US012741966B2

(12) United States Patent
Vaswani et al.

(10) Patent No.: US 12,741,966 B2
(45) **Date of Patent: *Sep. 22, 2026**

(54) BRM/BRG1 INHIBITORS AND USES THEREOF

(71) Applicant: FOGHORN THERAPEUTICS INC., Watertown, MA (US)

(72) Inventors: Rishi G. Vaswani, Lexington, MA (US); Neville John Anthony, Northborough, MA (US); David Simon Millan, Stow, MA (US); Shawn E.R. Schiller, Haverhill, MA (US); Kevin J. Wilson, Roslindale, MA (US); David S. Huang, Watertown, MA (US)

(73) Assignee: FOGHORN THERAPEUTICS INC., Watertown, MA (US)

( * ) Notice: Subject to any disclaimer, the term of this patent is extended or adjusted under 35 U.S.C. 154(b) by 1072 days.

This patent is subject to a terminal disclaimer.

(21) Appl. No.: 17/425,140

(22) PCT Filed: Jan. 29, 2020

(86) PCT No.: PCT/US2020/015723

§ 371 (c)(1),
(2) Date: Jul. 22, 2021

(87) PCT Pub. No.: WO2020/160180

PCT Pub. Date: Aug. 6, 2020

(65) Prior Publication Data

US 2023/0079819 A1 Mar. 16, 2023

Related U.S. Application Data

(60) Provisional application No. 62/938,415, filed on Nov. 21, 2019, provisional application No. 62/881,275, filed on Jul. 31, 2019, provisional application No. 62/798,406, filed on Jan. 29, 2019.

(51) Int. Cl.

| | |
|---|---|
| ***C07D 417/14*** | (2006.01) |
| ***A61P 35/00*** | (2006.01) |
| ***C07D 417/12*** | (2006.01) |
| ***C07D 471/04*** | (2006.01) |
| ***C07D 487/04*** | (2006.01) |
| ***C07D 491/048*** | (2006.01) |
| ***C07D 491/08*** | (2006.01) |
| ***C07D 491/107*** | (2006.01) |
| ***C07D 498/04*** | (2006.01) |

(52) U.S. Cl.

CPC ............ *C07D 417/14* (2013.01); *A61P 35/00* (2018.01); *C07D 417/12* (2013.01); *C07D 471/04* (2013.01); *C07D 487/04* (2013.01); *C07D 491/048* (2013.01); *C07D 491/08* (2013.01); *C07D 491/107* (2013.01); *C07D 498/04* (2013.01)

(58) Field of Classification Search

CPC .. C07D 401/00; C07D 403/00; C07D 405/00; C07D 407/00; C07D 409/00; C07D 417/14; C07D 417/12; C07D 491/048; C07D 491/08; A61P 35/00

See application file for complete search history.

(56) References Cited

U.S. PATENT DOCUMENTS

| | | | |
|---|---|---|---|
| 2,788,341 | A | 4/1957 | Schwyzer et al. |
| 3,717,642 | A | 2/1973 | Von Strandtmann |
| 4,109,496 | A | 8/1978 | Allemann et al. |
| 4,650,796 | A | 3/1987 | George et al. |
| 4,868,103 | A | 9/1989 | Stavrianopoulos et al. |
| 5,223,409 | A | 6/1993 | Ladner et al. |
| 5,225,422 | A | 7/1993 | Nagata et al. |
| 5,283,317 | A | 2/1994 | Saifer et al. |
| 5,631,169 | A | 5/1997 | Lakowicz et al. |
| 5,677,158 | A | 10/1997 | Zhou et al. |
| 5,801,030 | A | 9/1998 | McVey et al. |
| 5,858,358 | A | 1/1999 | June et al. |
| 5,883,223 | A | 3/1999 | Gray |
| 6,180,612 | B1 | 1/2001 | Hockensmith et al. |
| 6,309,634 | B1 | 10/2001 | Bankiewicz et al. |
| 6,352,694 | B1 | 3/2002 | June et al. |
| 6,551,786 | B2 | 4/2003 | Manfredi |

(Continued)

FOREIGN PATENT DOCUMENTS

| | | | |
|---|---|---|---|
| CN | 103038231 | A | 4/2013 |
| CN | 105473141 | A | 4/2016 |

(Continued)

OTHER PUBLICATIONS

Albany Molecular Research, Inc., RN 858073-83-3, 2005, STN Registry, Answer 2510 of 2521 (Year: 2005).*

Aurora Fine Chemicals, RN 924410-17-3, CHEMCATS, Entered STN Mar. 2, 2007 (Year: 2007).*

Aurora Fine Chemicals, RN 924420-04-2, CHEMCATS, Entered STN Mar. 2, 2007 (Year: 2007).*

Enamine, RN 1223164-86-0, CHEMCATS, Entered STN May 14, 2010 (Year: 2010).*

FCH Group, RN 1300403-14-8, Entered STN May 25, 2011 (Year: 2011).*

"FLI1 gene," MedlinePlus, published May 1, 2012, <https://medlineplus.gov/genetics/> (3 pages).

(Continued)

*Primary Examiner* — Brenda L Coleman
*Assistant Examiner* — Madeline E Braun
(74) *Attorney, Agent, or Firm* — Clark & Elbing LLP

(57) ABSTRACT

The compounds disclosed herein may be inhibitors of BRG1 (Brahma-related gene-1) and/or BRM (Brahma). The compounds or pharmaceutically acceptable salts thereof are useful for the treatment of disorders associated with an alteration in a BAF complex, e.g., a disorder associated with an alteration in one or both of the BRG1 and BRM proteins. Also disclosed are pharmaceutical compositions containing the compounds or pharmaceutically acceptable salts thereof and methods of their preparation and use.

16 Claims, 13 Drawing Sheets

(56) References Cited

U.S. PATENT DOCUMENTS 6,683,058 B1 1/2004 Tuszynski
6,692,964 B1 2/2004 June et al.
6,716,662 B2 4/2004 Akai
6,797,514 B2 9/2004 Berenson et al.
6,867,041 B2 3/2005 Berenson et al.
6,887,466 B2 5/2005 June et al.
6,905,680 B2 6/2005 June et al.
6,905,681 B1 6/2005 June et al.
6,905,874 B2 6/2005 Berenson et al.
6,995,011 B2 2/2006 Itoh et al.
7,067,318 B2 6/2006 June et al.
7,144,575 B2 12/2006 June et al.
7,172,869 B2 2/2007 June et al.
7,175,843 B2 2/2007 June et al.
7,205,103 B2 4/2007 Emerson
7,232,566 B2 6/2007 June et al.
7,348,326 B2 3/2008 DeSimone et al.
7,572,631 B2 8/2009 Berenson et al.
8,324,367 B2 12/2012 Kaemmerer et al.
8,642,660 B2 2/2014 Goldfarb
8,697,359 B1 4/2014 Zhang
8,703,761 B2 4/2014 Forster et al.
8,771,945 B1 7/2014 Zhang
8,795,965 B2 8/2014 Zhang
8,865,406 B2 10/2014 Zhang et al.
8,945,861 B2 2/2015 Bomgarden et al.
8,946,268 B2 2/2015 Lau et al.
9,072,052 B2 6/2015 Griffin et al.
9,126,985 B2 9/2015 Kley et al.
9,353,051 B2 5/2016 Byrd et al.
9,403,843 B2 8/2016 Thatcher et al.
9,410,943 B2 8/2016 Kadoch et al.
9,546,206 B2 1/2017 Ring et al.
9,546,296 B2 1/2017 Wang et al.
9,636,323 B2 5/2017 Lin et al.
9,656,959 B2 5/2017 Ni et al.
9,694,084 B2 7/2017 Bradner et al.
9,708,338 B2 7/2017 Yukimasa et al.
9,708,348 B2 7/2017 Castro et al.
9,850,543 B2 12/2017 Jagani et al.
9,919,998 B2 3/2018 Ebright et al.
9,932,340 B2 4/2018 Dai et al.
10,105,420 B2 10/2018 Kadoch et al.
10,131,637 B2 11/2018 Abdel-Meguid et al.
10,207,998 B2 2/2019 Derbyshire et al.
10,239,888 B2 3/2019 Bradner et al.
10,266,850 B2 4/2019 Doudna et al.
10,308,614 B2 6/2019 Albrecht et al.
10,464,925 B2 11/2019 Bradner et al.
10,472,376 B2 11/2019 Yamamoto et al.
10,646,575 B2 5/2020 Phillips et al.
10,660,968 B2 5/2020 Phillips et al.
10,669,253 B2 6/2020 Bradner et al.
10,849,982 B2 12/2020 Phillips et al.
10,905,768 B1 2/2021 Phillips et al.
10,976,320 B2 4/2021 Dykhuizen et al.
11,149,254 B2 10/2021 Szalay et al.
11,419,859 B2 8/2022 Agresta
11,485,732 B2 11/2022 Vaswani et al.
11,497,752 B2 11/2022 Anthony et al.
11,639,345 B2 5/2023 Bloch et al.
11,773,085 B2 10/2023 Zhou et al.
11,793,802 B2 10/2023 Bearss et al.
11,851,445 B2 12/2023 Ruppel et al.
11,865,114 B2 1/2024 Ramachandra et al.
12,282,014 B2 4/2025 Kadoch et al.
12,383,555 B2 8/2025 Centore et al.
12,383,560 B2 8/2025 Anthony et al.
12,441,726 B2 10/2025 Wilson et al.
12,486,262 B2 12/2025 Vaswani et al.
2002/0022018 A1 2/2002 Curiel et al.
2002/0037281 A1 3/2002 Davidson et al.
2002/0106632 A1 8/2002 Manfredi
2003/0022375 A1 1/2003 Itoh et al.
2003/0027335 A1 2/2003 Ruley et al.
2004/0216178 A1 10/2004 Jones et al.
2005/0079512 A1 4/2005 Emerson et al.
2005/0130919 A1 6/2005 Xu et al.
2006/0058255 A1 3/2006 Chen et al.
2006/0121005 A1 6/2006 Berenson et al.
2007/0105181 A1 5/2007 Pope et al.
2008/0221157 A1 9/2008 Chakravarty et al.
2009/0163545 A1 6/2009 Goldfarb
2010/0048565 A1 2/2010 Frenkel et al.
2010/0197621 A1 8/2010 Henry et al.
2010/0284990 A1 11/2010 Kaemmerer et al.
2011/0003809 A1 1/2011 Ahrendt
2011/0230486 A1 9/2011 Lau et al.
2012/0034867 A1 2/2012 Griffin et al.
2012/0035244 A1 2/2012 Chinnaiyan et al.
2012/0308484 A1 12/2012 Szalay et al.
2013/0034867 A1 2/2013 Bomgarden et al.
2014/0068797 A1 3/2014 Doudna et al.
2014/0287931 A1 9/2014 Bernards et al.
2015/0057169 A1 2/2015 Siu et al.
2015/0376139 A1 12/2015 Abdel-Meguid et al.
2016/0032402 A1 2/2016 Jagani et al.
2016/0039903 A1 2/2016 Ring et al.
2016/0130663 A1 5/2016 Kohno et al.
2016/0176916 A1 6/2016 Bradner et al.
2016/0200721 A1 7/2016 Yukimasa et al.
2016/0347708 A1 12/2016 Ebright et al.
2018/0086720 A1 3/2018 Albrecht et al.
2018/0105500 A1 4/2018 Derbyshire et al.
2018/0140722 A1 5/2018 Willis et al.
2018/0258491 A1 9/2018 Jagani et al.
2018/0303808 A1 10/2018 Agresta
2018/0328913 A1 11/2018 Kadoch et al.
2020/0069669 A1 3/2020 Grassian et al.
2020/0206344 A1 7/2020 Kadoch et al.
2020/0261434 A1 8/2020 Choe et al.
2021/0009568 A1 1/2021 Zhou et al.
2021/0038611 A1 2/2021 Anthony et al.
2021/0171958 A1 6/2021 Chan et al.
2021/0230154 A1 7/2021 Vaswani et al.
2021/0230190 A1 7/2021 Ruppel et al.
2021/0251988 A1 8/2021 Zhou et al.
2021/0260171 A1 8/2021 Zhou et al.
2021/0388040 A1 12/2021 Kadoch et al.
2022/0016083 A1 1/2022 Centore et al.
2022/0079940 A1 3/2022 Centore et al.
2022/0098190 A1 3/2022 Ruppel et al.
2022/0119378 A1 4/2022 Anthony et al.
2022/0125776 A1 4/2022 Bearss et al.
2022/0396604 A1 12/2022 Kadoch et al.
2023/0035235 A1 2/2023 Kadoch et al.
2023/0121497 A1 4/2023 Vaswani et al.
2023/0129003 A1 4/2023 Vaswani et al.
2023/0138480 A1 5/2023 Anthony et al.
2023/0145003 A1 5/2023 Wilson et al.
2023/0149414 A1 5/2023 Anthony et al.
2024/0101550 A1 3/2024 Vaswani et al.
2024/0158387 A1 5/2024 Vaswani et al.
2024/0189318 A1 6/2024 Huang
2025/0241931 A1 7/2025 Reilly et al.
2025/0325553 A1 10/2025 Schuck et al.
2025/0339441 A1 11/2025 Schuck et al.

FOREIGN PATENT DOCUMENTS

CN 104530013 B 6/2016
CN 107531668 A 1/2018
EA 202192101 A1 12/2021
JP 2000-095767 A 4/2000
JP 2008-505963 A 2/2008
JP 2011-507910 A 3/2011
JP 2011-528016 A 11/2011
JP 2016-520515 A 7/2016
WO WO-94/10300 A1 5/1994
WO WO-95/30761 A2 11/1995
WO WO-2000/024392 A1 5/2000
WO WO-00/59888 A1 10/2000
WO WO-00/59905 A1 10/2000
WO WO-2005/039643 A2 5/2005

(56) References Cited

FOREIGN PATENT DOCUMENTS

| | | | | |
|---|---|---|---|---|
| WO | WO-2005/112620 A2 | 12/2005 | | |
| WO | WO-2006/005941 A1 | 1/2006 | | |
| WO | WO-2006/051063 A1 | 5/2006 | | |
| WO | WO-2006/070806 A1 | 7/2006 | | |
| WO | WO-2008/022396 A1 | 2/2008 | | |
| WO | WO-2008/157500 A1 | 12/2008 | | |
| WO | WO-2009/086303 A2 | 7/2009 | | |
| WO | WO-2009/111277 A1 | 9/2009 | | |
| WO | WO-2010/007046 A2 | 1/2010 | | |
| WO | WO-2011/115998 A2 | 9/2011 | | |
| WO | WO-2011/132175 A2 | 10/2011 | | |
| WO | WO-2012/085650 A1 | 6/2012 | | |
| WO | WO-2013/116663 A1 | 8/2013 | | |
| WO | WO-2013116682 A1 | 8/2013 | | |
| WO | WO-2014/150395 A1 | 9/2014 | | |
| WO | WO-2015/005473 A1 | 1/2015 | | |
| WO | WO-2015002230 A1 | 1/2015 | | |
| WO | WO-2015/103317 A1 | 7/2015 | | |
| WO | WO-2015/120320 A1 | 8/2015 | | |
| WO | WO-2015/121688 A1 | 8/2015 | | |
| WO | WO-2016/054491 A1 | 4/2016 | | |
| WO | WO-2016/138114 A1 | 9/2016 | | |
| WO | WO-2016/160718 A1 | 10/2016 | | |
| WO | WO-2016/207212 A1 | 12/2016 | | |
| WO | WO-2017/024318 A1 | 2/2017 | | |
| WO | WO-2017060470 A1 | 4/2017 | | |
| WO | WO-2017/087885 A1 | 5/2017 | | |
| WO | WO-2017/118734 A1 | 7/2017 | | |
| WO | WO-2017/158381 A1 | 9/2017 | | |
| WO | WO-2018/148443 A1 | 8/2018 | | |
| WO | WO-2018/160636 A1 | 9/2018 | | |
| WO | WO-2018/175324 A1 | 9/2018 | | |
| WO | WO-2019/038215 A1 | 2/2019 | | |
| WO | WO-2019/040098 A1 | 2/2019 | | |
| WO | WO-2019/138017 A1 | 7/2019 | | |
| WO | WO-2019/142192 A1 | 7/2019 | | |
| WO | WO-2019/152437 A1 | 8/2019 | | |
| WO | WO-2019/152440 A1 | 8/2019 | | |
| WO | WO-2019/226915 A1 | 11/2019 | | |
| WO | WO-2020/035779 A1 | 2/2020 | | |
| WO | WO-2020/081556 A2 | 4/2020 | | |
| WO | WO-2020/081588 A1 | 4/2020 | | |
| WO | WO-2020106915 A1 * | 5/2020 | ......... | A61K 31/4184 |
| WO | WO-2020/127685 A1 | 6/2020 | | |
| WO | WO-2020/160100 A1 | 8/2020 | | |
| WO | WO-2020/160180 A1 | 8/2020 | | |
| WO | WO-2021/081032 A1 | 4/2021 | | |
| WO | WO-2021/155262 A1 | 8/2021 | | |
| WO | WO-2021/155264 A1 | 8/2021 | | |
| WO | WO-2021/155316 A1 | 8/2021 | | |
| WO | WO-2021/155320 A1 | 8/2021 | | |
| WO | WO-2021/155321 A2 | 8/2021 | | |
| WO | WO-2021/183218 A1 | 9/2021 | | |
| WO | WO-2021/236080 A1 | 11/2021 | | |
| WO | WO-2022/192621 A1 | 9/2022 | | |
| WO | WO-2022/198043 A1 | 9/2022 | | |
| WO | WO-2023/009834 A2 | 2/2023 | | |
| WO | WO-2023/196560 A1 | 10/2023 | | |
| WO | WO-2023/196565 A1 | 10/2023 | | |
| WO | WO-2023/196567 A2 | 10/2023 | | |
| WO | WO-2024/024428 A1 | 2/2024 | | |
| WO | WO-2024/031875 A1 | 2/2024 | | |
| WO | WO-2024/086577 A1 | 4/2024 | | |
| WO | WO-2024/249769 A2 | 12/2024 | | |
| WO | WO-2025/080767 A1 | 4/2025 | | |
| WO | WO-2025/080769 A1 | 4/2025 | | |

OTHER PUBLICATIONS

Adam et al., International Application No. PCT/US2024/024407, filed Apr. 12, 2024 by applicant Foghorn Therapeutics Inc. (42 pages).

Adam et al., International Application No. PCT/US2024/024428, filed Apr. 12, 2024 by applicant Foghorn Therapeutics Inc. (40 pages).

Boulay et al., "Cancer-Specific Retargeting of BAF Complexes by a Prion-like Domain," Cell 171(1):163-78 (Sep. 21, 2017).

Centore et al., "Abstract 1224: Discovery of novel BAF inhibitors for the treatment of transcription factor-driven cancers," Poster Presentations—Proffered abstracts, Cancer Research 81(13_ Supplement): 1224 (Jul. 1, 2021) (2 pages).

Coban et al., "Synthesis, biological activity screening and molecular modeling study of acylaminoacetamide derivatives," Med Chem Res. 24(10):3710-29 (Jul. 25, 2015).

Database Registry, RN 1323542-96-6, entered Aug. 26, 2011 (1 page).

Décor et al., "Design, synthesis and biological evaluation of novel aminothiazoles as antiviral compounds acting against human rhinovirus," Bioorg Med Chem Lett. 23(13):3841-7 (Jul. 1, 2013).

Extended European Search Report for European Application No. 21748261.1, dated Jan. 29, 2024 (17 pages).

Fadul et al., "EWS/FLI utilizes NKX2-2 to repress mesenchymal features of Ewing sarcoma," Genes Cancer 6(3-4):129-43 (Mar. 2015).

Gingras et al., "Advances in protein complex analysis using mass spectrometry," J Physiol. 563(Pt 1):11-21 (Feb. 15, 2005).

Grohar et al., "Ecteinascidin 743 interferes with the activity of EWS-FLI1 in Ewing sarcoma cells," Neoplasia 13(2):145-53 (Feb. 2011).

Herrero-Martin et al., "Stable interference of EWS-FLI1 in an Ewing sarcoma cell line impairs IGF-1/IGF-1R signalling and reveals TOPK as a new target," Br J Cancer 101(1):80-90 (Jul. 7, 2009).

Hohmann et al., "Sensitivity and engineered resistance of myeloid leukemia cells to BRD9 inhibition," Nat Chem Biol. 12(9): 672-679 (Sep. 2016) (12 pages).

International Preliminary Report on Patentability for International Application No. PCT/US2019/056312, mailed Apr. 29, 2021 (10 pages). Incorrect date. /MEB/.

International Preliminary Report on Patentability for International Application No. PCT/US2022/019506, issued Sep. 12, 2023 (6 pages).

International Preliminary Report on Patentability for International Application No. PCT/US2022/020943, issued Sep. 12, 2023 (5 pages).

International Search Report and Written Opinion for International Application No. PCT/US18/000339 dated Jan. 28, 2019 (13 pages).

International Search Report and Written Opinion for International Application No. PCT/US19/56312, dated Jan. 14, 2020 (14 pages).

International Search Report and Written Opinion for International Application No. PCT/US2023/077088, mailed Mar. 4, 2024 (17 pages).

International Search Report and Written Opinion for International Application No. PCT/US2024/024407, mailed Jun. 24, 2024 (15 pages).

Jones et al., "A novel series of potent and selective ketone histone deacetylase inhibitors with antitumor activity in vivo," J Med Chem. 51(8):2350-3 (Apr. 24, 2008).

Kedage et al., "An Interaction with Ewing's Sarcoma Breakpoint Protein EWS Defines a Specific Oncogenic Mechanism of ETS Factors Rearranged in Prostate Cancer," Cell Rep. 17(5):1289-301 (Oct. 25, 2016).

Michel et al., "Abstract PR15: BRD9 defines a novel mammalian SWI/SNF (BAF) complex configuration which supports proliferation in AML," Clin Cancer Res. 23(24_Suppl) Abstract PR15 (2017) (4 pages).

Mill et al., "RUNX1-targeted therapy for AML expressing somatic or germline mutation in RUNX1," Blood 134(1):59-73 (Jul. 4, 2019).

Partial Supplementary European Search Report for European Patent Application No. 20936213.6, dated Feb. 8, 2024 (20 pages).

Pescatore et al., "Optimization of a series of potent and selective ketone histone deacetylase inhibitors," Bioorg Med Chem Lett. 18(20):5528-32 (Oct. 15, 2008).

Piel et al., International Application No. PCT/US2024/031875, filed May 31, 2024 by applicant Foghorn Therapeutics Inc. (47 pages).

(56) References Cited

OTHER PUBLICATIONS

Rago et al., "Exquisite Sensitivity to Dual BRG1/BRM ATPase Inhibitors Reveals Broad SWI/SNF Dependencies in Acute Myeloid Leukemia," Mol Cancer Res. 20(3):361-72 (Mar. 1, 2022).
Ramos et al., "Current Approaches in the Treatment of Relapsed and Refractory Acute Myeloid Leukemia," J Clin Med. 4(4):665-95 (Apr. 2015).
Riggi et al., "EWS-FLI1 utilizes divergent chromatin remodeling mechanisms to directly activate or repress enhancer elements in Ewing sarcoma," Cancer Cell 26(5):668-81 (Nov. 10, 2014).
Sankar et al., "Promiscuous partnerships in Ewing's sarcoma," Cancer Genet. 204(7):351-65 (Jul. 2011).
Schiefer et al., "Design, synthesis, and optimization of novel epoxide incorporating peptidomimetics as selective calpain inhibitors," J Med Chem. 56(15):6054-68 (Aug. 8, 2013).
Spickler et al., "Phosphatidylinositol 4-kinase III beta is essential for replication of human rhinovirus and its inhibition causes a lethal phenotype in vivo," Antimicrob Agents Chemother. 57(7):3358-68 (Jul. 2013).
STN Registry Database, RN 1010893-05-6, entered Mar. 30, 2008 (2 pages).
STN Registry Database, RN 1049271-26-2, entered Sep. 14, 2008 (2 pages).
STN Registry Database, RN 1081662-32-9, entered Dec. 8, 2008 (2 pages).
STN Registry Database, RN 1209112-42-4, entered Mar. 12, 2010 (2 pages).
STN Registry Database, RN 1246047-75-5, entered Oct. 12, 2010 (2 pages).
STN Registry Database, RN 1308280-67-2, entered Jun. 9, 2011 (2 pages).
STN Registry Database, RN 1351682-19-3, entered Dec. 22, 2011 (2 pages).
STN Registry Database, RN 1401558-47-1, entered Oct. 22, 2012 (2 pages).
STN Registry Database, RN 1455783-72-8, entered Oct. 6, 2013 (2 pages).
STN Registry Database, RN 1576383-94-2, entered Mar. 31, 2014 (2 pages).
STN Registry Database, RN 1586193-45-4, entered Apr. 17, 2014 (2 pages).
STN Registry Database, RN 1827759-12-5, entered Dec. 13, 2015 (2 pages).
STN Registry Database, RN 1831899-24-1, entered Dec. 17, 2015 (2 pages).
STN Registry Database, RN 1839545-15-1, entered Dec. 31, 2015 (2 pages).
STN Registry Database, RN 923768-18-7, entered Feb. 28, 2007 (2 pages).
STN Registry Database, RN 923809-79-4, entered Feb. 28, 2007 (2 pages).
STN Registry Database, RN 931893-54-8, entered Apr. 23, 2007 (2 pages).
STN Registry Database, RN 932130-00-2, entered Apr. 24, 2007 (2 pages).
STN Registry Database, RN 938283-11-5, entered Jun. 22, 2007 (2 pages).
Takigami et al., "Synthetic siRNA targeting the breakpoint of EWS/Fli-1 inhibits growth of Ewing sarcoma xenografts in a mouse model," Int J Cancer 128(1):216-26 (Jan. 1, 2011).
Triandafillidi et al., "tert-Butyl ester or benzylamide of the dipeptide Pro-Gly as organocatalysts for the asymmetric aldol reaction," Tetrahedron 71:932-40 (2015).
Wahedy et al., "Facile Synthesis and In-Vitro Antimicrobial Activity of Some Novel 2-Hetroamido-5-Amino Benzimidazoles," Am J PharmTech Res. 3(2):868-82 (2013).
Wu et al., "Targeting the chromatin remodeling enzyme BRG1 increases the efficacy of chemotherapy drugs in breast cancer cells," Oncotarget 7(19):27158-75 (May 10, 2016).
Zhang et al., "Discovery of novel dual-action antidiabetic agents that inhibit glycogen phosphorylase and activate glucokinase," Eur J Med Chem. 58:624-39 (Dec. 2012).
U.S. Appl. No. 18/281,022, Vaswani et al.
U.S. Appl. No. 18/282,279, Huang, Liyue.
U.S. Appl. No. 18/373,518, Huang et al.
Adamo et al., "The oncogene ERG: a key factor in prostate cancer," Oncogene 35(4):403-14 (Jan. 28, 2016).
Advani et al., "A Phase 1 study of imatinib mesylate in combination with cytarabine and daunorubicin for c-kit positive relapsed acute myeloid leukemia," Leuk Res. 34(12):1622-6 (Dec. 2010).
Alazawi, "Foghorn Therapeutics," Blackseed Bio, last updated Mar. 4, 2022, retrieved Jul. 24, 2023, from <https://blackseedbio.com/reports/fhtx#pipeline> (26 pages).
Anders et al., "HTSeq—a Python framework to work with high-throughput sequencing data," Bioinformatics 31(2):166-9 (Jan. 15, 2015).
Asangani et al., "Therapeutic targeting of BET bromodomain proteins in castration-resistant prostate cancer," available in PMC Dec. 12, 2014. Published in final edited form as: Nature. 510(7504):278-82 (2014) (44 pages).
Attard et al., "Duplication of the fusion of TMPRSS2 to ERG sequences identifies fatal human prostate cancer," available in PMC Feb. 24, 2009. Published in final edited form as: Oncogene. 27(3):253-63 (2008) (19 pages).
Basuyaux et al., "The Ets transcription factors interact with each other and with the c-Fos/c-Jun complex via distinct protein domains in a DNA-dependent and -independent manner," J Biol Chem. 272(42):26188-95 (1997).
Bendall et al., "Prevention of amino acid conversion in SILAC experiments with embryonic stem cells," Mol Cell Proteomics. 7(9):1587-97 (2008).
Berger et al., "Androgen-induced differentiation and tumorigenicity of human prostate epithelial cells," Cancer Res. 64(24):8867-75 (2004).
Börno et al., "Genome-wide DNA methylation events in TMPRSS2-ERG fusion-negative prostate cancers implicate an EZH2-dependent mechanism with miR-26a hypermethylation," Cancer Discov. 2(11):1024-35 (2012).
Camuzeaux et al., "Imaging Erg and Jun transcription factor interaction in living cells using fluorescence resonance energy transfer analyses," Biochem Biophys Res Commun. 332(4):1107-14 (2005).
Cancer Genome Atlas Research Network, "The Molecular Taxonomy of Primary Prostate Cancer," Cell. 163(4):1011-25 (2015) (16 pages).
Carell et al., "A novel procedure for the synthesis of libraries containing small organic molecules," Angew Chem Int Ed Engl. 33(20):2059-2061 (1994).
Carell et al., "A Solution-Phase Screening Procedure for the Isolation of Active Compounds from a Library of Molecules," Angewandte Chemie International Edition in English. 33(20): 2061-2064 (1994).
Chen et al., "ETS factors reprogram the androgen receptor cistrome and prime prostate tumorigenesis in response to PTEN loss," available in PMC Feb. 1, 2014. Published in final edited form as: Nat Med. 19(8):1023-9 (2013) (21 pages).
Chng et al., "A transcriptional repressor co-regulatory network governing androgen response in prostate cancers," EMBO J. 31(12):2810-23 (2012).
Cho et al., "An unnatural biopolymer," Science. 261(5126):1303-1305 (1993).
Cull et al., "Screening for receptor ligands using large libraries of peptides linked to the C terminus of the lac repressor," Proc Natl Acad Sci. 89(5):1865-1869. (1992).
Cwirla et al., "Peptides on phage: A vast library of peptides for identifying ligands," Proc Nati Acad Sci. 87:6378-6382 (1990).
Database Registry, RN 1004932-80-2, entered Feb. 21, 2008 (1 page).
Database Registry, RN 1175782-23-6, entered Aug. 26, 2009 (1 page).
Database Registry, RN 1315743-98-6, entered Aug. 11, 2011 (1 page).
Database Registry, RN 878254-76-3, entered Mar. 28, 2006 (1 page).

(56) References Cited

OTHER PUBLICATIONS

Delattre et al., "Gene fusion with an ETS DNA-binding domain caused by chromosome translocation in human tumours," Nature. 359(6391):162-5 (1992).
Demichelis et al., "TMPRSS2:ERG gene fusion associated with lethal prostate cancer in a watchful waiting cohort," Oncogene 26:4596-4599 (2007).
Devlin et al., "Random Peptide Libraries: a Source of Specific Protein Binding Molecules," Science. 249(4967):404-406 (1990).
DeWitt et al., "Diversomers': an approach to nonpeptide, nonoligomeric chemical diversity," Proc Natl Acad Sci. 90(15):6909-6913 (1993).
Dobin et al., "STAR: ultrafast universal RNA-seq aligner," Bioinformatics. 29(1):15-21 (2013).
Dominguez et al. "Beyond editing: Repurposing CRISPR-Cas9 for Precision Genome Regulation and Interrogation," available in PMC Jun. 27, 2016, published in final edited form as: Nat Rev Mol Cell Biol. 17(1):5-15 (Jan. 2016) (24 pages).
Donaldson et al., "Solution structure of the ETS domain from murine Ets-1: a winged helix-turn-helix DNA binding motif," EMBO J. 15(1):125-34 (1996).
Erb et al., "Recursive deconvolution of combinatorial chemical libraries," Proc Natl Acad Sci. 91(24):11422-11426 (1994).
Extended European Search Report for European Application No. 19748410.8, dated Sep. 24, 2021 (10 pages).
Extended European Search Report for European Application No. 19887386.1, dated Dec. 5, 2022 (18 pages).
Extended European Search Report for European Application No. 20749261.2, dated Oct. 18, 2022 (8 pages).
Fathi et al., "Differentiation syndrome with lower-intensity treatments for acute myeloid leukemia," Am J Hematol. 96(6):735-46 (Jun. 1, 2021) (13 Pages).
Felici et al., "Selection of antibody ligands from a large library of oligopeptides expressed on a multivalent exposition vector," J Mol Biol. 222(2):301-10 (1991).
Feng et al., "GFOLD: a generalized fold change for ranking differentially expressed genes from RNA-seq data," Bioinformatics. 28(21):2782-8 (2012).
Fodor et al., "Multiplexed biochemical assays with biological chips," Nature. 364:555-556 (1993).
Gaj et al. "ZFN, TALEN and CRISPR/Cas-based Methods for Genome Engineering," available in PMC Jul. 1, 2014, published in final edited form as: Trends Biotechnol. 31(7):397-405 (Jul. 2013) (20 pages).
Gallop et al., "Applications of Combinatorial Technologies to Drug Discovery. 1. Background and Peptide Combinatorial Libraries," J Med Chem 37(9):1233-51 (1994).
Gene Ontology Consortium, "Gene Ontology Consortium: going forward," Nucleic Acids Res. 43(Database issue): D1049-56 (2015).
Godwin et al., "Gemtuzumab ozogamicin in acute myeloid leukemia," Leukemia 31(9):1855-68 (Sep. 2017).
Helgeson et al., "Characterization of TMPRSS2:ETV5 and SLC45A3:ETV5 gene fusions in prostate cancer," Cancer Res. 68(1):73-80 (2008).
Ho et al., "An embryonic stem cell chromatin remodeling complex, esBAF, is essential for embryonic stem cell self-renewal and pluripotency," Proc Natl Acad Sci U S A. 106(13):5181-6 (2009).
Houghten et al., "The use of synthetic peptide combinatorial libraries for the identification of bioactive peptides," Biotechniques. 13(3):412-21 (1992).
Ichikawa et al., "An RNA-binding protein gene, TLS/FUS, is fused to ERG in human myeloid leukemia with t(16;21) chromosomal translocation," Cancer Res. 54(11):2865-8 (1994).
International Preliminary Report on Patentability for International Application No. PCT/US2016/062911 issued May 22, 2018 (13 pages).
International Preliminary Report on Patentability for International Application No. PCT/US2019/015722, issued Aug. 4, 2020 (6 pages).
International Preliminary Report on Patentability for International Application No. PCT/US2020/033829, issued Nov. 17, 2022 (6 pages).
International Search Report and Written Opinion for International Application No. PCT/US19/15722, mailed May 31, 2019 (12 pages).
International Search Report and Written Opinion for International Application No. PCT/US2016/062911 dated Mar. 3, 2017 (16 pages).
International Search Report and Written Opinion for International Application No. PCT/US2020/015605, mailed Jun. 16, 2020 (15 pages).
International Search Report and Written Opinion for International Application No. PCT/US2020/015723, mailed Jul. 2, 2020 (15 pages).
International Search Report and Written Opinion for International Application No. PCT/US2020/033829, mailed Aug. 17, 2020 (14 pages).
International Search Report and Written Opinion for International Application No. PCT/US2022/019506, dated Jun. 7, 2022 (9 pages).
International Search Report and Written Opinion for International Application No. PCT/US2023/017839, mailed Sep. 6, 2023 (11 pages).
International Search Report and Written Opinion for International Application No. PCT/US21/15876, mailed on Apr. 7, 2021 (23 pages).
International Search Report and Written Opinion for International Application No. PCT/US21/15878, dated Jun. 4, 2021 (10 pages).
International Search Report and Written Opinion for International Application No. PCT/US23/17821, mailed Jun. 30, 2023 (9 pages).
International Search Report and Written Opinion for International Application No. PCT/US23/17829, mailed Aug. 23, 2023 (15 pages).
International Search Report and Written Opinion for International Patent Application No. PCT/US2019/062525, mailed Feb. 18, 2020 (14 pages).
International Search Report and Written Opinion for PCT/US2022/020943, dated Jun. 14, 2022 (17 pages).
Kadoch et al. "Reversible Disruption of mSWI/SNF (BAF) Complexes by the SS18-SSX Oncogenic Fusion in Synovial Sarcoma," available in PMC May 16, 2013, published in final edited form as: Cell. 153(1):71-85 (Mar. 2013) (26 pages).
Kadoch et al., "Mammalian SWI/SNF chromatin remodeling complexes and cancer: Mechanistic insights gained from human genomics," Sci Adv. 1(5):e1500447 (2015) (17 pages).
Kadoch et al., "Proteomic and bioinformatic analysis of mammalian SWI/SNF complexes identifies extensive roles in human malignancy," Nat Genet. 45(6):592-601 (2013) (11 pages).
Karim et al., "The ETS-domain: a new DNA-binding motif that recognizes a purine-rich core DNA sequence," Genes Dev. 4(9):1451-3 (1990).
Klezovitch et al., "A causal role for ERG in neoplastic transformation of prostate epithelium," Proc Natl Acad Sci U S A. 105(6):2105-10 (2008).
Kumar-Sinha et al., "Recurrent gene fusions in prostate cancer," available in PMC Jul. 16, 2009. Published in final edited form as: Nat Rev Cancer. 8(7):497-511 (2008) (29 pages).
Kunderfranco et al., "ETS transcription factors control transcription of EZH2 and epigenetic silencing of the tumor suppressor gene Nkx3.1 in prostate cancer," PLoS One. 5(5):e10547 (2010) (17 pages).
Lam et al., "A new type of synthetic peptide library for identifying ligand-binding activity," Nature. 354(6348):82-84 (1991).
Lam, "Application of combinatorial library methods in cancer research and drug discovery," Anticancer Drug Des. 12(3):145-67 (1997).
Langmead et al., "Fast gapped-read alignment with Bowtie 2," available in PMC Apr. 1, 2013. Published in final edited form as: Nat Methods. 9(4):357-9 (2012) (8 pages).
Link et al., "Targeting the BAF57 SWI/SNF subunit in prostate cancer: a novel platform to control androgen receptor activity," Cancer Res. 68(12):4551-8 (2008).

(56) References Cited

OTHER PUBLICATIONS

Love et al., "Moderated estimation of fold change and dispersion for RNA-seq data with DESeq2," Genome Biol. 15(12):550 (2014) (21 pages).

Lupien et al., "FoxA1 translates epigenetic signatures into enhancer-driven lineage-specific transcription," Cell. 132(6):958-70 (2008).

Machanick et al., "MEME-ChIP: motif analysis of large DNA datasets," Bioinformatics. 27(12):1696-7 (2011).

MacKereth et al., "Diversity in structure and function of the Ets family PNT domains," J Mol Biol. 342(4):1249-64 (2004).

Madura et al., "N-recognin/Ubc2 interactions in the N-end rule pathway," J Biol Chem. 268(16):12046-54 (1993).

McBride et al., "Disruption of mammalian SWI/SNF and polycomb complexes in human sarcomas: mechanisms and therapeutic opportunities," J Pathol. 244(5): 638-649 (Apr. 2018).

Mele et al., "The human transcriptome across tissues and individuals," available in PMC Aug. 24, 2015. Published in final edited form as: Science. 348(6235):660-5 (2015) (12 pages).

Mounir et al., "ERG signaling in prostate cancer is driven through PRMT5-dependent methylation of the Androgen Receptor," Elife. 5:e13964 (2016) (19 pages).

Nagaich et al., "Rapid periodic binding and displacement of the glucocorticoid receptor during chromatin remodeling," Mol Cell. 14(2):163-74 (2004).

Nam et al., "Expression of the TMPRSS2:ERG fusion gene predicts cancer recurrence after surgery for localised prostate cancer," Br J Cancer. 97(12):1690-5 (2007).

Office Action for Chinese Patent Application No. 201980023925.9, dated Apr. 20, 2022 (13 pages).

Ong et al., "A practical recipe for stable isotope labeling by amino acids in cell culture (SILAC)," Nat Protoc. 1(6):2650-60 (2006).

Papillon et al., "Discovery of Orally Active Inhibitors of Brahma Homolog (BRM)/SMARCA2 ATPase Activity for the Treatment of Brahma Related Gene 1 (BRG1)/SMARCA4-Mutant Cancers," J Med Chem. 61(22):10155-72 (Nov. 2018).

Partial Supplementary European Search Report for European Patent Application No. 19887386.1, dated Jul. 20, 2022 (23 pages).

Paulo et al., "FLI1 is a novel ETS transcription factor involved in gene fusions in prostate cancer," Genes Chromosomes Cancer. 51(3):240-9 (2012).

Petrovics et al., "Frequent overexpression of ETS-related gene-1 (ERG1) in prostate cancer transcriptome," Oncogene. 24(23):3847-52 (2005).

Pomerantz et al., "The androgen receptor cistrome is extensively reprogrammed in human prostate tumorigenesis," available in PMC May 1, 2016. Published in final edited form as: Nat Genet. 47(11):1346-51 (2015) (17 pages).

Prensner et al., "The long noncoding RNA SChLAP1 promotes aggressive prostate cancer and antagonizes the SWI/SNF complex," available in PMC May 1, 2014. Published in final edited form as: Nat Genet. 45(11):1392-8 (2013) (26 pages).

PubChem CID 117640569, "N-[2-[[4-(4-Methoxyphenyl)-1,3-thiazol-2-yl]amino]-2-oxoethyl]-1,3-thiazole-5-carboxamide," https://pubchem.ncbi.nlm.nih.gov/compound/117640569, created Feb. 23, 2016 (9 pages).

PubChem CID 56442706, "1-(4-Methoxyphenyl)-N-[2-oxo-2-[4-(1,2,4-triazol-1-yl) anilino]ethyl]pyrazole-3-carboxamide," https://pubchem.ncbi.nlm.nih.gov/compound/56442706, created Jan. 25, 2012 (8 pages).

PubChem CID 91946137, "N-[2-[(1-Ethylpyrazol-3-yl}amino]-2-oxoethyl]-1-methylpyrazole-3-carboxamide," https://pubchem.ncbi.nlm.nih.gov/compound/91946137, created Oct. 22, 2015 (8 pages).

PubChem Compound Summary for CID 155037309, dated Dec. 19, 2020 (9 pages).

PubChem Compound Summary for CID No. 136572628, "4-Chloro-N-[2-(cyclopentylamino)-2-oxoethyl]-5-nitro-1H-pyrazole-3-carboxamide," created Jan. 24, 2019, <https://pubchem.ncbi.nlm.nih.gov/compound/136572628>, (7 pages).

PubChem Compound Summary for CID No. 49726797, "N-Methyl-N-(2-oxo-2-((4-(pyridin-3-yl)thiazol-2-yl)amino)ethyl)-1H-indole-3-carboxamide," created Nov. 27, 2010, <https://pubchem.ncbi.nlm.nih.gov/compound/49726797>, (8 pages).

PubChem Compound Summary for CID No. 91945707, "N-[2-[(4,5-Dimethyl-1,3-thiazol-2-yl)amino]-2-oxoethyl]-1-methylpyrazole-3-carboxamide," created Oct. 22, 2015 <https://pubchem.ncbi.nlm.nih.gov/compound/91945707>, (8 pages).

PubChem Compound Summary for PubChem CID 49726798, "N-(2-((4-(Furan-2-yl)thiazol-2-yl)amino)-2-oxoethyl)-N-methyl-1H-indole-3-carboxamide," created Nov. 27, 2010 <https://pubchem.ncbi.nih.gov/compound/49726798> (8 pages).

PubChem Compound Summary for SID 172131678, dated Dec. 9, 2014 (8 pages).

PubChem, "Compound Summary for CID 108452511," <https://pubchem.ncbi.nlm.nih.gov/compound/108452511>, created Jan. 15, 2016, retrieved Jan. 4, 2021 (7 pages).

PubChem, "Compound Summary for CID 2955118," <https://pubchem.ncbi.nlm.nih.gov/compound/2955118>, created Jul. 29, 2005, retrieved Mar. 22, 2017 (13 pages).

PubChem, "Compound Summary for CID 7325930," <https://pubchem.ncbi.nlm.nih.gov/compound/7325930>, created Jul. 29, 2006, retrieved Mar. 22, 2017 (11 pages).

PubChem, "Compound Summary for CID 970466," <https://pubchem.ncbi.nlm.nih.gov/compound/970466>, created Jul. 9, 2005, retrieved Mar. 22, 2017 (11 pages).

Quinlan et al., "BEDTools: a flexible suite of utilities for comparing genomic features," Bioinformatics. 26(6):841-2 (2010).

Rajput et al., "Frequency of the TMPRSS2:ERG gene fusion is increased in moderate to poorly differentiated prostate cancers," J Clin Pathol. 60(11):1238-43 (2007).

Rappsilber et al., "Protocol for micro-purification, enrichment, pre-fractionation and storage of peptides for proteomics using StageTips," Nat Protoc. 2(8):1896-906 (2007).

Scott et al., "Searching for peptide ligands with an epitope library," Science. 249(4967):386-390 (1990).

Shen et al., "The SWI/SNF ATPase Brm is a gatekeeper of proliferative control in prostate cancer," Cancer Res. 68(24):10154-62 (Dec. 2008).

Shi et al., "Role of SWI/SNF in acute leukemia maintenance and enhancer-mediated Myc regulation," Genes Dev. 27(24):2648-62 (Dec. 2013).

Siegel et al., "Cancer statistics, 2015," CA Cancer J Clin. 65(1):5-29 (2015).

Subramanian et al., "Gene set enrichment analysis: a knowledge-based approach for interpreting genome-wide expression profiles," Proc Natl Acad Sci USA. 102(43):15545-50 (2005).

Sun et al., "TMPRSS2-ERG fusion, a common genomic alteration in prostate cancer activates C-MYC and abrogates prostate epithelial differentiation," available in PMC Oct. 4, 2020. Published in final edited form as: Oncogene. 27(40)5348-53 (2008) (12 pages).

Tikdari et al., "Reaction of 2-Aminothiazoles with 5-Oxazolones," ChemInform. 18(47):Abstract 199 (1987) (1 page).

Tikdari et al., "Reaction of 2-Aminothiazoles with 5-Oxazolones," Indian Journal of Chemistry 26B:478-9 (May 1987).

Tomlins et al., "Recurrent fusion of TMPRSS2 and ETS transcription factor genes in prostate cancer," Science.310(5748):644-8 (2005).

Tomlins et al., "Role of the TMPRSS2-ERG gene fusion in prostate cancer," Neoplasia. 10(2):177-88 (2008) (21 pages).

Tomlins et al., "TMPRSS2: ETV4 gene fusions define a third molecular subtype of prostate cancer," Cancer Res. 66(7):3396-400 (2006).

Tsai et al. "Dimeric CRISPR RNA-guided FokI Nucleases for Highly Specific Genome Editing," available in PMC Dec. 1, 2014, published in final edited form as: Nat Biotechnol. 32(6):569-576 (Jun. 2014) (22 pages).

Tuoc et al., "Chromatin regulation by BAF170 controls cerebral cortical size and thickness," Dev Cell. 25(3):256-69 (May 2013).

Vachtenheim et al., "SWI/SNF chromatin remodeling complex is critical for the expression of microphthalmia-associated transcription factor in melanoma cells," Biochemical and Biophysical Research Communications. 392(3):454-459 (2010).

Varambally et al., "The polycomb group protein EZH2 is involved in progression of prostate cancer," Nature. 419(6907):624-9 (2002).

(56) References Cited

OTHER PUBLICATIONS

Vela et al., "Discovery of Enhancers of the Secretion of Leukemia Inhibitory Factor for the Treatment of Multiple Sclerosis," J Biomol Screen. 21(5):437-45 (Jun. 2016).
Verger et al., "Identification of amino acid residues in the ETS transcription factor Erg that mediate Erg-Jun/Fos-DNA ternary complex formation," J Biol Chem. 276(20):17181-9 (2001).
Wollenick et al., "Synthetic transactivation screening reveals ETV4 as broad coactivator of hypoxia-inducible factor signaling," Nucleic Acids Res. 40(5):1928-43 (2012).
Yang et al., "EZH2, an epigenetic driver of prostate cancer," Protein Cell. 4(5):331-41 (2013).
Yildirim et al., "Mbd3/NURD complex regulates expression of 5-hydroxymethylcytosine marked genes in embryonic stem cells," Cell. 147(7):1498-510 (2011).
Yu et al., "An integrated network of androgen receptor, polycomb, and TMPRSS2-ERG gene fusions in prostate cancer progression," Cancer Cell. 17(5):443-54 (2010).
Yu et al., "Direct recruitment of polycomb repressive complex 1 to chromatin by core binding transcription factors," Mol Cell. 45(3):330-43 (2012).
Zervos et al., "Mxi1, a protein that specifically interacts with Max to bind Myc-Max recognition sites," Cell. 72(2):223-32 (1993).
Zhang et al., "Model-based analysis of ChIP-Seq (MACS)," Genome Biol. 9(9):R137 (2008) (9 pages).
Zong et al., "ETS family transcription factors collaborate with alternative signaling pathways to induce carcinoma from adult murine prostate cells," Proc Natl Acad Sci U S A. 106(30):12465-70 (Jul. 2009).
Zuckermann et al., "Discovery of Nanomolar Ligands for 7-Transmembrane G-Protein-Coupled Receptors from a Diverse N-(Substituted)glycine Peptoid Library," J Med Chem. 37(17):2678-2685 (1994).
Zvarec et al., "5-Benzylidenerhodanine and 5-benzylidene-2-4-thiazolidinedione based antibacterials," Bioorg Med Chem Lett. 22(8):2720-2 (2012).
Chandler et al., "ARID1a-DNA interactions are required for promoter occupancy by SWI/SNF," Mol Cell Biol. 33(2):265-80 (Jan. 2013).
Chattopadhyay et al., "Uveal melanoma: From diagnosis to treatment and the science in between," Cancer. 122(15):2299-2312 (26 pages) (Aug. 2016).
Danziger et al., Automated site-directed drug design: a general algorithm for knowledge acquisition about hydrogen-bonding regions at protein surfaces, Proc R Soc Lond B Biol Sci. 236(1283): 101-113 (Mar. 1989) (14 pages).
Database Registry, RN 1323331-37-8, entered Aug. 25, 2011 (1 page).
Database Registry, RN 1324163-01-0, entered Aug. 28, 2011 (1 page).
Database Registry, RN 1327304-26-6, entered Sep. 2, 2011 (1 page).
International Search Report and Written Opinion for International Application No. PCT/US19/56365 dated Jan. 30, 2020 (8 pages).
International Search Report and Written Opinion for International Application No. PCT/US2024/024428, mailed Jul. 16, 2024 (18 pages).
International Search Report and Written Opinion for International Patent Application No. PCT/US2024/031875, mailed Oct. 18, 2024 (15 pages).
Simone, Part XIV: Oncology: Introduction, Textbook of Medicine, Bennett et al., 20(1), 1004-1010 (1997).
U.S. Appl. No. 63/543,464, Wan et al.
U.S. Appl. No. 63/543,467, Piel et al.
U.S. Appl. No. 63/707,938, Adam et al.
"Compound Summary: N-[(S)-1-[[4-[6-[(2R,6S)-2,6-Dimethylmorpholino]-2-pyridyl]-2-thiazolyl]amino]-3-methoxy-1-oxo-2-propyl]-1-(methylsulfonyl)-1H-pyrrole-3-carboxamide," PubChem. CID: 156818027, <https://pubchem.ncbi.nlm.nih.gov/compound/156818027>, created Nov. 10, 2021, accessed Jan. 19, 2025 (9 pages).
"Form S-1 Registration Statement: Foghorn Therapeutics Inc.," as filed with the United States Securities and Exchange Commission on Oct. 2, 2020 (230 pages).
Caira, Mino R. "Crystalline polymorphism of organic compounds." Design of Organic Solids (1998): 163-208.
Collins et al., "Abstract 2122: The dual BRM/BRG1 (SMARCA2/4) inhibitor FHD-286 induces differentiation in preclinical models of AML," Cancer Res. 83(7_Supplement) (Apr. 2023) (5 pages).
Fiskus et al., "Pre-Clinical Efficacy of Targeting Baf Complexes through Inhibition of the Dual Atpases BRG1 and BRM by FHD-286 in Cellular Models of AML of Diverse Genetic Background," Blood. 140(Supplement 1):8819-20 (Nov. 2022) (15 pages).
Hentemann, "Abstract ND14: Pharmacological profile and anti-tumor properties of FHD-286: A novel BAF inhibitor for the treatment of transcription factor-driven cancers," Cancer Res. 82(12_Supplement): ND14 (Jun. 2022) (4 pages).
International Search Report and Written Opinion for International Patent Application No. PCT/US2024/050665, mailed Jan. 28, 2025 (15 pages).
International Search Report and Written Opinion for PCT/US2024/050660, mailed Nov. 26, 2024 (12 pages).
Piel et al., International Application No. PCT/US2024/050660, filed Oct. 10, 2024 by applicant Foghorn Therapeutics Inc. (35 pages).
Selleck Chemicals, "Safety Data Sheet: FHD-286," <https://www.selleckchem.com/msds/MSDS_E1178.pdf>, revised May 1, 2014 (2 pages).
Wan et al., International Application No. PCT/US2024/050665, filed Oct. 10, 2024 by applicant Foghorn Therapeutics Inc. (112 pages).
CAS RN: 1212404-62-0; 2010. C18H17N3O4.
CAS RN: 1644411-35-7; 2015. C24H32ClN8O4.
CAS, "FHD-286 Cas registration information," dated Feb. 19, 2025 (6 pages).
Kumar et al., "Diazanaphthalen-3-yl carboxamides as inhibitors of proteins of the Wnt pathway and their preparation," Database Caplus. (Jan. 2019) (12 pages).
PubChem CID 60478710, 5-nitro-N-(1-phenylbenzimidazol-2-yl)furan-2-carboxamide. National Center for Biotechnology Information (2025). Retrieved Sep. 4, 2025 from https://pubchem.ncbi.nlm.nih.gov/compound/60478710, (8 pages).
PubChem CID 110712084, N-[(1- cyclopropylbenzimidazol-2-yl)methyl]furan-2-carboxamide. National Center for Biotechnology Information (2025). Retrieved Sep. 4, 2025 from https://pubchem.ncbi.nlm.nih.gov/compound/110712084, (8 pages).
U.S. Appl. No. 19/121,614, Wan et al.
U.S. Appl. No. 19/474,359, Adam et al.
Adam et al., International Application No. PCT/US25/51009, filed by Foghorn Therapeutics Inc. (65 pages).

* cited by examiner

BRM/BRG1 INHIBITORS AND USES THEREOF

BACKGROUND

The invention relates to compounds useful for modulating BRG1- or BRM-associated factors (BAF) complexes. In particular, the invention relates to compounds useful for treatment of disorders associated with BAF complex function.

Chromatin regulation is essential for gene expression, and ATP-dependent chromatin remodeling is a mechanism by which such gene expression occurs. The human Switch/Sucrose Non-Fermentable (SWI/SNF) chromatin remodeling complex, also known as BAF complex, has two SWI2-like ATPases known as BRG1 (Brahma-related gene-1) and BRM (Brahma). The transcription activator BRG1, also known as ATP-dependent chromatin remodeler SMARCA4, is encoded by the SMARCA4 gene on chromosome 19. BRG1 is overexpressed in some cancer tumors and is needed for cancer cell proliferation. BRM, also known as probable global transcription activator SNF2L2 and/or ATP-dependent chromatin remodeler SMARCA2, is encoded by the SMARCA2 gene on chromosome 9 and has been shown to be essential for tumor cell growth in cells characterized by loss of BRG1 function mutations. Deactivation of BRG and/or BRM results in downstream effects in cells, including cell cycle arrest and tumor suppression.

SUMMARY

The present invention features compounds useful for modulating a BAF complex. In some embodiments, the compounds are useful for the treatment of disorders associated with an alteration in a BAF complex, e.g., a disorder associated with an alteration in one or both of the BRG1 and BRM proteins. The compounds of the invention, alone or in combination with other pharmaceutically active agents, can be used for treating such disorders.

In one aspect, the invention features a compound having the structure:

Formula A

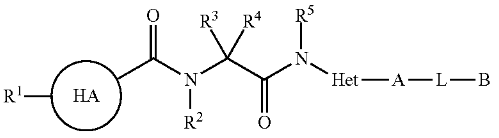

where $R^1$ is absent, H, optionally substituted $C_1$-$C_6$ acyl, optionally substituted $C_1$-$C_6$ alkyl, optionally substituted $C_3$-$C_8$ cycloalkyl, optionally substituted $C_1$-$C_6$ heteroalkyl, optionally substituted $C_2$-$C_9$ heterocyclyl, or —$SO_2R^6$;

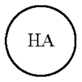

is 5- or 6-membered heteroarylene;

each of $R^2$ and $R^5$ is, independently, H or optionally substituted $C_1$-$C_6$ alkyl;

$R^3$ is H or optionally substituted $C_1$-$C_6$ alkyl; and $R^4$ is H, optionally substituted $C_1$-$C_6$ alkyl, or optionally substituted $C_1$-$C_6$ heteroalkyl; or $R^3$ and $R^4$, together with the carbon atom to which each is attached, form an optionally substituted $C_3$-$C_6$ cycloalkyl;

$R^6$ is optionally substituted $C_1$-$C_6$ alkyl or —$NR^7R^8$;

$R^7$ and $R^8$ are, independently, optionally substituted $C_1$-$C_6$ alkyl;

Het is optionally substituted 5-membered heteroarylene, optionally substituted 6-membered heteroarylene, or

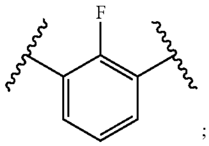 [SMILES: *c1cccc(*)c1F]

;

A is optionally substituted $C_6$-$C_{10}$ arylene, optionally substituted $C_2$-$C_9$ heterocyclylene, or optionally substituted $C_2$-$C_9$ heteroarylene;

L is absent, —O—, optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted $C_2$-$C_9$ heterocyclylene, optionally substituted $C_2$-$C_9$ heterocyclyl $C_1$-$C_6$ alkylene, optionally substituted $C_2$-$C_9$ heteroarylene, or optionally substituted $C_2$-$C_9$ heteroaryl $C_1$-$C_6$ alkylene; and B is H, halogen, cyano, optionally substituted $C_6$-$C_{10}$ aryl, optionally substituted $C_3$-$C_{10}$ cycloalkyl, optionally substituted $C_2$-$C_9$ heterocyclyl, or optionally substituted $C_2$-$C_9$ heteroaryl, or a pharmaceutically acceptable salt thereof.

In some embodiments,

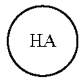

is 6-membered heteroarylene. In some embodiments,

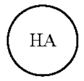

is 5-membered heteroarylene.

In some embodiments,

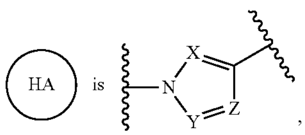

, where each of X, Y, and Z is, independently, N or CH.

In some embodiments, the compound of Formula A has the structure of Formula I:

Formula I

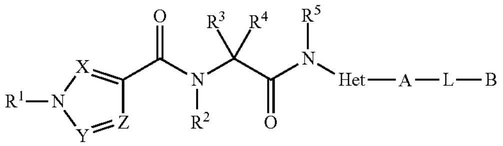

where each of X, Y, and Z is, independently, N or CH;

$R^1$ is H, optionally substituted $C_1$-$C_6$ acyl, optionally substituted $C_1$-$C_6$ alkyl, optionally substituted $C_1$-$C_6$ heteroalkyl, optionally substituted $C_3$-$C_8$ cycloalkyl, optionally substituted $C_2$-$C_9$ heterocyclyl, or —$SO_2R^6$;

each of $R^2$, $R^3$, and $R^5$ is, independently, H or optionally substituted $C_1$-$C_6$ alkyl;

$R^4$ is H, optionally substituted $C_1$-$C_6$ alkyl, or optionally substituted $C_1$-$C_6$ heteroalkyl;

$R^6$ is optionally substituted $C_1$-$C_6$ alkyl or —$NR^7R^8$;

each of $R^7$ and $R^8$ is, independently, optionally substituted $C_1$-$C_6$ alkyl;

Het is optionally substituted 5-membered heteroarylene, optionally substituted 6-membered heteroarylene, or

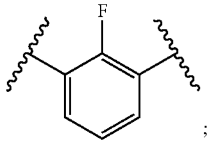 [SMILES: *c1cccc(*)c1F]

;

A is optionally substituted $C_6$-$C_{10}$ arylene, optionally substituted $C_2$-$C_9$ heterocyclylene, or optionally substituted $C_2$-$C_9$ heteroarylene;

L is absent, —O—, optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted $C_2$-$C_9$ heterocyclylene, optionally substituted $C_2$-$C_9$ heterocyclyl $C_1$-$C_6$ alkylene, optionally substituted $C_2$-$C_9$ heteroarylene, or optionally substituted $C_2$-$C_9$ heteroaryl $C_1$-$C_6$ alkylene; and B is H, halogen, cyano, optionally substituted $C_6$-$C_{10}$ aryl, optionally substituted $C_3$-$C_{10}$ cycloalkyl, optionally substituted $C_2$-$C_9$ heterocyclyl, or optionally substituted $C_2$-$C_9$ heteroaryl, or a pharmaceutically acceptable salt thereof.

In some embodiments, X, Y, and Z are CH; X is N and Y and Z are CH; Z is N and X and Y are CH; Y is N and X and Z are CH; X is CH and Y and Z are N; Z is CH and X and y are N; Y is CH and X and Z are N; or X, Y, and Z are N.

In some embodiments, the compound of Formula I has the structure of Formula Ia:

Formula Ia

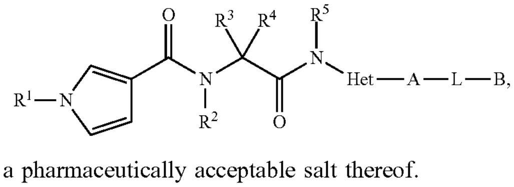

or a pharmaceutically acceptable salt thereof.

In some embodiments, the compound of Formula I has the structure of Formula Ib:

Formula Ib

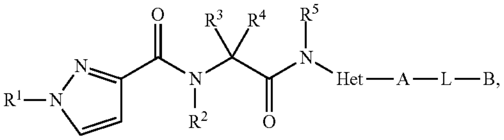

or a pharmaceutically acceptable salt thereof.

In some embodiments, the compound of Formula I has the structure of Formula Ic:

Formula Ic

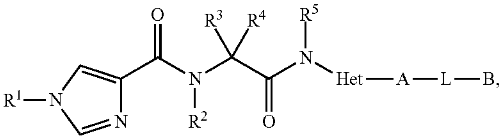

or a pharmaceutically acceptable salt thereof.

In some embodiments, the compound of Formula I has the structure of Formula Id:

Formula Id

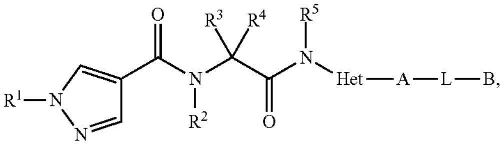

or a pharmaceutically acceptable salt thereof.

In some embodiments,

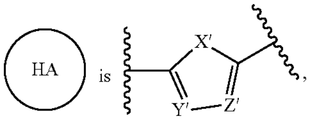

where X' is O or S; Y' is N or CH; and Z' is N or CH.

In some embodiments, the compound of Formula A has the structure of Formula II:

Formula II

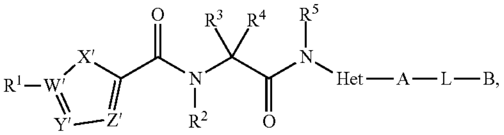

where

W' is C or N;

X' is O, S, or N—$CH_3$;

Y' is N or CH;

Z' is N or CH;

$R^1$ is absent, H, optionally substituted $C_1$-$C_6$ acyl, optionally substituted $C_1$-$C_6$ alkyl, optionally substituted $C_1$-$C_6$ heteroalkyl, optionally substituted $C_3$-$C_8$ cycloalkyl, optionally substituted $C_2$-$C_9$ heterocyclyl, or —$SO_2R^6$;

each of $R^2$, $R^3$, and $R^5$ is, independently, H or optionally substituted $C_1$-$C_6$ alkyl;

$R^4$ is H, optionally substituted $C_1$-$C_6$ alkyl, or optionally substituted $C_1$-$C_6$ heteroalkyl;

$R^6$ is optionally substituted $C_1$-$C_6$ alkyl or —$NR^7R^8$;

each of $R^7$ and $R^8$ is, independently, optionally substituted $C_1$-$C_6$ alkyl;

Het is optionally substituted 5-membered heteroarylene, optionally substituted 6-membered heteroarylene, or

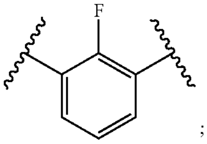 [SMILES: *c1cccc(*)c1F]

;

A is optionally substituted $C_6$-$C_{10}$ arylene, optionally substituted $C_2$-$C_9$ heterocyclylene, or optionally substituted $C_2$-$C_9$ heteroarylene;

L is absent, —O—, optionally substituted $C_1$-$C_6$ alkylene, optionally substituted $C_1$-$C_6$ heteroalkylene, optionally substituted $C_1$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted $C_2$-$C_9$ heterocyclylene, optionally substituted $C_2$-$C_9$ heterocyclyl $C_1$-$C_6$ alkylene, optionally substituted $C_2$-$C_9$ heteroarylene, or optionally substituted $C_2$-$C_9$ heteroaryl $C_1$-$C_6$ alkylene; and B is H, halogen, cyano, optionally substituted $C_6$-$C_{10}$ aryl, optionally substituted $C_3$-$C_{10}$ cycloalkyl, optionally substituted $C_2$-$C_9$ heterocyclyl, or optionally substituted $C_2$-$C_9$ heteroaryl, or a pharmaceutically acceptable salt thereof.

In some embodiments, X' is O, Y' is CH, and Z' is N; X' is S, Y' is CH, and Z' is N; X' is O, Y' is N, and Z' is CH; X' is S, Y' is N, and Z' is CH; X' is O, Y' is N, and Z' is N; or X' is S, Y' is N, and Z' is N.

In some embodiments, the compound of Formula II has the structure of Formula IIa:

Formula IIa

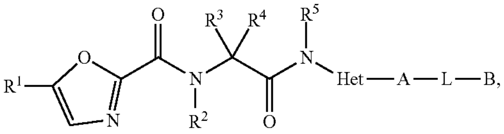

or a pharmaceutically acceptable salt thereof.

In some embodiments, the compound of Formula II has the structure of Formula IIb:

Formula IIb

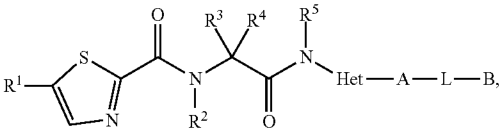

or a pharmaceutically acceptable salt thereof.

In some embodiments, $R^2$ is H.

In some embodiments, $R^5$ is H. In other embodiments, $R^5$ is optionally substituted $C_1$-$C_6$ alkyl, e.g., methyl.

In some embodiments, $R^3$ is H. In some embodiments, $R^3$ is optionally substituted $C_1$-$C_6$ alkyl, e.g., $R^3$ is methyl.

In further embodiments, $R^4$ is H. In other embodiments, $R^4$ is optionally substituted $C_1$-$C_6$ alkyl, e.g., methyl, tert-butyl, iso-propyl, iso-butyl, or tert-pentyl. In further embodiments, $R^4$ is optionally substituted $C_1$-$C_6$ heteroalkyl, e.g.,

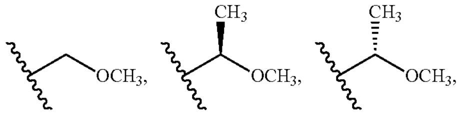

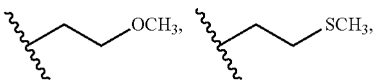

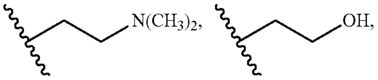

or

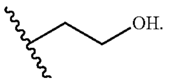

In some embodiments, $R^4$ is

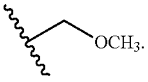 [SMILES: *COC]

In some embodiments, $R^3$ is H and $R^4$ is

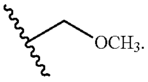 [SMILES: *COC]

In some embodiments, $R^3$ and $R^4$, together with the carbon atom to which each is attached, form optionally substituted $C_3$-$C_6$ cycloalkyl.

In some embodiments, $R^3$ and $R^4$, together with the carbon atom to which each is attached, form $C_3$-$C_6$ cycloalkyl.

In some embodiments, $R^3$ and $R^4$, together with the carbon atom to which each is attached, form

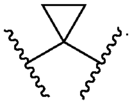 [SMILES: *C1(*)CC1]

In some embodiments, Het is optionally substituted 5-membered heteroarylene.

In some embodiments, Het is

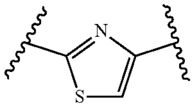

.

In further embodiments, Het is

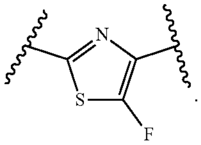 [SMILES: *c1nc(*)c(F)s1]

.

In some embodiments, Het is optionally substituted 6-membered heteroarylene.

In some embodiments, Het is

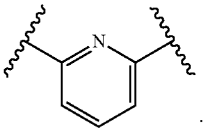 [SMILES: *c1cccc(*)n1]

.

In some embodiments, Het is

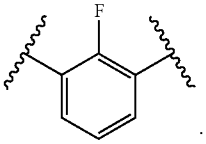 [SMILES: *c1cccc(*)c1F]

.

In some embodiments, L is absent. In some embodiments, L is —O—. In some embodiments, L is optionally substituted $C_1$-$C_6$ alkylene, e.g., L is

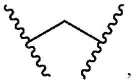, 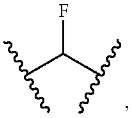, 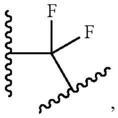, 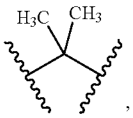, 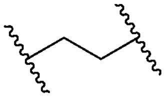, 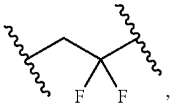, 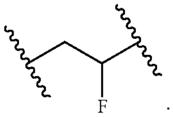.

In further embodiments, L is optionally substituted $C_1$-$C_6$ heteroalkylene, e.g., L is

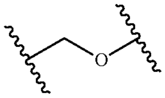, 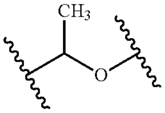, 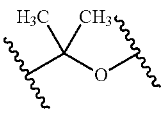,

-continued

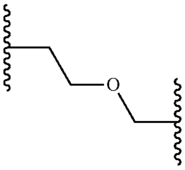, 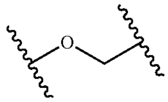, 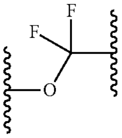,

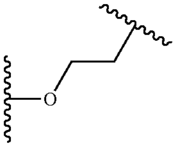, 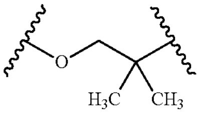,

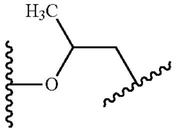, 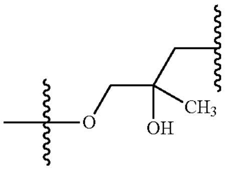,

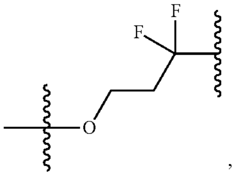, 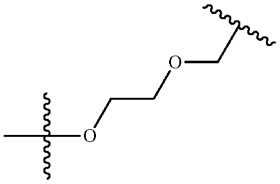,

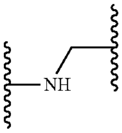, 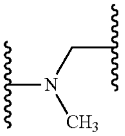, 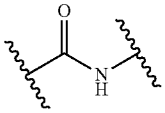,

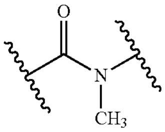, 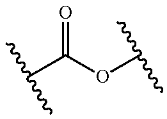, or

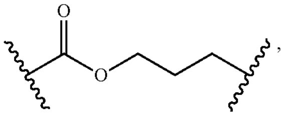,

In some embodiments, L is In particular embodiments, L is optionally substituted $C_1$-$C_6$ alkenylene, e.g.,

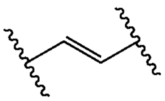.

In further embodiments, L is optionally substituted $C_2$-$C_6$ heteroalkenylene. In other embodiments, L is optionally substituted $C_2$-$C_6$ alkynylene, e.g., L is

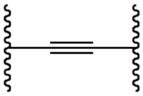 or 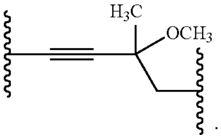.

In still other embodiments, L is optionally substituted $C_2$-$C_6$ heteroalknylene, e.g., L is

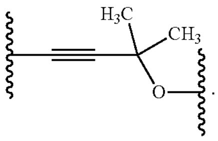 [SMILES: *C#CC(C)(C)O*]

In some embodiments, L is optionally substituted $C_2$-$C_9$ heterocyclylene, e.g., L is

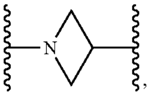 , 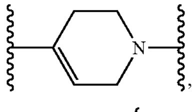 , 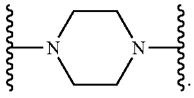 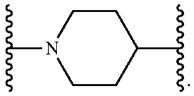 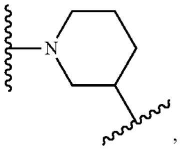 , 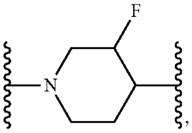 , or 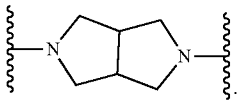

In further embodiments, L is optionally substituted $C_2$-$C_9$ heterocyclyl $C_1$-$C_6$ alkylene, e.g., L is

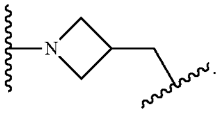 [SMILES: *CC1CN(*)C1]

In other embodiments, L is optionally substituted $C_2$-$C_9$ heteroarylene. In still other embodiments, L is optionally substituted $C_2$-$C_9$ heteroaryl $C_1$-$C_6$ alkylene.

In some embodiments, A is optionally substituted $C_6$-$C_{10}$ arylene, e.g.,

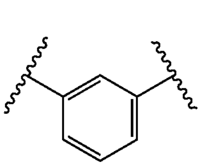 , 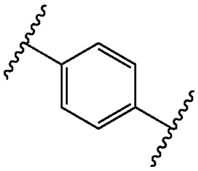 , 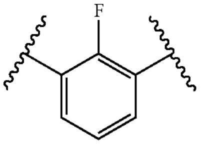 , 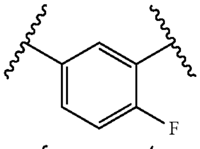 , 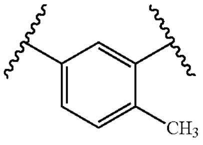 , 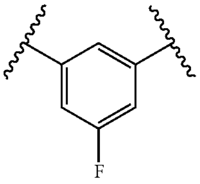 ,

-continued

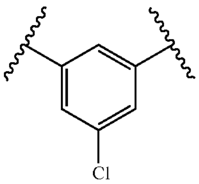 , 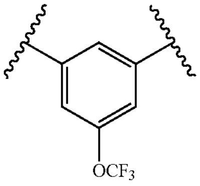 , 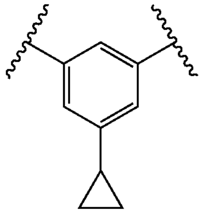 , 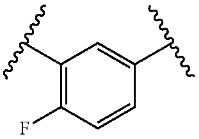 , 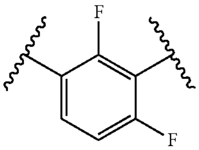 , or 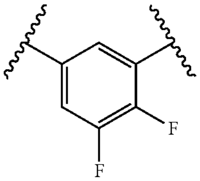 .

In other embodiments, A is optionally substituted $C_2$-$C_9$ heteroarylene, e.g.,

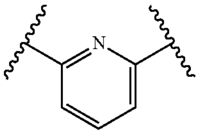 , 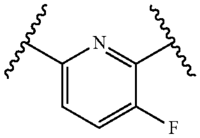 , 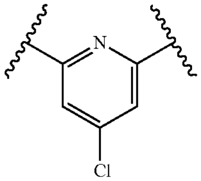 , 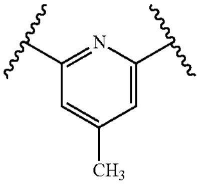 , 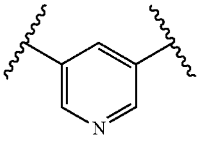 , 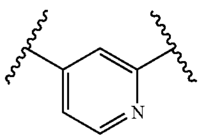 , 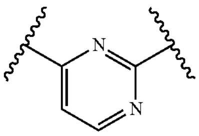 , 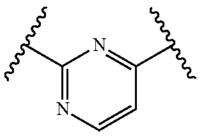 , 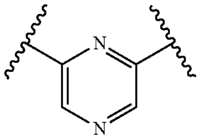 , 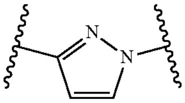 , 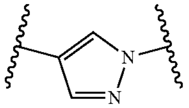 , 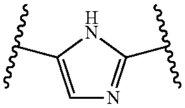 , -continued
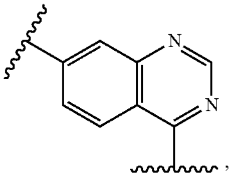,
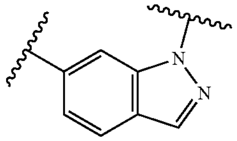,
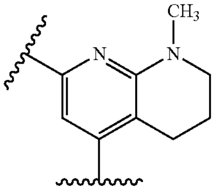,
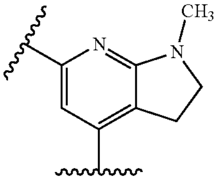, or
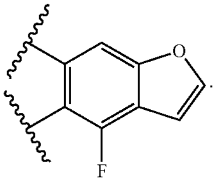
In further embodiments, A is optionally substituted $C_2$-$C_9$ heterocyclylene, e.g.,
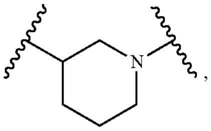
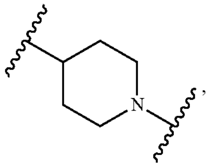
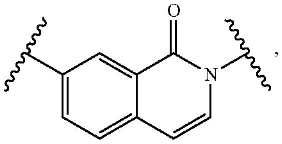
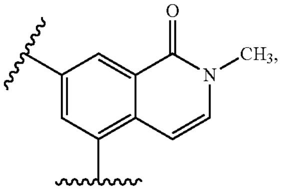
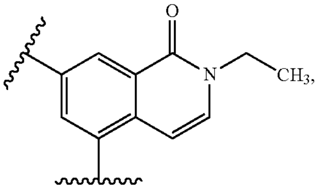
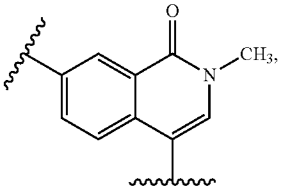
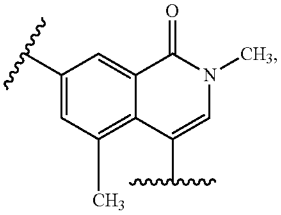
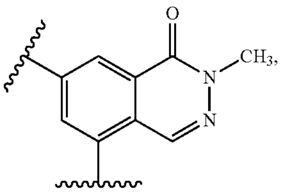
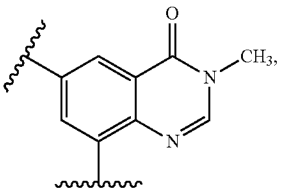
-continued
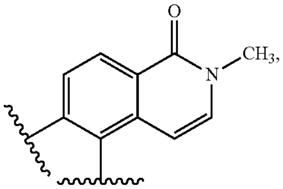
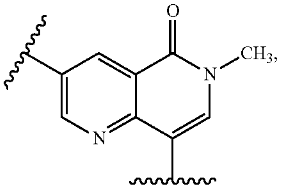
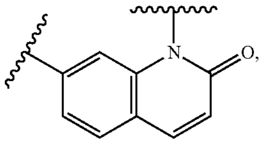
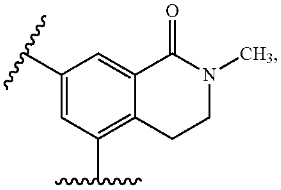
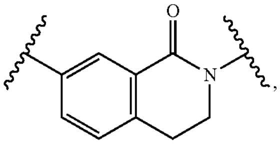
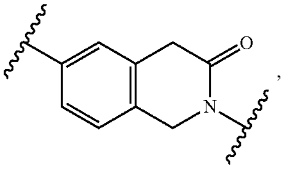
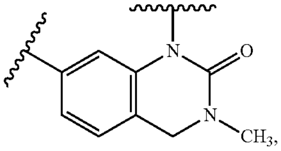
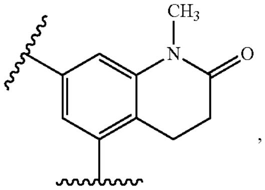
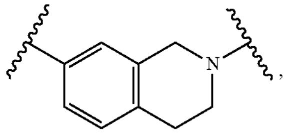
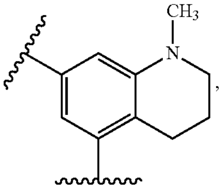
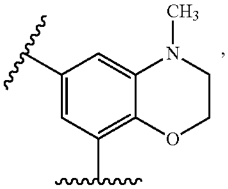
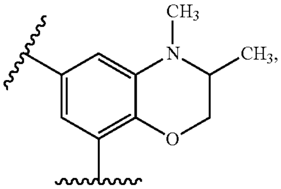
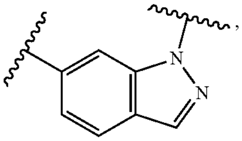
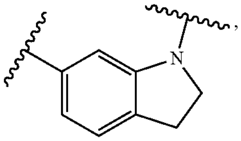
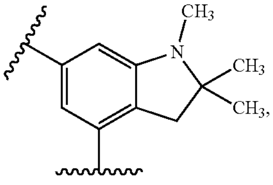
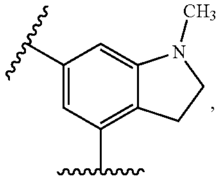
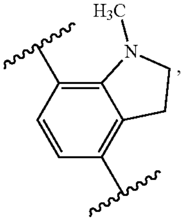
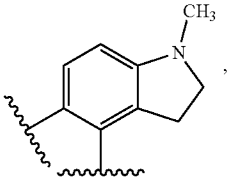

-continued
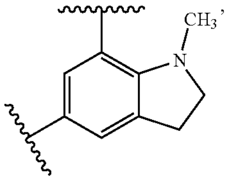
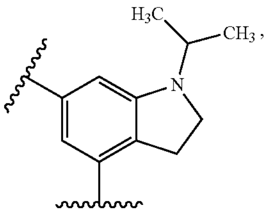
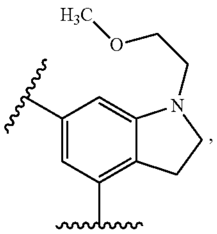
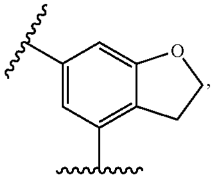
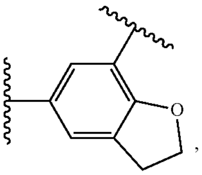
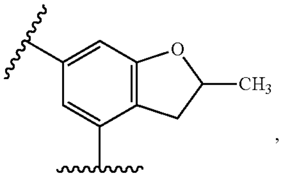
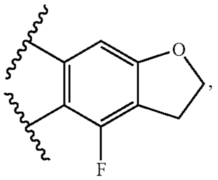
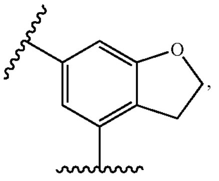
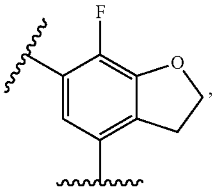
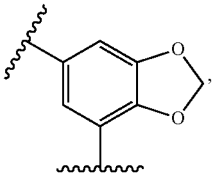
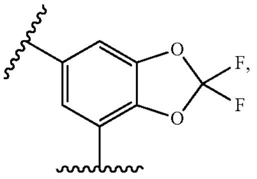
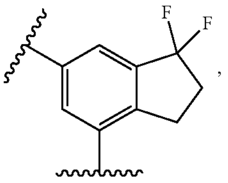
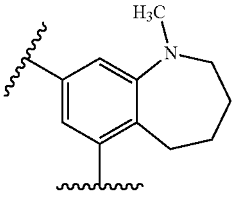
or
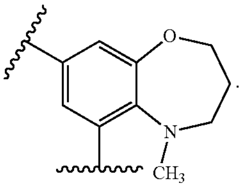
In some embodiments, A is
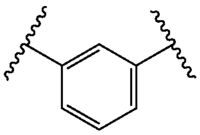
or
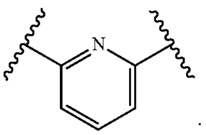
.
In some embodiments, A is
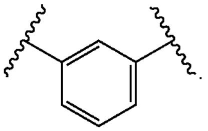
In some embodiments, A is
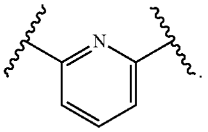 [SMILES: *c1cccc(*)n1]
In some embodiments, B is H. In other embodiments, B is cyano. In further embodiments, B is optionally substituted $C_6$-$C_{10}$ aryl, e.g.,
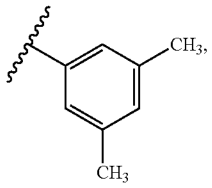
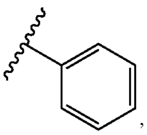
, or
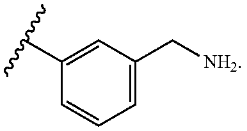
In still further embodiments, B is optionally substituted $C_2$-$C_9$ heterocyclyl, e.g.,
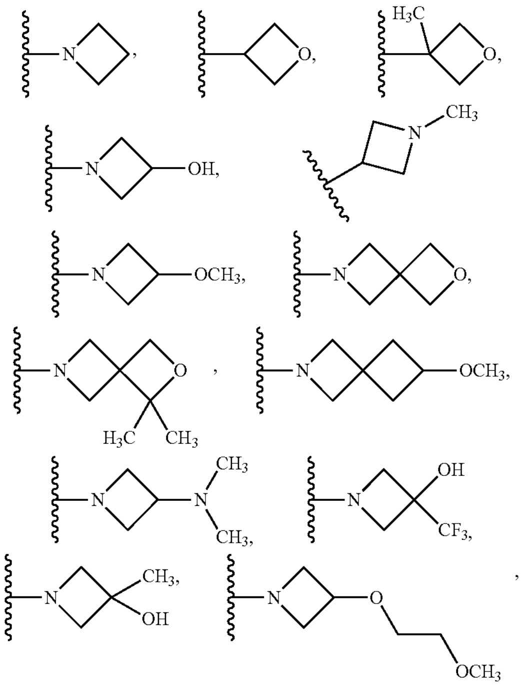

-continued
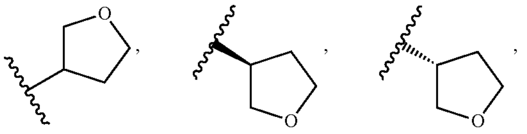
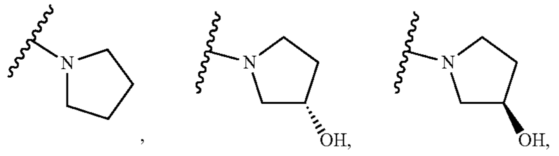
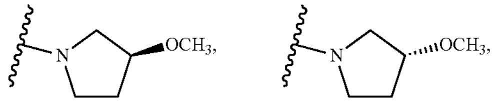
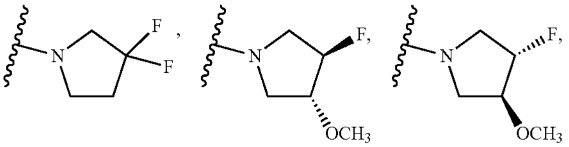
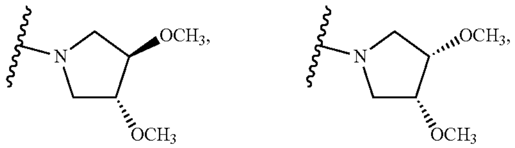
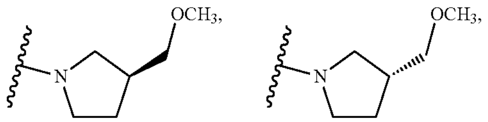
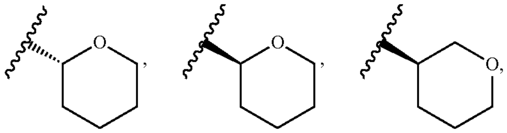
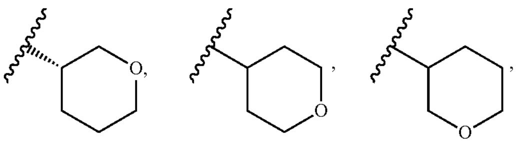
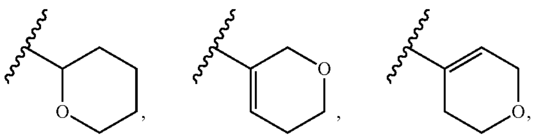
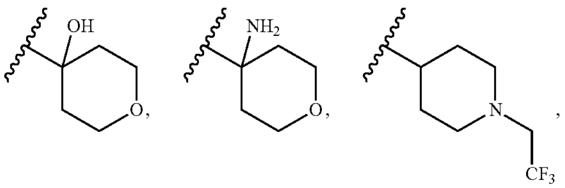
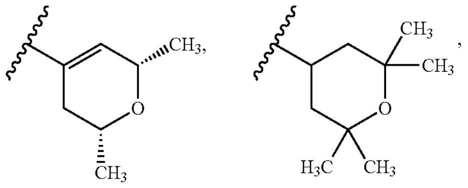
-continued
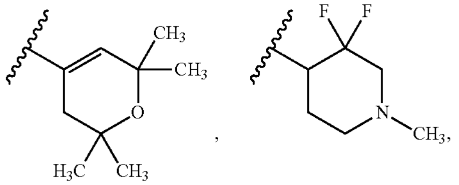
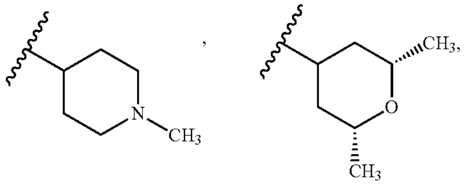
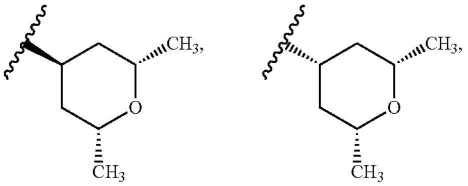
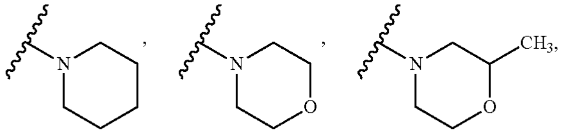
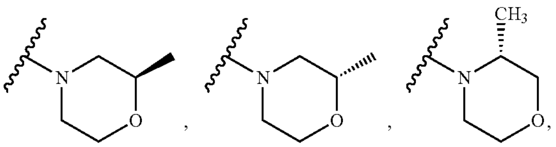
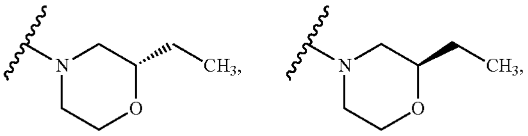
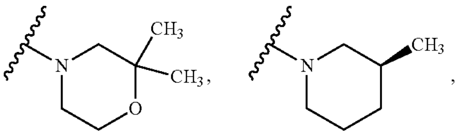
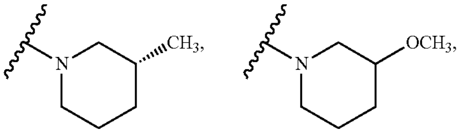
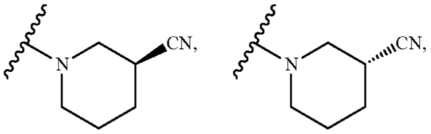
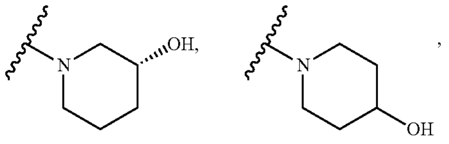
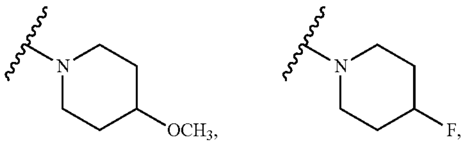

-continued
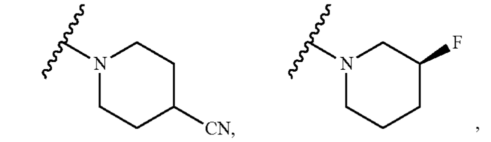
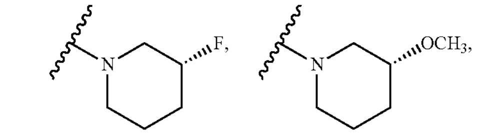
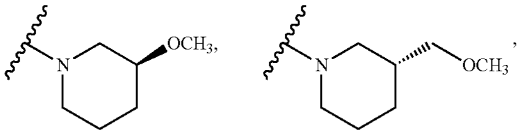
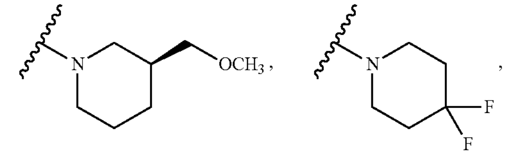
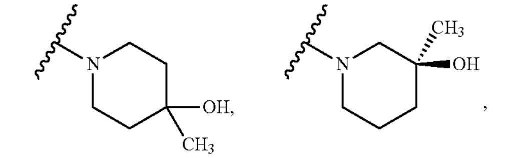
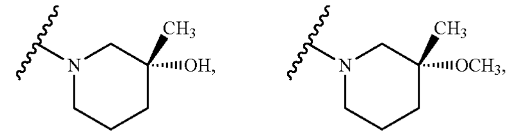
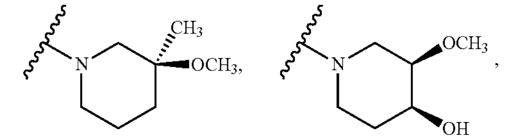
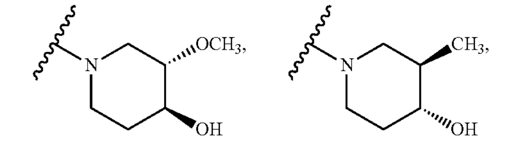
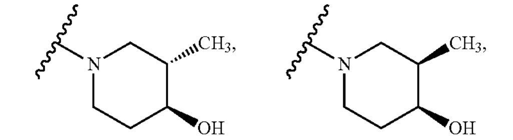
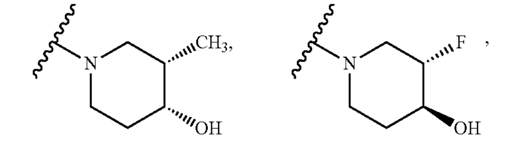
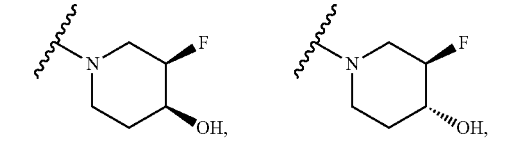
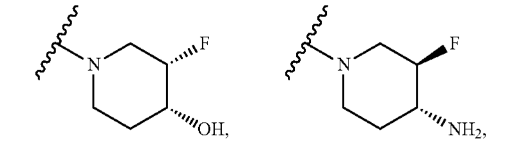
-continued
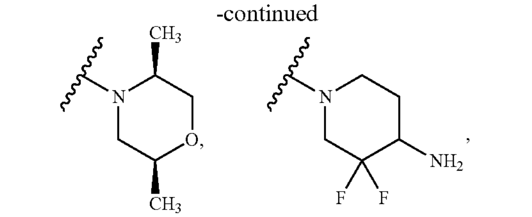
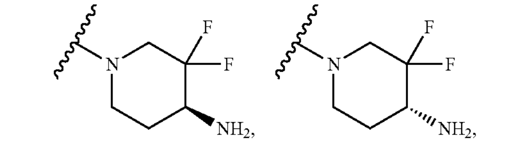
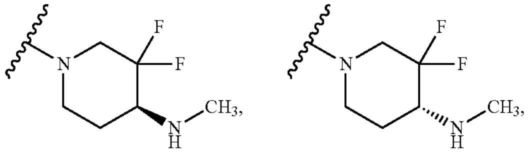
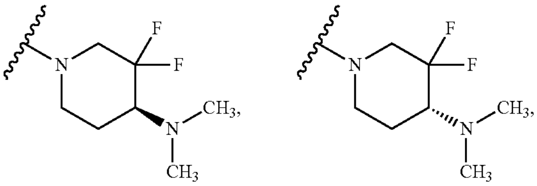
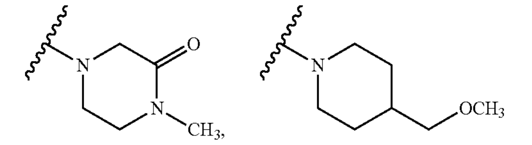
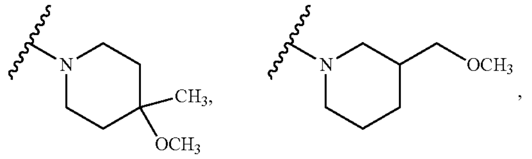
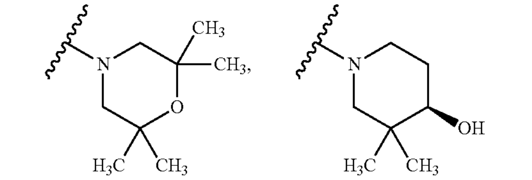
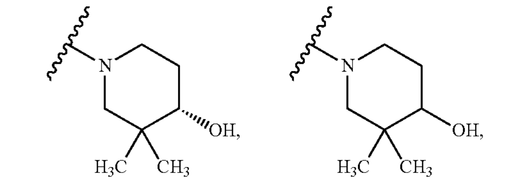
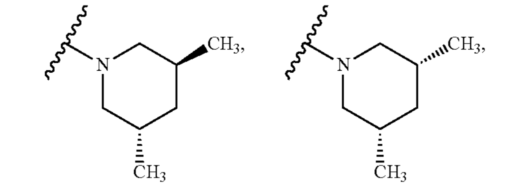
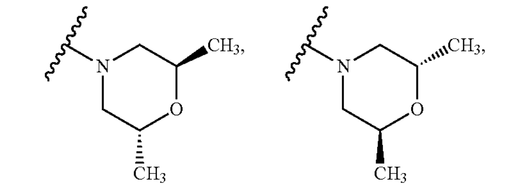

-continued

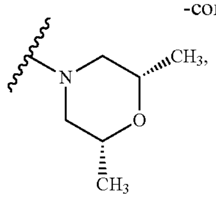 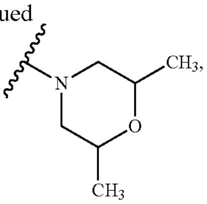

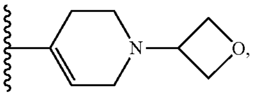 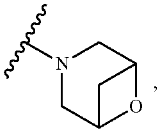 ,

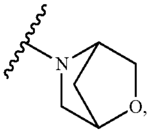 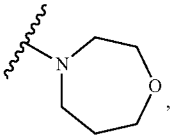

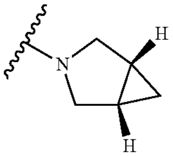 , 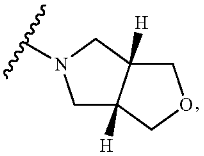

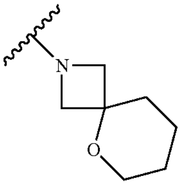 , 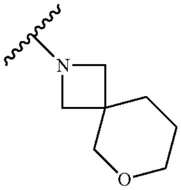 ,

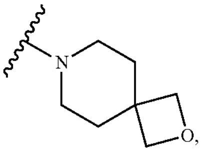 or 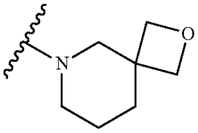 ,

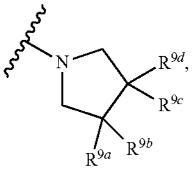 or 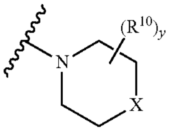 .

In some embodiments, each one of $R^{9a}$, $R^{9b}$, $R^{9c}$, and $R^{9d}$ is, independently, H, halogen, hydroxyl, optionally substituted $C_{1-6}$ alkyl, or optionally substituted $C_{1-6}$ heteroalkyl. In other embodiments, X is O or $C(R^{10})_2$; y can be 0, 1, 2, 3, 4, 5, 6, 7, or 8; and each $R^{10}$ is, independently, H, halogen, cyano, amino, hydroxyl, allyl, heteroallyl, optionally substituted $C_{1-6}$ alkyl, optionally substituted $C_{1-6}$ heteroalkyl, or two combine with the carbon to which they are attached to form C═O.

In some embodiments, B is mopholino. In some embodiments, B is

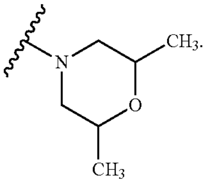 [SMILES: *N1CC(C)OC(C)C1]

In some embodiments, B is

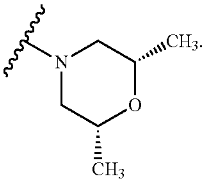 [SMILES: *N1C[C@@H](C)O[C@@H](C)C1]

In yet other embodiments, B is optionally substituted $C_2$-$C_9$ heteroaryl, e.g.,

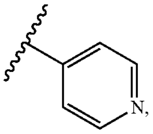 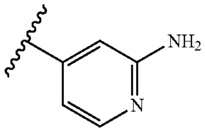 ,

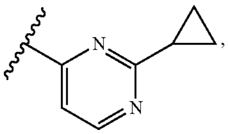 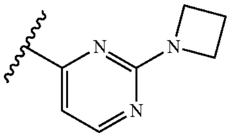 ,

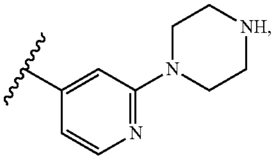

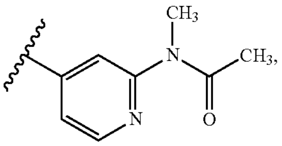

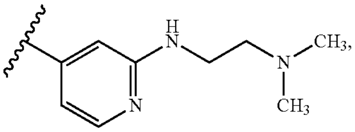

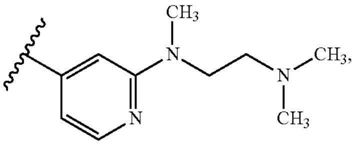

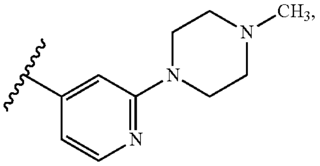

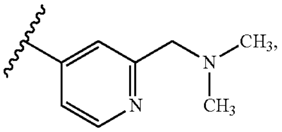

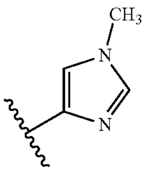 , 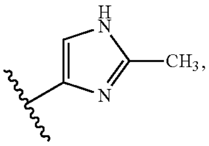

-continued
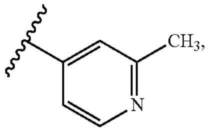
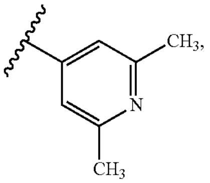
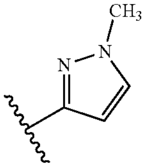
,
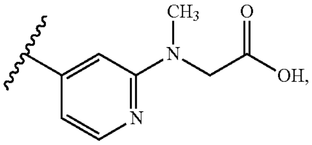
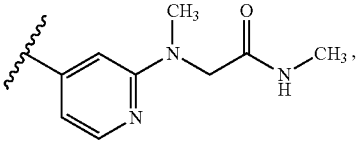
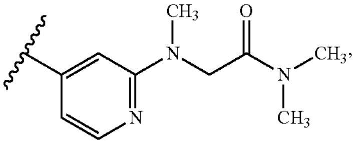
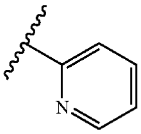
,
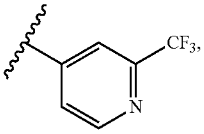
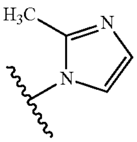
,
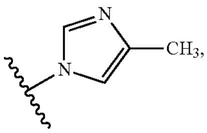
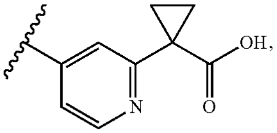
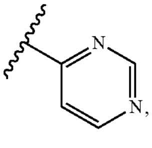
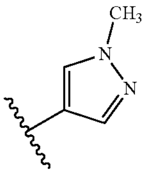
,
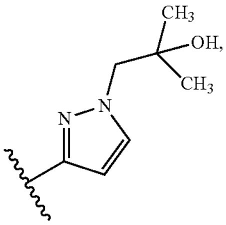
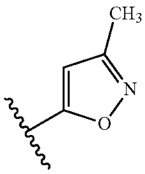
,
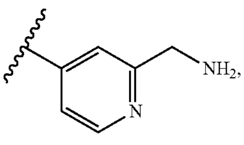
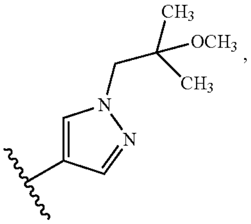
-continued
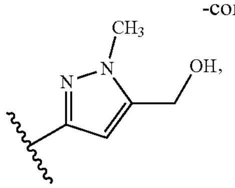
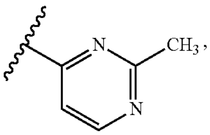
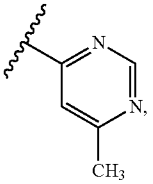
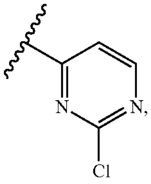
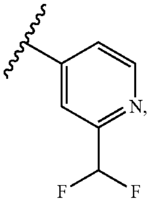
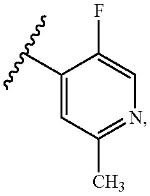
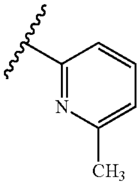
,
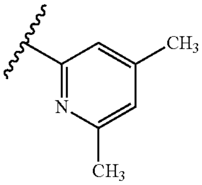
,
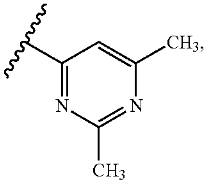
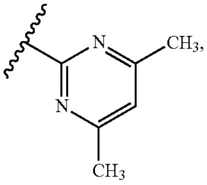
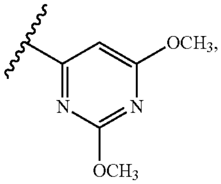
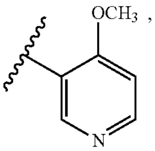
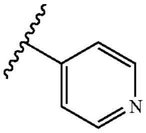
,
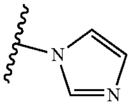
,
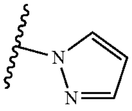
,
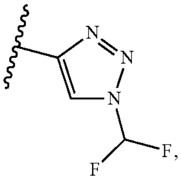
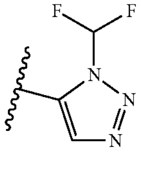
,
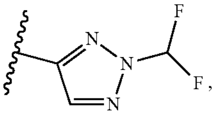
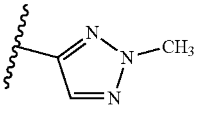
,
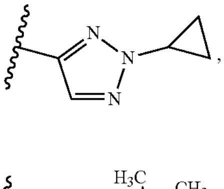
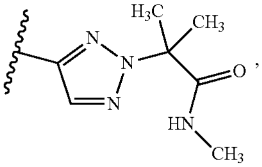
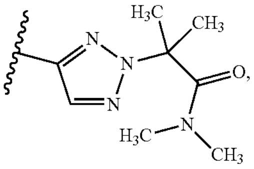
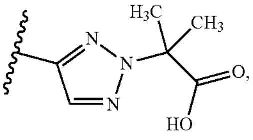

-continued

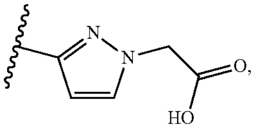 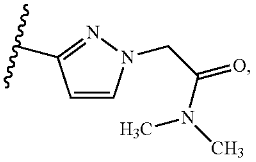,

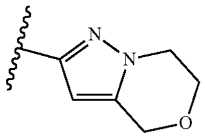, 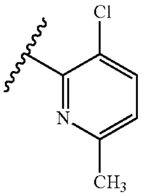,

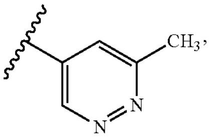, 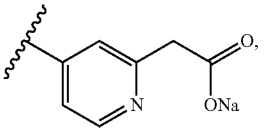 or

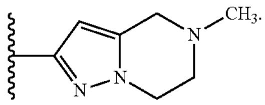

In further embodiments, B is optionally substituted $C_3$-$C_{10}$ cycloalkyl, e.g.,

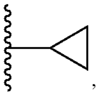, 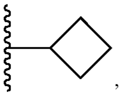, 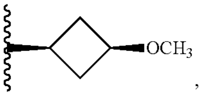,

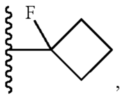, 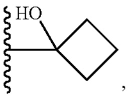, 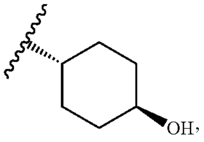

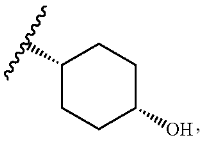 or 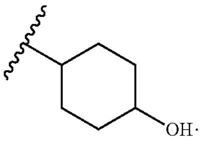

In certain embodiments, $R^1$ is H. In other embodiments, $R^1$ is optionally substituted $C_1$-$C_6$ acyl, e.g., acetyl. In further embodiments, $R^1$ is optionally substituted $C_1$-$C_6$ alkyl, e.g., methyl, tert-butyl, iso-propyl, or

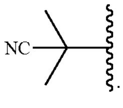

In yet other embodiments, $R^1$ is optionally substituted $C_1$-$C_6$ heteroalkyl, e.g.,

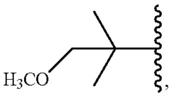, 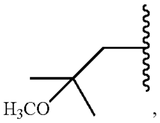, 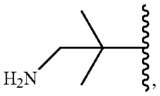,

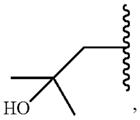, or 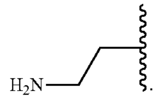

In some embodiments, $R^1$ is optionally substituted $C_2$-$C_9$ heterocyclyl, e.g.,

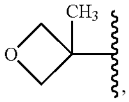, or 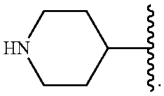

In further embodiments, $R^1$ is $—SO_2R^6$. In some embodiments, $R^6$ is optionally substituted $C_1$-$C_6$ alkyl, e.g., methyl, iso-propyl, or

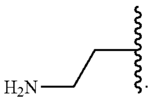

In some embodiments, $R^6$ is $—NR^7R^8$. In some embodiments, $R^7$ is methyl. In some embodiments, $R^8$ is methyl.

In some embodiments, the compound is any one of compounds 1-827 in Table 1. In some embodiments, the compound, or pharmaceutically acceptable salt thereof, has the structure of any one of compounds 1-421 in Table 1.

In some embodiments, the compound is any one of compounds 1-156 in Table 1. In other embodiments, the compound is any one of compounds 157-421 in Table 1. In some embodiments, the compound is any one of compounds 422-827 in Table 1.

In some embodiments, the compound is any one of compounds 1-776 in Table 1. In some embodiments, the compound is any one of compounds 777-819 in Table 1. In some embodiments, the compound is any one of compounds 820-827 in Table 1.

TABLE 1
| Compounds of the invention | |
|---|---|
| # | Compound |
| 1 | 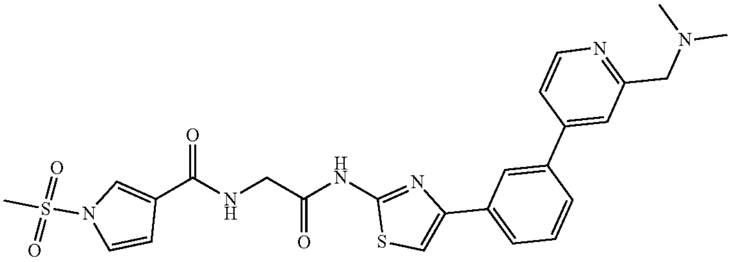 |
| 2 | 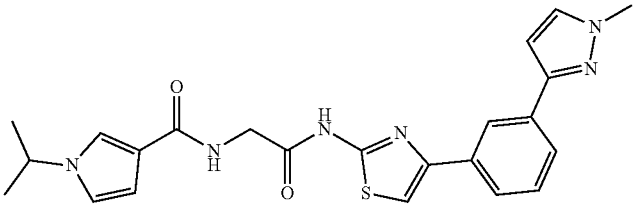 [SMILES: CC(C)n1ccc(C(=O)NCC(=O)Nc2nc(-c3cccc(-c4ccn(C)n4)c3)cs2)c1] |
| 3 | 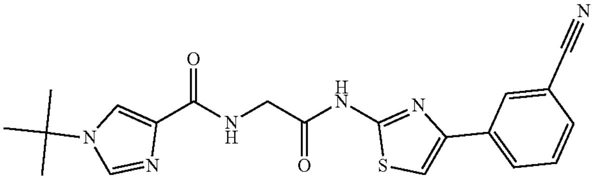 |
| 4 | 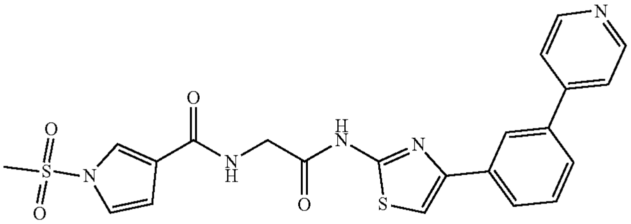 |
| 5 | 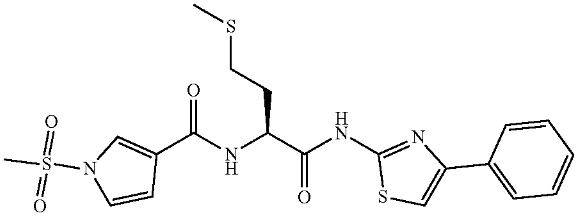 [SMILES: CSCC[C@H](NC(=O)c1ccn(S(C)(=O)=O)c1)C(=O)Nc1nc(-c2ccccc2)cs1] |
| 6 | 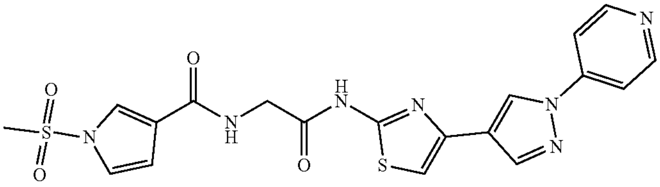 [SMILES: CS(=O)(=O)n1ccc(C(=O)NCC(=O)Nc2nc(-c3cnn(-c4ccncc4)c3)cs2)c1] |
| 7 | 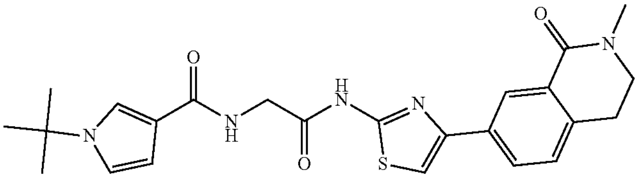 [SMILES: CN1CCc2ccc(-c3csc(NC(=O)CNC(=O)c4ccn(C(C)(C)C)c4)n3)cc2C1=O] |

TABLE 1-continued
| Compounds of the invention | |
|---|---|
| # | Compound |
| 8 | 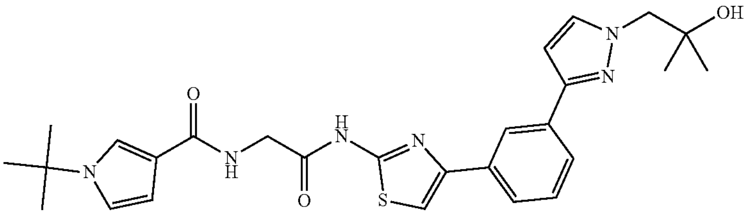 [SMILES: CC(C)(O)Cn1ccc(-c2cccc(-c3csc(NC(=O)CNC(=O)c4ccn(C(C)(C)C)c4)n3)c2)n1] |
| 9 | 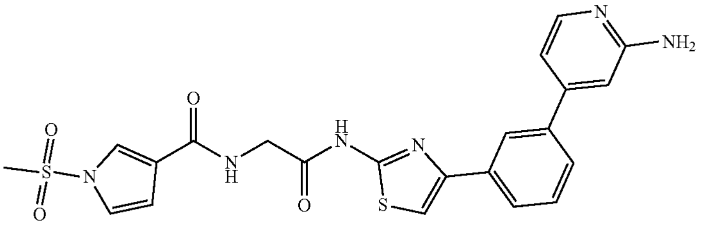 [SMILES: CS(=O)(=O)n1ccc(C(=O)NCC(=O)Nc2nc(-c3cccc(-c4ccnc(N)c4)c3)cs2)c1] |
| 10 | 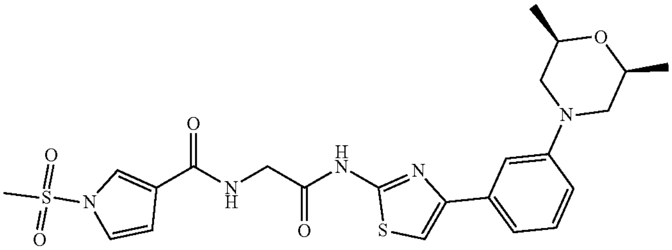 |
| 11 | 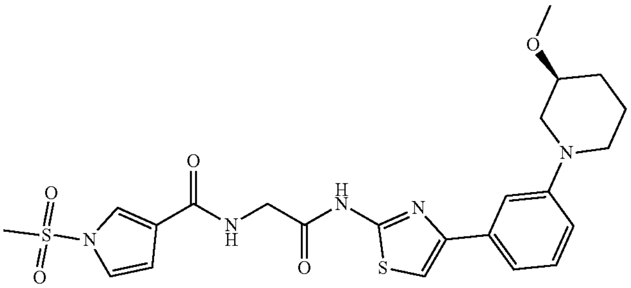 [SMILES: CO[C@H]1CCCN(c2cccc(-c3csc(NC(=O)CNC(=O)c4ccn(S(C)(=O)=O)c4)n3)c2)C1] |
| 12 | 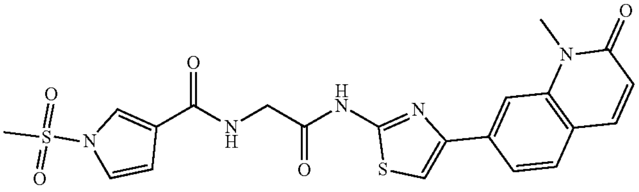 [SMILES: Cn1c(=O)ccc2ccc(-c3csc(NC(=O)CNC(=O)c4ccn(S(C)(=O)=O)c4)n3)cc21] |
| 13 | 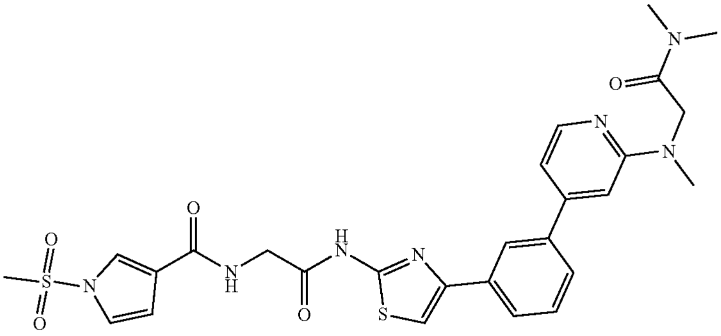 |

TABLE 1-continued
| Compounds of the invention | |
|---|---|
| # | Compound |
| 14 | 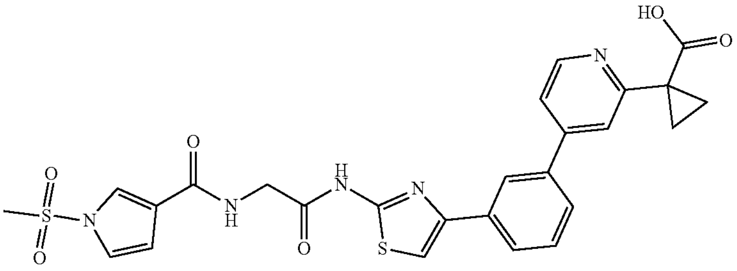 [SMILES: CS(=O)(=O)n1ccc(C(=O)NCC(=O)Nc2nc(-c3cccc(-c4ccnc(C5(C(=O)O)CC5)c4)c3)cs2)c1] |
| 15 | 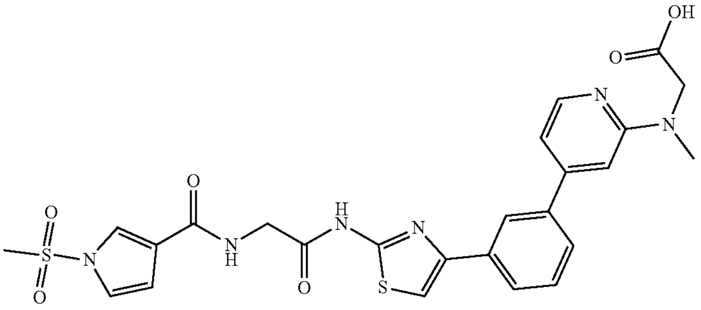 |
| 16 | 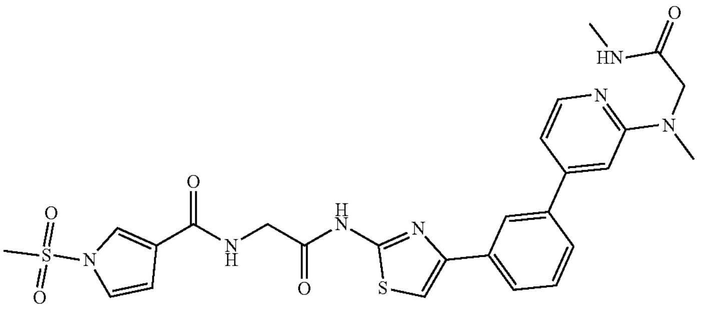 |
| 17 | 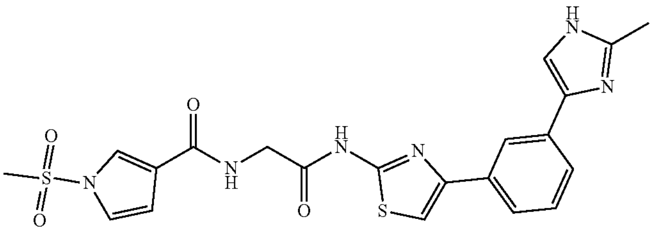 |
| 18 | 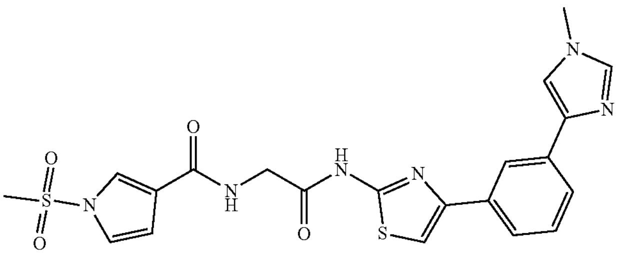 [SMILES: Cn1cnc(-c2cccc(-c3csc(NC(=O)CNC(=O)c4ccn(S(C)(=O)=O)c4)n3)c2)c1] |

TABLE 1-continued
| Compounds of the invention | |
|---|---|
| # | Compound |
| 19 | 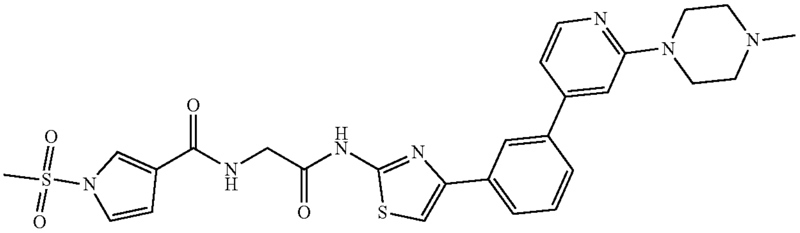 |
| 20 | 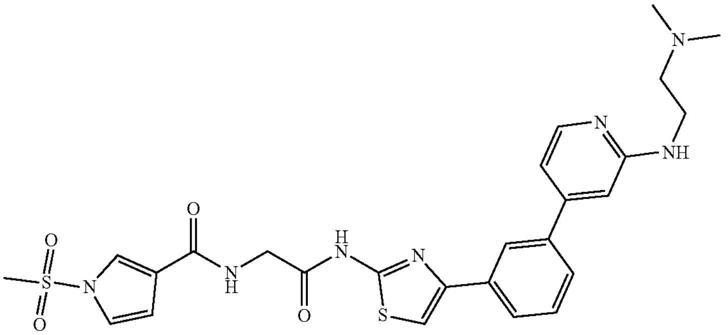 |
| 21 | 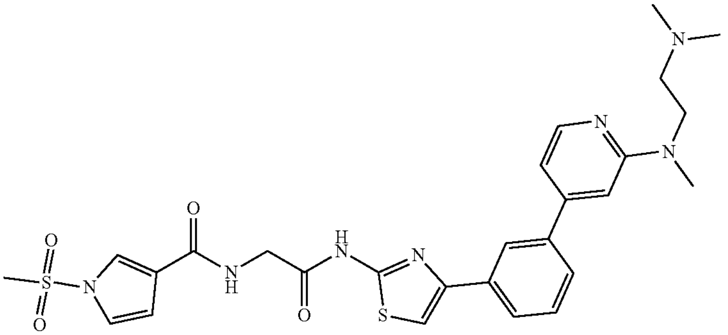 |
| 22 | 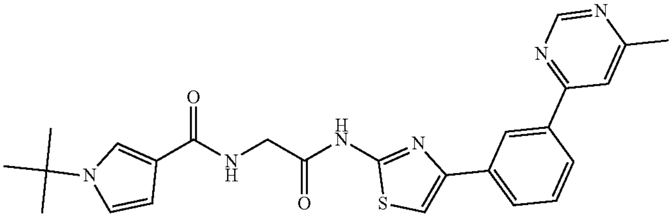 [SMILES: Cc1cc(-c2cccc(-c3csc(NC(=O)CNC(=O)c4ccn(C(C)(C)C)c4)n3)c2)ncn1] |
| 23 | 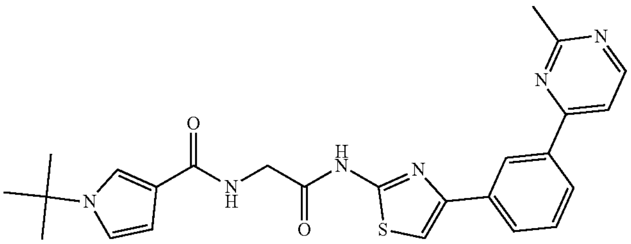 [SMILES: Cc1nccc(-c2cccc(-c3csc(NC(=O)CNC(=O)c4ccn(C(C)(C)C)c4)n3)c2)n1] |

TABLE 1-continued
| Compounds of the invention | |
|---|---|
| # | Compound |
| 24 | 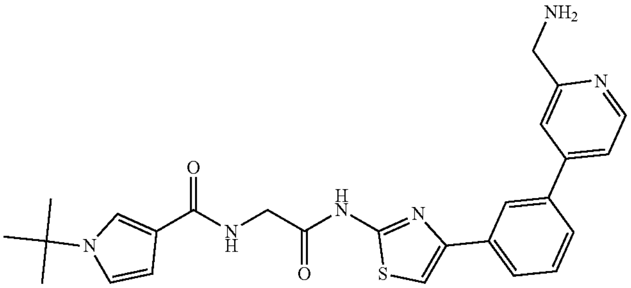 [SMILES: CC(C)(C)n1ccc(C(=O)NCC(=O)Nc2nc(-c3cccc(-c4ccnc(CN)c4)c3)cs2)c1] |
| 25 | 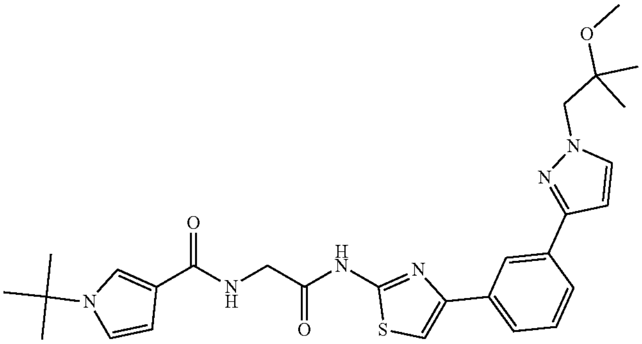 [SMILES: COC(C)(C)Cn1ccc(-c2cccc(-c3csc(NC(=O)CNC(=O)c4ccn(C(C)(C)C)c4)n3)c2)n1] |
| 26 | 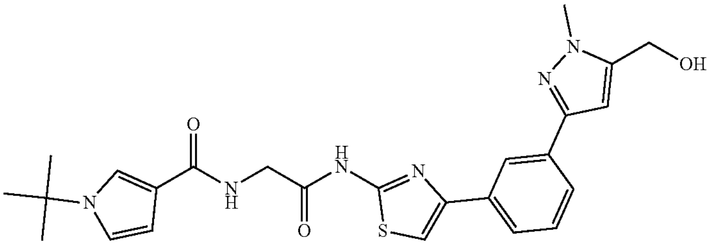 [SMILES: Cn1nc(-c2cccc(-c3csc(NC(=O)CNC(=O)c4ccn(C(C)(C)C)c4)n3)c2)cc1CO] |
| 27 | 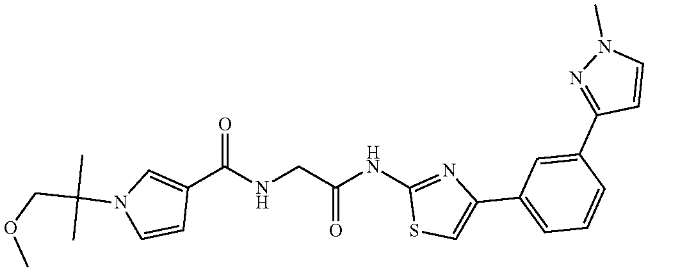 [SMILES: COCC(C)(C)n1ccc(C(=O)NCC(=O)Nc2nc(-c3cccc(-c4ccn(C)n4)c3)cs2)c1] |
| 28 | 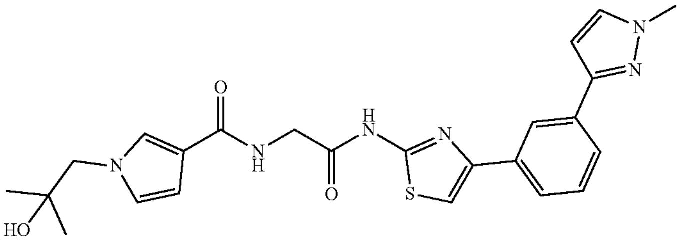 [SMILES: Cn1ccc(-c2cccc(-c3csc(NC(=O)CNC(=O)c4ccn(CC(C)(C)O)c4)n3)c2)n1] |

TABLE 1-continued
| Compounds of the invention | |
|---|---|
| # | Compound |
| 29 | 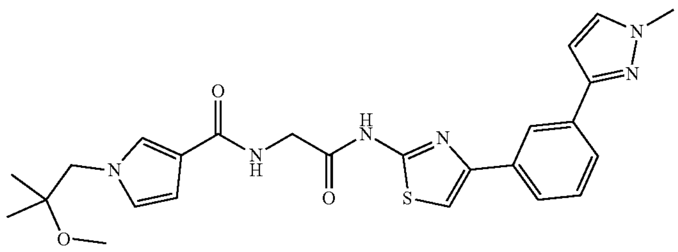 [SMILES: COC(C)(C)Cn1ccc(C(=O)NCC(=O)Nc2nc(-c3cccc(-c4ccn(C)n4)c3)cs2)c1] |
| 30 | 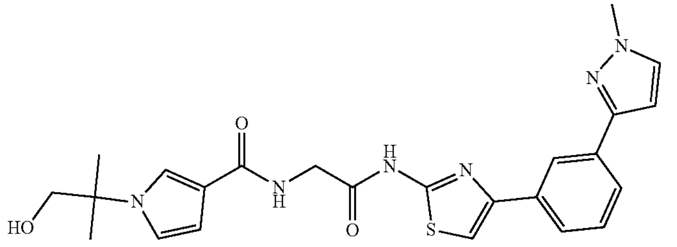 [SMILES: Cn1ccc(-c2cccc(-c3csc(NC(=O)CNC(=O)c4ccn(C(C)(C)CO)c4)n3)c2)n1] |
| 31 | 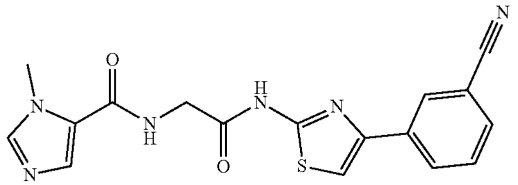 [SMILES: Cn1cncc1C(=O)NCC(=O)Nc1nc(-c2cccc(C#N)c2)cs1] |
| 32 | 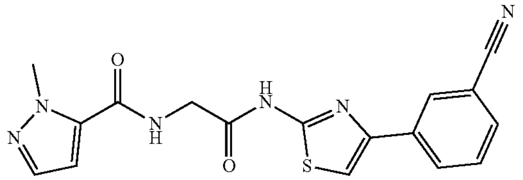 [SMILES: Cn1nccc1C(=O)NCC(=O)Nc1nc(-c2cccc(C#N)c2)cs1] |
| 33 | 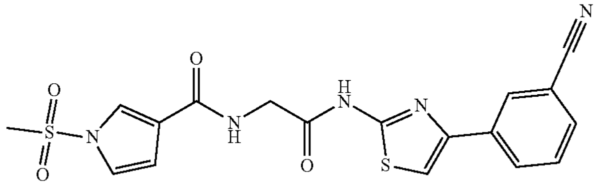 [SMILES: CS(=O)(=O)n1ccc(C(=O)NCC(=O)Nc2nc(-c3cccc(C#N)c3)cs2)c1] |
| 34 | 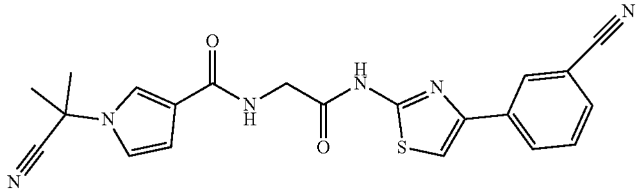 [SMILES: CC(C)(C#N)n1ccc(C(=O)NCC(=O)Nc2nc(-c3cccc(C#N)c3)cs2)c1] |
| 35 | 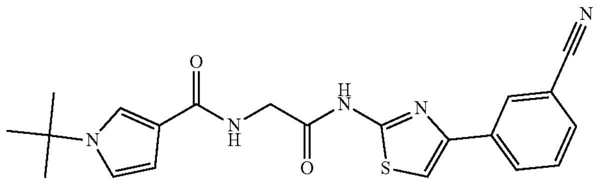 [SMILES: CC(C)(C)n1ccc(C(=O)NCC(=O)Nc2nc(-c3cccc(C#N)c3)cs2)c1] |

TABLE 1-continued
| Compounds of the invention | |
|---|---|
| # | Compound |
| 36 | 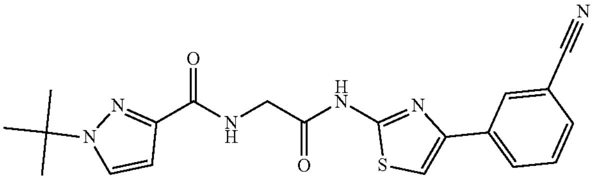 [SMILES: CC(C)(C)n1ccc(C(=O)NCC(=O)Nc2nc(-c3cccc(C#N)c3)cs2)n1] |
| 37 | 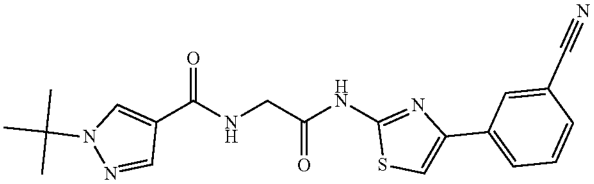 [SMILES: CC(C)(C)n1cc(C(=O)NCC(=O)Nc2nc(-c3cccc(C#N)c3)cs2)cn1] |
| 38 | 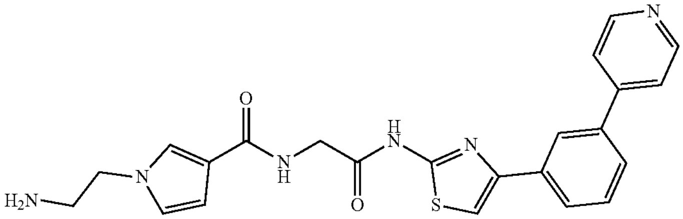 [SMILES: NCCn1ccc(C(=O)NCC(=O)Nc2nc(-c3cccc(-c4ccncc4)c3)cs2)c1] |
| 39 | 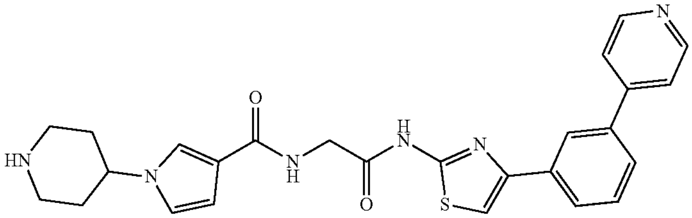 [SMILES: O=C(CNC(=O)c1ccn(C2CCNCC2)c1)Nc1nc(-c2cccc(-c3ccncc3)c2)cs1] |
| 40 | 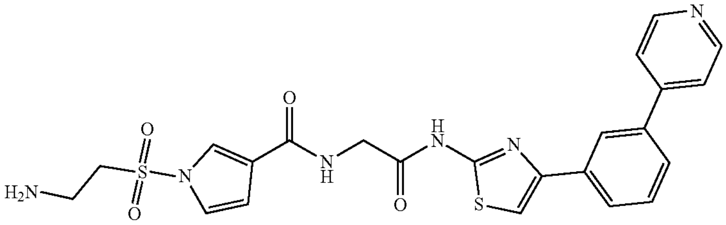 [SMILES: NCCS(=O)(=O)n1ccc(C(=O)NCC(=O)Nc2nc(-c3cccc(-c4ccncc4)c3)cs2)c1] |
| 41 | 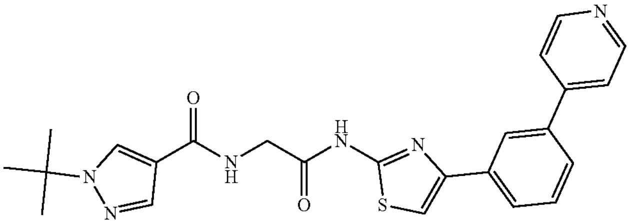 [SMILES: CC(C)(C)n1cc(C(=O)NCC(=O)Nc2nc(-c3cccc(-c4ccncc4)c3)cs2)cn1] |
| 42 | 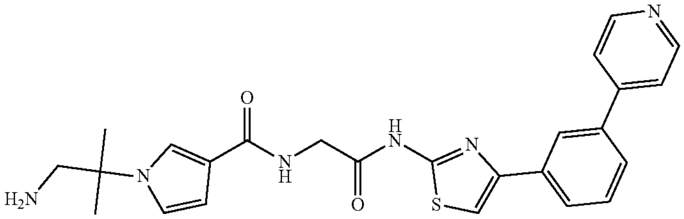 [SMILES: CC(C)(CN)n1ccc(C(=O)NCC(=O)Nc2nc(-c3cccc(-c4ccncc4)c3)cs2)c1] |

TABLE 1-continued
| Compounds of the invention | |
|---|---|
| # | Compound |
| 43 | 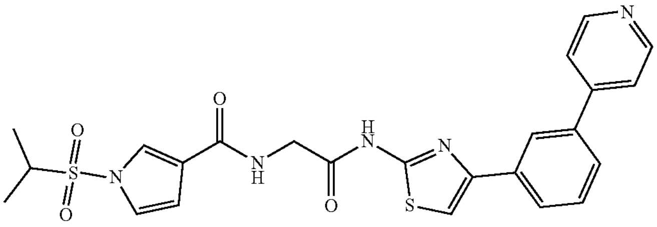 [SMILES: CC(C)S(=O)(=O)n1ccc(C(=O)NCC(=O)Nc2nc(-c3cccc(-c4ccncc4)c3)cs2)c1] |
| 44 | 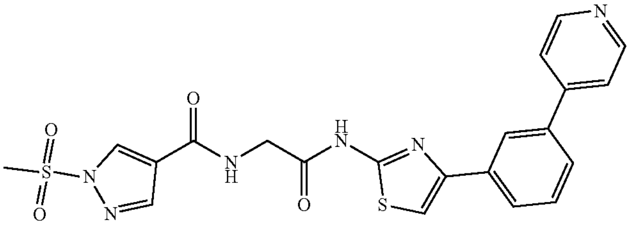 [SMILES: CS(=O)(=O)n1cc(C(=O)NCC(=O)Nc2nc(-c3cccc(-c4ccncc4)c3)cs2)cn1] |
| 45 | 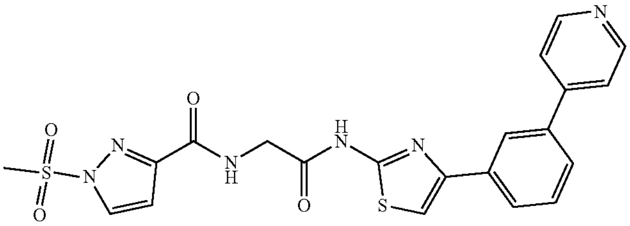 |
| 46 | 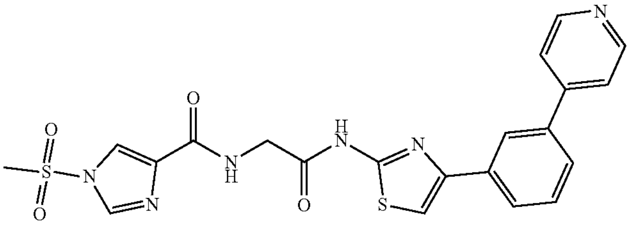 [SMILES: CS(=O)(=O)n1cnc(C(=O)NCC(=O)Nc2nc(-c3cccc(-c4ccncc4)c3)cs2)c1] |
| 47 | 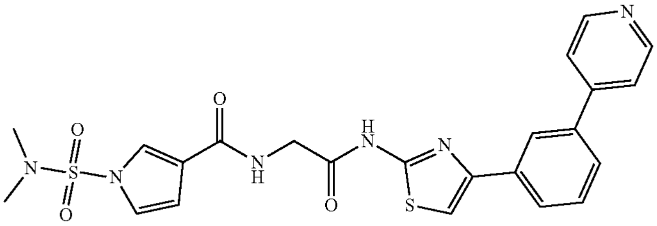 [SMILES: CN(C)S(=O)(=O)n1ccc(C(=O)NCC(=O)Nc2nc(-c3cccc(-c4ccncc4)c3)cs2)c1] |
| 48 | 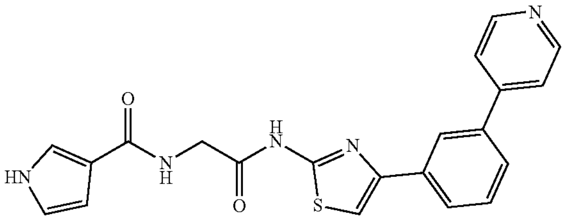 [SMILES: O=C(CNC(=O)c1cc[nH]c1)Nc1nc(-c2cccc(-c3ccncc3)c2)cs1] |

TABLE 1-continued
Compounds of the invention
| # | Compound |
|---|---|
| 49 | 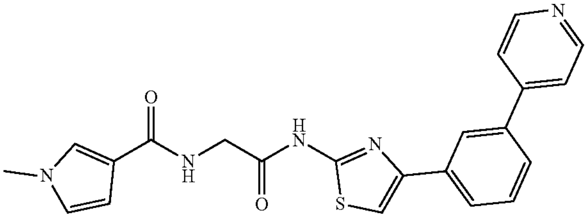 [SMILES: Cn1ccc(C(=O)NCC(=O)Nc2nc(-c3cccc(-c4ccncc4)c3)cs2)c1] |
| 50 | 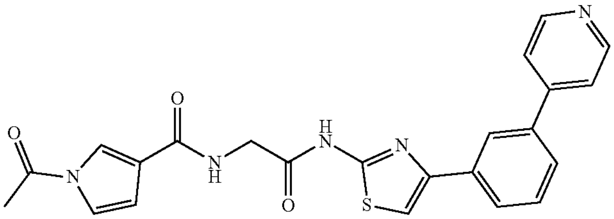 [SMILES: CC(=O)n1ccc(C(=O)NCC(=O)Nc2nc(-c3cccc(-c4ccncc4)c3)cs2)c1] |
| 51 | 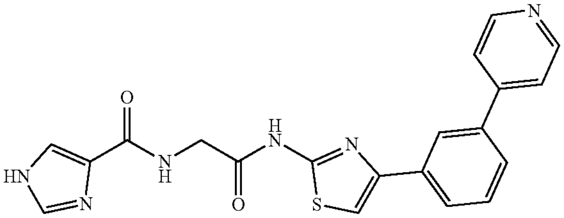 [SMILES: O=C(CNC(=O)c1c[nH]cn1)Nc1nc(-c2cccc(-c3ccncc3)c2)cs1] |
| 52 | 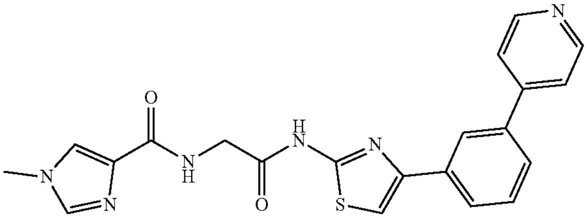 [SMILES: Cn1cnc(C(=O)NCC(=O)Nc2nc(-c3cccc(-c4ccncc4)c3)cs2)c1] |
| 53 | 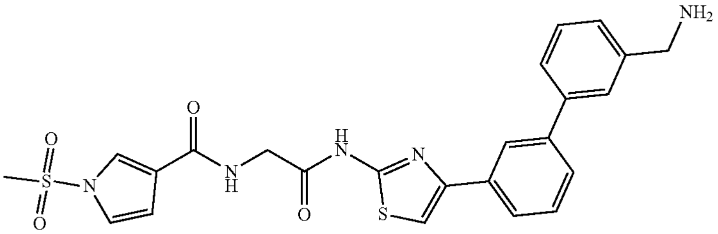 [SMILES: CS(=O)(=O)n1ccc(C(=O)NCC(=O)Nc2nc(-c3cccc(-c4cccc(CN)c4)c3)cs2)c1] |
| 54 | 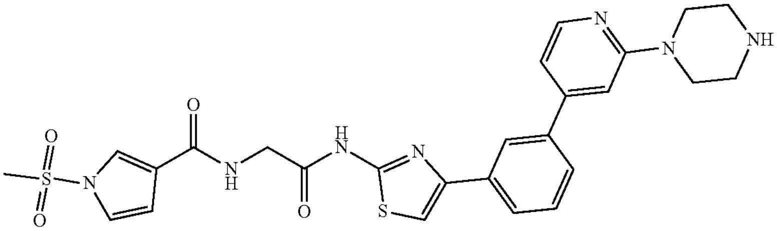 [SMILES: CS(=O)(=O)n1ccc(C(=O)NCC(=O)Nc2nc(-c3cccc(-c4ccnc(N5CCNCC5)c4)c3)cs2)c1] |

TABLE 1-continued
| Compounds of the invention | |
|---|---|
| # | Compound |
| 55 | 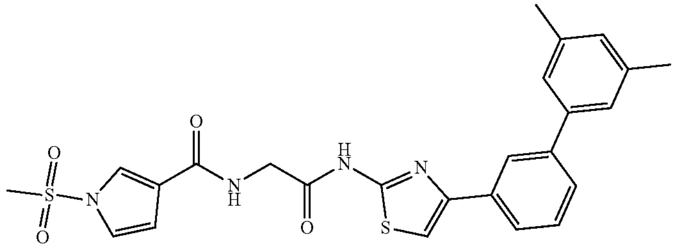 |
| 56 | 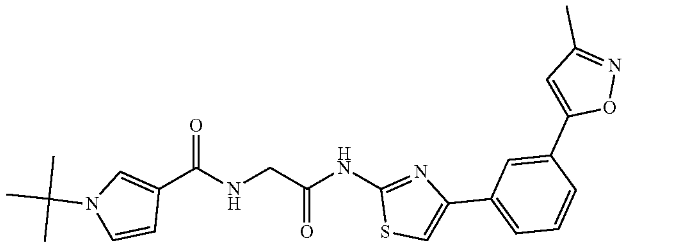 [SMILES: Cc1cc(-c2cccc(-c3csc(NC(=O)CNC(=O)c4ccn(C(C)(C)C)c4)n3)c2)on1] |
| 57 | 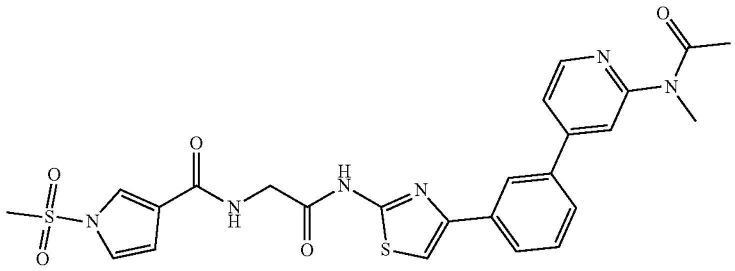 [SMILES: CC(=O)N(C)c1cc(-c2cccc(-c3csc(NC(=O)CNC(=O)c4ccn(S(C)(=O)=O)c4)n3)c2)ccn1] |
| 58 | 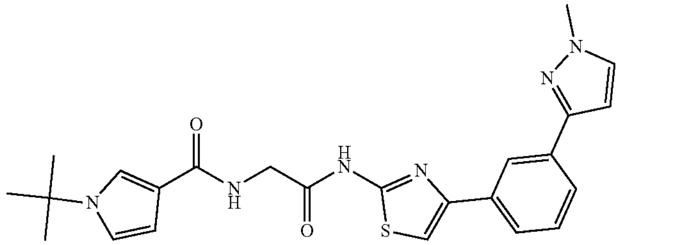 [SMILES: Cn1ccc(-c2cccc(-c3csc(NC(=O)CNC(=O)c4ccn(C(C)(C)C)c4)n3)c2)n1] |
| 59 | 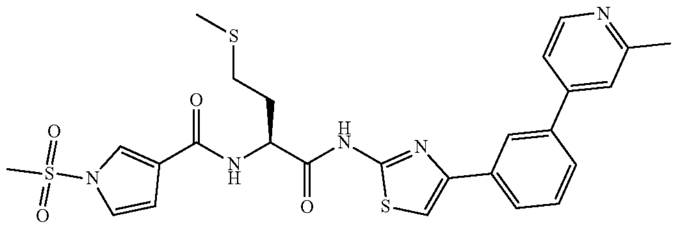 |
| 60 | 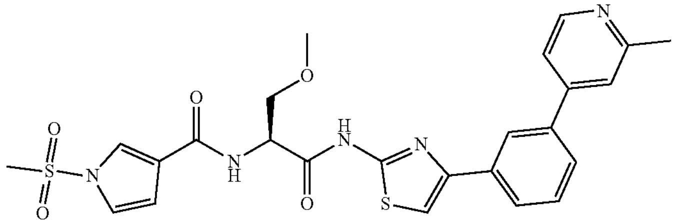 |

TABLE 1-continued
| Compounds of the invention | |
|---|---|
| # | Compound |
| 61 | 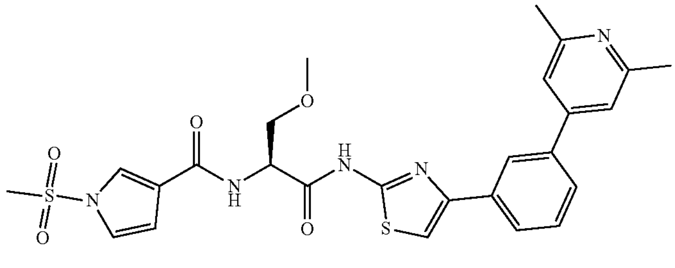 |
| 62 | 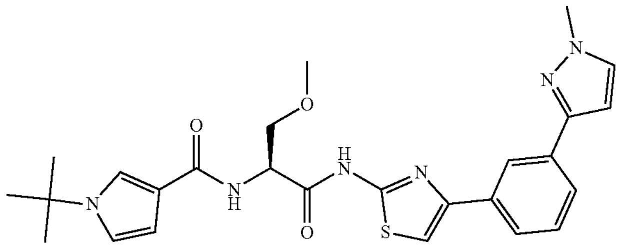 [SMILES: COC[C@H](NC(=O)c1ccn(C(C)(C)C)c1)C(=O)Nc1nc(-c2cccc(-c3ccn(C)n3)c2)cs1] |
| 63 | 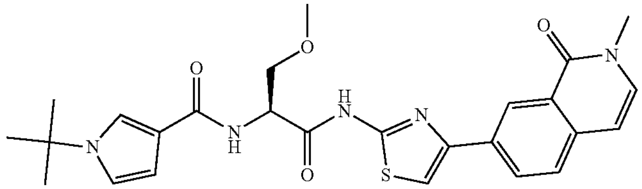 [SMILES: COC[C@H](NC(=O)c1ccn(C(C)(C)C)c1)C(=O)Nc1nc(-c2ccc3ccn(C)c(=O)c3c2)cs1] |
| 64 | 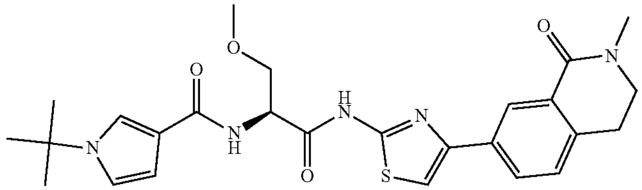 [SMILES: COC[C@H](NC(=O)c1ccn(C(C)(C)C)c1)C(=O)Nc1nc(-c2ccc3c(c2)C(=O)N(C)CC3)cs1] |
| 65 | 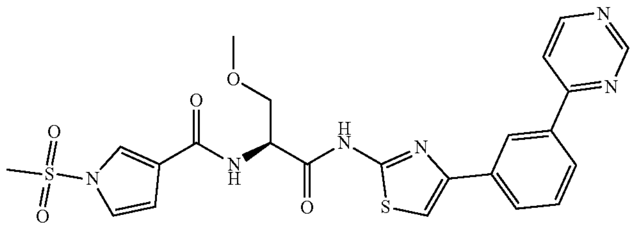 [SMILES: COC[C@H](NC(=O)c1ccn(S(C)(=O)=O)c1)C(=O)Nc1nc(-c2cccc(-c3ccncn3)c2)cs1] |
| 66 | 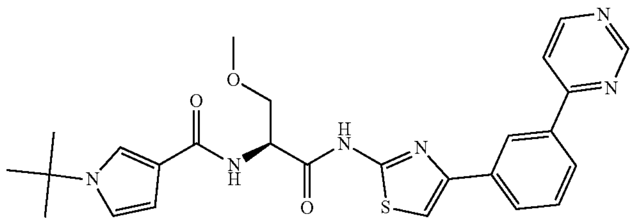 [SMILES: COC[C@H](NC(=O)c1ccn(C(C)(C)C)c1)C(=O)Nc1nc(-c2cccc(-c3ccncn3)c2)cs1] |

TABLE 1-continued
| Compounds of the invention | |
|---|---|
| # | Compound |
| 67 | 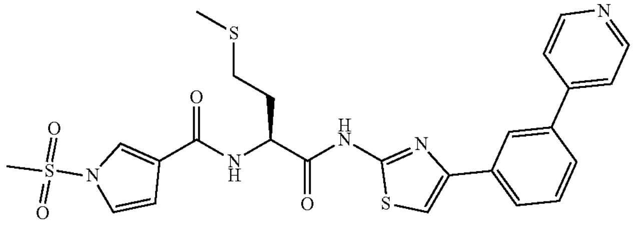 [SMILES: CSCC[C@H](NC(=O)c1ccn(S(C)(=O)=O)c1)C(=O)Nc1nc(-c2cccc(-c3ccncc3)c2)cs1] |
| 68 | 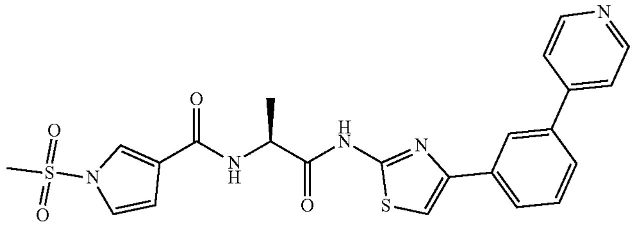 [SMILES: C[C@H](NC(=O)c1ccn(S(C)(=O)=O)c1)C(=O)Nc1nc(-c2cccc(-c3ccncc3)c2)cs1] |
| 69 | 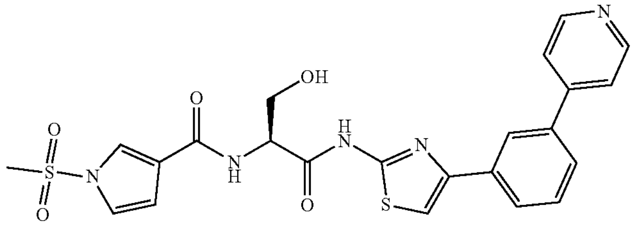 [SMILES: CS(=O)(=O)n1ccc(C(=O)N[C@@H](CO)C(=O)Nc2nc(-c3cccc(-c4ccncc4)c3)cs2)c1] |
| 70 | 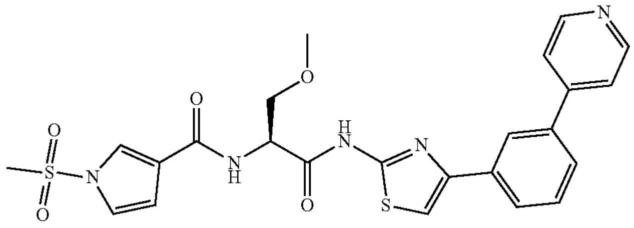 [SMILES: COC[C@H](NC(=O)c1ccn(S(C)(=O)=O)c1)C(=O)Nc1nc(-c2cccc(-c3ccncc3)c2)cs1] |
| 71 | 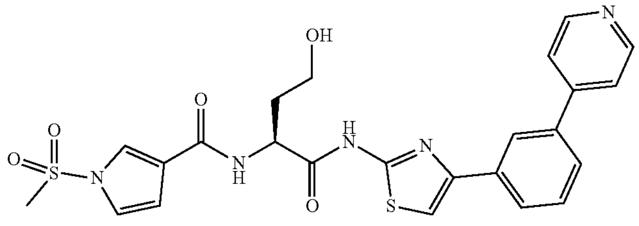 [SMILES: CS(=O)(=O)n1ccc(C(=O)N[C@@H](CCO)C(=O)Nc2nc(-c3cccc(-c4ccncc4)c3)cs2)c1] |
| 72 | 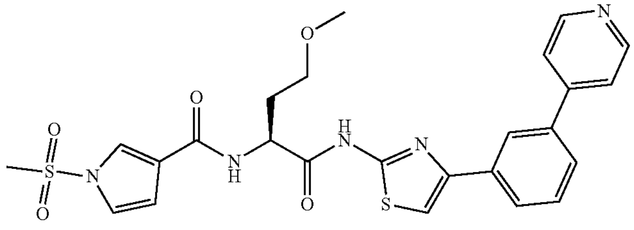 [SMILES: COCC[C@H](NC(=O)c1ccn(S(C)(=O)=O)c1)C(=O)Nc1nc(-c2cccc(-c3ccncc3)c2)cs1] |

TABLE 1-continued
| Compounds of the invention | |
|---|---|
| # | Compound |
| 73 | 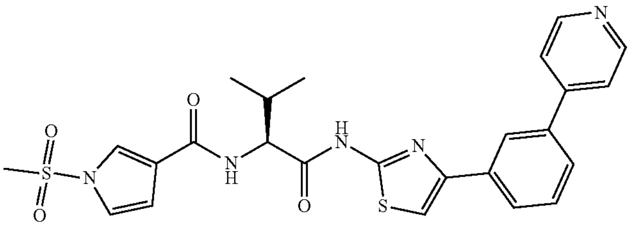 [SMILES: CC(C)[C@H](NC(=O)c1ccn(S(C)(=O)=O)c1)C(=O)Nc1nc(-c2cccc(-c3ccncc3)c2)cs1] |
| 74 | 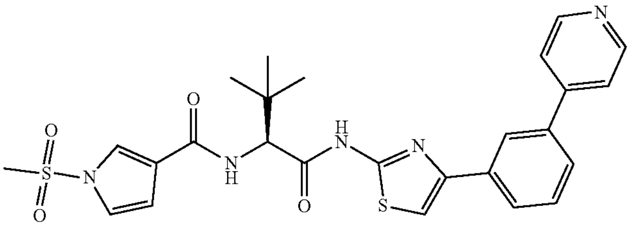 [SMILES: CC(C)(C)[C@H](NC(=O)c1ccn(S(C)(=O)=O)c1)C(=O)Nc1nc(-c2cccc(-c3ccncc3)c2)cs1] |
| 75 | 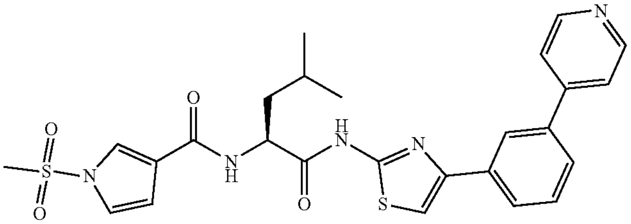 [SMILES: CC(C)C[C@H](NC(=O)c1ccn(S(C)(=O)=O)c1)C(=O)Nc1nc(-c2cccc(-c3ccncc3)c2)cs1] |
| 76 | 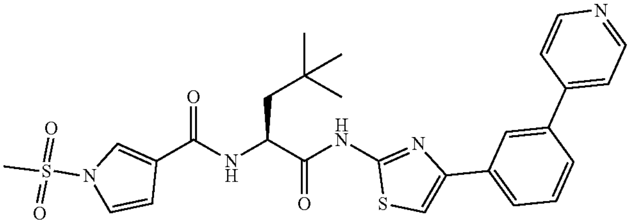 [SMILES: CC(C)(C)C[C@H](NC(=O)c1ccn(S(C)(=O)=O)c1)C(=O)Nc1nc(-c2cccc(-c3ccncc3)c2)cs1] |
| 77 | 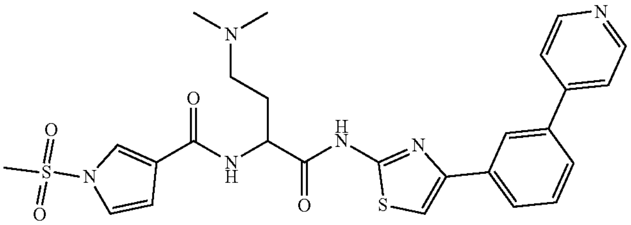 [SMILES: CN(C)CCC(NC(=O)c1ccn(S(C)(=O)=O)c1)C(=O)Nc1nc(-c2cccc(-c3ccncc3)c2)cs1] |
| 78 | 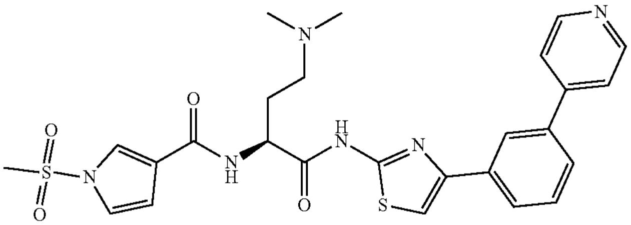 [SMILES: CN(C)CC[C@H](NC(=O)c1ccn(S(C)(=O)=O)c1)C(=O)Nc1nc(-c2cccc(-c3ccncc3)c2)cs1] |

TABLE 1-continued
| Compounds of the invention | |
|---|---|
| # | Compound |
| 79 | 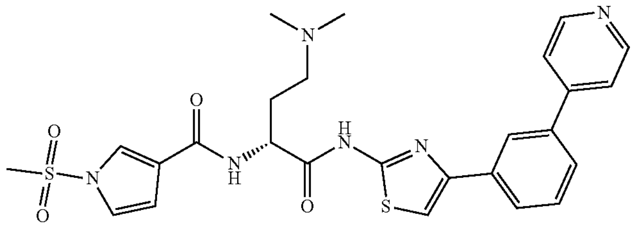 [SMILES: CN(C)CC[C@@H](NC(=O)c1ccn(S(C)(=O)=O)c1)C(=O)Nc1nc(-c2cccc(-c3ccncc3)c2)cs1] |
| 80 | 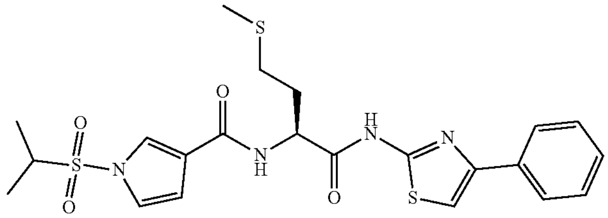 [SMILES: CSCC[C@H](NC(=O)c1ccn(S(=O)(=O)C(C)C)c1)C(=O)Nc1nc(-c2ccccc2)cs1] |
| 81 | 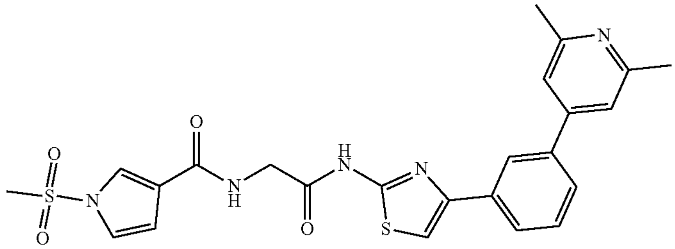 |
| 82 | 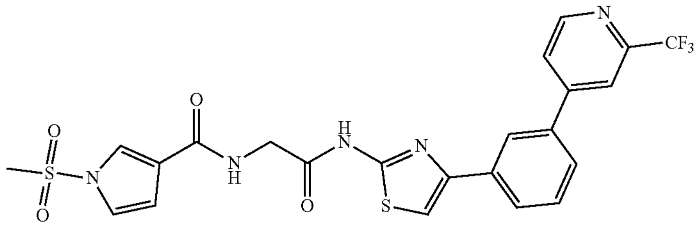 [SMILES: CS(=O)(=O)n1ccc(C(=O)NCC(=O)Nc2nc(-c3cccc(-c4ccnc(C(F)(F)F)c4)c3)cs2)c1] |
| 83 | 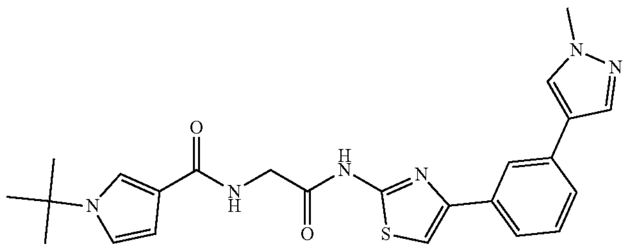 [SMILES: Cn1cc(-c2cccc(-c3csc(NC(=O)CNC(=O)c4ccn(C(C)(C)C)c4)n3)c2)cn1] |
| 84 | 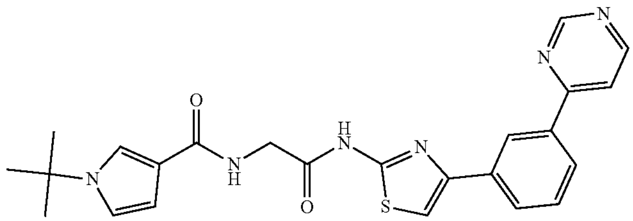 |

TABLE 1-continued
| Compounds of the invention | |
|---|---|
| # | Compound |
| 85 | 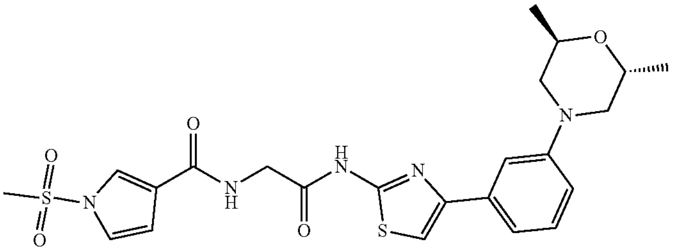 |
| 86 | 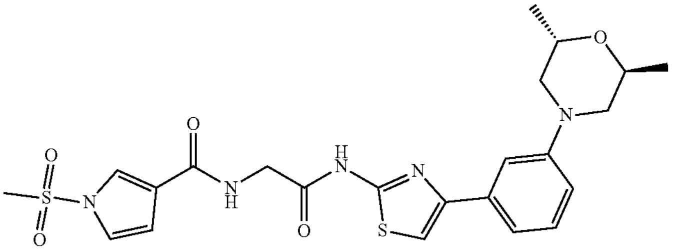 |
| 87 | 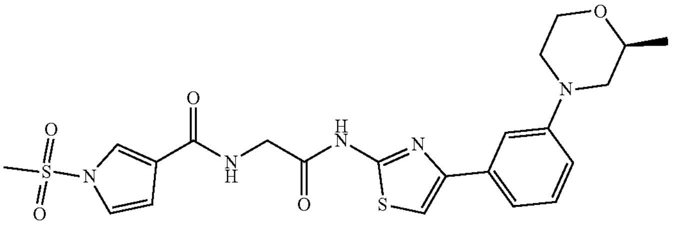 |
| 88 | 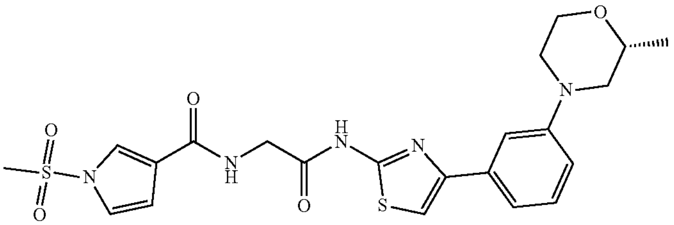 |
| 89 | 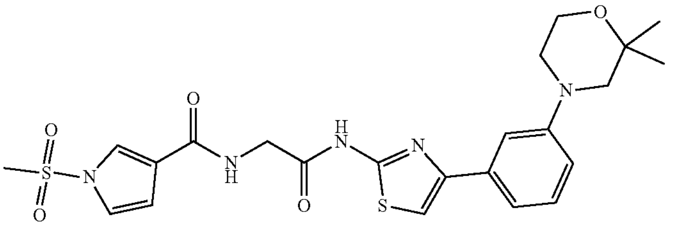 |
| 90 | 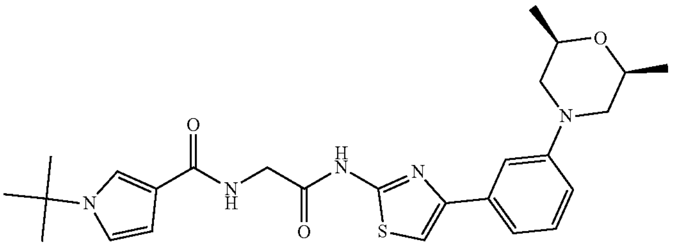 [SMILES: C[C@@H]1CN(c2cccc(-c3csc(NC(=O)CNC(=O)c4ccn(C(C)(C)C)c4)n3)c2)C[C@H](C)O1] |

TABLE 1-continued
| Compounds of the invention | |
|---|---|
| # | Compound |
| 91 | 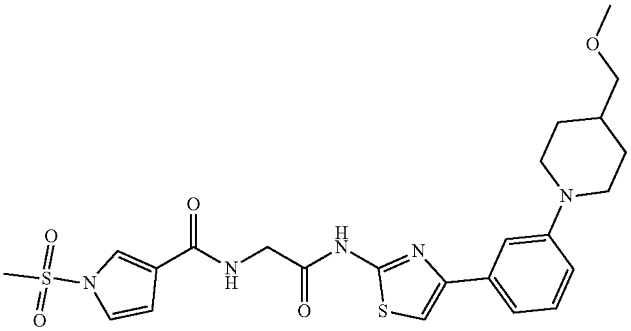 [SMILES: COCC1CCN(c2cccc(-c3csc(NC(=O)CNC(=O)c4ccn(S(C)(=O)=O)c4)n3)c2)CC1] |
| 92 | 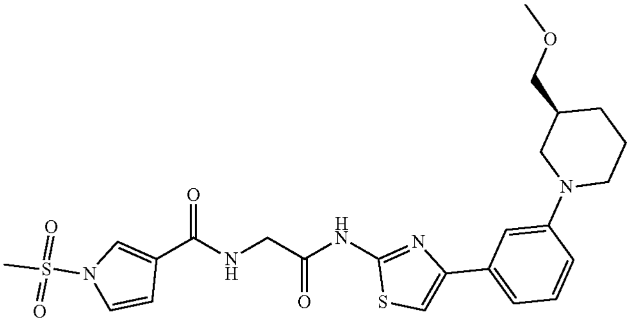 [SMILES: COC[C@H]1CCCN(c2cccc(-c3csc(NC(=O)CNC(=O)c4ccn(S(C)(=O)=O)c4)n3)c2)C1] |
| 93 | 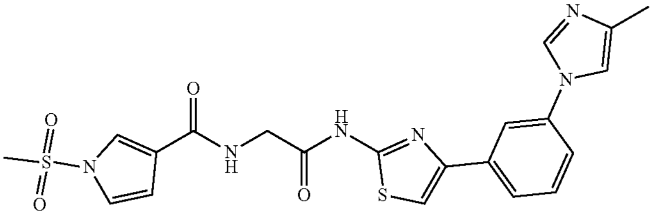 |
| 94 | 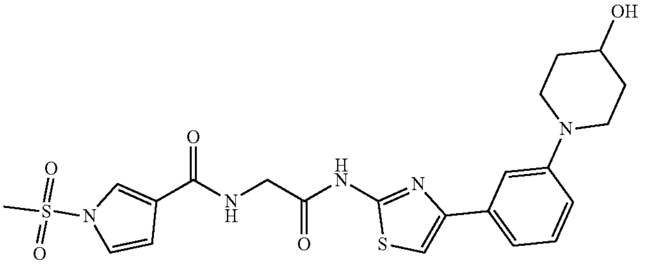 |
| 95 | 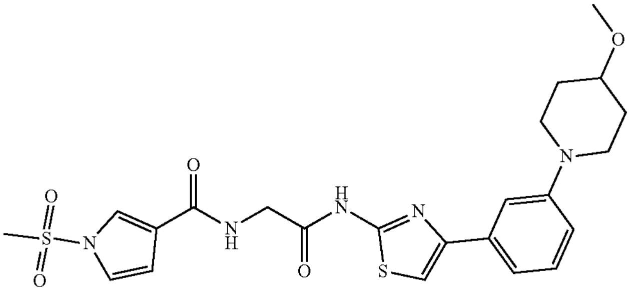 [SMILES: COC1CCN(c2cccc(-c3csc(NC(=O)CNC(=O)c4ccn(S(C)(=O)=O)c4)n3)c2)CC1] |

TABLE 1-continued
| Compounds of the invention | |
|---|---|
| # | Compound |
| 96 | 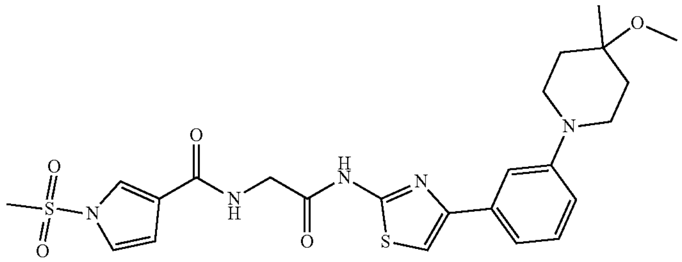 |
| 97 | 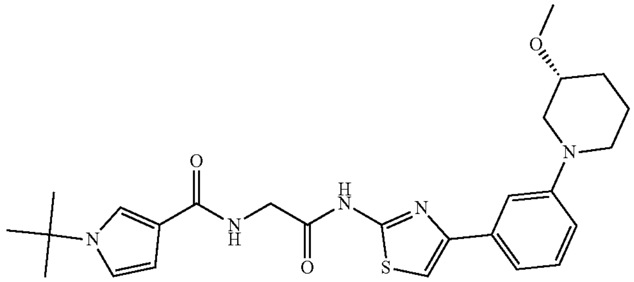 [SMILES: CO[C@@H]1CCCN(c2cccc(-c3csc(NC(=O)CNC(=O)c4ccn(C(C)(C)C)c4)n3)c2)C1] |
| 98 | 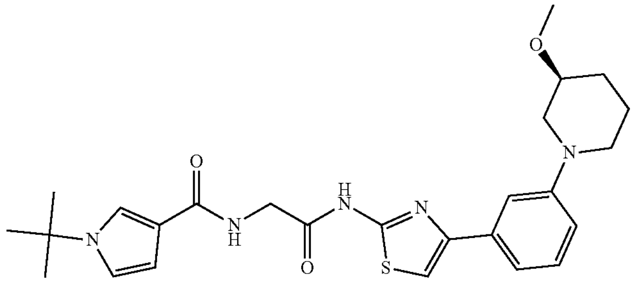 [SMILES: CO[C@H]1CCCN(c2cccc(-c3csc(NC(=O)CNC(=O)c4ccn(C(C)(C)C)c4)n3)c2)C1] |
| 99 | 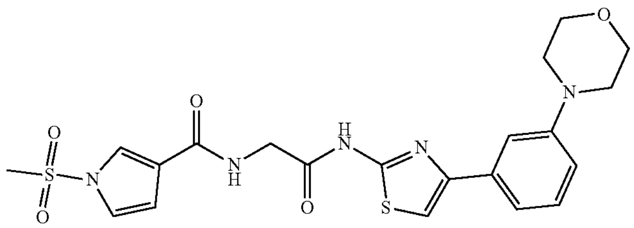 [SMILES: CS(=O)(=O)n1ccc(C(=O)NCC(=O)Nc2nc(-c3cccc(N4CCOCC4)c3)cs2)c1] |
| 100 | 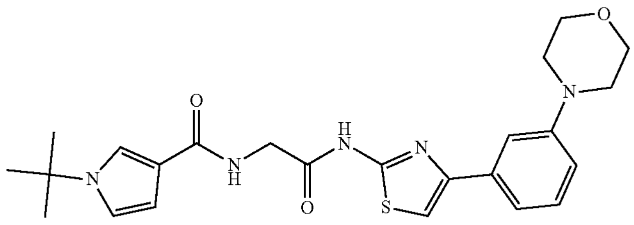 [SMILES: CC(C)(C)n1ccc(C(=O)NCC(=O)Nc2nc(-c3cccc(N4CCOCC4)c3)cs2)c1] |
| 101 | 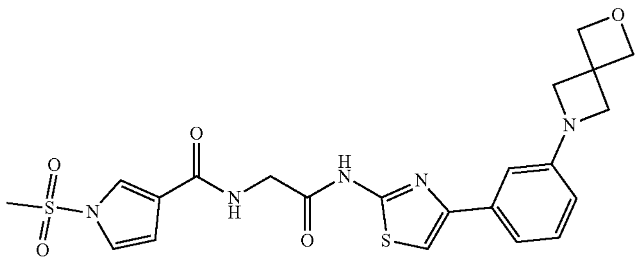 [SMILES: CS(=O)(=O)n1ccc(C(=O)NCC(=O)Nc2nc(-c3cccc(N4CC5(COC5)C4)c3)cs2)c1] |

TABLE 1-continued
| Compounds of the invention | |
|---|---|
| # | Compound |
| 102 | 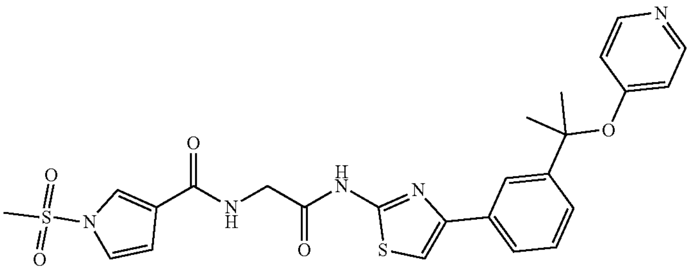 [SMILES: CC(C)(Oc1ccncc1)c1cccc(-c2csc(NC(=O)CNC(=O)c3ccn(S(C)(=O)=O)c3)n2)c1] |
| 103 | 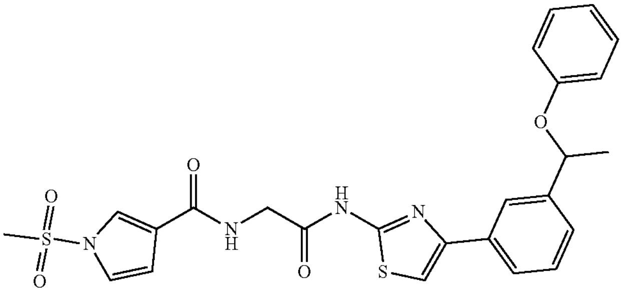 [SMILES: CC(Oc1ccccc1)c1cccc(-c2csc(NC(=O)CNC(=O)c3ccn(S(C)(=O)=O)c3)n2)c1] |
| 104 | 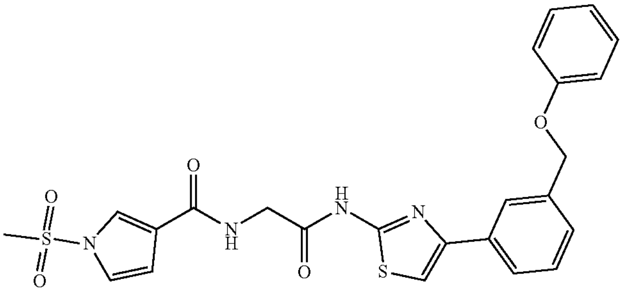 [SMILES: CS(=O)(=O)n1ccc(C(=O)NCC(=O)Nc2nc(-c3cccc(COc4ccccc4)c3)cs2)c1] |
| 105 | 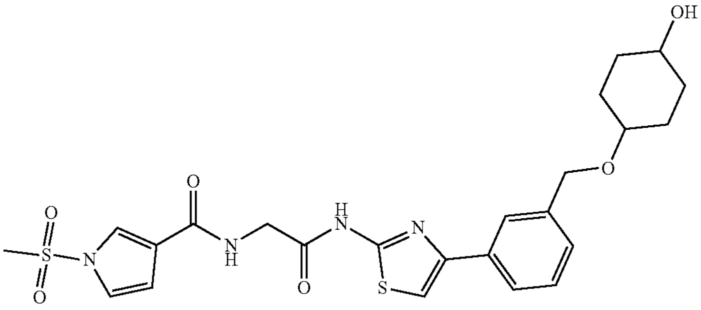 [SMILES: CS(=O)(=O)n1ccc(C(=O)NCC(=O)Nc2nc(-c3cccc(COC4CCC(O)CC4)c3)cs2)c1] |
| 106 | 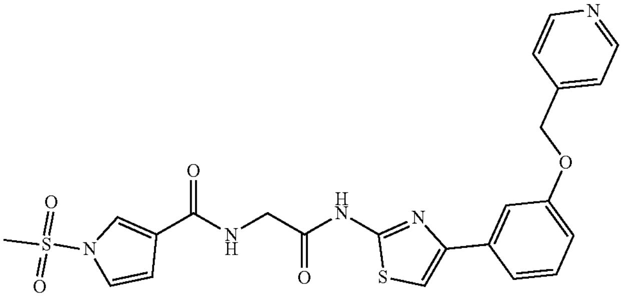 [SMILES: CS(=O)(=O)n1ccc(C(=O)NCC(=O)Nc2nc(-c3cccc(OCc4ccncc4)c3)cs2)c1] |

TABLE 1-continued
| Compounds of the invention | |
|---|---|
| # | Compound |
| 107 | 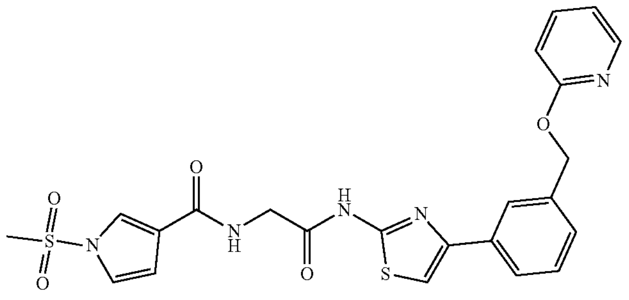 [SMILES: CS(=O)(=O)n1ccc(C(=O)NCC(=O)Nc2nc(-c3cccc(COc4ccccn4)c3)cs2)c1] |
| 108 | 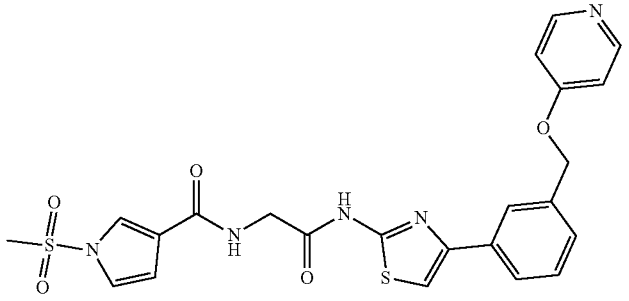 [SMILES: CS(=O)(=O)n1ccc(C(=O)NCC(=O)Nc2nc(-c3cccc(COc4ccncc4)c3)cs2)c1] |
| 109 | 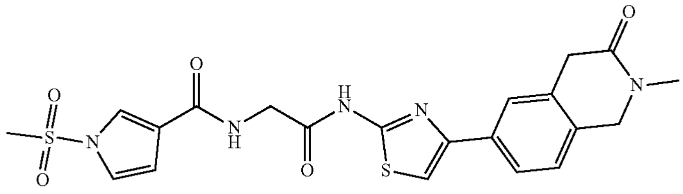 |
| 110 | 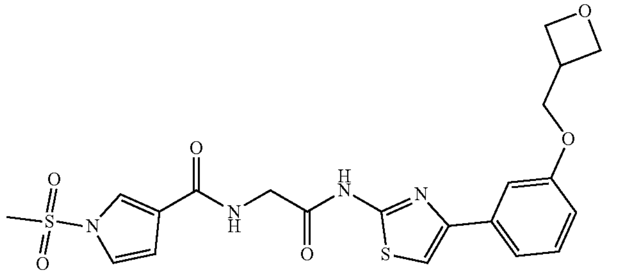 [SMILES: CS(=O)(=O)n1ccc(C(=O)NCC(=O)Nc2nc(-c3cccc(OCC4COC4)c3)cs2)c1] |
| 111 | 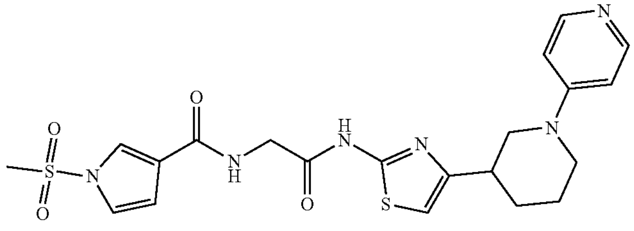 [SMILES: CS(=O)(=O)n1ccc(C(=O)NCC(=O)Nc2nc(C3CCCN(c4ccncc4)C3)cs2)c1] |
| 112 | 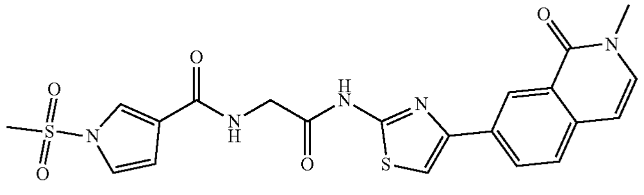 [SMILES: Cn1ccc2ccc(-c3csc(NC(=O)CNC(=O)c4ccn(S(C)(=O)=O)c4)n3)cc2c1=O]

TABLE 1-continued
| # | Compound |
|---|---|
| 113 | 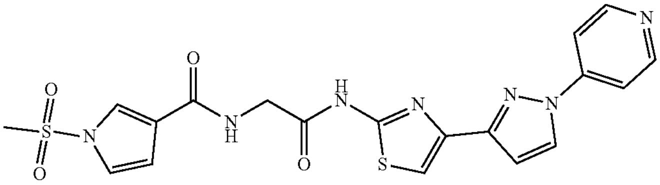 [SMILES: CS(=O)(=O)n1ccc(C(=O)NCC(=O)Nc2nc(-c3ccn(-c4ccncc4)n3)cs2)c1] |
| 114 | 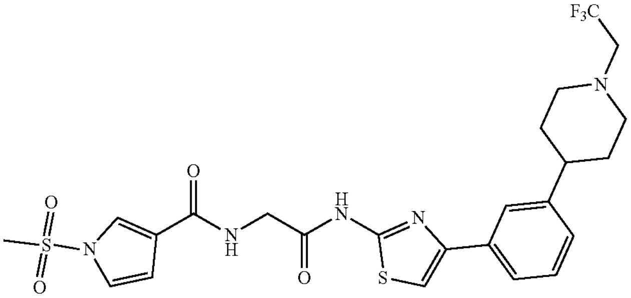 [SMILES: CS(=O)(=O)n1ccc(C(=O)NCC(=O)Nc2nc(-c3cccc(C4CCN(CC(F)(F)F)CC4)c3)cs2)c1] |
| 115 | 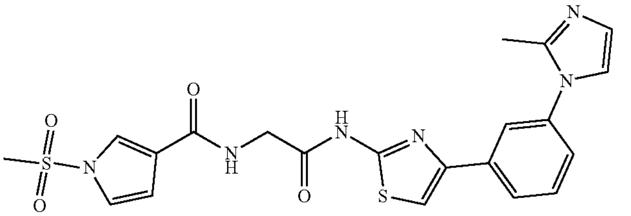 [SMILES: Cc1nccn1-c1cccc(-c2csc(NC(=O)CNC(=O)c3ccn(S(C)(=O)=O)c3)n2)c1] |
| 116 | 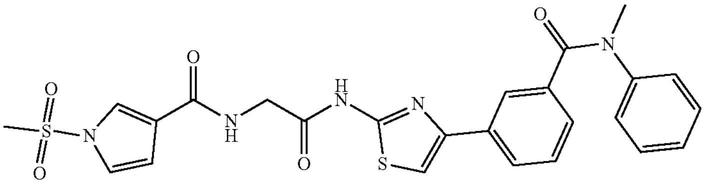 [SMILES: CN(C(=O)c1cccc(-c2csc(NC(=O)CNC(=O)c3ccn(S(C)(=O)=O)c3)n2)c1)c1ccccc1] |
| 117 | 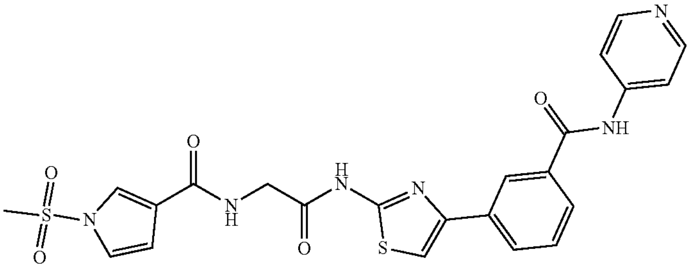 [SMILES: CS(=O)(=O)n1ccc(C(=O)NCC(=O)Nc2nc(-c3cccc(C(=O)Nc4ccncc4)c3)cs2)c1] |
| 118 | 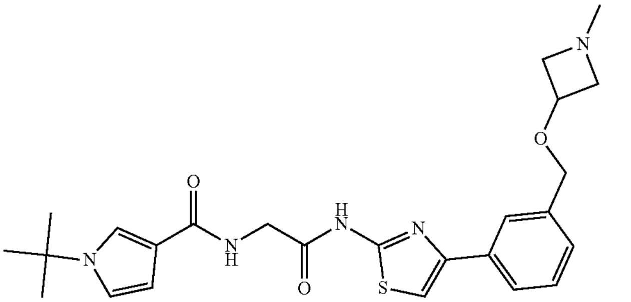 [SMILES: CN1CC(OCc2cccc(-c3csc(NC(=O)CNC(=O)c4ccn(C(C)(C)C)c4)n3)c2)C1] |
Compounds of the invention TABLE 1-continued
| Compounds of the invention | |
|---|---|
| # | Compound |
| 119 | 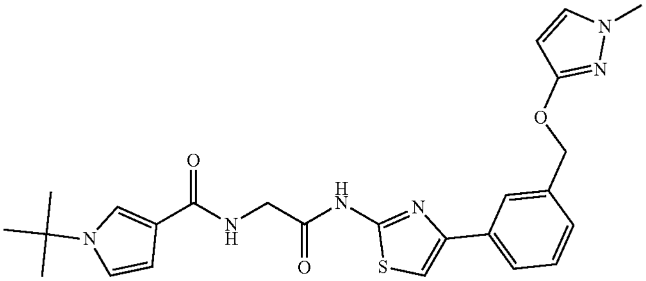 [SMILES: Cn1ccc(OCc2cccc(-c3csc(NC(=O)CNC(=O)c4ccn(C(C)(C)C)c4)n3)c2)n1] |
| 120 | 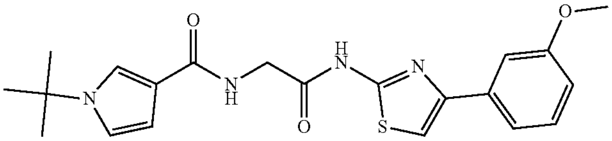 [SMILES: COc1cccc(-c2csc(NC(=O)CNC(=O)c3ccn(C(C)(C)C)c3)n2)c1] |
| 121 | 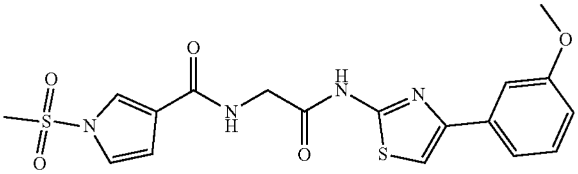 [SMILES: COc1cccc(-c2csc(NC(=O)CNC(=O)c3ccn(S(C)(=O)=O)c3)n2)c1] |
| 122 | 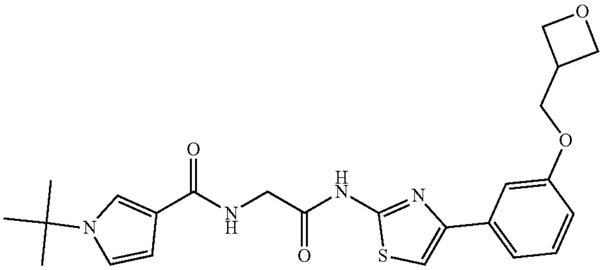 [SMILES: CC(C)(C)n1ccc(C(=O)NCC(=O)Nc2nc(-c3cccc(OCC4COC4)c3)cs2)c1] |
| 123 | 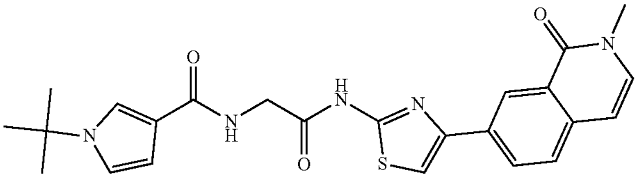 [SMILES: Cn1ccc2ccc(-c3csc(NC(=O)CNC(=O)c4ccn(C(C)(C)C)c4)n3)cc2c1=O] |
| 124 | 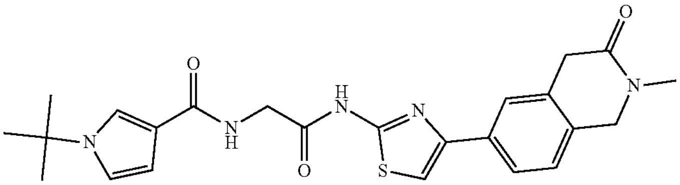 [SMILES: CN1Cc2ccc(-c3csc(NC(=O)CNC(=O)c4ccn(C(C)(C)C)c4)n3)cc2CC1=O] |

TABLE 1-continued
| Compounds of the invention | |
|---|---|
| # | Compound |
| 125 | 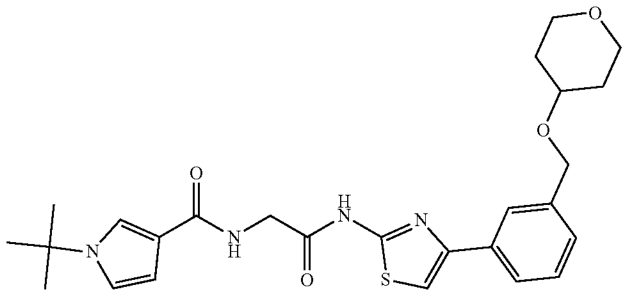 [SMILES: CC(C)(C)n1ccc(C(=O)NCC(=O)Nc2nc(-c3cccc(COC4CCOCC4)c3)cs2)c1] |
| 126 | 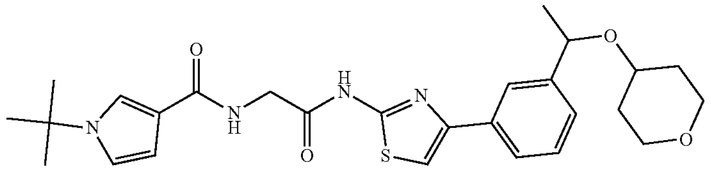 [SMILES: CC(OC1CCOCC1)c1cccc(-c2csc(NC(=O)CNC(=O)c3ccn(C(C)(C)C)c3)n2)c1] |
| 127 | 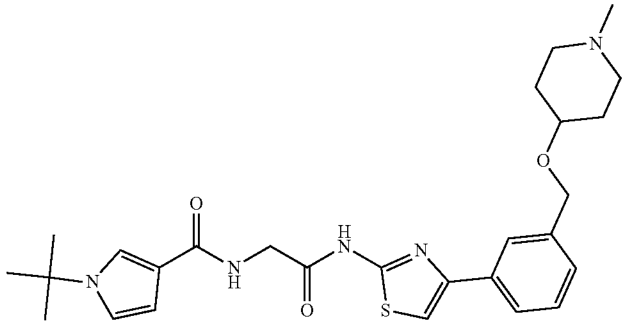 [SMILES: CN1CCC(OCc2cccc(-c3csc(NC(=O)CNC(=O)c4ccn(C(C)(C)C)c4)n3)c2)CC1] |
| 128 | 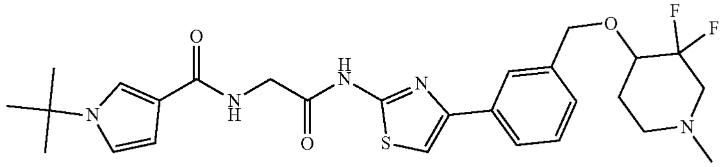 [SMILES: CN1CCC(OCc2cccc(-c3csc(NC(=O)CNC(=O)c4ccn(C(C)(C)C)c4)n3)c2)C(F)(F)C1] |
| 129 | 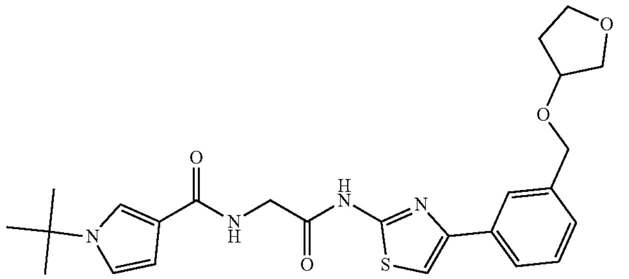 [SMILES: CC(C)(C)n1ccc(C(=O)NCC(=O)Nc2nc(-c3cccc(COC4CCOC4)c3)cs2)c1] |
| 130 | 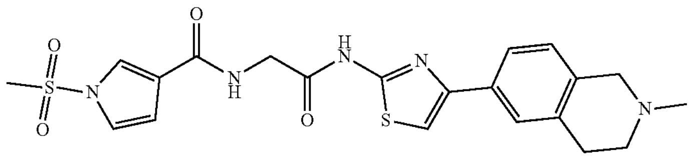 |

TABLE 1-continued
| Compounds of the invention | |
|---|---|
| # | Compound |
| 131 | 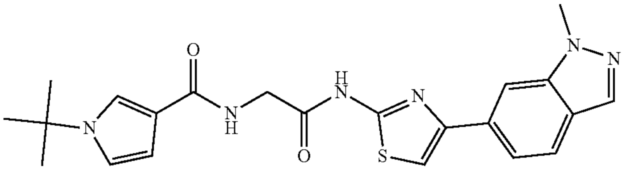 [SMILES: Cn1ncc2ccc(-c3csc(NC(=O)CNC(=O)c4ccn(C(C)(C)C)c4)n3)cc21] |
| 132 | 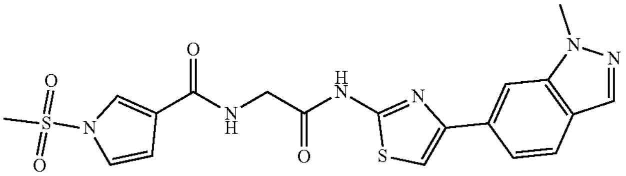 [SMILES: Cn1ncc2ccc(-c3csc(NC(=O)CNC(=O)c4ccn(S(C)(=O)=O)c4)n3)cc21] |
| 133 | 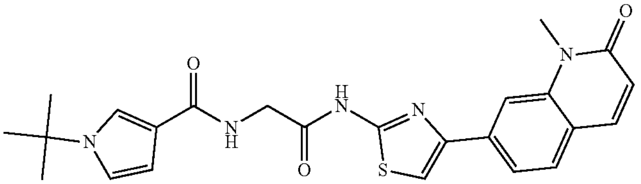 [SMILES: Cn1c(=O)ccc2ccc(-c3csc(NC(=O)CNC(=O)c4ccn(C(C)(C)C)c4)n3)cc21] |
| 134 | 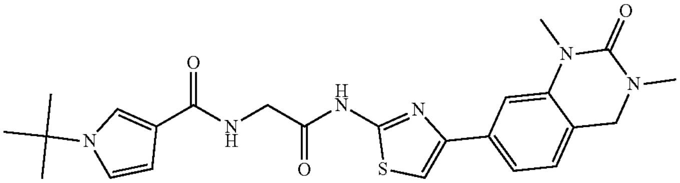 [SMILES: CN1Cc2ccc(-c3csc(NC(=O)CNC(=O)c4ccn(C(C)(C)C)c4)n3)cc2N(C)C1=O] |
| 135 | 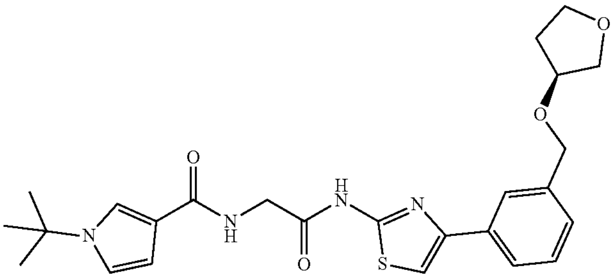 [SMILES: CC(C)(C)n1ccc(C(=O)NCC(=O)Nc2nc(-c3cccc(CO[C@H]4CCOC4)c3)cs2)c1] |
| 136 | 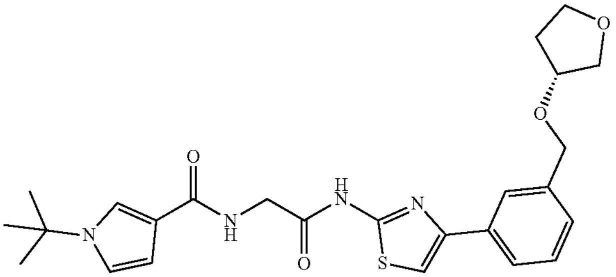 [SMILES: CC(C)(C)n1ccc(C(=O)NCC(=O)Nc2nc(-c3cccc(CO[C@@H]4CCOC4)c3)cs2)c1] |
| 137 | 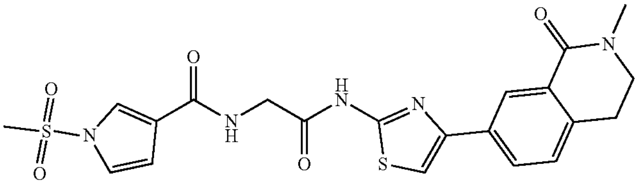 [SMILES: CN1CCc2ccc(-c3csc(NC(=O)CNC(=O)c4ccn(S(C)(=O)=O)c4)n3)cc2C1=O] |

TABLE 1-continued
| Compounds of the invention | |
|---|---|
| # | Compound |
| 138 | 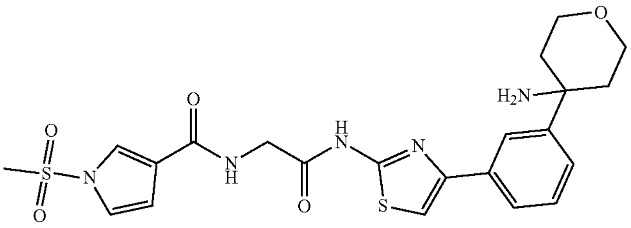 [SMILES: CS(=O)(=O)n1ccc(C(=O)NCC(=O)Nc2nc(-c3cccc(C4(N)CCOCC4)c3)cs2)c1] |
| 139 | 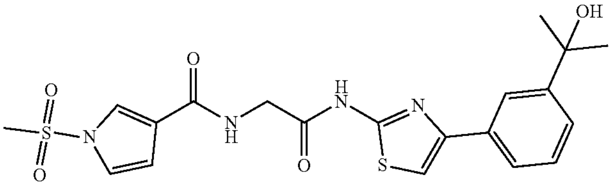 [SMILES: CC(C)(O)c1cccc(-c2csc(NC(=O)CNC(=O)c3ccn(S(C)(=O)=O)c3)n2)c1] |
| 140 | 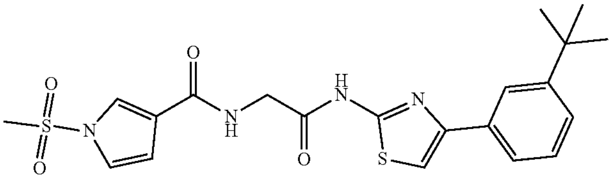 [SMILES: CC(C)(C)c1cccc(-c2csc(NC(=O)CNC(=O)c3ccn(S(C)(=O)=O)c3)n2)c1] |
| 141 | 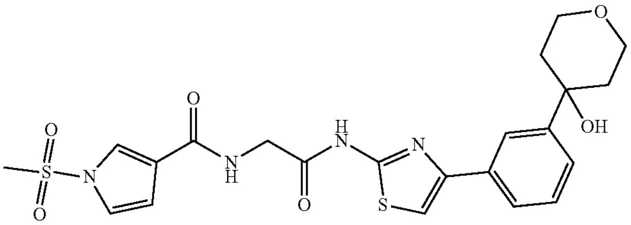 [SMILES: CS(=O)(=O)n1ccc(C(=O)NCC(=O)Nc2nc(-c3cccc(C4(O)CCOCC4)c3)cs2)c1] |
| 142 | 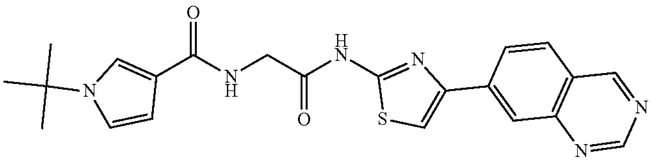 [SMILES: CC(C)(C)n1ccc(C(=O)NCC(=O)Nc2nc(-c3ccc4cncnc4c3)cs2)c1] |
| 143 | 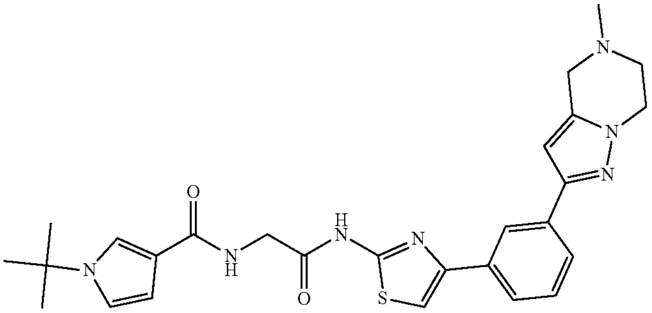 [SMILES: CN1CCn2nc(-c3cccc(-c4csc(NC(=O)CNC(=O)c5ccn(C(C)(C)C)c5)n4)c3)cc2C1] |
| 144 | 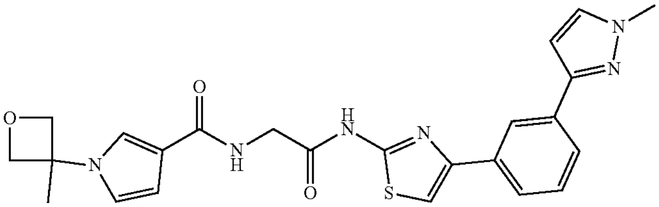 [SMILES: Cn1ccc(-c2cccc(-c3csc(NC(=O)CNC(=O)c4ccn(C5(C)COC5)c4)n3)c2)n1] |

TABLE 1-continued
| Compounds of the invention | |
|---|---|
| # | Compound |
| 145 | 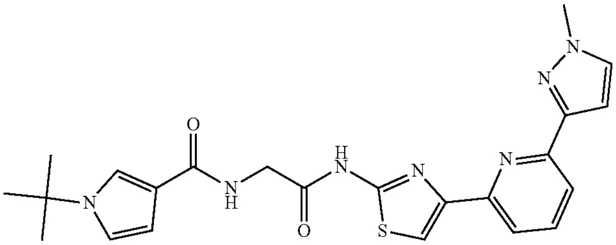 [SMILES: Cn1ccc(-c2cccc(-c3csc(NC(=O)CNC(=O)c4ccn(C(C)(C)C)c4)n3)n2)n1] |
| 146 | 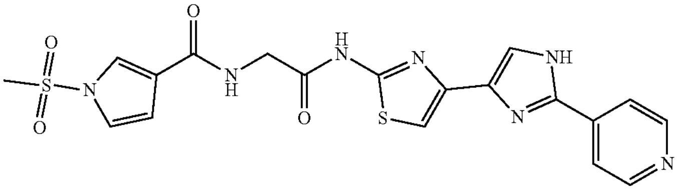 [SMILES: CS(=O)(=O)n1ccc(C(=O)NCC(=O)Nc2nc(-c3c[nH]c(-c4ccncc4)n3)cs2)c1] |
| 147 | 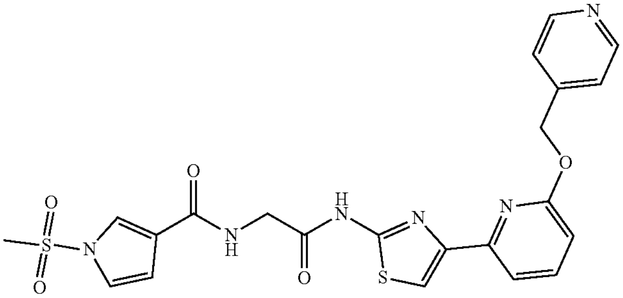 [SMILES: CS(=O)(=O)n1ccc(C(=O)NCC(=O)Nc2nc(-c3cccc(OCc4ccncc4)n3)cs2)c1] |
| 148 | 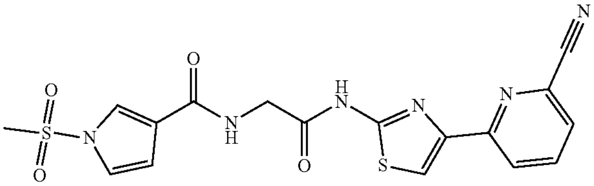 [SMILES: CS(=O)(=O)n1ccc(C(=O)NCC(=O)Nc2nc(-c3cccc(C#N)n3)cs2)c1] |
| 149 | 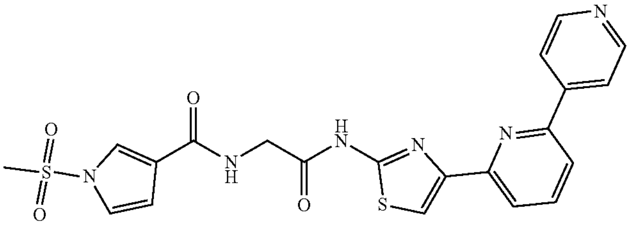 |
| 150 | 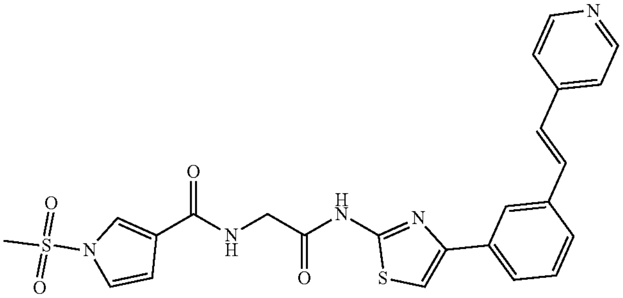 [SMILES: CS(=O)(=O)n1ccc(C(=O)NCC(=O)Nc2nc(-c3cccc(/C=C/c4ccncc4)c3)cs2)c1] |

TABLE 1-continued
| Compounds of the invention | |
|---|---|
| # | Compound |
| 151 | 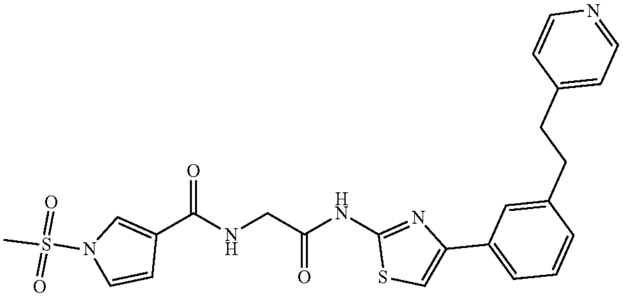 |
| 152 | 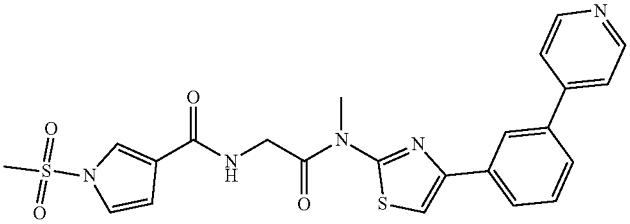 [SMILES: CN(C(=O)CNC(=O)c1ccn(S(C)(=O)=O)c1)c1nc(-c2cccc(-c3ccncc3)c2)cs1] |
| 153 | 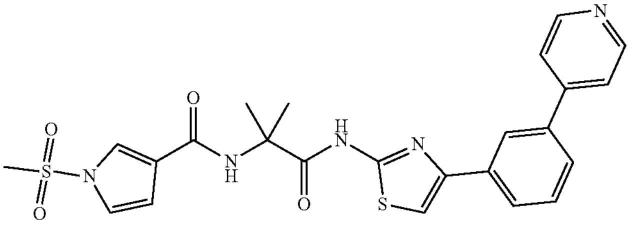 [SMILES: CC(C)(NC(=O)c1ccn(S(C)(=O)=O)c1)C(=O)Nc1nc(-c2cccc(-c3ccncc3)c2)cs1] |
| 154 | 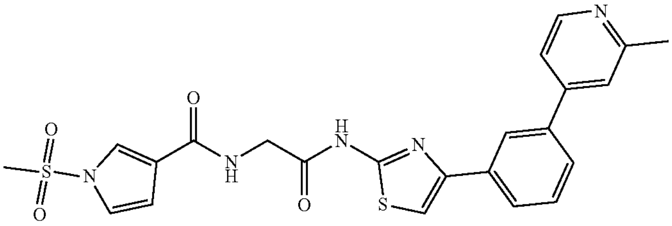 |
| 155 | 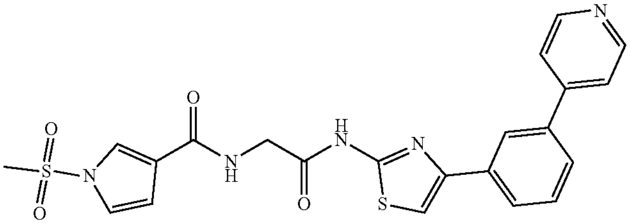 |
| 156 | 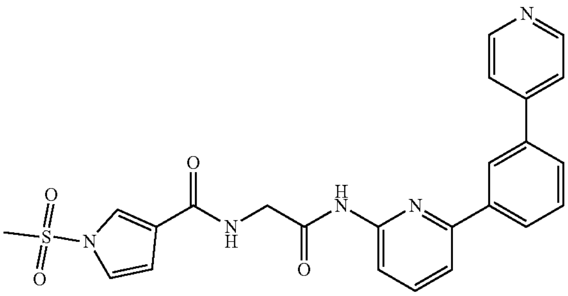 [SMILES: CS(=O)(=O)n1ccc(C(=O)NCC(=O)Nc2cccc(-c3cccc(-c4ccncc4)c3)n2)c1] |

TABLE 1-continued
| Compounds of the invention | |
|---|---|
| # | Compound |
| 157 | 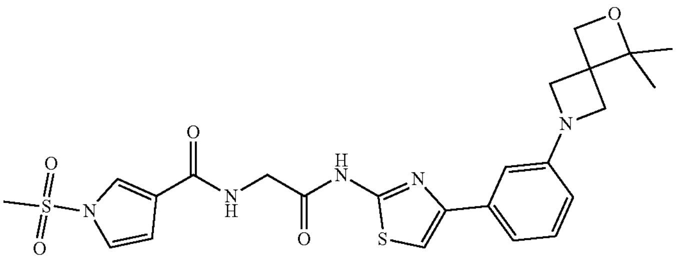 |
| 158 | 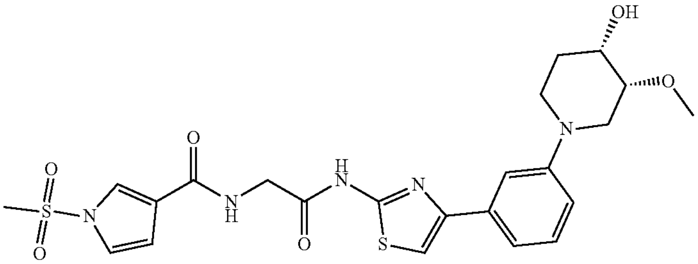 (±) |
| 159 | 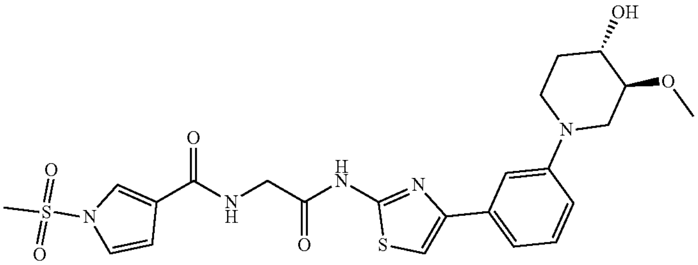 (±) |
| 160 | 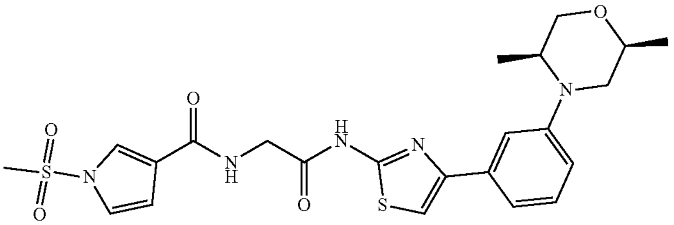 |
| 161 | 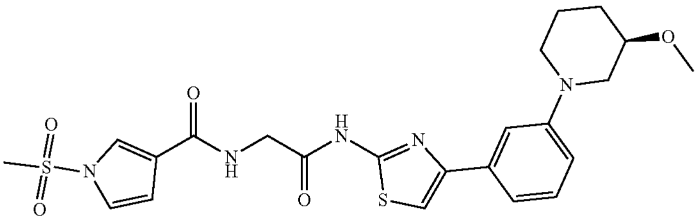 |

TABLE 1-continued
| Compounds of the invention | |
|---|---|
| # | Compound |
| 162 | 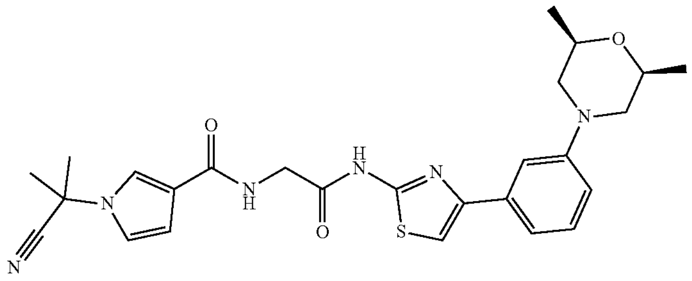 [SMILES: C[C@@H]1CN(c2cccc(-c3csc(NC(=O)CNC(=O)c4ccn(C(C)(C)C#N)c4)n3)c2)C[C@H](C)O1] |
| 163 | 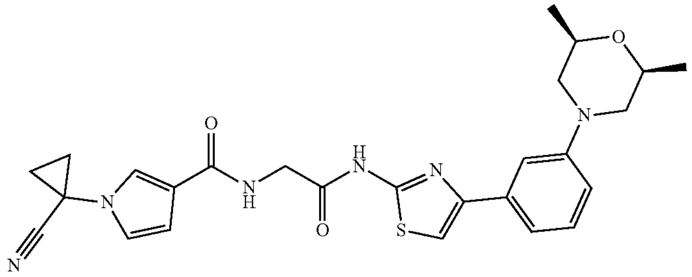 [SMILES: C[C@@H]1CN(c2cccc(-c3csc(NC(=O)CNC(=O)c4ccn(C5(C#N)CC5)c4)n3)c2)C[C@H](C)O1] |
| 164 | 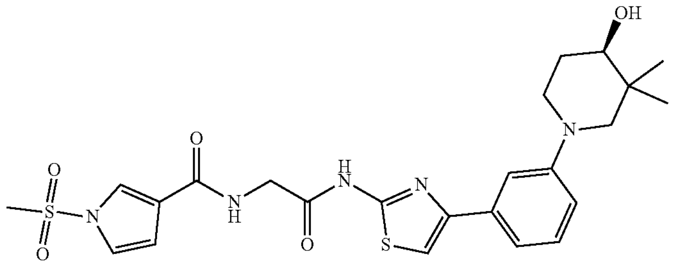 |
| 165 | 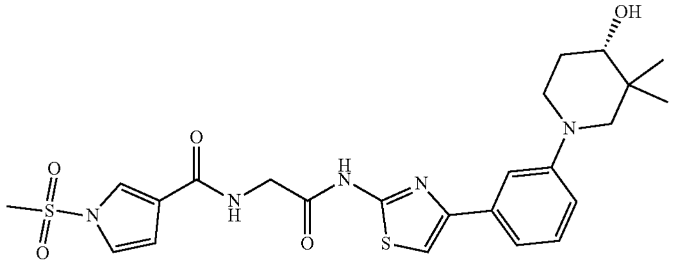 |
| 166 | 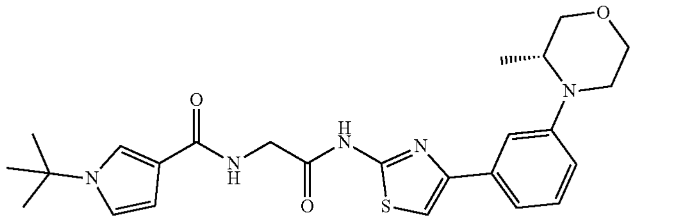 [SMILES: C[C@@H]1COCCN1c1cccc(-c2csc(NC(=O)CNC(=O)c3ccn(C(C)(C)C)c3)n2)c1] |
| 167 | 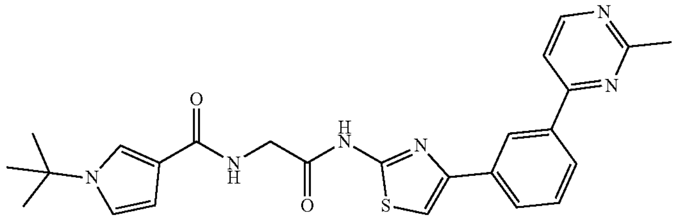 [SMILES: Cc1nccc(-c2cccc(-c3csc(NC(=O)CNC(=O)c4ccn(C(C)(C)C)c4)n3)c2)n1] |

TABLE 1-continued
| Compounds of the invention | |
|---|---|
| # | Compound |
| 168 | 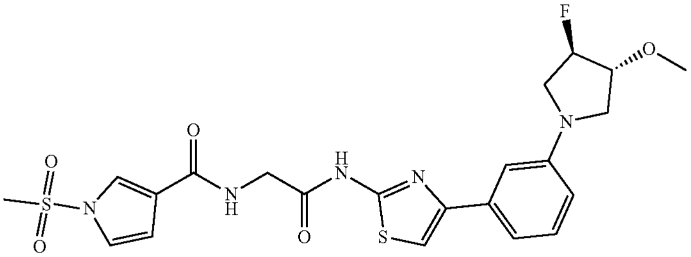 |
| 169 | 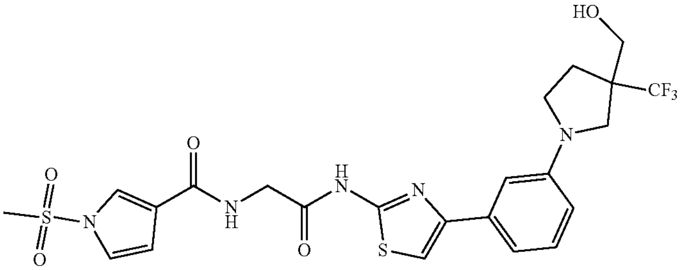 [SMILES: CS(=O)(=O)n1ccc(C(=O)NCC(=O)Nc2nc(-c3cccc(N4CCC(CO)(C(F)(F)F)C4)c3)cs2)c1] |
| 170 | 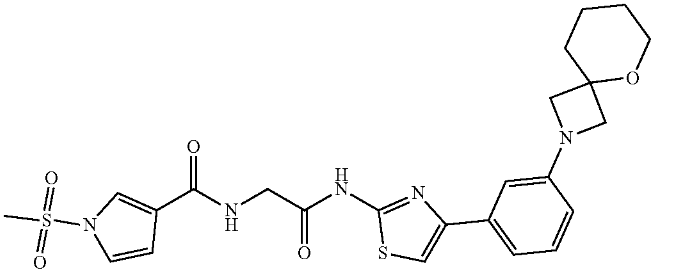 [SMILES: CS(=O)(=O)n1ccc(C(=O)NCC(=O)Nc2nc(-c3cccc(N4CC5(CCCCO5)C4)c3)cs2)c1] |
| 171 | 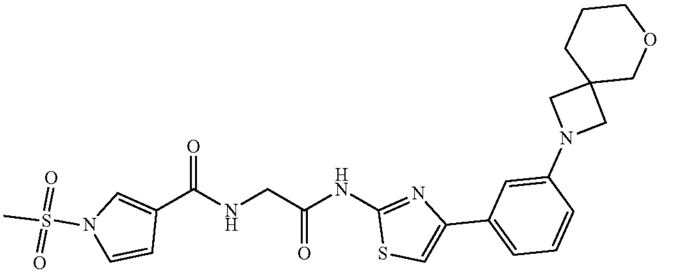 [SMILES: CS(=O)(=O)n1ccc(C(=O)NCC(=O)Nc2nc(-c3cccc(N4CC5(CCCOC5)C4)c3)cs2)c1] |
| 172 | 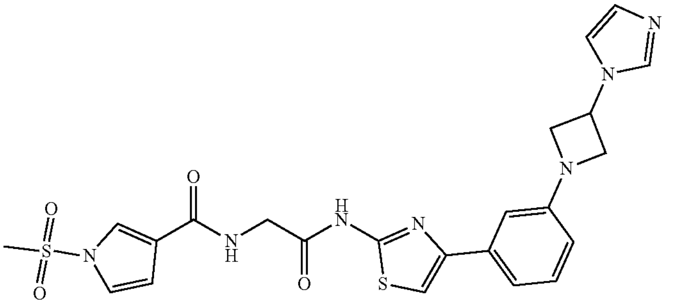 [SMILES: CS(=O)(=O)n1ccc(C(=O)NCC(=O)Nc2nc(-c3cccc(N4CC(n5ccnc5)C4)c3)cs2)c1] |

TABLE 1-continued
| Compounds of the invention | |
|---|---|
| # | Compound |
| 173 | 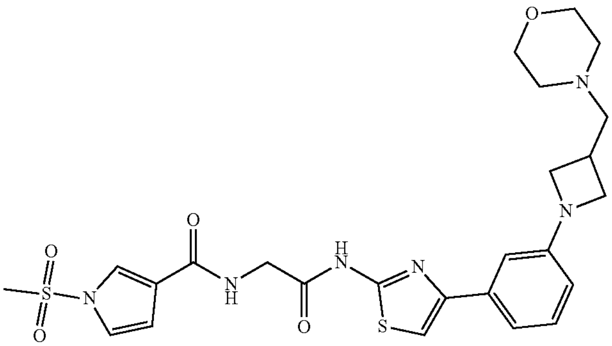 [SMILES: CS(=O)(=O)n1ccc(C(=O)NCC(=O)Nc2nc(-c3cccc(N4CC(CN5CCOCC5)C4)c3)cs2)c1] |
| 174 | 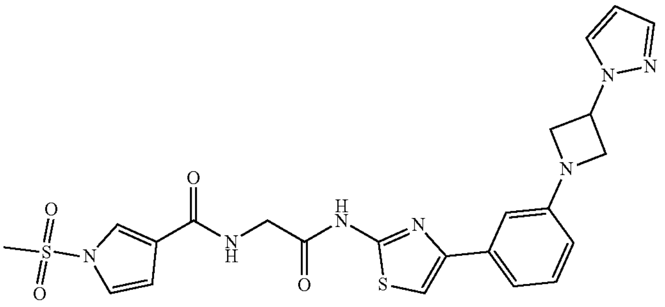 [SMILES: CS(=O)(=O)n1ccc(C(=O)NCC(=O)Nc2nc(-c3cccc(N4CC(n5cccn5)C4)c3)cs2)c1] |
| 175 | 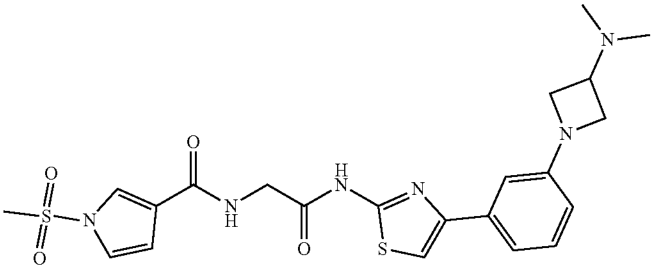 |
| 176 | 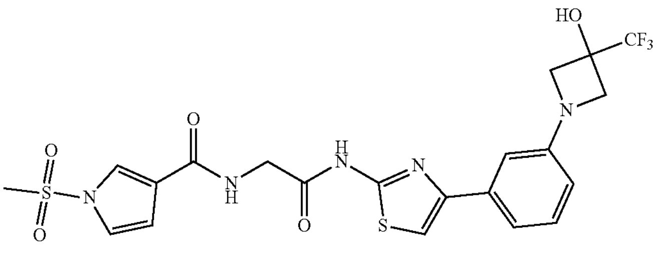 [SMILES: CS(=O)(=O)n1ccc(C(=O)NCC(=O)Nc2nc(-c3cccc(N4CC(O)(C(F)(F)F)C4)c3)cs2)c1] |
| 177 | 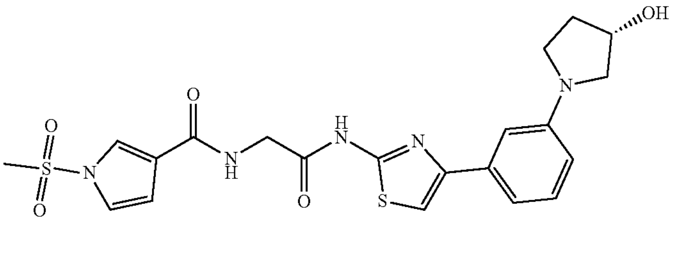 [SMILES: CS(=O)(=O)n1ccc(C(=O)NCC(=O)Nc2nc(-c3cccc(N4CC[C@H](O)C4)c3)cs2)c1] |

TABLE 1-continued
| Compounds of the invention | |
|---|---|
| # | Compound |
| 178 | 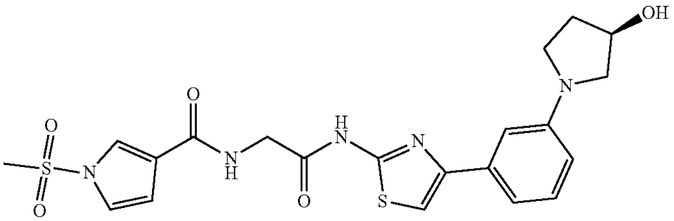 [SMILES: CS(=O)(=O)n1ccc(C(=O)NCC(=O)Nc2nc(-c3cccc(N4CC[C@@H](O)C4)c3)cs2)c1] |
| 179 | 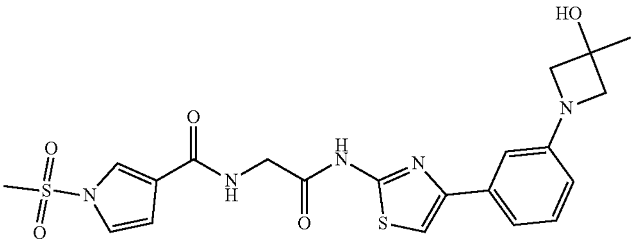 |
| 180 | 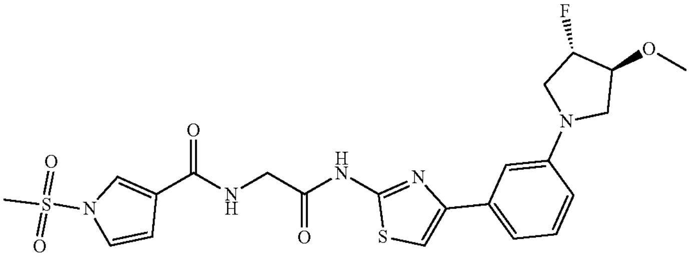 |
| 181 | 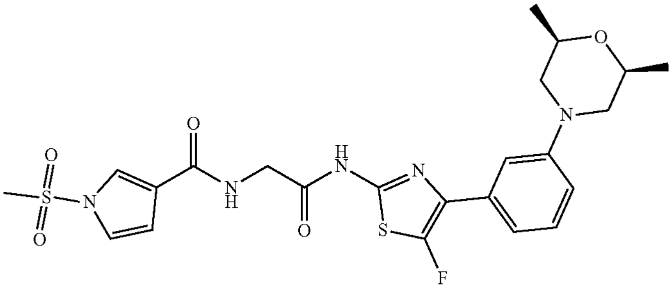 |
| 182 | 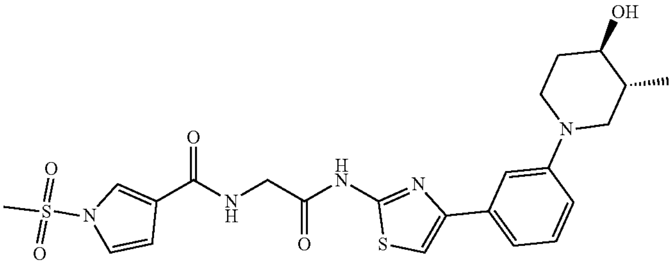 |

TABLE 1-continued
| Compounds of the invention | |
|---|---|
| # | Compound |
| 183 | 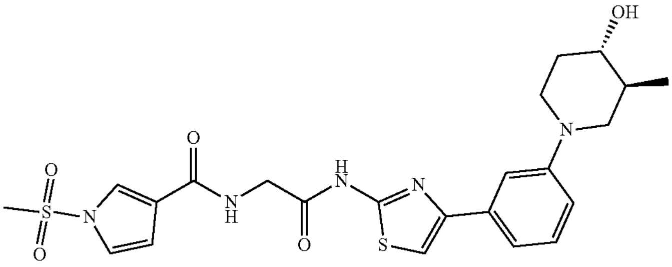 |
| 184 | 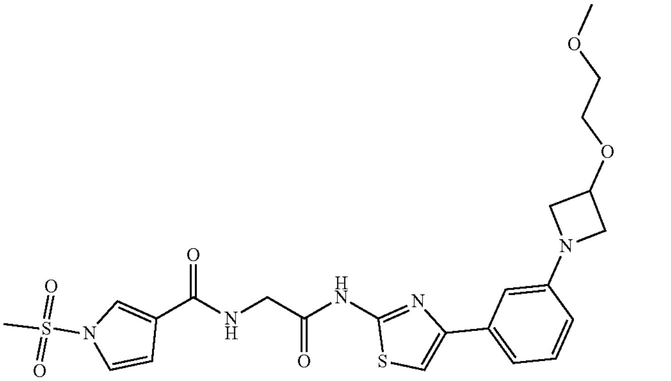 [SMILES: COCCOC1CN(c2cccc(-c3csc(NC(=O)CNC(=O)c4ccn(S(C)(=O)=O)c4)n3)c2)C1] |
| 185 | 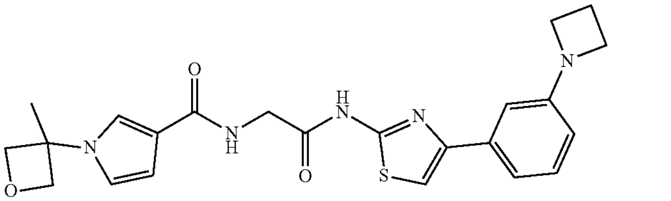 [SMILES: CC1(n2ccc(C(=O)NCC(=O)Nc3nc(-c4cccc(N5CCC5)c4)cs3)c2)COC1] |
| 186 | 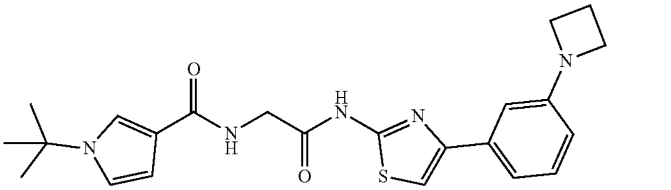 [SMILES: CC(C)(C)n1ccc(C(=O)NCC(=O)Nc2nc(-c3cccc(N4CCC4)c3)cs2)c1] |
| 187 | 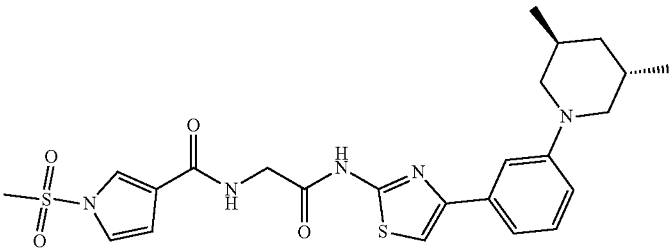 (±) |

TABLE 1-continued
| Compounds of the invention | |
|---|---|
| # | Compound |
| 188 | 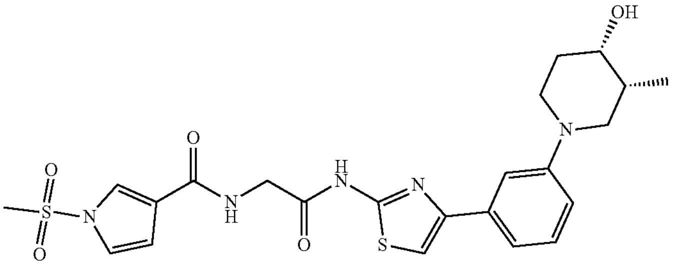 |
| 189 | 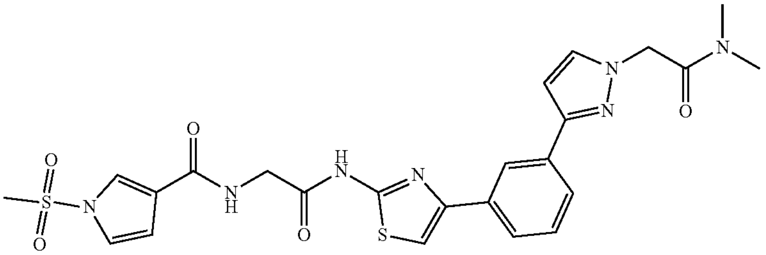 |
| 190 | 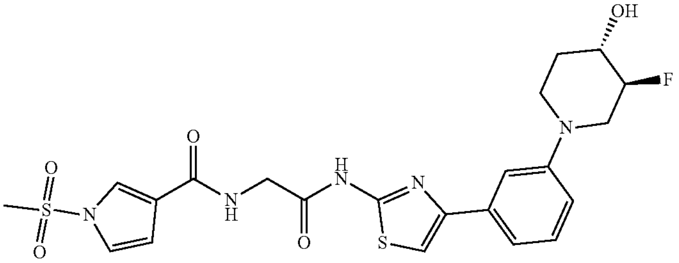 [SMILES: CS(=O)(=O)n1ccc(C(=O)NCC(=O)Nc2nc(-c3cccc(N4CC[C@H](O)[C@@H](F)C4)c3)cs2)c1] |
| 191 | 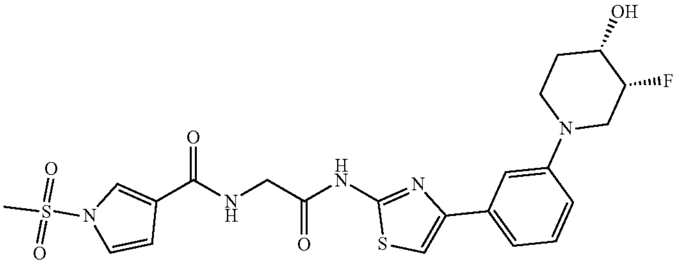 [SMILES: CS(=O)(=O)n1ccc(C(=O)NCC(=O)Nc2nc(-c3cccc(N4CC[C@H](O)[C@H](F)C4)c3)cs2)c1] |
| 192 | 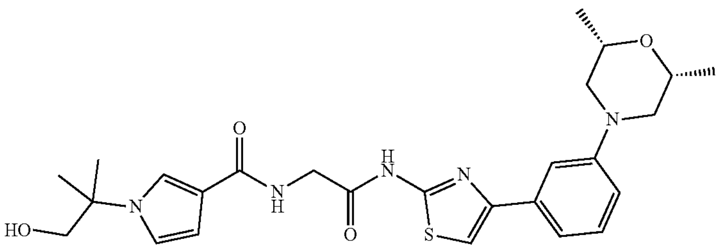 [SMILES: C[C@@H]1CN(c2cccc(-c3csc(NC(=O)CNC(=O)c4ccn(C(C)(C)CO)c4)n3)c2)C[C@H](C)O1] |

TABLE 1-continued
| Compounds of the invention | |
|---|---|
| # | Compound |
| 193 | 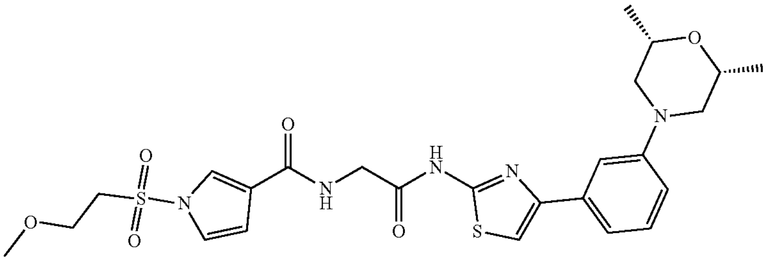 |
| 194 | 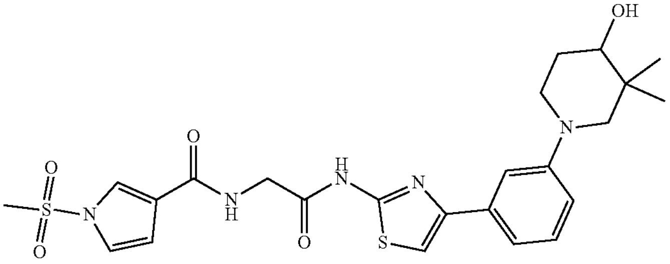 |
| 195 | 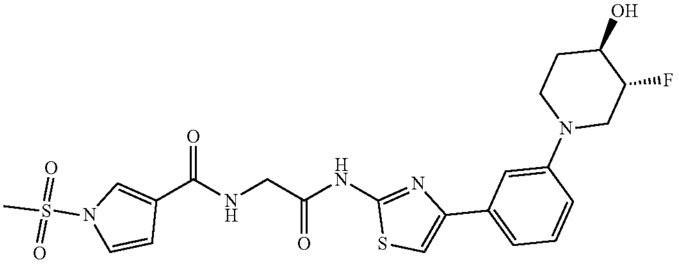 [SMILES: CS(=O)(=O)n1ccc(C(=O)NCC(=O)Nc2nc(-c3cccc(N4CC[C@@H](O)[C@H](F)C4)c3)cs2)c1] |
| 196 | 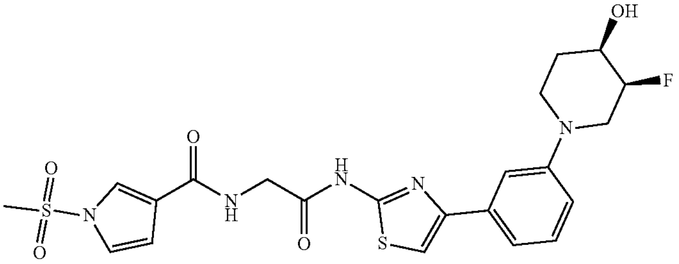 [SMILES: CS(=O)(=O)n1ccc(C(=O)NCC(=O)Nc2nc(-c3cccc(N4CC[C@@H](O)[C@@H](F)C4)c3)cs2)c1] |
| 197 | 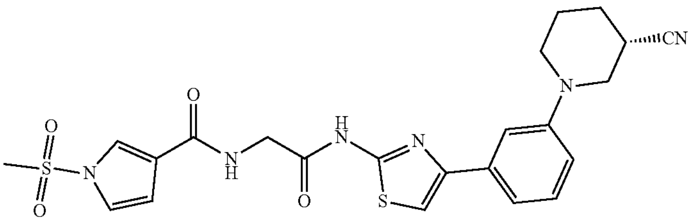 [SMILES: CS(=O)(=O)n1ccc(C(=O)NCC(=O)Nc2nc(-c3cccc(N4CCC[C@H](C#N)C4)c3)cs2)c1] |

TABLE 1-continued
Compounds of the invention
| # | Compound |
|---|---|
| 198 | 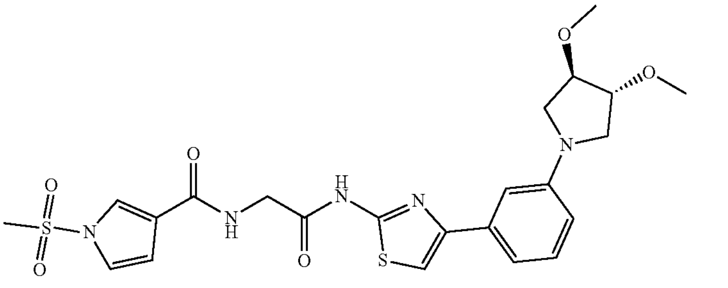 (±) |
| 199 | 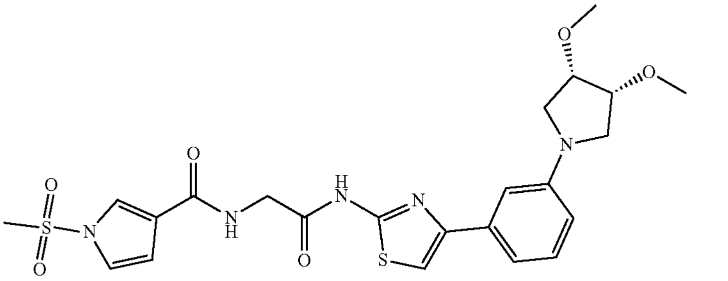 |
| 200 | 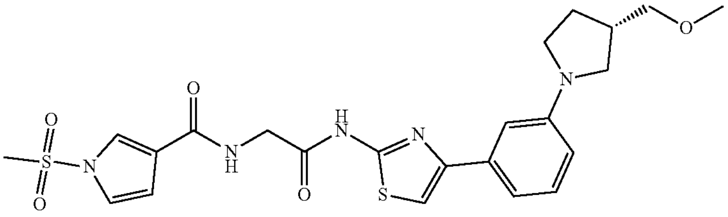 |
| 201 | 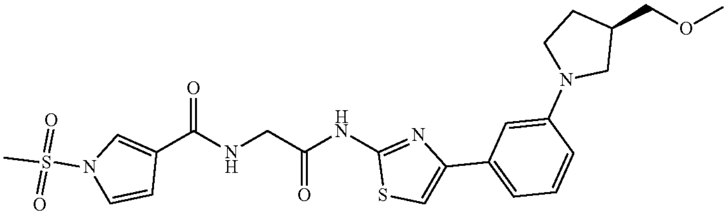 |
| 202 | 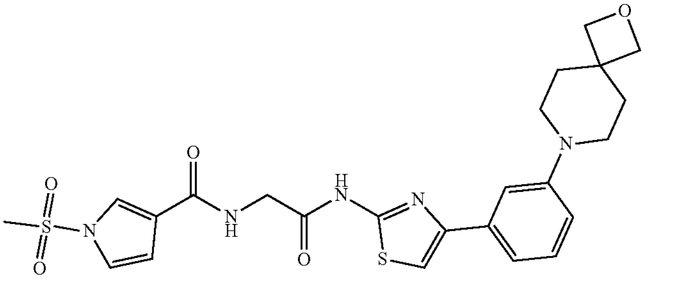 [SMILES: CS(=O)(=O)n1ccc(C(=O)NCC(=O)Nc2nc(-c3cccc(N4CCC5(CC4)COC5)c3)cs2)c1] |

TABLE 1-continued
| Compounds of the invention | |
|---|---|
| # | Compound |
| 203 | 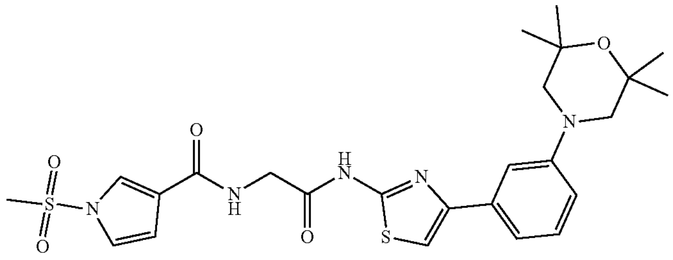 |
| 204 | 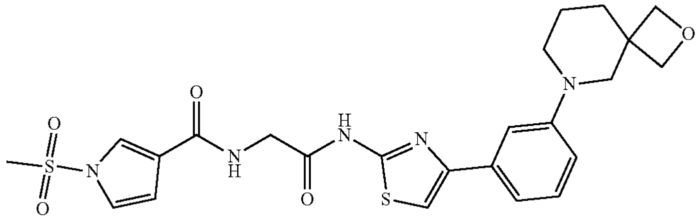 [SMILES: CS(=O)(=O)n1ccc(C(=O)NCC(=O)Nc2nc(-c3cccc(N4CCCC5(COC5)C4)c3)cs2)c1] |
| 205 | 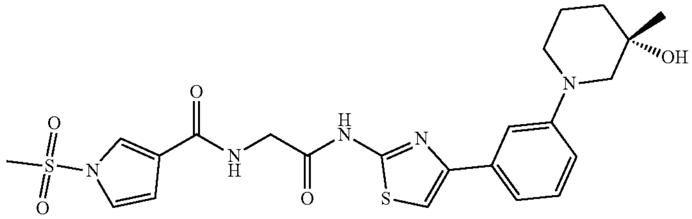 [SMILES: C[C@]1(O)CCCN(c2cccc(-c3csc(NC(=O)CNC(=O)c4ccn(S(C)(=O)=O)c4)n3)c2)C1] |
| 206 | 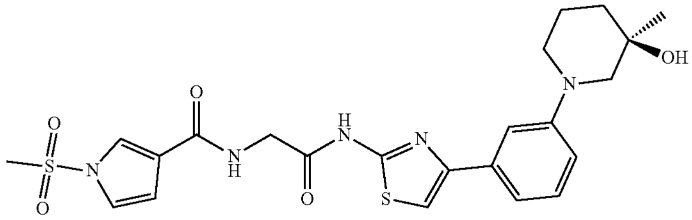 [SMILES: C[C@@]1(O)CCCN(c2cccc(-c3csc(NC(=O)CNC(=O)c4ccn(S(C)(=O)=O)c4)n3)c2)C1] |
| 207 | 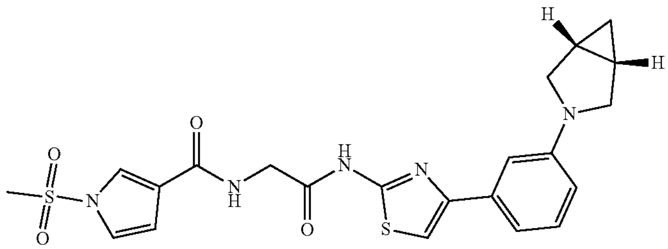 [SMILES: CS(=O)(=O)n1ccc(C(=O)NCC(=O)Nc2nc(-c3cccc(N4C[C@H]5C[C@H]5C4)c3)cs2)c1] |
| 208 | 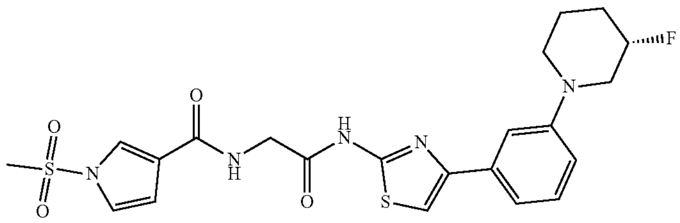 [SMILES: CS(=O)(=O)n1ccc(C(=O)NCC(=O)Nc2nc(-c3cccc(N4CCC[C@H](F)C4)c3)cs2)c1] |

TABLE 1-continued
Compounds of the invention
| # | Compound |
|---|---|
| 209 | 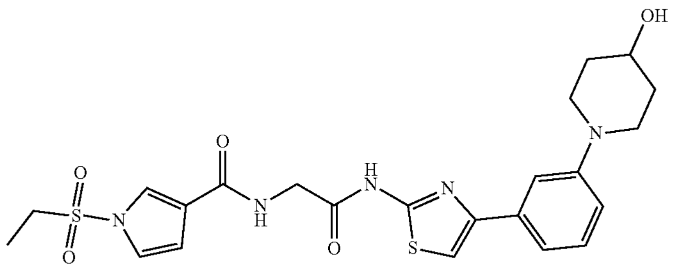 [SMILES: CCS(=O)(=O)n1ccc(C(=O)NCC(=O)Nc2nc(-c3cccc(N4CCC(O)CC4)c3)cs2)c1] |
| 210 | 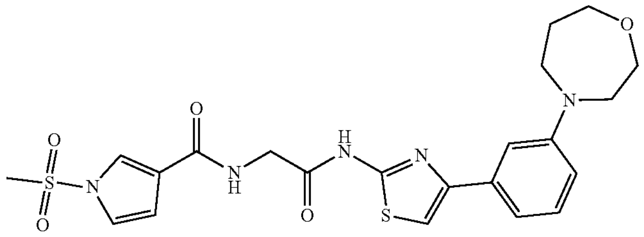 [SMILES: CS(=O)(=O)n1ccc(C(=O)NCC(=O)Nc2nc(-c3cccc(N4CCCOCC4)c3)cs2)c1] |
| 211 | 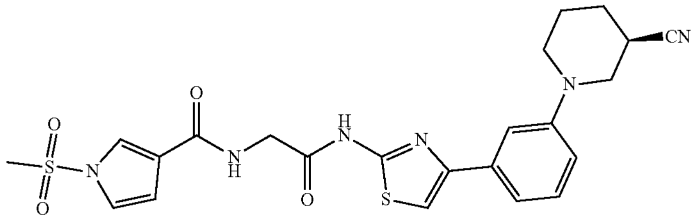 |
| 212 | 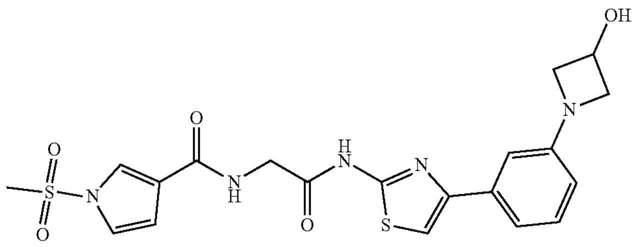 [SMILES: CS(=O)(=O)n1ccc(C(=O)NCC(=O)Nc2nc(-c3cccc(N4CC(O)C4)c3)cs2)c1] |
| 213 | 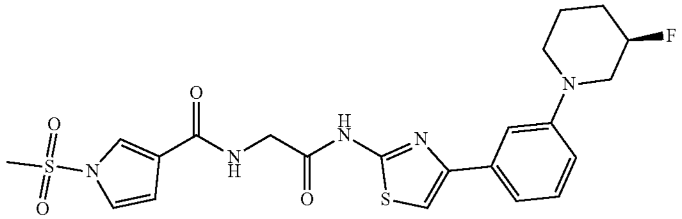 [SMILES: CS(=O)(=O)n1ccc(C(=O)NCC(=O)Nc2nc(-c3cccc(N4CCC[C@@H](F)C4)c3)cs2)c1] |
| 214 | 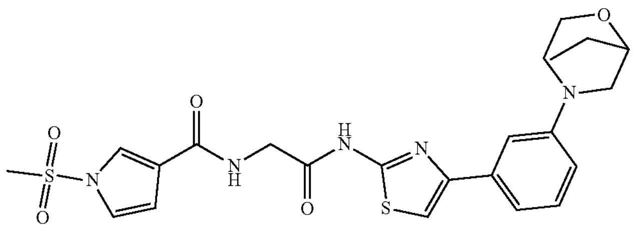 |

TABLE 1-continued
| # | Compound |
|---|---|
| 215 | 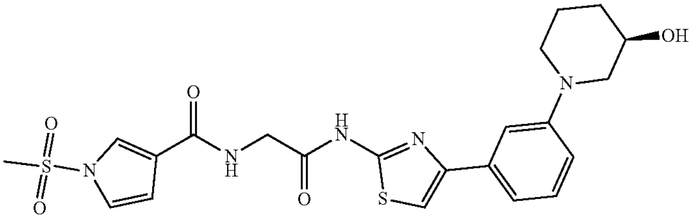 |
| 216 | 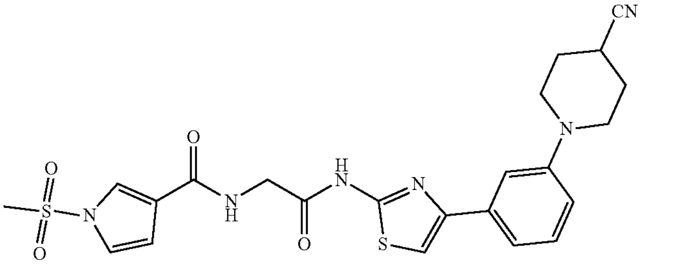 [SMILES: CS(=O)(=O)n1ccc(C(=O)NCC(=O)Nc2nc(-c3cccc(N4CCC(C#N)CC4)c3)cs2)c1] |
| 217 | 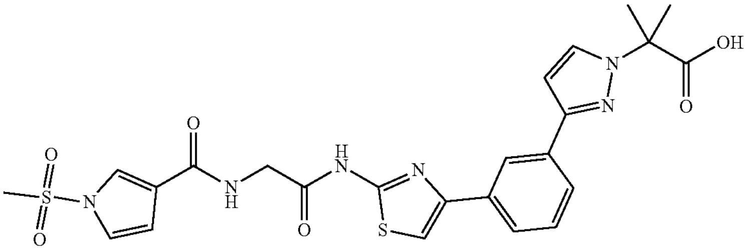 [SMILES: CC(C)(C(=O)O)n1ccc(-c2cccc(-c3csc(NC(=O)CNC(=O)c4ccn(S(C)(=O)=O)c4)n3)c2)n1] |
| 218 | 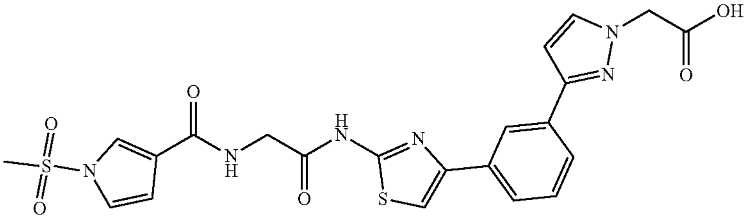 [SMILES: CS(=O)(=O)n1ccc(C(=O)NCC(=O)Nc2nc(-c3cccc(-c4ccn(CC(=O)O)n4)c3)cs2)c1] |
| 219 | 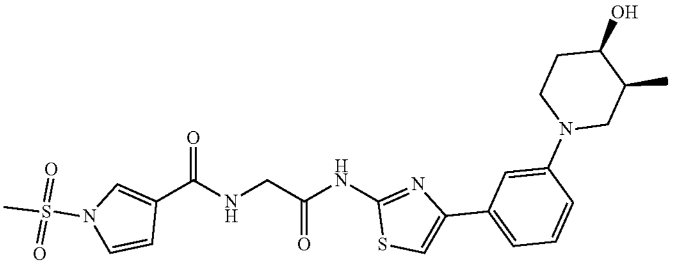 |
| 220 | 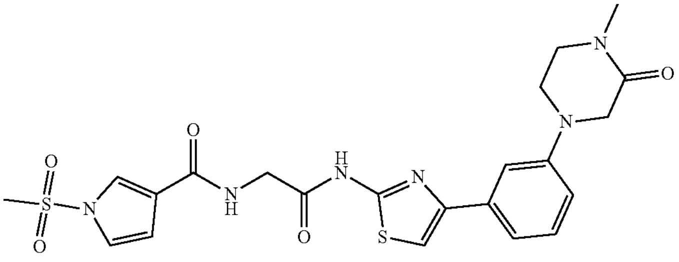 [SMILES: CN1CCN(c2cccc(-c3csc(NC(=O)CNC(=O)c4ccn(S(C)(=O)=O)c4)n3)c2)CC1=O] |
Compounds of the invention TABLE 1-continued
| Compounds of the invention | |
|---|---|
| # | Compound |
| 221 | 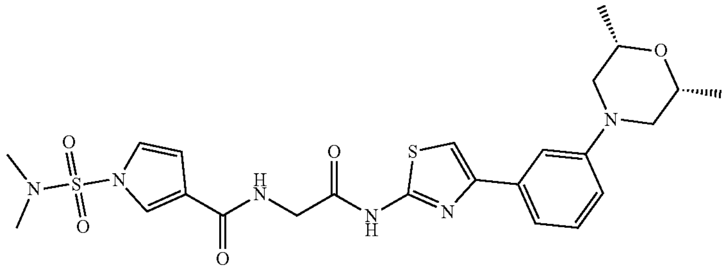 |
| 222 | 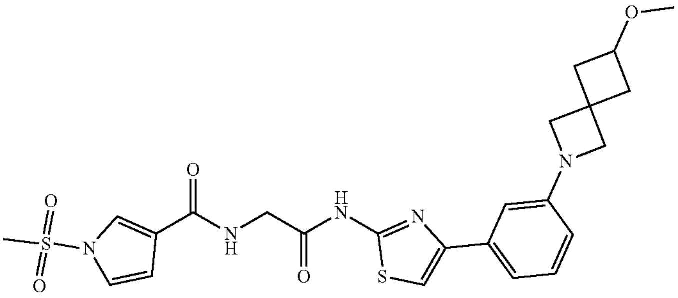 |
| 223 | 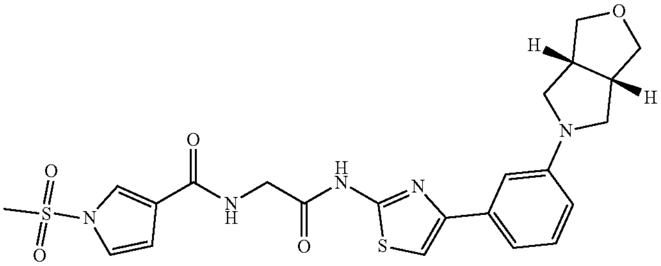 [SMILES: CS(=O)(=O)n1ccc(C(=O)NCC(=O)Nc2nc(-c3cccc(N4C[C@H]5COC[C@H]5C4)c3)cs2)c1] |
| 224 | 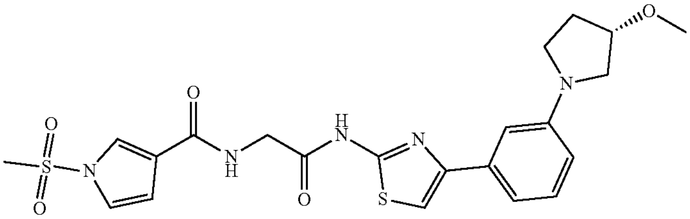 |
| 225 | 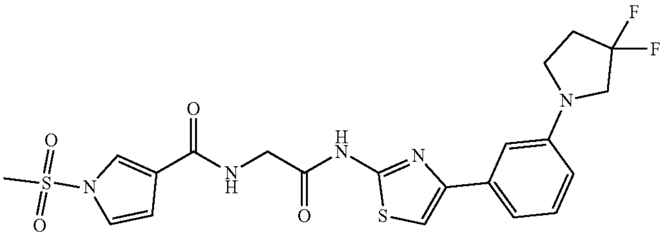 [SMILES: CS(=O)(=O)n1ccc(C(=O)NCC(=O)Nc2nc(-c3cccc(N4CCC(F)(F)C4)c3)cs2)c1] |
| 226 | 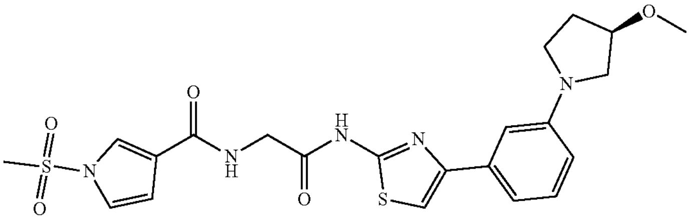 |

TABLE 1-continued
| Compounds of the invention | |
|---|---|
| # | Compound |
| 227 | 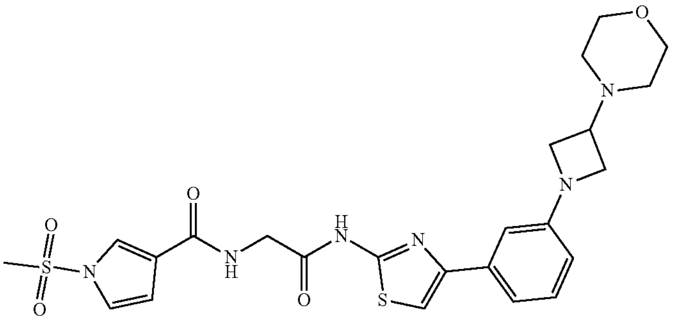 [SMILES: CS(=O)(=O)n1ccc(C(=O)NCC(=O)Nc2nc(-c3cccc(N4CC(N5CCOCC5)C4)c3)cs2)c1] |
| 228 | 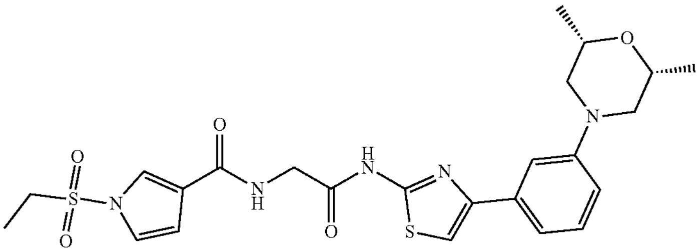 [SMILES: CCS(=O)(=O)n1ccc(C(=O)NCC(=O)Nc2nc(-c3cccc(N4C[C@@H](C)O[C@@H](C)C4)c3)cs2)c1] |
| 229 | 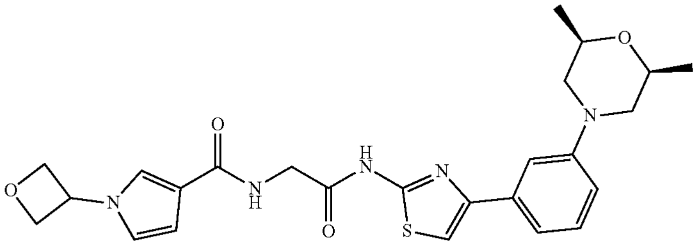 [SMILES: C[C@@H]1CN(c2cccc(-c3csc(NC(=O)CNC(=O)c4ccn(C5COC5)c4)n3)c2)C[C@H](C)O1] |
| 230 | 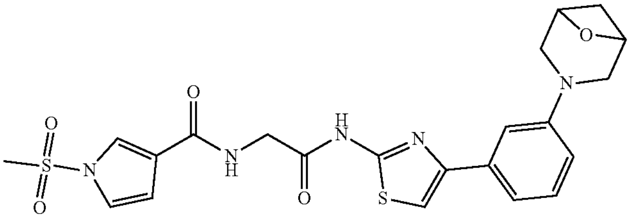 [SMILES: CS(=O)(=O)n1ccc(C(=O)NCC(=O)Nc2nc(-c3cccc(N4CC5CC(C4)O5)c3)cs2)c1] |
| 231 | 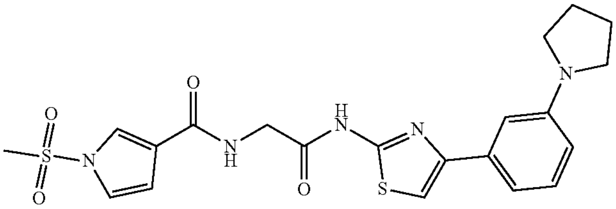 [SMILES: CS(=O)(=O)n1ccc(C(=O)NCC(=O)Nc2nc(-c3cccc(N4CCCC4)c3)cs2)c1] |
| 232 | 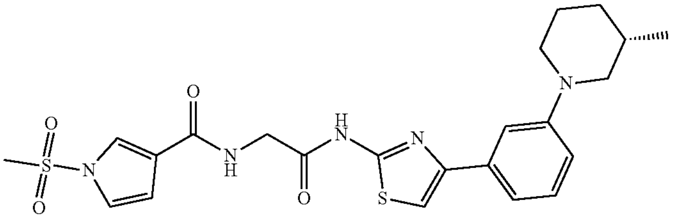 |

TABLE 1-continued
| Compounds of the invention | |
|---|---|
| # | Compound |
| 233 | 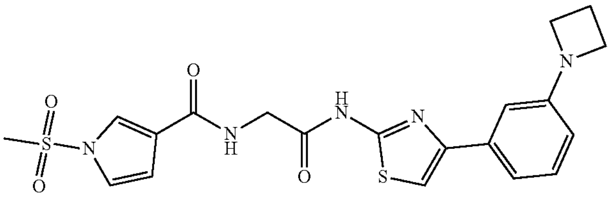 [SMILES: CS(=O)(=O)n1ccc(C(=O)NCC(=O)Nc2nc(-c3cccc(N4CCC4)c3)cs2)c1] |
| 234 | 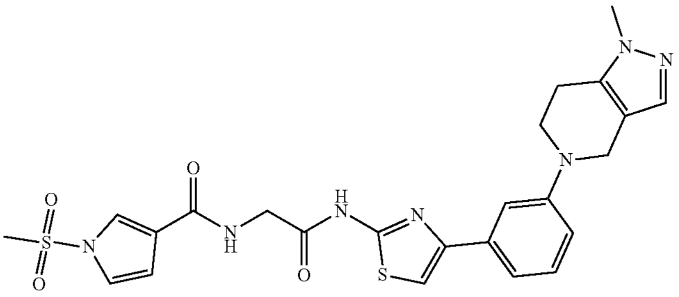 [SMILES: Cn1ncc2c1CCN(c1cccc(-c3csc(NC(=O)CNC(=O)c4ccn(S(C)(=O)=O)c4)n3)c1)C2] |
| 235 | 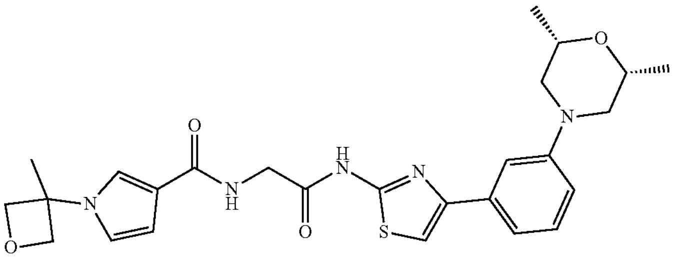 [SMILES: C[C@@H]1CN(c2cccc(-c3csc(NC(=O)CNC(=O)c4ccn(C5(C)COC5)c4)n3)c2)C[C@H](C)O1] |
| 236 | 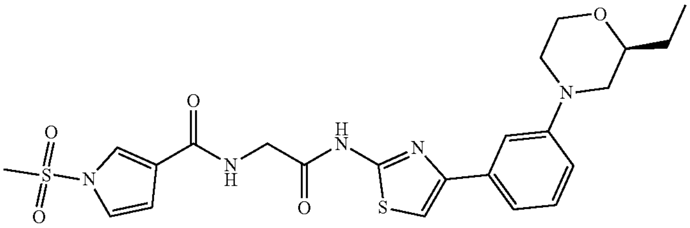 [SMILES: CC[C@H]1CN(c2cccc(-c3csc(NC(=O)CNC(=O)c4ccn(S(C)(=O)=O)c4)n3)c2)CCO1] |
| 237 | 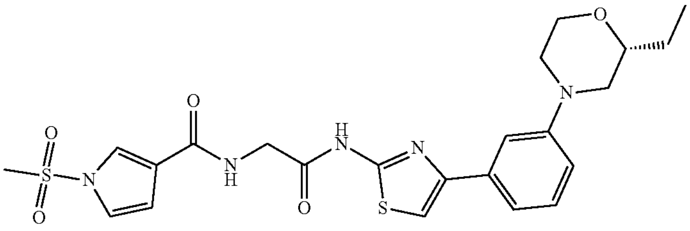 [SMILES: CC[C@@H]1CN(c2cccc(-c3csc(NC(=O)CNC(=O)c4ccn(S(C)(=O)=O)c4)n3)c2)CCO1] |
| 238 | 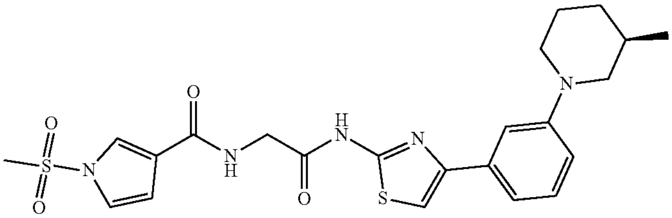 |

TABLE 1-continued
| Compounds of the invention | |
|---|---|
| # | Compound |
| 239 | 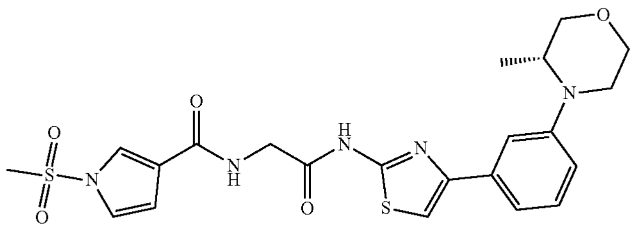 [SMILES: C[C@@H]1COCCN1c1cccc(-c2csc(NC(=O)CNC(=O)c3ccn(S(C)(=O)=O)c3)n2)c1] |
| 240 | 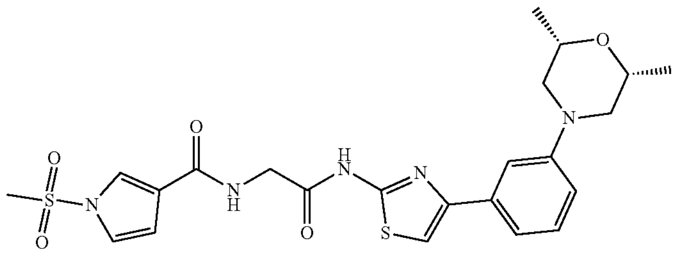 |
| 241 | 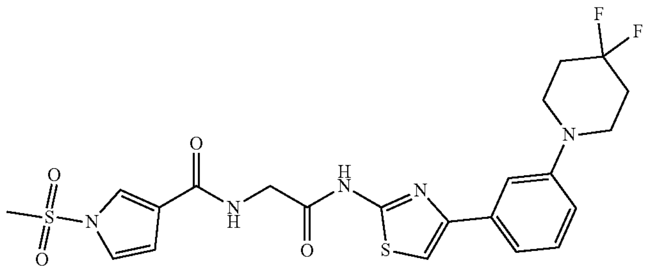 [SMILES: CS(=O)(=O)n1ccc(C(=O)NCC(=O)Nc2nc(-c3cccc(N4CCC(F)(F)CC4)c3)cs2)c1] |
| 242 | 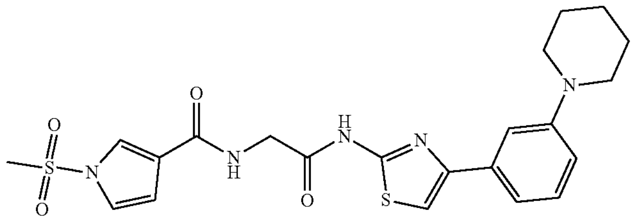 [SMILES: CS(=O)(=O)n1ccc(C(=O)NCC(=O)Nc2nc(-c3cccc(N4CCCCC4)c3)cs2)c1] |
| 243 | 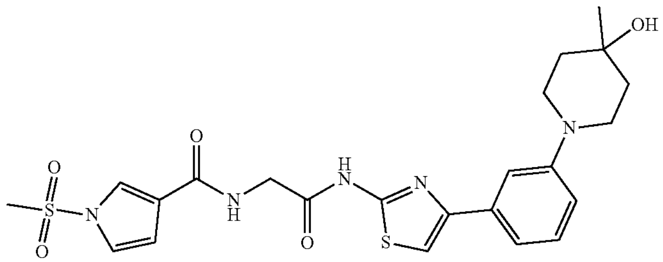 [SMILES: CC1(O)CCN(c2cccc(-c3csc(NC(=O)CNC(=O)c4ccn(S(C)(=O)=O)c4)n3)c2)CC1] |
| 244 | 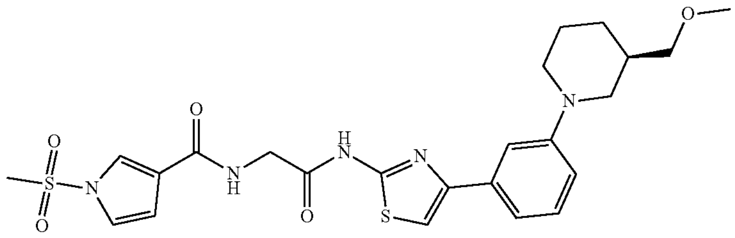 |

TABLE 1-continued
| Compounds of the invention | |
|---|---|
| # | Compound |
| 245 | 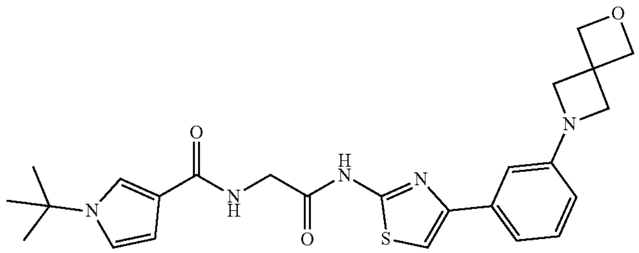 [SMILES: CC(C)(C)n1ccc(C(=O)NCC(=O)Nc2nc(-c3cccc(N4CC5(COC5)C4)c3)cs2)c1] |
| 246 | 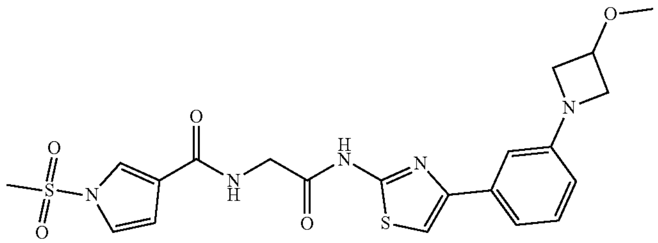 |
| 247 | 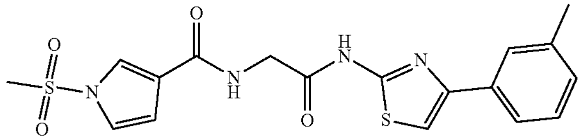 [SMILES: Cc1cccc(-c2csc(NC(=O)CNC(=O)c3ccn(S(C)(=O)=O)c3)n2)c1] |
| 248 | 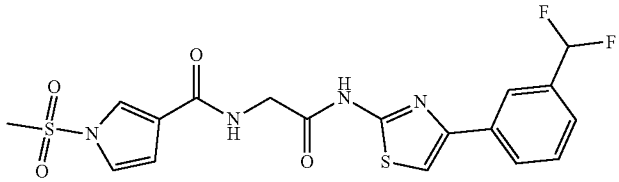 [SMILES: CS(=O)(=O)n1ccc(C(=O)NCC(=O)Nc2nc(-c3cccc(C(F)F)c3)cs2)c1] |
| 249 | 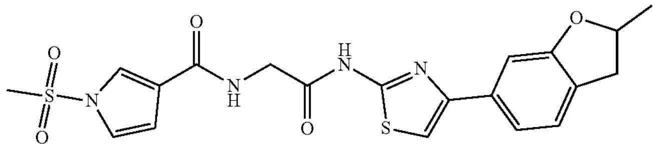 (±) |
| 250 | 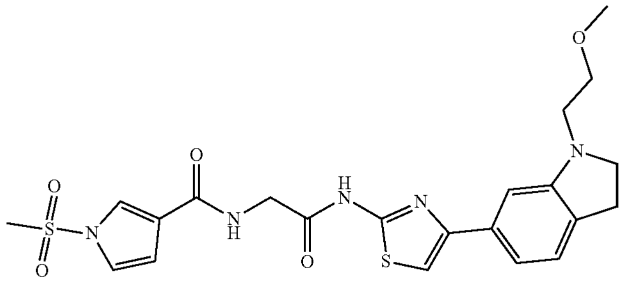 [SMILES: COCCN1CCc2ccc(-c3csc(NC(=O)CNC(=O)c4ccn(S(C)(=O)=O)c4)n3)cc21] |

TABLE 1-continued
| Compounds of the invention | |
|---|---|
| # | Compound |
| 251 | 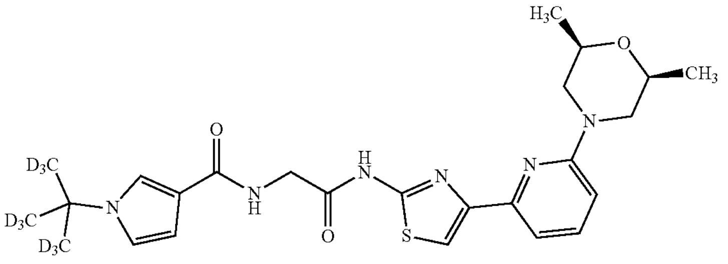 [SMILES: [2H]C([2H])([2H])C(n1ccc(C(=O)NCC(=O)Nc2nc(-c3cccc(N4C[C@@H](C)O[C@@H](C)C4)n3)cs2)c1)(C([2H])([2H])[2H])C([2H])([2H])[2H]] |
| 252 | 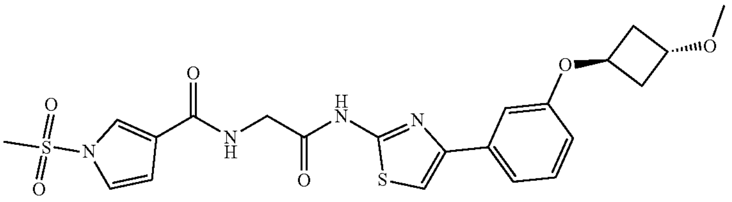 |
| 253 | 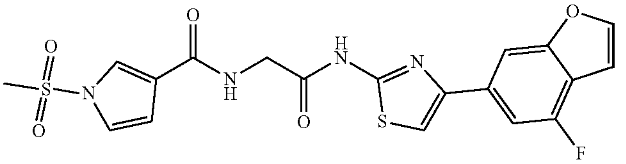 [SMILES: CS(=O)(=O)n1ccc(C(=O)NCC(=O)Nc2nc(-c3cc(F)c4ccoc4c3)cs2)c1] |
| 254 | 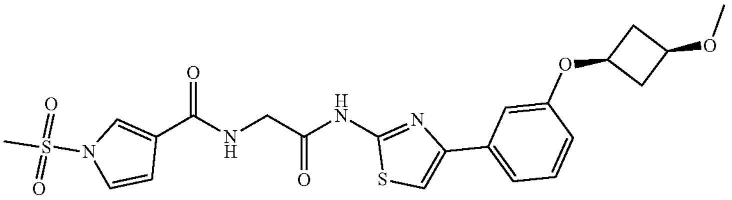 |
| 255 | 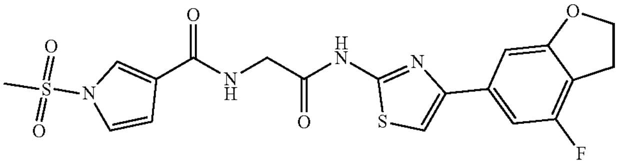 [SMILES: CS(=O)(=O)n1ccc(C(=O)NCC(=O)Nc2nc(-c3cc(F)c4c(c3)OCC4)cs2)c1] |
| 256 | 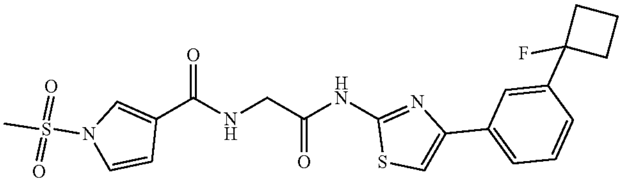 [SMILES: CS(=O)(=O)n1ccc(C(=O)NCC(=O)Nc2nc(-c3cccc(C4(F)CCC4)c3)cs2)c1] |
| 257 | 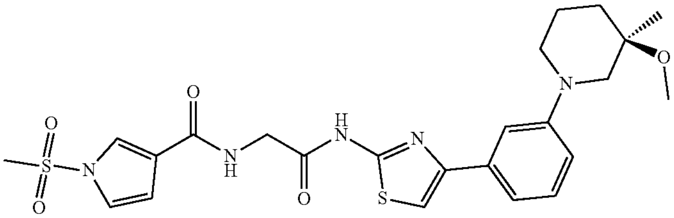 |

TABLE 1-continued
| Compounds of the invention | |
|---|---|
| # | Compound |
| 258 | 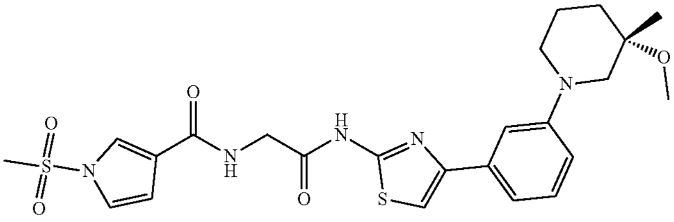 |
| 259 | 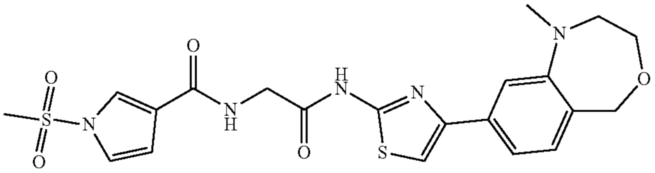 [SMILES: CN1CCOCc2ccc(-c3csc(NC(=O)CNC(=O)c4ccn(S(C)(=O)=O)c4)n3)cc21] |
| 260 | 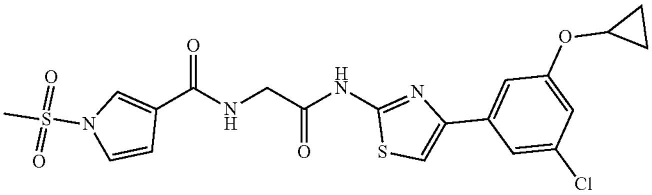 |
| 261 | 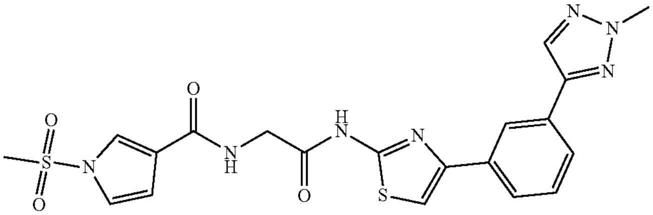 |
| 262 | 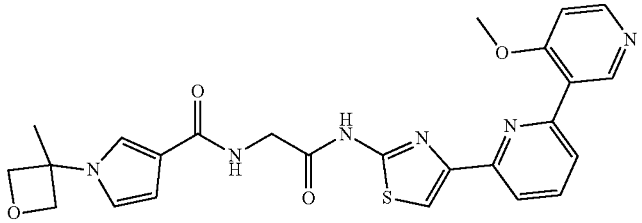 [SMILES: COc1ccncc1-c1cccc(-c2csc(NC(=O)CNC(=O)c3ccn(C4(C)COC4)c3)n2)n1] |
| 263 | 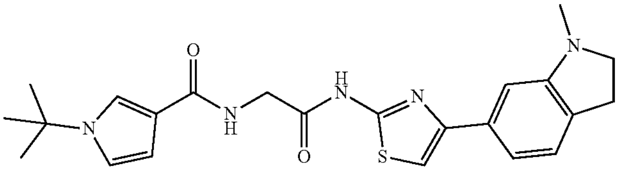 [SMILES: CN1CCc2ccc(-c3csc(NC(=O)CNC(=O)c4ccn(C(C)(C)C)c4)n3)cc21] |
| 264 | 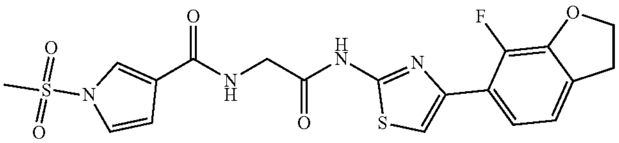 [SMILES: CS(=O)(=O)n1ccc(C(=O)NCC(=O)Nc2nc(-c3ccc4c(c3F)OCC4)cs2)c1] |

TABLE 1-continued
| Compounds of the invention | |
|---|---|
| # | Compound |
| 265 | 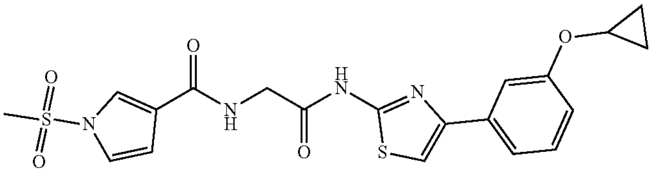 [SMILES: CS(=O)(=O)n1ccc(C(=O)NCC(=O)Nc2nc(-c3cccc(OC4CC4)c3)cs2)c1] |
| 266 | 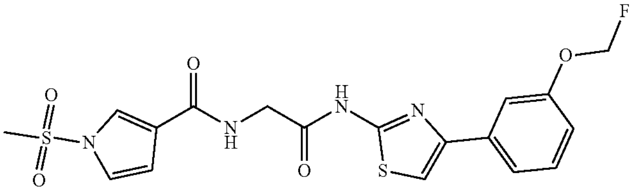 [SMILES: CS(=O)(=O)n1ccc(C(=O)NCC(=O)Nc2nc(-c3cccc(OCF)c3)cs2)c1] |
| 267 | 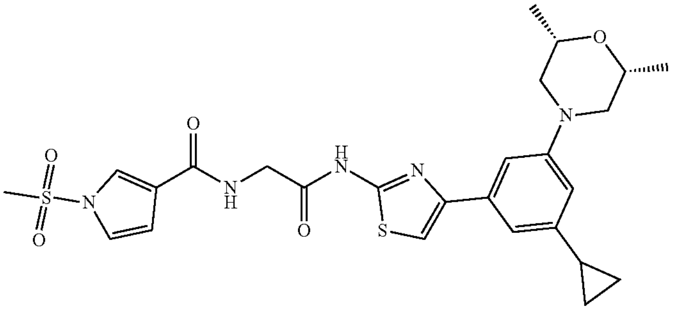 |
| 268 | 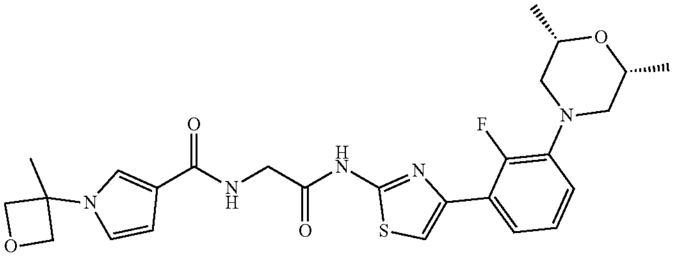 [SMILES: C[C@@H]1CN(c2cccc(-c3csc(NC(=O)CNC(=O)c4ccn(C5(C)COC5)c4)n3)c2F)C[C@H](C)O1] |
| 269 | 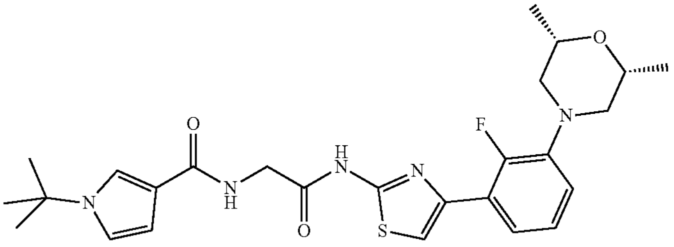 [SMILES: C[C@@H]1CN(c2cccc(-c3csc(NC(=O)CNC(=O)c4ccn(C(C)(C)C)c4)n3)c2F)C[C@H](C)O1] |
| 270 | 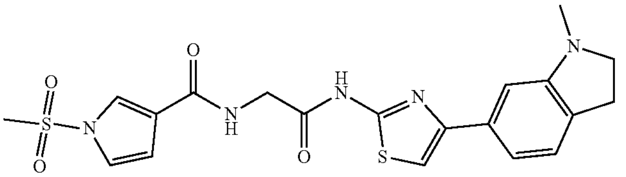 [SMILES: CN1CCc2ccc(-c3csc(NC(=O)CNC(=O)c4ccn(S(C)(=O)=O)c4)n3)cc21] |
| 271 | 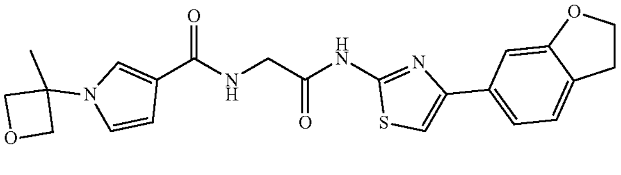 [SMILES: CC1(n2ccc(C(=O)NCC(=O)Nc3nc(-c4ccc5c(c4)OCC5)cs3)c2)COC1] |

TABLE 1-continued
| Compounds of the invention | |
| --- | --- |
| # | Compound |
| 272 | 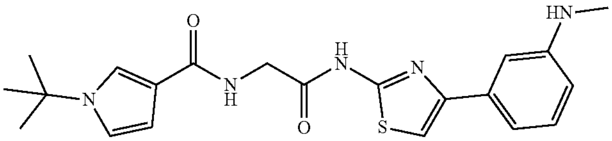 [SMILES: CNc1cccc(-c2csc(NC(=O)CNC(=O)c3ccn(C(C)(C)C)c3)n2)c1] |
| 273 | 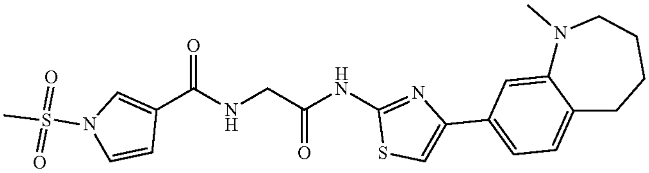 [SMILES: CN1CCCCc2ccc(-c3csc(NC(=O)CNC(=O)c4ccn(S(C)(=O)=O)c4)n3)cc21] |
| 274 | 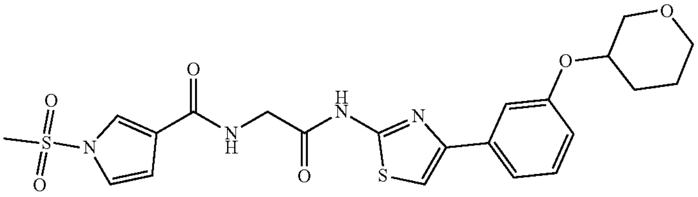 (±) |
| 275 | 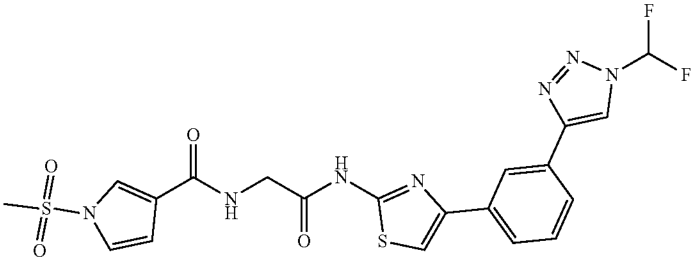 [SMILES: CS(=O)(=O)n1ccc(C(=O)NCC(=O)Nc2nc(-c3cccc(-c4cn(C(F)F)nn4)c3)cs2)c1] |
| 276 | 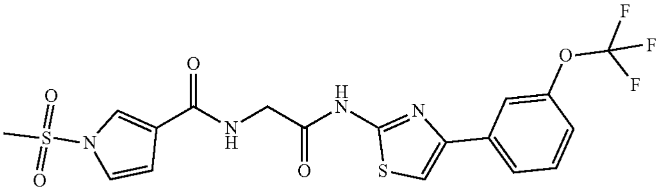 [SMILES: CS(=O)(=O)n1ccc(C(=O)NCC(=O)Nc2nc(-c3cccc(OC(F)(F)F)c3)cs2)c1] |
| 277 | 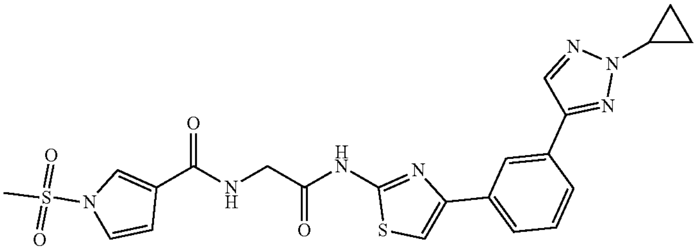 [SMILES: CS(=O)(=O)n1ccc(C(=O)NCC(=O)Nc2nc(-c3cccc(-c4cnn(C5CC5)n4)c3)cs2)c1] |
| 278 | 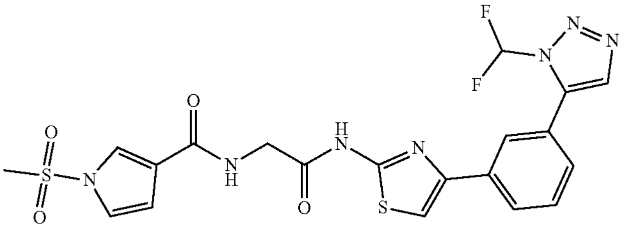 [SMILES: CS(=O)(=O)n1ccc(C(=O)NCC(=O)Nc2nc(-c3cccc(-c4cnnn4C(F)F)c3)cs2)c1] |

TABLE 1-continued
| Compounds of the invention | |
|---|---|
| # | Compound |
| 279 | 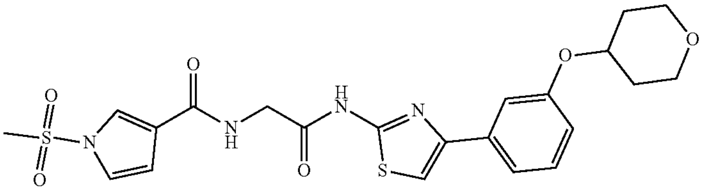 [SMILES: CS(=O)(=O)n1ccc(C(=O)NCC(=O)Nc2nc(-c3cccc(OC4CCOCC4)c3)cs2)c1] |
| 280 | 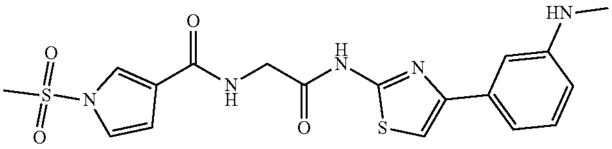 |
| 281 | 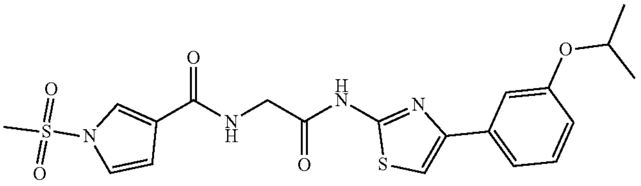 [SMILES: CC(C)Oc1cccc(-c2csc(NC(=O)CNC(=O)c3ccn(S(C)(=O)=O)c3)n2)c1] |
| 282 | 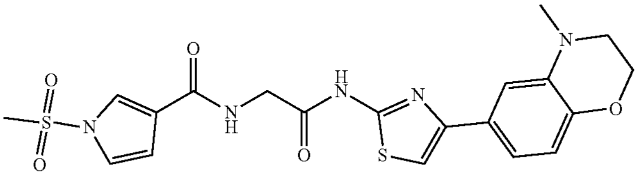 [SMILES: CN1CCOc2ccc(-c3csc(NC(=O)CNC(=O)c4ccn(S(C)(=O)=O)c4)n3)cc21] |
| 283 | 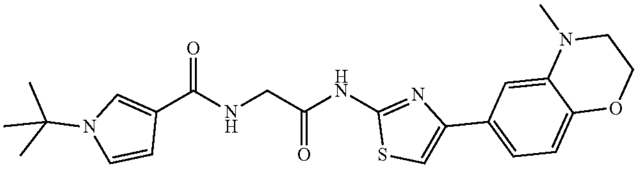 [SMILES: CN1CCOc2ccc(-c3csc(NC(=O)CNC(=O)c4ccn(C(C)(C)C)c4)n3)cc21] |
| 284 | 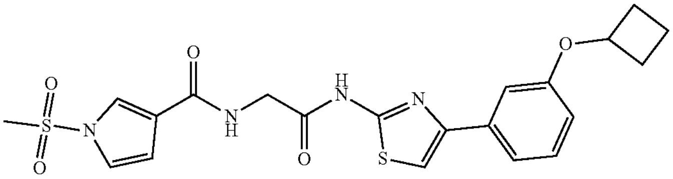 [SMILES: CS(=O)(=O)n1ccc(C(=O)NCC(=O)Nc2nc(-c3cccc(OC4CCC4)c3)cs2)c1] |
| 285 | 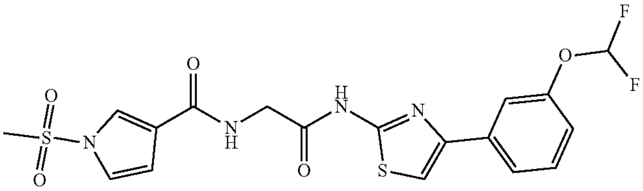 [SMILES: CS(=O)(=O)n1ccc(C(=O)NCC(=O)Nc2nc(-c3cccc(OC(F)F)c3)cs2)c1] |
| 286 | 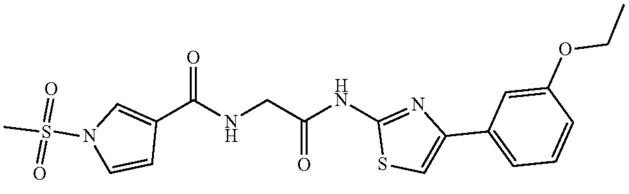 [SMILES: CCOc1cccc(-c2csc(NC(=O)CNC(=O)c3ccn(S(C)(=O)=O)c3)n2)c1] |

TABLE 1-continued
| Compounds of the invention | |
|---|---|
| # | Compound |
| 287 | 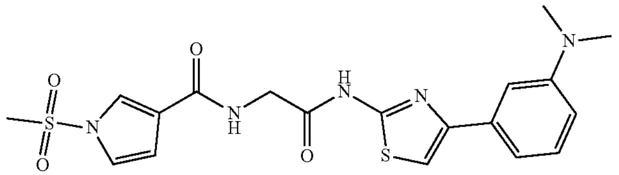 |
| 288 | 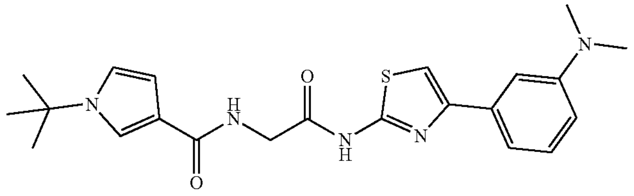 [SMILES: CN(C)c1cccc(-c2csc(NC(=O)CNC(=O)c3ccn(C(C)(C)C)c3)n2)c1] |
| 289 | 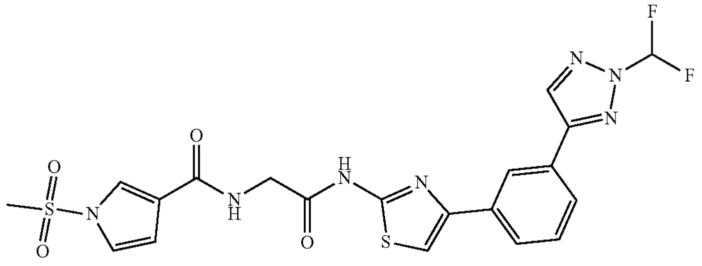 [SMILES: CS(=O)(=O)n1ccc(C(=O)NCC(=O)Nc2nc(-c3cccc(-c4cnn(C(F)F)n4)c3)cs2)c1] |
| 290 | 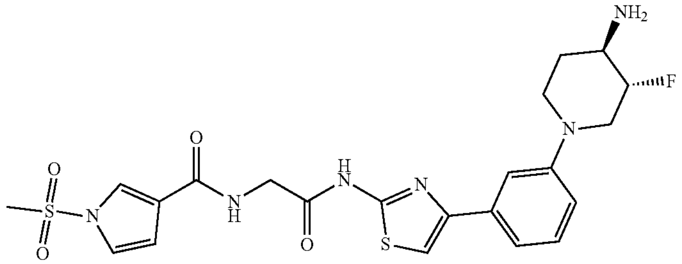 [SMILES: CS(=O)(=O)n1ccc(C(=O)NCC(=O)Nc2nc(-c3cccc(N4CC[C@@H](N)[C@H](F)C4)c3)cs2)c1] |
| 291 | 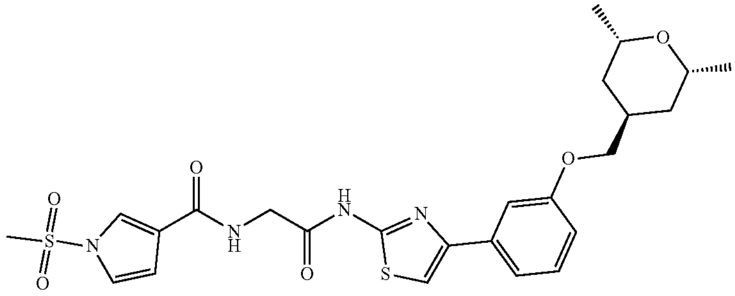 |
| 292 | 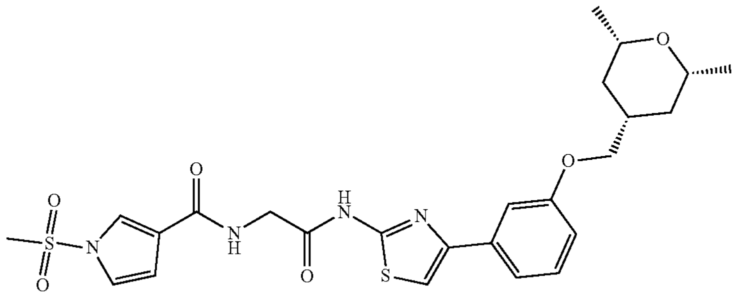 |

TABLE 1-continued
| Compounds of the invention | |
|---|---|
| # | Compound |
| 293 | 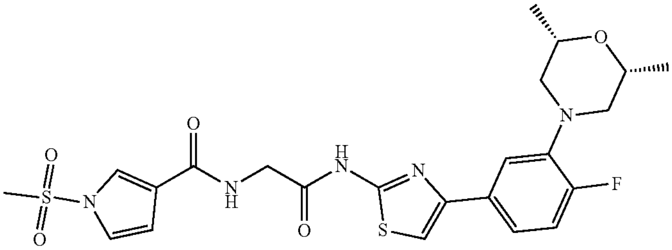 |
| 294 | 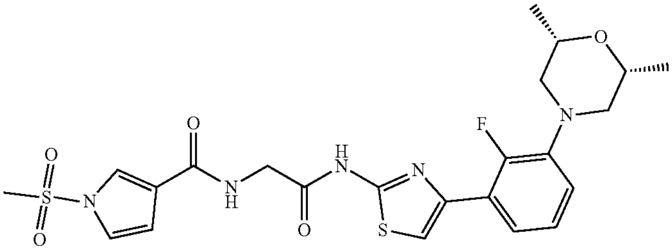 |
| 295 | 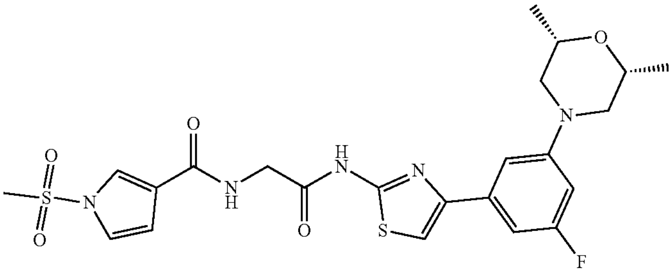 |
| 296 | 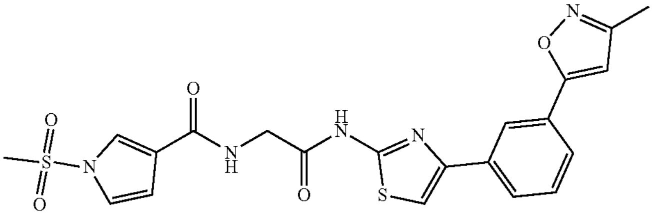 |
| 297 | 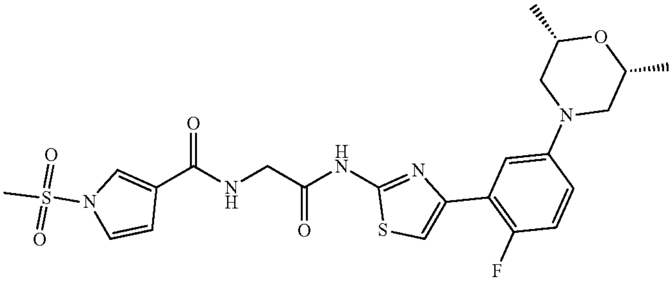 |
| 298 | 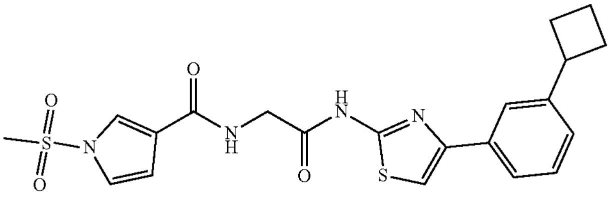 [SMILES: CS(=O)(=O)n1ccc(C(=O)NCC(=O)Nc2nc(-c3cccc(C4CCC4)c3)cs2)c1] |

TABLE 1-continued
| Compounds of the invention | |
|---|---|
| # | Compound |
| 299 | 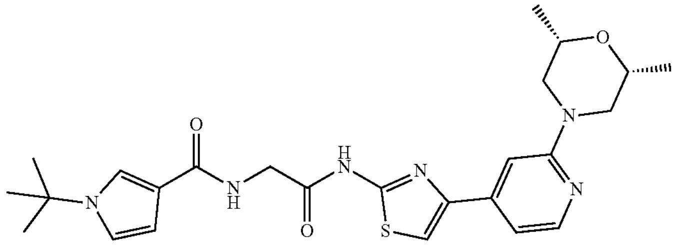 [SMILES: C[C@@H]1CN(c2cc(-c3csc(NC(=O)CNC(=O)c4ccn(C(C)(C)C)c4)n3)ccn2)C[C@H](C)O1] |
| 300 | 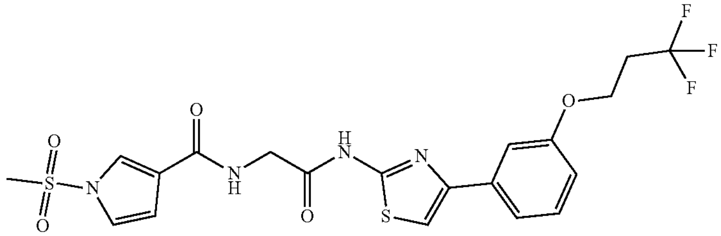 [SMILES: CS(=O)(=O)n1ccc(C(=O)NCC(=O)Nc2nc(-c3cccc(OCCC(F)(F)F)c3)cs2)c1] |
| 301 | 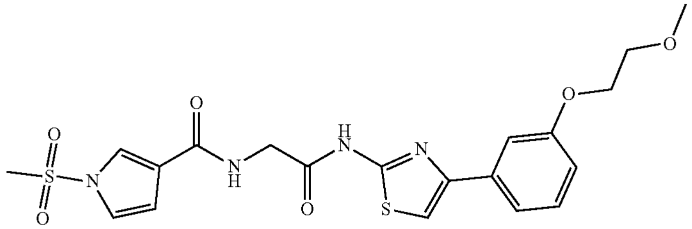 |
| 302 | 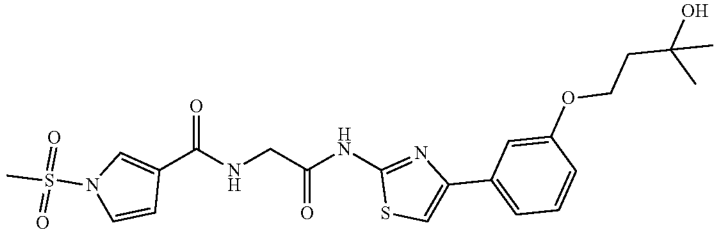 [SMILES: CC(C)(O)CCOc1cccc(-c2csc(NC(=O)CNC(=O)c3ccn(S(C)(=O)=O)c3)n2)c1] |
| 303 | 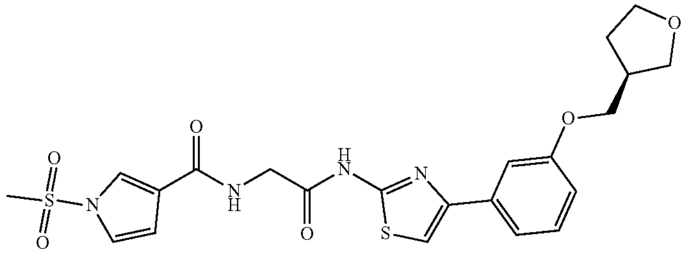 [SMILES: CS(=O)(=O)n1ccc(C(=O)NCC(=O)Nc2nc(-c3cccc(OC[C@H]4CCOC4)c3)cs2)c1] |
| 304 | 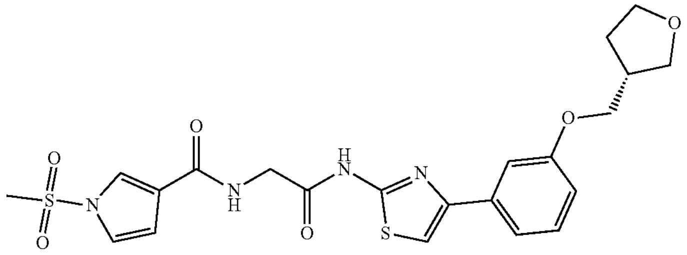 [SMILES: CS(=O)(=O)n1ccc(C(=O)NCC(=O)Nc2nc(-c3cccc(OC[C@@H]4CCOC4)c3)cs2)c1] |

TABLE 1-continued
| Compounds of the invention | |
|---|---|
| # | Compound |
| 305 | 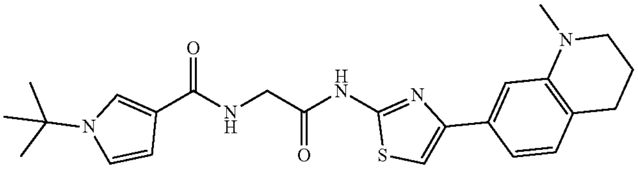 [SMILES: CN1CCCc2ccc(-c3csc(NC(=O)CNC(=O)c4ccn(C(C)(C)C)c4)n3)cc21] |
| 306 | 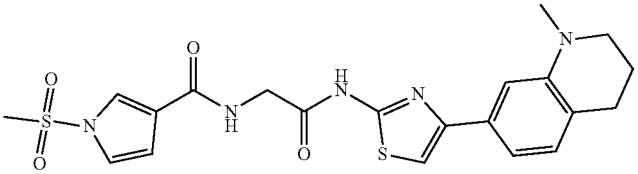 [SMILES: CN1CCCc2ccc(-c3csc(NC(=O)CNC(=O)c4ccn(S(C)(=O)=O)c4)n3)cc21] |
| 307 | 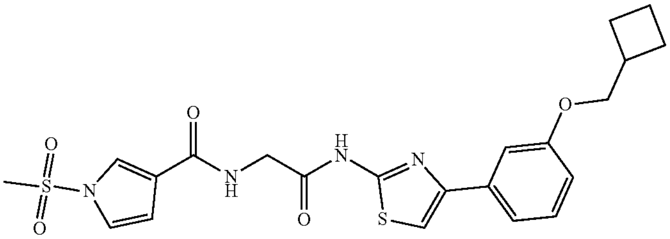 [SMILES: CS(=O)(=O)n1ccc(C(=O)NCC(=O)Nc2nc(-c3cccc(OCC4CCC4)c3)cs2)c1] |
| 308 | 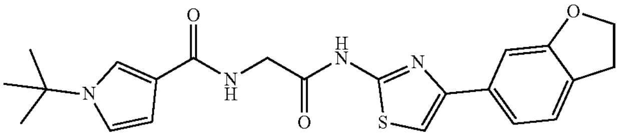 [SMILES: CC(C)(C)n1ccc(C(=O)NCC(=O)Nc2nc(-c3ccc4c(c3)OCC4)cs2)c1] |
| 309 | 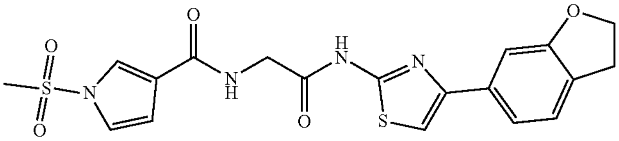 [SMILES: CS(=O)(=O)n1ccc(C(=O)NCC(=O)Nc2nc(-c3ccc4c(c3)OCC4)cs2)c1] |
| 310 | 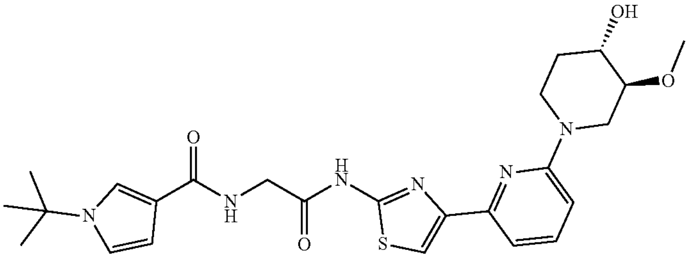<br>(±) |
| 311 | 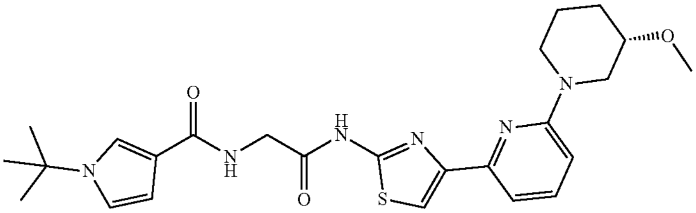 [SMILES: CO[C@H]1CCCN(c2cccc(-c3csc(NC(=O)CNC(=O)c4ccn(C(C)(C)C)c4)n3)n2)C1] |

TABLE 1-continued
| Compounds of the invention | |
|---|---|
| # | Compound |
| 312 | 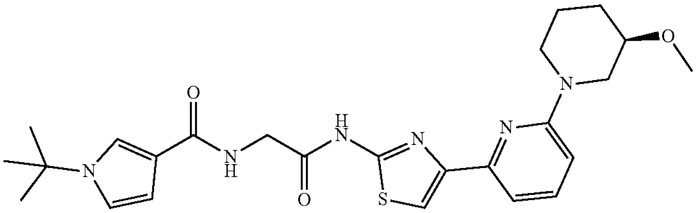 [SMILES: CO[C@@H]1CCCN(c2cccc(-c3csc(NC(=O)CNC(=O)c4ccn(C(C)(C)C)c4)n3)n2)C1] |
| 313 | 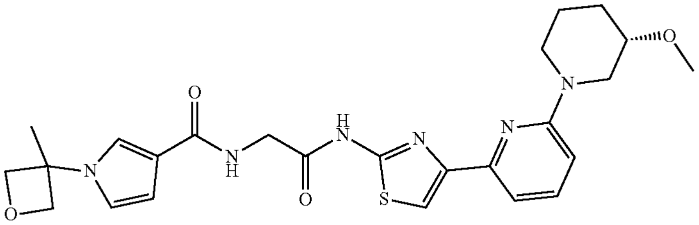 [SMILES: CO[C@H]1CCCN(c2cccc(-c3csc(NC(=O)CNC(=O)c4ccn(C5(C)COC5)c4)n3)n2)C1] |
| 314 | 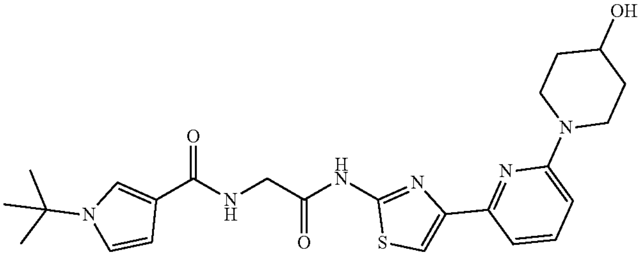 [SMILES: CC(C)(C)n1ccc(C(=O)NCC(=O)Nc2nc(-c3cccc(N4CCC(O)CC4)n3)cs2)c1] |
| 315 | 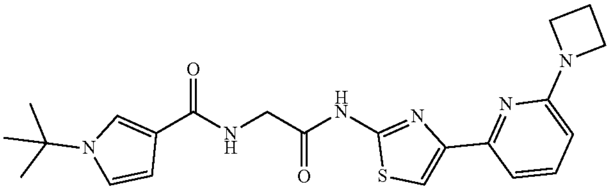 [SMILES: CC(C)(C)n1ccc(C(=O)NCC(=O)Nc2nc(-c3cccc(N4CCC4)n3)cs2)c1] |
| 316 | 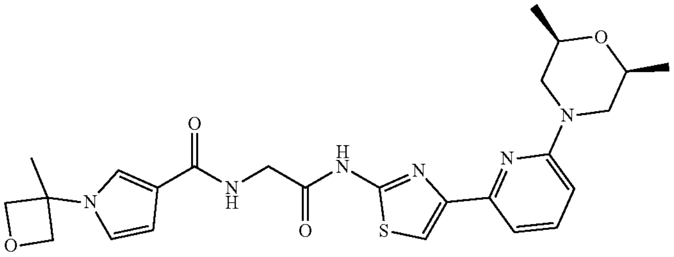 [SMILES: C[C@@H]1CN(c2cccc(-c3csc(NC(=O)CNC(=O)c4ccn(C5(C)COC5)c4)n3)n2)C[C@H](C)O1] |
| 317 | 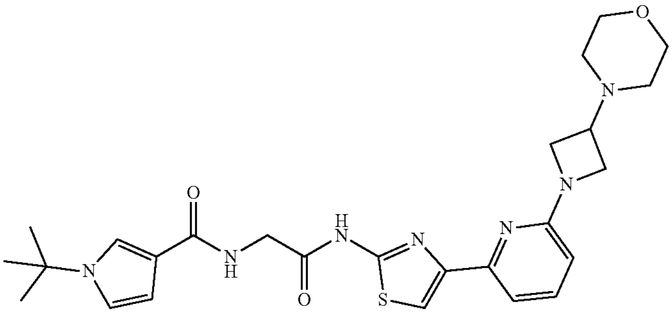 [SMILES: CC(C)(C)n1ccc(C(=O)NCC(=O)Nc2nc(-c3cccc(N4CC(N5CCOCC5)C4)n3)cs2)c1] |

TABLE 1-continued
Compounds of the invention
| # | Compound |
|---|---|
| 318 | 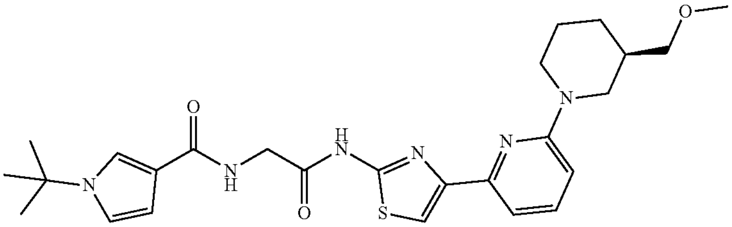 [SMILES: COC[C@@H]1CCCN(c2cccc(-c3csc(NC(=O)CNC(=O)c4ccn(C(C)(C)C)c4)n3)n2)C1] |
| 319 | 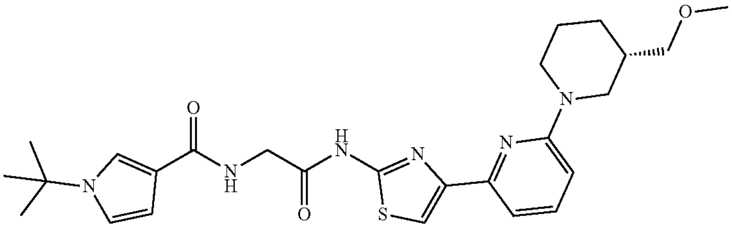 [SMILES: COC[C@H]1CCCN(c2cccc(-c3csc(NC(=O)CNC(=O)c4ccn(C(C)(C)C)c4)n3)n2)C1] |
| 320 | 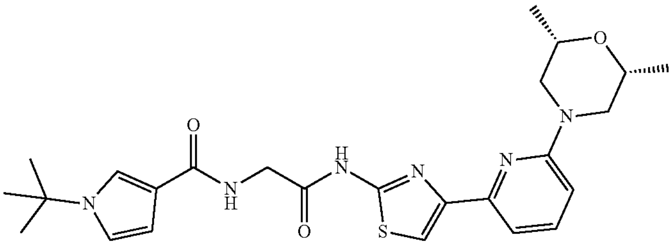 [SMILES: C[C@@H]1CN(c2cccc(-c3csc(NC(=O)CNC(=O)c4ccn(C(C)(C)C)c4)n3)n2)C[C@H](C)O1] |
| 321 | 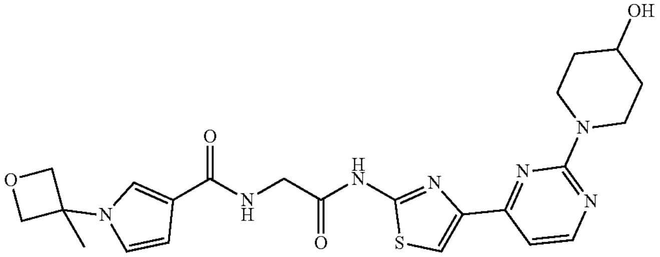 [SMILES: CC1(n2ccc(C(=O)NCC(=O)Nc3nc(-c4ccnc(N5CCC(O)CC5)n4)cs3)c2)COC1] |
| 322 | 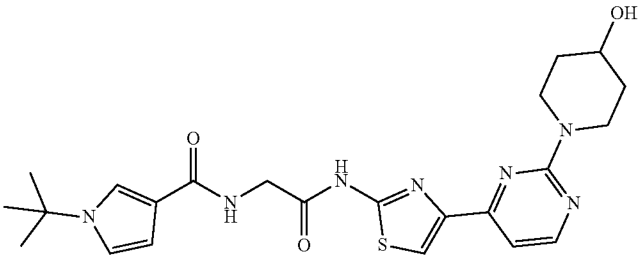 [SMILES: CC(C)(C)n1ccc(C(=O)NCC(=O)Nc2nc(-c3ccnc(N4CCC(O)CC4)n3)cs2)c1] |
| 323 | 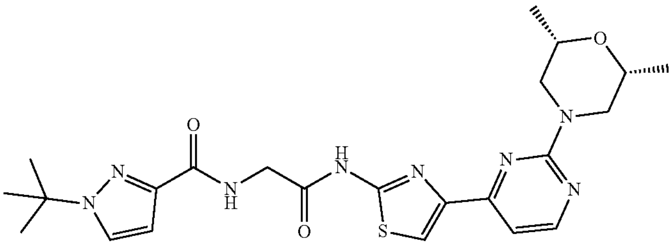 [SMILES: C[C@@H]1CN(c2nccc(-c3csc(NC(=O)CNC(=O)c4ccn(C(C)(C)C)n4)n3)n2)C[C@H](C)O1] |

TABLE 1-continued
Compounds of the invention
| # | Compound |
|---|---|
| 324 | 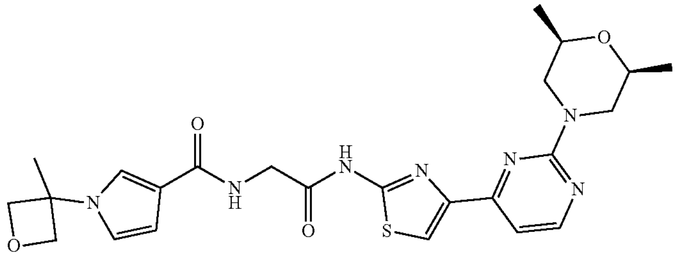 [SMILES: C[C@@H]1CN(c2nccc(-c3csc(NC(=O)CNC(=O)c4ccn(C5(C)COC5)c4)n3)n2)C[C@H](C)O1] |
| 325 | 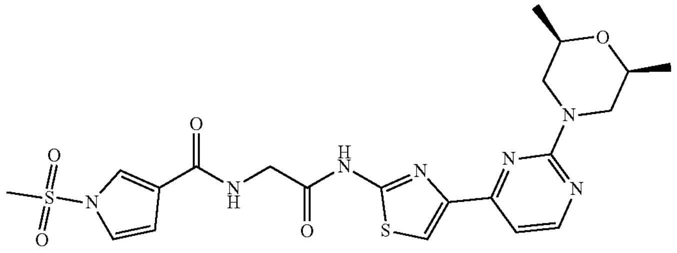 |
| 326 | 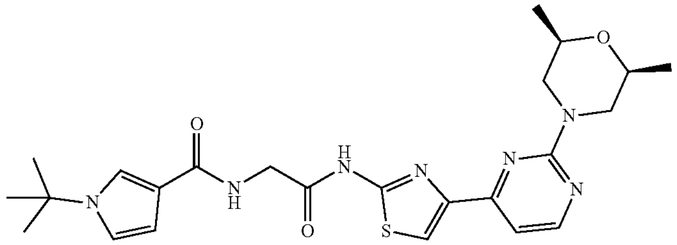 [SMILES: C[C@@H]1CN(c2nccc(-c3csc(NC(=O)CNC(=O)c4ccn(C(C)(C)C)c4)n3)n2)C[C@H](C)O1] |
| 327 | 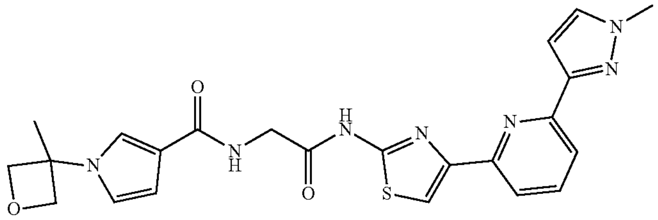 [SMILES: Cn1ccc(-c2cccc(-c3csc(NC(=O)CNC(=O)c4ccn(C5(C)COC5)c4)n3)n2)n1] |
| 328 | 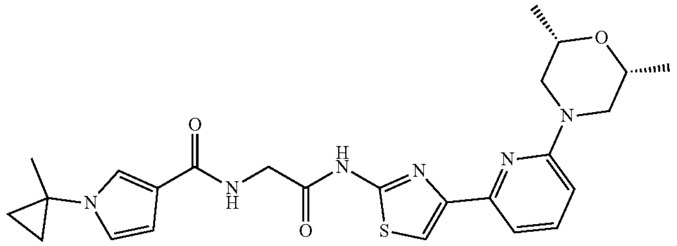 [SMILES: C[C@@H]1CN(c2cccc(-c3csc(NC(=O)CNC(=O)c4ccn(C5(C)CC5)c4)n3)n2)C[C@H](C)O1] |
| 329 | 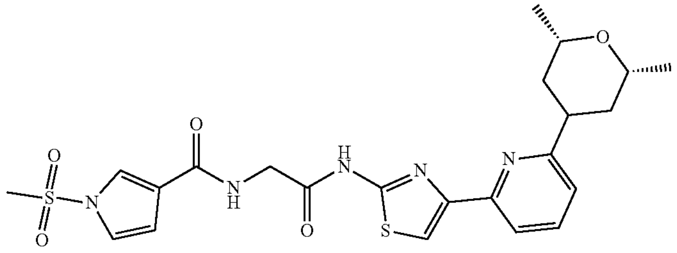 |

TABLE 1-continued
| Compounds of the invention | |
|---|---|
| # | Compound |
| 330 | 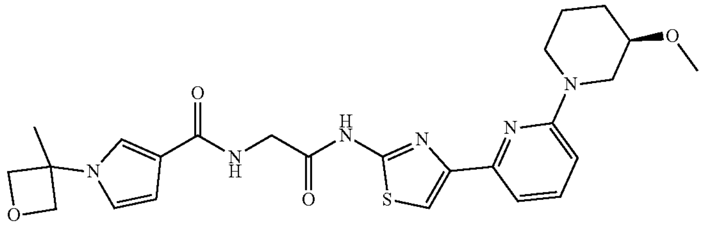 [SMILES: CO[C@@H]1CCCN(c2cccc(-c3csc(NC(=O)CNC(=O)c4ccn(C5(C)COC5)c4)n3)n2)C1] |
| 331 | 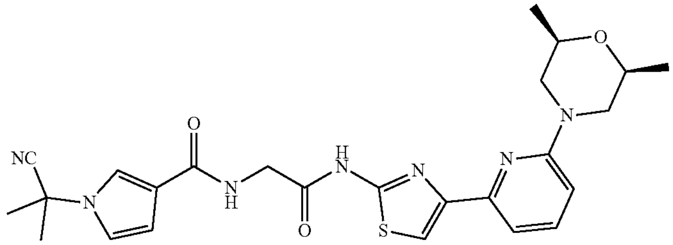 [SMILES: C[C@@H]1CN(c2cccc(-c3csc(NC(=O)CNC(=O)c4ccn(C(C)(C)C#N)c4)n3)n2)C[C@H](C)O1] |
| 332 | 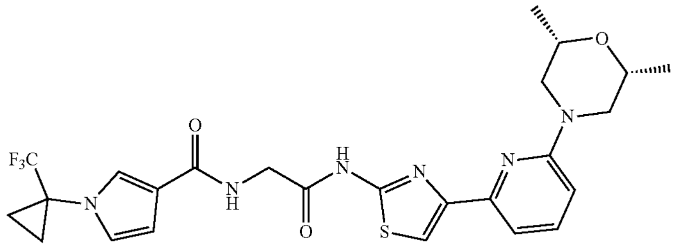 [SMILES: C[C@@H]1CN(c2cccc(-c3csc(NC(=O)CNC(=O)c4ccn(C5(C(F)(F)F)CC5)c4)n3)n2)C[C@H](C)O1] |
| 333 | 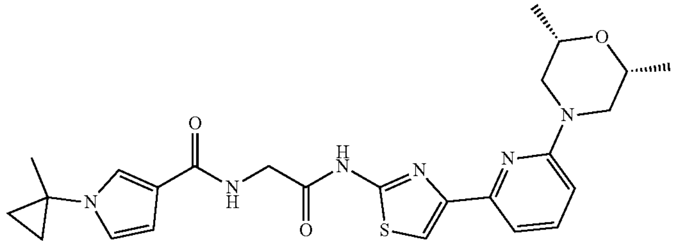 [SMILES: C[C@@H]1CN(c2cccc(-c3csc(NC(=O)CNC(=O)c4ccn(C5(C)CC5)c4)n3)n2)C[C@H](C)O1] |
| 334 | 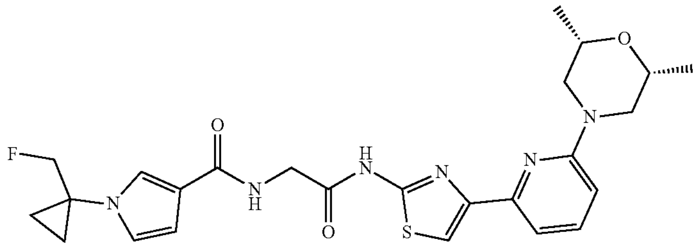 [SMILES: C[C@@H]1CN(c2cccc(-c3csc(NC(=O)CNC(=O)c4ccn(C5(CF)CC5)c4)n3)n2)C[C@H](C)O1] |
| 335 | 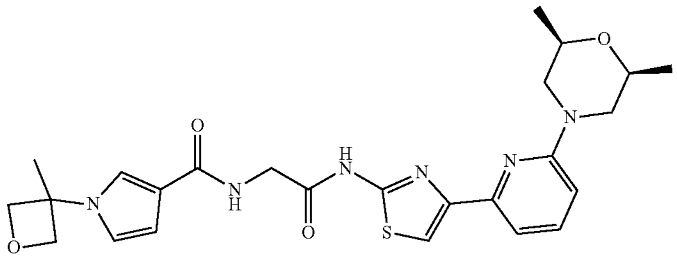 [SMILES: C[C@@H]1CN(c2cccc(-c3csc(NC(=O)CNC(=O)c4ccn(C5(C)COC5)c4)n3)n2)C[C@H](C)O1] |

TABLE 1-continued
| Compounds of the invention | |
|---|---|
| # | Compound |
| 336 | 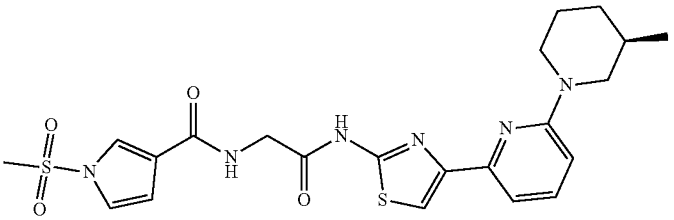 |
| 337 | 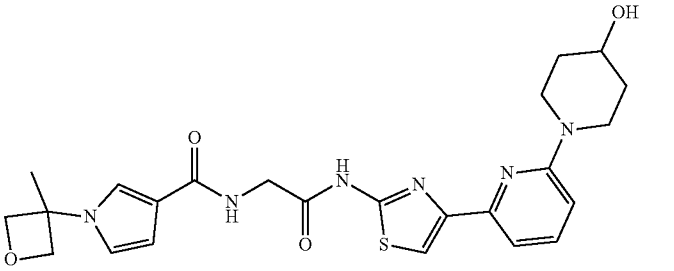 [SMILES: CC1(n2ccc(C(=O)NCC(=O)Nc3nc(-c4cccc(N5CCC(O)CC5)n4)cs3)c2)COC1] |
| 338 | 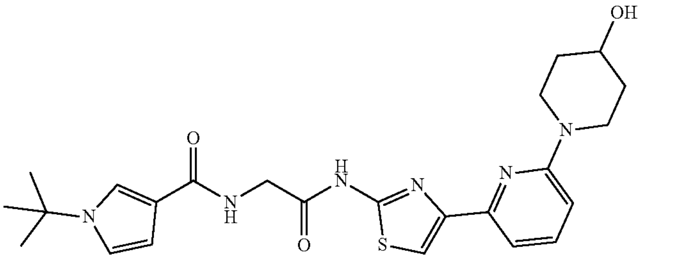 [SMILES: CC(C)(C)n1ccc(C(=O)NCC(=O)Nc2nc(-c3cccc(N4CCC(O)CC4)n3)cs2)c1] |
| 339 | 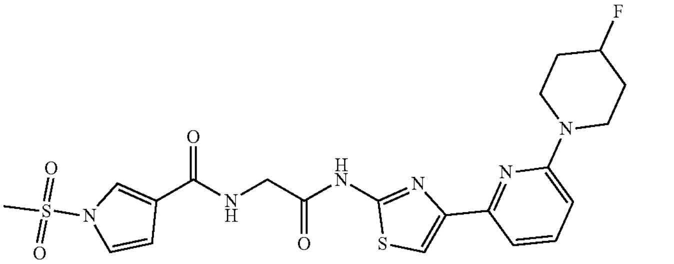 [SMILES: CS(=O)(=O)n1ccc(C(=O)NCC(=O)Nc2nc(-c3cccc(N4CCC(F)CC4)n3)cs2)c1] |
| 340 | 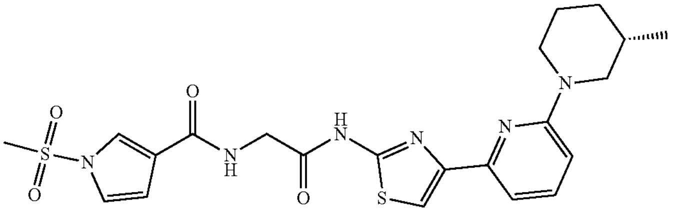 |
| 341 | 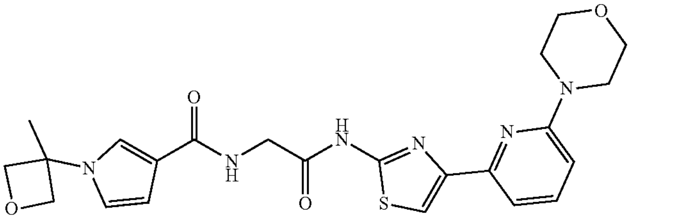 [SMILES: CC1(n2ccc(C(=O)NCC(=O)Nc3nc(-c4cccc(N5CCOCC5)n4)cs3)c2)COC1] |

TABLE 1-continued
Compounds of the invention
| # | Compound |
|---|---|
| 342 | 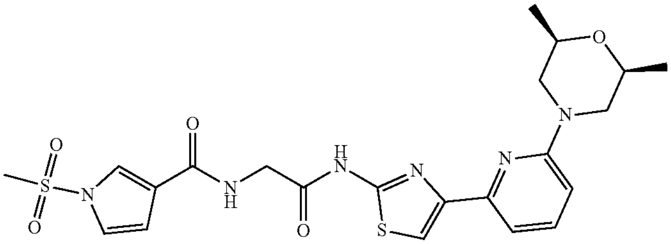 |
| 343 | 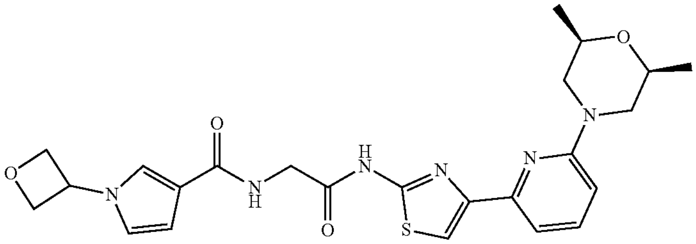 [SMILES: C[C@@H]1CN(c2cccc(-c3csc(NC(=O)CNC(=O)c4ccn(C5COC5)c4)n3)n2)C[C@H](C)O1] |
| 344 | 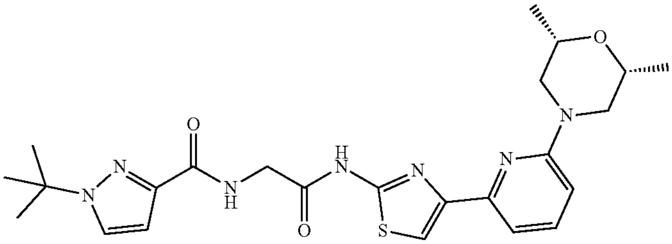 [SMILES: C[C@@H]1CN(c2cccc(-c3csc(NC(=O)CNC(=O)c4ccn(C(C)(C)C)n4)n3)n2)C[C@H](C)O1] |
| 345 | 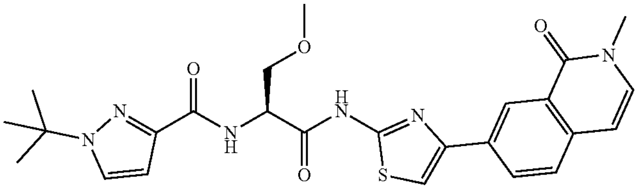 [SMILES: COC[C@H](NC(=O)c1ccn(C(C)(C)C)n1)C(=O)Nc1nc(-c2ccc3ccn(C)c(=O)c3c2)cs1] |
| 346 | 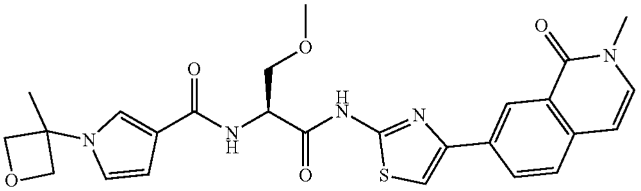 [SMILES: COC[C@H](NC(=O)c1ccn(C2(C)COC2)c1)C(=O)Nc1nc(-c2ccc3ccn(C)c(=O)c3c2)cs1] |
| 347 | 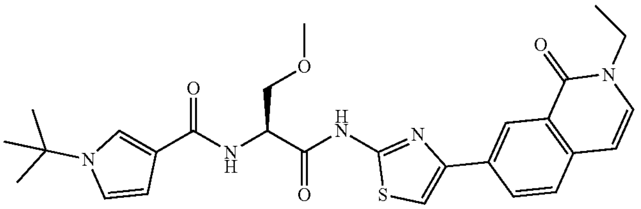 [SMILES: CCn1ccc2ccc(-c3csc(NC(=O)[C@H](COC)NC(=O)c4ccn(C(C)(C)C)c4)n3)cc2c1=O] |
| 348 | 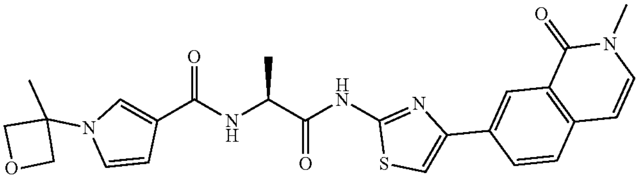 [SMILES: C[C@H](NC(=O)c1ccn(C2(C)COC2)c1)C(=O)Nc1nc(-c2ccc3ccn(C)c(=O)c3c2)cs1] |

TABLE 1-continued
Compounds of the invention
| # | Compound |
|---|---|
| 349 | 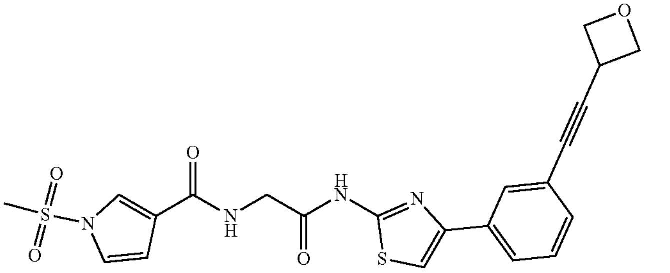 [SMILES: CS(=O)(=O)n1ccc(C(=O)NCC(=O)Nc2nc(-c3cccc(C#CC4COC4)c3)cs2)c1] |
| 350 | 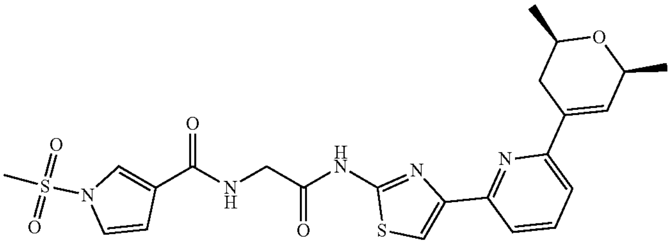 ± |
| 351 | 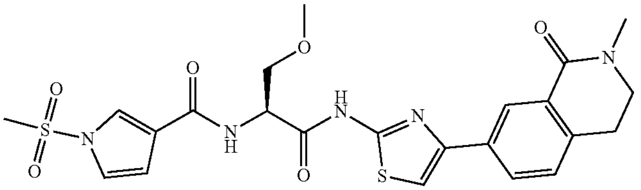 [SMILES: COC[C@H](NC(=O)c1ccn(S(C)(=O)=O)c1)C(=O)Nc1nc(-c2ccc3c(c2)C(=O)N(C)CC3)cs1] |
| 352 | 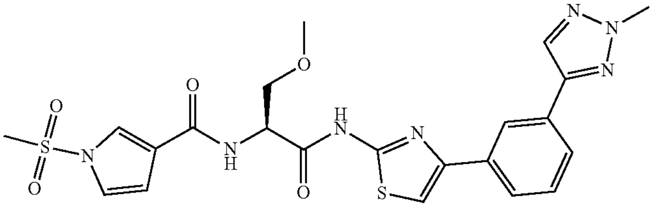 |
| 353 | 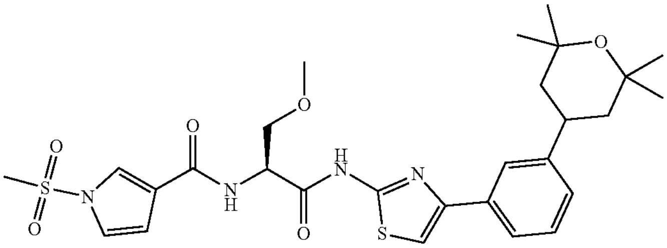 |
| 354 | 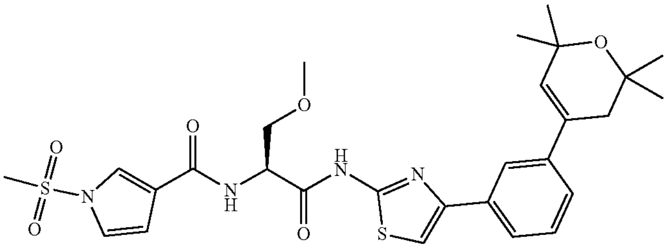 |

TABLE 1-continued
| # | Compound |
| --- | --- |
| Compounds of the invention | |
| 355 | 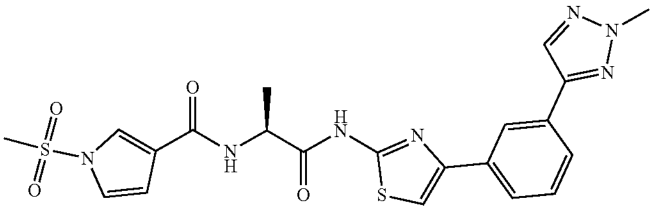 |
| 356 | 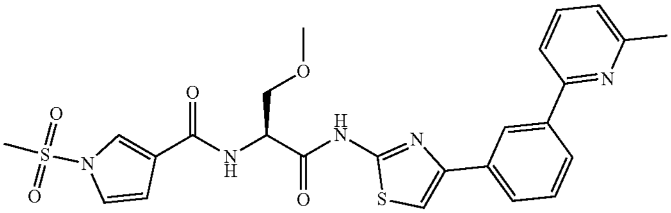 |
| 357 | 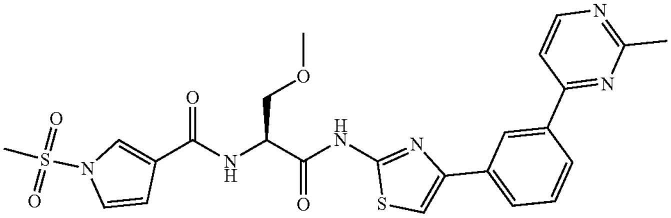 |
| 358 | 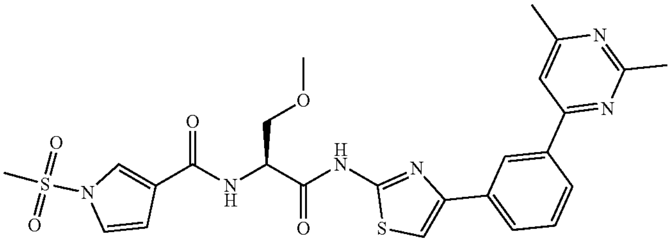 |
| 359 | 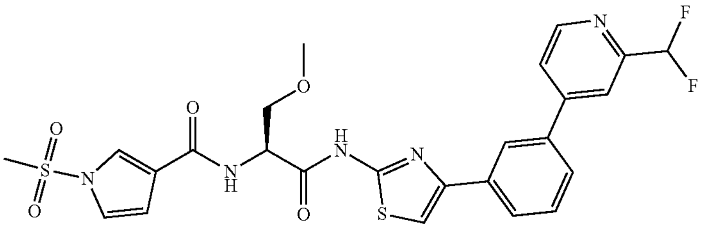 [SMILES: COC[C@H](NC(=O)c1ccn(S(C)(=O)=O)c1)C(=O)Nc1nc(-c2cccc(-c3ccnc(C(F)F)c3)c2)cs1] |
| 360 | 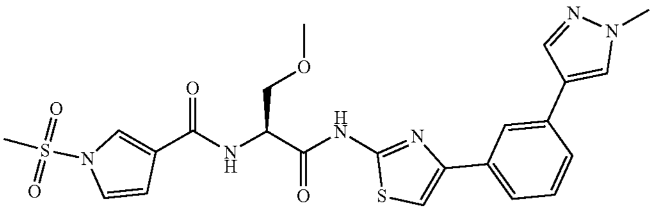 |

TABLE 1-continued
| # | Compound |
|---|---|
| | Compounds of the invention |
| 361 | 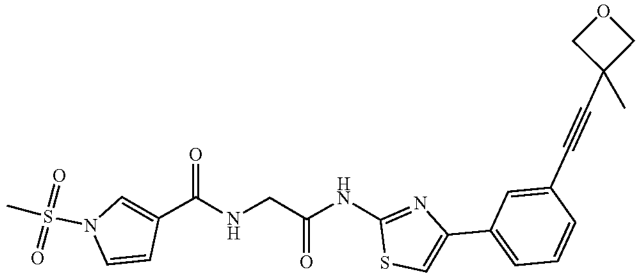 [SMILES: CC1(C#Cc2cccc(-c3csc(NC(=O)CNC(=O)c4ccn(S(C)(=O)=O)c4)n3)c2)COC1] |
| 362 | 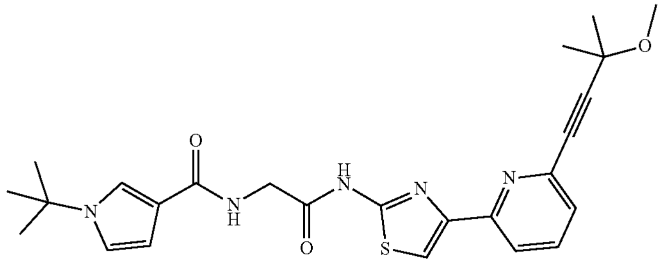 [SMILES: COC(C)(C)C#Cc1cccc(-c2csc(NC(=O)CNC(=O)c3ccn(C(C)(C)C)c3)n2)n1] |
| 363 | 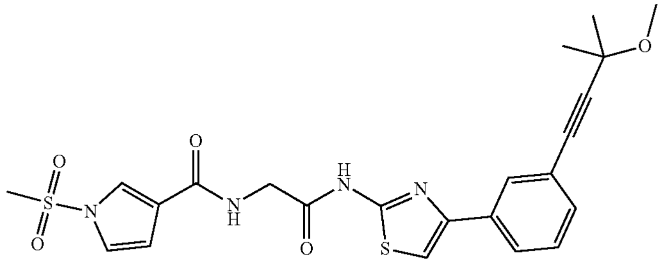 |
| 364 | 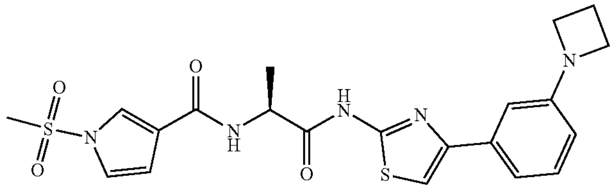 [SMILES: C[C@H](NC(=O)c1ccn(S(C)(=O)=O)c1)C(=O)Nc1nc(-c2cccc(N3CCC3)c2)cs1] |
| 365 | 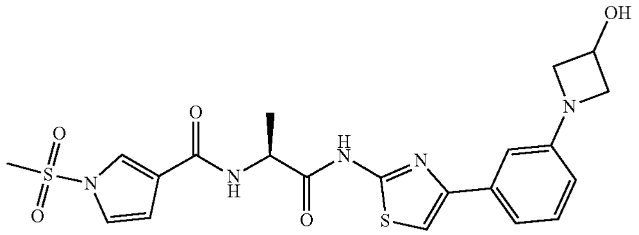 [SMILES: C[C@H](NC(=O)c1ccn(S(C)(=O)=O)c1)C(=O)Nc1nc(-c2cccc(N3CC(O)C3)c2)cs1] |
| 366 | 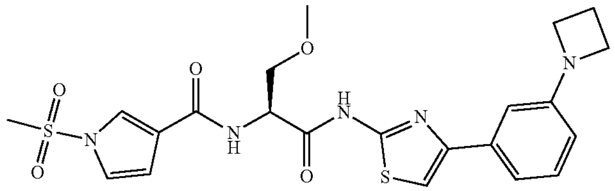 [SMILES: COC[C@H](NC(=O)c1ccn(S(C)(=O)=O)c1)C(=O)Nc1nc(-c2cccc(N3CCC3)c2)cs1] |

TABLE 1-continued
Compounds of the invention
| # | Compound |
|---|---|
| 367 | 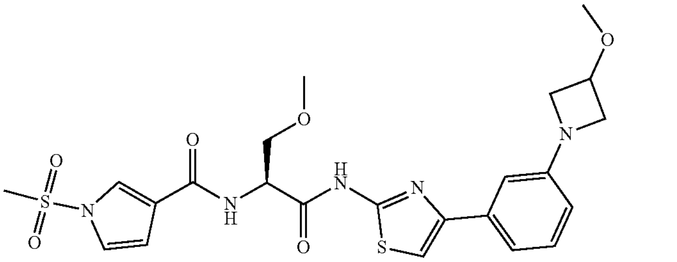 [SMILES: COC[C@H](NC(=O)c1ccn(S(C)(=O)=O)c1)C(=O)Nc1nc(-c2cccc(N3CC(OC)C3)c2)cs1] |
| 368 | 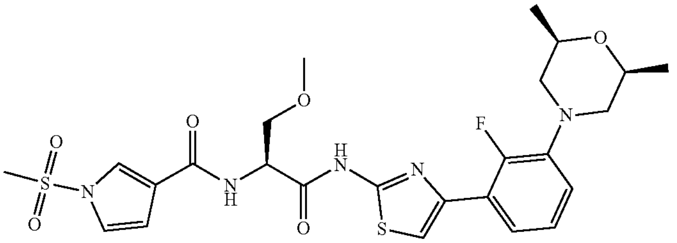 |
| 369 | 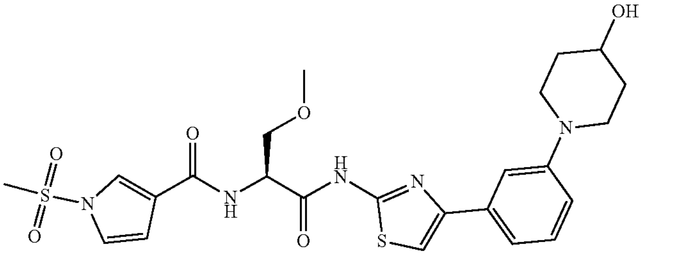 [SMILES: COC[C@H](NC(=O)c1ccn(S(C)(=O)=O)c1)C(=O)Nc1nc(-c2cccc(N3CCC(O)CC3)c2)cs1] |
| 370 | 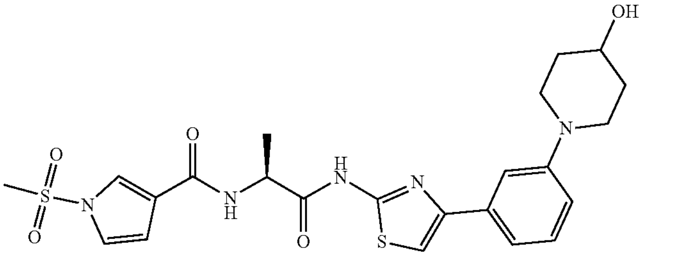 [SMILES: C[C@H](NC(=O)c1ccn(S(C)(=O)=O)c1)C(=O)Nc1nc(-c2cccc(N3CCC(O)CC3)c2)cs1] |
| 371 | 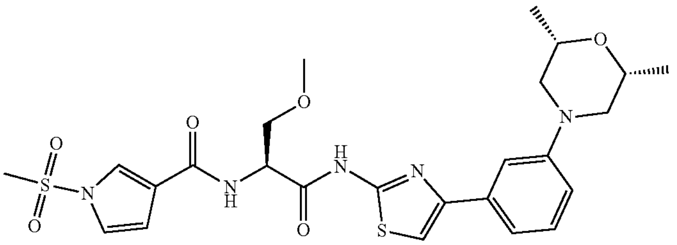 |
| 372 | 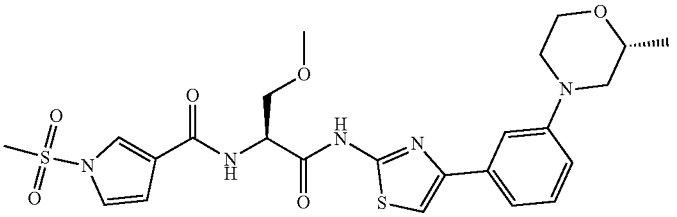 |

TABLE 1-continued
| Compounds of the invention | |
|---|---|
| # | Compound |
| 373 | 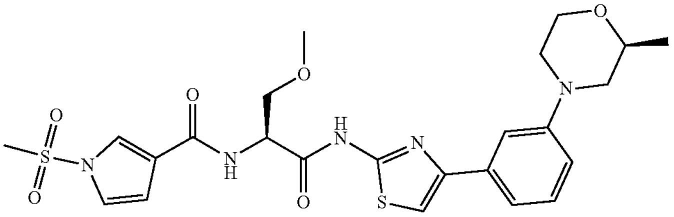 |
| 374 | 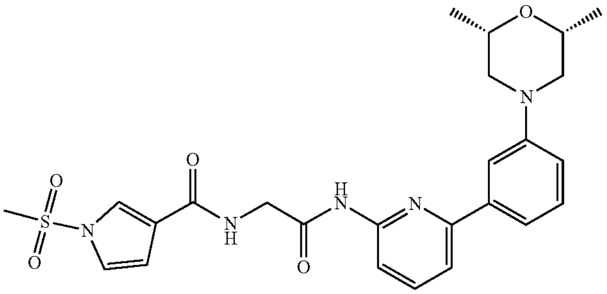 |
| 375 | 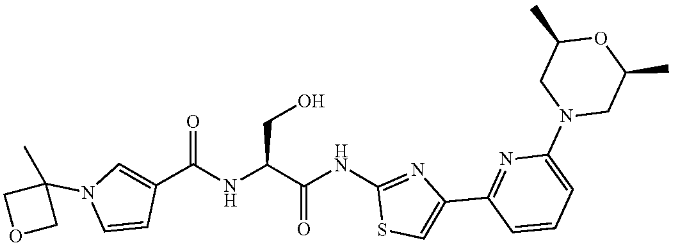 [SMILES: C[C@@H]1CN(c2cccc(-c3csc(NC(=O)[C@H](CO)NC(=O)c4ccn(C5(C)COC5)c4)n3)n2)C[C@H](C)O1] |
| 376 | 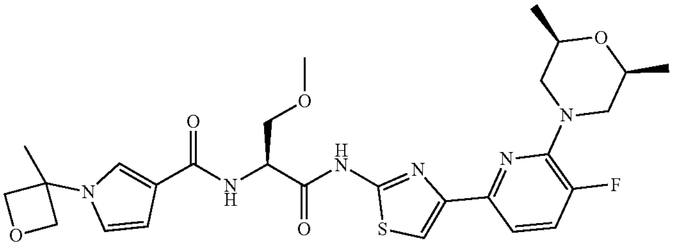 [SMILES: COC[C@H](NC(=O)c1ccn(C2(C)COC2)c1)C(=O)Nc1nc(-c2ccc(F)c(N3C[C@@H](C)O[C@@H](C)C3)n2)cs1] |
| 377 | 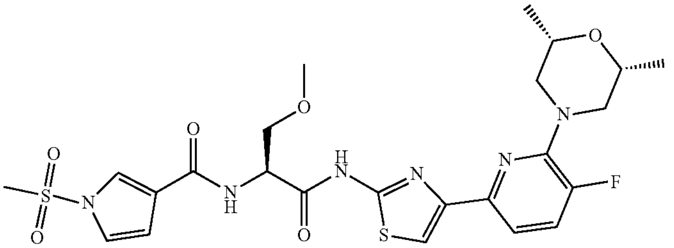 |
| 378 | 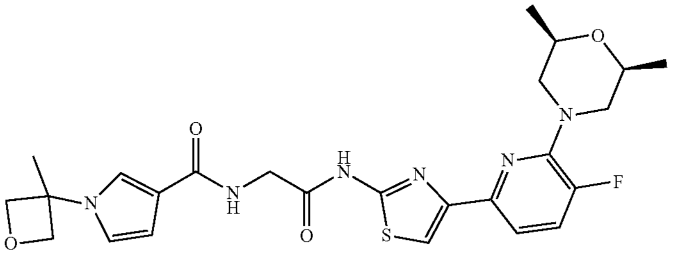 [SMILES: C[C@@H]1CN(c2nc(-c3csc(NC(=O)CNC(=O)c4ccn(C5(C)COC5)c4)n3)ccc2F)C[C@H](C)O1] |

TABLE 1-continued
| Compounds of the invention | |
|---|---|
| # | Compound |
| 379 | 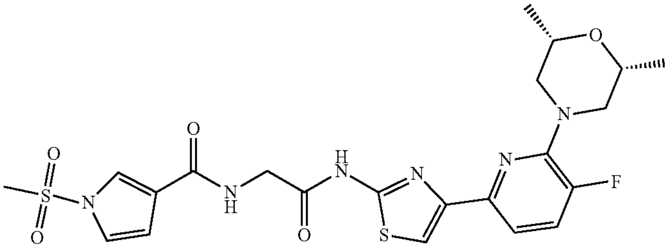 |
| 380 | 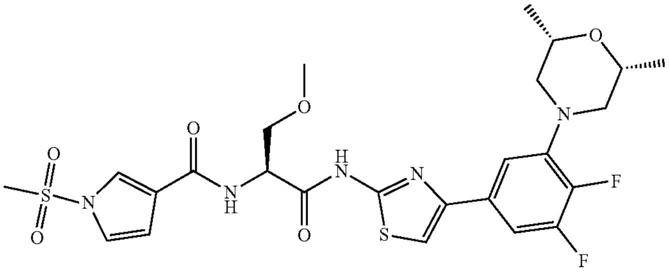 |
| 381 | 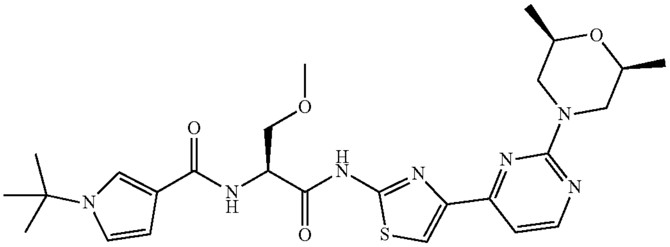 [SMILES: COC[C@H](NC(=O)c1ccn(C(C)(C)C)c1)C(=O)Nc1nc(-c2ccnc(N3C[C@@H](C)O[C@@H](C)C3)n2)cs1] |
| 382 | 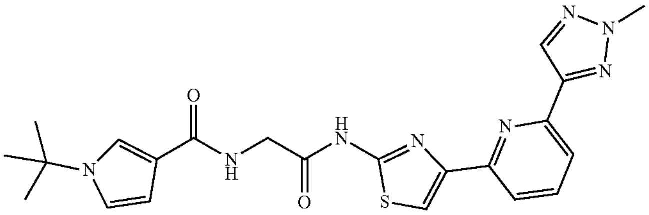 [SMILES: Cn1ncc(-c2cccc(-c3csc(NC(=O)CNC(=O)c4ccn(C(C)(C)C)c4)n3)n2)n1] |
| 383 | 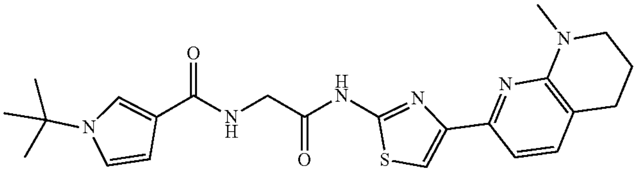 [SMILES: CN1CCCc2ccc(-c3csc(NC(=O)CNC(=O)c4ccn(C(C)(C)C)c4)n3)nc21] |
| 384 | 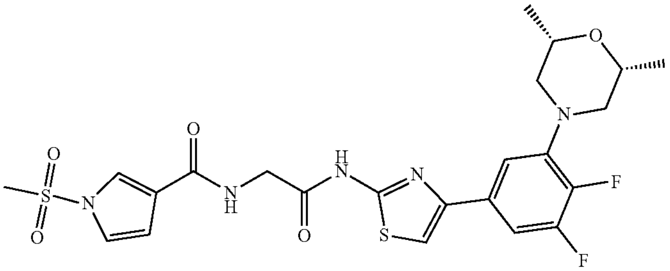 |

TABLE 1-continued
| Compounds of the invention | |
|---|---|
| # | Compound |
| 385 | 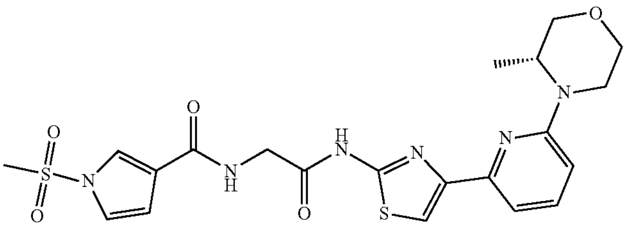 [SMILES: C[C@@H]1COCCN1c1cccc(-c2csc(NC(=O)CNC(=O)c3ccn(S(C)(=O)=O)c3)n2)n1] |
| 386 | 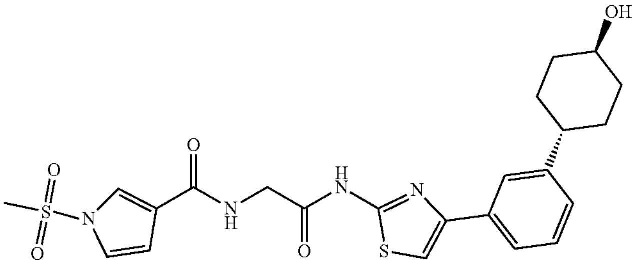 [SMILES: CS(=O)(=O)n1ccc(C(=O)NCC(=O)Nc2nc(-c3cccc([C@H]4CC[C@H](O)CC4)c3)cs2)c1] |
| 387 | 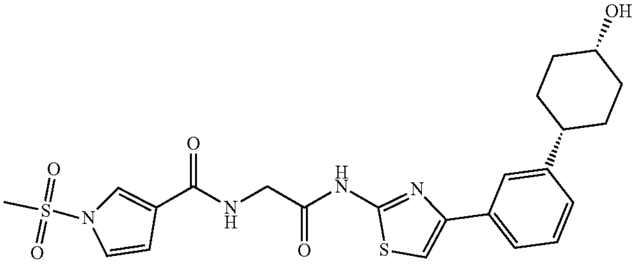 [SMILES: CS(=O)(=O)n1ccc(C(=O)NCC(=O)Nc2nc(-c3cccc([C@H]4CC[C@@H](O)CC4)c3)cs2)c1] |
| 388 | 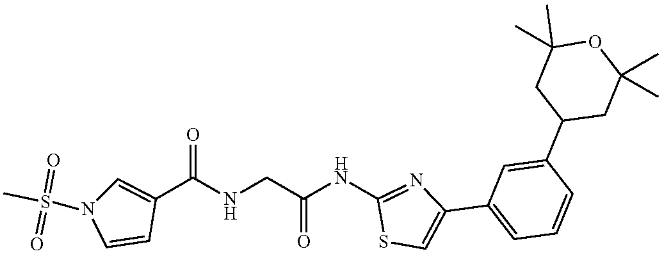 |
| 389 | 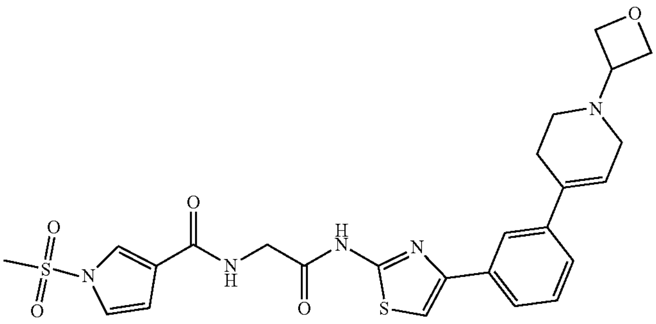 [SMILES: CS(=O)(=O)n1ccc(C(=O)NCC(=O)Nc2nc(-c3cccc(C4=CCN(C5COC5)CC4)c3)cs2)c1] |

TABLE 1-continued
| Compounds of the invention | |
|---|---|
| # | Compound |
| 390 | 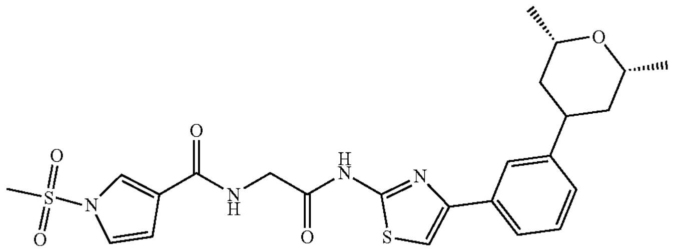 |
| 391 | 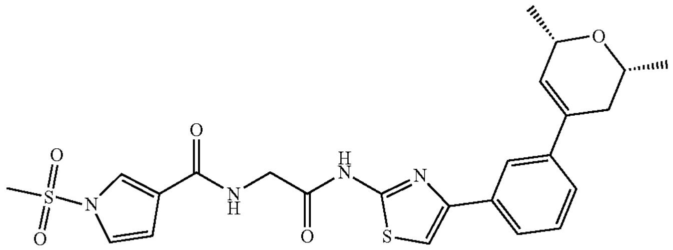<br>(±) |
| 392 | 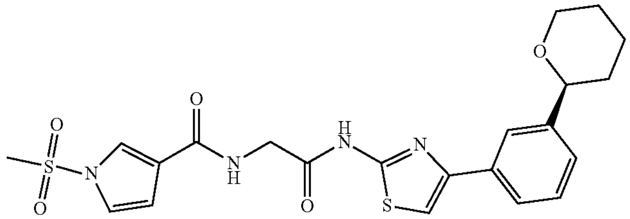<br>± |
| 393 | 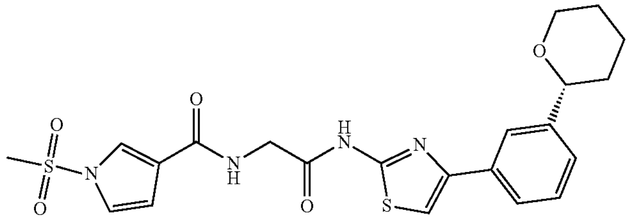 [SMILES: CS(=O)(=O)n1ccc(C(=O)NCC(=O)Nc2nc(-c3cccc([C@H]4CCCCO4)c3)cs2)c1] |
| 394 | 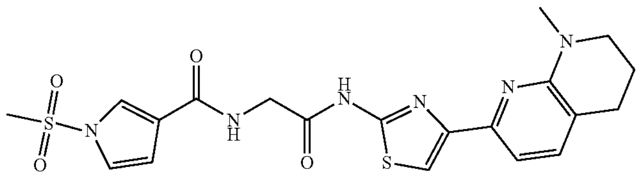 [SMILES: CN1CCCc2ccc(-c3csc(NC(=O)CNC(=O)c4ccn(S(C)(=O)=O)c4)n3)nc21] |
| 395 | 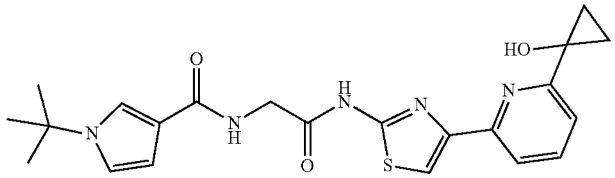 [SMILES: CC(C)(C)n1ccc(C(=O)NCC(=O)Nc2nc(-c3cccc(C4(O)CC4)n3)cs2)c1] |

TABLE 1-continued
| Compounds of the invention | |
|---|---|
| # | Compound |
| 396 | 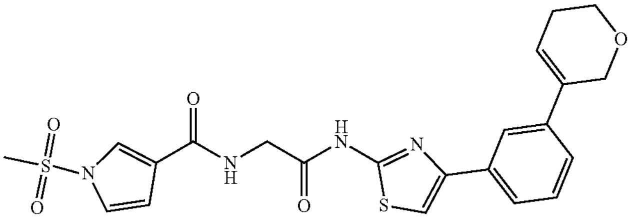 [SMILES: CS(=O)(=O)n1ccc(C(=O)NCC(=O)Nc2nc(-c3cccc(C4=CCCOC4)c3)cs2)c1] |
| 397 | 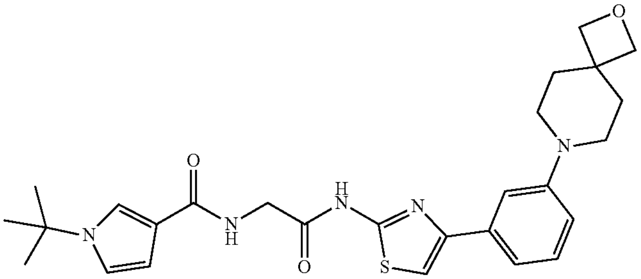 [SMILES: CC(C)(C)n1ccc(C(=O)NCC(=O)Nc2nc(-c3cccc(N4CCC5(CC4)COC5)c3)cs2)c1] |
| 398 | 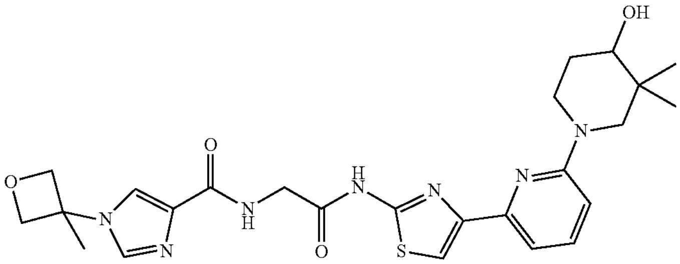 [SMILES: CC1(C)CN(c2cccc(-c3csc(NC(=O)CNC(=O)c4cn(C5(C)COC5)cn4)n3)n2)CCC1O] |
| 399 | 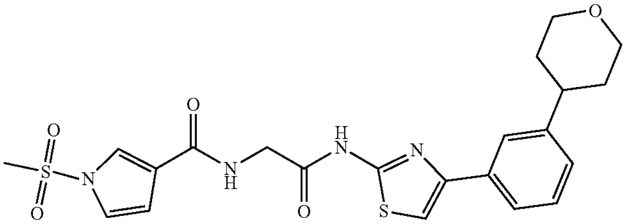 [SMILES: CS(=O)(=O)n1ccc(C(=O)NCC(=O)Nc2nc(-c3cccc(C4CCOCC4)c3)cs2)c1] |
| 400 | 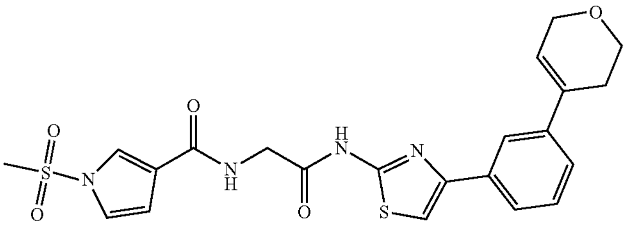 |
| 401 | 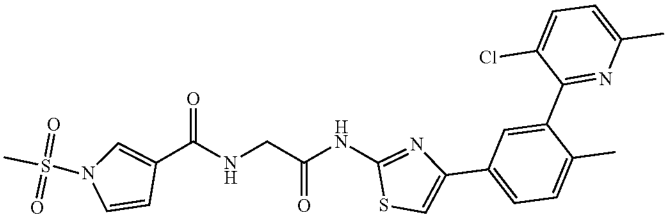 |

TABLE 1-continued
| Compounds of the invention | |
|---|---|
| # | Compound |
| 402 | 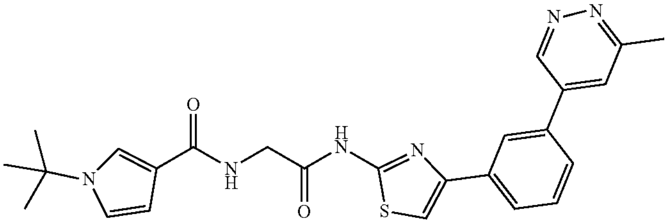 [SMILES: Cc1cc(-c2cccc(-c3csc(NC(=O)CNC(=O)c4ccn(C(C)(C)C)c4)n3)c2)cnn1] |
| 403 | 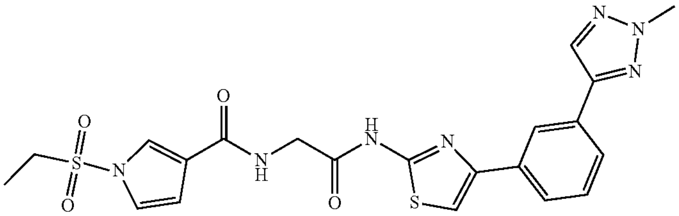 [SMILES: CCS(=O)(=O)n1ccc(C(=O)NCC(=O)Nc2nc(-c3cccc(-c4cnn(C)n4)c3)cs2)c1] |
| 404 | 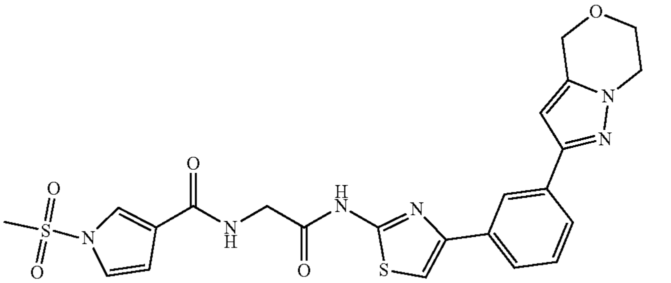 [SMILES: CS(=O)(=O)n1ccc(C(=O)NCC(=O)Nc2nc(-c3cccc(-c4cc5n(n4)CCOC5)c3)cs2)c1] |
| 405 | 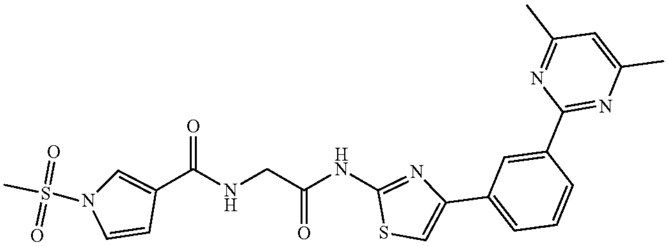 |
| 406 | 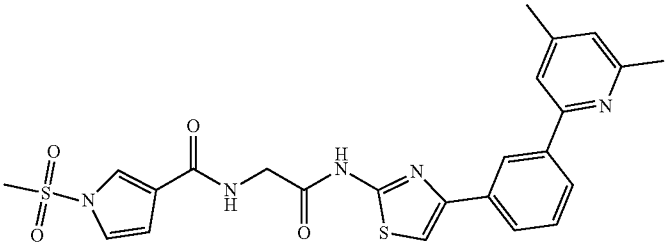 |
| 407 | 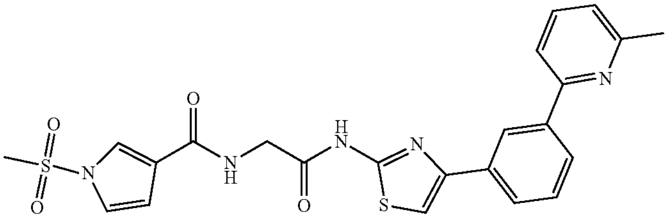 |

TABLE 1-continued
| Compounds of the invention |
| --- |
| # | Compound |
| --- | --- |
| 408 | 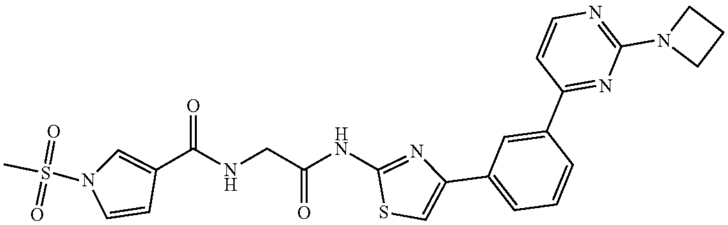 [SMILES: CS(=O)(=O)n1ccc(C(=O)NCC(=O)Nc2nc(-c3cccc(-c4ccnc(N5CCC5)n4)c3)cs2)c1] |
| 409 | 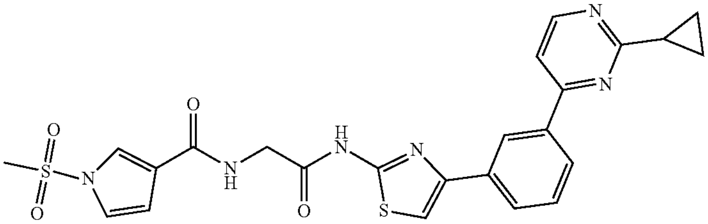 [SMILES: CS(=O)(=O)n1ccc(C(=O)NCC(=O)Nc2nc(-c3cccc(-c4ccnc(C5CC5)n4)c3)cs2)c1] |
| 410 | 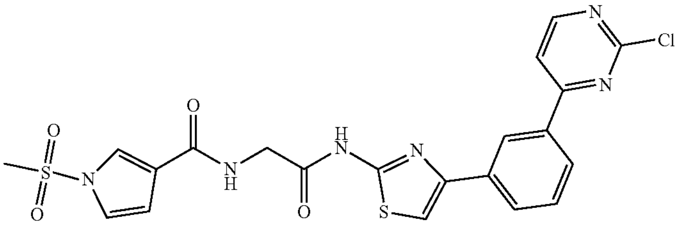 [SMILES: CS(=O)(=O)n1ccc(C(=O)NCC(=O)Nc2nc(-c3cccc(-c4ccnc(Cl)n4)c3)cs2)c1] |
| 411 | 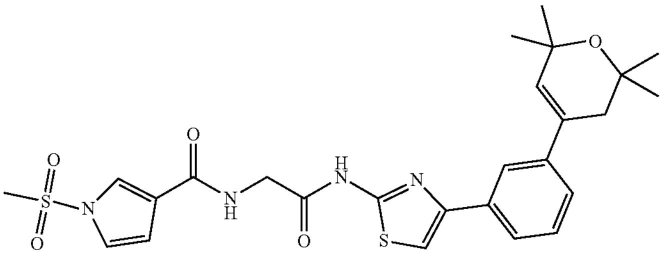 |
| 412 | 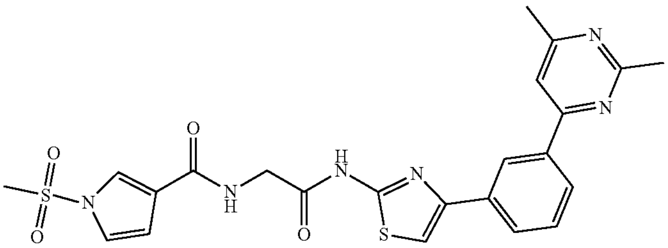 |
| 413 | 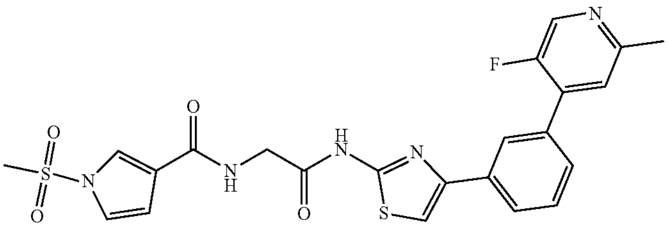 |

TABLE 1-continued
| Compounds of the invention | |
|---|---|
| # | Compound |
| 414 | 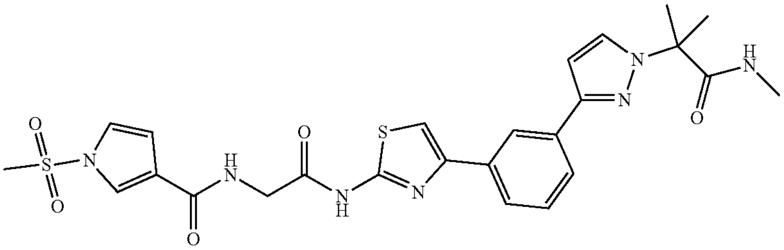 |
| 415 | 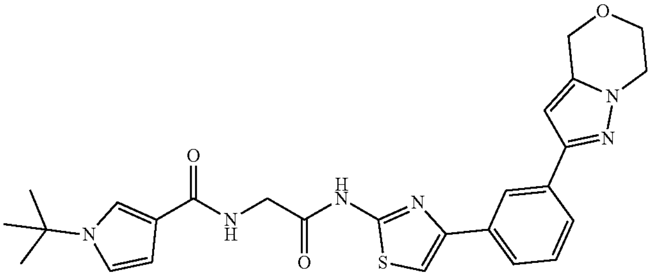 [SMILES: CC(C)(C)n1ccc(C(=O)NCC(=O)Nc2nc(-c3cccc(-c4cc5n(n4)CCOC5)c3)cs2)c1] |
| 416 | 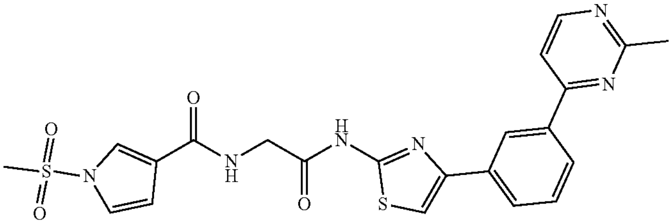 |
| 417 | 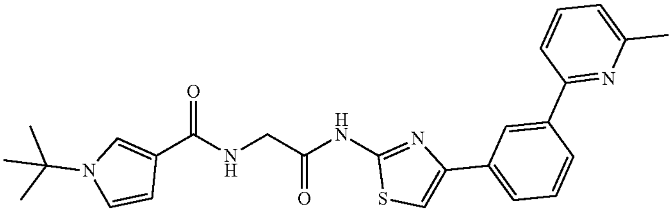 [SMILES: Cc1cccc(-c2cccc(-c3csc(NC(=O)CNC(=O)c4ccn(C(C)(C)C)c4)n3)c2)n1] |
| 418 | 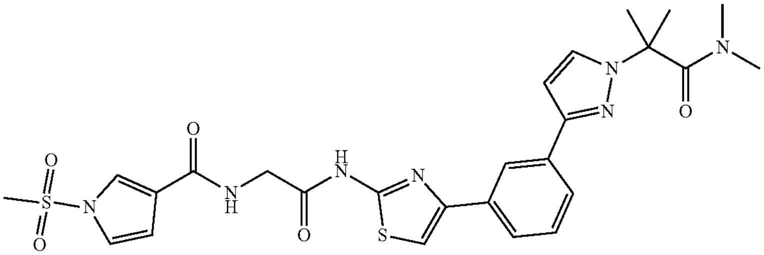 |
| 419 | 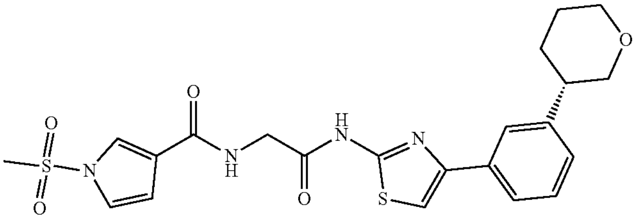 [SMILES: CS(=O)(=O)n1ccc(C(=O)NCC(=O)Nc2nc(-c3cccc([C@@H]4CCCOC4)c3)cs2)c1] |

TABLE 1-continued
| Compounds of the invention | |
|---|---|
| # | Compound |
| 420 | 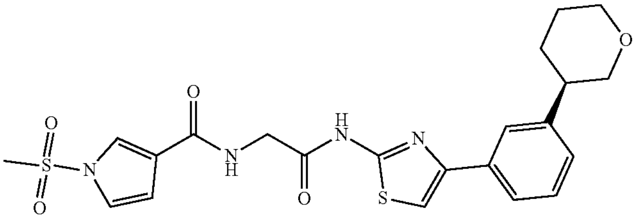 [SMILES: CS(=O)(=O)n1ccc(C(=O)NCC(=O)Nc2nc(-c3cccc([C@H]4CCCOC4)c3)cs2)c1] |
| 421 | 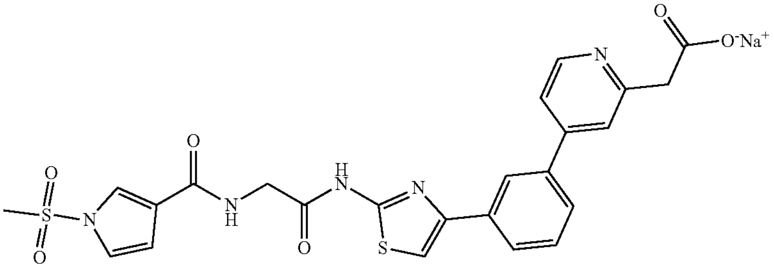 |
| 422 | 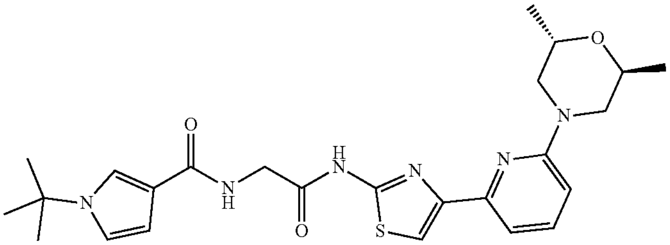 [SMILES: C[C@H]1CN(c2cccc(-c3csc(NC(=O)CNC(=O)c4ccn(C(C)(C)C)c4)n3)n2)C[C@H](C)O1] |
| 423 | 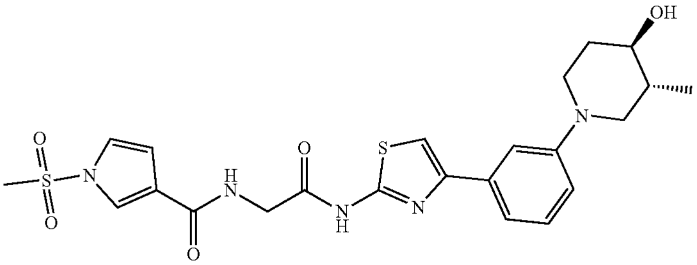 |
| 424 | 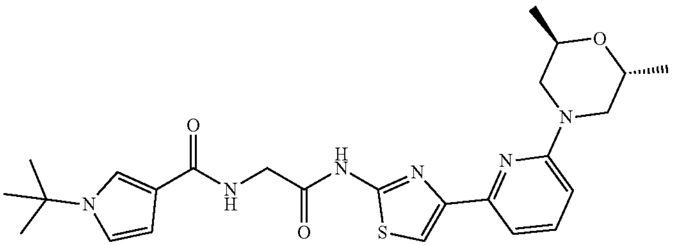 [SMILES: C[C@@H]1CN(c2cccc(-c3csc(NC(=O)CNC(=O)c4ccn(C(C)(C)C)c4)n3)n2)C[C@@H](C)O1] |
| 425 | 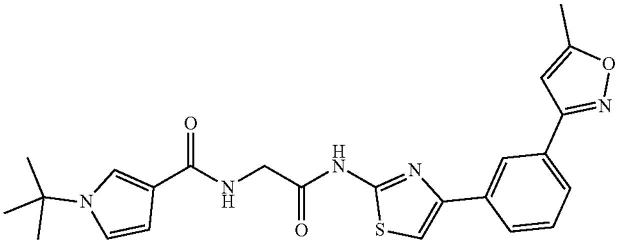 [SMILES: Cc1cc(-c2cccc(-c3csc(NC(=O)CNC(=O)c4ccn(C(C)(C)C)c4)n3)c2)no1] |

TABLE 1-continued
| Compounds of the invention | |
|---|---|
| # | Compound |
| 426 | 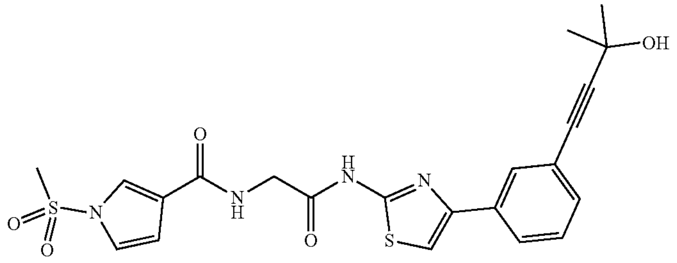 [SMILES: CC(C)(O)C#Cc1cccc(-c2csc(NC(=O)CNC(=O)c3ccn(S(C)(=O)=O)c3)n2)c1] |
| 427 | 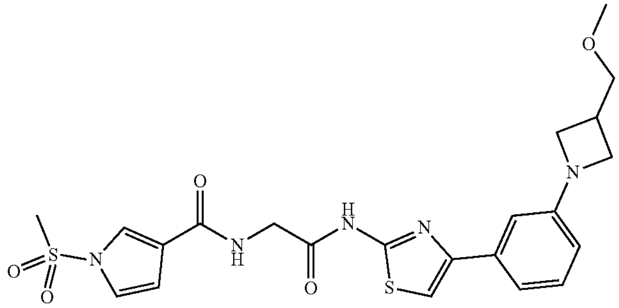 [SMILES: COCC1CN(c2cccc(-c3csc(NC(=O)CNC(=O)c4ccn(S(C)(=O)=O)c4)n3)c2)C1] |
| 428 | 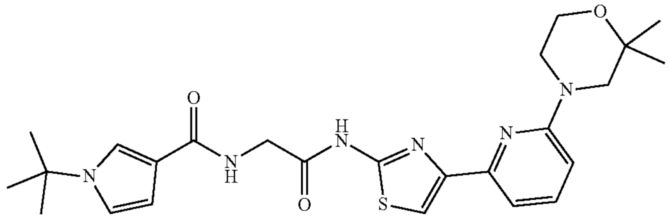 [SMILES: CC1(C)CN(c2cccc(-c3csc(NC(=O)CNC(=O)c4ccn(C(C)(C)C)c4)n3)n2)CCO1] |
| 429 | 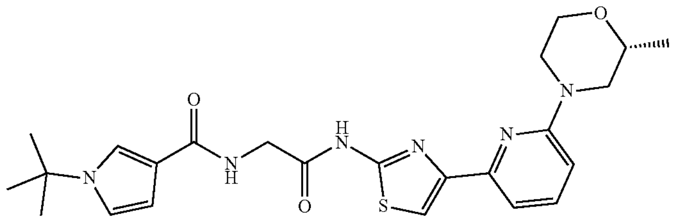 [SMILES: C[C@@H]1CN(c2cccc(-c3csc(NC(=O)CNC(=O)c4ccn(C(C)(C)C)c4)n3)n2)CCO1] |
| 430 | 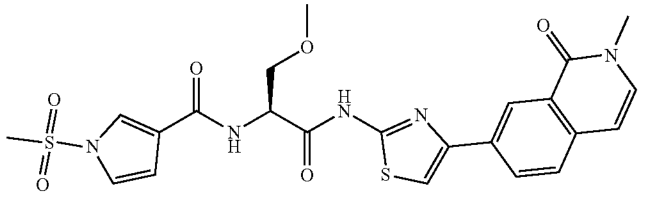 [SMILES: COC[C@H](NC(=O)c1ccn(S(C)(=O)=O)c1)C(=O)Nc1nc(-c2ccc3ccn(C)c(=O)c3c2)cs1] |
| 431 | 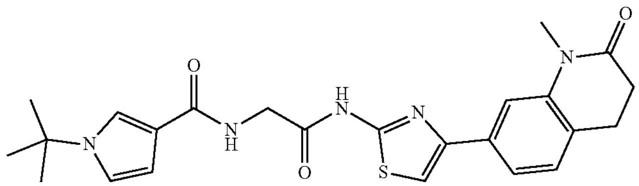 [SMILES: CN1C(=O)CCc2ccc(-c3csc(NC(=O)CNC(=O)c4ccn(C(C)(C)C)c4)n3)cc21] |

TABLE 1-continued
| Compounds of the invention | |
|---|---|
| # | Compound |
| 432 | 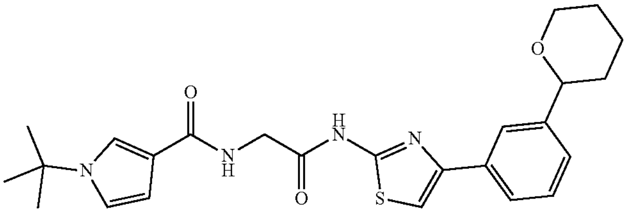 [SMILES: CC(C)(C)n1ccc(C(=O)NCC(=O)Nc2nc(-c3cccc(C4CCCCO4)c3)cs2)c1] |
| 433 | 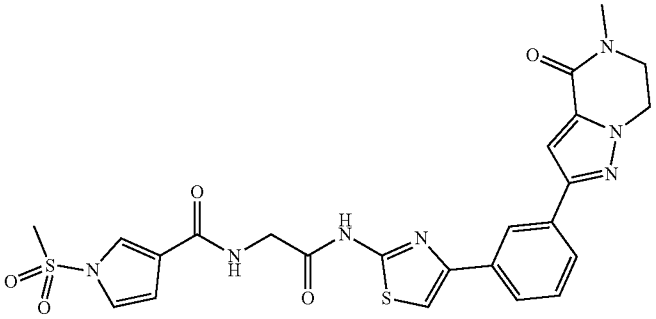 [SMILES: CN1CCn2nc(-c3cccc(-c4csc(NC(=O)CNC(=O)c5ccn(S(C)(=O)=O)c5)n4)c3)cc2C1=O] |
| 434 | 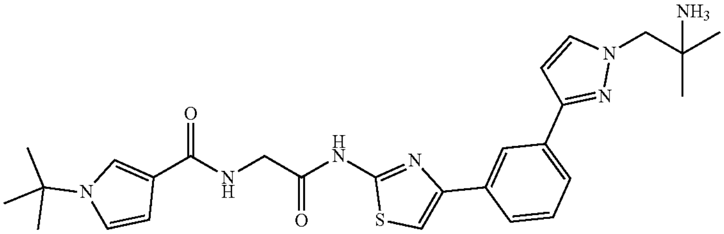 [SMILES: CC(C)(N)Cn1ccc(-c2cccc(-c3csc(NC(=O)CNC(=O)c4ccn(C(C)(C)C)c4)n3)c2)n1] |
| 435 | 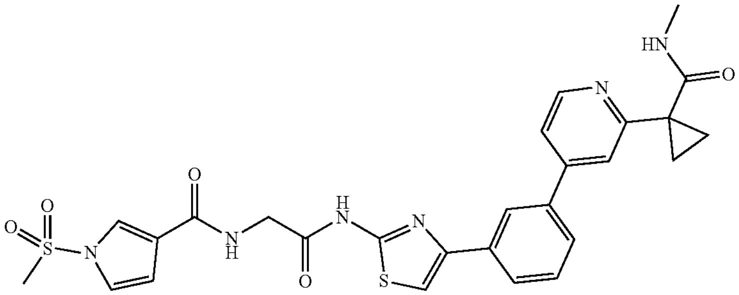 [SMILES: CNC(=O)C1(c2cc(-c3cccc(-c4csc(NC(=O)CNC(=O)c5ccn(S(C)(=O)=O)c5)n4)c3)ccn2)CC1] |
| 436 | 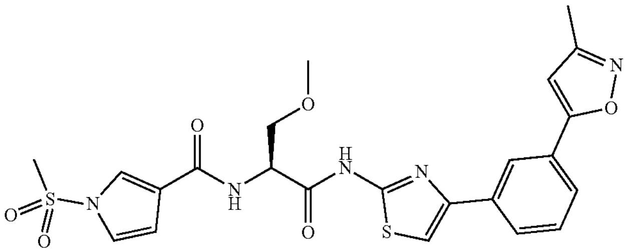 [SMILES: COC[C@H](NC(=O)c1ccn(S(C)(=O)=O)c1)C(=O)Nc1nc(-c2cccc(-c3cc(C)no3)c2)cs1] |

TABLE 1-continued
| Compounds of the invention | |
|---|---|
| # | Compound |
| 437 | 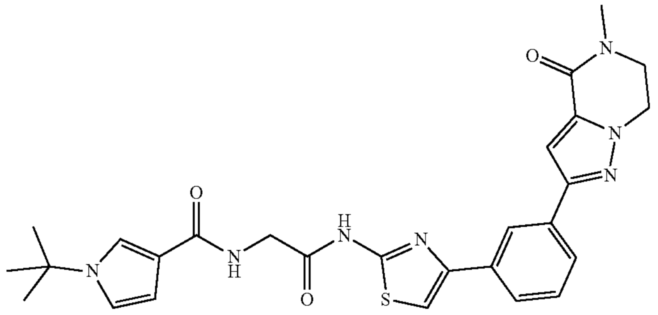 [SMILES: CN1CCn2nc(-c3cccc(-c4csc(NC(=O)CNC(=O)c5ccn(C(C)(C)C)c5)n4)c3)cc2C1=O] |
| 438 | 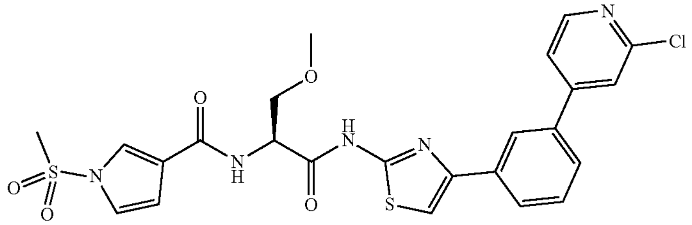 [SMILES: COC[C@H](NC(=O)c1ccn(S(C)(=O)=O)c1)C(=O)Nc1nc(-c2cccc(-c3ccnc(Cl)c3)c2)cs1] |
| 439 | 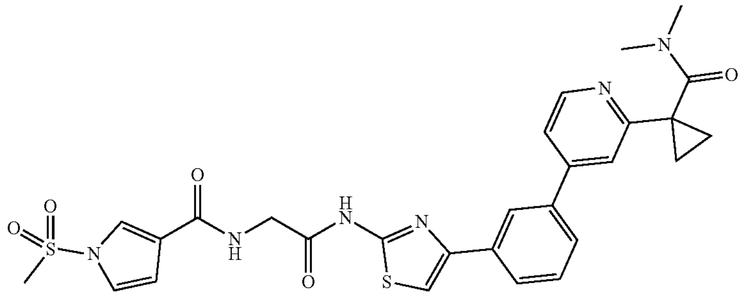 [SMILES: CN(C)C(=O)C1(c2cc(-c3cccc(-c4csc(NC(=O)CNC(=O)c5ccn(S(C)(=O)=O)c5)n4)c3)ccn2)CC1] |
| 440 | 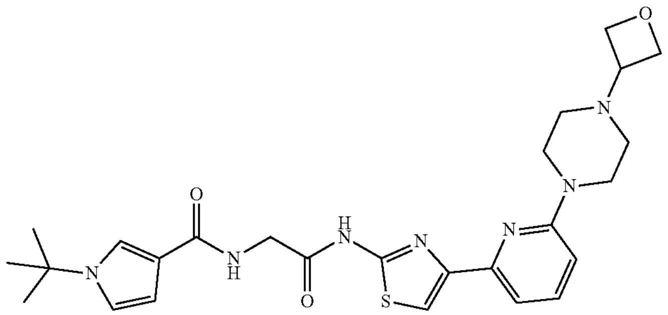 [SMILES: CC(C)(C)n1ccc(C(=O)NCC(=O)Nc2nc(-c3cccc(N4CCN(C5COC5)CC4)n3)cs2)c1] |
| 441 | 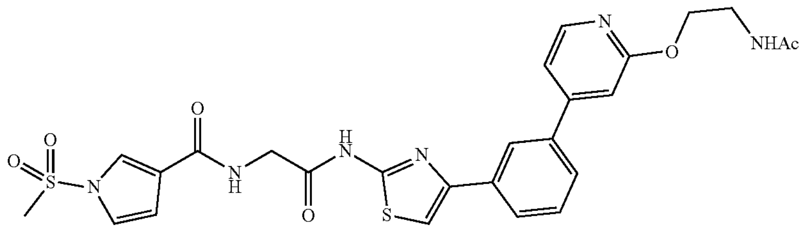 [SMILES: CC(=O)NCCOc1cc(-c2cccc(-c3csc(NC(=O)CNC(=O)c4ccn(S(C)(=O)=O)c4)n3)c2)ccn1] |

TABLE 1-continued
| Compounds of the invention | |
|---|---|
| # | Compound |
| 442 | 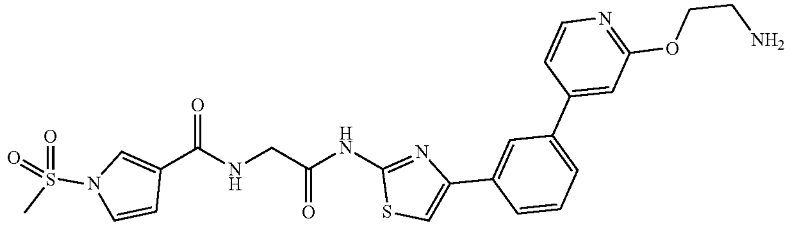 [SMILES: CS(=O)(=O)n1ccc(C(=O)NCC(=O)Nc2nc(-c3cccc(-c4ccnc(OCCN)c4)c3)cs2)c1] |
| 443 | 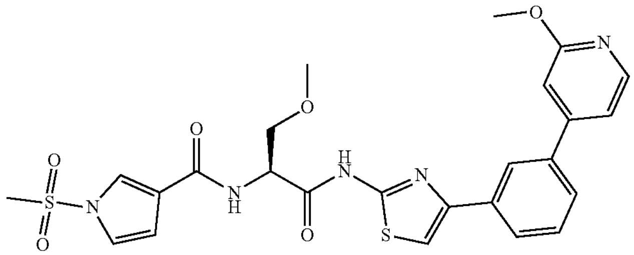 [SMILES: COC[C@H](NC(=O)c1ccn(S(C)(=O)=O)c1)C(=O)Nc1nc(-c2cccc(-c3ccnc(OC)c3)c2)cs1] |
| 444 | 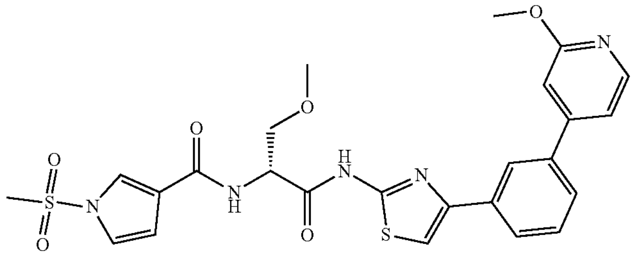 [SMILES: COC[C@@H](NC(=O)c1ccn(S(C)(=O)=O)c1)C(=O)Nc1nc(-c2cccc(-c3ccnc(OC)c3)c2)cs1] |
| 445 | 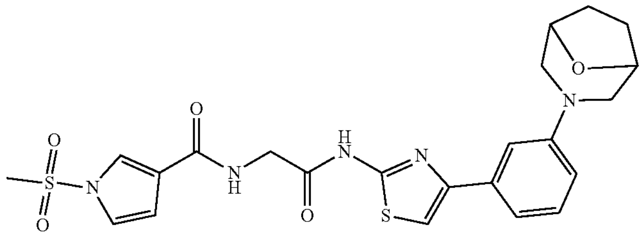 [SMILES: CS(=O)(=O)n1ccc(C(=O)NCC(=O)Nc2nc(-c3cccc(N4CC5CCC(C4)O5)c3)cs2)c1] |
| 446 | 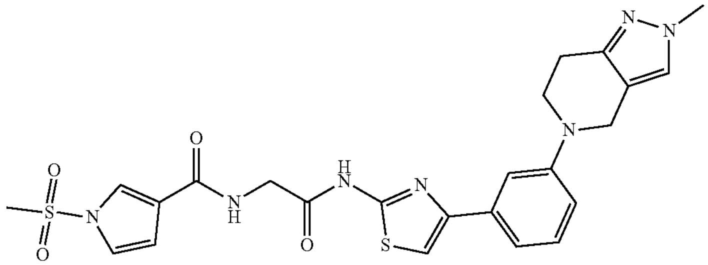 |
| 447 | 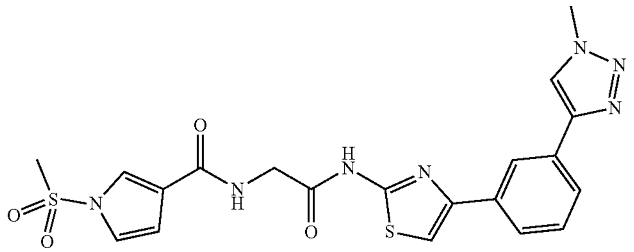 [SMILES: Cn1cc(-c2cccc(-c3csc(NC(=O)CNC(=O)c4ccn(S(C)(=O)=O)c4)n3)c2)nn1] |

TABLE 1-continued
| Compounds of the invention | |
|---|---|
| # | Compound |
| 448 | 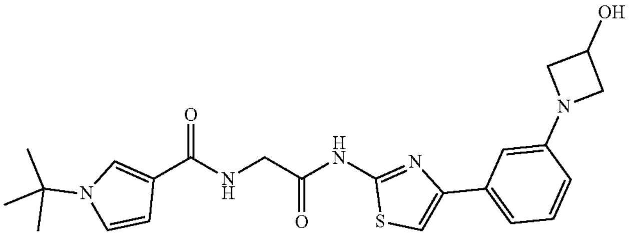 [SMILES: CC(C)(C)n1ccc(C(=O)NCC(=O)Nc2nc(-c3cccc(N4CC(O)C4)c3)cs2)c1] |
| 449 | 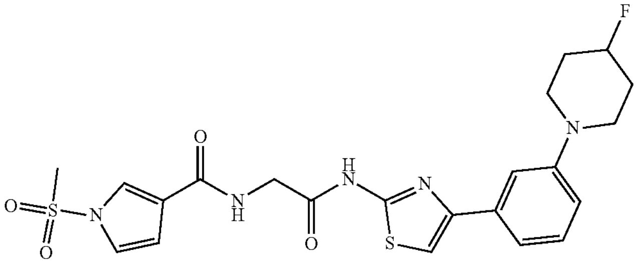 [SMILES: CS(=O)(=O)n1ccc(C(=O)NCC(=O)Nc2nc(-c3cccc(N4CCC(F)CC4)c3)cs2)c1] |
| 450 | 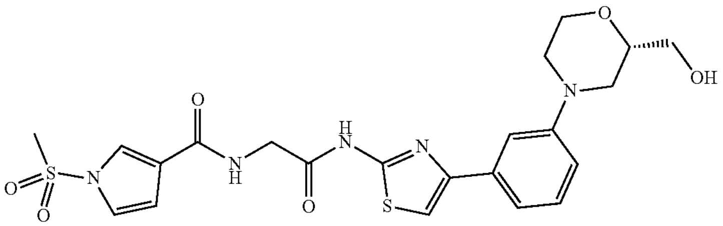 [SMILES: CS(=O)(=O)n1ccc(C(=O)NCC(=O)Nc2nc(-c3cccc(N4CCO[C@H](CO)C4)c3)cs2)c1] |
| 451 | 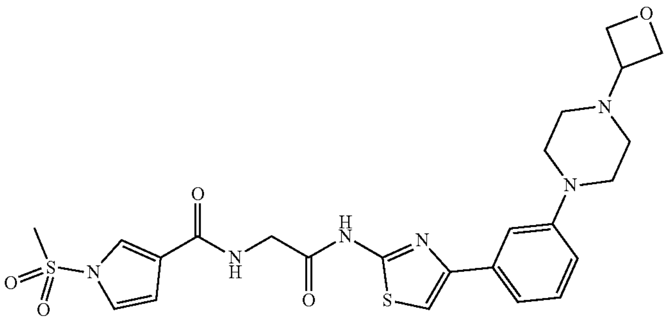 [SMILES: CS(=O)(=O)n1ccc(C(=O)NCC(=O)Nc2nc(-c3cccc(N4CCN(C5COC5)CC4)c3)cs2)c1] |
| 452 | 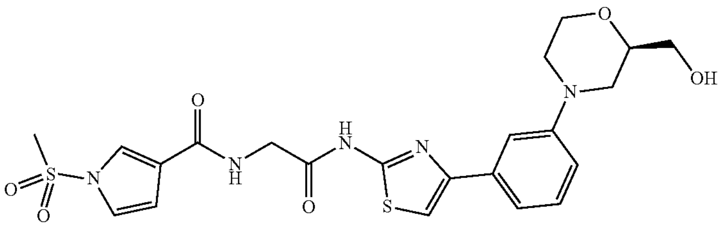 [SMILES: CS(=O)(=O)n1ccc(C(=O)NCC(=O)Nc2nc(-c3cccc(N4CCO[C@@H](CO)C4)c3)cs2)c1] |
| 453 | 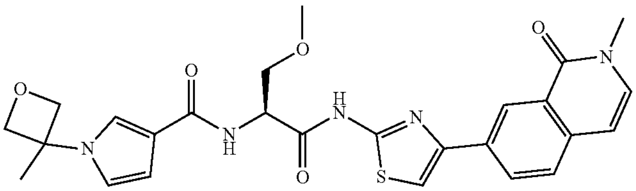 [SMILES: COC[C@H](NC(=O)c1ccn(C2(C)COC2)c1)C(=O)Nc1nc(-c2ccc3ccn(C)c(=O)c3c2)cs1] |

TABLE 1-continued
Compounds of the invention
| # | Compound |
|---|---|
| 454 | 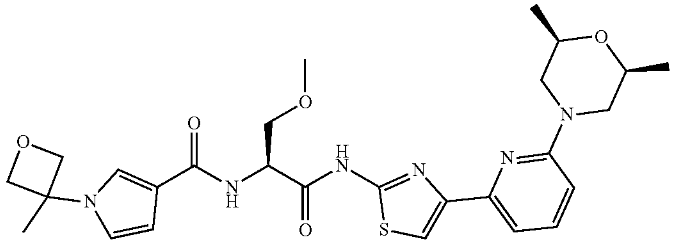 [SMILES: COC[C@H](NC(=O)c1ccn(C2(C)COC2)c1)C(=O)Nc1nc(-c2cccc(N3C[C@@H](C)O[C@@H](C)C3)n2)cs1] |
| 455 | 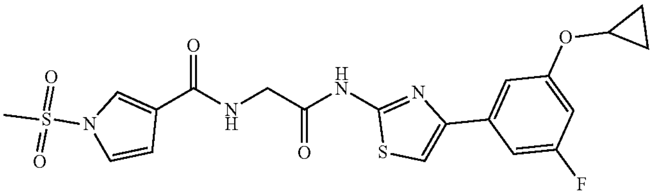 [SMILES: CS(=O)(=O)n1ccc(C(=O)NCC(=O)Nc2nc(-c3cc(F)cc(OC4CC4)c3)cs2)c1] |
| 456 | 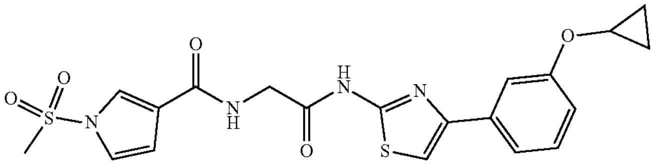 [SMILES: CS(=O)(=O)n1ccc(C(=O)NCC(=O)Nc2nc(-c3cccc(OC4CC4)c3)cs2)c1] |
| 457 | 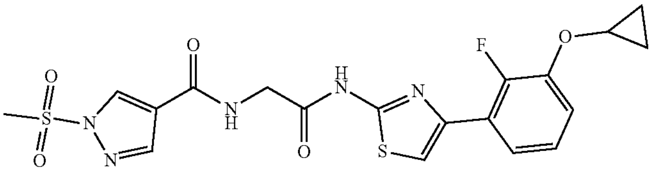 |
| 458 | 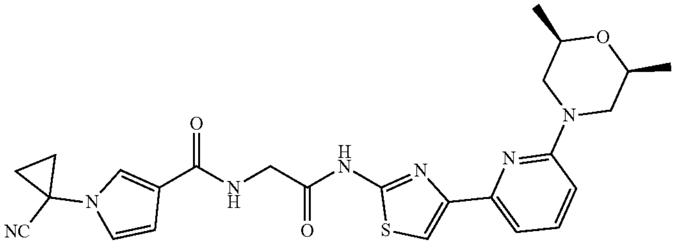 [SMILES: C[C@@H]1CN(c2cccc(-c3csc(NC(=O)CNC(=O)c4ccn(C5(C#N)CC5)c4)n3)n2)C[C@H](C)O1] |
| 459 | 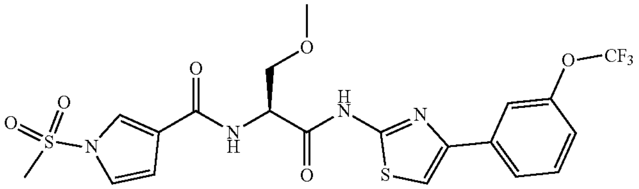 [SMILES: COC[C@H](NC(=O)c1ccn(S(C)(=O)=O)c1)C(=O)Nc1nc(-c2cccc(OC(F)(F)F)c2)cs1] |
| 460 | 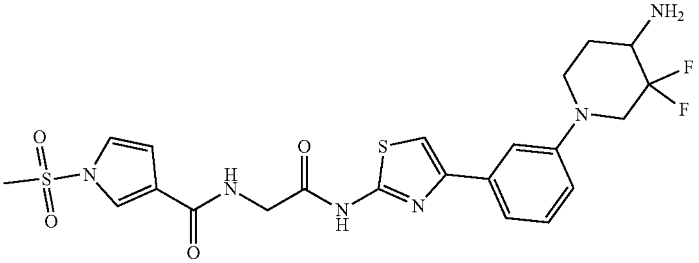 [SMILES: CS(=O)(=O)n1ccc(C(=O)NCC(=O)Nc2nc(-c3cccc(N4CCC(N)C(F)(F)C4)c3)cs2)c1] |

TABLE 1-continued
| Compounds of the invention | |
|---|---|
| # | Compound |
| 461 | 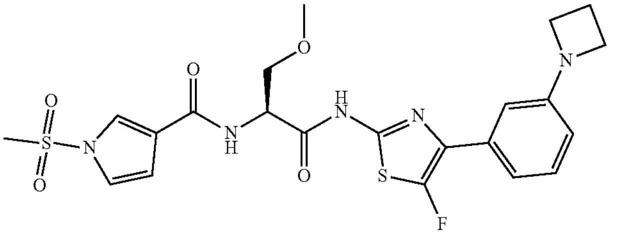 [SMILES: COC[C@H](NC(=O)c1ccn(S(C)(=O)=O)c1)C(=O)Nc1nc(-c2cccc(N3CCC3)c2)c(F)s1] |
| 462 | 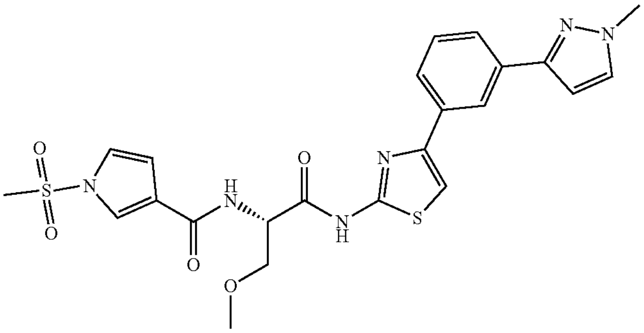 |
| 463 | 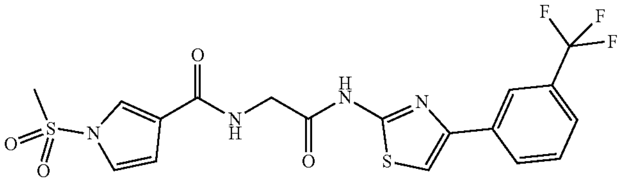 [SMILES: CS(=O)(=O)n1ccc(C(=O)NCC(=O)Nc2nc(-c3cccc(C(F)(F)F)c3)cs2)c1] |
| 464 | 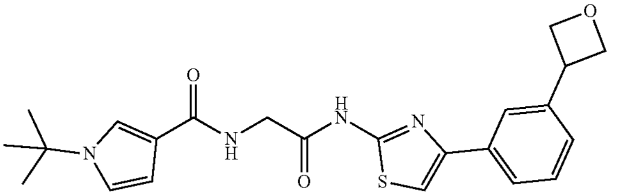 [SMILES: CC(C)(C)n1ccc(C(=O)NCC(=O)Nc2nc(-c3cccc(C4COC4)c3)cs2)c1] |
| 465 | 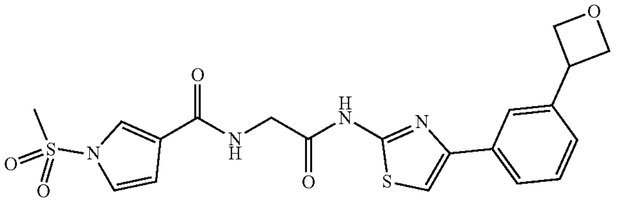 [SMILES: CS(=O)(=O)n1ccc(C(=O)NCC(=O)Nc2nc(-c3cccc(C4COC4)c3)cs2)c1] |
| 466 | 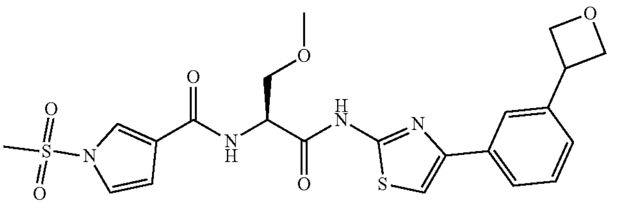 [SMILES: COC[C@H](NC(=O)c1ccn(S(C)(=O)=O)c1)C(=O)Nc1nc(-c2cccc(C3COC3)c2)cs1] |

TABLE 1-continued
| Compounds of the invention | |
|---|---|
| # | Compound |
| 467 | 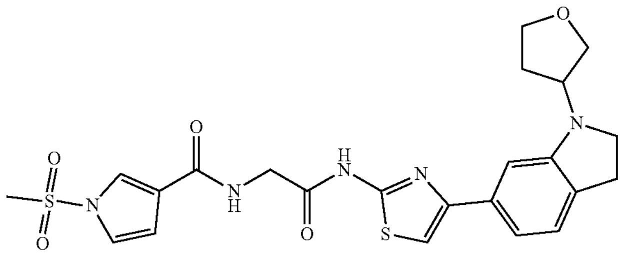 (±) |
| 468 | 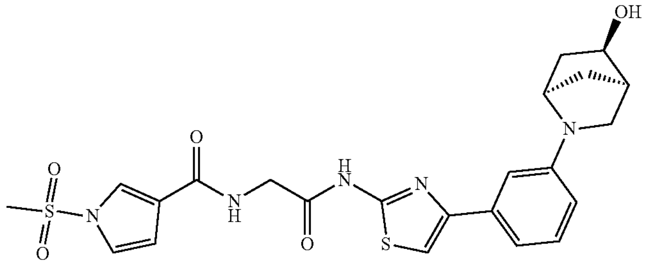 (±) |
| 469 | 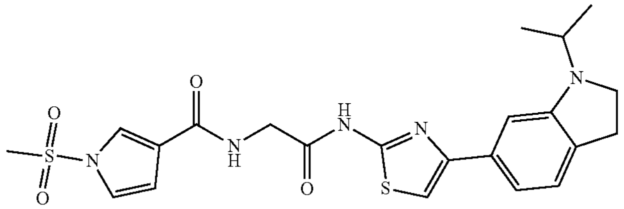 [SMILES: CC(C)N1CCc2ccc(-c3csc(NC(=O)CNC(=O)c4ccn(S(C)(=O)=O)c4)n3)cc21] |
| 470 | 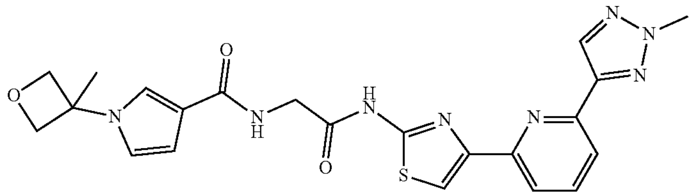 [SMILES: Cn1ncc(-c2cccc(-c3csc(NC(=O)CNC(=O)c4ccn(C5(C)COC5)c4)n3)n2)n1] |
| 471 | 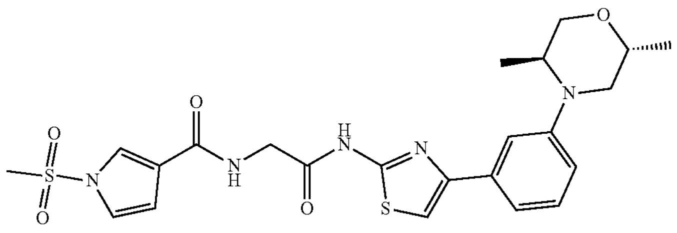 |
| 472 | 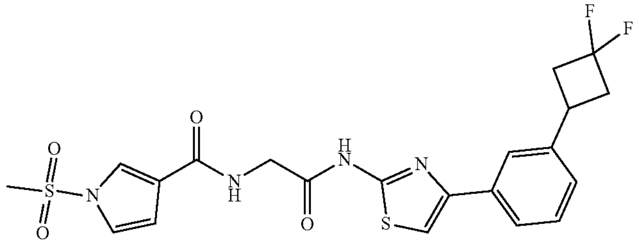 [SMILES: CS(=O)(=O)n1ccc(C(=O)NCC(=O)Nc2nc(-c3cccc(C4CC(F)(F)C4)c3)cs2)c1] |

TABLE 1-continued
| Compounds of the invention | |
|---|---|
| # | Compound |
| 473 | 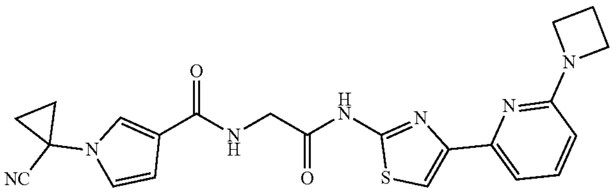 [SMILES: N#CC1(n2ccc(C(=O)NCC(=O)Nc3nc(-c4cccc(N5CCC5)n4)cs3)c2)CC1] |
| 474 | 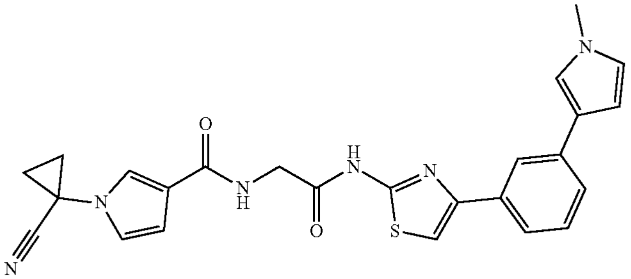 [SMILES: Cn1ccc(-c2cccc(-c3csc(NC(=O)CNC(=O)c4ccn(C5(C#N)CC5)c4)n3)c2)c1] |
| 475 | 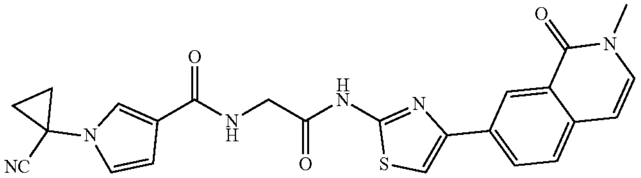 [SMILES: Cn1ccc2ccc(-c3csc(NC(=O)CNC(=O)c4ccn(C5(C#N)CC5)c4)n3)cc2c1=O] |
| 476 | 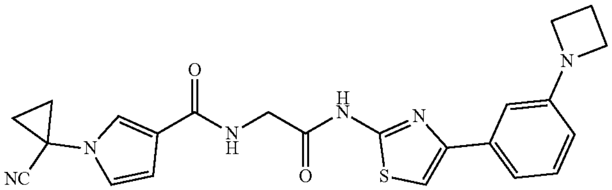 [SMILES: N#CC1(n2ccc(C(=O)NCC(=O)Nc3nc(-c4cccc(N5CCC5)c4)cs3)c2)CC1] |
| 477 | 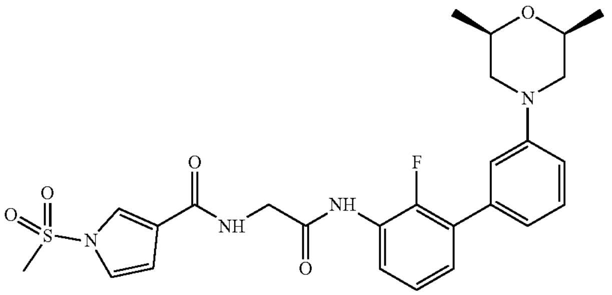 [SMILES: C[C@@H]1CN(c2cccc(-c3cccc(NC(=O)CNC(=O)c4ccn(S(C)(=O)=O)c4)c3F)c2)C[C@H](C)O1] |
| 478 | 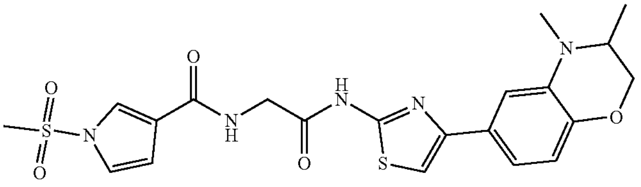 |
(±)

TABLE 1-continued
| Compounds of the invention | |
|---|---|
| # | Compound |
| 479 | 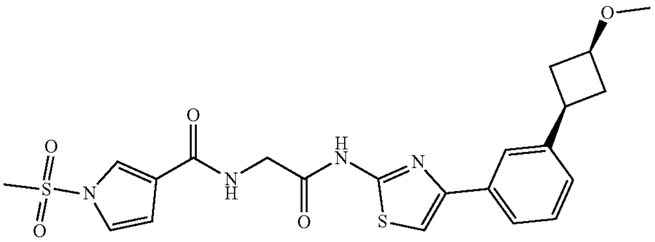 |
| 480 | 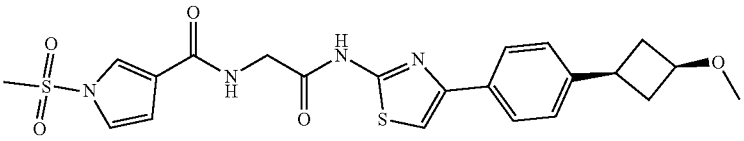 |
| 481 | 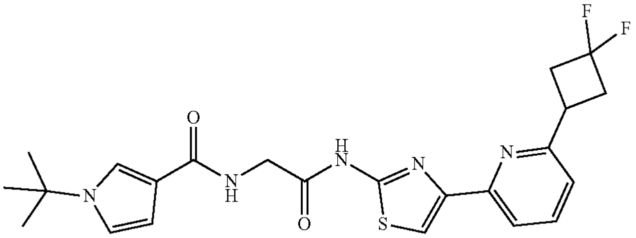 [SMILES: CC(C)(C)n1ccc(C(=O)NCC(=O)Nc2nc(-c3cccc(C4CC(F)(F)C4)n3)cs2)c1] |
| 482 | 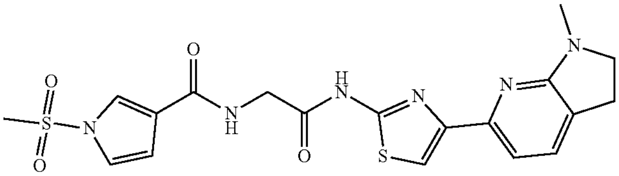 [SMILES: CN1CCc2ccc(-c3csc(NC(=O)CNC(=O)c4ccn(S(C)(=O)=O)c4)n3)nc21] |
| 483 | 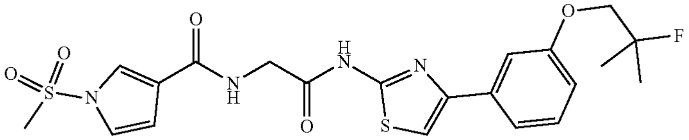 [SMILES: CC(C)(F)COc1cccc(-c2csc(NC(=O)CNC(=O)c3ccn(S(C)(=O)=O)c3)n2)c1] |
| 484 | 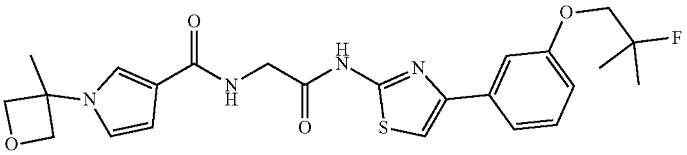 [SMILES: CC(C)(F)COc1cccc(-c2csc(NC(=O)CNC(=O)c3ccn(C4(C)COC4)c3)n2)c1] |
| 485 | 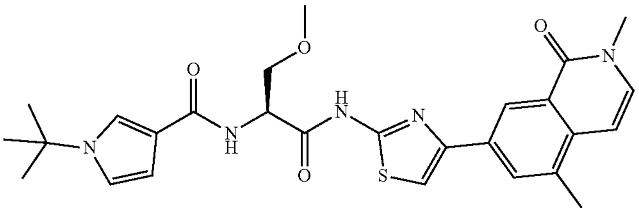 [SMILES: COC[C@H](NC(=O)c1ccn(C(C)(C)C)c1)C(=O)Nc1nc(-c2cc(C)c3ccn(C)c(=O)c3c2)cs1] |

TABLE 1-continued
Compounds of the invention
| # | Compound |
|---|---|
| 486 | 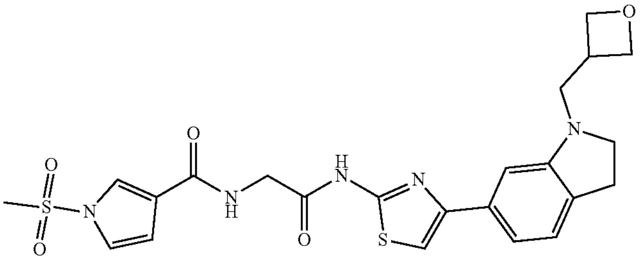 [SMILES: CS(=O)(=O)n1ccc(C(=O)NCC(=O)Nc2nc(-c3ccc4c(c3)N(CC3COC3)CC4)cs2)c1] |
| 487 | 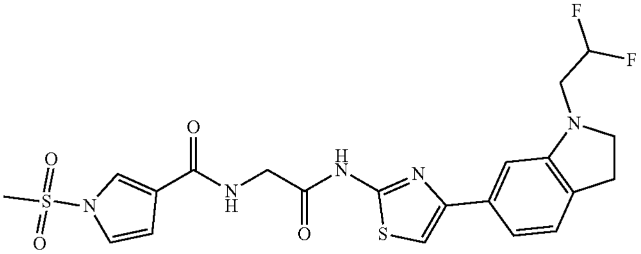 [SMILES: CS(=O)(=O)n1ccc(C(=O)NCC(=O)Nc2nc(-c3ccc4c(c3)N(CC(F)F)CC4)cs2)c1] |
| 488 | 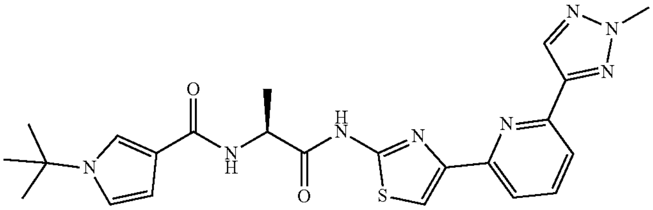 [SMILES: C[C@H](NC(=O)c1ccn(C(C)(C)C)c1)C(=O)Nc1nc(-c2cccc(-c3cnn(C)n3)n2)cs1] |
| 489 | 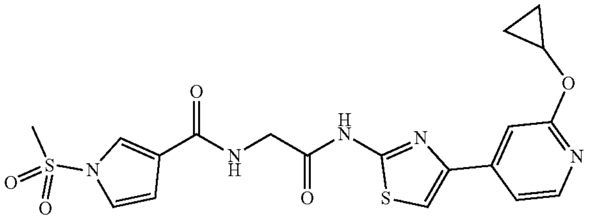 [SMILES: CS(=O)(=O)n1ccc(C(=O)NCC(=O)Nc2nc(-c3ccnc(OC4CC4)c3)cs2)c1] |
| 490 | 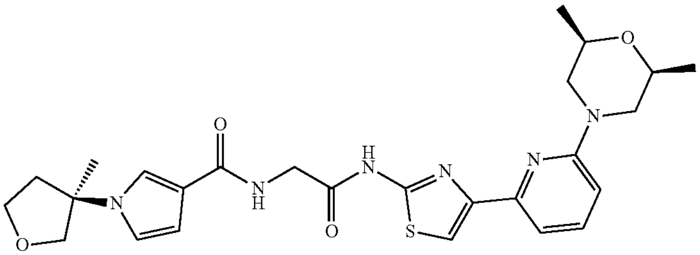 [SMILES: C[C@@H]1CN(c2cccc(-c3csc(NC(=O)CNC(=O)c4ccn([C@]5(C)CCOC5)c4)n3)n2)C[C@H](C)O1] |
| 491 | 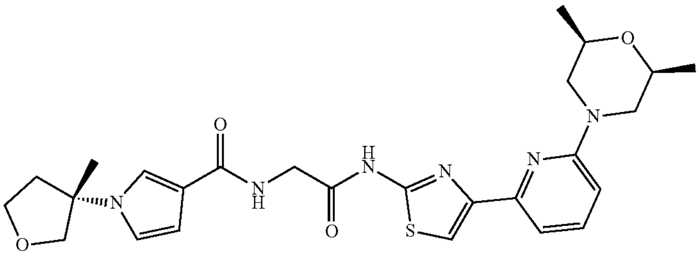 [SMILES: C[C@@H]1CN(c2cccc(-c3csc(NC(=O)CNC(=O)c4ccn([C@@]5(C)CCOC5)c4)n3)n2)C[C@H](C)O1] |

TABLE 1-continued
Compounds of the invention
| # | Compound |
|---|---|
| 492 | 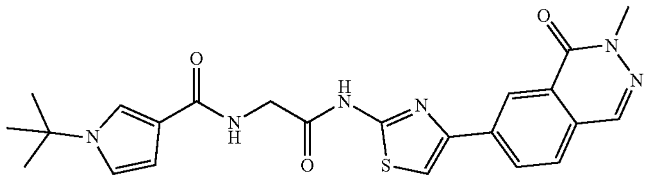 [SMILES: Cn1ncc2ccc(-c3csc(NC(=O)CNC(=O)c4ccn(C(C)(C)C)c4)n3)cc2c1=O] |
| 493 | 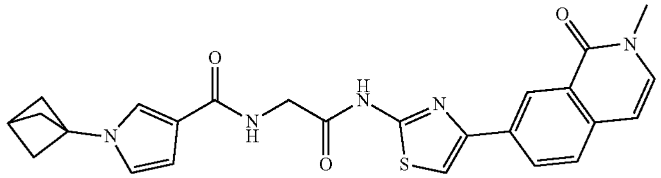 [SMILES: Cn1ccc2ccc(-c3csc(NC(=O)CNC(=O)c4ccn(C56CC(C5)C6)c4)n3)cc2c1=O] |
| 494 | 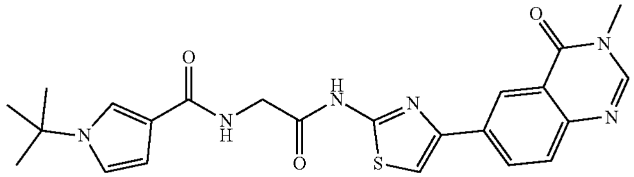 [SMILES: Cn1cnc2ccc(-c3csc(NC(=O)CNC(=O)c4ccn(C(C)(C)C)c4)n3)cc2c1=O] |
| 495 | 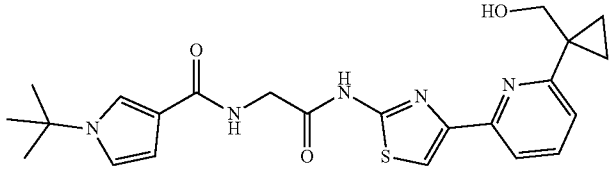 [SMILES: CC(C)(C)n1ccc(C(=O)NCC(=O)Nc2nc(-c3cccc(C4(CO)CC4)n3)cs2)c1] |
| 496 | 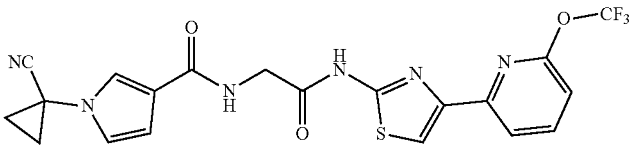 [SMILES: N#CC1(n2ccc(C(=O)NCC(=O)Nc3nc(-c4cccc(OC(F)(F)F)n4)cs3)c2)CC1] |
| 497 | 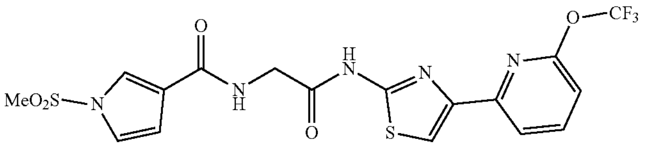 [SMILES: CS(=O)(=O)n1ccc(C(=O)NCC(=O)Nc2nc(-c3cccc(OC(F)(F)F)n3)cs2)c1] |
| 498 | 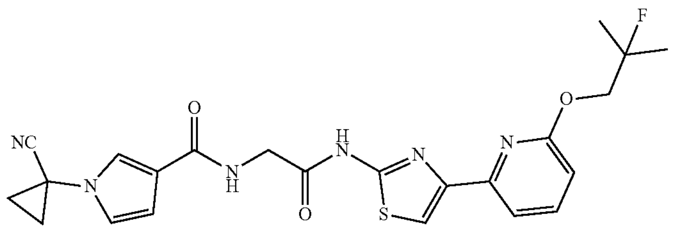 [SMILES: CC(C)(F)COc1cccc(-c2csc(NC(=O)CNC(=O)c3ccn(C4(C#N)CC4)c3)n2)n1] |
| 499 | 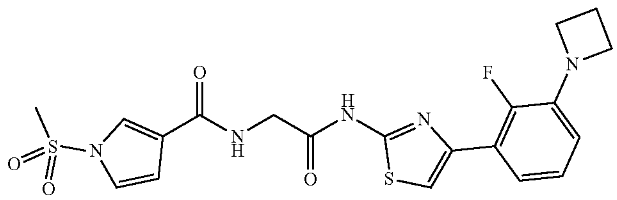 [SMILES: CS(=O)(=O)n1ccc(C(=O)NCC(=O)Nc2nc(-c3cccc(N4CCC4)c3F)cs2)c1] |

TABLE 1-continued
| Compounds of the invention | |
|---|---|
| # | Compound |
| 500 | 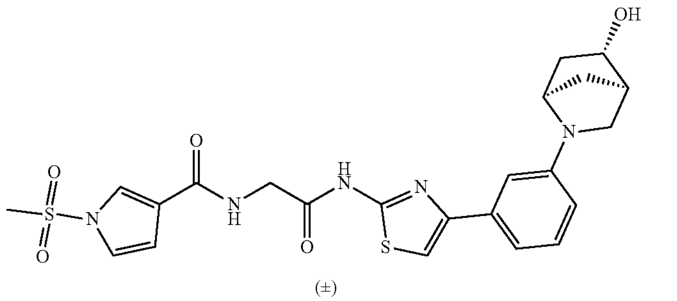 [SMILES: CS(=O)(=O)n1ccc(C(=O)NCC(=O)Nc2nc(-c3cccc(N4C[C@H]5C[C@@H]4C[C@@H]5O)c3)cs2)c1] |
| 501 | 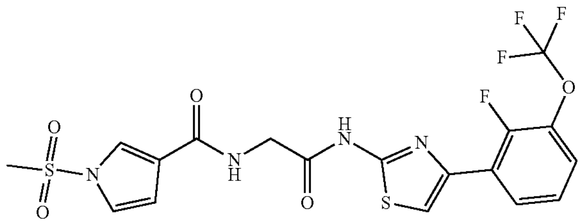 [SMILES: CS(=O)(=O)n1ccc(C(=O)NCC(=O)Nc2nc(-c3cccc(OC(F)(F)F)c3F)cs2)c1] |
| 502 | 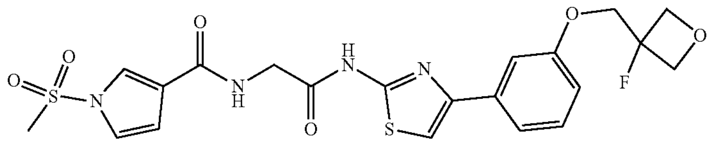 [SMILES: CS(=O)(=O)n1ccc(C(=O)NCC(=O)Nc2nc(-c3cccc(OCC4(F)COC4)c3)cs2)c1] |
| 503 | 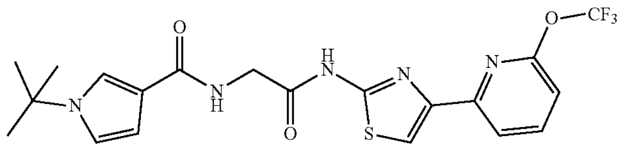 [SMILES: CC(C)(C)n1ccc(C(=O)NCC(=O)Nc2nc(-c3cccc(OC(F)(F)F)n3)cs2)c1] |
| 504 | 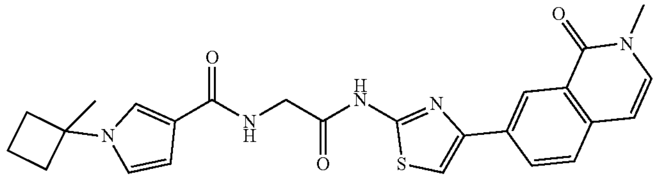 [SMILES: Cn1ccc2ccc(-c3csc(NC(=O)CNC(=O)c4ccn(C5(C)CCC5)c4)n3)cc2c1=O] |
| 505 | 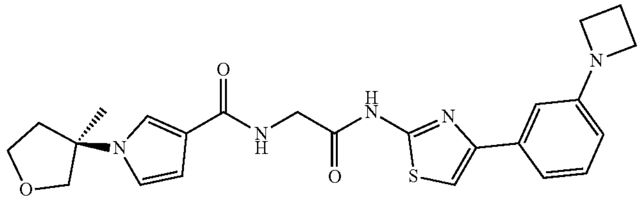 [SMILES: C[C@@]1(n2ccc(C(=O)NCC(=O)Nc3nc(-c4cccc(N5CCC5)c4)cs3)c2)CCOC1] |
| 506 | 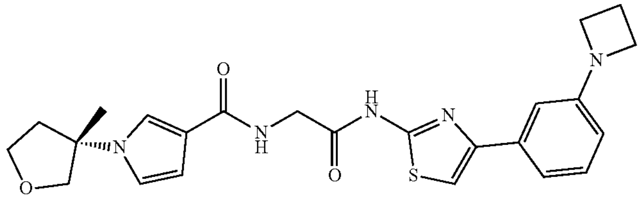 [SMILES: C[C@]1(n2ccc(C(=O)NCC(=O)Nc3nc(-c4cccc(N5CCC5)c4)cs3)c2)CCOC1] |

TABLE 1-continued
| Compounds of the invention | |
|---|---|
| # | Compound |
| 507 | 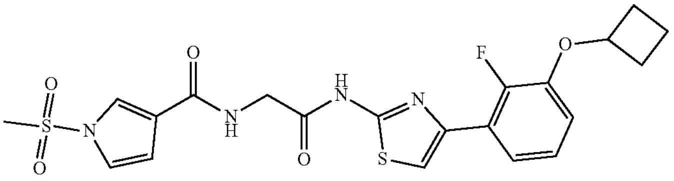 [SMILES: CS(=O)(=O)n1ccc(C(=O)NCC(=O)Nc2nc(-c3cccc(OC4CCC4)c3F)cs2)c1] |
| 508 | 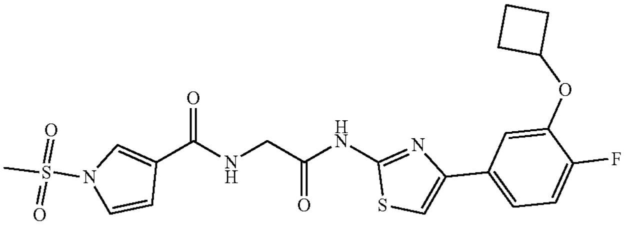 [SMILES: CS(=O)(=O)n1ccc(C(=O)NCC(=O)Nc2nc(-c3ccc(F)c(OC4CCC4)c3)cs2)c1] |
| 509 | 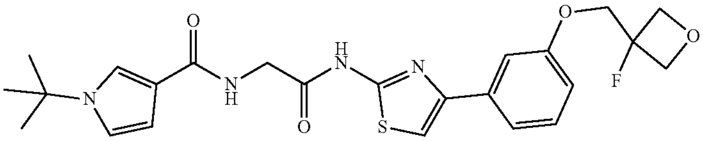 [SMILES: CC(C)(C)n1ccc(C(=O)NCC(=O)Nc2nc(-c3cccc(OCC4(F)COC4)c3)cs2)c1] |
| 510 | 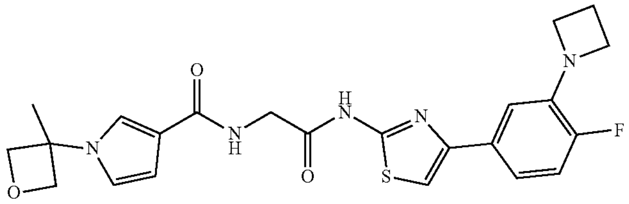 [SMILES: CC1(n2ccc(C(=O)NCC(=O)Nc3nc(-c4ccc(F)c(N5CCC5)c4)cs3)c2)COC1] |
| 511 | 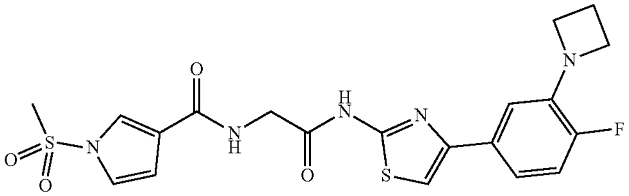 [SMILES: CS(=O)(=O)n1ccc(C(=O)NCC(=O)Nc2nc(-c3ccc(F)c(N4CCC4)c3)cs2)c1] |
| 512 | 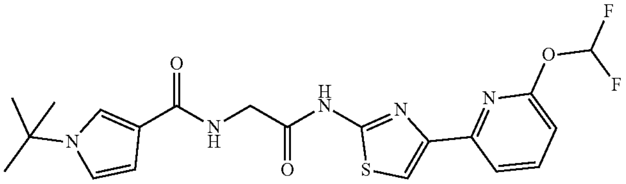 [SMILES: CC(C)(C)n1ccc(C(=O)NCC(=O)Nc2nc(-c3cccc(OC(F)F)n3)cs2)c1] |
| 513 | 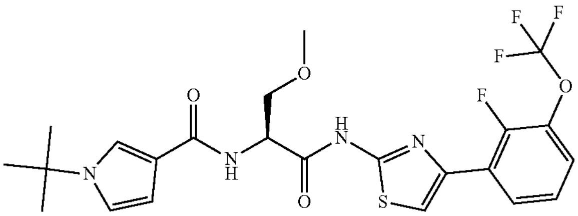 [SMILES: COC[C@H](NC(=O)c1ccn(C(C)(C)C)c1)C(=O)Nc1nc(-c2cccc(OC(F)(F)F)c2F)cs1] |

TABLE 1-continued
| Compounds of the invention | |
|---|---|
| # | Compound |
| 514 | 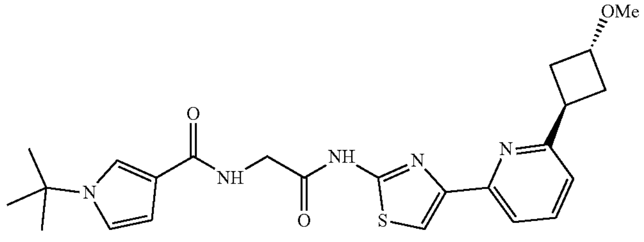 [SMILES: CO[C@H]1C[C@H](c2cccc(-c3csc(NC(=O)CNC(=O)c4ccn(C(C)(C)C)c4)n3)n2)C1] |
| 515 | 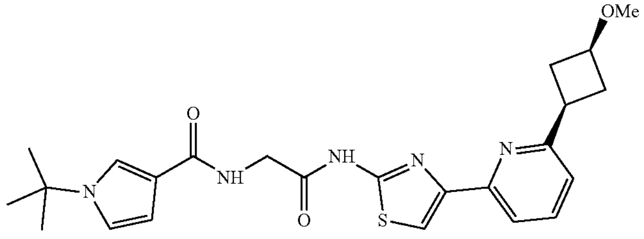 [SMILES: CO[C@H]1C[C@@H](c2cccc(-c3csc(NC(=O)CNC(=O)c4ccn(C(C)(C)C)c4)n3)n2)C1] |
| 516 | 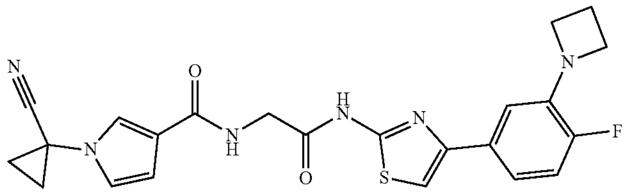 [SMILES: N#CC1(n2ccc(C(=O)NCC(=O)Nc3nc(-c4ccc(F)c(N5CCC5)c4)cs3)c2)CC1] |
| 517 | 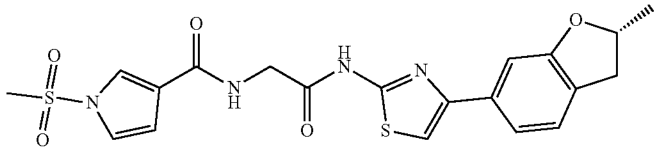 |
| 518 | 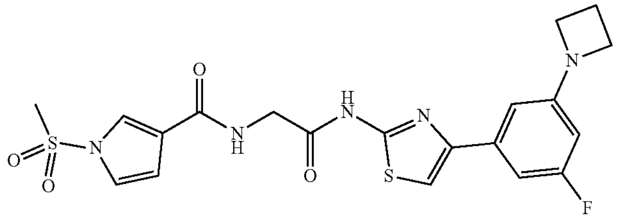 [SMILES: CS(=O)(=O)n1ccc(C(=O)NCC(=O)Nc2nc(-c3cc(F)cc(N4CCC4)c3)cs2)c1] |
| 519 | 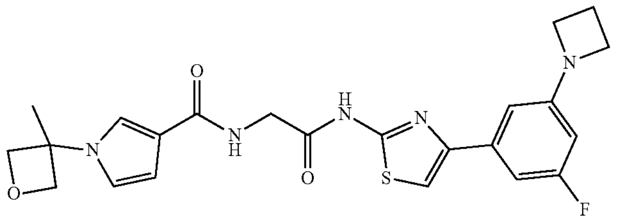 [SMILES: CC1(n2ccc(C(=O)NCC(=O)Nc3nc(-c4cc(F)cc(N5CCC5)c4)cs3)c2)COC1] |

TABLE 1-continued
| Compounds of the invention | |
|---|---|
| # | Compound |
| 520 | 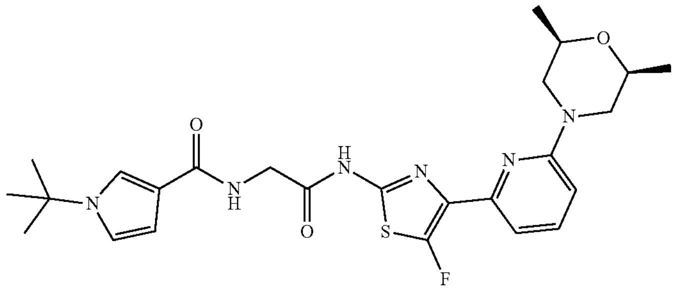 [SMILES: C[C@@H]1CN(c2cccc(-c3nc(NC(=O)CNC(=O)c4ccn(C(C)(C)C)c4)sc3F)n2)C[C@H](C)O1] |
| 521 | 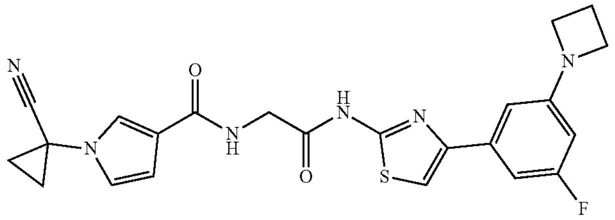 [SMILES: N#CC1(n2ccc(C(=O)NCC(=O)Nc3nc(-c4cc(F)cc(N5CCC5)c4)cs3)c2)CC1] |
| 522 | 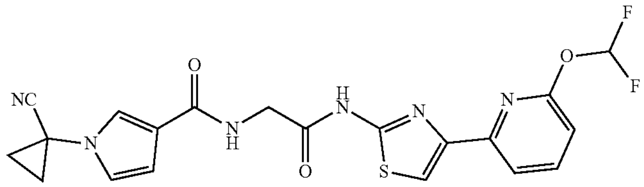 [SMILES: N#CC1(n2ccc(C(=O)NCC(=O)Nc3nc(-c4cccc(OC(F)F)n4)cs3)c2)CC1] |
| 523 | 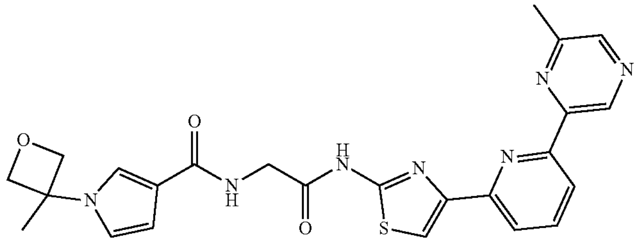 [SMILES: Cc1cncc(-c2cccc(-c3csc(NC(=O)CNC(=O)c4ccn(C5(C)COC5)c4)n3)n2)n1] |
| 524 | 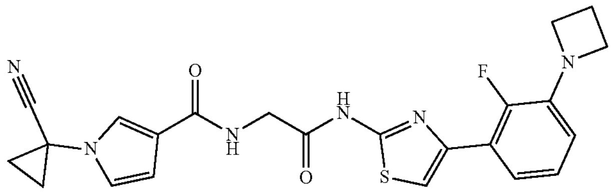 [SMILES: N#CC1(n2ccc(C(=O)NCC(=O)Nc3nc(-c4cccc(N5CCC5)c4F)cs3)c2)CC1] |
| 525 | 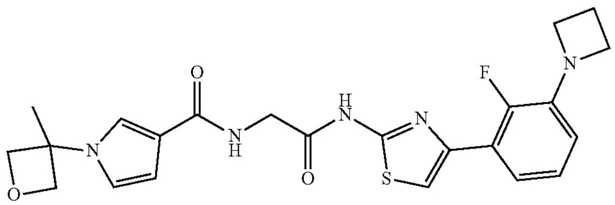 [SMILES: CC1(n2ccc(C(=O)NCC(=O)Nc3nc(-c4cccc(N5CCC5)c4F)cs3)c2)COC1] |

TABLE 1-continued
| Compounds of the invention | |
|---|---|
| # | Compound |
| 526 | 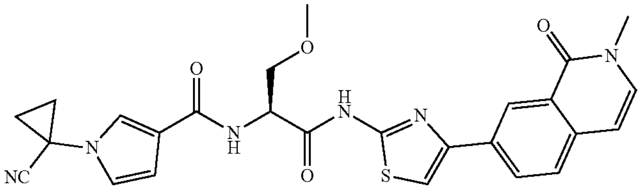 [SMILES: COC[C@H](NC(=O)c1ccn(C2(C#N)CC2)c1)C(=O)Nc1nc(-c2ccc3ccn(C)c(=O)c3c2)cs1] |
| 527 | 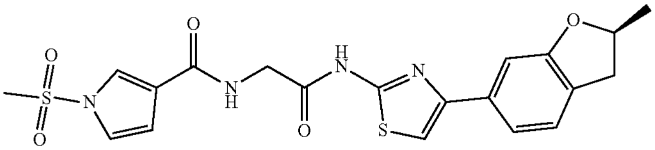 |
| 528 | 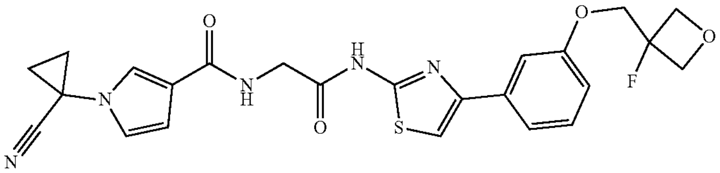 [SMILES: N#CC1(n2ccc(C(=O)NCC(=O)Nc3nc(-c4cccc(OCC5(F)COC5)c4)cs3)c2)CC1] |
| 529 | 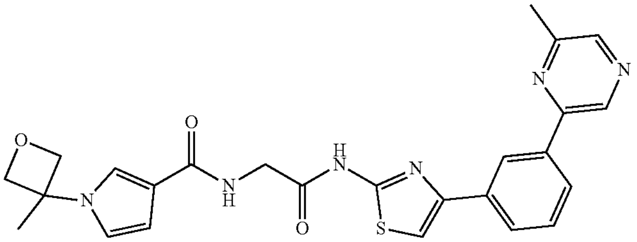 [SMILES: Cc1cncc(-c2cccc(-c3csc(NC(=O)CNC(=O)c4ccn(C5(C)COC5)c4)n3)c2)n1] |
| 530 | 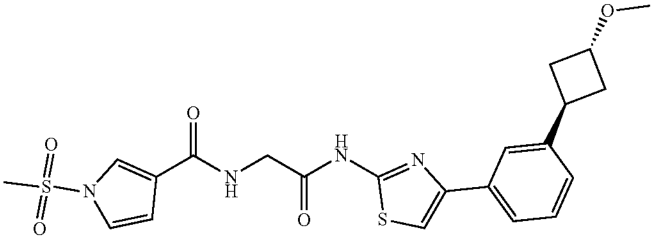 |
| 531 | 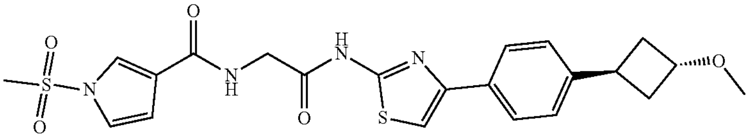 |
| 532 | 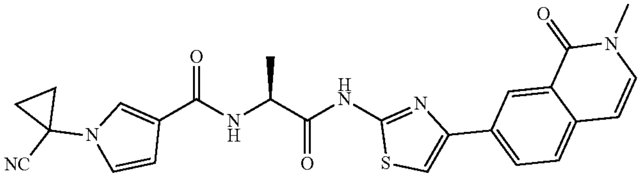 [SMILES: C[C@H](NC(=O)c1ccn(C2(C#N)CC2)c1)C(=O)Nc1nc(-c2ccc3ccn(C)c(=O)c3c2)cs1] |

TABLE 1-continued
Compounds of the invention
| # | Compound |
|---|---|
| 533 | 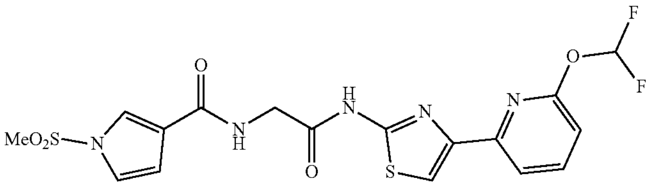 [SMILES: CS(=O)(=O)n1ccc(C(=O)NCC(=O)Nc2nc(-c3cccc(OC(F)F)n3)cs2)c1] |
| 534 | 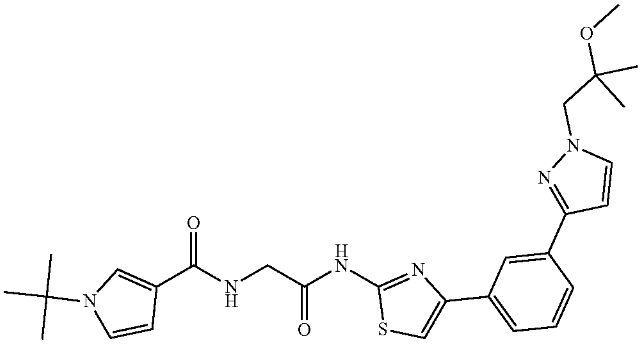 [SMILES: COC(C)(C)Cn1ccc(-c2cccc(-c3csc(NC(=O)CNC(=O)c4ccn(C(C)(C)C)c4)n3)c2)n1] |
| 535 | 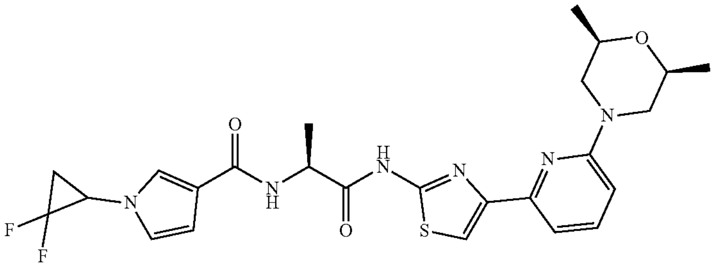 (±) |
| 536 | 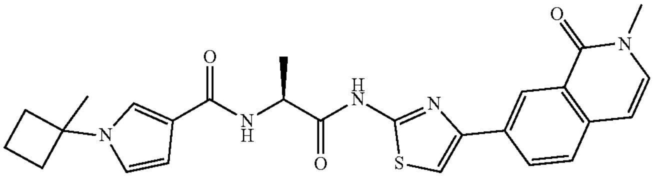 [SMILES: C[C@H](NC(=O)c1ccn(C2(C)CCC2)c1)C(=O)Nc1nc(-c2ccc3ccn(C)c(=O)c3c2)cs1] |
| 537 | 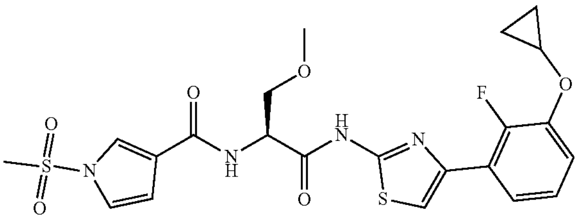 [SMILES: COC[C@H](NC(=O)c1ccn(S(C)(=O)=O)c1)C(=O)Nc1nc(-c2cccc(OC3CC3)c2F)cs1] |
| 538 | 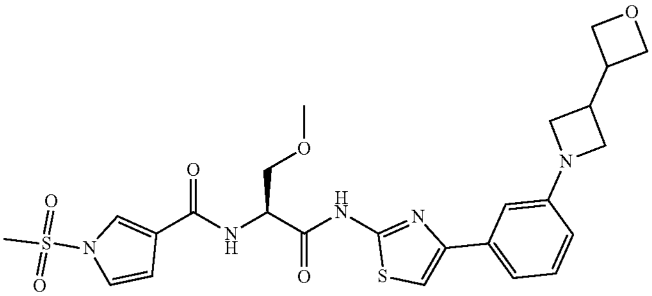 [SMILES: COC[C@H](NC(=O)c1ccn(S(C)(=O)=O)c1)C(=O)Nc1nc(-c2cccc(N3CC(C4COC4)C3)c2)cs1] |

TABLE 1-continued
| Compounds of the invention | |
|---|---|
| # | Compound |
| 539 | 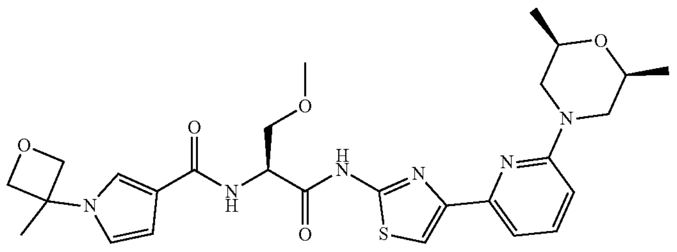 [SMILES: COC[C@H](NC(=O)c1ccn(C2(C)COC2)c1)C(=O)Nc1nc(-c2cccc(N3C[C@@H](C)O[C@@H](C)C3)n2)cs1] |
| 540 | 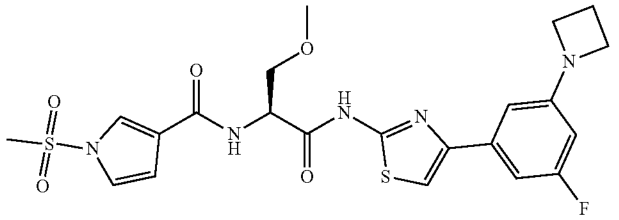 [SMILES: COC[C@H](NC(=O)c1ccn(S(C)(=O)=O)c1)C(=O)Nc1nc(-c2cc(F)cc(N3CCC3)c2)cs1] |
| 541 | 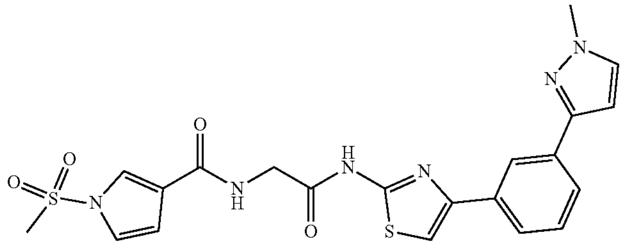 [SMILES: Cn1ccc(-c2cccc(-c3csc(NC(=O)CNC(=O)c4ccn(S(C)(=O)=O)c4)n3)c2)n1] |
| 542 | 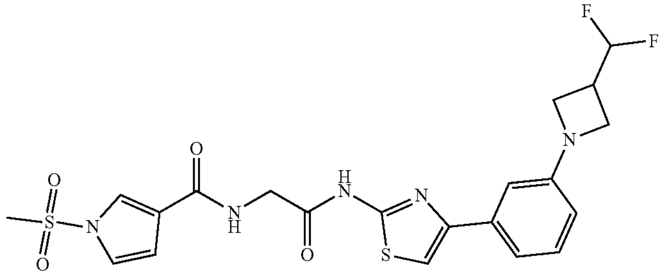 [SMILES: CS(=O)(=O)n1ccc(C(=O)NCC(=O)Nc2nc(-c3cccc(N4CC(C(F)F)C4)c3)cs2)c1] |
| 543 | 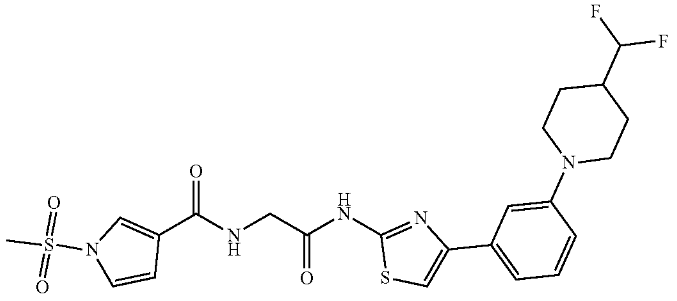 [SMILES: CS(=O)(=O)n1ccc(C(=O)NCC(=O)Nc2nc(-c3cccc(N4CCC(C(F)F)CC4)c3)cs2)c1] |
| 544 | 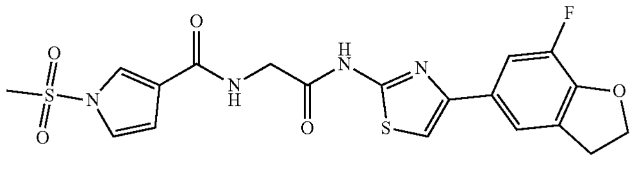 [SMILES: CS(=O)(=O)n1ccc(C(=O)NCC(=O)Nc2nc(-c3cc(F)c4c(c3)CCO4)cs2)c1] |

TABLE 1-continued
Compounds of the invention
| # | Compound |
|---|---|
| 545 | 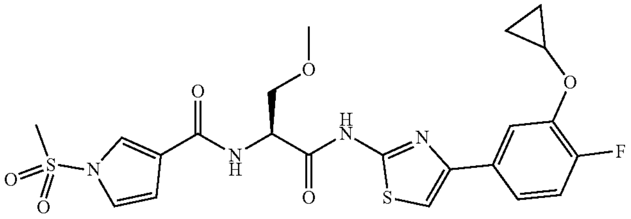 [SMILES: COC[C@H](NC(=O)c1ccn(S(C)(=O)=O)c1)C(=O)Nc1nc(-c2ccc(F)c(OC3CC3)c2)cs1] |
| 546 | 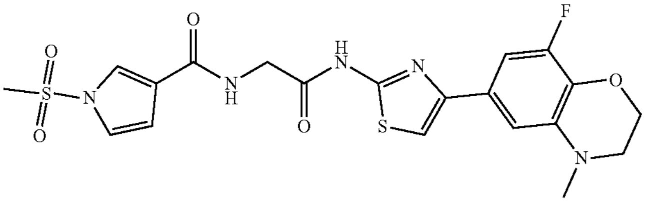 [SMILES: CN1CCOc2c(F)cc(-c3csc(NC(=O)CNC(=O)c4ccn(S(C)(=O)=O)c4)n3)cc21] |
| 547 | 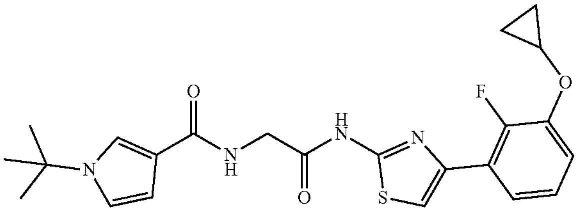 [SMILES: CC(C)(C)n1ccc(C(=O)NCC(=O)Nc2nc(-c3cccc(OC4CC4)c3F)cs2)c1] |
| 548 | 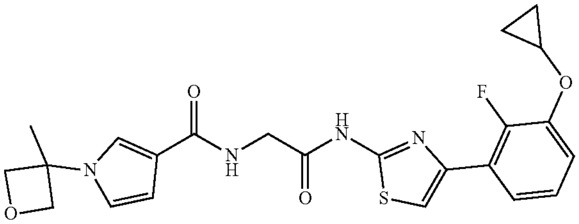 [SMILES: CC1(n2ccc(C(=O)NCC(=O)Nc3nc(-c4cccc(OC5CC5)c4F)cs3)c2)COC1] |
| 549 | 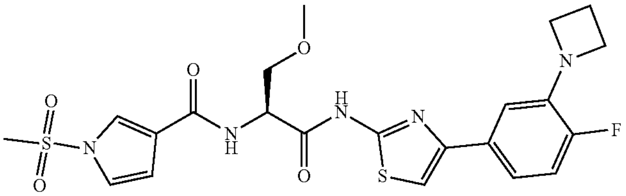 [SMILES: COC[C@H](NC(=O)c1ccn(S(C)(=O)=O)c1)C(=O)Nc1nc(-c2ccc(F)c(N3CCC3)c2)cs1] |
| 550 | 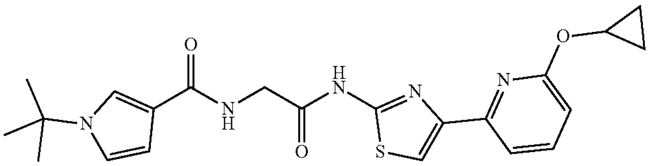 [SMILES: CC(C)(C)n1ccc(C(=O)NCC(=O)Nc2nc(-c3cccc(OC4CC4)n3)cs2)c1] |
| 551 | 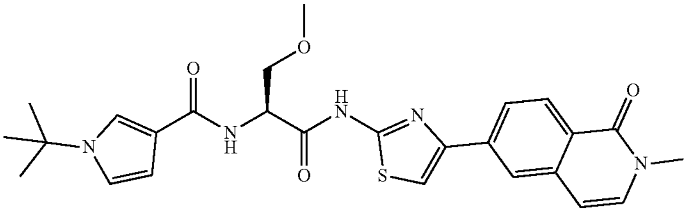 [SMILES: COC[C@H](NC(=O)c1ccn(C(C)(C)C)c1)C(=O)Nc1nc(-c2ccc3c(=O)n(C)ccc3c2)cs1] |

TABLE 1-continued
| Compounds of the invention | |
|---|---|
| # | Compound |
| 552 | 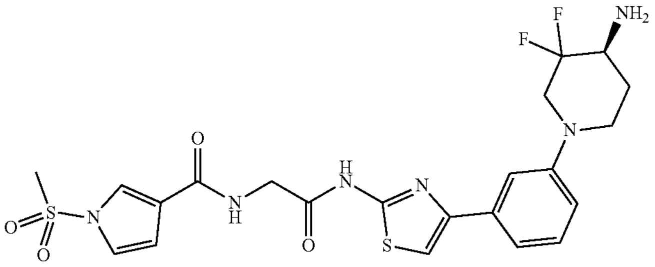 [SMILES: CS(=O)(=O)n1ccc(C(=O)NCC(=O)Nc2nc(-c3cccc(N4CC[C@H](N)C(F)(F)C4)c3)cs2)c1] |
| 553 | 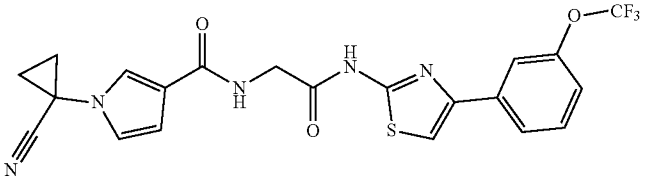 [SMILES: N#CC1(n2ccc(C(=O)NCC(=O)Nc3nc(-c4cccc(OC(F)(F)F)c4)cs3)c2)CC1] |
| 554 | 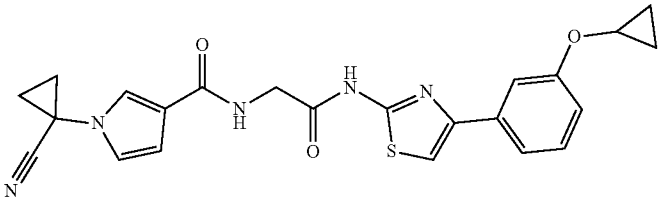 [SMILES: N#CC1(n2ccc(C(=O)NCC(=O)Nc3nc(-c4cccc(OC5CC5)c4)cs3)c2)CC1] |
| 555 | 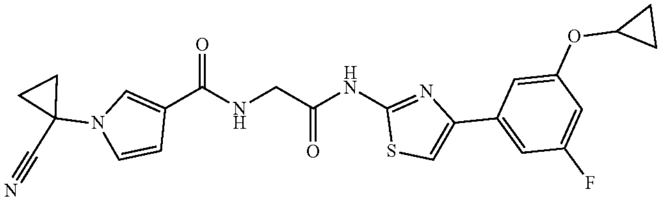 [SMILES: N#CC1(n2ccc(C(=O)NCC(=O)Nc3nc(-c4cc(F)cc(OC5CC5)c4)cs3)c2)CC1] |
| 556 | 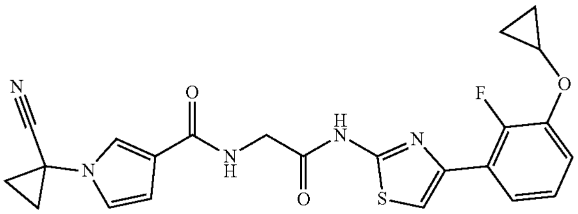 [SMILES: N#CC1(n2ccc(C(=O)NCC(=O)Nc3nc(-c4cccc(OC5CC5)c4F)cs3)c2)CC1] |
| 557 | 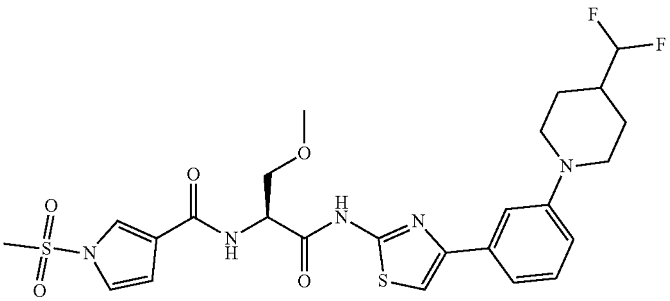 [SMILES: COC[C@H](NC(=O)c1ccn(S(C)(=O)=O)c1)C(=O)Nc1nc(-c2cccc(N3CCC(C(F)F)CC3)c2)cs1] |

TABLE 1-continued
| Compounds of the invention | |
|---|---|
| # | Compound |
| 558 | 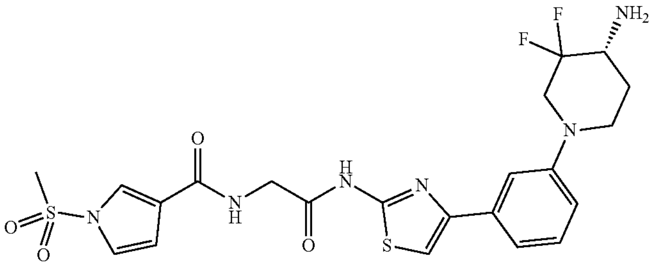 [SMILES: CS(=O)(=O)n1ccc(C(=O)NCC(=O)Nc2nc(-c3cccc(N4CC[C@@H](N)C(F)(F)C4)c3)cs2)c1] |
| 559 | 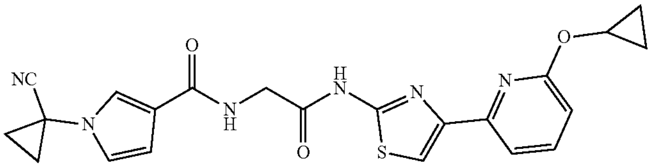 [SMILES: N#CC1(n2ccc(C(=O)NCC(=O)Nc3nc(-c4cccc(OC5CC5)n4)cs3)c2)CC1] |
| 560 | 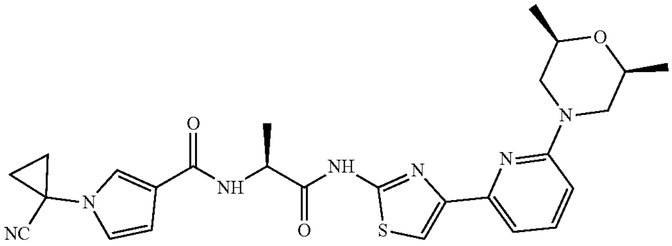 [SMILES: C[C@@H]1CN(c2cccc(-c3csc(NC(=O)[C@H](C)NC(=O)c4ccn(C5(C#N)CC5)c4)n3)n2)C[C@H](C)O1] |
| 561 | 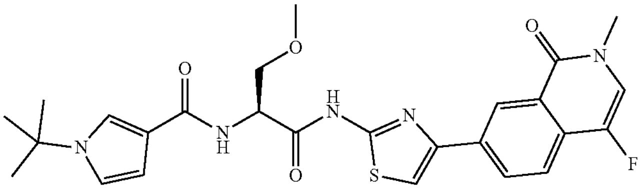 [SMILES: COC[C@H](NC(=O)c1ccn(C(C)(C)C)c1)C(=O)Nc1nc(-c2ccc3c(F)cn(C)c(=O)c3c2)cs1] |
| 562 | 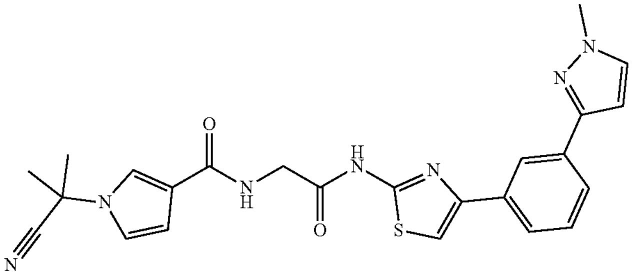 [SMILES: Cn1ccc(-c2cccc(-c3csc(NC(=O)CNC(=O)c4ccn(C(C)(C)C#N)c4)n3)c2)n1] |
| 563 | 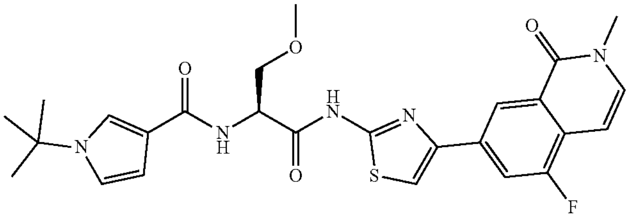 [SMILES: COC[C@H](NC(=O)c1ccn(C(C)(C)C)c1)C(=O)Nc1nc(-c2cc(F)c3ccn(C)c(=O)c3c2)cs1] |

TABLE 1-continued
| Compounds of the invention | |
|---|---|
| # | Compound |
| 564 | 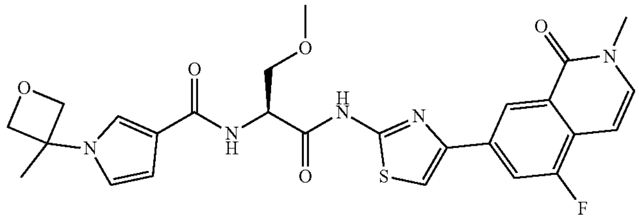 [SMILES: COC[C@H](NC(=O)c1ccn(C2(C)COC2)c1)C(=O)Nc1nc(-c2cc(F)c3ccn(C)c(=O)c3c2)cs1] |
| 565 | 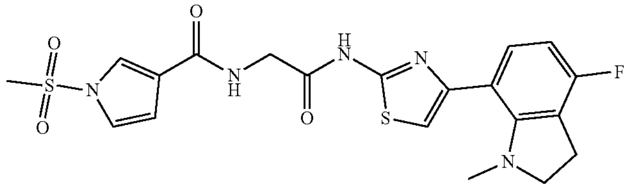 [SMILES: CN1CCc2c(F)ccc(-c3csc(NC(=O)CNC(=O)c4ccn(S(C)(=O)=O)c4)n3)c21] |
| 566 | 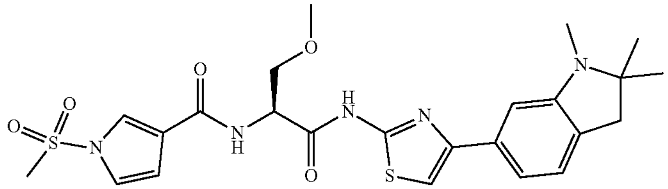 [SMILES: COC[C@H](NC(=O)c1ccn(S(C)(=O)=O)c1)C(=O)Nc1nc(-c2ccc3c(c2)N(C)C(C)(C)C3)cs1] |
| 567 | 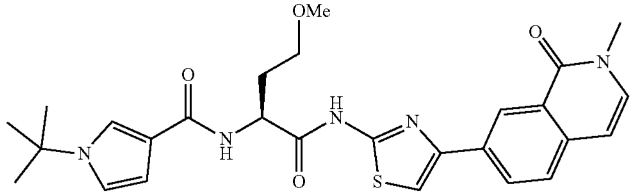 [SMILES: COCC[C@H](NC(=O)c1ccn(C(C)(C)C)c1)C(=O)Nc1nc(-c2ccc3ccn(C)c(=O)c3c2)cs1] |
| 568 | 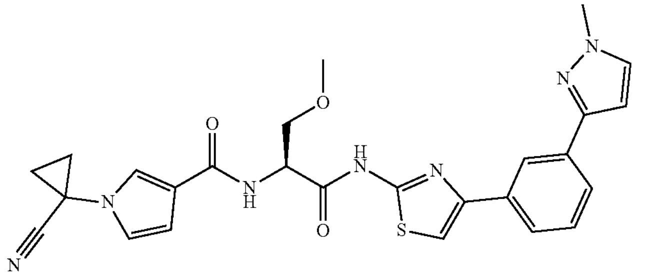 [SMILES: COC[C@H](NC(=O)c1ccn(C2(C#N)CC2)c1)C(=O)Nc1nc(-c2cccc(-c3ccn(C)n3)c2)cs1] |
| 569 | 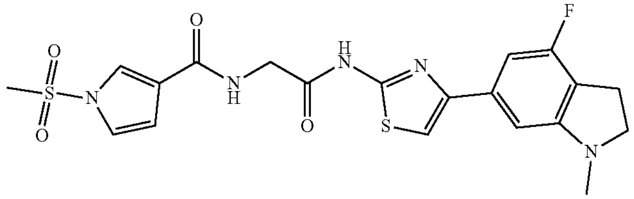 [SMILES: CN1CCc2c(F)cc(-c3csc(NC(=O)CNC(=O)c4ccn(S(C)(=O)=O)c4)n3)cc21] |
| 570 | 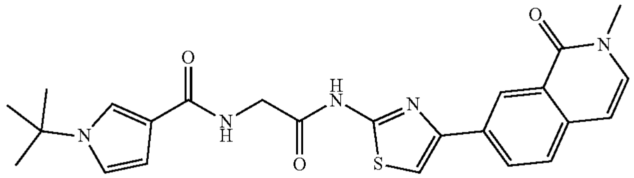 [SMILES: Cn1ccc2ccc(-c3csc(NC(=O)CNC(=O)c4ccn(C(C)(C)C)c4)n3)cc2c1=O] |

TABLE 1-continued
Compounds of the invention
| # | Compound |
|---|---|
| 571 | 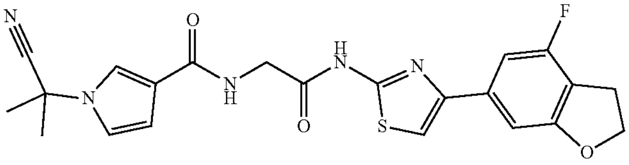 [SMILES: CC(C)(C#N)n1ccc(C(=O)NCC(=O)Nc2nc(-c3cc(F)c4c(c3)OCC4)cs2)c1] |
| 572 | 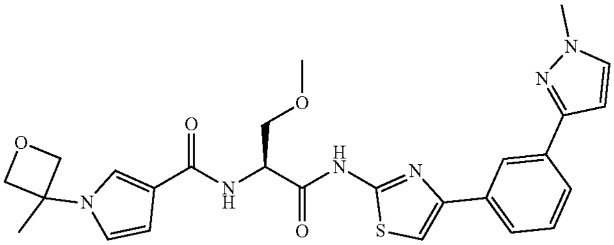 [SMILES: COC[C@H](NC(=O)c1ccn(C2(C)COC2)c1)C(=O)Nc1nc(-c2cccc(-c3ccn(C)n3)c2)cs1] |
| 573 | 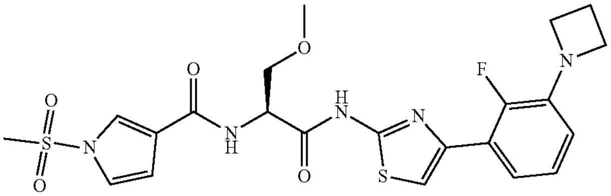 [SMILES: COC[C@H](NC(=O)c1ccn(S(C)(=O)=O)c1)C(=O)Nc1nc(-c2cccc(N3CCC3)c2F)cs1] |
| 574 | 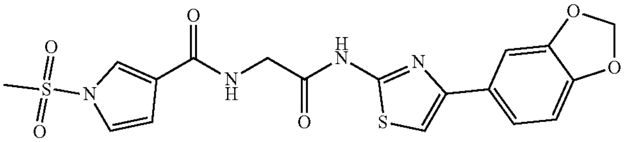 [SMILES: CS(=O)(=O)n1ccc(C(=O)NCC(=O)Nc2nc(-c3ccc4c(c3)OCO4)cs2)c1] |
| 575 | 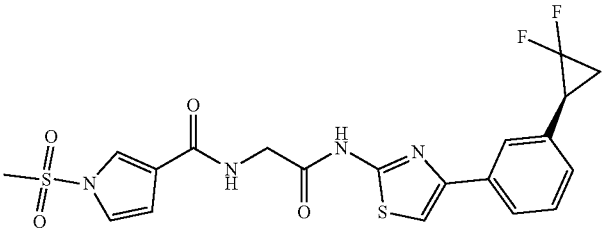 |
| 576 | 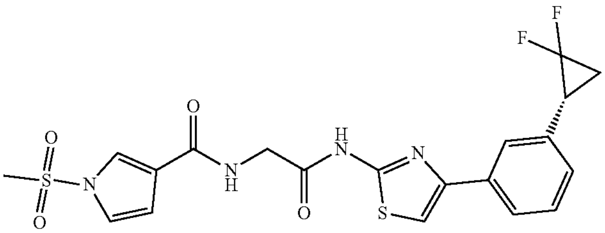 |
| 577 | 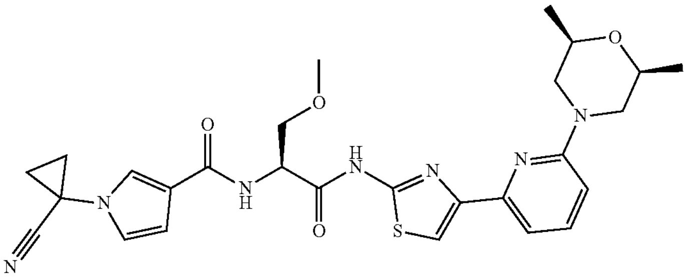 [SMILES: COC[C@H](NC(=O)c1ccn(C2(C#N)CC2)c1)C(=O)Nc1nc(-c2cccc(N3C[C@@H](C)O[C@@H](C)C3)n2)cs1] |

TABLE 1-continued
| Compounds of the invention | |
|---|---|
| # | Compound |
| 578 | 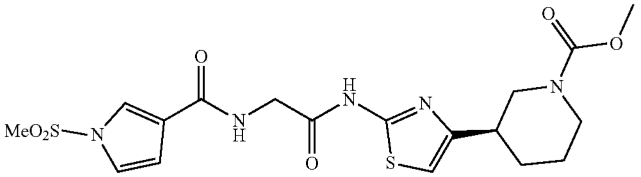 [SMILES: COC(=O)N1CCC[C@@H](c2csc(NC(=O)CNC(=O)c3ccn(S(C)(=O)=O)c3)n2)C1] |
| 579 | 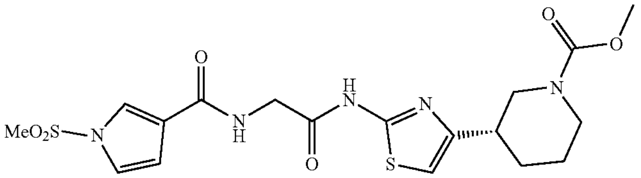 [SMILES: COC(=O)N1CCC[C@H](c2csc(NC(=O)CNC(=O)c3ccn(S(C)(=O)=O)c3)n2)C1] |
| 580 | 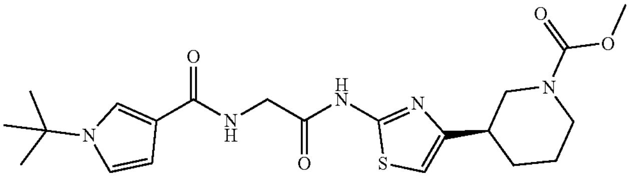 [SMILES: COC(=O)N1CCC[C@@H](c2csc(NC(=O)CNC(=O)c3ccn(C(C)(C)C)c3)n2)C1] |
| 581 | 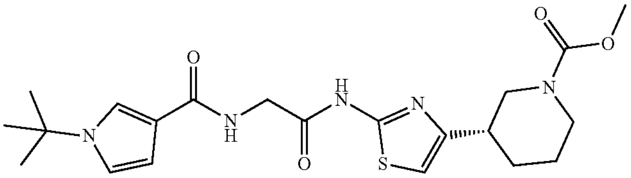 [SMILES: COC(=O)N1CCC[C@H](c2csc(NC(=O)CNC(=O)c3ccn(C(C)(C)C)c3)n2)C1] |
| 582 | 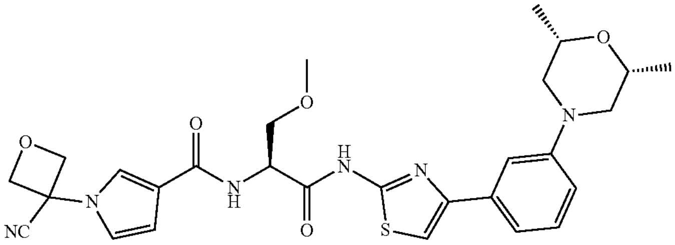 [SMILES: COC[C@H](NC(=O)c1ccn(C2(C#N)COC2)c1)C(=O)Nc1nc(-c2cccc(N3C[C@@H](C)O[C@@H](C)C3)c2)cs1] |
| 583 | 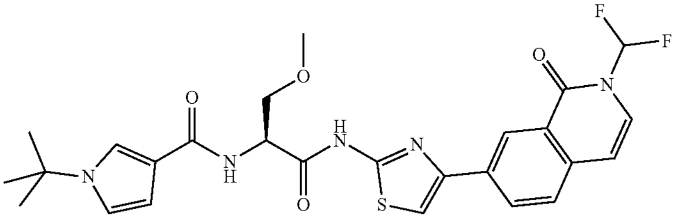 [SMILES: COC[C@H](NC(=O)c1ccn(C(C)(C)C)c1)C(=O)Nc1nc(-c2ccc3ccn(C(F)F)c(=O)c3c2)cs1] |
| 584 | 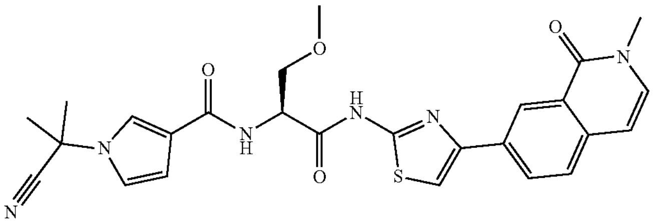 [SMILES: COC[C@H](NC(=O)c1ccn(C(C)(C)C#N)c1)C(=O)Nc1nc(-c2ccc3ccn(C)c(=O)c3c2)cs1] |

TABLE 1-continued
| Compounds of the invention | |
|---|---|
| # | Compound |
| 585 | 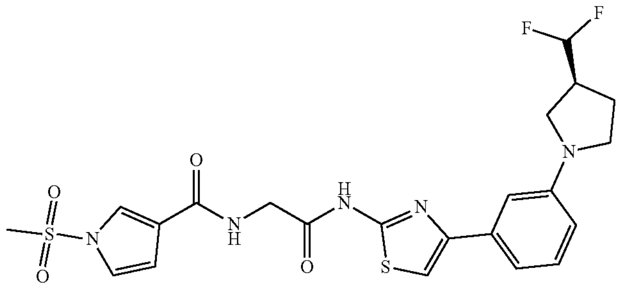 [SMILES: CS(=O)(=O)n1ccc(C(=O)NCC(=O)Nc2nc(-c3cccc(N4CC[C@H](C(F)F)C4)c3)cs2)c1] |
| 586 | 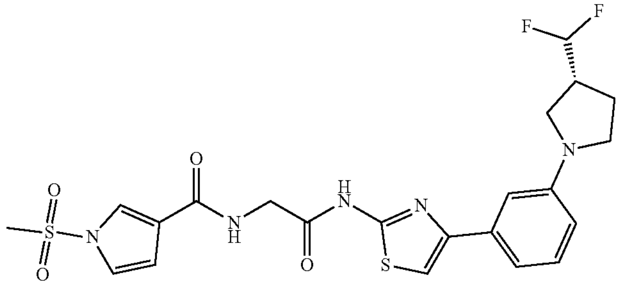 [SMILES: CS(=O)(=O)n1ccc(C(=O)NCC(=O)Nc2nc(-c3cccc(N4CC[C@@H](C(F)F)C4)c3)cs2)c1] |
| 587 | 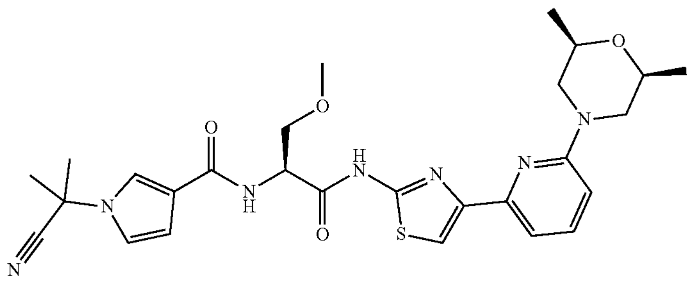 [SMILES: COC[C@H](NC(=O)c1ccn(C(C)(C)C#N)c1)C(=O)Nc1nc(-c2cccc(N3C[C@@H](C)O[C@@H](C)C3)n2)cs1] |
| 588 | 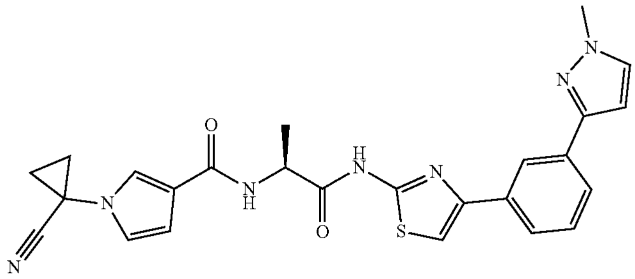 [SMILES: C[C@H](NC(=O)c1ccn(C2(C#N)CC2)c1)C(=O)Nc1nc(-c2cccc(-c3ccn(C)n3)c2)cs1] |
| 589 | 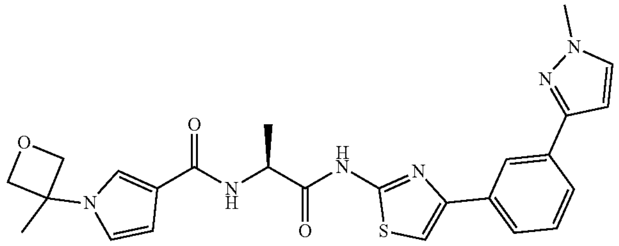 [SMILES: C[C@H](NC(=O)c1ccn(C2(C)COC2)c1)C(=O)Nc1nc(-c2cccc(-c3ccn(C)n3)c2)cs1] |

TABLE 1-continued
| Compounds of the invention | |
|---|---|
| # | Compound |
| 590 | 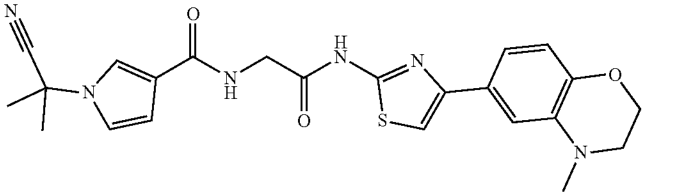 [SMILES: CN1CCOc2ccc(-c3csc(NC(=O)CNC(=O)c4ccn(C(C)(C)C#N)c4)n3)cc21] |
| 591 | 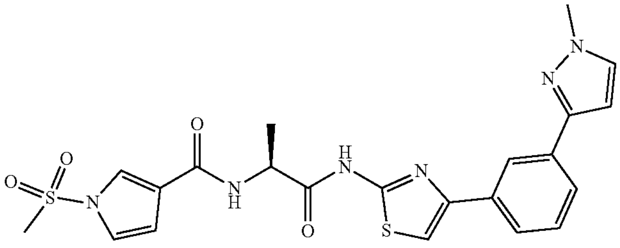 [SMILES: C[C@H](NC(=O)c1ccn(S(C)(=O)=O)c1)C(=O)Nc1nc(-c2cccc(-c3ccn(C)n3)c2)cs1] |
| 592 | 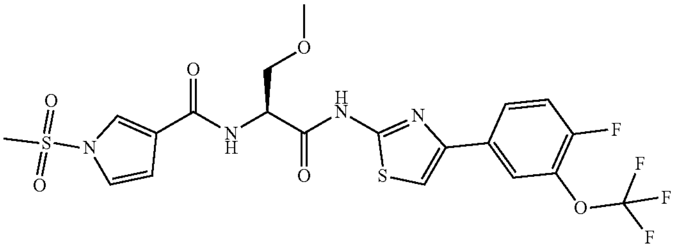 [SMILES: COC[C@H](NC(=O)c1ccn(S(C)(=O)=O)c1)C(=O)Nc1nc(-c2ccc(F)c(OC(F)(F)F)c2)cs1] |
| 593 | 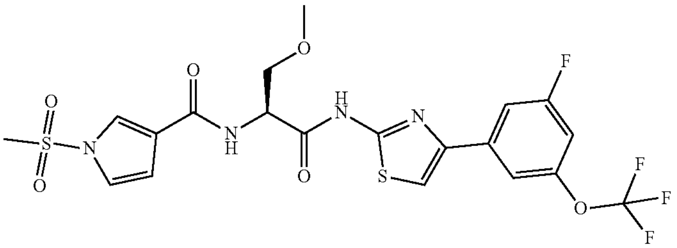 [SMILES: COC[C@H](NC(=O)c1ccn(S(C)(=O)=O)c1)C(=O)Nc1nc(-c2cc(F)cc(OC(F)(F)F)c2)cs1] |
| 594 | 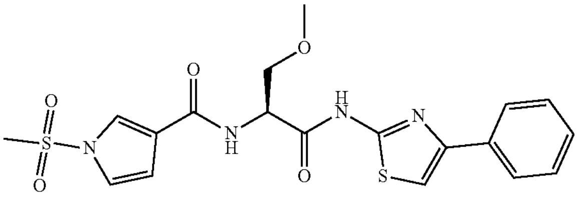 [SMILES: COC[C@H](NC(=O)c1ccn(S(C)(=O)=O)c1)C(=O)Nc1nc(-c2ccccc2)cs1] |
| 595 | 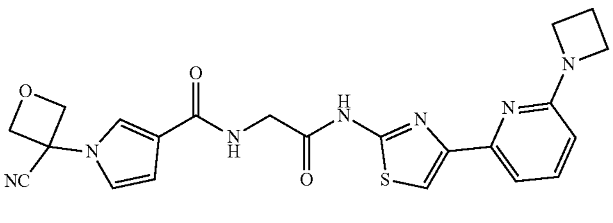 [SMILES: N#CC1(n2ccc(C(=O)NCC(=O)Nc3nc(-c4cccc(N5CCC5)n4)cs3)c2)COC1] |

TABLE 1-continued
| Compounds of the invention | |
|---|---|
| # | Compound |
| 596 | 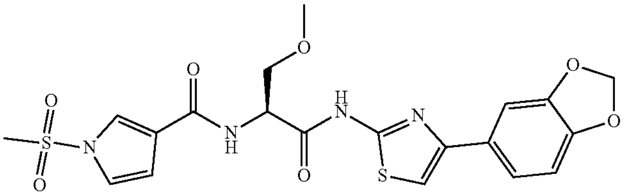 [SMILES: COC[C@H](NC(=O)c1ccn(S(C)(=O)=O)c1)C(=O)Nc1nc(-c2ccc3c(c2)OCO3)cs1] |
| 597 | 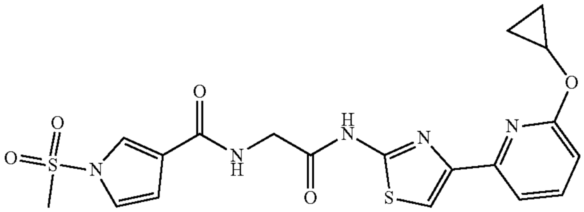 [SMILES: CS(=O)(=O)n1ccc(C(=O)NCC(=O)Nc2nc(-c3cccc(OC4CC4)n3)cs2)c1] |
| 598 | 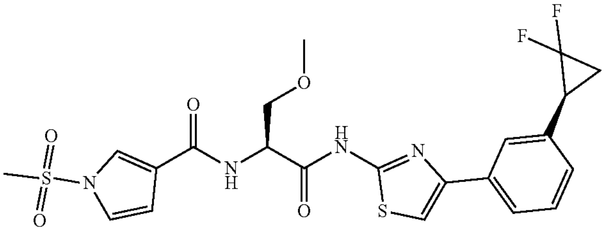 [SMILES: COC[C@H](NC(=O)c1ccn(S(C)(=O)=O)c1)C(=O)Nc1nc(-c2cccc([C@@H]3CC3(F)F)c2)cs1] |
| 599 | 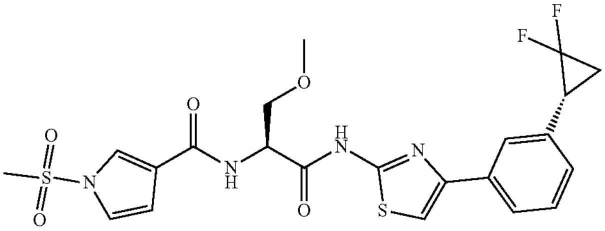 [SMILES: COC[C@H](NC(=O)c1ccn(S(C)(=O)=O)c1)C(=O)Nc1nc(-c2cccc([C@H]3CC3(F)F)c2)cs1] |
| 600 | 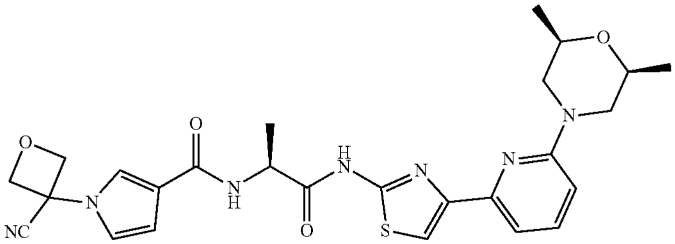 [SMILES: C[C@@H]1CN(c2cccc(-c3csc(NC(=O)[C@H](C)NC(=O)c4ccn(C5(C#N)COC5)c4)n3)n2)C[C@H](C)O1] |
| 601 | 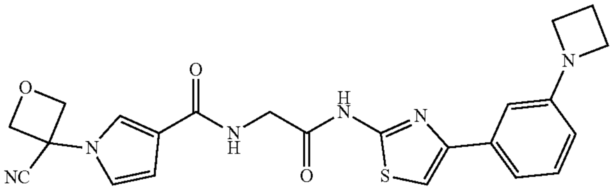 [SMILES: N#CC1(n2ccc(C(=O)NCC(=O)Nc3nc(-c4cccc(N5CCC5)c4)cs3)c2)COC1] |

TABLE 1-continued
| Compounds of the invention | |
|---|---|
| # | Compound |
| 602 | 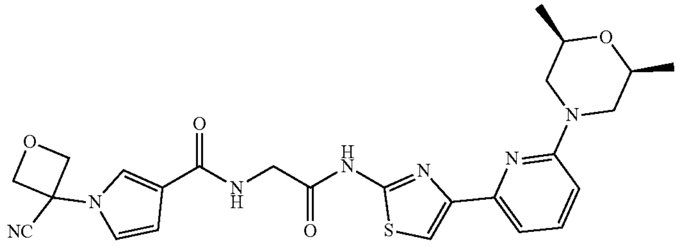 [SMILES: C[C@@H]1CN(c2cccc(-c3csc(NC(=O)CNC(=O)c4ccn(C5(C#N)COC5)c4)n3)n2)C[C@H](C)O1] |
| 603 | 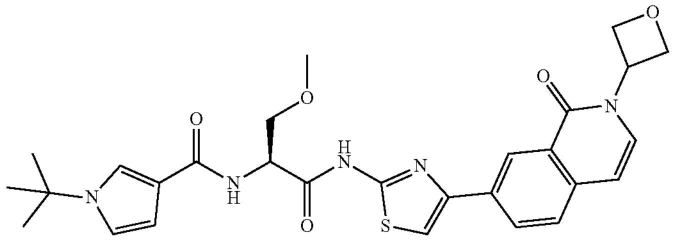 [SMILES: COC[C@H](NC(=O)c1ccn(C(C)(C)C)c1)C(=O)Nc1nc(-c2ccc3ccn(C4COC4)c(=O)c3c2)cs1] |
| 604 | 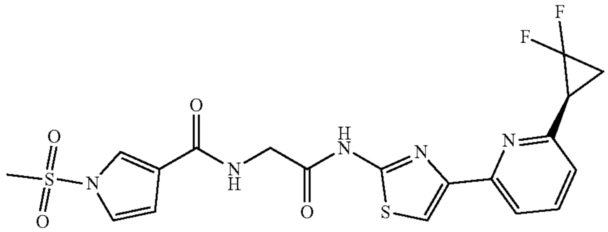 [SMILES: CS(=O)(=O)n1ccc(C(=O)NCC(=O)Nc2nc(-c3cccc([C@@H]4CC4(F)F)n3)cs2)c1] |
| 605 | 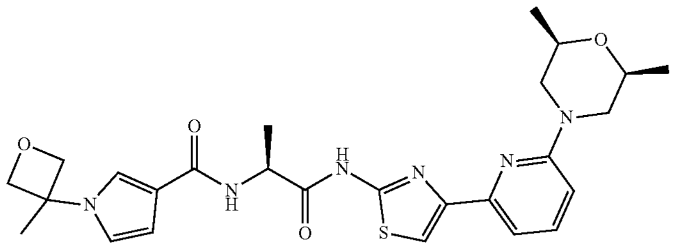 [SMILES: C[C@@H]1CN(c2cccc(-c3csc(NC(=O)[C@H](C)NC(=O)c4ccn(C5(C)COC5)c4)n3)n2)C[C@H](C)O1] |
| 606 | 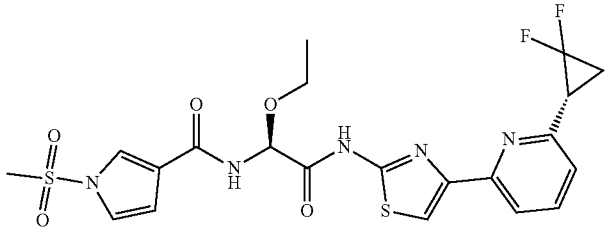 [SMILES: CCO[C@H](NC(=O)c1ccn(S(C)(=O)=O)c1)C(=O)Nc1nc(-c2cccc([C@H]3CC3(F)F)n2)cs1] |
| 607 | 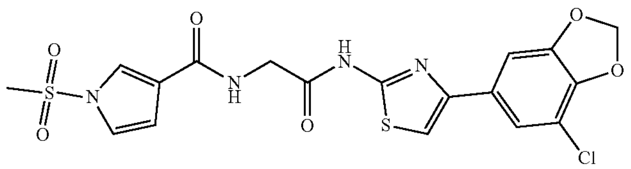 [SMILES: CS(=O)(=O)n1ccc(C(=O)NCC(=O)Nc2nc(-c3cc(Cl)c4c(c3)OCO4)cs2)c1] |

TABLE 1-continued
| Compounds of the invention | |
|---|---|
| # | Compound |
| 608 | 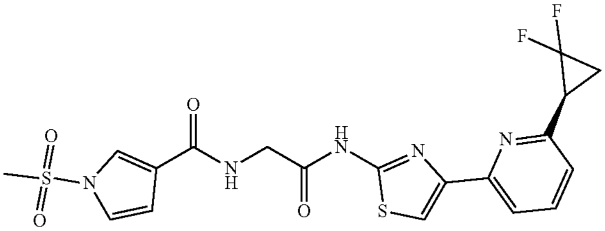 [SMILES: CS(=O)(=O)n1ccc(C(=O)NCC(=O)Nc2nc(-c3cccc([C@@H]4CC4(F)F)n3)cs2)c1] |
| 609 | 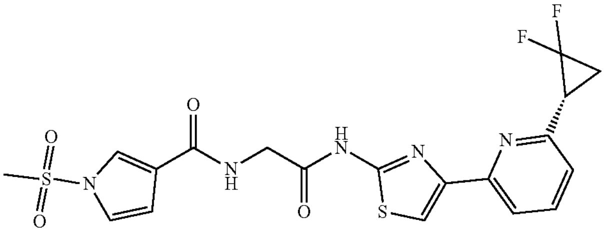 [SMILES: CS(=O)(=O)n1ccc(C(=O)NCC(=O)Nc2nc(-c3cccc([C@H]4CC4(F)F)n3)cs2)c1] |
| 610 | 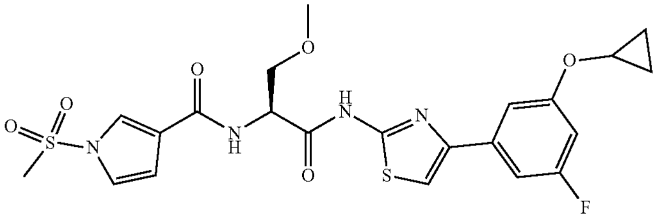 [SMILES: COC[C@H](NC(=O)c1ccn(S(C)(=O)=O)c1)C(=O)Nc1nc(-c2cc(F)cc(OC3CC3)c2)cs1] |
| 611 | 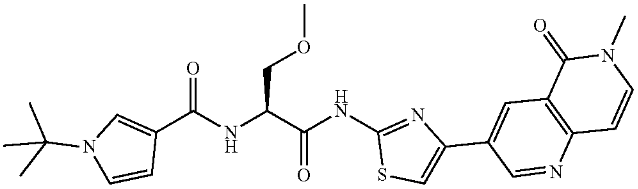 [SMILES: COC[C@H](NC(=O)c1ccn(C(C)(C)C)c1)C(=O)Nc1nc(-c2cnc3ccn(C)c(=O)c3c2)cs1] |
| 612 | 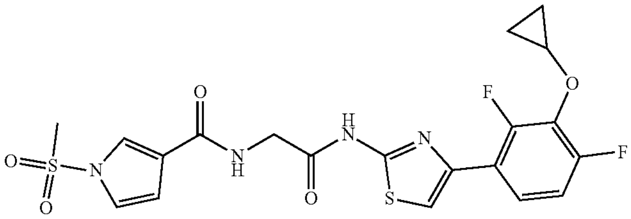 [SMILES: CS(=O)(=O)n1ccc(C(=O)NCC(=O)Nc2nc(-c3ccc(F)c(OC4CC4)c3F)cs2)c1] |
| 613 | 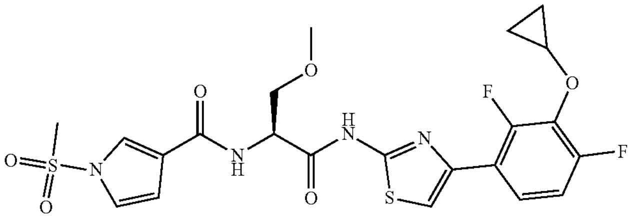 [SMILES: COC[C@H](NC(=O)c1ccn(S(C)(=O)=O)c1)C(=O)Nc1nc(-c2ccc(F)c(OC3CC3)c2F)cs1]

TABLE 1-continued
| Compounds of the invention | |
|---|---|
| # | Compound |
| 614 | 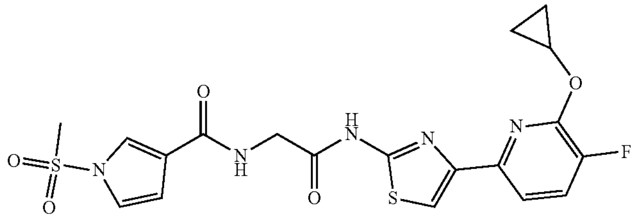 [SMILES: CS(=O)(=O)n1ccc(C(=O)NCC(=O)Nc2nc(-c3ccc(F)c(OC4CC4)n3)cs2)c1] |
| 615 | 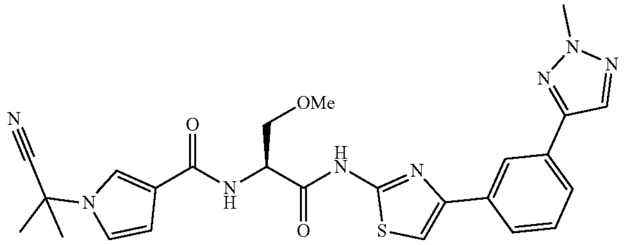 [SMILES: COC[C@H](NC(=O)c1ccn(C(C)(C)C#N)c1)C(=O)Nc1nc(-c2cccc(-c3cnn(C)n3)c2)cs1] |
| 616 | 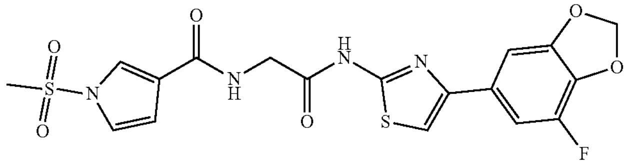 |
| 617 | 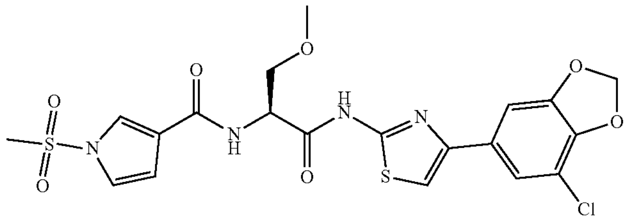 [SMILES: COC[C@H](NC(=O)c1ccn(S(C)(=O)=O)c1)C(=O)Nc1nc(-c2cc(Cl)c3c(c2)OCO3)cs1] |
| 618 | 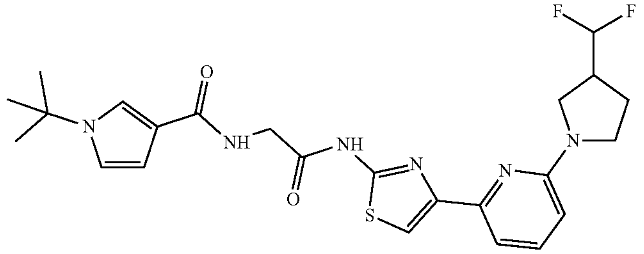 [SMILES: CC(C)(C)n1ccc(C(=O)NCC(=O)Nc2nc(-c3cccc(N4CCC(C(F)F)C4)n3)cs2)c1] |
| 619 | 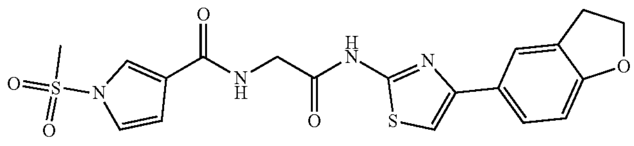 [SMILES: CS(=O)(=O)n1ccc(C(=O)NCC(=O)Nc2nc(-c3ccc4c(c3)CCO4)cs2)c1] |
| 620 | 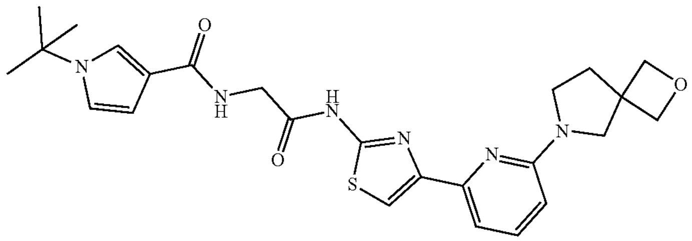 [SMILES: CC(C)(C)n1ccc(C(=O)NCC(=O)Nc2nc(-c3cccc(N4CCC5(COC5)C4)n3)cs2)c1] |

TABLE 1-continued
| Compounds of the invention | |
|---|---|
| # | Compound |
| 621 | 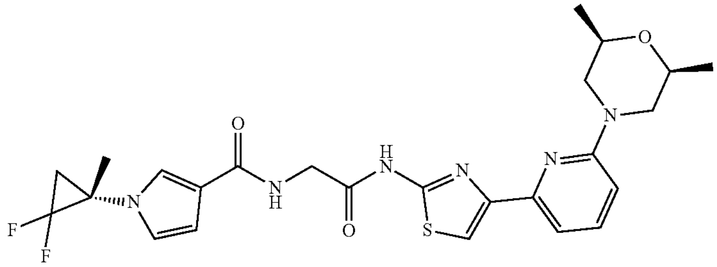 [SMILES: C[C@@H]1CN(c2cccc(-c3csc(NC(=O)CNC(=O)c4ccn([C@@]5(C)CC5(F)F)c4)n3)n2)C[C@H](C)O1] |
| 622 | 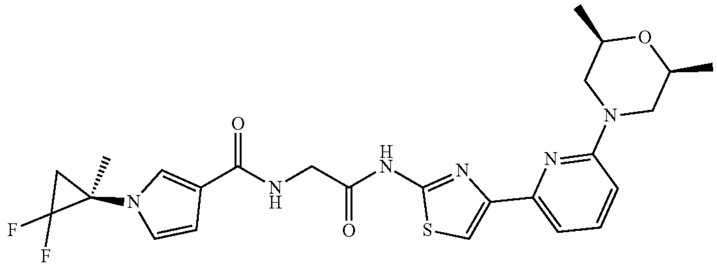 [SMILES: C[C@@H]1CN(c2cccc(-c3csc(NC(=O)CNC(=O)c4ccn([C@]5(C)CC5(F)F)c4)n3)n2)C[C@H](C)O1] |
| 623 | 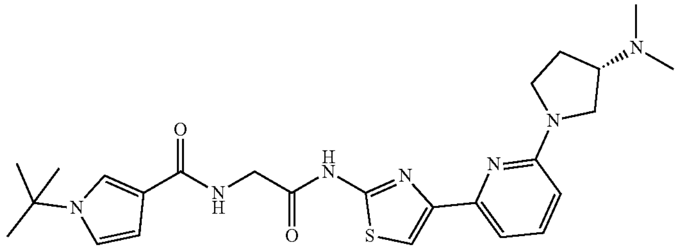 [SMILES: CN(C)[C@H]1CCN(c2cccc(-c3csc(NC(=O)CNC(=O)c4ccn(C(C)(C)C)c4)n3)n2)C1] |
| 624 | 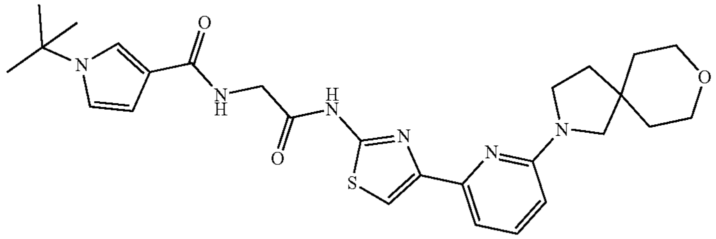 [SMILES: CC(C)(C)n1ccc(C(=O)NCC(=O)Nc2nc(-c3cccc(N4CCC5(CCOCC5)C4)n3)cs2)c1] |
| 625 | 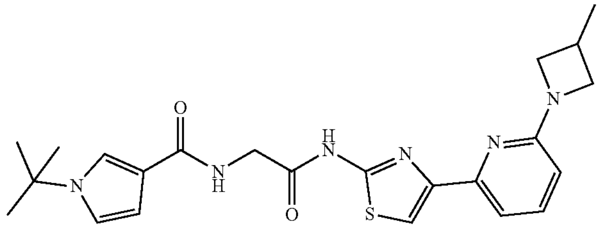 [SMILES: CC1CN(c2cccc(-c3csc(NC(=O)CNC(=O)c4ccn(C(C)(C)C)c4)n3)n2)C1] |
| 626 | 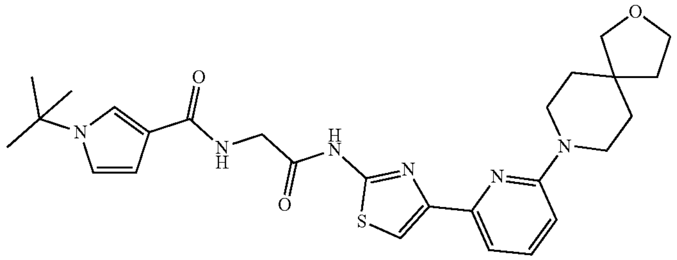 [SMILES: CC(C)(C)n1ccc(C(=O)NCC(=O)Nc2nc(-c3cccc(N4CCC5(CCOC5)CC4)n3)cs2)c1] |

TABLE 1-continued
| Compounds of the invention |
| --- |
| # Compound |
627
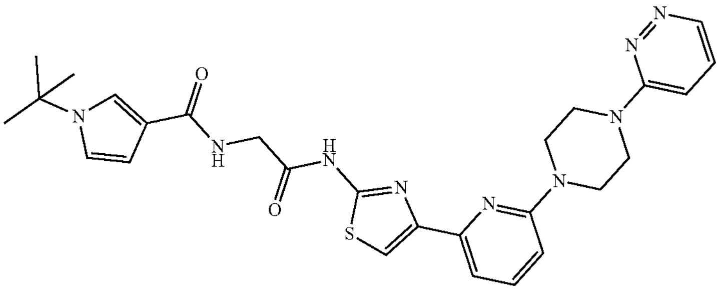 [SMILES: CC(C)(C)n1ccc(C(=O)NCC(=O)Nc2nc(-c3cccc(N4CCN(c5cccnn5)CC4)n3)cs2)c1]
628
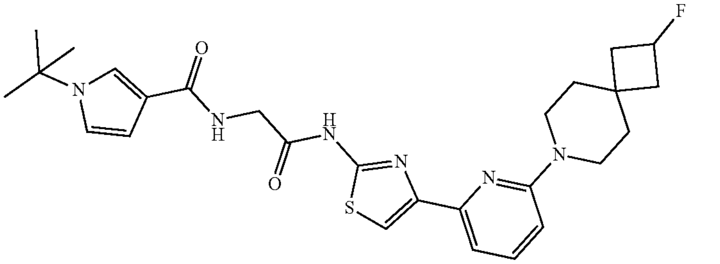 [SMILES: CC(C)(C)n1ccc(C(=O)NCC(=O)Nc2nc(-c3cccc(N4CCC5(CC4)CC(F)C5)n3)cs2)c1]
629
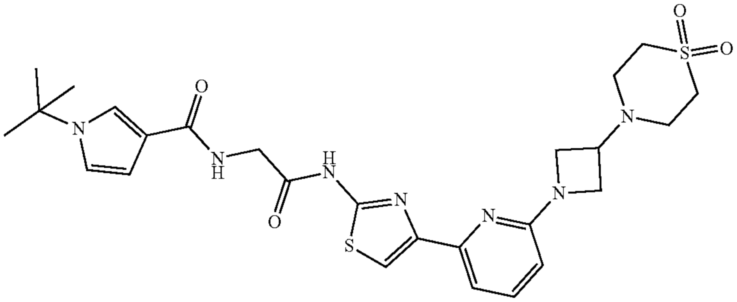 [SMILES: CC(C)(C)n1ccc(C(=O)NCC(=O)Nc2nc(-c3cccc(N4CC(N5CCS(=O)(=O)CC5)C4)n3)cs2)c1]
630
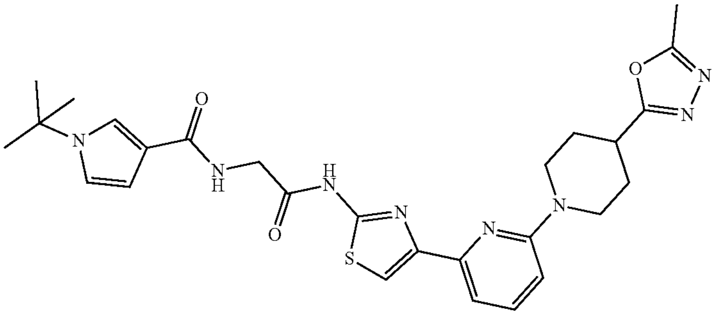 [SMILES: Cc1nnc(C2CCN(c3cccc(-c4csc(NC(=O)CNC(=O)c5ccn(C(C)(C)C)c5)n4)n3)CC2)o1]
631
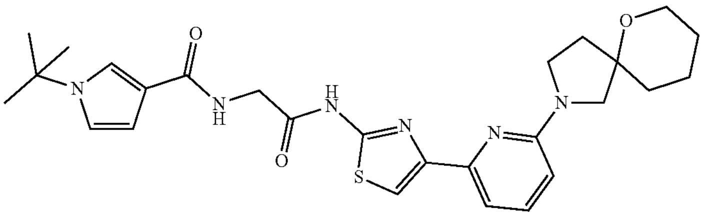 [SMILES: CC(C)(C)n1ccc(C(=O)NCC(=O)Nc2nc(-c3cccc(N4CCC5(CCCCO5)C4)n3)cs2)c1]

TABLE 1-continued
Compounds of the invention
| # | Compound |
|---|---|
| 632 | 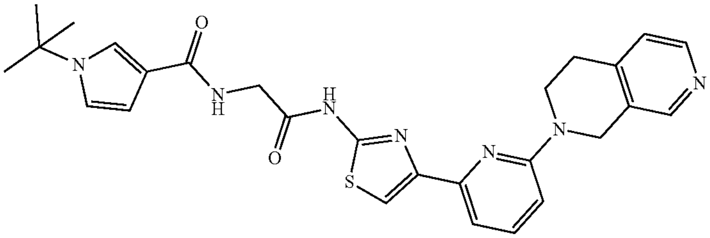 [SMILES: CC(C)(C)n1ccc(C(=O)NCC(=O)Nc2nc(-c3cccc(N4CCc5ccncc5C4)n3)cs2)c1] |
| 633 | 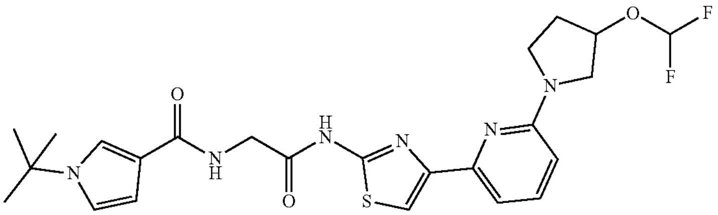 [SMILES: CC(C)(C)n1ccc(C(=O)NCC(=O)Nc2nc(-c3cccc(N4CCC(OC(F)F)C4)n3)cs2)c1] |
| 634 | 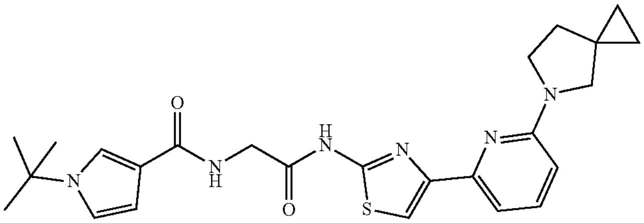 [SMILES: CC(C)(C)n1ccc(C(=O)NCC(=O)Nc2nc(-c3cccc(N4CCC5(CC5)C4)n3)cs2)c1] |
| 635 | 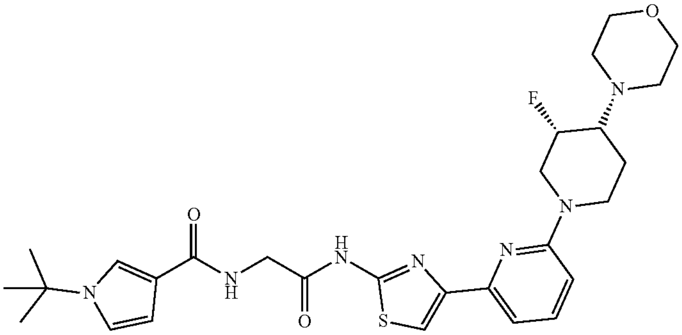 |
| 636 | 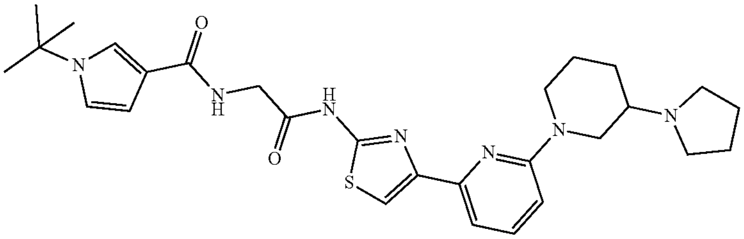 [SMILES: CC(C)(C)n1ccc(C(=O)NCC(=O)Nc2nc(-c3cccc(N4CCCC(N5CCCC5)C4)n3)cs2)c1] |
| 637 | 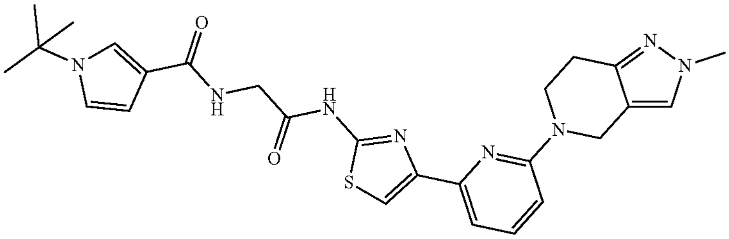 [SMILES: Cn1cc2c(n1)CCN(c1cccc(-c3csc(NC(=O)CNC(=O)c4ccn(C(C)(C)C)c4)n3)n1)C2] |

TABLE 1-continued
| Compounds of the invention | |
|---|---|
| # | Compound |
| 638 | 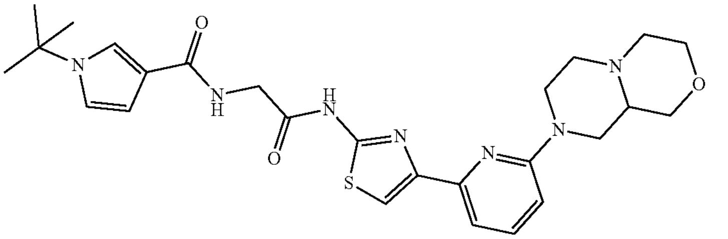 [SMILES: CC(C)(C)n1ccc(C(=O)NCC(=O)Nc2nc(-c3cccc(N4CCN5CCOCC5C4)n3)cs2)c1] |
| 639 | 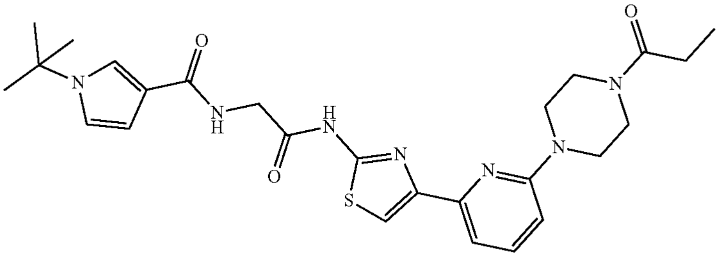 [SMILES: CCC(=O)N1CCN(c2cccc(-c3csc(NC(=O)CNC(=O)c4ccn(C(C)(C)C)c4)n3)n2)CC1] |
| 640 | 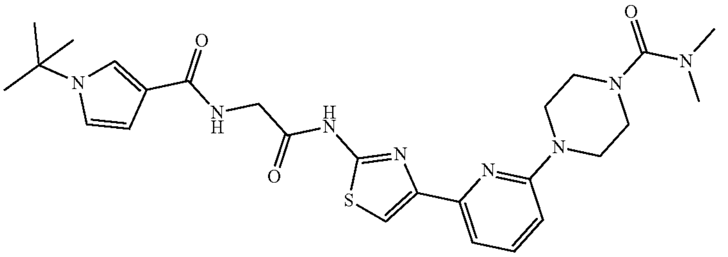 [SMILES: CN(C)C(=O)N1CCN(c2cccc(-c3csc(NC(=O)CNC(=O)c4ccn(C(C)(C)C)c4)n3)n2)CC1] |
| 641 | 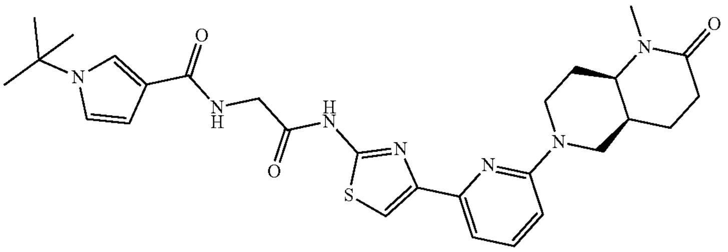 [SMILES: CN1C(=O)CC[C@H]2CN(c3cccc(-c4csc(NC(=O)CNC(=O)c5ccn(C(C)(C)C)c5)n4)n3)CC[C@H]21] |
| 642 | 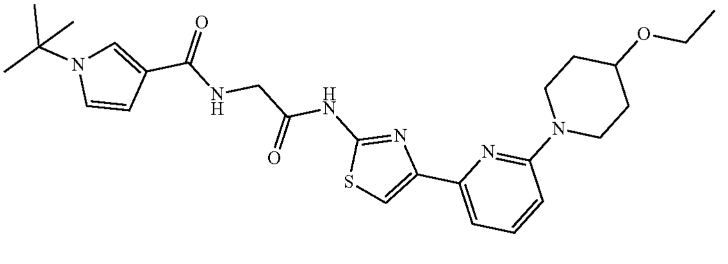 [SMILES: CCOC1CCN(c2cccc(-c3csc(NC(=O)CNC(=O)c4ccn(C(C)(C)C)c4)n3)n2)CC1] |

TABLE 1-continued
| Compounds of the invention | |
|---|---|
| # | Compound |
| 643 | 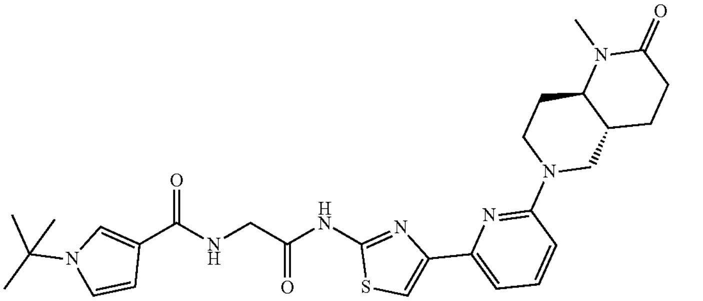 [SMILES: CN1C(=O)CC[C@@H]2CN(c3cccc(-c4csc(NC(=O)CNC(=O)c5ccn(C(C)(C)C)c5)n4)n3)CC[C@H]21] |
| 644 | 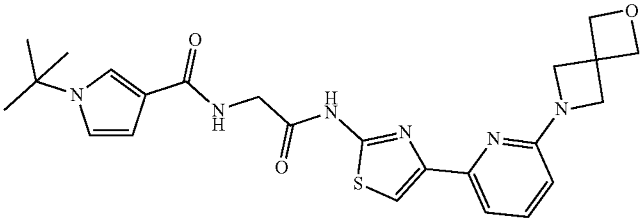 [SMILES: CC(C)(C)n1ccc(C(=O)NCC(=O)Nc2nc(-c3cccc(N4CC5(COC5)C4)n3)cs2)c1] |
| 645 | 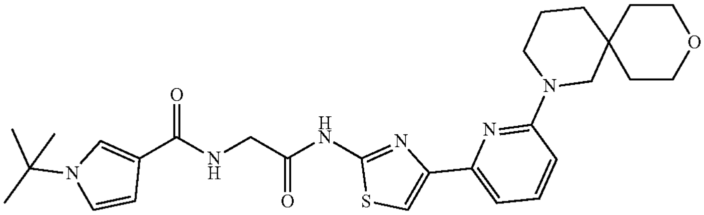 [SMILES: CC(C)(C)n1ccc(C(=O)NCC(=O)Nc2nc(-c3cccc(N4CCCC5(CCOCC5)C4)n3)cs2)c1] |
| 646 | 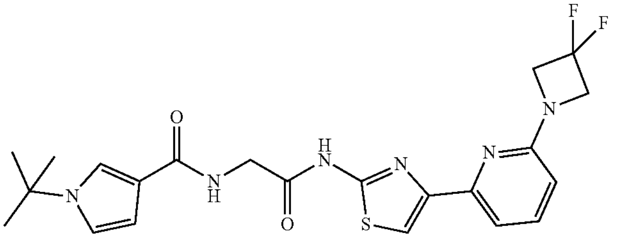 [SMILES: CC(C)(C)n1ccc(C(=O)NCC(=O)Nc2nc(-c3cccc(N4CC(F)(F)C4)n3)cs2)c1] |
| 647 | 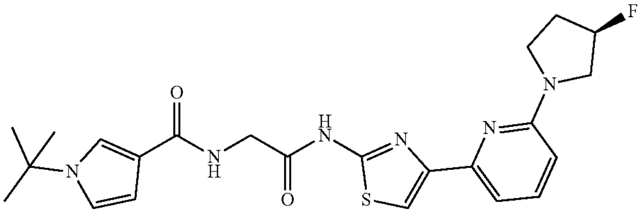 [SMILES: CC(C)(C)n1ccc(C(=O)NCC(=O)Nc2nc(-c3cccc(N4CC[C@@H](F)C4)n3)cs2)c1] |
| 648 | 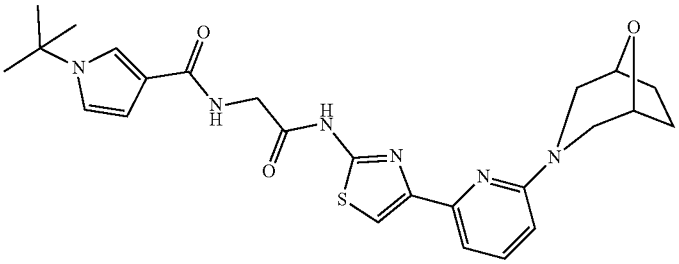 [SMILES: CC(C)(C)n1ccc(C(=O)NCC(=O)Nc2nc(-c3cccc(N4CC5CCC(C4)O5)n3)cs2)c1] |

TABLE 1-continued
| Compounds of the invention | |
|---|---|
| # | Compound |
| 649 | 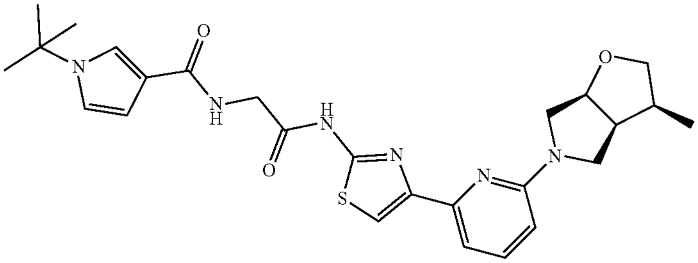 (±) |
| 650 | 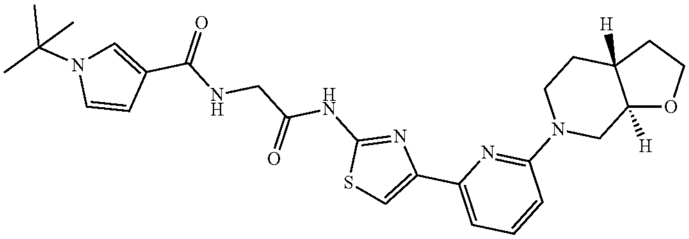 (±) |
| 651 | 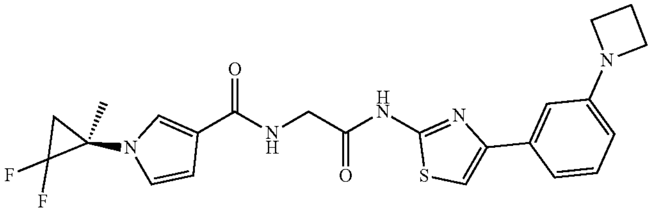 [SMILES: C[C@@]1(n2ccc(C(=O)NCC(=O)Nc3nc(-c4cccc(N5CCC5)c4)cs3)c2)CC1(F)F] |
| 652 | 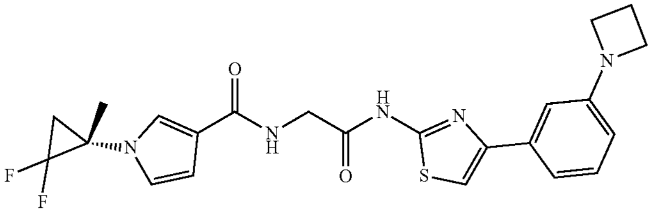 [SMILES: C[C@]1(n2ccc(C(=O)NCC(=O)Nc3nc(-c4cccc(N5CCC5)c4)cs3)c2)CC1(F)F] |
| 653 | 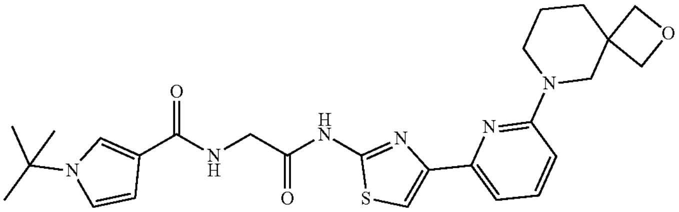 [SMILES: CC(C)(C)n1ccc(C(=O)NCC(=O)Nc2nc(-c3cccc(N4CCCC5(COC5)C4)n3)cs2)c1] |
| 654 | 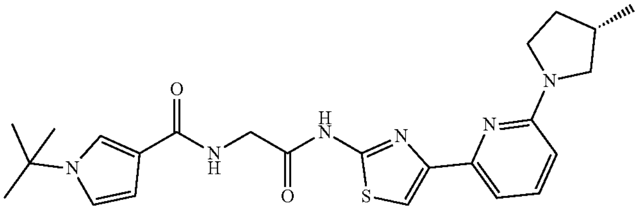 [SMILES: C[C@H]1CCN(c2cccc(-c3csc(NC(=O)CNC(=O)c4ccn(C(C)(C)C)c4)n3)n2)C1] |

TABLE 1-continued
| Compounds of the invention | |
|---|---|
| # | Compound |
| 655 | 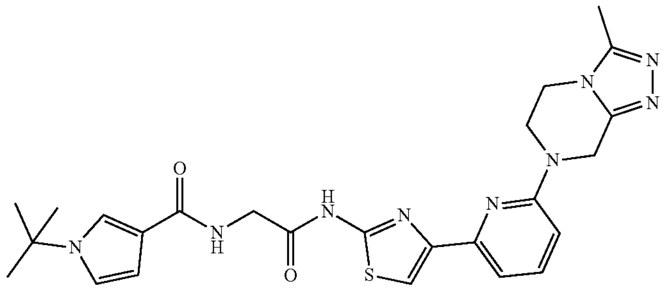 [SMILES: Cc1nnc2n1CCN(c1cccc(-c3csc(NC(=O)CNC(=O)c4ccn(C(C)(C)C)c4)n3)n1)C2] |
| 656 | 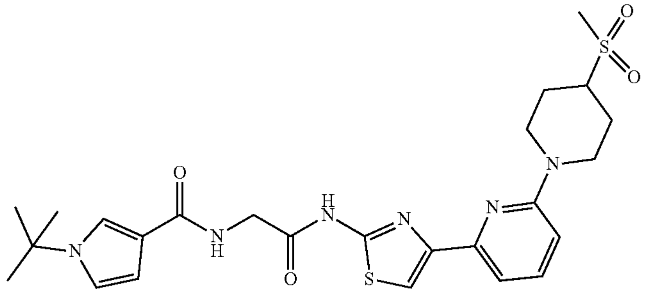 [SMILES: CC(C)(C)n1ccc(C(=O)NCC(=O)Nc2nc(-c3cccc(N4CCC(S(C)(=O)=O)CC4)n3)cs2)c1] |
| 657 | 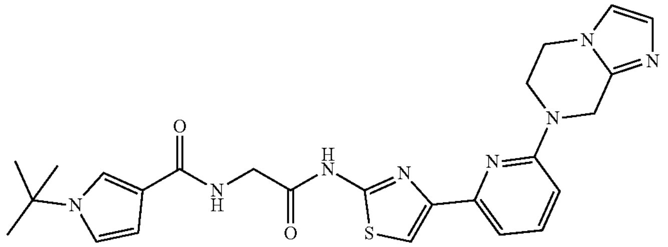 [SMILES: CC(C)(C)n1ccc(C(=O)NCC(=O)Nc2nc(-c3cccc(N4CCn5ccnc5C4)n3)cs2)c1] |
| 658 | 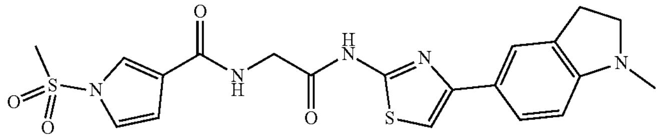 [SMILES: CN1CCc2cc(-c3csc(NC(=O)CNC(=O)c4ccn(S(C)(=O)=O)c4)n3)ccc21] |
| 659 | 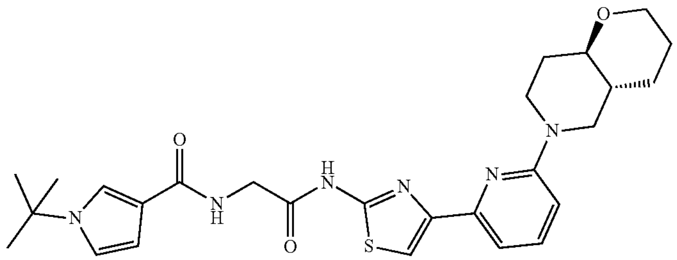 [SMILES: CC(C)(C)n1ccc(C(=O)NCC(=O)Nc2nc(-c3cccc(N4CC[C@H]5OCCC[C@@H]5C4)n3)cs2)c1] |
| 660 | 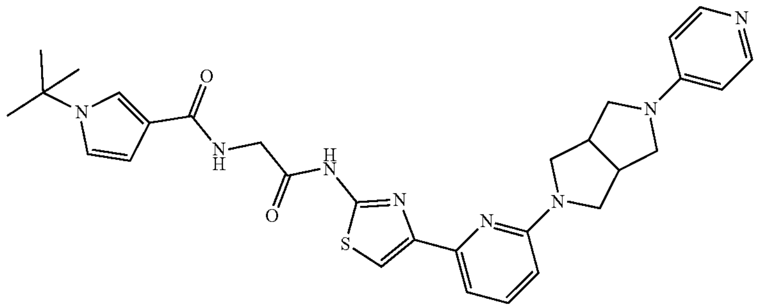 [SMILES: CC(C)(C)n1ccc(C(=O)NCC(=O)Nc2nc(-c3cccc(N4CC5CN(c6ccncc6)CC5C4)n3)cs2)c1] |

TABLE 1-continued
Compounds of the invention
| # | Compound |
|---|---|
| 661 | 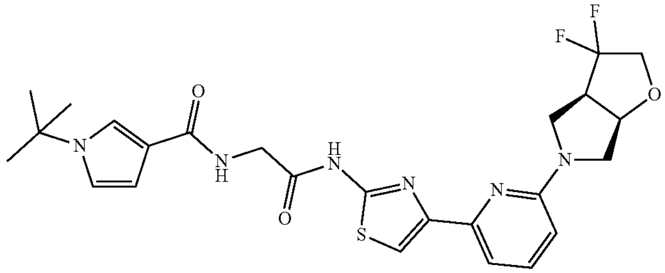 [SMILES: CC(C)(C)n1ccc(C(=O)NCC(=O)Nc2nc(-c3cccc(N4C[C@@H]5OCC(F)(F)[C@@H]5C4)n3)cs2)c1] |
| 662 | 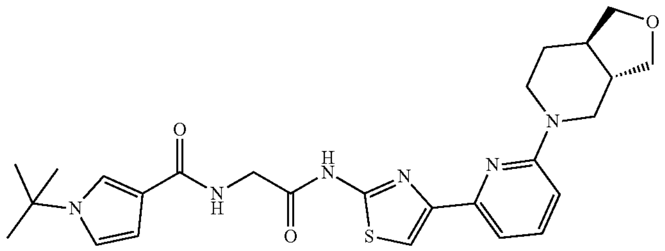 [SMILES: CC(C)(C)n1ccc(C(=O)NCC(=O)Nc2nc(-c3cccc(N4CC[C@H]5COC[C@@H]5C4)n3)cs2)c1] |
| 663 | 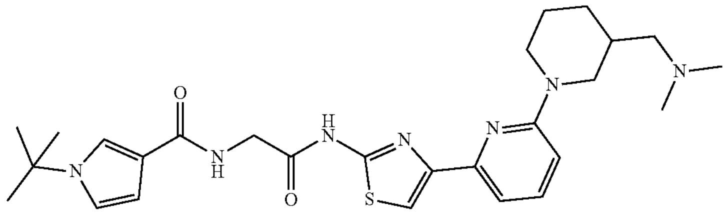 [SMILES: CN(C)CC1CCCN(c2cccc(-c3csc(NC(=O)CNC(=O)c4ccn(C(C)(C)C)c4)n3)n2)C1] |
| 664 | 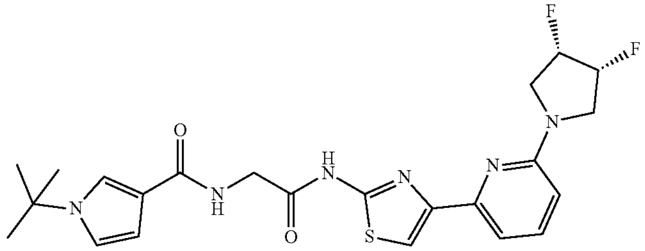 [SMILES: CC(C)(C)n1ccc(C(=O)NCC(=O)Nc2nc(-c3cccc(N4C[C@@H](F)[C@@H](F)C4)n3)cs2)c1] |
| 665 | 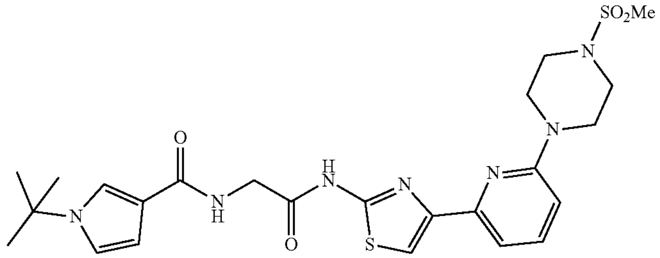 [SMILES: CC(C)(C)n1ccc(C(=O)NCC(=O)Nc2nc(-c3cccc(N4CCN(S(C)(=O)=O)CC4)n3)cs2)c1] |
| 666 | 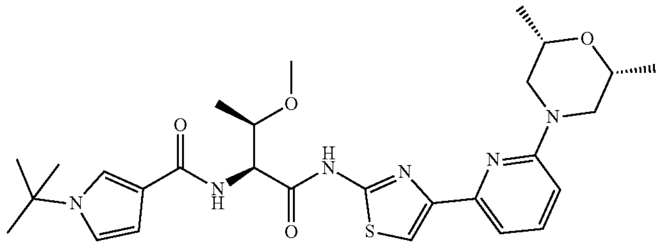 [SMILES: CO[C@H](C)[C@H](NC(=O)c1ccn(C(C)(C)C)c1)C(=O)Nc1nc(-c2cccc(N3C[C@@H](C)O[C@@H](C)C3)n2)cs1] |

TABLE 1-continued
| Compounds of the invention | |
|---|---|
| # | Compound |
| 667 | 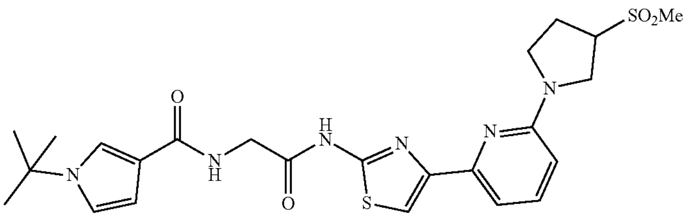 [SMILES: CC(C)(C)n1ccc(C(=O)NCC(=O)Nc2nc(-c3cccc(N4CCC(S(C)(=O)=O)C4)n3)cs2)c1] |
| 668 | 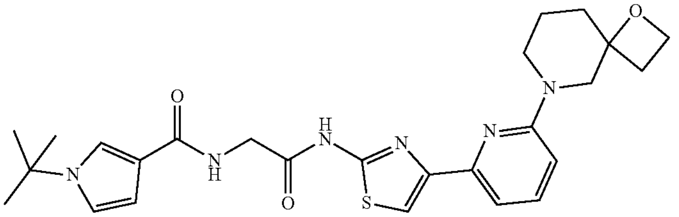 [SMILES: CC(C)(C)n1ccc(C(=O)NCC(=O)Nc2nc(-c3cccc(N4CCCC5(CCO5)C4)n3)cs2)c1] |
| 669 | 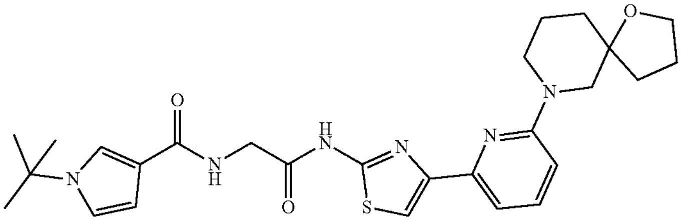 [SMILES: CC(C)(C)n1ccc(C(=O)NCC(=O)Nc2nc(-c3cccc(N4CCCC5(CCCO5)C4)n3)cs2)c1] |
| 670 | 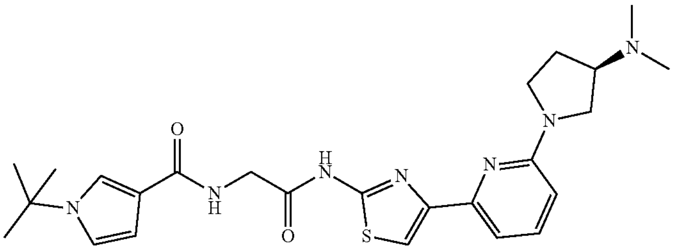 [SMILES: CN(C)[C@@H]1CCN(c2cccc(-c3csc(NC(=O)CNC(=O)c4ccn(C(C)(C)C)c4)n3)n2)C1] |
| 671 | 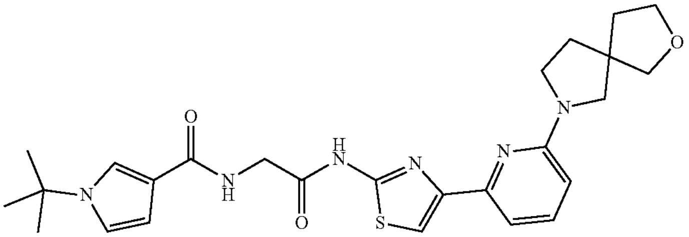 [SMILES: CC(C)(C)n1ccc(C(=O)NCC(=O)Nc2nc(-c3cccc(N4CCC5(CCOC5)C4)n3)cs2)c1] |
| 672 | 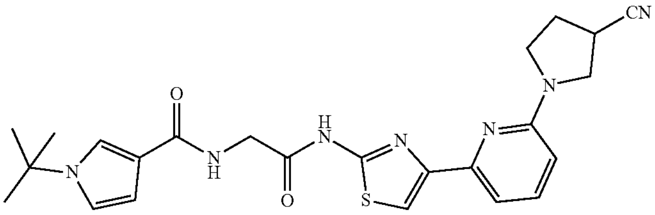 [SMILES: CC(C)(C)n1ccc(C(=O)NCC(=O)Nc2nc(-c3cccc(N4CCC(C#N)C4)n3)cs2)c1] |

TABLE 1-continued
| Compounds of the invention | |
|---|---|
| # | Compound |
| 673 | 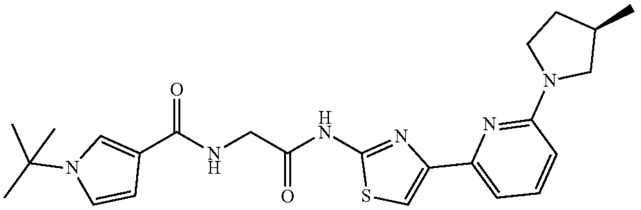 [SMILES: C[C@@H]1CCN(c2cccc(-c3csc(NC(=O)CNC(=O)c4ccn(C(C)(C)C)c4)n3)n2)C1] |
| 674 | 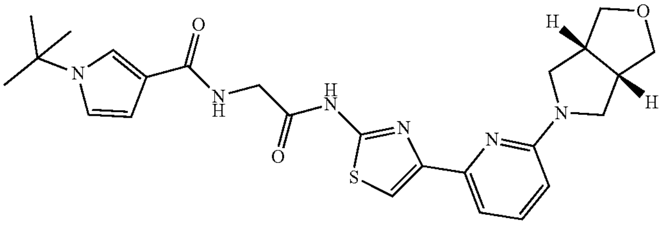 [SMILES: CC(C)(C)n1ccc(C(=O)NCC(=O)Nc2nc(-c3cccc(N4C[C@H]5COC[C@H]5C4)n3)cs2)c1] |
| 675 | 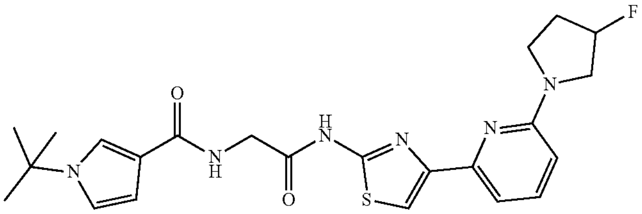 [SMILES: CC(C)(C)n1ccc(C(=O)NCC(=O)Nc2nc(-c3cccc(N4CCC(F)C4)n3)cs2)c1] |
| 676 | 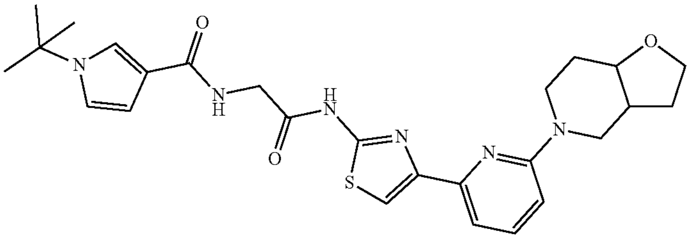 [SMILES: CC(C)(C)n1ccc(C(=O)NCC(=O)Nc2nc(-c3cccc(N4CCC5OCCC5C4)n3)cs2)c1] |
| 677 | 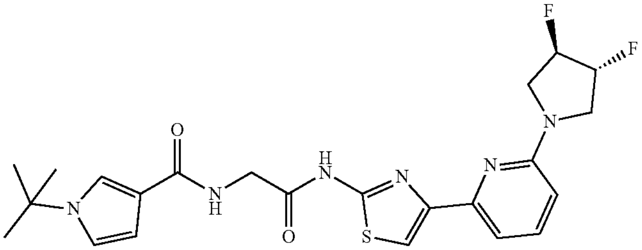 [SMILES: CC(C)(C)n1ccc(C(=O)NCC(=O)Nc2nc(-c3cccc(N4C[C@@H](F)[C@H](F)C4)n3)cs2)c1] |
| 678 | 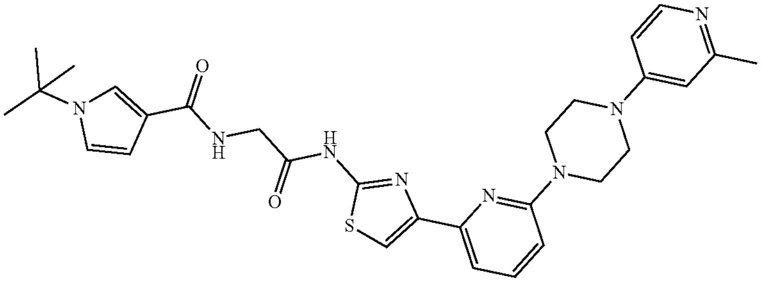 [SMILES: Cc1cc(N2CCN(c3cccc(-c4csc(NC(=O)CNC(=O)c5ccn(C(C)(C)C)c5)n4)n3)CC2)ccn1] |

TABLE 1-continued
| Compounds of the invention | |
|---|---|
| # | Compound |
| 679 | 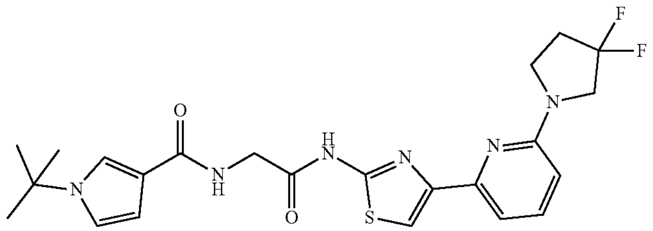 [SMILES: CC(C)(C)n1ccc(C(=O)NCC(=O)Nc2nc(-c3cccc(N4CCC(F)(F)C4)n3)cs2)c1] |
| 680 | 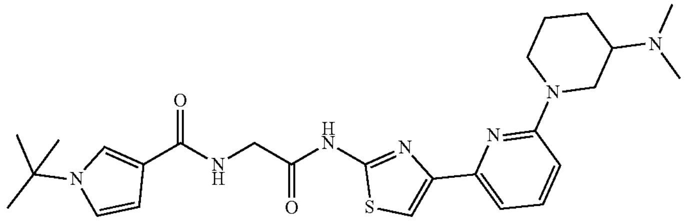 [SMILES: CN(C)C1CCCN(c2cccc(-c3csc(NC(=O)CNC(=O)c4ccn(C(C)(C)C)c4)n3)n2)C1] |
| 681 | 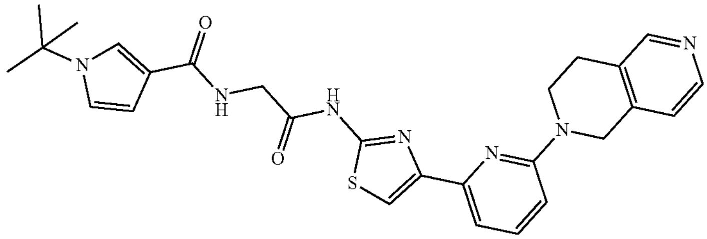 [SMILES: CC(C)(C)n1ccc(C(=O)NCC(=O)Nc2nc(-c3cccc(N4CCc5cnccc5C4)n3)cs2)c1] |
| 682 | 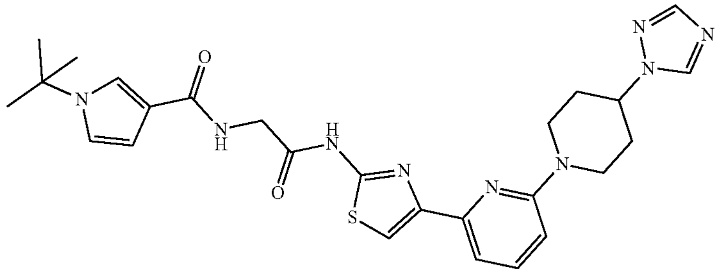 [SMILES: CC(C)(C)n1ccc(C(=O)NCC(=O)Nc2nc(-c3cccc(N4CCC(n5cncn5)CC4)n3)cs2)c1] |
| 683 | 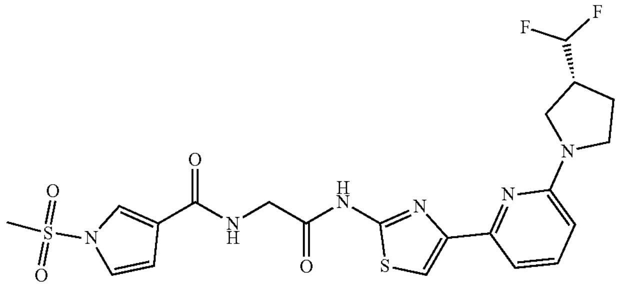 [SMILES: CS(=O)(=O)n1ccc(C(=O)NCC(=O)Nc2nc(-c3cccc(N4CC[C@@H](C(F)F)C4)n3)cs2)c1] |
| 684 | 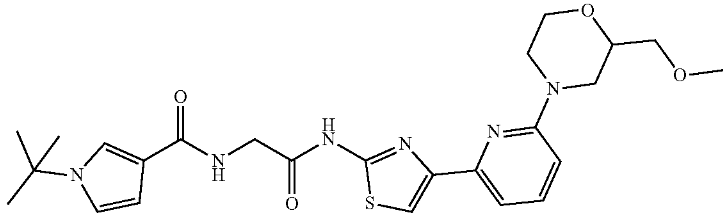 [SMILES: COCC1CN(c2cccc(-c3csc(NC(=O)CNC(=O)c4ccn(C(C)(C)C)c4)n3)n2)CCO1]

TABLE 1-continued
| Compounds of the invention | |
|---|---|
| # | Compound |
| 685 | 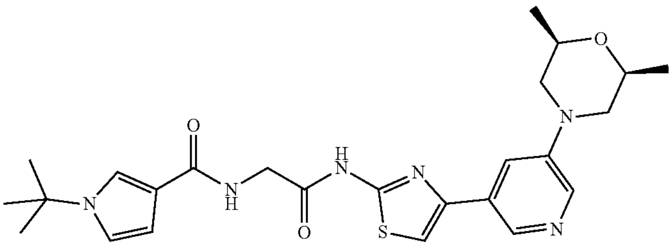 [SMILES: C[C@@H]1CN(c2cncc(-c3csc(NC(=O)CNC(=O)c4ccn(C(C)(C)C)c4)n3)c2)C[C@H](C)O1] |
| 686 | 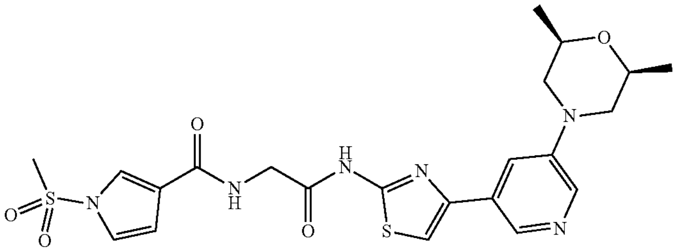 [SMILES: C[C@@H]1CN(c2cncc(-c3csc(NC(=O)CNC(=O)c4ccn(S(C)(=O)=O)c4)n3)c2)C[C@H](C)O1] |
| 687 | 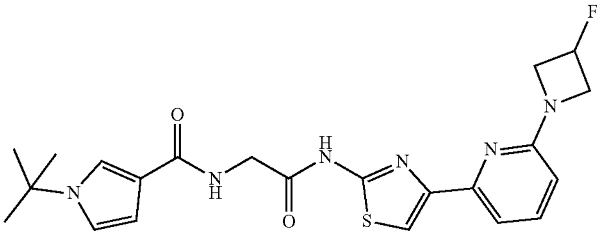 [SMILES: CC(C)(C)n1ccc(C(=O)NCC(=O)Nc2nc(-c3cccc(N4CC(F)C4)n3)cs2)c1] |
| 688 | 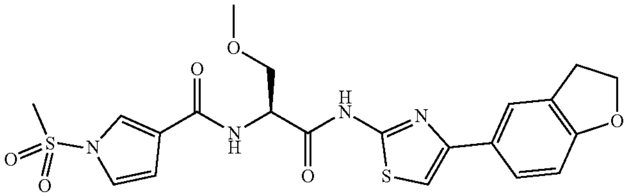 [SMILES: COC[C@H](NC(=O)c1ccn(S(C)(=O)=O)c1)C(=O)Nc1nc(-c2ccc3c(c2)CCO3)cs1] |
| 689 | 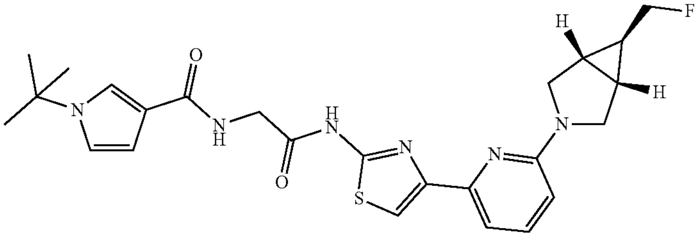 [SMILES: CC(C)(C)n1ccc(C(=O)NCC(=O)Nc2nc(-c3cccc(N4C[C@@H]5[C@@H](CF)[C@@H]5C4)n3)cs2)c1] |
| 690 | 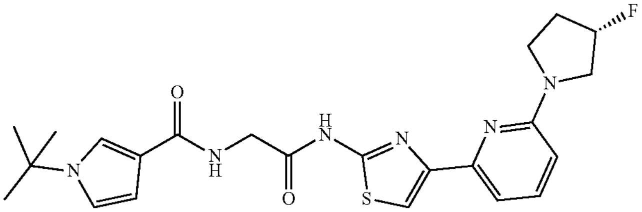 [SMILES: CC(C)(C)n1ccc(C(=O)NCC(=O)Nc2nc(-c3cccc(N4CC[C@H](F)C4)n3)cs2)c1] |

TABLE 1-continued
| Compounds of the invention | |
|---|---|
| # | Compound |
| 691 | 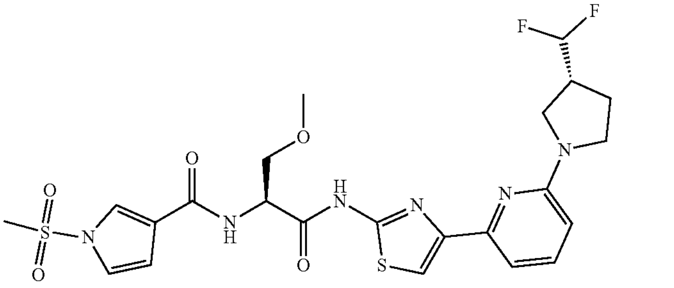 [SMILES: COC[C@H](NC(=O)c1ccn(S(C)(=O)=O)c1)C(=O)Nc1nc(-c2cccc(N3CC[C@@H](C(F)F)C3)n2)cs1] |
| 692 | 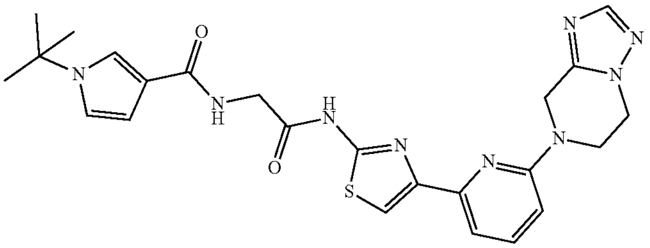 [SMILES: CC(C)(C)n1ccc(C(=O)NCC(=O)Nc2nc(-c3cccc(N4CCn5ncnc5C4)n3)cs2)c1] |
| 693 | 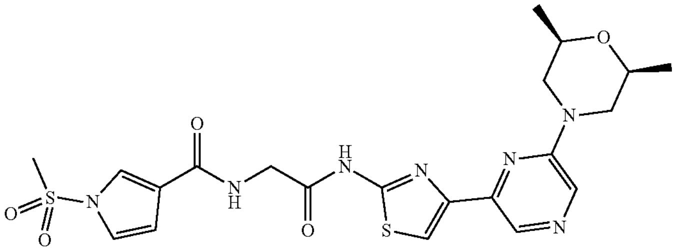 [SMILES: C[C@@H]1CN(c2cncc(-c3csc(NC(=O)CNC(=O)c4ccn(S(C)(=O)=O)c4)n3)n2)C[C@H](C)O1] |
| 694 | 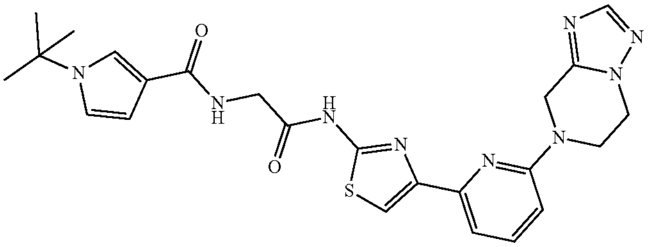 [SMILES: CC(C)(C)n1ccc(C(=O)NCC(=O)Nc2nc(-c3cccc(N4CCn5ncnc5C4)n3)cs2)c1] |
| 695 | 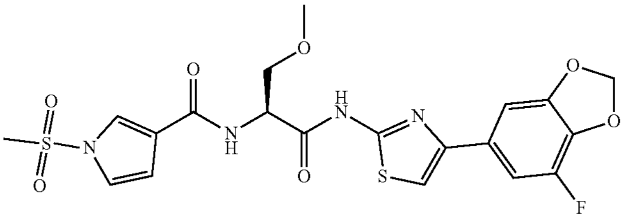 [SMILES: COC[C@H](NC(=O)c1ccn(S(C)(=O)=O)c1)C(=O)Nc1nc(-c2cc(F)c3c(c2)OCO3)cs1] |

TABLE 1-continued
Compounds of the invention
| # | Compound |
|---|---|
| 696 | 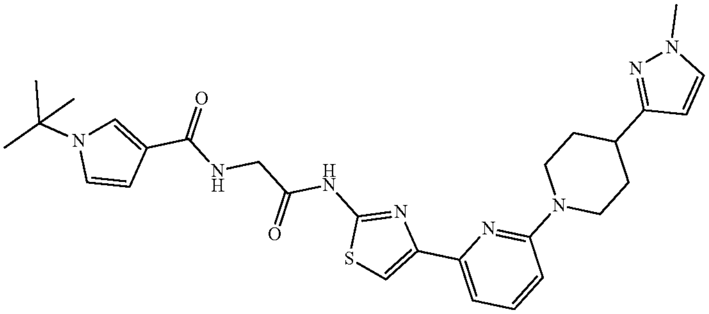 [SMILES: Cn1ccc(C2CCN(c3cccc(-c4csc(NC(=O)CNC(=O)c5ccn(C(C)(C)C)c5)n4)n3)CC2)n1] |
| 697 | 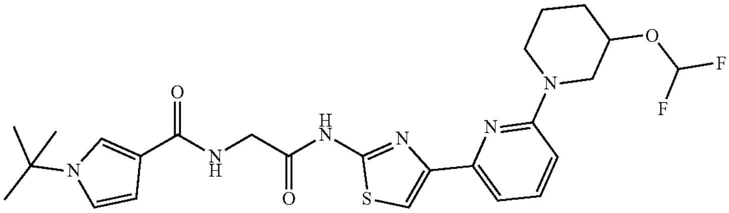 [SMILES: CC(C)(C)n1ccc(C(=O)NCC(=O)Nc2nc(-c3cccc(N4CCCC(OC(F)F)C4)n3)cs2)c1] |
| 698 | 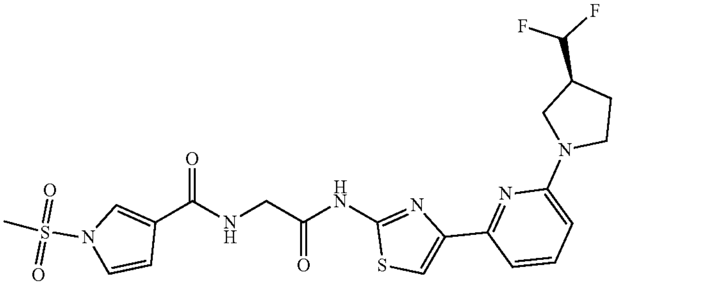 [SMILES: CS(=O)(=O)n1ccc(C(=O)NCC(=O)Nc2nc(-c3cccc(N4CC[C@H](C(F)F)C4)n3)cs2)c1] |
| 699 | 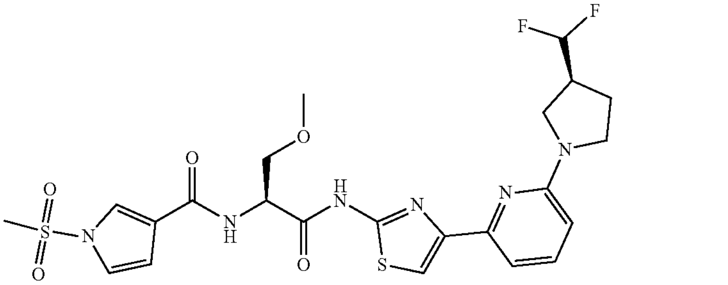 [SMILES: COC[C@H](NC(=O)c1ccn(S(C)(=O)=O)c1)C(=O)Nc1nc(-c2cccc(N3CC[C@H](C(F)F)C3)n2)cs1] |
| 700 | 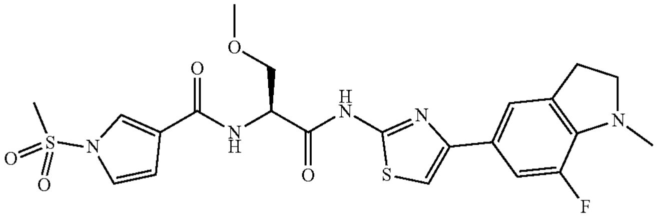 [SMILES: COC[C@H](NC(=O)c1ccn(S(C)(=O)=O)c1)C(=O)Nc1nc(-c2cc(F)c3c(c2)CCN3C)cs1] |
| 701 | 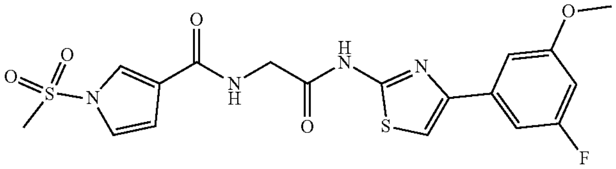 [SMILES: COc1cc(F)cc(-c2csc(NC(=O)CNC(=O)c3ccn(S(C)(=O)=O)c3)n2)c1] |

TABLE 1-continued
| Compounds of the invention | |
|---|---|
| # | Compound |
| 702 | 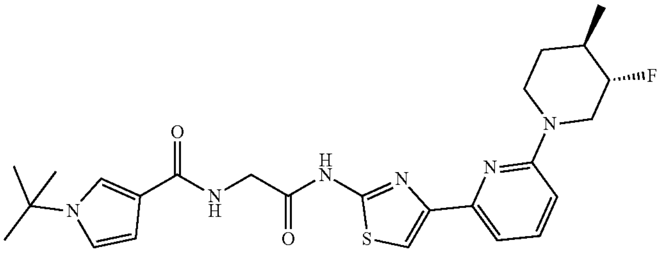 (±) |
| 703 | 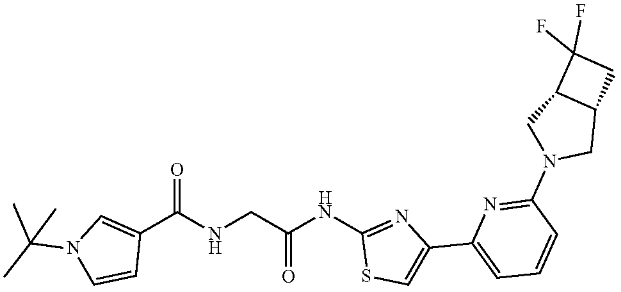 (±) |
| 704 | 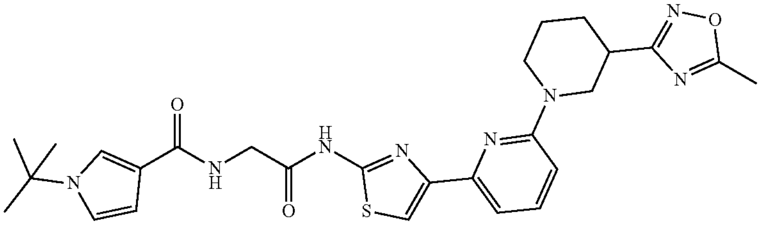 [SMILES: Cc1nc(C2CCCN(c3cccc(-c4csc(NC(=O)CNC(=O)c5ccn(C(C)(C)C)c5)n4)n3)C2)no1] |
| 705 | 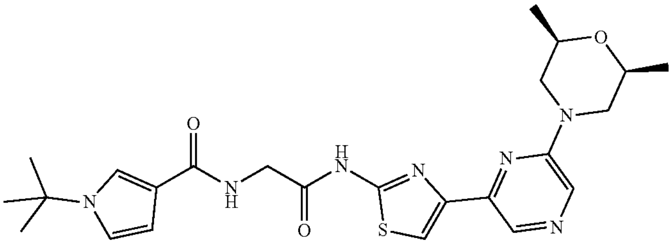 [SMILES: C[C@@H]1CN(c2cncc(-c3csc(NC(=O)CNC(=O)c4ccn(C(C)(C)C)c4)n3)n2)C[C@H](C)O1] |
| 706 | 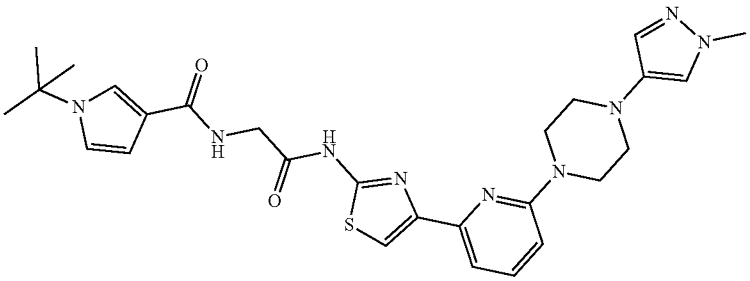 [SMILES: Cn1cc(N2CCN(c3cccc(-c4csc(NC(=O)CNC(=O)c5ccn(C(C)(C)C)c5)n4)n3)CC2)cn1] |

TABLE 1-continued
| Compounds of the invention | |
|---|---|
| # | Compound |
| 707 | 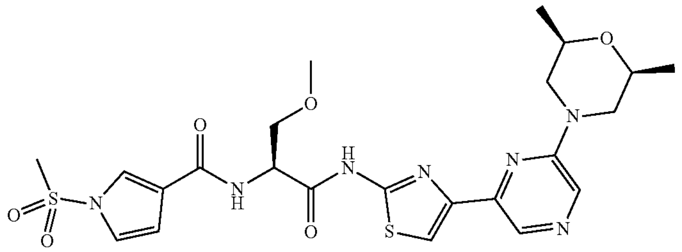 [SMILES: COC[C@H](NC(=O)c1ccn(S(C)(=O)=O)c1)C(=O)Nc1nc(-c2cncc(N3C[C@@H](C)O[C@@H](C)C3)n2)cs1] |
| 708 | 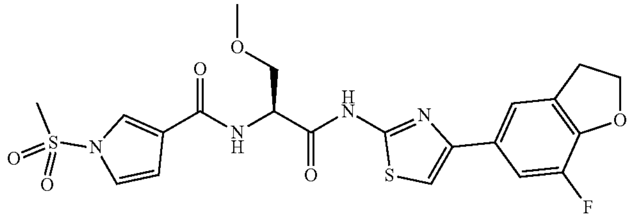 [SMILES: COC[C@H](NC(=O)c1ccn(S(C)(=O)=O)c1)C(=O)Nc1nc(-c2cc(F)c3c(c2)CCO3)cs1] |
| 709 | 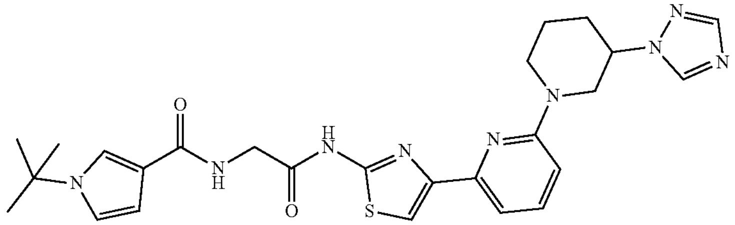 [SMILES: CC(C)(C)n1ccc(C(=O)NCC(=O)Nc2nc(-c3cccc(N4CCCC(n5cncn5)C4)n3)cs2)c1] |
| 710 | 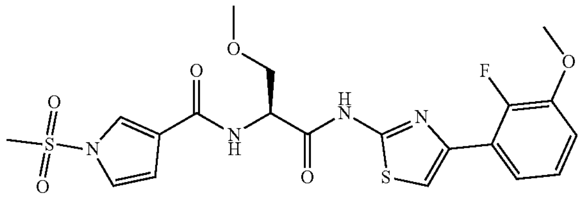 [SMILES: COC[C@H](NC(=O)c1ccn(S(C)(=O)=O)c1)C(=O)Nc1nc(-c2cccc(OC)c2F)cs1] |
| 711 | 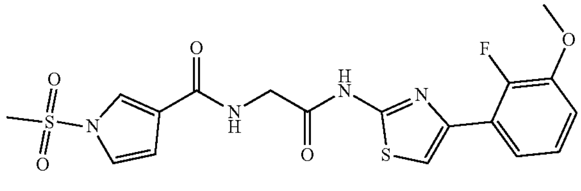 [SMILES: COc1cccc(-c2csc(NC(=O)CNC(=O)c3ccn(S(C)(=O)=O)c3)n2)c1F] |
| 712 | 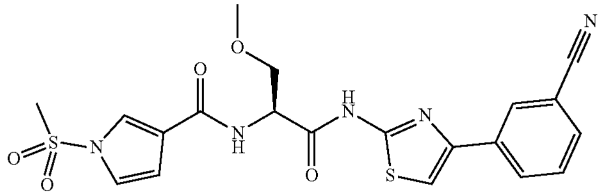 [SMILES: COC[C@H](NC(=O)c1ccn(S(C)(=O)=O)c1)C(=O)Nc1nc(-c2cccc(C#N)c2)cs1] |

TABLE 1-continued
Compounds of the invention
| # | Compound |
|---|---|
| 713 | 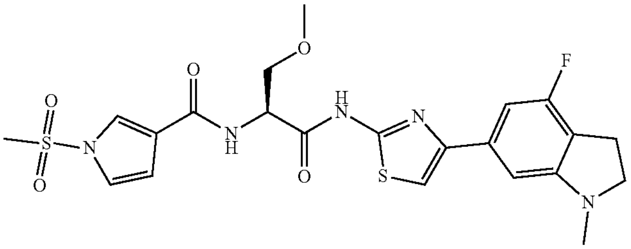 [SMILES: COC[C@H](NC(=O)c1ccn(S(C)(=O)=O)c1)C(=O)Nc1nc(-c2cc(F)c3c(c2)N(C)CC3)cs1] |
| 714 | 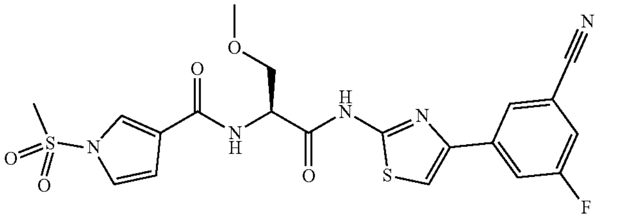 [SMILES: COC[C@H](NC(=O)c1ccn(S(C)(=O)=O)c1)C(=O)Nc1nc(-c2cc(F)cc(C#N)c2)cs1] |
| 715 | 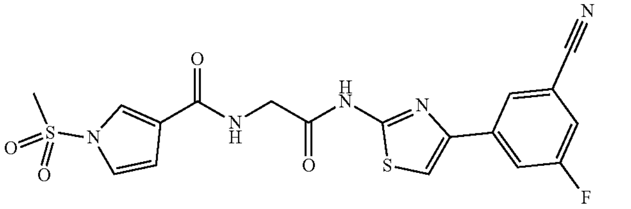 [SMILES: CS(=O)(=O)n1ccc(C(=O)NCC(=O)Nc2nc(-c3cc(F)cc(C#N)c3)cs2)c1] |
| 716 | 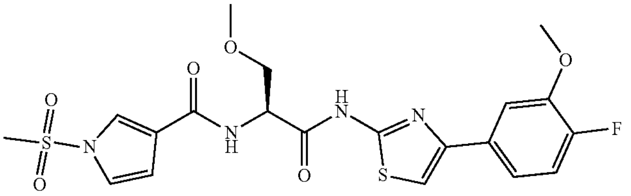 [SMILES: COC[C@H](NC(=O)c1ccn(S(C)(=O)=O)c1)C(=O)Nc1nc(-c2ccc(F)c(OC)c2)cs1] |
| 717 | 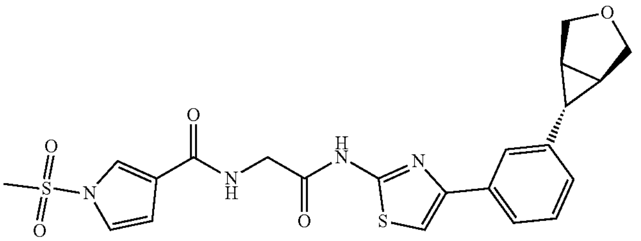 [SMILES: CS(=O)(=O)n1ccc(C(=O)NCC(=O)Nc2nc(-c3cccc([C@H]4[C@@H]5COC[C@@H]54)c3)cs2)c1] |
| 718 | 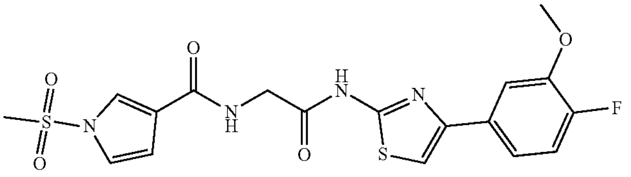 [SMILES: COc1cc(-c2csc(NC(=O)CNC(=O)c3ccn(S(C)(=O)=O)c3)n2)ccc1F] |
| 719 | 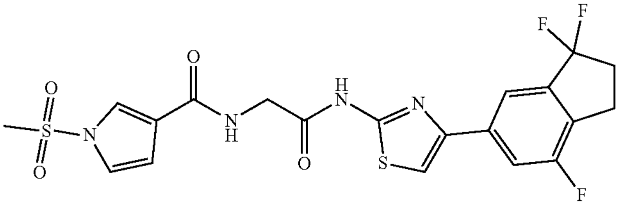 [SMILES: CS(=O)(=O)n1ccc(C(=O)NCC(=O)Nc2nc(-c3cc(F)c4c(c3)C(F)(F)CC4)cs2)c1] |

TABLE 1-continued
| Compounds of the invention | |
|---|---|
| # | Compound |
| 720 | 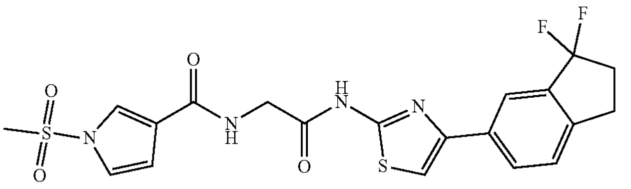 [SMILES: CS(=O)(=O)n1ccc(C(=O)NCC(=O)Nc2nc(-c3ccc4c(c3)C(F)(F)CC4)cs2)c1] |
| 721 | 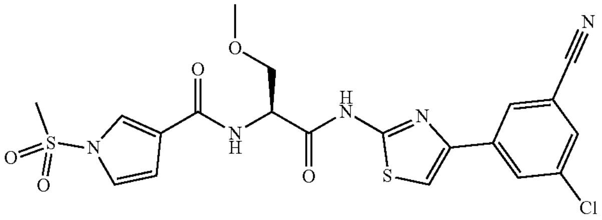 [SMILES: COC[C@H](NC(=O)c1ccn(S(C)(=O)=O)c1)C(=O)Nc1nc(-c2cc(Cl)cc(C#N)c2)cs1] |
| 722 | 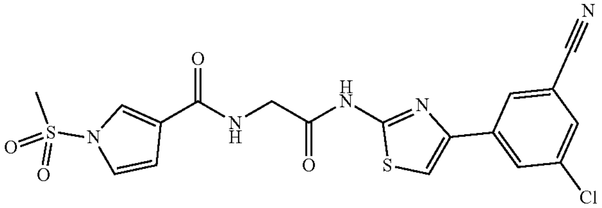 [SMILES: CS(=O)(=O)n1ccc(C(=O)NCC(=O)Nc2nc(-c3cc(Cl)cc(C#N)c3)cs2)c1] |
| 723 | 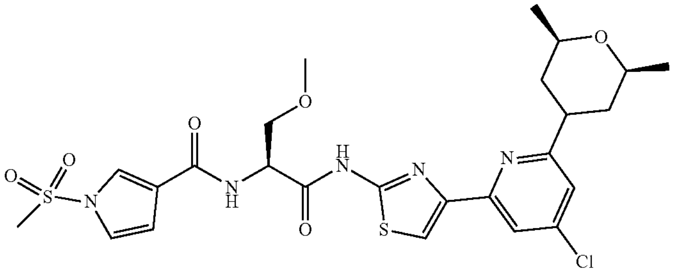 [SMILES: COC[C@H](NC(=O)c1ccn(S(C)(=O)=O)c1)C(=O)Nc1nc(-c2cc(Cl)cc(C3C[C@@H](C)O[C@@H](C)C3)n2)cs1] |
| 724 | 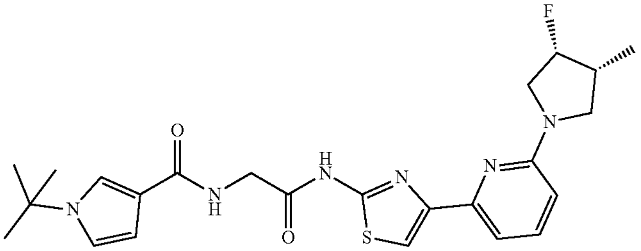 (±) |
| 725 | 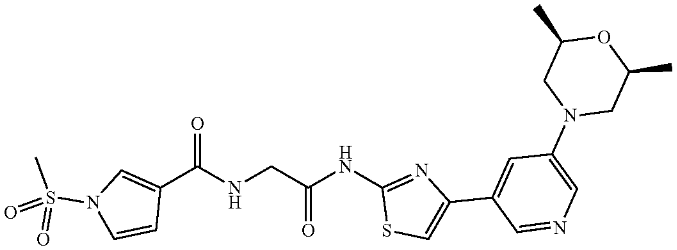 [SMILES: C[C@@H]1CN(c2cncc(-c3csc(NC(=O)CNC(=O)c4ccn(S(C)(=O)=O)c4)n3)c2)C[C@H](C)O1] |

TABLE 1-continued
| Compounds of the invention | |
|---|---|
| # | Compound |
| 726 | 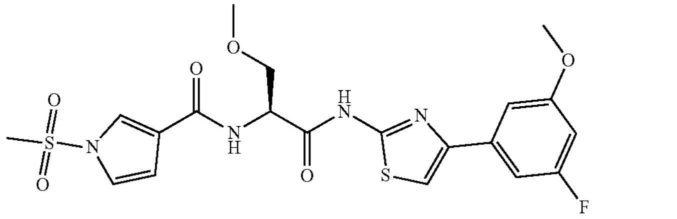 [SMILES: COC[C@H](NC(=O)c1ccn(S(C)(=O)=O)c1)C(=O)Nc1nc(-c2cc(F)cc(OC)c2)cs1] |
| 727 | 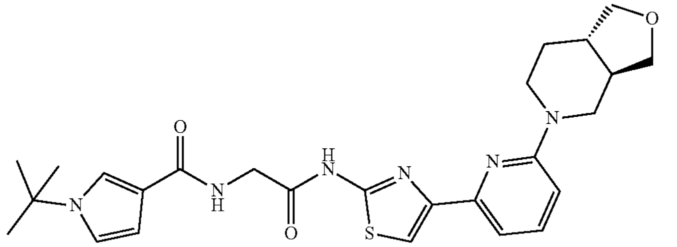 [SMILES: CC(C)(C)n1ccc(C(=O)NCC(=O)Nc2nc(-c3cccc(N4CC[C@@H]5COC[C@H]5C4)n3)cs2)c1] |
| 728 | 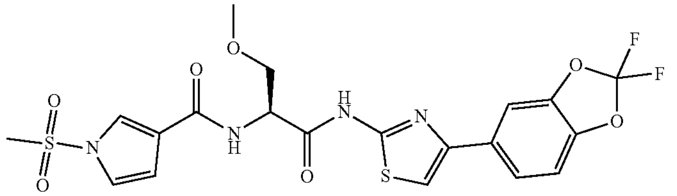 [SMILES: COC[C@H](NC(=O)c1ccn(S(C)(=O)=O)c1)C(=O)Nc1nc(-c2ccc3c(c2)OC(F)(F)O3)cs1] |
| 729 | 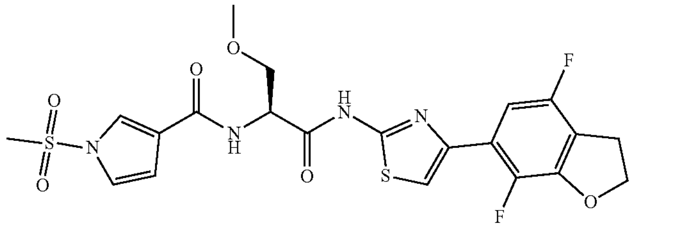 [SMILES: COC[C@H](NC(=O)c1ccn(S(C)(=O)=O)c1)C(=O)Nc1nc(-c2cc(F)c3c(c2F)OCC3)cs1] |
| 730 | 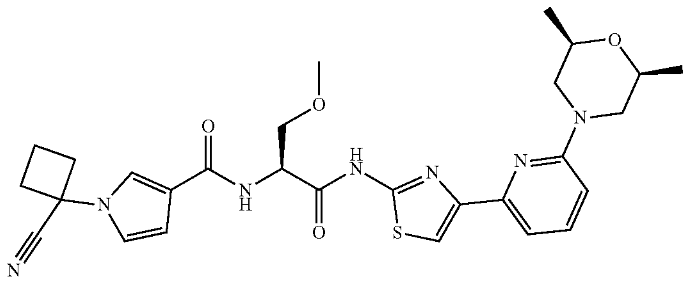 [SMILES: COC[C@H](NC(=O)c1ccn(C2(C#N)CCC2)c1)C(=O)Nc1nc(-c2cccc(N3C[C@@H](C)O[C@@H](C)C3)n2)cs1] |
| 731 | 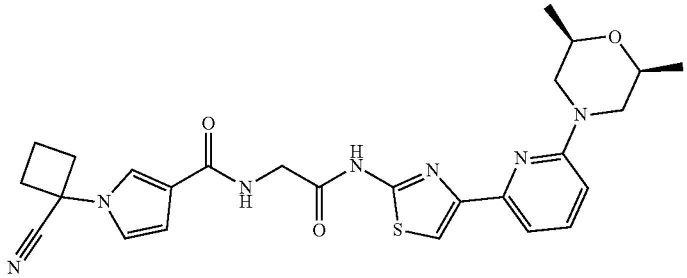 [SMILES: C[C@@H]1CN(c2cccc(-c3csc(NC(=O)CNC(=O)c4ccn(C5(C#N)CCC5)c4)n3)n2)C[C@H](C)O1] |

TABLE 1-continued
| Compounds of the invention | |
|---|---|
| # | Compound |
| 732 | 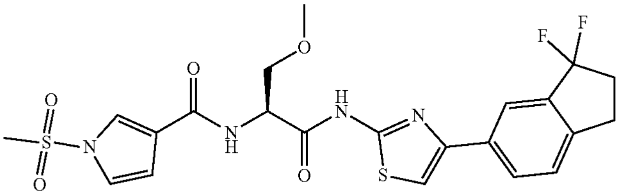 [SMILES: COC[C@H](NC(=O)c1ccn(S(C)(=O)=O)c1)C(=O)Nc1nc(-c2ccc3c(c2)C(F)(F)CC3)cs1] |
| 733 | 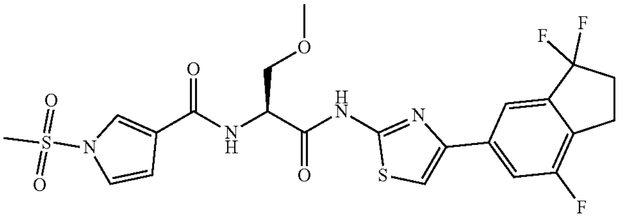 [SMILES: COC[C@H](NC(=O)c1ccn(S(C)(=O)=O)c1)C(=O)Nc1nc(-c2cc(F)c3c(c2)C(F)(F)CC3)cs1] |
| 734 | 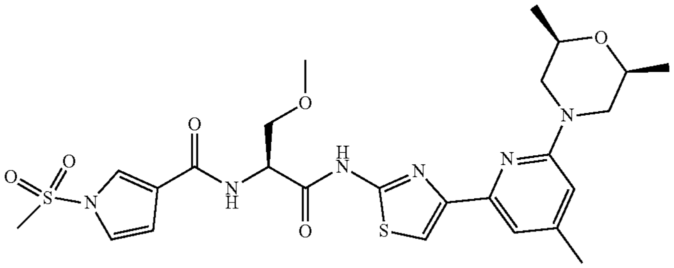 [SMILES: COC[C@H](NC(=O)c1ccn(S(C)(=O)=O)c1)C(=O)Nc1nc(-c2cc(C)cc(N3C[C@@H](C)O[C@@H](C)C3)n2)cs1] |
| 735 | 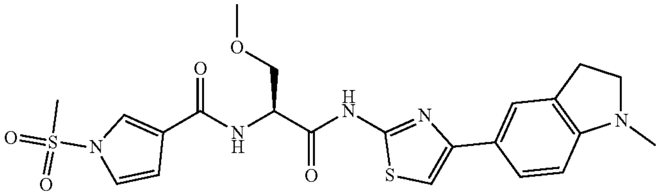 [SMILES: COC[C@H](NC(=O)c1ccn(S(C)(=O)=O)c1)C(=O)Nc1nc(-c2ccc3c(c2)CCN3C)cs1] |
| 736 | 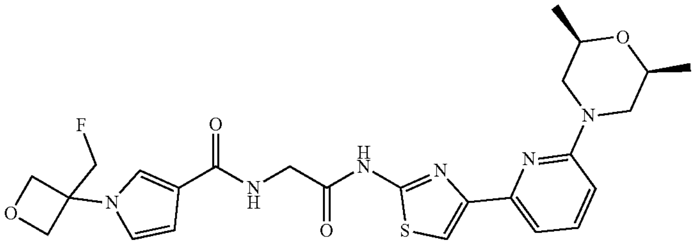 [SMILES: C[C@@H]1CN(c2cccc(-c3csc(NC(=O)CNC(=O)c4ccn(C5(CF)COC5)c4)n3)n2)C[C@H](C)O1] |
| 737 | 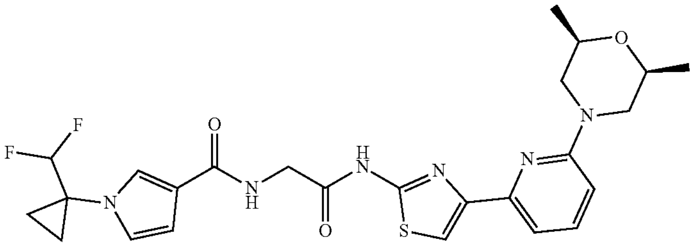 [SMILES: C[C@@H]1CN(c2cccc(-c3csc(NC(=O)CNC(=O)c4ccn(C5(C(F)F)CC5)c4)n3)n2)C[C@H](C)O1] |

TABLE 1-continued
| Compounds of the invention | |
|---|---|
| # | Compound |
| 738 | 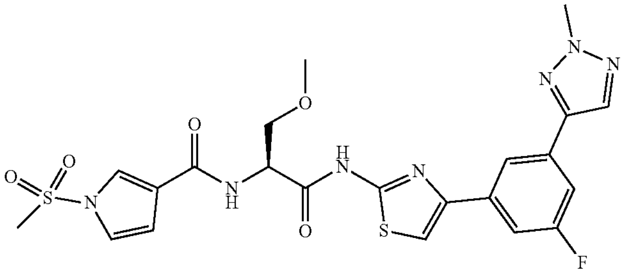 [SMILES: COC[C@H](NC(=O)c1ccn(S(C)(=O)=O)c1)C(=O)Nc1nc(-c2cc(F)cc(-c3cnn(C)n3)c2)cs1] |
| 739 | 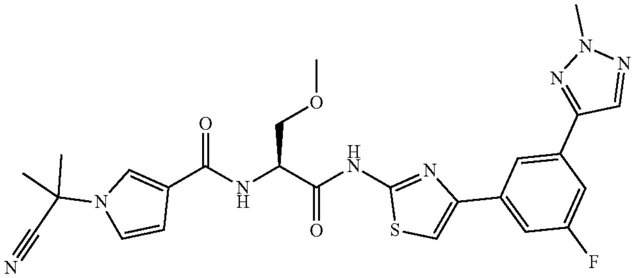 [SMILES: COC[C@H](NC(=O)c1ccn(C(C)(C)C#N)c1)C(=O)Nc1nc(-c2cc(F)cc(-c3cnn(C)n3)c2)cs1] |
| 740 | 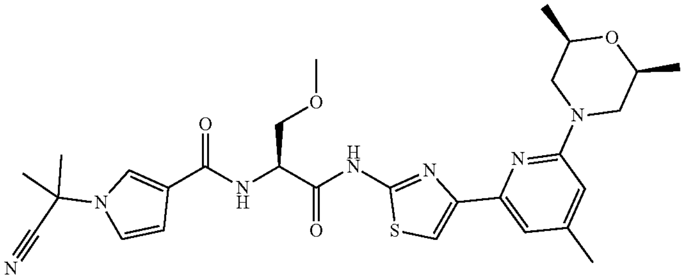 [SMILES: COC[C@H](NC(=O)c1ccn(C(C)(C)C#N)c1)C(=O)Nc1nc(-c2cc(C)cc(N3C[C@@H](C)O[C@@H](C)C3)n2)cs1] |
| 741 | 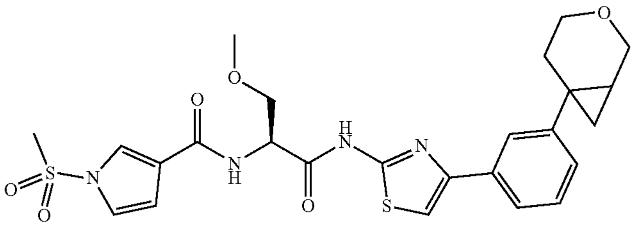 [SMILES: COC[C@H](NC(=O)c1ccn(S(C)(=O)=O)c1)C(=O)Nc1nc(-c2cccc(C34CCOCC3C4)c2)cs1] |
| 742 | 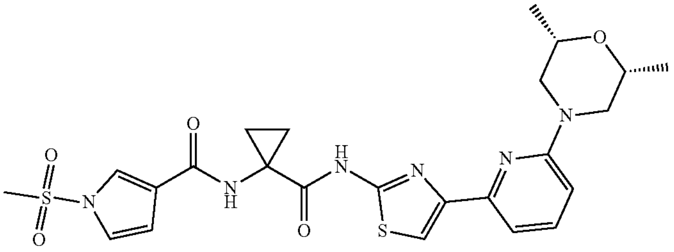 |

TABLE 1-continued
| Compounds of the invention | |
|---|---|
| # | Compound |
| 743 | 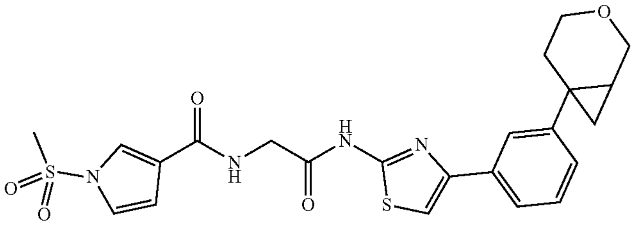 (±) |
| 744 | 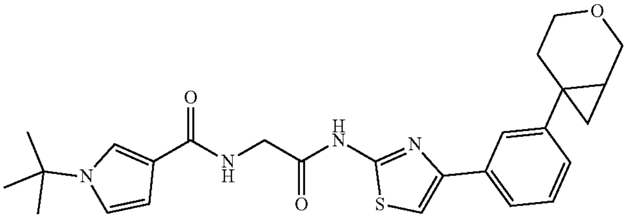 (±) |
| 745 | 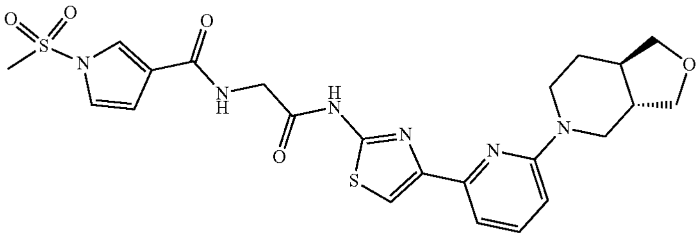 [SMILES: CS(=O)(=O)n1ccc(C(=O)NCC(=O)Nc2nc(-c3cccc(N4CC[C@H]5COC[C@@H]5C4)n3)cs2)c1] |
| 746 | 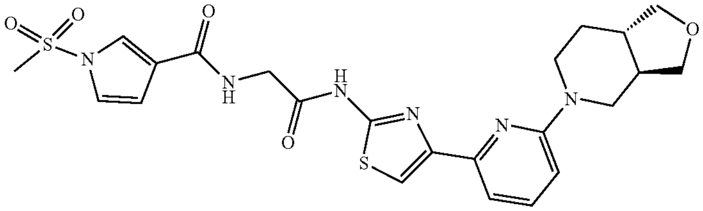 [SMILES: CS(=O)(=O)n1ccc(C(=O)NCC(=O)Nc2nc(-c3cccc(N4CC[C@@H]5COC[C@H]5C4)n3)cs2)c1] |
| 747 | 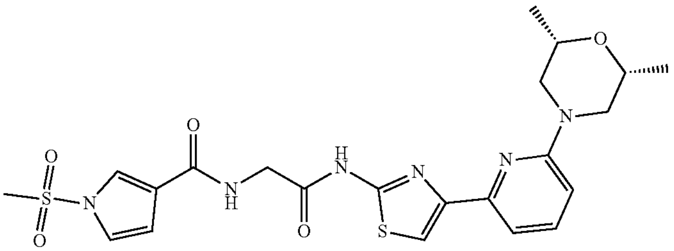 |
| 748 | 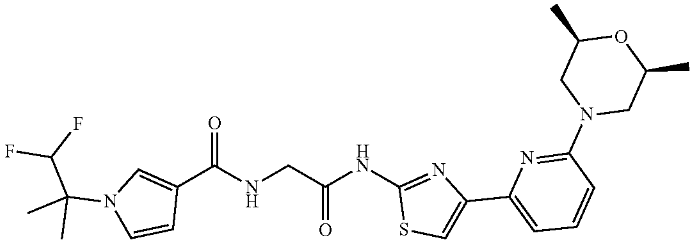 |

TABLE 1-continued
| Compounds of the invention | |
|---|---|
| # | Compound |
| 749 | 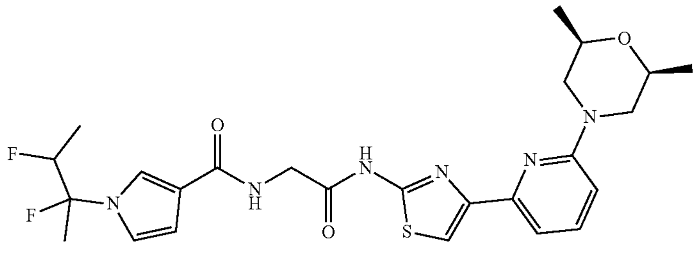 |
| 750 | 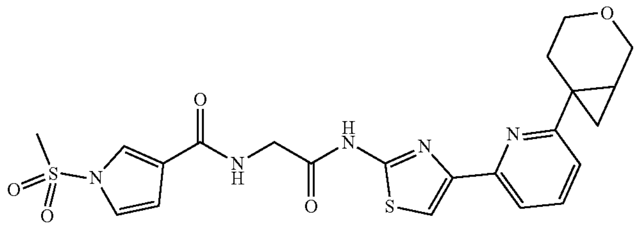 [SMILES: CS(=O)(=O)n1ccc(C(=O)NCC(=O)Nc2nc(-c3cccc(C45CCOCC4C5)n3)cs2)c1] |
| 751 | 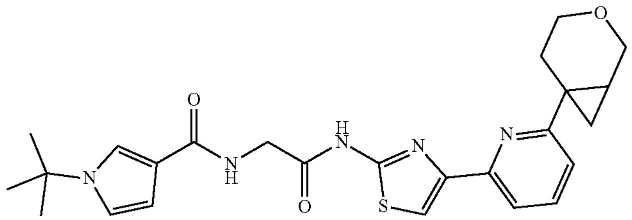 [SMILES: CC(C)(C)n1ccc(C(=O)NCC(=O)Nc2nc(-c3cccc(C45CCOCC4C5)n3)cs2)c1] |
| 752 | 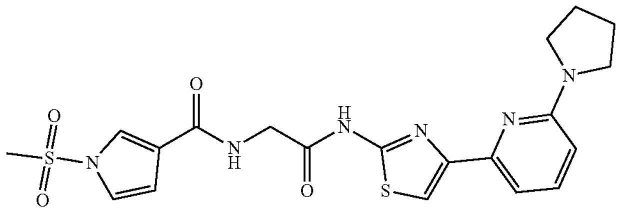 [SMILES: CS(=O)(=O)n1ccc(C(=O)NCC(=O)Nc2nc(-c3cccc(N4CCCC4)n3)cs2)c1] |
| 753 | 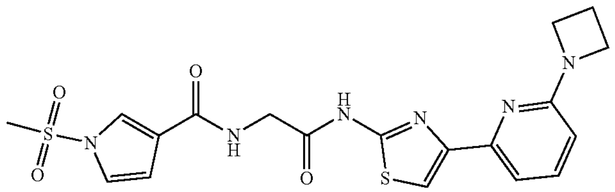 [SMILES: CS(=O)(=O)n1ccc(C(=O)NCC(=O)Nc2nc(-c3cccc(N4CCC4)n3)cs2)c1] |
| 754 | 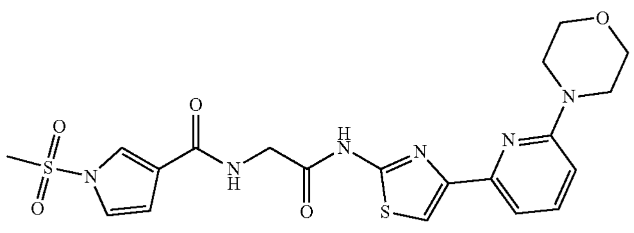 [SMILES: CS(=O)(=O)n1ccc(C(=O)NCC(=O)Nc2nc(-c3cccc(N4CCOCC4)n3)cs2)c1] |

TABLE 1-continued
| Compounds of the invention | |
|---|---|
| # | Compound |
| 755 | 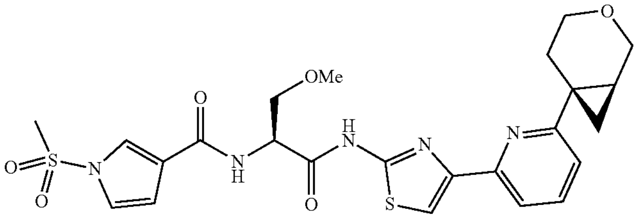 [SMILES: COC[C@H](NC(=O)c1ccn(S(C)(=O)=O)c1)C(=O)Nc1nc(-c2cccc([C@]34CCOC[C@H]3C4)n2)cs1] |
| 756 | 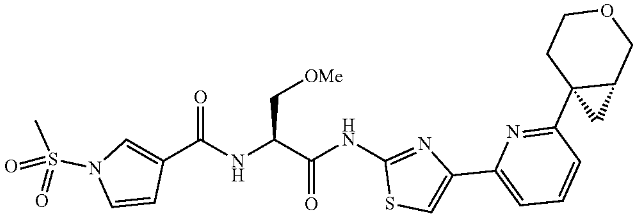 [SMILES: COC[C@H](NC(=O)c1ccn(S(C)(=O)=O)c1)C(=O)Nc1nc(-c2cccc([C@@]34CCOC[C@@H]3C4)n2)cs1] |
| 757 | 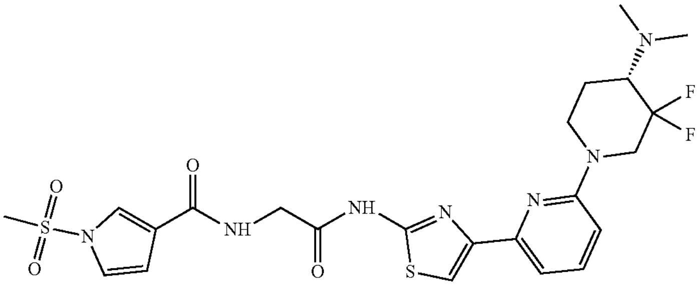 [SMILES: CN(C)[C@H]1CCN(c2cccc(-c3csc(NC(=O)CNC(=O)c4ccn(S(C)(=O)=O)c4)n3)n2)CC1(F)F] |
| 758 | 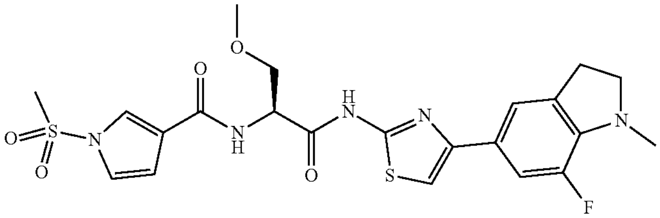 [SMILES: COC[C@H](NC(=O)c1ccn(S(C)(=O)=O)c1)C(=O)Nc1nc(-c2cc(F)c3c(c2)CCN3C)cs1] |
| 759 | 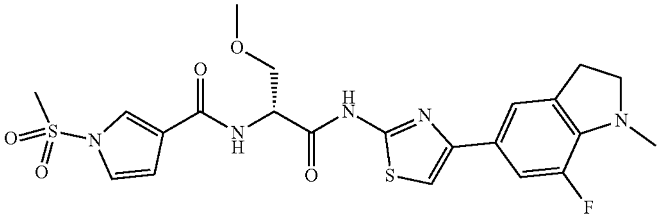 [SMILES: COC[C@@H](NC(=O)c1ccn(S(C)(=O)=O)c1)C(=O)Nc1nc(-c2cc(F)c3c(c2)CCN3C)cs1] |
| 760 | 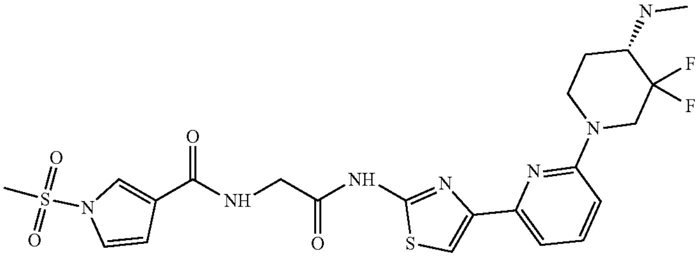 [SMILES: CN[C@H]1CCN(c2cccc(-c3csc(NC(=O)CNC(=O)c4ccn(S(C)(=O)=O)c4)n3)n2)CC1(F)F] |

TABLE 1-continued
| Compounds of the invention | |
|---|---|
| # | Compound |
| 761 | 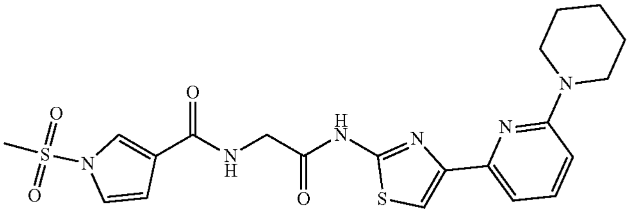 [SMILES: CS(=O)(=O)n1ccc(C(=O)NCC(=O)Nc2nc(-c3cccc(N4CCCCC4)n3)cs2)c1] |
| 762 | 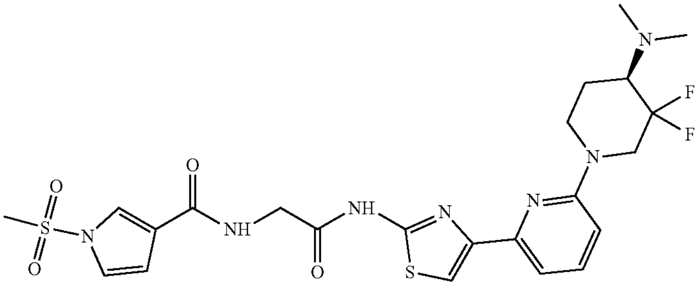 [SMILES: CN(C)[C@@H]1CCN(c2cccc(-c3csc(NC(=O)CNC(=O)c4ccn(S(C)(=O)=O)c4)n3)n2)CC1(F)F] |
| 763 | 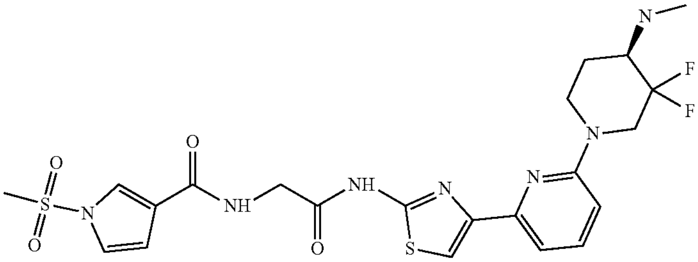 [SMILES: CN[C@@H]1CCN(c2cccc(-c3csc(NC(=O)CNC(=O)c4ccn(S(C)(=O)=O)c4)n3)n2)CC1(F)F] |
| 764 | 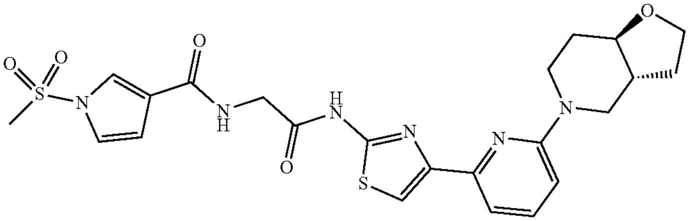 [SMILES: CS(=O)(=O)n1ccc(C(=O)NCC(=O)Nc2nc(-c3cccc(N4CC[C@H]5OCC[C@@H]5C4)n3)cs2)c1] |
| 765 | 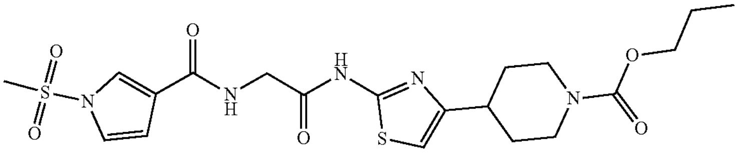 [SMILES: CCCOC(=O)N1CCC(c2csc(NC(=O)CNC(=O)c3ccn(S(C)(=O)=O)c3)n2)CC1] |
| 766 | 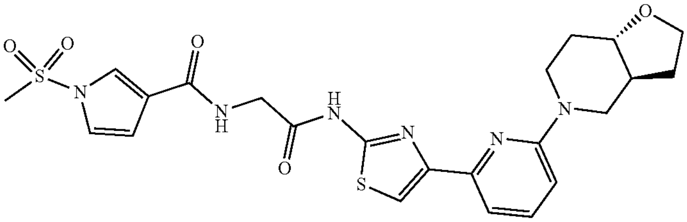 [SMILES: CS(=O)(=O)n1ccc(C(=O)NCC(=O)Nc2nc(-c3cccc(N4CC[C@@H]5OCC[C@H]5C4)n3)cs2)c1] |

TABLE 1-continued
| Compounds of the invention | |
|---|---|
| # | Compound |
| 767 | 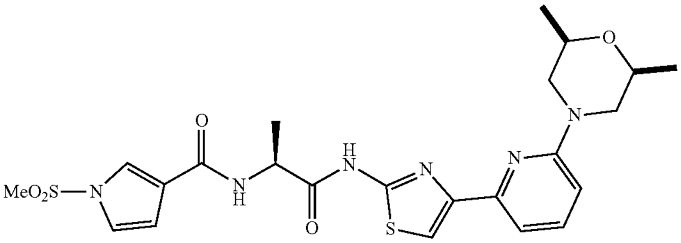 [SMILES: C[C@@H]1CN(c2cccc(-c3csc(NC(=O)[C@H](C)NC(=O)c4ccn(S(C)(=O)=O)c4)n3)n2)C[C@H](C)O1] |
| 768 | 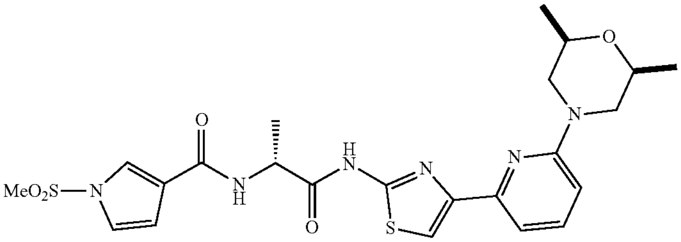 [SMILES: C[C@@H]1CN(c2cccc(-c3csc(NC(=O)[C@@H](C)NC(=O)c4ccn(S(C)(=O)=O)c4)n3)n2)C[C@H](C)O1] |
| 769 | 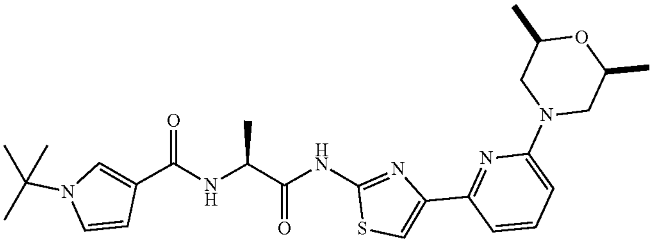 [SMILES: C[C@@H]1CN(c2cccc(-c3csc(NC(=O)[C@H](C)NC(=O)c4ccn(C(C)(C)C)c4)n3)n2)C[C@H](C)O1] |
| 770 | 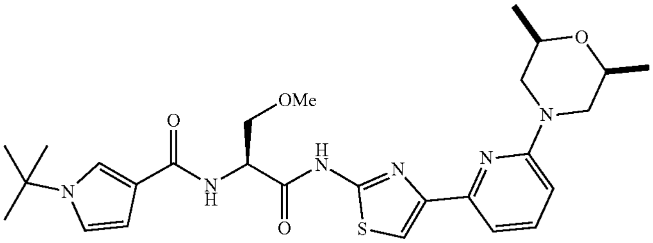 [SMILES: COC[C@H](NC(=O)c1ccn(C(C)(C)C)c1)C(=O)Nc1nc(-c2cccc(N3C[C@@H](C)O[C@@H](C)C3)n2)cs1] |
| 771 | 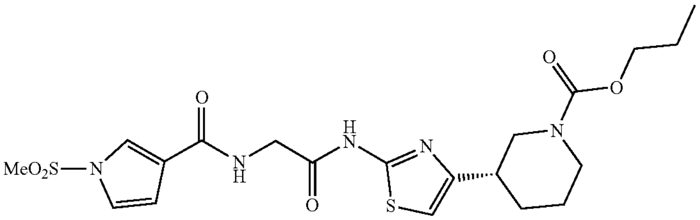 [SMILES: CCCOC(=O)N1CCC[C@H](c2csc(NC(=O)CNC(=O)c3ccn(S(C)(=O)=O)c3)n2)C1] |
| 772 | 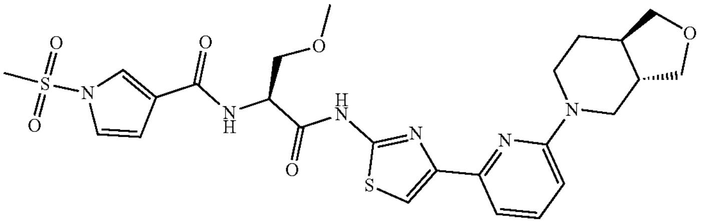 [SMILES: COC[C@H](NC(=O)c1ccn(S(C)(=O)=O)c1)C(=O)Nc1nc(-c2cccc(N3CC[C@H]4COC[C@@H]4C3)n2)cs1] |

TABLE 1-continued
| Compounds of the invention | |
|---|---|
| # | Compound |
| 773 | 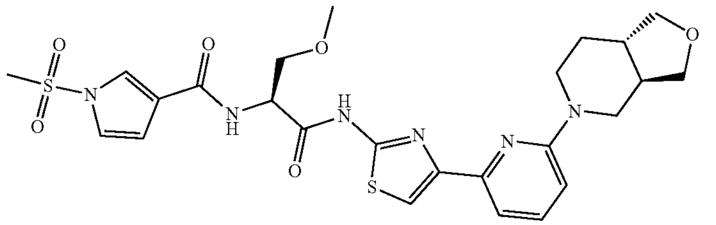 [SMILES: COC[C@H](NC(=O)c1ccn(S(C)(=O)=O)c1)C(=O)Nc1nc(-c2cccc(N3CC[C@@H]4COC[C@H]4C3)n2)cs1] |
| 774 | 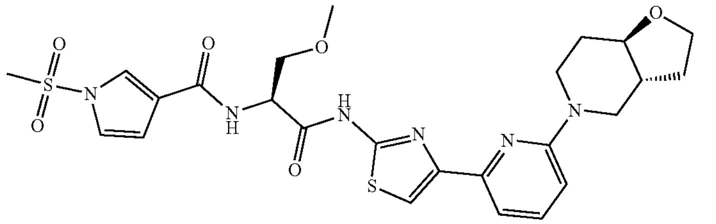 [SMILES: COC[C@H](NC(=O)c1ccn(S(C)(=O)=O)c1)C(=O)Nc1nc(-c2cccc(N3CC[C@H]4OCC[C@@H]4C3)n2)cs1] |
| 775 | 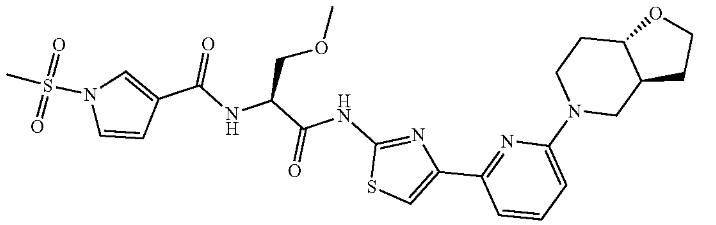 [SMILES: COC[C@H](NC(=O)c1ccn(S(C)(=O)=O)c1)C(=O)Nc1nc(-c2cccc(N3CC[C@@H]4OCC[C@H]4C3)n2)cs1] |
| 776 | 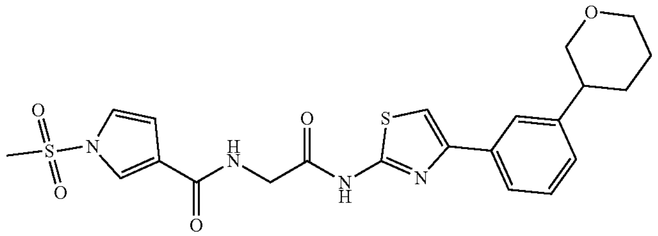 [SMILES: CS(=O)(=O)n1ccc(C(=O)NCC(=O)Nc2nc(-c3cccc(C4CCCOC4)c3)cs2)c1] |
| 777 | 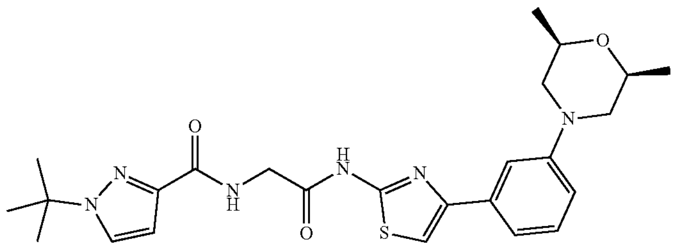 [SMILES: C[C@@H]1CN(c2cccc(-c3csc(NC(=O)CNC(=O)c4ccn(C(C)(C)C)n4)n3)c2)C[C@H](C)O1] |
| 778 | 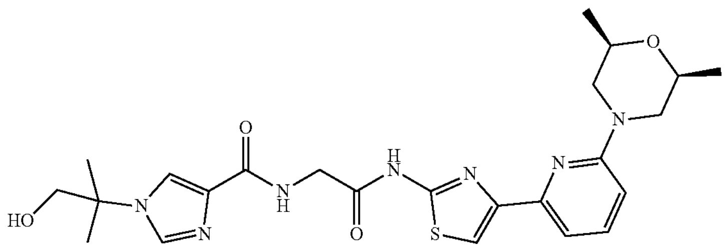 [SMILES: C[C@@H]1CN(c2cccc(-c3csc(NC(=O)CNC(=O)c4cn(C(C)(C)CO)cn4)n3)n2)C[C@H](C)O1] |

TABLE 1-continued
| Compounds of the invention | |
|---|---|
| # | Compound |
| 779 | 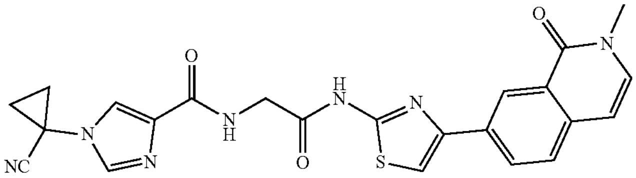 [SMILES: Cn1ccc2ccc(-c3csc(NC(=O)CNC(=O)c4cn(C5(C#N)CC5)cn4)n3)cc2c1=O] |
| 780 | 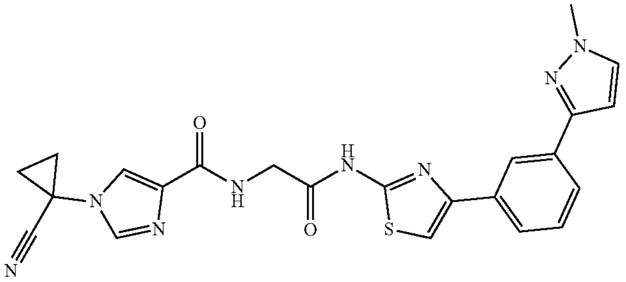 [SMILES: Cn1ccc(-c2cccc(-c3csc(NC(=O)CNC(=O)c4cn(C5(C#N)CC5)cn4)n3)c2)n1] |
| 781 | 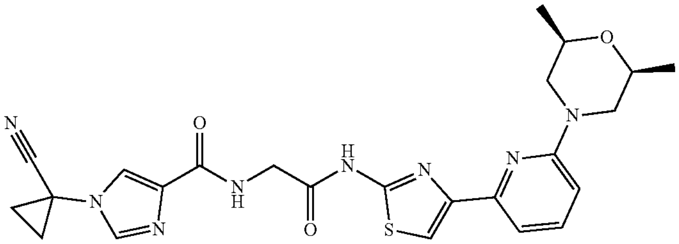 [SMILES: C[C@@H]1CN(c2cccc(-c3csc(NC(=O)CNC(=O)c4cn(C5(C#N)CC5)cn4)n3)n2)C[C@H](C)O1] |
| 782 | 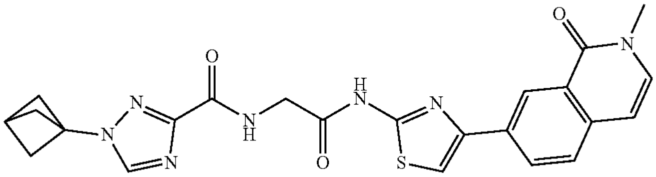 [SMILES: Cn1ccc2ccc(-c3csc(NC(=O)CNC(=O)c4ncn(C56CC(C5)C6)n4)n3)cc2c1=O] |
| 783 | 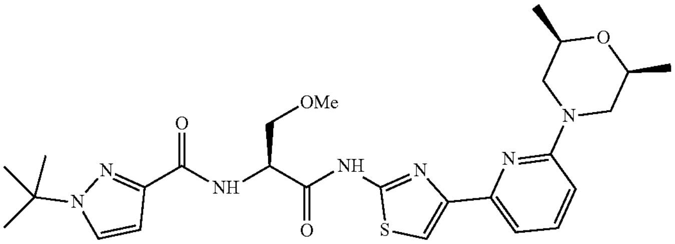 [SMILES: COC[C@H](NC(=O)c1ccn(C(C)(C)C)n1)C(=O)Nc1nc(-c2cccc(N3C[C@@H](C)O[C@@H](C)C3)n2)cs1] |
| 784 | 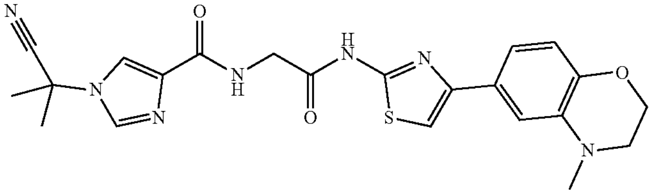 [SMILES: CN1CCOc2ccc(-c3csc(NC(=O)CNC(=O)c4cn(C(C)(C)C#N)cn4)n3)cc21] |
| 785 | 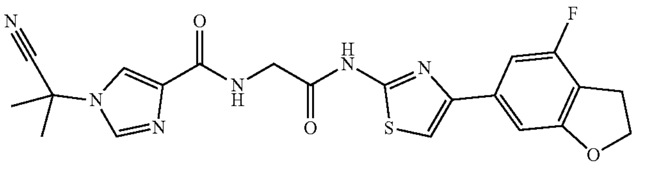 [SMILES: CC(C)(C#N)n1cnc(C(=O)NCC(=O)Nc2nc(-c3cc(F)c4c(c3)OCC4)cs2)c1] |

TABLE 1-continued
| Compounds of the invention | |
|---|---|
| # | Compound |
| 786 | 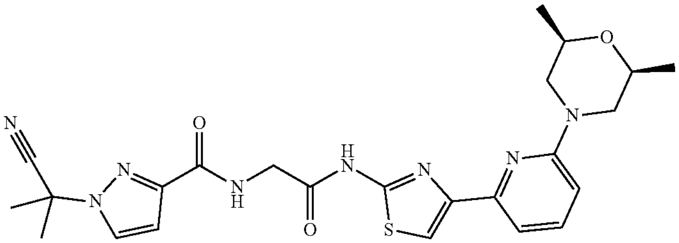 [SMILES: C[C@@H]1CN(c2cccc(-c3csc(NC(=O)CNC(=O)c4ccn(C(C)(C)C#N)n4)n3)n2)C[C@H](C)O1] |
| 787 | 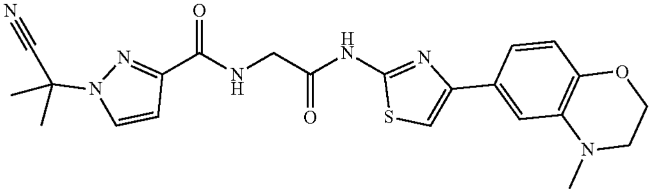 [SMILES: CN1CCOc2ccc(-c3csc(NC(=O)CNC(=O)c4ccn(C(C)(C)C#N)n4)n3)cc21] |
| 788 | 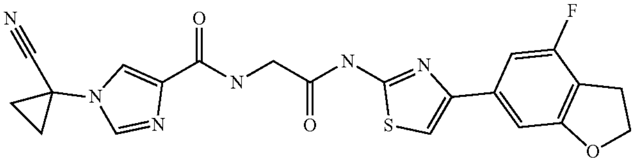 [SMILES: N#CC1(n2cnc(C(=O)NCC(=O)Nc3nc(-c4cc(F)c5c(c4)OCC5)cs3)c2)CC1] |
| 789 | 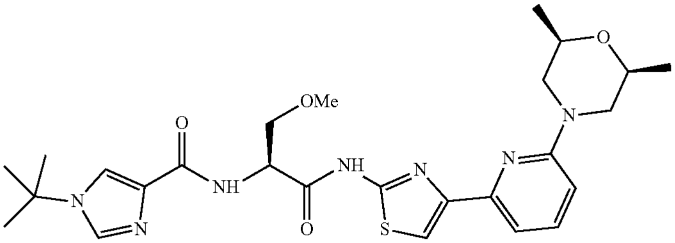 [SMILES: COC[C@H](NC(=O)c1cn(C(C)(C)C)cn1)C(=O)Nc1nc(-c2cccc(N3C[C@@H](C)O[C@@H](C)C3)n2)cs1] |
| 790 | 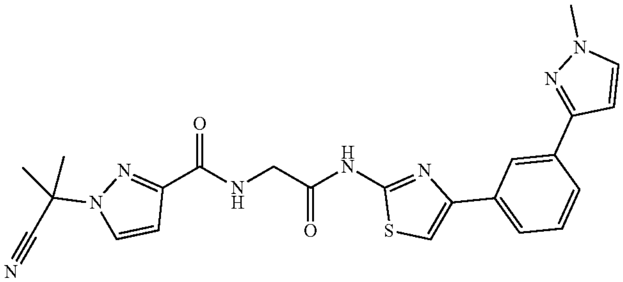 [SMILES: Cn1ccc(-c2cccc(-c3csc(NC(=O)CNC(=O)c4ccn(C(C)(C)C#N)n4)n3)c2)n1] |
| 791 | 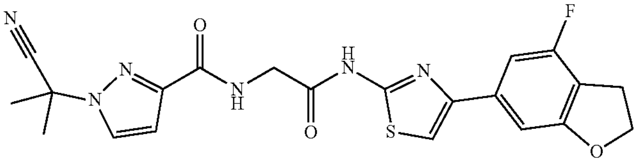 [SMILES: CC(C)(C#N)n1ccc(C(=O)NCC(=O)Nc2nc(-c3cc(F)c4c(c3)OCC4)cs2)n1] |
| 792 | 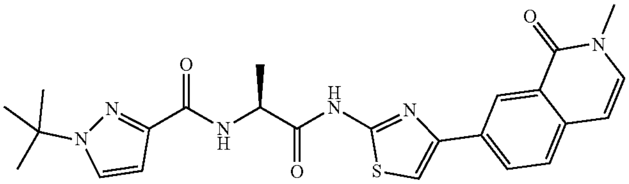 [SMILES: C[C@H](NC(=O)c1ccn(C(C)(C)C)n1)C(=O)Nc1nc(-c2ccc3ccn(C)c(=O)c3c2)cs1] |

TABLE 1-continued
| Compounds of the invention | |
|---|---|
| # | Compound |
| 793 | 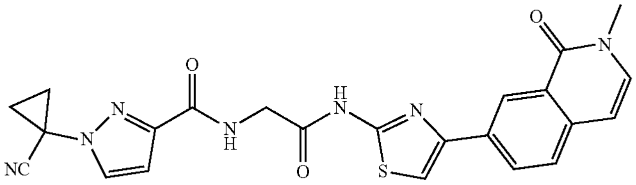 [SMILES: Cn1ccc2ccc(-c3csc(NC(=O)CNC(=O)c4ccn(C5(C#N)CC5)n4)n3)cc2c1=O] |
| 794 | 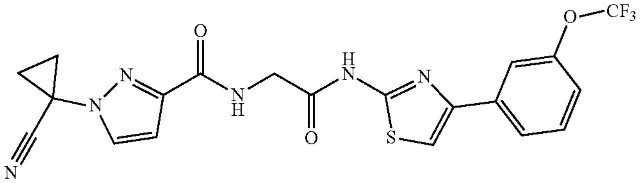 [SMILES: N#CC1(n2ccc(C(=O)NCC(=O)Nc3nc(-c4cccc(OC(F)(F)F)c4)cs3)n2)CC1] |
| 795 | 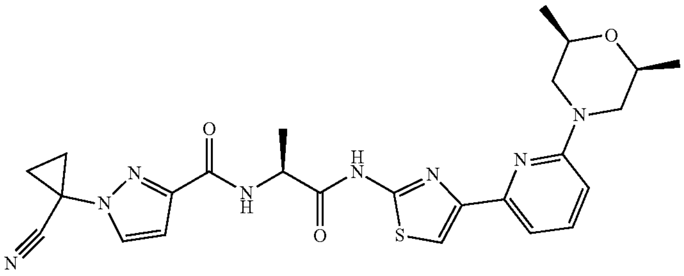 [SMILES: C[C@@H]1CN(c2cccc(-c3csc(NC(=O)[C@H](C)NC(=O)c4ccn(C5(C#N)CC5)n4)n3)n2)C[C@H](C)O1] |
| 796 | 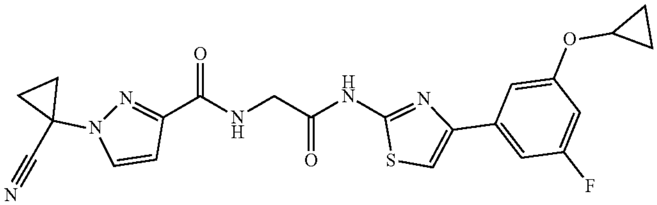 [SMILES: N#CC1(n2ccc(C(=O)NCC(=O)Nc3nc(-c4cc(F)cc(OC5CC5)c4)cs3)n2)CC1] |
| 797 | 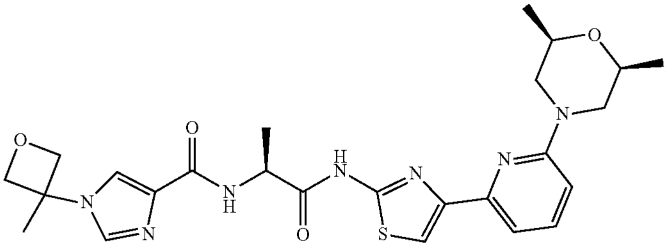 [SMILES: C[C@@H]1CN(c2cccc(-c3csc(NC(=O)[C@H](C)NC(=O)c4cn(C5(C)COC5)cn4)n3)n2)C[C@H](C)O1] |
| 798 | 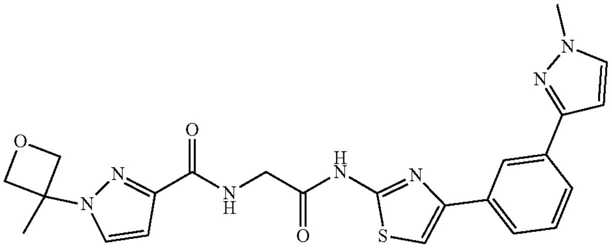 [SMILES: Cn1ccc(-c2cccc(-c3csc(NC(=O)CNC(=O)c4ccn(C5(C)COC5)n4)n3)c2)n1]

TABLE 1-continued
| Compounds of the invention | |
|---|---|
| # | Compound |
| 799 | 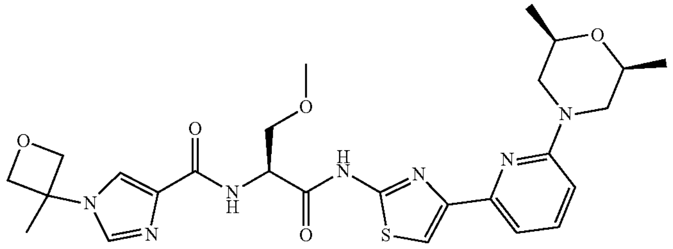 [SMILES: COC[C@H](NC(=O)c1cn(C2(C)COC2)cn1)C(=O)Nc1nc(-c2cccc(N3C[C@@H](C)O[C@@H](C)C3)n2)cs1] |
| 800 | 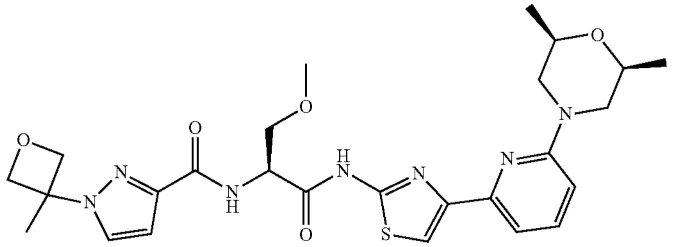 |
| 801 | 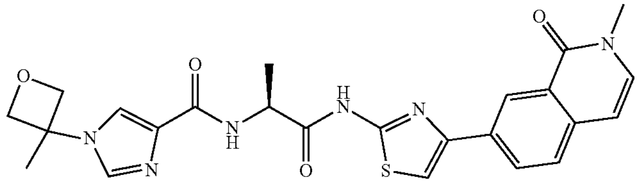 [SMILES: C[C@H](NC(=O)c1cn(C2(C)COC2)cn1)C(=O)Nc1nc(-c2ccc3ccn(C)c(=O)c3c2)cs1] |
| 802 | 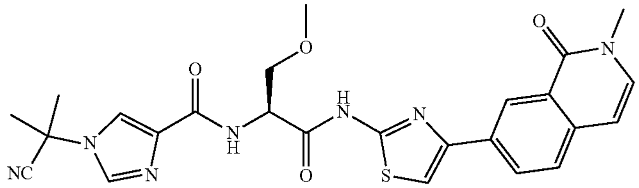 [SMILES: COC[C@H](NC(=O)c1cn(C(C)(C)C#N)cn1)C(=O)Nc1nc(-c2ccc3ccn(C)c(=O)c3c2)cs1] |
| 803 | 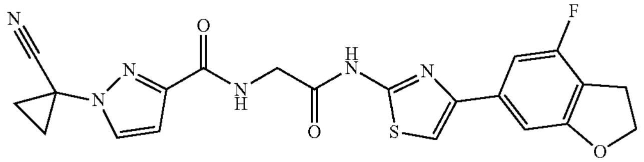 [SMILES: N#CC1(n2ccc(C(=O)NCC(=O)Nc3nc(-c4cc(F)c5c(c4)OCC5)cs3)n2)CC1] |
| 804 | 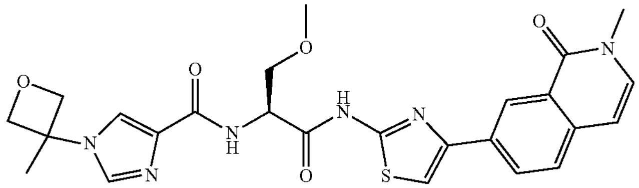 [SMILES: COC[C@H](NC(=O)c1cn(C2(C)COC2)cn1)C(=O)Nc1nc(-c2ccc3ccn(C)c(=O)c3c2)cs1] |
| 805 | 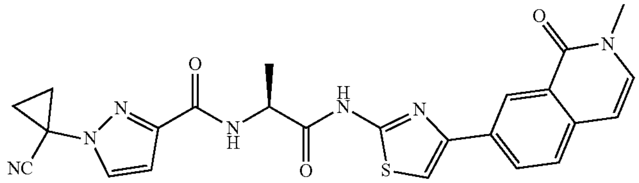 [SMILES: C[C@H](NC(=O)c1ccn(C2(C#N)CC2)n1)C(=O)Nc1nc(-c2ccc3ccn(C)c(=O)c3c2)cs1] |

TABLE 1-continued
| Compounds of the invention | |
|---|---|
| # | Compound |
| 806 | 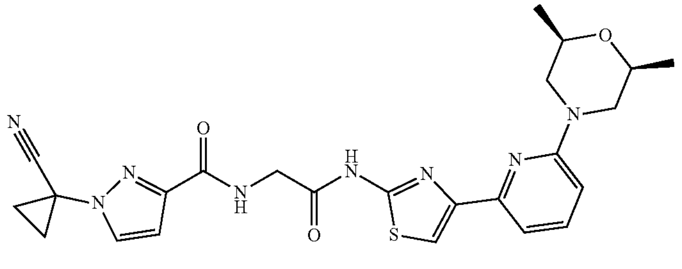 [SMILES: C[C@@H]1CN(c2cccc(-c3csc(NC(=O)CNC(=O)c4ccn(C5(C#N)CC5)n4)n3)n2)C[C@H](C)O1] |
| 807 | 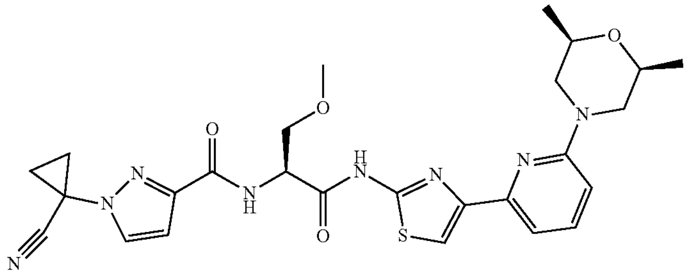 [SMILES: COC[C@H](NC(=O)c1ccn(C2(C#N)CC2)n1)C(=O)Nc1nc(-c2cccc(N3C[C@@H](C)O[C@@H](C)C3)n2)cs1] |
| 808 | 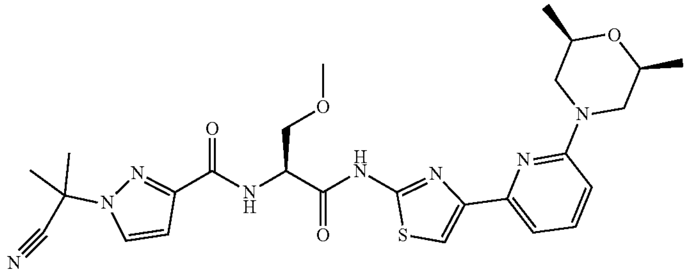 [SMILES: COC[C@H](NC(=O)c1ccn(C(C)(C)C#N)n1)C(=O)Nc1nc(-c2cccc(N3C[C@@H](C)O[C@@H](C)C3)n2)cs1] |
| 809 | 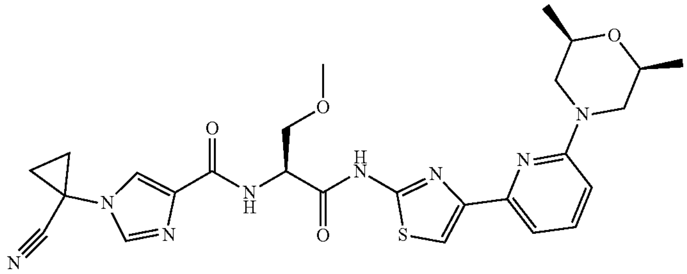 [SMILES: COC[C@H](NC(=O)c1cn(C2(C#N)CC2)cn1)C(=O)Nc1nc(-c2cccc(N3C[C@@H](C)O[C@@H](C)C3)n2)cs1] |
| 810 | 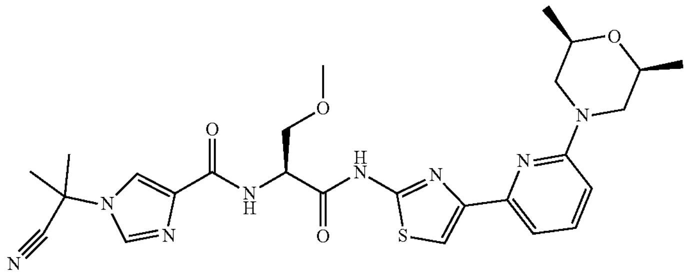 [SMILES: COC[C@H](NC(=O)c1cn(C(C)(C)C#N)cn1)C(=O)Nc1nc(-c2cccc(N3C[C@@H](C)O[C@@H](C)C3)n2)cs1] |

TABLE 1-continued
| Compounds of the invention | |
|---|---|
| # | Compound |
| 811 | 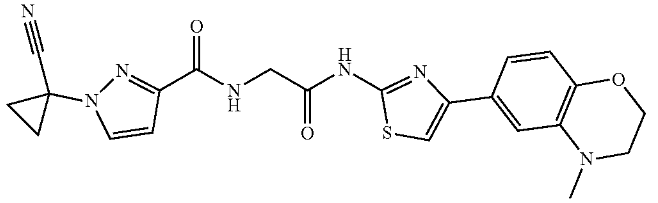 [SMILES: CN1CCOc2ccc(-c3csc(NC(=O)CNC(=O)c4ccn(C5(C#N)CC5)n4)n3)cc21] |
| 812 | 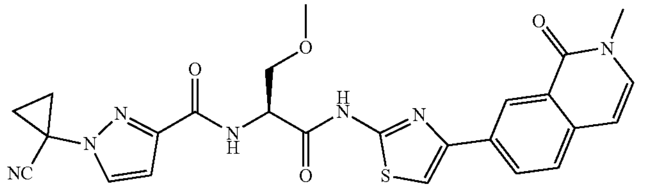 [SMILES: COC[C@H](NC(=O)c1ccn(C2(C#N)CC2)n1)C(=O)Nc1nc(-c2ccc3ccn(C)c(=O)c3c2)cs1] |
| 813 | 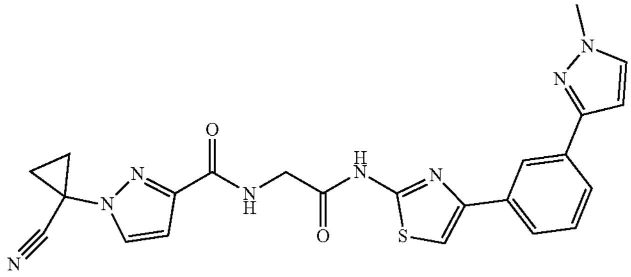 [SMILES: Cn1ccc(-c2cccc(-c3csc(NC(=O)CNC(=O)c4ccn(C5(C#N)CC5)n4)n3)c2)n1] |
| 814 | 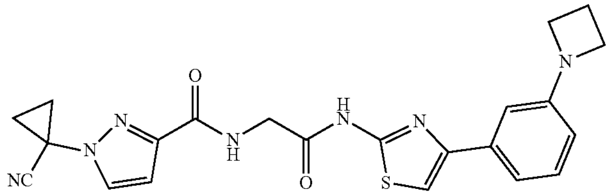 [SMILES: N#CC1(n2ccc(C(=O)NCC(=O)Nc3nc(-c4cccc(N5CCC5)c4)cs3)n2)CC1] |
| 815 | 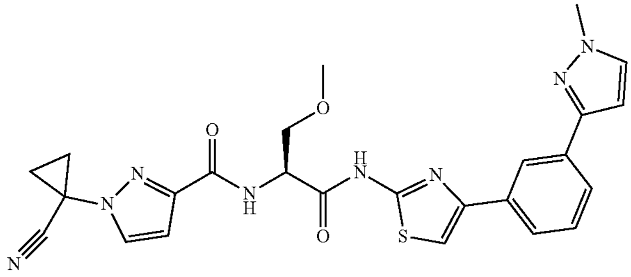 [SMILES: COC[C@H](NC(=O)c1ccn(C2(C#N)CC2)n1)C(=O)Nc1nc(-c2cccc(-c3ccn(C)n3)c2)cs1] |
| 816 | 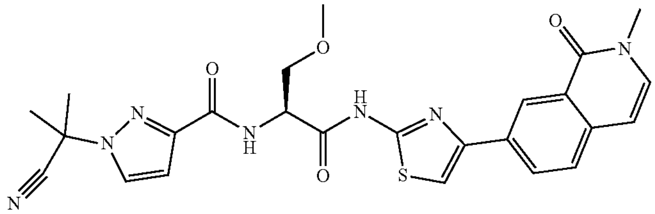 [SMILES: COC[C@H](NC(=O)c1ccn(C(C)(C)C#N)n1)C(=O)Nc1nc(-c2ccc3ccn(C)c(=O)c3c2)cs1] |

TABLE 1-continued
Compounds of the invention
| # | Compound |
|---|---|
| 817 | 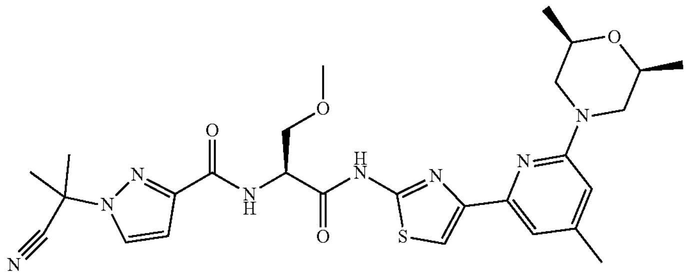 [SMILES: COC[C@H](NC(=O)c1ccn(C(C)(C)C#N)n1)C(=O)Nc1nc(-c2cc(C)cc(N3C[C@@H](C)O[C@@H](C)C3)n2)cs1] |
| 818 | 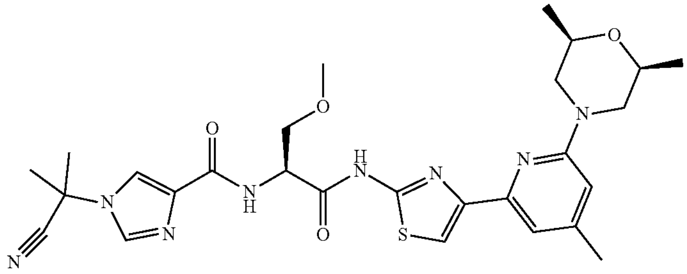 [SMILES: COC[C@H](NC(=O)c1cn(C(C)(C)C#N)cn1)C(=O)Nc1nc(-c2cc(C)cc(N3C[C@@H](C)O[C@@H](C)C3)n2)cs1] |
| 819 | 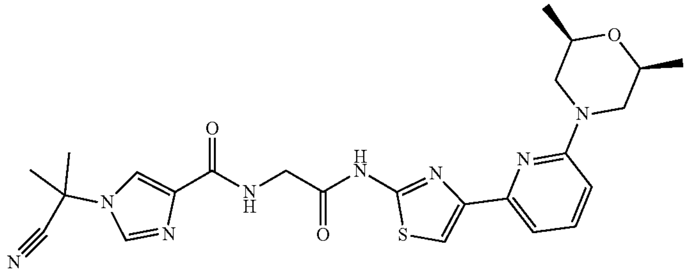 [SMILES: C[C@@H]1CN(c2cccc(-c3csc(NC(=O)CNC(=O)c4cn(C(C)(C)C#N)cn4)n3)n2)C[C@H](C)O1] |
| 820 | 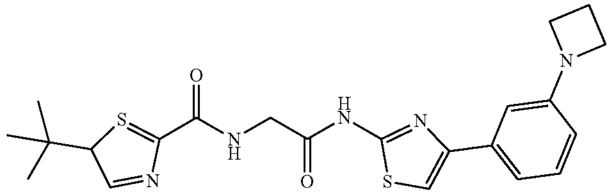 |
| 821 | 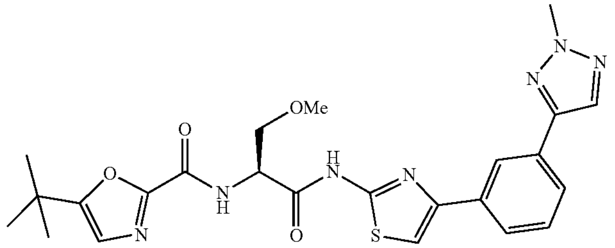 [SMILES: COC[C@H](NC(=O)c1ncc(C(C)(C)C)o1)C(=O)Nc1nc(-c2cccc(-c3cnn(C)n3)c2)cs1] |
| 822 | 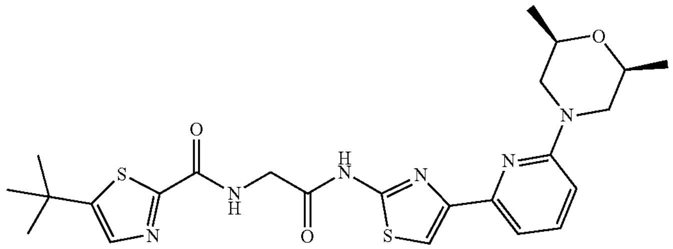 [SMILES: C[C@@H]1CN(c2cccc(-c3csc(NC(=O)CNC(=O)c4ncc(C(C)(C)C)s4)n3)n2)C[C@H](C)O1] |

TABLE 1-continued

| Compounds of the invention | |
|---|---|
| # | Compound |
| 823 | 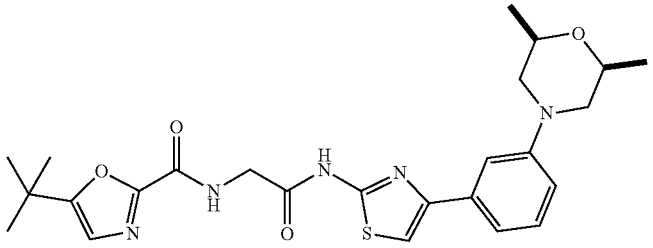 [SMILES: C[C@@H]1CN(c2cccc(-c3csc(NC(=O)CNC(=O)c4ncc(C(C)(C)C)o4)n3)c2)C[C@H](C)O1] |
| 824 | 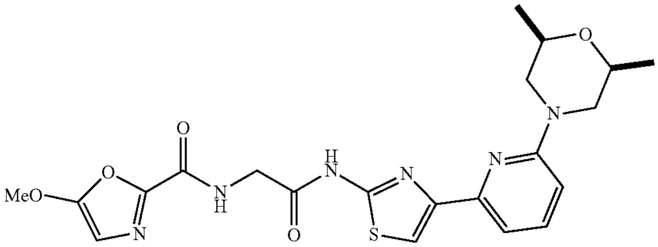 [SMILES: COc1cnc(C(=O)NCC(=O)Nc2nc(-c3cccc(N4C[C@@H](C)O[C@@H](C)C4)n3)cs2)o1] |
| 825 | 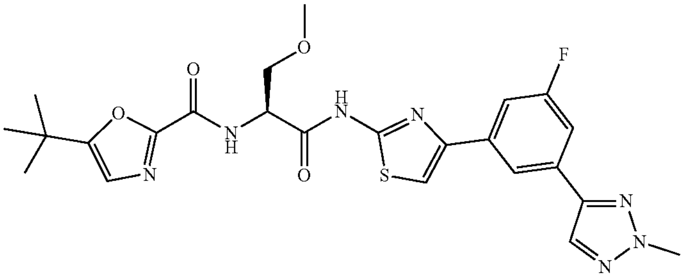 [SMILES: COC[C@H](NC(=O)c1ncc(C(C)(C)C)o1)C(=O)Nc1nc(-c2cc(F)cc(-c3cnn(C)n3)c2)cs1] |
| 826 | 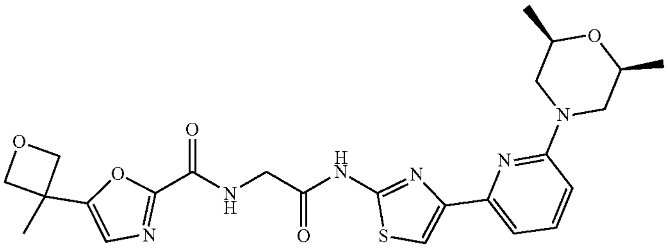 [SMILES: C[C@@H]1CN(c2cccc(-c3csc(NC(=O)CNC(=O)c4ncc(C5(C)COC5)o4)n3)n2)C[C@H](C)O1] |
| 827 | 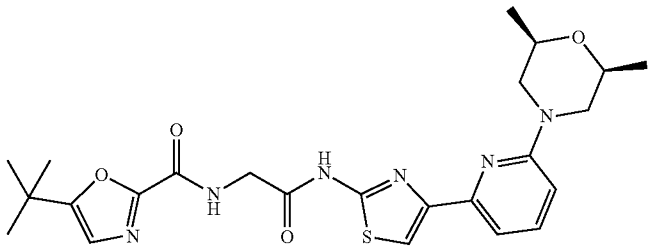 [SMILES: C[C@@H]1CN(c2cccc(-c3csc(NC(=O)CNC(=O)c4ncc(C(C)(C)C)o4)n3)n2)C[C@H](C)O1] |

In another aspect, the invention features a pharmaceutical composition including any one of the above compounds and a pharmaceutically acceptable excipient.

In another aspect, the invention features a method of decreasing the activity of a BAF complex in a cell, the method involving contacting the cell with an effective amount of any of the foregoing compounds or a pharmaceutical composition thereof.

In some embodiments, the cell is a cancer cell.

In another aspect, the invention features a method of treating a BAF complex-related disorder in a subject in need thereof, the method involving administering to the subject an effective amount of any of the foregoing compounds or a pharmaceutical composition thereof.

In some embodiments, the BAF complex-related disorder is cancer.

In a further aspect, the invention features a method of inhibiting BRM, the method involving contacting a cell with an effective amount of any of the foregoing compounds or a pharmaceutical composition thereof. In some embodiments, the cell is a cancer cell.

In another aspect, the invention features a method of inhibiting BRG1, the method involving contacting the cell with an effective amount of any of the foregoing compounds or a pharmaceutical composition thereof. In some embodiments, the cell is a cancer cell.

In a further aspect, the invention features a method of inhibiting BRM and BRG1, the method involving contacting the cell with an effective amount of any of the foregoing compounds or a pharmaceutical composition thereof. In some embodiments, the cell is a cancer cell.

In another aspect, the invention features a method of treating a disorder related to a BRG1 loss of function mutation in a subject in need thereof, the method involving administering to the subject an effective amount of any of the foregoing compounds or a pharmaceutical composition thereof.

In some embodiments, the disorder related to a BRG1 loss of function mutation is cancer. In other embodiments, the subject is determined to have a BRG1 loss of function disorder, for example, is determined to have a BRG1 loss of function cancer (for example, the cancer has been determined to include cancer cells with loss of BRG1 function).

In another aspect, the invention features a method of inducing apoptosis in a cell, the method involving contacting the cell with an effective amount of any of the foregoing compounds or a pharmaceutical composition thereof. In some embodiments, the cell is a cancer cell.

In a further aspect, the invention features a method of treating cancer in a subject in need thereof, the method including administering to the subject an effective amount of any of the foregoing compounds or a pharmaceutical composition thereof.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, or penile cancer.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, or penile cancer.

In some embodiments of any of the foregoing methods, the cancer is a drug resistant cancer or has failed to respond to a prior therapy (e.g., vemurafenib, dacarbazine, a CTLA4 inhibitor, a PD1 inhibitor, interferon therapy, a BRAF inhibitor, a MEK inhibitor, radiotherapy, temozolimide, irinotecan, a CAR-T therapy, herceptin, perjeta, tamoxifen, xeloda, docetaxol, platinum agents such as carboplatin, taxanes such as paclitaxel and docetaxel, ALK inhibitors, MET inhibitors, alimta, abraxane, Adriamycin®, gemcitabine, avastin, halaven, neratinib, a PARP inhibitor, ARN810, an mTOR inhibitor, topotecan, gemzar, a VEGFR2 inhibitor, a folate receptor antagonist, demcizumab, fosbretabulin, or a PDL1 inhibitor).

In some embodiments of any of the foregoing methods, the cancer has or has been determined to have BRG1 mutations. In some embodiments of any of the foregoing methods, the BRG1 mutations are homozygous. In some embodiments of any of the foregoing methods, the cancer does not have, or has been determined not to have, an epidermal growth factor receptor (EGFR) mutation. In some embodiments of any of the foregoing methods, the cancer does not have, or has been determined not to have, an anaplastic lymphoma kinase (ALK) driver mutation. In some embodiments of any of the foregoing methods, the cancer has, or has been determined to have, a KRAS mutation. In some embodiments of any of the foregoing methods, the BRG1 mutation is in the ATPase catalytic domain of the protein. In some embodiments of any of the foregoing methods, the BRG1 mutation is a deletion at the C-terminus of BRG1.

In another aspect, the disclosure provides a method treating a disorder related to BAF (e.g., cancer or viral infections) in a subject in need thereof. This method includes contacting a cell with an effective amount of any of the foregoing compounds, or pharmaceutically acceptable salts thereof, or any of the foregoing pharmaceutical compositions. In some embodiments, the disorder is a viral infection is an infection with a virus of the Retroviridae family such as the lentiviruses (e.g., Human immunodeficiency virus (HIV) and deltaretroviruses (e.g., human T cell leukemia virus I (HTLV-I), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g., Human Papillomavirus (HPV, HPV E1)), Parvoviridae family (e.g., Parvovirus B19), Polyomaviridae family (e.g., JC virus and BK virus), Paramyxoviridae family (e.g., Measles virus), Togaviridae family (e.g., Rubella virus). In some embodiments, the disorder is Coffin Siris, Neurofibromatosis (e.g., NF-1, NF-2, or Schwannomatosis), or Multiple Meningioma.

In another aspect, the disclosure provides a method for treating a viral infection in a subject in need thereof. This method includes administering to the subject an effective amount of any of the foregoing compounds, or pharmaceutically acceptable salts thereof, or any of the foregoing pharmaceutical compositions. In some embodiments, the viral infection is an infection with a virus of the Retroviridae family such as the lentiviruses (e.g., Human immunodeficiency virus (HIV) and deltaretroviruses (e.g., human T cell leukemia virus I (HTLV-I), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g., Human Papillomavirus (HPV, HPV E1)), Parvoviridae family (e.g., Parvovirus B19), Polyomaviridae family (e.g., JC virus and BK virus), Paramyxoviridae family (e.g., Measles virus), or Togaviridae family (e.g., Rubella virus).

In another aspect, the invention features a method of treating melanoma, prostate cancer, breast cancer, bone cancer, renal cell carcinoma, or a hematologic cancer in a subject in need thereof, the method including administering to the subject an effective amount of any of the foregoing compounds or pharmaceutical compositions thereof.

In another aspect, the invention features a method of reducing tumor growth of melanoma, prostate cancer, breast cancer, bone cancer, renal cell carcinoma, or a hematologic cancer in a subject in need thereof, the method including administering to the subject an effective amount of any of the foregoing compounds or pharmaceutical compositions thereof.

In another aspect, the invention features a method of suppressing metastatic progression of melanoma, prostate cancer, breast cancer, bone cancer, renal cell carcinoma, or a hematologic cancer in a subject, the method including administering an effective amount of any of the foregoing compounds or pharmaceutical compositions thereof.

In another aspect, the invention features a method of suppressing metastatic colonization of melanoma, prostate cancer, breast cancer, bone cancer, renal cell carcinoma, or a hematologic cancer in a subject, the method including administering an effective amount of any of the foregoing compounds or pharmaceutical compositions thereof.

In another aspect, the invention features a method of reducing the level and/or activity of BRG1 and/or BRM in a melanoma, prostate cancer, breast cancer, bone cancer, renal cell carcinoma, or hematologic cancer cell, the method including contacting the cell with an effective amount of any of the foregoing compounds or pharmaceutical compositions thereof.

In some embodiments of any of the above aspects, the melanoma, prostate cancer, breast cancer, bone cancer, renal cell carcinoma, or hematologic cell is in a subject.

In some embodiments of any of the above aspects, the effective amount of the compound reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the compound that reduces the level and/or activity of BRG1 by at least 50% (e.g., 55%, 60%, 65%, 70%, 75%, 80%, 85%, 90%, or 95%) as compared to a reference. In some embodiments, the effective amount of the compound that reduces the level and/or activity of BRG1 by at least 90% (e.g., 91%, 92%, 93%, 94%, 95%, 96%, 97%, 98%, or 99%).

In some embodiments, the effective amount of the compound reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the compound that reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments of any of the above aspects, the effective amount of the compound reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the compound that reduces the level and/or activity of BRM by at least 50% (e.g., 55%, 60%, 65%, 70%, 75%, 80%, 85%, 90%, or 95%) as compared to a reference. In some embodiments, the effective amount of the compound that reduces the level and/or activity of BRM by at least 90% (e.g., 91%, 92%, 93%, 94%, 95%, 96%, 97%, 98%, or 99%).

In some embodiments, the effective amount of the compound reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the compound that reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments, the subject has cancer. In some embodiments, the cancer expresses BRG1 and/or BRM protein and/or the cell or subject has been identified as expressing BRG1 and/or BRM. In some embodiments, the cancer expresses BRG1 protein and/or the cell or subject has been identified as expressing BRG1. In some embodiments, the cancer expresses BRM protein and/or the cell or subject has been identified as expressing BRM. In some embodiments, the cancer is melanoma (e.g., uveal melanoma, mucosal melanoma, or cutaneous melanoma). In some embodiments, the cancer is prostate cancer. In some embodiments, the cancer is a hematologic cancer, e.g., multiple myeloma, large cell lymphoma, acute T-cell leukemia, acute myeloid leukemia, myelodysplastic syndrome, immunoglobulin A lambda myeloma, diffuse mixed histiocytic and lymphocytic lymphoma, B-cell lymphoma, acute lymphoblastic leukemia (e.g., T-cell acute lymphoblastic leukemia or B-cell acute lymphoblastic leukemia), diffuse large cell lymphoma, or non-Hodgkin's lymphoma. In some embodiments, the cancer is breast cancer (e.g., an ER positive breast cancer, an ER negative breast cancer, triple positive breast cancer, or triple negative breast cancer). In some embodiments, the cancer is a bone cancer (e.g., Ewing's sarcoma). In some embodiments, the cancer is a renal cell carcinoma (e.g., a Microphthalmia Transcription Factor (MITF) family translocation renal cell carcinoma (tRCC)). In some embodiments, the cancer is metastatic (e.g., the cancer has spread to the liver). The metastatic cancer can include cells exhibiting migration and/or invasion of migrating cells and/or include cells exhibiting endothelial recruitment and/or angiogenesis. In other embodiments, the migrating cancer is a cell migration cancer. In still other embodiments, the cell migration cancer is a non-metastatic cell migration cancer. The metastatic cancer can be a cancer spread via seeding the surface of the peritoneal, pleural, pericardial, or subarachnoid spaces. Alternatively, the metastatic cancer can be a cancer spread via the lymphatic system, or a cancer spread hematogenously. In some embodiments, the effective amount of an agent that reduces the level and/or activity of BRG1 and/or BRM is an amount effective to inhibit metastatic colonization of the cancer to the liver.

In some embodiments the cancer harbors a mutation in GNAQ. In some embodiments the cancer harbors a mutation in GNA11. In some embodiments the cancer harbors a mutation in PLCB4. In some embodiments the cancer harbors a mutation in CYSLTR2. In some embodiments the cancer harbors a mutation in BAP1. In some embodiments the cancer harbors a mutation in SF3B1. In some embodiments the cancer harbors a mutation in EIF1AX. In some embodiments the cancer harbors a TFE3 translocation. In some embodiments the cancer harbors a TFEB translocation. In some embodiments the cancer harbors a MITF translocation. In some embodiments the cancer harbors an EZH2 mutation. In some embodiments the cancer harbors a SUZ12 mutation. In some embodiments the cancer harbors an EED mutation.

In some embodiments, the method further includes administering to the subject or contacting the cell with an anticancer therapy, e.g., a chemotherapeutic or cytotoxic agent, immunotherapy, surgery, radiotherapy, thermotherapy, or photocoagulation. In some embodiments, the anticancer therapy is a chemotherapeutic or cytotoxic agent, e.g., an antimetabolite, antimitotic, antitumor antibiotic, asparagine-specific enzyme, bisphosphonates, antineoplastic, alkylating agent, DNA-Repair enzyme inhibitor, histone deacetylase inhibitor, corticosteroid, demethylating agent, immunomodulatory, janus-associated kinase inhibitor, phosphinositide 3-kinase inhibitor, proteasome inhibitor, or tyrosine kinase inhibitor.

In some embodiments, the compound of the invention is used in combination with another anti-cancer therapy used for the treatment of uveal melanoma such as surgery, a MEK inhibitor, and/or a PKC inhibitor. For example, in some embodiments, the method further comprises performing surgery prior to, subsequent to, or at the same time as administration of the compound of the invention. In some embodiments, the method further comprises administration of a MEK inhibitor and/or a PKC inhibitor prior to, subsequent to, or at the same time as administration of the compound of the invention.

In some embodiments, the anticancer therapy and the compound of the invention are administered within 28 days of each other and each in an amount that together are effective to treat the subject.

In some embodiments, the subject or cancer has and/or has been identified as having a BRG1 loss of function mutation. In some embodiments, the subject or cancer has and/or has been identified as having a BRM loss of function mutation.

In some embodiments, the cancer is resistant to one or more chemotherapeutic or cytotoxic agents (e.g., the cancer has been determined to be resistant to chemotherapeutic or cytotoxic agents such as by genetic markers, or is likely to be resistant, to chemotherapeutic or cytotoxic agents such as a cancer that has failed to respond to a chemotherapeutic or cytotoxic agent). In some embodiments, the cancer has failed to respond to one or more chemotherapeutic or cytotoxic agents. In some embodiments, the cancer is resistant or has failed to respond to dacarbazine, temozolomide, cisplatin, treosulfan, fotemustine, IMCgp100, a CTLA-4 inhibitor (e.g., ipilimumab), a PD-1 inhibitor (e.g., Nivolumab or pembrolizumab), a PD-L1 inhibitor (e.g., atezolizumab, avelumab, or durvalumab), a mitogen-activated protein kinase (MEK) inhibitor (e.g., selumetinib, binimetinib, or tametinib), and/or a protein kinase C (PKC) inhibitor (e.g., sotrastaurin or IDE196).

In some embodiments, the cancer is resistant to or failed to respond to a previously administered therapeutic used for the treatment of uveal melanoma such as a MEK inhibitor or PKC inhibitor. For example, in some embodiments, the cancer is resistant to or failed to respond to a mitogen-activated protein kinase (MEK) inhibitor (e.g., selumetinib, binimetinib, or tametinib), and/or a protein kinase C (PKC) inhibitor (e.g., sotrastaurin or IDE196).

Chemical Terms

The terminology employed herein is for the purpose of describing particular embodiments and is not intended to be limiting.

For any of the following chemical definitions, a number following an atomic symbol indicates that total number of atoms of that element that are present in a particular chemical moiety. As will be understood, other atoms, such as H atoms, or substituent groups, as described herein, may be present, as necessary, to satisfy the valences of the atoms. For example, an unsubstituted $C_2$ alkyl group has the formula $—CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

The term "acyl," as used herein, represents a H or an alkyl group that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, 1 to 6 carbon atoms, or 1 to 3 carbon atoms).

An alkylene is a divalent alkyl group. The term "alkenyl," as used herein, alone or in combination with other groups, refers to a straight chain or branched hydrocarbon residue having a carbon-carbon double bond and having 2 to 20 carbon atoms (e.g., 2 to 16 carbon atoms, 2 to 10 carbon atoms, 2 to 6 carbon atoms, or 2 carbon atoms).

The term "alkynyl," as used herein, alone or in combination with other groups, refers to a straight chain or branched hydrocarbon residue having a carbon-carbon triple bond and having 2 to 20 carbon atoms (e.g., 2 to 16 carbon atoms, 2 to 10 carbon atoms, 2 to 6 carbon atoms, or 2 carbon atoms).

The term "amino," as used herein, represents $—N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., $—NH_2$) or a substituted amino (i.e., $—N(R^{N1})_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl. An "arylene" is a divalent aryl group.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_1$-$C_6$ alkyl $C_6$-$C_{10}$ aryl, $C_1$-$C_{10}$ alkyl $C_6$-$C_{10}$ aryl, or $C_1$-$C_{20}$ alkyl $C_6$-$C_{10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a $—N_3$ group.

The term "bridged polycycloalkyl," as used herein, refers to a bridged polycyclic group of 5 to 20 carbons, containing from 1 to 3 bridges.

The term "cyano," as used herein, represents a —CN group.

The term "carbocyclyl," as used herein, refers to a non-aromatic $C_3$-$C_{12}$ monocyclic, bicyclic, or tricyclic structure in which the rings are formed by carbon atoms. Carbocyclyl structures include cycloalkyl groups and unsaturated carbocyclyl radicals.

The term "cycloalkyl," as used herein, refers to a saturated, non-aromatic, and monovalent mono- or polycarbocyclic radical of 3 to 10, preferably 3 to 6 carbon atoms. This term is further exemplified by radicals such as cyclopropyl, cyclobutyl, cyclopentyl, cyclohexyl, cycloheptyl, norbornyl, and adamantyl.

The term "halo," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group. The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group. The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic mono- or polycyclic radical of 5 to 12 atoms having at least one aromatic ring containing 1, 2, or 3 ring atoms selected from nitrogen, oxygen, and sulfur, with the remaining ring atoms being carbon. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl. A "heteroarylene" is a divalent heteroaryl group.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_1$-$C_6$ alkyl $C_2$-$C_9$ heteroaryl, $C_1$-$C_{10}$ alkyl $C_2$-$C_9$ heteroaryl, or $C_1$-$C_{20}$ alkyl $C_2$-$C_9$ heteroaryl). In some embodiments, the alkyl and the heteroaryl each can be further substituted with 1, 2, 3, or 4 substituent groups as defined herein for the respective groups.

The term "heterocyclyl," as used herein, refers a mono- or polycyclic radical having 3 to 12 atoms having at least one non-aromatic ring containing 1, 2, 3, or 4 ring atoms selected from N, O or S and no aromatic ring containing any N, O, or S atoms. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl. A "heterocyclene" is a divalent heterocyclyl group.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_1$-$C_6$ alkyl $C_2$-$C_9$ heterocyclyl, $C_1$-$C_{10}$ alkyl $C_2$-$C_9$ heterocyclyl, or $C_1$-$C_{20}$ alkyl $C_2$-$C_9$ heterocyclyl). In some embodiments, the alkyl and the heterocyclyl each can be further substituted with 1, 2, 3, or 4 substituent groups as defined herein for the respective groups.

The term "hydroxyalkyl," as used herein, represents alkyl group substituted with an —OH group.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999). N-protecting groups include, but are not limited to, acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L, or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-20 dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an $—NO_2$ group.

The term "oxo," as used herein, represents an =O group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: alkyl (e.g., unsubstituted and substituted, where the substituents include any group described herein, e.g., aryl, halo, hydroxy), aryl (e.g., substituted and unsubstituted phenyl), carbocyclyl (e.g., substituted and unsubstituted cycloalkyl), halo (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), azido, cyano, nitro, oxo, sulfonyl, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. “Enantiomer” means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. “Racemate” or “racemic mixture” means a compound containing two enantiomers, wherein such mixtures exhibit no optical activity; i.e., they do not rotate the plane of polarized light. “Geometric isomer” means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. “R,” “S,” “S*,” “R*,” “E,” “Z,” “cis,” and “trans,” indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Compounds of the present disclosure also include all of the isotopes of the atoms occurring in the intermediate or final compounds. “Isotopes” refers to atoms having the same atomic number but different mass numbers resulting from a different number of neutrons in the nuclei. For example, isotopes of hydrogen include tritium and deuterium.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term “a” may be understood to mean “at least one”; (ii) the term “or” may be understood to mean “and/or”; and (iii) the terms “comprising” and “including” may be understood to encompass itemized components or steps whether presented by themselves or together with one or more additional components or steps.

As used herein, the terms “about” and “approximately” refer to a value that is within 10% above or below the value being described. For example, the term “about 5 nM” indicates a range of from 4.5 to 5.5 nM.

As used herein, the term “administration” refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term “BAF complex” refers to the BRG1- or HBRM-associated factors complex in a human cell.

As used herein, the term “BAF complex-related disorder” refers to a disorder that is caused or affected by the level of activity of a BAF complex.

As used herein, the term “BRG1 loss of function mutation” refers to a mutation in BRG1 that leads to the protein having diminished activity (e.g., at least 1% reduction in BRG1 activity, for example 2%, 5%, 10%, 25%, 50%, or 100% reduction in BRG1 activity). Exemplary BRG1 loss of function mutations include, but are not limited to, a homozygous BRG1 mutation and a deletion at the C-terminus of BRG1.

As used herein, the term “BRG1 loss of function disorder” refers to a disorder (e.g., cancer) that exhibits a reduction in BRG1 activity (e.g., at least 1% reduction in BRG1 activity, for example 2%, 5%, 10%, 25%, 50%, or 100% reduction in BRG1 activity).

The term “cancer” refers to a condition caused by the proliferation of malignant neoplastic cells, such as tumors, neoplasms, carcinomas, sarcomas, leukemias, and lymphomas.

As used herein, a “combination therapy” or “administered in combination” means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

By “determining the level” of a protein or RNA is meant the detection of a protein or an RNA, by methods known in the art, either directly or indirectly. “Directly determining” means performing a process (e.g., performing an assay or test on a sample or “analyzing a sample” as that term is defined herein) to obtain the physical entity or value. “Indirectly determining” refers to receiving the physical entity or value from another party or source (e.g., a third party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure RNA levels are known in the art and include, but are not limited to, quantitative polymerase chain reaction (qPCR) and Northern blot analyses.

By a "decreased level" or an "increased level" of a protein or RNA is meant a decrease or increase, respectively, in a protein or RNA level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, μg/mL, ng/mL) or percentage relative to total protein in a sample.

By "decreasing the activity of a BAF complex" is meant decreasing the level of an activity related to a BAF complex, or a related downstream effect. A non-limiting example of decreasing an activity of a BAF complex is Sox2 activation. The activity level of a BAF complex may be measured using any method known in the art, e.g., the methods described in Kadoch et al. Cell, 2013, 153, 71-85, the methods of which are herein incorporated by reference.

As used herein, the term "inhibiting BRM" refers to blocking or reducing the level or activity of the ATPase catalytic binding domain or the bromodomain of the protein. BRM inhibition may be determined using methods known in the art, e.g., a BRM ATPase assay, a Nano DSF assay, or a BRM Luciferase cell assay.

As used herein, the term "LXS196," also known as IDE196, refers to the PKC inhibitor having the structure:

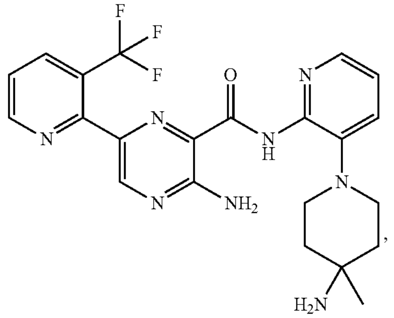 [SMILES: CC1(N)CCN(c2cccnc2NC(=O)c2nc(-c3ncccc3C(F)(F)F)cnc2N)CC1]

or a pharmaceutically acceptable salt thereof.

The term "pharmaceutical composition," as used herein, represents a composition containing a compound described herein formulated with a pharmaceutically acceptable excipient and appropriate for administration to a mammal, for example a human. Typically, a pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers to any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of a compound, for example, any compound of Formula I. Pharmaceutically acceptable salts of any of the compounds described herein may include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

By a "reference" is meant any useful reference used to compare protein or RNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound of the invention; a sample from a subject that has been treated by a compound of the invention; or a sample of a purified protein or RNA (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound of the invention. In preferred embodiments, the reference sample, standard, or level is matched to the sample subject sample by at least one of the following criteria: age, weight, sex, disease stage, and overall health. A standard curve of levels of a purified protein or RNA, e.g., any described herein, within the normal reference range can also be used as a reference.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean therapeutic treatment or any measures whose object is to slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total); an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. Compounds of the invention may also be used to "prophylactically treat" or "prevent" a disorder, for example, in a subject at increased risk of developing the disorder.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material. The details of one or more embodiments of the invention are set forth in the description below. Other features, objects, and advantages of the invention will be apparent from the description and from the claims.

DETAILED DESCRIPTION

Figure 1:
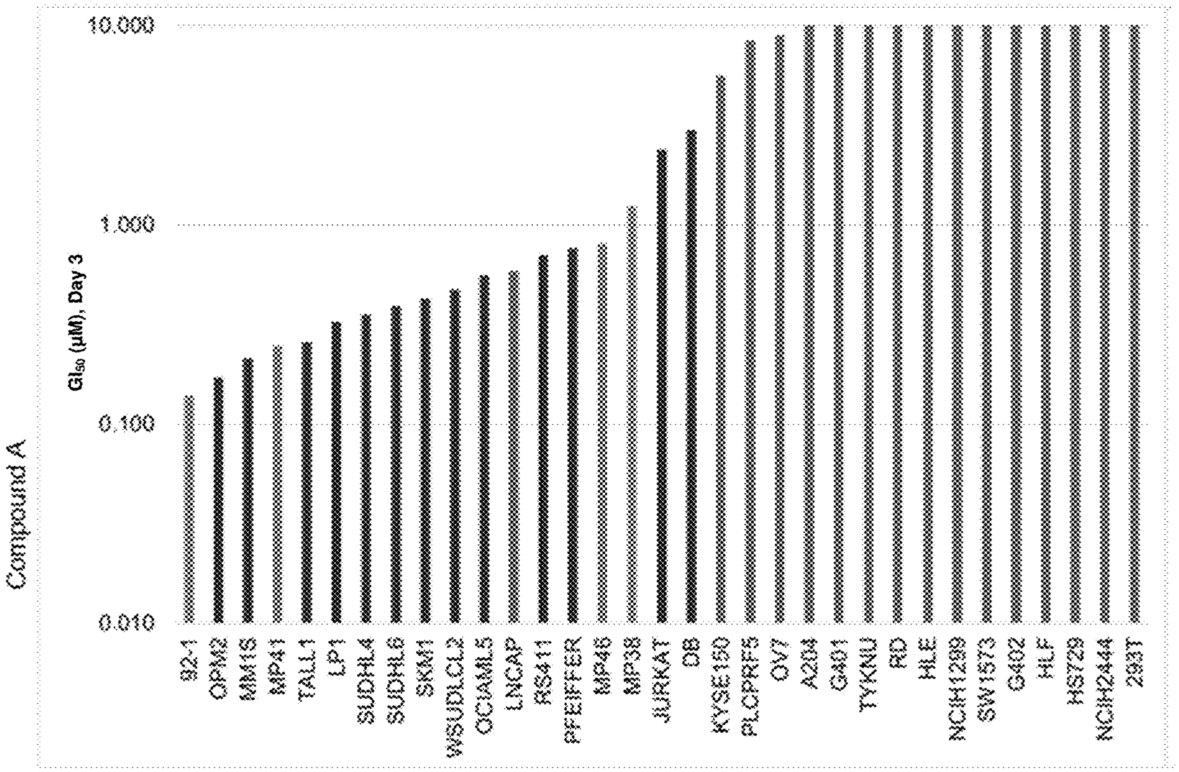
FIG. 1 is a graph illustrating inhibition of cell proliferation of several cancer cell lines by a BRG1/BRM inhibitor (Compound A).

The present disclosure features compounds useful for the inhibition of BRG1 and/or BRM. These compounds may be used to modulate the activity of a BAF complex, for example, for the treatment of a BAF-related disorder, such as cancer. Exemplary compounds described herein include compounds having a structure according to Formula A:

Formula A

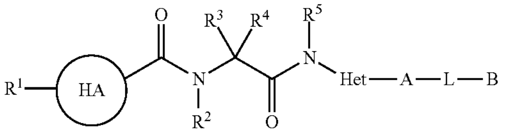

where $R^1$ is H, optionally substituted $C_1$-$C_6$ acyl, optionally substituted $C_1$-$C_6$ alkyl, optionally substituted $C_3$-$C_8$ cycloalkyl, optionally substituted $C_1$-$C_6$ heteroalkyl, optionally substituted $C_2$-$C_9$ heterocyclyl, or —$SO_2R^6$;

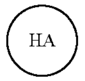

is 5- or 6-membered heteroarylene; each of $R^2$, $R^3$, and $R^5$ is, independently, H or optionally substituted $C_1$-$C_6$ alkyl; $R^4$ is H, optionally substituted $C_1$-$C_6$ alkyl, or optionally substituted $C_1$-$C_6$ heteroalkyl; $R^6$ is optionally substituted $C_1$-$C_6$ alkyl or —$NR^7R^8$; $R^7$ and $R^8$ are, independently, optionally substituted $C_1$-$C_6$ alkyl; Het is optionally substituted 5- or 6-membered heteroarylene; A is optionally substituted $C_6$-$C_{10}$ arylene, optionally substituted $C_2$-$C_9$ heterocyclylene, or optionally substituted $C_2$-$C_9$ heteroarylene; L is absent, —O—, optionally substituted $C_1$-$C_6$ alkylene, optionally substituted $C_1$-$C_6$ alkenylene, optionally substituted $C_1$-$C_6$ heteroalkylene, optionally substituted $C_2$-$C_9$ heterocyclyl $C_1$-$C_6$ alkylene, or optionally substituted $C_2$-$C_9$ heteroaryl $C_1$-$C_6$ alkylene; and B is H, halogen, cyano, optionally substituted $C_6$-$C_{10}$ aryl, optionally substituted $C_3$-$C_{10}$ cycloalkyl, optionally substituted $C_2$-$C_9$ heterocyclyl, or optionally substituted $C_2$-$C_9$ heteroaryl, or a pharmaceutically acceptable salt thereof.

In some embodiments, the compound, or pharmaceutically acceptable salt thereof, has the structure of Formula I:

Formula I

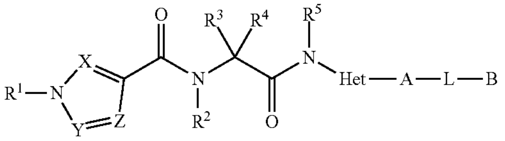

where each of X, Y, and Z is, independently, N or CH; $R^1$ is hydrogen, optionally substituted $C_1$-$C_6$ acyl, optionally substituted $C_1$-$C_6$ alkyl, optionally substituted $C_1$-$C_6$ heteroalkyl, optionally substituted $C_2$-$C_9$ heterocyclyl, or —$SO_2R^6$; each of $R^2$, $R^3$, and $R^5$ is, independently, H or optionally substituted $C_1$-$C_6$ alkyl; $R^4$ is hydrogen, optionally substituted $C_1$-$C_6$ alkyl, or optionally substituted $C_1$-$C_6$ heteroalkyl; $R^6$ is optionally substituted $C_1$-$C_6$ alkyl or —$NR^7R^8$; each of $R^7$ and $R^8$ is, independently, optionally substituted $C_1$-$C_6$ alkyl; Het is a 5- or 6-membered heteroarylene; Het is a 5- or 6-membered heteroarylene; A is optionally substituted $C_6$-$C_{10}$ arylene, optionally substituted $C_2$-$C_9$ heterocyclylene, or optionally substituted $C_2$-$C_9$ heteroarylene; L is absent, —O—, optionally substituted $C_1$-$C_6$ alkylene, optionally substituted $C_1$-$C_6$ alkenylene, optionally substituted $C_1$-$C_6$ heteroalkylene, optionally substituted $C_2$-$C_9$ heterocyclyl $C_1$-$C_6$ alkylene, or optionally substituted $C_2$-$C_9$ heteroaryl $C_1$-$C_6$ alkylene; and B is hydrogen, halogen, cyano, optionally substituted $C_6$-$C_{10}$ aryl, optionally substituted $C_3$-$C_{10}$ cycloalkyl, optionally substituted $C_2$-$C_9$ heterocyclyl, or optionally substituted $C_2$-$C_9$ heteroaryl, or a pharmaceutically acceptable salt thereof.

In some embodiments, the compound, or pharmaceutically acceptable salt thereof, has the structure of Formula II:

Formula II

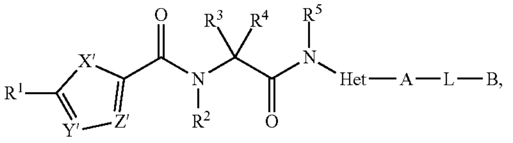

where X' is O or S; Y' is N or CH; Z' is N or CH; $R^1$ is H, optionally substituted $C_1$-$C_6$ acyl, optionally substituted $C_1$-$C_6$ alkyl, optionally substituted $C_1$-$C_6$ heteroalkyl, optionally substituted $C_3$-$C_8$ cycloalkyl, optionally substituted $C_2$-$C_9$ heterocyclyl, or —$SO_2R^6$; each of $R^2$, $R^3$, and $R^5$ is, independently, H or optionally substituted $C_1$-$C_6$ alkyl; $R^4$ is H, optionally substituted $C_1$-$C_6$ alkyl, or optionally substituted $C_1$-$C_6$ heteroalkyl; $R^6$ is optionally substituted $C_1$-$C_6$ alkyl or —$NR^7R^8$; each of $R^7$ and $R^8$ is, independently, optionally substituted $C_1$-$C_6$ alkyl; Het is a 5- or 6-membered heteroarylene; A is optionally substituted $C_6$-$C_{10}$ arylene, optionally substituted $C_2$-$C_9$ heterocyclylene, or optionally substituted $C_2$-$C_9$ heteroarylene; L is absent, —O—, optionally substituted $C_1$-$C_6$ alkylene, optionally substituted $C_1$-$C_6$ alkenylene, optionally substituted $C_1$-$C_6$ heteroalkylene, optionally substituted $C_2$-$C_9$ heterocyclyl $C_1$-$C_6$ alkylene, or optionally substituted $C_2$-$C_9$ heteroaryl $C_1$-$C_6$ alkylene; and B is H, halogen, cyano, optionally substituted $C_6$-$C_{10}$ aryl, optionally substituted $C_3$-$C_{10}$ cycloalkyl, optionally substituted $C_2$-$C_9$ heterocyclyl, or optionally substituted $C_2$-$C_9$ heteroaryl, or a pharmaceutically acceptable salt thereof.

In some embodiments, the compound is any one of compounds 1-827 in Table 1. In some embodiments, the compound, or pharmaceutically acceptable salt thereof, has the structure of any one of compounds 1-421 in Table 1. In some embodiments, the compound, or pharmaceutically acceptable salt thereof, has the structure of any one of compounds 1-156 in Table 1. In some embodiments, the compound, or pharmaceutically acceptable salt thereof, has the structure of any one of compounds 157-421 in Table 1. In some embodiments, the compound is any one of compounds 422-827 in Table 1.

In some embodiments, the compound is any one of compounds 1-776 in Table 1. In some embodiments, the compound is any one of compounds 777-819 in Table 1. In some embodiments, the compound is any one of compounds 820-827 in Table 1.

Other embodiments, as well as exemplary methods for the synthesis of production of these compounds, are described herein.

Pharmaceutical Uses

The compounds described herein are useful in the methods of the invention and, while not bound by theory, are believed to exert their ability to modulate the level, status, and/or activity of a BAF complex, i.e., by inhibiting the activity of the BRG1 and/or BRM proteins within the BAF complex in a mammal. BAF complex-related disorders include, but are not limited to, BRG1 loss of function mutation-related disorders.

An aspect of the present invention relates to methods of treating disorders related to BRG1 loss of function mutations such as cancer (e.g., non-small cell lung cancer, colorectal cancer, bladder cancer, cancer of unknown primary, glioma, breast cancer, melanoma, non-melanoma skin cancer, endometrial cancer, or penile cancer) in a subject in need thereof. In some embodiments, the compound is administered in an amount and for a time effective to result in one or more (e.g., two or more, three or more, four or more) of: (a) reduced tumor size, (b) reduced rate of tumor growth, (c) increased tumor cell death (d) reduced tumor progression, (e) reduced number of metastases, (f reduced rate of metastasis, (g) decreased tumor recurrence (h) increased survival of subject, (i) increased progression free survival of subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with a pharmaceutically acceptable salt of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of the invention. A decrease in the mortality rate of a population may also be measured, for example, by calculating for a population the average number of disease-related deaths per unit time following completion of a first round of treatment with a pharmaceutically acceptable salt of the invention.

Exemplary cancers that may be treated by the invention include, but are not limited to, non-small cell lung cancer, small-cell lung cancer, colorectal cancer, bladder cancer, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer and penile cancer.

Combination Formulations and Uses Thereof

The compounds of the invention can be combined with one or more therapeutic agents. In particular, the therapeutic agent can be one that treats or prophylactically treats any cancer described herein.

Combination Therapies

A compound of the invention can be used alone or in combination with an additional therapeutic agent, e.g., other agents that treat cancer or symptoms associated therewith, or in combination with other types of treatment to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6, 2005). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed Engl. 33:183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, Adriamycin® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), ABraxane®, cremophor-free, albumin-engineered nanoparticle formulation of paclitaxel (American Pharmaceutical Partners, Schaumberg, Ill.), and Taxotere® doxetaxel (Rhone-Poulenc Rorer, Antony, France); chloranbucil; Gemzar® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al. (1999) Proc ASCO 18:233a and Douillard et al. (2000) Lancet 355:1041-7.

In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (Avastin®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include Rituxan (Rituximab); Zenapax (Daclizumab); Simulect (Basiliximab); Synagis (Palivizumab); Remicade (Infliximab); Herceptin (Trastuzumab); Mylotarg (Gemtuzumab ozogamicin); Campath (Alemtuzumab); Zevalin (Ibritumomab tiuxetan); Humira (Adalimumab); Xolair (Omalizumab); Bexxar (Tositumomab-1-131); Raptiva (Efalizumab); Erbitux (Cetuximab); Avastin (Bevacizumab); Tysabri (Natalizumab); Actemra (Tocilizumab); Vectibix (Panitumumab); Lucentis (Ranibizumab); Soliris (Eculizumab); Cimzia (Certolizumab pegol); Simponi (Golimumab); Ilaris (Canakinumab); Stelara (Ustekinumab); Arzerra (Ofatumumab); Prolia (Denosumab); Numax (Motavizumab); ABThrax (Raxibacumab); Benlysta (Belimumab); Yervoy (Ipilimumab); Adcetris (Brentuximab Vedotin); Perjeta (Pertuzumab); Kadcyla (Ado-trastuzumab emtansine); and Gazyva (Obinutuzumab). Also included are antibody-drug conjugates.

The second agent may be a therapeutic agent which is a non-drug treatment. For example, the second therapeutic agent is radiation therapy, cryotherapy, hyperthermia and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody such as ipilimumab/Yervoy or tremelimumab). In some embodiments, the inhibitor of checkpoint is an inhibitor (e.g., an inhibitory antibody or small molecule inhibitor) of PD-1 (e.g., nivolumab/Opdivo®; pembrolizumab/

Keytruda®; pidilizumab/CT-011). In some embodiments, the inhibitor of checkpoint is an inhibitor (e.g., an inhibitory antibody or small molecule inhibitor) of PDL1 (e.g., MPDL3280A/RG7446; MEDI4736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK1, CHK2, A2aR, B-7 family ligands, or a combination thereof.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Pharmaceutical Compositions

The compounds of the invention are preferably formulated into pharmaceutical compositions for administration to a mammal, preferably, a human, in a biologically compatible form suitable for administration in vivo. Accordingly, in an aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, and wafers. A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, 20th ed.) and in The United States Pharmacopeia: The National Formulary (USP 24 NF19), published in 1999. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter. A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

Alternatively, the dosage amount can be calculated using the body weight of the patient. For example, the dose of a compound, or pharmaceutical composition thereof, administered to a patient may range from 0.1-100 mg/kg (e.g., 0.1-50 mg/kg, 0.25-25 mg/kg). In exemplary, non-limiting embodiments, the dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

EXAMPLES

The following abbreviations are used throughout the Examples below.

2-bipy 2-(2-pyridyl)pyridine
Ac acetyl
ACN or MeCN acetonitrile
AcOH acetic acid
$Ac_2O$ acetic anhydride
$AlMe_3$ trimethylaluminum
aq. aqueous
BINAP 2,2'-bis(diphenylphosphino)-1,1'-binaphthalene
Bn benzyl
Boc tert-butoxycarbonyl
BPin 4,4,5,5-tetramethyl-1,3,2-dioxaborolan-2-yl
$B_2pin_2$ 4,4,5,5-tetramethyl-2-(4,4,5,5-tetramethyl-1,3,2-dioxaborolan-2-yl)-1,3,2-dioxaborolane
Bu or n-Bu butyl
CDI 1,1'-carbonyldiimidazole
DAST (diethylamino)sulfur trifluoride
DBU 1,8-diazabicyclo[5.4.0]undec-7-ene
DCE or 1,2-DCE 1,2-dichloroethane
DCM dichloromethane
dcpp 1,3-bis(dicyclohexylphosphino)propane
DIAD diisopropyl azodicarboxylate
DIPEA or DIEA N.N-diisopropylethylamine
DMAP 4-(dimethylamino)pyridine
DME 1,2-dimethoxyethane
DMF N.N-dimethylformamide
DMSO dimethyl sulfoxide
EA or EtOAc ethyl acetate
EDCI N-(3-dimethylaminopropyl)-N'-ethylcarbodiimide hydrochloride
EEDQ 2-ethoxy-1-ethoxycarbonyl-1,2-dihydroquinoline
eq equivalents
$Et_3N$ or TEA triethylamine
EtOH ethyl alcohol
FA formic acid
Fmoc 9-fluorenylmethoxycarbonyl
Fmoc-OSuc 9-fluorenylmethyl N-succinimidyl carbonate
h or hr hour
HATU 1-[bis(dimethylamino)methylene]-1H-1,2,3-triazolo[4,5-b]pyridinium 3-oxid hexafluorophosphate
HOBt or HOBT 1-hydroxybenzotriazole hydrate
iPr Isopropyl
iPrMgCl isopropylmagnesium chloride
KHMDS potassium bis(trimethylsilyl)amide
KOAc or AcOK potassium acetate
LDA lithium diisopropylamide
LED light-emitting diode
MeMgBr methylmagnesium bromide
$MeNH_2$ methyl amine
MeOH methyl alcohol
$Me_4$t-BuXphos ditert-butyl-[2,3,4,5-tetramethyl-6-(2,4,6-triisopropylphenyl)phenyl]phosphane
MsCl methanesulfonyl chloride
MTBE tert-butyl methyl ether
NaHMDS sodium bis(trimethylsilyl)amide
NaOtBu or t-BuONa sodium tert-butoxide
NBS N-bromosuccinimide
n-BuLi n-butylithium
NMP 1-methyl-2-pyrrolidinone
OAc acetate
Pd/C palladium on carbon
$PdCl_2$(dtbpf) or Pd(dtbpf)$Cl_2$ dichloro[1,1'-bis(di-t-butylphosphino)ferrocene]palladium(II)
$PdCl_2$(dppf) or Pd(dppf)$Cl_2$ [1,1'-bis(diphenylphosphino)ferrocene]dichloropalladium(II)
$Pd_2(dba)_3$ tris(dibenzylideneacetone)dipalladium(0)
$Pd(PPh_3)_4$ tetrakis(triphenylphosphine)palladium(0
$Pd(PPh_3)_2Cl_2$ dichlorobis(triphenylphosphine)palladium (II)
PE petroleum ether
$PPh_3$ triphenylphosphine
Pr n-propyl
Py pyridine
rac racemic
Rf retention factor
r.t. or rt room temperature
RuPhos Precat G4 methanesulfonato(2-dicyclohexylphosphino-2',6'-di-i-propoxy-1,1'-biphenyl)(2'-methylamino-1,1'-biphenyl-2-yl)palladium(II)
sat. saturated
SFC supercritical fluid chromatography
TBAF tetrabutylammonium fluoride
TBDPS tert-butyldiphenylsilyl
TBS tert-butyldimethylsilyl
t-Bu tert-butyl
t-BuOK potassium tert-butoxide
tBuXphos-Pd-G3 or [2-(2-aminophenyl)phenyl]-tBuXphos Pd G3 or methylsulfonyloxypalladium; ditert-butyl-[2-(2,4,6-t-BuXphos-Pd (gen triisopropylphenyl) phenyl]phosphane 3)
TCFH chloro-N,N,N',N'-tetramethylformamidinium hexafluorophosphate
TFA trifluoroacetic acid
$Tf_2O$ trifluoromethanesulfonic anhydride
THF tetrahydrofuran
TLC thin layer chromatography
TMS trimethylsilyl
$TMSCHN_2$ (diazomethyl)trimethylsilane
TsOH p-toluenesulfonic acid
Ts p-toluenesulfonyl
Xantphos-Pd-G3 [2-(2-aminophenyl)phenyl]-methylsulfonyloxy-palladium; (5-diphenylphosphanyl-9,9-dimethyl-xanthen-4-yl)-diphenyl-phosphane Example 1. Preparation of N-(2-((4-(3-(2-((dimethylamino)methyl)pyridin-4-yl)phenyl)thiazol-2-yl)amino)-2-oxoethyl)-1-(methylsulfonyl)-1H-pyrrole-3-carboxamide (Compound 1)
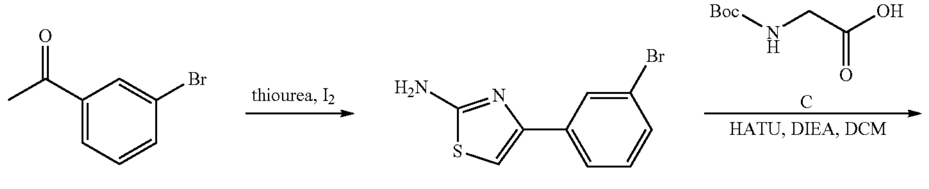
A B
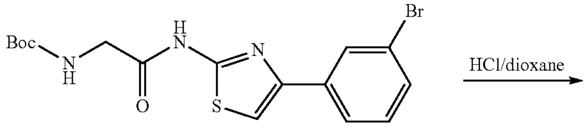
D
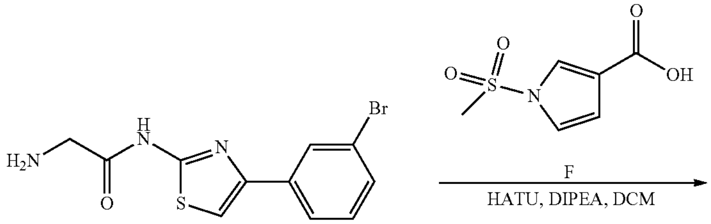
E
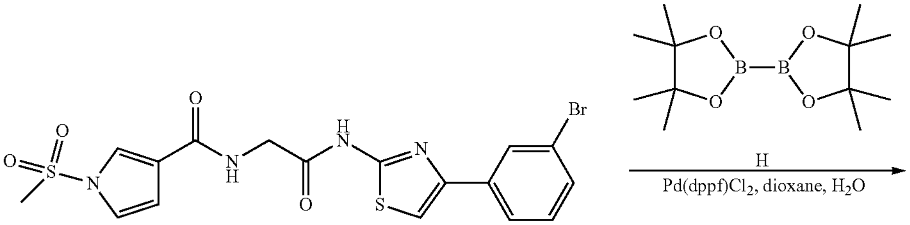
G
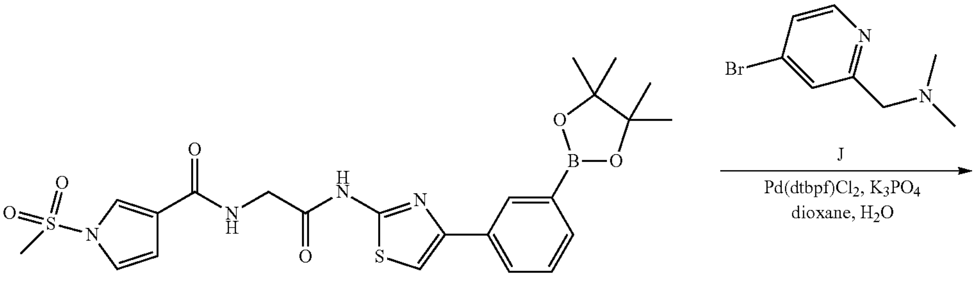
I
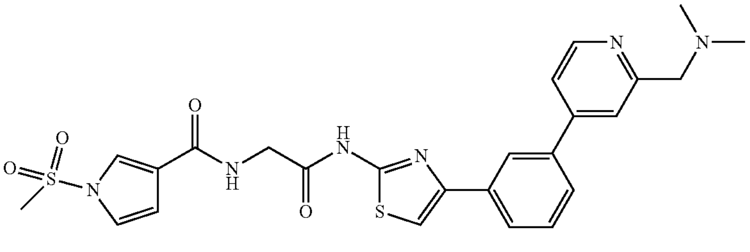
Compound 1

Step 1: Preparation of 4-(3-bromophenyl)thiazol-2-amine (Intermediate B)

B

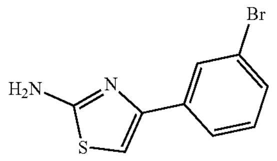

To a mixture of 1-(3-bromophenyl)ethanone (473 g, 2.38 mol, 313.25 mL) and thiourea (361.78 g, 4.75 mol) was added $I_2$ (603.14 g, 2.38 mol, 478.68 mL, 1 eq). The mixture was stirred at 110° C. for 16 h. After cooling, the reaction mixture was triturated with MTBE (5 L), and then filtered to remove any unreacted iodine and acetophenone. The filter cake was put in ice water (4 L) and treated with 25% $NH_3 \cdot H_2O$ to pH~9-10. The suspension was stirred at 25° C. for 15 min, then filtered and washed with water (1 L) to give wet solid. The wet solid was dissolved in EtOAc (4 L) and washed with sat. $NaHCO_3$ (1 L×2) and brine (1 L). The EtOAc layer was dried over $Na_2SO_4$, filtered and concentrated under reduced pressure to give a residue. The residue was triturated with PE/EA=100:1 (4 L) at 25° C. for 3 h, then the suspension was filtered, the filter cake was washed with PE (1 L) and dried in vacuum to give intermediate B (450 g, 1.69 mol, 71.20% yield, 95.93% purity) as a pink solid. LCMS (ESI) m/z [M+H$^+$]=254.9; $^1$H NMR (400 MHz, DMSO-$d_6$) δ 7.98-7.97 (m, 1H), 7.80-7.77 (m, 1H), 7.43-7.42 (m, 1H), 7.34-7.30 (m, 1H), 7.15 (s, 1H), 7.10 (s, 2H).

Step 2: Preparation of tert-butyl N-[2-[[4-(3-bromophenyl)thiazol-2-yl]amino]-2-oxo-ethyl]carbamate (Intermediate D)

D

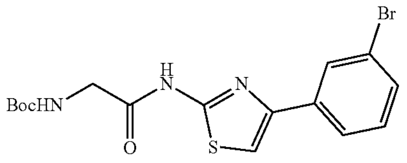

To a solution of 2-(tert-butoxycarbonylamino)acetic acid (82.40 g, 470.34 mmol), HATU (178.84 g, 470.34 mmol) and DIEA (151.97 g, 1.18 mol, 204.81 mL) in DCM (1000.00 mL) was added intermediate B (100.00 g, 391.95 mmol), the mixture was stirred at 30° C. for 16 h. The reaction mixture was washed with saturated citric acid (500 mL×4) and brine (500 mL), dried over $Na_2SO_4$, filtered and concentrated under reduced pressure to give a residue. The residue was triturated with MeOH (200.0 mL), filtered and dried in vacuum to give Intermediate D (100 g, 241.89 mmol, 61.71% yield) as a white solid. LCMS (ESI) m/z [M+H]$^+$=413.8. $^1$H NMR (400 MHz, DMSO-$d_6$) δ 12.29 (s, 1H), 8.09-8.09 (m, 1H), 7.89 (d, J=7.6 Hz, 1H), 7.76 (s, 1H), 7.52-7.49 (m, 1H), 7.41-7.37 (m, 1H), 7.16-7.13 (m, 1H), 3.87-3.81 (m, 2H), 1.39 (s, 9H).

Step 3: Preparation of 2-amino-N-(4-(3-bromophenyl)thiazol-2-yl)acetamide (Intermediate E)

E

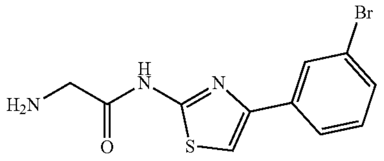

A mixture of Intermediate D (10 g, 24.25 mmol) in HCl/dioxane (100 mL) was stirred at 30° C. for 2 h. The reaction mixture was concentrated in vacuum to give Intermediate E (8.4 g, crude, HCl) as a white solid, which was used for next step directly. LCMS (ESI) m/z [M+H]$^+$=313.8.

Step 4: Preparation of N-(2-((4-(3-bromophenyl)thiazol-2-yl)amino)-2-oxoethyl)-1-(methylsulfonyl)-1H-pyrrole-3-carboxamide (Intermediate G)

G

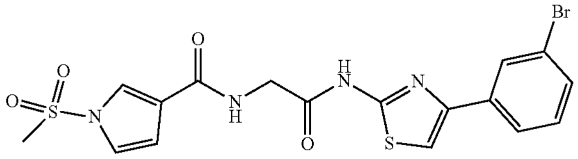

To a solution of Intermediate E (8.4 g, 24.09 mmol, HCl), 1-methylsulfonylpyrrole-3-carboxylic acid [prepared according to the method in Example 4] (5.47 g, 28.91 mmol) in DCM (100 mL) was added HATU (10.99 g, 28.91 mmol) and DIEA (18.68 g, 144.56 mmol, 25.18 mL). The mixture was stirred at 20° C. for 16 h. Then the reaction mixture was filtered and washed with MTBE (50 mL×2) to give a filter cake, the filter cake was dried in vacuum to give Intermediate G (10 g, 20.58 mmol, 85.43% yield) a white solid, which was used into the next step without purification. LCMS (ESI) m/z [M+H]$^+$=484.8. $^1$H NMR (400 MHz, DMSO-d6) δ 12.40-12.35 (m, 1H), 8.69-8.66 (m, 1H), 8.11-8.10 (m, 1H), 7.92-7.90 (m, 1H), 7.85-7.84 (m, 1H), 7.78 (s, 1H), 7.53-7.51 (m, 1H), 7.42-7.38 (m, 1H), 7.32-7.30 (m, 1H), 6.78-6.77 (m, 1H), 4.14 (d, J=6.0 Hz, 2H), 3.57 (s, 3H).

Step 5: Preparation of 1-(methylsulfonyl)-N-(2-oxo-2-((4-(3-(4,4,5,5-tetramethyl-1,3,2-dioxaborolan-2-yl)phenyl)thiazol-2-yl)amino)ethyl)-1H-pyrrole-3-carboxamide (Intermediate I)

I

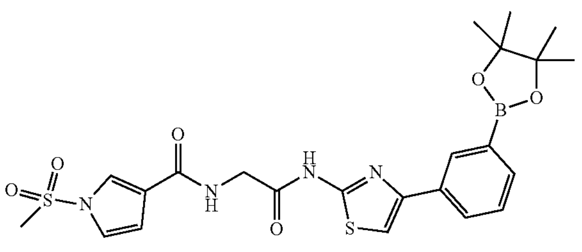

To a solution of Intermediate G (1.5 g, 3.10 mmol) and 4,4,5,5-tetramethyl-2-(4,4,5,5-tetramethyl-1,3,2-dioxaborolan-2-yl)-1,3,2-dioxaborolane (1.18 g, 4.65 mmol) in dioxane (15 mL) was added Pd(dppf)$Cl_2$ (227.07 mg, 310.33 μmol) and KOAc (913.69 mg, 9.31 mmol). Then the mixture was stirred at 80° C. for 2 h. The reaction mixture was poured into water (100 mL) and extracted with EtOAc (100 mL×3). The combined organic layer was washed with brine (50 mL), dried over $Na_2SO_4$, filtered thought silica gel and concentrated to give a residue. The residue was triturated with solution (PE:EA=1:1, 20 mL), filtered and concentrated in vacuum to give Intermediate I (6.5 g, 12.00 mmol, 96.71% yield) as a brown solid. LCMS (ESI) m/z $[M+H]^+$= 531.2; $^1$H NMR (400 MHz, DMSO-d6) δ 12.45 (s, 1H), 8.67 (t, J=6.0 Hz, 1H), 8.29 (s, 1H), 8.01 (br d, J=7.6 Hz, 1H), 7.84 (s, 1H), 7.65 (s, 1H), 7.62 (d, J=7.2 Hz, 1H), 7.44 (t, J=7.6 Hz, 1H), 7.31 (t, J=2.8 Hz, 1H), 6.78 (d, J=1.6 Hz, 1H), 4.14 (d, J=6.0 Hz, 2H), 3.57 (s, 3H), 1.31 (s, 12H).

Step 6: Preparation of N-(2-((4-(3-(2-((dimethylamino)methyl)pyridin-4-yl)phenyl)thiazol-2-yl)amino)-2-oxoethyl)-1-(methylsulfonyl)-1H-pyrrole-3-carboxamide (Compound 1)

Compound 1

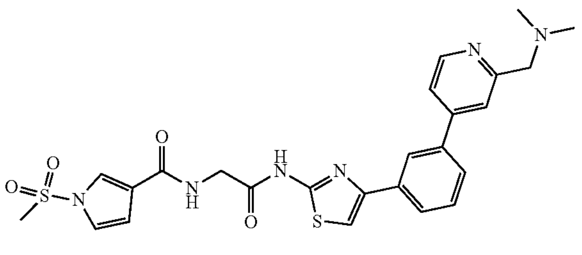

To a mixture of 1-(4-bromo-2-pyridyl)-N,N-dimethyl-methanamine (30 mg, 139.48 μmol), Intermediate I (88.78 mg, 167.37 μmol), $K_3PO_4$ (118.42 mg, 557.91 μmol) in dioxane (1.5 mL)/$H_2O$ (0.2 mL) was added 1,1'-bis(di-tert-butylphosphino)ferrocene]dichloropalladium(II) (9.09 mg, 13.95 μmol), then the reaction mixture was stirred at 100° C. for 2 hours under $N_2$. The reaction mixture was diluted with water (10 mL) and extracted with EtOAc (10 mL×2). The combined organic layers were washed with brine (10 mL×2), dried over $Na_2SO_4$, filtered and concentrated under reduced pressure to give a residue. The residue was purified by Prep-HPLC (mobile phase: [water (0.05% ammonia hydroxide v/v)-acetonitrile]; B %: 22%-52%) and lyophilized to give Compound 1 (12.36 mg, 22.49 μmol, 16.12% yield, 98% purity) as a yellow solid. LCMS (ESI) m/z $[M+H]^+$=539.4; $^1$H NMR (400 MHz, DMSO-$d_6$) δ 12.45 (s, 1H), 8.70-8.59 (m, 2H), 8.28 (s, 1H), 8.01 (d, J=8 Hz, 1H), 7.85-7.74 (m, 4H), 7.66-7.58 (m, 2H), 7.32-7.31 (m, 1H), 6.79-6.77 (m, 1H), 4.15 (d, J=5.6 Hz, 2H), 3.68 (s, 2H), 3.57 (s, 3H), 2.29 (s, 6H).

Example 2. Preparation of 1-isopropyl-N-(2-((4-(3-(1-methyl-1H-pyrazol-3-yl)phenyl)thiazol-2-yl)amino)-2-oxoethyl)-1H-pyrrole-3-carboxamide (Compound 2)

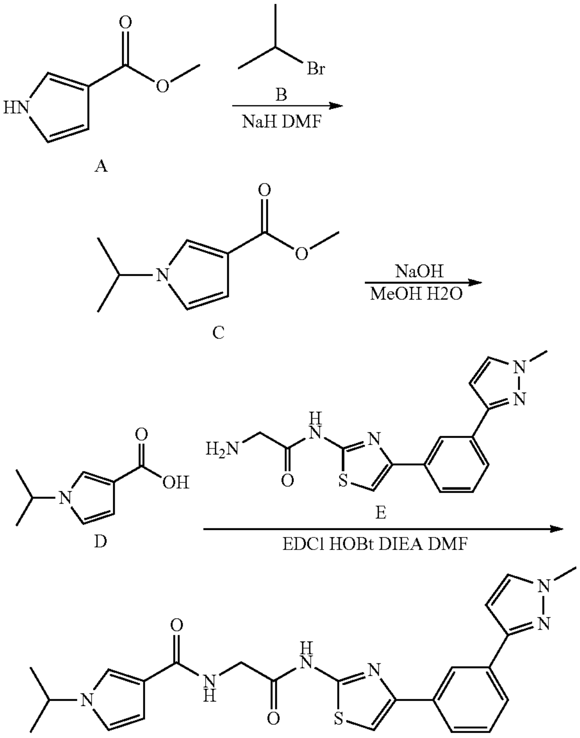

Compound 2

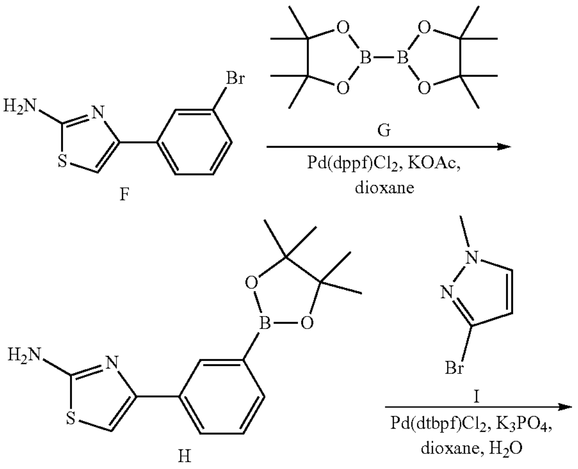

-continued

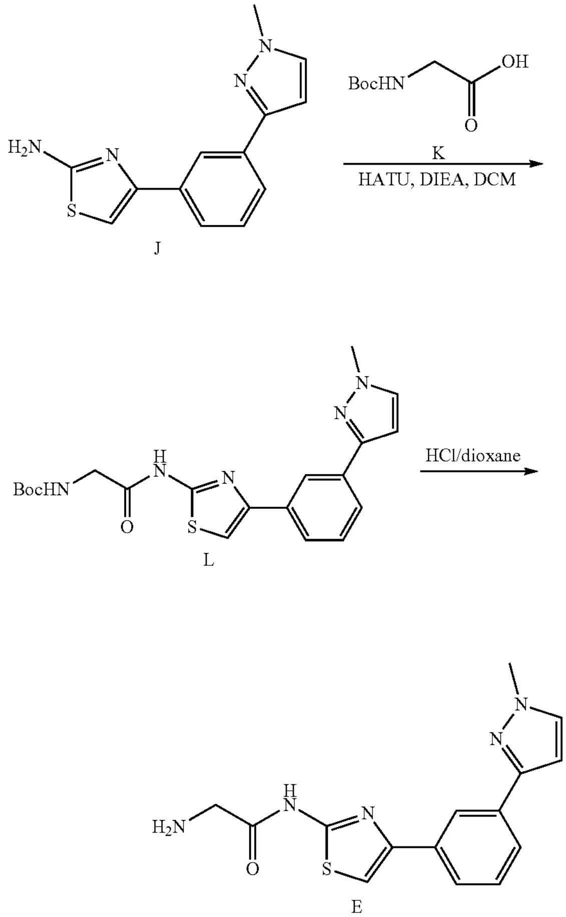

J

L

E

Step 1: Preparation of methyl 1-isopropyl-1H-pyrrole-3-carboxylate (Intermediate C)

C

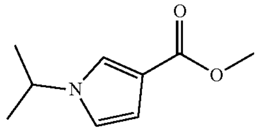

To a solution of methyl 1H-pyrrole-3-carboxylate (500 mg, 4.00 mmol) in DMF (10 mL) was added NaH (239.74 mg, 5.99 mmol, 60% purity) at 25° C., then the mixture was stirred at this temperature for 1 h, and then 2-iodopropane (679.29 mg, 4.00 mmol, 399.58 μL) was added. The resulting mixture was stirred at this temperature for 1 h and then quenched by $NH_4Cl$ (3 mL), extracted with EtOAc (10 mL×3). The combined organic layers were washed with brine (20 mL×2), dried over $Na_2SO_4$, filtered and concentrated under reduced pressure to give Intermediate C (0.49 g, 1.22 mmol, 30.43% yield) as yellow oil, which was used into the next step without further purification. LCMS (ESI) m/z $[M+H]^+$=168.1.

Step 2: Preparation of 1-isopropyl-1H-pyrrole-3-carboxylic acid (Intermediate D)

D

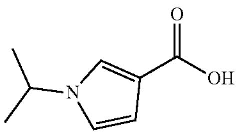

To a solution of Intermediate C (200 mg, 1.20 mmol) in MeOH (1 mL) and $H_2O$ (3 mL) was added NaOH (96.00 mg, 2.40 mmol), then the mixture was stirred at 25° C. for 2 h. The reaction mixture was concentrated in vacuum and then purified by reversed phase (FA condition) and concentrated under reduced pressure to remove acetonitrile. Then the residue was extracted with EtOAc (10 mL×3). The combined organic layers were dried over $Na_2SO_4$, filtered and concentrated under reduced pressure to give Intermediate D (68 mg, 435.89 μmol, 36.32% yield) as a white solid. LCMS (ESI) m/z $[M+H]^+$=154.2; $^1H$ NMR (400 MHz, DMSO-$d_6$) δ 11.79-11.48 (m, 1H), 7.44-7.42 (m, 1H), 6.89-6.87 (m, 1H), 6.35 (dd, J=2.0, 2.8 Hz, 1H), 4.39-4.24 (m, 1H), 1.41-1.34 (m, 6H).

Step 3: Preparation of 4-(3-(4,4,5,5-tetramethyl-1,3,2-dioxaborolan-2-yl)phenyl)thiazol-2-amine (Intermediate H)

H

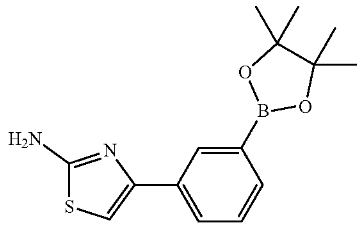

To a solution of 4-(3-bromophenyl)thiazol-2-amine (20 g, 78.39 mmol), 4,4,5,5-tetramethyl-2-(4,4,5,5-tetramethyl-1,3,2-dioxaborolan-2-yl)-1,3,2-dioxaborolane (21.90 g, 86.23 mmol) and Pd(dppf)$Cl_2$ (2 g, 2.73 mmol) in dioxane (300 mL) was added KOAc (23.08 g, 235.17 mmol) under $N_2$, the mixture was stirred at 80° C. for 2 h. The reaction mixture was concentrated under reduced pressure to give a residue. The residue was diluted with water (300 mL) and extracted with EtOAc (200 mL×3). The combined organic layers were washed with brine (400 mL), dried over $Na_2SO_4$, filtered and concentrated under reduced pressure to give a crude Intermediate H (23.69 g, crude) as a brown solid, which was used to the next step without further purification. LCMS (ESI) m/z $[M+H]^+$=303.2.

Step 4: Preparation of 4-(3-(1-methyl-1H-pyrazol-3-yl)phenyl)thiazol-2-amine (Intermediate J)

J

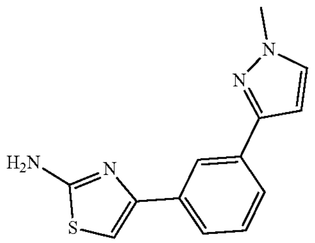

To a solution of Intermediate H (23 g, 76.11 mmol), 3-bromo-1-methyl-pyrazole (12.25 g, 76.11 mmol) and [1,1'-bis(di-tert-butylphosphino)ferrocene]dichloropalladium(II) (3 g, 4.60 mmol) in dioxane (200 mL) and water (50 mL) was added $K_3PO_4$ (48.47 g, 228.33 mmol), the mixture was stirred at 80° C. for 4 h. The reaction mixture was concentrated under reduced pressure to give a residue. The residue was purified by column chromatography ($SiO_2$, Petroleum ether/EtOAc=3:1-2:1) and concentrated under reduced pressure to give Intermediate J (15 g, 58.52 mmol, 76.89% yield) as a gray solid. LCMS (ESI) m/z $[M+H]^+$=257.1; $^1$H NMR (400 MHz, DMSO-$d_6$) δ 8.25-8.24 (m, 1H), 7.73-7.63 (m, 3H), 7.38-7.34 (m, 1H), 7.08-6.06 (m, 3H), 6.69-6.68 (m, 1H), 3.89 (s, 3H).

Step 5: Preparation of tert-butyl (2-((4-(3-(1-methyl-1H-pyrazol-3-yl)phenyl)thiazol-2-yl)amino)-2-oxoethyl)carbamate (Intermediate L)

L

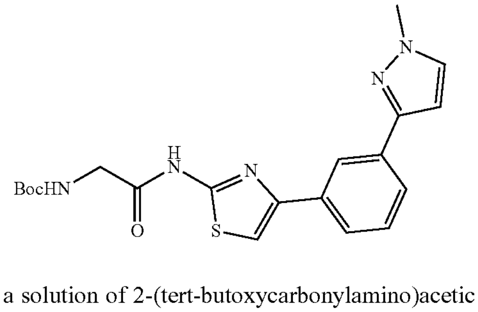

To a solution of 2-(tert-butoxycarbonylamino)acetic acid (4.10 g, 23.41 mmol), DIEA (6.05 g, 46.82 mmol, 8.15 mL) and HATU (8.90 g, 23.41 mmol) in DCM (40 mL) was added Intermediate J (4 g, 15.61 mmol), the mixture was stirred at 30° C. for 2 h. The reaction mixture was concentrated under reduced pressure to give a residue. The residue was purified by reverse phase (FA) and lyophilized to give Intermediate L (2 g, 4.44 mmol, 28.45% yield) as a brown solid. LCMS (ESI) m/z $[M+H]^+$=414.1.

Step 6: Preparation of 2-amino-N-(4-(3-(1-methyl-1H-pyrazol-3-yl)phenyl)thiazol-2-yl)acetamide (Intermediate E)

E

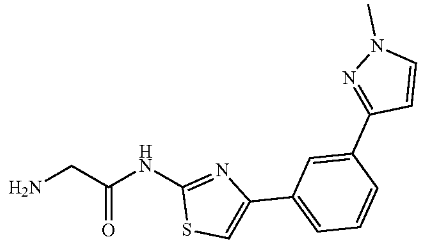

The solution of Intermediate L (2 g, 4.84 mmol) in 4 M HCl/dioxane (20 mL) was stirred at 30° C. for 1 hr. The reaction mixture was concentrated under reduced pressure to give a residue. The residue was triturated with MTBE (50.0 mL), then filtered and concentrated under reduced pressure to give Intermediate E (2 g, crude, HCl salt) as a brown solid. LCMS (ESI) m/z $[M+H]^+$=313.9; 1H NMR (400 MHz, DMSO-$d_6$) δ 12.80 (s, 1H), 8.51 (s, 3H), 8.39 (s, 1H), 7.82-7.72 (m, 4H), 7.47-7.43 (m, 1H), 6.74-6.73 (m, 1H), 3.93-3.90 (m, 5H).

Step 7: Preparation of 1-isopropyl-N-(2-((4-(3-(1-methyl-1H-pyrazol-3-yl)phenyl)thiazol-2-yl)amino)-2-oxoethyl)-1H-pyrrole-3-carboxamide (Compound 2)

Compound 2

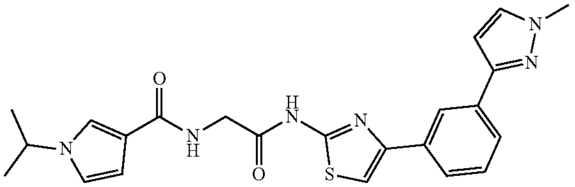

A mixture of Intermediate D (65 mg, 424.34 μmol), Intermediate E (199.47 mg, 636.51 μmol), HOBt (114.68 mg, 848.69 μmol), EDCI (162.69 mg, 848.69 μmol) and DIEA (164.53 mg, 1.27 mmol, 221.74 μL) in DMF (2 mL) was degassed and purged with $N_2$ for 3 times, and then the mixture was stirred at 25° C. for 12 h. The reaction mixture was concentrated in vacuum. The residue was purified by reversed phase (basic condition) and lyophilized to give Compound 2 (64 mg, 142.69 μmol, 33.62% yield) as a yellow solid. LCMS (ESI) m/z $[M+H]^+$=449.4; $^1$H NMR (400 MHz, DMSO-$d_6$) δ 12.40 (s, 1H), 8.39 (s, 1H), 8.18-8.16 (m, 1H), 7.83-7.68 (m, 4H), 7.48-7.40 (m, 2H), 6.88-6.86 (m, 1H), 6.73 (d, J=2.2 Hz, 1H), 6.48 (dd, J=2.0, 2.8 Hz, 1H), 4.32 (m, 1H), 4.10 (d, J=5.6 Hz, 2H), 3.91 (s, 3H), 1.39 (d, J=6.8 Hz, 6H).

Example 3. Preparation of 1-(tert-butyl)-N-(2-((4-(3-cyanophenyl)thiazol-2-yl)amino)-2-oxoethyl)-1H-imidazole-4-carboxamide (Compound 3)

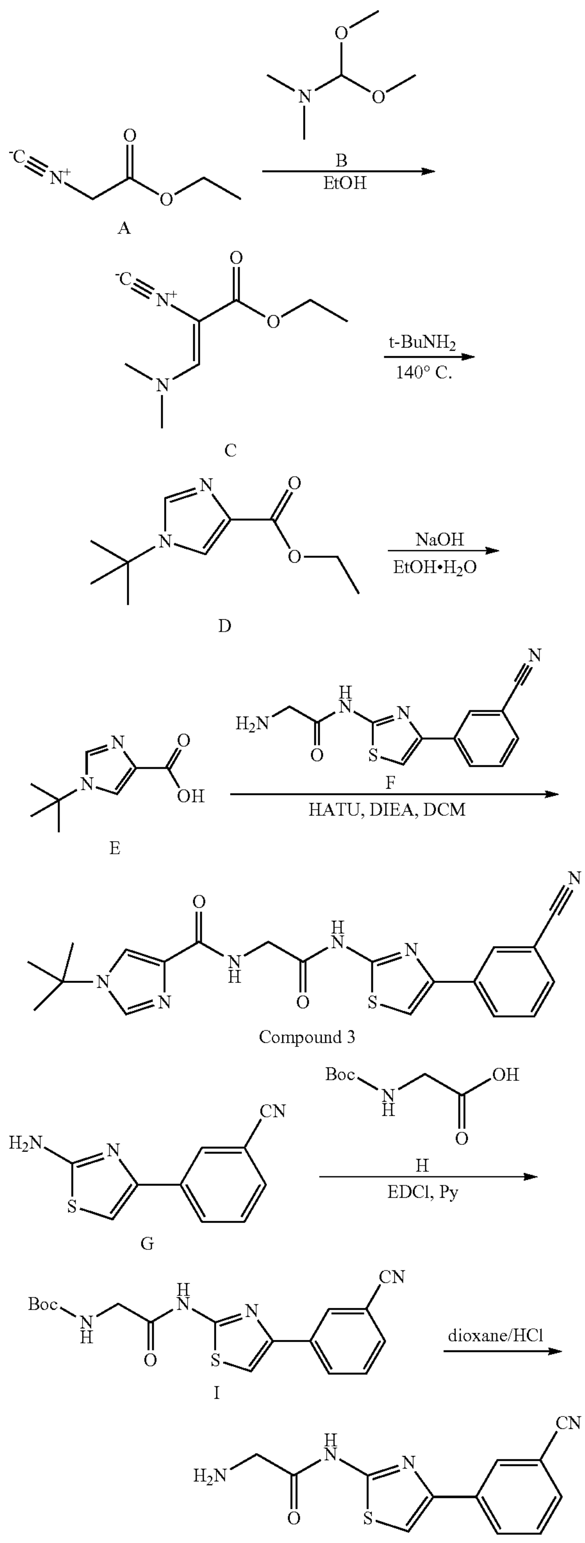

F

Step 1: Preparation of (Z)-ethyl 3-(dimethylamino)-2-isocyanoacrylate (Intermediate C)

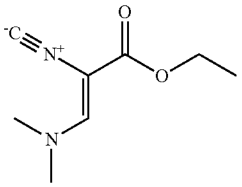
C

To a solution of ethyl 2-isocyanoacetate (1 g, 8.84 mmol, 970.87 μL) in EtOH (10 mL) was added 1,1-dimethoxy-N,Ndimethyl-methanamine (2.11 g, 17.68 mmol, 2.35 mL) dropwise at 0° C., the mixture was stirred at 30° C. for 16 h under $N_2$. The reaction mixture was concentrated to give a residue. The residue was purified by column chromatography ($SiO_2$, Petroleum ether/EtOAc=30/1 to 10:1) and concentrated to give Intermediate C (1 g, crude) as brown oil. LCMS (ESI) m/z $[M+H]^+$=169.2. $^1H$ NMR (400 MHz, Methanol-$d_4$) δ 7.34-7.31 (s, 1H), 4.20-4.13 (m, 2H), 3.31-3.24 (m, 6H), 1.29-1.25 (m, 3H).

Step 2: Preparation of ethyl 1-(tert-butyl)-1H-imidazole-4-carboxylate (Intermediate D)

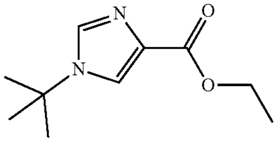
D

A mixture of Intermediate C (1 g, 5.95 mmol) and 2-methylpropan-2-amine (1.30 g, 17.84 mmol, 1.87 mL) was stirred at 140° C. for 24 h. The reaction mixture was concentrated to give a residue. The crude product was purified by reversed-phase HPLC (0.1% $NH_3 \cdot H_2O$), the solution was extracted with EtOAc (20 mL×3), the combined organic layer was washed with brine (50 mL), dried over $Na_2SO_4$ and filtered. The filtrate was concentrated to give Intermediate D (200 mg, 847.00 μmol, 14.25% yield) as a yellow oil. LCMS (ESI) m/z $[M+H]^+$=197.3.

Step 3: Preparation of 1-(tert-butyl)-1H-imidazole-4-carboxylic acid (Intermediate E)

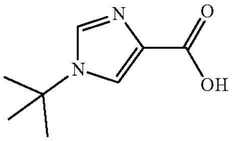
E

To solution of Intermediate D (80 mg, 407.65 μmol) in $H_2O$ (1 mL) and EtOH (1 mL) was added NaOH (16.30 mg, 407.65 μmol), the mixture was stirred at 30° C. for 2 h. The reaction mixture was concentrated in vacuum to give Intermediate E (60 mg, crude) as a yellow solid, which was used for next step directly. LCMS (ESI) m/z $[M+H]^+$=169.1.

Step 4: Preparation of tert-butyl (2-((4-(3-cyanophenyl)thiazol-2-yl)amino)-2-oxoethyl)carbamate (Intermediate I)

I

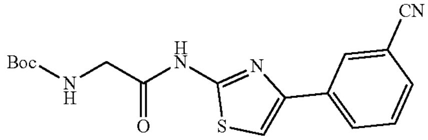

To a solution of 3-(2-aminothiazol-4-yl)benzonitrile (7 g, 34.78 mmol) and 2-(tert-butoxycarbonylamino)acetic acid (9.14 g, 52.17 mmol) in Pyridine (140 mL) was added EDCI (20.00 g, 104.35 mmol), the mixture was stirred at 30° C. for 2 h. The reaction mixture was concentrated to give a residue. The residue was poured into aq. citric acid solution (200 mL), the solution was stirred at 30° C. for 30 min. The mixture was extracted with EtOAc (100 mL×3), the combined organic layers were washed with brine (200 mL), dried over $Na_2SO_4$ and filtered. The filtrate was concentrated to give a residue. The residue was triturated with EtOAc (20 mL), then filtered and dried in vacuum to give Intermediate I (6.6 g, 15.98 mmol, 45.93% yield) as a white solid. LCMS (ESI) m/z $[M+H-56]^+$=303.0; $^1H$ NMR (400 MHz, DMSO-$d_6$) δ 12.39-12.31 (m, 1H), 8.34-8.29 (m, 1H), 8.25-8.18 (m, 1H), 7.88-7.84 (m, 1H), 7.81-7.76 (m, 1H), 7.70-7.62 (m, 1H), 7.24-7.12 (m, 1H), 3.94-3.80 (m, 2H), 1.48-1.32 (m, 9H).

Step 5: Preparation of 2-amino-N-(4-(3-cyanophenyl)thiazol-2-yl)acetamide (Intermediate F)

F

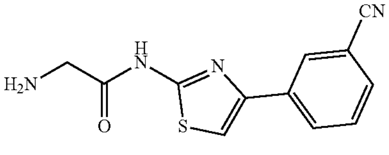

A mixture of Intermediate I (6.6 g, 18.19 mmol) in HCl/dioxane (70 mL) was stirred at 30° C. for 2 h. The reaction mixture was concentrated to give a residue. The residue was triturated with MTBE (10 mL), then filtered and dried in vacuum to give intermediate F (6.1 g, crude, HCl salt) as a white solid. LCMS (ESI) m/z $[M+H]^+$=258.9. $^1H$ NMR (400 MHz, Methanol-$d_4$) δ 8.27 (s, 1H), 8.20 (d, J=8.0 Hz, 1H), 7.66-7.64 (m, 2H), 7.60-7.56 (m, 1H), 4.02 (s, 2H).

Step 6: Preparation of 1-(tert-butyl)-N-(2-((4-(3-cyanophenyl)thiazol-2-yl)amino)-2-oxoethyl)-1H-imidazole-4-carboxamide (Compound 3)

Compound 3

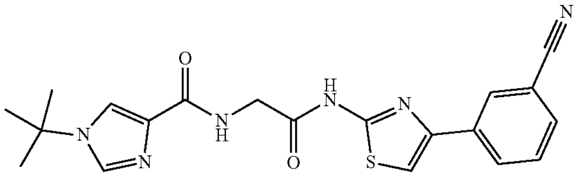

To a solution of Intermediate E (60 mg, 356.73 μmol) and intermediate F (52.58 mg, 178.37 μmol, HCl salt) in DCM (2 mL) was added HATU (81.38 mg, 214.04 μmol) and DIEA (115.26 mg, 891.83 μmol, 155.34 μL), the mixture was stirred at 30° C. for 16 h. The reaction mixture was concentrated to give a residue. The residue was purified by Prep-HPLC (mobile phase: [water (0.225% FA)-acetonitrile]; B %: 22%-52%) and lyophilized to give Compound 3 (33.52 mg, 82.06 μmol, 46.01% yield) as a white solid. LCMS (ESI) m/z $[M+H]^+$=409.2; $^1H$ NMR (400 MHz, DMSO-$d_6$) δ 12.39 (s, 1H), 8.32 (s, 1H), 8.23-8.21 (m, 2H), 7.89-7.86 (m, 3H), 7.78 (d, J=7.6 Hz, 1H), 7.67-7.63 (m, 1H), 4.17 (d, J=6.0 Hz, 2H), 1.53 (s, 9H).

Example 4. Preparation of 1-(methylsulfonyl)-N-(2-oxo-2-((4-(3-(pyridin-4-yl)phenyl)thiazol-2-yl)amino)ethyl)-1H-pyrrole-3-carboxamide (Compound 4)

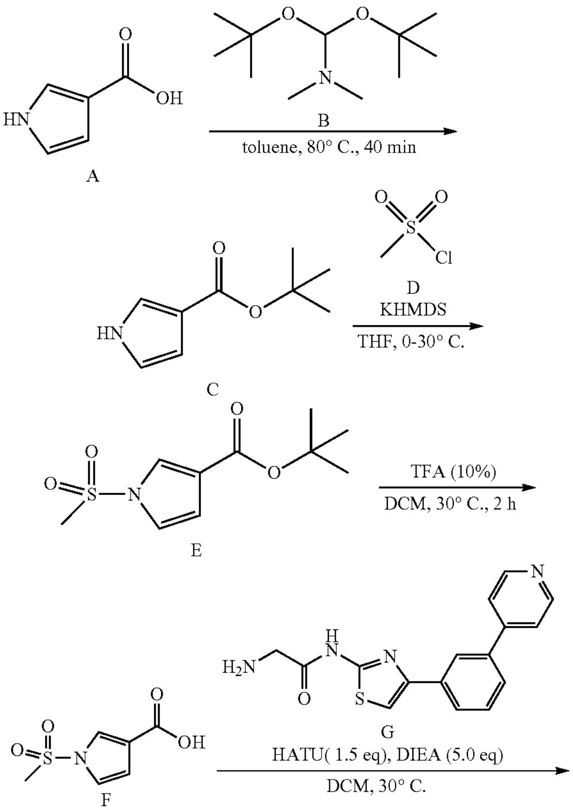

-continued

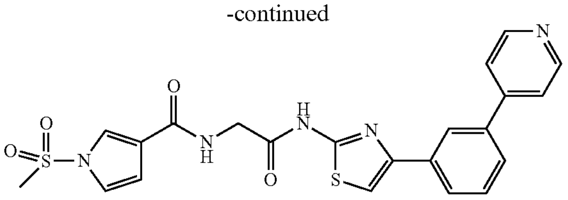

Compound 4

Step 1: Preparation of tert-butyl 1H-pyrrole-3-carboxylate (Intermediate C)

C

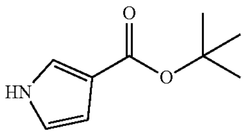

To a mixture of 1H-pyrrole-3-carboxylic acid (500 mg, 4.50 mmol) in toluene (15 mL) was added 1,1-di-tert-butoxy-N,N-dimethylmethanamine (3.66 g, 18.00 mmol, 4.32 mL) dropwisely at 80° C. within 20 min. The reaction mixture was stirred at 80° C. for 10 min. The reaction mixture was cooled to room temperature (30° C.), diluted with EtOAc (40 mL), washed with $H_2O$ (60 mL) and extracted with EtOAc (60 mL×3). The combined organic layers were washed with brine (30 mL), dried over anhydrous $Na_2SO_4$, filtered and concentrated under reduced pressure to afford a residue. The residue was purified by reverse phase column ($NH_3 \cdot H_2O$ condition) and lyophilized to afford Intermediate C (450 mg, 2.69 mmol, 59.80% yield) as yellow solid. $^1H$ NMR (400 MHz, $CDCl_3$) δ 8.52 (br s, 1H), 7.37-7.35 (m, 1H), 6.74-6.72 (m, 1H), 6.62-6.60 (m, 1H), 1.56 (s, 9H).

Step 2: Preparation of tert-butyl 1-(methylsulfonyl)-1H-pyrrole-3-carboxylate (Intermediate E)

E

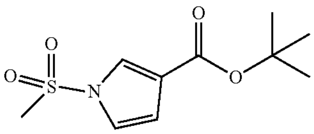

To a solution of Intermediate C (620 mg, 3.71 mmol) in THF (25 mL) was added KHMDS (1 M, 7.42 mL) slowly at 0° C. under $N_2$. The reaction mixture was stirred at 0° C. for 30 min under $N_2$. Then to the reaction mixture was added methanesulfonyl chloride (509.71 mg, 4.45 mmol, 344.40 μL) slowly at 0° C. under $N_2$. The reaction mixture was warmed to 30° C. and stirred at 30° C. for 16 h under $N_2$. The reaction mixture was poured into $H_2O$ (60 mL) slowly and extracted with EtOAc (60 mL×3). The combined organic layers was washed with brine (30 mL), dried over anhydrous $Na_2SO_4$, filtered and concentrated under reduced pressure to afford a residue. The residue was purified by reverse phase column ($NH_3 \cdot H_2O$ condition) to afford Intermediate E (510 mg, 2.01 mmol, 54.19% yield) as yellow solid. LCMS (ESI) m/z[M+Na]$^+$=268.2. $^1H$ NMR (400 MHz, $CDCl_3$) δ 7.65-7.64 (m, 1H), 7.09-7.08 (m, 1H), 6.72-6.71 (m, 1H), 3.21 (s, 3H), 1.56 (s, 9H).

Step 3: Preparation of 1-methylsulfonylpyrrole-3-carboxylic acid [Prepared According to the Method in Example 4] (Intermediate F)

F

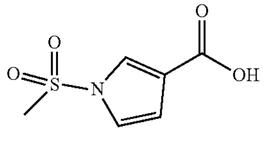

To a solution of Intermediate E (560 mg, 2.28 mmol) in DCM (25 mL) was added TFA (3.85 g, 33.77 mmol, 2.5 mL) slowly at 30° C. The reaction mixture was stirred at 30° C. for 2 h. The reaction mixture was concentrated under reduced pressure to afford a residue. The residue was purified by reverse phase column (FA condition) to afford Intermediate F (310 mg, 1.57 mmol, 68.57% yield) as white solid. LCMS (ESI) m/z [M+H]$^+$=190.0. $^1H$ NMR (400 MHz, Methanol-$d_4$) δ 7.77-7.76 (m, 1H), 7.24-7.22 (m, 1H), 6.71-6.70 (m, 1H), 3.37 (s, 3H).

Preparation of 2-amino-N-[4-[3-(4-pyridyl)phenyl]thiazol-2-yl]acetamide (Intermediate G)

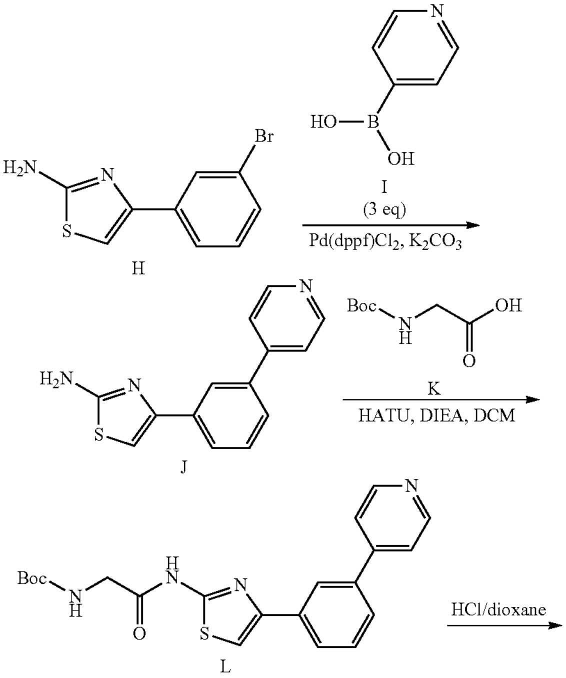

-continued

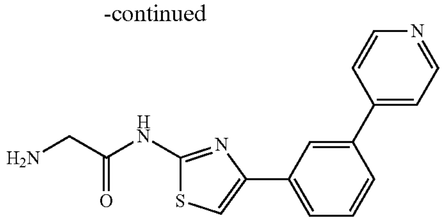

G

Step 4: Preparation of 4-[3-(4-pyridyl)phenyl]thiazol-2-amine (Intermediate J)

J

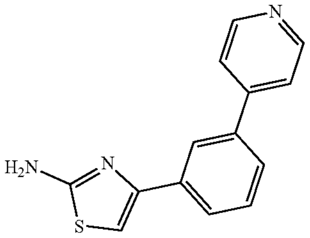

To a solution of 4-(3-bromophenyl)thiazol-2-amine (10 g, 39.20 mmol), 4-pyridylboronic acid (14.45 g, 117.59 mmol) and $K_2CO_3$ (16.25 g, 117.59 mmol) in dioxane (120 mL) and Water (30 mL) was added Pd(dppf)$Cl_2$ (1 g, 1.37 mmol) under $N_2$, the mixture was stirred at 100° C. for 4 h. The reaction mixture was diluted with water (500 mL), extracted with EtOAc (500 mL) and concentrated under reduced pressure to give a residue. The residue was purified by crystallization from DCM/MTBE=1:20 (200 mL) and filtered to give intermediate J (9.5 g, 36.33 mmol, 92.69% yield) as a brown solid. LCMS (ESI) m/z $[M+H]^+$=254.2; $^1$H NMR (400 MHz, DMSO-d6) δ 8.66 (d, J=6.0 Hz, 2H), 8.19 (s, 1H), 7.90 (d, J=8.0 Hz, 1H), 7.76-7.70 (m, 2H), 7.68 (d, J=8.0 Hz, 1H), 7.52 (t, J=8.0 Hz, 1H), 7.21 (s, 1H), 7.11 (s, 2H).

Step 5: Preparation of tert-butyl N-[2-oxo-2-[[4-[3-(4-pyridyl)phenyl]thiazol-2-yl]amino]ethyl]carbamate (Intermediate L)

L

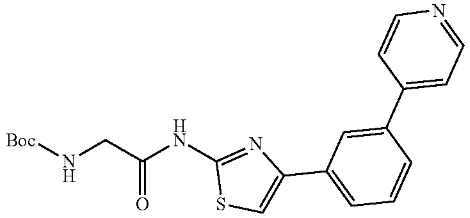

To a solution of 2-(tert-butoxycarbonylamino)acetic acid (9.85 g, 56.25 mmol), HATU (21.39 g, 56.25 mmol) and DIPEA (14.54 g, 112.51 mmol) in DCM (200 mL) was added Intermediate C (9.5 g, 37.50 mmol, 1 eq), the mixture was stirred at 30° C. for 16 h. A precipitate was formed. The reaction mixture was filtered to give a yellow solid. The crude product was triturated with EtOAc (300.0 mL) and MeOH (50.0 mL) and dried in vacuum to give intermediate L (11 g, 25.89 mmol, 69.03% yield) as a white solid. LCMS (ESI) m/z $[M+H]^+$=411.3. $^1$H NMR (400 MHz, DMSO-d6) δ 12.32 (br s, 1H), 8.69-8.67 (m, 2H), 8.30 (s, 1H), 8.01 (d, J=7.8 Hz, 1H), 7.83 (s, 1H), 7.80-7.76 (m, 3H), 7.64-7.60 (m, 1H), 7.20-7.15 (m, 1H), 3.88 (d, J=6.4 Hz, 2H), 1.44 (s, 9H).

Step 6: Preparation of 2-amino-N-[4-[3-(4-pyridyl)phenyl]thiazol-2-yl]acetamide (Intermediate G)

G

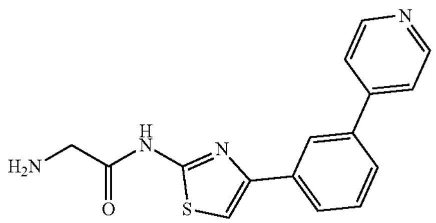

To a solution of Intermediate L (11 g, 26.80 mmol) in MeOH (20 mL) was added 4 M HCl/EtOAc (20 mL). The mixture was stirred at 20° C. for 2 h. The reaction mixture was concentrated under reduced pressure to give a residue. The residue was purified by triturated with EtOAc (200 mL) and MTBE (50 mL) and dried in vacuum to give intermediate G (12 g, HCl salt) a light yellow solid. LCMS (ESI) m/z $[M+H]^+$=311.3. $^1$H NMR (400 MHz, Methanol-d4) δ8.92 (d, J=6.8 Hz, 2H), 8.52-8.47 (m, 3H), 8.22 (d, J=8.0 Hz, 1H), 7.94 (m, J=8.4 Hz, 1H), 7.75-7.66 (m, 2H), 4.04 (s, 2H).

Step 7: Preparation of 1-(methylsulfonyl)-N-(2-oxo-2-((4-(3-(pyridin-4-yl)phenyl)thiazol-2-yl)amino)ethyl)-1H-pyrrole-3-carboxamide (Compound 4)

Compound 4

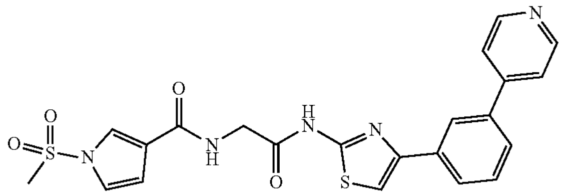

To a mixture of Intermediate F (248.74 mg, 1.31 mmol) in DCM (15 mL) was added DIPEA (708.01 mg, 5.48 mmol, 954.19 μL), HATU (624.88 mg, 1.64 mmol) and 2-amino-N-(4-(3-(pyridin-4-yl)phenyl)thiazol-2-yl)acetamide (380 mg, 1.10 mmol, HCl salt) at 30° C. The reaction mixture was stirred at 30° C. for 13 h. The reaction mixture was filtered and the filter cake was washed with DCM (50 mL) and MeOH (20 mL) to afford a yellow solid (600 mg). The yellow solid was triturated with EtOH (50 mL) at 30° C. for 15 min and filtered to afford a yellow solid (270 mg). The yellow solid was triturated with MeCN (20 mL) and 10 drops of TFA at 30° C. for 20 min and filtered to afford Compound 4 (257.10 mg, 419.77 μmol, 38.31% yield, TFA salt) as white solid. LCMS (ESI) m/z $[M+H]^+$=481.9; $^1$H NMR (400 MHz, DMSO) δ 12.46 (s, 1H), 8.85 (d, J=5.2 Hz, 2H), 8.71-8.69 (m, 1H), 8.40 (s, 1H), 8.13-8.08 (m, 3H), 7.89-7.84 (m, 3H), 7.68-7.64 (m, 1H), 7.33-7.31 (m, 1H), 6.78-6.77 (m, 1H), 4.15 (d, J=5.6 Hz, 2H), 3.58 (s, 3H).

Example 5. Preparation of (S)-1-(methylsulfonyl)-N-(4-(methylthio)-1-oxo-1-((4-phenylthiazol-2-yl)amino)butan-2-yl)-1H-pyrrole-3-carboxamide (Compound 5)

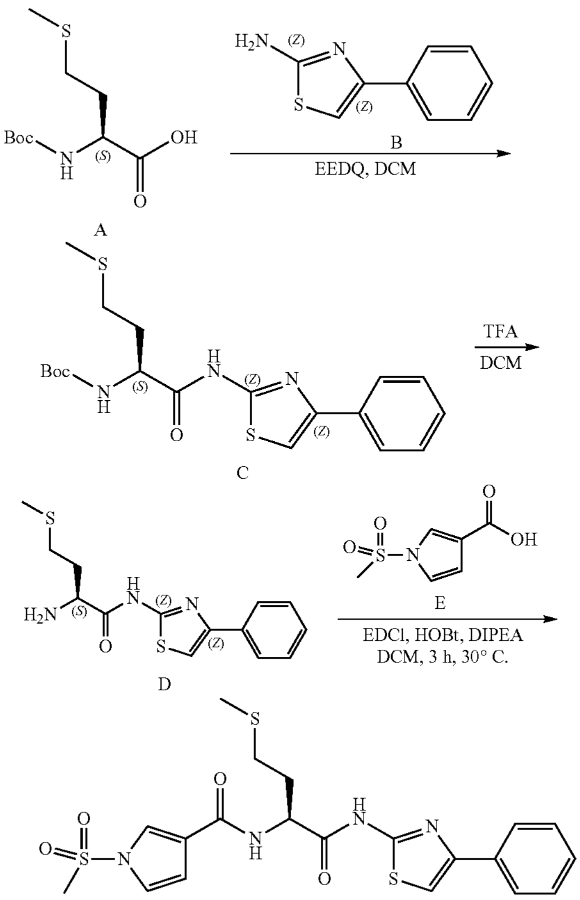

Compound 5

Step 1: Preparation of (S)-tert-butyl (4-(methylthio)-1-oxo-1-((4-phenylthiazol-2-yl)amino)butan-2-yl)carbamate (Intermediate C)

C

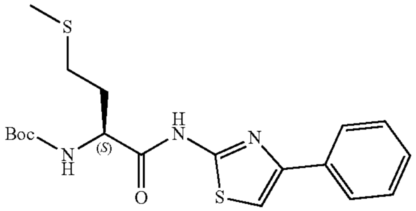

To a solution of (2S)-2-(tert-butoxycarbonylamino)-4-methylsulfanyl-butanoic acid (5.0 g, 20.05 mmol) in DCM (20.0 mL) was added EEDQ (6.20 g, 25.07 mmol), then 4-phenylthiazol-2-amine (2.95 g, 16.71 mmol) was added to the mixture. The mixture was stirred at 25° C. for 3 h. 10% of Citric acid (800.0 mL) was added and the reaction mixture was extracted with EtOAc (200 mL). The combined organic layers were washed with brine (100 mL), dried over $Na_2SO_4$, filtered and concentrated under reduced pressure to give a residue. The residue was purified by column chromatography ($SiO_2$, Petroleum ether/EtOAc=50/1 to 8:1) to give intermediate C (5.8 g, 14.23 mmol, 85.16% yield) as a white solid. LCMS (ESI) m/z $[M+H]^+$=408.0; ee %=100%.

Step 2: Preparation of (S)-2-amino-4-(methylthio)-N-(4-phenylthiazol-2-yl) butanamide (Intermediate D)

D

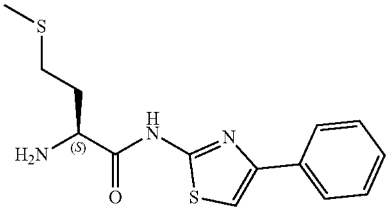

To a solution of intermediate C (5.8 g, 14.23 mmol) in DCM (20.0 mL) was added TFA (4.0 mL). The mixture was stirred at 10° C. for 2 h. The reaction mixture was concentrated under reduced pressure to remove DCM. The crude product intermediate D (7 g, crude, TFA salt) was lyophilized and used into the next step without further purification as a white solid. LCMS (ESI) m/z $[M+H]^+$=307.9; ee %=100%.

Step 3: Preparation of (S)-1-(methylsulfonyl)-N-(4-(methylthio)-1-oxo-1-((4-phenylthiazol-2-yl)amino) butan-2-yl)-1H-pyrrole-3-carboxamide (Compound 5)

Compound 5

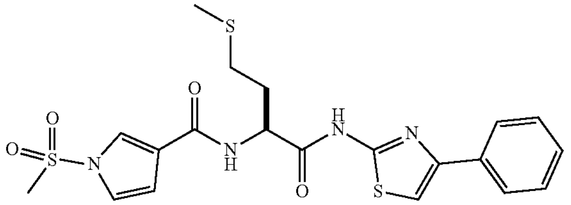

To a solution of 1-methylsulfonylpyrrole-3-carboxylic acid [prepared according to the method in Example 4] (300 mg, 1.59 mmol) and intermediate D (487.50 mg, 1.59 mmol) in DCM (10 mL) was added DIPEA (614.81 mg, 4.76 mmol, 828.59 μL), EDCI (455.97 mg, 2.38 mmol) and HOBt (321.39 mg, 2.38 mmol) at 30° C. The reaction mixture was stirred at 30° C. for 3 h. The reaction mixture was concentrated under reduced pressure to afford a residue. The residue was purified by reverse phase column (FA condition) and lyophilized to afford Compound 5 (507.03 mg, 1.05 mmol, 66.35% yield) as white solid. LCMS (ESI) m/z $[M+H]^+$=478.9; $^1H$ NMR (400 MHz, Methanol-$d_4$) δ 7.93-7.85 (m, 3H), 7.42-7.35 (m, 3H), 7.30 (d, J=7.2 Hz, 1H), 7.28-7.24 (m, 1H), 6.84-6.82 (m, 1H), 4.90-4.88 (m, 1H), 3.36 (s, 3H), 2.73-2.57 (m, 2H), 2.31-2.11 (m, 5H); ee %=100%.

Example 6. Preparation of 1-(methylsulfonyl)-N-(2-oxo-2-((4-(1-(pyridin-4-yl)-1H-pyrazol-4-yl)thiazol-2-yl)amino)ethyl)-1H-pyrrole-3-carboxamide (Compound 6)

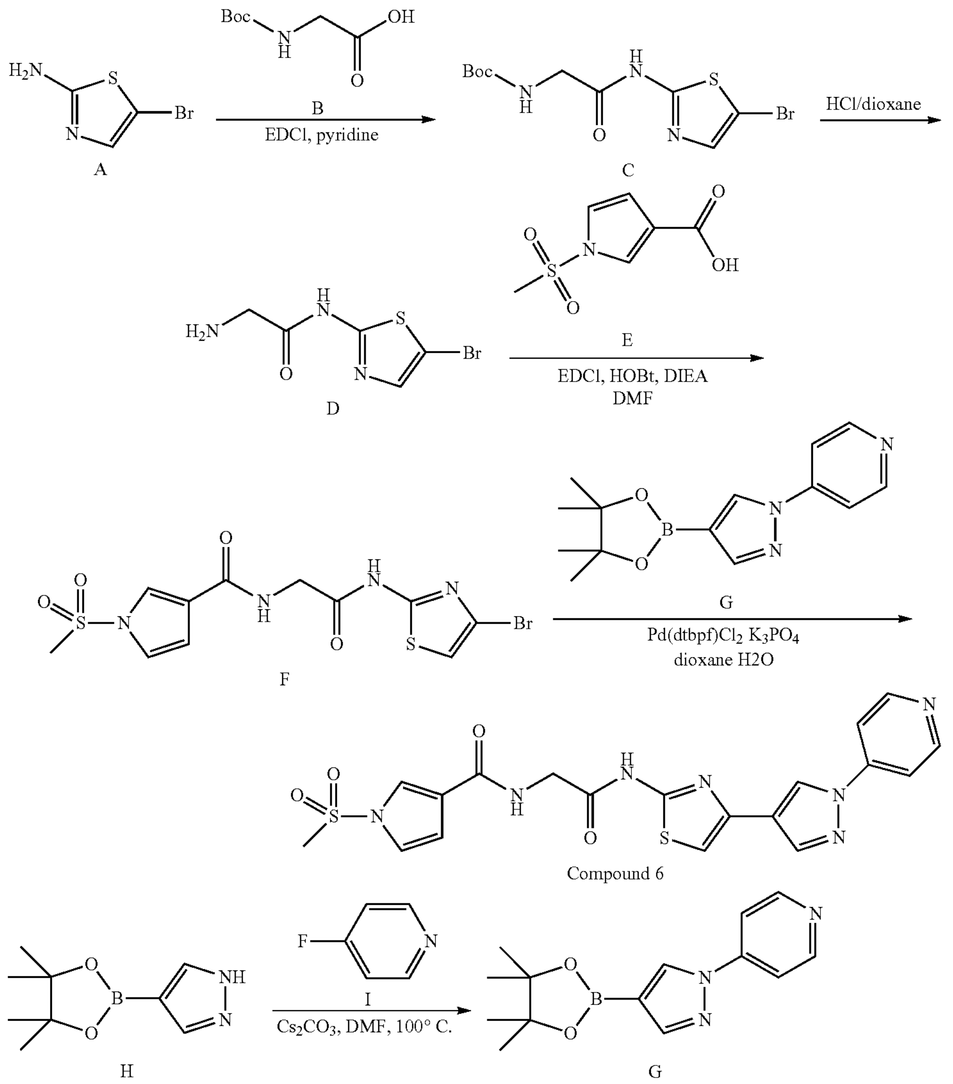

Step 1: Preparation of tert-butyl (2-((4-bromothiazol-2-yl)amino)-2-oxoethyl)carbamate (Intermediate C)

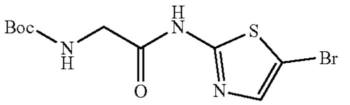

C

To a solution of 2-(tert-butoxycarbonylamino)acetic acid (14.68 g, 83.78 mmol) and 4-bromothiazol-2-amine (10 g, 55.85 mmol) in pyridine (150 mL) was added EDCI (53.54 g, 279.27 mmol) at 25° C. The reaction mixture was stirred at 25° C. for 16 h. The reaction mixture was extracted with EtOAc (50 mL×3). The combined organic phase was washed with brine (50 mL), dried with anhydrous $Na_2SO_4$, filtered and concentrated in vacuum. The residue was purified by flash silica gel chromatography (Petroleum ether/EtOAc=1:0 to 0:1) to give a solid. The solid was triturated with MTBE (20 mL), filtered and dried in vacuum to give Intermediate C (8 g, 21.65 mmol, 38.77% yield) as a white solid. LCMS (ESI) $[M+H]^+$=336.1/338.1; $^1$H NMR (400 MHz, DMSO-$d_6$) δ 12.44 (s, 1H), 7.29 (s, 1H), 7.17 (s, 1H), 6.59-6.56 (m, 1H), 3.84 (d, J=6.4 Hz, 2H), 1.39 (s, 9H).

Step 2: Preparation of 2-amino-N-(4-bromothiazol-2-yl)acetamide (Intermediate D)

D

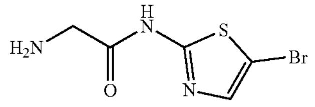

A solution of intermediate C (5 g, 14.87 mmol) in HCl/dioxane (4 M, 50 mL) was stirred at 25° C. for 2 hours. The reaction mixture was filtered and the solid was dried in vacuum to afford Intermediate D (4.2 g, HCl salt) as a yellow solid. LCMS (ESI) m/z $[M+H]^+$=236.2/238.2.

Step 3: Preparation of N-(2-((4-bromothiazol-2-yl) amino)-2-oxoethyl)-1-(methylsulfonyl)-1H-pyrrole-3-carboxamide (Intermediate F)

F

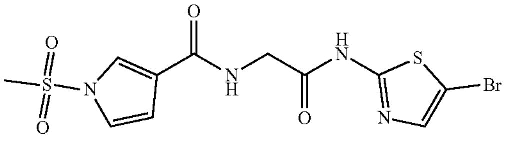

The solution of 1-methylsulfonylpyrrole-3-carboxylic acid [prepared according to the method in Example 4] (1.67 g, 8.81 mmol), DIEA (2.85 g, 22.01 mmol) and HATU (4.19 g, 11.01 mmol) in DCM (20 mL) was stirred at 25° C. for 5 minutes. Then Intermediate D (2 g, 7.34 mmol) was added at 25° C. The reaction mixture was stirred at 25° C. for 16 hours. The reaction mixture was filtered to afford a brown solid. The solid was triturated with DCM (5 mL) and then dissolved with DMSO (5 mL) and repurified by reversed-phase HPLC (FA), concentrated and extracted with EtOAc (20 mL×2), the combined organic layers was dried over anhydrous $Na_2SO_4$ and concentrated to afford intermediate F (550 mg, 1.31 mmol, 17.83% yield) as a white solid. LCMS (ESI) $[M+H]^+$=407.1/409.1; $^1H$ NMR (400 MHz, DMSO-d6) δ 12.54 (br s, 1H), 8.69-8.67 (m, 1H), 7.83-7.83 (m, 1H), 7.33-7.28 (m, 2H), 6.76-6.75 (m, 1H), 4.10 (d, J=5.8 Hz, 2H), 3.57 (s, 3H).

Step 4: Preparation of 4-[4-(4,4,5,5-tetramethyl-1,3,2-dioxaborolan-2-yl)pyrazol-1-yl]pyridine (Intermediate G)

G

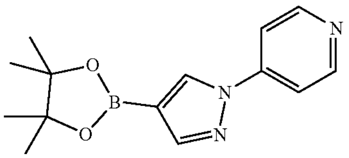

To a solution of 4-(4,4,5,5-tetramethyl-1,3,2-dioxaborolan-2-yl)-1H-pyrazole (500 mg, 2.58 mmol) and 4-fluoropyridine (375.28 mg, 2.81 mmol, 1.09 eq, HCl) in DMF (5 mL) was added $Cs_2CO_3$ (1.68 g, 5.15 mmol). Then the mixture was stirred at 100° C. for 16 h. The reaction mixture was diluted with brine (10 mL) and then extracted with EtOAc (5 mL×2). The combined organic layers were dried over anhydrous $Na_2SO_4$, filtered and concentrated under reduced pressure to give intermediate G (1.5 g, crude) as yellow oil, which was used directly in the next step. LCMS (ESI) $[M+H]^+$=272.1.

Step 5: Preparation of 1-(methylsulfonyl)-N-(2-oxo-2-((4-(1-(pyridin-4-yl)-1H-pyrazol-4-yl)thiazol-2-yl) amino)ethyl)-1H-pyrrole-3-carboxamide (Compound 6)

Compound 6

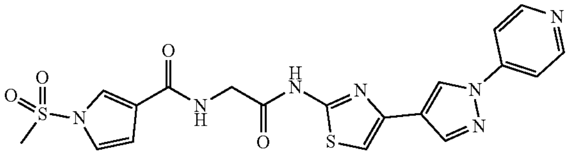

To a solution of Intermediate F (100 mg, 245.54 μmol) and intermediate G (332.86 mg, 1.23 mmol) in Dixoane/$H_2O$=4/1 (5 mL) was added $K_3PO_4$ (156.36 mg, 736.62 μmol) and [1,1'-bis(di-tert-butylphosphino)ferrocene]dichloropalladium(II) (32.01 mg, 49.11 μmol). The mixture was stirred at 75° C. under $N_2$ for 16 h. To the mixture was added $H_2O$ (0.5 mL) and a yellow solid was precipitate from the mixture, the solid was filtered to afford the crude product. The crude product was purified by reversed phase (0.1% FA condition) and lyophilized to afford Compound 6 (11.15 mg, 20.62 μmol, 8.40% yield, FA salt) as a white solid. LCMS (ESI) m/z $[M+H]^+$=472.3; $^1H$ NMR (400 MHz, DMSO-$d_6$) δ 12.41 (br s, 1H), 8.98 (s, 1H), 8.68-8.66 (m, 3H), 8.22 (s, 1H), 7.90-7.88 (m, 2H), 7.85-7.84 (m, 1H), 7.41 (s, 1H), 7.32-7.32 (m, 1H), 6.78-6.78 (m, 1H), 4.22-4.07 (m, 2H), 3.66-3.50 (m, 3H).

Example 7. Preparation of 1-(tert-butyl)-N-(2-((4-(2-methyl-1-oxo-1,2,3,4-tetrahydroisoquinolin-7-yl) thiazol-2-yl)amino)-2-oxoethyl)-1H-pyrrole-3-carboxamide (Compound 7)

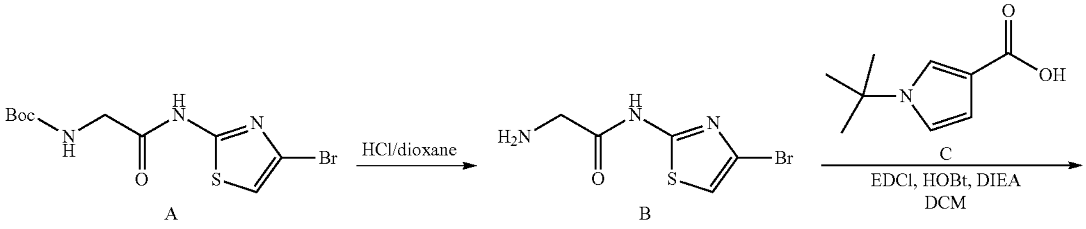

-continued

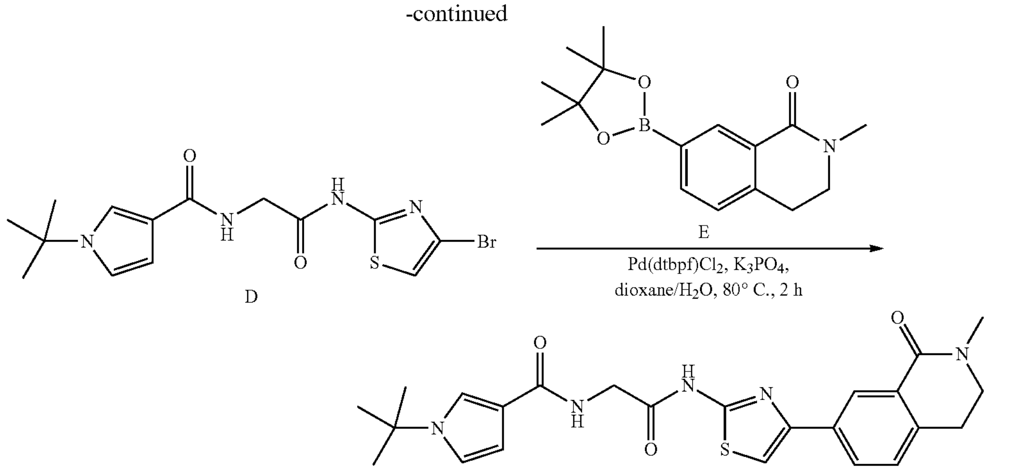

D

E

Compound 7

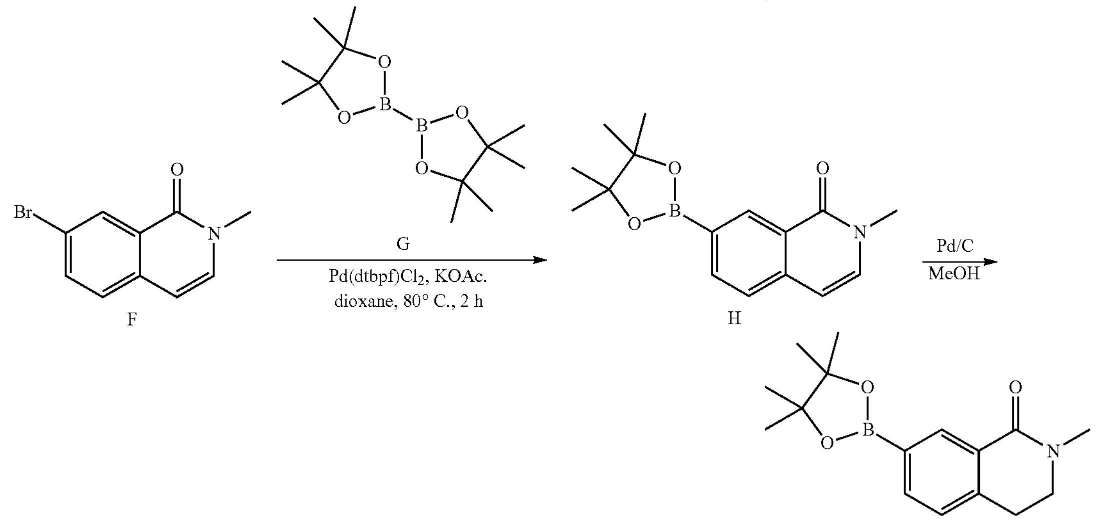

F

G

H

E

Step 1: Preparation of N-(2-((4-bromothiazol-2-yl) amino)-2-oxoethyl)-1-(tert-butyl)-1H-pyrrole-3-carboxamide (Intermediate D)

D

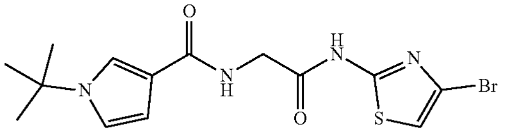

To a solution of 1-tert-butylpyrrole-3-carboxylic acid [prepared according to the method in Example 34] (73.62 mg, 440.29 μmol) in DCM (4 mL) was added EDCI (105.50 mg, 550.36 μmol), DIEA (189.68 mg, 1.47 mmol, 255.63 μL) and HOBt (74.37 mg, 550.36 μmol). Then 2-amino-N-(4-bromothiazol-2-yl)acetamide [prepared according to the method in Example 6] (100 mg, 366.90 μmol, HCl salt) was added. The mixture was stirred at 25° C. for 2 h. Water (20 mL) was added and the reaction mixture was extracted with EtOAc (50 mL×2). The combined organic layers were washed with brine (20 mL), dried over $Na_2SO_4$, filtered and concentrated under reduced pressure to give a residue. The residue was purified by flash silica gel chromatography (EtOAc/Petroleum ether gradient) and concentrated to give Intermediate D (120 mg, 303.55 μmol, 82.73% yield) as a white solid. LCMS (ESI) m/z $[M+H]^+$=387.0.

Step 2: Preparation of 2-methyl-7-(4,4,5,5-tetramethyl-1,3,2-dioxaborolan-2-yl)isoquinolin-1(2H)-one (Intermediate H)

H

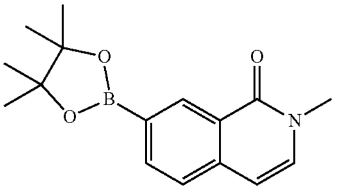

A mixture of 7-bromo-2-methyl-isoquinolin-1-one (300 mg, 1.26 mmol), 4,4,5,5-tetramethyl-2-(4,4,5,5-tetramethyl-1,3,2-dioxaborolan-2-yl)-1,3,2-dioxaborolane (351.98 mg, 1.39 mmol), KOAc (371.00 mg, 3.78 mmol) and [1,1'-bis(di-tert-butylphosphino)ferrocene]dichloropalladium(II)

(82.12 mg, 126.01 μmol) in dioxane (4 mL) was degassed and purged with $N_2$ for 3 times, and then the mixture was stirred at 80° C. for 2 h under $N_2$ atmosphere. Water (20 mL) was added and the reaction mixture was extracted with EtOAc (50 mL×2). The combined organic layers were washed with brine (20 mL), dried over $Na_2SO_4$, filtered and concentrated under reduced pressure to give Intermediate H (300 mg, crude) as a yellow solid, which was used for the next step without further purification. LCMS (ESI) m/z $[M+H]^+$=286.2.

Step 3: Preparation of 2-methyl-7-(4,4,5,5-tetramethyl-1,3,2-dioxaborolan-2-yl)-3,4-dihydroisoquinolin-1(2H)-one (Intermediate E)

E

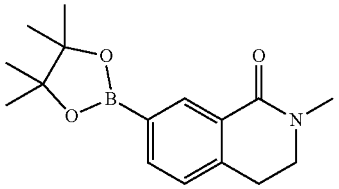

To a solution of Intermediate H (80 mg, 280.56 μmol) in MeOH (5 mL) was added Pd/C (10 mg, 280.56 μmol, 10% purity). The mixture was stirred under $H_2$ (15 psi) at 25° C. for 12 hours. The reaction mixture was filtered and concentrated under reduced pressure to give Intermediate E (70 mg, crude) as a white solid, which was used for the next step without further purification. LCMS (ESI) m/z $[M+H]^+$=287.8.

Step 4: Preparation of 1-(tert-butyl)-N-(2-((4-(2-methyl-1-oxo-1,2,3,4-tetrahydroisoquinolin-7-yl)thiazol-2-yl)amino)-2-oxoethyl)-1H-pyrrole-3-carboxamide (Compound 7)

Compound 7

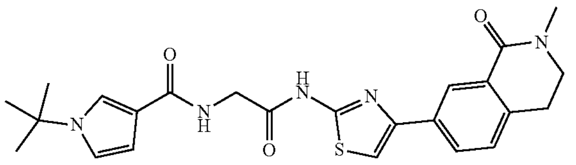

A mixture of N-(2-((4-bromothiazol-2-yl)amino)-2-oxoethyl)-1-(tert-butyl)-1H-pyrrole-3-carboxamide (50 mg, 129.78 μmol), Intermediate E (48.45 mg, 168.71 μmol), $K_3PO_4$ (82.64 mg, 389.34 μmol) and [1,1'-bis(di-tert-butylphosphino)ferrocene]dichloropalladium(II) (16.92 mg, 25.96 μmol) in dioxane (2 mL) and $H_2O$ (0.5 mL) was degassed and purged with $N_2$ for 3 times, and then the mixture was stirred at 80° C. for 2 h under $N_2$ atmosphere. Water (20 mL) was added and the reaction mixture was extracted with EtOAc (50 mL×2). The combined organic layers were washed with brine (20 mL), dried over $Na_2SO_4$, filtered and concentrated under reduced pressure to give a residue. The residue was purified by Prep-HPLC (mobile phase: [water (0.05% ammonia hydroxide v/v)-acetonitrile]; B %: 28%-58%) and lyophilized to give Compound 7 (7 mg, 15.04 μmol, 11.59% yield) as a white solid. LCMS (ESI) m/z $[M+H]^+$=466.2; $^1H$ NMR (400 MHz, DMSO-$d_6$) δ 12.36 (s, 1H), 8.46 (d, J=2.0 Hz, 1H), 8.17-8.14 (m, 1H), 7.98-7.95 (m, 1H), 7.65 (s, 1H), 7.52-7.50 (m, 1H), 7.35 (d, J=8.0 Hz, 1H), 6.97-6.95 (m, 1H), 6.47-6.46 (m, 1H), 4.09 (d, J=5.6 Hz, 2H), 3.58-3.55 (m, 2H), 3.04-2.98 (m, 5H), 1.50 (s, 9H).

Example 8. Preparation of 1-(tert-butyl)-N-(2-((4-(3-(1-(2-hydroxy-2-methylpropyl)-1H-pyrazol-3-yl)phenyl)thiazol-2-yl)amino)-2-oxoethyl)-1H-pyrrole-3-carboxamide (Compound 8)

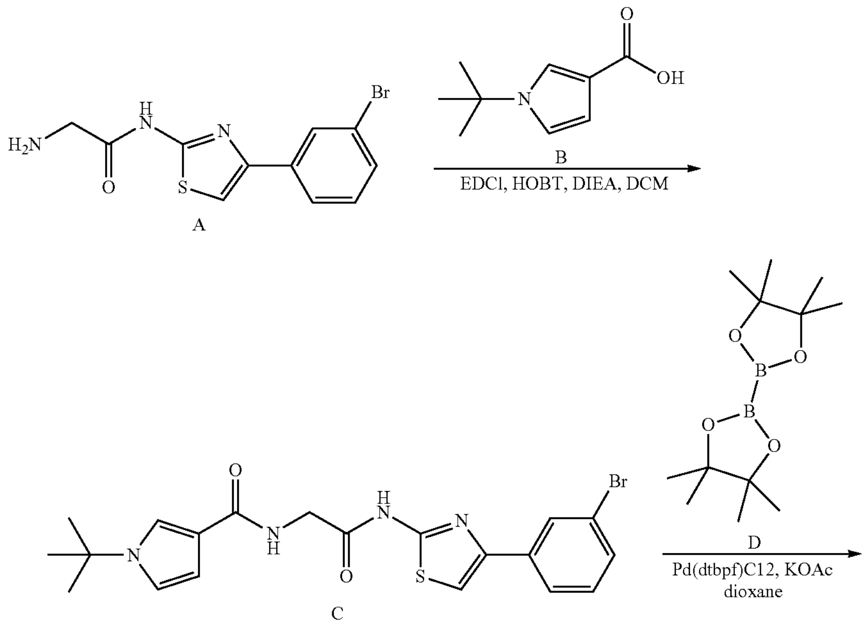

A

B

C

D

-continued

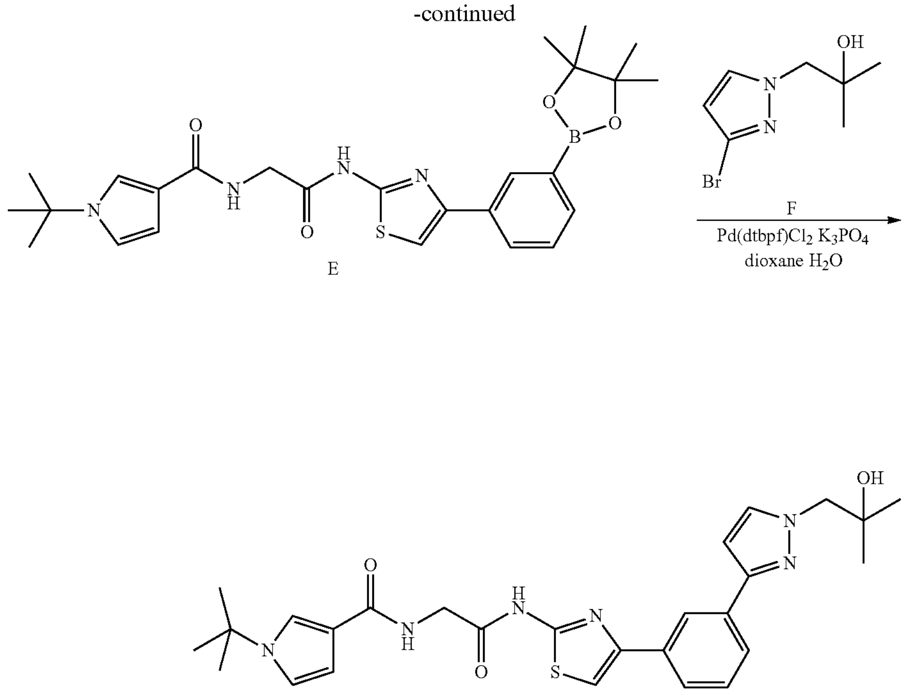

E

Compound 8

Step 1: Preparation of N-(2-((4-(3-bromophenyl)thiazol-2-yl)amino)-2-oxoethyl)-1-(tert-butyl)-1H-pyrrole-3-carboxamide (Intermediate C)

C

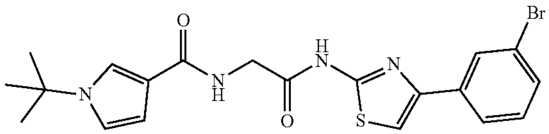

To a solution of 2-amino-N-[4-(3-bromophenyl)thiazol-2-yl]acetamide (prepared according to the method in Example 1) (2.09 g, 5.98 mmol, HCl salt) in DCM (20 mL) was added EDCI (1.72 g, 8.97 mmol), DIEA (3.86 g, 29.90 mmol, 5.21 mL) and HOBt (1.21 g, 8.97 mmol). The mixture was stirred at 25° C. for 30 min, then 1-tert-butylpyrrole-3-carboxylic acid [prepared according to the method in Example 34](1 g, 5.98 mmol) was added at 25° C. and stirred for 16 h. The mixture was cooled to 25° C. and concentrated in reduced pressure at 40° C. The residue was poured into ice-water (20 mL). The aqueous phase was extracted with EtOAc (20 mL×3). The combined organic phase was washed with brine (20 mL), dried with anhydrous $Na_2SO_4$, filtered and concentrated in vacuum to afford a residue. The residue was purified by silica gel column chromatography (Petroleum ether/EtOAc=1:0, 0:1)) and concentrated to afford Intermediate C (1.5 g, 3.25 mmol, 54.36% yield) as yellow solid. LCMS (ESI) m/z $[M+H]^+$=463.0; $^1H$ NMR (400 MHz, DMSO-$d_6$) δ 12.37 (s, 1H), 8.24-8.17 (m, 1H), 8.12 (d, J=1.6 Hz, 1H), 7.95-7.88 (m, 1H), 7.78 (s, 1H), 7.57-7.49 (m, 2H), 7.41 (s, 1H), 6.99-6.97 (m, 1H), 6.48-6.47 (m, 1H), 4.13-4.07 (m, 2H), 1.50 (s, 9H).

Step 2: Preparation of 1-(tert-butyl)-N-(2-oxo-2-((4-(3-(4,4,5,5-tetramethyl-1,3,2-dioxaborolan-2-yl)phenyl)thiazol-2-yl)amino)ethyl)-1H-pyrrole-3-carboxamide (Intermediate E)

E

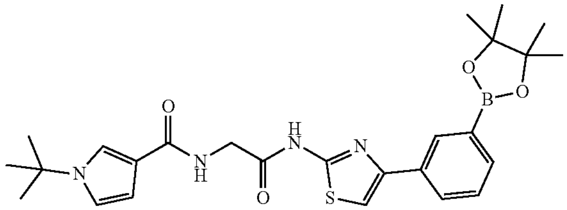

A mixture of Intermediate C (500 mg, 1.08 mmol), 4,4,5,5-tetramethyl-2-(4,4,5,5-tetramethyl-1,3,2-dioxaborolan-2-yl)-1,3,2-dioxaborolane (825.59 mg, 3.25 mmol), $Pd(dppf)Cl_2$ (158.59 mg, 216.74 μmol), KOAc (319.08 mg, 3.25 mmol) in dioxane (5 mL) was degassed and purged with $N_2$ for 3 times, and then the mixture was stirred at 80° C. for 4 h under $N_2$ atmosphere. The mixture was cooled to 25° C. and concentrated in reduced pressure at 40° C. The residue was poured into ice-water (10 mL). The aqueous phase was extracted with EtOAc (10 mL×3). The combined organic phase was washed with brine (10 mL), dried with anhydrous $Na_2SO_4$, filtered and concentrated in vacuum to afford a residue. The residue was purified by silica gel chromatography (Petroleum ether/EtOAc=10/1, 0/1) and concentrated to afford Intermediate E (500 mg, 973.57 μmol, 89.84% yield) as yellow solid. LCMS (ESI) m/z $[M+H]^+$=509.4.

Step 3: Preparation of 1-(tert-butyl)-N-(2-((4-(3-(1-(2-hydroxy-2-methylpropyl)-1H-pyrazol-3-yl)phenyl)thiazol-2-yl)amino)-2-oxoethyl)-1H-pyrrole-3-carboxamide (Compound 8)

Compound 8

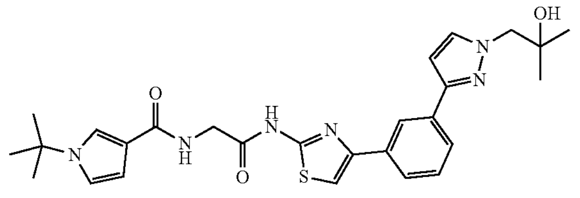

To a mixture of 1-(3-bromopyrazol-1-yl)-2-methyl-propan-2-ol (50 mg, 228.23 μmol) and Intermediate E (116.04 mg, 228.23 μmol) in dioxane (1.2 mL) and $H_2O$ (0.3 mL) was added [1,1'-bis(di-tert-butylphosphino)ferrocene]dichloropalladium(II) (29.75 mg, 45.65 μmol) and $K_3PO_4$ (145.34 mg, 684.69 μmol) at 25° C. under $N_2$. The reaction mixture was heated to 75° C. and stirred at 75° C. for 2 h. The mixture was cooled to 25° C. and concentrated in reduced pressure at 40° C. The residue was poured into ice-water (10 mL). The aqueous phase was extracted with EtOAc (10 mL×3). The combined organic phase was washed with brine (10 mL), dried with anhydrous $Na_2SO_4$, filtered and concentrated in vacuum to afford a residue. The residue was purified by reversed phase HPLC (FA) and lyophilized to afford Compound 8 (20.86 mg, 39.67 μmol, 17.38% yield) as yellow solid. LCMS (ESI) m/z $[M+H]^+$= 521.3; $^1$HNMR (400 MHz, Methanol-$d_4$) δ 8.39-8.30 (m, 1H), 7.87-7.79 (m, 1H), 7.75-7.67 (m, 2H), 7.60-7.56 (m, 1H), 7.46-7.40 (m, 2H), 6.98-6.93 (m, 1H), 6.73-6.67 (m, 1H), 6.60-6.54 (m, 1H), 4.27-4.20 (m, 2H), 4.18-4.12 (m, 2H), 1.57 (s, 9H), 1.22 (s, 6H).

Example 9. Preparation of N-(2-((4-(3-(2-aminopyridin-4-yl)phenyl)thiazol-2-yl)amino)-2-oxoethyl)-1-(methylsulfonyl)-1H-pyrrole-3-carboxamide (Compound 9)

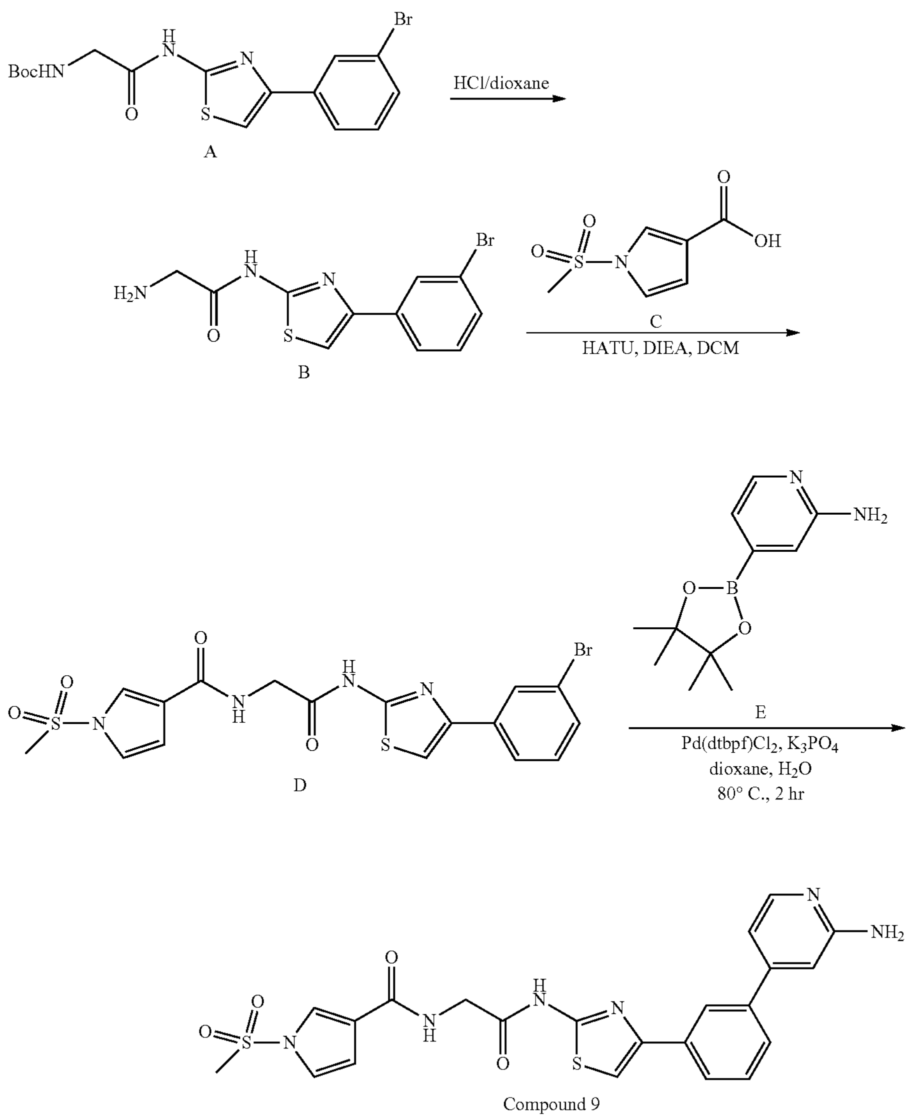

Compound 9

Step 1: Preparation of N-(2-((4-(3-(2-aminopyridin-4-yl)phenyl)thiazol-2-yl)amino)-2-oxoethyl)-1-(methylsulfonyl)-1H-pyrrole-3-carboxamide (Compound 9)

Compound 9

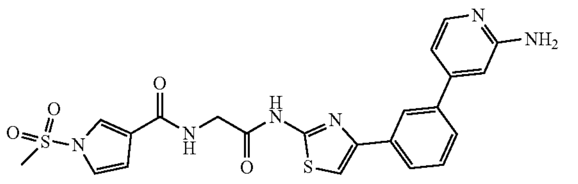

To a solution of N-(2-((4-(3-bromophenyl)thiazol-2-yl)amino)-2-oxoethyl)-1-(methylsulfonyl)-1H-pyrrole-3-carboxamide [prepared according the method in Example 1] (50 mg, 96.26 μmol) and 4-(4,4,5,5-tetramethyl-1,3,2-dioxaborolan-2-yl)pyridin-2-amine (31.78 mg, 144.40 μmol) in dioxane (2 mL) and $H_2O$ (0.2 mL) was added $K_3PO_4$ (61.30 mg, 288.79 μmol) and [1,1'-bis(di-tert-butylphosphino)ferrocene]dichloropalladium(II) (12.55 mg, 19.25 μmol) under $N_2$. The reaction mixture was stirred at 80° C. for 2 h. The reaction mixture was poured into water (5 mL), the solution was extracted with EtOAc (5 mL×3). The combined organic layer was washed with brine (20 mL), dried over $Na_2SO_4$ and filtered. The filtrate was concentrated to give a residue. The residue was purified by Pre-HPLC (mobile phase: [water (0.225% FA)-acetonitrile]; B %: 15%-36%) to give Compound 9 (4.95 mg, 9.97 μmol, 10.36% yield) as a white solid. LCMS (ESI) m/z $[M+H]^+$=497.1. $^1H$ NMR (400 MHz, DMSO-$d_6$) δ 12.78-12.43 (m, 1H), 8.69-8.67 (m, 1H), 8.25 (s, 1H), 8.16 (s, 1H), 7.99 (d, J=5.6 Hz, 1H), 7.98 (s, 1H), 7.85-7.83 (m, 1H), 7.75 (s, 1H), 7.56-7.55 (m, 2H), 7.30 (s, 1H), 6.81 (dd, J=1.6, 5.4 Hz, 1H), 6.77 (d, J=1.6 Hz, 1H), 6.73 (s, 1H), 5.98 (s, 2H), 4.14 (d, J=6.0 Hz, 2H), 3.56 (s, 3H).

Example 10. Preparation of N-(2-((4-(3-cis-2,6-dimethylmorpholino)phenyl)thiazol-2-yl)amino)-2-oxoethyl)-1-(methylsulfonyl)-1H-pyrrole-3-carboxamide (Compound 10)

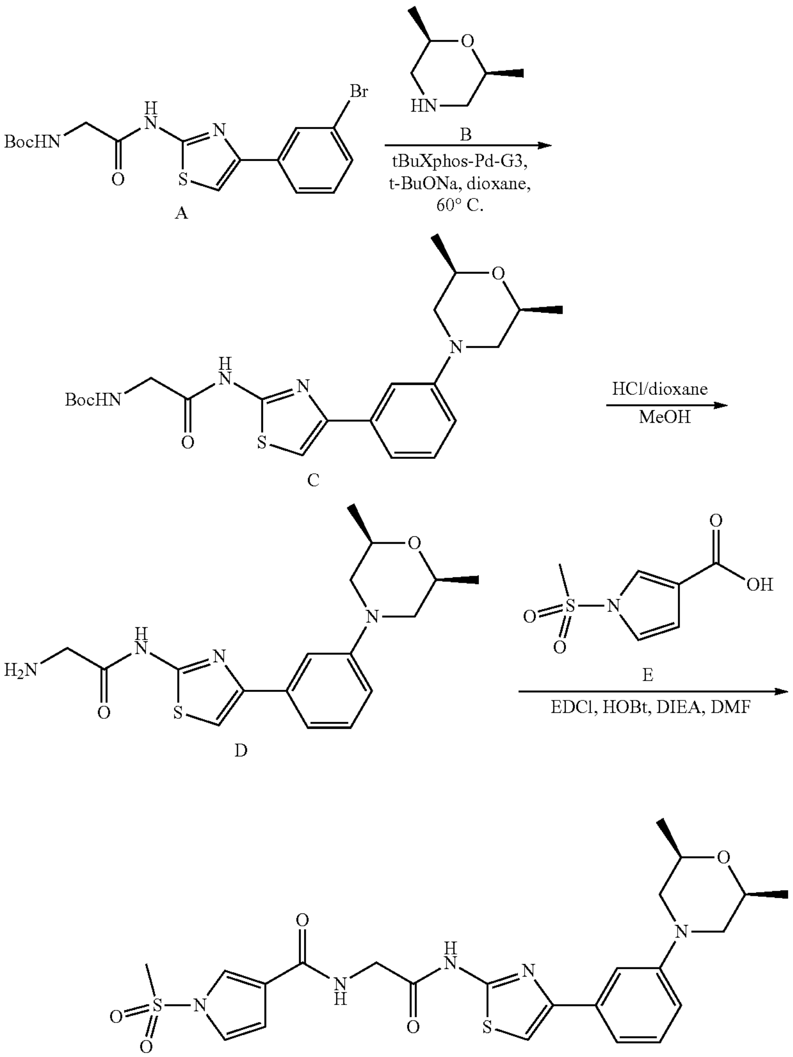

Compound 10

Step 1: Preparation of tert-butyl (2-((4-(3-cis-2,6-dimethylmorpholino)phenyl)thiazol-2-yl)amino)-2-oxoethyl)carbamate (Intermediate C)

C

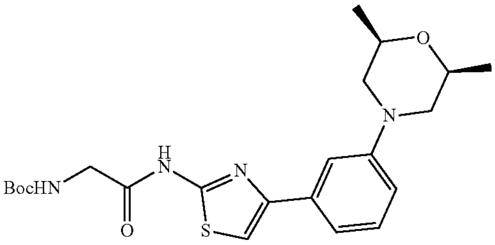

A mixture of tert-butyl N-[2-[[4-(3-bromophenyl)thiazol-2-yl]amino]-2-oxo-ethyl]carbamate (400 mg, 970.17 μmol) (prepared according to the method in Example 1), cis-2,6-dimethylmorpholine (167.61 mg, 1.46 mmol), [2-(2-aminophenyl)phenyl]-methylsulfonyloxypalladium; ditert-butyl-[2-(2,4,6-triisopropylphenyl)phenyl]phosphane (77.07 mg, 97.02 μmol) and t-BuONa (279.71 mg, 2.91 mmol) in dioxane (4 mL) was degassed and purged with $N_2$ for 3 times, and then the mixture was stirred at 60° C. for 12 h under $N_2$ atmosphere. Water (20 mL) was added and the reaction mixture was extracted with EtOAc (50 mL×2). The combined organic layers were washed with brine (20 mL), dried over $Na_2SO_4$, filtered and concentrated under reduced pressure to give a residue. The residue was purified by flash silica gel chromatography (Eluent of 10-60% Ethyl acetate/Petroleum ether gradient) and concentrated in vacuum to give Intermediate C (200 mg, 362.77 μmol, 37.39% yield) as yellow oil. LCMS (ESI) m/z $[M+H]^+$=447.3.

Step 2: Preparation of 2-amino-N-(4-(3-cis-2,6-dimethylmorpholino)phenyl)thiazol-2-yl)acetamide (Intermediate D)

D

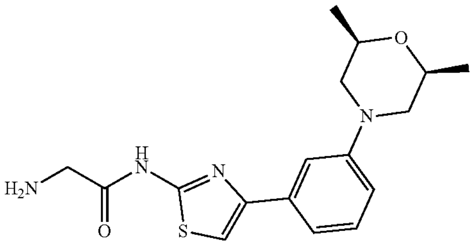

To a solution of Intermediate C (180 mg, 403.08 μmol) in MeOH (2 mL) was added HCl/dioxane (2 mL). The mixture was stirred at 25° C. for 2 h. The reaction mixture was concentrated under reduced pressure to give Intermediate D (160 mg, crude, HCl salt) as a yellow solid, which was used into the next step without further purification. LCMS (ESI) m/z $[M+H]^+$=347.2.

Step 3: Preparation of N-(2-((4-(3-cis-2,6-dimethylmorpholino)phenyl)thiazol-2-yl)amino)-2-oxoethyl)-1-(methylsulfonyl)-1H-pyrrole-3-carboxamide (Compound 10)

Compound 10

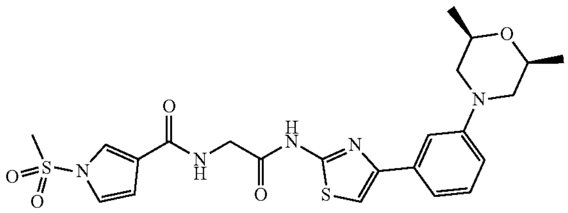

To a solution of 1-methylsulfonylpyrrole-3-carboxylic acid [prepared according to the method in Example 4] (47.43 mg, 250.71 μmol) in DMF (2 mL) was added EDCI (60.08 mg, 313.39 μmol), DIEA (108.01 mg, 835.71 μmol, 145.57 μL) and HOBt (42.35 mg, 313.39 μmol), then Intermediate D (80 mg, 208.93 μmol, HCl salt) was added. The mixture was stirred at 25° C. for 2 h. The reaction mixture was concentrated under reduced pressure to give a residue. The residue was purified by Prep-HPLC (mobile phase: [water (0.075% TFA)-acetonitrile]; B %: 30%-60%) and lyophilized to give Compound 10 (40 mg, 60.79 μmol, 29.10% yield, TFA salt) as a white solid. LCMS (ESI) m/z $[M+H]^+$=518.3. $^1H$ NMR (400 MHz, DMSO-$d_6$) δ 12.35 (s, 1H), 8.67-8.65 (m, 1H), 7.84 (s, 1H), 7.61 (s, 1H), 7.44 (s, 1H), 7.36-7.30 (m, 2H), 7.29-7.24 (m, 1H), 6.93 (d, J=8.0 Hz, 1H), 6.79-6.75 (m, 1H), 4.13 (d, J=5.6 Hz, 2H), 3.78-3.67 (m, 2H), 3.62 (d, J=11.0 Hz, 2H), 3.57 (s, 3H), 2.32-2.25 (m, 2H), 1.17 (d, J=6.0 Hz, 6H); ee %=100%.

Example 11. Preparation of (S)—N-(2-((4-(3-(3-methoxypiperidin-1-yl)phenyl)thiazol-2-yl)amino)-2-oxoethyl)-1-(methylsulfonyl)-1H-pyrrole-3-carboxamide (Compound 11)

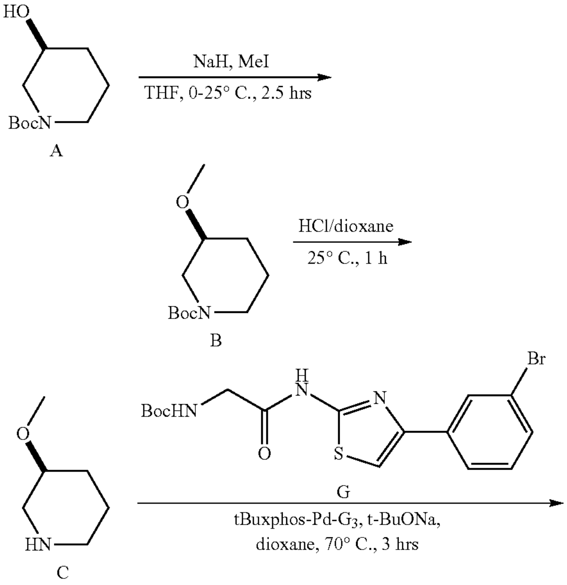

-continued

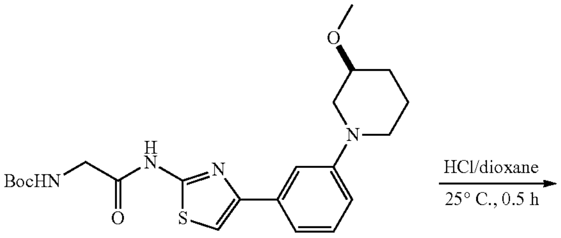

D

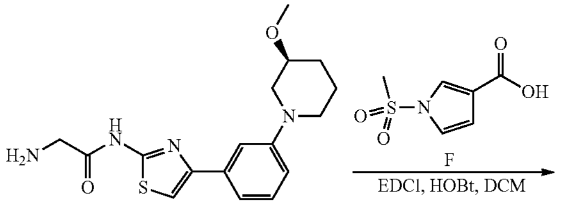

E

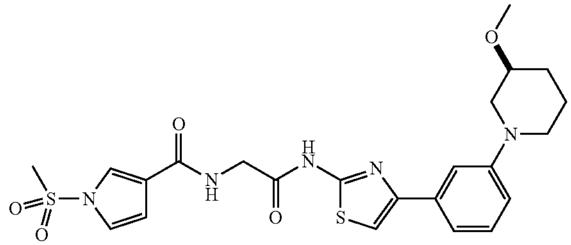

Compound 11

Step 1: Preparation of (S)-tert-butyl 3-methoxypiperidine-1-carboxylate (Intermediate B)

B

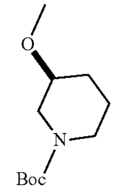

To a solution of tert-butyl (3S)-3-hydroxypiperidine-1-carboxylate (2 g, 9.94 mmol) in THF (20 mL) was added NaH (794.91 mg, 19.87 mmol, 60% purity) at 0° C., and stirred at 0° C. for 30 min, then MeI (2.12 g, 14.91 mmol, 927.95 μL) was added to the mixture and stirred at 25° C. for 2 h. The mixture was poured into aq. $NH_4Cl$ (80 mL), then extracted with EtOAc (30 mL×3). The combined organic layers were washed with brine (25 mL×2), dried over $Na_2SO_4$, filtered and concentrated under reduced pressure to give Intermediate B (2.14 g, crude) as a black brown oil, which was used to next step without further purification. LCMS (ESI) m/z $[M+Na]^+$=237.9.

Step 2: Preparation of (S)-3-methoxypiperidine (Intermediate C)

C

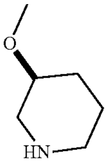

A solution of Intermediate B (1.78 g g, 8.27 mmol) in HCl/dioxane (4 M, 12.82 mL) was stirred at 25° C. for 1 h. The reaction mixture was concentrated under vacuum to give Intermediate C (1.2 g, crude, HCl salt) as a black brown solid, which was used to next step without further purification.

$^1$H NMR (400 MHz, methanol-$d_4$) δ 3.63 (s, 1H), 3.39 (s, 3H), 3.27 (s, 1H), 3.22-3.12 (m, 2H), 3.05-3.00 (m, 1H), 2.01-1.94 (m, 2H), 1.76-1.66 (m, 2H).

Step 3: Preparation of (S)-tert-butyl (2-((4-(3-(3-methoxypiperidin-1-yl)phenyl)thiazol-2-yl)amino)-2-oxoethyl)carbamate (Intermediate D)

D

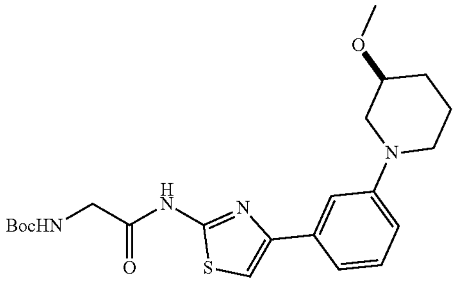

A mixture of tert-butyl N-[2-[[4-(3-bromophenyl)thiazol-2-yl]amino]-2-oxo-ethyl]carbamate (prepared according to the method in Example 1) (250 mg, 606.35 μmol), Intermediate C (137.92 mg, 909.53 μmol, HCl salt), t-BuONa (233.08 mg, 2.43 mmol) and [2-(2-aminophenyl)phenyl]-methylsulfonyloxy-palladium; ditert-butyl-[2-(2,4,6-triisopropylphenyl)phenyl]phosphane (48.17 mg, 60.64 μmol) in dioxane (5 mL) was degassed and purged with $N_2$ for 3 times, and then the mixture was stirred at 70° C. for 3 h under $N_2$. The reaction mixture was diluted with water (100 mL) and extracted with EtOAc (150 mL×3). The combined organic layers were washed with brine (45 mL×2), dried over $Na_2SO_4$, filtered and concentrated under reduced pressure to give a residue. The residue was purified by column chromatography ($SiO_2$, Petroleum ether/EtOAc=20/1 to 1:1) and concentrated in vacuum to give Intermediate D (340 mg, 723.30 μmol, 59.64% yield) as a white solid. LCMS (ESI) m/z $[M+H]^+$=447.5.

Step 4: Preparation of (S)-2-amino-N-(4-(3-(3-methoxypiperidin-1-yl)phenyl)thiazol-2-yl)acetamide (Intermediate E)

E

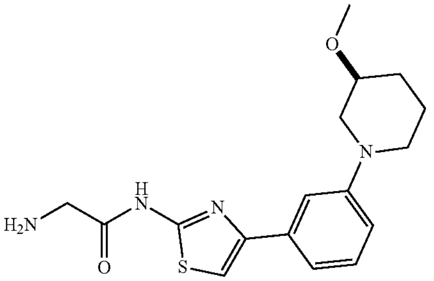

A mixture of Intermediate D (300 mg, 671.80 μmol) in HCl/dioxane (4 M, 3 mL) was stirred at 25° C. for 0.5 h under $N_2$. The reaction mixture was concentrated under vacuum to give Intermediate E (300 mg, crude, HCl salt) as a brown solid, which was used to next step directly.

Step 5: Preparation of (S)—N-(2-((4-(3-(3-methoxypiperidin-1-yl)phenyl)thiazol-2-yl)amino)-2-oxoethyl)-1-(methylsulfonyl)-1H-pyrrole-3-carboxamide (Compound 11)

Compound 11

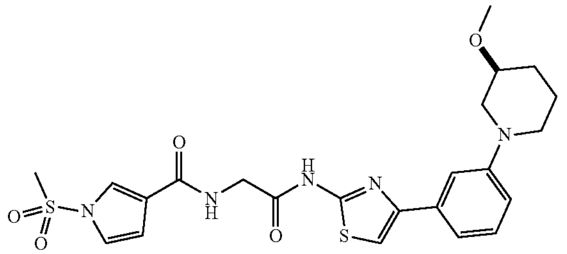

To a solution of Intermediate E (60 mg, 156.70 μmol, HCl salt), 1-methylsulfonylpyrrole-3-carboxylic acid [prepared according to the method in Example 4] (35.57 mg, 188.04 μmol) and DIEA (101.26 mg, 783.48 μmol, 136.46 μL) in DCM (2 mL) was added HOBt (25.41 mg, 188.04 μmol) and EDCI (90.12 mg, 470.09 μmol), the reaction mixture was stirred at 25° C. for 2 h. The reaction mixture was concentrated under vacuum to give residue. The residue was purified by Pre-HPLC (mobile phase: [water (0.1% TFA)-acetonitrile]; B %: 20%-40%) and lyophilized to give Compound 11 (88.55 mg, 140.19 μmol, 89.47% yield, TFA salt) as a white solid. LCMS (ESI) m/z $[M+H]^+$=518.4. $^1H$ NMR (400 MHz, DMSO-$d_6$) δ 8.12-8.00 (m, 2H), 7.83 (s, 1H), 7.62-7.51 (m, 3H), 7.28-7.27 (m, 1H), 6.81-6.80 (m, 1H), 4.26 (s, 2H), 3.80-3.72 (m, 3H), 3.64-3.59 (m, 1H), 3.55-3.51 (m, 1H), 3.48 (s, 3H), 3.38 (s, 3H), 2.28-2.20 (m, 1H), 2.04-1.99 (m, 1H), 1.95-1.87 (m, 2H); ee %=100%.

Example 12. Preparation of N-(2-((4-(1-methyl-2-oxo-1,2-dihydroquinolin-7-yl)thiazol-2-yl)amino)-2-oxoethyl)-1-(methylsulfonyl)-1H-pyrrole-3-carboxamide (Compound 12)

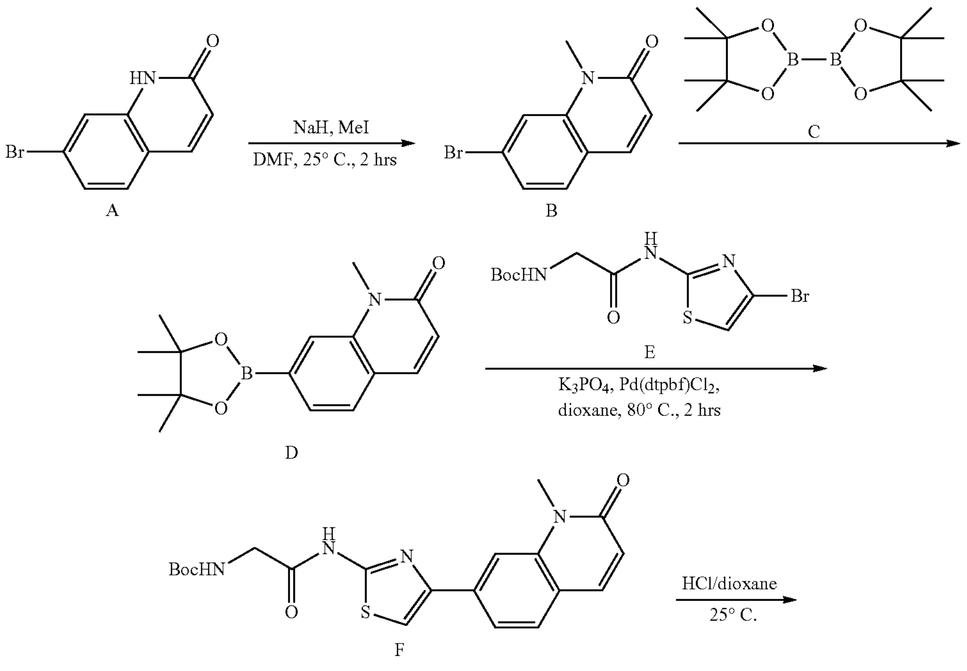

-continued

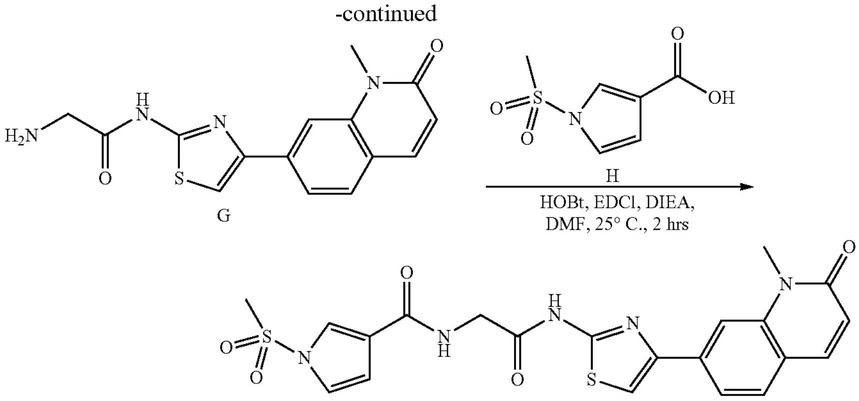

Compound 12

Step 1: Preparation of 7-bromo-1-methylquinolin-2(1H)-one (Intermediate B)

B

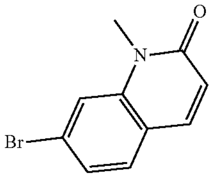

To a solution of 7-bromo-1H-quinolin-2-one (500 mg, 2.23 mmol) in DMF (5 mL) was added NaH (107.11 mg, 2.68 mmol, 60% purity) at 0° C. and stirred at 0° C. for 0.5 h. Then MeI (610 mg mg, 4.30 mmol, 267.54 μL) was added at 0° C. and stirred at 25° C. for 1.5 h. The reaction mixture was quenched by addition water (2 mL), and then diluted with EtOAc (15 mL) and extracted with EtOAc (10 mL×2). The combined organic layers were dried over anhydrous $Na_2SO_4$ and filtered and concentrated under reduced pressure to give Intermediate B (400 mg, 1.68 mmol, 75.29% yield) as a brown solid, which was used for the next step directly without further purification. $^1H$ NMR (400 MHz, DMSO-$d_6$) δ 7.91 (d, J=9.6 Hz, 1H), 7.74 (s, 1H), 7.67 (d, J=8.4 Hz, 1H), 7.46-7.44 (m, 1H), 6.65 (d, J=9.2 Hz, 1H), 3.60 (s, 3H).

Step 2: Preparation of 1-methyl-7-(4,4,5,5-tetramethyl-1,3,2-dioxaborolan-2-yl)quinolin-2(1H)-one (Intermediate D)

D

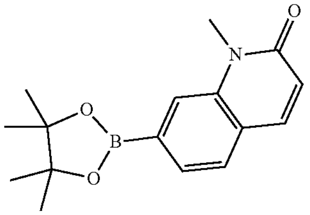

To a solution of Intermediate B (400 mg, 1.68 mmol) in dioxane (5 mL) was added 4,4,5,5-tetramethyl-2-(4,4,5,5-tetramethyl-1,3,2-dioxaborolan-2-yl)-1,3,2-dioxaborolane (639.96 mg, 2.52 mmol) and KOAc (494.67 mg, 5.04 mmol) and Pd(dppf)$Cl_2$ (122.93 mg, 168.01 μmol). The mixture was stirred at 80° C. for 2 h. The mixture was diluted with water (3 mL) and extracted with EtOAc (20 mL×2). The combined organic layers were dried over anhydrous $Na_2SO_4$ and concentrated in vacuum. The residue was purified by column chromatography ($SiO_2$, Petroleum ether/EtOAc=20/1 to 1:1) and concentrated to give Intermediate D (204 mg, 715.43 μmol, 42.58% yield) as a white solid. LCMS (ESI) m/z $[M+H]^+$=286.3; $^1H$ NMR (400 MHz, DMSO-$d_6$) δ 7.82 (s, 1H), 7.69-7.65 (m, 2H), 7.56 (d, J=7.6 Hz, 1H), 6.76 (d, J=9.6 Hz, 1H), 3.80 (s, 3H), 1.39 (s, 12H).

Step 3: Preparation of tert-butyl (2-((4-(1-methyl-2-oxo-1,2-dihydroquinolin-7-yl)thiazol-2-yl)amino)-2-oxoethyl)carbamate (Intermediate F)

F

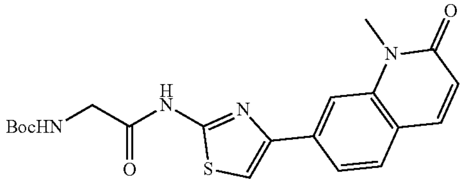

A mixture of tert-butyl N-[2-[(4-bromothiazol-2-yl)amino]-2-oxo-ethyl]carbamate (prepared according to the method in Example 6) (160 mg, 475.90 μmol), Intermediate D (203.55 mg, 713.85 μmol), $K_3PO_4$ (303.05 mg, 1.43 mmol) in dioxane (3 mL) and $H_2O$ (0.6 mL) was added [1,1'-bis(di-tert-butylphosphino)ferrocene]dichloropalladium(II) (31.02 mg, 47.59 μmol) was degassed and purged with $N_2$ for 3 times, and then the mixture was stirred at 80° C. for 2 h under $N_2$ atmosphere. The residue was diluted with $H_2O$ (10 mL) and extracted with EtOAc (10 mL×3). The combined organic layers were dried over anhydrous $Na_2SO_4$, filtered and concentrated under reduced pressure to give a residue. The residue was purified by flash silica gel chromatography (PE:EtOAc=1:1 to 0:1) and concentrated to give Intermediate F (140 mg, 336.90 μmol, 70.79% yield) as light yellow solid. LCMS (ESI) m/z $[M+H]^+$=415.1; $^1H$ NMR (400 MHz, DMSO-d6) δ 12.35 (s, 1H), 7.97 (s, 1H), 7.90-7.88 (m, 2H), 7.80-7.73 (m, 2H), 7.16-7.13 (m, 1H), 6.59 (d, J=9.6 Hz, 1H), 3.86 (d, J=6.4 Hz, 2H), 3.66 (s, 3H), 1.38 (s, 9H).

Step 4: Preparation of 2-amino-N-(4-(1-methyl-2-oxo-1,2-dihydroquinolin-7-yl)thiazol-2-yl)acetamide (Intermediate G)

G

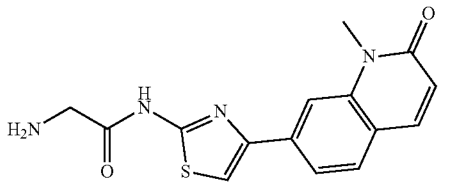

To a solution of Intermediate F (40 mg, 96.51 μmol) in dioxane (0.5 mL) was added HCl/dioxane (4 M, 241.27 μL). The mixture was stirred at 25° C. for 2 h. The reaction mixture was concentrated under reduced pressure to give Intermediate G (35 mg, crude, HCl salt) as yellow solid, which was used to the next step directly. LCMS (ESI) m/z $[M+H]^+$=315.0.

Step 5: Preparation of N-(2-((4-(1-methyl-2-oxo-1,2-dihydroquinolin-7-yl)thiazol-2-yl)amino)-2-oxoethyl)-1-(methylsulfonyl)-1H-pyrrole-3-carboxamide (Compound 12)

Compound 12

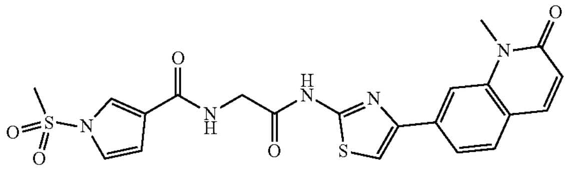

To a solution of 1-methylsulfonylpyrrole-3-carboxylic acid [prepared according to the method in Example 4] (22.65 mg, 119.72 μmol) in DMF (0.5 mL) was added EDCI (28.69 mg, 149.65 μmol), HOBt (20.22 mg, 149.65 μmol), DIEA (38.68 mg, 299.30 μmol, 52.13 μL) and Intermediate G (35 mg, 99.77 μmol, HCl salt). The mixture was stirred at 25° C. for 2 h. The reaction mixture was diluted with $H_2O$ (5 mL) and extracted with EtOAc (5 mL×3). The combined organic layers were washed with saturated brine (5 mL×3), dried over anhydrous $Na_2SO_4$, filtered and concentrated under reduced pressure to give a residue. The residue was purified by Pre-HPLC (mobile phase: [water (0.05% ammonia hydroxide v/v)-acetonitrile]; B %: 10%-40%) and lyophilized to give Compound 12 (12.98 mg, 26.30 μmol, 26.36% yield) as yellow solid. LCMS (ESI) m/z $[M+H]^+$ =486.0; $^1$H NMR (400 MHz, DMSO-$d_6$) δ 8.63 (s, 1H), 8.06-7.98 (m, 1H), 7.95-7.73 (m, 5H), 7.31 (s, 1H), 6.78 (s, 1H), 6.60 (d, J=9.2 Hz, 1H), 4.13 (d, J=4.4 Hz, 2H), 3.68 (s, 3H), 3.57 (s, 3H).

Example 13. Preparation of N-(2-((4-(3-(2-((2-(dimethylamino)-2-oxoethyl)(methyl)amino)pyridin-4-yl)phenyl)thiazol-2-yl)amino)-2-oxoethyl)-1-(methylsulfonyl)-1H-pyrrole-3-carboxamide (Compound 13)

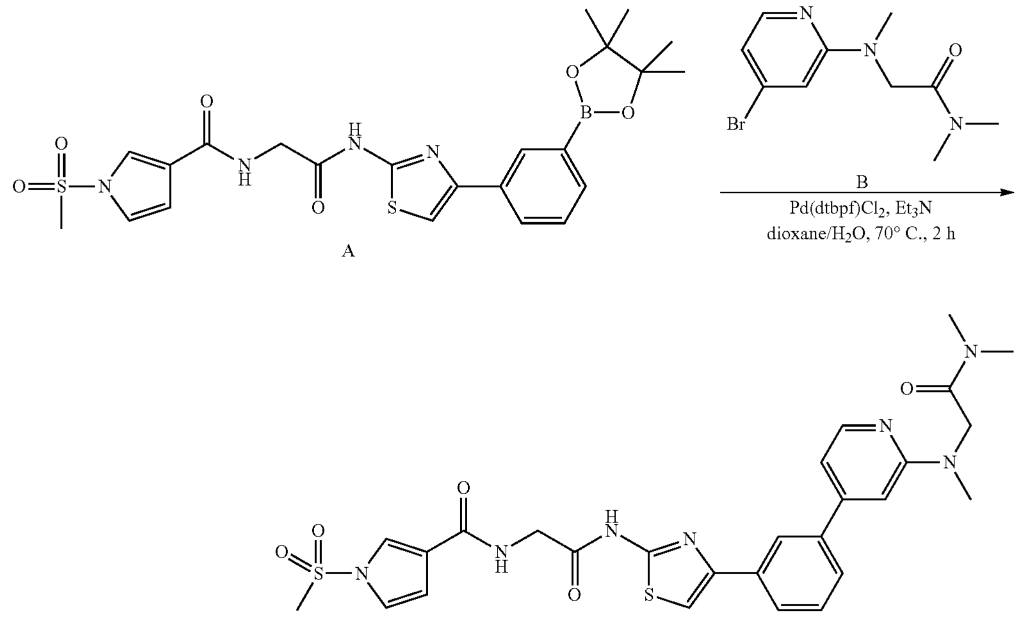

Compound 13

To a mixture of 1-methylsulfonyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (prepared according to the method in Example 1) (75 mg, 141.40 μmol) and 2-[(4-bromo-2-pyridyl)-methyl-amino]-N,N-dimethylacetamide (38.48 mg, 141.40 μmol) in dioxane (1.6 mL) and $H_2O$ (0.4 mL) was added $Et_3N$ (42.92 mg, 424.19 μmol, 59.04 μL) and [1,1'-bis(di-tert-butylphosphino)ferrocene]dichloropalladium(II) (9.22 mg, 14.14 μmol) at 30° C. under $N_2$. The reaction mixture was heated to 70° C. and stirred at 70° C. for 2 h under $N_2$. The reaction mixture was concentrated under reduced pressure to afford a residue. The residue was purified by reverse phase column (neutral condition) to afford Compound 13 (39.01 mg, 64.90 μmol, 45.90% yield) as a yellow solid. LCMS (ESI) m/z $[M+H]^+$ =596.2. $^1H$ NMR (400 MHz, $DMSO-d_{67}$) δ 12.41 (br s, 1H), 8.73-8.61 (m, 1H), 8.21 (s, 1H), 8.12 (d, J=5.2 Hz, 1H), 7.97 (d, J=7.6 Hz, 1H), 7.85 (s, 1H), 7.80 (s, 1H), 7.68 (d, J=7.6 Hz, 1H), 7.61-7.52 (m, 1H), 7.36-7.27 (m, 1H), 6.92-6.83 (m, 2H), 6.79-6.77 (m, 1H), 4.51 (s, 2H), 4.15 (d, J=5.6 Hz, 2H), 3.57 (s, 3H), 3.12-3.00 (m, 6H), 2.81 (s, 3H).

Example 14. Preparation of 1-(4-(3-(2-(2-(1-(methylsulfonyl)-1H-pyrrole-3-carboxamido)acetamido)thiazol-4-yl)phenyl)pyridin-2-yl)cyclopropanecarboxylic acid (Compound 14)

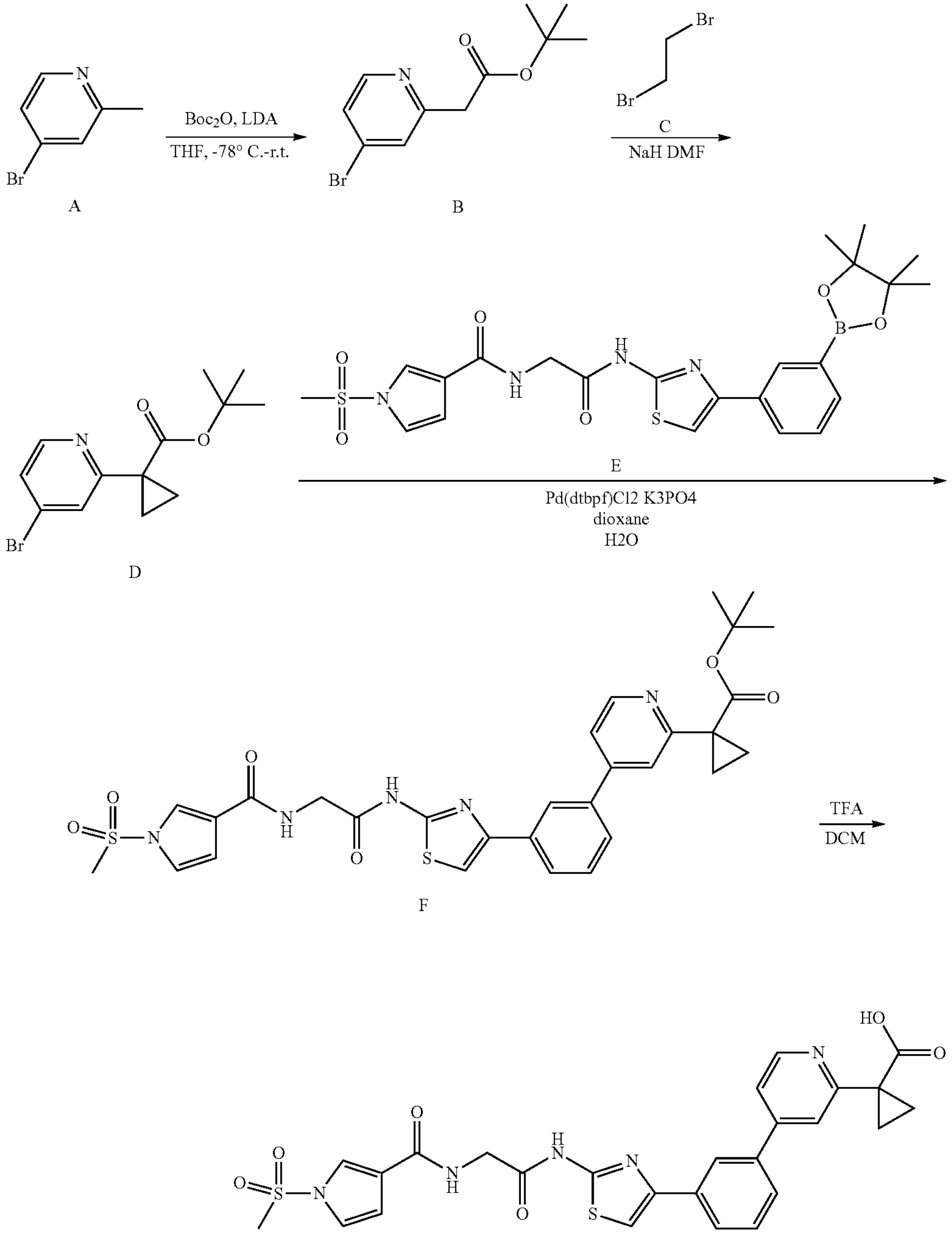

A
B
D
E
F

Compound 14

Step 1: Preparation of tert-butyl 2-(4-bromopyridin-2-yl)acetate (Intermediate B)

B

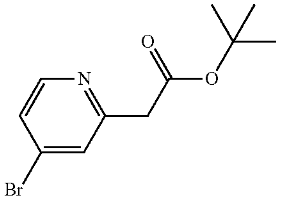

To a solution of 4-bromo-2-methyl-pyridine (1.4 g, 8.14 mmol) in THF (20 mL) was added LDA (2 M, 4.88 mL) at −70° C. dropwise. After addition, the mixture was stirred at this temperature for 1 h. Then $Boc_2O$ (1.95 g, 8.95 mmol, 2.06 mL) was added dropwise at −70° C. The resulting mixture was stirred at 25° C. for 11 h. The reaction mixture was quenched by addition water (30 mL), and extracted with EtOAc (10 mL×3). The combined organic layers were washed with brine (10 mL×3), dried over $Na_2O_4$, filtered and concentrated under reduced pressure to give a residue. The residue was purified by reversed phase (FA) and lyophilized to give Intermediate B (500 mg, 1.84 mmol, 22.58% yield) as yellow oil. $^1H$ NMR (400 MHz, $CDCl_3$) δ 8.38 (d, J=5.4 Hz, 1H), 7.50 (d, J=1.6 Hz, 1H), 7.37 (dd, J=1.8, 5.4 Hz, 1H), 3.74 (s, 2H), 1.47 (s, 9H).

Step 2: Preparation of tert-butyl 1-(4-bromopyridin-2-yl)cyclopropanecarboxylate (Intermediate D)

D

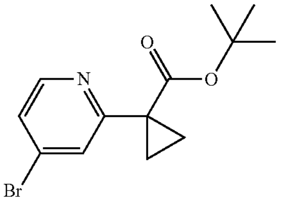

To a solution of Intermediate B (450 mg, 1.65 mmol) in DMF (5 mL) was added NaH (198.43 mg, 4.96 mmol, 60% purity) at 25° C. After additional, the mixture was stirred at this temperature for 1 h, and then 1,2-dibromoethane (621.28 mg, 3.31 mmol, 249.51 μL) was added dropwise at 25° C. The resulting mixture was stirred at 25° C. for 1 h. The reaction mixture was quenched by addition water (10 mL), and extracted with EtOAc (10 mL×3). The combined organic layers were washed with brine (10 mL×3), dried over $Na_2SO_4$, filtered and concentrated under reduced pressure to give a residue. The residue was purified by reversed phase (FA) and lyophilized to give Intermediate D (400 mg, 1.34 mmol, 81.13% yield) as yellow oil. LCMS (ESI) m/z $[M+H-56]^+$=242.0.

Step 3: Preparation of tert-butyl 1-(4-(3-(2-(2-(1-(methylsulfonyl)-1H-pyrrole-3-carboxamido)acetamido)thiazol-4-yl)phenyl)pyridin-2-yl)cyclopropanecarboxylate (Intermediate F)

F

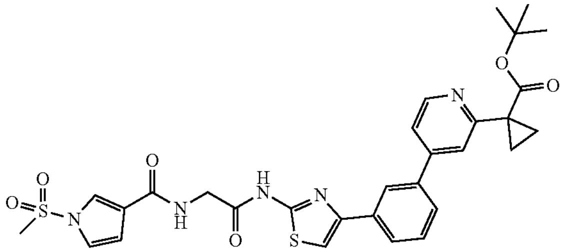

A mixture of Intermediate D (200 mg, 670.75 μmol), 1-methylsulfonyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (prepared according to the method in Example 1) (391.36 mg, 737.83 μmol), $K_3PO_4$ (427.14 mg, 2.01 mmol), [1,1'-bis(di-tert-butylphosphino)ferrocene]dichloropalladium(II) (43.72 mg, 67.08 μmol) in dioxane (2 mL) $H_2O$ (0.5 mL) was degassed and purged with $N_2$ for 3 times, and then the mixture was stirred at 80° C. for 12 h under $N_2$ atmosphere. The reaction mixture was quenched by addition water (10 mL) and extracted with EtOAc (10 mL×3). The combined organic layers were washed with NaCl (10 mL×3), dried over $Na_2SO_4$, filtered and concentrated under reduced pressure to give a residue. The residue was purified by reversed phase (FA) and lyophilized to give Intermediate F (200 mg, 321.69 μmol, 47.96% yield) as a yellow solid. LCMS (ESI) m/z $[M+H]^+$=622.4.

Step 4: Preparation of 1-(4-(3-(2-(2-(1-(methylsulfonyl)-1H-pyrrole-3-carboxamido)acetamido)thiazol-4-yl)phenyl)pyridin-2-yl)cyclopropanecarboxylic acid (Compound 14)

Compound 14

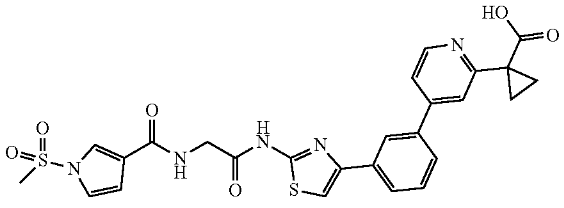

A mixture of Intermediate F (100 mg, 160.84 μmol), TFA (183.39 mg, 1.61 mmol, 119.09 μL) in DCM (1 mL) was degassed and purged with $N_2$ for 3 times, and then the mixture was stirred at 25° C. for 1 h under $N_2$ atmosphere. The mixture was concentrated to give the residue. The residue was purified by reversed phase (FA) and lyophilized to give Compound 14 (43 mg, 76.02 μmol, 47.27% yield) as a white solid. LCMS (ESI) m/z $[M+H]^+$=566.4; $^1H$ NMR (400 MHz, DMSO-$d_6$) δ 12.66-12.27 (m, 1H), 8.72-8.70 (m, 1H), 8.57 (d, J=5.4 Hz, 1H), 8.28 (s, 1H), 8.02 (d, J=8.0 Hz, 1H), 7.88-7.83 (m, 3H), 7.76 (d, J=8.2 Hz, 1H), 7.65-7.57 (m, 2H), 7.32 (dd, J=2.4, 3.4 Hz, 1H), 6.78 (dd, J=1.6, 3.4 Hz, 1H), 4.15 (d, J=5.8 Hz, 2H), 3.58 (s, 3H), 1.61-1.46 (m, 4H).

Example 15. Preparation of 2-(methyl(4-(3-(2-(2-(1-(methylsulfonyl)-1H-pyrrole-3-carboxamido)acetamido)thiazol-4-yl)phenyl)pyridin-2-yl)amino)acetic acid (Compound 15) and N-(2-((4-(3-(2-(methyl(2-(methylamino)-2-oxoethyl)amino)pyridin-4-yl)phenyl)thiazol-2-yl)amino)-2-oxoethyl)-1-(methylsulfonyl)-1H-pyrrole-3-carboxamide (Compound 16)

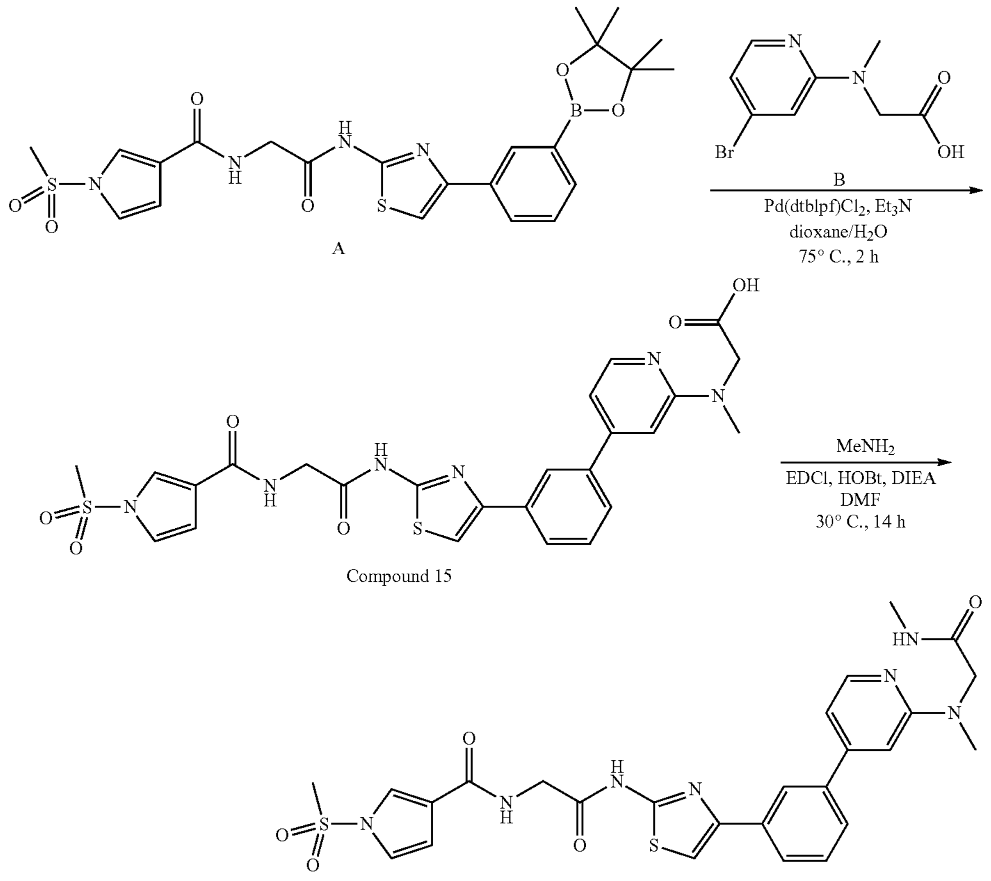

A

Compound 15

Compound 16

Step 1: Preparation of 2-(methyl(4-(3-(2-(2-(1-(methylsulfonyl)-1H-pyrrole-3-carboxamido)acetamido)thiazol-4-yl)phenyl)pyridin-2-yl)amino)acetic acid (Compound 15)

Compound 15

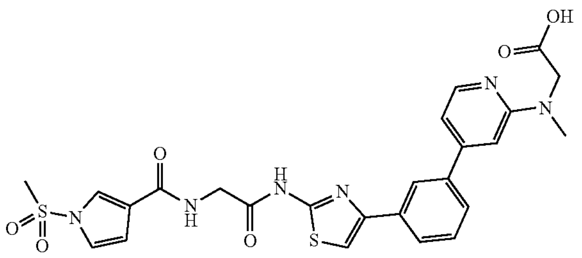

To a mixture of 1-methylsulfonyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (prepared according to the method in Example 1) (100 mg, 188.53 μmol) and 2-[(4-bromo-2-pyridyl)-methyl-amino]-N-methylacetamide (48.66 mg, 188.53 μmol) in dioxane (2 mL) and $H_2O$ (0.5 mL) was added [1,1'-bis(di-tert-butylphosphino)ferrocene] dichloropalladium(II) (12.29 mg, 18.85 μmol) and $Et_3N$ (57.23 mg, 565.59 μmol, 78.72 μL) at 30° C. under $N_2$. The reaction mixture was heated to 70° C. and stirred at 70° C. for 2 h under $N_2$. The reaction mixture was concentrated under reduced pressure to afford a residue. The residue was purified by reverse phase column (FA condition) to afford Compound 15 (60 mg, 97.62 μmol, 51.78% yield, FA salt) as green solid. This product was a hydrolyzed by-product. LCMS (ESI) m/z $[M+H]^+$=569.1; $^1H$ NMR (400 MHz, DMSO-$d_6$) δ 8.70-8.67 (m, 1H), 8.22 (s, 1H), 8.15 (d, J=5.2 Hz, 1H), 7.98 (d, J=7.6 Hz, 1H), 7.88-7.80 (m, 2H), 7.69 (d, J=7.6 Hz, 1H), 7.60-7.54 (m, 1H), 7.35-7.30 (m, 1H), 6.97-6.85 (m, 2H), 6.79-6.77 (m, 1H), 4.29 (s, 2H), 4.15 (d, J=6.0 Hz, 2H), 3.57 (s, 3H), 3.21-3.06 (m, 2H).

Step 2: Preparation of N-(2-((4-(3-(2-(methyl(2-(methylamino)-2-oxoethyl)amino)pyridin-4-yl)phenyl)thiazol-2-yl)amino)-2-oxoethyl)-1-(methylsulfonyl)-1H-pyrrole-3-carboxamide (Compound 16)

Compound 16

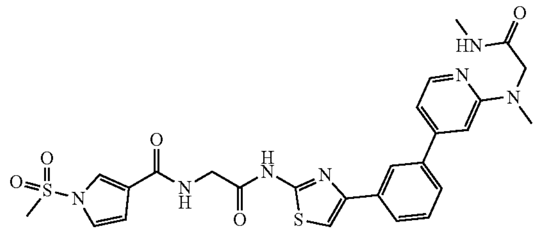

To a mixture of Compound 101 (60 mg, 97.62 μmol, FA salt) in DMF (1 mL) was added EDCI (28.07 mg, 146.43 μmol), HOBt (19.78 mg, 146.43 μmol), DIPEA (63.08 mg, 488.10 μmol, 85.01 μL) and methanamine (31.84 mg, 471.58 μmol, 35.78 μL, HCl salt) at 30° C. The reaction mixture was stirred at 30° C. for 14 h. The reaction mixture was filtered to afford a black solution. The black solution was purified by reverse phase column (neutral condition) to afford Compound 16 (26.92 mg, 44.88 μmol, 45.97% yield) as yellow solid. LCMS (ESI) m/z $[M+H]^+$=582.2; $^1H$ NMR (400 MHz, DMSO-$d_6$) δ 12.42 (s, 1H), 8.69-8.66 (m, 1H), 8.21 (s, 1H), 8.15 (d, J=5.6 Hz, 1H), 7.98 (d, J=7.6 Hz, 1H), 7.86-7.84 (m, 1H), 7.79 (s, 1H), 7.78-7.73 (m, 1H), 7.69 (d, J=7.6 Hz, 1H), 7.59-7.55 (m, 1H), 7.33-7.31 (m, 1H), 6.95-6.92 (m, 1H), 6.87 (s, 1H), 6.79-6.77 (m, 1H), 4.20 (s, 2H), 4.16 (d, J=6.0 Hz, 2H), 3.57 (s, 3H), 3.13 (s, 3H), 2.60 (d, J=4.8 Hz, 3H).

Example 16. Preparation of N-(2-((4-(3-(2-((dimethylamino)methyl)pyridin-4-yl)phenyl)thiazol-2-yl)amino)-2-oxoethyl)-1-(methylsulfonyl)-1H-pyrrole-3-carboxamide (Compound 17)

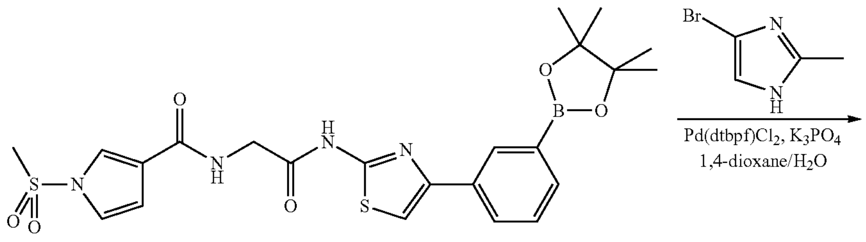

A

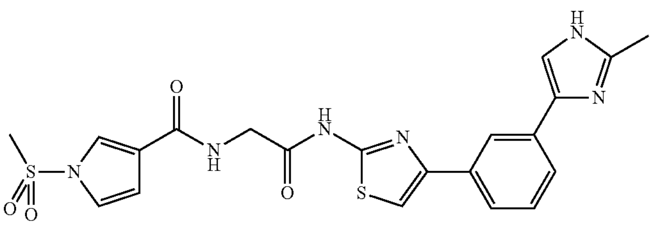

Compound 17

To a solution of 4-bromo-2-methyl-1H-imidazole (30 mg, 186.34 μmol) and 1-methylsulfonyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (prepared according to the method in Example 1) (98.84 mg, 186.34 μmol) in dioxane (2 mL)/$H_2O$ (0.2 mL) was added $K_3PO_4$ (118.66 mg, 559.01 μmol) and [1,1'-bis(di-tert-butylphosphino)ferrocene]dichloropalladium(II) (12.14 mg, 18.63 μmol) under $N_2$. The mixture was stirred at 100° C. for 2 h. The reaction mixture was diluted with water (10 mL) and extracted with EtOAc (12 mL×3). The combined organic layers were washed with brine (10 mL×2), dried over $Na_2SO_4$, filtered and concentrated under reduced pressure to give a residue. The residue was purified by Prep-HPLC (mobile phase: [water (0.1% TFA)-acetonitrile]; B %: 22%-52%) and lyophilized to give Compound 17 (11.21 mg, 22.90 μmol, 12.29% yield) as a gray solid. LCMS (ESI) m/z $[M+H]^+$=485.0; $^1H$ NMR (400 MHz, Methanol-$d_4$) δ 8.22-8.21 (m, 1H), 8.01-7.99 (m, 1H), 7.83-7.82 (m, 1H), 7.78 (s, 1H), 7.63-7.60 (m, 1H), 7.56-7.51 (m, 2H), 7.28-7.26 (m, 1H), 6.81-6.79 (m, 1H), 4.25 (s, 2H), 3.37 (s, 3H), 2.70 (s, 3H).

Example 17. Preparation of N-(2-((4-(3-(1-methyl-1H-imidazol-4-yl)phenyl)thiazol-2-yl)amino)-2-oxoethyl)-1-(methylsulfonyl)-1H-pyrrole-3-carboxamide (Compound 18)

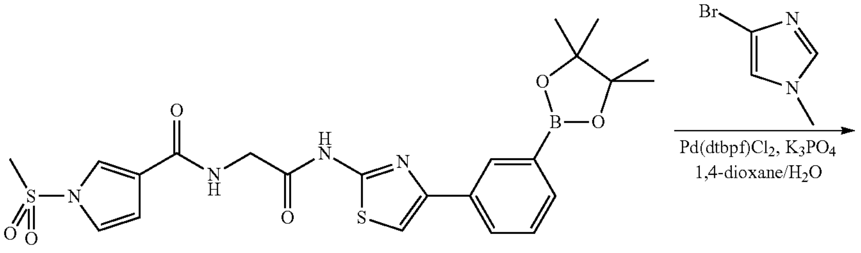

A

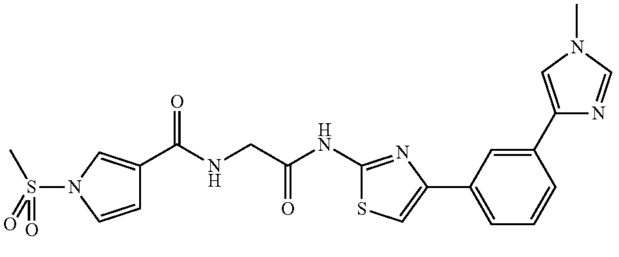

Compound 18

A mixture of 4-bromo-1-methyl-imidazole (36.42 mg, 226.23 μmol), 1-methylsulfonyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (prepared according to the method in Example 1) (100 mg, 188.53 μmol), $K_3PO_4$ (120.05 mg, 565.59 μmol) and [1,1'-bis(di-tert-butylphosphino)ferrocene]dichloropalladium(II) (24.57 mg, 37.71 μmol) in dioxane (2 mL) and $H_2O$ (0.5 mL) was degassed and purged with $N_2$ for 3 times, and then the mixture was stirred at 80° C. for 12 h under $N_2$ atmosphere. Water (20 mL) was added and the reaction mixture was extracted with EtOAc (50 mL×2). The combined organic layers were washed with brine (20 mL), dried over $Na_2SO_4$, filtered and concentrated under reduced pressure to give a residue. The residue was purified by Prep-HPLC (mobile phase: [water (0.075% TFA)-acetonitrile]; B %: 12%-42%) and lyophilized to give Compound 18 (18.25 mg, 30.49 μmol, 16.17% yield, TFA salt) as a white solid. LCMS (ESI) m/z $[M+H]^+$=485.1; $^1H$ NMR (400 MHz, DMSO-$d_6$) δ 12.41 (s, 1H), 9.05 (s, 1H), 8.69-8.68 (m, 1H), 8.28 (s, 1H), 8.13 (s, 1H), 7.95 (d, J=8.0 Hz, 1H), 7.85-7.84 (m, 1H), 7.71-7.68 (m, 2H), 7.60-7.56 (m, 1H), 7.32-7.31 (m, 1H), 6.78-6.76 (m, 1H), 4.15 (d, J=5.6 Hz, 2H), 3.90 (s, 3H), 3.57 (s, 3H).

Example 18. Preparation of N-(2-((4-(3-(2-(4-methylpiperazin-1-yl)pyridin-4-yl)phenyl)thiazol-2-yl)amino)-2-oxoethyl)-1-(methylsulfonyl)-1H-pyrrole-3-carboxamide (Compound 19)

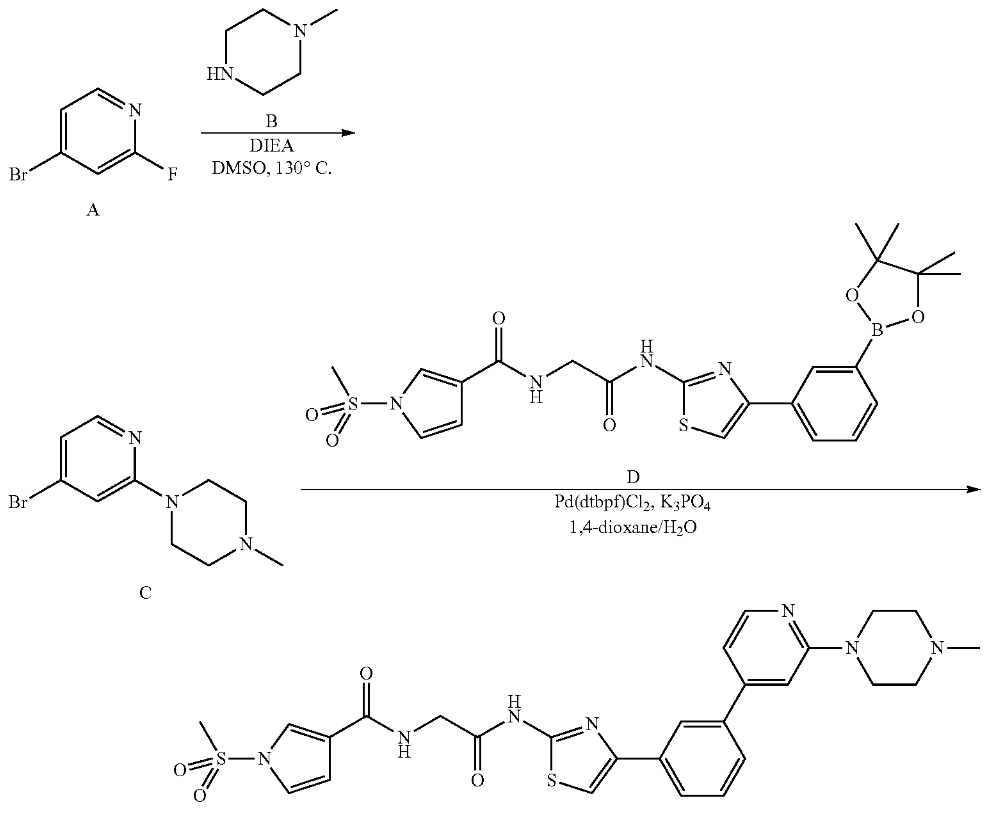

Compound 19

Step 1: Preparation of 1-(4-bromopyridin-2-yl)-4-methylpiperazine (Intermediate C)

C

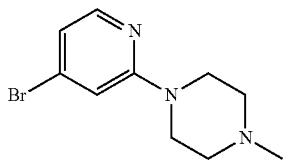

To a solution of 4-bromo-2-fluoropyridine (500 mg, 2.84 mmol) and 1-methylpiperazine (313.03 mg, 3.13 mmol, 346.66 μL) in DMSO (5 mL) was added DIPEA (1.10 g, 8.52 mmol, 1.48 mL), then the mixture was stirred at 130° C. for 2 h. The reaction mixture was poured into water (50.0 mL) and extracted with EtOAc (30.0 mL×3). The combined organics were washed with water and brine, dried over $Na_2SO_4$, filtered and filtration was evaporated to dryness to give Intermediate C (720 mg, crude) as yellow oil. $^1$H NMR (400 MHz, Methanol-$d_4$) δ 7.93 (d, J=5.6 Hz, 1H), 7.00 (d, J=1.2 Hz, 1H), 6.83-6.81 (m, 1H), 3.56-3.54 (m, 4H), 2.56-2.49 (m, 4H), 2.33 (s, 3H). LCMS (ESI) m/z $[M+H]^+$=258.0.

Step 2: Preparation of N-(2-((4-(3-(2-(4-methylpiperazin-1-yl)pyridin-4-yl)phenyl)thiazol-2-yl)amino)-2-oxoethyl)-1-(methylsulfonyl)-1H-pyrrole-3-carboxamide (Compound 19)

Compound 19

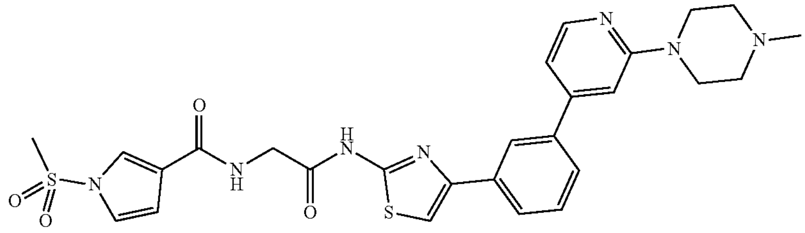

1-(methylsulfonyl)-N-(2-oxo-2-((4-(3-(4,4,5,5-tetramethyl-1,3,2-dioxaborolan-2-yl)phenyl)thiazol-2-yl)amino)ethyl)-1H-pyrrole-3-carboxamide (prepared according to the method in Example 1) (60 mg, 113.12 μmol), Intermediate C (86.92 mg, 339.35 μmol), [1,1'-bis(di-tert-butylphosphino)ferrocene]dichloropalladium(II) (14.74 mg, 22.62 μmol) and $K_3PO_4$ (96.05 mg, 452.47 μmol) were added into dioxane (1.5 mL) and $H_2O$ (0.3 mL), the mixture was purged with $N_2$ three times and then stirred at 80° C. for 2 h. The reaction mixture was filtered and filtration was evaporated to dryness. The residue was purified by Prep-HPLC (mobile phase: [water (0.1% TFA)-acetonitrile]; B %: 8%-38%) and lyophilized to give Compound 19 (33.80 mg, 48.72 μmol, 43.07% yield, TFA salt) as yellow solid. LCMS (ESI) m/z $[M+H]^+$=580.2; $^1$H NMR (400 MHz, Methanol-$d_4$) δ 8.25-8.24 (m, 2H), 8.01 (d, J=8.0 Hz, 1H), 7.84-7.83 (m, 1H), 7.68-7.66 (m, 1H), 7.56-7.52 (m, 2H), 7.29-7.28 (m, 2H), 7.20-7.18 (m, 1H), 6.82-6.80 (m, 1H), 4.26 (s, 2H), 3.86-3.34 (m, 11H), 2.98 (s, 3H).

Example 19. Preparation of N-(2-((4-(3-(2-((2-(dimethylamino)ethyl)amino)pyridin-4-yl)phenyl)thiazol-2-yl)amino)-2-oxoethyl)-1-(methylsulfonyl)-1H-pyrrole-3-carboxamide (Compound 20)

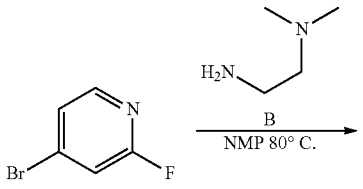

A

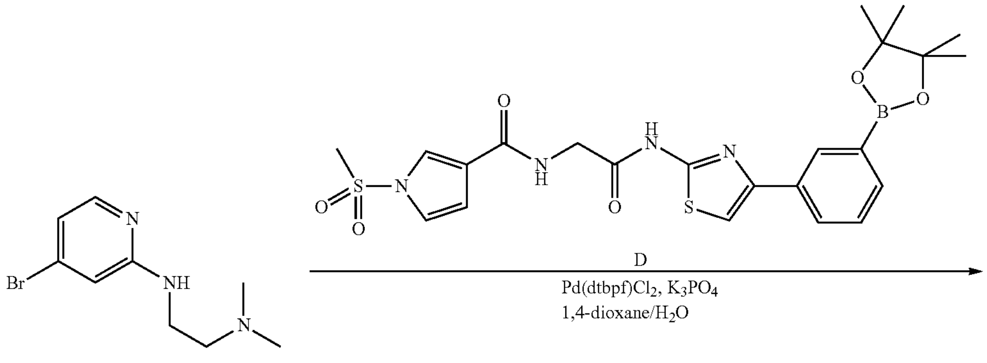

C

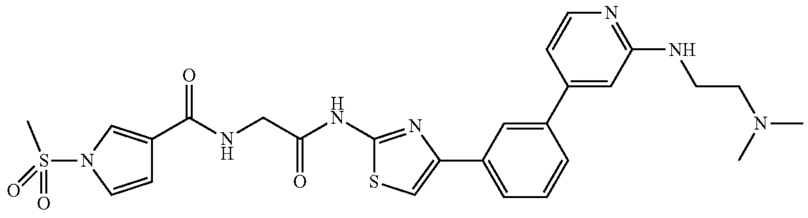

Compound 20

Step 1: Preparation of N1-(4-bromopyridin-2-yl)-N2,N2-dimethylethane-1,2-diamine (Intermediate C)

C

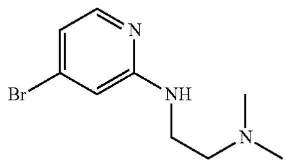

A solution of 4-bromo-2-fluoro-pyridine (1 g, 5.68 mmol) and N',N'-dimethylethane-1,2-diamine (525.94 mg, 5.97 mmol, 651.72 μL) in NMP (5 mL) was stirred at 80° C. for 2 h. The mixture was poured into water (50 mL) and extracted with EtOAc (10 mL×3). The combined organic layer was washed with water (5 mL×3) and brine (5 mL×2), then dried over $Na_2SO_4$, filtered and concentrated under vacuum to give Intermediate C (1.2 g, 4.92 mmol, 86.50% yield) as yellow oil. The crude product was used to next step directly without further purification. LCMS (ESI) m/z $[M+H]^+$=246.2.

Step 2: Preparation of N-(2-((4-(3-(2-((2-(dimethylamino)ethyl)amino)pyridin-4-yl)phenyl)thiazol-2-yl)amino)-2-oxoethyl)-1-(methylsulfonyl)-1H-pyrrole-3-carboxamide (Compound 20)

Compound 20

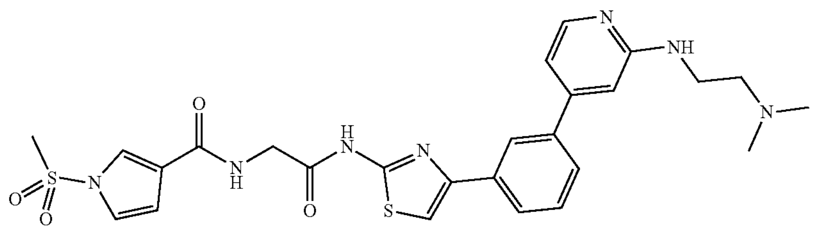

To a solution of Intermediate C (60 mg, 245.77 μmol), 1-methylsulfonyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (prepared according to the method in Example 1) (108.64 mg, 204.81 μmol), $K_3PO_4$ (130.42 mg, 614.43 μmol) in dioxane (3 mL) and water (0.5 mL) was added [1,1'-bis(di-tert-butylphosphino)ferrocene]dichloropalladium(II) (26.70 mg, 40.96 μmol). The mixture was stirred at 90° C. for 2 h. The reaction was through silica pad and the pad was washed with EtOAc (30 mL), MeOH (30 mL) and DMF (2 mL). The combined organic layer was washed with water (5 mL×3) and brine (5 mL×2), then dried over $Na_2SO_4$, filtered and concentrated under vacuum. The residue was purified by Prep-HPLC (FA condition) and lyophilized to give Compound 20 (40 mg, 64.98 μmol, 31.73% yield, FA salt) as yellow solid. LCMS (ESI) m/z $[M+H]^+$=568.2; $^1$H NMR (400 MHz, DMSO-$d_6$) δ 12.43 (br s, 1H), 8.70-8.67 (m, 1H), 8.21-8.17 (m, 2H), 8.07 (d, J=5.4 Hz, 1H), 7.96 (d, J=7.6 Hz, 1H), 7.86-7.85 (m, 1H), 7.78 (s, 1H), 7.64-7.52 (m, 2H), 7.32-7.30 (m, 1H), 6.86-6.80 (m, 2H), 6.79-6.77 (m, 1H), 6.53-6.42 (m, 1H), 4.15 (d, J=5.8 Hz, 2H), 3.58 (s, 3H), 3.43 (br d, J=5.8 Hz, 2H), 2.58-2.54 (m, 2H), 2.29 (s, 6H).

Example 20. Preparation of N-(2-((4-(3-(2-((2-(dimethylamino)ethyl)(methyl)amino)pyridin-4-yl)phenyl)thiazol-2-yl)amino)-2-oxoethyl)-1-(methylsulfonyl)-1H-pyrrole-3-carboxamide (Compound 21)

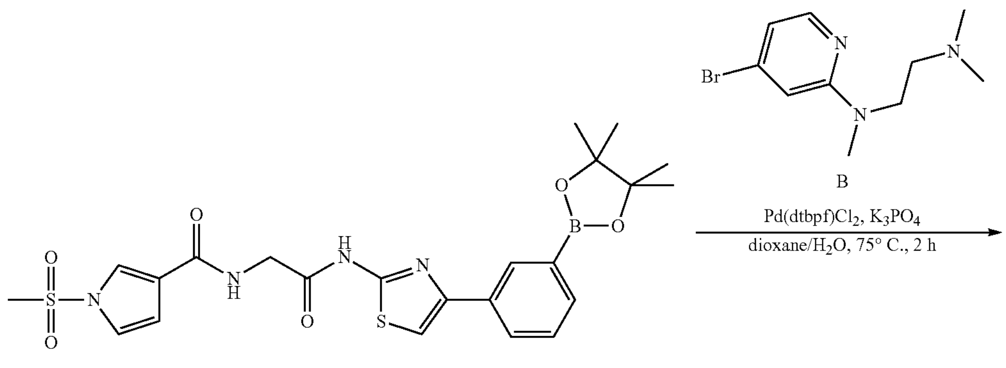

A

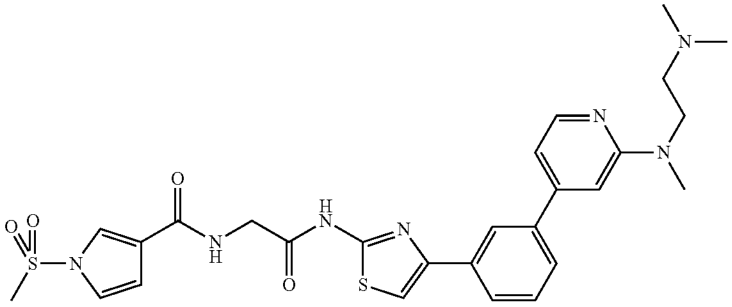

Compound 21

Step 1: Preparation of N-(2-((4-(3-(2-((2-(dimethylamino)ethyl)(methyl)amino)pyridin-4-yl)phenyl)thiazol-2-yl)amino)-2-oxoethyl)-1-(methylsulfonyl)-1H-pyrrole-3-carboxamide (Compound 21)

Compound 21

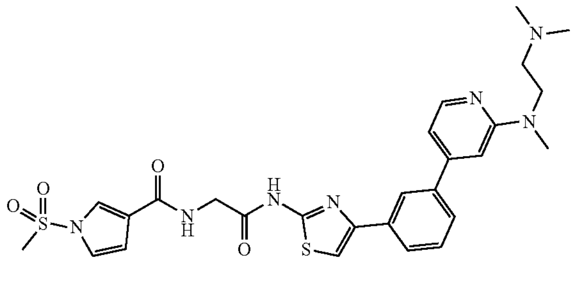

To a mixture of 1-methylsulfonyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (prepared according to the method in Example 1) (100 mg, 188.53 μmol) and N'-(4-bromo-2-pyridyl)-N,N,N'-trimethyl-ethane-1,2-diamine (40.56 mg, 157.11 μmol) in dioxane (2 mL) and $H_2O$ (0.5 mL) was added $K_3PO_4$ (100.05 mg, 471.33 μmol) and [1,1'-bis(di-tert-butylphosphino)ferrocene]dichloropalladium(II) (10.24 mg, 15.71 μmol) at 30° C. The reaction mixture was heated to 75° C. and stirred at 75° C. for 2 h. The reaction mixture was concentrated under reduced pressure to afford a residue. The residue was purified by Prep-HPLC (mobile phase: [water (0.225% FA)-acetonitrile]; B %: 25%-55%) and lyophilized to give Compound 21 (47.01 mg, 73.26 μmol, 46.63% yield, FA salt) as yellow solid. LCMS (ESI) m/z $[M+H]^+$=582.0; $^1H$ NMR (400 MHz, DMSO-$d_6$) δ 12.41 (br s, 1H), 8.70-8.67 (m, 1H), 8.21 (s, 2H), 8.17 (d, J=5.2 Hz, 1H), 7.97 (d, J=8.0 Hz, 1H), 7.86-7.85 (m, 1H), 7.79 (s, 1H), 7.69 (d, J=8.0 Hz, 1H), 7.61-7.52 (m, 1H), 7.33-7.31 (m, 1H), 6.89-6.87 (m, 1H), 6.83 (s, 1H), 6.79-6.77 (m, 1H), 4.16 (d, J=5.6 Hz, 2H), 3.75-3.71 (m, 2H), 3.57 (s, 3H), 3.09 (s, 3H), 2.54 (s, 2H), 2.27 (s, 6H).

Example 21. Preparation of 1-(tert-butyl)-N-(2-((4-(3-(6-methylpyrimidin-4-yl)phenyl)thiazol-2-yl)amino)-2-oxoethyl)-1H-pyrrole-3-carboxamide (Compound 22)

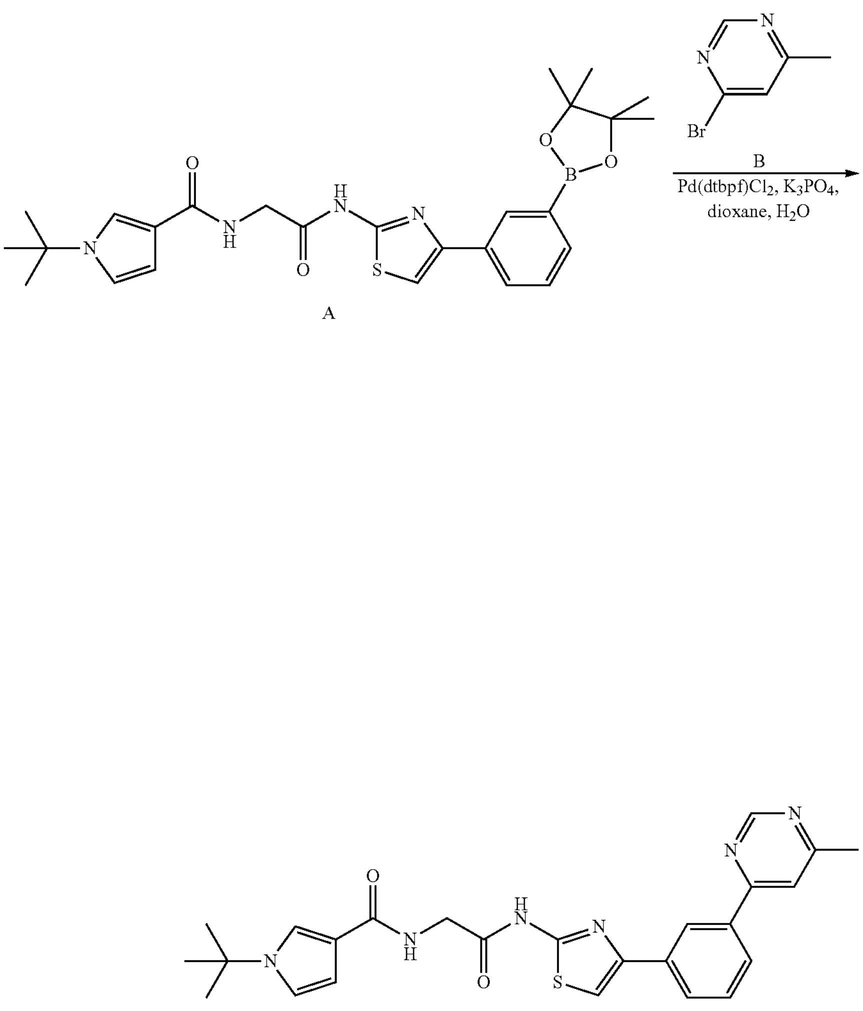

A

Compound 22

Step 1: Preparation of 1-(tert-butyl)-N-(2-((4-(3-(6-methylpyrimidin-4-yl)phenyl)thiazol-2-yl)amino)-2-oxoethyl)-1H-pyrrole-3-carboxamide (Compound 22)

Compound 22

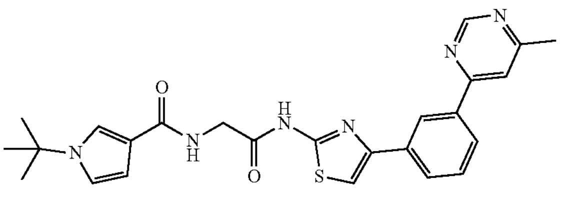

A mixture of 1-tert-butyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (Prepared according to the method in Example 8) (100 mg, 196.68 μmol), 4-bromo-6-methyl-pyrimidine (51.04 mg, 295.02 μmol), [1,1'-bis(di-tert-butylphosphino)ferrocene]dichloropalladium(II) (12.82 mg, 19.67 μmol), $K_3PO_4$ (125.25 mg, 590.04 μmol) in dioxane (2 mL) and $H_2O$ (0.4 mL) was degassed and purged with $N_2$ for 3 times, and then the mixture was stirred at 100° C. for 2 h under $N_2$ atmosphere. The reaction mixture was diluted with water (10 mL) and extracted with EtOAc (5 mL×3). The combined organic layers were washed with brine (5 mL), dried over $Na_2SO_4$, filtered though silica gel and concentrated under reduced pressure to give a residue. The residue was triturated with MTBE (5 mL) for 10 min at 20° C. Then the mixture was filtered and washed with MTBE (3 mL) to give a brown solid. Then the solid was dissolved in $H_2O/CH_3CN$ (4:1, 30 mL) and then lyophilized to give Compound 22 (67.24 mg, 138.96 μmol, 70.65% yield) as a brown solid. LCMS (ESI) m/z $[M+H]^+$=475.3; $^1H$ NMR (400 MHz, methanol-$d_4$) δ 9.05 (d, J=0.8 Hz, 1H), 8.69 (s, 1H), 8.08-8.06 (m, 2H), 7.95 (s, 1H), 7.58-7.54 (m, 3H), 6.96-6.94 (m, 1H), 6.58-6.57 (m, 1H), 4.24 (s, 2H), 2.61 (s, 3H), 1.56 (s, 9H) ppm.

Example 22. Preparation of 1-(tert-butyl)-N-(2-((4-(3-(2-methylpyrimidin-4-yl)phenyl)thiazol-2-yl)amino)-2-oxoethyl)-1H-pyrrole-3-carboxamide (Compound 23)

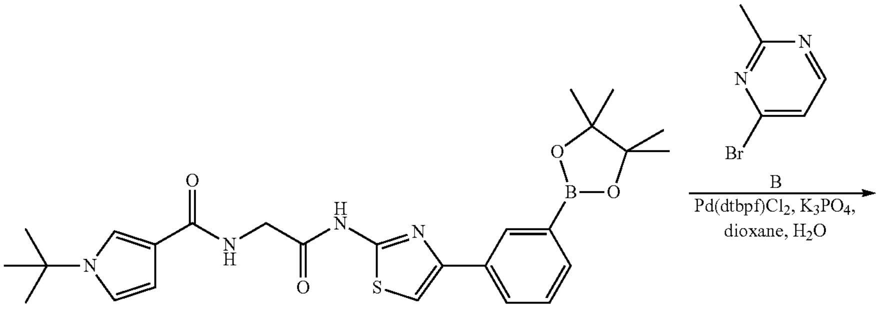

A

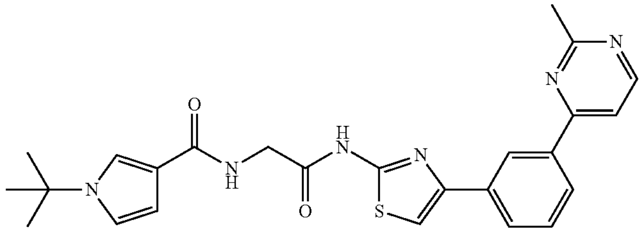

Compound 23

Step 1: Preparation of 1-(tert-butyl)-N-(2-((4-(3-(2-methylpyrimidin-4-yl)phenyl)thiazol-2-yl)amino)-2-oxoethyl)-1H-pyrrole-3-carboxamide (Compound 23)

Compound 23

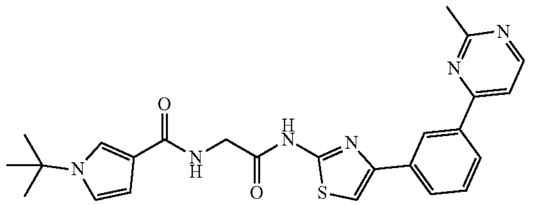

A mixture of 1-tert-butyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (prepared according to the method in Example 8) (50 mg, 98.34 μmol), 4-bromo-2-methyl-pyrimidine (25.52 mg, 147.51 μmol), [1,1'-bis(di-tert-butylphosphino)ferrocene]dichloropalladium(II) (6.41 mg, 9.83 μmol), $K_3PO_4$ (62.62 mg, 295.02 μmol) in dioxane (1 mL) and $H_2O$ (0.2 mL) was degassed and purged with $N_2$ for 3 times, and then the mixture was stirred at 100° C. for 2 h under $N_2$ atmosphere. The reaction mixture was diluted with water (5 mL) and extracted with EtOAc (3 mL×3). The combined organic layers were washed with brine (3 mL), dried over $Na_2SO_4$, filtered and concentrated under reduced pressure to give a residue. The residue was triturated with MTBE (3 mL) for 10 min at 20° C. Then the mixture was filtered and washed with MTBE (3 mL) to give a yellow solid. The solid was dissolved in $H_2O/CH_3CN$ (4:1, 30 mL) and then lyophilized to give Compound 23 (20.96 mg, 44.17 μmol, 44.91% yield) as a yellow solid. LCMS (ESI) m/z $[M+H]^+$=475.3; $^1H$ NMR (400 MHz, Methanol-$d_4$) δ 8.73-8.70 (m, 2H), 8.08 (d, J=7.6 Hz, 2H), 7.84 (d, J=5.2 Hz, 1H), 7.59-7.55 (m, 3H), 6.96-6.95 (m, 1H), 6.58-6.57 (m, 1H), 4.24 (s, 2H), 2.76 (s, 3H), 1.57 (s, 9H).

Example 23. Preparation of N-(2-((4-(3-(2-(aminomethyl)pyridin-4-yl)phenyl)thiazol-2-yl)amino)-2-oxoethyl)-1-(tert-butyl)-1H-pyrrole-3-carboxamide (Compound 24)

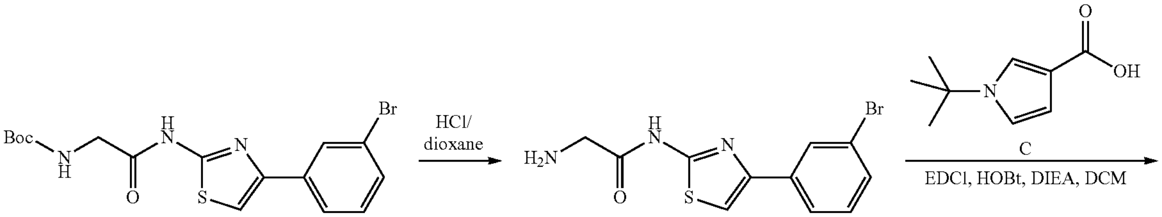

A B

-continued

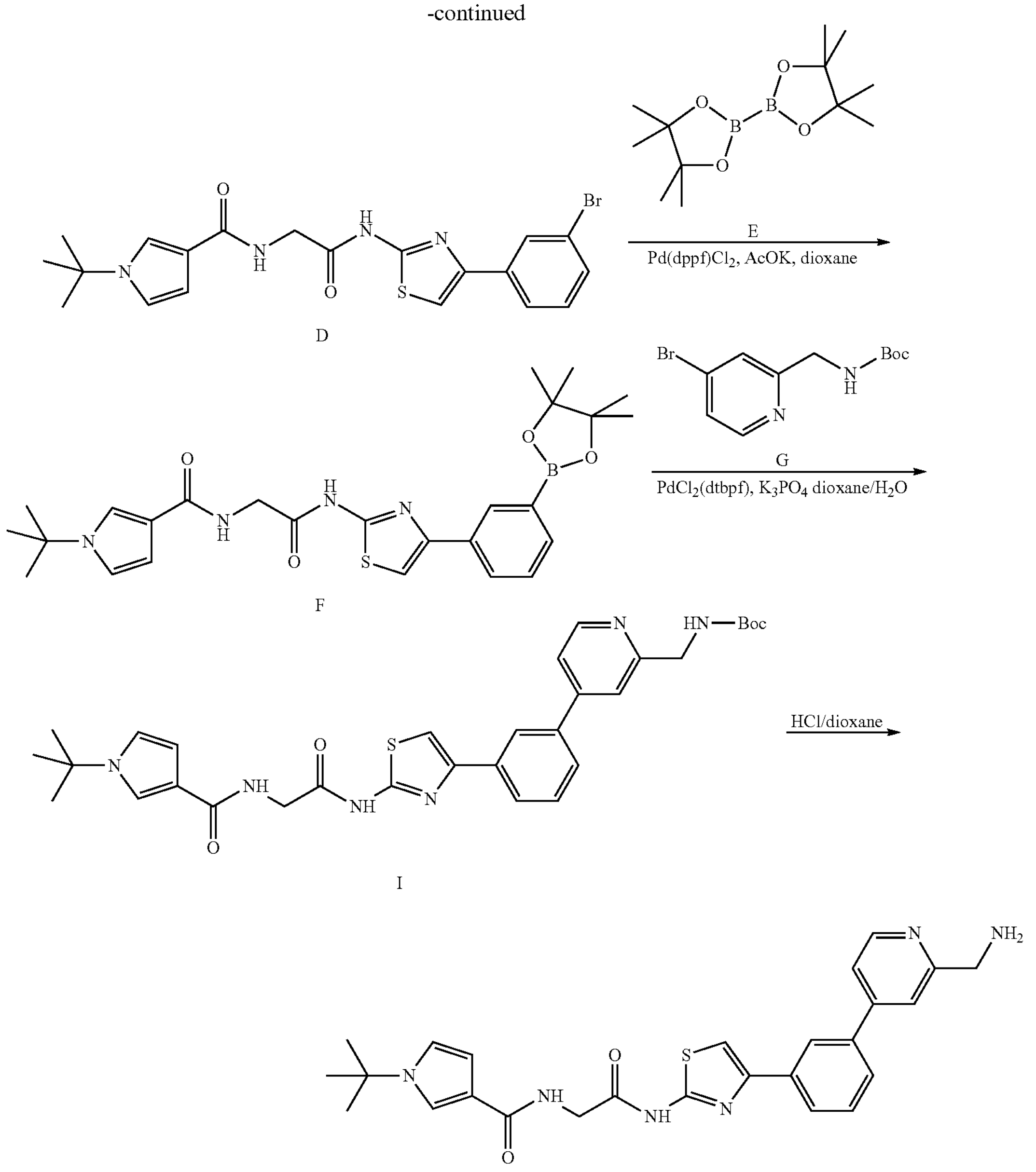

D

F

I

Compound 24

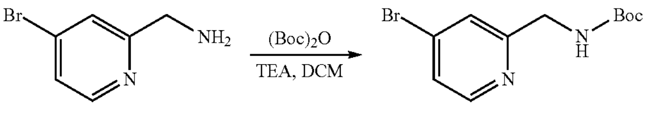

H G

Step 1: Preparation of tert-butyl ((4-bromopyridin-2-yl)methyl)carbamate (Intermediate G)

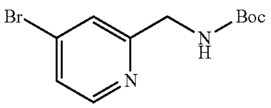

G

A mixture of (4-bromo-2-pyridyl)methanamine (200 mg, 894.86 μmol, HCl salt), $Boc_2O$ (234.36 mg, 1.07 mmol, 246.70 μL), TEA (271.65 mg, 2.68 mmol, 373.66 μL), in DCM (3 mL) was stirred at 25° C. for 4 h. The reaction was diluted with water (5 mL) and extract with DCM (2 mL×3), the combined organic layer was concentrated in vacuum. The residue was purified by reversed-phase HPLC (0.1% FA condition) and lyophilized to give Intermediate G (150 mg, 475.36 μmol, 53.12% yield) as a white solid. LCMS (ESI) m/z $[M+H]^+$=289.0.

Step 2: Preparation of tert-butyl ((4-(3-(2-(2-(1-(tert-butyl)-1H-pyrrole-3-carboxamido)acetamido)thiazol-4-yl)phenyl)pyridin-2-yl)methyl)carbamate (Intermediate I)

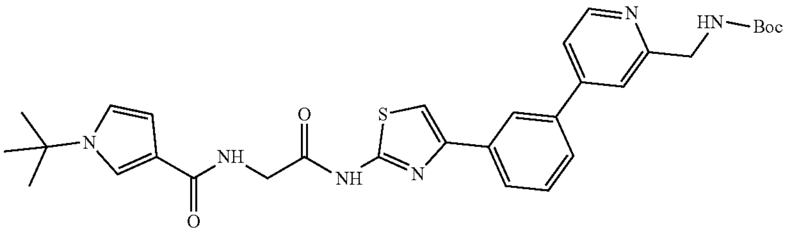

I

A mixture of 1-(tert-butyl)-N-(2-oxo-2-((4-(3-(4,4,5,5-tetramethyl-1,3,2-dioxaborolan-2-yl)phenyl)thiazol-2-yl)amino)ethyl)-1H-pyrrole-3-carboxamide [prepared according to the method in 8] (50 mg, 98.34 μmol), Intermediate G (33.89 mg, 118.01 μmol), $K_3PO_4$ (62.62 mg, 295.02 μmol), [1,1'-bis(di-tert-butylphosphino)ferrocene]dichloropalladium(II) (6.41 mg, 9.83 μmol) in dioxane (0.5 mL) and $H_2O$ (0.25 mL) was degassed and purged with $N_2$ for 3 times, and then the mixture was stirred at 80° C. for 14 h under $N_2$ atmosphere. The reaction was diluted with water (5 mL), filtered to give a solid. The solid was dissolved with DMSO (1 mL) and purified by reversed-phase HPLC (0.1% FA condition) and lyophilized to give Intermediate I (15 mg, 22.17 μmol, 22.54% yield) as yellow oil. LCMS (ESI) m/z $[M+H]^+$=589.2.

Step 3: Preparation of N-(2-((4-(3-(2-(aminomethyl)pyridin-4-yl)phenyl)thiazol-2-yl)amino)-2-oxoethyl)-1-(tert-butyl)-1H-pyrrole-3-carboxamide (Compound 24)

Compound 24

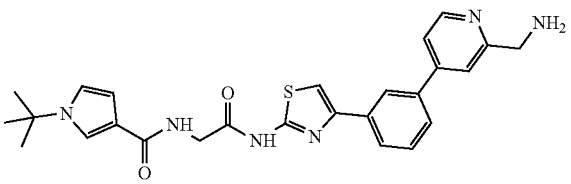

To a solution of Intermediate I (15 mg, 22.17 μmol) in MeOH (0.1 mL) was added HCl/dioxane (0.2 mL). The mixture was stirred at 25° C. for 6 h. The reaction mixture was concentrated in vacuum. The crude product was purified by reversed-phase HPLC (0.1% FA condition) and lyophilized to give Compound 24 (1.65 mg, 2.90 μmol, 13.07% yield, FA salt) as a yellow solid. LCMS (ESI) m/z $[M+H]^+$=489.1. $^1$H NMR (400 MHz, Methanol-$d_4$) δ 8.61-8.59 (m, 1H), 8.19 (s, 1H), 7.93 (d, J=7.6 Hz, 1H), 7.70 (s, 1H), 7.66-7.59 (m, 2H), 7.48-7.43 (m, 3H), 6.87-6.85 (m, 1H), 6.48-6.47 (m, 1H), 4.26 (s, 2H), 4.14 (s, 2H), 1.46 (s, 9H).

Example 24. Preparation of 1-(tert-butyl)-N-(2-((4-(3-(1-(2-methoxy-2-methylpropyl)-1H-pyrazol-3-yl)phenyl)thiazol-2-yl)amino)-2-oxoethyl)-1H-pyrrole-3-carboxamide (Compound 25)

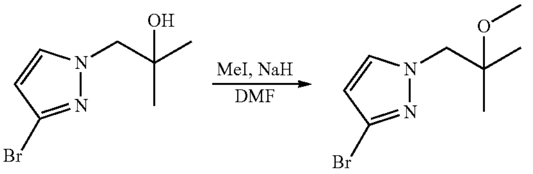

A B

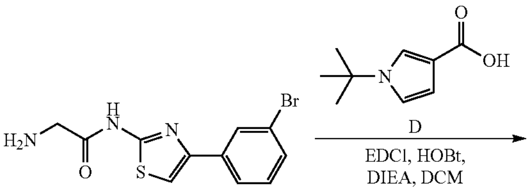

C

-continued

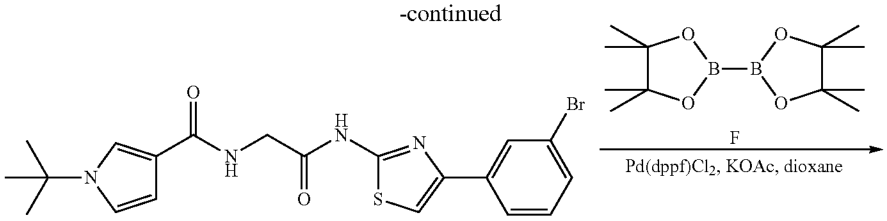

E

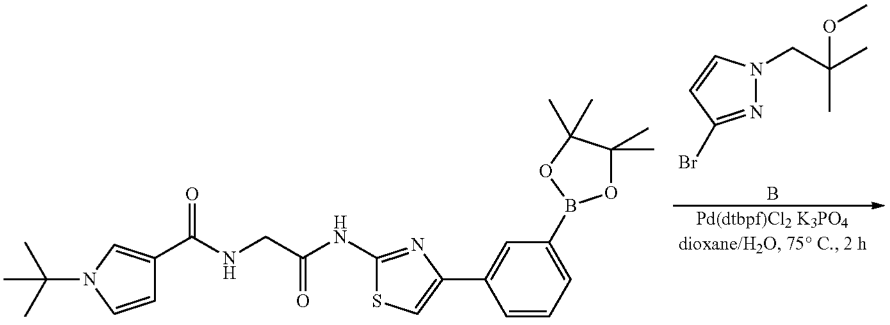

G

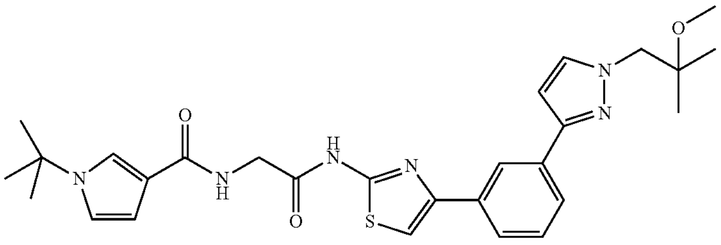

Compound 25

Step 1: Preparation of 3-bromo-1-(2-methoxy-2-methylpropyl)-1H-pyrazole (Intermediate B)

B

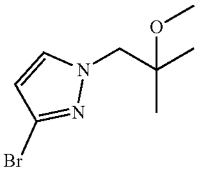

To a mixture of 1-(3-bromopyrazol-1-yl)-2-methyl-propan-2-ol (200 mg, 912.91 μmol) and MeI (259.15 mg, 1.83 mmol, 113.66 μL) in DMF (2 mL) was added NaH (43.82 mg, 1.10 mmol, 60% purity) in portions at 0° C. The reaction mixture was warmed to 25° C. and stirred at 25° C. for 2 h. The reaction mixture was poured into saturated $NH_4Cl$ aqueous solution (5 mL) and extracted with EtOAc (5 mL×3). The organic phase was washed with brine (5 mL×2), dried over anhydrous $Na_2SO_4$, filtered and concentrated under reduced pressure to afford a residue. The residue was purified by reverse phase column (FA condition) and lyophilized to afford Intermediate B (90 mg, 386.09 μmol, 42.29% yield) as yellow oil. LCMS (ESI) m/z [M+H]+=233.9. $^1$H NMR (400 MHz, CDCl3) δ 7.41 (d, J=2.4 Hz, 1H), 6.28 (d, J=2.0 Hz, 1H), 4.10 (s, 2H), 3.25 (s, 3H), 1.16 (s, 6H).

Step 2: Preparation of 1-(tert-butyl)-N-(2-((4-(3-(1-(2-methoxy-2-methylpropyl)-1H-pyrazol-3-yl)phenyl)thiazol-2-yl)amino)-2-oxoethyl)-1H-pyrrole-3-carboxamide (Compound 25)

Compound 25

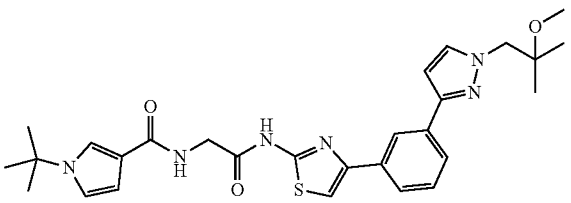

To a mixture of Intermediate B (22.92 mg, 98.34 μmol) and 1-(tert-butyl)-N-(2-oxo-2-((4-(3-(4,4,5,5-tetramethyl-1,3,2-dioxaborolan-2-yl)phenyl)thiazol-2-yl)amino)ethyl)-1H-pyrrole-3-carboxamide [prepared according to the method in 8] (50 mg, 98.34 μmol) in dioxane (0.8 mL) and $H_2O$ (0.2 mL) was added $K_3PO_4$ (62.62 mg, 295.02 μmol) and [1,1'-bis(di-tert-butylphosphino)ferrocene]dichloropalladium(II) (6.41 mg, 9.83 μmol) at 25° C. under $N_2$. The reaction mixture was heated to 75° C. and stirred at 75° C. for 2 h. The reaction mixture was poured into $H_2O$ (2 mL) and extracted with EtOAc (2 mL×5), the combined organic phase was dried over $Na_2SO_4$, filtered and concentrated under reduced pressure to afford a residue. The residue was purified by silica gel column chromatography (PE/

EtOAc=3/1-EtOAc) (TLC: EtOAc, Rf=0.7) to afford a yellow solid. The yellow solid was purified by reverse phase column (FA condition) and lyophilized to afford Compound 25 (3.51 mg, 6.04 μmol, 6.15% yield, FA salt) as white solid. LCMS (ESI) m/z $[M+H]^+$=535.2; $^1H$ NMR (400 MHz, Methanol-$d_4$) δ 8.50 (s, 1H), 8.34 (s, 1H), 7.83 (d, J=8.0 Hz, 1H), 7.71 (d, J=7.6 Hz, 1H), 7.65 (d, J=2.4 Hz, 1H), 7.59-7.58 (m, 1H), 7.47-7.39 (m, 2H), 6.96-6.94 (m, 1H), 6.68 (d, J=2.0 Hz, 1H), 6.58-6.57 (m, 1H), 4.24 (s, 2H), 4.21 (s, 2H), 3.30 (br s, 3H), 1.57 (s, 9H), 1.19 (s, 6H).

Example 25. Preparation of 1-(tert-butyl)-N-(2-((4-(3-(5-(hydroxymethyl)-1-methyl-1H-pyrazol-3-yl)phenyl)thiazol-2-yl)amino)-2-oxoethyl)-1H-pyrrole-3-carboxamide (Compound 26)

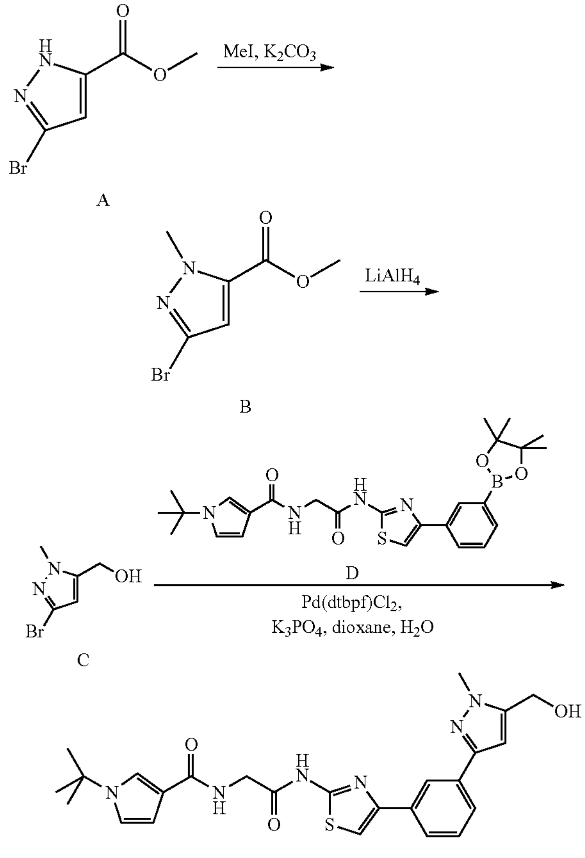

Compound 26

Step 1: Preparation of methyl 3-bromo-1-methyl-1H-pyrazole-5-carboxylate (Intermediate B)

B

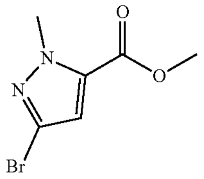

To a solution of methyl 3-bromo-1H-pyrazole-5-carboxylate (500 mg, 2.44 mmol) and MeI (1.73 g, 12.19 mmol, 759.16 μL) in DMF (5 mL) was added $K_2CO_3$ (505.61 mg, 3.66 mmol), the mixture was stirred at 60° C. for 2 h. The reaction mixture was diluted with water (50 Ml) and extracted with EtOAc (50 mL×3). The combined organic layers were washed with brine (100 mL), dried over $Na_2SO_4$, filtered and concentrated under reduced pressure to give a residue. The residue was purified by column chromatography ($SiO_2$, Petroleum ether/EtOAc=3/1 to 1:1) and concentrated to give Intermediate B (330 mg, 1.51 mmol, 61.77% yield) as a white solid. LCMS (ESI) m/z $[M+H]^+$=220.8; $^1H$ NMR (400 MHz, DMSO-$d_6$) δ 6.99 (s, 1H), 4.06 (s, 3H), 3.84 (s, 3H).

Step 2: Preparation of (3-bromo-1-methyl-1H-pyrazol-5-yl methanol (Intermediate C)

C

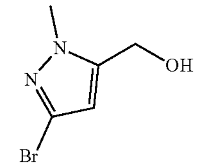

To a solution of $LiAlH_4$ (110.90 mg, 2.92 mmol) in THF (4 mL) was added the solution of Intermediate B (320 mg, 1.46 mmol) in THF (2 mL) at 0° C., then the mixture was warmed to 30° C. and stirred at 30° C. for 1 h. The reaction mixture was quenched by addition EtOAc 10 mL at 0° C., and then diluted with water (0.11 mL), 15% NaOH solution (0.11 mL), water (0.4 mL) and 2 g $Na_2SO_4$, then filtered. The combined organic layers were concentrated under reduced pressure to give a residue. The residue was purified by column chromatography ($SiO_2$, Petroleum ether/EtOAc=3/1 to 2:1) and concentrated under reduced pressure to give Intermediate C (110 mg, 575.84 μmol, 39.42% yield) as a white solid. LCMS (ESI) m/z $[M+H]^+$=191.1; $^1H$ NMR (400 MHz, DMSO-$d_6$) δ 6.26 (s, 1H), 5.37-5.34 (m, 1H), 4.45 (d, J=5.6 Hz, 2H), 3.74 (s, 3H).

Step 3: Preparation of 1-(tert-butyl)-N-(2-((4-(3-(5-(hydroxymethyl)-1-methyl-1H-pyrazol-3-yl)phenyl)thiazol-2-yl)amino)-2-oxoethyl)-1H-pyrrole-3-carboxamide (Compound 26)

Compound 26

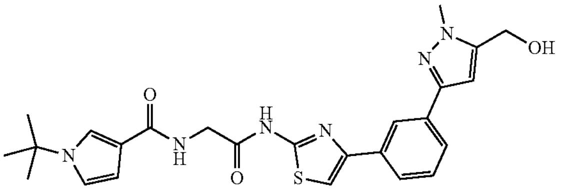

To a solution of 1-tert-butyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (prepared according to the method in Example 8) (100 mg, 196.68 μmol), Intermediate C (45.09 mg, 236.02 μmol) and [1,1'-bis(di-tert-butylphosphino)ferrocene]dichloropalladium(II) (12.82 mg, 19.67 μmol) in dioxane (1 mL) and Water (0.25 mL) was added $K_3PO_4$ (125.25 mg, 590.04 μmol) under $N_2$, the mixture was stirred at 80° C. for 1 h. The reaction mixture was diluted with water (10 mL) and extracted with EtOAc (10 mL×3). The combined organic layers were washed with brine (20 mL), dried over $Na_2SO_4$, filtered and concentrated under reduced pressure to give a residue. The residue was purified by column chromatography ($SiO_2$, Petroleum ether/EtOAc=0:1) (PE/EtOAc=0:1, Rf=0.6) and concentrated under reduced pressure to give Compound 26 (23.60 mg, 47.29 μmol, 24.04% yield) as a white solid. LCMS (ESI) m/z $[M+H]^+$=493.4; $^1H$ NMR (400 MHz, Methanol-$d_4$) δ 8.31-8.30 (m, 1H), 7.84-7.82 (m, 1H), 7.69 (d, J=8.0 Hz, 1H), 7.59-7.58 (m, 1H), 7.43-7.39 (m, 2H), 6.96-6.94 (m, 1H), 6.64 (s, 1H), 6.58-6.57 (m, 1H), 4.67 (s, 2H), 4.24 (s, 2H), 3.93 (s, 3H), 1.56 (s, 9H).

Example 26. Preparation of 1-(1-methoxy-2-methylpropan-2-yl)-N-(2-((4-(3-(1-methyl-1H-pyrazol-3-yl)phenyl)thiazol-2-yl)amino)-2-oxoethyl)-1H-pyrrole-3-carboxamide (Compound 27)

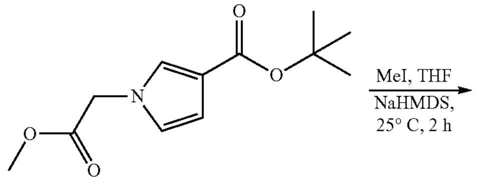

A

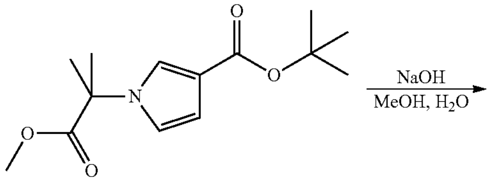

B

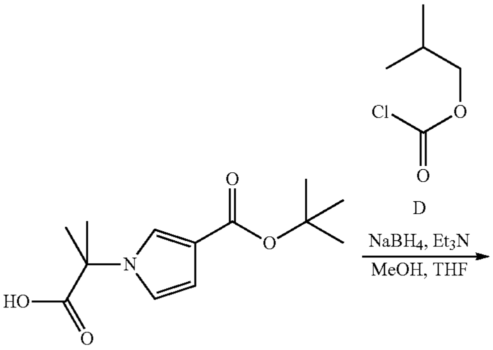

D

C

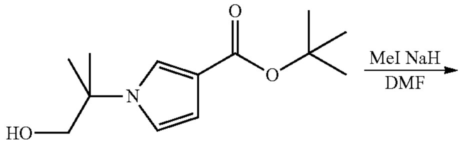

E

-continued

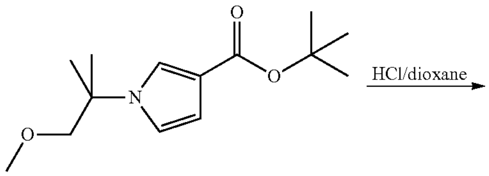

F

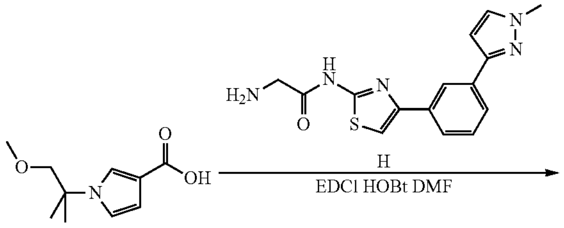

G

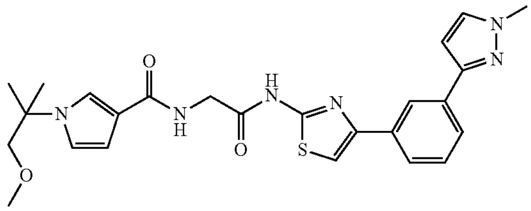

Compound 27

Step 1: Preparation of tert-butyl 1-(1-methoxy-2-methyl-1-oxopropan-2-yl)-1H-pyrrole-3-carboxylate (Intermediate B)

B

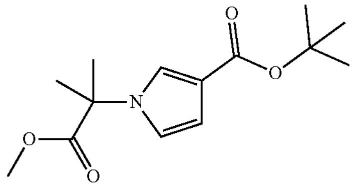

To a solution of tert-butyl 1-(2-methoxy-2-oxo-ethyl) pyrrole-3-carboxylate (500 mg, 2.09 mmol) MeI (1.19 g, 8.36 mmol, 520.38 μL) in THF (5 mL) was added NaHMDS (1 M, 10.45 mL) at 0° C. After addition, the resulting mixture was stirred at 25° C. for 1 h. The reaction mixture was quenched by addition water (10 mL), and extracted with EtOAc (10 mL×3). The combined organic layers were washed with NaCl (10 mL×3), dried over $Na_2SO_4$, filtered and concentrated under reduced pressure to give Intermediate B (440 mg, crude) as yellow oil, which was directly used to next step without further purification. LCMS (ESI) m/z $[M+H-56]^+$=212.1.

Step 2: Preparation of 2-(3-(tert-butoxycarbonyl)-1H-pyrrol-1-yl)-2-methylpropanoic acid (Intermediate C)

C

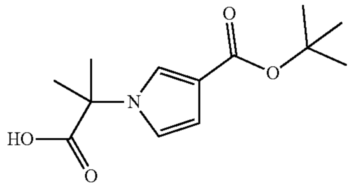

To a solution of Intermediate B (400 mg, 1.50 mmol) in $H_2O$ (2 mL) and MeOH (6 mL) was added NaOH (119.71 mg, 2.99 mmol). The mixture was stirred at 25° C. for 12 h. The residue was purified by reversed phase (FA condition) and lyophilized to give Intermediate C (224 mg, 809.27 μmol, 54.08% yield) as light yellow oil. LCMS (ESI) m/z $[M+H-56]^+$=198.1. $^1H$ NMR (400 MHz, DMSO-$d_6$) δ 13.19-13.08 (m, 1H), 7.38-7.36 (m, 1H), 6.93-6.91 (m, 1H), 6.35-6.34 (m, 1H), 1.71 (s, 6H), 1.48 (s, 9H).

Step 3: Preparation of tert-butyl 1-(1-hydroxy-2-methylpropan-2-yl)-1H-pyrrole-3-carboxylate (Intermediate E)

E

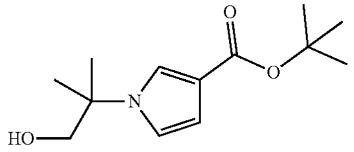

To a solution of Intermediate C (200 mg, 789.60 μmol), $Et_3N$ (119.85 mg, 1.18 mmol, 164.85 μL) in THF (2 mL) was added isobutyl chloroformate (129.41 mg, 947.52 μmol, 124.43 μL) at 0° C. After additional, the mixture was stirred at this temperature for 1 h, and then $NaBH_4$ (268.83 mg, 7.11 mmol) in MeOH (0.4 mL) was added dropwise at 0° C. The resulting mixture was stirred at 25° C. for 1 h. The reaction mixture was quenched by addition water (10 mL) and extracted with EtOAc (10 mL×3). The combined organic layers were washed with brine (10 mL×3), dried over $Na_2SO_4$, filtered and concentrated under reduced pressure to give a residue. The residue was purified by reversed phase (FA condition) and lyophilized to give Intermediate E (170 mg, 710.38 μmol, 89.97% yield) as a white solid. LCMS (ESI) m/z $[M+H-56]^+$=184.1. $^1H$ NMR (400 MHz, DMSO-$d_6$) δ 7.37-7.35 (m, 1H), 6.96-6.90 (m, 1H), 6.31 (dd, J=1.8, 3.0 Hz, 1H), 5.06-5.53 (m, 1H), 3.48 (d, J=5.4 Hz, 2H), 1.48 (s, 9H), 1.42 (s, 6H).

Step 4: Preparation of tert-butyl 1-(1-methoxy-2-methylpropan-2-yl)-1H-pyrrole-3-carboxylate (Intermediate F)

F

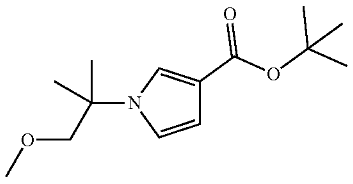

To a solution of Intermediate E (90 mg, 376.08 μmol) in THF (1 mL) was added MeI (106.76 mg, 752.16 μmol, 46.83 μL) at 25° C., and then NaH (30.09 mg, 752.16 μmol, 60% purity) was added at 0° C. The resulting mixture was stirred at 25° C. for 1 h. The reaction mixture was quenched by addition water (3 mL), and extracted with EtOAc (2 mL×3). The combined organic layers were washed with brine (2 mL×3), dried over $Na_2SO_4$, filtered and concentrated under reduced pressure to give Intermediate F (130 mg, crude) as a yellow oil which was directly used to next step without further purification. LCMS (ESI) m/z $[M+H-56]^+$=198.1. $^1H$ NMR (400 MHz, $CDCl_3$) δ 7.36-7.29 (m, 1H), 6.71-6.70 (m, 1H), 6.45 (dd, J=1.8, 3.0 Hz, 1H), 3.35 (s, 2H), 3.21 (s, 3H), 1.49-1.43 (m, 15H).

Step 5: Preparation of 1-(1-methoxy-2-methylpropan-2-yl)-1H-pyrrole-3-carboxylic acid (Intermediate G)

G

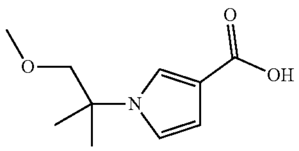

A solution of Intermediate F (130 mg, 513.15 μmol) in HCl/dioxane (4 M, 1.28 mL) was stirred at 25° C. for 2 h. The mixture was concentrated in vacuum to give Intermediate G (50 mg, crude) as yellow oil, which was used to next step without further purification. LCMS (ESI) m/z $[M+H]^+$=198.1.

Step 6: Preparation of 1-(1-methoxy-2-methylpropan-2-yl)-N-(2-((4-(3-(1-methyl-1H-pyrazol-3-yl)phenyl)thiazol-2-yl)amino)-2-oxoethyl)-1H-pyrrole-3-carboxamide (Compound 27)

Compound 27

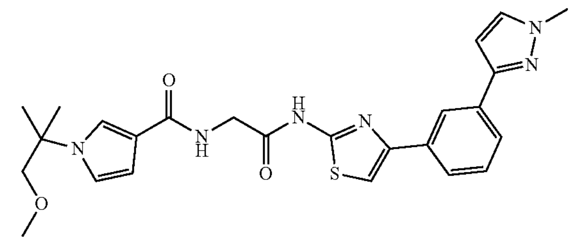

A mixture of Intermediate G (50 mg, 253.51 μmol), 2-amino-N-[4-[3-(1-methylpyrazol-3-yl)phenyl]thiazol-2-yl]acetamide (prepared according to the method in Example 2) (119.17 mg, 340.63 μmol, HCl salt), DIEA (163.82 mg, 1.27 mmol, 220.78 μL), EDCI (97.20 mg, 507.02 μmol) and HOBt (68.51 mg, 507.02 μmol) in DMF (2 mL) was degassed and purged with $N_2$ for 3 times, and then the mixture was stirred at 25° C. for 1 h under $N_2$ atmosphere. The reaction mixture was quenched by addition water (10 mL), and extracted with EtOAc (3 mL×2). The combined organic layers were washed with brine (3 mL×2), dried over $Na_2SO_4$, filtered and concentrated under reduced pressure to give a residue. The residue was purified by Prep-HPLC (TFA condition) and lyophilized to give Compound 27 (11 mg, 21.88 μmol, 8.63% yield, TFA salt) as brown oil. LCMS (ESI) m/z $[M+H]^+$=493.4; $^1H$ NMR (400 MHz, DMSO-$d_6$) δ 12.39 (s, 1H), 8.38 (s, 1H), 8.21-8.20 (m, 1H), 7.85-7.64 (m, 4H), 7.53-7.40 (m, 2H), 6.95-6.94 (m, 1H), 6.73 (d, J=2.2 Hz, 1H), 6.51-6.44 (m, 1H), 4.10 (br d, J=6.0 Hz, 2H), 3.90 (s, 3H), 3.22-3.20 (m, 3H), 1.48-1.43 (m, 6H).

Example 27. Preparation of 1-(2-hydroxy-2-methylpropyl)-N-(2-((4-(3-(1-methyl-1H-pyrazol-3-yl)phenyl)thiazol-2-yl)amino)-2-oxoethyl)-1H-pyrrole-3-carboxamide (Compound 28)

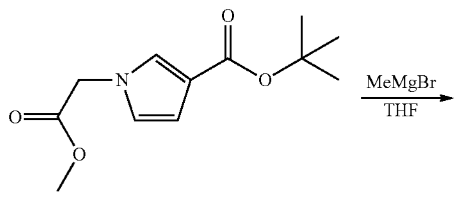

A

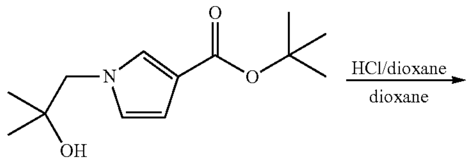

B

-continued

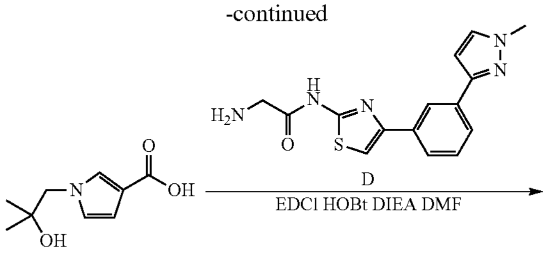

C

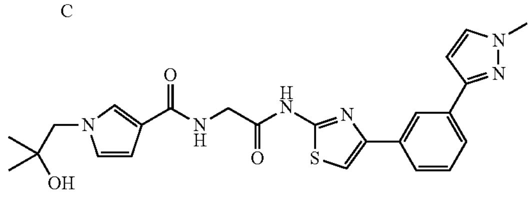

Compound 28

Step 1: Preparation of 1-(2-hydroxy-2-methylpropyl)-1H-pyrrole-3-carboxylic acid (Intermediate C)

C

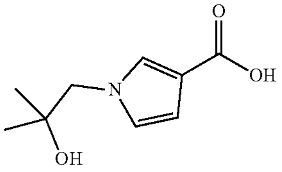

To a solution of tert-butyl 1-(1-hydroxy-2-methylpropan-2-yl)-1H-pyrrole-3-carboxylate [prepared according to the method described in Example 26] (50 mg, 208.93 μmol) in dioxane (0.5 mL) was added HCl/dioxane (4 M, 522.34 μL), then the mixture was stirred at 25° C. for 12 h. The reaction mixture was concentrated under reduced pressure to give Intermediate C (23 mg, crude) as a brown solid. LCMS (ESI) m/z $[M+H]^+$=184.1.

Step 2: Preparation of 1-(2-hydroxy-2-methylpropyl)-N-(2-((4-(3-(1-methyl-1H-pyrazol-3-yl)phenyl)thiazol-2-yl)amino)-2-oxoethyl)-1H-pyrrole-3-carboxamide (Compound 28)

Compound 28

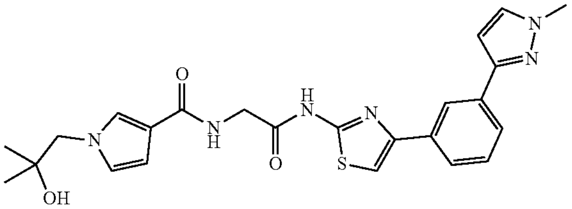

A mixture of Intermediate C (20 mg, 109.17 μmol), 2-amino-N-[4-[3-(1-methylpyrazol-3-yl)phenyl]thiazol-2-yl]acetamide (prepared according to the method in Example 2) (51.32 mg, 146.69 μmol, HCl salt), DIEA (42.33 mg, 327.50 μmol, 57.05 μL), HOBt (29.50 mg, 218.34 μmol) and EDCI (41.86 mg, 218.34 μmol) in DMF (1 mL) was degassed and purged with $N_2$ for 3 times, and then the mixture was stirred at 25° C. for 12 h under $N_2$ atmosphere. The reaction mixture was concentrated in vacuum. The residue was purified through Prep-HPLC (FA condition) and lyophilized to give Compound 28 (8 mg, 15.74 μmol, 14.42% yield) as a yellow solid. LCMS (ESI) m/z $[M+H]^+=$ 479.2; $^1H$ NMR (400 MHz, DMSO-$d_6$) δ 12.81-11.85 (m, 1H), 8.45 (s, 1H), 8.39 (s, 1H), 8.20-8.18 (m, 1H), 7.84-7.67 (m, 4H), 7.46-7.44 (m, 1H), 7.32 (s, 1H), 6.76-6.71 (m, 2H), 6.48-6.44 (m, 1H), 4.66 (br s, 1H), 4.10 (d, J=6.0 Hz, 2H), 3.91 (s, 3H), 3.80 (s, 2H), 1.06 (s, 6H).

Example 28. Preparation of 1-(2-methoxy-2-methylpropyl)-N-(2-((4-(3-(1-methyl-1H-pyrazol-3-yl)phenyl)thiazol-2-yl)amino)-2-oxoethyl)-1H-pyrrole-3-carboxamide (Compound 29)

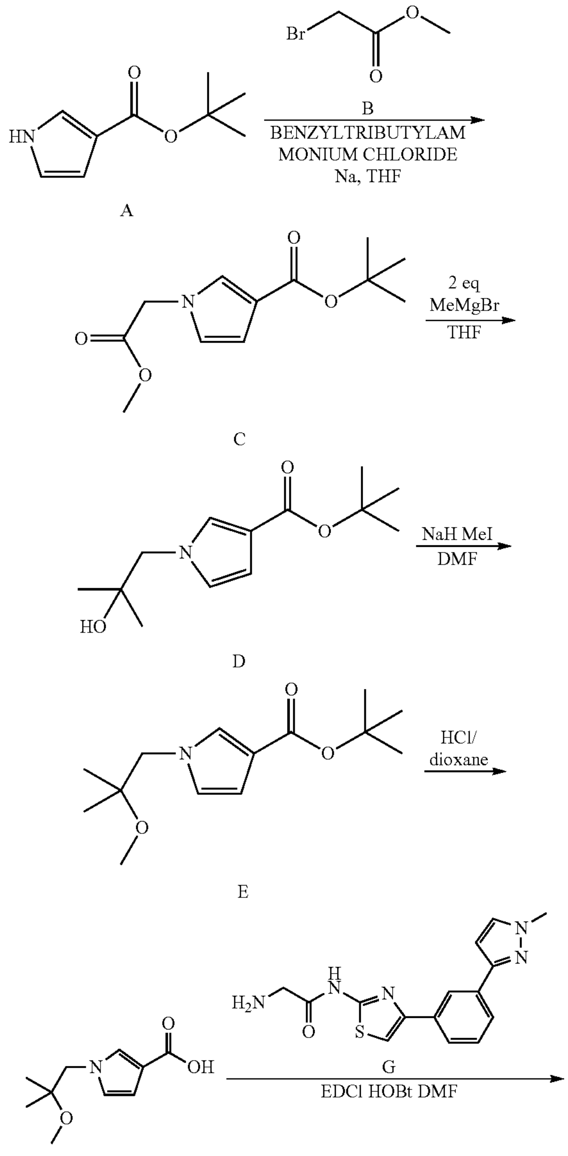

B
A
C
D
E
G
F

-continued

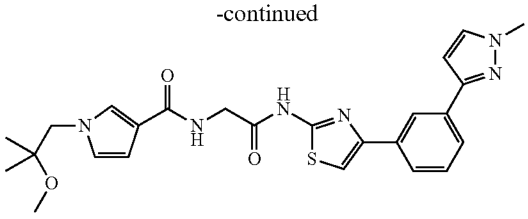

Compound 29

Step 1: Preparation of tert-butyl 1-(2-hydroxy-2-methylpropyl)-1H-pyrrole-3-carboxylate (Intermediate D)

D

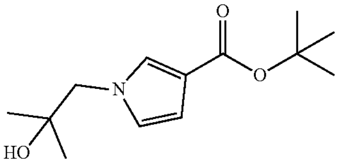

To a solution of tert-butyl 1-(2-methoxy-2-oxoethyl)-1H-pyrrole-3-carboxylate [prepared according to the method described in Example 27] (500 mg, 2.09 mmol) in THF (3 mL) was added MeMgBr (3 M, 2.79 mL) at 0° C. After addition, the mixture was stirred at 25° C. for 12 h. The reaction mixture was quenched by $NH_4Cl$ (3 mL), and then extracted with EtOAc (10 mL×3). The combined organic layers were dried over $Na_2SO_4$, filtered and concentrated under reduced pressure to give a residue. The residue was purified by flash silica gel chromatography (Eluent of 0-50% Ethyl acetate/Petroleum ether gradient 40 mL/min) and concentrated to give Intermediate D (202 mg, 774.62 μmol, 37.07% yield) as a light yellow solid. LCMS (ESI) m/z $[M+H-56]^+=184.1$.

Step 2: Preparation of tert-butyl 1-(2-methoxy-2-methylpropyl)-1H-pyrrole-3-carboxylate (Intermediate E)

E

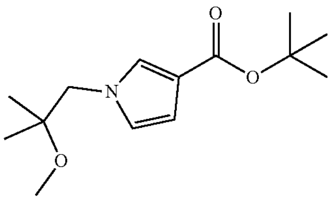

To a solution of Intermediate D (50 mg, 208.93 μmol) in DMF (1 mL) was added NaH (16.71 mg, 417.87 μmol, 60% purity) at 0° C. After additional, the mixture was stirred at this temperature for 1 h, and then MeI (44.48 mg, 313.40 μmol, 19.51 μL) was added at 0° C. The resulting mixture was stirred at 25° C. for 1 h. The reaction mixture was quenched by addition water (2 mL), and extracted with EtOAc (5 mL×3). The combined organic layers were washed with brine (5 mL×3), dried over $Na_2SO_4$, filtered and concentrated under reduced pressure to give Intermediate E (50 mg, crude) as a yellow oil, which was directly used to next step without further purification. LCMS (ESI) m/z $[M+H-56]^+$=198.1.

Step 3: Preparation of 1-(2-methoxy-2-methylpropyl)-1H-pyrrole-3-carboxylic acid (Intermediate F)

F

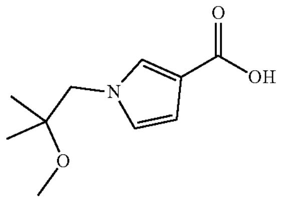

A mixture of Intermediate E (50 mg, 132.24 μmol) in HCl/dioxane (4 M, 330.59 μL) was stirred at 25° C. for 12 h. The mixture was concentrated in vacuum to give Intermediate F (40 mg, crude) as yellow oil. LCMS (ESI) m/z $[M+H]^+$=198.1.

Step 4: Preparation of 1-(2-methoxy-2-methylpropyl)-N-(2-((4-(3-(1-methyl-1H-pyrazol-3-yl)phenyl) thiazol-2-yl)amino)-2-oxoethyl)-1H-pyrrole-3-carboxamide (Compound 29)

Compound 29

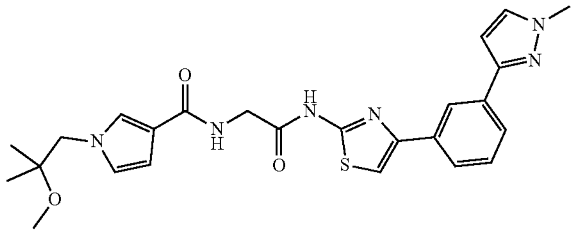

A mixture of Intermediate F (40 mg, 202.81 μmol), 2-amino-N-[4-[3-(1-methylpyrazol-3-yl)phenyl]thiazol-2-yl]acetamide (prepared according to the method in Example 2) (127.11 mg, 363.34 μmol, HCl salt), EDCI (77.76 mg, 405.62 μmol), HOBt (54.81 mg, 405.62 μmol) and DIEA (131.06 mg, 1.01 mmol, 176.62 μL) in DMF (1 mL) was degassed and purged with $N_2$ for 3 times, and then the mixture was stirred at 25° C. for 1 h under $N_2$ atmosphere. The reaction mixture was quenched by addition water (2 mL), and extracted with EtOAc (1 mL×3). The combined organic layers were washed with brine (3 mL), dried over $Na_2SO_4$, filtered and concentrated under reduced pressure to give a residue. The residue was purified by reversed phase (FA) and lyophilized to give Compound 29 (12 mg, 24.12 μmol, 11.89% yield) as a yellow solid. LCMS (ESI) m/z $[M+H]^+$=493.4. $^1H$ NMR (400 MHz, DMSO-$d_6$) δ 12.53-12.25 (m, 1H), 8.39 (s, 1H), 8.22-8.20 (m, 1H), 7.83-7.68 (m, 4H), 7.46-7.44 (m, 1H), 7.29-7.27 (m, 1H), 6.79-6.70 (m, 2H), 6.51-6.39 (m, 1H), 4.10 (br d, J=5.8 Hz, 2H), 3.91 (s, 5H), 3.17 (s, 3H), 1.06 (s, 6H).

Example 29. Preparation of 1-(1-hydroxy-2-methylpropan-2-yl)-N-(2-((4-(3-(1-methyl-1H-pyrazol-3-yl)phenyl)thiazol-2-yl)amino)-2-oxoethyl)-1H-pyrrole-3-carboxamide (Compound 30)

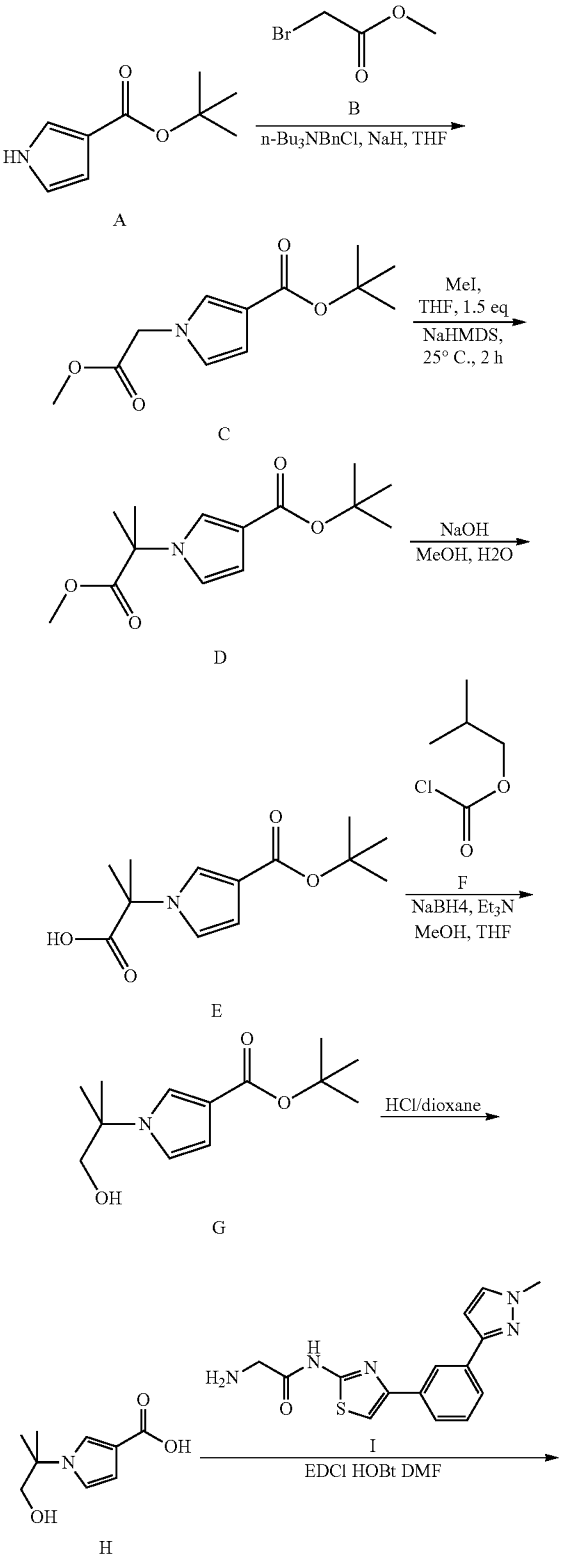

-continued

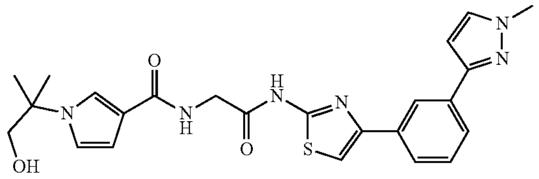

Compound 30

Step 1: Preparation of 1-(1-hydroxy-2-methylpropan-2-yl)-1H-pyrrole-3-carboxylic acid (Intermediate H)

H

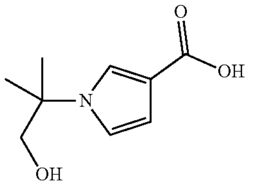

A mixture of tert-butyl 1-(1-hydroxy-2-methylpropan-2-yl)-1H-pyrrole-3-carboxylate [prepared according to the method described in Example 26] (70 mg, 292.51 μmol), HCl/dioxane (4 M, 731.27 μL) was degassed and then the mixture was stirred at 25° C. for 12 h under $N_2$ atmosphere. The mixture was concentrated in vacuum to give Intermediate H (50 mg, crude) as yellow oil. LCMS (ESI) m/z $[M+H]^+$=184.1.

Step 2: Preparation of 1-(1-hydroxy-2-methylpropan-2-yl)-N-(2-((4-(3-(1-methyl-1H-pyrazol-3-yl)phenyl)thiazol-2-yl)amino)-2-oxoethyl)-1H-pyrrole-3-carboxamide (Compound 30)

Compound 30

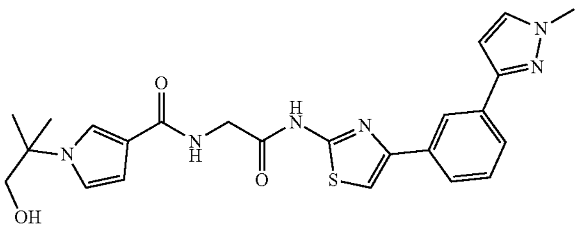

A mixture of Intermediate H (50 mg, 272.92 μmol), 2-amino-N-[4-[3-(1-methylpyrazol-3-yl)phenyl]thiazol-2-yl]acetamide (prepared according to the method in Example 2) (128.29 mg, 409.38 μmol), DIEA (176.36 mg, 1.36 mmol, 237.68 μL), EDCI (104.64 mg, 545.84 μmol) and HOBt (73.75 mg, 545.84 μmol) in DMF (1 mL) was degassed and purged with $N_2$ for 3 times, and then the mixture was stirred at 25° C. for 1 h under $N_2$ atmosphere. The reaction mixture was quenched by addition water (5 mL), and extracted with EtOAc (3 mL×2). The combined organic layers were washed with brine (3 mL×2), dried over $Na_2SO_4$, filtered and concentrated under reduced pressure to give a residue. The residue was purified by reversed phase (FA condition) and lyophilized to give Compound 30 (10 mg, 20.90 μmol, 7.66% yield) as a white solid. LCMS (ESI) m/z $[M+H]^+$=479.3; $^1H$ NMR (400 MHz, DMSO-$d_6$) δ 12.50-12.25 (m, 1H), 8.39 (s, 1H), 8.17-8.15 (m, 1H), 7.87-7.65 (m, 4H), 7.54-7.39 (m, 2H), 6.94-6.92 (m, 1H), 6.73 (d, J=2.4 Hz, 1H), 6.51-6.42 (m, 1H), 5.08-5.06 (m, 1H), 4.10 (d, J=6.0 Hz, 2H), 3.91 (s, 3H), 3.49 (d, J=5.4 Hz, 2H), 1.44 (s, 6H).

Example 30. Preparation of N-(2-((4-(3-cyanophenyl)thiazol-2-yl)amino)-2-oxoethyl)-1-methyl-1H-imidazole-5-carboxamide (Compound 31)

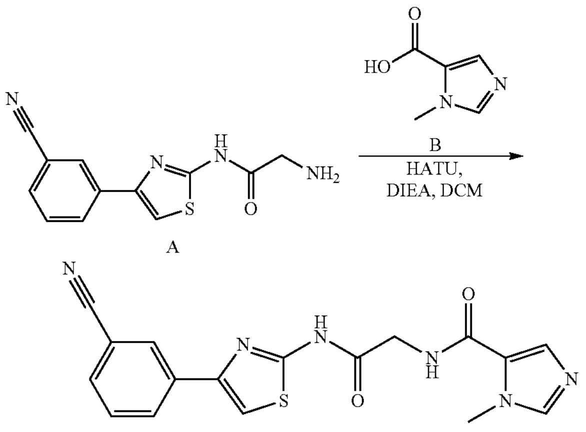

Compound 31

Step 1: Preparation of N-(2-((4-(3-cyanophenyl)thiazol-2-yl)amino)-2-oxoethyl)-1-methyl-1H-imidazole-5-carboxamide (Compound 31)

Compound 31

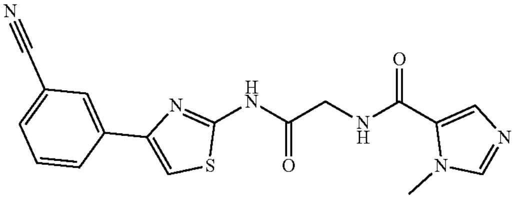

To a solution of 3-methylimidazole-4-carboxylic acid (24.41 mg, 193.56 μmol) in DCM (1 mL) was added HATU (88.32 mg, 232.28 μmol) and DIEA (125.09 mg, 967.87 μmol, 168.58 μL) and the mixture was stirred at 25° C. for 5 min. Then 2-amino-N-[4-(3-cyanophenyl)thiazol-2-yl]acetamide (prepared according to the method in Example 3) (50 mg, 169.63 μmol, HCl salt) was added and the mixture was stirred at 25° C. for 1 h. A white solid was formed and the formed precipitate was collected by filtration. The solid was triturated with MeOH (2 mL), then filtered and dried in vacuum to give Compound 31 (27.74 mg, 75.38 μmol, 44.44% yield) as a white solid. LCMS (ESI) m/z $[M+H]^+$=367.0; $^1H$ NMR (400 MHz, DMSO-$d_6$) δ 8.71-8.68 (m, 1H), 8.33-8.32 (m, 1H), 8.24-8.21 (m, 1H), 7.87 (s, 1H), 7.80-7.77 (m, 2H), 7.67-7.64 (m, 2H), 4.14 (d, J=6.0 Hz, 2H), 3.80 (s, 3H).

Example 31. Preparation of N-(2-((4-(3-cyanophenyl)thiazol-2-yl)amino)-2-oxoethyl)-1-methyl-1H-pyrazole-5-carboxamide (Compound 32)

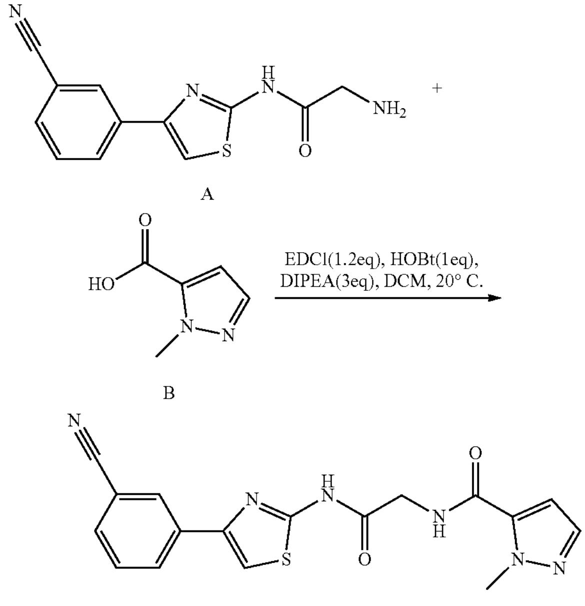

Compound 32

Step 1: Preparation of N-(2-((4-(3-cyanophenyl)thiazol-2-yl)amino)-2-oxoethyl)-1-methyl-1H-pyrazole-5-carboxamide (Compound 32)

Compound 32

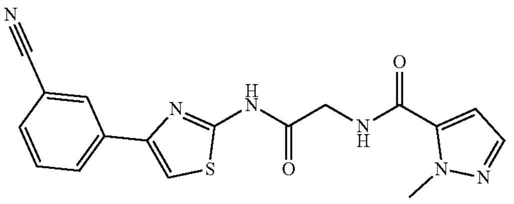

To a solution of 2-amino-N-[4-(3-cyanophenyl)thiazol-2-yl]acetamide (prepared according to the method in Example 3) (50 mg, 169.63 μmol, HCl salt) in DCM (3 mL) was added 2-methylpyrazole-3-carboxylic acid (21.39 mg, 169.63 μmol) HOBt (22.92 mg, 169.63 μmol), DIEA (65.77 mg, 508.89 μmol, 88.64 μL) and EDCI (39.02 mg, 203.56 μmol). The mixture was stirred at 25° C. for 16 h. The reaction mixture was concentrated to dryness to give a residue. The residue was triturated with MeOH (5 mL) at 25° C. for 30 min and filtered and dried in vacuum to afford Compound 32 (22.07 mg, 59.42 μmol, 35.03% yield) as white solid. LCMS (ESI) m/z $[M+H]^+$=367.1; $^1H$ NMR (400 MHz, DMSO-$d_6$) δ 12.50 (br s, 1H), 8.93-8.91 (m, 1H), 8.37-8.30 (m, 1H), 8.27-8.21 (m, 1H), 7.89 (s, 1H), 7.83-7.76 (m, 1H), 7.70-7.63 (m, 1H), 7.50 (d, J=2.0 Hz, 1H), 6.94 (d, J=2.0 Hz, 1H), 4.19-4.17 (m, 2H), 4.06 (s, 3H).

Example 32. Preparation of N-(2-((4-(3-cyanophenyl)thiazol-2-yl)amino)-2-oxoethyl)-1-(methylsulfonyl)-1H-pyrrole-3-carboxamide (Compound 33)

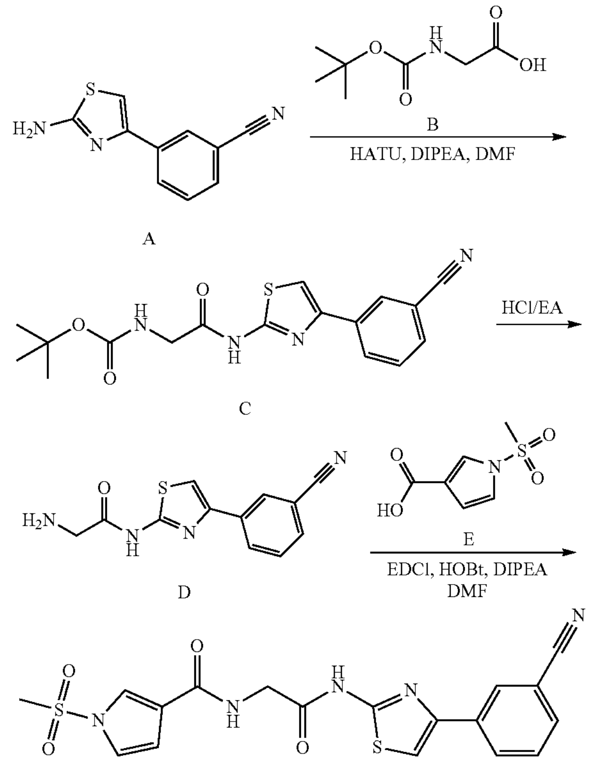

Compound 33

Step 1: Preparation of N-(2-((4-(3-cyanophenyl)thiazol-2-yl)amino)-2-oxoethyl)-1-(methylsulfonyl)-1H-pyrrole-3-carboxamide (Compound 33)

Compound 33

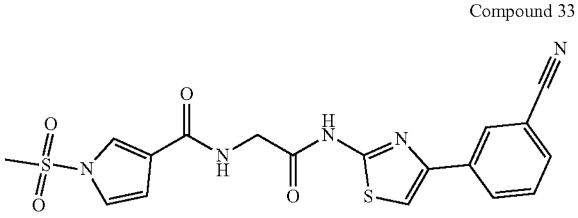 [SMILES: CS(=O)(=O)n1ccc(C(=O)NCC(=O)Nc2nc(-c3cccc(C#N)c3)cs2)c1]

To the solution of 1-(methylsulfonyl)-1H-pyrrole-3-carboxylic acid [prepared according to the method in Example 4] (21.97 mg, 116.14 μmol), EDCI (33.40 mg, 174.22 μmol), HOBt (23.54 mg, 174.22 μmol) and DIPEA (45.03 mg, 348.43 μmol, 60.69 μL) in DMF (0.5 mL) was added 2-amino-N-[4-(3-cyanophenyl)thiazol-2-yl]acetamide (prepared according to the method in Example 3) (30 mg, 116.14 μmol) at 25° C. The reaction mixture was stirred at 30° C. for 16 hours. The reaction mixture was poured into water (2 mL), and filtered to afford crude desired compound as white solid. The residue was dissolved in DMSO (2 mL) and purified by Prep-HPLC (mobile phase: [water (0.225%

FA)-acetonitrile]; B %: 40%-70%) and lyophilized to give Compound 33 (21.25 mg, 44.29 μmol, 38.14% yield, FA salt) as white solid. LCMS (ESI) m/z $[M+H]^+$=430.0; $^1H$ NMR (400 MHz, DMSO-d6) δ 12.43 (br s, 1H), 8.67-8.65 (m, 1H), 8.32 (s, 1H), 8.23 (d, J=8.0 Hz, 1H), 7.88-7.82 (m, 2H), 7.79 (d, J=7.8 Hz, 1H), 7.67-7.65 (m, 1H), 7.31-7.30 (m, 1H), 6.77-6.76 (m, 1H), 4.14 (d, J=5.6 Hz, 2H), 3.57 (s, 3H).

Example 33. Preparation of N-(2-((4-(3-cyanophenyl)thiazol-2-yl)amino)-2-oxoethyl)-1-(2-cyanopropan-2-yl)-1H-pyrrole-3-carboxamide (Compound 34)

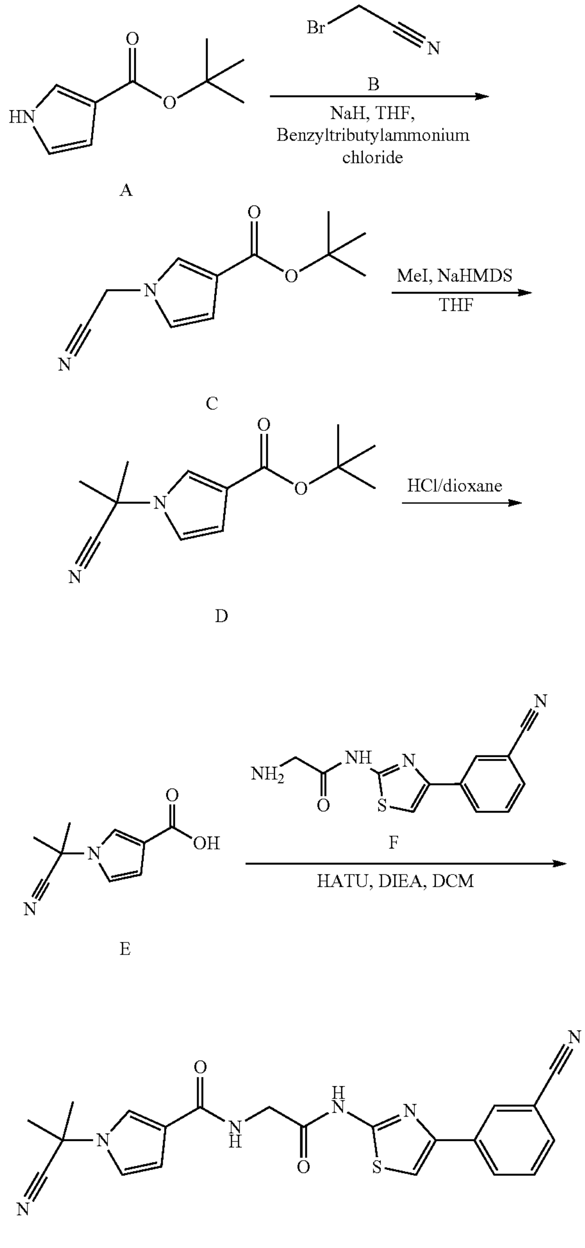

Compound 34

Step 1: Preparation of tert-butyl 1-(cyanomethyl)-1H-pyrrole-3-carboxylate (Intermediate C)

C

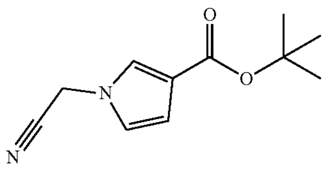

A mixture of tert-butyl 1H-pyrrole-3-carboxylate (500 mg, 2.99 mmol), 2-bromoacetonitrile (430.42 mg, 3.59 mmol, 239.12 μL) and benzyltributylammonium chloride (93.28 mg, 299.03 μmol) in THF (10 mL) was stirred at 0° C. under $N_2$ atmosphere, then NaH (179.42 mg, 4.49 mmol, 60% purity) was added and the reaction mixture was warmed up to 25° C. and stirred for another 2 h. The reaction mixture was poured into $NH_4Cl$ (15 mL) and extracted with EtOAc (15 mL×2), the combined organic layers were washed with brine (10 mL×mL×2) and then concentrated under vacuum to give residue. The residue was purified by reversed phase HPLC (0.1% FA), the solution was extracted with EtOAc (15 mL×2), concentrated under vacuum to give Intermediate C (304 mg, 1.36 mmol, 45.35% yield) as black-brown oil. LCMS (ESI) m/z $[M+H-56]^+$=150.9; $^1H$ NMR (400 MHz, $CDCl_3$) δ 7.29-7.28 (m, 1H), 6.68-6.67 (m, 1H), 6.63-6.62 (m, 1H), 4.82 (s, 2H), 1.55 (s, 9H).

Step 2: Preparation of tert-butyl 1-(2-cyanopropan-2-yl)-1H-pyrrole-3-carboxylate (Intermediate D)

D

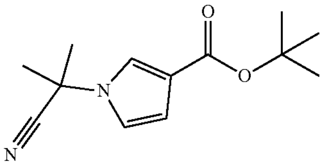

To a solution of Intermediate C (304 mg, 1.36 mmol) and MeI (769.93 mg, 5.42 mmol, 337.69 μL) in THF (8 mL) was added NaHMDS (1 M, 6.78 mL) at 0° C., then the reaction mixture was stirred at 25° C. for 2 h. The reaction mixture was quenched by addition $NH_4Cl$ (25 mL) at 25° C., and then diluted with water (10 mL) and extracted with EtOAc (10 mL×2). The combined organic layers were washed with brine (15 mL×3), dried over $Na_2SO_4$, filtered and concentrated under reduced pressure to give a residue. The residue was purified by reversed phase (0.1% FA), then the solution was extracted with EtOAc (10 mL×2). The combined organic layers were dried over $Na_2SO_4$, filtered and concentrated under reduced pressure to give Intermediate D (285 mg, 1.12 mmol, 82.52% yield) as brown oil. LCMS (ESI) m/z $[M+H-56]^+$=178.9.

Step 3: Preparation of 1-(2-cyanopropan-2-yl)-1H-pyrrole-3-carboxylic acid (Intermediate E)

E

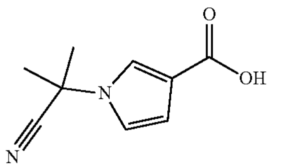

Intermediate D (100 mg, 426.82 μmol) was dissolved in HCl/dioxane (4 M, 1 mL) and the reaction mixture was stirred at 25° C. for 2 h. The reaction mixture was concentrated under vacuum to give Intermediate E (76 mg, crude) as brown oil, which was used to next step without further purification. LCMS (ESI) m/z $[M+H]^+$=178.9.

Step 4: Preparation of N-(2-((4-(3-cyanophenyl)thiazol-2-yl)amino)-2-oxoethyl)-1-(2-cyanopropan-2-yl)-1H-pyrrole-3-carboxamide (Compound 34)

Compound 34

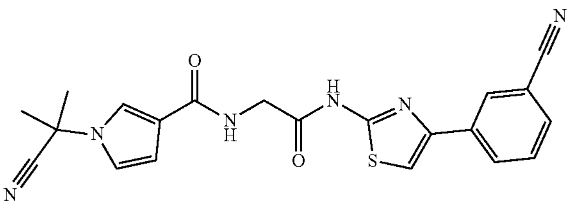

To a solution of Intermediate E (72.54 mg, 407.11 μmol), HATU (154.80 mg, 407.11 μmol) and DIEA (175.39 mg, 1.36 mmol, 236.37 μL) in DCM (2 mL) was added 2-amino-N-[4-(3-cyanophenyl)thiazol-2-yl]acetamide (prepared according to the method in Example 3) (80 mg, 271.41 μmol, HCl salt), then the reaction mixture was stirred at 25° C. for 2 h. The reaction mixture was concentrated under reduced pressure to give a residue. The residue was purified by Prep-HPLC (mobile phase: [water (0.1% TFA)-acetonitrile]; B %: 46%-58%) and lyophilized to give Compound 34 (12.28 mg, 29.05 μmol, 10.70% yield) as a white solid. LCMS (ESI) m/z $[M+H]^+$=419.0; $^1H$ NMR (400 MHz, DMSO-$d_6$) δ 12.40 (s, 1H), 8.39-8.32 (m, 2H), 8.23-8.21 (m, 1H), 7.86 (s, 1H), 7.80-7.78 (m, 1H), 7.68-7.64 (m, 2H), 7.15-7.14 (m, 1H), 6.61-6.60 (m, 1H), 4.12 (d, J=6.0 Hz, 2H), 1.95 (s, 6H).

Example 34. Preparation of 1-(tert-butyl)-N-(2-((4-(3-cyanophenyl)thiazol-2-yl)amino)-2-oxoethyl)-1H-pyrrole-3-carboxamide (Compound 35)

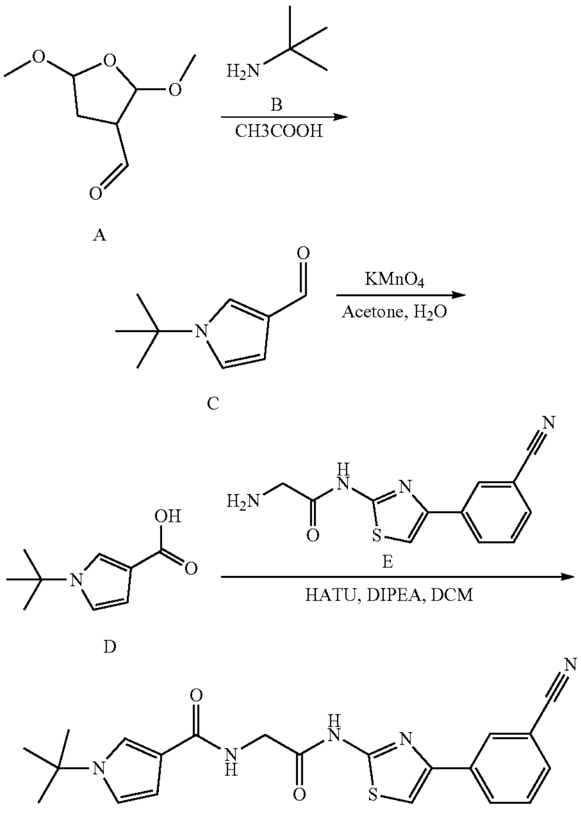

Compound 35

Step 1: Preparation of 1-(tert-butyl)-1H-pyrrole-3-carbaldehyde (Intermediate C)

C

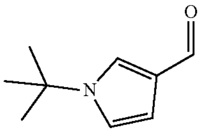

A solution of 2,5-dimethoxytetrahydrofuran-3-carbaldehyde (800 mg, 4.99 mmol, 707.96 μL) and 2-methylpropan-2-amine (365.30 mg, 4.99 mmol, 524.86 μL) in $CH_3COOH$ (25 mL) was stirred at 120° C. for 2 h. The mixture was poured into water (50 mL) and extracted with EtOAc (10 mL×mL×3). The combined organic layer was washed with water (5 mL×mL×3) and brine (5 mL×mL×2), then dried over $Na_2SO_4$, filtered and concentrated under vacuum to give Intermediate C (800 mg, crude) as a yellow solid. LCMS (ESI) m/z $[M+H]^+$=152.0; $^1H$ NMR (400 MHz, $CDCl_3$) δ 9.67 (s, 1H), 7.39-7.38 (m, 1H), 6.80-6.79 (m, 1H), 6.57-6.56 (m, 1H), 1.49 (s, 9H).

Step 2: Preparation of 1-(tert-butyl)-1H-pyrrole-3-carboxylic acid (Intermediate D)

D

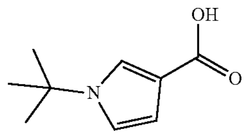

$KMnO_4$ (1.25 g, 7.94 mmol) was portionwise added to a cooled (0° C.) suspension of Intermediate C (800 mg, 5.29 mmol) in Acetone (40 mL) and water (8 mL). Each small addition was made after the disappearance of the violet color of the oxidizing agent. After the additions were completed, the mixture was stirred at 30° C. for 2 hrs. The excess of potassium permanganate was quenched with a 38% of sodium hydrogen sulfite solution and the solution acidified with HCl (6N) to pH=4-5. The mixture was extracted with EtOAc (10 mL×3). The combined organic layers were washed with water (10 mL×3) and brine (10 mL×2), then dried over $Na_2SO_4$, filtered and concentrated under vacuum. The residue was purified by reverse phase flash (FA condition) and extracted by EtOAc (10 mL×3). The combined organic layer was washed with water (10 mL×3) and brine (10 mL×2), then dried over $Na_2SO_4$, filtered and concentrated under vacuum to give Intermediate D (400 mg, crude) as white solid. LCMS (ESI) m/z $[M+H]^+$=168.0; $^1H$ NMR (400 MHz, $CDCl_3$) δ 7.53-7.42 (m, 1H), 6.77-6.71 (m, 1H), 6.56-6.55 (m, 1H), 1.48 (s, 9H).

Step 3: Preparation of 1-(tert-butyl)-N-(2-((4-(3-cyanophenyl)thiazol-2-yl)amino)-2-oxoethyl)-1H-pyrrole-3-carboxamide (Compound 35)

Compound 35

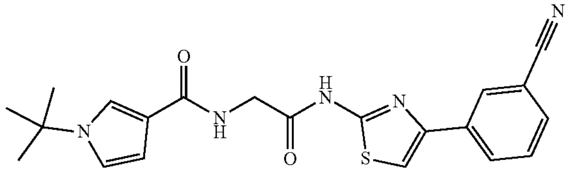

To a solution of Intermediate D (34.04 mg, 203.56 μmol) in DCM (3 mL) was added HATU (96.75 mg, 254.44 μmol) and DIEA (65.77 mg, 508.89 μmol, 88.64 μL). Then 2-amino-N-[4-(3-cyanophenyl)thiazol-2-yl]acetamide (prepared according to the method in Example 3) (50 mg, 169.63 μmol, HCl salt) was added. The mixture was stirred at 30° C. for 2 h. The mixture was diluted with DCM (30 mL) and washed with water (5 mL×3) and brine (5 mL×2), dried over $Na_2SO_4$, filtered and concentrated under vacuum. The residue was purified by Prep-HPLC (mobile phase: [water (10 mM $NH_4HCO_3$)-acetonitrileacetonitrile]; B %: 25%-55%) and lyophilized to give Compound 35 (6 mg, 14.72 μmol, 8.68% yield) as white solid. LCMS (ESI) m/z $[M+H]^+$=408.2; $^1H$ NMR (400 MHz, DMSO-$d_6$) δ 12.36 (br s, 1H), 8.33 (s, 1H), 8.24 (d, J=8.4 Hz, 1H), 8.18 (s, 1H), 7.87 (s, 1H), 7.80 (d, J=7.8 Hz, 1H), 7.70-7.63 (m, 1H), 7.52-7.51 (m, 1H), 6.98-6.96 (m, 1H), 6.48-6.47 (m, 1H), 4.10 (d, J=5.6 Hz, 2H), 3.29 (s, 2H), 1.50 (s, 9H).

Example 35. Preparation of 1-(tert-butyl)-N-(2-((4-(3-cyanophenyl)thiazol-2-yl)amino)-2-oxoethyl)-1H-pyrazole-3-carboxamide (Compound 36)

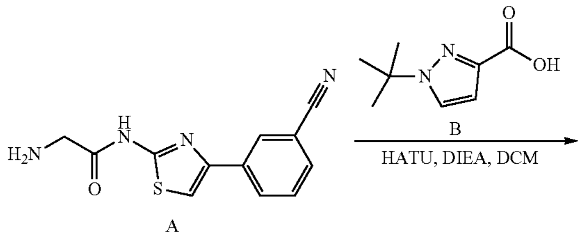

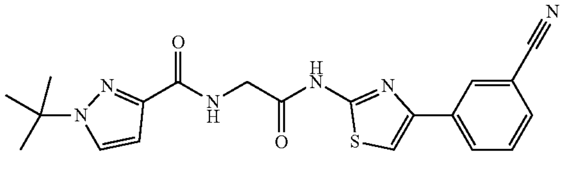

Compound 36

Step 1: Preparation of 1-(tert-butyl)-N-(2-((4-(3-cyanophenyl)thiazol-2-yl)amino)-2-oxoethyl)-1H-pyrazole-3-carboxamide (Compound 36)

Compound 36

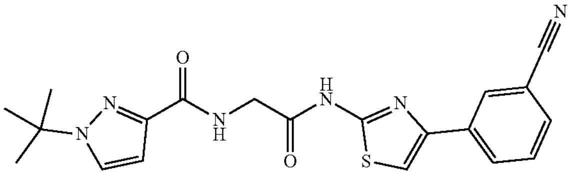

To a solution of 2-amino-N-[4-(3-cyanophenyl)thiazol-2-yl]acetamide (prepared according to the method in Example 3) (50 mg, 169.63 μmol, HCl salt) and 1-tertbutylpyrazole-3-carboxylic acid (34.24 mg, 203.56 μmol) in DCM (2 mL) was added HATU (77.40 mg, 203.56 μmol) and DIEA (109.62 mg, 848.15 μmol, 147.73 μL), the mixture was stirred at 30° C. for 16 h. The reaction mixture was poured into MeOH (2 mL), the solution was filtered to give a solid and the solid was dried under vacuum to give Compound 36 (15.63 mg, 37.81 μmol, 22.29% yield) as a white solid. LCMS (ESI) m/z $[M+H]^+$=409.2; $^1H$ NMR (400 MHz, DMSO-$d_6$) δ 12.44 (s, 1H), 8.33-8.22 (m, 3H), 7.94 (d, J=2.4 Hz, 1H), 7.88 (s, 1H), 7.80 (d, J=7.6 Hz, 1H), 7.68-7.65 (m, 1H), 6.65 (d, J=2.4 Hz, 1H), 4.19 (d, J=6.0 Hz, 2H), 1.58 (s, 9H).

Example 36. Preparation of 1-(tert-butyl)-N-(2-((4-(3-cyanophenyl)thiazol-2-yl)amino)-2-oxoethyl)-1H-pyrazole-4-carboxamide (Compound 37)

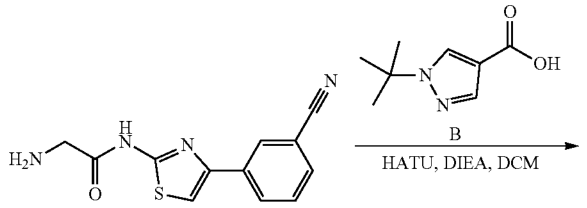

A

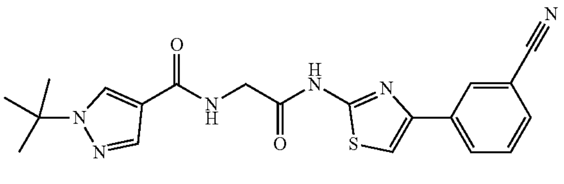

Compound 37

Step 1: Preparation of 2-(tert-butyl)-N-(2-((4-(3-cyanophenyl)thiazol-2-yl)amino)-2-oxoethyl)-1H-pyrazole-4-carboxamide (Compound 37)

Compound 37

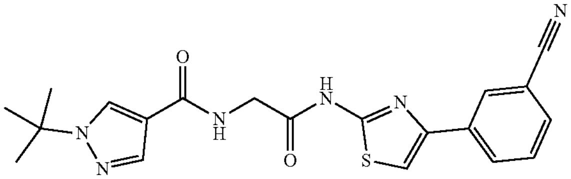

To a solution of 2-amino-N-[4-(3-cyanophenyl)thiazol-2-yl]acetamide (prepared according to the method in Example 3) (50 mg, 193.57 μmol) and 1-tert-butylpyrazole-4-carboxylic acid (39.07 mg, 232.29 μmol) in DCM (2 mL) was added HATU (88.32 mg, 232.29 μmol) and DIEA (125.09 mg, 967.87 μmol, 168.59 μL), the mixture was stirred at 30° C. for 16 h. The reaction mixture was concentrated to give a residue. The residue was purified by Prep-HPLC (mobile phase: [water (0.225% FA)-acetonitrile]; B %: 29%-59%) and lyophilized to give Compound 37 (22.12 mg, 54.15 μmol, 27.98% yield) as a white solid. LCMS (ESI) m/z $[M+H]^+$=409.1; $^1H$ NMR (400 MHz, DMSO-$d_6$) δ 12.42 (s, 1H), 8.50-8.48 (m, 1H), 8.32-8.31 (m, 2H), 8.23-8.21 (m, 1H), 7.88 (d, J=10.0 Hz, 2H), 7.79 (d, J=7.6 Hz, 1H), 7.67-7.64 (m, 1H), 4.14 (d, J=6.0 Hz, 2H), 1.53 (s, 9H).

Example 37. Preparation of 1-(2-aminoethyl)-N-(2-oxo-2-((4-(3-(pyridin-4-yl)phenyl)thiazol-2-yl)amino)ethyl)-1H-pyrrole-3-carboxamide (Compound 38)

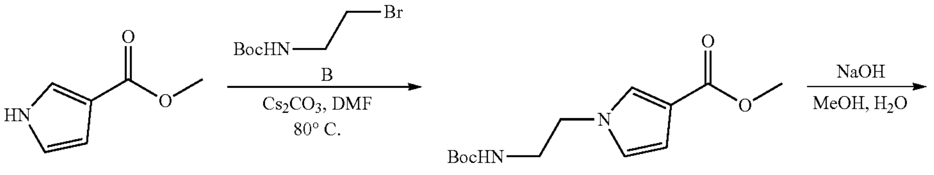

A

C

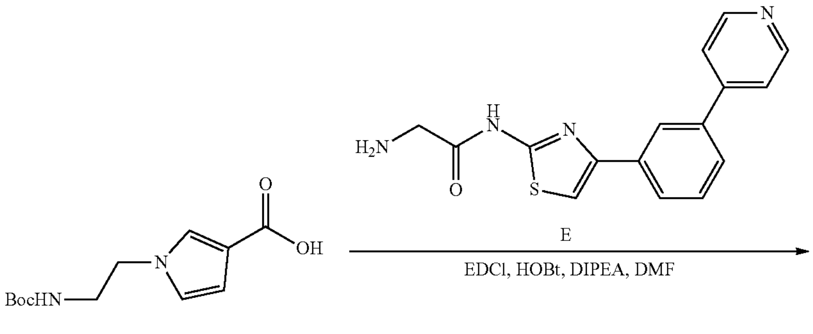

D

-continued

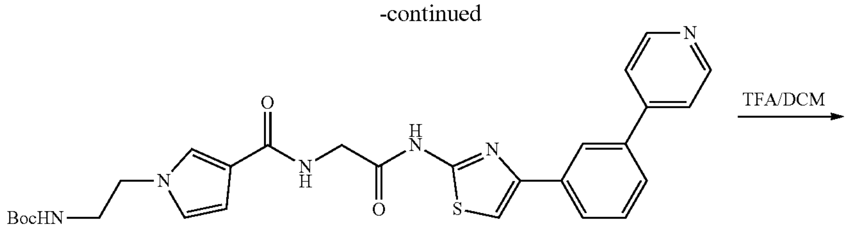

F

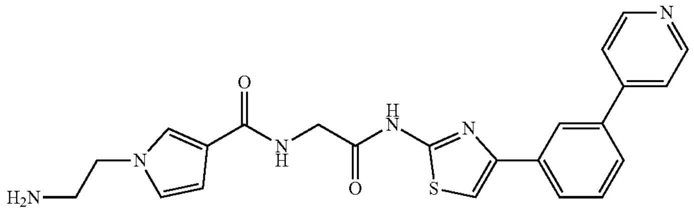

Compound 38

Step 1: Preparation of methyl 1-(2-((tert-butoxycarbonyl)amino)ethyl)-1H-pyrrole-3-carboxylate (Intermediate C)

C

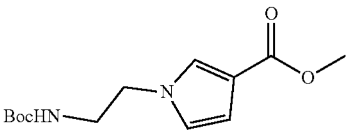

To a solution of methyl 1H-pyrrole-3-carboxylate (300 mg, 2.40 mmol) in DMF (5 mL) was added $Cs_2CO_3$ (2.34 g, 7.19 mmol) at 0° C. under $N_2$ and the mixture was stirred at 0° C. for 0.5 h. Then tert-butyl (2-bromoethyl)carbamate (805.94 mg, 3.60 mmol) was added and the mixture was stirred at 80° C. for 16 h. The reaction mixture was filtered and filtration was evaporated to dryness. The residue was purified by Prep-HPLC (FA condition) and lyophilized to give Intermediate C (420 mg, 1.55 mmol, 64.64% yield) as yellow solid. $^1H$ NMR (400 MHz, Methanol-$d_4$) δ 7.34 (s, 1H), 6.70-6.69 (m, 1H), 6.49 (br s, 1H), 4.01-3.98 (m, 2H), 3.76 (s, 3H), 3.36-3.33 (m, 2H), 1.40 (s, 9H).

Step 2: Preparation of 1-(2-((tert-butoxycarbonyl)amino)ethyl)-1H-pyrrole-3-carboxylic acid (Intermediate D)

D

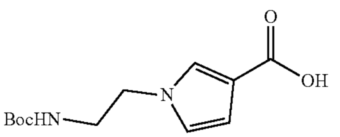

To a solution of Intermediate C (250 mg, 931.76 μmol) in MeOH (1 mL) was added aq. NaOH (2 M, 559.06 μL), the mixture was stirred at 30° C. for 1 h. 1.5 ml of aq. HCl (1M) and water (30.0 mL) was added and the mixture was extracted with EtOAc (30.0 mL×3). The combined organics were washed with water and brine, dried over $Na_2SO_4$, filtered and filtration was evaporated to dryness to give Intermediate D (200 mg, 786.53 μmol, 84.41% yield) as yellow oil, which was used for the next step directly. $^1H$ NMR (400 MHz, Methanol-$d_4$) δ 7.33 (s, 1H), 6.70-6.69 (m, 1H), 6.49 (br s, 1H), 4.01-3.98 (m, 2H), 3.36-3.33 (m, 2H), 1.41 (s, 9H).

Step 3: Preparation of tert-butyl (2-(3-((2-oxo-2-((4-(3-(pyridin-4-yl)phenyl)thiazol-2-yl)amino)ethyl)carbamoyl)-1H-pyrrol-1-yl)ethyl)carbamate (Intermediate F)

F

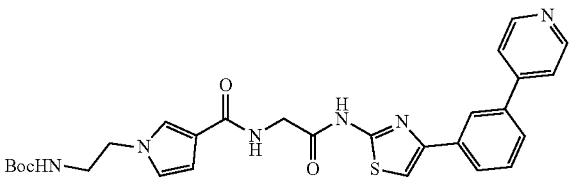

To a mixture of Intermediate D (50 mg, 196.63 μmol) and 2-amino-N-(4-(3-(pyridin-4-yl)phenyl)thiazol-2-yl)acetamide (prepared according to the method in Example 4) (68.20 mg, 196.63 μmol, HCl salt) in DMF (2 mL) was added DIPEA (101.65 mg, 786.53 μmol, 137.00 μL). The mixture was stirred at 30° C. for 15 min, then EDCI (56.54 mg, 294.95 μmol) and HOBt (39.85 mg, 294.95 μmol) was added and stirred at 30° C. for 6 hours. The reaction solution was poured into $H_2O$ (3 mL) and stirred for 5 min. The precipitate was collected by filtration and washed with MeOH (3 mL) and dried in vacuum to give Intermediate F (90 mg, 163.00 μmol, 82.89% yield) as white solid. LCMS (ESI) m/z$[M+H]^+$=547.2.

Step 4: Preparation of 1-(2-aminoethyl)-N-(2-oxo-2-((4-(3-(pyridin-4-yl)phenyl)thiazol-2-yl)amino)ethyl)-1H-pyrrole-3-carboxamide (Compound 38)

Compound 38

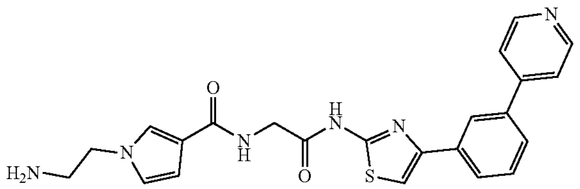

To a mixture of Intermediate F (40 mg, 73.17 μmol) in DCM (0.5 mL) was added TFA (166.87 mg, 1.46 mmol, 108.36 μL). The mixture was stirred at 30° C. for 0.5 hours. The reaction mixture was evaporated to dryness. The residue was triturated in MTBE (5 mL) and stirred for 5 min. The precipitate was collected by filtration and washed with MTBE (5 mL) and dried in vacuum to give Compound 38 (18.52 mg, 33.04 μmol, 45.15% yield, TFA salt) as yellow solid. LCMS (ESI) m/z $[M+H]^+$=447.1; $^1H$ NMR (400 MHz, Methanol-$d_4$) δ 8.85 (d, J=6.8 Hz, 2H), 8.48-8.47 (m, 1H), 8.36-8.34 (m, 2H), 8.18 (d, J=8.0 Hz, 1H), 7.90 (d, J=8.4 Hz, 1H), 7.69-7.65 (m, 1H), 7.62 (s, 1H), 7.43-7.42 (m, 1H), 6.86-6.85 (m, 1H), 6.67-6.66 (m, 1H), 4.29-4.26 (m, 4H), 3.39-3.35 (m, 2H).

Example 38. Preparation of N-(2-oxo-2-((4-(3-(pyridin-4-yl)phenyl)thiazol-2-yl)amino)ethyl)-1-(piperidin-4-yl)-1H-pyrrole-3-carboxamide (Compound 39)

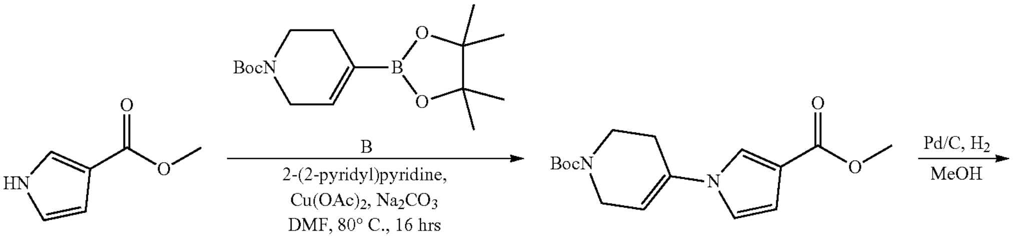

A

C

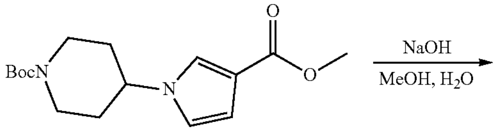

D

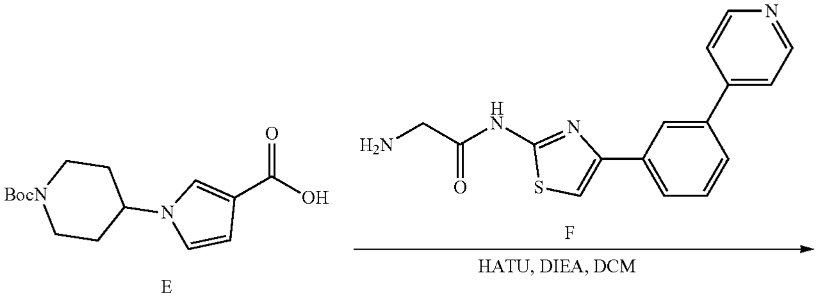

E

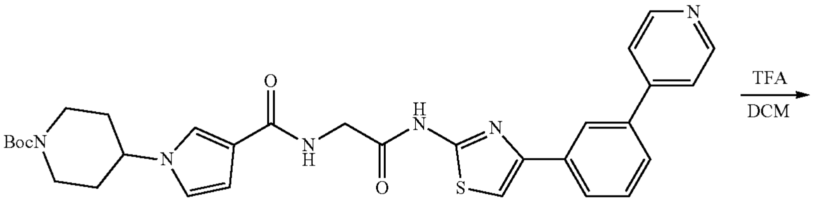

G

-continued

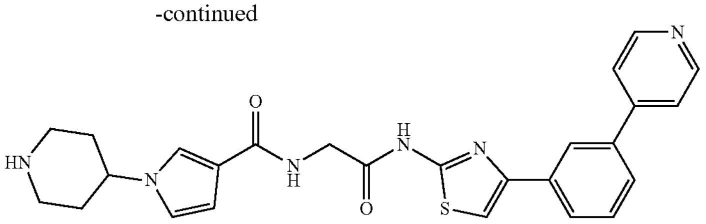

Compound 39

Step 1: Preparation of tert-butyl 4-(3-(methoxycarbonyl)-1H-pyrrol-1-yl)-5,6-dihydropyridine-1(2H)-carboxylate (Intermediate C)

C

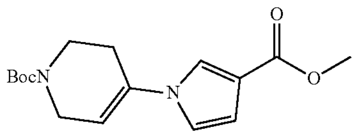

A mixture of methyl 1H-pyrrole-3-carboxylate (500 mg, 4.00 mmol), tert-butyl 4-(4,4,5,5-tetramethyl-1,3,2-dioxaborolan-2-yl)-3,6-dihydro-2H-pyridine-1-carboxylate (2.47 g, 7.99 mmol), copper (II) acetate (870.95 mg, 4.80 mmol), 2-(2-pyridyl)pyridine (624.10 mg, 4.00 mmol) and $Na_2CO_3$ (847.07 mg, 7.99 mmol) in DMF (30 mL) was stirred at 80° C. for 16 h. The mixture was poured into water (50 mL) and extracted with EtOAc (30 mL×3). The combined organic layer was washed with water (15 mL×3) and brine (15 mL×2), then dried over $Na_2SO_4$, filtered and concentrated under vacuum. The residue was purified by column chromatography ($SiO_2$, PE:EtOAc=20:1-1:1) to give Intermediate C (360 mg, 1.18 mmol, 29.41% yield) as yellow oil. LCMS (ESI) m/z $[M+H-56]^+$=251.1; $^1H$ NMR (400 MHz, $CDCl_3$) δ 7.54-7.47 (m, 1H), 6.89-6.85 (m, 1H), 6.67-6.62 (m, 1H), 5.77 (br s, 1H), 4.09 (br d, J=2.8 Hz, 2H), 3.83 (s, 3H), 3.71-3.68 (m, 2H), 2.64-2.50 (m, 2H), 1.51 (s, 9H).

Step 2: Preparation of tert-butyl 4-(3-(methoxycarbonyl)-1H-pyrrol-1-yl)piperidine-1-carboxylate (Intermediate D)

D

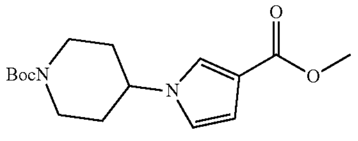

To a solution of Intermediate C (300 mg, 979.25 μmol) in MeOH (30 mL) was added ammonium formate (617.48 mg, 9.79 mmol) and Pd/C (200 mg, 10% purity). The mixture was stirred at 70° C. for 16 h. The mixture was diluted with MeOH (30 mL) and filtered to remove Pd/C. The filtrate was concentrated under vacuum to give Intermediate D (300 mg, crude) as yellow oil, which was used to next step directly without further purification. LCMS (ESI) m/z $[M+Na]^+$= 331.2; $^1H$ NMR (400 MHz, chloroform-d) δ 7.29-7.28 (m, 1H), 6.59-6.58 (m, 1H), 6.54-6.48 (m, 1H), 4.19 (br d, J=6.0 Hz, 2H), 3.92-3.84 (m, 1H), 3.72 (s, 3H), 2.78-2.76 (m, 2H), 1.98 (br d, J=12.0 Hz, 2H), 1.78-1.68 (m, 2H), 1.41 (s, 9H).

Step 3: Preparation of 1-(1-(tert-butoxycarbonyl)piperidin-4-yl)-1H-pyrrole-3-carboxylic acid (Intermediate E)

E

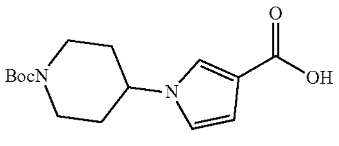

To a solution of Intermediate D (300 mg, 972.85 μmol) in MeOH (10 mL) was added Water (10 mL) and NaOH (38.91 mg, 972.85 μmol). The mixture was stirred at 30° C. for 3 h. The mixture was diluted with water (50 mL) and extracted with EtOAc (10 mL×3). The organic layers were discarded and the aqueous was treated with HCl (2M) to adjusted pH to 6-7, then extracted with EtOAc (10 mL×5). The combined organic layer was washed with water (5 mL×3) and brine (5 mL×2), then dried over $Na_2SO_4$, filtered and concentrated under vacuum to give Intermediate E (140 mg, 475.63 μmol, 48.89% yield) as yellow oil, which was used to next step directly without further purification. $^1H$ NMR (400 MHz, $CDCl_3$) δ 7.36 (br s, 1H), 6.58 (br d, J=17.2 Hz, 2H), 4.21 (br s, 2H), 3.92-3.86 (m, 1H), 2.78-2.73 (m, 2H), 1.98 (br d, J=11.4 Hz, 2H), 1.81-1.65 (m, 2H), 1.41 (s, 9H).

Step 4: Preparation of tert-butyl 4-(3-((2-oxo-2-((4-(3-(pyridin-4-yl)phenyl)thiazol-2-yl)amino)ethyl)carbamoyl)-1H-pyrrol-1-yl)piperidine-1-carboxylate (Intermediate G)

G

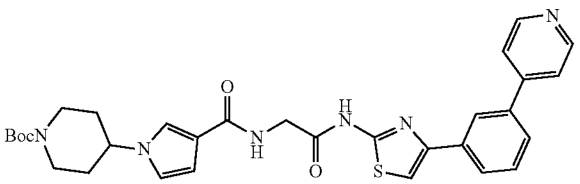

To a solution of intermediate E (20 mg, 67.95 μmol) in DMF (2 mL) was added HATU (32.29 mg, 84.93 μmol) and DIEA (21.95 mg, 169.87 μmol). Then 2-amino-N-[4-[3-(4-pyridyl)phenyl]thiazol-2-yl]acetamide (prepared according to the method in Example 4) (19.64 mg, 56.62 μmol, HCl salt) was added. The mixture was stirred at 30° C. for 2 h. The mixture was poured into water (30 mL) and extracted with EtOAc (10 mL×3). The combined organic layer was washed with water (5 mL×3) and brine (5 mL×2), then dried over $Na_2SO_4$, filtered and concentrated under vacuum to give Intermediate G (30 mg, crude) as yellow oil which was used to next step directly. LCMS (ESI) m/z $[M+H]^+$=587.2.

Step 5: Preparation of N-(2-oxo-2-((4-(3-(pyridin-4-yl)phenyl)thiazol-2-yl)amino)ethyl)-1-(piperidin-4-yl)-1H-pyrrole-3-carboxamide (Compound 39)

Compound 39

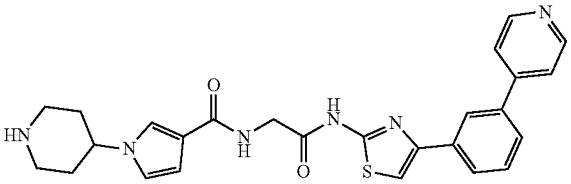

A mixture of Intermediate G (25 mg, 42.61 μmol) in DCM (3 mL) and TFA (0.5 mL) was stirred at 30° C. for 2 h. The mixture was diluted with DCM (30 mL) and concentrated under reduced pressure. This operation was repeated three times. The residue was purified by Prep-HPLC (mobile phase: [water (0.1% TFA)-acetonitrile]; B %: 5%-35%, 9 min) and lyophilized to give Compound 39 (15.28 mg, 25.44 μmol, 59.70% yield, TFA salt) as yellow solid. LCMS (ESI) m/z $[M+H]^+$=487.2; $^1H$ NMR (400 MHz, DMSO-$d_6$) δ 12.39 (s, 1H), 8.82 (d, J=6.4 Hz, 2H), 8.73 (br d, J=10.0 Hz, 1H), 8.46 (br d, J=10.0 Hz, 1H), 8.38 (s, 1H), 8.28-8.25 (m, 1H), 8.07 (d, J=7.8 Hz, 1H), 8.03 (d, J=6.2 Hz, 2H), 7.88-7.83 (m, 2H), 7.66-7.63 (m, 1H), 7.42-7.41 (m, 1H), 6.87-6.86 (m, 1H), 6.55-6.54 (m, 1H), 4.35-4.23 (m, 1H), 4.12 (br d, J=5.6 Hz, 2H), 3.43 (br d, J=12.8 Hz, 2H), 3.13-2.99 (m, 2H), 2.18 (br d, J=12.2 Hz, 2H), 2.07-1.91 (m, 2H).

Example 39. Preparation of 1-((2-aminoethyl)sulfonyl)-N-(2-oxo-2-((4-(3-(pyridin-4-yl)phenyl)thiazol-2-yl)amino)ethyl)-1H-pyrrole-3-carboxamide (Compound 40)

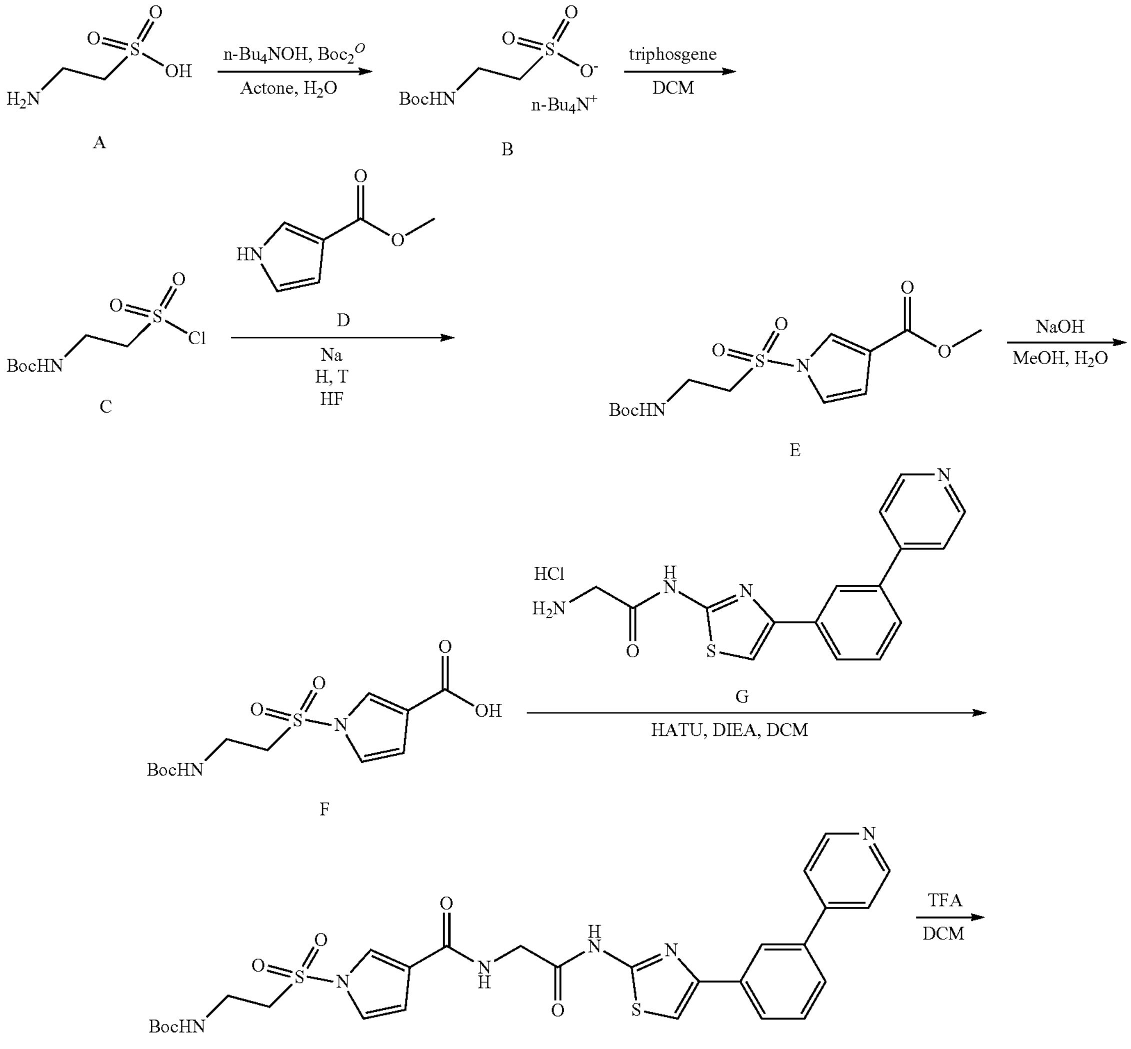

A B C E F

H

-continued

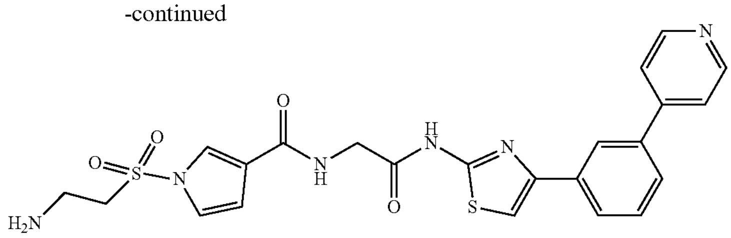

Compound 40

Step 1: Preparation of tetrabutylammonium 2-((tert-butoxycarbonyl)amino)ethanesulfonate (Intermediate B)

B

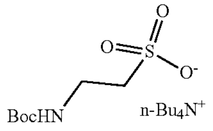

2-aminoethanesulfonic acid (1.25 g, 9.99 mmol, 1.25 mL) was dissolved in $H_2O$ (10 mL), and then tetrabutylammonium; hydroxide (6.48 g, 9.99 mmol, 8.10 mL, 40% purity) was added. Then $Boc_2O$ (2.18 g, 9.99 mmol, 2.29 mL) in acetone (30 mL) was added dropwise. The mixture was stirred at 25° C. for 16 h. The reaction mixture was concentrated under reduced pressure to remove acetone. The aqueous layer was extracted with DCM (20 mL×3). The combined organic layers were washed with brine (20 mL), dried over $Na_2SO_4$, filtered and concentrated under reduced pressure to give Intermediate B (4 g, crude) as colorless oil.

Step 2: Preparation of tert-butyl (2-(chlorosulfonyl)ethyl)carbamate (Intermediate C)

C

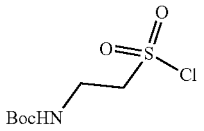

To a solution of Intermediate B (1.8 g, 3.86 mmol) in DCM (13 mL) was added triphosgene (457.79 mg, 1.54 mmol) and DMF (28.19 mg, 385.67 μmol, 29.67 μL) in one portion at 20° C. under $N_2$. The mixture was stirred at 20° C. for 0.5 hour. The reaction mixture was concentrated under reduced pressure to give a residue. The residue was dissolved in PE/EtOAc (2:1, v/v, 5 mL), then purified by column chromatography ($SiO_2$, Petroleum ether/EtOAc=2:1) and concentrated under reduced pressure to give Intermediate C (500 mg, crude) as a white solid. $^1H$ NMR (400 MHz, $CDCl_3$) δ 5.11 (br s, 1H), 3.92-3.90 (m, 2H), 3.80-3.76 (m, 2H), 1.46 (s, 9H).

Step 3: Preparation of methyl 1-((2-((tert-butoxycarbonyl)amino)ethyl)sulfonyl)-1H-pyrrole-3-carboxylate (Intermediate E)

E

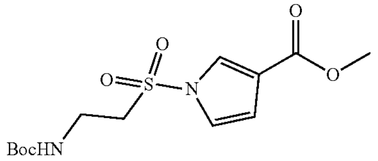

To methyl 1H-pyrrole-3-carboxylate (100 mg, 799.20 μmol) in THF (2 mL) was added NaH (95.89 mg, 2.40 mmol, 60% purity) in one portion at 0° C. under $N_2$. The mixture was stirred at 0° C. for 30 min, then Intermediate C (233.73 mg, 959.04 μmol) was added to this solution and heated to 20° C. and stirred for 0.5 hours. The reaction mixture was quenched by addition $NH_4Cl$ 20 mL at 20° C. and extracted with EtOAc (20 mL×3). The combined organic layers were washed with brine (30 MI), dried over $Na_2SO_4$, filtered and concentrated under reduced pressure to give a residue. The reaction was purified by reversed phase ($NH_3 \cdot H_2O$), concentrated under reduced pressure to remove MeCN and extracted with EtOAc 30 mL (10 mL×3). The combined organic layers were washed with brine (20 mL), dried over $Na_2SO_4$, filtered and concentrated under reduced pressure to give Intermediate E (100 mg, 288.83 μmol, 36.14% yield) as a light yellow solid. $^1H$ NMR (400 MHz, $CDCl_3$) δ 7.72-7.71 (m, 1H), 7.10-7.09 (m, 1H), 6.78-6.77 (m, 1H), 4.86 (br s, 1H), 3.85 (s, 3H), 3.52 (br s, 4H), 1.41 (s, 9H).

Step 4: Preparation of 1-((2-((tert-butoxycarbonyl)amino)ethyl)sulfonyl)-1H-pyrrole-3-carboxylic acid (Intermediate F)

F

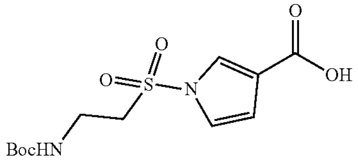

To a solution of Intermediate E (50 mg, 150.43 μmol) in MeOH (0.2 mL) and THF (0.1 mL) was added aq. NaOH (2 M, 225.65 μL). The mixture was stirred at 25° C. for 0.5 h. The reaction mixture was acidified with 2N HCl to pH=6-7, then the mixture was concentrated in vacuum to give Intermediate F (50 mg, crude) as a yellow solid. LCMS (ESI) m/z $[M+H-100]^+$=218.2.

Step 5: Preparation of tert-butyl (2-((3-((2-oxo-2-((4-(3-(pyridin-4-yl)phenyl)thiazol-2-yl)amino)ethyl)carbamoyl)-1H-pyrrol-1-yl)sulfonyl)ethyl)carbamate (Intermediate H)

H

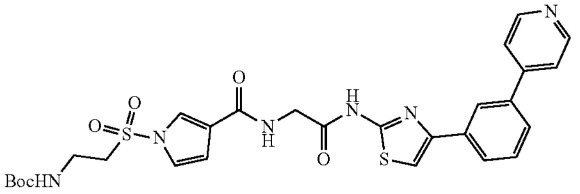

To a solution of Intermediate F (49.23 mg, 154.65 μmol), HATU (58.80 mg, 154.65 μmol) and DIEA (99.94 mg, 773.26 μmol, 134.69 μL) in DCM (0.6 mL) was added 2-amino-N-(4-(3-(pyridin-4-yl)phenyl)thiazol-2-yl)acetamide (prepared according to the method in Example 4) (40 mg, 115.33 μmol, HCl salt). The mixture was stirred at 25° C. for 2 h. Then the mixture was concentrated under reduced pressure to give a residue. The crude product was purified by reversed-phase HPLC (0.1% $NH_3 \cdot H_2O$). The solution was concentrated in vacuum to remove MeCN, then the aqueous layer was extracted with EtOAc (50 mL×3). The combined organic phases were concentrated in vacuum to give Intermediate H. (20 mg, 28.29 μmol, 21.95% yield) as a yellow solid. LCMS (ESI) m/z $[M+H]^+$=611.2.

Step 6: Preparation of 1-((2-aminoethyl)sulfonyl)-N-(2-oxo-2-((4-(3-(pyridin-4-yl)phenyl)thiazol-2-yl)amino)ethyl)-1H-pyrrole-3-carboxamide (Compound 40)

Compound 40

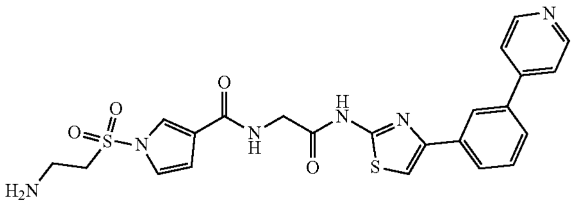

A mixture of Intermediate H (20 mg, 32.75 μmol) in TFA (0.05 mL) and DCM (0.5 mL) was stirred at 25° C. for 1 h under $N_2$ atmosphere. The reaction mixture was concentrated under reduced pressure to give a residue. The residue was purified by prep-HPLC (mobile phase: [water (0.1% TFA)-acetonitrile]; B %: 5%-35%) and lyophilized to give Compound 40 (6.76 mg, 13.24 μmol, 40.43% yield) as a white solid. LCMS (ESI) m/z $[M+H]^+$=511.1; $^1H$ NMR (400 MHz, Methanol-$d_4$) δ 8.86-8.84 (m, 2H), 8.47 (s, 1H), 8.37-8.35 (m, 2H), 8.18 (d, J=8.30 Hz, 1H), 7.91-7.87 (m, 2H), 7.69-7.65 (m, 1H), 7.63 (s, 1H), 7.36-7.35 (m, 1H), 6.90-6.89 (m, 1H), 4.28 (s, 2H), 3.92-3.88 (m, 2H), 3.33-3.30 (m, 2H).

Example 40. Preparation of 1-(tert-butyl)-N-(2-oxo-2-((4-(3-(pyridin-4-yl)phenyl)thiazol-2-yl)amino)ethyl)-1H-pyrrole-3-carboxamide (Compound 41)

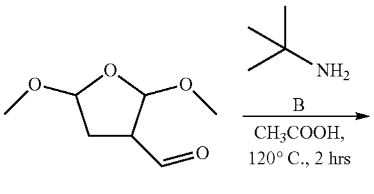

A

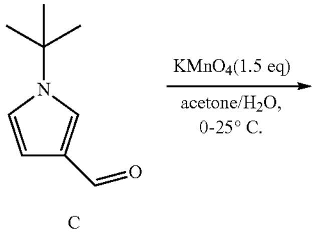

C

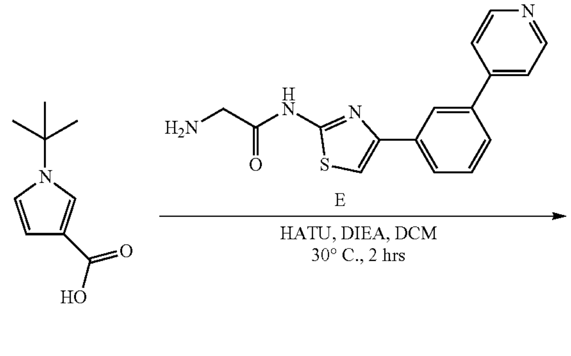

D

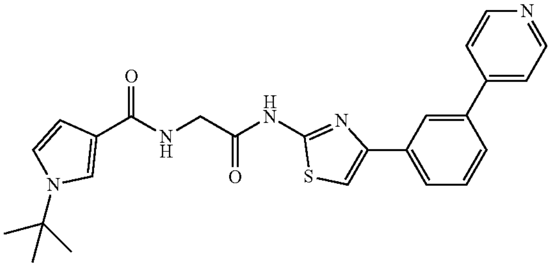

Compound 41

Step 1: Preparation of 1-(tert-butyl)-N-(2-oxo-2-((4-(3-(pyridin-4-yl)phenyl)thiazol-2-yl)amino)ethyl)-1H-pyrrole-3-carboxamide (Compound 41)

Compound 41

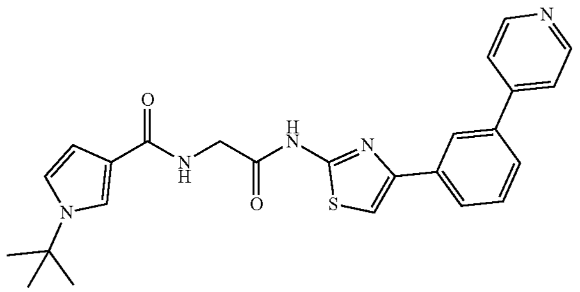

To a solution of 1-(tert-butyl)-1H-pyrrole-3-carboxylic acid [prepared according to the method in Example 34] (36.16 mg, 216.24 μmol) in DCM (3 mL) was added HATU (82.22 mg, 216.24 μmol) and DIEA (55.89 mg, 432.48 μmol, 75.33 μL). Then 2-amino-N-[4-[3-(4-pyridyl)phenyl]thiazol-2-yl]acetamide [prepared according to the method in Example 4] (50 mg, 144.16 μmol, HCl salt) was added. The mixture was stirred at 30° C. for 2 h. The mixture was diluted with DCM (30 mL) and washed with water (5 mL×3) and brine (5 mL×2), dried over $Na_2SO_4$, filtered and concentrated under vacuum. The residue was purified by Prep-HPLC (mobile phase: [water (0.1% TFA)-acetonitrile]; B %: 25%-55%) and lyophilized to give Compound 41 (23.32 mg, 40.66 μmol, 28.20% yield, TFA salt) as a white solid. LCMS (ESI) m/z $[M+H]^+$=460.3; $^1$H NMR (400 MHz, DMSO-$d_6$) δ 12.36 (s, 1H), 8.85 (br d, J=6.6 Hz, 2H), 8.40 (s, 1H), 8.21-8.16 (m, 1H), 8.15-8.06 (m, 3H), 7.90-7.83 (m, 2H), 7.68-7.62 (m, 1H), 7.53 (s, 1H), 6.98-6.97 (m, 1H), 6.50-6.46 (m, 1H), 4.11 (d, J=6.0 Hz, 2H), 1.50 (s, 9H).

Example 41. Preparation of 1-(1-amino-2-methylpropan-2-yl)-N-(2-oxo-2-((4-(3-(pyridin-4-yl)phenyl)thiazol-2-yl)amino)ethyl)-1H-pyrrole-3-carboxamide (Compound 42)

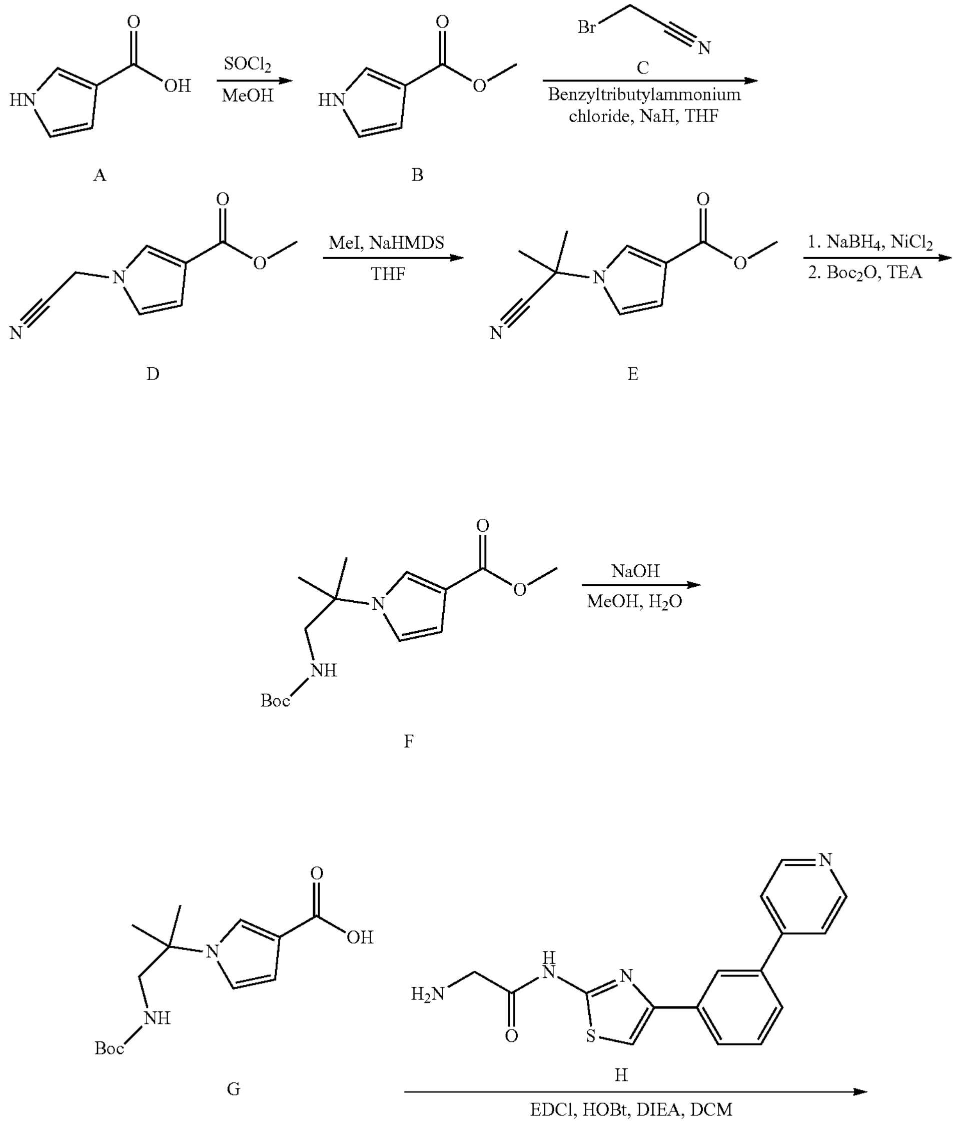

-continued

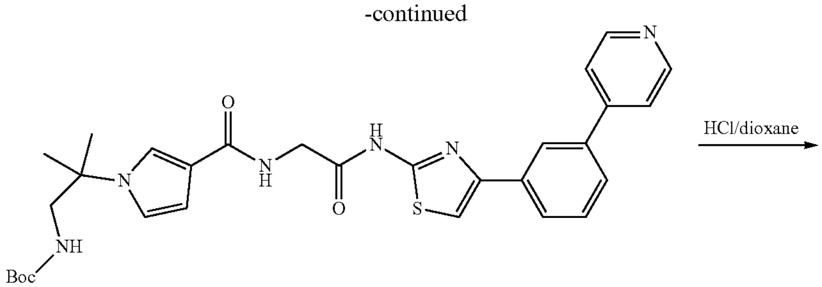

I

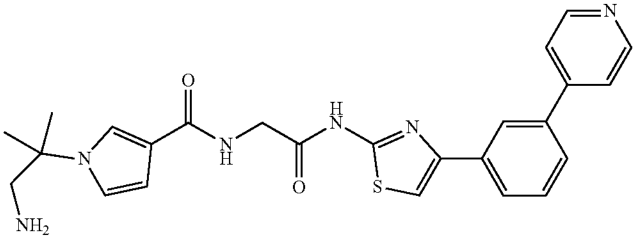

Compound 42

Step 1: Preparation of methyl 1-[2-(tert-butoxycarbonylamino)-1,1-dimethyl-ethyl]pyrrole-3-carboxylate (Intermediate F)

F

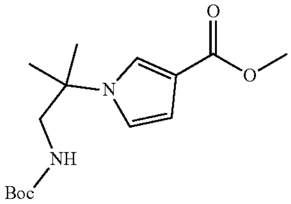

To a solution of methyl 1-(2-cyanopropan-2-yl)-1H-pyrrole-3-carboxylate [prepared according to method in Example 33] (2 g, 9.47 mmol, 1 eq) and NiCl2·6H2O (5.63 g, 23.67 mmol) in MeOH (50 mL) was added $NaBH_4$ (3.58 g, 94.69 mmol) at 0° C. and stirred for 1 hour, then TEA (2.87 g, 28.41 mmol, 3.95 mL) and $Boc_2O$ (4.13 g, 18.94 mmol, 4.35 mL) was added to the reaction mixture, and stirred at 25° C. for another 2 h. The reaction mixture was acidified to pH=5 by aq. HCl (2 M), extracted with EtOAc (150 mL×3). The combined organic layers were washed with brine (50 mL), dried over $Na_2SO_4$, filtered and concentrated under reduced pressure to give a residue. The residue was purified by column chromatography ($SiO_2$, Petroleum ether/EtOAc=50/1 to 5:1) and concentrated in vacuum to give Intermediate F (1.93 g, 6.19 mmol, 65.34% yield) as a yellow oil. LCMS (ESI) m/z $[M+H-100]^+$=197.3. $^1H$ NMR (400 MHz, $CDCl_3$) δ 7.44 (s, 1H), 6.76 (s, 1H), 6.62 (s, 1H), 4.30 (s, 1H), 3.80 (s, 3H), 3.41 (s, 2H), 1.53 (s, 6H), 1.40 (s, 9H).

Step 2: Preparation of 1-[2-(tert-butoxycarbonylamino)-1,1-dimethyl-ethyl]pyrrole-3-carboxylic acid (Intermediate G)

G

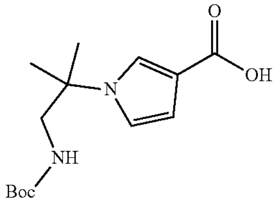

A solution of Intermediate F (1.87 g, 6.31 mmol) and NaOH (2 M, 6.31 mL) in MeOH (20 mL) was stirred at 25° C. for 2 h, then another batch of NaOH (504.75 mg, 12.62 mmol) was added to the reaction mixture. The reaction mixture was stirred at 55° C. for another 2 hr. The reaction mixture was adjusted pH=6 with aq. HCl (2 M) and extracted by EtOAc (50 mL×3). The combined organic layers were washed with brine (15 mL×3), dried over $Na_2SO_4$, filtered and concentrated under reduced pressure to give a residue. The residue was purified by reversed phase HPLC (FA condition), the combined fraction was extracted by EtOAc (100 mL×3). The combined organic layers were washed with brine (255 mL×3), dried over $Na_2SO_4$, filtered and concentrated under reduced pressure to give Intermediate G (1.47 g, 5.21 mmol, 82.51% yield) as yellow oil. LCMS (ESI) m/z $[M+23]^+$=305.0. $^1H$ NMR (400 MHz, Methanol-$d_4$) δ 7.49 (s, 1H), 6.89 (d, J=5.6 Hz, 1H), 6.51 (d, J=5.2 Hz, 1H), 3.32 (s, 2H), 1.52 (s, 6H), 1.39 (s, 9H).

Step 3: Preparation of tert-butyl (2-methyl-2-(3-((2-oxo-2-((4-(3-(pyridin-4-yl)phenyl)thiazol-2-yl)amino)ethyl)carbamoyl)-1H-pyrrol-1-yl)propyl)carbamate (Intermediate I)

I

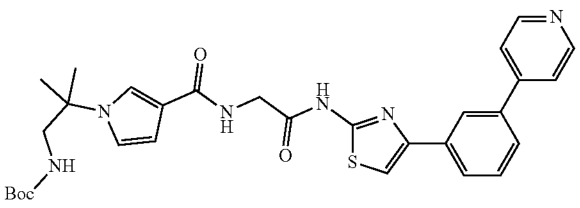

To a solution of Intermediate G (97.68 mg, 345.99 μmol), EDCI (66.33 mg, 345.99 μmol), HOBt (46.75 mg, 345.99 μmol) and DIEA (186.32 mg, 1.44 mmol, 251.10 μL) in DCM (2 mL) was added 2-amino-N-[4-[3-(4-pyridyl)phenyl]thiazol-2-yl]acetamide [prepared according to method in Example 4] (100 mg, 288.32 μmol, HCl salt), then the mixture was stirred at 25° C. for 2 h. The reaction mixture was concentrated under vacuum to give residue. The residue was triturated with MeOH (10 mL) at 25° C. for 15 min, then filtered and dried in vacuum to give Intermediate I (70 mg, 110.84 μmol, 38.44% yield) as a white solid. LCMS (ESI) m/z $[M+H]^+$=575.5.

Step 4: Preparation of 1-(1-amino-2-methylpropan-2-yl)-N-(2-oxo-2-((4-(3-(pyridin-4-yl)phenyl)thiazol-2-yl)amino)ethyl)-1H-pyrrole-3-carboxamide (Compound 42)

Compound 42

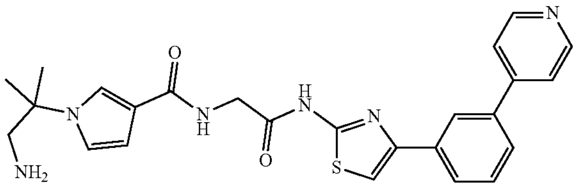

A solution of Intermediate I (68 mg, 118.32 μmol) in HCl/dioxane (1 mL) was stirred at 25° C. for 2 hr. The reaction mixture was concentrated under vacuum to give residue. The residue was purified by reversed phase HPLC (0.1% FA), the fraction was lyophilized to give Compound 42 (26.23 mg, 48.87 μmol, 41.30% yield, FA salt) as a white solid. LCMS (ESI) m/z $[M+H]^+$=475.0; $^1H$ NMR (400 MHz, DMSO-$d_6$) δ 8.69-8.68 (m, 2H), 8.31-8.30 (m, 1H), 8.23-8.20 (m, 2H), 8.03-8.00 (m, 1H), 7.83-7.76 (m, 4H), 7.62-7.58 (m, 1H), 7.50 (s, 1H), 6.94 (s, 1H), 6.51 (s, 1H), 4.10 (d, J=6.0 Hz, 2H), 2.83 (s, 2H), 1.46 (s, 6H).

Example 42. Preparation of 1-isopropylsulfonyl-N-[2-oxo-2-[[4-[3-(4-pyridyl)phenyl]thiazol-2-yl]amino]ethyl]pyrrole-3-carboxamide (Compound 43)

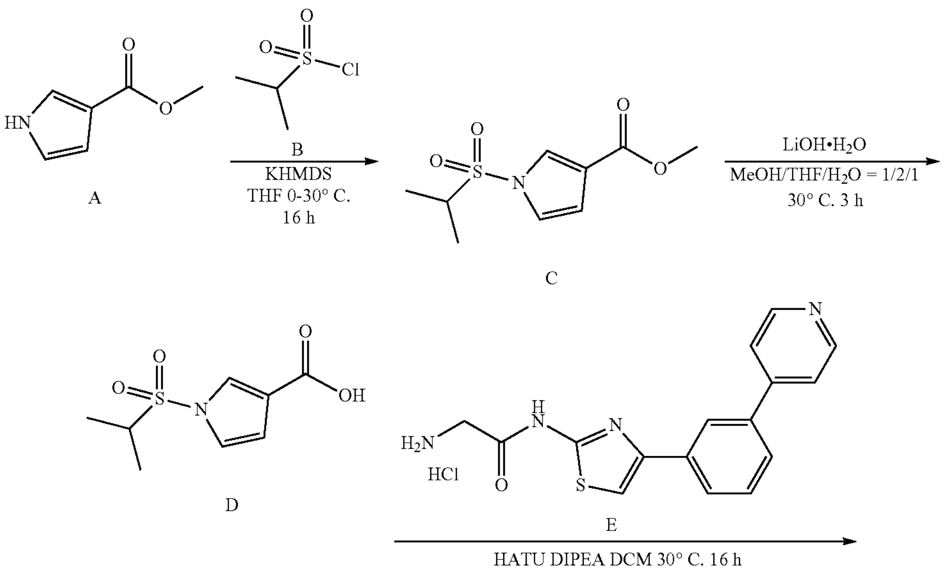

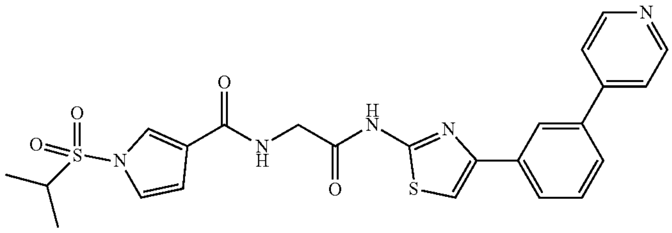

Compound 43

Step 1: Preparation of methyl 1-isopropylsulfonylpyrrole-3-carboxylate (Intermediate C)

C

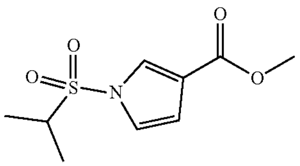

To a solution of methyl 1H-pyrrole-3-carboxylate (500 mg, 4.00 mmol) in THF (20 mL) was added KHMDS (1 M, 7.99 mL) slowly at 0° C. under $N_2$. The reaction mixture was stirred at 0° C. for 30 min under $N_2$. Then to the reaction mixture was added propane-2-sulfonyl chloride (683.82 mg, 4.80 mmol, 534.23 μL) slowly at 0° C. under $N_2$. The reaction mixture was warmed to 30° C. and stirred at 30° C. for 16 h under $N_2$. The reaction mixture was poured into $H_2O$ (100 mL) slowly and extracted with EtOAc (100 mL×3). The combined organic layers were washed with brine (50 mL), dried over anhydrous $Na_2SO_4$, filtered and concentrated under reduced pressure to afford a residue. The residue was purified by reverse phase column (FA condition) and lyophilized to afford Intermediate C (490 mg, 2.12 mmol, 53% yield) as white solid. LCMS (ESI) m/z $[M+H]^+$=232.0; $^1H$ NMR (400 MHz, $CDCl_3$) δ 7.70-7.69 (m, 1H), 7.07-7.06 (m, 1H), 6.75-6.74 (m, 1H), 3.85 (s, 3H), 3.49-3.39 (m, 1H), 1.36 (d, J=6.8 Hz, 6H).

Step 2: Preparation of 1-isopropylsulfonylpyrrole-3-carboxylic acid (Intermediate D)

D

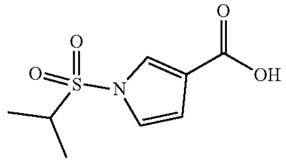

To a mixture of Intermediate C (490 mg, 2.12 mmol) in THF (10 mL) and MeOH (5 mL) was added a solution of $LiOH \cdot H_2O$ (266.73 mg, 6.36 mmol) in $H_2O$ (5 mL) at 25° C. The reaction mixture was stirred at 25° C. for 3 h. The reaction mixture was quenched by addition HCl aqueous solution (1M) to pH=4 and extracted with EtOAc (20 mL×4). The combined organic layers were dried over anhydrous $Na_2SO_4$, filtered and concentrated under reduced pressure to afford a residue. The residue was purified by reverse phase column (FA condition) to afford Intermediate D (360 mg, 1.66 mmol, 78% yield) as white solid. LCMS (ESI) m/z $[M+H]^+$=218.0; $^1H$ NMR (400 MHz, $CDCl_3$) δ 7.80-7.79 (m, 1H), 7.12-7.11 (m, 1H), 6.80-6.79 (m, 1H), 3.53-3.42 (m, 1H), 1.39 (d, J=7.2 Hz, 6H).

Step 3: Preparation of 1-isopropylsulfonyl-N-[2-oxo-2-[[4-[3-(4-pyridyl)phenyl]thiazol-2-yl]amino]ethyl]pyrrole-3-carboxamide (Compound 43)

Compound 43

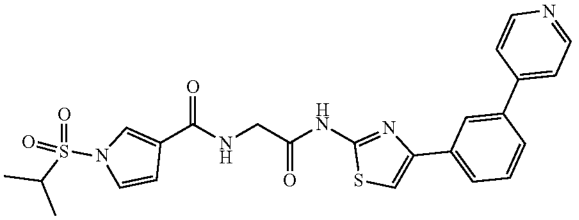

To a mixture of Intermediate D (17.00 mg, 78.27 μmol) in DCM (1 mL) was added DIPEA (50.58 mg, 391.34 μmol, 68.16 μL), HATU (44.64 mg, 117.40 μmol) and 2-amino-N-[4-[3-(4-pyridyl)phenyl]thiazol-2-yl]acetamide [prepared according to method in Example 4] (30 mg, 78.27 μmol, 2HCl salt) at 30° C. The reaction mixture was stirred at 30° C. for 16 h. The reaction mixture was filtered and the filter cake was washed with DCM (5 mL) and MeOH (2 mL) to afford Compound 43 (8.59 mg, 15.85 μmol, 20% yield) as yellow solid. LCMS (ESI) m/z $[M+H]^+$=510.1; $^1H$ NMR (400 MHz, DMSO-$d_6$) δ 12.43 (br s, 1H), 8.72-8.69 (m, 3H), 8.31 (s, 1H), 8.02 (d, J=8.0 Hz, 1H), 7.83-7.82 (m, 2H), 7.77-7.76 (m, 3H), 7.62-7.58 (m, 1H), 7.30-7.27 (m, 1H), 6.80-6.79 (m, 1H), 4.16 (d, J=5.6 Hz, 2H), 3.91-3.85 (m, 1H), 1.24 (d, J=6.8 Hz, 6H).

Example 43. Preparation of 1-(methylsulfonyl)-N-(2-oxo-2-((4-(3-(pyridin-4-yl)phenyl)thiazol-2-yl)amino)ethyl)-1H-pyrazole-4-carboxamide (Compound 44)

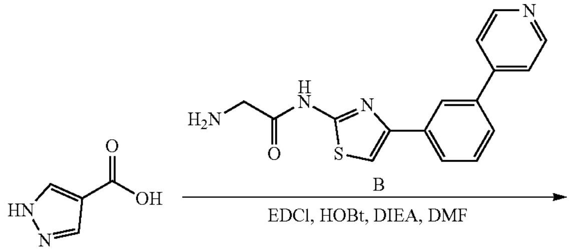

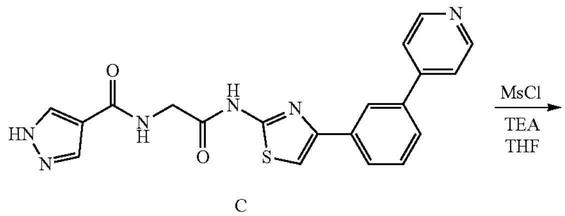

-continued

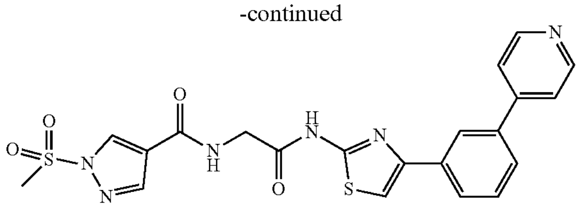

Compound 44

Step 1: Preparation of N-(2-oxo-2-((4-(3-(pyridin-4-yl)phenyl)thiazol-2-yl)amino)ethyl)-1H-pyrazole-4-carboxamide (Intermediate C)

C

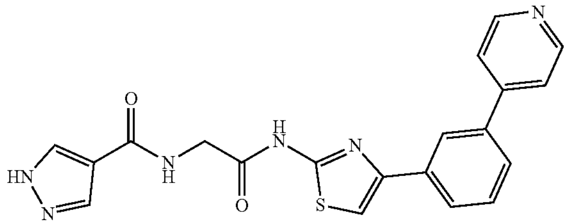

To a mixture of 1H-pyrazole-4-carboxylic acid (60 mg, 535.30 μmol), 2-amino-N-[4-[3-(4-pyridyl)phenyl]thiazol-2-yl]acetamide [prepared according to method in Example 4] (166.14 mg, 479.03 μmol, HCl salt) and DIEA (345.92 mg, 2.68 mmol, 466.20 μL) in DMF (3 mL) was added HOBt (86.80 mg, 642.36 μmol) and EDCI (123.14 mg, 642.36 μmol), and then the mixture was stirred at 25° C. for 2 h under $N_2$ atmosphere. The reaction mixture was pureed into water (5 mL), filtered and filter cake dried in the air to give crude product. The crude product was triturated with MeOH (3 mL) at 25° C. for 30 min, filtered and dried in vacuum to give Intermediate C (140 mg, 318.46 μmol, 59.49% yield) as a white solid. LCMS (ESI) m/z $[M+H]^+$= 405.0.

Step 2: Preparation of 1-(methylsulfonyl)-N-(2-oxo-2-((4-(3-(pyridin-4-yl)phenyl)thiazol-2-yl)amino)ethyl)-1H-pyrazole-4-carboxamide (Compound 44)

Compound 44

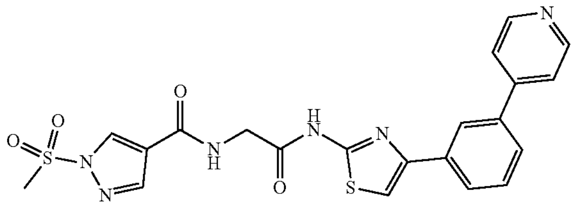

To a solution of Intermediate C (50 mg, 123.63 μmol) in THF (2 mL) was added TEA (100.08 mg, 989.01 μmol, 137.66 μL) and added MsCl (42.48 mg, 370.88 μmol, 28.71 μL) drop wise. The mixture was stirred at 25° C. for 0.5 h. The reaction mixture was diluted with water 3 mL, some of precipitate was formed, and the mixture was filtered to give filtered cake, dried in air to give crude product. The crude product was purified by Prep-HPLC (mobile phase: [water (0.1% TFA)-acetonitrile; B %: 13%-37%) and lyophilized to give Compound 44 (35.18 mg, 57.20 μmol, 46.27% yield, TFA salt) as a yellow solid. LCMS (ESI) m/z $[M+H]^+$= 482.9; $^1H$ NMR (400 MHz, DMSO-$d_6$) δ 12.47 (s, 1H), 8.95-8.92 (m, 1H), 8.82-8.81 (m, 3H), 8.37 (s, 1H), 8.29 (s, 1H), 8.08-8.05 (m, 3H), 7.86-7.84 (d, J=8.8 Hz, 2H), 7.66-7.62 (m, 1H), 4.19-4.18 (d, J=6 Hz, 2H), 3.64 (s, 3H).

Example 44. Preparation of 1-(methylsulfonyl)-N-(2-oxo-2-((4-(3-(pyridin-4-yl)phenyl)thiazol-2-yl)amino)ethyl)-1H-pyrazole-3-carboxamide (Compound 45)

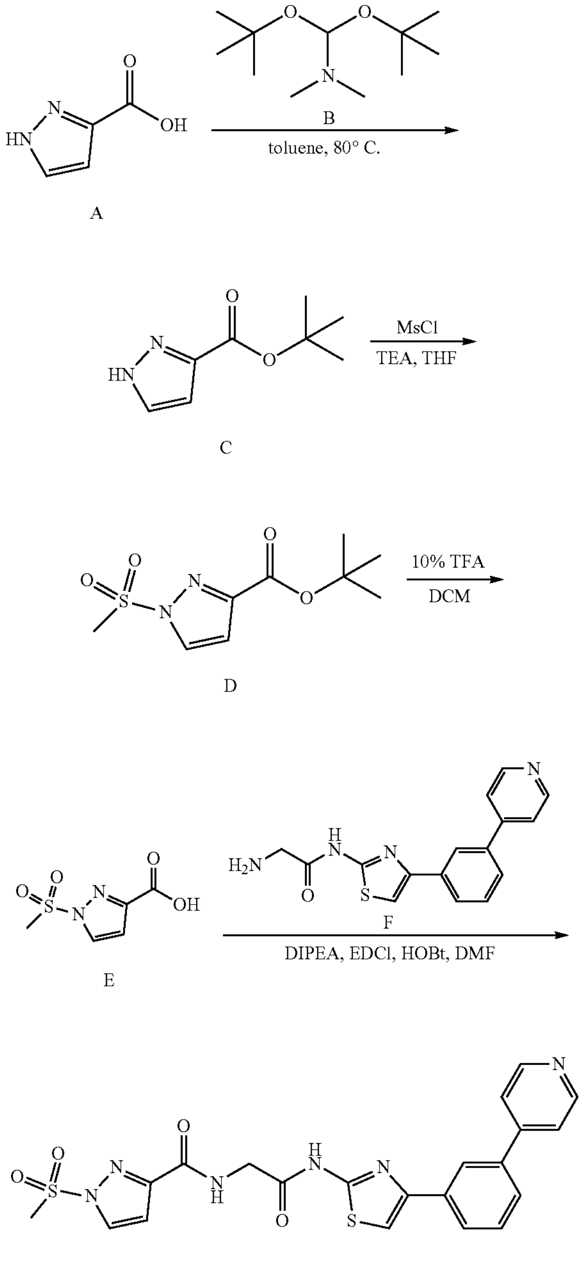

Compound 45

Step 1: Preparation of tert-butyl 1H-pyrazole-3-carboxylate (Intermediate C)

C

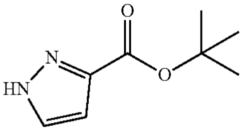

To a solution of 1H-pyrazole-3-carboxylic acid (600 mg, 5.35 mmol) in toluene (10 mL) was added 1,1-di-tert-butoxy-N,N-dimethylmethanamine (4.35 g, 21.41 mmol, 5.13 mL) at 80° C., the mixture was stirred at 80° C. for 2 h. The reaction mixture was poured into water (50.0 mL) and extracted with EtOAc (50.0 mL×3). The combined organics were washed with water and brine, dried over $Na_2SO_4$, filtered and filtration was evaporated to dryness. To the residue was added MTBE (10 mL) and stirred for 10 min, then filtered and dried in vacuum to give Intermediate C (600 mg, 3.46 mmol, 64.64% yield) as yellow solid. LCMS (ESI) m/z $[M+Na]^+$=191.3; $^1$H NMR (400 MHz, DMSO-$d_6$) δ 13.77-13.34 (m, 1H), 7.80-7.57 (m, 1H), 6.72-6.64 (m, 1H), 1.51 (s, 9H).

Step 2: Preparation of tert-butyl 1-(methylsulfonyl)-1H-pyrazole-3-carboxylate (Intermediate D)

D

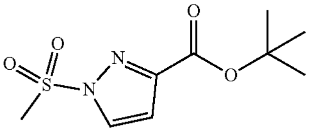

To a solution of Intermediate C (150 mg, 891.83 μmol) in THF (3 mL) was added TEA (270.73 mg, 2.68 mmol, 372.40 μL) at 0° C. under $N_2$ and the mixture was stirred at 0° C. for 10 min. Then MsCl (132.81 mg, 1.16 mmol, 89.74 μL) was added and the mixture was stirred at 30° C. for 1 h. The reaction mixture was poured into cool $NH_4Cl$ solution (50.0 mL), and extracted with EtOAc (30 mL×3). The combined organics were washed with water and brine, dried over $Na_2SO_4$, filtered and concentrated in vacuum to give Intermediate D (210 mg, crude) as yellow solid, which was used for the next step directly. LCMS (ESI) m/z $[M+H-56]^+$=190.8. $^1$H NMR (400 MHz, Methanol-$d_4$) δ 8.24 (d, J=2.8 Hz, 1H), 6.88 (d, J=2.4 Hz, 1H), 3.49 (s, 3H), 1.60 (s, 9H).

Step 3: Preparation of 1-(methylsulfonyl)-1H-pyrazole-3-carboxylic acid (Intermediate E)

E

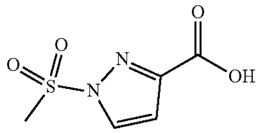

To a mixture of Intermediate D (100 mg, 406.04 μmol) in DCM (3 mL) was added TFA (462.98 mg, 4.06 mmol, 300.63 μL). The mixture was stirred at 30° C. for 1 hour. The reaction mixture was evaporated to dryness to give Intermediate E (75 mg, crude) as yellow solid. $^1$H NMR (400 MHz, Methanol-$d_4$) δ 8.27 (d, J=2.8 Hz, 1H), 6.95 (d, J=2.8 Hz, 1H), 3.51 (s, 3H).

Step 4: Preparation of 1-(methylsulfonyl)-N-(2-oxo-2-((4-(3-(pyridin-4-yl)phenyl)thiazol-2-yl)amino)ethyl)-1H-pyrazole-3-carboxamide (Compound 45)

Compound 45

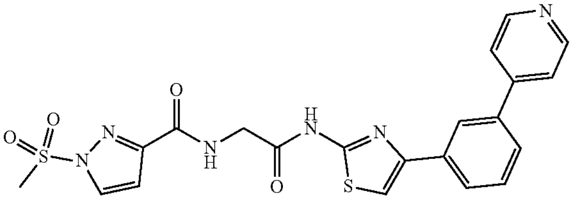

To a mixture of Intermediate E (70 mg, 368.08 μmol) and 2-amino-N-(4-(3-(pyridin-4-yl)phenyl)thiazol-2-yl)acetamide [prepared according to method in Example 4] (140.43 mg, 404.89 μmol, HCl salt) in DMF (1 mL) was added DIPEA (190.29 mg, 1.47 mmol, 256.45 μL). The mixture was stirred at 30° C. for 15 min, then EDCI (105.84 mg, 552.12 μmol) and HOBt (74.60 mg, 552.12 μmol) was added and stirred at 30° C. for 1 hours. The reaction mixture was poured into water (30.0 mL) and extracted with EtOAc (30.0 mL×3). The combined organics were washed with water and brine, dried over $Na_2SO_4$, filtered and filtration was evaporated to dryness. The residue was purified by Prep-HPLC (mobile phase: [water (0.225% FA)-acetonitrile]; B %: 10%-40%) and lyophilized to give Compound 45 (45 mg, 85.14 μmol, 23.13% yield, FA salt) as yellow solid. LCMS (ESI) m/z $[M+H]^+$=483.1; $^1$H NMR (400 MHz, DMSO-d6) δ 12.48 (br s, 1H), 8.85-8.82 (m, 1H), 8.68-8.67 (m, 2H), 8.41 (d, J=2.8 Hz, 1H), 8.30 (s, 1H), 8.01 (d, J=8.0 Hz, 1H), 7.82 (s, 1H), 7.77-7.75 (m, 3H), 7.61-7.57 (m, 1H), 6.96 (d, J=2.8 Hz, 1H), 4.20 (d, J=6.0 Hz, 2H), 3.68 (s, 3H).

Example 45. Preparation of 1-(methylsulfonyl)-N-(2-oxo-2-((4-(3-(pyridin-4-yl)phenyl)thiazol-2-yl)amino)ethyl)-1H-imidazole-4-carboxamide (Compound 46)

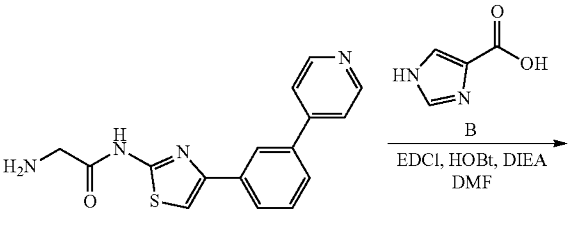

A

-continued

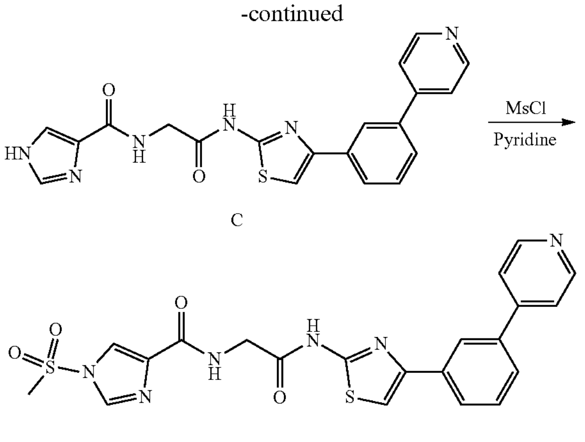

C

Compound 46

Step 1: Preparation of N-(2-oxo-2-((4-(3-(pyridin-4-yl)phenyl)thiazol-2-yl)amino)ethyl)-1H-imidazole-4-carboxamide (Intermediate C)

C

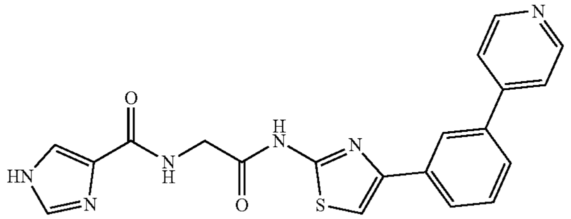

To a mixture of 2-amino-N-[4-[3-(4-pyridyl)phenyl]thiazol-2-yl]acetamide [prepared according to method in Example 4] (250 mg, 720.81 μmol, HCl salt) and 1H-imidazole-4-carboxylic acid (105.03 mg, 937.05 μmol) in DMF (4 mL) was added DIEA (372.63 mg, 2.88 mmol, 502.19 μL), EDCI (207.27 mg, 1.08 mmol) and HOBt (146.09 mg, 1.08 mmol). The resulting mixture was stirred at 25° C. for 4 h. The mixture was poured into water (30 mL) and the precipitate was collected by filtration. The precipitate was triturated in MeOH (10 mL) and stirred for 5 min. Then the precipitate was collected by filtration and washed with MTBE (2 mL) and dried in vacuum to give Intermediate C (180 mg, 417.86 μmol, 57.97% yield) as a yellow solid. LCMS (ESI) m/z $[M+H]^+$=405.2.

Step 2: Preparation of 1-(methylsulfonyl)-N-(2-oxo-2-((4-(3-(pyridin-4-yl)phenyl)thiazol-2-yl)amino)ethyl)-1H-imidazole-4-carboxamide (Compound 46)

Compound 46

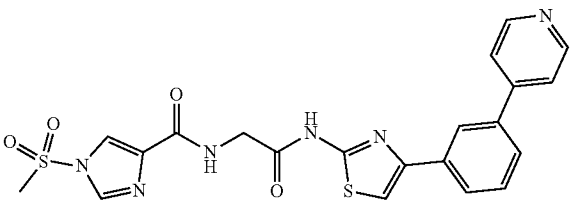

To a mixture of Intermediate C (100 mg, 247.25 μmol) in pyridine (2 mL) was added MsCl (1.42 g, 12.36 mmol, 956.86 μL) slowly at 25° C. and then the mixture was stirred at 25° C. for 0.5 h. The mixture was poured into water (50 mL) and the precipitate was collected by filtration. The precipitate was triturated in MeOH (10 mL) and stirred for 5 min. Then the precipitate was collected by filtration and washed with MTBE (3 mL) and dried in vacuum to give Compound 46 (56.32 mg, 115.20 μmol, 46.59% yield) as a yellow solid. LCMS (ESI) m/z $[M+H]^+$=482.8; $^1$H NMR (400 MHz, DMSO-$d_6$) δ 12.44 (s, 1H), 8.70-8.68 (m, 2H), 8.59-8.56 (m, 1H), 8.32-8.30 (m, 2H), 8.15 (d, J=1.2 Hz, 1H), 8.02-8.00 (m, 1H), 7.83 (s, 1H), 7.80-7.76 (m, 3H), 7.62-7.58 (m, 1H), 4.15 (d, J=6.0 Hz, 2H), 3.77 (s, 3H).

Example 46. Preparation of 1-(N,N-dimethylsulfamoyl)-N-(2-oxo-2-((4-(3-(pyridin-4-yl)phenyl)thiazol-2-yl)amino)ethyl)-1H-pyrrole-3-carboxamide (Compound 47)

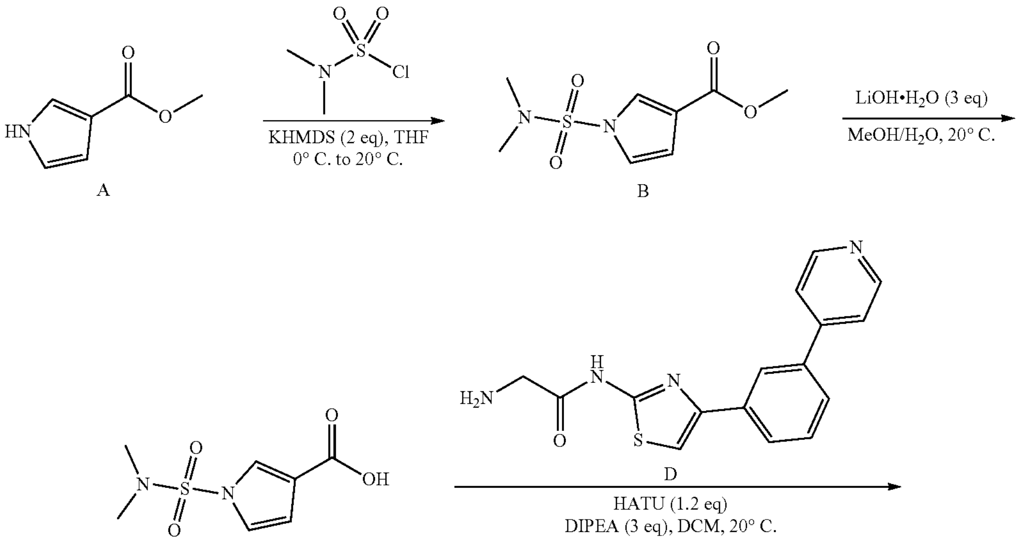

A

B

D

C

-continued

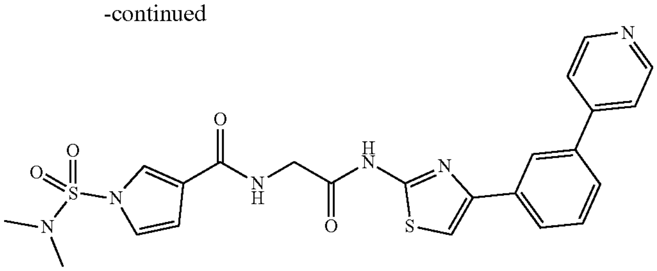

Compound 47

Step 1: Preparation of methyl 1-(N,N-dimethylsulfamoyl)-1H-pyrrole-3-carboxylate (Intermediate B)

B

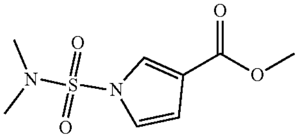

To a solution of methyl 1H-pyrrole-3-carboxylate (100 mg, 799.20 μmol) in THF (3 mL) was added KHMDS (1 M, 1.60 mL) at 0° C. The mixture was stirred at 0° C. for 30 min under $N_2$. N,N-dimethylsulfamoyl chloride (137.71 mg, 959.04 μmol, 102.77 μL) was added at 0° C. and the mixture was stirred at 20° C. for 16 h under $N_2$. The reaction was quenched by adding water (10 mL) and the resulting mixture was extracted with EtOAc (15 mL×2). The combined organic phases were washed with water (10 mL), dried over $Na_2SO_4$ and concentrated to give a residue. The residue was purified by column chromatography ($SiO_2$, Petroleum ether/EtOAc=2/1) to give Intermediate B (60 mg, 258.34 μmol, 32.32% yield) as colorless oil. LCMS (ESI) m/z $[M+H]^+$= 233.2; $^1$H NMR (400 MHz, $CDCl_3$) δ 7.70 (dd, J=2.0 Hz, 1.6 Hz, 1H) 7.07 (dd, J=3.2 Hz, 2.0 Hz, 1H), 6.73 (dd, J=3.2 Hz, 1.6 Hz, 1H), 3.86 (s, 3H), 2.86 (s, 6H).

Step 2: Preparation of 1-(N,N-dimethylsulfamoyl)-1H-pyrrole-3-carboxylic acid (Intermediate C)

C

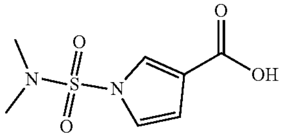

To a solution of Intermediate B (50 mg, 215.28 μmol) in MeOH (2 mL) and $H_2O$ (2 mL) was added $LiOH{\cdot}H_2O$ (18.07 mg, 430.56 μmol). The mixture was stirred at 20° C. for 16 h. The reaction mixture was adjusted pH to 4 with 1 N HCl solution and the resulting mixture was extracted with EtOAc (15 mL×2). The combined organic phases were washed with water (5 mL), dried over $Na_2SO_4$ and concentrated to afford Intermediate C (35 mg, 160.38 μmol, 74.50% yield) as yellow solid. The product was used for the next step without further purification. LCMS (ESI) m/z $[M+H]^+$= 219.2; $^1$H NMR (400 MHz, $CDCl_3$) δ 7.69 (m, 1H) 7.00 (dd, J=3.2 Hz, 1.6 Hz, 1H), 6.68 (dd, J=3.2 Hz, 1.6 Hz, 1H), 2.79 (s, 6H).

Step 3: Preparation of 1-(N,N-dimethylsulfamoyl)-N-(2-oxo-2-((4-(3-(pyridin-4-yl)phenyl)thiazol-2-yl)amino)ethyl)-1H-pyrrole-3-carboxamide (Compound 47)

Compound 47

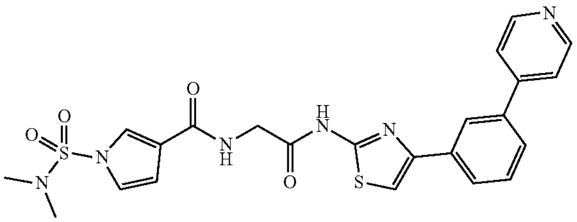

To a solution of Intermediate C (30 mg, 137.47 μmol) in DCM (3 mL) was added DIPEA (53.30 mg, 412.41 μmol, 71.83 μL) and HATU (62.72 mg, 164.96 μmol). The mixture was stirred at 20° C. for 10 min. 2-amino-N-[4-[3-(4-pyridyl)phenyl]thiazol-2-yl]acetamide [prepared according to method in Example 4] (47.68 mg, 137.47 μmol, HCl salt) was added and the mixture was stirred at 20° C. for 16 h. The reaction mixture was filtered and the filtrated cake was washed with DCM (10 mL) and dried in vacuum to afford Compound 47 (44.55 mg, 85.84 μmol, 62.44% yield) as white solid. LCMS (ESI) m/z $[M+H]^+$=511.2; $^1$H NMR (400 MHz, DMSO-$d_6$) δ 12.44 (br s, 1H), 8.72-8.64 (m, 3H), 8.31 (s, 1H), 8.02 (d, J=8.0. Hz, 1H), 7.86-7.80 (m, 2H), 7.79-7.74 (m, 3H), 7.65-7.56 (m, 1H), 7.29 (d, J=3.2 Hz, 2.0 Hz, 1H), 6.76 (d, J=3.2 Hz, 2.0 Hz, 1H), 4.16 (m, 2H), 2.81 (s, 6H).

Example 47. Preparation of N-(2-oxo-2-((4-(3-(pyridin-4-yl)phenyl)thiazol-2-yl)amino)ethyl)-1H-pyrrole-3-carboxamide (Compound 48)

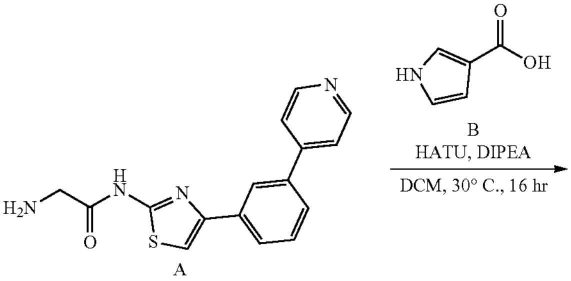

-continued

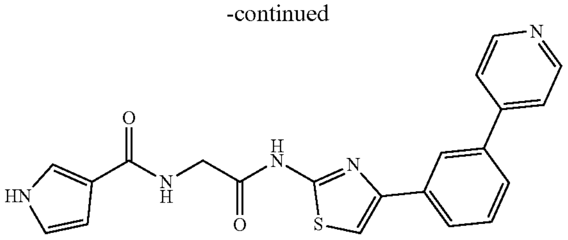

Compound 48

To a mixture of 1H-pyrrole-3-carboxylic acid (20 mg, 180.02 μmol) in DCM (2 mL) was added DIPEA (116.33 mg, 900.10 μmol, 156.78 μL), HATU (102.67 mg, 270.03 μmol) and 2-amino-N-(4-(3-(pyridin-4-yl)phenyl)thiazol-2-yl)acetamide [prepared according to method in Example 4] (69.00 mg, 180.02 μmol, 2HCl salt) at 30° C. The reaction mixture was stirred at 30° C. for 16 h. The reaction mixture was filtered and the filter cake was washed with DCM (10 mL) and MeOH (3 mL) to afford a brown solid, which was further purified by Prep-HPLC (mobile phase: [water (10 mM $NH_4HCO_3$)-acetonitrile]; B %: 23%-53%) to afford Compound 48 (2.03 mg, 4.89 μmol, 2.72% yield) as white solid. LCMS (ESI) m/z $[M+H]^+$=404.0; $^1$H NMR (400 MHz, DMSO-$d_6$) δ 12.30 (br s, 1H), 11.18 (br s, 1H), 8.69-8.67 (m, 2H), 8.31 (s, 1H), 8.18-8.17 (m, 1H), 8.02 (d, J=8.0 Hz, 1H), 7.81 (s, 1H), 7.77-7.75 (m, 3H), 7.62-7.58 (m, 1H), 7.36-7.35 (m, 1H), 6.79-6.77 (m, 1H), 6.51-6.50 (m, 1H), 4.11 (d, J=6.0 Hz, 2H).

Example 48. Preparation of 1-methyl-N-(2-oxo-2-((4-(3-(pyridin-4-yl)phenyl)thiazol-2-yl)amino)ethyl)-1H-pyrrole-3-carboxamide (Compound 49)

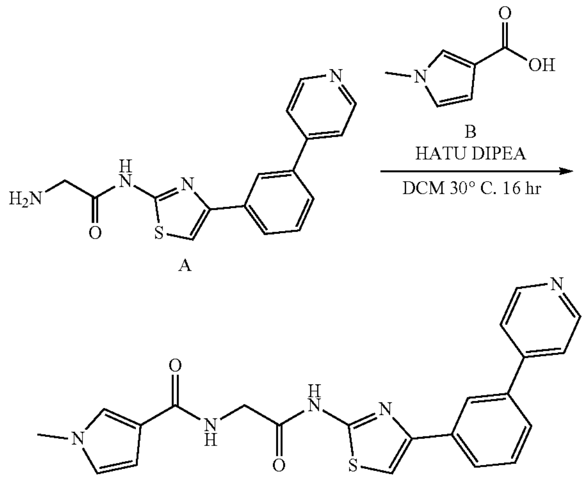

Compound 49

To a mixture of 1-methyl-1H-pyrrole-3-carboxylic acid (10.82 mg, 86.50 μmol) in DCM (1 mL) was added DIPEA (55.89 mg, 432.48 μmol, 75.33 μL), HATU (49.33 mg, 129.75 μmol) and 2-amino-N-(4-(3-(pyridin-4-yl)phenyl)thiazol-2-yl)acetamide [prepared according to method in Example 4] (30 mg, 86.50 μmol, HCl salt) at 30° C. The reaction mixture was stirred at 30° C. for 16 h. The reaction mixture was filtered and the filter cake was washed with DCM (5 mL) and MeOH (2 mL) to afford a yellow solid. The yellow solid was purified by Prep-HPLC (mobile phase: [water (10 mM $NH_4HCO_3$)-acetonitrile]; B %: 23%-56%, 11 min) to afford a yellow solid. The yellow solid was further purified by Prep-HPLC (mobile phase: [water (0.225% FA)-acetonitrile]; B %: 20%-50%) to afford Compound 49 (9.2 mg, 19.44 μmol, 22.47% yield, FA salt) as white solid. LCMS (ESI) m/z $[M+H]^+$=418.0; $^1$H NMR (400 MHz, DMSO-$d_6$) δ 12.33 (br s, 1H), 8.68 (d, J=6.0 Hz, 2H), 8.30 (s, 1H), 8.18-8.16 (m, 1H), 8.01 (d, J=8.0 Hz, 1H), 7.81 (s, 1H), 7.76-7.74 (m, 3H), 7.61-7.57 (m, 1H), 7.28 (s, 1H), 6.73-6.71 (m, 1H), 6.47-6.46 (m, 1H), 4.09 (d, J=5.6 Hz, 2H), 3.64 (s, 3H).

Example 49. Preparation of 1-acetyl-N-(2-oxo-2-((4-(3-(pyridin-4-yl)phenyl)thiazol-2-yl)amino)ethyl)-1H-pyrrole-3-carboxamide (Compound 50)

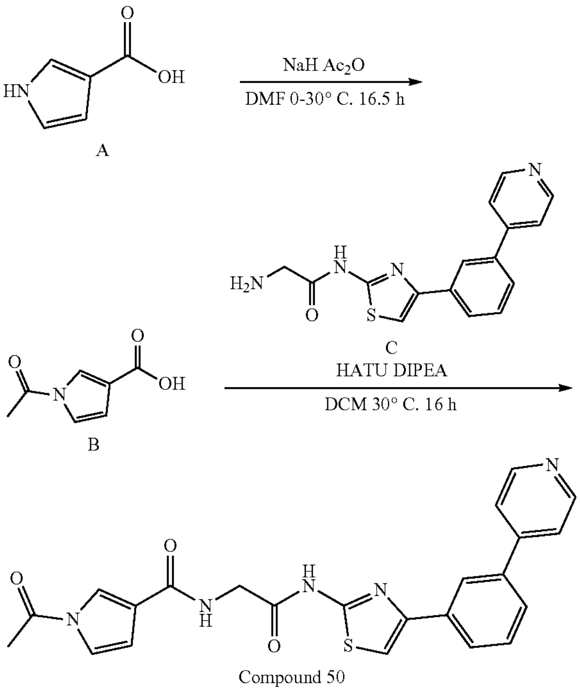

Compound 50

Step 1: Preparation of 1-acetyl-1H-pyrrole-3-carboxylic acid (Intermediate B)

B

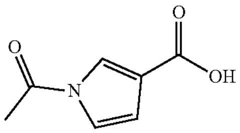

To a solution of 1H-pyrrole-3-carboxylic acid (50 mg, 450.05 μmol) in DMF (2 mL) was added NaH at 0° C. under $N_2$. The reaction mixture was stirred at 0° C. for 30 min. To the reaction mixture was added $Ac_2O$ (50.54 mg, 495.05 μmol, 46.37 μL) dropwisely at 0° C. The reaction mixture was warmed to 30° C. and stirred at 30° C. for 16 h. The reaction mixture was poured into $H_2O$ (2 mL) slowly. To the mixture was added HCl (2M) and adjusted pH=2 to afford a red solution. The red solution was purified by reverse phase column (FA condition) and lyophilized to afford Intermediate B (25 mg, 135.69 μmol, 30.15% yield) as yellow solid. LCMS (ESI) m/z $[M+H]^+$=154.0; $^1H$ NMR (400 MHz, DMSO-$d_6$) δ 7.91-7.90 (m, 1H), 7.50-7.43 (m, 1H), 6.56-6.55 (m, 1H), 2.60 (s, 3H).

Step 2: Preparation of 1-acetyl-N-(2-oxo-2-((4-(3-(pyridin-4-yl)phenyl)thiazol-2-yl)amino)ethyl)-1H-pyrrole-3-carboxamide (Compound 50)

Compound 50

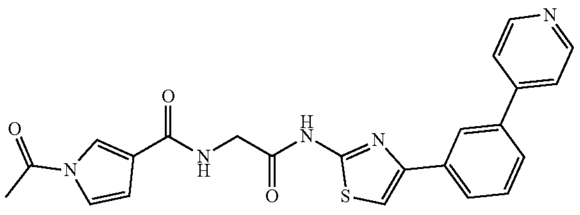

To a mixture of Intermediate B (15 mg, 97.95 μmol) in DCM (1 mL) was added DIPEA (63.30 mg, 489.76 μmol, 85.31 μL), HATU (55.87 mg, 146.93 μmol) and 2-amino-N-(4-(3-(pyridin-4-yl)phenyl)thiazol-2-yl)acetamide [prepared according to method in Example 4] (33.97 mg, 97.95 μmol, HCl salt) at 30° C. The reaction mixture was stirred at 30° C. for 16 h. The reaction mixture was filtered and the filter cake was washed with DCM (5 mL) and MeOH (2 mL) to afford a yellow solid. The yellow solid was further purified by Prep-HPLC (mobile phase: [water (0.225% FA)-acetonitrile]; B %: 12%-36%) and lyophilized to afford Compound 50 (7.59 mg, 15.44 μmol, 15.76% yield, FA salt) as white solid. LCMS (ESI) m/z $[M+H]^+$=446.1; $^1H$ NMR (400 MHz, DMSO-$d_6$) δ 12.25 (br s, 1H), 8.69-8.67 (m, 2H), 8.64-8.61 (m, 1H), 8.44 (br s, 1H), 8.31 (s, 1H), 8.03-8.00 (m, 2H), 7.82 (s, 1H), 7.77-7.76 (m, 3H), 7.62-7.58 (m, 1H), 7.48-7.46 (m, 1H), 6.71-6.70 (m, 1H), 4.16 (d, J=5.6 Hz, 2H), 2.61 (s, 3H).

Example 50. Preparation of N-(2-oxo-2-((4-(3-(pyridin-4-yl)phenyl)thiazol-2-yl)amino)ethyl)-1H-imidazole-4-carboxamide (Compound 51)

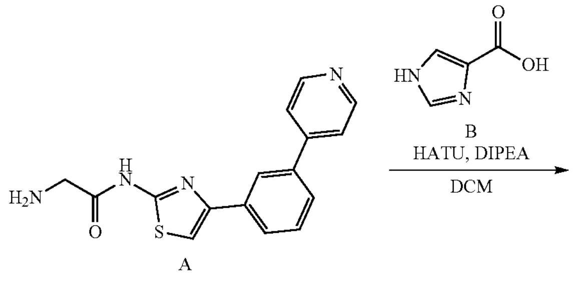

-continued

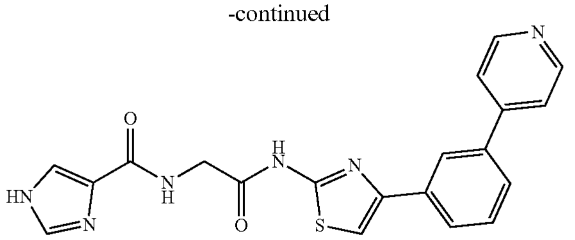

Compound 51

To a mixture of 1H-imidazole-4-carboxylic acid (15 mg, 133.82 μmol) and 2-amino-N-[4-[3-(4-pyridyl)phenyl]thiazol-2-yl]acetamide [prepared according to method in Example 4] (46.41 mg, 133.82 μmol, HCl salt) in DCM (1 mL) was added DIEA (51.89 mg, 401.47 μmol, 69.93 μL) and HATU (61.06 mg, 160.59 μmol). The resulting mixture was stirred at 30° C. for 1 h. The precipitate was collected by filtration. The solid was slurried in MeOH (2 mL) and stirred for 5 min. The precipitate was collected by filtration. Then the solid was further purified by Prep-HPLC (mobile phase: [water (0.1% TFA)-acetonitrile]; B %: 1%-30%) and lyophilized to give Compound 51 (5.44 mg, 13.45 μmol, 10.05% yield) as a white solid. LCMS (ESI) m/z $[M+H]^+$=405.2; $^1H$ NMR (400 MHz, DMSO-$d_6$) δ 12.50 (s, 1H), 8.87-8.82 (m, 3H), 8.55 (s, 1H), 8.40-8.38 (m, 1H), 8.10-7.85 (m, 7H), 7.67-7.63 (m, 1H), 4.23 (d, J=5.6 Hz, 2H).

Example 51. Preparation of 1-methyl-N-(2-oxo-2-((4-(3-(pyridin-4-yl)phenyl)thiazol-2-yl)amino)ethyl)-1H-imidazole-4-carboxamide (Compound 52)

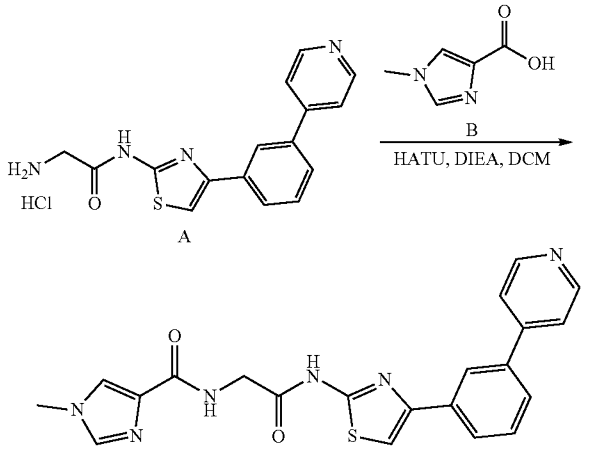

Compound 52

To a solution of 1-methyl-1H-imidazole-4-carboxylic acid (21.82 mg, 172.99 μmol), HATU (65.78 mg, 172.99 μmol) and DIEA (93.16 mg, 720.81 μmol, 125.55 μL) in DCM (0.5 mL) was added 2-amino-N-(4-(3-(pyridin-4-yl)phenyl)thiazol-2-yl)acetamide [prepared according to method in Example 4] (50 mg, 144.16 μmol, HCl salt), the mixture was stirred at 30° C. for 1 h. The reaction mixture was concentrated under reduced pressure to give a residue. The residue was triturated with MeOH (5.0 mL) and filtered, dried in vacuum to give Compound 52 (32.73 mg, 77.90 μmol, 54.04% yield) as a gray solid. LCMS (ESI) m/z $[M+H]^+$=419.2; $^1H$ NMR (400 MHz, DMSO-$d_6$) δ 12.36 (brs, 1H), 8.68-8.66 (m, 2H), 8.30-8.29 (m, 1H), 8.21-8.18 (m, 1H), 8.01 (d, J=8.0 Hz, 1H), 7.82 (s, 1H), 7.76-7.74 (m, 3H), 7.69-7.66 (m, 2H), 7.61-7.57 (m, 1H), 4.16 (d, J=6.0 Hz, 2H), 3.70 (s, 3H).

Example 52. Preparation of N-(2-((4-(3'-(aminomethyl)-[1,1'-biphenyl]-3-yl)thiazol-2-yl)amino)-2-oxoethyl)-1-(methylsulfonyl)-1H-pyrrole-3-carboxamide (Compound 53)

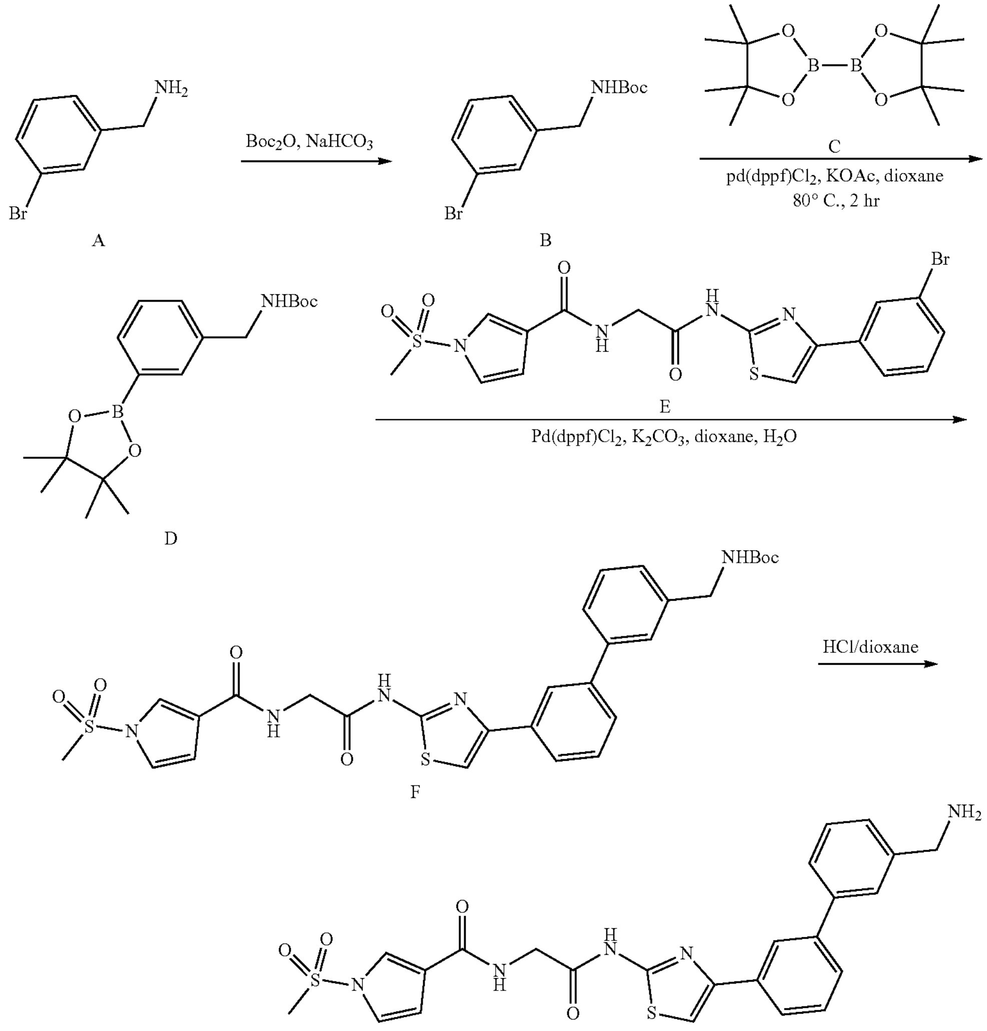

Compound 53

Step 1: Preparation of tert-butyl 3-bromobenzylcarbamate (Intermediate B)

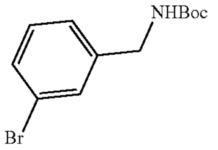

B

To a solution of (3-bromophenyl)methanamine (3.7 g, 19.89 mmol) in THF (20 mL) was added $NaHCO_3$ (3.34 g, 39.77 mmol, 1.55 mL) and $Boc_2O$ (4.77 g, 21.88 mmol, 5.03 mL), the mixture was stirred at 30° C. for 16 h. The reaction mixture was filtered to give a filtrate. The filtrate was concentrated to give Intermediate B (5.6 g, 16.67 mmol, 83.85% yield) as a white solid was used for next step directly. LCMS (ESI) m/z $[M+H-56]^+$=231.9.

Step 2: Preparation of tert-butyl 3-(4,4,5,5-tetramethyl-1,3,2-dioxaborolan-2-yl)benzylcarbamate (Intermediate D)

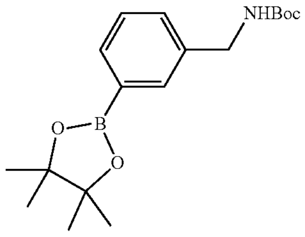

D

To a solution of Intermediate B (5.6 g, 16.67 mmol) and 4,4,5,5-tetramethyl-2-(4,4,5,5-tetramethyl-1,3,2-dioxaborolan-2-yl)-1,3,2-dioxaborolane (5.08 g, 20.01 mmol) in dioxane (60 mL) was added dichloro 1,1'-bis(diphenylphosphino)ferrocene palladium (II) dichloromethane (1.36 g, 1.67 mmol) and KOAc (4.91 g, 50.02 mmol), the mixture was stirred at 80° C. for 2 h. The reaction mixture was poured into water (100 mL), the solution was extracted with EtOAc (100 mL×3). The combined organic layer was washed with brine (200 mL), dried over $Na_2SO_4$ and filtered. The filtrate was concentrated to give a residue. The residue was purified by column chromatography ($SiO_2$, Petroleum ether/EtOAc=1:0-10:1) and concentrated in vacuum to give Intermediate D (5.5 g, 16.51 mmol, 98.98% yield) as a white solid. $^1H$ NMR (400 MHz, DMSO-$d_6$) δ 7.58 (s, 1H), 7.53 (d, J=6.8 Hz, 1H), 7.35-7.32 (m, 3H), 4.13 (d, J=6.0 Hz, 2H), 1.39 (s, 9H), 1.29 (s, 12H).

Step 3: Preparation of tert-butyl ((3'-(2-(2-(1-(methylsulfonyl)-1H-pyrrole-3-carboxamido)acetamido) thiazol-4-yl)-[1,1'-biphenyl]-3-yl)methyl)carbamate (Intermediate F)

F

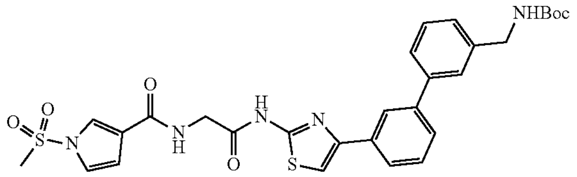

To a solution of N-[2-[[4-(3-bromophenyl)thiazol-2-yl] amino]-2-oxo-ethyl]-1-methylsulfonyl-pyrrole-3-carboxamide (prepared according to the method in Example 1) (500 mg, 1.03 mmol) and Intermediate D (413.64 mg, 1.24 mmol) in dioxane (5 mL) and $H_2O$ (0.5 mL) was added Pd(dppf)$Cl_2$ (75.69 mg, 103.44 μmol) and $K_2CO_3$ (428.89 mg, 3.10 mmol), the mixture was stirred at 80° C. for 2 h. The reaction mixture was concentrated to give a residue. The crude product was purified by reversed-phase HPLC (0.1% FA condition) and lyophilized to give Intermediate F (600 mg, crude) as a yellow solid. LCMS (ESI) m/z $[M+H]^+$= 610.2.

Step 4: Preparation of N-(2-((4-(3'-(aminomethyl)-[1,1'-biphenyl]-3-yl)thiazol-2-yl)amino)-2-oxo-ethyl)-1-(methylsulfonyl)-1H-pyrrole-3-carboxamide (Compound 53)

Compound 53

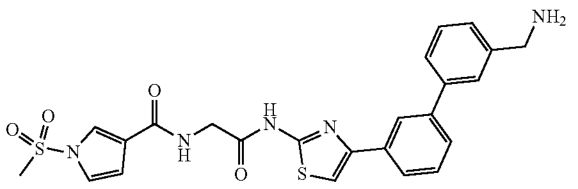

A mixture of Intermediate F (400 mg, 656.04 μmol) in HCl/dioxane (5 mL) was stirred 30° C. for 2 h. The reaction mixture was concentrated to give a residue. The residue was triturated with MTBE (2 mL) and then filtered to give a yellow solid. The yellow solid was purified by twice Prep-HPLC (mobile phase: [water (0.05% HCl)-acetonitrile]; B %: 18%-38%) and then (mobile phase: [water (0.225% FA)-acetonitrile]; B %:10%-40%) and the solution was lyophilized to give Compound 53 (68.49 mg, 134.40 μmol, 56.45% yield) as a white solid. LCMS (ESI) m/z $[M+H]^+$= 510.2; $^1H$ NMR (400 MHz, DMSO-$d_6$) δ 8.69-8.67 (m, 1H), 8.33 (s, 1H), 8.20 (s, 1H), 7.90 (d, J=8.0 Hz, 1H), 7.85-7.83 (m, 1H), 7.75 (s, 2H), 7.64-7.60 (m, 2H), 7.55-7.52 (m, 1H), 7.49-7.45 (m, 1H), 7.40-7.38 (m, 1H), 7.32-7.30 (m, 1H), 6.78 (dd, J=1.6, 3.2 Hz, 1H), 4.15 (d, J=5.6 Hz, 2H), 3.92 (s, 2H), 3.57 (s, 3H).

Example 53. Preparation of 1-(methylsulfonyl)-N-(2-oxo-2-((4-(3-(2-(piperazin-1-yl)pyridin-4-yl)phenyl)thiazol-2-yl)amino)ethyl)-1H-pyrrole-3-carboxamide (Compound 54)

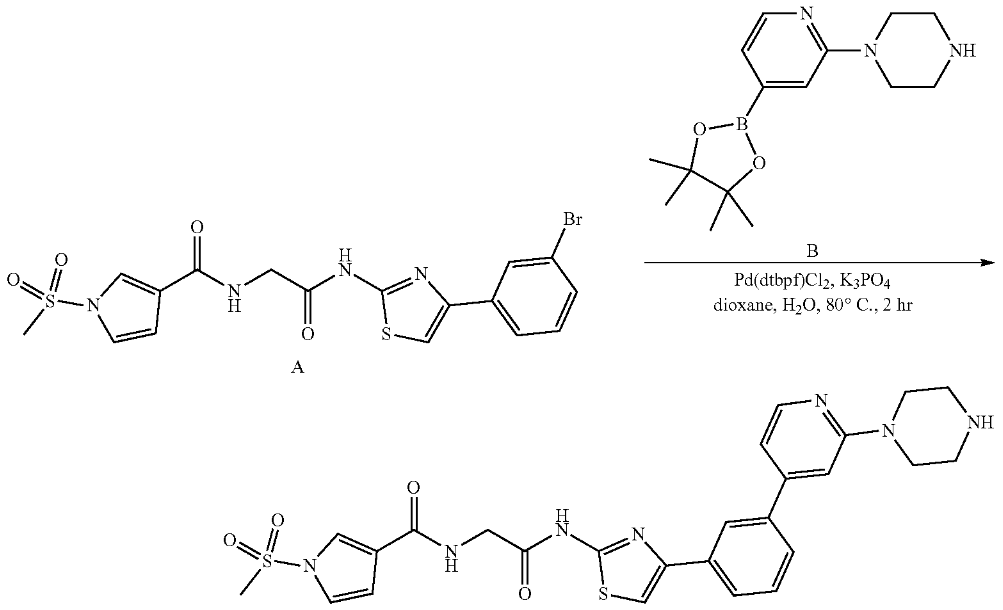

Compound 54

To a solution of N-[2-[[4-(3-bromophenyl)thiazol-2-yl]amino]-2-oxo-ethyl]-1-methylsulfonyl-pyrrole-3-carboxamide (prepared according to the method in Example 1) (50 mg, 96.26 μmol) and 1-[4-(4,4,5,5-tetramethyl-1,3,2-dioxaborolan-2-yl)-2-pyridyl]piperazine (41.76 mg, 144.40 μmol) in dioxane (0.5 mL) and $H_2O$ (0.05 mL) was added $K_3PO_4$ (61.30 mg, 288.79 μmol) and [1,1'-bis(di-tert-butylphosphino)ferrocene]dichloropalladium(II) (12.55 mg, 19.25 μmol) under $N_2$. The reaction mixture was stirred at 80° C. for 2 h. The reaction mixture was poured into water (5 mL), the solution was extracted with EtOAc (5 mL×3). The combined organic layer was washed with brine (20 mL), dried over $Na_2SO_4$ and filtered. The filtrate was concentrated to give a residue. The residue was purified by Prep-HPLC (mobile phase: [water (0.225% FA)-acetonitrile]; B %: 10%-34%) to give Compound 54 (18.81 mg, 33.25 μmol, 34.54% yield) as a white solid. LCMS (ESI) m/z $[M+H]^+$=566.2; $^1H$ NMR (400 MHz, DMSO-$d_6$) δ 8.70 (br t, J=5.6 Hz, 1H), 8.67-8.26 (m, 3H), 8.22-8.20 (m, 1H), 7.85 (s, 1H), 7.81 (s, 1H), 7.71 (br d, J=7.6 Hz, 1H), 7.62-7.52 (m, 1H), 7.32 (dd, J=2.4, 3.2 Hz, 1H), 7.08 (s, 1H), 6.99 (d, J=5.2 Hz, 1H), 6.78-6.77 (m, 1H), 4.15 (d, J=5.6 Hz, 2H), 3.58 (s, 7H), 2.88 (br s, 4H).

Example 54. Preparation of N-(2-((4-(3',5'-dimethyl-[1,1'-biphenyl]-3-yl)thiazol-2-yl)amino)-2-oxoethyl)-1-(methylsulfonyl)-1H-pyrrole-3-carboxamide (Compound 55)

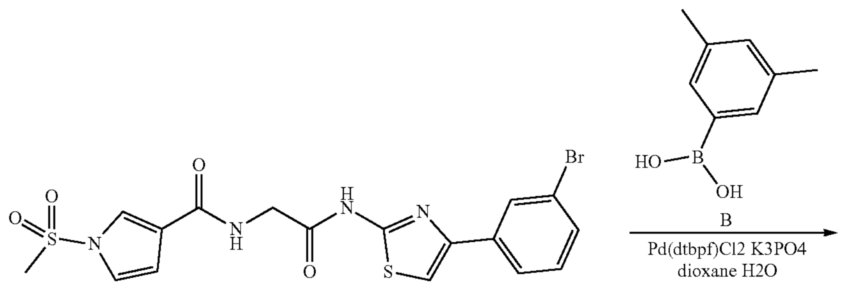

A

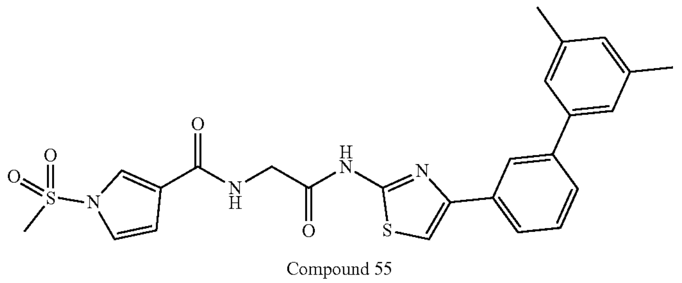

Compound 55

The solution of N-[2-[[4-(3-bromophenyl)thiazol-2-yl]amino]-2-oxo-ethyl]-1-methylsulfonyl-pyrrole-3-carboxamide (prepared according to the method in Example 1) (100 mg, 206.89 μmol), (3,5-dimethylphenyl)boronic acid (62.06 mg, 413.77 μmol) and $K_3PO_4$ (131.74 mg, 620.66 μmol) in dioxane (0.8 mL) and $H_2O$ (0.2 mL) was added [1,1'-bis(di-tert-butylphosphino)ferrocene]dichloropalladium(II) (13.48 mg, 20.69 μmol) at 25° C. under $N_2$. The reaction mixture was stirred at 80° C. under $N_2$ for 16 h. The reaction mixture was poured into water (10 mL) and extracted with EtOAc (10 mL×3), the combined organic layers was dried over anhydrous $Na_2SO_4$ then concentrated to afford a brown solid. The brown solid was dissolved with DMSO (2 mL) and purified by reversed-phase HPLC (FA), then concentrated and lyophilized to afford Compound 55 (57.31 mg, 110.37 μmol, 53.35% yield) as an off-white solid. LCMS (ESI) m/z $[M+H]^+$=509.1; $^1H$ NMR (400 MHz, DMSO-$d_6$) δ 12.40 (br s, 1H), 8.67-8.66 (m, 1H), 8.16 (s, 1H), 7.87 (d, J=7.8 Hz, 1H), 7.84-7.83 (m, 1H), 7.75 (s, 1H), 7.58 (d, J=7.8 Hz, 1H), 7.53-7.46 (m, 1H), 7.31 (s, 3H), 7.02 (s, 1H), 6.77-6.76 (m, 1H), 4.14 (d, J=5.6 Hz, 2H), 3.57 (s, 3H), 2.35 (s, 6H).

Example 55. Preparation of 1-(tert-butyl)-N-(2-((4-(3-(3-methylisoxazol-5-yl)phenyl)thiazol-2-yl)amino)-2-oxoethyl)-1H-pyrrole-3-carboxamide (Compound 56)

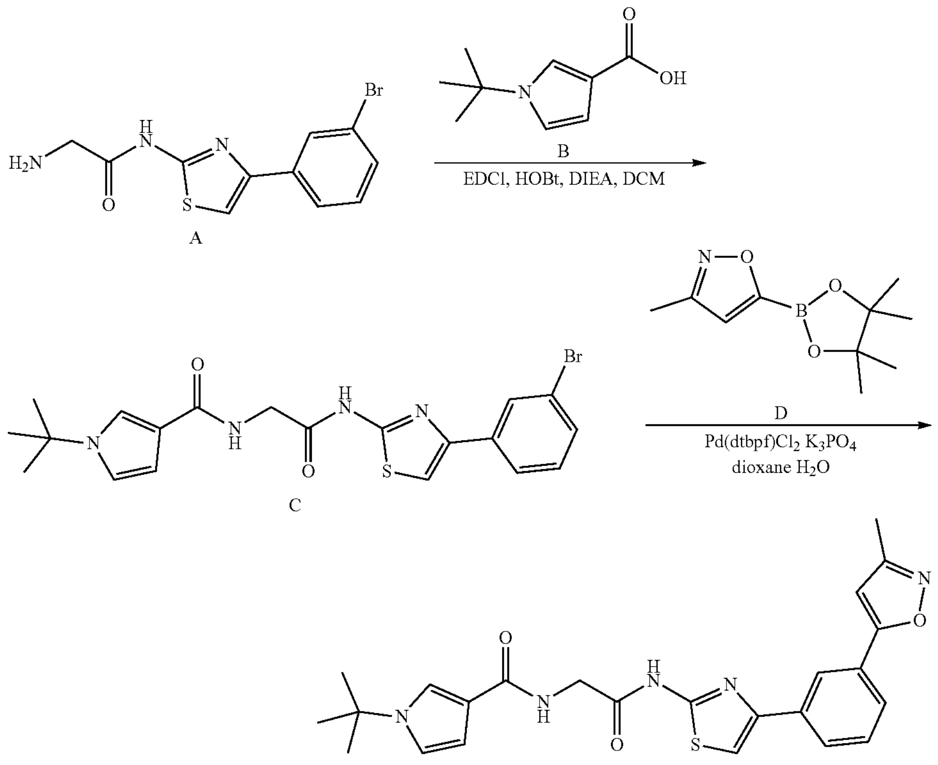

Compound 56

To a solution of N-[2-[[4-(3-bromophenyl)thiazol-2-yl]amino]-2-oxo-ethyl]-1-tert-butyl-pyrrole-3-carboxamide [prepared according to the method in Example 8] (70 mg, 151.72 μmol) in dioxane (1 mL) and water (0.2 mL) was added 3-methyl-5-(4,4,5,5-tetramethyl-1,3,2-dioxaborolan-2-yl)isoxazole (38.06 mg, 182.06 μmol) and $K_3PO_4$ (96.62 mg, 455.16 μmol) and [1,1'-bis(di-tert-butylphosphino)ferrocene]dichloropalladium(II) (9.89 mg, 15.17 μmol) under $N_2$ atmosphere. The mixture was stirred at 100° C. for 2 h. The mixture was diluted with water (3 mL) and extracted with EtOAc (10 mL×3). The organic layer was dried over anhydrous $Na_2SO_4$ and concentrated to afford residue. The residue was purified by reversed-phase HPLC (0.1% $NH_3 \cdot H_2O$) and lyophilized to give Compound 56 (2.53 mg, 5.46 μmol, 3.60% yield) as a white solid. LCMS (ESI) m/z $[M+H]^+$=464.3; $^1$H NMR (400 MHz, $CDCl_3$) δ 10.29 (s, 1H), 8.25 (s, 1H), 7.88 (d, J=7.6 Hz, 1H), 7.71 (d, J=7.6 Hz, 1H), 7.57-7.55 (m, 1H), 7.49-7.47 (m, 1H), 7.23 (s, 1H), 6.86-6.84 (m, 1H), 6.47-6.45 (m, 3H), 4.37 (d, J=6.0 Hz, 2H), 2.38 (s, 3H), 1.56 (s, 9H).

Example 56. Preparation of N-(2-((4-(3-(2-(N-methylacetamido)pyridin-4-yl)phenyl)thiazol-2-yl)amino)-2-oxoethyl)-1-(methylsulfonyl)-1H-pyrrole-3-carboxamide (Compound 57)

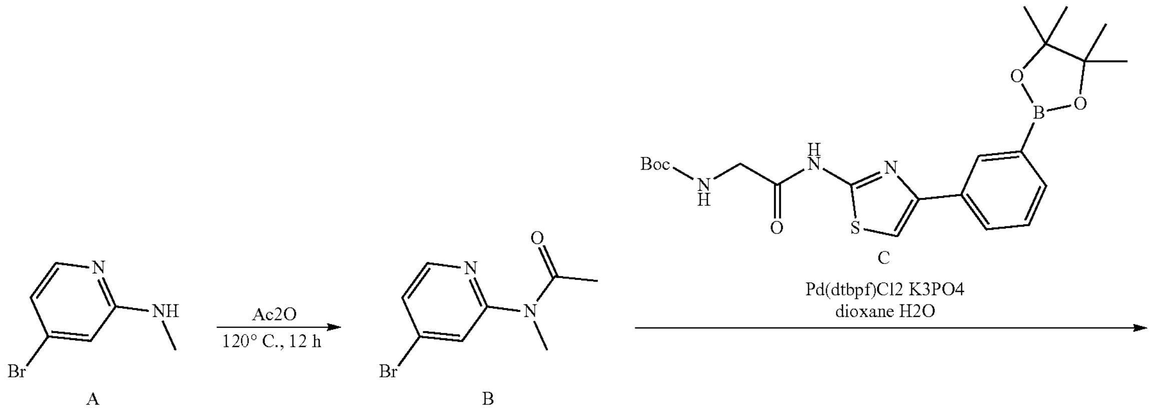

-continued

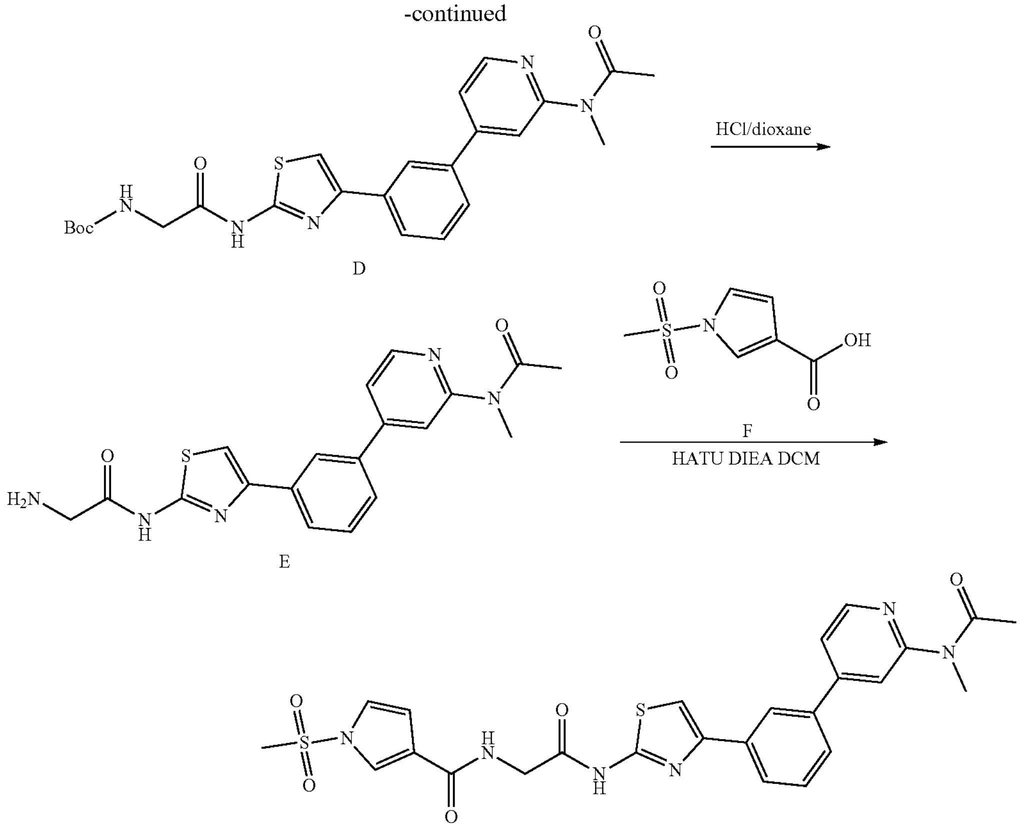

D

E

Compound 57

Step 1: Preparation of N-(4-bromopyridin-2-yl)-N-methylacetamide (Intermediate B)

B

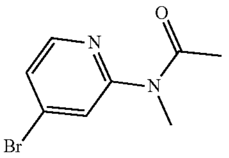

A mixture of 4-bromo-N-methylpyridin-2-amine (200 mg, 1.07 mmol) in acetic anhydride (3.27 g, 32.03 mmol, 3 mL) was stirred at 120° C. for 4 hours. The mixture was concentrated in reduced pressure at 50° C. to give Intermediate B (180 mg, 785.77 μmol, 73.48% yield) as yellow oil. The oil was taken to the next step without purification. LCMS (ESI) m/z $[M+H]^+=229.1$; $^1H$ NMR (400 MHz, Methanol-$d_4$) δ 8.33 (d, J=5.4 Hz, 1H), 7.99 (s, 1H), 7.54 (d, J=5.4 Hz, 1H), 3.35 (s, 3H), 2.10 (s, 3H).

Step 2: Preparation of tert-butyl (2-((4-(3-(2-(N-methylacetamido)pyridin-4-yl)phenyl)thiazol-2-yl)amino)-2-oxoethyl)carbamate (Intermediate D)

D

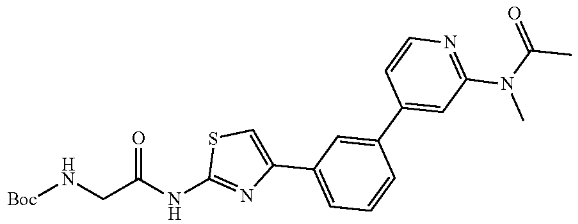

To a mixture of tert-butyl (2-oxo-2-((4-(3-(4,4,5,5-tetramethyl-1,3,2-dioxaborolan-2-yl)phenyl)thiazol-2-yl)amino)ethyl)carbamate [prepared according to the method in Example 57] (200 mg, 435.38 μmol) and Intermediate B (129.66 mg, 566.00 μmol) in dioxane (10 mL) and $H_2O$ (2 mL) was added [1,1'-bis(di-tert-butylphosphino)ferrocene] dichloropalladium(II) (28.38 mg, 43.54 μmol) and $K_3PO_4$ (184.84 mg, 870.77 μmol) in one portion at 25° C. under $N_2$. The mixture was stirred at 75° C. under $N_2$ for 12 hours. The mixture was poured into water (40 mL) and stirred for 5 min. The aqueous phase was extracted with EtOAc (30 mL×3). The combined organic phase was washed with brine (10 mL), dried with anhydrous $Na_2SO_4$, filtered and concentrated in vacuum to give Intermediate D (180 mg, 373.78 μmol, 85.85% yield) as yellow oil. The oil was used for the next step directly without purification. LCMS (ESI) m/z $[M+H]^+=482.0$.

Step 3: Preparation of 2-amino-N-(4-(3-(2-(N-methylacetamido)pyridin-4-yl)phenyl)thiazol-2-yl) acetamide (Intermediate E)

E

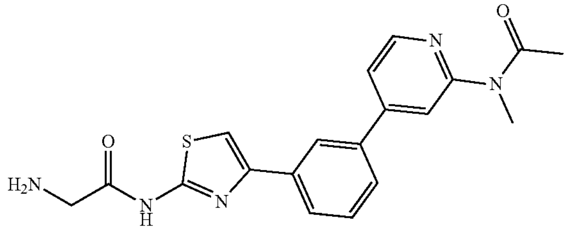

To a mixture of Intermediate D (180 mg, 373.78 μmol) in EA (5 mL) was added HCl/EtOAc (4 M, 93.45 μL) in one portion at 25° C. The mixture was stirred at 25° C. for 1 hour. The mixture was filtered and the solid was dried in vacuum to give Intermediate E (100 mg, 239.28 μmol, 64.02% yield, HCl salt) as black brown solid. $^{1}$H NMR (400 MHz, DMSO-$d_6$) δ 8.59 (d, J=5.2 Hz, 1H), 8.39-8.28 (m, 1H), 8.04 (d, J=7.2 Hz, 1H), 7.95 (d, J=3.2 Hz, 2H), 7.82 (d, J=7.0 Hz, 1H), 7.75 (d, J=4.4 Hz, 1H), 7.66-7.57 (m, 1H), 3.92 (d, J=4.8 Hz, 2H), 3.35 (s, 3H), 2.09 (s, 3H).

Step 4: Preparation of N-(2-((4-(3-(2-(N-methylacetamido)pyridin-4-yl)phenyl)thiazol-2-yl)amino)-2-oxoethyl)-1-(methylsulfonyl)-1H-pyrrole-3-carboxamide (Compound 57)

Compound 57

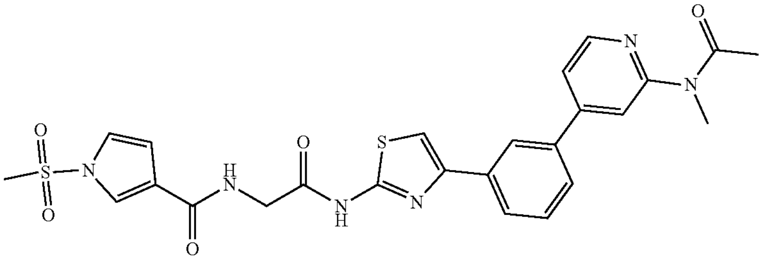

To a mixture of 1-methylsulfonylpyrrole-3-carboxylic acid [prepared according to the method in Example 4] (16.30 mg, 86.14 μmol) and DIEA (46.39 mg, 358.93 μmol, 62.52 μL) in DCM (1 mL) was added HATU (40.94 mg, 107.68 μmol) in one portion at 25° C. under $N_2$. The mixture was stirred at 25° C. for 5 min, then Intermediate E (30 mg, 71.79 μmol, HCl) was added to the mixture and stirred at 25° C. for 2 hours. The reaction mixture was concentrated in vacuum and the residue was purified by reverse phase column (FA) and then lyophilized to give Compound 57 (11.70 mg, 19.22 μmol, 26.78% yield, FA salt) as off-white solid. LCMS (ESI) m/z $[M+H]^+$=553.3; $^{1}$H NMR (400 MHz, DMSO-$d_6$) δ 8.56 (d, J=5.2 Hz, 1H), 8.29 (s, 1H), 8.00 (d, J=7.8 Hz, 1H), 7.86 (s, 1H), 7.84-7.83 (m, 1H), 7.81 (s, 1H), 7.78 (d, J=7.8 Hz, 1H), 7.68-7.66 (m, 1H), 7.61-7.60 (m, 1H), 7.32-7.31 (m, 1H), 6.78-6.77 (m, 1H), 4.14 (s, 2H), 3.55 (s, 3H), 3.33 (s, 3H), 2.06 (m, 3H).

Example 57. Preparation of 1-(tert-butyl)-N-(2-((4-(3-(1-methyl-1H-pyrazol-3-yl)phenyl)thiazol-2-yl)amino)-2-oxoethyl)-1H-pyrrole-3-carboxamide (Compound 58)

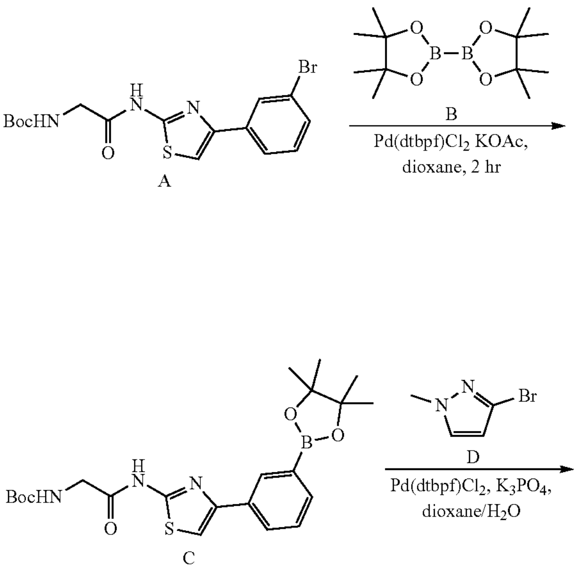

-continued

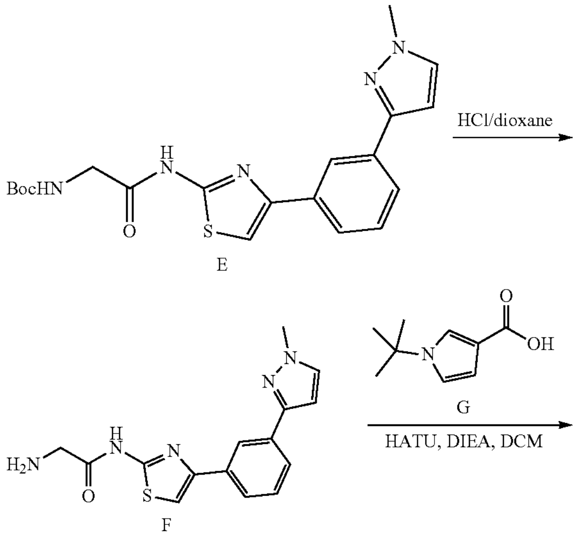

-continued

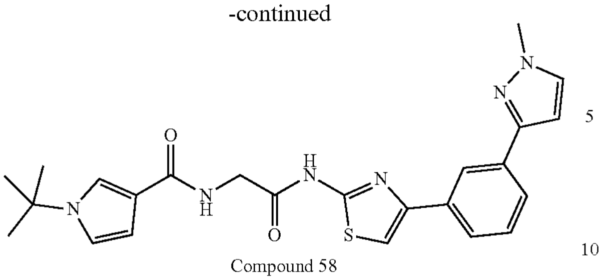

Compound 58

Step 1: Preparation of tert-butyl (2-oxo-2-((4-(3-(4,4,5,5-tetramethyl-1,3,2-dioxaborolan-2-yl)phenyl)thiazol-2-yl)amino)ethyl)carbamate (Intermediate C)

C

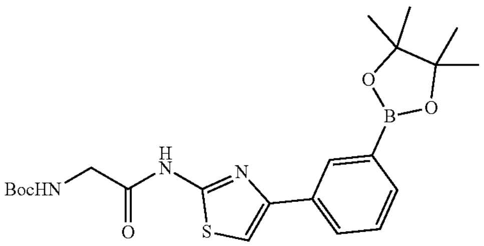

tert-Butyl N-[2-[[4-(3-bromophenyl)thiazol-2-yl]amino]-2-oxo-ethyl]carbamate (6 g, 14.55 mmol), 4,4,5,5-tetramethyl-2-(4,4,5,5-tetramethyl-1,3,2-dioxaborolan-2-yl)-1,3,2-dioxaborolane (4.06 g, 16.01 mmol), [1,1'-bis(di-tert-butylphosphino)ferrocene]dichloropalladium(II) (948.45 mg, 1.46 mmol) and KOAc (2.86 g, 29.10 mmol) were taken up in dioxane (60 mL), the mixture was purged with $N_2$ three times. Then the resulting mixture was stirred at 100° C. for 2 h. The reaction mixture was filtered and filtration was evaporated to dryness to give Intermediate C (6.68 g, crude) as black oil. LCMS (ESI) m/z $[M+H]^+$=460.3.

Step 2: Preparation of tert-butyl (2-((4-(3-(1-methyl-1H-pyrazol-3-yl)phenyl)thiazol-2-yl)amino)-2-oxoethyl)carbamate (Intermediate E)

E

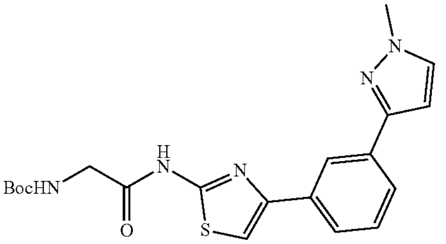

Intermediate C (6.68 g, 14.54 mmol), 3-bromo-1-methyl-pyrazole (2.34 g, 14.54 mmol), [1,1'-bis(di-tert-butylphosphino)ferrocene]dichloropalladium(II) (947.76 mg, 1.45 mmol) and $K_3PO_4$ (6.17 g, 29.08 mmol) were taken up in dioxane (50 mL) and $H_2O$ (10 mL), the mixture was purged with $N_2$ three times. Then the resulting mixture was stirred at 80° C. for 4 h. The reaction mixture was diluted with water (100 mL) and extracted with EtOAc (50 mL×3). The combined organic layers were washed with brine (50 mL), dried over $Na_2SO_4$, filtered and concentrated under reduced pressure to give a residue. The residue was purified by column chromatography ($SiO_2$, Petroleum ether/EtOAc=5/1 to 1:1) and concentrated in vacuum to give Intermediate E (3 g, 7.26 mmol, 49.89% yield) as yellow solid. LCMS (ESI) m/z $[M+H]^+$=414.1.

Step 3: Preparation of 2-amino-N-(4-(3-(1-methyl-1H-pyrazol-3-yl)phenyl)thiazol-2-yl)acetamide (Intermediate F)

F

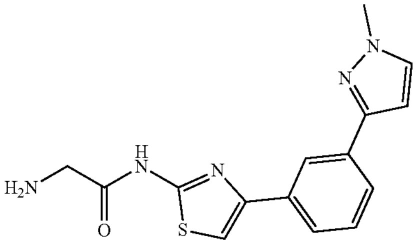

Intermediate E (3 g, 7.26 mmol) was dissolved in HCl/dioxane (20 mL). The mixture was stirred at 30° C. for 1 hr. The reaction mixture was evaporated to dryness to give Intermediate F (4.2 g, crude, HCl salt) as a yellow solid, which was used for the next step directly. LCMS (ESI) m/z $[M+H]^+$=314.2.

Step 4: Preparation of 1-(tert-butyl)-N-(2-((4-(3-(1-methyl-1H-pyrazol-3-yl)phenyl)thiazol-2-yl)amino)-2-oxoethyl)-1H-pyrrole-3-carboxamide (Compound 58)

Compound 58

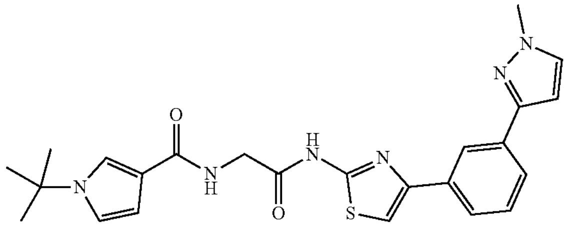

To a mixture of 1-tert-butylpyrrole-3-carboxylic acid [prepared according to the method in Example 34] (1.43 g, 8.58 mmol) in DCM (20 mL) was added HATU (2.61 g, 6.86 mmol) and DIPEA (3.69 g, 28.58 mmol, 4.98 mL). The mixture was stirred at 30° C. for 15 min, then Intermediate F (2 g, 5.72 mmol, HCl salt) was added and stirred for 1 hours. The reaction mixture was poured into water (50.0 mL) and extracted with EtOAc (50.0 mL×3). The combined organics were washed with water and brine, dried over $Na_2SO_4$, filtered and filtration was evaporated to dryness. The residue was purified by column chromatography ($SiO_2$, DCM/MeOH=100/1 to 80:1) and concentrated in vacuum to give Compound 58 (1.5 g, 3.18 mmol, 55.64% yield) as a white solid. LCMS (ESI) m/z $[M+H]^+$=463.3; 1H NMR (400 MHz, DMSO-$d_6$) δ 12.39 (s, 1H), 8.38 (s, 1H), 8.19-8.16 (m, 1H), 7.81 (d, J=8.0 Hz, 1H), 7.76 (d, J=2.0 Hz, 1H), 7.72 (d, J=7.6 Hz, 1H), 7.68 (s, 1H), 7.53-7.52 (m, 1H), 7.46-7.42 (m, 1H), 6.98-6.96 (m, 1H), 6.73 (d, J=2.0 Hz, 1H), 6.48-6.47 (m, 1H), 4.10 (d, J=6.0 Hz, 2H), 3.90 (s, 3H), 1.49 (s, 9H).

Example 58. Preparation of (S)—N-(1-((4-(3-(2-methylpyridin-4-yl)phenyl)thiazol-2-yl)amino)-4-(methylthio)-1-oxobutan-2-yl)-1-(methylsulfonyl)-1H-pyrrole-3-carboxamide (Compound 59)

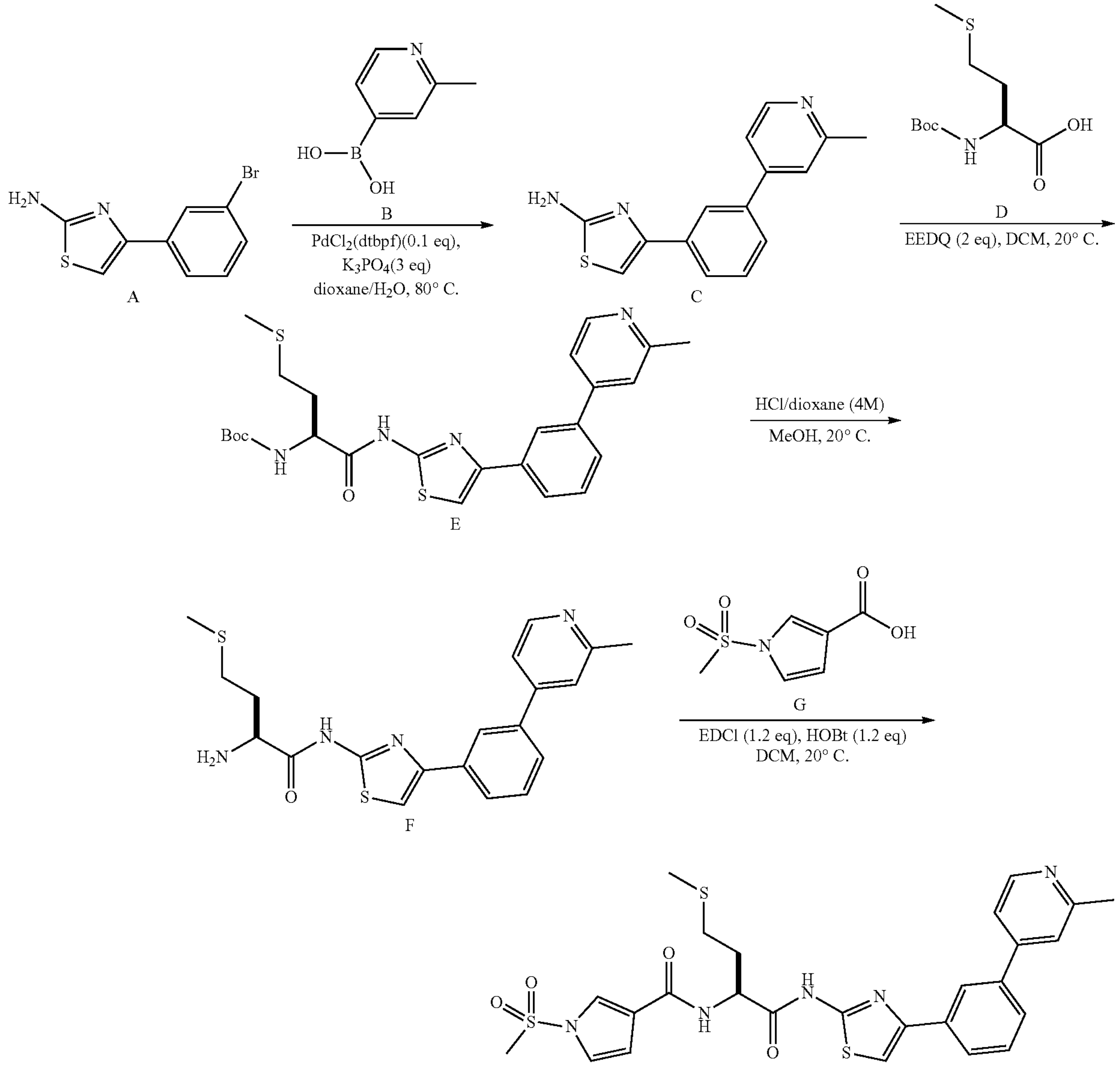

Compound 59

Step 1: Preparation of 4-(3-(2-methylpyridin-4-yl) phenyl)thiazol-2-amine (Intermediate C)

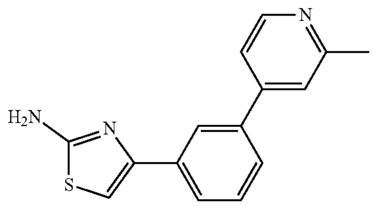

C

A mixture of 4-(3-bromophenyl)thiazol-2-amine (1 g, 3.92 mmol), (2-methyl-4-pyridyl)boronic acid (590.43 mg, 4.31 mmol), $K_2CO_3$ (1.63 g, 11.76 mmol) and $Pd(dppf)Cl_2$ (286.79 mg, 391.95 μmol) in dioxane (10 mL) and $H_2O$ (3 mL) was degassed and purged with $N_2$ for 3 times, and then the mixture was stirred at 80° C. for 2 h under $N_2$ atmosphere. The reaction mixture was concentrated under reduced pressure to give a residue. The residue was purified by column chromatography ($SiO_2$, Petroleum ether/EtOAc=3/1) and concentrated to afford Intermediate C (1 g, 3.74 mmol, 95.43% yield) as yellow solid. LCMS (ESI) m/z $[M+H]^+$=268.2; $^1H$ NMR (400 MHz, $CDCl_3$) δ 8.57 (d, J=5.2 Hz, 1H), 8.10-8.08 (m, 1H), 7.85-7.83 (m, 1H), 7.59-7.54 (m, 1H), 7.53-7.47 (m, 1H), 7.45 (s, 1H), 7.40-7.38 (m, 1H), 6.84 (s, 1H), 5.04 (br s, 2H), 2.66 (s, 3H).

Step 2: Preparation of (S)-tert-butyl (1-((4-(3-(2-methylpyridin-4-yl)phenyl)thiazol-2-yl)amino)-4-(methylthio)-1-oxobutan-2-yl)carbamate (Intermediate E)

E

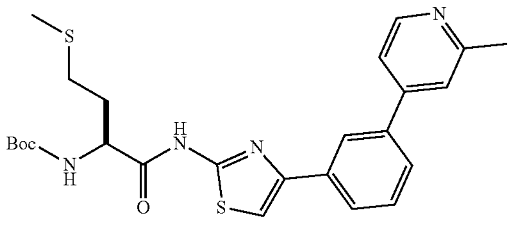

To a solution of Intermediate C (0.5 g, 1.87 mmol) and 2-(tert-butoxycarbonylamino)-4-methylsulfanyl-butanoic acid (699.45 mg, 2.81 mmol) in DCM (8 mL) was added EEDQ (924.97 mg, 3.74 mmol). The mixture was stirred at 25° C. for 16 h. The reaction mixture was concentrated under reduced pressure to give a residue. The residue was purified by column chromatography ($SiO_2$, Petroleum ether/EtOAc=1/1) and concentrated to afford Intermediate E (0.74 g, 1.48 mmol, 79.35% yield) as yellow oil. LCMS (ESI) m/z $[M+H]^+$=499.1; 100% ee value.

Step 3: Preparation of (S)-2-amino-N-(4-(3-(2-methylpyridin-4-yl)phenyl)thiazol-2-yl)-4-(methylthio)butanamide (Intermediate F)

F

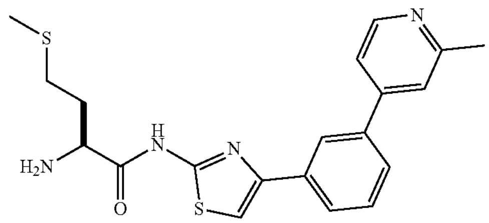

To a solution of Intermediate E (0.7 g, 1.40 mmol) in MeOH (5 mL) was added HCl/dioxane (4 M, 5 mL). The mixture was stirred at 25° C. for 1 h. The reaction mixture was concentrated to dryness to give Intermediate F (0.6 g, crude, HCl salt) as yellow solid, which was used for the next step without further purification. LCMS (ESI) m/z $[M+H]^+$=399.0.

Step 4: Preparation of (S)—N-(1-((4-(3-(2-methylpyridin-4-yl)phenyl)thiazol-2-yl)amino)-4-(methylthio)-1-oxobutan-2-yl)-1-(methylsulfonyl)-1H-pyrrole-3-carboxamide (Compound 59)

Compound 59

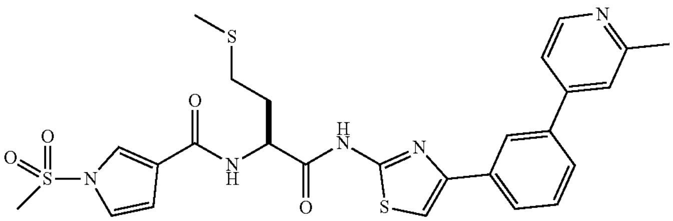

To a solution of Intermediate F (200 mg, 459.76 μmol, HCl salt) in DCM (3 mL) was added 1-methylsulfonylpyrrole-3-carboxylic acid [prepared according to the method in Example 4] (95.68 mg, 505.74 μmol), HOBt (62.12 mg, 459.76 μmol), DIEA (237.68 mg, 1.84 mmol, 320.32 μL) and EDCI (105.76 mg, 551.72 μmol). The mixture was stirred at 25° C. for 2 h. The reaction mixture was concentrated to dryness to give a residue. The residue was purified with Prep-HPLC (mobile phase: [water (0.1% TFA)-acetonitrile]; B %: 18%-48%) and lyophilized to afford Compound 59 (95.37 mg, 167.40 μmol, 36.41% yield) as white solid. LCMS (ESI) m/z $[M+H]^+$=570.0; $^1H$ NMR (400 MHz, DMSO-$d_6$) δ 12.53 (s, 1H), 8.84 (br s, 1H), 8.53-8.41 (m, 2H), 8.33-8.07 (m, 3H), 7.99-7.86 (m, 3H), 7.70-7.68 (m, 1H), 7.37-7.26 (m, 1H), 6.79 (dd, J=3.2 Hz, 1.60 Hz, 1H), 4.78-4.65 (m, 1H), 3.58 (s, 3H), 2.76 (br d, J=2.4 Hz, 3H), 2.16-1.96 (m, 6H); ee %=100%.

Example 59. Preparation of (S)—N-(3-methoxy-1-((4-(3-(2-methylpyridin-4-yl)phenyl)thiazol-2-yl)amino)-1-oxopropan-2-yl)-1-(methylsulfonyl)-1H-pyrrole-3-carboxamide (Compound 60)

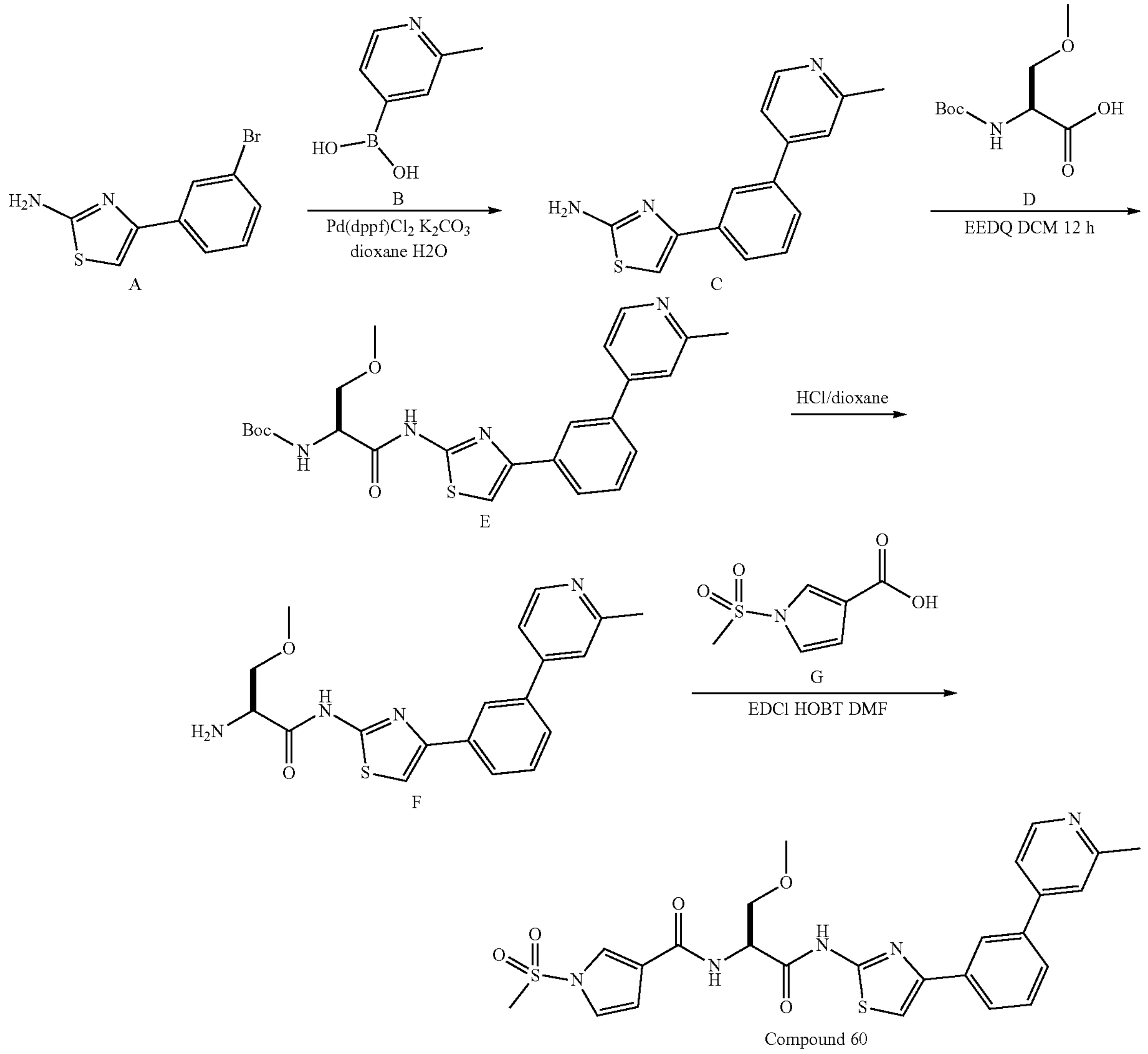

Step 1: Preparation of (S)-tert-butyl (3-methoxy-1-((4-(3-(2-methylpyridin-4-yl)phenyl)thiazol-2-yl)amino)-1-oxopropan-2-yl)carbamate (Intermediate E)

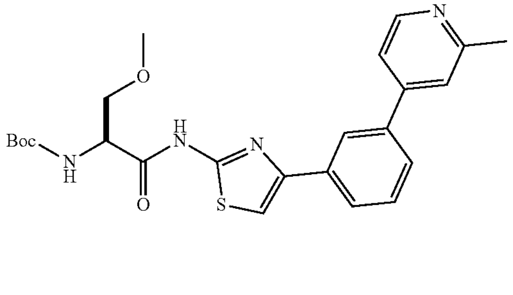

E

A mixture of 4-(3-(2-methylpyridin-4-yl)phenyl)thiazol-2-amine [prepared according to the method in Example 58] (950 mg, 3.55 mmol), 2-(tert-butoxycarbonylamino)-3-methoxy-propanoic acid (934.84 mg, 4.26 mmol), EEDQ (1.76 g, 7.11 mmol) in DCM (10 mL) was degassed and purged with $N_2$ for 3 times, and then the mixture was stirred at 25° C. for 12 h under $N_2$ atmosphere. The reaction mixture was quenched by addition water (20 mL), and extracted with EtOAc (20 mL×3). The combined organic layers were washed with brine (10 mL×3), dried over $Na_2SO_4$, filtered and concentrated under reduced pressure to give a residue. The residue was purified by reversed phase ($NH_{30}H$) and lyophilized to give Intermediate E (1.3 g, 2.77 mmol, 78.08% yield) as a yellow solid. LCMS (ESI) m/z $[M+H]^+$= 469.4; $^1$H NMR (400 MHz, DMSO-$d_6$) δ 12.43 (s, 1H), 8.54 (d, J=5.2 Hz, 1H), 8.29 (s, 1H), 8.00 (d, J=7.8 Hz, 1H), 7.83 (s, 1H), 7.74 (d, J=7.8 Hz, 1H), 7.67-7.48 (m, 3H), 7.17

(br d, J=7.6 Hz, 1H), 4.52 (br d, J=6.6 Hz, 1H), 3.58 (br d, J=5.6 Hz, 2H), 3.27 (s, 3H), 2.56 (s, 3H), 1.44-1.25 (m, 9H).

Step 2: Preparation of (S)-2-amino-3-methoxy-N-(4-(3-(2-methylpyridin-4-yl)phenyl)thiazol-2-yl) propanamide (Intermediate F)

F

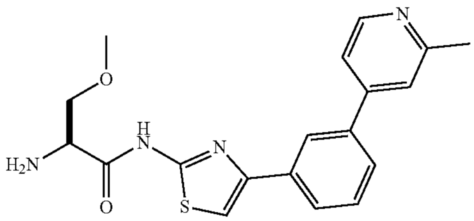

A mixture of Intermediate E (300 mg, 640.25 μmol) in HCl/dioxane (4 M, 1.60 mL) was degassed and purged with $N_2$ for 3 times, and then the mixture was stirred at 25° C. for 2 h under $N_2$ atmosphere. The mixture was concentrated to remove the solvent to obtain Intermediate F (350 mg, crude, HCl salt) as a yellow solid. LCMS (ESI) m/z $[M+H]^+$=369.2.

Step 3: Preparation of (S)—N-(3-methoxy-1-((4-(3-(2-methylpyridin-4-yl)phenyl)thiazol-2-yl)amino)-1-oxopropan-2-yl)-1-(methylsulfonyl)-1H-pyrrole-3-carboxamide (Compound 60)

Compound 60

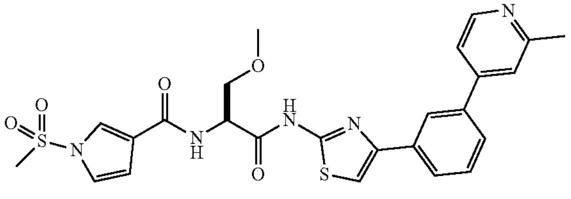

A mixture of Intermediate F (250 mg, 617.42 μmol, HCl salt), 1-methylsulfonylpyrrole-3-carboxylic acid [prepared according to the method in Example 4] (140.17 mg, 740.90 μmol), DIEA (398.97 mg, 3.09 mmol, 537.70 μL), HOBt (166.85 mg, 1.23 mmol) and EDCI (236.72 mg, 1.23 mmol) in DMF (3 mL) was degassed and purged with $N_2$ for 3 times, and then the mixture was stirred at 25° C. for 12 h under $N_2$ atmosphere. To the reaction mixture was added water (10 mL), extracted with EtOAc (10 mL×3). The combined organic layers were washed with brine (10 mL×3), dried over $Na_2SO_4$, filtered and concentrated under reduced pressure to give a residue. The residue was purified by reversed phase (FA) and lyophilized to give Compound 60 (160 mg, 296.50 μmol, 48.02% yield, FA salt) as a yellow solid. LCMS (ESI) m/z $[M+H]^+$=540.2. $^1$H NMR (400 MHz, DMSO-$d_6$) δ 8.48 (d, J=5.4 Hz, 1H), 8.27-8.21 (m, 1H), 8.13 (s, 1H), 8.01-7.90 (m, 2H), 7.76-7.68 (m, 2H), 7.66-7.52 (m, 3H), 7.28 (dd, J=2.2, 3.4 Hz, 1H), 6.79 (dd, J=1.8 Hz, 3.2 Hz, 1H), 4.86-4.84 (m, 1H), 3.79-3.63 (m, 2H), 3.47 (s, 3H), 3.29 (s, 3H), 2.53 (br s, 3H); ee %=95.212%.

Example 60. Preparation of (S)—N-(1-((4-(3-(2,6-dimethylpyridin-4-yl)phenyl)thiazol-2-yl)amino)-3-methoxy-1-oxopropan-2-yl)-1-(methylsulfonyl)-1H-pyrrole-3-carboxamide (Compound 61)

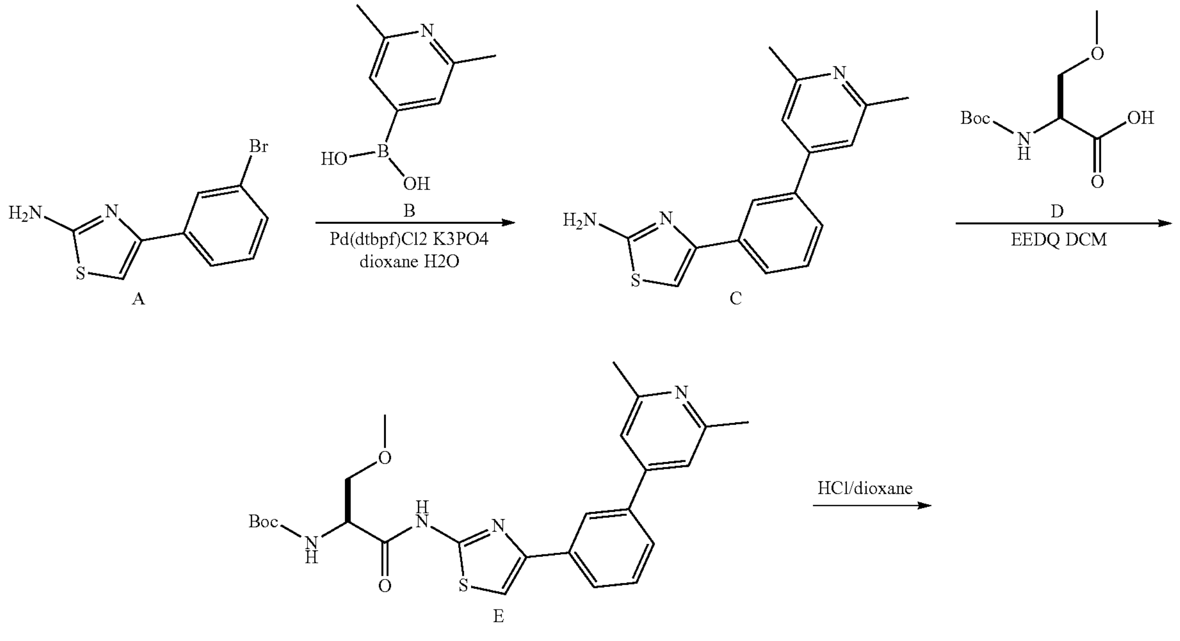

-continued

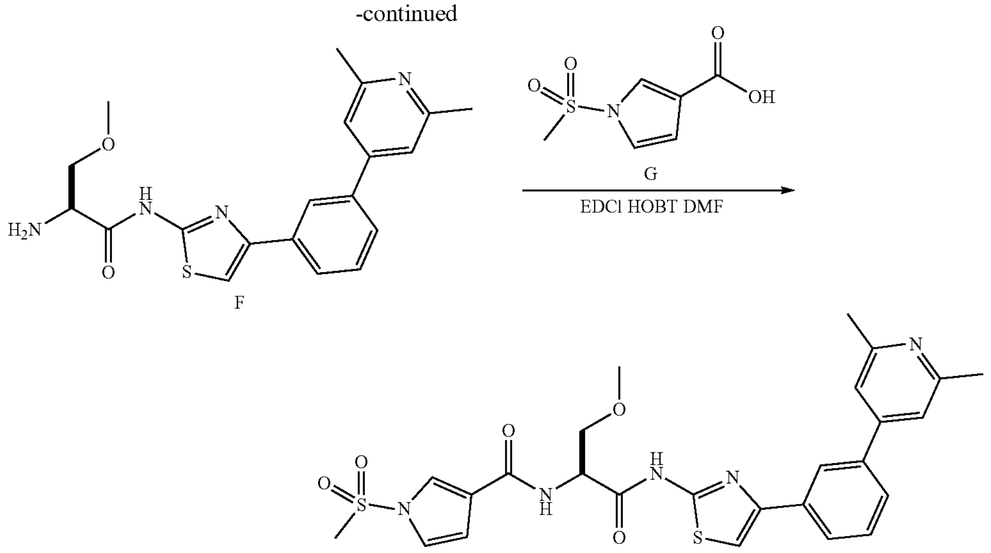

F

Compound 61

Step 1: Preparation of 4-(3-(2,6-dimethylpyridin-4-yl)phenyl)thiazol-2-amine (Intermediate C)

C

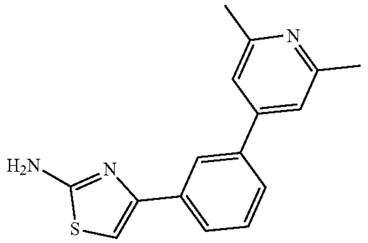

To a solution of 4-(3-bromophenyl)thiazol-2-amine (600 mg, 2.35 mmol) and (2,6-dimethyl-4-pyridyl) boronic acid (532.56 mg, 3.53 mmol) in dioxane/$H_2O$=4/1 (10 mL) was added $K_3PO_4$ (1.50 g, 7.06 mmol) and [1,1'-bis(di-tert-butylphosphino)ferrocene]dichloropalladium(II) (229.91 mg, 352.76 μmol). The mixture was stirred at 75° C. under $N_2$ for 4 h. The reaction mixture was diluted with $H_2O$ (20 mL) and extracted with EtOAc (20 mL×2). The combined organic layers were dried over anhydrous $Na_2SO_4$, filtered and concentrated under reduced pressure to give a residue. The residue was purified by column chromatography ($SiO_2$, Petroleum ether/EtOAc=1/0 to 1:1) and concentrated in vacuum to give Intermediate C (400 mg, 1.42 mmol, 60.45% yield) as a yellow solid. LCMS (ESI) m/z $[M+H]^+$=282.0; $^1$H NMR (400 MHz, Methanol-$d_4$) δ 8.11 (m, 1H), 7.83-7.81 (m, 1H), 7.61 (m, 1H), 7.50-7.48 (m, 1H), 7.42 (s, 2H), 6.96 (s, 1H), 2.56 (s, 6H).

Step 2: Preparation of (S)-tert-butyl (1-((4-(3-(2,6-dimethylpyridin-4-yl)phenyl)thiazol-2-yl)amino)-3-methoxy-1-oxopropan-2-yl)carbamate (Intermediate E)

E

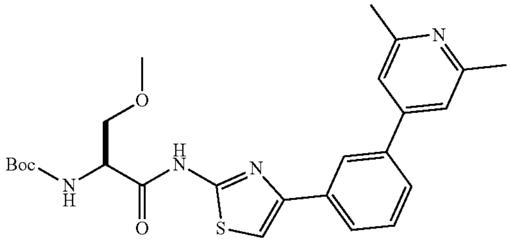

To a solution of (2S)-2-(tert-butoxycarbonylamino)-3-methoxy-propanoic acid (397.37 mg, 1.81 mmol) in DCM (5 mL) was added EEDQ (597.63 mg, 2.42 mmol), the mixture was stirred at 30° C. for 0.5 h. Then Intermediate C (340 mg, 1.21 mmol) was added to the mixture. The mixture was stirred at 30° C. for 16 h. The reaction mixture was diluted with $H_2O$ (10 mL) and extracted with EtOAc (10 mL×2). The combined organic layers were dried over anhydrous $Na_2SO_4$, filtered and concentrated under reduced pressure to give the residue. The residue was purified by reversed phase (0.1% FA condition) and concentrated to remove the acetonitrile, then extracted with EtOAc (20 mL×2), the combined organic layers were dried over anhydrous $Na_2SO_4$, filtered and concentrated to afford Intermediate E (300 mg, 621.64 μmol, 51.45% yield) as a white solid. LCMS (ESI) m/z $[M+H]^+$=483.1; 1H NMR (400 MHz, $CDCl_3$) δ 9.88-9.80 (m, 1H), 8.09 (s, 1H), 7.87 (d, J=7.6 Hz, 1H), 7.58-7.49 (m, 2H), 7.25 (d, J=4.0 Hz, 3H), 5.47-5.46 (m, 1H), 4.55 (br d, J=2.0 Hz, 1H), 3.98-3.95 (m, 1H), 3.63-3.61 (m, 1H), 3.44 (s, 3H), 1.62 (br s, 6H), 1.50 (s, 9H).

Step 3: Preparation of (S)-2-amino-N-(4-(3-(2,6-dimethylpyridin-4-yl)phenyl)thiazol-2-yl)-3-methoxypropanamide (Intermediate F)

F

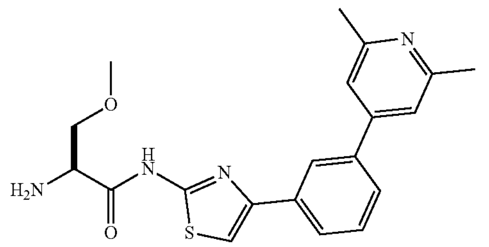

A solution of Intermediate E (300 mg, 621.64 μmol) in HCl/dioxane (4 M, 5 mL) was stirred at 30° C. for 0.5 h. The reaction mixture was concentrated directly to afford Intermediate F (260 mg, 620.61 μmol, 99.83% yield, HCl salt) as a white solid, which was used directly in the next step. LCMS (ESI) m/z $[M+H]^+$=383.2; $^1$H NMR (400 MHz, DMSO-$d_6$) δ 13.02-12.95 (m, 1H), 8.65-8.62 (m, 3H), 8.46 (s, 1H), 8.20 (s, 2H), 8.16 (d, J=8.4 Hz, 1H), 8.00 (s, 1H), 7.96-7.94 (m, 1H), 7.73-7.69 (m, 1H), 4.37 (br d, J=4.4 Hz, 1H), 3.92-3.79 (m, 2H), 3.32 (s, 3H), 2.79 (s, 6H).

Step 4: Preparation of (S)—N-(1-((4-(3-(2,6-dimethylpyridin-4-yl)phenyl)thiazol-2-yl)amino)-3-methoxy-1-oxopropan-2-yl)-1-(methylsulfonyl)-1H-pyrrole-3-carboxamide (Compound 61)

Compound 61

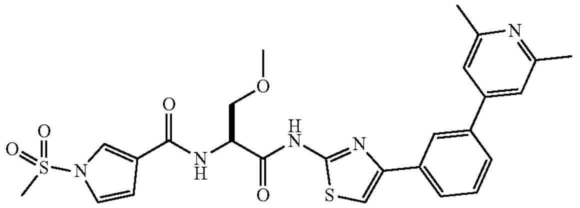

To a solution of Intermediate F (150 mg, 358.05 μmol, HCl salt) in DMF (2 mL) was added 1-methylsulfonylpyrrole-3-carboxylic acid [prepared according to the method in Example 4] (74.51 mg, 393.85 μmol) and DIEA (231.37 mg, 1.79 mmol, 311.82 μL), then EDCI (102.96 mg, 537.07 μmol) and HOBt (58.06 mg, 429.66 μmol) was added to the mixture. The mixture was stirred at 30° C. for 16 h. The reaction mixture was concentrated in vacuum and then the residue was purified by reversed phase (0.1% FA condition) and lyophilized to afford Compound 61 (109.15 mg, 182.01 μmol, 50.84% yield, FA salt) as a white solid. LCMS (ESI) m/z $[M+H]^+$=554.2; $^1$H NMR (400 MHz, Methanol-$d_4$) δ 8.26 (br d, J=2.4 Hz, 1H), 8.02-7.95 (m, 1H), 7.91-7.90 (m, 1H), 7.70-7.63 (m, 1H), 7.54-7.47 (m, 4H), 7.26-7.25 (m, 1H), 6.83 (m, 1H), 4.97-4.95 (m, 1H), 3.88-3.82 (m, 2H), 3.81-3.79 (m, 3H), 3.44-3.42 (m, 3H), 2.58 (d, J=1.6 Hz, 6H); ee %=100%.

Example 61. Preparation (S)-1-(tert-butyl)-N-(3-methoxy-1-((4-(3-(1-methyl-1H-pyrazol-3-yl)phenyl)thiazol-2-yl)amino)-1-oxopropan-2-yl)-1H-pyrrole-3-carboxamide (Compound 62)

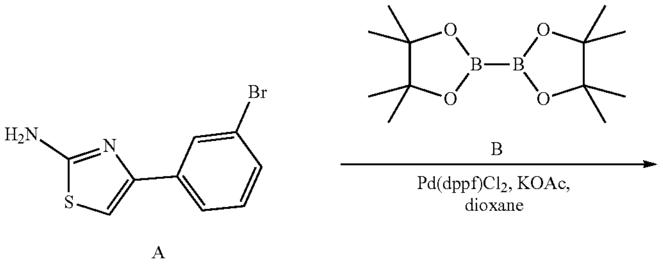

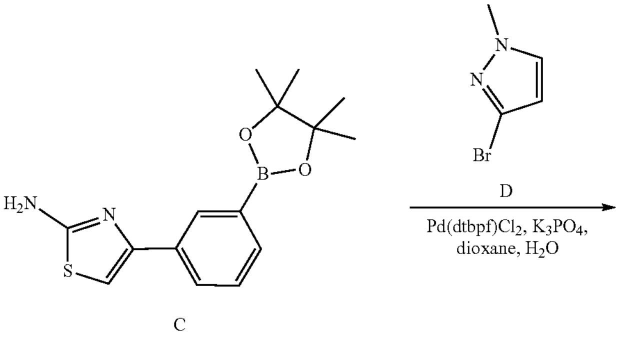

-continued
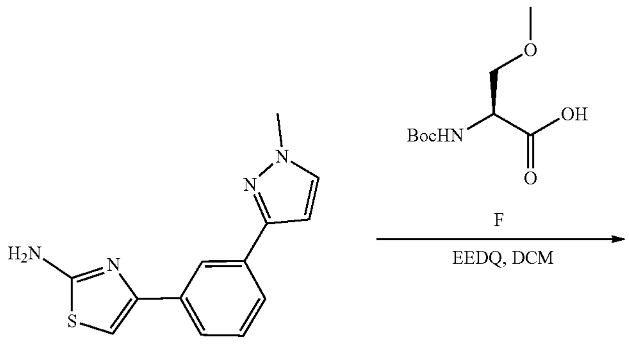
E
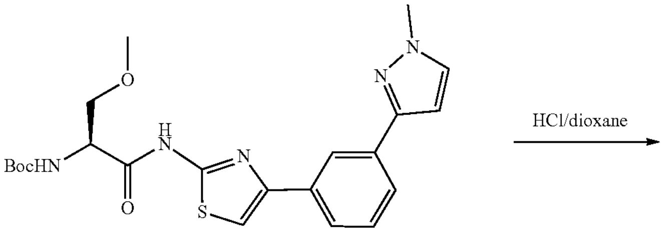
G
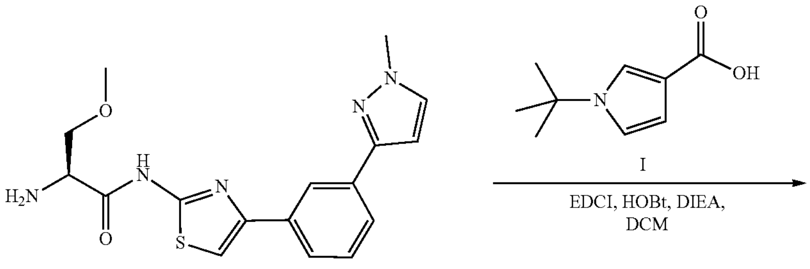
H
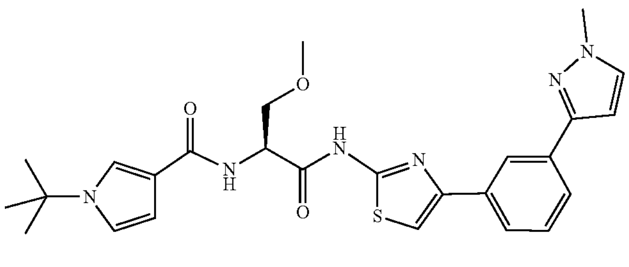
Compound 62

Step 1: Preparation of (S)-tert-butyl (3-methoxy-1-((4-(3-(1-methyl-1H-pyrazol-3-yl)phenyl)thiazol-2-yl)amino)-1-oxopropan-2-yl)carbamate (Intermediate G)

G

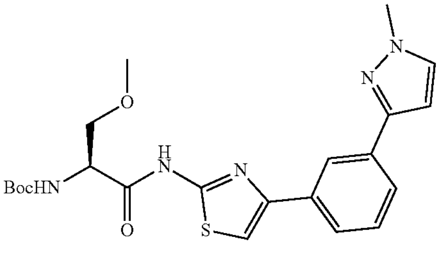

To a solution of 4-(3-(1-methyl-1H-pyrazol-3-yl)phenyl) thiazol-2-amine (prepared according to the method in Example 2) (500 mg, 1.95 mmol) and (2S)-2-(tertbutoxycarbonylamino)-3-methoxy-propanoic acid (513.18 mg, 2.34 mmol) in DCM (5 mL) was added EEDQ (723.56 mg, 2.93 mmol), the mixture was stirred at 30° C. for 12 h. The reaction mixture was concentrated under reduced pressure to give a residue. The residue was purified by column chromatography ($SiO_2$, Petroleum ether/EtOAc=3/1 to 2:1) and concentrated to give Intermediate G (800 mg, 1.71 mmol, 87.84% yield) as a white solid. LCMS (ESI) m/z $[M+H]^+$= 458.4; ee %=100%.

Step 2: Preparation of (S)-2-amino-3-methoxy-N-(4-(3-(1-methyl-1H-pyrazol-3-yl)phenyl)thiazol-2-yl)propanamide (Intermediate H)

H

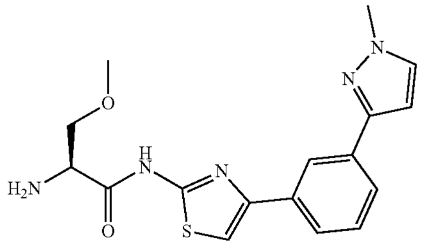

A solution of Intermediate G (0.8 g, 1.75 mmol) in 4 M HCl/dioxane (10 mL) was stirred at 30° C. for 1 h. The reaction mixture was concentrated under reduced pressure to give a crude product. The crude product was triturated with MTBE (10 mL), filtered and dried in vacuum to give Intermediate H (600 mg, 1.52 mmol, 87.12% yield, HCl salt) as a white solid. LCMS (ESI) m/z $[M+H]^+$=358.4; $^1H$ NMR (400 MHz, DMSO-$d_6$) δ 12.99 (br s, 1H), 8.70-8.69 (m, 3H), 8.39-8.38 (m, 1H), 7.82-7.77 (m, 4H), 7.46-7.43 (m, 1H), 6.74-6.73 (m, 1H), 4.34-4.32 (m, 1H), 3.93-3.81 (m, 5H), 3.31 (m, 3H); ee %=100%.

Step 3: Preparation of (S)-1-(tert-butyl)-N-(3-methoxy-1-((4-(3-(1-methyl-1H-pyrazol-3-yl)phenyl)thiazol-2-yl)amino)-1-oxopropan-2-yl)-1H-pyrrole-3-carboxamide (Compound 62)

Compound 62

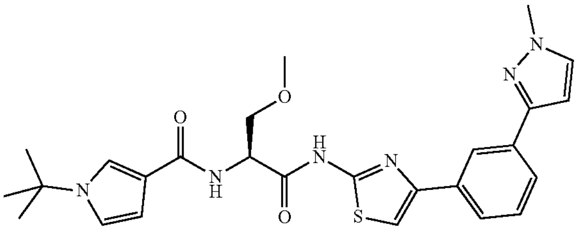

To a solution of 1-tert-butylpyrrole-3-carboxylic acid [prepared according to the method in Example 34] (63.67 mg, 380.82 μmol), EDCI (97.34 mg, 507.76 μmol), HOBt (68.61 mg, 507.76 μmol) and DIEA (164.06 mg, 1.27 mmol, 221.10 μL) in DCM (1 mL) was added Intermediate H (100 mg, 253.88 μmol, HCl salt), the mixture was stirred at 30° C. for 2 h. The reaction mixture was concentrated under reduced pressure to give a residue. The residue was purified by reverse phase (FA) and lyophilized to give Compound 62 (31.20 mg, 60.69 μmol, 23.90% yield) as a white solid. LCMS (ESI) m/z $[M+H]^+$=507.4; $^1H$ NMR (400 MHz, Methanol-$d_4$) δ 8.33-8.32 (m, 1H), 7.84-7.82 (m, 1H), 7.71-7.69 (m, 1H), 7.64-7.61 (m, 2H), 7.45-7.40 (m, 2H), 6.95-6.94 (m, 1H), 6.67-6.66 (m, 1H), 6.61-6.59 (m, 1H), 4.97-4.94 (m, 1H), 3.95 (s, 3H), 3.86-3.82 (m, 2H), 3.43 (s, 3H), 1.56 (s, 9H); ee %=100%.

Example 62. Preparation of (S)-1-(tert-butyl)-N-(3-methoxy-1-((4-(2-methyl-1-oxo-1,2-dihydroisoquinolin-7-yl)thiazol-2-yl)amino)-1-oxopropan-2-yl)-1H-pyrrole-3-carboxamide (Compound 63)

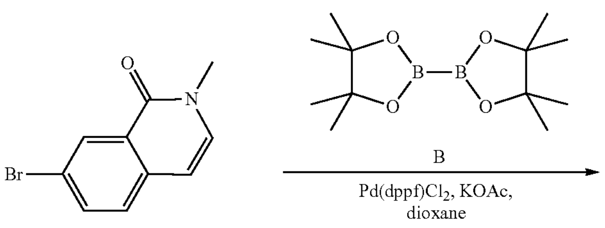

A

-continued
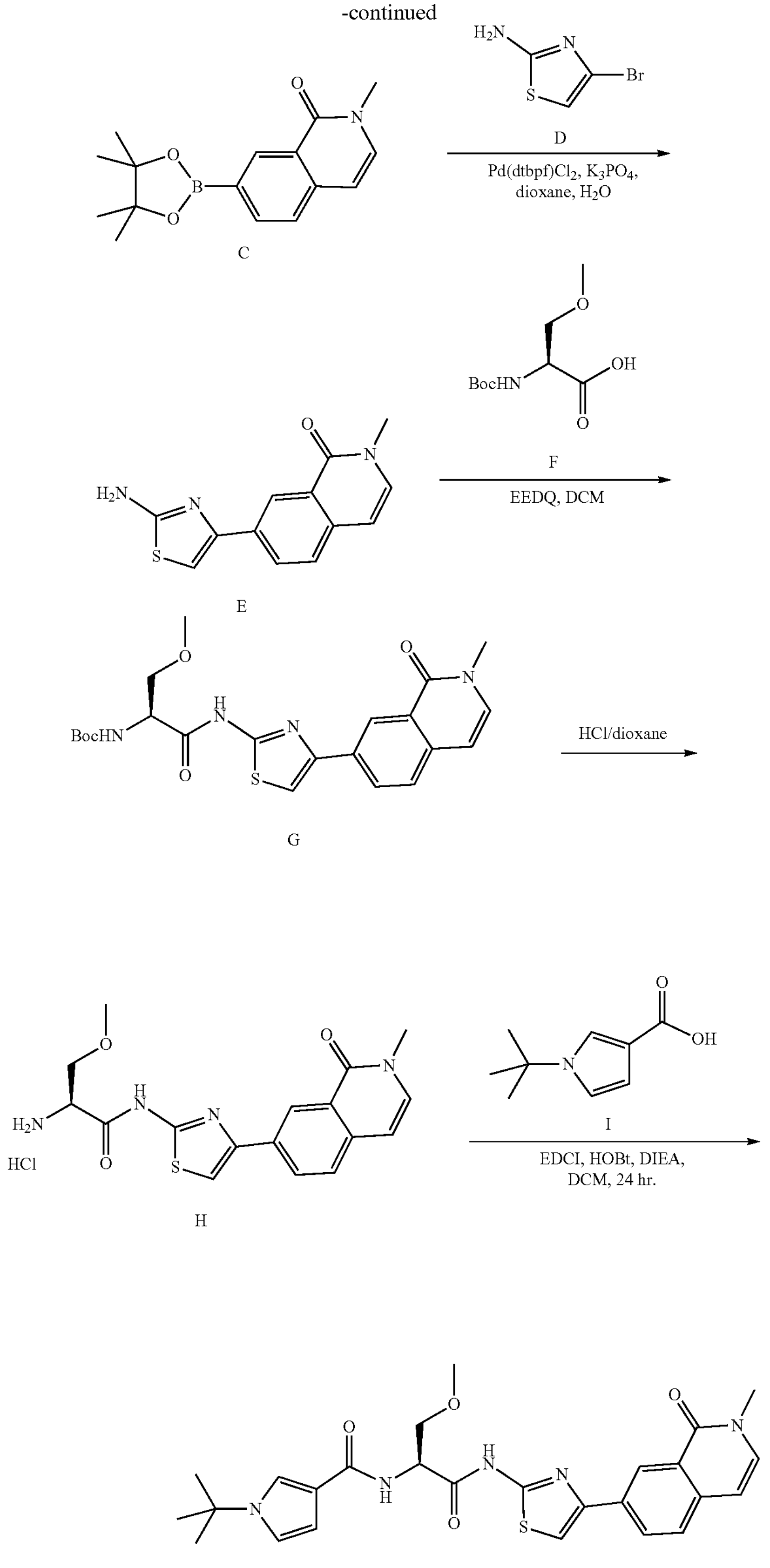
Compound 63

Step 1: Preparation of 7-(2-aminothiazol-4-yl)-2-methylisoquinolin-1(2H)-one (Intermediate E)

E

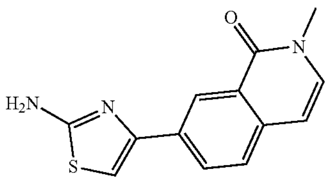

A mixture of 4-bromothiazol-2-amine (500 mg, 2.79 mmol), 2-methyl-7-(4,4,5,5-tetramethyl-1,3,2-dioxaborolan-2-yl)isoquinolin-1(2H)-one [prepared according to the method in Example 7] (955.59 mg, 3.35 mmol), $K_3PO_4$ (1.78 g, 8.38 mmol) and [1,1'-bis(di-tert-butylphosphino)ferrocene]dichloropalladium(II) (182.01 mg, 279.27 μmol) in dioxane (8 mL) and $H_2O$ (2 mL) was degassed and purged with $N_2$ for 3 times, and then the mixture was stirred at 100° C. for 2 h under $N_2$ atmosphere. Water (50 mL) was added and the reaction mixture was extracted with EtOAc (200 mL). The combined organic layers were washed with brine (50 mL), dried over $Na_2SO_4$, filtered and concentrated under reduced pressure to give a residue. The crude product was purified by reversed-phase HPLC (0.1% $NH_3{\cdot}H_2O$) and lyophilized to give Intermediate E (400 mg, 1.37 mmol, 48.98% yield) as a yellow solid. LCMS (ESI) m/z $[M+H]^+$=258.3.

Step 2: Preparation of (S)-tert-butyl (3-methoxy-1-((4-(2-methyl-1-oxo-1,2-dihydroisoquinolin-7-yl)thiazol-2-yl)amino)-1-oxopropan-2-yl)carbamate (Intermediate G)

G

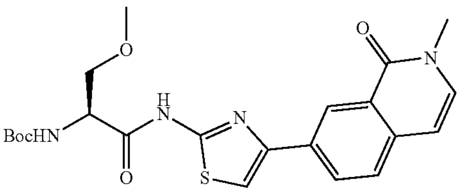

To a solution of Intermediate E (330 mg, 1.28 mmol) and (2S)-2-(tertbutoxycarbonylamino)-3-methoxy-propanoic acid (337.40 mg, 1.54 mmol) in DCM (20 mL) was added EEDQ (475.72 mg, 1.92 mmol). The mixture was stirred at 25° C. for 2 h. The reaction mixture was concentrated under reduced pressure to remove DCM. The crude product was triturated with MeOH (20 mL) at 25° C. for 10 min, then filtered and dried in vacuum to give Intermediate G (400 mg, 817.74 μmol, 63.76% yield) as a white solid. LCMS (ESI) m/z $[M+H]^+$=459.0.

Step 3: Preparation of (S)-2-amino-3-methoxy-N-(4-(2-methyl-1-oxo-1,2-dihydroisoquinolin-7-yl)thiazol-2-yl)propanamide (Intermediate H)

H

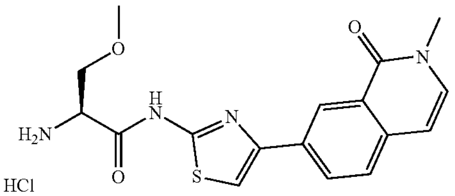

To a solution of Intermediate G (200 mg, 436.18 μmol) in dioxane (2 mL) was added HCl/dioxane (2 mL). The mixture was stirred at 25° C. for 2 h. The reaction mixture was concentrated under reduced pressure to give Intermediate H (180 mg, crude, HCl salt) as a brown solid. LCMS (ESI) m/z $[M+H]^+$=359.1.

Step 4: Preparation of (S)-1-(tert-butyl)-N-(3-methoxy-1-((4-(2-methyl-1-oxo-1,2-dihydroisoquinolin-7-yl)thiazol-2-yl)amino)-1-oxopropan-2-yl)-1H-pyrrole-3-carboxamide (Compound 63)

Compound 63

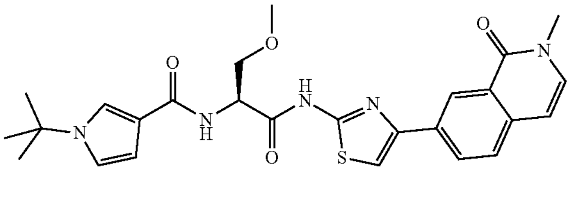

To a solution of [prepared according to the method in Example 34] (50.81 mg, 303.89 μmol) in DCM (2 mL) was added EDCI (58.26 mg, 303.89 μmol), HOBt (41.06 mg, 303.89 μmol) and DIEA (104.74 mg, 810.38 μmol, 141.15 μL), then Intermediate H (80 mg, 202.60 μmol, HCl salt) was added. The mixture was stirred at 25° C. for 12 h. Water (30 mL) was added and the reaction mixture was extracted with EtOAc (50 mL×2). The combined organic layers were washed with brine (20 mL), dried over $Na_2SO_4$, filtered and concentrated under reduced pressure to give a residue. The residue was purified by Prep-HPLC (mobile phase: [water (0.075% TFA)-acetonitrile]; B %: 35%-65%) and then re-purified by Prep-TLC ($SiO_2$, DCM:EtOAc=2:1) to give Compound 63 (17 mg, 33.49 μmol, 16.53% yield) as a white solid. LCMS (ESI) m/z $[M+H]^+$=508.4. $^1H$ NMR (400 MHz, DMSO-$d_6$) δ 12.51 (s, 1H), 8.82 (d, J=2.0 Hz, 1H), 8.22-8.20 (m, 1H), 7.93 (d, J=7.6 Hz, 1H), 7.78 (s, 1H), 7.70 (d, J=8.4 Hz, 1H), 7.63-7.61 (m, 1H), 7.48 (d, J=7.2 Hz, 1H), 6.96-6.95 (m, 1H), 6.63 (d, J=6.8 Hz, 1H), 6.51-6.50 (m, 1H), 4.94-4.89 (m, 1H), 3.75-3.67 (m, 2H), 3.52 (s, 3H), 3.32-3.31 (m, 3H), 1.49 (s, 9H); ee %=89.392%.

Example 63. Preparation of (S)-1-(tert-butyl)-N-(3-methoxy-1-((4-(2-methyl-1-oxo-1,2,3,4-tetrahydroisoquinolin-7-yl)thiazol-2-yl)amino)-1-oxopropan-2-yl)-1H-pyrrole-3-carboxamide (Compound 64)
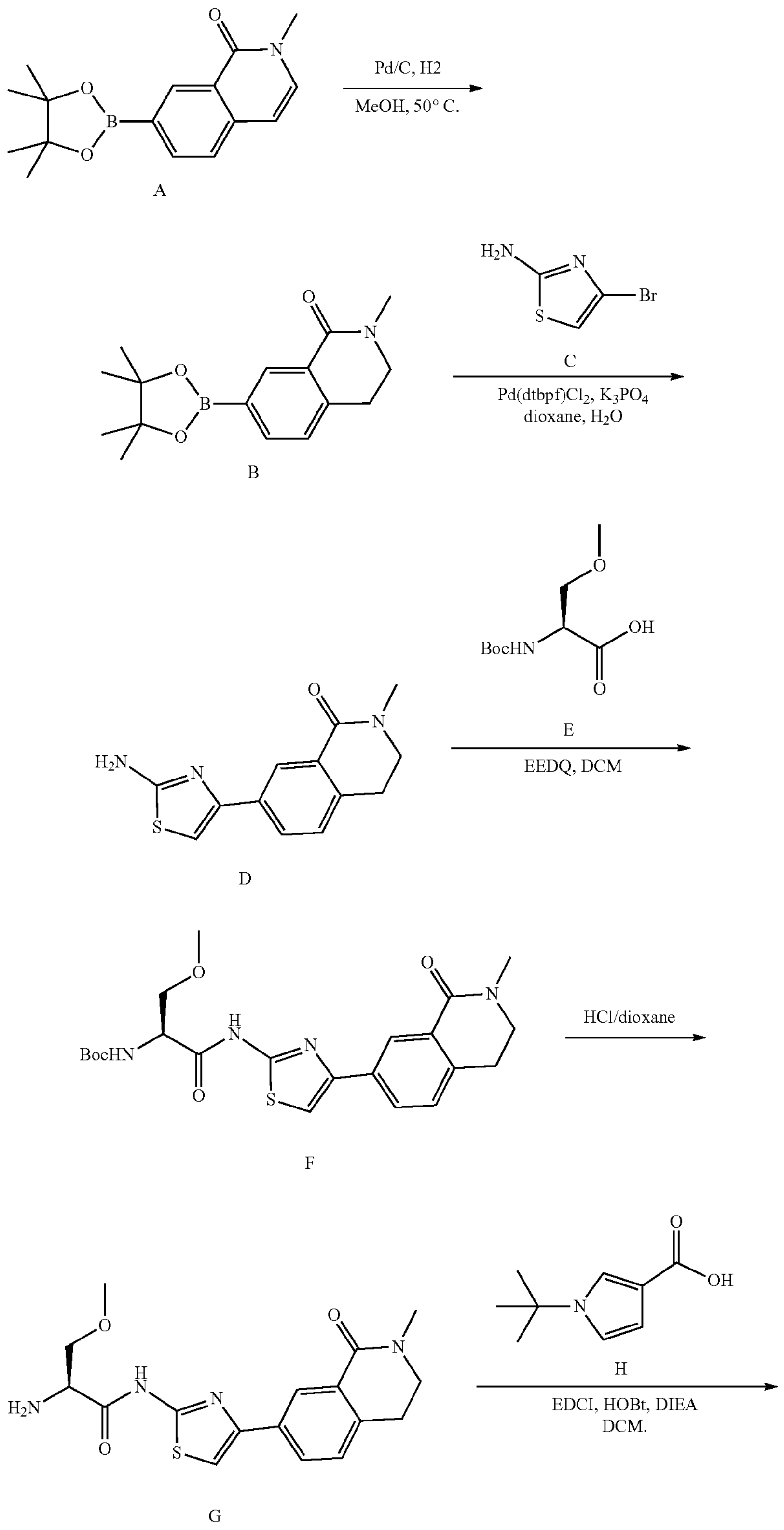

-continued

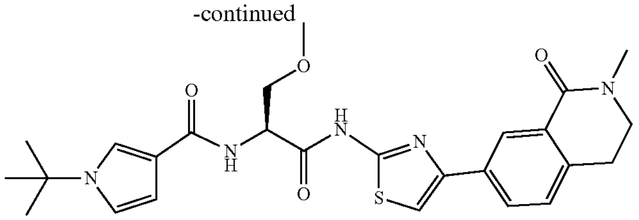

Compound 64

Step 1: Preparation of 7-(2-aminothiazol-4-yl)-2-methyl-3,4-dihydroisoquinolin-1(2H)-one (Intermediate D)

D

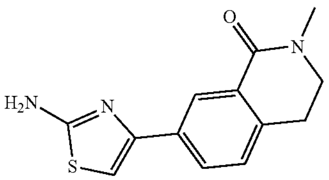

A mixture of 2-methyl-7-(4,4,5,5-tetramethyl-1,3,2-dioxaborolan-2-yl)-3,4-dihydroisoquinolin-1(2H)-one [prepared according to the method in Example 7] (200 mg, 696.47 μmol), 4-bromothiazol-2-amine (124.70 mg, 696.47 μmol), $K_3PO_4$ (591.35 mg, 2.79 mmol) and [1,1'-bis(di-tert-butylphosphino)ferrocene]dichloropalladium(II) (45.39 mg, 69.65 μmol) in dioxane (2 mL) and $H_2O$ (0.5 mL) was degassed and purged with $N_2$ for 3 times, and then the mixture was stirred at 100° C. for 2 h under $N_2$ atmosphere. Water (20 mL) was added and the reaction mixture was extracted with EtOAc (50 mL×2). The combined organic layers were washed with brine (20 mL), dried over $Na_2SO_4$, filtered and concentrated under reduced pressure to give a residue. The crude product was triturated with MeOH (10 mL) at 25° C. for 10 min, then filtered and dried in vacuum to give Intermediate D (180 mg, 691.75 μmol, 99.32% yield) as a white solid. LCMS (ESI) m/z $[M+H]^+$=260.1.

Step 2: Preparation of (S)-tert-butyl (3-methoxy-1-((4-(2-methyl-1-oxo-1,2,3,4-tetrahydroisoquinolin-7-yl)thiazol-2-yl)amino)-1-oxopropan-2-yl)carbamate (Intermediate F)

F

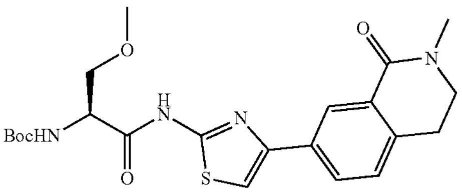

To a solution of Intermediate D (110.86 mg, 427.50 μmol) and (2S)-2-(tert-butoxycarbonylamino)-3-methoxy-propanoic acid (103.09 mg, 470.25 μmol) in DCM (2 mL) was added EEDQ (158.57 mg, 641.25 μmol). The mixture was stirred at 25° C. for 2 h. The reaction mixture was concentrated under reduced pressure to remove DCM. The crude product was triturated with MeOH (5 mL) at 25° C. for 10 min, then filtered and dried in vacuum to give Intermediate F (150 mg, 325.70 μmol, 76.19% yield) as a brown solid. LCMS (ESI) m/z $[M+H]^+$=461.4.

Step 3: Preparation of (S)-2-amino-3-methoxy-N-(4-(2-methyl-1-oxo-1,2,3,4-tetrahydroisoquinolin-7-yl)thiazol-2-yl)propanamide (Intermediate G)

G

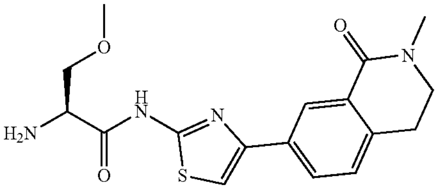

To a solution of Intermediate F (100 mg, 217.13 μmol) in MeOH (2 mL) was added HCl/dioxane (2 mL). The mixture was stirred at 30° C. for 2 h. The reaction mixture was concentrated under reduced pressure to give Intermediate G (80 mg, crude, HCl salt) as a yellow solid, which was used into the next step without further purification. LCMS (ESI) m/z $[M+H]^+$=361.2.

Step 4: Preparation of (S)-1-(tert-butyl)-N-(3-methoxy-1-((4-(2-methyl-1-oxo-1,2,3,4-tetrahydroisoquinolin-7-yl)thiazol-2-yl)amino)-1-oxopropan-2-yl)-1H-pyrrole-3-carboxamide (Compound 64)

Compound 64

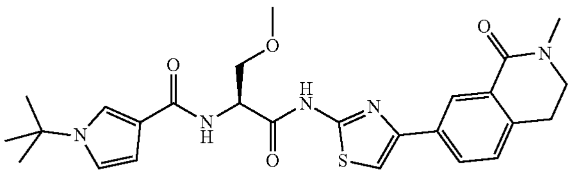

To a solution of [prepared according to the method in Example 34] (50.55 mg, 302.35 μmol) in DMF (2 mL) was added EDCI (57.96 mg, 302.35 μmol), HOBt (40.85 mg, 302.35 μmol) and DIEA (104.20 mg, 806.27 μmol, 140.43 μL), then Intermediate G (80 mg, 201.57 μmol, HCl salt) was added. The mixture was stirred at 25° C. for 12 h. Water (30 mL) was added and the reaction mixture was extracted with EtOAc (50 mL×2). The combined organic layers were washed with brine (20 mL), dried over $Na_2SO_4$, filtered and concentrated under reduced pressure to give a residue. The residue was purified by Prep-HPLC (mobile phase: [water (0.075% TFA)-acetonitrile]; B %: 35%-65%) and then re-purified by Prep-TLC ($SiO_2$, DCM:EtOAc=2:1) and concentrated to give Compound 64 (17 mg, 33.36 μmol, 16.55% yield) as a white solid. LCMS (ESI) m/z $[M+H]^+$=510.3; $^1H$ NMR (400 MHz, DMSO-$d_6$) δ 12.48 (s, 1H), 8.47 (d, J=2.0 Hz, 1H), 7.98-7.91 (m, 2H), 7.68 (s, 1H), 7.62-7.61 (m, 1H), 7.35 (d, J=8.0 Hz, 1H), 6.96-6.95 (m, 1H), 6.50-6.49 (m, 1H), 4.93-4.88 (m, 1H), 3.74-3.66 (m, 2H), 3.58-3.55 (m, 2H), 3.31 (s, 3H), 3.05 (s, 3H), 3.01-2.98 (m, 2H), 1.49 (s, 9H); ee %=100%.

Example 64. (S)—N-(3-methoxy-1-oxo-1-((4-(3-(pyrimidin-4-yl)phenyl)thiazol-2-yl)amino)propan-2-yl)-1-(methylsulfonyl)-1H-pyrrole-3-carboxamide (Compound 65)

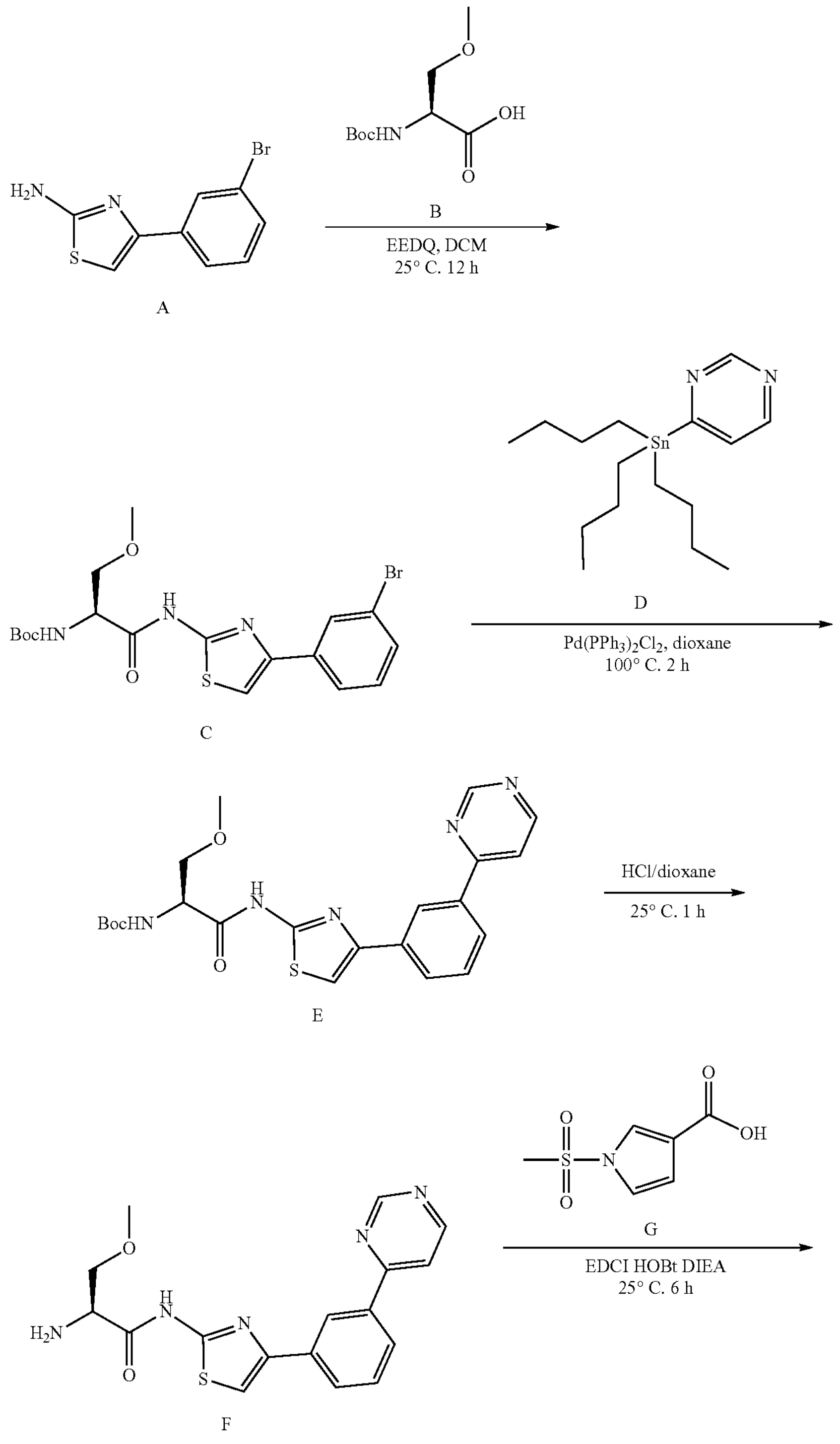

-continued

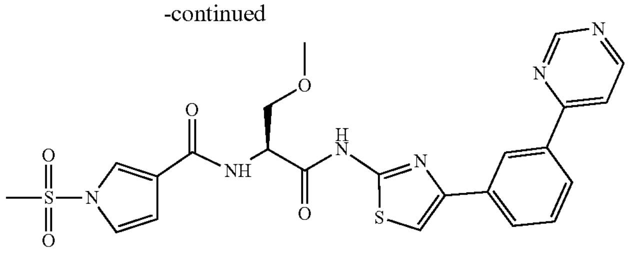

Compound 65

Step 1: Preparation of (S)-tert-butyl (1-((4-(3-bromophenyl)thiazol-2-yl)amino)-3-methoxy-1-oxopropan-2-yl)carbamate (Intermediate C)

C

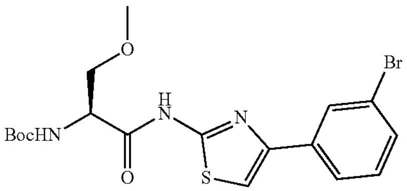

A mixture of (2S)-2-(tert-butoxycarbonylamino)-3-methoxy-propanoic acid (300 mg, 1.37 mmol), 4-(3-bromophenyl)thiazol-2-amine (418.95 mg, 1.64 mmol), EEDQ (676.78 mg, 2.74 mmol) in DCM (5 mL) was degassed and purged with $N_2$ for 3 times, and then the mixture was stirred at 25° C. for 12 h under $N_2$ atmosphere. The reaction mixture was poured into $H_2O$ (10 mL), and then extracted with EtOAc (3 mL×4). The combined organic layers were dried over $Na_2SO_4$, filtered and concentrated under reduced pressure to give a residue. The residue was purified by reversed phase (FA) and lyophilized to give Intermediate C (410 mg, 843.62 μmol, 61.65% yield) as a white gum. LCMS (ESI) m/z $[M+H]^+$=458.0; $^1$H NMR (400 MHz, DMSO-$d_6$) δ 12.53-12.30 (m, 1H), 8.11 (s, 1H), 7.95-7.88 (m, 1H), 7.79 (s, 1H), 7.54-7.50 (m, 1H), 7.41 (s, 1H), 7.17 (d, J=6.8 Hz, 1H), 4.50 (d, J=5.6 Hz, 1H), 3.57 (d, J=5.2 Hz, 2H), 3.27 (s, 4H), 1.39 (s, 9H).

Step 2: Preparation of (S)-tert-butyl (3-methoxy-1-oxo-1-((4-(3-(pyrimidin-4-yl)phenyl)thiazol-2-yl)amino)propan-2-yl)carbamate (Intermediate E)

E

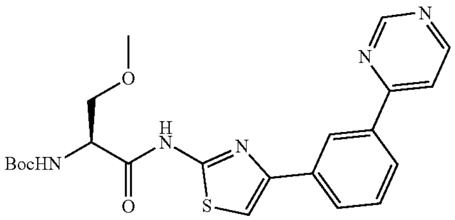

A mixture of Intermediate C (300 mg, 657.39 μmol), tributyl(pyrimidin-4-yl)stannane (363.99 mg, 986.08 μmol), $Pd(PPh_3)_2Cl_2$ (46.14 mg, 65.74 μmol) in dioxane (3 mL) was degassed and purged with $N_2$ for 3 times, and then the mixture was stirred at 100° C. for 2 h under $N_2$ atmosphere. The reaction mixture was poured into aq. KF (5 mL) and stirred for 30 min, then extracted with EtOAc (2 mL×3). The combined organic layers were dried over $Na_2SO_4$, filtered and concentrated under reduced pressure to give a residue. The residue was purified by flash silica gel chromatography (Eluent of 0-80% Ethyl acetate/Petroleum ether gradient) and concentrated under reduced pressure to give Intermediate E (265 mg, 431.88 μmol, 65.70% yield) as a light yellow solid. LCMS (ESI) m/z $[M+H]^+$=456.1; $^1$H NMR (400 MHz, DMSO-$d_6$) δ 12.52 (s, 1H), 9.30 (d, J=1.2 Hz, 1H), 8.92 (d, J=5.2 Hz, 1H), 8.83-8.82 (m, 1H), 8.19-8.15 (m, 2H), 8.10 (d, J=8.4 Hz, 1H), 7.84 (s, 1H), 7.65-7.61 (m, 2H), 7.22-7.17 (m, 1H), 4.58-4.47 (m, 1H), 3.58 (d, J=5.6 Hz, 2H), 3.28 (s, 3H), 1.40 (s, 9H).

Step 3: Preparation of (S)-2-amino-3-methoxy-N-(4-(3-(pyrimidin-4-yl)phenyl)thiazol-2-yl)propanamide (Intermediate F)

F

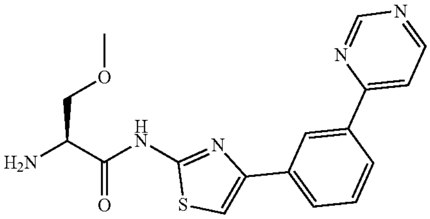

To a solution of Intermediate E (100 mg, 219.52 μmol) in dioxane (1 mL) was added HCl/dioxane (4 M, 548.81 μL), and then the mixture was stirred at 25° C. for 1 h. The reaction mixture was concentrated under reduced pressure to give a residue, and the residue was washed with MTBE (6 mL) and concentrated in vacuum to give Intermediate F (78 mg, crude) as light yellow solid, which was used into the next step without further purification. LCMS (ESI) m/z $[M+H]^+$=356.2.

Step 4: Preparation of (S)—N-(3-methoxy-1-oxo-1-((4-(3-(pyrimidin-4-yl)phenyl)thiazol-2-yl)amino)propan-2-yl)-1-(methylsulfonyl)-1H-pyrrole-3-carboxamide (Compound 65)

Compound 65

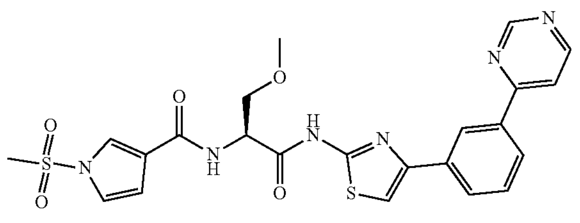

To a solution of 1-methylsulfonylpyrrole-3-carboxylic acid [prepared according to the method in Example 4] (26.62 mg, 140.68 μmol) and Intermediate F (50 mg, 140.68 μmol) in DMF (0.3 mL) was added HOBT (38.02 mg, 281.36 μmol), EDCI (53.94 mg, 281.36 μmol) and DIEA (54.55 mg, 422.04 μmol). The resulting mixture was stirred at 25° C. for 6 h. The reaction mixture was poured into water (5 mL), and extracted with EtOAc (5 mL×3). The combined organic layers were washed with brine (5 mL×2), dried over $Na_2SO_4$, filtered and concentrated under reduced pressure to give a residue. The residue was purified by flash silica gel chromatography (Eluent of 0-100% Ethyl acetate/Petroleum ether gradient) and then re-purified through Prep-HPLC (TFA condition) and lyophilized to give Compound 65 (18 mg, 27.22 μmol, 19.35% yield, TFA salt) as an off-white solid. LCMS (ESI) m/z $[M+H]^+$=527.2; $^1$H NMR (400 MHz, DMSO+$D_2O$) δ 9.27 (d, J=1.2 Hz, 1H), 8.89 (d, J=5.2 Hz, 1H), 8.79 (s, 1H), 8.15-8.12 (m, 2H), 8.09 (d, J=7.6 Hz, 1H), 7.98-7.97 (m, 1H), 7.79 (s, 1H), 7.66-7.61 (m, 1H), 7.31-7.28 (m, 1H), 6.80-6.79 (m, 1H), 4.94-4.89 (m, 1H), 3.74-3.71 (m, 2H), 3.54 (s, 3H), 3.32 (s, 3H); ee %=100%.

Example 65. Preparation of (S)-1-(tert-butyl)-N-(3-methoxy-1-oxo-1-((4-(3-(pyrimidin-4-yl)phenyl)thiazol-2-yl)amino)propan-2-yl)-1H-pyrrole-3-carboxamide (Compound 66)

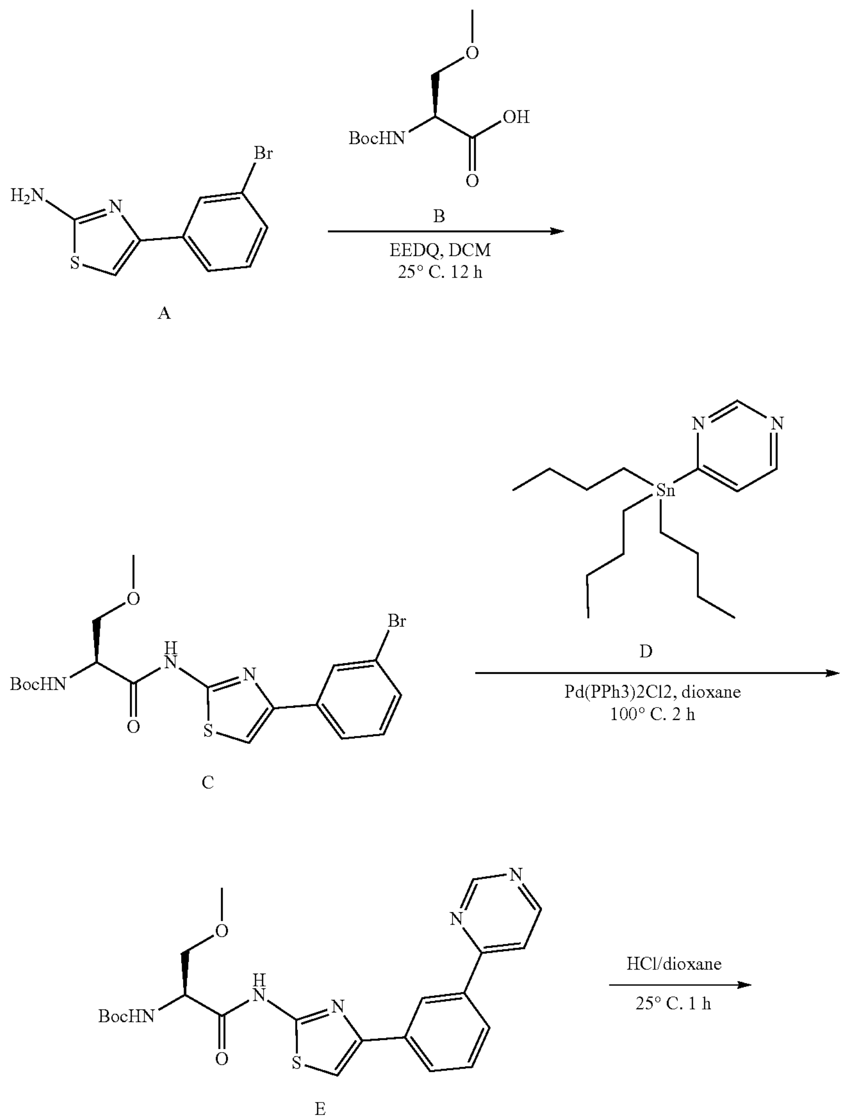

A

C

E

-continued

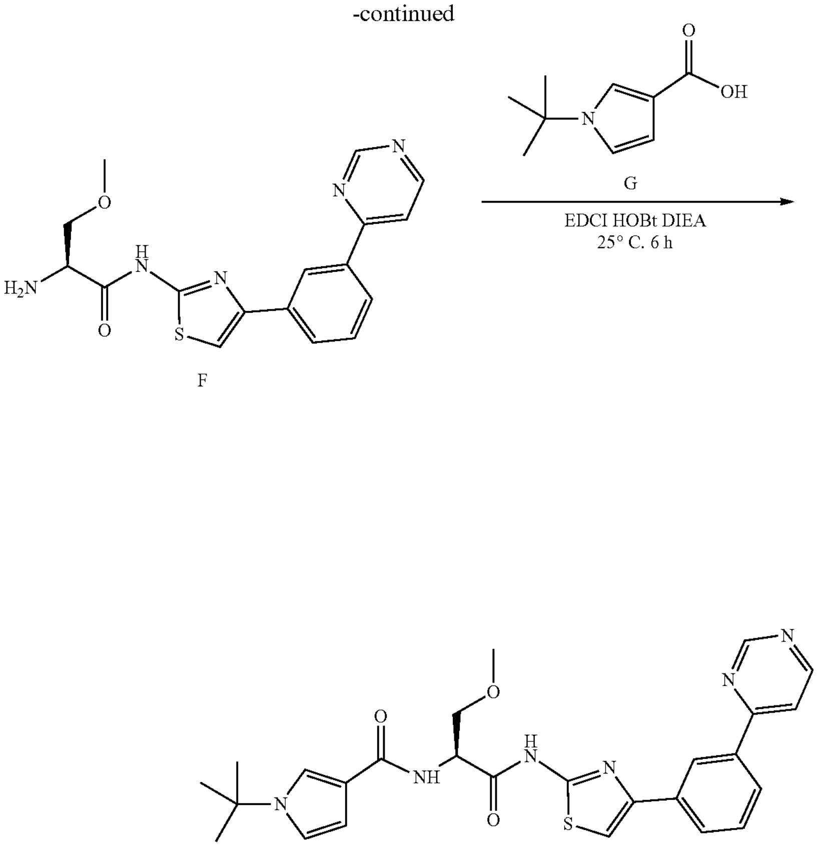

F

G

Compound 66

To a solution of (S)-2-amino-3-methoxy-N-(4-(3-(pyrimidin-4-yl)phenyl)thiazol-2-yl)propanamide [prepared according to the method in Example 64] (50 mg, 140.68 μmol, HCl salt) and 1-tert-butylpyrrole-3-carboxylic acid [prepared according to the method in Example 34] (23.52 mg, 140.68 μmol) in DMF (0.3 mL) were added HOBt (38.02 mg, 281.36 μmol), EDCI (53.94 mg, 281.36 μmol) and DIEA (54.54 mg, 422.04 μmol). The resulting mixture was stirred at 25° C. for 6 h. The reaction mixture was poured into $H_2O$ (5 mL), and extracted with EtOAc (5 mL×3). The combined organic layers were washed with brine (5 mL×2), dried over $Na_2SO_4$, filtered and concentrated under reduced pressure to give a residue. The residue was purified by flash silica gel chromatography (Eluent of 0-100% Ethyl acetate/Petroleum ether gradient 30 mL/min) and concentrated to give Compound 66 (20 mg, 39.64 μmol, 28.17% yield) as an off-white solid. LCMS (ESI) m/z $[M+H]^+$=505.4; $^1H$ NMR (400 MHz, DMSO-$d_6$) δ 12.63-12.43 (m, 1H), 9.30 (s, 1H), 8.96-8.89 (m, 1H), 8.83 (s, 1H), 8.20-8.07 (m, 3H), 7.97-7.91 (m, 1H), 7.82 (s, 1H), 7.69-7.59 (m, 2H), 6.97 (br s, 1H), 6.58-6.48 (m, 1H), 4.96-4.91 (m, 1H), 3.73-3.71 (m, 2H), 2.70 (d, J=1.0 Hz, 3H), 1.50 (s, 9H); ee %=94.616%.

Example 66. Preparation of (S)-1-(methylsulfonyl)-N-(4-(methylthio)-1-oxo-1-((4-(3-(pyridin-4-yl)phenyl)thiazol-2-yl)amino)butan-2-yl)-1H-pyrrole-3-carboxamide (Compound 67)

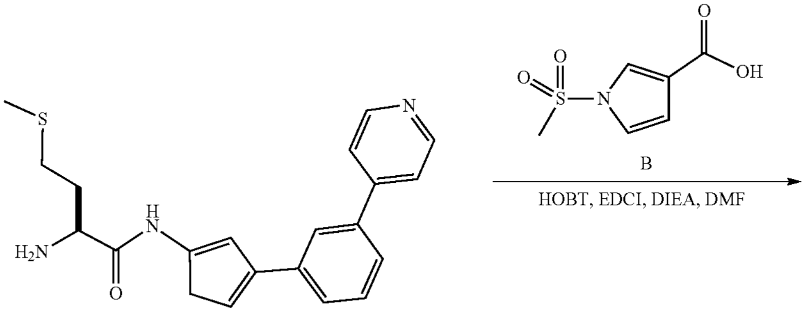

A

B

-continued

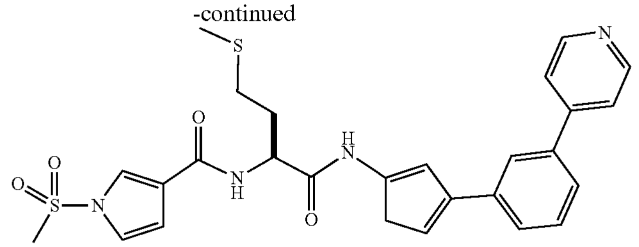

Compound 67

To a mixture of (2S)-2-amino-4-methylsulfanyl-N-[4-[3-(4-pyridyl)phenyl]thiazol-2-yl]butanamide (2 g, 4.75 mmol, HCl salt) and 1-methylsulfonylpyrrole-3-carboxylic acid [prepared according to the method in Example 4] (898.81 mg, 4.75 mmol) in DMF (20 mL) was added EDCI (1.37 g, 7.13 mmol), HOBt (962.92 mg, 7.13 mmol) and DIEA (2.46 g, 19.00 mmol, 3.31 mL) and the mixture was stirred at 25° C. for 3 hr. The mixture was poured into $H_2O$ (100 mL) and the precipitate was collected by filtration. The solid was triturated in MeOH (20 mL) and the precipitate was collected by filtration. The solid was dissolved in DMSO (10 mL) and then the mixture was poured into MeOH (50 mL) and the formed precipitate was collected by filtration and lyophilized to give Compound 67 (2.05 g, 3.66 mmol, 77.01% yield) as a white solid. LCMS (ESI) m/z $[M+H]^+$=555.9; $^1$H NMR (400 MHz, DMSO-$d_6$) δ 12.49 (s, 1H), 8.68-8.66 (m, 2H), 8.46 (d, J=7.2 Hz, 1H), 8.31-8.30 (m, 1H), 8.02-8.00 (m, 1H), 7.94-7.96 (m, 1H), 7.83 (s, 1H), 7.73-7.74 (m, 3H), 7.61-7.57 (m, 1H), 7.31-7.29 (m, 1H), 6.79-6.77 (m, 1H), 4.74-4.69 (m, 1H), 3.57 (s, 3H), 2.67-2.53 (m, 2H), 2.13-2.01 (m, 5H); ee %=100%.

Example 67. Preparation of N-[(1S)-1-methyl-2-oxo-2-[[4-[3-(4-pyridyl)phenyl]thiazol-2-yl]amino]ethyl]-1-methylsulfonyl-pyrrole-3-carboxamide (Compound 68)

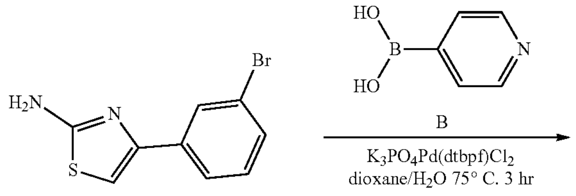

A

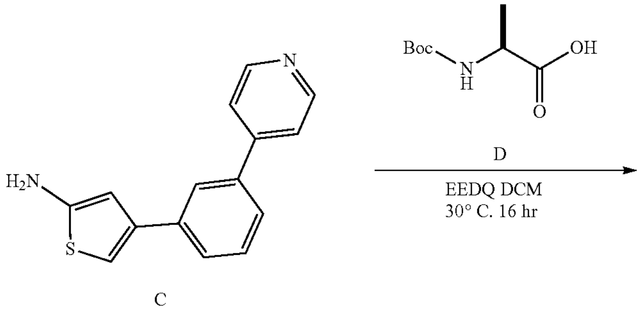

C

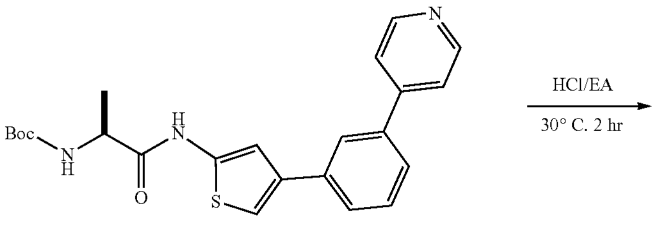

E

-continued

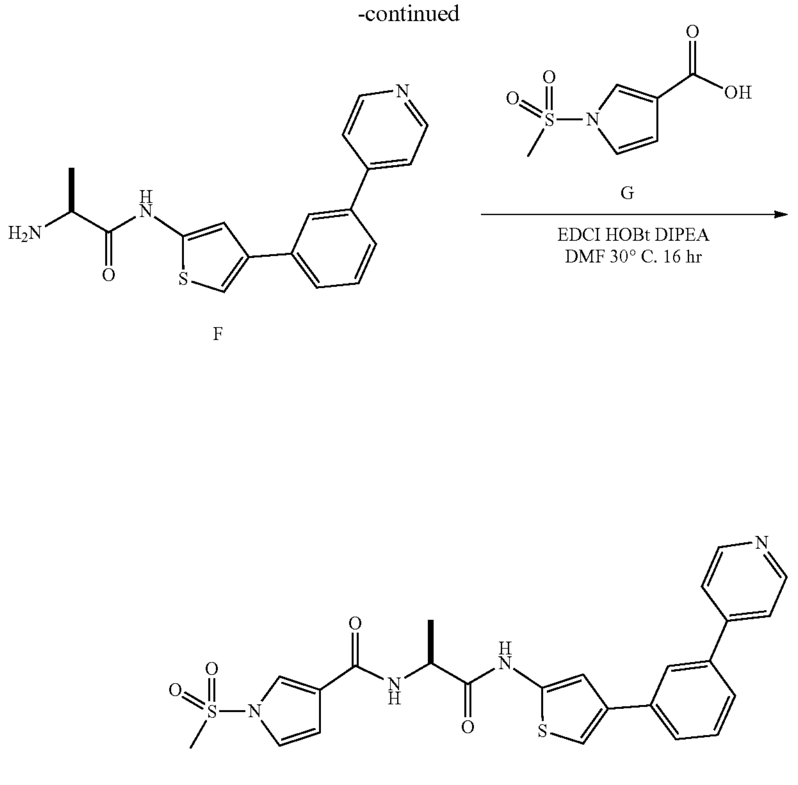

Compound 68

Step 1: Preparation of tert-butyl N-[(1S)-1-methyl-2-oxo-2-[[4-[3-(4-pyridyl)phenyl]thiazol-2-yl]amino]ethyl]carbamate (Intermediate E)

E

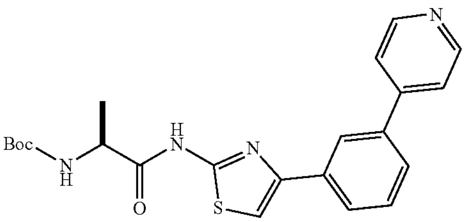

To a mixture of -[3-(4-pyridyl)phenyl]thiazol-2-amine [prepared according to method in Example 4] (205 mg, 809.25 μmol) and (2S)-2-(tertbutoxycarbonylamino)propanoic acid (153.12 mg, 809.25 μmol) in DCM (7 mL) was added EEDQ (400.24 mg, 1.62 mmol) at 30° C. The reaction mixture was stirred at 30° C. for 16 h. The reaction mixture was concentrated under reduced pressure to afford a residue. The residue was purified by reverse phase column ($NH_3 \cdot H_2O$ condition) to afford Intermediate E (80 mg, 188.45 μmol) as yellow solid. LCMS (ESI) m/z $[M+H]^+$=425.3; $^1H$ NMR (400 MHz, DMSO-$d_6$) δ 12.34 (s, 1H), 8.69-8.67 (m, 2H), 8.31 (s, 1H), 8.02 (d, J=8.0 Hz, 1H), 7.84 (s, 1H), 7.77-7.75 (m, 3H), 7.62-7.58 (m, 1H), 7.26 (d, J=6.8 Hz, 1H), 4.29-4.25 (m, 1H), 1.39 (s, 9H), 1.30-1.28 (m, 3H). Chiral HPLC: OJ-3-MeOH (DEA)-5-40-3 mL-35T, t=1.744 min, ee %=100%.

Step 2: Preparation of (2S)-2-amino-N-[4-[3-(4-pyridyl)phenyl]thiazol-2-yl]propanamide (Intermediate F)

F

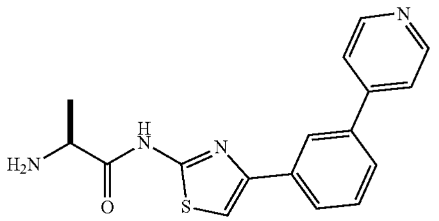

To a mixture of Intermediate E (80 mg, 188.45 μmol) in dioxane (2 mL) was added HCl/dioxane (4 M, 2 mL) at 30° C. The reaction mixture was stirred at 30° C. for 2 h. The reaction mixture was filtered and dried in vacuum to afford Intermediate F (75 mg, 172.20 μmol, 91% yield, HCl salt) as yellow solid. LCMS (ESI) m/z $[M+H]^+$=325.1; $^1H$ NMR (400 MHz, DMSO-$d_6$) δ 12.89 (br s, 1H), 9.00 (d, J=6.8 Hz, 2H), 8.53 (br s, 2H), 8.48 (s, 1H), 8.43 (d, J=6.8 Hz, 2H), 8.16 (d, J=7.6 Hz, 1H), 8.02 (s, 1H), 7.99 (d, J=8.4 Hz, 1H), 7.73-7.69 (m, 1H), 4.23-4.15 (m, 1H), 1.51 (d, J=7.2 Hz, 3H).

Step 3: Preparation of N-[(1S)-1-methyl-2-oxo-2-[[4-[3-(4-pyridyl)phenyl]thiazol-2-yl]amino]ethyl]-1-methylsulfonyl-pyrrole-3-carboxamide (Compound 68)

Compound 68

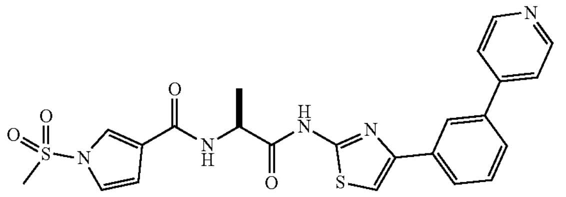

To a mixture of Intermediate F (30 mg, 83.13 μmol, HCl salt) and 1-methylsulfonylpyrrole-3-carboxylic acid [prepared according to the method in Example 4] (15.73 mg, 83.13 μmol) in DMF (1 mL) was added DIPEA (53.72 mg, 415.67 μmol, 72.40 μL), EDCI (23.91 mg, 124.70 μmol) and HOBt (16.85 mg, 124.70 μmol) at 30° C. The reaction mixture was stirred at 30° C. for 16 h. The reaction mixture was concentrated in vacuum and then purified by reverse phase column ($NH_3 \cdot H_2O$ condition) and lyophilized to afford Compound 68 (12.52 mg, 25.26 μmol, 30% yield) as white solid. LCMS (ESI) m/z $[M+H]^+$=496.0; $^1$H NMR (400 MHz, DMSO-$d_6$) δ 12.43 (s, 1H), 8.68 (d, J=6.0 Hz, 2H), 8.50 (d, J=6.4 Hz, 1H), 8.30 (s, 1H), 8.01 (d, J=8.0 Hz, 1H), 7.95-7.94 (m, 1H), 7.83 (s, 1H), 7.77-7.75 (m, 3H), 7.61-7.57 (m, 1H), 7.30-7.29 (m, 1H), 6.79-6.78 (m, 1H), 4.68-4.61 (m, 1H), 3.56 (s, 3H), 1.43 (d, J=7.2 Hz, 3H); ee %=100%.

Example 68. Preparation of (S)—N-(3-hydroxy-1-oxo-1-((4-(3-(pyridin-4-yl)phenyl)thiazol-2-yl)amino)propan-2-yl)-1-(methylsulfonyl)-1H-pyrrole-3-carboxamide (Compound 69)

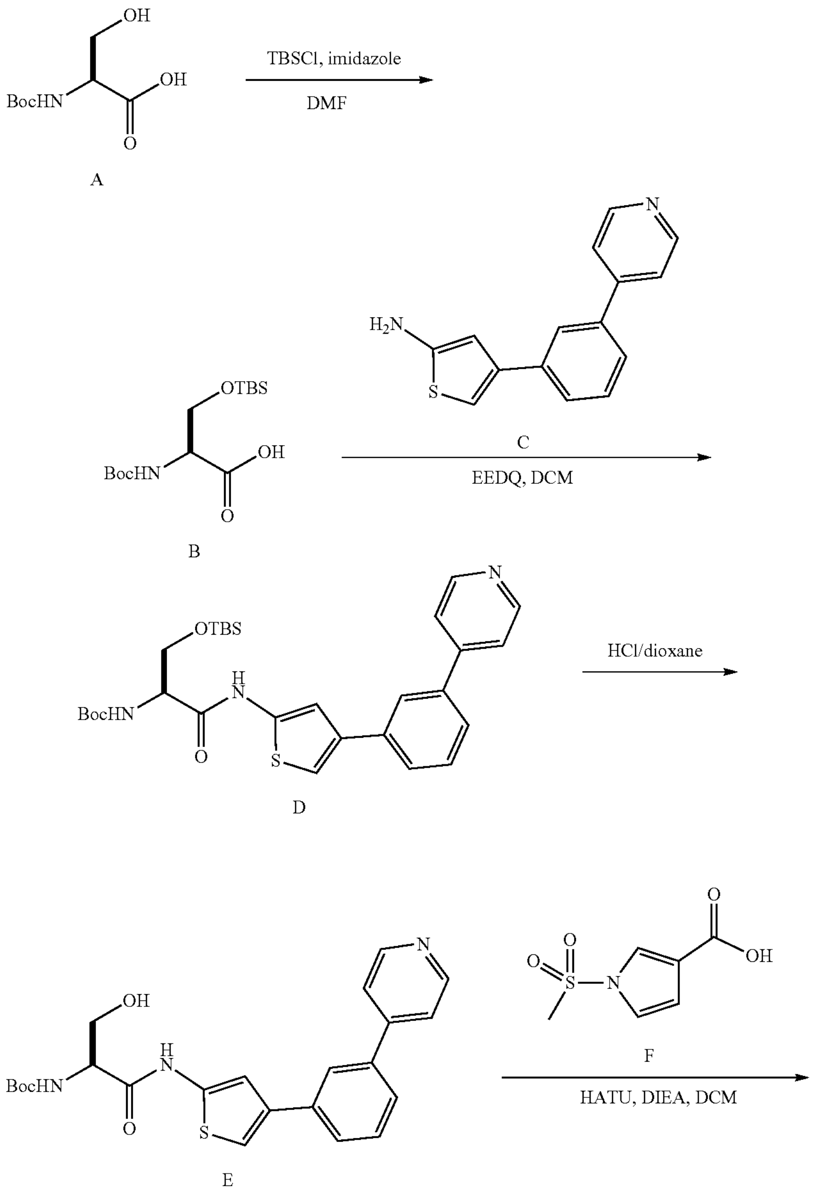

-continued

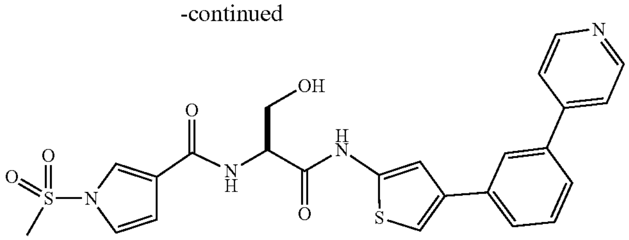

Compound 69

Step 1: Preparation of (S)-2-((tert-butoxycarbonyl) amino)-3-((tert-butyldimethylsilyl)oxy)propanoic acid (Intermediate B)

B

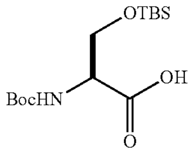

To a solution of (S)-2-((tert-butoxycarbonyl)amino)-3-hydroxypropanoic acid (1.0 g, 4.87 mmol) and imidazole (663.10 mg, 9.75 mmol) in DMF (10 mL) was added tert-butyl-chloro-dimethyl-silane (770.71 mg, 5.12 mmol, 626.59 μL) dropwise at 0° C., the mixture was stirred at 30° C. for 2 h. The reaction mixture was diluted with water (100.0 mL) and extracted with EtOAc (150 mL). The organic layer was washed with water (400.0 mL), dried over $Na_2SO_4$, filtered and concentrated under reduced pressure to give Intermediate B (700 mg, crude) as light yellow oil. $^1H$ NMR (400 MHz, $CDCl_3$) δ 5.32 (br s, 1H), 4.35 (br s, 1H), 4.11-4.08 (m, 1H), 3.83-3.80 (m, 1H), 1.47 (s, 9H), 0.89 (m, 9H), 0.08 (d, J=2.0 Hz, 6H).

Step 2: Preparation of (S)-tert-butyl (3-((tert-butyldimethylsilyl)oxy)-1-oxo-1-((4-(3-(pyridin-4-yl)phenyl)thiazol-2-yl)amino)propan-2-yl)carbamate (Intermediate D)

D

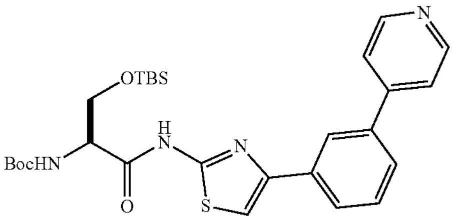

To a solution of 4-(3-(pyridin-4-yl)phenyl)thiazol-2-amine (prepared according to the method in Example 4) (300 mg, 1.18 mmol) and Intermediate B (567.50 mg, 1.78 mmol) in DCM (10 mL) was added EEDQ (439.29 mg, 1.78 mmol), the mixture was stirred at 30° C. for 4 h. The mixture was concentrated under reduced pressure to give a residue. The residue was purified by column chromatography ($SiO_2$, Petroleum ether/EtOAc=4/1 to 3:1) and concentrated under reduced pressure to give Intermediate D (300 mg, 535.35 μmol, 45.37% yield) as a light yellow oil. LCMS (ESI) m/z $[M+H]^+$=555.3; ee=100%.

Step 3: Preparation of (S)-2-amino-3-hydroxy-N-(4-(3-(pyridin-4-yl)phenyl)thiazol-2-yl)propanamide (Intermediate E)

E

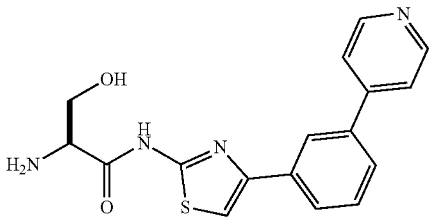

The solution of Intermediate D (300 mg, 540.76 μmol) in HCl/dioxane (4 M, 3 mL) was stirred at 30° C. for 0.25 h. The reaction mixture was concentrated under reduced pressure to give the crude product. The crude product was triturated with MTBE (5.0 mL), filtered and dried in vacuum to give Intermediate E (200 mg, 520.09 μmol, 96.18% yield, HCl salt) as a white solid. LCMS (ESI) m/z $[M+H]^+$=341.1; ee=95.398%.

Step 4: Preparation of (S)—N-(3-hydroxy-1-oxo-1-((4-(3-(pyridin-4-yl)phenyl)thiazol-2-yl)amino)propan-2-yl)-1-(methylsulfonyl)-1H-pyrrole-3-carboxamide (Compound 69)

Compound 69

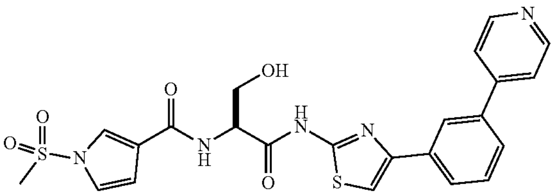

To a solution of Intermediate E (20 mg, 58.75 μmol, HCl salt), 1-methylsulfonylpyrrole-3-carboxylic acid [prepared according to the method in Example 4] (9.04 mg, 47.78 μmol) and DIEA (34.29 mg, 265.32 μmol, 46.21 μL) in DCM (0.5 mL) was added HATU (24.21 mg, 63.67 μmol), the mixture was stirred at 30° C. for 2 h. The reaction mixture was concentrated under reduced pressure to give a residue. The residue was purified by Prep-HPLC (mobile phase: water (0.1% TFA)-acetonitrile; B %: 18%-48%, 9 min) and lyophilized to give Compound 69 (15.31 mg, 24.47 μmol, 41.65% yield, TFA salt) as a white solid. LCMS (ESI) m/z $[M+H]^+$=512.1. $^1$H NMR (400 MHz, DMSO-$d_6$) δ 12.42 (s, 1H), 8.87 (d, J=6.4 Hz, 2H), 8.42 (s, 1H), 8.29 (d, J=7.2 Hz, 1H), 8.19 (br d, J=6.0 Hz, 2H), 8.10 (d, J=7.6 Hz, 1H), 7.95-7.95 (m, 1H), 7.90-7.87 (m, 2H), 7.68-7.64 (m, 1H), 7.31-7.30 (m, 1H), 6.78 (dd, J=1.6, 3.2 Hz, 1H), 6.78-6.77 (m, 1H), 4.75-4.70 (m, 1H), 3.85-3.77 (m, 2H), 3.57 (s, 3H); ee=100%.

Example 69. Preparation of (S)—N-(3-methoxy-1-oxo-1-((4-(3-(pyridin-4-yl)phenyl)thiazol-2-yl)amino)propan-2-yl)-1-(methylsulfonyl)-1H-pyrrole-3-carboxamide (Compound 70)

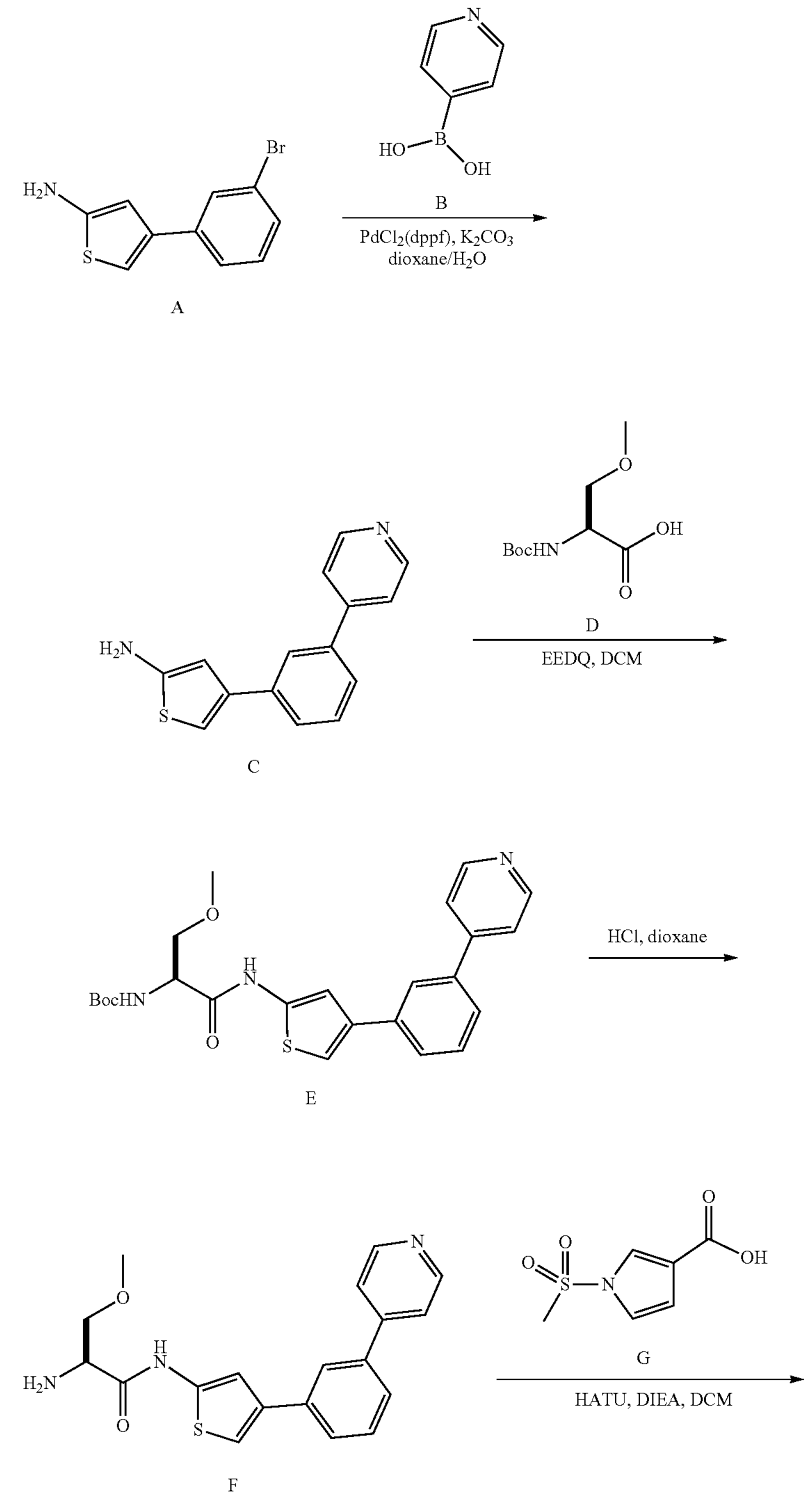

-continued

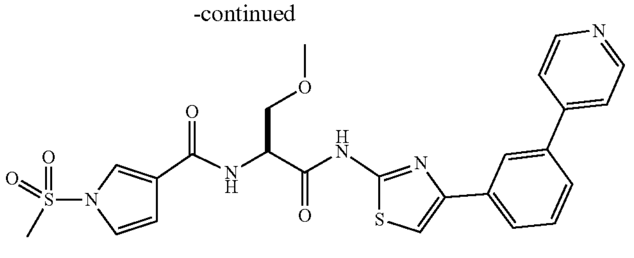

Compound 70

Step 1: Preparation of (S)-tert-butyl (3-methoxy-1-oxo-1-((4-(3-(pyridin-4-yl)phenyl)thiazol-2-yl)amino)propan-2-yl)carbamate (Intermediate E)

E

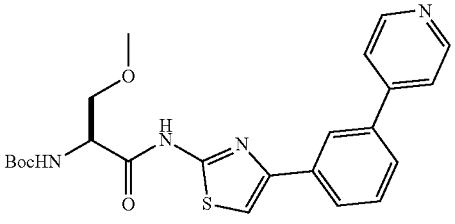

To a solution of 4-(3-(pyridin-4-yl)phenyl)thiazol-2-amine [prepared according to the method in Example 4] (12 g, 47.37 mmol) and (2S)-2-(tert-butoxycarbonylamino)-3-methoxy-propanoic acid (10.39 g, 47.37 mmol) in DCM (500 mL) was added EEDQ (23.43 g, 94.74 mmol). The mixture was stirred at 20° C. for 16 h. The reaction mixture was concentrated to give a residue. The residue was triturated with MTBE (100 mL) at 20° C. for 30 min and filtered to afford the crude product (6 g, brown solid), the crude product was further triturated with DCM (10 mL) at 20° C. for 30 min and filtered to afford the product (4.4 g, white solid) as the first batch. The mother liquid was concentrated to dryness and the residue was purified with column chromatography ($SiO_2$, DCM:MeOH=50:1) to afford the product (1.3 g, white solid) as the second batch. So Intermediate E (5.7 g, 12.37 mmol, 26.12% yield) was obtained as white solid for two batches. LCMS (ESI) m/z $[M+H]^+$=455.0; $^1H$ NMR (400 MHz, $CDCl_3$) δ 10.25 (br s, 1H), 8.81-8.70 (m, 2H), 8.20 (s, 1H), 7.95-7.87 (m, 1H), 7.65-7.60 (m, 3H), 7.59-7.53 (m, 1H), 7.27 (s, 1H), 5.49 (br s, 1H), 4.60 (br s, 1H), 3.98-3.97 (m 1H), 3.66-3.65 (m, 1H), 3.46 (s, 3H), 1.52 (s, 9H); ee %=100%.

Step 2: Preparation of (S)-2-amino-3-methoxy-N-(4-(3-(pyridin-4-yl)phenyl)thiazol-2-yl)propanamide (Intermediate F)

F

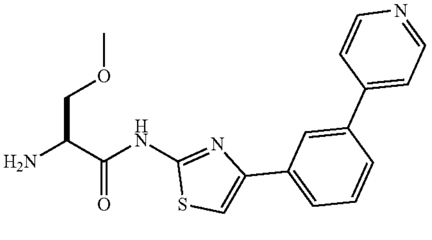

To a solution of Intermediate E (1.5 g, 3.30 mmol) in MeOH (5 mL) was added HCl/dioxane (4 M, 8.57 mL). The mixture was stirred at 20° C. for 30 min. The reaction mixture was concentrated to give Intermediate F (1.2 g, 3.07 mmol, 93.03% yield, HCl salt) as white solid, which was used in next step without further purification. LCMS (ESI) m/z $[M+H]^+$=355.0.

Step 3: Preparation of (S)—N-(3-methoxy-1-oxo-1-((4-(3-(pyridin-4-yl)phenyl)thiazol-2-yl)amino)propan-2-yl)-1-(methylsulfonyl)-1H-pyrrole-3-carboxamide (Compound 70)

Compound 70

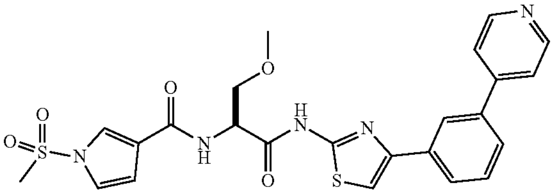

To a solution of 1-methylsulfonylpyrrole-3-carboxylic acid [prepared according to the method in Example 4] (2.02 g, 10.69 mmol) in DCM (20 mL) was added Intermediate F (3.8 g, 9.72 mmol, HCl salt), DIPEA (6.28 g, 48.61 mmol, 8.47 mL), HOBt (1.31 g, 9.72 mmol) and EDCI (2.80 g, 14.58 mmol). The mixture was stirred at 20° C. for 16 h. The reaction mixture was filtered and the solid was washed with DCM (15 mL) and dried in vacuum to give title compound (3.46 g, 6.41 mmol, 65.90% yield, ee %=100%, white solid). LCMS (ESI) m/z $[M+H]^+$=526.0; $^1H$ NMR (400 MHz, DMSO-$d_6$) δ 12.56 (s, 1H), 8.71-8.64 (m, 2H), 8.51 (d, J=7.2 Hz, 1H), 8.32 (s, 1H), 8.05-7.96 (m, 2H), 7.85 (s, 1H), 7.79-7.74 (m, 3H), 7.62-7.61 (m, 1H), 7.38-7.24 (m, 1H), 6.81-6.80 (m, 1H), 4.95-4.94 (m, 1H), 3.78-3.69 (m, 2H), 3.57 (s, 3H), 3.30 (br s, 3H); ee %=100%.

Example 70. Preparation of (S)—N-(4-hydroxy-1-oxo-1-((4-(3-(pyridin-4-yl)phenyl)thiazol-2-yl)amino)butan-2-yl)-1-(methylsulfonyl)-1H-pyrrole-3-carboxamide (Compound 71)
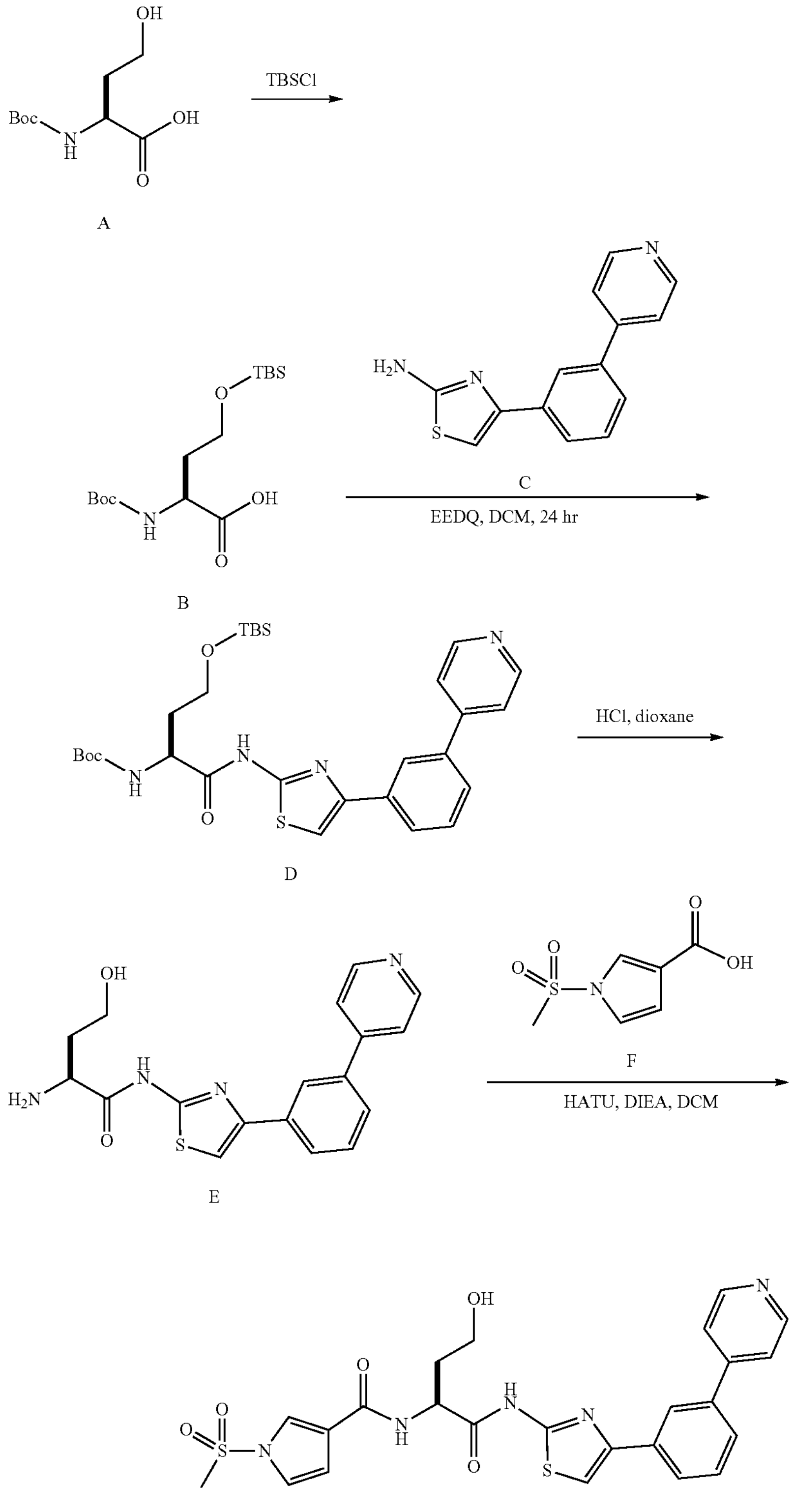
Compound 71

Step 1: Preparation of (S)-2-((tert-butoxycarbonyl) amino)-4-((tert-butyldimethylsilyl)oxy)butanoic acid (Intermediate B)

B

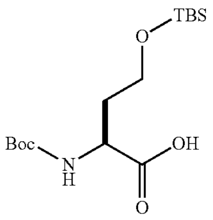

To a solution of (2S)-2-(tert-butoxycarbonylamino)-4-hydroxy-butanoic acid (1 g, 4.56 mmol) and imidazole (621.04 mg, 9.12 mmol) in DMF (10 mL) was added TBSCI (721.86 mg, 4.79 mmol, 586.88 μL) dropwise at 0° C. The mixture was stirred at 25° C. for 2 h. Water (20 mL) was added and the reaction mixture was extracted with EtOAc (50 mL×2). The combined organic layers were washed with brine (20 mL), dried over $Na_2SO_4$, filtered and concentrated under reduced pressure to give a residue. The residue was purified by flash silica gel chromatography (Eluent of 0-95% Ethyl acetate/Petroleum ether gradient) and concentrated in vacuum to give Intermediate B (900 mg, 2.70 mmol, 59.16% yield) as a colorless oil.

Step 2: Preparation of (S)-tert-butyl (4-((tert-butyldimethylsilyl)oxy)-1-oxo-1-((4-(3-(pyridin-4-yl)phenyl)thiazol-2-yl)amino)butan-2-yl)carbamate (Intermediate D)

D

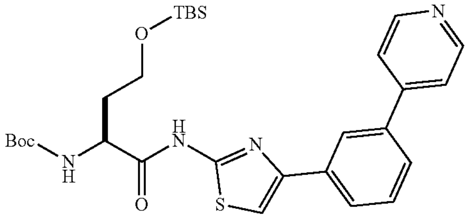

To a solution of 4-(3-(pyridin-4-yl)phenyl)thiazol-2-amine [prepared according to the method in Example 4] (300 mg, 1.18 mmol) and Intermediate B (592.42 mg, 1.78 mmol) in DCM (12 mL) was added EEDQ (585.71 mg, 2.37 mmol). The mixture was stirred at 25° C. for 2 h. The reaction mixture was concentrated under reduced pressure to remove DCM. The residue was purified by flash silica gel chromatography (Eluent of 0-95% Ethyl acetate/Petroleum ether gradient) and concentrated in vacuum to give Intermediate D (300 mg, 511.60 μmol, 43.20% yield) as a white solid. LCMS (ESI) m/z $[M+H]^+$=569.3; ee %=100%.

Step 3: Preparation of (S)-2-amino-4-hydroxy-N-(4-(3-(pyridin-4-yl)phenyl)thiazol-2-yl)butanamide (Intermediate E)

E

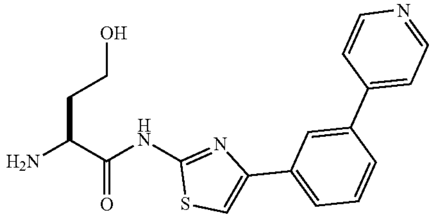

To a solution of Intermediate D (220 mg, 386.78 μmol) in dioxane (3 mL) was added HCl/dioxane (3 mL). The mixture was stirred at 25° C. for 2 h. The reaction mixture was concentrated under reduced pressure to give crude product Intermediate E (140 mg, crude, HCl salt) as a white solid, which was used for the next step without further purification. LCMS (ESI) m/z $[M+H]^+$=355.2.

Step 4: Preparation of (S)—N-(4-hydroxy-1-oxo-1-((4-(3-(pyridin-4-yl)phenyl)thiazol-2-yl)amino)butan-2-yl)-1-(methylsulfonyl)-1H-pyrrole-3-carboxamide (Compound 71)

Compound 71

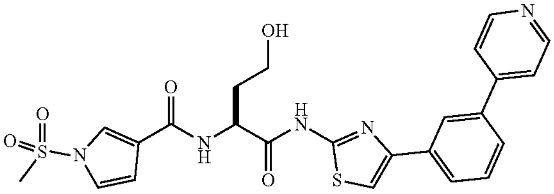

To a solution of Intermediate E (70 mg, 179.08 μmol, HCl salt) and 1-methylsulfonylpyrrole-3-carboxylic acid [prepared according to the method in Example 4] (33.88 mg, 179.08 μmol) in DCM (4 mL) was added DIEA (69.43 mg, 537.24 μmol, 93.58 μL), then HATU (136.18 mg, 358.16 μmol) was added. The mixture was stirred at 25° C. for 2 h. The reaction mixture was concentrated under reduced pressure to remove DCM. The residue was purified by Prep-HPLC (mobile phase:[water (0.1% TFA)-acetonitrile]; B %: 15%-45%) and lyophilized to give Compound 71 (23.76 mg, 37.15 μmol, 20.74% yield, TFA salt) as a white solid. LCMS (ESI) m/z $[M+H]^+$=526.2; $^1H$ NMR (400 MHz, DMSO-$d_6$) δ 12.39 (s, 1H), 8.84 (s, 2H), 8.43-8.40 (m, 2H), 8.09-8.07 (d, J=7.6 Hz, 3H), 7.95-7.94 (m, 1H), 7.86 (s, 2H), 7.67-7.63 (m, 1H), 7.31-7.29 (m, 1H), 6.77-6.76 (m, 1H), 4.71-4.66 (m, 1H), 3.56 (s, 3H), 3.53-3.52 (m, 2H), 1.98-1.97 (m, 2H); ee %=96.562%.

Example 71. Preparation of (S)—N-(4-methoxy-1-oxo-1-((4-(3-(pyridin-4-yl)phenyl)thiazol-2-yl)amino)butan-2-yl)-1-(methylsulfonyl)-1H-pyrrole-3-carboxamide (Compound 72)
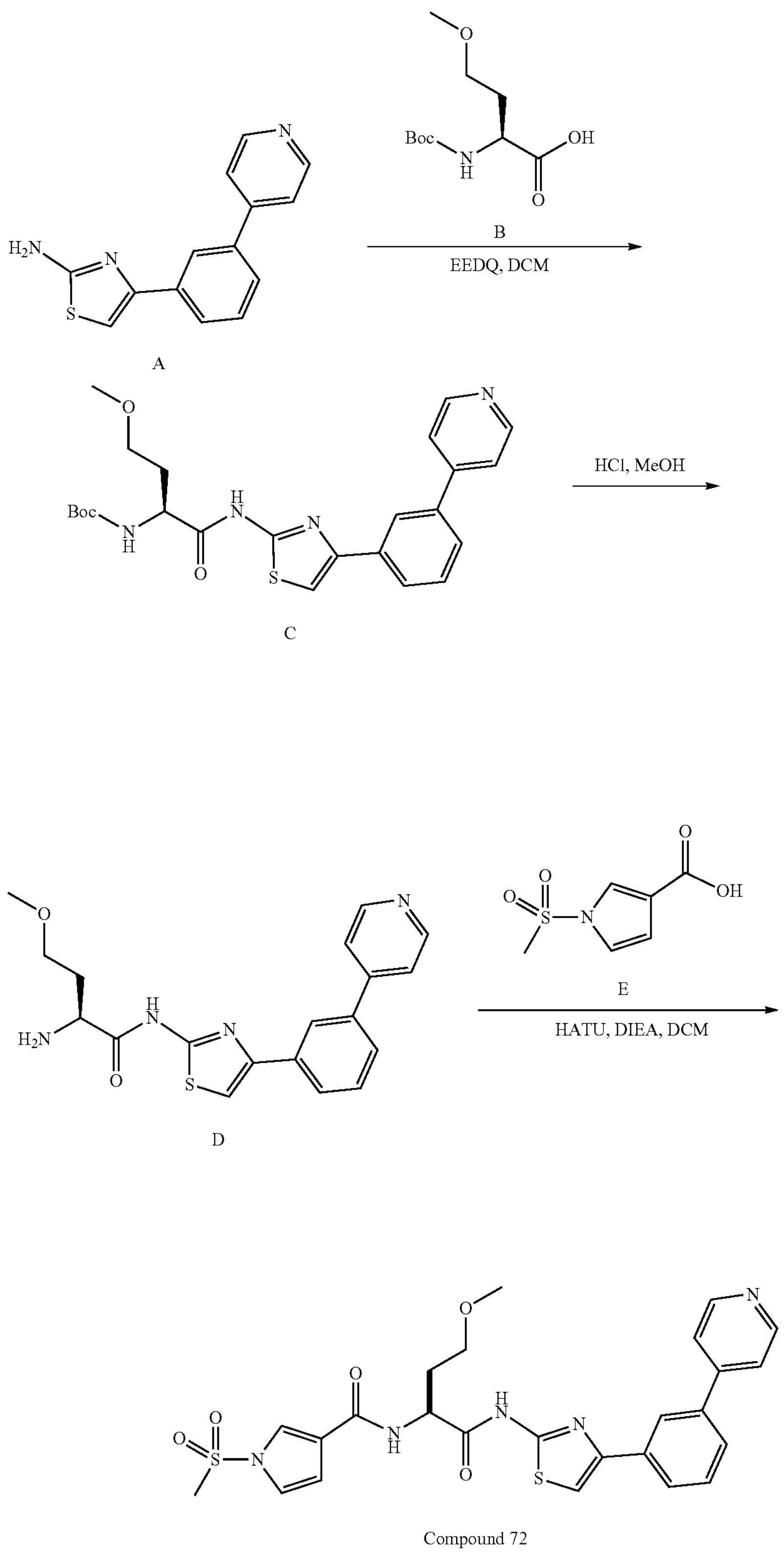
Compound 72

Step 1: Preparation of (S)-tert-butyl (4-methoxy-1-oxo-1-((4-(3-(pyridin-4-yl)phenyl)thiazol-2-yl)amino)butan-2-yl)carbamate (Intermediate C)

C

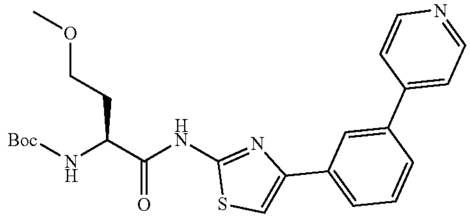

To a mixture of 4-(3-(pyridin-4-yl)phenyl)thiazol-2-amine [prepared according to the method in Example 4] (300 mg, 1.18 mmol) and (S)-2-((tert-butoxycarbonyl)amino)-4-methoxybutanoic acid (276.24 mg, 1.18 mmol) in DCM (5 mL) was added EEDQ (585.71 mg, 2.37 mmol) at 30° C. The mixture was stirred at 30° C. for 16 hours. The reaction mixture was evaporated to dryness. The residue was purified by prep-HPLC (FA condition) to give Intermediate C (330 mg, 704.27 μmol, 59.47% yield) as yellow solid. LCMS (ESI) m/z $[M+H]^+$=469.2.

Step 2: Preparation of (S)-2-amino-4-methoxy-N-(4-(3-(pyridin-4-yl)phenyl)thiazol-2-yl)butanamide (Intermediate D)

D

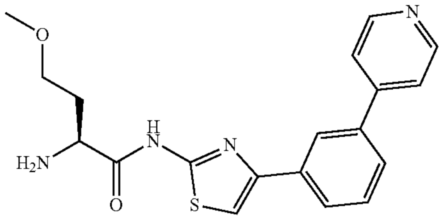

Intermediate C (100 mg, 213.42 μmol) was dissolved in HCl/MeOH (1 mL). The solution was stirred at 30° C. for 1 hr. The reaction mixture was evaporated to dryness to give Intermediate D (86 mg, crude, HCl salt) as yellow solid. LCMS (ESI) m/z$[M+H]^+$=369.2.

Step 3: Preparation of (S)—N-(4-methoxy-1-oxo-1-((4-(3-(pyridin-4-yl)phenyl)thiazol-2-yl)amino)butan-2-yl)-1-(methylsulfonyl)-1H-pyrrole-3-carboxamide (Compound 72)

Compound 72

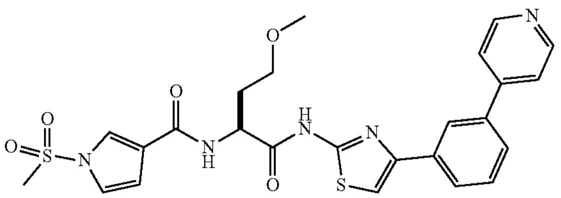

To a mixture of 1-methylsulfonylpyrrole-3-carboxylic acid [prepared according to the method in Example 4] (28.03 mg, 148.18 μmol) in DCM (1 mL) was added HATU (75.12 mg, 197.57 μmol) and DIPEA (51.07 mg, 395.15 μmol, 68.83 μL). The mixture was stirred at 30° C. for 15 min, then Intermediate D (40 mg, 98.79 μmol, HCl salt) was added and the solution was stirred at 30° C. for 1 hours. The reaction mixture was poured into water (30.0 mL) and extracted with EtOAc (30.0 mL×3). The combined organics were washed with water and brine, dried over $Na_2SO_4$, filtered and filtration was evaporated to dryness. The residue was purified by Prep-HPLC (FA condition) and lyophilized to give Compound 72 (12.42 mg, 21.00 μmol, 21.25% yield, FA salt) as white solid. LCMS (ESI) m/z $[M+H]^+$=540.2; $^1H$ NMR (400 MHz, DMSO-d6) δ 12.49 (br s, 1H), 8.68-8.67 (m, 2H), 8.47 (d, J=7.2 Hz, 1H), 8.31 (s, 1H), 8.02 (d, J=7.6 Hz, 1H), 7.96-7.95 (m, 1H), 7.84 (s, 1H), 7.77-7.75 (m, 3H), 7.62-7.58 (m, 1H), 7.31-7.30 (m, 1H), 6.78-6.77 (m, 1H), 4.70-4.65 (m, 1H), 3.57 (s, 3H), 3.46 (br s, 2H), 3.23 (s, 3H), 2.12-2.07 (m, 1H), 2.04-1.97 (m, 1H); ee %=100%.

Example 72. Preparation of (S)—N-(3-methyl-1-oxo-1-((4-(3-(pyridin-4-yl)phenyl)thiazol-2-yl)amino)butan-2-yl)-1-(methylsulfonyl)-1H-pyrrole-3-carboxamide (Compound 73)

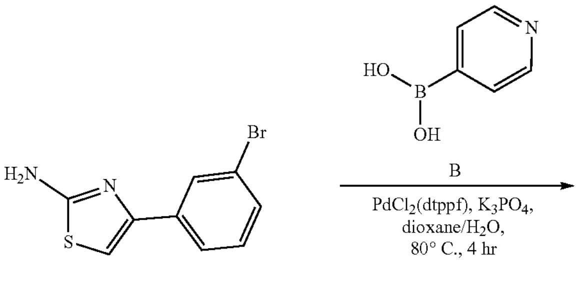

A

-continued

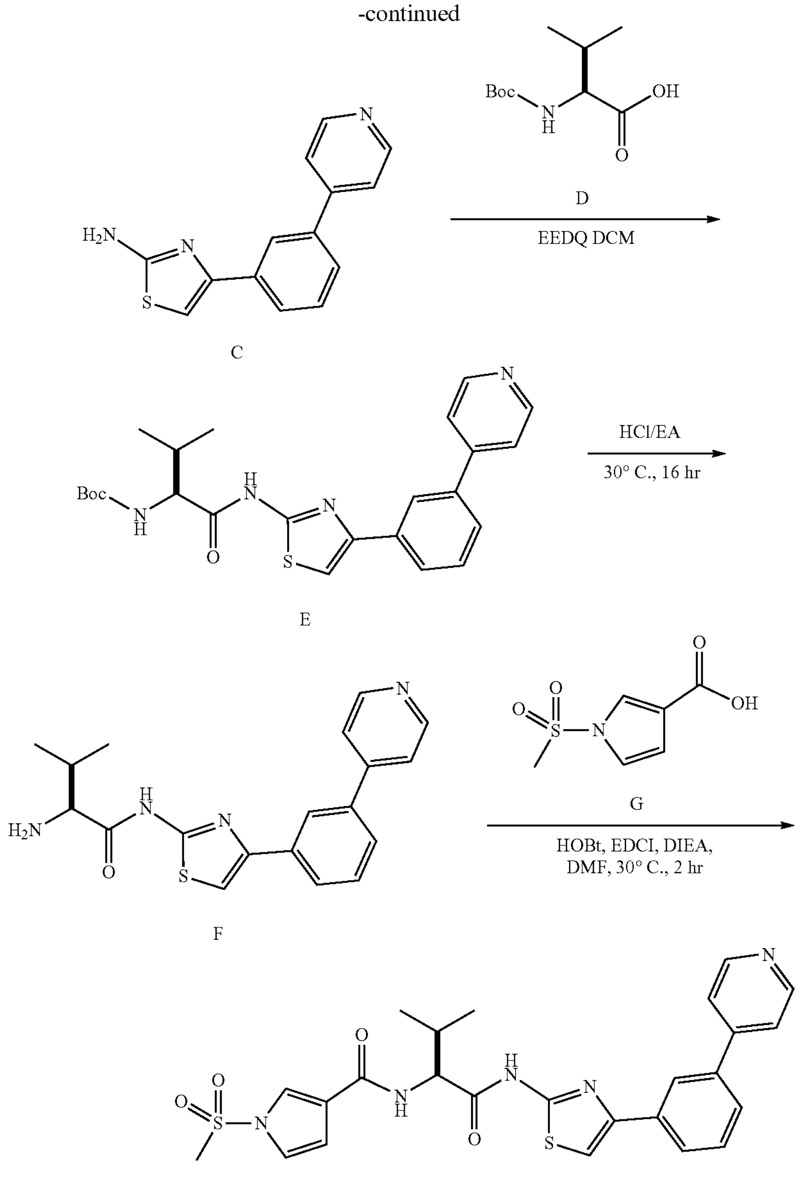

Compound 73

Step 1: Preparation of (S)-tert-butyl (3-methyl-1-oxo-1-((4-(3-(pyridin-4-yl)phenyl)thiazol-2-yl) amino)butan-2-yl)carbamate (Intermediate E)

E

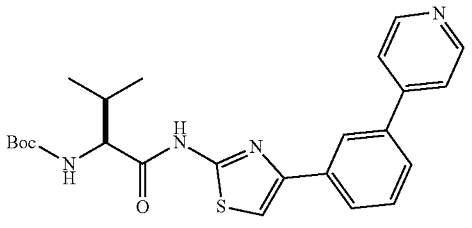

To a solution of 4-(3-(pyridin-4-yl)phenyl)thiazol-2-amine [prepared according to the method in Example 4] (582.99 mg, 2.30 mmol) in DCM (10 mL) was added EEDQ (1.14 g, 4.60 mmol), the mixture was stirred at 30° C. for 0.5 h. Then (S)-2-((tert-butoxycarbonyl)amino)-3-methylbutanoic acid (500 mg, 2.30 mmol) was added to the mixture. The mixture was stirred at 30° C. for 24 h. The reaction mixture was diluted with $H_2O$ (10 mL) and extracted with EtOAc (10 mL×2). The combined organic layers were dried over anhydrous $Na_2SO_4$, filtered and concentrated under reduced pressure to give the residue. The residue was purified by reversed phase (0.1% FA condition) and lyophilized to afford Intermediate E (310 mg, 684.98 μmol, 29.76% yield) as a yellow solid. LCMS (ESI) m/z $[M+H]^+$= 453.1.

Step 2: Preparation of (S)-2-amino-3-methyl-N-(4-(3-(pyridin-4-yl)phenyl)thiazol-2-yl)butanamide (Intermediate F)

F

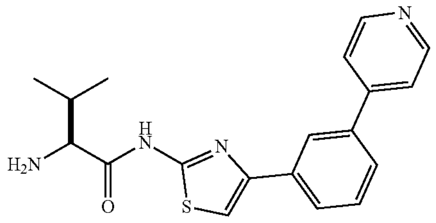

A solution of Intermediate E (160.00 mg, 353.54 μmol) in HCl/EA (4 M, 5 mL) was stirred at 30° C. for 0.5 h. The white solid was formed. The precipitate was collected by filtration, the solid was washed with EtOAc (5 mL) and dried under high vacuum to afford Intermediate F (100 mg, 257.13 μmol, 72.73% yield, HCl salt) as a white solid, which was used directly in the next step. LCMS (ESI) m/z $[M+H]^+$= 353.1; $^1$H NMR (400 MHz, DMSO-$d_6$) δ 12.92 (br s, 1H), 8.987 (d, J=6.4 Hz, 2H), 8.52 (br s, 3H), 8.47 (s, 1H), 8.39 (br d, J=5.2 Hz, 2H), 8.15 (d, J=7.6 Hz, 1H), 8.01 (s, 1H), 7.98 (br d, J=7.6 Hz, 1H), 7.72-7.70 (m, 1H), 3.94 (br d, J=4.4 Hz, 1H), 2.29-2.20 (m, 1H), 1.01-0.98 (m, 6H).

Step 3: Preparation of (S)—N-(3-methyl-1-oxo-1-((4-(3-(pyridin-4-yl)phenyl)thiazol-2-yl)amino)butan-2-yl)-1-(methylsulfonyl)-1H-pyrrole-3-carboxamide (Compound 73)

Compound 73

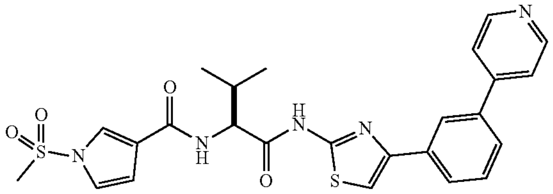

To a solution of Intermediate F (50 mg, 128.56 μmol, HCl salt) in DMF (1 mL) was added 1-methylsulfonylpyrrole-3-carboxylic acid [prepared according to the method in Example 4] (26.76 mg, 141.42 μmol) and DIEA (83.08 mg, 642.82 μmol, 111.96 μL), then EDCI (36.97 mg, 192.84 μmol) and HOBT (20.85 mg, 154.28 μmol) was added to the mixture. The mixture was stirred at 30° C. for 4 h. The reaction mixture was diluted with $H_2O$ (2 mL) and extracted with EtOAc (2 mL×2). The combined organic layers were dried over anhydrous $Na_2SO_4$, filtered and concentrated under reduced pressure to give a residue. The reaction was purified by reversed phase (0.1% FA condition) to afford Compound 73 (23.27 mg, 40.31 μmol, 31.35% yield, FA salt) as an off-white solid. LCMS (ESI) m/z $[M+H]^+$=524.2; $^1$H NMR (400 MHz, DMSO-$d_6$) δ 12.48 (br s, 1H), 8.69-8.67 (m, 2H), 8.31-8.26 (m, 2H), 8.04-8.01 (m, 2H), 7.83 (s, 1H), 7.78-7.76 (m, 3H), 7.75-7.60 (m, 1H), 7.29 (m, 1H), 6.80 (m, 1H), 4.54-4.50 (m, 1H), 3.57 (s, 3H), 2.24-2.15 (m, 1H), 1.01-0.95 (m, 6H); ee %=100%.

Example 73. Preparation of (S)—N-(3,3-dimethyl-1-oxo-1-((4-(3-(pyridin-4-yl)phenyl)thiazol-2-yl)amino)butan-2-yl)-1-(methylsulfonyl)-1H-pyrrole-3-carboxamide (Compound 74)

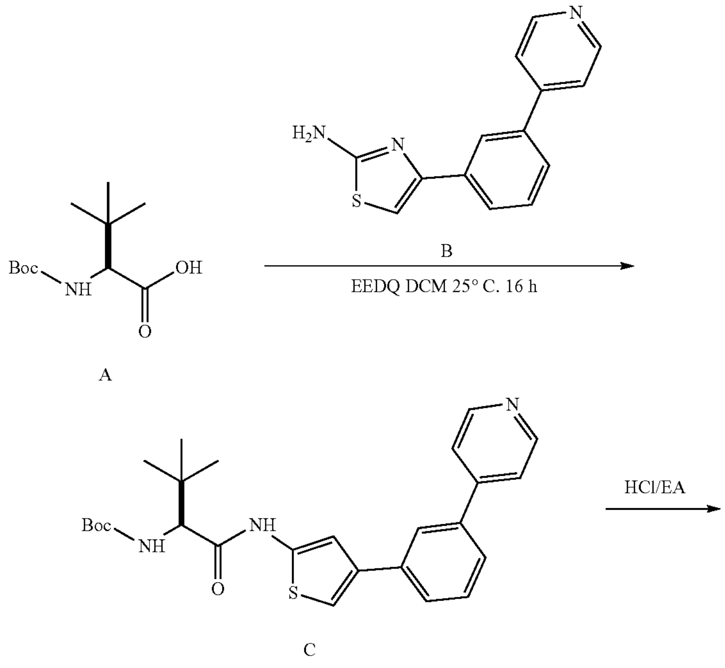

-continued

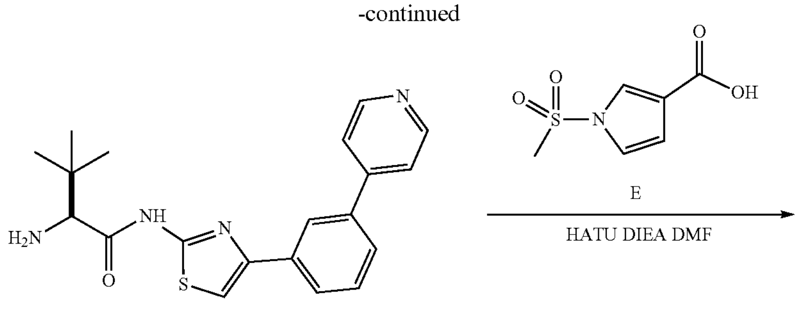

D

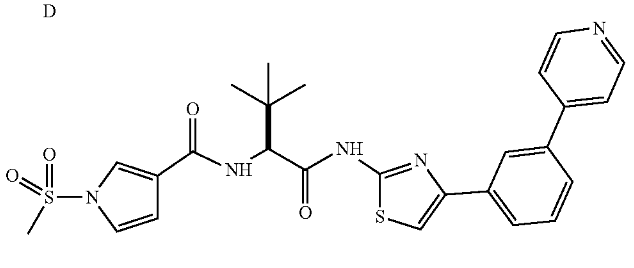

Compound 74

Step 1: Preparation of (S)-tert-butyl (3,3-dimethyl-1-oxo-1-((4-(3-(pyridin-4-yl)phenyl)thiazol-2-yl)amino)butan-2-yl)carbamate (Intermediate C)

C

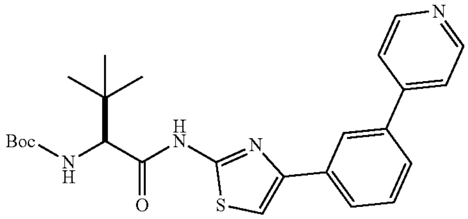

The solution of (S)-2-((tert-butoxycarbonyl)amino)-3,3-dimethylbutanoic acid (500 mg, 2.16 mmol) and EEDQ (534.59 mg, 2.16 mmol) in DCM (5 mL) was added 4-(3-(pyridin-4-yl)phenyl)thiazol-2-amine [prepared according to the method in Example 4] (273.82 mg, 1.08 mmol) at 25° C. The reaction mixture was stirred at 25° C. for 16 hours. The reaction mixture was diluted with water (10 mL), then extracted with EtOAc (20 mL×3), concentrated to afford a yellow oil. The oil was dissolved with MeOH (2 mL), then purified by reversed-phase HPLC (FA), extracted with EtOAc (20 mL×2), concentrated to afford Intermediate C (280 mg, 516.08 μmol, 47.75% yield) as yellow oil. LCMS (ESI) m/z $[M+H]^+$=467.1.

Step 2: Preparation of 2-(methylamino)-N-(4-(3-(pyridin-4-yl)phenyl)thiazol-2-yl)acetamide (Intermediate D)

D

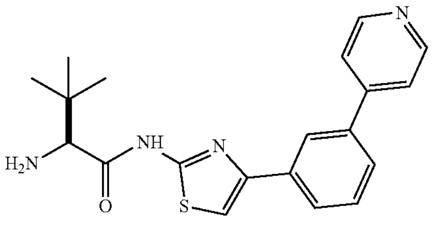

The solution of Intermediate C (280 mg, 516.08 μmol) in HCl/EtOAc (5 mL) was stirred at 25° C. for 16 hours. The reaction mixture was concentrated to afford Intermediate D (200 mg, 437.24 μmol, 84.72% yield, HCl salt) as a yellow residue. LCMS (ESI) m/z $[M+H]^+$=367.1.

Step 3: Preparation of (S)—N-(3,3-dimethyl-1-oxo-1-((4-(3-(pyridin-4-yl)phenyl)thiazol-2-yl)amino)butan-2-yl)-1-(methylsulfonyl)-1H-pyrrole-3-carboxamide (Compound 74)

Compound 74

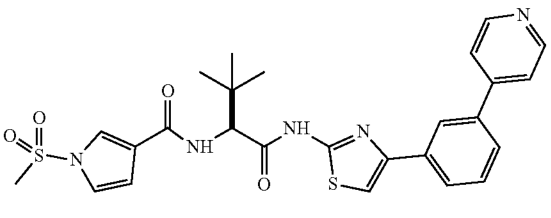

To a solution of 1-methylsulfonylpyrrole-3-carboxylic acid [prepared according to the method in Example 4] (90.95 mg, 480.74 μmol) and HATU (137.09 mg, 360.55 μmol) and DIEA (93.20 mg, 721.11 μmol, 125.60 μL) in DMF (0.5 mL) was added Intermediate D (100 mg, 240.37 μmol) at 25° C. The reaction mixture was stirred at 25° C. for 3 hours. The reaction was poured into water (10 mL), then extracted with EtOAc (10 mL×2) and concentrated in vacuum. The residue was purified by reversed-phase HPLC (FA), lyophilized to afford Compound 74 (2.19 mg, 3.75 μmol, 1.56% yield, FA salt) as white solid. LCMS (ESI) m/z $[M+H]^+$=538.3; $^1H$ NMR (400 MHz, Methanol-$d_4$) δ 8.61 (d, J=6.0 Hz, 2H), 8.33 (s, 1H), 8.03 (d, J=7.8 Hz, 1H), 7.94-7.93 (m, 1H), 7.78 (d, J=6.0 Hz, 2H), 7.71 (br d, J=7.2 Hz, 1H), 7.60-7.53 (m, 2H), 7.26-7.25 (m, 1H), 6.84-6.83 (m, 1H), 4.77 (s, 1H), 3.37 (s, 3H), 1.14 (s, 9H); ee %=100%.

Example 74. Preparation of (S)—N-(4-methyl-1-oxo-1-((4-(3-(pyridin-4-yl)phenyl)thiazol-2-yl)amino)pentan-2-yl)-1-(methylsulfonyl)-1H-pyrrole-3-carboxamide (Compound 75)

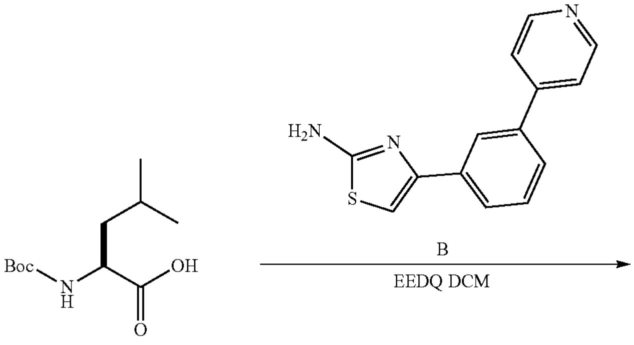

A

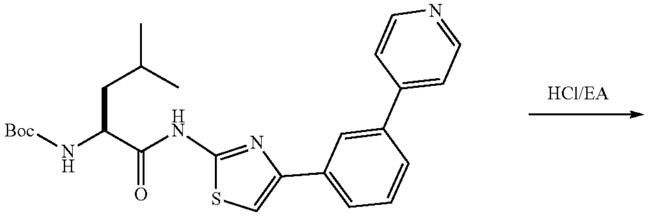

C

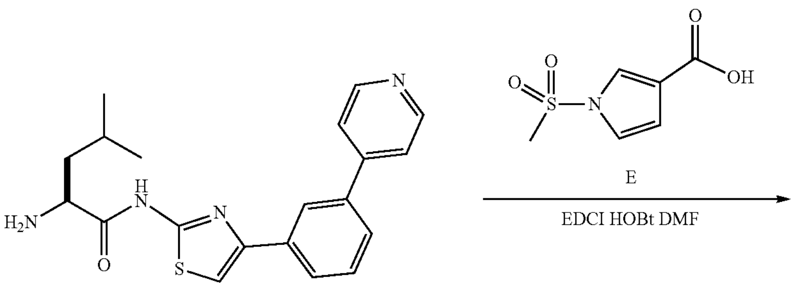

D

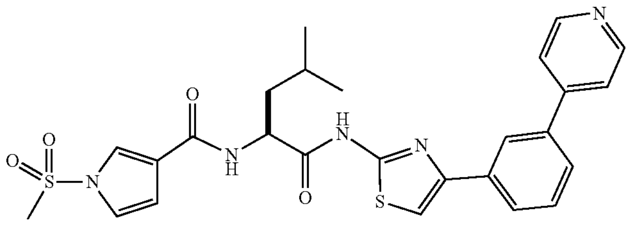

Compound 75

Step 1: Preparation of (S)-tert-butyl (4-methyl-1-oxo-1-((4-(3-(pyridin-4-yl)phenyl)thiazol-2-yl)amino)pentan-2-yl)carbamate (Intermediate C)

C

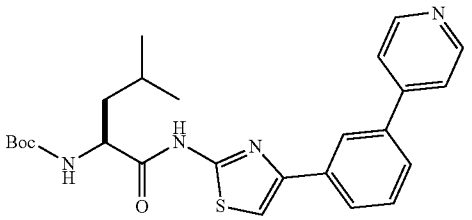

To a solution of 4-(3-(pyridin-4-yl)phenyl)thiazol-2-amine [prepared according to the method in Example 4] (304.84 mg, 1.20 mmol) in DCM (10 mL) was added EEDQ (595.16 mg, 2.41 mmol), the mixture was stirred at 30° C. for 0.5 h. Then (S)-2-((tert-butoxycarbonyl)amino)-4-methylpentanoic acid (360.00 mg, 1.44 mmol) was added. The mixture was stirred at 30° C. for 16 h. The reaction mixture was diluted with $H_2O$ (10 mL) and extracted with EtOAc (10 mL×2). The combined organic layers were dried over anhydrous $Na_2SO_4$, filtered and concentrated under reduced pressure to give the residue. The residue was purified by reversed phase (0.1% FA condition) to afford Intermediate C (300 mg, 642.96 μmol, 53.43% yield) as a yellow solid. LCMS (ESI) m/z $[M+H]^+$=467.1.

Step 2: Preparation of (S)-2-amino-4-methyl-N-(4-(3-(pyridin-4-yl)phenyl)thiazol-2-yl)pentanamide (Intermediate D)

D

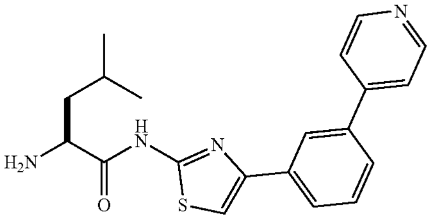

A solution of Intermediate C (300 mg, 642.96 μmol) in HCl/EA (4 M, 5 mL) was stirred at 30° C. for 0.5 h. The reaction mixture was concentrated directly to afford the crude product. The mixture was diluted with $H_2O$ (2 mL) and added 1 N HCl to adjust the pH=8, then extracted with EtOAc (5 mL×2). The combined organic layers were dried over anhydrous $Na_2SO_4$, filtered and concentrated under reduced pressure to give Intermediate D (70 mg, crude) as a white solid, which used directly in the next step. LCMS (ESI) m/z $[M+H]^+$=367.3.

Step 3: Preparation of (S)—N-(4-methyl-1-oxo-1-((4-(3-(pyridin-4-yl)phenyl)thiazol-2-yl)amino)pentan-2-yl)-1-(methylsulfonyl)-1H-pyrrole-3-carboxamide (Compound 75)

Compound 75

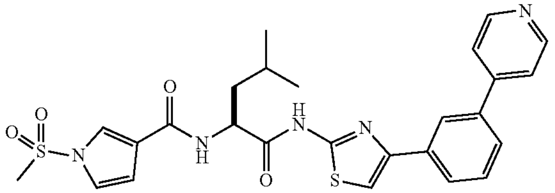

To a solution of Intermediate D (65 mg, 177.36 μmol) in DMF (1 mL) was added 1-methylsulfonylpyrrole-3-carboxylic acid [prepared according to the method in Example 4] (36.91 mg, 195.10 μmol) and DIEA (114.61 mg, 886.82 μmol, 154.46 μL), then EDCI (51.00 mg, 266.05 μmol) and HOBt (28.76 mg, 212.84 μmol) were added. The mixture was stirred at 30° C. for 16 h. The reaction mixture was diluted with $H_2O$ (2 mL) and extracted with EtOAc (2 mL×2). The combined organic layers were dried over anhydrous $Na_2SO_4$, filtered and concentrated under reduced pressure to give a residue. The reaction was purified by reversed phase (0.1% FA condition) and lyophilized to afford Compound 75 (18.16 mg, 31.11 μmol, 17.54% yield, FA salt) as a yellow solid. LCMS (ESI) m/z $[M+H]^+$=538.3; $^1H$ NMR (400 MHz, DMSO-$d_6$) δ 12.51 (br s, 1H), 8.68 (d, J=6.0 Hz, 2H), 8.38 (d, J=7.6 Hz, 1H), 8.31 (s, 1H), 8.01 (d, J=8.0 Hz, 1H), 7.97-7.96 (m, 1H), 7.82 (s, 1H), 7.77 (br d, J=6.0 Hz, 3H), 7.59 (m, 1H), 7.30-7.28 (m, 1H), 6.79-6.78 (m, 1H), 4.75-4.70 (m, 1H), 3.58-3.55 (m, 3H), 1.78-1.74 (m, 2H), 1.60-1.57 (m, 1H), 0.96-0.90 (m, 6H); ee %=100%.

Example 75. Preparation of (S)—N-(4,4-dimethyl-1-oxo-1-((4-(3-(pyridin-4-yl)phenyl)thiazol-2-yl)amino)pentan-2-yl)-1-(methylsulfonyl)-1H-pyrrole-3-carboxamide (Compound 76)

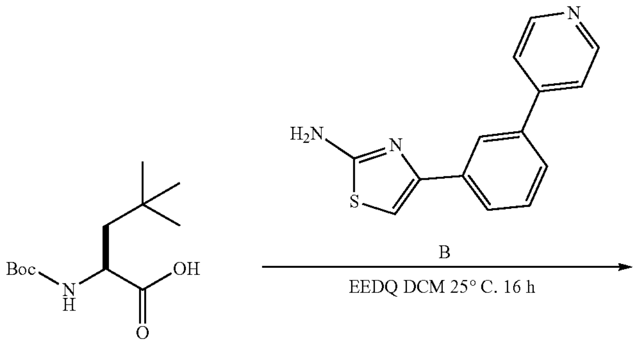

A

-continued

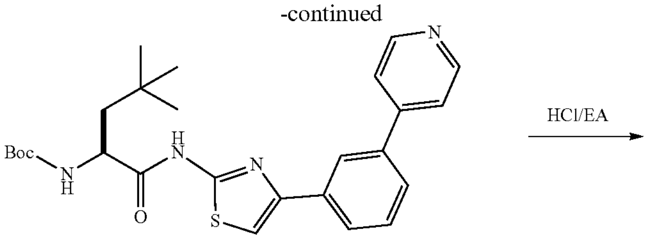

C

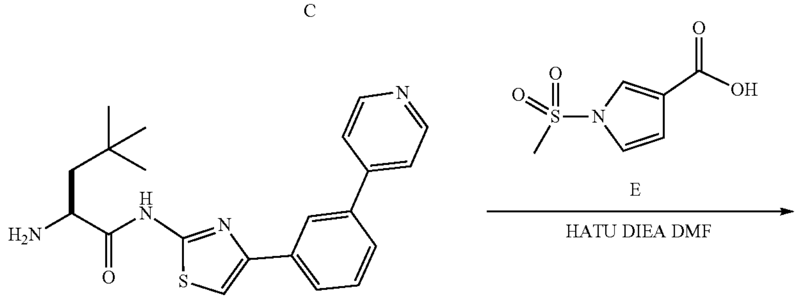

E

D

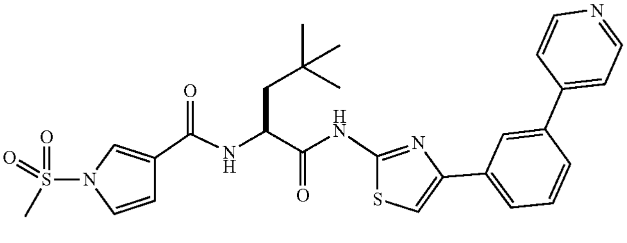

Compound 76

Step 1: Preparation of (S)-tert-butyl (4,4-dimethyl-1-oxo-1-((4-(3-(pyridin-4-yl)phenyl)thiazol-2-yl)amino)pentan-2-yl)carbamate (Intermediate C)

C

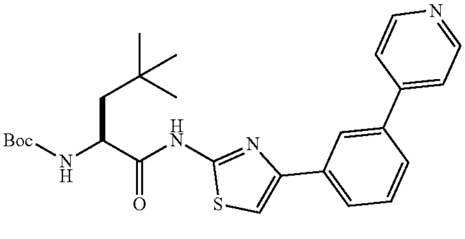

The solution of (S)-2-((tert-butoxycarbonyl)amino)-4,4-dimethylpentanoic acid (300 mg, 1.22 mmol) and EEDQ (302.42 mg, 1.22 mmol) in DCM (3 mL) was added 4-(3-(pyridin-4-yl)phenyl)thiazol-2-amine [prepared according to the method in Example 4] (154.90 mg, 611.46 μmol) at 25° C. Then the reaction mixture was stirred at 25° C. for 16 hours. The reaction mixture was diluted with water (10 mL), then extracted with EtOAc (20 mL×2), concentrated in vacuum to afford a yellow oil. The oil was dissolved with MeOH (2 mL), then purified by reversed-phase HPLC (FA), then extracted with EtOAc (20 mL×2), concentrated to afford Intermediate C (200 mg, 382.84 μmol, 62.61% yield) as yellow solid. LCMS (ESI) m/z $[M+H]^+$=481.1; 1H NMR (400 MHz, DMSO-d6) δ 12.34 (br s, 1H), 8.70-8.65 (m, 2H), 8.31 (s, 1H), 8.13 (s, 1H), 8.01 (d, J=7.8 Hz, 1H), 7.82 (s, 1H), 7.79-7.73 (m, 3H), 7.63-7.56 (m, 1H), 4.43-4.31 (m, 1H), 1.63-1.57 (m, 2H), 1.41-1.34 (m, 9H), 0.94 (s, 9H); ee %=100%.

Step 2: Preparation of (S)-2-amino-4,4-dimethyl-N-(4-(3-(pyridin-4-yl)phenyl)thiazol-2-yl)pentanamide (Intermediate D)

D

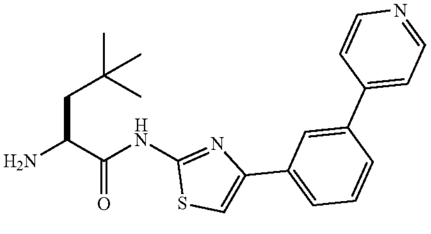

The solution of Intermediate C (200 mg, 416.13 μmol) in HCl/EtOAc (2 mL) was stirred at 25° C. for 16 hours. The reaction mixture was concentrated to afford Intermediate D (150 mg, 334.81 μmol, 80.46% yield, HCl salt) as yellow oil. LCMS (ESI) m/z $[M+H]^+$=381.1.

Step 3: Preparation of (S)—N-(4,4-dimethyl-1-oxo-1-((4-(3-(pyridin-4-yl)phenyl)thiazol-2-yl)amino)pentan-2-yl)-1-(methylsulfonyl)-1H-pyrrole-3-carboxamide (Compound 76)

Compound 76

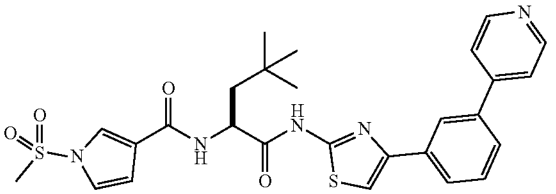

To a solution of 1-methylsulfonylpyrrole-3-carboxylic acid [prepared according to the method in Example 4] (74.58 mg, 394.21 μmol) and HATU (112.42 mg, 295.66 μmol) and DIEA (76.42 mg, 591.32 μmol, 103.00 μL) in DMF (0.5 mL) was added Intermediate D (75 mg, 197.11 μmol) at 25° C. The reaction mixture was stirred at 25° C. for 3 hours. The reaction was poured into water (10 mL), then extracted with EtOAc (10 mL×2), concentrated to afford a yellow liquid. The liquid was purified by reversed-phase HPLC (FA), lyophilized to afford Compound 76 (10.07 mg, 16.85 μmol, 8.55% yield, FA salt) as white solid. LCMS (ESI) m/z $[M+H]^+=552.3$; $^1H$ NMR (400 MHz, Methanol-$d_4$) δ 8.63-8.59 (m, 2H), 8.31-8.30 (m, 1H), 8.04-7.98 (m, 1H), 7.87-7.86 (m, 1H), 7.80-7.76 (m, 2H), 7.71-7.70 (m, 1H), 7.59-7.53 (m, 2H), 7.26-7.25 (m, 1H), 6.83-6.82 (m, 1H), 4.92-4.88 (m, 1H), 3.37 (s, 3H), 1.96-1.83 (m, 2H), 1.05 (s, 9H); ee %=100%.

Example 76. Preparation of N-(4-(dimethylamino)-1-oxo-1-((4-(3-(pyridin-4-yl)phenyl)thiazol-2-yl)amino)butan-2-yl)-1-(methylsulfonyl)-1H-pyrrole-3-carboxamide (Compound 77)

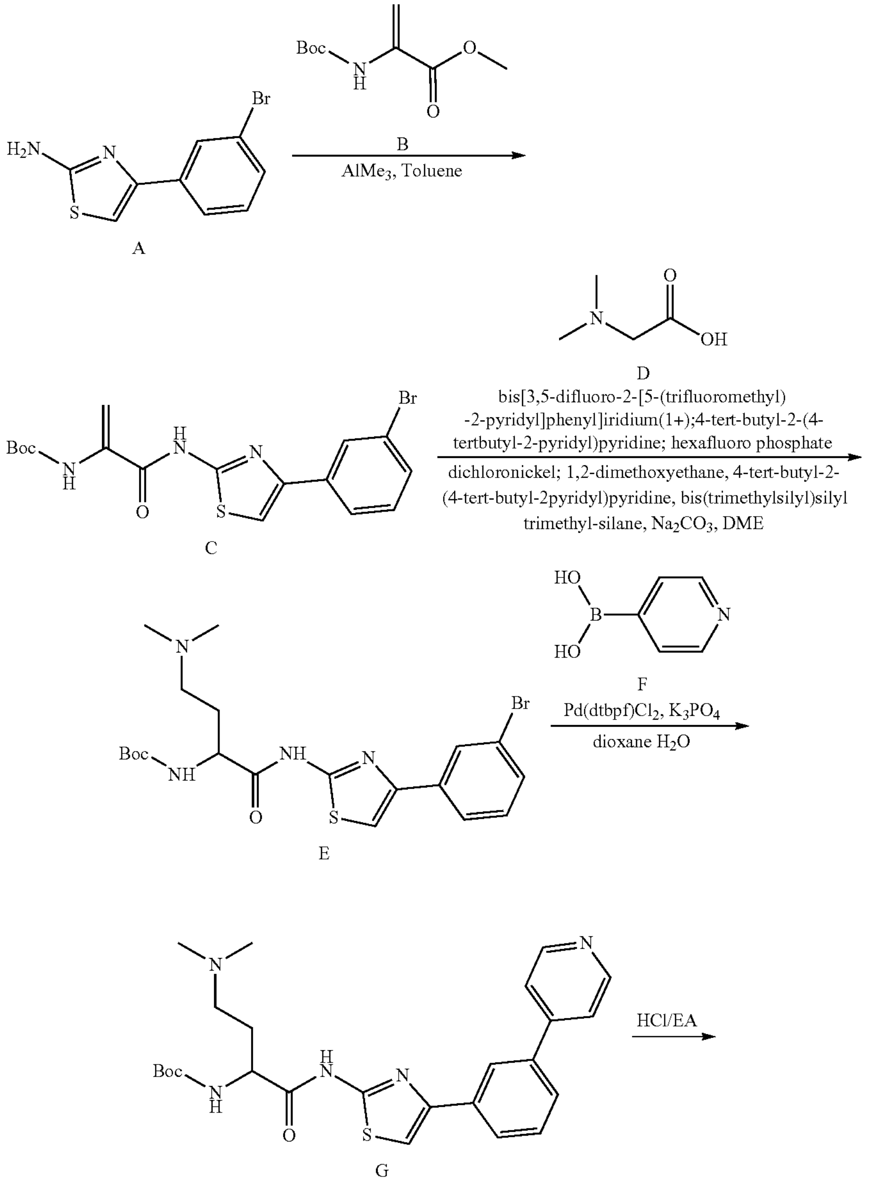

-continued

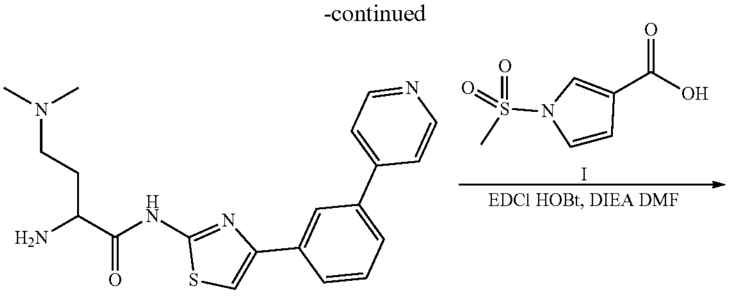

H

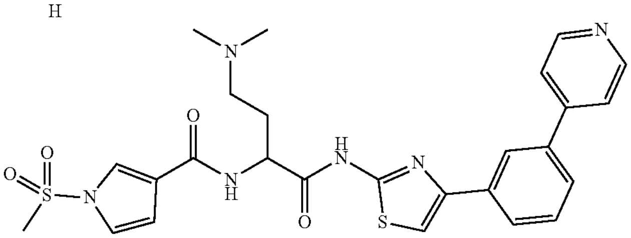

Compound 77

Step 1: Preparation of tert-butyl (3-((4-(3-bromophenyl)thiazol-2-yl)amino)-3-oxoprop-1-en-2-yl) carbamate (Intermediate C)

C

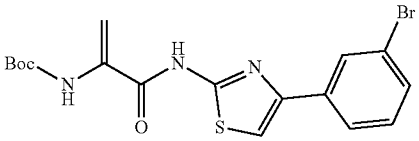

To a solution of 4-(3-(pyridin-4-yl)phenyl)thiazol-2-amine [prepared according to the method in Example 4] (1.27 g, 4.97 mmol) in toluene (8 mL) was added $AlMe_3$ (2 M, 2.48 mL). The reaction mixture was stirred at 100° C. for 0.5 h. Methyl 2-(tert-butoxycarbonylamino)prop-2-enoate (1 g, 4.97 mmol) was added at 100° C. The reaction mixture was stirred at 100° C. for 0.5 h. The reaction mixture was poured into water (50 mL) and extracted with EtOAc (50 mL×2). The combined organic layer was dried over anhydrous $Na_2SO_4$ and concentrated in vacuum. The residue was purified by silica gel chromatography column (PE-PE/EA=1/1) and concentrated to give Intermediate C (450 mg, 896.16 μmol, 18.03% yield) as yellow solid. LCMS (ESI) m/z $[M+H]^+$=423.9.

Step 2: Preparation of tert-butyl (1-((4-(3-bromophenyl)thiazol-2-yl)amino)-4-(dimethylamino)-1-oxobutan-2-yl)carbamate (Intermediate E)

E

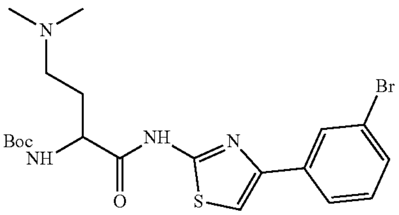

To a solution of Intermediate C (400 mg, 942.70 μmol), 2-(dimethylamino)acetic acid (97.21 mg, 942.70 μmol), bis[3,5-difluoro-2-[5-(trifluoromethyl)-2-pyridyl]phenyl] iridium(1+); 4-tert-butyl-2-(4-tert-butyl-2-pyridyl)pyridine; hexafluorophosphate (10.58 mg, 9.43 μmol), dichloronickel; 1,2-dimethoxyethane (1.04 mg, 4.71 μmol), 4-tert-butyl-2-(4-tert-butyl-2-pyridyl)pyridine (1.52 mg, 5.66 μmol), bis(trimethylsilyl)silyl-trimethyl-silane (234.41 mg, 942.70 μmol, 290.83 μL) in DME (1 mL) was added $Na_2CO_3$ (199.83 mg, 1.89 mmol). The reaction was stirred and irradiated with a 34 W blue LED lamp (7 cm away, with cooling fan to keep the reaction temperature at 25° C. for 1 h). The reaction mixture was concentrated to get the crude product. The crude product was purified by reverse phase column (FA) and lyophilized to give Intermediate E (200 mg, 345.87 μmol, 36.69% yield) as a white solid. LCMS (ESI) m/z $[M+H]^+$=483.0.

Step 3: Preparation of tert-butyl (4-(dimethylamino)-1-oxo-1-((4-(3-(pyridin-4-yl)phenyl)thiazol-2-yl)amino)butan-2-yl)carbamate (Intermediate G)

G

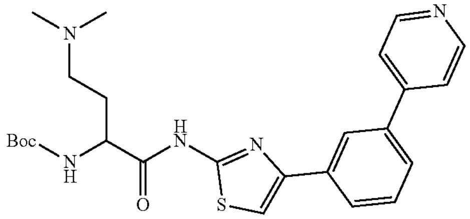

To a solution of Intermediate E (200 mg, 413.72 μmol), 4-(4,4,5,5-tetramethyl-1,3,2-dioxaborolan-2-yl)pyridine (169.67 mg, 827.44 μmol), $K_3PO_4$ (263.45 mg, 1.24 mmol) in dioxane (2 mL) and $H_2O$ (0.4 mL) was added [1,1'-bis(di-tert-butylphosphino)ferrocene]dichloropalladium(II) (26.96 mg, 41.37 μmol). Then the mixture was stirred at 70° C. for 1 h under $N_2$. The reaction mixture was concentrated to get the crude product. The crude product was purified by reverse phase column (FA) and lyophilized to give Intermediate G (100 mg, 177.02 μmol, 42.79% yield, FA salt) as white solid. LCMS (ESI) m/z $[M+H]^+$=482.1.

Step 4: Preparation of 2-amino-4-(dimethylamino)-N-(4-(3-(pyridin-4-yl)phenyl)thiazol-2-yl)butanamide (Intermediate H)

H

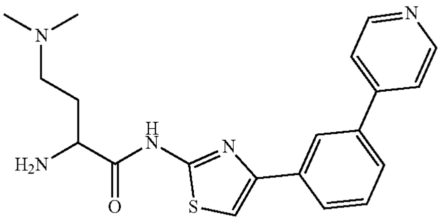

A solution of Intermediate G (100 mg, 189.53 μmol, FA salt) in HCl/EtOAc (2 mL) was stirred at 25° C. for 1 h. The reaction mixture was concentrated to get Intermediate H (80 mg, 153.89 μmol, 81.20% yield, HCl salt) as white solid. LCMS (ESI) m/z $[M+H]^+$=382.1.

Step 5: Preparation of N-(4-(dimethylamino)-1-oxo-1-((4-(3-(pyridin-4-yl)phenyl)thiazol-2-yl)amino)butan-2-yl)-1-(methylsulfonyl)-1H-pyrrole-3-carboxamide (Compound 77)

Compound 77

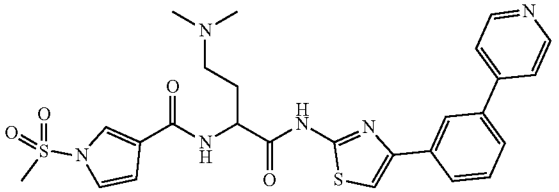

To a solution of Intermediate H (35 mg, 83.74 μmol, HCl salt), 1-methylsulfonylpyrrole-3-carboxylic acid [prepared according to the method in Example 4] (19.01 mg, 100.49 μmol), EDCI (32.11 mg, 167.48 μmol), HOBt (22.63 mg, 167.48 μmol) in DMF (0.5 mL) was added DIEA (54.11 mg, 418.71 μmol, 72.93 μL). Then the mixture was stirred at 25° C. for 1 h. The reaction mixture was concentrated to get the crude product. The crude product was purified by reverse phase column (FA) and lyophilized to get Compound 77 (25 mg, 41.76 μmol, 49.87% yield, FA salt) as white solid. LCMS (ESI) m/z $[M+H]^+$=533.3; $^1$H NMR (400 MHz, DMSO-$d_6$) δ 8.71-8.66 (m, 2H), 8.62 (d, J=7.2 Hz, 1H), 8.32 (s, 1H), 8.22 (s, 1H), 8.02 (d, J=7.8 Hz, 1H), 7.94 (m, 1H), 7.83 (s, 1H), 7.79-7.73 (m, 3H), 7.64-7.56 (m, 1H), 7.32 (m, 1H), 6.78 (m, 1H), 4.72-4.63 (m, 1H), 3.58 (s, 3H), 2.48 (br s, 2H), 2.26 (s, 6H), 2.10-2.01 (m, 1H), 1.98-1.89 (m, 1H).

Example 77. Preparation of (S)—N-(4-(dimethylamino)-1-oxo-1-((4-(3-(pyridin-4-yl)phenyl)thiazol-2-yl)amino)butan-2-yl)-1-(methylsulfonyl)-1H-pyrrole-3-carboxamide (Compound 78) and (R)—N-(4-(dimethylamino)-1-oxo-1-((4-(3-(pyridin-4-yl)phenyl)thiazol-2-yl)amino)butan-2-yl)-1-(methylsulfonyl)-1H-pyrrole-3-carboxamide (Compound 79)

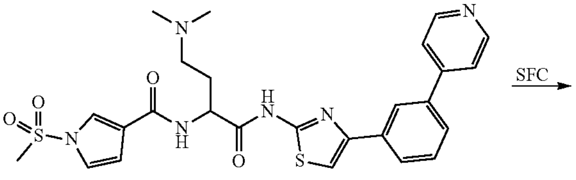

A

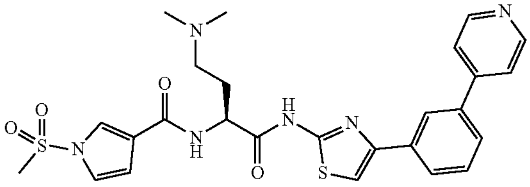

Compound 78

+

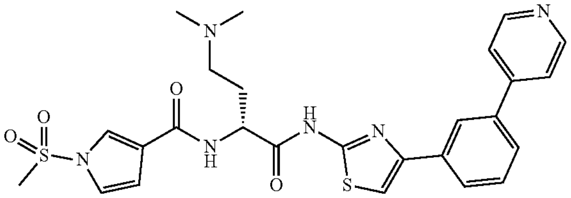

Compound 79

The N-[3-(dimethylamino)-1-[[4-[3-(4-pyridyl)phenyl]thiazol-2-yl]carbamoyl]propyl]-1-methylsulfonyl-pyrrole-3-carboxamide (18 mg, 32.57 μmol) was purified by SFC purification and concentrated to get Compound 78 (7.44 mg, 13.46 μmol, 41.33% yield) as off-white solid and Compound 79 (8.16 mg, 14.76 μmol, 45.33% yield) as off-white solid.

Compound 78: LCMS (ESI) m/z $[M+H]^+$=553.3; $^1$H NMR (400 MHz, DMSO-$d_6$) δ 8.70-8.66 (m, 2H), 8.62 (d, J=7.2 Hz, 1H), 8.32 (s, 1H), 8.02 (d, J=7.8 Hz, 1H), 7.93 (m, 1H), 7.83 (s, 1H), 7.80-7.74 (m, 3H), 7.60 (m, 1H), 7.31 (m, 1H), 6.77 (m, 1H), 4.72-4.62 (m, 1H), 3.58 (s, 3H), 2.39 (m, 2H), 2.19 (s, 6H), 2.01 (m, 1H), 1.90 (m, 1H); ee %=79.7%.

Compound 79: LCMS (ESI) m/z $[M+H]^+$=553.2; $^1$H NMR (400 MHz, DMSO-$d_6$) δ 8.70-8.66 (m, 2H), 8.62 (d, J=7.0 Hz, 1H), 8.32 (s, 1H), 8.02 (d, J=7.8 Hz, 1H), 7.93 (m, 1H), 7.83 (s, 1H), 7.79-7.74 (m, 3H), 7.64-7.57 (m, 1H), 7.31 (m, 1H), 6.77 (m, 1H), 4.66 (m, 1H), 3.58 (s, 3H), 2.38 (m, 2H), 2.18 (s, 6H), 2.04-1.96 (m, 1H), 1.94-1.86 (m, 1H); ee %=74.5%.

Example 78. Preparation of (S)-1-(isopropylsulfonyl)-N-(4-(methylthio)-1-oxo-1-((4-phenylthiazol-2-yl)amino)butan-2-yl)-1H-pyrrole-3-carboxamide (Compound 80)

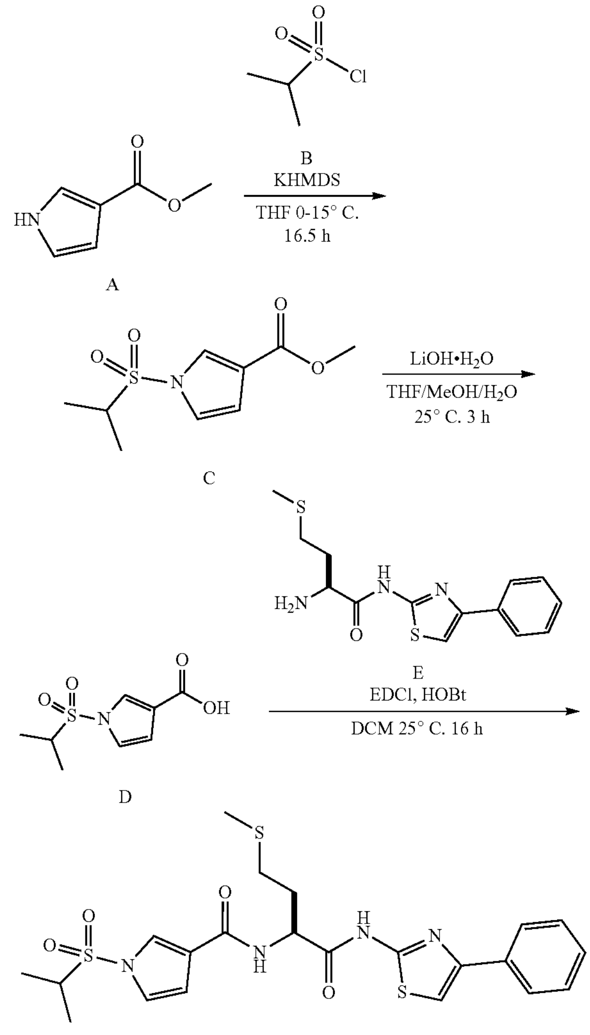

Compound 80

To a solution of 1-isopropylsulfonylpyrrole-3-carboxylic acid [prepared according to the method in Example 42] (25 mg, 115.08 μmol) and (2S)-2-amino-4-methylsulfanyl-N-(4-phenylthiazol-2-yl)butanamide (prepared according to the method in Example 5) (35.27 mg, 114.72 μmol) in DCM (1 mL) was added DIPEA (44.62 mg, 345.24 μmol, 60.13 μL), EDCI (33.09 mg, 172.62 μmol) and HOBt (23.32 mg, 172.62 μmol) at 25° C. The reaction mixture was stirred at 25° C. for 16 h. The reaction mixture was concentrated under reduced pressure to afford a residue. The residue was purified by reverse phase column (FA condition) and lyophilized to give Compound 80 (26.32 mg, 51.95 μmol, 45% yield) as white solid. LCMS (ESI) m/z $[M+H]^+$=507.1. $^1H$ NMR (400 MHz, Methanol-$d_4$) δ 7.89 (d, J=7.6 Hz, 2H), 7.86-7.85 (m, 1H), 7.40-7.36 (m, 3H), 7.31-7.27 (m, 1H), 7.22-7.20 (m, 1H), 6.85-6.84 (m, 1H), 4.89-4.85 (m, 1H), 3.68-3.62 (m, 1H), 2.72-2.59 (m, 2H), 2.27-2.13 (m, 5H), 1.32 (d, J=6.8 Hz, 6H). Chiral HPLC: Cellucoat-MeOH (DEA)-5-40-3 mL-35T, t=2.217 min, ee %=100%.

Example 79. Preparation of N-(2-((4-(3-(2,6-dimethylpyridin-4-yl)phenyl)thiazol-2-yl)amino)-2-oxoethyl)-1-(methylsulfonyl)-1H-pyrrole-3-carboxamide (Compound 81)

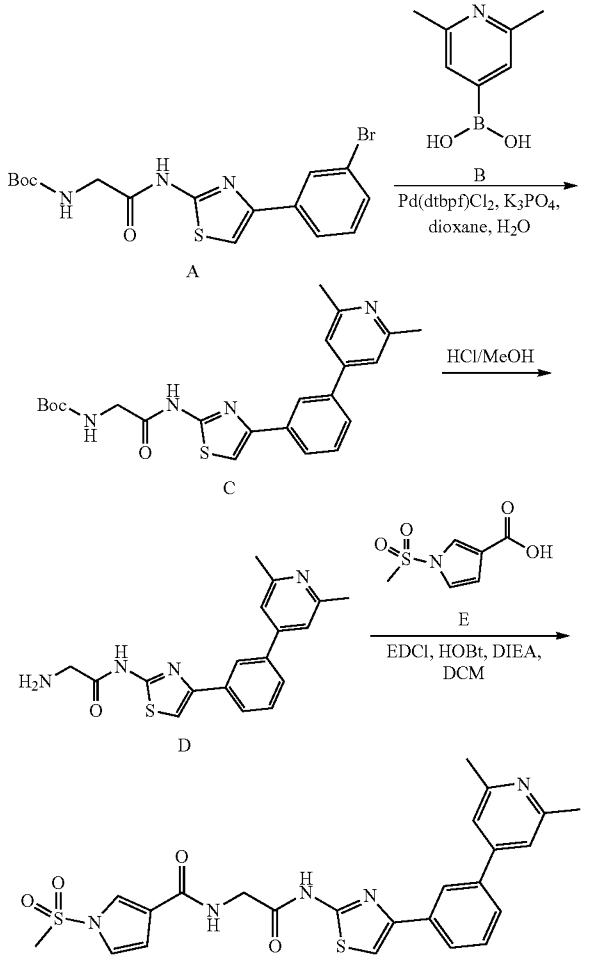

Compound 81

Step 1: Preparation of tert-butyl (2-((4-(3-(2,6-dimethylpyridin-4-yl)phenyl)thiazol-2-yl)amino)-2-oxoethyl)carbamate (Intermediate C)

C

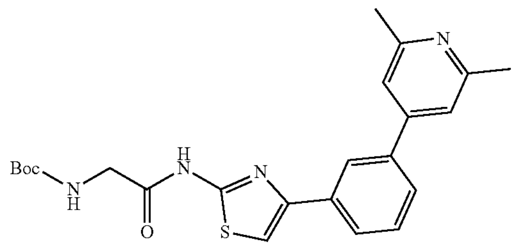

A mixture of tert-butyl N-[2-[[4-(3-bromophenyl)thiazol-2-yl]amino]-2-oxo-ethyl]carbamate [prepared according to the method in Example 1] (1 g, 2.43 mmol), (2,6-dimethyl-4-pyridyl)boronic acid (549.25 mg, 3.64 mmol), [1,1'-bis (di-tert-butylphosphino)ferrocene]dichloropalladium(II) (158.08 mg, 242.54 μmol), $K_3PO_4$ (1.54 g, 7.28 mmol) in dioxane (18 mL) and $H_2O$ (2 mL) was degassed and purged with $N_2$ for 3 times, and then the mixture was stirred at 80° C. for 2 h under $N_2$ atmosphere. The reaction mixture was concentrated under reduced pressure to give a residue. The residue was purified by column chromatography ($SiO_2$, Petroleum ether/EtOAc=1:1 to 0:1), then concentrated in vacuum to give Intermediate C (0.96 g, 2.19 mmol, 90.26% yield) as a yellow solid. LCMS (ESI) m/z $[M+H]^+$=439.2; $^1H$ NMR (400 MHz, Methanol-$d_4$) δ 8.26 (s, 1H), 7.97 (d, J=8.0 Hz, 1H), 7.67-7.64 (m, 1H), 7.54-7.50 (m, 2H), 7.42 (s, 2H), 3.99 (s, 2H), 2.57 (s, 6H), 1.48 (s, 9H).

Step 2: Preparation of 2-amino-N-(4-(3-(2,6-dimethylpyridin-4-yl)phenyl)thiazol-2-yl)acetamide (Intermediate D)

D

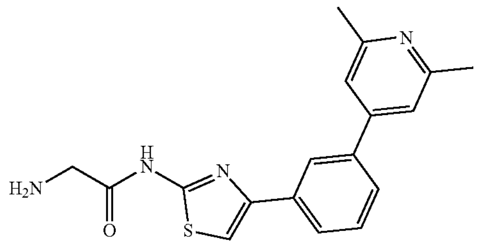

A mixture of Intermediate C (0.96 g, 2.19 mmol) in HCl/MeOH (4 M, 20 mL) was stirred at 25° C. for 2 h. The reaction mixture was concentrated under reduced pressure to give a residue. The residue was triturated with MTBE: MeOH=20:1 (20 mL) at 25° C. for 0.5 h, then the solid was collected by filtered, washed with MTBE (10 mL) and dried in vacuum to give Intermediate D (900 mg, crude, HCl) as a white solid. LCMS (ESI) m/z $[M+H]^+$=339.3.

Step 3: Preparation of N-(2-((4-(3-(2,6-dimethylpyridin-4-yl)phenyl)thiazol-2-yl)amino)-2-oxoethyl)-1-(methylsulfonyl)-1H-pyrrole-3-carboxamide (Compound 81)

Compound 81

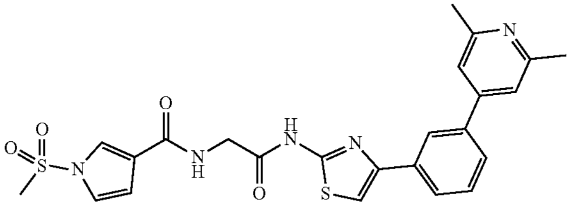

To a solution of 1-methylsulfonylpyrrole-3-carboxylic acid [prepared according to the method in Example 4] (242.23 mg, 1.28 mmol), EDCI (245.45 mg, 1.28 mmol), HOBt (173.01 mg, 1.28 mmol) and TEA (809.76 mg, 8.00 mmol, 1.11 mL) in DCM (8 mL) was added Intermediate D (400 mg, 1.07 mmol, HCl salt). The mixture was stirred at 25° C. for 16 h. The reaction suspension was diluted with MeOH (3 mL), then the solid was collected by filtered, washed with MeOH (1 mL) and dried in vacuum to give Compound 81 (231.39 mg, 454.06 μmol, 42.56% yield) as a white solid. LCMS (ESI) m/z $[M+H]^+$=510.1; $^1H$ NMR (400 MHz, Methanol-$d_4$) δ 8.27-8026 (m, 1H), 7.99-7.97 (m, 1H), 7.84-7.83 (m, 1H), 7.67-7.64 (m, 1H), 7.54-7.51 (m, 2H), 7.42 (s, 2H), 7.28-7.27 (m, 1H), 6.82-6.80 (m, 1H), 4.26 (s, 2H), 3.38 (s, 3H), 2.57 (s, 6H).

Example 80. Preparation of 1-(methylsulfonyl)-N-(2-oxo-2-((4-(3-(2-(trifluoromethyl)pyridin-4-yl)phenyl)thiazol-2-yl)amino)ethyl)-1H-pyrrole-3-carboxamide (Compound 82)

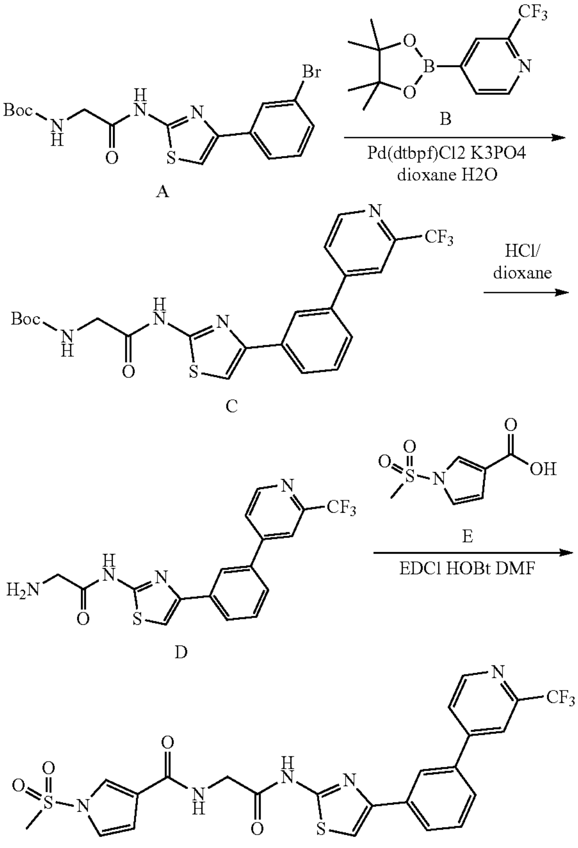

A
B
C
D
E
Compound 82

Step 1: Preparation of tert-butyl (2-oxo-2-((4-(3-(2-(trifluoromethyl)pyridin-4-yl)phenyl)thiazol-2-yl)amino)ethyl)carbamate (intermediate C)

C

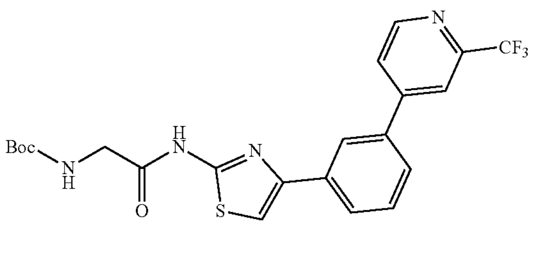

To a solution of tert-butyl (2-((4-(3-bromophenyl)thiazol-2-yl)amino)-2-oxoethyl)carbamate (prepared according to the method in Example 1) (1.2 g, 2.91 mmol), 4-(4,4,5,5-tetramethyl-1,3,2-dioxaborolan-2-yl)-2-(trifluoromethyl) pyridine (953.68 mg, 3.49 mmol), $K_3PO_4$ (1.85 g, 8.73 mmol) in dioxane (20 mL) and $H_2O$ (4 mL) was added [1,1'-bis(di-tert-butylphosphino)ferrocene]dichloropalladium(II) (189.69 mg, 291.05 μmol). Then the mixture was stirred at 70° C. for 1 h under $N_2$. The reaction mixture was poured into water (50 mL) and extracted with EtOAc (50 mL×2), the organic layer was washed with brine (50 mL) and dried over $Na_2SO_4$, concentrated in vacuum. The crude product was purified by reverse phase column (FA) and then extracted with EtOAc and then concentrated in vacuum to give Intermediate C (1.20 g, 2.39 mmol, 82.20% yield) as yellow solid. LCMS (ESI) m/z $[M+H]^+$=479.0; $^1H$ NMR (400 MHz, DMSO-$d_6$) δ 12.33 (s, 1H), 8.87 (d, J=5.2 Hz, 1H), 8.39 (m, 1H), 8.26 (d, J=1.0 Hz, 1H), 8.11 (m, 1H), 8.07 (d, J=7.8 Hz, 1H), 7.91-7.85 (m, 2H), 7.64 (m, 1H), 7.18 (s, 1H), 3.33 (s, 2H), 1.47-1.32 (m, 9H).

Step 2: Preparation of 2-amino-N-(4-(3-(2-(trifluoromethyl)pyridin-4-yl)phenyl)thiazol-2-yl)acetamide (Intermediate D)

D

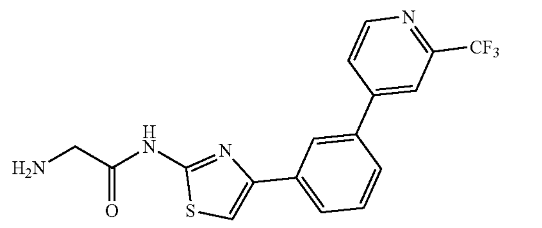

A solution of Intermediate C (1.2 g, 2.51 mmol) in HCl/EtOAc (20 mL) was stirred at 25° C. for 1 h. The reaction mixture was concentrated to get the crude product. The crude product was purified by triturated with (PE: EtOAc=1:1) at 25° C. for 30 min, then filtered and dried in vacuum to give Intermediate D (1 g, 2.28 mmol, 90.83% yield, HCl salt) as off-white solid. LCMS (ESI) m/z$[M+H]^+$ =379.0.

Step 3: Preparation of 1-(methylsulfonyl)-N-(2-oxo-2-((4-(3-(2-(trifluoromethyl)pyridin-4-yl)phenyl) thiazol-2-yl)amino)ethyl)-1H-pyrrole-3-carboxamide (Compound 82)

Compound 82

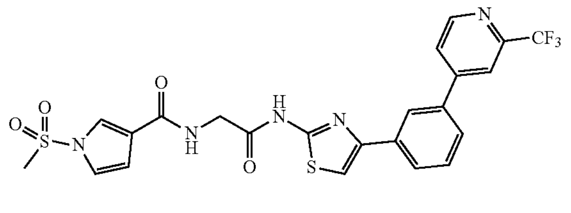

To a solution of Intermediate D (800 mg, 1.93 mmol, HCl salt), 1-methylsulfonylpyrrole-3-carboxylic acid [prepared according to the method in Example 4] (401.33 mg, 2.12 mmol), EDCI (739.39 mg, 3.86 mmol), HOBt (521.17 mg, 3.86 mmol) in DMF (10 mL) was added DIEA (1.25 g, 9.64 mmol, 1.68 mL). Then the mixture was stirred at 25° C. for 1 h. The reaction mixture was poured into water (30 mL) and extracted with EtOAc (20 mL×2), the organic layer was washed with brine (30 mL) and dried over $Na_2SO_4$, concentrated in vacuum. The crude product was triturated with EtOAc:MeOH=3:1 (10 mL) at 25° C. for 30 min, then filtered and dried in vacuum to give Compound 82 (500 mg, 905.30 μmol, 46.94% yield) as white solid. LCMS (ESI) m/z $[M+H]^+$=550.2; $^1H$ NMR (400 MHz, DMSO-$d_6$) δ 12.46 (s, 1H), 8.87 (d, J=5.2 Hz, 1H), 8.71 (m, 1H), 8.39 (s, 1H), 8.26 (s, 1H), 8.16-8.03 (m, 2H), 7.92-7.83 (m, 3H), 7.64 (m, 1H), 7.36-7.30 (m, 1H), 6.79 (m, 1H), 4.16 (d, J=5.6 Hz, 2H), 3.59 (s, 3H).

Example 81. Preparation of 1-(tert-butyl)-N-(2-((4-(3-(1-methyl-1H-pyrazol-4-yl)phenyl)thiazol-2-yl) amino)-2-oxoethyl)-1H-pyrrole-3-carboxamide (Compound 83)

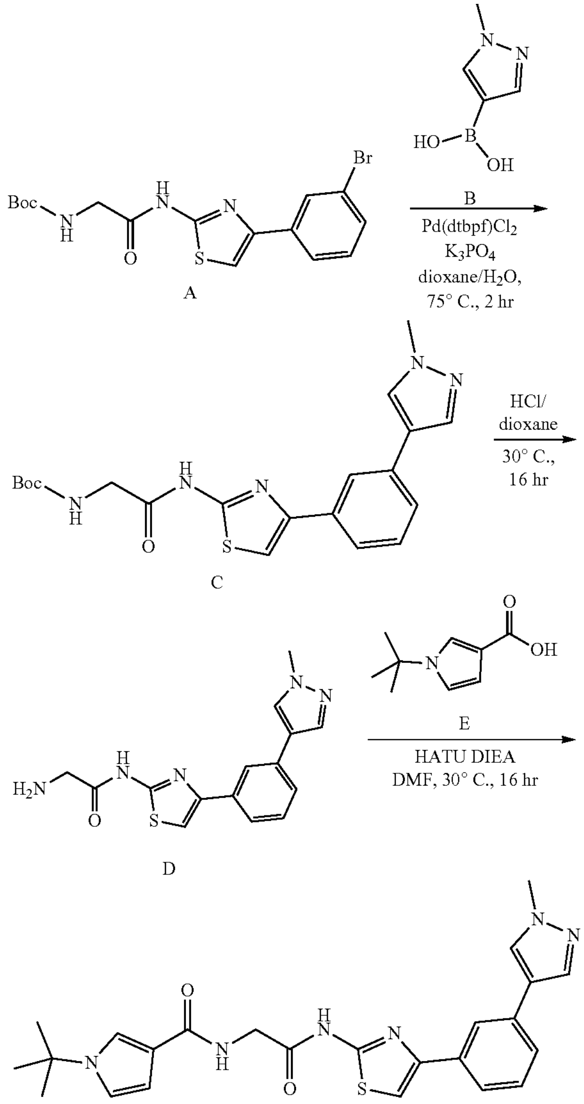

A
C
D

Compound 83

Step 1: Preparation of tert-butyl (2-((4-(3-(1-methyl-1H-pyrazol-4-yl)phenyl)thiazol-2-yl)amino)-2-oxoethyl)carbamate (Intermediate C)

C

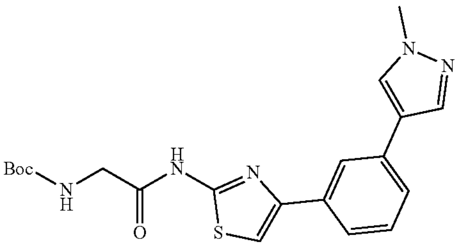

To a mixture of tert-butyl N-[2-[[4-(3-bromophenyl)thiazol-2-yl]amino]-2-oxo-ethyl]carbamate (prepared according to the method in Example 1) (250 mg, 606.35 μmol) and (1-methylpyrazol-4-yl)boronic acid (229.06 mg, 1.82 mmol) in dioxane (6 mL) and $H_2O$ (1.5 mL) was added $K_3PO_4$ (386.12 mg, 1.82 mmol) and [1,1'-bis(di-tert-butylphosphino)ferrocene]dichloropalladium(II) (39.52 mg, 60.64 μmol) at 30° C. under $N_2$. The reaction mixture was heated to 75° C. and stirred at 75° C. for 2 h. The reaction mixture was poured into $H_2O$ (20 mL) and extracted with EtOAc (20 mL×3), the combined organic layers were washed with brine (20 mL), dried over $Na_2SO_4$, filtered and concentrated under reduced pressure to afford a residue. The residue was purified by reverse phase column (FA condition) and lyophilized to afford Intermediate C (250 mg, 571.38 μmol, 94.23% yield) as yellow solid. LCMS (ESI) m/z $[M+H]^+$=414.0; $^1H$ NMR (400 MHz, DMSO-$d_6$) δ 12.28 (br s, 1H), 8.16 (s, 1H), 8.07-8.06 (m, 1H), 7.89 (s, 1H), 7.75-7.68 (m, 2H), 7.54-7.48 (m, 1H), 7.45-7.37 (m, 1H), 7.16-7.14 (m, 1H), 3.93-3.84 (m, 5H), 1.41 (s, 9H).

Step 2: Preparation of 2-amino-N-(4-(3-(1-methyl-1H-pyrazol-4-yl)phenyl)thiazol-2-yl)acetamide (Intermediate D)

D

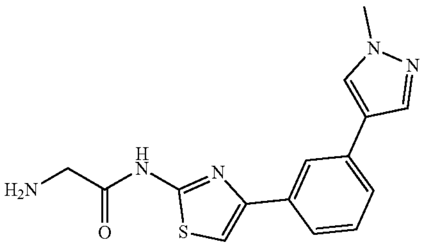

To a mixture of Intermediate C (250 mg, 604.61 μmol) in dioxane (2 mL) was added HCl/dioxane (4 M, 2 mL) at 30° C. The reaction mixture was stirred at 30° C. for 16 h. The reaction mixture was filtered and dried in vacuum to give Intermediate D (190 mg, 439.79 μmol, 72.74% yield, HCl salt) as yellow solid. LCMS (ESI) m/z $[M+H]^+$=314.3.

Step 3: Preparation of 1-(tert-butyl)-N-(2-((4-(3-(1-methyl-1H-pyrazol-4-yl)phenyl)thiazol-2-yl)amino)-2-oxoethyl)-1H-pyrrole-3-carboxamide (Compound 83)

Compound 83

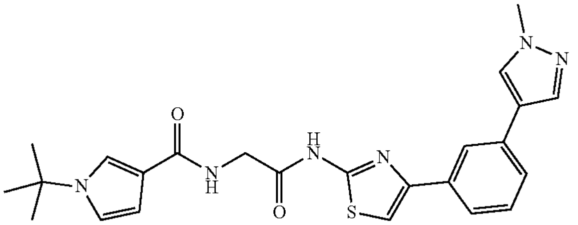

To a mixture of [prepared according to the method in Example 34] (28.68 mg, 171.51 μmol) in DCM (1 mL) was added DIEA (110.83 mg, 857.54 μmol, 149.37 μL), HATU (97.82 mg, 257.26 μmol) and Intermediate D (60 mg, 171.51 μmol, HCl salt) at 30° C. The reaction mixture was stirred at 30° C. for 16 h. The reaction mixture was washed with citric acid aqueous solution (2M, 1 mL) and saturated $NaHCO_3$ solution (1 mL). The organic phase was concentrated under reduced pressure to afford a residue. The residue was purified by reverse phase column (FA) and lyophilized to give Compound 83 (22.60 mg, 44.44 μmol, 25.91% yield, FA salt) as a white solid. LCMS (ESI) m/z $[M+H]^+$=463.0; 1H NMR (400 MHz, Methanol-$d_4$) δ 8.32-8.25 (m, 1H), 8.10-8.04 (m, 1H), 7.98 (s, 1H), 7.85 (s, 1H), 7.74 (d, J=8.0 Hz, 1H), 7.59-7.57 (m, 1H), 7.51-7.46 (m, 1H), 7.44 (s, 1H), 7.41-7.34 (m, 1H), 6.96-6.94 (m, 1H), 6.59-6.57 (m, 1H), 4.24 (s, 2H), 3.94 (s, 3H), 1.57 (s, 9H).

Example 82. Preparation of 1-(tert-butyl)-N-(2-oxo-2-((4-(3-(pyrimidin-4-yl)phenyl)thiazol-2-yl)amino)ethyl)-1H-pyrrole-3-carboxamide (Compound 84)

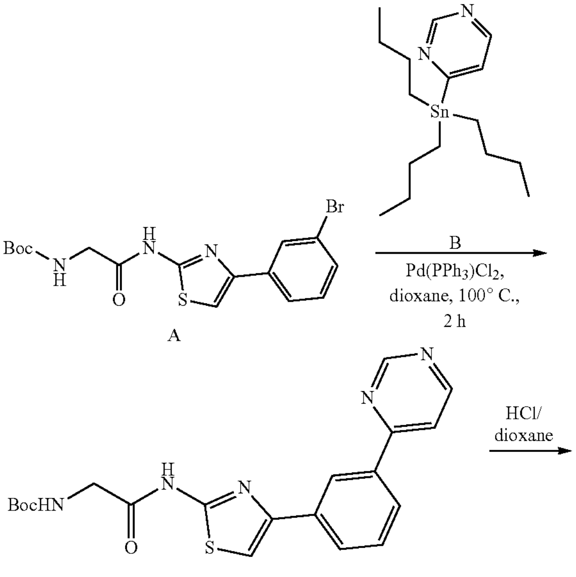

-continued

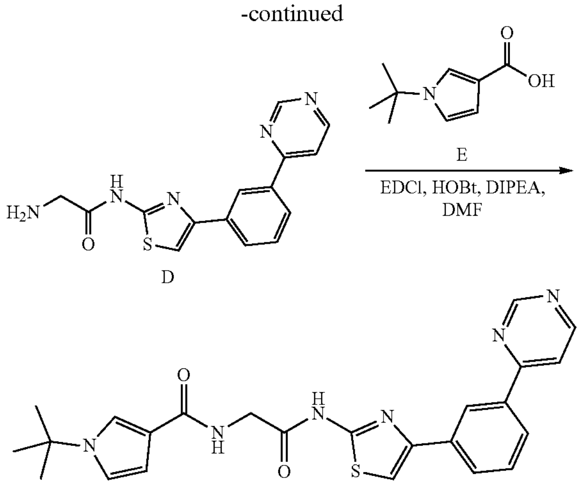

Compound 84

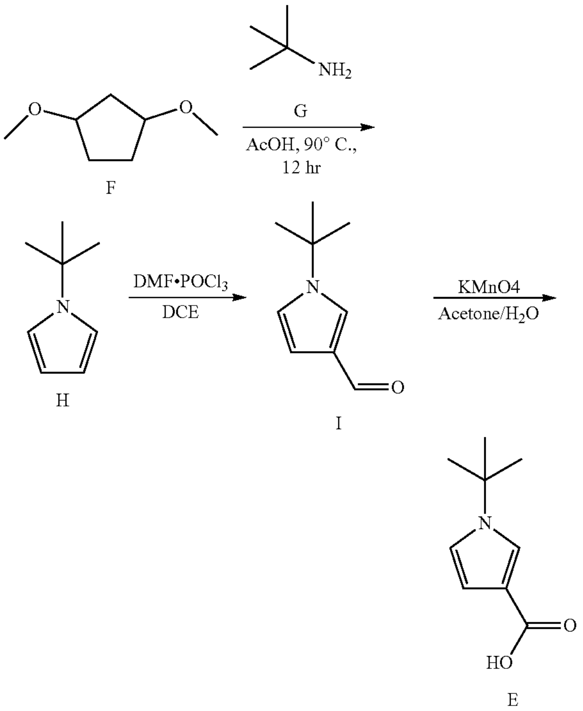

Step 1: Preparation of tert-butyl (2-oxo-2-((4-(3-(pyrimidin-4-yl)phenyl)thiazol-2-yl)amino)ethyl) carbamate (Intermediate C)

C

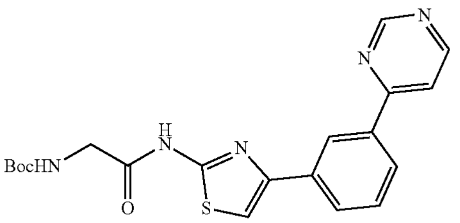

A mixture of tert-butyl N-[2-[[4-(3-bromophenyl)thiazol-2-yl]amino]-2-oxo-ethyl]carbamate (500 mg, 1.21 mmol), tributyl(pyrimidin-4-yl)stannane (805.77 mg, 2.18 mmol), $Pd(PPh_3)_2Cl_2$ (85.12 mg, 121.27 μmol) in dioxane (5 mL) was degassed and purged with $N_2$ for 3 times, and then the mixture was stirred at 100° C. for 4 h under $N_2$ atmosphere. The reaction mixture was poured into saturated aq. KF (15 mL) and stirred for 30 min. Then the solution was extracted with EtOAc (10 mL×3). The combined organic layer was concentrated in vacuum. The residue was purified by column chromatography (SiO2, DCM:MeOH=1:0 to 20:1) and concentrated to give Intermediate C (450 mg, 1.05 mmol, 86.19% yield) as a white solid. LCMS (ESI) m/z $[M+H]^+$=412.1; $^1$HNMR (400 MHz, DMSO-$d_6$) δ 12.62-12.25 (m, 1H), 9.29 (s, 1H), 8.90 (d, J=5.6 Hz, 1H), 8.81 (s, 1H), 8.18-8.12 (m, 2H), 8.08 (d, J=7.6 Hz, 1H), 7.76 (s, 1H), 7.63-7.59 (m, 1H), 7.10 (s, 1H), 3.86 (d, J=5.6 Hz, 2H), 1.40 (s, 9H).

Step 2: Preparation of 2-amino-N-(4-(3-(pyrimidin-4-yl)phenyl)thiazol-2-yl)acetamide (Intermediate D)

D

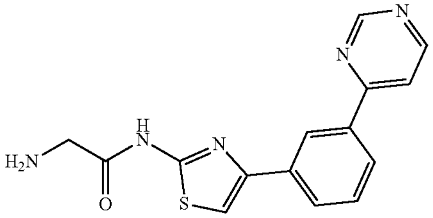

To a solution of Intermediate C (250 mg, 607.57 μmol) in dioxane (2 mL) was added HCl/dioxane (4 M, 1.52 mL). The mixture was stirred at 25° C. for 2 h. The reaction mixture was concentrated under reduced pressure to give a residue. The residue was washed with MTBE (5 mL) and dried in vacuum to give Intermediate D (200 mg, 517.51 μmol, 85.18% yield, HCl salt) as yellow solid. LCMS (ESI) m/z $[M+H]^+$=312.1; $^1$H NMR (400 MHz, DMSO-$d_6$) δ 9.32 (d, J=0.8 Hz, 1H), 8.93 (d, J=5.6 Hz, 1H), 8.83 (s, 1H), 8.47 (s, 1H), 8.22-8.14 (m, 2H), 8.10 (d, J=8.0 Hz, 1H), 7.90 (s, 1H), 7.66-7.62 (m, 1H), 3.92 (d, J=5.6 Hz, 2H).

Step 3: Preparation of 1-(tert-butyl)-N-(2-oxo-2-((4-(3-(pyrimidin-4-yl)phenyl)thiazol-2-yl)amino)ethyl)-1H-pyrrole-3-carboxamide (Compound 84)

Compound 84

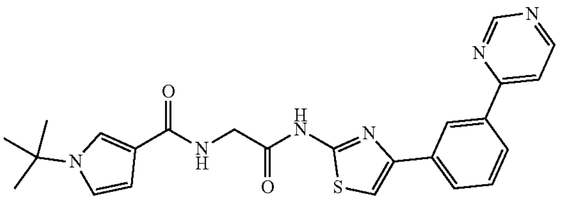

To a solution of 1-tert-butylpyrrole-3-carboxylic acid [prepared according to the method in Example 34] (96.14 mg, 575.01 μmol) in DCM (3 mL) was added Intermediate D (200 mg, 575.01 μmol, HCl salt), EDCI (165.34 mg, 862.51 μmol), HOBt (116.54 mg, 862.51 μmol) and DIEA (371.57 mg, 2.88 mmol, 500.77 μL). The mixture was stirred at 25° C. for 2 h. After the reaction MeOH (5 mL) was added and white solid was formed. The mixture was filtered and the solid was washed with MTBE (5 mL×2) and dried in vacuum to give Compound 84 (74.22 mg, 159.61 μmol, 27.76% yield) as off-white solid. LCMS (ESI) m/z $[M+H]^+$= 461.0; $^1H$ NMR (400 MHz, DMSO-$d_6$) δ 12.43 (s, 1H), 9.30 (d, J=0.8 Hz, 1H), 8.91 (d, J=5.6 Hz, 1H), 8.82 (s, 1H), 8.21-8.13 (m, 3H), 8.09 (d, J=7.6 Hz, 1H), 7.80 (s, 1H), 7.84-7.60 (m, 1H), 7.53-7.52 (m, 1H), 6.98-6.96 (m, 1H), 6.49-6.48 (m, 1H), 4.11 (d, J=5.6 Hz, 2H), 1.49 (s, 9H).

Example 83. Preparation of N-(2-((4-(3-((2R, 6R)-2,6-dimethylmorpholino)phenyl)thiazol-2-yl) amino)-2-oxoethyl)-1-(methylsulfonyl)-1H-pyrrole-3-carboxamide (Compound 85)

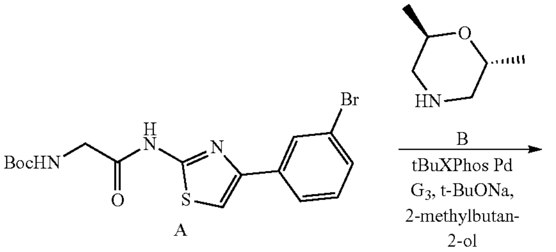

A

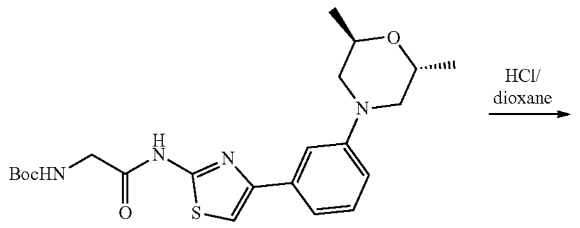

C

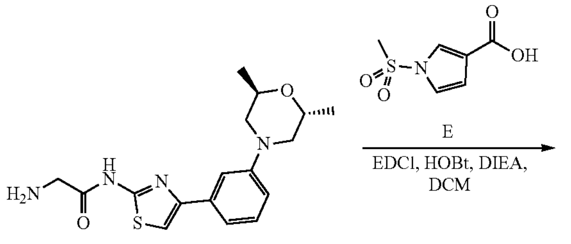

D

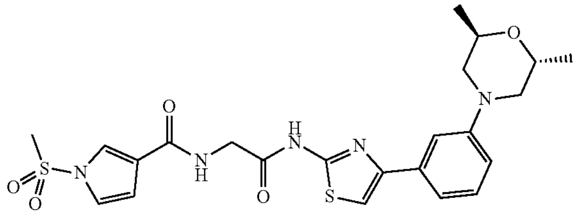

Compound 85

Step 1: Preparation of tert-butyl (2-((4-(3-((2R, 6R)-2,6-dimethylmorpholino)phenyl)thiazol-2-yl) amino)-2-oxoethyl)carbamate (Intermediate C)

C

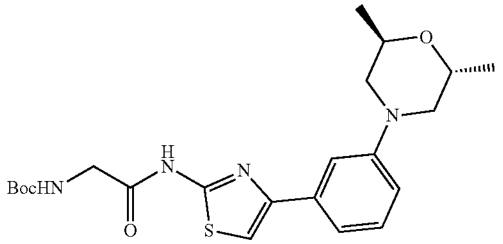

To a solution of tert-butyl N-[2-[[4-(3-bromophenyl)thiazol-2-yl]amino]-2-oxo-ethyl]carbamate (prepared according to the method in Example 1) (300 mg, 727.62 μmol) and (2R,6R)-2,6-dimethylmorpholine (125.70 mg, 1.09 mmol) in 2-methylbutan-2-ol (3 mL) were added t-BuXPhos-Pd-G3 (57.80 mg, 72.76 μmol) and t-BuONa (209.78 mg, 2.18 mmol) under $N_2$, the mixture was stirred at 60° C. for 4 h. The mixture was poured into waster (20 mL), the solution was extracted with EtOAc (20 mL×3). The combined organic layer was washed with brine (50 mL), dried over $Na_2SO_4$, filtered and concentrated in vacuum to give a residue. The residue was purified by column chromatography ($SiO_2$, PE:EA=10:1-5:1) and concentrated in vacuum to give Intermediate C (300 mg, 639.42 μmol, 87.88% yield) as a yellow oil. LCMS (ESI) m/z $[M+H]^+$=447.3.

Step 2: Preparation of 2-amino-N-(4-(3-((2R, 6R)-2,6-dimethylmorpholino)phenyl)thiazol-2-yl)acetamide (Intermediate D)

D

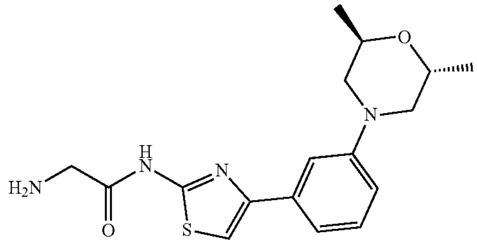

A solution of Intermediate C (290 mg, 618.10 μmol) in HCl/dioxane (3 mL) was stirred at 30° C. for 1 h. The reaction mixture was concentrated to give a residue. The residue was triturated with MTBE (5 mL), then filtered and dried in vacuum to give Intermediate D (200 mg, crude, HCl salt) as a yellow solid. LCMS (ESI) m/z $[M+H]^+$=347.2.

Step 3: Preparation of N-(2-((4-(3-((2R, 6R)-2,6-dimethylmorpholino)phenyl)thiazol-2-yl)amino)-2-oxoethyl)-1-(methylsulfonyl)-1H-pyrrole-3-carboxamide (Compound 85)

Compound 85

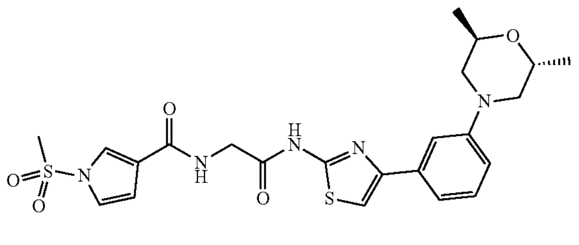

To a solution of Intermediate D (100 mg, 261.16 μmol, HCl salt) and 1-methylsulfonylpyrrole-3-carboxylic acid [prepared according to the method in Example 4] (59.29 mg, 313.39 μmol) in DCM (2 mL) was added EDCI (60.08 mg, 313.39 μmol), DIEA (168.77 mg, 1.31 mmol, 227.45 μL) and HOBt (42.35 mg, 313.39 μmol), the mixture was stirred at 30° C. for 16 h. The reaction mixture was poured into water (5 mL), the solution was extracted with EtOAc (5 mL×3), the combined organic layers were washed with brine (20 mL), dried over $Na_2SO_4$ and filtered. The filtrate was concentrated to give a residue. The residue was purified by reversed-phase HPLC (0.1% FA condition) and lyophilized to give Compound 85 (62.71 mg, 117.54 μmol, 45.01% yield) as a white solid. LCMS (ESI) m/z $[M+H]^+$=518.2; $^1H$ NMR (400 MHz, DMSO-$d_6$) δ 12.36 (s, 1H), 8.67-8.64 (m, 1H), 7.85-7.83 (m, 1H), 7.60 (s, 1H), 7.42 (s, 1H), 7.32-7.30 (m, 2H), 7.27-7.23 (m, 1H), 6.90-6.88 (m, 1H), 6.78-6.76 (m, 1H), 4.13-4.09 (m, 2H), 4.08-4.06 (m, 2H), 3.56 (s, 3H), 3.23-3.19 (m, 2H), 2.90-2.86 (m, 2H), 1.22 (d, J=6.8 Hz, 6H). Chiral HPLC: OJ-3-MeOH (DEA)-40-3ML-35T.lcm, Rt=1.971 min; ee %=87.63%.

Example 84. Preparation of N-(2-((4-(3-((2S, 6S)-2,6-dimethylmorpholino)phenyl)thiazol-2-yl)amino)-2-oxoethyl)-1-(methylsulfonyl)-1H-pyrrole-3-carboxamide (Compound 86)

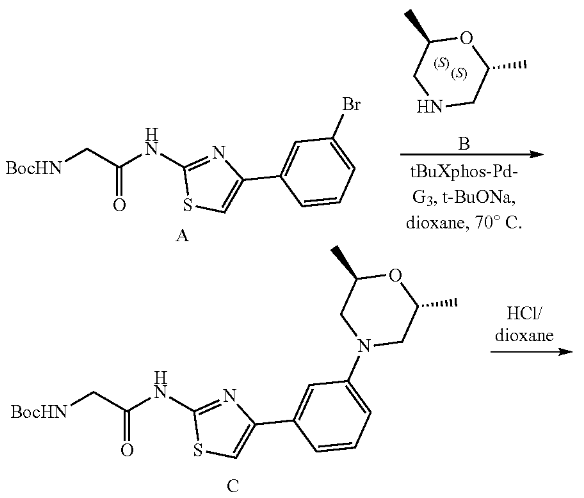

-continued

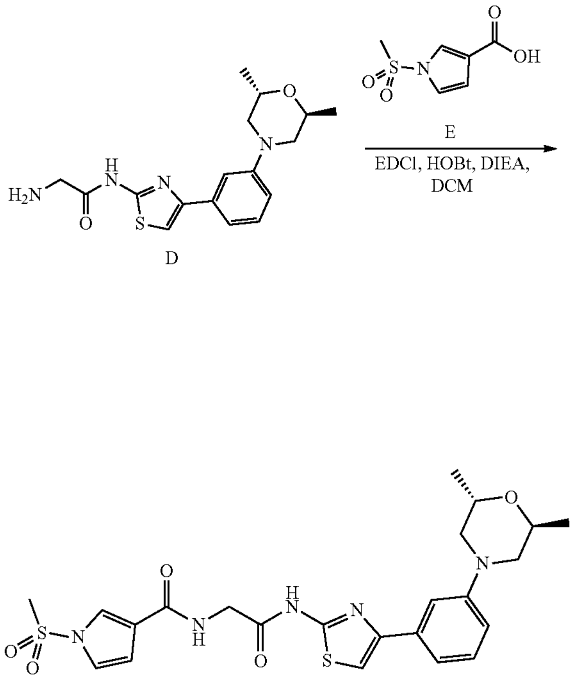

Compound 86

Step 1: Preparation of tert-butyl (2-((4-(3-((2S, 6S)-2,6-dimethylmorpholino)phenyl)thiazol-2-yl)amino)-2-oxoethyl)carbamate (Intermediate C)

C

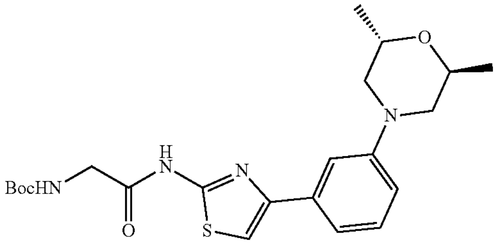

To a solution of tert-butyl N-[2-[[4-(3-bromophenyl)thiazol-2-yl]amino]-2-oxo-ethyl]carbamate (prepared according to the method in Example 1) (300 mg, 727.62 μmol), (2S,6S)-2,6-dimethylmorpholine (125.70 mg, 1.09 mmol) and t-BuONa (209.78 mg, 2.18 mmol) in dioxane (2.5 mL) was added [2-(2-aminophenyl)phenyl]-methylsulfonyloxy-palladium; ditert-butyl-[2-(2,4,6-triisopropylphenyl)phenyl]phosphane (57.80 mg, 72.76 μmol) under $N_2$, the mixture was stirred at 70° C. for 3 hours. The reaction mixture was diluted with water (20 mL) and extracted with EtOAc (10 mL×3). The combined organic layers were washed with brine (20 mL), dried over $Na_2SO_4$, filtered and concentrated under reduced pressure to give a residue. The residue was purified by column chromatography ($SiO_2$, Petroleum ether/EtOAc=2/1) and concentrated under reduced pressure to give Intermediate C (90 mg, 192.71 μmol, 26.49% yield) as a white solid. LCMS (ESI) m/z $[M+H]^+$=447.5.

Step 2: Preparation of 2-amino-N-(4-(3-((2S, 6S)-2,6-dimethylmorpholino)phenyl)thiazol-2-yl)acetamide (Intermediate D)

D

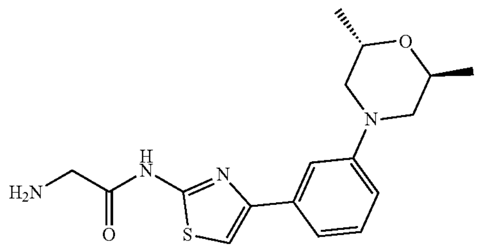

A solution of Intermediate C (90 mg, 201.54 μmol) in 4 M HCl/dioxane (2 mL) was stirred at 30° C. for 1 h. The reaction mixture was concentrated under reduced pressure to give Intermediate D (80 mg, crude, HCl salt) as a yellow solid, which was used to the next step without further purification.

Step 3: Preparation of N-(2-((4-(3-((2S, 6S)-2,6-dimethylmorpholino)phenyl)thiazol-2-yl)amino)-2-oxoethyl)-1-(methylsulfonyl)-1H-pyrrole-3-carboxamide (Compound 86)

Compound 86

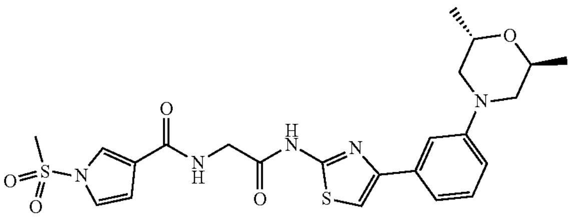

To a solution of 1-methylsulfonylpyrrole-3-carboxylic acid [prepared according to the method in Example 4] (39.53 mg, 208.93 μmol), EDCI (60.08 mg, 313.39 μmol), HOBt (42.35 mg, 313.39 μmol) and DIEA (135.01 mg, 1.04 mmol, 181.96 μL) in DCM (1 mL) was added Intermediate D (80 mg, 208.93 μmol, HCl salt), the mixture was stirred at 30° C. for 1 h. The reaction mixture was concentrated under reduced pressure to give a residue. The residue was purified by reverse phase (FA) and lyophilized to give Compound 86 (47.85 mg, 83.59 μmol, 40.01% yield, FA salt) as a white solid. LCMS (ESI) m/z $[M+H]^+$=518.2; $^1H$ NMR (400 MHz, DMSO-$d_6$) δ 12.38 (br s, 1H), 8.69-8.66 (m, 1H), 7.84-7.83 (m, 1H), 7.61 (s, 1H), 7.42 (s, 1H), 7.33-7.24 (m, 3H), 6.91-6.88 (m, 1H), 6.77-6.76 (m, 1H), 4.13-4.06 (m, 4H), 3.57 (s, 3H), 3.23-3.19 (m, 2H), 2.90-2.86 (m, 2H), 1.22 (d, J=6.4 Hz, 6H); ee %=100%.

Example 85. Preparation of (S)—N-(2-((4-(3-(2-methylmorpholino)phenyl)thiazol-2-yl)amino)-2-oxoethyl)-1-(methylsulfonyl)-1H-pyrrole-3-carboxamide (Compound 87)

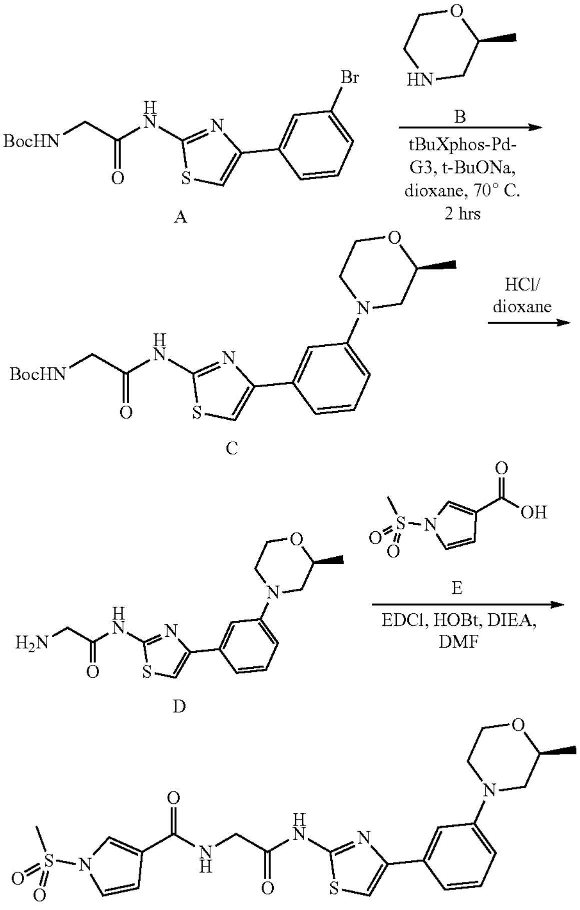

Compound 87

Step 1: Preparation of (S)-tert-butyl (2-((4-(3-(2-methylmorpholino)phenyl)thiazol-2-yl)amino)-2-oxoethyl)carbamate (Intermediate C)

C

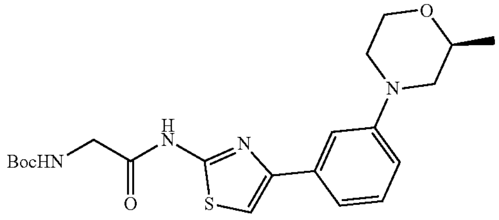

To a solution of tert-butyl N-[2-[[4-(3-bromophenyl)thiazol-2-yl]amino]-2-oxo-ethyl]carbamate (prepared according to the method in Example 1) (500 mg, 1.21 mmol), (2S)-2-methylmorpholine (245.32 mg, 2.43 mmol) and t-BuONa (349.64 mg, 3.64 mmol) in dioxane (5 mL) was added t-BuXPhos-Pd-G3 (96.33 mg, 121.27 μmol) at 25° C. under $N_2$. The reaction mixture was stirred at 70° C. under $N_2$ for 2 hours. The reaction mixture was diluted with water (20 mL) and extracted with EtOAc (15 mL×3), the combined organic layers was dried over anhydrous $Na_2SO_4$ and concentrated. The residue was purified by flash silica gel chromatography (Eluent of 0-60% Ethyl acetate/Petroleum ether gradient) and concentrated in vacuum to give Intermediate C (300 mg, 549.67 μmol, 45.33% yield) as a yellow oil. LCMS (ESI) m/z $[M+H]^+$=433.1; $^1H$ NMR (400 MHz, $CDCl_3$) δ 10.24-9.91 (m, 1H), 7.39 (s, 1H), 7.34-7.28 (m, 2H), 7.15 (s, 1H), 6.89-6.88 (m, 1H), 5.14 (s, 1H), 4.06-3.92 (m, 3H), 3.86-3.73 (m, 2H), 3.58-3.43 (m, 2H), 2.87-2.86 (m, 1H), 2.54-2.50 (m, 1H), 1.48 (s, 9H), 1.28-1.25 (m, 3H).

Step 2: Preparation of (S)-2-amino-N-(4-(3-(2-methylmorpholino)phenyl)thiazol-2-yl)acetamide (Intermediate D)

D

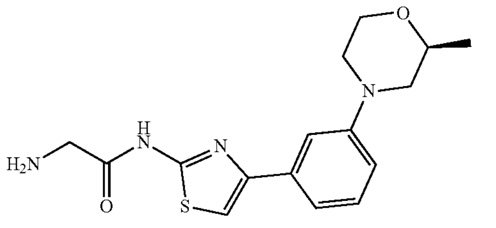

To a solution of Intermediate C (300 mg, 693.59 μmol) in dioxane (1.5 mL) was added HCl/dioxane (1.5 mL), then the mixture was stirred at 25° C. for 2 hours. The reaction mixture was concentrated to give Intermediate D (200 mg, 471.48 μmol, 67.98% yield, HCl salt) as a yellow solid, which was used to the next step without further purification. LCMS (ESI) m/z $[M+H]^+$=333.2; $^1H$ NMR (400 MHz, DMSO-$d_6$) δ 7.59 (s, 1H), 7.45 (s, 1H), 7.35-7.30 (m, 1H), 7.29-7.23 (m, 1H), 6.91-6.89 (m, 1H), 5.68-5.14 (m, 2H), 3.93-3.91 (m, 1H), 3.70-3.59 (m, 3H), 3.53 (d, J=12.0 Hz, 1H), 3.40 (s, 2H), 2.71-2.63 (m, 1H), 2.39-2.31 (m, 1H), 1.17 (d, J=6.0 Hz, 3H).

Step 3: Preparation of (S)—N-(2-((4-(3-(2-methylmorpholino)phenyl)thiazol-2-yl)amino)-2-oxoethyl)-1-(methylsulfonyl)-1H-pyrrole-3-carboxamide (Compound 87)

Compound 87

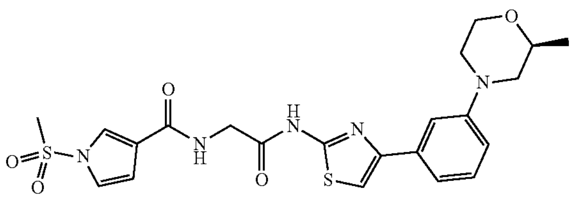

To a solution of 1-methylsulfonylpyrrole-3-carboxylic acid [prepared according to the method in Example 4] (50 mg, 264.29 μmol), EDCI (76.00 mg, 396.43 μmol), HOBt (53.57 mg, 396.43 μmol) and DIEA (102.47 mg, 792.86 μmol, 138.10 μL) in DMF (1 mL) was stirred at 25° C. for 5 minutes, then Intermediate D (107.24 mg, 290.71 μmol, HCl salt) was added. The reaction mixture was stirred at 25° C. for 2 hours. The reaction mixture was diluted with water (10 mL) and extracted with EtOAc (10 mL×4), the combined organic layers was dried over anhydrous $Na_2SO_4$ and concentrated to afford a yellow residue. The residue was purified by reversed-phase HPLC (FA), concentrated and extracted with EtOAc (10 mL×2). The combined organic layers were concentrated in vacuum. The residue was purified by reversed-phase HPLC (FA) and lyophilized to give Compound 87 (26.55 mg, 47.32 μmol, 17.90% yield, FA salt) as a white solid. LCMS (ESI) m/z $[M+H]^+$=504.2; $^1H$ NMR (400 MHz, DMSO-$d_6$) δ 12.37 (br s, 1H), 8.67-8.66 (m, 1H), 7.84-7.83 (m, 1H), 7.61 (s, 1H), 7.45 (s, 1H), 7.37-7.23 (m, 3H), 6.93-6.91 (m, 1H), 6.77-6.75 (m, 1H), 4.13 (d, J=5.6 Hz, 2H), 3.94-3.93 (m, 1H), 3.70-3.59 (m, 3H), 3.57 (s, 3H), 3.53 (d, J=12.0 Hz, 1H), 2.73-2.67 (m, 1H), 2.34 (br s, 1H), 1.17 (d, J=6.4 Hz, 3H); ee=100%.

Example 86. Preparation of (R)—N-(2-((4-(3-(2-methylmorpholino)phenyl)thiazol-2-yl)amino)-2-oxoethyl)-1-(methylsulfonyl)-1H-pyrrole-3-carboxamide (Compound 88)

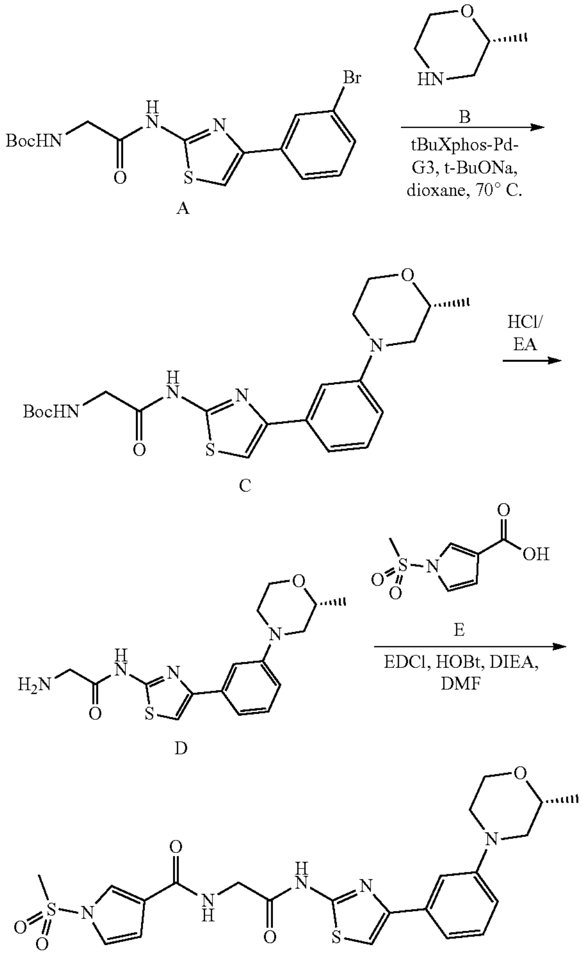

Compound 88

Step 1: Preparation of (R)-tert-butyl (2-((4-(3-(2-methylmorpholino)phenyl)thiazol-2-yl)amino)-2-oxoethyl)carbamate (Intermediate C)

C

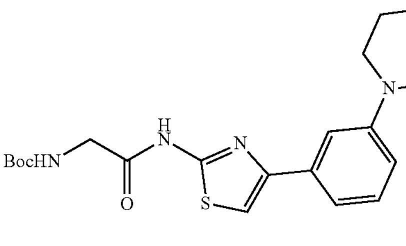

To a solution of tert-butyl N-[2-[[4-(3-bromophenyl)thiazol-2-yl]amino]-2-oxo-ethyl]carbamate (prepared according to the method in Example 1) (500 mg, 1.21 mmol), (2R)-2-methylmorpholine (183.99 mg, 1.82 mmol), t-BuONa (349.64 mg, 3.64 mmol) in dioxane (10 mL) was added t-BuXPhos-Pd-G3 (96.33 mg, 121.27 μmol). Then the mixture was stirred at 80° C. for 3 h under $N_2$. The reaction mixture was poured into water (10 mL) and extracted with EtOAc (10 mL×2). The organic layer was washed with brine (10 mL) and dried over $Na_2SO_4$, concentrated in vacuum to get a crude product. The crude product was purified by reverse phase column (FA), the solution was extracted with EtOAc (30 mL) and then concentrated in vacuum to give Intermediate C (200 mg, 362.05 μmol, 29.85% yield) as colorless oil. LCMS (ESI) m/z $[M+H]^+$=433.1.

Step 2: Preparation of (R)-2-amino-N-(4-(3-(2-methylmorpholino)phenyl)thiazol-2-yl)acetamide (Intermediate D)

D

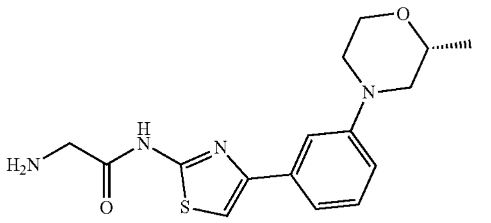

A solution of Intermediate C (200 mg, 462.39 μmol) in HCl/EtOAc (2 mL) was stirred at 25° C. for 0.5 h. The reaction mixture was concentrated. The residue was triturated with EtOAc (5 mL) at 25° C. for 10 min, then filtered and dried in vacuum to give Intermediate D (160 mg, 374.32 μmol, 80.95% yield, HCl salt) as white solid. LCMS (ESI) m/z $[M+H]^+$=333.2.

Step 3: Preparation of (R)—N-(2-((4-(3-(2-methylmorpholino)phenyl)thiazol-2-yl)amino)-2-oxoethyl)-1-(methylsulfonyl)-1H-pyrrole-3-carboxamide (Compound 88)

Compound 88

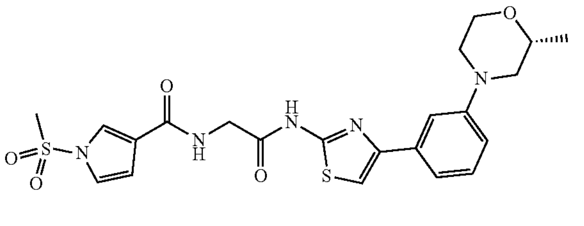

To a solution of Intermediate D (100 mg, 271.09 μmol, HCl salt), 1-methylsulfonylpyrrole-3-carboxylic acid [prepared according to the method in Example 4] (61.54 mg, 325.31 μmol), EDCI (103.94 mg, 542.18 μmol), HOBt (73.26 mg, 542.18 μmol) in DMF (1 mL) was added DIEA (175.18 mg, 1.36 mmol, 236.10 μL). Then the mixture was stirred at 25° C. for 1 h. The reaction mixture was concentrated to get the crude product. The crude product was purified by reverse phase column (FA) and lyophilized to give Compound 88 (68.13 mg, 117.14 μmol, 43.21% yield, FA salt) as a white solid. LCMS (ESI) m/z $[M+H]^+$=504.2; $^1$H NMR (400 MHz, DMSO-$d_6$) δ 12.37 (s, 1H), 8.68-9.67 (m, 1H), 7.86-7.85 (m, 1H), 7.62 (s, 1H), 7.46 (s, 1H), 7.40-7.25 (m, 3H), 6.94-6.93 (m, 1H), 6.79-6.78 (m, 1H), 4.14 (d, J=6.0 Hz, 2H), 3.96-3.95 (m, 1H), 3.74-3.61 (m, 3H), 3.59-3.51 (m, 4H), 2.75-2.65 (m, 1H), 2.39-2.38 (m, 1H), 1.18 (d, J=6.2 Hz, 3H); ee %=100%.

Example 87. Preparation of N-(2-((4-(3-(2,2-dimethylmorpholino)phenyl)thiazol-2-yl)amino)-2-oxoethyl)-1-(methylsulfonyl)-1H-pyrrole-3-carboxamide (Compound 89)

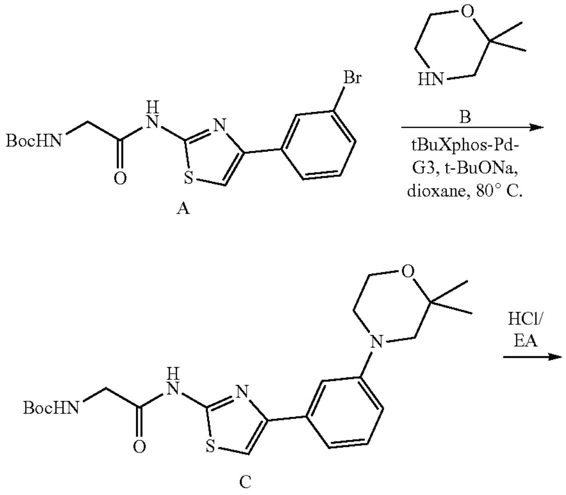

-continued

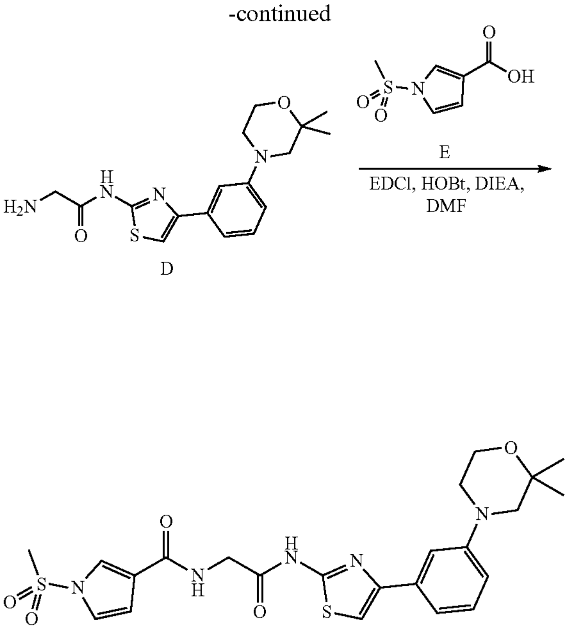

D

Compound 89

Step 1: Preparation of tert-butyl (2-((4-(3-(2,2-dimethylmorpholino)phenyl)thiazol-2-yl)amino)-2-oxoethyl)carbamate (Intermediate C)

C

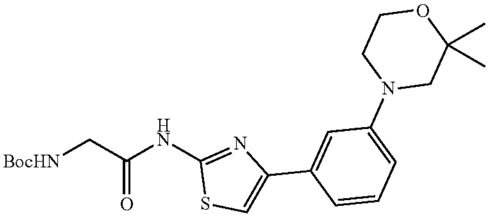

To a solution of tert-butyl N-[2-[[4-(3-bromophenyl)thiazol-2-yl]amino]-2-oxo-ethyl]carbamate (prepared according to the method in Example 1) (500 mg, 1.21 mmol), 2,2-dimethylmorpholine (209.51 mg, 1.82 mmol), t-BuONa (349.62 mg, 3.64 mmol) in dioxane (10 mL) was added t-BuXPhos-Pd-G3 (96.33 mg, 121.27 μmol). Then the mixture was stirred at 80° C. for 3 h under $N_2$. The reaction mixture was poured into water (10 mL) and extracted with EtOAc (10 mL×2), the organic layer was washed with brine (10 mL) and concentrated to get the crude product. The crude product was purified by reverse phase column (FA) and lyophilized to give Intermediate C (180 mg, 249.51 μmol, 20.57% yield) as colorless oil. LCMS (ESI) m/z $[M+H]^+$=447.1.

Step 2: Preparation of 2-amino-N-(4-(3-(2,2-dimethylmorpholino)phenyl)thiazol-2-yl)acetamide (Intermediate D)

D

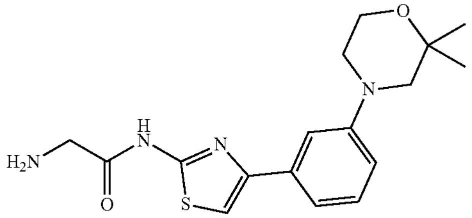

A solution of Intermediate C (180 mg, 403.08 μmol) in HCl/EtOAc (2 mL) was stirred at 25° C. for 0.5 h. The reaction mixture was concentrated to get the crude product. The crude product was triturated with EtOAc (5 mL) at 25° C. for 30 min, then filtered and concentrated in vacuum to give Intermediate D (100 mg, 258.55 μmol, 64.14% yield, HCl salt) as a white solid. LCMS (ESI) m/z $[M+H]^+$=347.2.

Step 3: Preparation of N-(2-((4-(3-(2,2-dimethylmorpholino)phenyl)thiazol-2-yl)amino)-2-oxoethyl)-1-(methylsulfonyl)-1H-pyrrole-3-carboxamide (Compound 89)

Compound 89

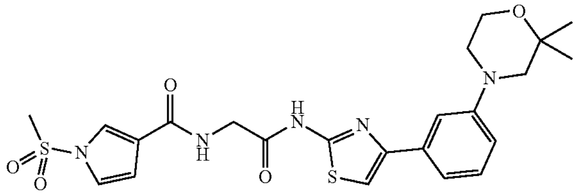

To a solution of Intermediate D (100 mg, 261.16 μmol, HCl salt), 1-methylsulfonylpyrrole-3-carboxylic acid [prepared according to the method in Example 4] (59.29 mg, 313.39 μmol), EDCI (100.13 mg, 522.32 μmol), HOBt (70.58 mg, 522.32 μmol) in DMF (1 mL) was added DIEA (168.77 mg, 1.31 mmol, 227.45 μL). Then the mixture was stirred at 25° C. for 1 h. The reaction mixture was concentrated to get the crude product. The crude product was purified by reverse phase (FA) and lyophilized to give Compound 89 (62.57 mg, 108.23 μmol, 41.44% yield, FA salt) as a white solid. LCMS (ESI) m/z $[M+H]^+$=518.2; $^1H$ NMR (400 MHz, DMSO-$d_6$) δ 12.37 (s, 1H), 8.73-8.63 (m, 1H), 7.85 (d, J=1.6 Hz, 1H), 7.62 (s, 1H), 7.44 (s, 1H), 7.37-7.23 (m, 3H), 6.92 (d, J=8.0 Hz, 1H), 6.78 (m, 1H), 4.14 (d, J=5.6 Hz, 2H), 3.83-3.75 (m, 2H), 3.61-3.53 (m, 3H), 3.14-3.07 (m, 2H), 2.99 (s, 2H), 1.26 (s, 6H).

Example 88. Preparation of 1-(tert-butyl)-N-(2-((4-(3-(cis-2,6-dimethylmorpholino)phenyl)thiazol-2-yl)amino)-2-oxoethyl)-1H-pyrrole-3-carboxamide (Compound 90)

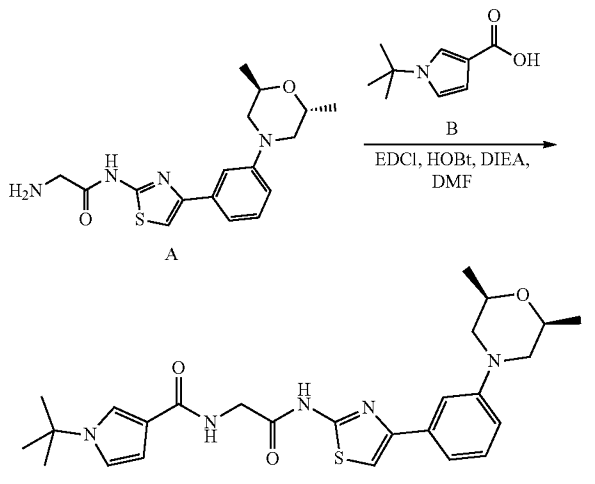

A

Compound 90

To a solution of 1-tert-butylpyrrole-3-carboxylic acid [prepared according to the method in Example 34] (41.92 mg, 250.71 μmol) in DMF (2 mL) was added EDCI (60.08 mg, 313.39 μmol), DIEA (108.01 mg, 835.71 μmol, 145.56 μL) and HOBt (42.35 mg, 313.39 μmol), then 2-amino-N-[4-[3-[cis-2,6-dimethylmorpholin-4-yl]phenyl]thiazol-2-yl]acetamide (prepared according to the method in Example 10) (80 mg, 208.93 μmol, HCl salt) was added. The mixture was stirred at 25° C. for 2 h. The reaction mixture was concentrated under reduced pressure to remove DMF. The residue was purified by Prep-HPLC (mobile phase: [water (0.075% TFA)-acetonitrile]; B %: 38%-68%) and lyophilized to give Compound 90 (45 mg, 70.82 μmol, 33.90% yield, TFA salt) as a white solid. LCMS (ESI) m/z $[M+H]^+$=496.4; $^1$H NMR (400 MHz, DMSO-$d_6$) δ 12.30 (s, 1H), 8.19-8.16 (m, 1H), 7.61 (s, 1H), 7.54-7.50 (m, 1H), 7.45 (s, 1H), 7.36-7.31 (m, 1H), 7.29-7.24 (m, 1H), 6.99-6.91 (m, 2H), 6.48-6.46 (m, 1H), 4.09-4.07 (d, J=6.0 Hz, 2H), 3.77-3.69 (m, 2H), 3.62 (d, J=10.4 Hz, 2H), 2.33-2.24 (m, 2H), 1.50-1.48 (m, 9H), 1.17 (d, J=6.4 Hz, 6H).

Example 89. Preparation of N-(2-((4-(3-(4-(methoxymethyl)piperidin-1-yl)phenyl)thiazol-2-yl)amino)-2-oxoethyl)-1-(methylsulfonyl)-1H-pyrrole-3-carboxamide (Compound 91)

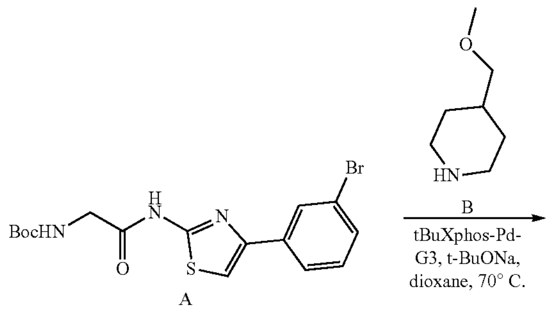

A

-continued

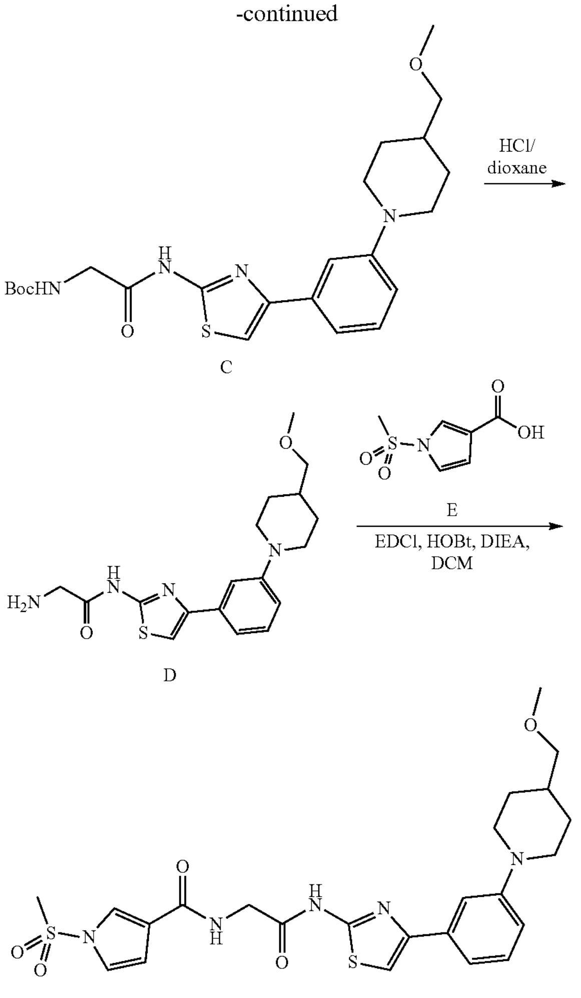

C

D

Compound 91

Step 1: Preparation of tert-butyl (2-((4-(3-(4-(methoxymethyl)piperidin-1-yl)phenyl)thiazol-2-yl)amino)-2-oxoethyl)carbamate (Intermediate C)

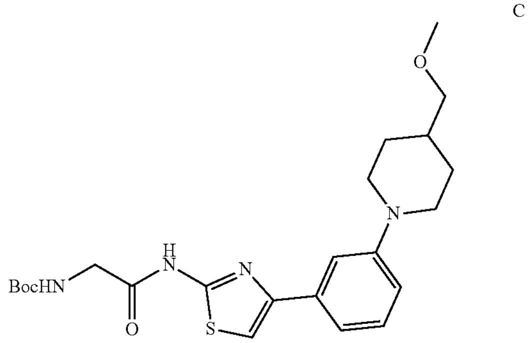 [SMILES: COCC1CCN(c2cccc(-c3csc(NC(=O)CNC(=O)OC(C)(C)C)n3)c2)CC1]

C

To a solution of tert-butyl N-[2-[[4-(3-bromophenyl)thiazol-2-yl]amino]-2-oxo-ethyl]carbamate (prepared according to the method in Example 1) (300 mg, 727.62 μmol), 4-(methoxymethyl)piperidine (141.01 mg, 1.09 mmol) and t-BuONa (209.78 mg, 2.18 mmol) in dioxane (2.5 mL) was added [2-(2-aminophenyl)phenyl]-methylsulfonyloxy-palladium; ditert-butyl-[2-(2,4,6-triisopropylphenyl)phenyl] phosphane (57.80 mg, 72.76 μmol) under $N_2$, the mixture was stirred at 70° C. for 3 h. The reaction mixture was diluted with water (20 mL) and extracted with EtOAc (10 mL×3). The combined organic layers were washed with brine (20 mL), dried over $Na_2SO_4$, filtered and concentrated under reduced pressure to give a residue. The residue was purified by column chromatography ($SiO_2$, Petroleum ether/EtOA c=2/1) and concentrated under reduced pressure to give Intermediate C (200 mg, 432.97 μmol, 59.50% yield) as a white solid. LCMS (ESI) m/z $[M+H]^+$=461.4.

Step 2: Preparation of 2-amino-N-(4-(3-(4-(methoxymethyl)piperidin-1-yl)phenyl)thiazol-2-yl) acetamide (Intermediate D)

D

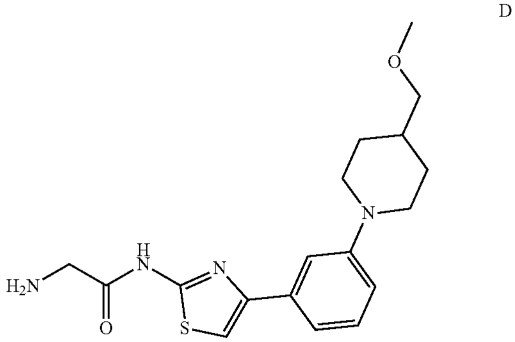 [SMILES: COCC1CCN(c2cccc(-c3csc(NC(=O)CN)n3)c2)CC1]

A solution of Intermediate C (200 mg, 434.23 μmol) in 4 M HCl/dioxane (2 mL) was stirred at 30° C. for 1 hr. The reaction mixture was concentrated under reduced pressure to give Intermediate D (180 mg, crude, HCl salt) as a light-yellow solid, which was used to the next step without further purification.

Step 3: Preparation of N-(2-((4-(3-(4-(methoxymethyl)piperidin-1-yl)phenyl)thiazol-2-yl)amino)-2-oxoethyl)-1-(methylsulfonyl)-1H-pyrrole-3-carboxamide (Compound 91)

Compound 91

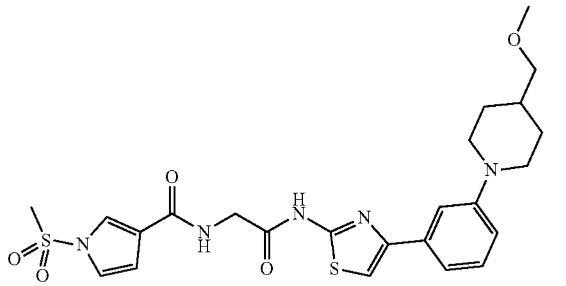

To a solution of 1-methylsulfonylpyrrole-3-carboxylic acid [prepared according to the method in Example 4] (38.13 mg, 201.54 μmol), EDCI (57.95 mg, 302.32 μmol), HOBt (40.85 mg, 302.32 μmol) and DIEA (130.24 mg, 1.01 mmol, 175.53 μL) in DCM (1 mL) was added Intermediate D (80 mg, 201.54 μmol, HCl). The mixture was stirred at 30° C. for 1 h. The reaction mixture was concentrated under reduced pressure to give a residue. The residue was purified by reverse phase (FA) and lyophilized to give Compound 91 (34.32 mg, 58.82 μmol, 29.18% yield, FA salt) as a white solid. LCMS (ESI) m/z $[M+H]^+$=532.2; $^1H$ NMR (400 MHz, DMSO-$d_6$) δ 12.38 (br s, 1H), 8.69-8.66 (m, 1H), 7.84-7.83 (m, 1H), 7.59 (s, 1H), 7.46 (s, 1H), 7.32-7.21 (m, 3H), 6.90-6.88 (m, 1H), 6.77-6.76 (m, 1H), 4.12 (d, J=5.6 Hz, 2H), 3.76-3.70 (m, 2H), 3.57 (s, 3H), 3.24-3.21 (m, 5H), 2.68-2.65 (m, 2H), 1.76-1.68 (m, 3H), 1.33-1.23 (m, 2H).

Example 90. Preparation of (S)—N-(2-((4-(3-(3-(methoxymethyl)piperidin-1-yl)phenyl)thiazol-2-yl) amino)-2-oxoethyl)-1-(methylsulfonyl)-1H-pyrrole-3-carboxamide (Compound 92)

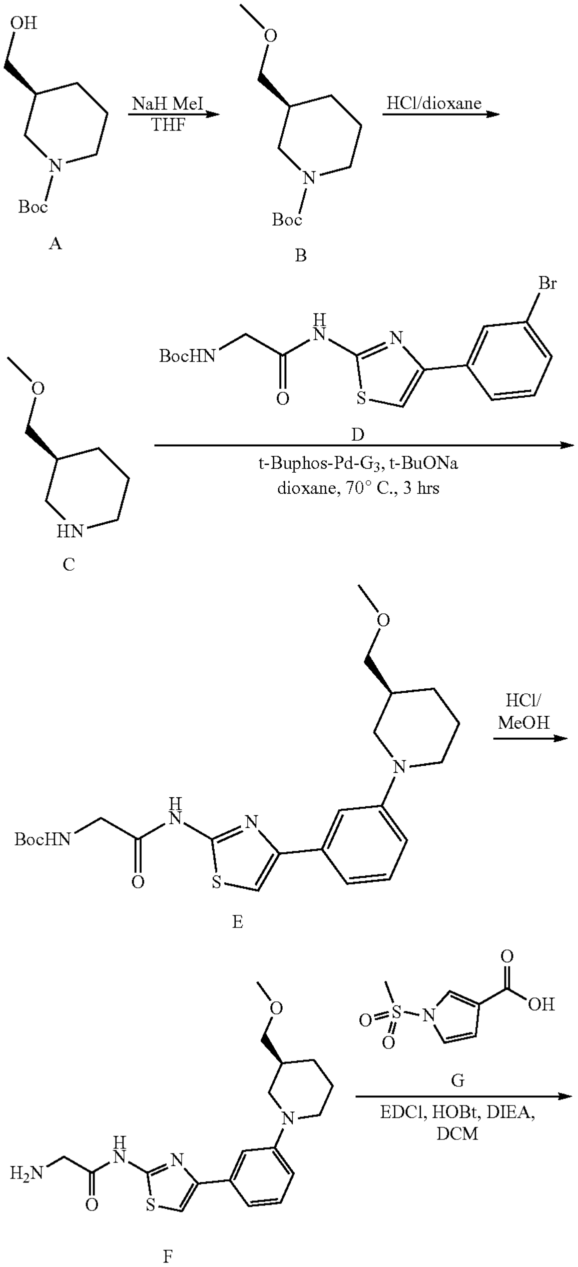

-continued

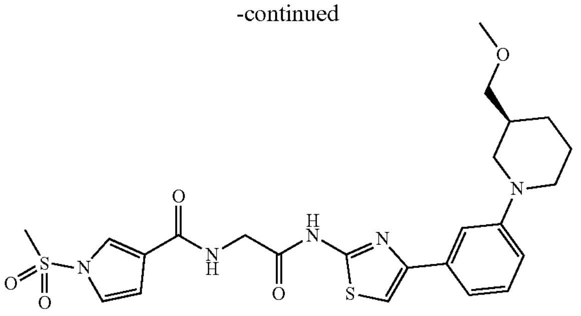

Compound 92

Step 1: Preparation of (S)-tert-butyl 3-(methoxymethyl)piperidine-1-carboxylate (Intermediate B)

B

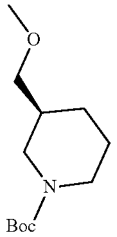

To a solution of tert-butyl (3S)-3-(hydroxymethyl)piperidine-1-carboxylate (1.00 g, 4.64 mmol) in THF (15 mL) was added NaH (557.34 mg, 13.93 mmol, 60% purity) at 0° C. After additional, the mixture was stirred at 25° C. for 0.5 h, and then MeI (1.98 g, 13.93 mmol, 867.49 μL) was added at 0° C. The resulting mixture was stirred at 25° C. for 2 h. The reaction was diluted with aq. $NH_4Cl$ (50 mL), extract with EtOAc (20 mL×3), the combined organic layers were dried over $Na_2SO_4$, concentrated to get the residue. The residue was purified by column chromatography ($SiO_2$, Petroleum ether/EtOAc=10/1 to 8:1) and concentrated in vacuum to give Intermediate B (1 g, 4.36 mmol, 93.88% yield) as yellow oil. LCMS (ESI) m/z $[M+H]^+$=230.1. $^1H$ NMR (400 MHz, DMSO-$d_6$) δ 3.84-3.72 (m, 2H), 3.23 (s, 3H), 3.19-3.14 (m, 2H), 2.79-2.76 (m, 1H), 1.65-1.54 (m, 3H), 1.39 (s, 9H), 1.33-1.15 (m, 3H).

Step 2: Preparation of (S)-3-(methoxymethyl)piperidine hydrochloride (Intermediate C)

C

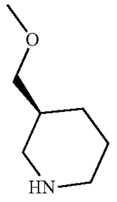

A solution of Intermediate B (1000.00 mg, 4.36 mmol) in HCl/dioxane (10 mL) was stirred at 25° C. for 1.5 h. The reaction mixture was concentrated to get the residue. The residue was triturated with MTBE (30 mL), then filtered and dried in vacuum to give Intermediate C (500 mg, 3.02 mmol, 69.21% yield, HCl salt) as a white solid. $^1H$ NMR (400 MHz, DMSO-d6) δ 3.37-3.31 (m, 4H), 3.29 (s, 3H), 2.88-2.82 (m, 1H), 2.72-2.66 (m, 1H), 2.04 (br s, 1H), 1.91 (br d, J=14.4 Hz, 1H), 1.80 (br d, J=13.2 Hz, 1H), 1.67-1.64 (m, 1H), 1.27-1.21 (m, 1H).

Step 3: Preparation of (S)-tert-butyl (2-((4-(3-(3-(methoxymethyl)piperidin-1-yl)phenyl)thiazol-2-yl)amino)-2-oxoethyl)carbamate (Intermediate E)

E

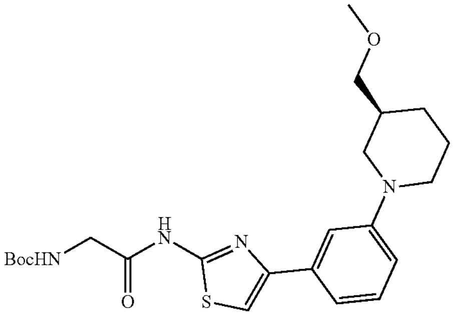

A mixture of tert-butyl N-[2-[[4-(3-bromophenyl)thiazol-2-yl]amino]-2-oxo-ethyl]carbamate (prepared according to the method in Example 1) (150 mg, 363.81 μmol), Intermediate C (94.01 mg, 727.62 μmol, HCl salt), t-BuONa (174.82 mg, 1.82 mmol), and [2-(2-aminophenyl)phenyl]-methylsulfonyloxypalladium; ditert-butyl-[2-(2,4,6-triisopropylphenyl)phenyl]phosphane (28.90 mg, 36.38 μmol) in dioxane (3 mL) was degassed and purged with $N_2$ for 3 times, and then the mixture was stirred at 70° C. for 3 hrs under $N_2$. The reaction was diluted with water (15 mL), extracted with EtOAc (5 mL×3). The combined organic layers were dried over $Na_2SO_4$, filtered and concentrated to get the residue. The residue was purified by column chromatography ($SiO_2$, Petroleum ether/EtOAc=8/1 to 2:1) and concentrated in vacuum to give Intermediate E (120 mg, 260.54 μmol, 71.61% yield) as yellow oil. LCMS (ESI) m/z $[M+H]^+$=461.2; $^1H$ NMR (400 MHz, $CDCl_3$) δ 7.43 (br s, 1H), 7.30 (s, 1H), 7.27-7.25 (m, 1H), 7.15 (s, 1H), 6.96 (d, J=8.0 Hz, 1H), 5.14 (d, J=3.2 Hz, 1H), 4.07 (d, J=4.0 Hz, 2H), 3.77-3.74 (m, 1H), 3.63 (d, J=12.0 Hz, 1H), 3.38 (s, 3H), 3.36-3.34 (m, 2H), 2.81-280 (m, 1H), 2.63-2.58 (m, 1H), 1.87-1.79 (m, 2H), 1.78-1.72 (m, 1H), 1.51 (s, 9H), 1.25-1.19 (m, 1H).

Step 4: Preparation of (S)-2-amino-N-(4-(3-(3-(methoxymethyl)piperidin-1-yl)phenyl)thiazol-2-yl) acetamide (Intermediate F)

F

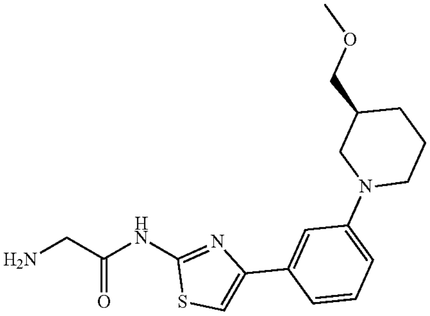

A solution of Intermediate E (120.00 mg, 260.54 μmol) in HCl/MeOH (3 mL) stirred at 25° C. for 1 h. The reaction was concentrated in vacuum. The residue was triturated by MTBE (10 mL), filtered and dried in vacuum to give Intermediate F (90 mg, 226.74 μmol, 87.03% yield, HCl salt) as a yellow solid. LCMS (ESI) m/z $[M+H]^+$=361.2; $^{1}$H NMR (400 MHz, Methanol-$d_4$) δ 8.31 (br d, J=14.0 Hz, 1H), 8.13-8.12 (m, 1H), 7.71 (d, J=1.2 Hz, 1H), 7.68 (d, J=5.6 Hz, 2H), 4.05 (s, 2H), 3.76-3.73 (m, 2H), 3.58-3.55 (m, 1H), 3.52-3.47 (m, 1H), 3.36 (s, 6H), 2.50-2.49 (m, 1H), 2.17 (d, J=2.0 Hz, 2H), 1.98 (d, J=12.4 Hz, 1H), 1.59-1.55 (m, 1H).

Step 5: Preparation of (S)—N-(2-((4-(3-(3-(methoxymethyl)piperidin-1-yl)phenyl)thiazol-2-yl) amino)-2-oxoethyl)-1-(methylsulfonyl)-1H-pyrrole-3-carboxamide (Compound 92)

Compound 92

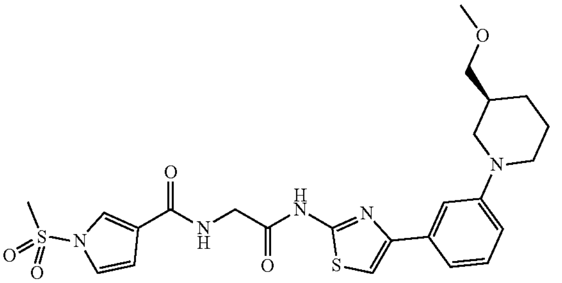

To a solution of 1-methylsulfonylpyrrole-3-carboxylic acid [prepared according to the method in Example 4] (25.17 mg, 133.02 μmol) in DCM (0.5 mL) was added EDCI (34.77 mg, 181.39 μmol), HOBt (24.51 mg, 181.39 μmol), DIPEA (62.52 mg, 483.71 μmol, 84.25 μL) at 25° C. After additional, the mixture was stirred at this temperature for 30 min, and then Intermediate F (43.59 mg, 120.93 μmol, HCl salt) was added at 25° C. The resulting mixture was stirred for another 2 h. The reaction mixture was diluted with water (5 mL) and extracted with DCM (3 mL×3). The combined organic layers were washed with $NH_4Cl$ (5 mL), dried over $Na_2SO_4$, filtered and concentrated under reduced pressure to give a residue. The residue was purified by column chromatography ($SiO_2$, Petroleum ether/EtOAc=6/1 to 3:1) and concentrated to give Compound 92 (25 mg, 47.02 μmol, 38.89% yield) as a yellow solid. LCMS (ESI) m/z $[M+H]^+$= 532.2; $^{1}$H NMR (400 MHz, Methanol-$d_4$) δ 7.86 (s, 1H), 7.57 (s, 1H), 7.36-7.34 (m, 2H), 7.30-7.24 (m, 2H), 6.96-6.94 (m, 1H), 6.83-6.82 (m, 1H), 4.27 (s, 2H), 3.78-3.71 (m, 1H), 3.64 (d, J=12.0 Hz, 1H), 3.39 (s, 3H), 3.39-3.36 (m, 5H), 2.75-2.73 (m, 1H), 2.57-2.51 (m, 1H), 2.04-2.02 (m, 1H), 1.84-1.81 (m, 2H), 1.78-1.67 (m, 1H), 1.22-1.18 (m, 1H); ee %=84.67%.

Example 91. Preparation of N-(2-((4-(3-(4-methyl-1H-imidazol-1-yl)phenyl)thiazol-2-yl)amino)-2-oxoethyl)-1-(methylsulfonyl)-1H-pyrrole-3-carboxamide (Compound 93)

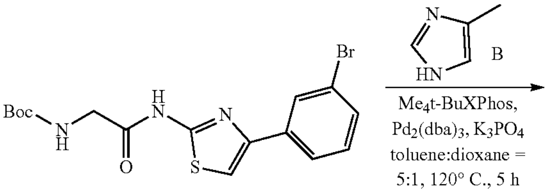

A

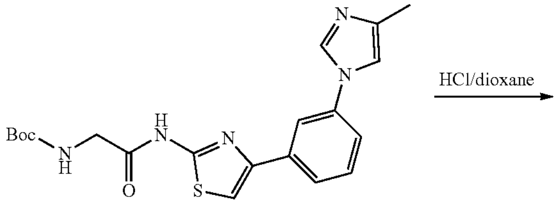

C

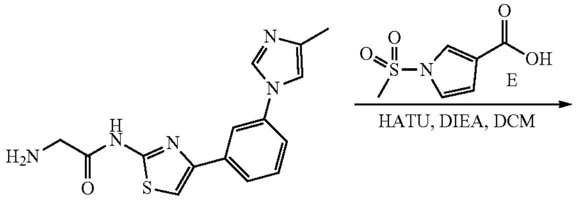

D

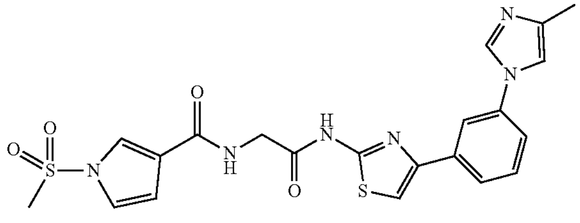

Compound 93

Step 1: Preparation of tert-butyl (2-((4-(3-(4-methyl-1H-imidazol-1-yl)phenyl)thiazol-2-yl)amino)-2-oxoethyl)carbamate (Intermediate C)

C

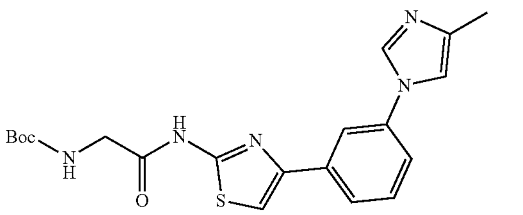

A mixture of $Pd_2(dba)_3$ (41.84 mg, 72.76 μmol), ditert-butyl-[2,3,4,5-tetramethyl-6-(2,4,6-triisopropylphenyl)phenyl]phosphane (69.96 mg, 145.52 μmol) in toluene (3 mL) and dioxane (0.6 mL) was degassed and purged with $N_2$ for 3 times, and then the mixture was stirred at 120° C. for 3 min under $N_2$ atmosphere. Then tert-butyl N-[2-[[4-(3-bromophenyl)thiazol-2-yl]amino]-2-oxo-ethyl]carbamate [prepared according to the method in Example 1] (300 mg, 727.62 μmol), 4-methyl-1H-imidazole (71.69 mg, 873.15 μmol) and $K_3PO_4$ (308.90 mg, 1.46 mmol) was added and stirred at 120° C. for 5 h. The reaction mixture was filtered and filtrate was evaporated to dryness. The residue was purified by Prep-HPLC (basic condition) and lyophilized to give Intermediate C (210 mg, 507.87 μmol, 69.80% yield) as a yellow solid. LCMS (ESI) m/z $[M+H]^+$=414.3.

Step 2: Preparation of 2-amino-N-(4-(3-(4-methyl-1H-imidazol-1-yl)phenyl)thiazol-2-yl)acetamide (Intermediate D)

D

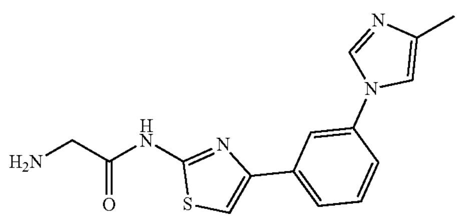

Intermediate C (100 mg, 241.84 μmol) was dissolved in HCl/dioxane (1 mL). The mixture was stirred at 30° C. for 1 hr. The mixture was evaporated to dryness and to give Intermediate D (75 mg, 214.39 μmol, 88.65% yield, HCl salt) as yellow solid, which was used for the next step directly. LCMS (ESI) m/z $[M+H]^+$=314.3.

Step 3: Preparation of N-(2-((4-(3-(4-methyl-1H-imidazol-1-yl)phenyl)thiazol-2-yl)amino)-2-oxoethyl)-1-(methylsulfonyl)-1H-pyrrole-3-carboxamide (Compound 93)

Compound 93

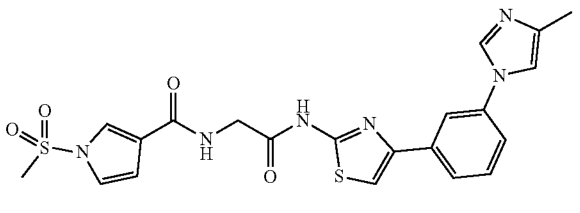

To a mixture of 1-methylsulfonylpyrrole-3-carboxylic acid [prepared according to the method in Example 4] (40.56 mg, 214.39 μmol) in DCM (1 mL) was added HATU (108.69 mg, 285.85 μmol) and DIPEA (110.83 mg, 857.54 μmol, 149.37 μL). The mixture was stirred at 30° C. for 15 min, then Intermediate D (50 mg, 142.92 μmol, HCl salt) was added and stirred at 30° C. for 1 hours. The reaction mixture was evaporated to dryness. To the residue was added MeOH (5 mL) and stirred for 10 min, the precipitate was collected by filtration and washed with MeOH (3 mL) and dried in vacuum to give Compound 93 (43.71 mg, 87.05 μmol, 60.91% yield) as yellow solid. LCMS (ESI) m/z $[M+H]^+$=485.3; $^1H$ NMR (400 MHz, DMSO-$d_6$) δ 12.43-12.38 (m, 1H), 8.69-8.66 (m, 1H), 8.18 (d, J=1.2 Hz, 1H), 8.06 (d, J=1.2 Hz, 1H), 7.87-7.83 (m, 3H), 7.55-7.54 (m, 2H), 7.48 (s, 1H), 7.32-7.30 (m, 1H), 6.78-6.76 (m, 1H), 4.15 (d, J=6.0 Hz, 2H), 3.57 (s, 3H), 2.18 (s, 3H).

Example 92. Preparation of N-(2-((4-(3-(4-hydroxypiperidin-1-yl)phenyl)thiazol-2-yl)amino)-2-oxoethyl)-1-(methylsulfonyl)-1H-pyrrole-3-carboxamide (Compound 94)

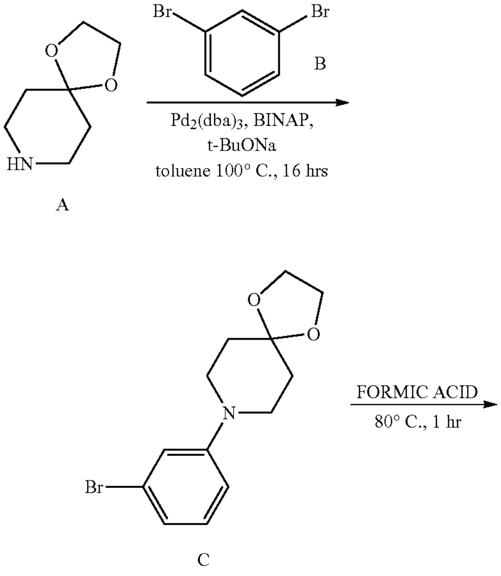

-continued

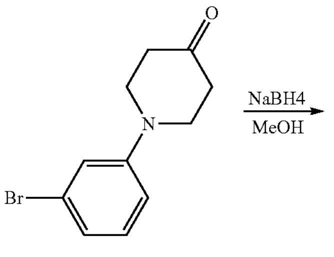

D

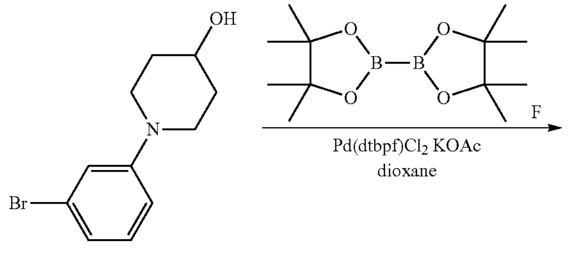

E

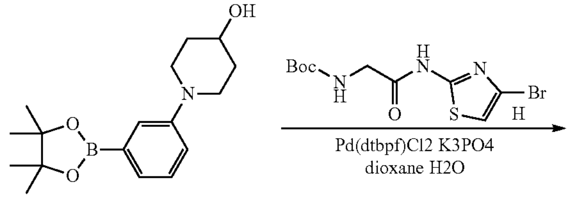

G

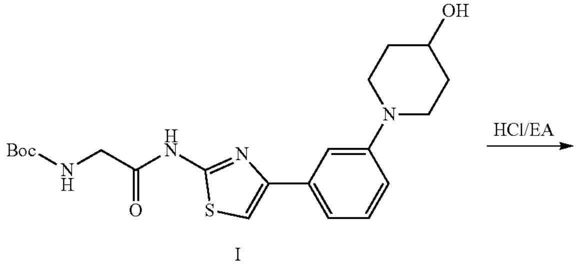

I

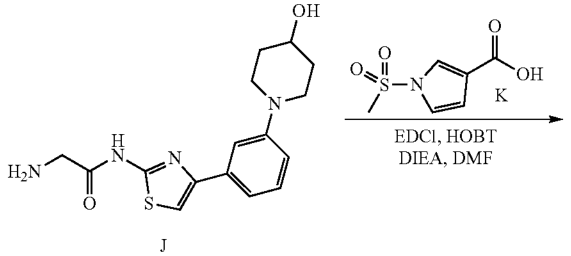

J

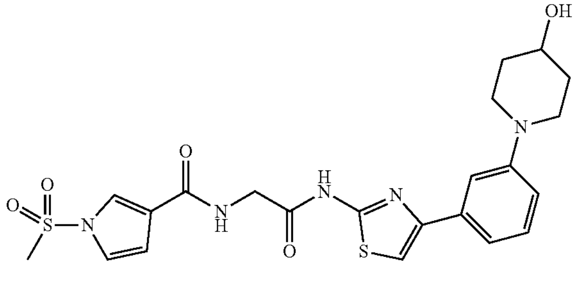

Compound 94

Step 1: Preparation of 8-(3-bromophenyl)-1,4-dioxa-8-azaspiro[4.5]decane (Intermediate C)

C

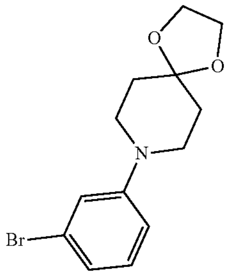

To a solution of 1,3-dibromobenzene (2 g, 8.48 mmol, 1.02 mL), 1,4-dioxa-8-azaspiro[4.5]decane (1.21 g, 8.48 mmol, 1.08 mL), t-BuONa (2.44 g, 25.43 mmol), BINAP (1.06 g, 1.70 mmol) in toluene (30 mL) was added $Pd_2(dba)_3$ (776.35 mg, 847.80 μmol). Then the mixture was stirred at 90° C. for 2 h under $N_2$. The reaction mixture was concentrated in vacuum. The residue was purified by column chromatography ($SiO_2$, PE:EtOAc=10:1 to 5:1) and concentrated to give Intermediate C (850 mg, 2.53 mmol, 29.86% yield) as yellow oil. LCMS (ESI) m/z $[M+H]^+$=298.0.

Step 2: Preparation of 1-(3-bromophenyl)piperidin-4-one (Intermediate D)

D

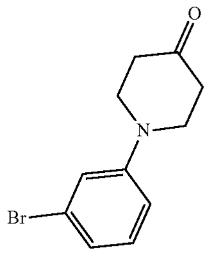

A solution of Intermediate C (800 mg, 2.68 mmol) in formic acid (10 mL) was stirred at 80° C. for 1 h. The reaction mixture was poured into water (20 mL) and extracted with EtOAc (20 mL×2), the organic layer was washed with brine (20 mL) and dried over $Na_2SO_4$ and concentrated. The crude product was purified by reverse phase column (FA) and lyophilized to give Intermediate D (550 mg, 2.16 mmol, 80.67% yield) as yellow oil. LCMS (ESI) m/z $[M+H]^+$=255.9.

Step 3: Preparation of 1-(3-bromophenyl)piperidin-4-ol (Intermediate E)

E

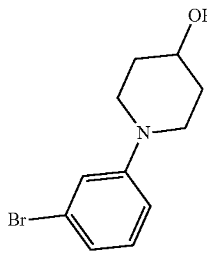

To a solution of Intermediate D (400 mg, 1.57 mmol) in MeOH (5 mL) was added $NaBH_4$ (89.33 mg, 2.36 mmol). Then the mixture was stirred at 25° C. for 0.5 h. The reaction mixture was poured into water (10 mL) and extracted with EtOAc (10 mL×2), the organic layer was washed with brine (10 mL) and dried over $Na_2SO_4$ and concentrated in vacuum to give Intermediate E (350 mg, 1.36 mmol, 86.12% yield) as yellow oil, which was used for next step without further purification. LCMS (ESI) m/z $[M+H]^+$=258.0.

Step 4: Preparation of 1-(3-(4,4,5,5-tetramethyl-1,3,2-dioxaborolan-2-yl)phenyl)piperidin-4-ol (Intermediate G)

G

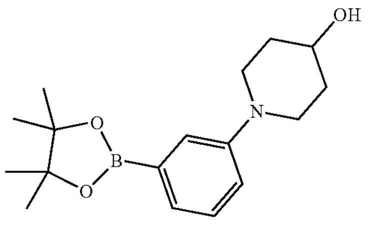

To a solution of Intermediate E (350 mg, 1.37 mmol), 4,4,4',4',5,5,5',5'-octamethyl-2,2'-bi(1,3,2-dioxaborolane) (693.99 mg, 2.73 mmol), KOAc (402.32 mg, 4.10 mmol) in dioxane (5 mL) was added [1,1'-bis(di-tert-butylphosphino)ferrocene]dichloropalladium(II) (89.06 mg, 136.64 μmol). Then the mixture was stirred at 70° C. for 1 h under $N_2$. The reaction mixture was concentrated to give the Intermediate G (400 mg, 790.23 μmol, 57.83% yield) as yellow oil, which was used for next step without further purification. LCMS (ESI) m/z $[M+H]^+$=304.1.

Step 5: Preparation of tert-butyl (2-((4-(3-(4-hydroxypiperidin-1-yl)phenyl)thiazol-2-yl)amino)-2-oxoethyl)carbamate (Intermediate I)

I

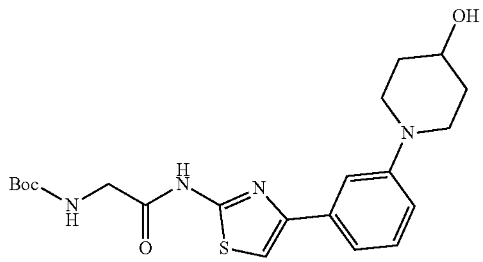

To a solution of tert-butyl (2-((4-bromothiazol-2-yl)amino)-2-oxoethyl)carbamate [prepared according to the method in Example 6] (100 mg, 297.44 μmol), Intermediate G (165.61 mg, 327.18 μmol), $K_3PO_4$ (189.41 mg, 892.31 μmol) in dioxane (1 mL) and $H_2O$ (0.2 mL) was added [1,1'-bis(di-tert-butylphosphino)ferrocene]dichloropalladium(II) (19.39 mg, 29.74 μmol). Then the mixture was stirred at 70° C. for 1 h under $N_2$. The reaction mixture was concentrated to get the crude product. The crude product was purified by Prep-HPLC (FA) and lyophilized to give Intermediate I (120 mg, 252.74 μmol, 84.97% yield) as a yellow solid. LCMS (ESI) m/z $[M+H]^+$=433.1.

Step 6: Preparation of 2-amino-N-(4-(3-(4-hydroxypiperidin-1-yl)phenyl)thiazol-2-yl)acetamide (Intermediate J)

J

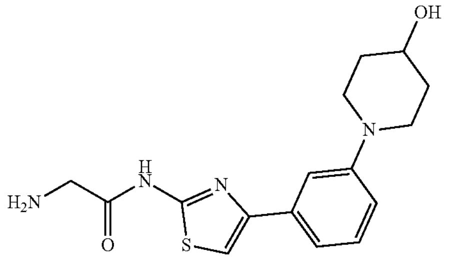

A solution of Intermediate I (120 mg, 277.43 μmol) in HCl/EtOAc (2 mL) was stirred at 25° C. for 1 h. The reaction mixture was concentrated to give the crude product. The crude product was triturated with PE:EA=1:1 (10 mL) at 25° C. for 30 min, then filtered and dried in vacuum to give Intermediate J (85 mg, 193.70 μmol, 69.82% yield, HCl salt) as a white solid. LCMS (ESI) m/z$[M+H]^+$=333.1.

Step 7: Preparation of N-(2-((4-(3-(4-hydroxypiperidin-1-yl)phenyl)thiazol-2-yl)amino)-2-oxoethyl)-1-(methylsulfonyl)-1H-pyrrole-3-carboxamide (Compound 94)

Compound 94

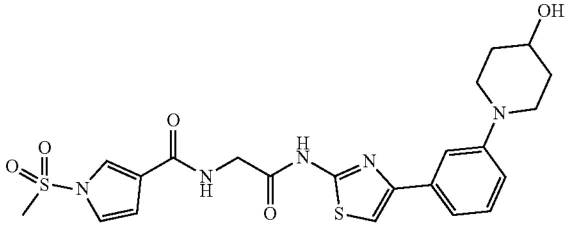

To a solution of Intermediate J (80 mg, 216.87 μmol, HCl salt), 1-methylsulfonylpyrrole-3-carboxylic acid [prepared according to the method in Example 4] (45.13 mg, 238.56 μmol), EDCI (83.15 mg, 433.74 μmol), HOBt (58.61 mg, 433.74 μmol) in DMF (2 mL) was added DIEA (140.15 mg, 1.08 mmol, 188.88 μL). Then the mixture was stirred at 25° C. for 1 h. The reaction mixture was concentrated to get the crude product. The crude product was purified by reverse phase ($NH_4OH$) and lyophilized to give Compound 94 (53.77 mg, 106.77 μmol, 49.23% yield) as a yellow solid. LCMS (ESI) m/z $[M+H]^+$=504.2. $^1H$ NMR (400 MHz, DMSO-$d_6$) δ 12.38 (s, 1H), 8.69-8.67 (m, 1H), 7.86-7.84 (m, 1H), 7.61 (s, 1H), 7.47 (s, 1H), 7.33-7.31 (m, 1H), 7.30-7.21 (m, 2H), 6.91-6.90 (m, 1H), 6.79-6.78 (m, 1H), 4.70 (d, J=4.4 Hz, 1H), 4.14 (d, J=6.0 Hz, 2H), 3.70-3.62 (m, 1H), 3.61-3.52 (m, 5H), 2.96-2.82 (m, 2H), 1.93-1.78 (m, 2H), 1.55-1.42 (m, 2H).

Example 93. Preparation of N-[2-[[4-[3-(4-methoxy-1-piperidyl)phenyl]thiazol-2-yl]amino]-2-oxo-ethyl]-1-methylsulfonyl-pyrrole-3-carboxamide (Compound 95)

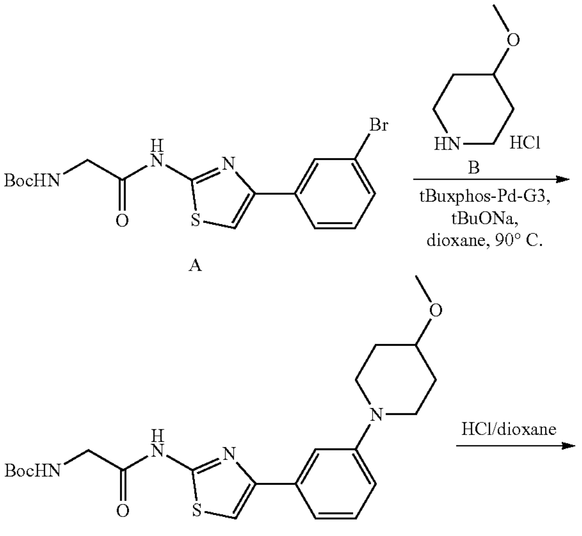

-continued

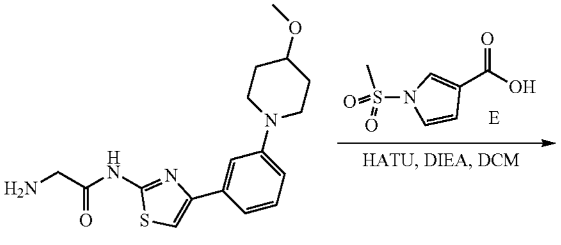

D

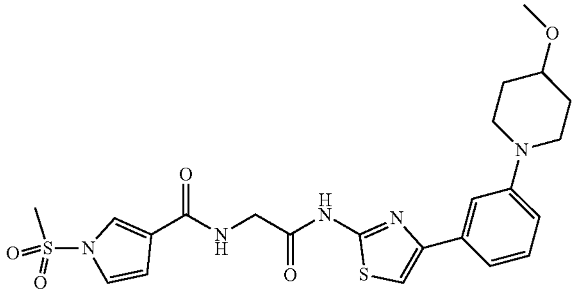

Compound 95

Step 1: Preparation of tert-butyl N-[2-[[4-[3-(4-methoxy-1-piperidyl)phenyl]thiazol-2-yl]amino]-2-oxo-ethyl]carbamate (Intermediate C)

C

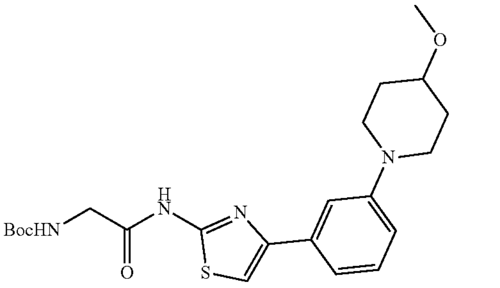

To a solution of tert-butyl N-[2-[[4-(3-bromophenyl)thiazol-2-yl]amino]-2-oxo-ethyl]carbamate [prepared according to the method in Example 1] (200 mg, 485.08 μmol) and 4-methoxypiperidine (88.27 mg, 582.10 μmol) in dioxane (10 mL) was added t-BuONa (186.47 mg, 1.94 mmol), then the mixture was degassed for three times and then[2-(2-aminophenyl)phenyl]-methylsulfonyloxy-palladium; ditert-butyl-[2-(2,4,6-triisopropylphenyl)phenyl]phosphane (38.53 mg, 48.51 μmol) was added. The mixture was stirred at 90° C. for 6 h. The reaction solution was concentrated in vacuum. The residue was purified through column chromatography ($SiO_2$, PE/EtOAc=10/1-1/1) and concentrated to give Intermediate C (140 mg, 313.51 μmol, 64.63% yield) as yellow oil, which was used for the next step directly. LCMS (ESI) m/z $[M+H]^+$=447.2.

Step 2: Preparation of 2-amino-N-[4-[3-(4-methoxy-1-piperidyl)phenyl]thiazol-2-yl]acetamide (Intermediate D)

D

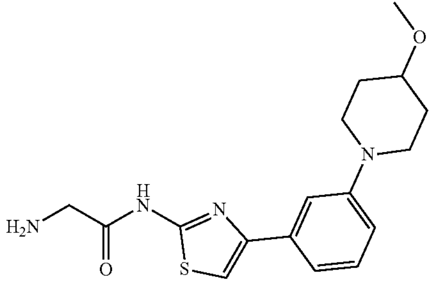

To a solution of Intermediate C (140 mg, 313.51 μmol) in dioxane (10 mL) was added HCl/dioxane (4 M, 10 mL), then the solution was stirred at 25° C. for 0.5 h. The reaction solution was concentrated in vacuum. The residue was washed with MTBE and dried in vacuum to give Intermediate D (120 mg, 313.39 μmol, 99.96% yield, HCl salt) as a white solid. LCMS (ESI) m/z $[M+H]^+$=347.2.

Step 3: Preparation of N-[2-[[4-[3-(4-methoxy-1-piperidyl)phenyl]thiazol-2-yl]amino]-2-oxo-ethyl]-1-methylsulfonyl-pyrrole-3-carboxamide (Compound 95)

Compound 95

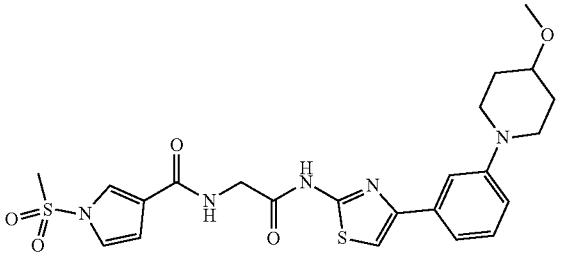

To a mixture of Intermediate D (60 mg, 156.70 μmol) and 1-methylsulfonylpyrrole-3-carboxylic acid [prepared according to the method in Example 4] (29.65 mg, 156.70 μmol) in DCM (4 mL) was added DIPEA (81.01 mg, 626.78 μmol), then HATU (77.45 mg, 203.70 μmol) was added. The solution was stirred at 25° C. for 12 h. The reaction solution was concentrated in vacuum. The residue was purified through reversed phase ($CH_3CN/H_2O$: 0%~60%, FA) and lyophilized to give Compound 95 (22 mg, 39.03 μmol, 24.91% yield, FA salt) as a white solid. LCMS (ESI) m/z $[M+H]^+$=518.2; $^1H$ NMR (400 MHz, DMSO-d6) δ 12.28 (s, 1H), 8.68-8.67 (m, 1H), 7.85-7.84 (m, 1H), 7.60 (s, 1H), 7.47 (s, 1H), 7.31-7.24 (m, 3H), 6.95-6.85 (m, 1H), 6.78-6.77 (m, 1H), 4.14 (d, J=5.6 Hz, 2H), 3.57-3.53 (m, 5H), 3.31-3.30 (m, 1H), 3.28 (s, 3H), 2.96-2.90 (m, 2H), 1.97-1.94 (m, 2H), 1.54-1.49 (m, 2H).

Example 94. Preparation of N-(2-((4-(3-(4-methoxy-4-methylpiperidin-1-yl)phenyl)thiazol-2-yl)amino)-2-oxoethyl)-1-(methylsulfonyl)-1H-pyrrole-3-carboxamide (Compound 96)

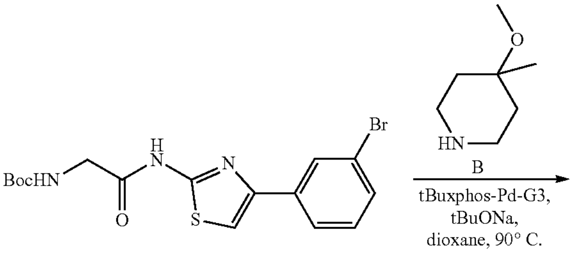

A

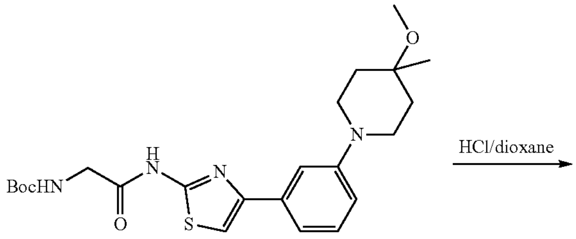

C

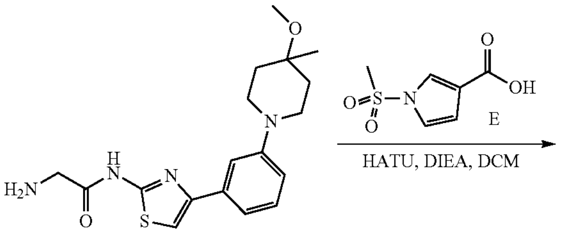

D

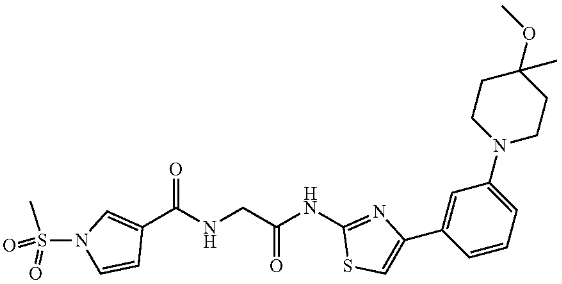

Compound 96

Step 1: Preparation of tert-butyl (2-((4-(3-(4-methoxy-4-methylpiperidin-1-yl)phenyl)thiazol-2-yl)amino)-2-oxoethyl)carbamate (Intermediate C)

C

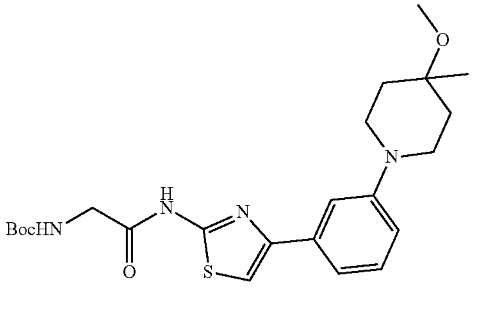

To a mixture of tert-butyl N-[2-[[4-(3-bromophenyl)thiazol-2-yl]amino]-2-oxo-ethyl]carbamate [prepared according to the method in Example 1] (500 mg, 1.21 mmol), 4-methoxy-4-methyl-piperidine (301.35 mg, 1.82 mmol, HCl salt) in dioxane (10 mL) was added t-BuONa (582.71 mg, 6.06 mmol) and [2-(2-aminophenyl)phenyl]-methylsulfonyloxy-palladium; ditert-butyl-[2-(2,4,6-triisopropylphenyl)phenyl]phosphane (96.33 mg, 121.27 μmol). The mixture was stirred at 70° C. for 2 h under protect of $N_2$. The mixture was poured into water (100 mL) and extracted with EtOAc (10 mL×3). The combined organic layer was washed with water (10 mL×3) and brine (10 mL×2), then dried over $Na_2SO_4$, filtered and concentrated under vacuum. The residue was purified by column chromatography ($SiO_2$, PE:EtOAc=10:1~1:1) and concentrated to give a crude product. The crude product was purified by Pre-TLC (PE:EA=2:1, Rf=0.4) to give Intermediate C (100 mg, 155.45 μmol, 12.82% yield) as yellow solid. LCMS (ESI) m/z $[M+H]^+$=461.3.

Step 2: Preparation of 2-amino-N-(4-(3-(4-methoxy-4-methylpiperidin-1-yl)phenyl)thiazol-2-yl)acetamide (Intermediate D)

D

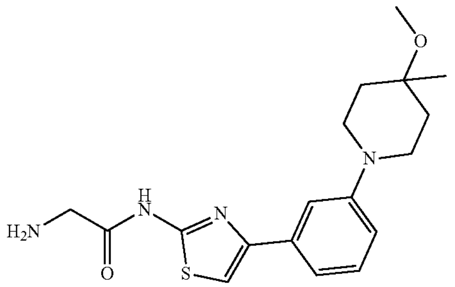

A mixture of Intermediate C (90 mg, 138.74 μmol) in HCl/dioxane (4 M, 2 mL) was stirred at 30° C. for 2 h. The mixture was diluted with DCM (20 mL) and concentrated under vacuum. This operation was repeated three times. The residue was washed by MTBE (5 mL×2) and concentrated in vacuum to give Intermediate D (60 mg, crude, HCl salt) as a yellow solid, which was used to next step directly. LCMS (ESI) m/z $[M+H]^+$=361.1.

Step 3: Preparation of N-(2-((4-(3-(4-methoxy-4-methylpiperidin-1-yl)phenyl)thiazol-2-yl)amino)-2-oxoethyl)-1-(methylsulfonyl)-1H-pyrrole-3-carboxamide (Compound 96)

Compound 96

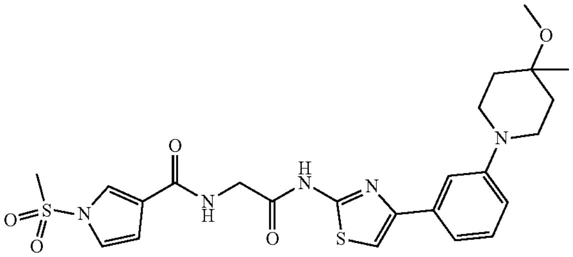

To a solution of 1-methylsulfonylpyrrole-3-carboxylic acid [prepared according to the method in Example 4] (26.21 mg, 138.56 μmol) in DCM (5 mL) was added HATU (71.84 mg, 188.95 μmol) and DIEA (48.84 mg, 377.90 μmol, 65.82 μL). Then Intermediate D (50 mg, 125.97 μmol, HCl salt) was added and the mixture was stirred at 30° C. for 2 h. The mixture was poured into water (50 mL) and extracted with DCM (10 mL×3). The combined organic layer was washed with water (10 mL×3) and brine (10 mL×2), then dried over $Na_2SO_4$, filtered and concentrated under vacuum. The residue was purified by reverse phase flash (FA condition) and lyophilized to give Compound 96 (18.34 mg, 30.99 μmol, 24.60% yield, FA salt) as an off-white solid. LCMS (ESI) m/z $[M+H]^+$=532.2; $^1H$ NMR (400 MHz, DMSO-$d_6$) δ 12.35 (s, 1H), 8.68-8.65 (m, 1H), 8.14 (s, 1H), 7.86-7.83 (m, 1H), 7.60 (s, 1H), 7.48 (s, 1H), 7.34-7.21 (m, 3H), 6.91 (d, J=8.0 Hz, 1H), 6.78-6.77 (m, 1H), 4.14 (d, J=5.6 Hz, 2H), 3.57 (s, 3H), 3.37 (s, 2H), 3.14 (s, 3H), 3.10-3.01 (m, 2H), 1.79 (d, J=13.2 Hz, 2H), 1.66-1.53 (m, 2H), 1.15 (s, 3H).

Example 95. Preparation of (R)-1-(tert-butyl)-N-(2-((4-(3-(3-methoxypiperidin-1-yl)phenyl)thiazol-2-yl)amino)-2-oxoethyl)-1H-pyrrole-3-carboxamide (Compound 97)

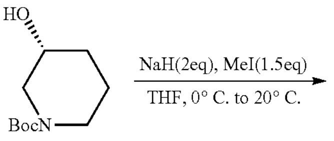

A

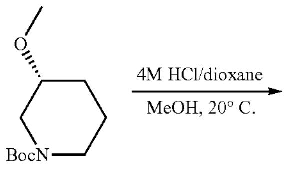

B

-continued

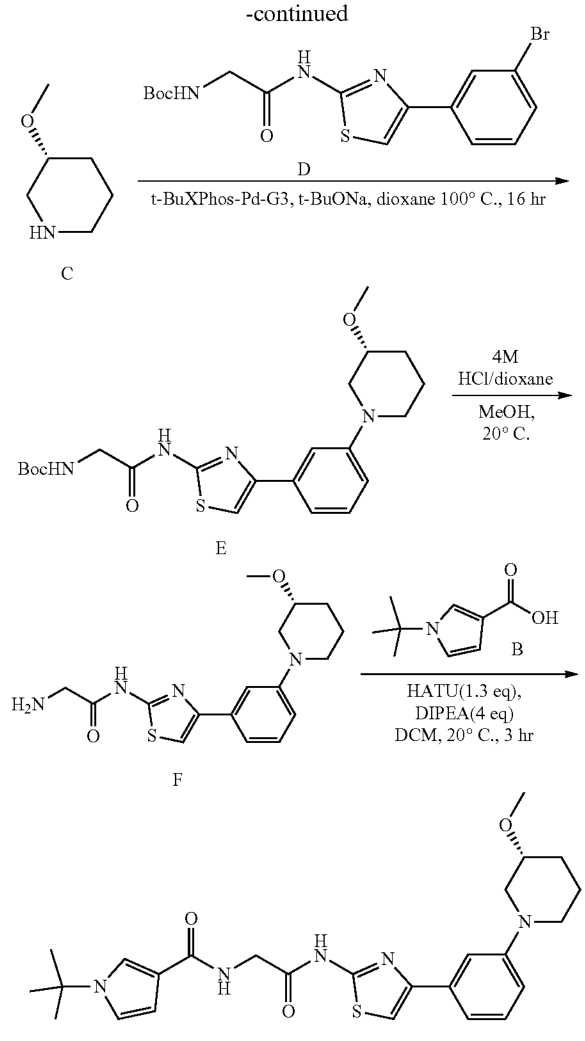

Compound 97

Step 1: Preparation of (R)-tert-butyl 3-methoxypiperidine-1-carboxylate (Intermediate B)

B

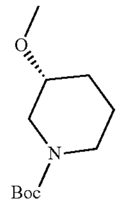

To a solution of tert-butyl (3R)-3-hydroxypiperidine-1-carboxylate (1 g, 4.97 mmol) in THF (5 mL) was added NaH (397.49 mg, 9.94 mmol, 60% purity) at 0° C. The mixture was stirred at 0° C. for 30 min. Iodomethane (1.06 g, 7.45 mmol, 463.97 μL) was added and the mixture was stirred at 20° C. for 16 h. The reaction mixture was quenched by addition Sat. $NH_4Cl$ solution (15 mL), and then extracted with EtOAc (10 mL×5). The combined organic layers were washed with brine (10 mL×3), dried over $Na_2SO_4$, filtered and concentrated under reduced pressure to give Intermediate B (0.9 g, 4.18 mmol, 84.14% yield) as yellow oil. $^1H$ NMR (400 MHz, $CDCl_3$) δ 4.02-3.68 (m, 1H), 3.66-3.56 (m, 1H), 3.40 (s, 3H), 3.23-3.21 (m, 1H), 3.07 (br s, 2H), 2.02-1.91 (m, 1H), 1.81-1.70 (m, 1H), 1.53-1.39 (m, 1OH), 0.95-0.84 (m, 1H).

Step 2: Preparation of (R)-3-methoxypiperidine (Intermediate C)

C

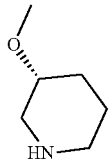

To a solution of Intermediate B (0.8 g, 3.72 mmol) in MeOH (1 mL) was added HCl/dioxane (4 M, 8.00 mL). The mixture was stirred at 20° C. for 30 min. The reaction mixture was concentrated to give Intermediate C (0.6 g, crude, HCl salt) as yellow solid, which was used in next step without further purification.

Step 3: Preparation of (R)-tert-butyl (2-((4-(3-(3-methoxypiperidin-1-yl)phenyl)thiazol-2-yl)amino)-2-oxoethyl)carbamate (Intermediate E)

E

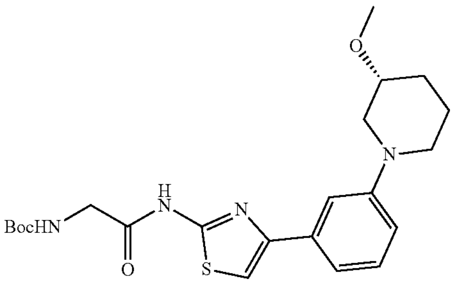

A mixture of tert-butyl N-[2-[[4-(3-bromophenyl)thiazol-2-yl]amino]-2-oxo-ethyl]carbamate [prepared according to the method in Example 1] (200 mg, 485.08 μmol), Intermediate C (88.27 mg, 582.10 μmol, HCl salt), t-BuONa (233.08 mg, 2.43 mmol) and t-BuXPhos Pd G3 (38.53 mg, 48.51 μmol) in dioxane (5 mL) was degassed and purged with $N_2$ for 3 times, and then the mixture was stirred at 100° C. for 16 h under $N_2$ atmosphere. The reaction mixture was concentrated to give a residue. The residue was purified by column chromatography ($SiO_2$, Petroleum ether/EtOAc=1/1) to afford Intermediate E (130 mg, 291.11 μmol, 60.01% yield) as yellow oil. LCMS (ESI) m/z $[M+H]^+$=447.5.

Step 4: Preparation of (R)-2-amino-N-(4-(3-(3-methoxypiperidin-1-yl)phenyl)thiazol-2-yl)acetamide (Intermediate F)

F

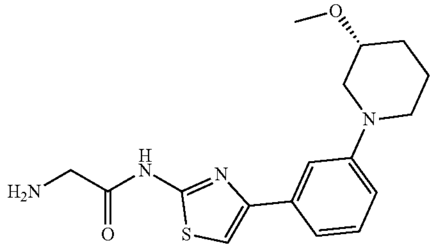

To a solution of Intermediate E (0.12 g, 268.72 μmol) in MeOH (1 mL) was added HCl/dioxane (4 M, 578.42 μL). The mixture was stirred at 20° C. for 30 min. The reaction mixture was concentrated to give Intermediate F (125 mg, crude, HCl salt) as yellow solid, which was used in next step without further purification. LCMS (ESI) m/z $[M+H]^+$=347.0.

Step 5: Preparation of (R)-1-(tert-butyl)-N-(2-((4-(3-(3-methoxypiperidin-1-yl)phenyl)thiazol-2-yl)amino)-2-oxoethyl)-1H-pyrrole-3-carboxamide (Compound 97)

Compound 97

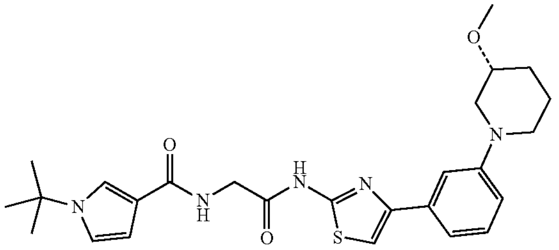

To a solution of 1-tert-butylpyrrole-3-carboxylic acid [prepared according to the method in Example 34] (31.44 mg, 188.04 μmol) in DCM (2 mL) was added 2-amino-N-[4-[3-[(3R)-3-methoxy-1-piperidyl]phenyl]thiazol-2-yl]acetamide (60 mg, 156.70 μmol, HCl salt), DIPEA (81.01 mg, 626.80 μmol, 109.17 μL) and HATU (89.37 mg, 235.05 μmol). The mixture was stirred at 20° C. for 2 h. The reaction mixture was concentrated to dryness to give a residue. The residue was purified by Prep-TLC ($SiO_2$, Petroleum ether/EtOAc=1/1) to give the crude product. The crude product was further purified by Prep-HPLC (mobile phase: [water (0.1% TFA)-acetonitrile]; B %: 25%-45%) and lyophilized to afford Compound 97 (6.38 mg, 10.46 μmol, 6.68% yield, TFA salt) as a white solid. LCMS (ESI) m/z $[M+H]^+$=496.1; $^1H$ NMR (400 MHz, DMSO-$d_6$) δ 12.28 (s, 1H), 8.17-8.15 (m, 1H), 7.61 (s, 1H), 7.55-7.46 (m, 2H), 7.40-7.20 (m, 2H), 6.98-6.96 (m, 2H), 6.48 (dd, J=2.8 Hz, 2.0 Hz, 1H), 4.10-4.08 (m, 2H), 3.70-3.68 (m, 1H), 3.41-3.39 (m, 2H), 3.33 (s, 3H), 2.85-2.83 (m, 1H), 2.77-2.75 (m, 1H), 2.02-2.00 (m, 1H), 1.82-1.80 (m, 1H), 1.60-1.58 (m, 1H), 1.50 (s, 9H), 1.38-1.36 (m, 1H); ee %=100%.

Example 96. Preparation of (S)-1-(tert-butyl)-N-(2-((4-(3-(3-methoxypiperidin-1-yl)phenyl)thiazol-2-yl)amino)-2-oxoethyl)-1H-pyrrole-3-carboxamide (Compound 98)

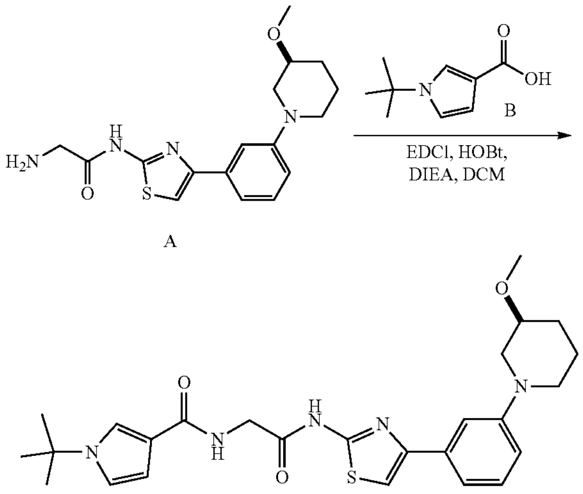

Compound 98

To a solution of 2-amino-N-[4-[3-[(3S)-3-methoxy-1-piperidyl]phenyl]thiazol-2-yl]acetamide (prepared according to the method in Example 11) (120 mg, 313.39 μmol, HCl salt), 1-tert-butylpyrrole-3-carboxylic acid [prepared according to the method in Example 34] (78.60 mg, 470.09 μmol) and DIEA (202.51 mg, 1.57 mmol, 272.93 μL) in DCM (0.5 mL) was added HOBt (50.81 mg, 376.07 μmol) and EDCI (180.23 mg, 940.18 μmol), the reaction mixture was stirred at 25° C. for 2 h. The reaction mixture was concentrated under vacuum to give residue. The residue was purified by Pre-HPLC (mobile phase: [water (0.1% TFA)-acetonitrile]; B %: 21%-51%) and lyophilized to give Compound 98 (78.98 mg, 129.55 μmol, 41.34% yield, TFA salt) as a white solid. LCMS (ESI) m/z $[M+H]^+$=496.5; $^1H$ NMR (400 MHz, Methanol-$d_4$) δ 8.09 (s, 1H), 7.97 (d, J=8.0 Hz, 1H), 7.61-7.53 (m, 3H), 7.50 (d, J=8.0 Hz, 1H), 6.97-6.95 (m, 1H), 6.58-6.56 (m, 1H), 4.23 (s, 2H), 3.81-3.69 (m, 3H), 3.48 (d, J=0.6 Hz, 5H), 2.25-2.23 (m, 1H), 2.08-1.96 (m, 1H), 1.95-1.84 (m, 2H), 1.57 (d, J=0.8 Hz, 9H); ee %=100%.

Example 97. Preparation of N-[2-[[4-[3-(4-methoxy-1-piperidyl)phenyl]thiazol-2-yl]amino]-2-oxo-ethyl]-1-methylsulfonyl-pyrrole-3-carboxamide (Compound 99)

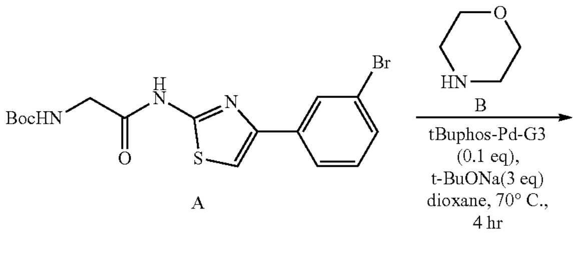

-continued

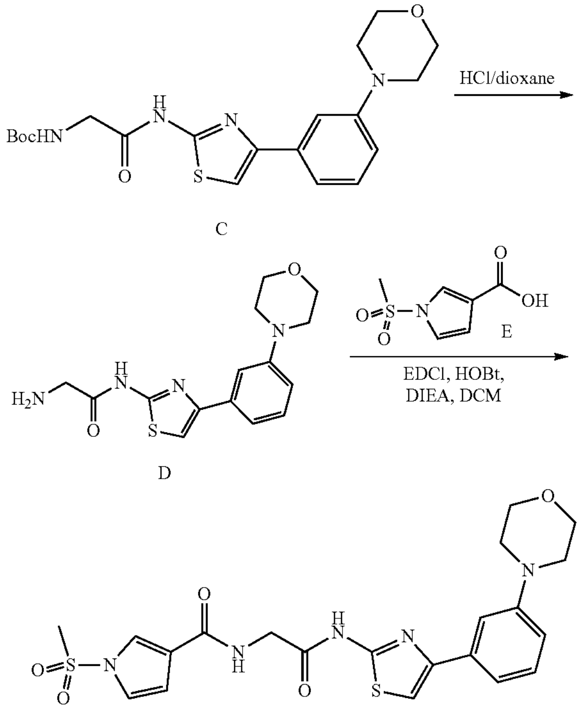

C

D

Compound 99

Step 1: Preparation of tert-butyl N-[2-[[4-(3-morpholinophenyl)thiazol-2-yl]amino]-2-oxo-ethyl]carbamate (Intermediate C)

C

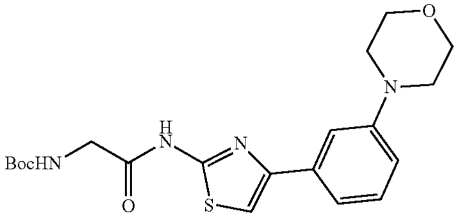

To a solution of tert-butyl N-[2-[[4-(3-bromophenyl)thiazol-2-yl]amino]-2-oxo-ethyl]carbamate [prepared according to the method in Example 1] (400 mg, 970.17 μmol) and morpholine (126.78 mg, 1.46 mmol) in tert-amylalcohol (8 mL) was added t-BuONa (372.95 mg, 3.88 mmol), then [2-(2-aminophenyl)phenyl]-methylsulfonyloxy-palladium; ditert-butyl-[2-(2,4,6-triisopropylphenyl)phenyl]phosphane (154.13 mg, 194.03 μmol) was added and the mixture was degassed for three times. The solution was stirred at 70° C. for 4 h. The reaction solution was poured into aq. $NH_4Cl$ (100 mL) and then extracted with EtOAc (200 mL). The organic layer was washed with brine (100 mL) and dried. The solution was concentrated in vacuum. The residue was purified through column chromatography ($SiO_2$, PE/EtOAc=5/1-2/1) and concentrated to give Intermediate C (200 mg, 477.89 μmol, 49.26% yield) as a yellow solid. LCMS (ESI) m/z $[M+H]^+$=419.2.

Step 2: Preparation of 2-amino-N-[4-(3-morpholinophenyl)thiazol-2-yl]acetamide (Intermediate D)

D

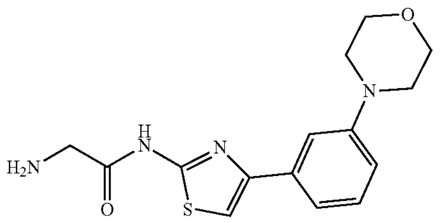

To a solution of Intermediate C (200 mg, 477.89 μmol) in dioxane (5 mL) was added HCl/dioxane (4 M, 10 mL), then the solution was stirred at 25° C. for 1 h. The reaction solution was concentrated in vacuum. The residue was washed with MBTE (50 mL). The solid was dried in vacuum to give Intermediate D (200 mg, crude, 2HCl salt) as a yellow solid, which was used for the next step directly. LCMS (ESI) m/z $[M+H]^+$=319.2.

Step 3: Preparation of 1-methylsulfonyl-N-[2-[[4-(3-morpholinophenyl)thiazol-2-yl]amino]-2-oxo-ethyl]pyrrole-3-carboxamide (Compound 99)

Compound 99

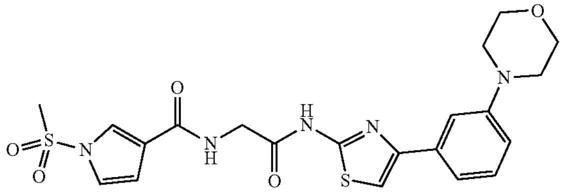

To a solution of Intermediate D (100 mg, 255.55 μmol) and 1-methylsulfonylpyrrole-3-carboxylic acid [prepared according to the method in Example 4] (58.02 mg, 306.66 μmol) in DCM (5 mL) was added DIPEA (165.14 mg, 1.28 mmol), then EDCI (58.79 mg, 306.66 μmol) and HOBt (41.44 mg, 306.66 μmol) were added. The solution was stirred at 25° C. for 12 h. The reaction solution was poured into aq. citric acid (50 mL) and then extracted with EtOAc (100 mL). The organic layer was washed with brine (100 mL) and dried. The solution was concentrated in vacuum. The residue was triturated in MeOH (20 mL) and filtered. The solid was dried in vacuum to give Compound 99 (38 mg, 75.90 μmol, 29.70% yield) as a white solid. LCMS (ESI) m/z $[M+H]^+$=490.1; $^1H$ NMR (400 MHz, DMSO-d6) δ 12.37 (s, 1H), 8.68-8.65 (m, 1H), 7.85-7.84 (m, 1H), 7.61 (s, 1H), 7.47 (s, 1H), 7.35-7.28 (m, 3H), 6.95-6.85 (m, 1H), 6.78-6.77 (m, 1H), 4.14 (d, J=5.6 Hz, 2H), 3.78-3.76 (m, 4H), 3.57 (s, 3H), 3.17-3.14 (m, 4H).

Example 98. Preparation of 1-tert-butyl-N-[2-[[4-(3-morpholinophenyl)thiazol-2-yl]amino]-2-oxo-ethyl]pyrrole-3-carboxamide (Compound 100)

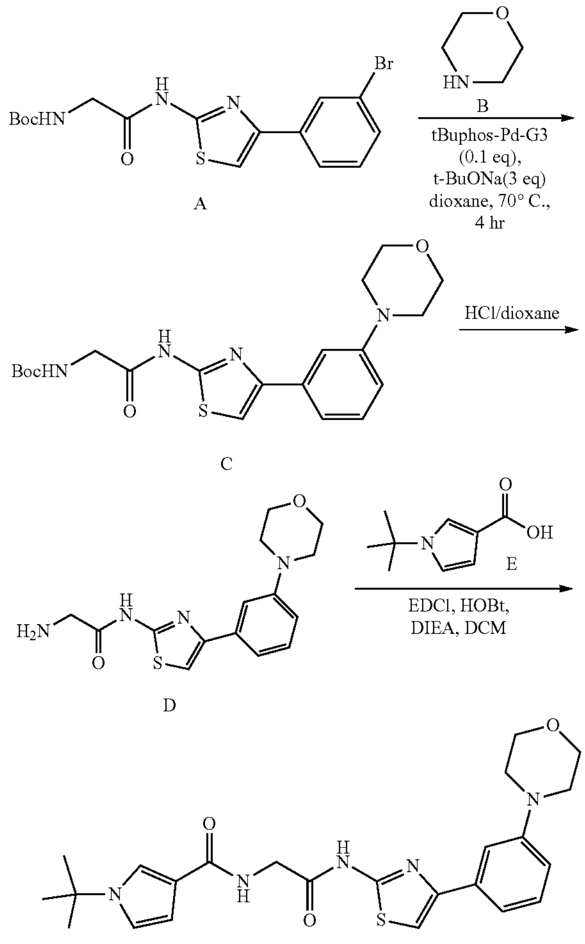

A

C

D

Compound 100

Step 1: Preparation of tert-butyl N-[2-[[4-(3-morpholinophenyl)thiazol-2-yl]amino]-2-oxo-ethyl]carbamate (Intermediate C)

C

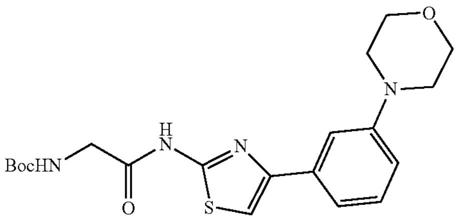

To a solution of tert-butyl N-[2-[[4-(3-bromophenyl)thiazol-2-yl]amino]-2-oxo-ethyl]carbamate [prepared according to the method in Example 1] (400 mg, 970.17 μmol) and morpholine (126.78 mg, 1.46 mmol) in tert-amylalcohol (8 mL) was added t-BuONa (372.95 mg, 3.88 mmol), then [2-(2-aminophenyl)phenyl]-methylsulfonyloxy-palladium; ditert-butyl-[2-(2,4,6-triisopropylphenyl)phenyl]phosphane (154.13 mg, 194.03 μmol) was added and the mixture was degassed for three times. The solution was stirred at 70° C. for 4 h. The reaction solution was poured into aq. $NH_4Cl$ (100 mL) and then extracted with EtOAc (200 mL). The organic layer was washed with brine (100 mL) and dried. The solution was concentrated in vacuum. The residue was purified through column chromatography ($SiO_2$, PE/EtOAc=5/1-2/1) and concentrated to give Intermediate C (200 mg, 477.89 μmol, 49.26% yield) as a yellow solid. LCMS (ESI) m/z $[M+H]^+$=419.2.

Step 2: Preparation of 2-amino-N-[4-(3-morpholinophenyl)thiazol-2-yl]acetamide (Intermediate D)

D

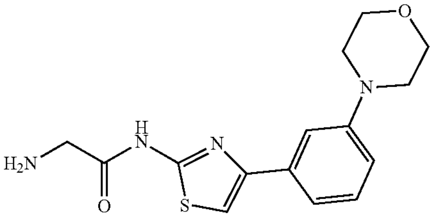

To a solution of Intermediate C (200 mg, 477.89 μmol) in dioxane (5 mL) was added HCl/dioxane (4 M, 10 mL), then the solution was stirred at 25° C. for 1 h. The reaction solution was concentrated in vacuum. The residue was washed with TBME (50 mL). The solid was dried in vacuum to give Intermediate D (200 mg, crude, 2HCl salt) as a yellow solid, which was used for the next step directly. LCMS (ESI) m/z $[M+H]^+$=319.2.

Step 3: Preparation of 1-tert-butyl-N-[2-[[4-(3-morpholinophenyl)thiazol-2-yl]amino]-2-oxo-ethyl]pyrrole-3-carboxamide (Compound 100)

Compound 100

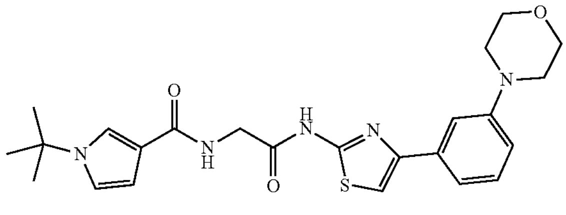

To a solution of Intermediate D (100 mg, 255.55 μmol) and 1-tert-butylpyrrole-3-carboxylic acid [prepared according to the method in Example 34]1-methylsulfonylpyrrole-3-carboxylic acid [prepared according to the method in Example 4] (58.02 mg, 306.66 μmol) in DCM (5 mL) was added DIPEA (165.14 mg, 1.28 mmol), then EDCI (58.79 mg, 306.66 μmol) and HOBt (41.44 mg, 306.66 μmol) were added. The solution was stirred at 25° C. for 12 h. The reaction solution was poured into aq. citric acid (50 mL) and then extracted with EtOAc (100 mL). The organic layer was washed with brine (100 mL) and dried. The solution was concentrated in vacuum. The residue was purified through Prep-HPLC (mobile phase: [water(0.1% TFA)-acetonitrile]; B %: 33%-63%) and lyophilized to give Compound 100 (40 mg, 68.78 μmol, 26.91% yield) as a white solid. LCMS (ESI) m/z $[M+H]^+$=468.4; $^1H$ NMR (400 MHz, DMSO-d6) δ 12.30 (s, 1H), 8.19-8.16 (m, 1H), 7.61 (s, 1H), 7.52-7.51 (m, 1H), 7.48-7.47 (m, 1H), 7.35-7.34 (m, 1H), 7.28-7.36 (m, 1H), 6.68-6.96 (m, 2H), 6.48-6.47 (m, 1H), 4.08 (d, J=5.6 Hz, 2H), 3.78-3.76 (m, 4H), 3.17-3.15 (m, 4H), 1.49 (s, 9H).

Example 99. Preparation of N-(2-((4-(3-(2-oxa-6-azaspiro[3.3]heptan-6-yl)phenyl)thiazol-2-yl)amino)-2-oxoethyl)-1-(methylsulfonyl)-1H-pyrrole-3-carboxamide (Compound 101)

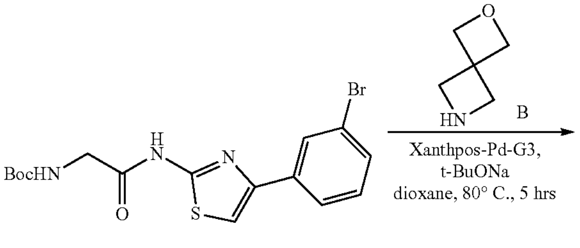

A

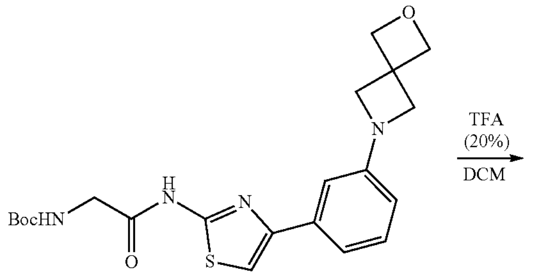

C

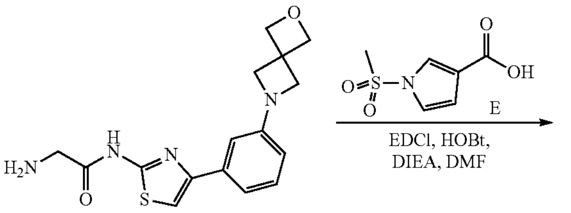

D

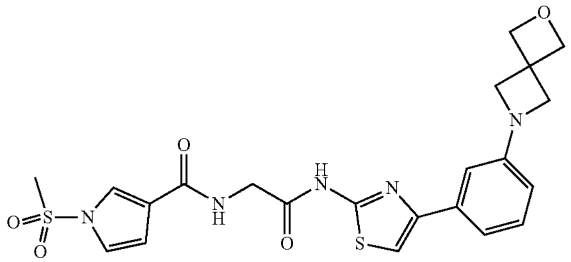

Compound 101

Step 1: Preparation of tert-butyl (2-((4-(3-(2-oxa-6-azaspiro[3.3]heptan-6-yl)phenyl)thiazol-2-yl)amino)-2-oxoethyl)carbamate (Intermediate C)

C

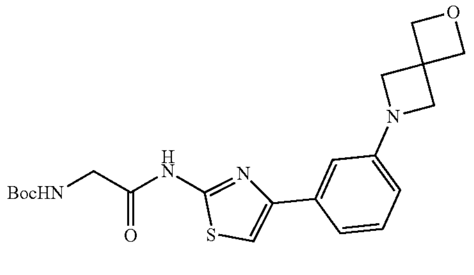

A mixture of tert-butyl N-[2-[[4-(3-bromophenyl)thiazol-2-yl]amino]-2-oxo-ethyl]carbamate [prepared according to the method in Example 1] (500 mg, 1.21 mmol), 2-oxa-6-azaspiro[3.3]heptane (275.28 mg, 1.46 mmol, oxalate), t-BuONa (466.16 mg, 4.85 mmol), and [2-(2-aminophenyl)phenyl]-methylsulfonyloxy-palladium; (5-diphenylphosphanyl-9,9-dimethyl-xanthen-4-yl)-diphenyl-phosphane (115.01 mg, 121.27 μmol) in dioxane (5 mL) was degassed and purged with $N_2$ for 3 times, and then the mixture was stirred at 80° C. for 5 h under $N_2$ atmosphere. Water (20 mL) was added and the reaction mixture was extracted with EtOAc (50 mL×2). The combined organic layers were washed with brine (20 mL), dried over $Na_2SO_4$, filtered and concentrated under reduced pressure to give a residue. The crude product was purified by reversed-phase HPLC (0.1% FA condition). Then sat. $NaHCO_3$ (20 mL) was added and the reaction mixture was extracted with EtOAc (50*2 mL). The combined organic layers were washed with brine (20 mL), dried over $Na_2SO_4$, filtered and concentrated under reduced pressure to give Intermediate C (150 mg, 331.00 μmol, 27.29% yield) as a white solid. LCMS (ESI) m/z $[M+H]^+$=431.3.

Step 2: Preparation of N-(4-(3-(2-oxa-6-azaspiro[3.3]heptan-6-yl)phenyl)thiazol-2-yl)-2-aminoacetamide (Intermediate D)

D

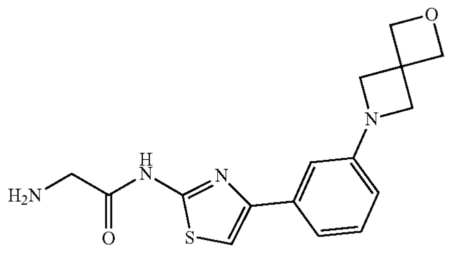

To a solution of Intermediate C (140 mg, 325.19 μmol) in DCM (5 mL) was added TFA (1 mL). The mixture was stirred at 0° C. for 2 h. Sat. $NaHCO_3$ (20 mL) was added and the reaction mixture was extracted with EtOAc 100 mL (50 mL×2). The combined organic layers were washed with brine (20 mL), dried over $Na_2SO_4$, filtered and concentrated under reduced pressure to give Intermediate D (80 mg, crude) as a yellow solid, which was used into the next step without further purification. LCMS (ESI) m/z $[M+H]^+$=331.1.

Step 3: Preparation of N-(2-((4-(3-(2-oxa-6-azaspiro[3.3]heptan-6-yl)phenyl)thiazol-2-yl)amino)-2-oxoethyl)-1-(methylsulfonyl)-1H-pyrrole-3-carboxamide (Compound 101)

Compound 101

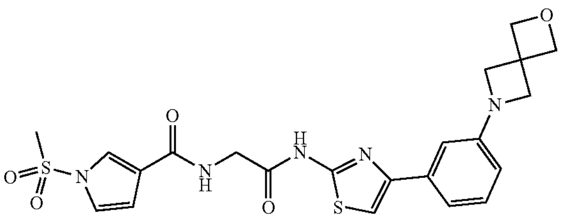

To a solution of 1-methylsulfonylpyrrole-3-carboxylic acid [prepared according to the method in Example 4] (48.10 mg, 254.23 μmol) in DMF (2 mL) was added EDCI (60.92 mg, 317.79 μmol), DIEA (82.14 mg, 635.59 μmol, 110.71 μL) and HOBt (42.94 mg, 317.79 μmol). Then Intermediate D (70 mg, 211.86 μmol) was added. The mixture was stirred at 25° C. for 25 h. The reaction mixture was diluted with MeOH (2 mL). The reaction mixture was purified by prep-HPLC (mobile phase: [water(0.075% TFA)-acetonitrile]; B %: 25%-55%) and lyophilized to give a crude product, the product was triturated with MeOH (20 mL) at 25° C. and collected by filtration to give Compound 101 (38 mg, 59.60 μmol, 28.13% yield, TFA salt) as a yellow solid. LCMS (ESI) m/z $[M+H]^+$=502.1; $^1H$ NMR (400 MHz, DMSO-$d_6$) δ 12.39 (s, 1H), 8.66-8.63 (m, 1H), 7.85-7.83 (m, 1H), 7.55 (s, 1H), 7.35-7.28 (m, 1H), 7.24-7.18 (m, 2H), 6.96 (s, 1H), 6.78-6.76 (m, 1H), 6.42-6.35 (m, 1H), 4.73 (s, 4H), 4.13 (d, J=6.0 Hz, 2H), 3.99 (s, 4H), 3.57 (s, 3H).

Example 100. Preparation of 1-(methylsulfonyl)-N-(2-oxo-2-((4-(3-(2-(pyridin-4-yloxy)propan-2-yl)phenyl)thiazol-2-yl)amino)ethyl)-1H-pyrrole-3-carboxamide (Compound 102)

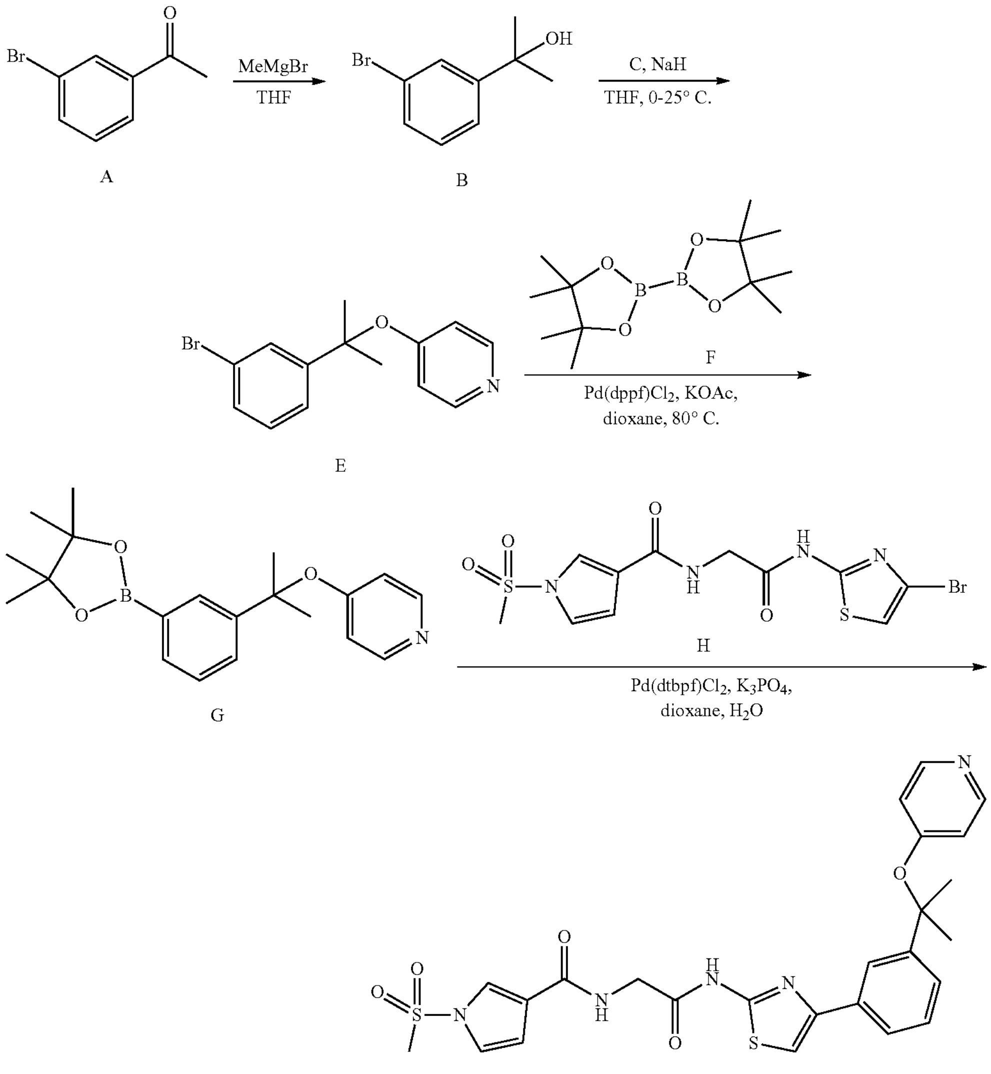

Compound 102

-continued

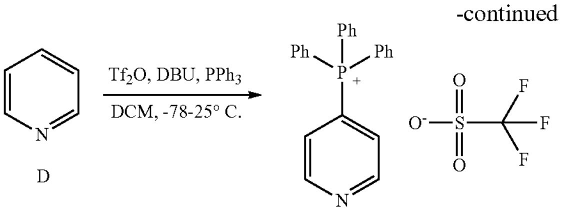

D

C

Step 1: Preparation of 2-(3-bromophenyl)propan-2-ol (Intermediate B)

B

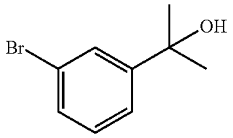

A mixture of 1-(3-bromophenyl)ethanone (2 g, 10.05 mmol, 1.32 mL) was degassed and purged with $N_2$ for 3 times, and then MeMgBr/THF (3 M, 10.05 mL) was added at 0° C. The mixture was stirred at 25° C. for 2 h under $N_2$ atmosphere. Water (80 mL) was added and the reaction mixture was extracted with EtOAc (200 mL×2). The combined organic layers were washed with brine (80 mL), dried over $Na_2SO_4$, filtered and concentrated under reduced pressure to give a residue. The residue was purified by flash silica gel chromatography (Eluent of 0-20% Ethylacetate/Petroleum ether gradient) and concentrated to give Intermediate B (2 g, 9.30 mmol, 92.54% yield) as colorless oil.

Step 2: Preparation of triphenyl(pyridin-4-yl)phosphonium trifluoromethanesulfonate (Intermediate C)

C

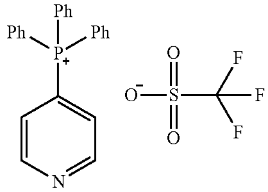

Triphenyl(pyridin-4-yl)phosphonium trifluoromethanesulfonate was synthesized according to the method described in following reference: Hilton, M. C.; Ryan D. Dolewski, R. D.; McNally A. *Journal of the American Chemical Society* (2016) 138 (42), 13806-13809

To a solution of pyridine (500 mg, 6.32 mmol, 510.20 μL) in DCM (50 mL) was added $Tf_2O$ (1.78 g, 6.32 mmol, 1.04 mL) at −78° C. under $N_2$. The reaction was stirred for 30 min before $PPh_3$ (1.82 g, 6.95 mmol) was added. After the mixture was stirred for 30 min, the stated organic DBU (962.33 mg, 6.32 mmol, 952.80 μL) was added dropwise via syringe, the cooling bath was removed and the reaction was allowed to warm to 25° C. while stirring (30 minutes). Water (50 mL×3) was added and the reaction mixture was extracted with DCM (100 mL). The combined organic layers were washed with brine (50 mL), dried over $Na_2SO_4$, filtered and concentrated under reduced pressure to give a residue. The crude product was triturated with MTBE (40 mL) at 25° C. for 10 min, then filtered and dried in vacuum to give Intermediate C (2.5 g, 5.11 mmol, 80.81% yield) as a white solid. $^1$H NMR (400 MHz, Methanol-d$_4$) δ 8.79-8.78 (m, 2H), 7.98-7.80 (m, 3H), 7.73-7.87 (m, 14H).

Step 3: Preparation of 4-((2-(3-bromophenyl)propan-2-yl)oxy)pyridine (Intermediate E)

E

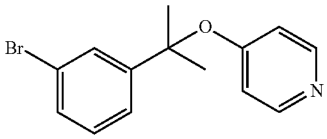

To a solution of Intermediate B (500 mg, 2.32 mmol) in THF (5 mL) was added NaH (139.47 mg, 3.49 mmol, 60% purity) at 0° C. under $N_2$. The mixture was stirred for 30 min before Intermediate C (1.14 g, 2.32 mmol) was added at 0° C. The mixture was stirred at 25° C. for 3 h. Water (20 mL) was added the reaction mixture was extracted with EtOAc (50 mL×2). The combined organic layers were washed with brine (20 mL), dried over $Na_2SO_4$, filtered and concentrated under reduced pressure to give a residue. The residue was purified by flash silica gel chromatography (Eluent of 0-90% Ethyl acetate/Petroleum ether gradient) and concentrated to give Intermediate E (120 mg, 410.72 μmol, 17.67% yield) as yellow oil. $^1$H NMR (400 MHz, $CDCl_3$) δ 8.26-8.25 (m, 2H), 7.55-7.53 (m, 1H), 7.45-7.43 (m, 1H), 7.33-7.31 (m, 1H), 7.25-7.21 (m, 1H), 6.52-6.50 (m, 2H), 1.76 (s, 6H).

Step 4: Preparation of 4-((2-(3-(4,4,5,5-tetramethyl-1,3,2-dioxaborolan-2-yl)phenyl)propan-2-yl)oxy)pyridine (Intermediate G)

G

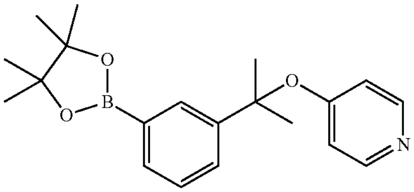

A mixture of Intermediate E (110 mg, 376.49 μmol), 4,4,5,5-tetramethyl-2-(4,4,5,5-tetramethyl-1,3,2-dioxaborolan-2-yl)-1,3,2-dioxaborolane (286.82 mg, 1.13 mmol), KOAc (147.80 mg, 1.51 mmol) and [1,1'-bis(di-tert-butylphosphino)ferrocene]dichloropalladium(II) (24.54 mg, 37.65 μmol) in dioxane (4 mL) was degassed and purged with $N_2$ for 3 times, and then the mixture was stirred at 80° C. for 2 h under $N_2$ atmosphere. Water (20 mL) was added and the reaction mixture was extracted with EtOAc (50 mL×2). The combined organic layers were washed with brine (20 mL), dried over $Na_2SO_4$, filtered and concentrated under reduced pressure to give a residue. The residue was purified by column chromatography ($SiO_2$, Petroleum ether/EtOAc=20/1 to 1:1) and concentrated to give Intermediate G (150 mg, crude) as a brown oil which was used into the next step without further purification.

Step 5: Preparation of 1-(methylsulfonyl)-N-(2-oxo-2-((4-(3-(2-(pyridin-4-yloxy)propan-2-yl)phenyl)thiazol-2-yl)amino)ethyl)-1H-pyrrole-3-carboxamide (Compound 102)

Compound 102

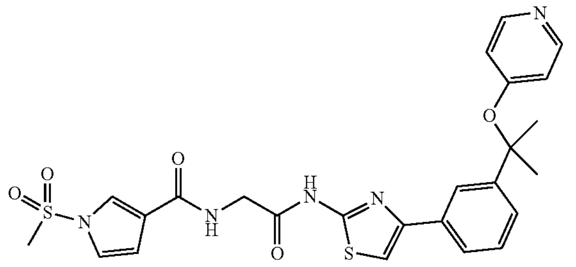

A mixture of N-[2-[(4-bromothiazol-2-yl)amino]-2-oxo-ethyl]-1-methylsulfonyl-pyrrole-3-carboxamide [prepared according to the method in Example 6] (120 mg, 294.65 μmol), Intermediate G (119.60 mg, 352.57 μmol), $K_3PO_4$ (250.18 mg, 1.18 mmol) and [1,1'-bis(di-tert-butylphosphino)ferrocene]dichloropalladium(II) (38.41 mg, 58.93 μmol) in dioxane (2 mL) and $H_2O$ (0.5 mL) was degassed and purged with $N_2$ for 3 times, and then the mixture was stirred at 100° C. for 2 h under $N_2$ atmosphere. Water (20 mL) was added and the reaction mixture was extracted with EtOAc (50 mL×2). The combined organic layers were washed with brine (20 mL), dried over $Na_2SO_4$, filtered and concentrated under reduced pressure to give a residue. The residue was purified by Prep-HPLC (mobile phase: [water (10 mM $NH_4HCO_3$)-acetonitrile]; B %: 20%-50%) and lyophilized to give Compound 102 (4.2 mg, 7.71 μmol, 2.62% yield) as a white solid. LCMS (ESI) m/z $[M+H]^+$=540.3; $^1H$ NMR (400 MHz, DMSO-$d_6$) δ 12.33 (s, 1H), 8.55 (s, 1H), 8.20-8.18 (m, 2H), 7.97 (s, 1H), 7.83-7.80 (m, 2H), 7.56 (s, 1H), 7.44-7.40 (m, 1H), 7.34 (d, J=7.6 Hz, 1H), 7.30-7.29 (m, 1H), 6.77-6.75 (m, 1H), 6.59-6.58 (m, 2H), 4.08 (d, J=5.2 Hz, 2H), 3.57 (s, 3H), 1.79 (s, 6H).

Example 101. Preparation of 1-(methylsulfonyl)-N-(2-oxo-2-((4-(3-(1-phenoxyethyl)phenyl)thiazol-2-yl)amino)ethyl)-1H-pyrrole-3-carboxamide (Compound 103)

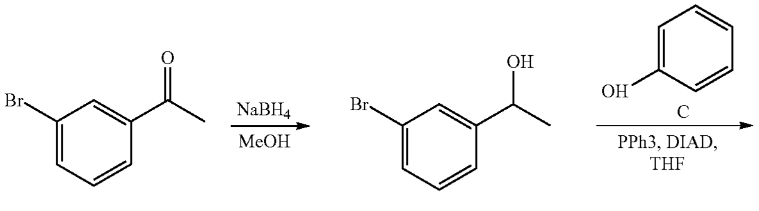

A

B

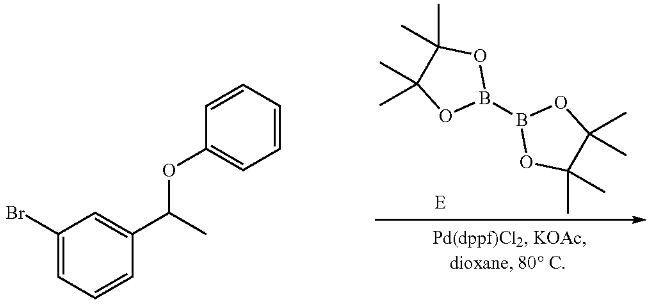

D

-continued

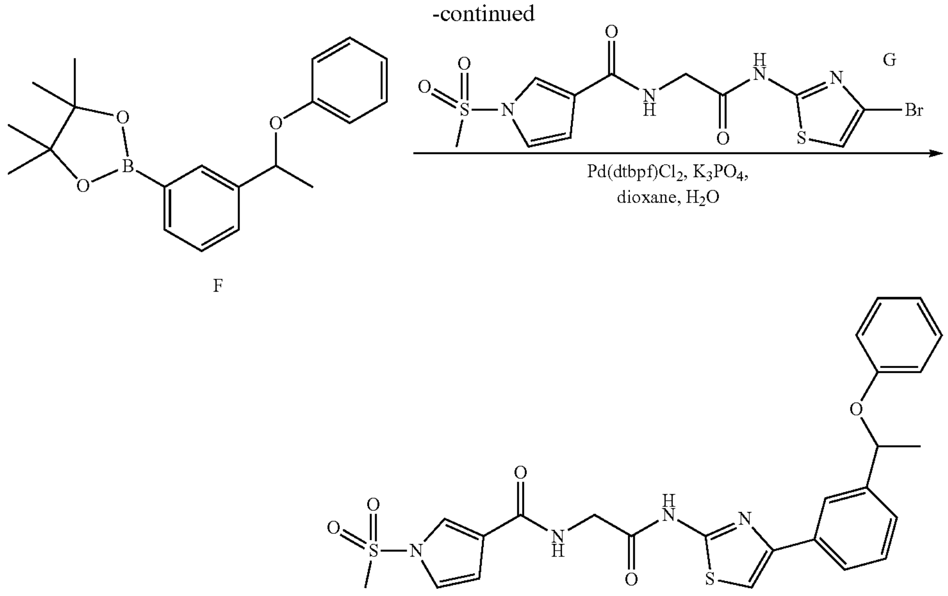

G

F

Compound 103

Step 1: Preparation of 1-(3-bromophenyl)ethanol (Intermediate B)

B

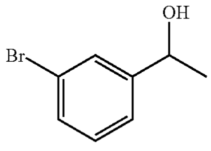

To a solution of 1-(3-bromophenyl)ethanone (1 g, 5.02 mmol, 662.25 μL) in MeOH (10 mL) was added $NaBH_4$ (380.14 mg, 10.05 mmol). The mixture was stirred at 25° C. for 2 h. 2N HCl (20 mL) and $H_2O$ (30 mL) was added and the reaction mixture was extracted with EtOAc (100 mL×2). The combined organic layers were washed with brine (50 mL), dried over $Na_2SO_4$, filtered and concentrated under reduced pressure to give Intermediate B (1.2 g, crude) as a colorless oil was used into the next step without further purification. $^1$H NMR (400 MHz, $CDCl_3$) δ 7.57 (s, 1H), 7.44 (d, J=7.6 Hz, 1H), 7.33-7.30 (m, 1H), 7.27-7.23 (m, 1H), 4.92-4.87 (m, 1H), 1.97 (s, 1H), 1.52 (d, J=6.4 Hz, 3H).

Step 2: Preparation of 1-bromo-3-(1-phenoxyethyl)benzene (Intermediate D)

D

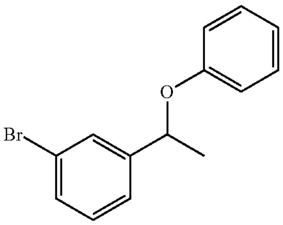

To a solution of Intermediate B (1 g, 4.97 mmol) in THF (10 mL) was added phenol (561.69 mg, 5.97 mmol, 524.94 μL) and DIAD (1.01 g, 4.97 mmol, 967.03 μL), then $PPh_3$ (1.57 g, 5.97 mmol) was add under $N_2$ at 0° C. The mixture was stirred at 25° C. for 2 h. Water (50 mL) was added and the reaction mixture was extracted with EtOAc (100 mL×2). The combined organic layers were washed with brine (50 mL), dried over $Na_2SO_4$, filtered and concentrated under reduced pressure to give a residue. The residue was purified by flash silica gel chromatography (Eluent of 0-10% Ethyl acetate/Petroleum ether gradient) and concentrated to give Intermediate D (600 mg, 2.16 mmol, 43.53% yield) as yellow oil. $^1$H NMR (400 MHz, $CDCl_3$) δ 7.55-7.54 (m, 1H), 7.40-7.38 (m, 1H), 7.32-7.30 (m, 1H), 7.25-7.19 (m, 3H), 6.93-6.89 (m, 1H), 6.87-6.84 (m, 2H), 5.29-5.24 (m, 1H), 1.63 (d, J=6.4 Hz, 3H).

Step 3: Preparation of 4,4,5,5-tetramethyl-2-(3-(1-phenoxyethyl)phenyl)-1,3,2-dioxaborolane (Intermediate F)

F

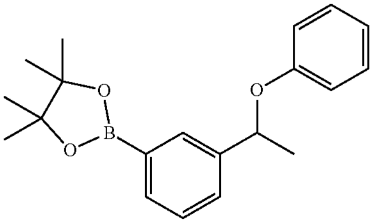

A mixture of Intermediate D (200 mg, 721.62 μmol), 4,4,5,5-tetramethyl-2-(4,4,5,5-tetramethyl-1,3,2-dioxaborolan-2-yl)-1,3,2-dioxaborolane (219.89 mg, 865.94 μmol), KOAc (212.46 mg, 2.16 mmol) and Pd(dppf)$Cl_2$ (52.80 mg, 72.16 μmol) in dioxane (2 mL) was degassed and purged with $N_2$ for 3 times, and then the mixture was stirred at 80° C. for 2 h under $N_2$ atmosphere. Water (30 mL) was added and the reaction mixture was extracted with EtOAc (50 mL×2). The combined organic layers were washed with brine (20 mL), dried over $Na_2SO_4$, filtered and concentrated under reduced pressure to give a residue. The residue was purified by flash silica gel chromatography (Eluent of 0-20% Ethyl acetate/Petroleum ether gradient) and concentrated to give Intermediate F (100 mg, 308.43 μmol, 42.74% yield) as yellow oil, which was used into the next step without further purification.

Step 4: Preparation of 1-(methylsulfonyl)-N-(2-oxo-2-((4-(3-(1-phenoxyethyl)phenyl)thiazol-2-yl)amino)ethyl)-1H-pyrrole-3-carboxamide (Compound 103)

Compound 103

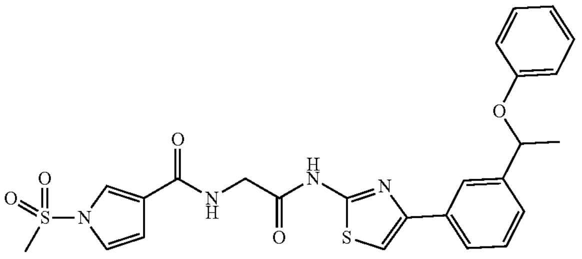

A mixture of N-[2-[(4-bromothiazol-2-yl)amino]-2-oxo-ethyl]-1-methylsulfonyl-pyrrole-3-carboxamide [prepared according to the method in Example 6] (50 mg, 122.77 μmol), Intermediate F (79.61 mg, 245.54 μmol), $K_3PO_4$ (78.18 mg, 368.31 μmol) and [1,1'-bis(di-tert-butylphosphino)ferrocene]dichloropalladium(II) (16.00 mg, 24.55 μmol) in dioxane (2 mL) and $H_2O$ (0.5 mL) was degassed and purged with $N_2$ for 3 times, and then the mixture was stirred at 100° C. for 2 h under $N_2$ atmosphere. Water (20 mL) was added and the reaction mixture was extracted with EtOAc (50 mL×2). The combined organic layers were washed with brine (20 mL), dried over $Na_2SO_4$, filtered and concentrated under reduced pressure to give a residue. The residue was purified by Prep-HPLC (mobile phase: [water (0.075% TFA)-acetonitrile]; B %: 48%-78%) and lyophilized to give Compound 103 (13 mg, 24.78 μmol, 20.18% yield) as a white solid. LCMS (ESI) m/z $[M+H]^+$=525.4; $^1H$ NMR (400 MHz, DMSO-$d_6$) δ 12.39 (s, 1H), 8.67-8.64 (m, 1H), 7.96 (s, 1H), 7.84-7.83 (m, 1H), 7.77 (d, J=7.2 Hz, 1H), 7.61 (s, 1H), 7.41-7.35 (m, 2H), 7.31-7.30 (m, 1H), 7.22-7.18 (m, 2H), 6.91 (d, J=8.0 Hz, 2H), 6.86-6.83 (m, 1H), 6.77-6.76 (m, 1H), 5.53-5.49 (m, 1H), 4.13 (d, J=6.0 Hz, 2H), 3.56 (s, 3H), 1.57 (d, J=6.4 Hz, 3H).

Example 102. Preparation of 1-(methylsulfonyl)-N-(2-oxo-2-((4-(3-(phenoxymethyl)phenyl)thiazol-2-yl)amino)ethyl)-1H-pyrrole-3-carboxamide (Compound 104)

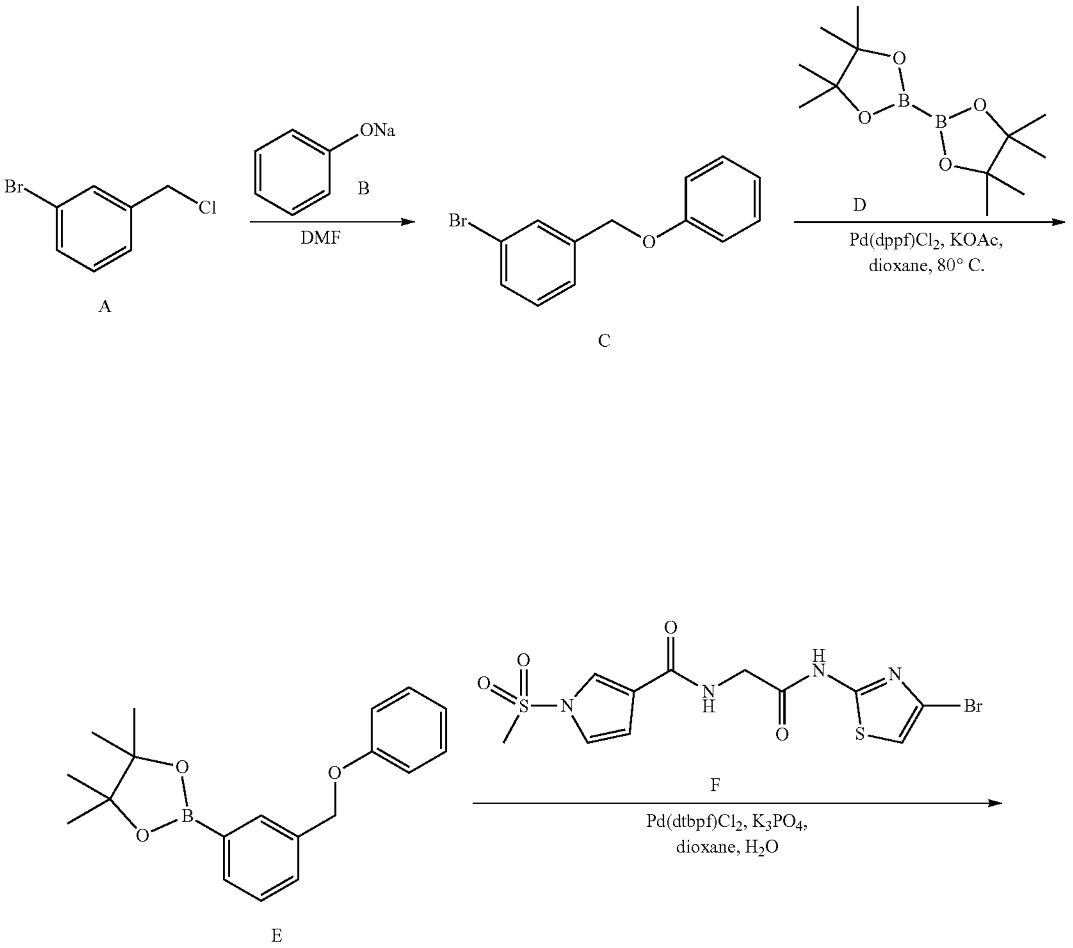

-continued

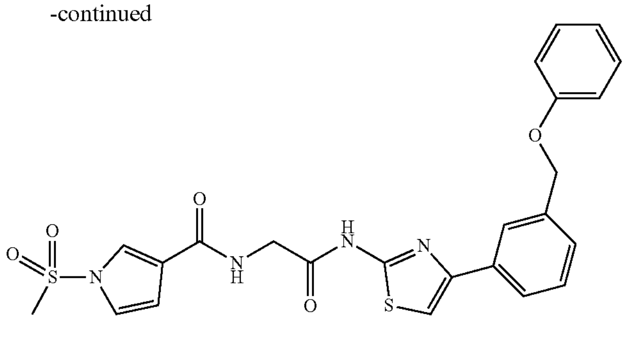

Compound 104

Step 1: Preparation of 1-bromo-3-(phenoxymethyl)benzene (Intermediate C)

C

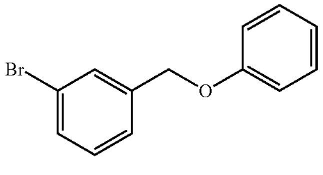

To a solution of phenoxysodium (564.99 mg, 4.87 mmol, 856.68 μL) in DMF (10 mL) was added 1-bromo-3-(chloromethyl)benzene (500 mg, 2.43 mmol). The mixture was stirred at 25° C. for 2 h. Water (50 mL) was added and the reaction mixture was extracted with EtOAc (100 mL×2). The combined organic layers were washed with brine (50 mL), dried over $Na_2SO_4$, filtered and concentrated under reduced pressure to give a residue. The residue was purified by flash silica gel chromatography (Eluent of 0-20% Ethyl acetate/Petroleum ether gradient) and concentrated to give Intermediate C (600 mg, 2.28 mmol, 93.71% yield) as colorless oil.

$^1$H NMR (400 MHz, $CDCl_3$) δ 7.63 (s, 1H), 7.48 (d, J=8.0 Hz, 1H), 7.39 (d, J=7.6 Hz, 1H), 7.34-7.25 (m, 3H), 7.00-6.98 (m, 3H), 5.06 (s, 2H).

Step 2: Preparation of 4,4,5,5-tetramethyl-2-(3-(phenoxymethyl)phenyl)-1,3,2-dioxaborolane (Intermediate E)

E

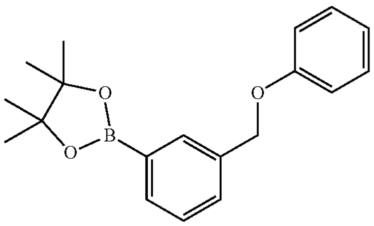

A mixture of Intermediate C (200 mg, 760.08 μmol), 4,4,5,5-tetramethyl-2-(4,4,5,5-tetramethyl-1,3,2-dioxaborolan-2-yl)-1,3,2-dioxaborolane (231.62 mg, 912.10 μmol), KOAc (223.79 mg, 2.28 mmol) and Pd(dppf)$Cl_2$ (55.62 mg, 76.01 μmol) in dioxane (2 mL) was degassed and purged with $N_2$ for 3 times, and then the mixture was stirred at 80° C. for 2 h under $N_2$ atmosphere. The reaction mixture was concentrated under reduced pressure to remove dioxane. The residue was purified by flash silica gel chromatography (Eluent of 0-20% Ethyl acetate/Petroleum ether gradient) and concentrated to give Intermediate E (120 mg, 386.85 μmol, 50.90% yield) as a yellow solid. $^1$H NMR (400 MHz, Methanol-d4) δ 7.82 (s, 1H), 7.72-7.68 (m, 1H), 7.58-7.53 (m, 1H), 7.29-7.24 (m, 1H), 7.31-7.23 (m, 2H), 7.04-6.97 (m, 3H), 5.06 (s, 2H), 1.35 (s, 12H).

Step 3: Preparation of 1-(methylsulfonyl)-N-(2-oxo-2-((4-(3-(phenoxymethyl)phenyl)thiazol-2-yl)amino)ethyl)-1H-pyrrole-3-carboxamide (Compound 104)

Compound 104

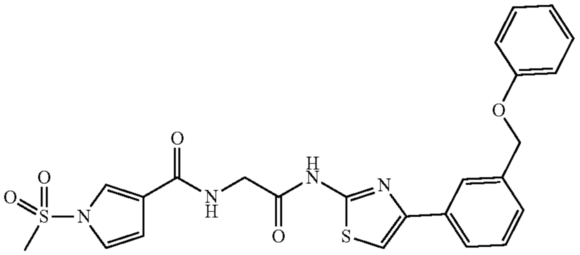

A mixture of N-[2-[(4-bromothiazol-2-yl)amino]-2-oxo-ethyl]-1-methylsulfonyl-pyrrole-3-carboxamide [prepared according to the method in Example 6] (50 mg, 122.77 μmol), Intermediate E (76.17 mg, 245.54 μmol), $K_3PO_4$ (78.18 mg, 368.31 μmol) and [1,1'-bis(di-tert-butylphosphino)ferrocene]dichloropalladium(II) (16.00 mg, 24.55 μmol) in dioxane (2 mL) and $H_2O$ (0.5 mL) was degassed and purged with $N_2$ for 3 times, and then the mixture was stirred at 100° C. for 2 h under $N_2$ atmosphere. Water (20 mL) was added and the reaction mixture was extracted with EtOAc (50 mL×2). The combined organic layers were washed with brine (20 mL), dried over $Na_2SO_4$, filtered and concentrated under reduced pressure to give a residue. The residue was purified by Prep-HPLC (mobile phase: [water (0.075% TFA)-acetonitrile]; B %: 48%-78%) and lyophilized to give Compound 104 (16.19 mg, 31.71 μmol, 25.83% yield) as a white solid. LCMS (ESI) m/z $[M+H]^+$=511.3; $^1$HNMR (400 MHz, DMSO-$d_6$) δ 12.39 (s, 1H), 8.67-8.65 (m, 1H), 8.00 (s, 1H), 7.85-7.83 (m, 2H) 7.65 (s, 1H), 7.46-7.39 (m, 2H), 7.31-7.27 (m, 3H), 7.03 (d, J=8.0 Hz, 2H), 6.96-6.92 (m, 1H), 6.77-6.76 (m, 1H), 5.15 (s, 2H), 4.13 (d, J=6.0 Hz, 2H), 3.57 (s, 3H).

Example 103. Preparation of N-(2-((4-(3-((((1R, 4R)-4-hydroxycyclohexyl)oxy)methyl)phenyl)thiazol-2-yl)amino)-2-oxoethyl)-1-(methylsulfonyl)-1H-pyrrole-3-carboxamide (Compound 105)
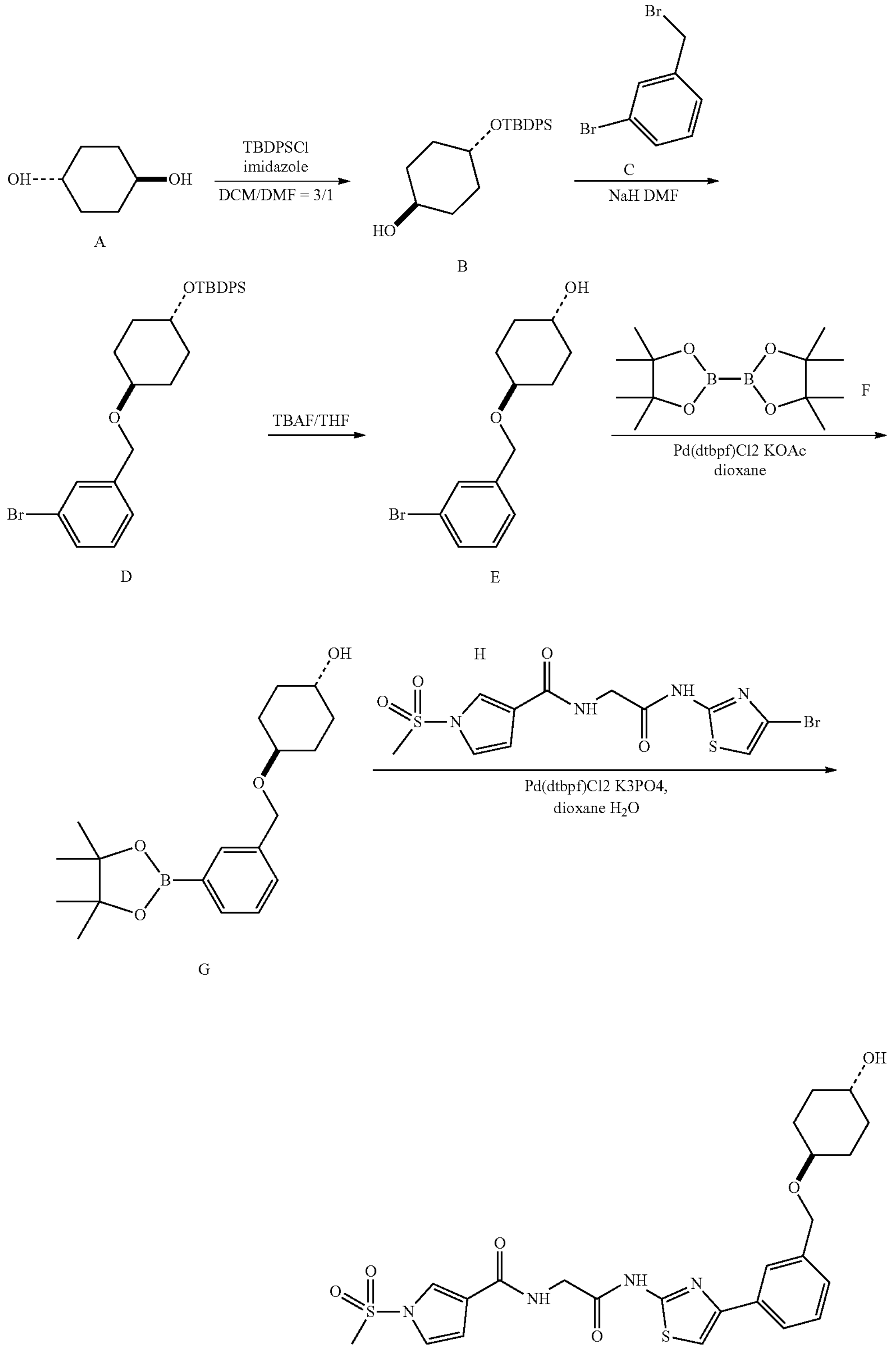
Compound 105

Step 1: Preparation of (1R,4R)-4-((tert-butyldiphenylsilyl)oxy)cyclohexanol (Intermediate B)

B

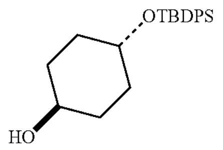

The solution of cyclohexane-1,4-diol (3 g, 25.83 mmol) and TBDPSCl (7.10 g, 25.83 mmol, 6.63 mL) in DCM (60 mL) and DMF (30 mL) was added a solution of imidazole (1.76 g, 25.83 mmol) in DCM (30 mL). The reaction mixture was stirred at 25° C. for 16 hours. The reaction mixture was diluted with water (50 mL), extracted with DCM (30 mL×3), the combined organic layers was washed with brine and dried over anhydrous $Na_2SO_4$ and concentrated to afford a white solid. The solid was dispersed in DCM (5 mL) and filtered, the filter liquid was purified by flash silica gel chromatography (Eluent of 0-30% Ethyl acetate/Petroleum ether gradient), concentrated to afford Intermediate B (5.00 g, 11.28 mmol, 43.68% yield) as light yellow oil. $^1$H NMR (400 MHz, DMSO-$d_6$) δ 7.59-7.58 (m, 4H), 7.47-7.39 (m, 6H), 4.39 (d, J=4.4 Hz, 1H), 3.66-3.59 (m, 1H), 3.45-3.40 (m, 1H), 1.75-1.66 (m, 4H), 1.38-1.28 (m, 2H), 1.09-1.03 (m, 2H), 0.99 (s, 9H).

Step 2: Preparation of (((1R,4R)-4-((3-bromobenzyl)oxy)cyclohexyl)oxy)(tert-butyl)diphenylsilane (Intermediate D)

D

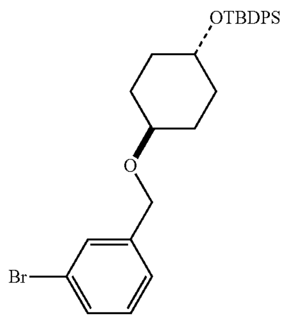

To the mixture of NaH (676.84 mg, 16.92 mmol, 60% purity) in THF (30 mL) was added a solution of Intermediate B (3 g, 8.46 mmol, 917.43 μL) in THF (5 mL) dropwise at 0° C., the reaction mixture was stirred at 0° C. for 15 minutes, then a solution of 1-bromo-3-(bromomethyl)benzene (3.17 g, 12.69 mmol) in THF (5 mL) was added drop wise at 0° C. The reaction mixture was warmed to 25° C. and stirred for 4 hours. The reaction mixture was quenched with saturated $NH_4Cl$ (50 mL), and extracted with EtOAc (20 mL×2), the combined organic layers was dried over anhydrous $Na_2SO_4$ and concentrated to afford a yellow oil. The oil was purified by flash silica gel chromatography (Eluent of 0-20% Ethyl acetate/Petroleum ether gradient), concentrated to afford Intermediate D (3.30 g, crude) as a yellow oil. $^1$H NMR (400 MHz, DMSO-$d_6$) δ 7.62-7.58 (m, 4H), 7.53-7.49 (m, 1H), 7.46-7.42 (m, 7H), 7.27 (d, J=5.2 Hz, 2H), 4.69 (s, 2H), 3.79-3.69 (m, 1H), 3.43-3.40 (m, 1H), 1.95-1.86 (m, 2H), 1.72 (d, J=9.8 Hz, 2H), 1.43 (br s, 2H), 1.32-1.21 (m, 2H), 1.00 (s, 9H).

Step 3: Preparation of (1R,4R)-4-((3-bromobenzyl)oxy)cyclohexanol (Intermediate E)

E

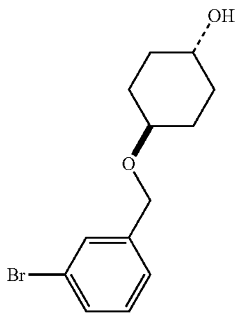

The solution of Intermediate D (200 mg, 381.99 μmol) in TBAF/THF (1M, 2 mL) was stirred at 80° C. for 16 hours. The reaction mixture was diluted with water (5 mL) and extracted with EtOAc (5 mL×2), the combined organic layers was dried over anhydrous $Na_2SO_4$ and concentrated to afford yellow oil. The oil was dissolved with DCM (1 mL) and purified by silica gel chromatography (PE/EA=5/1 to 0/1), concentrated to afford Intermediate E (90 mg, 252.48 μmol, 66.09% yield) a yellow oil. $^1$H NMR (400 MHz, DMSO-$d_6$) δ 7.49 (s, 1H), 7.47-7.43 (m, 1H), 7.32-7.29 (m, 2H), 4.50 (d, J=4.0 Hz, 1H), 4.48 (s, 2H), 3.44-3.41 (m, 1H), 3.31-3.26 (m, 1H), 1.96-1.89 (m, 2H), 1.83-1.74 (m, 2H), 1.32-1.23 (m, 2H), 1.20-1.12 (m, 2H).

Step 4: Preparation of (1R,4R)-4-((3-(4,4,5,5-tetramethyl-1,3,2-dioxaborolan-2-yl)benzyl)oxy)cyclohexanol (Intermediate G)

G

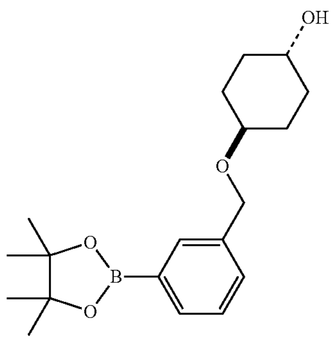

The solution of Intermediate E (90 mg, 315.59 μmol), 4,4,5,5-tetramethyl-2-(4,4,5,5-tetramethyl-1,3,2-dioxaborolan-2-yl)-1,3,2-dioxaborolane (104.18 mg, 410.27 μmol) and KOAc (92.92 mg, 946.78 μmol) in dioxane (1 mL) was added [1,1'-bis(di-tert-butylphosphino)ferrocene]dichloropalladium(II) (20.57 mg, 31.56 μmol) at 25° C. under $N_2$. The reaction mixture was stirred at 80° C. under $N_2$ for 3 hours. The reaction mixture was diluted with water (5 mL) and extracted with EtOAc (3 mL×3), the combined organic layers was dried over anhydrous $Na_2SO_4$ and concentrated to afford Intermediate G (100 mg, crude) as a black brown oil, which was used to the next step without further purification. LCMS (ESI) m/z $[M+H]^+$=333.0.

Step 5: Preparation of N-(2-((4-(3-((((1R,4R)-4-hydroxycyclohexyl)oxy)methyl)phenyl)thiazol-2-yl)amino)-2-oxoethyl)-1-(methylsulfonyl)-1H-pyrrole-3-carboxamide (Compound 105)

Compound 105

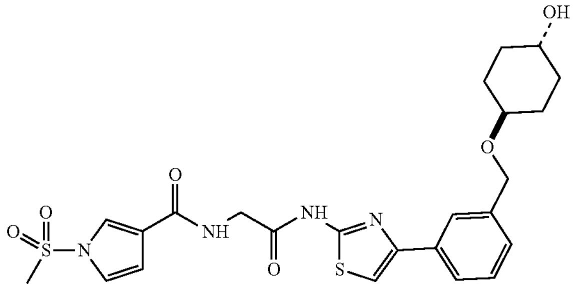

The solution of N-[2-[(4-bromothiazol-2-yl)amino]-2-oxo-ethyl]-1-methylsulfonyl-pyrrole-3-carboxamide [prepared according to the method in Example 6] (61.29 mg, 150.49 μmol), Intermediate G (100 mg, 300.99 μmol) and $K_3PO_4$ (95.83 mg, 451.48 μmol) in dioxane (0.8 mL) and $H_2O$ (0.2 mL) was added [1,1'-bis(di-tert-butylphosphino)ferrocene]dichloropalladium(II) (9.81 mg, 15.05 μmol) at 25° C. under $N_2$. The reaction mixture was stirred at 75° C. under $N_2$ for 4 h. The reaction mixture was diluted with water (5 mL) and extracted with EtOAc (4 mL×3), the combined organic layers was dried over anhydrous $Na_2SO_4$ and concentrated to afford black brown oil. The oil was dissolved with DCM (2 mL) and purified by Prep-TLC (EA), concentrated to afford a white residue. The residue was dissolved with DMSO (1 mL) and purified by Prep-HPLC (FA), concentrated and lyophilized to afford Compound 105 (3.00 mg, 5.37 μmol, 3.57% yield) as white solid. LCMS (ESI) m/z $[M+H]^+$=533.1; $^1H$ NMR (400 MHz, Methanol-$d_4$) δ 7.90 (s, 1H), 7.84-7.83 (m, 1H), 7.81 (d, J=7.6 Hz, 1H), 7.39 (s, 1H), 7.38-7.34 (m, 1H), 7.31-7.26 (m, 2H), 6.81-6.80 (m, 1H), 4.58 (s, 2H), 4.26 (s, 2H), 3.66-3.55 (m, 1H), 3.48-3.40 (m, 1H), 3.38 (s, 3H), 2.13-2.04 (m, 2H), 1.99-1.91 (m, 2H), 1.43-1.26 (m, 4H).

Example 104. Preparation of 1-(methylsulfonyl)-N-(2-oxo-2-((4-(3-(pyridin-4-ylmethoxy)phenyl)thiazol-2-yl)amino)ethyl)-1H-pyrrole-3-carboxamide (Compound 106)

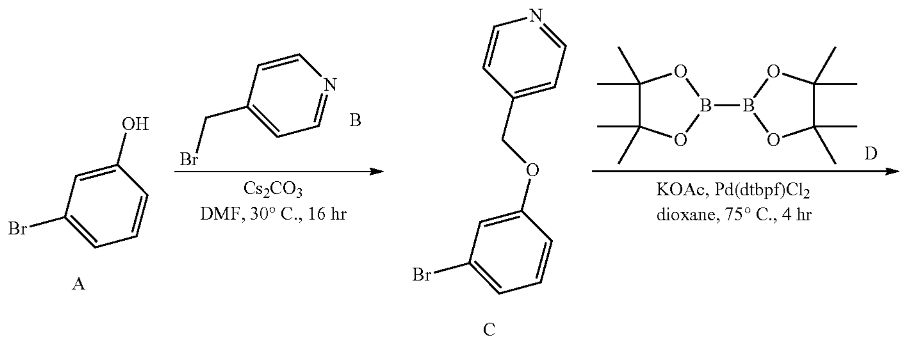

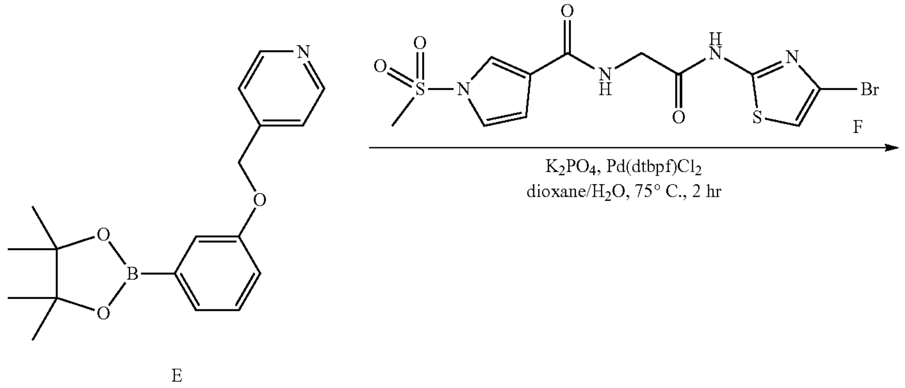

-continued

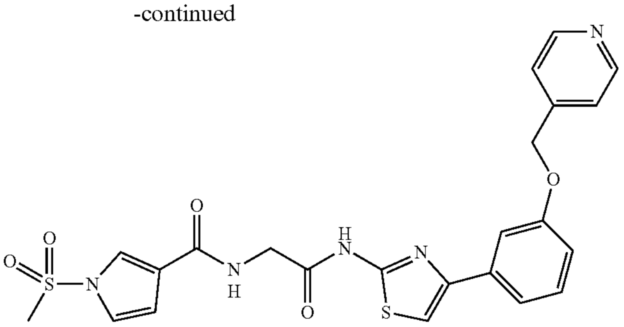

Compound 106

Step 1: Preparation of 4-((3-bromophenoxy)methyl)pyridine (Intermediate C)

C

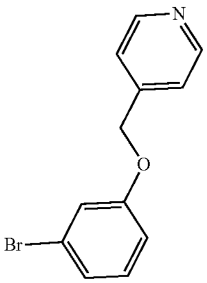

To a mixture of 3-bromophenol (300 mg, 1.73 mmol) and 4-(bromomethyl)pyridine (357.95 mg, 2.08 mmol) in DMF (5 mL) was added $Cs_2CO_3$ (1.13 g, 3.47 mmol) at 30° C. The reaction mixture was stirred at 30° C. for 16 h. The reaction mixture was poured into $H_2O$ (30 mL), extracted with EtOAc (30 mL×3). The combined organic layers were washed with brine (30 mL×3), dried over anhydrous $Na_2SO_4$, filtered and concentrated under reduced pressure to afford a residue. The residue was purified by silica gel chromatography (PE/EA=5/1-3/1) and concentrated to afford Intermediate C (300 mg, 1.08 mmol, 62.23% yield) as yellow oil. LCMS (ESI) m/z $[M+H]^+$=266.0; $^1$H NMR (400 MHz, $CDCl_3$) δ 8.68-8.58 (m, 2H), 7.35 (d, J=6.0 Hz, 2H), 7.15 (s, 3H), 6.91 (s, 1H), 5.09 (s, 2H).

Step 2: Preparation of 4-((3-(4,4,5,5-tetramethyl-1,3,2-dioxaborolan-2-yl)phenoxy)methyl)pyridine (Intermediate E)

E

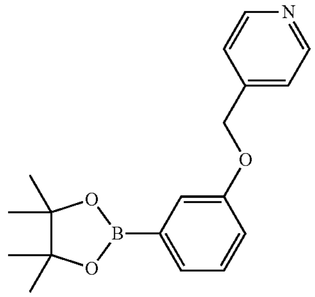

To a mixture of Intermediate C (300 mg, 1.14 mmol) and 4,4,5,5-tetramethyl-2-(4,4,5,5-tetramethyl-1,3,2-dioxaborolan-2-yl)-1,3,2-dioxaborolane (346.12 mg, 1.36 mmol) in dioxane (5 mL) was added KOAc (334.43 mg, 3.41 mmol) and [1,1'-bis(di-tert-butylphosphino)ferrocene]dichloropalladium(II) (74.03 mg, 113.59 μmol) at 30° C. under $N_2$. The reaction mixture was heated to 75° C. and stirred at 75° C. for 4 h under $N_2$. The reaction mixture was filtered and concentrated under reduced pressure to afford a residue. The residue was purified by silica gel chromatography (PE/EA=5/1-1/1) and concentrated in vacuum to give Intermediate E (310 mg, 897.76 μmol, 79.04% yield) as brown oil. LCMS (ESI) m/z $[M+H]^+$=312.1; $^1$H NMR (400 MHz, $CDCl_3$) δ 8.63 (d, J=6.0 Hz, 2H), 7.46 (d, J=7.2 Hz, 1H), 7.39 (br d, J=6.0 Hz, 3H), 7.35-7.30 (m, 1H), 7.11-7.05 (m, 1H), 5.13 (s, 2H), 1.36 (s, 12H).

Step 3: Preparation of 1-(methylsulfonyl)-N-(2-oxo-2-((4-(3-(pyridin-4-ylmethoxy)phenyl)thiazol-2-yl)amino)ethyl)-1H-pyrrole-3-carboxamide (Compound 106)

Compound 106

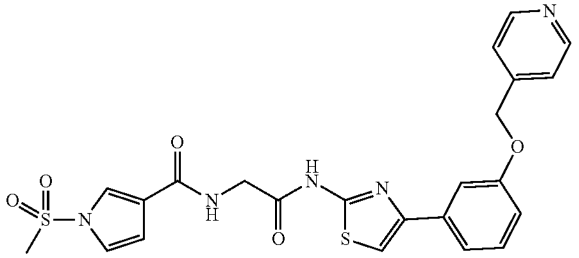

To a mixture of N-[2-[(4-bromothiazol-2-yl)amino]-2-oxo-ethyl]-1-methylsulfonyl-pyrrole-3-carboxamide [prepared according to the method in Example 6] (60 mg, 147.32 μmol) and Intermediate E (91.69 mg, 294.65 μmol) in dioxane (1.2 mL) and $H_2O$ (0.3 mL) was added $K_3PO_4$ (93.82 mg, 441.97 μmol) and [1,1'-bis(di-tert-butylphosphino)ferrocene]dichloropalladium(II) (9.60 mg, 14.73 μmol) at 30° C. under $N_2$. The reaction mixture was heated to 75° C. and stirred at 75° C. for 2 h. The reaction mixture was filtered and the filter cake was washed with MeOH (5 mL) to afford a yellow solid. The yellow solid was purified by reverse phase column (FA condition) and lyophilized to afford Compound 106 (21.13 mg, 37.89 μmol, 25.72% yield, FA salt) as a white solid. LCMS (ESI) m/z $[M+H]^+$=512.2; $^1$H NMR (400 MHz, DMSO-$d_6$) δ 12.38 (br s, 1H), 8.66 (s, 1H), 8.63-8.57 (m, 2H), 7.83-7.85 (m, 1H), 7.66 (s, 1H), 7.59-7.55 (m, 1H), 7.52 (d, J=8.0 Hz, 1H), 7.47 (d, J=6.0 Hz, 2H), 7.38-7.34 (m, 1H), 7.32-7.30 (m, 1H), 7.00-6.97 (m, 1H), 6.78-6.76 (m, 1H), 5.24 (s, 2H), 4.14 (d, J=5.6 Hz, 2H), 3.57 (s, 3H).

Example 105. Preparation of 1-(methylsulfonyl)-N-(2-oxo-2-((4-(3-((pyridin-2-yloxy)methyl)phenyl)thiazol-2-yl)amino)ethyl)-1H-pyrrole-3-carboxamide (Compound 107)

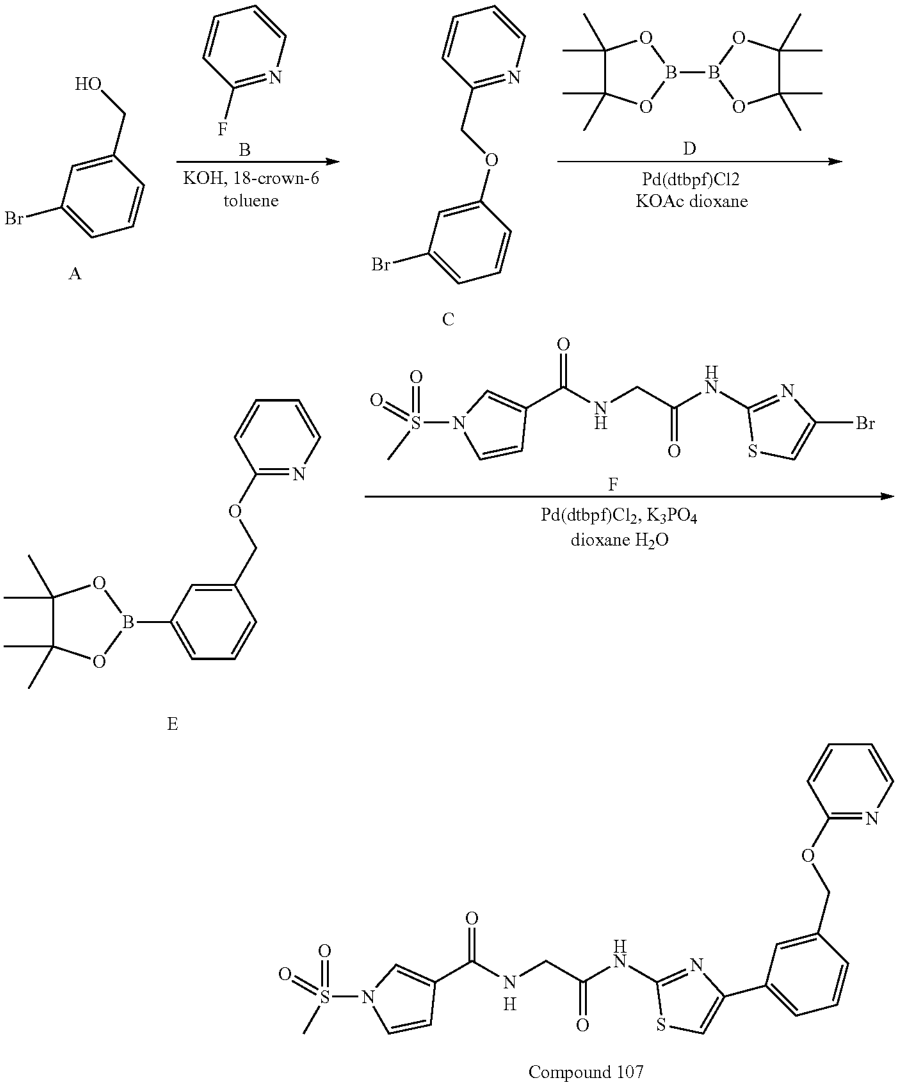

Compound 107

Step 1: Preparation of 2-((3-bromobenzyl)oxy)pyridine (Intermediate C)

C

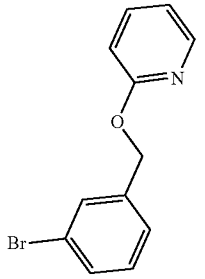

To a mixture of (3-bromophenyl)methanol (5 g, 26.73 mmol, 3.21 mL) and 2-fluoropyridine (3.89 g, 40.10 mmol, 3.45 mL) in toluene (100 mL) was added KOH (6.00 g, 106.93 mmol) and 18-crown-6 (7.77 g, 29.41 mmol) in one portion at 25° C. The mixture was stirred at 25° C. for 12 hours. The mixture was poured into ice-water (200 mL) and stirred for 2 min. The aqueous phase was extracted with EtOAc (100 mL×2). The combined organic phase was washed with brine (100 mL), dried with anhydrous $Na_2SO_4$, filtered and concentrated in vacuum to give Intermediate C (6.2 g, 23.47 mmol, 87.81% yield) as yellow oil. LCMS (ESI) m/z $[M+H]^+$=264.0; $^1$H NMR (400 MHz, Methanol-$d_4$) δ 8.15-8.13 (m, 1H), 7.75-7.67 (m, 1H), 7.62 (s, 1H), 7.45-7.42 (m, 2H), 7.29 (d, J=16.8 Hz, 1H), 6.97-6.95 (m, 1H), 6.88 (d, J=8.4 Hz, 1H), 5.35 (s, 2H).

Step 2: Preparation of 2-((3-(4,4,5,5-tetramethyl-1,3,2-dioxaborolan-2-yl)benzyl)oxy)pyridine (Intermediate E)

E

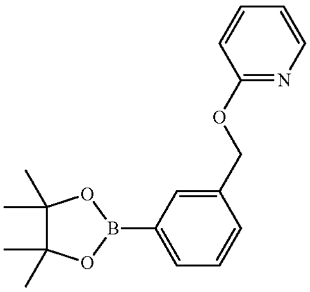

To a mixture of Intermediate C (2 g, 7.57 mmol) and 4,4,5,5-tetramethyl-2-(4,4,5,5-tetramethyl-1,3,2-dioxaborolan-2-yl)-1,3,2-dioxaborolane (2.31 g, 9.08 mmol) in dioxane (20 mL) was added KOAc (1.49 g, 15.14 mmol) and $Pd(dppf)Cl_2$ (276.95 mg, 378.50 μmol) in one portion at 25° C. under $N_2$. The mixture was stirred at 100° C. for 4 hours. The mixture was concentrated in vacuum. The residue was purified by column (PE/EA=10/1) and concentrated to afford Intermediate E (2.5 g, crude) as yellow oil. LCMS (ESI) m/z $[M+H]^+$=312.1; $^1$HNMR (400 MHz, Methanol-$d_4$) δ 8.16-8.04 (m, 1H), 7.83 (s, 1H), 7.71-7.69 (m, 2H), 7.57-7.55 (m, 1H), 7.44-7.34 (m, 1H), 6.97-6.87 (m, 1H), 6.88-6.87 (m, 1H), 5.36 (s, 2H), 1.36 (s, 12H).

Step 3: Preparation of 1-(methylsulfonyl)-N-(2-oxo-2-((4-(3-((pyridin-2-yloxy)methyl)phenyl)thiazol-2-yl)amino)ethyl)-1H-pyrrole-3-carboxamide (Compound 107)

Compound 107

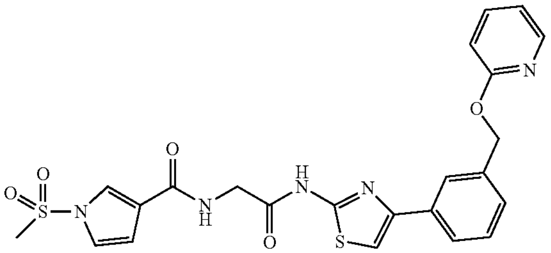

To a mixture of N-[2-[(4-bromothiazol-2-yl)amino]-2-oxo-ethyl]-1-methylsulfonyl-pyrrole-3-carboxamide [prepared according to the method in Example 6] (100 mg, 245.54 μmol) and Intermediate E (229.22 mg, 736.62 μmol) in dioxane (5 mL) and $H_2O$ (1 mL) was added [1,1'-bis(di-tert-butylphosphino)ferrocene]dichloropalladium(II) (16.00 mg, 24.55 μmol) and $K_3PO_4$ (104.24 mg, 491.08 μmol) in one portion at 25° C. under $N_2$. The mixture was stirred at 75° C. for 4 hours. The mixture was poured into water (30 mL) and extracted with EtOAc (30 mL×2). The combined organic phase was washed with brine (20 mL), dried over anhydrous $Na_2SO_4$, filtered and concentrated in vacuum. The residue was purified by reverse phase column (FA) and lyophilized to afford Compound 107 (33.94 mg, 60.62 μmol, 24.69% yield, FA salt) as a yellow solid. LCMS (ESI) m/z $[M+H]^+$=512.2; $^1$H NMR (400 MHz, DMSO-$d_6$) δ 12.42 (br s, 1H), 8.70-8.67 (m, 1H), 8.22-8.18 (m, 1H), 8.00 (s, 1H), 7.89-7.85 (m, 2H), 7.75-7.73 (m, 1H), 7.65 (s, 1H), 7.48-7.38 (m, 2H), 7.32-7.29 (m, 1H), 7.01-6.99 (m, 1H), 6.91 (d, J=8.2 Hz, 1H), 6.78-6.76 (m, 1H), 5.40 (s, 2H), 4.14 (d, J=5.6 Hz, 2H), 3.58 (s, 3H).

Example 106. Preparation of 1-(methylsulfonyl)-N-(2-oxo-2-((4-(3-((pyridin-4-yloxy)methyl)phenyl)thiazol-2-yl)amino)ethyl)-1H-pyrrole-3-carboxamide (Compound 108)
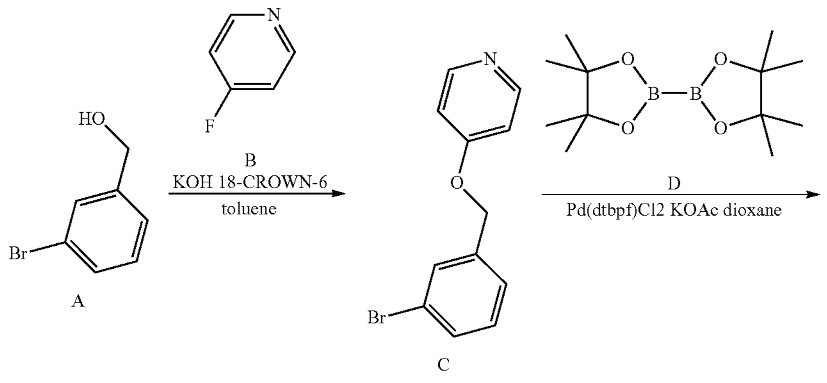
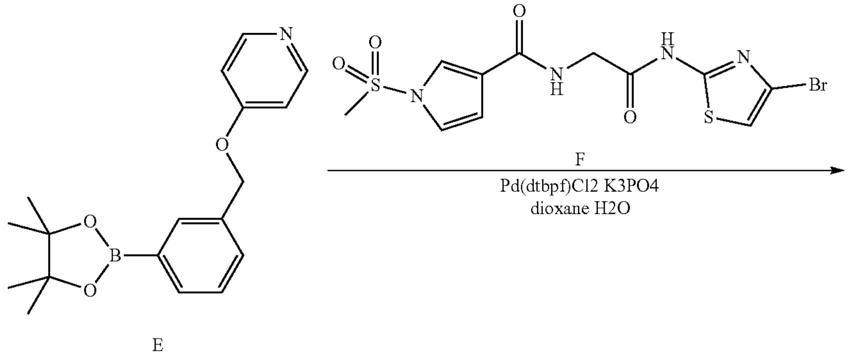
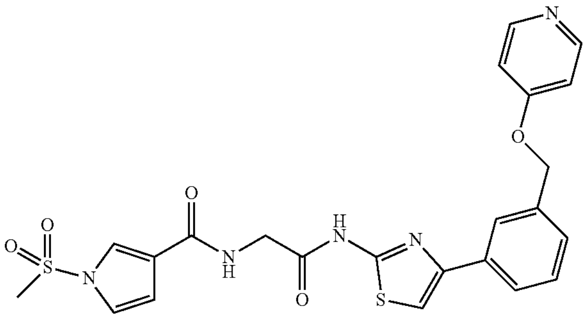
Compound 108

Step 1: Preparation of 4-((3-bromobenzyl)oxy)pyridine (Intermediate C)

C

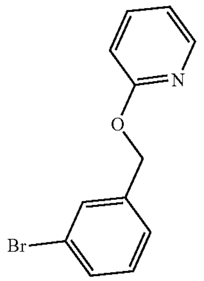

The solution of 3-bromophenyl)methanol (500 mg, 2.67 mmol, 320.51 μL) and 4-fluoropyridine (389.33 mg, 4.01 mmol) in toluene (5 mL) was added KOH (599.95 mg, 10.69 mmol) and 18-CROWN-6 (777.26 mg, 2.94 mmol) at 25° C. The reaction mixture was stirred at 25° C. for 16 hours. The reaction mixture was poured into water (20 mL) and extracted with EtOAc (20 mL×2), the combined organic layers was dried over anhydrous $Na_2SO_4$, concentrated to afford Intermediate C (800 mg, crude) as a yellow oil. LCMS (ESI) m/z $[M+H]^+$=263.9; $^1H$ NMR (400 MHz, DMSO-$d_6$) δ 8.42-8.38 (m, 2H), 7.68-7.67 (m, 1H), 7.58-7.53 (m, 1H), 7.47 (d, J=8.0 Hz, 1H), 7.40-7.34 (m, 1H), 7.06-7.02 (m, 2H), 5.20 (s, 2H).

Step 2: Preparation of 4-((3-(4,4,5,5-tetramethyl-1,3,2-dioxaborolan-2-yl)benzyl)oxy)pyridine (Intermediate E)

E

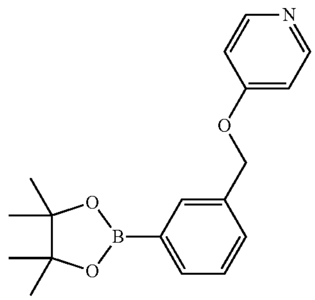

The solution of Intermediate C (800 mg, 3.03 mmol), 4,4,5,5-tetramethyl-2-(4,4,5,5-tetramethyl-1,3,2-dioxaborolan-2-yl)-1,3,2-dioxaborolane (1.54 g, 6.06 mmol) and KOAc (891.81 mg, 9.09 mmol) in dioxane (8 mL) was added [1,1'-bis(di-tert-butylphosphino)ferrocene]dichloropalladium(II) (197.41 mg, 302.90 μmol) at 25° C. under $N_2$. The reaction mixture was stirred at 70° C. under $N_2$ for 16 hours. The reaction mixture was diluted with EtOAc (2 mL). The mixture was purified by silica gel chromatography (PE/EA=10/1 to 3/1) and concentrated to afford Intermediate E (350 mg, 1.00 mmol, 33.17% yield) as black brown solid. LCMS (ESI) m/z $[M+H]^+$=312.2; $^1H$ NMR (400 MHz, DMSO-$d_6$) δ 8.40 (br s, 1H), 7.91 (s, 1H), 7.76 (s, 1H), 7.64 (d, J=7.2 Hz, 1H), 7.58 (d, J=7.6 Hz, 1H), 7.42-7.41 (m, 1H), 7.04 (d, J=4.6 Hz, 2H), 5.21 (s, 2H), 1.29 (s, 12H).

Step 3: Preparation of 1-(methylsulfonyl)-N-(2-oxo-2-((4-(3-((pyridin-4-yloxy)methyl)phenyl)thiazol-2-yl)amino)ethyl)-1H-pyrrole-3-carboxamide (Compound 108)

Compound 108

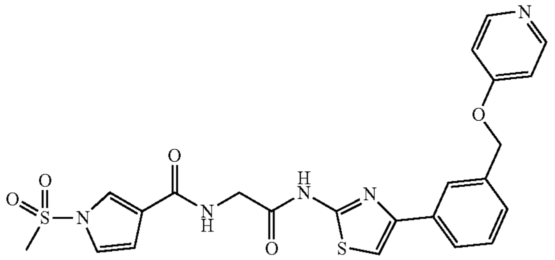

The solution of N-[2-[(4-bromothiazol-2-yl)amino]-2-oxo-ethyl]-1-methylsulfonyl-pyrrole-3-carboxamide [prepared according to the method in Example 6] (100 mg, 245.54 μmol), Intermediate E (342.14 mg, 982.17 μmol) and $K_3PO_4$ (156.36 mg, 736.62 μmol) in dioxane (0.8 mL) and $H_2O$ (0.2 mL) was added [1,1'-bis(di-tert-butylphosphino)ferrocene]dichloropalladium(II) (16.00 mg, 24.55 μmol) at 25° C. under $N_2$. The reaction mixture was stirred at 80° C. under $N_2$ for 16 hours. The reaction mixture was diluted with water (10 mL) and extracted with EtOAc (10 mL×3), the combined organic layers was dried over anhydrous $Na_2SO_4$ and concentrated to afford a brown solid. The solid was dissolved with DMSO (2 mL), then purified by reversed-phase HPLC (FA), concentrated and lyophilized to afford Compound 108 (14.77 mg, 26.06 μmol, 10.61% yield, FA salt) as a yellow solid. LCMS (ESI) m/z $[M+H]^+$=512.2; $^1H$ NMR (400 MHz, DMSO-$d_6$) δ 12.53-12.32 (m, 1H), 8.69-8.68 (m, 1H), 8.41 (d, J=5.6 Hz, 2H), 8.25 (br s, 1H), 8.00 (s, 1H), 7.91-7.83 (m, 2H), 7.66 (s, 1H), 7.50-7.40 (m, 2H), 7.33-7.29 (m, 1H), 7.06 (d, J=5.6 Hz, 2H), 6.77 (br s, 1H), 5.25 (s, 2H), 4.13 (d, J=6.0 Hz, 2H), 3.57 (s, 3H).

Example 107. Preparation of N-(2-((4-(2-methyl-3-oxo-1,2,3,4-tetrahydroisoquinolin-6-yl)thiazol-2-yl)amino)-2-oxoethyl)-1-(methylsulfonyl)-1H-pyrrole-3-carboxamide (Compound 109)

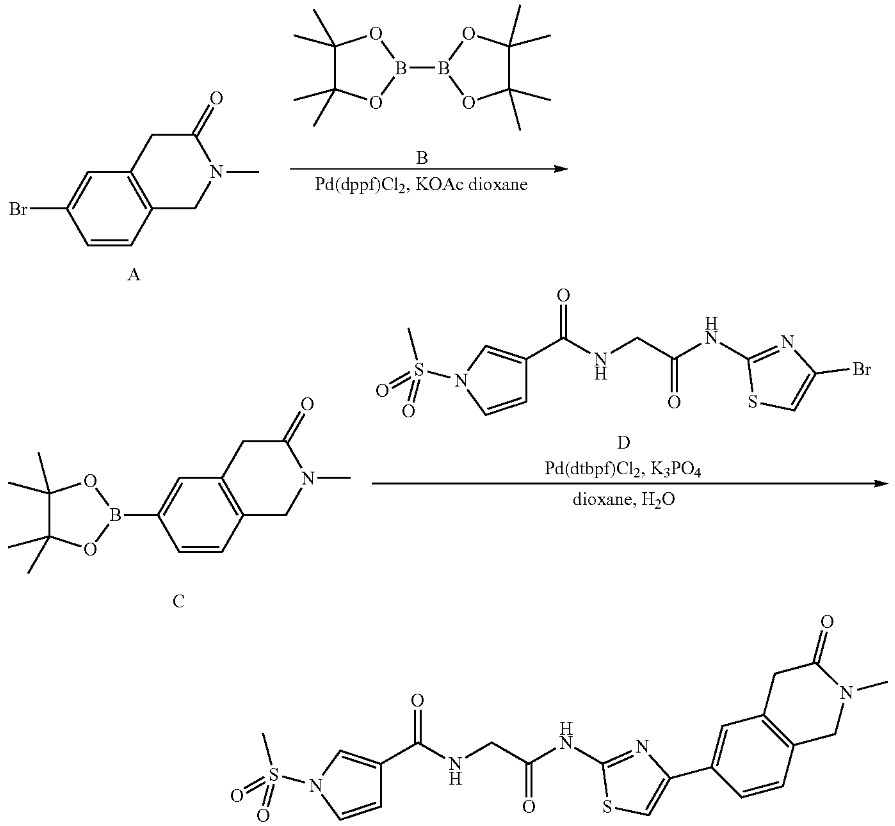

Compound 109

Step 1: Preparation of 2-methyl-6-(4,4,5,5-tetramethyl-1,3,2-dioxaborolan-2-yl)-1,2-dihydroisoquinolin-3(4H)-one (Intermediate C)

C

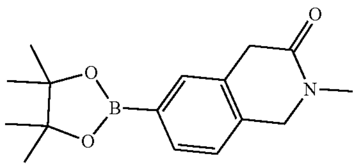

6-bromo-2-methyl-1,4-dihydroisoquinolin-3-one (50 mg, 208.25 μmol), 4,4,5,5-tetramethyl-2-(4,4,5,5-tetramethyl-1,3,2-dioxaborolan-2-yl)-1,3,2-dioxaborolane (58.17 mg, 229.07 μmol), $Pd(dppf)Cl_2$ (15.24 mg, 20.82 μmol) and KOAc (40.88 mg, 416.50 μmol) were taken up in dioxane (0.5 mL), the mixture was purged with $N_2$ three times. Then the resulting mixture was stirred at 80° C. for 2 hr. The reaction mixture was diluted with water (5 mL) and extracted with EtOAc (5 mL×3). The combined organic layers were washed with brine (5 mL), dried over $Na_2SO_4$, filtered and concentrated under reduced pressure to give Intermediate C (50 mg, crude) as yellow solid, which was used for the next step directly. LCMS (ESI) m/z $[M+H]^+$=288.2.

Step 2: Preparation of N-(2-((4-(2-methyl-3-oxo-1,2,3,4-tetrahydroisoquinolin-6-yl)thiazol-2-yl)amino)-2-oxoethyl)-1-(methylsulfonyl)-1H-pyrrole-3-carboxamide (Compound 109)

Compound 109

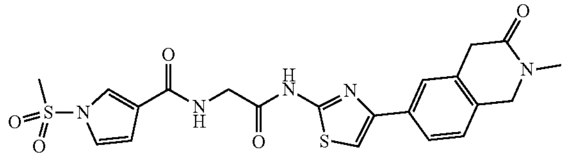

Intermediate C (45 mg, 156.71 μmol), N-[2-[(4-bromothiazol-2-yl)amino]-2-oxo-ethyl]-1-methylsulfonyl-pyrrole-3-carboxamide [prepared according to the method in Example 6] (63.82 mg, 156.71 μmol), [1,1'-bis(di-tert-butylphosphino)ferrocene]dichloropalladium(II) (10.21 mg, 15.67 μmol) and $K_3PO_4$ (66.53 mg, 313.41 μmol) were taken up in dioxane (0.5 mL) and $H_2O$ (0.1 mL), the mixture was purged with $N_2$ three times. Then the resulting mixture was stirred at 80° C. for 2 hr. The reaction mixture was diluted with water (5 mL) and extracted with EtOAc (5 mL×3). The combined organic layers were washed with brine (5 mL), dried over $Na_2SO_4$, filtered and concentrated under reduced pressure to give product. The residue was purified by Prep-HPLC (FA condition) and lyophilized to give Compound 109 (16.13 mg, 32.09 μmol, 20.48% yield) as yellow solid. LCMS (ESI) m/z $[M+H]^+$=488.2; $^1H$ NMR (400 MHz, DMSO-$d_6$) δ 12.43 (br d, J=3.2 Hz, 1H), 8.69-8.67 (m, 1H), 7.84-7.83 (m, 1H), 7.77-7.72 (m, 2H), 7.60 (s, 1H), 7.32-7.30 (m, 2H), 6.77-6.76 (m, 1H), 4.53 (s, 2H), 4.13 (br d, J=6.0 Hz, 2H), 3.57 (s, 5H), 2.97 (s, 3H).

Example 108. Preparation of 1-(methylsulfonyl)-N-(2-((4-(3-(oxetan-3-ylmethoxy)phenyl)thiazol-2-yl)amino)-2-oxoethyl)-1H-pyrrole-3-carboxamide (Compound 110)

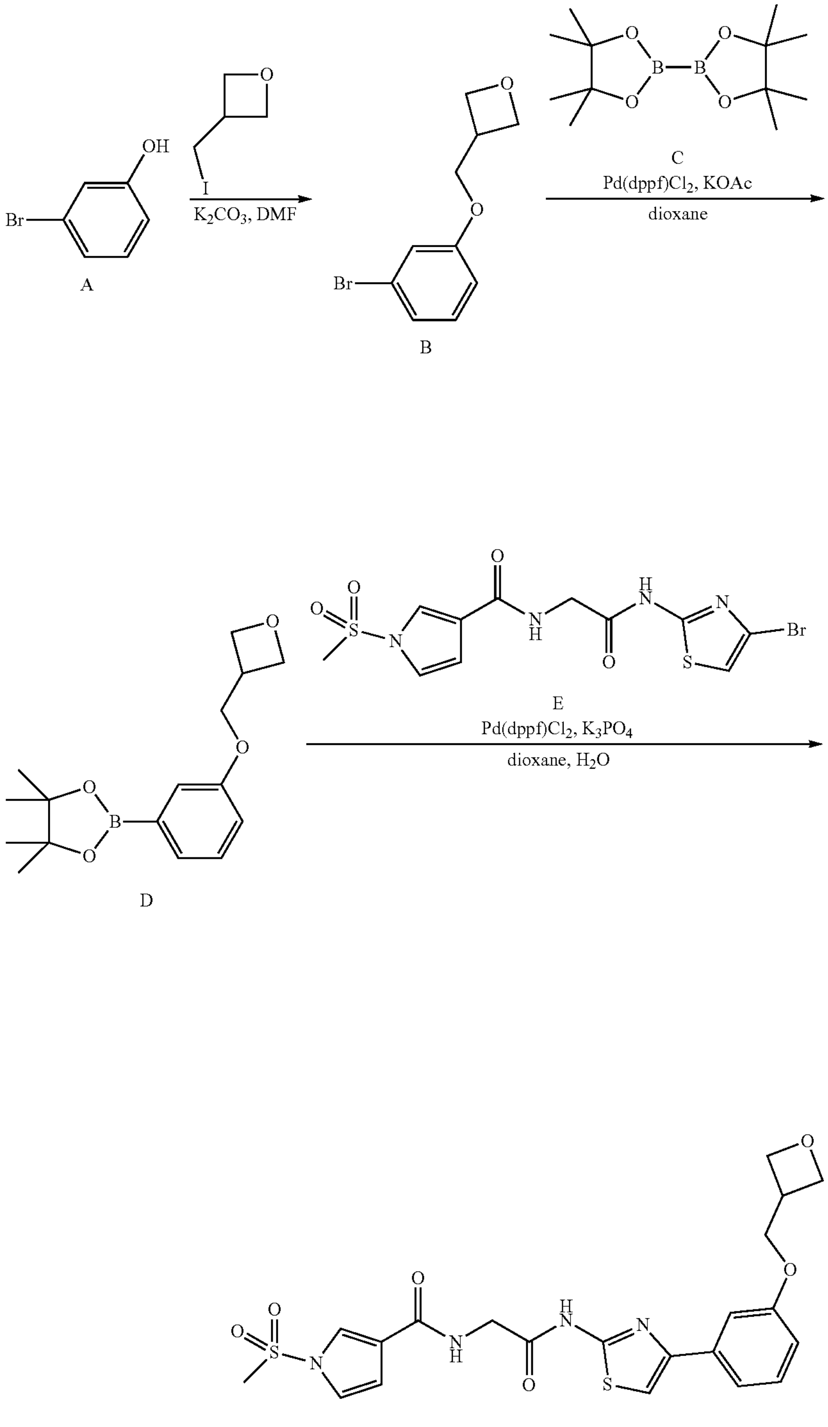

Compound 110

Step 1: Preparation of 3-((3-bromophenoxy)methyl)oxetane (Intermediate B)

B

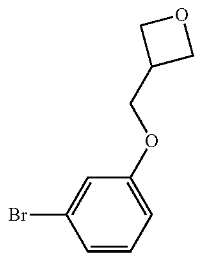

To a solution of 3-bromophenol (300 mg, 1.73 mmol) and 3-(iodomethyl)oxetane (343.34 mg, 1.73 mmol) in DMF (3 mL) was added $K_2CO_3$ (718.96 mg, 5.20 mmol), the mixture was stirred at 30° C. for 2 h. The mixture was diluted with water (20 mL) and extracted with EtOAc (20 mL×3). The combined organic layers were washed with brine (50 mL), dried over $Na_2SO_4$, filtered and concentrated under reduced pressure to give a residue. The residue was purified by reverse phase (FA) and lyophilized to give Intermediate B (300 mg, 1.23 mmol, 71.03% yield) as light yellow oil. LCMS (ESI) m/z $[M+H]^+$=243.0.

Step 2: Preparation of 4,4,5,5-tetramethyl-2-(3-(oxetan-3-ylmethoxy)phenyl)-1,3,2-dioxaborolane (Intermediate D)

D

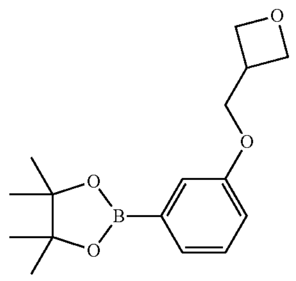

To a solution of Intermediate B (100 mg, 411.36 μmol), 4,4,5,5-tetramethyl-2-(4,4,5,5-tetramethyl-1,3,2-dioxaborolan-2-yl)-1,3,2-dioxaborolane (125.35 mg, 493.63 μmol) and Pd(dppf)$Cl_2$ (60.20 mg, 82.27 μmol) in dioxane (2 mL) was added KOAc (121.12 mg, 1.23 mmol) under $N_2$, the mixture was stirred at 80° C. for 1 h. The reaction mixture was diluted with water 10 mL and extracted with EtOAc (10 mL×3). The combined organic layers were washed with brine (30 mL), dried over $Na_2SO_4$, filtered and concentrated under reduced pressure to give Intermediate D (110 mg, crude) as black brown oil, which was used to the next step without further purification. LCMS (ESI) m/z $[M+H]^+$=291.3.

Step 3: Preparation of 1-(methylsulfonyl)-N-(2-((4-(3-(oxetan-3-ylmethoxy)phenyl)thiazol-2-yl)amino)-2-oxoethyl)-1H-pyrrole-3-carboxamide (Compound 110)

Compound 110

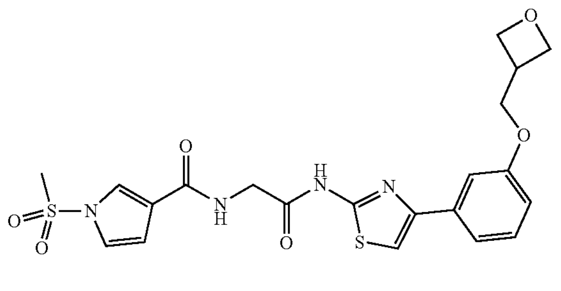

To a solution of Intermediate D (106.87 mg, 368.31 μmol), N-[2-[(4-bromothiazol-2-yl)amino]-2-oxo-ethyl]-1-methylsulfonyl-pyrrole-3-carboxamide [prepared according to the method in Example 7] (50 mg, 122.77 μmol) and [1,1'-bis(di-tert-butylphosphino)ferrocene]dichloropalladium(II) (16.00 mg, 24.55 μmol) in dioxane (1 mL) and water (0.25 mL) was added $K_3PO_4$ (78.18 mg, 368.31 μmol) under $N_2$, the mixture was stirred at 80° C. for 1 h. The reaction mixture was diluted with water (10 mL) and extracted with EtOAc 30 mL (10 mL×3). The combined organic layers were washed with brine (30 mL), dried over $Na_2SO_4$, filtered and concentrated under reduced pressure to give a residue. The residue was purified by column chromatography ($SiO_2$, Petroleum ether/EtOAc=0:1) and concentrated under reduced pressure to give Compound 110 (8.88 mg, 17.90 μmol, 14.58% yield) as a gray solid. LCMS (ESI) m/z $[M+H]^+$=491.2. $^1H$ NMR (400 MHz, DMSO-$d_6$) δ 12.37 (s, 1H), 8.68-8.65 (m, 1H), 7.84-7.83 (m, 1H), 7.67 (s, 1H), 7.50-7.49 (m, 2H), 7.36-7.30 (m, 2H), 6.93-6.91 (m, 1H), 6.77-6.76 (m, 1H), 4.74-4.71 (m, 2H), 4.46-4.43 (m, 2H), 4.25 (d, J=6.4 Hz, 2H), 4.13 (d, J=6.0 Hz, 2H), 3.57 (s, 3H), 3.44-3.37 (m, 1H).

Example 109. Preparation of 4-amino-N-(2-oxo-2-((4-(1-(pyridin-4-yl)piperidin-3-yl)thiazol-2-yl)amino)ethyl)benzamide (Compound 111)

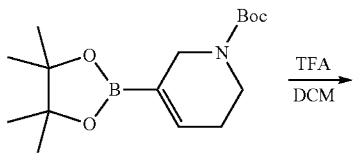

A

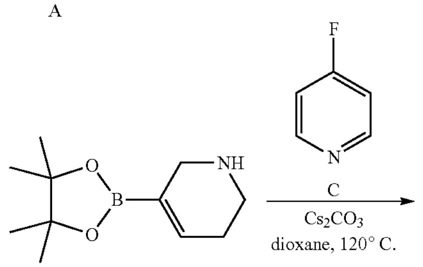

B

-continued

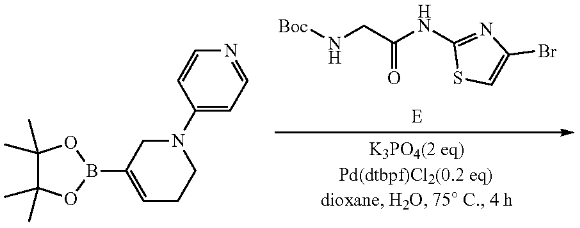

D

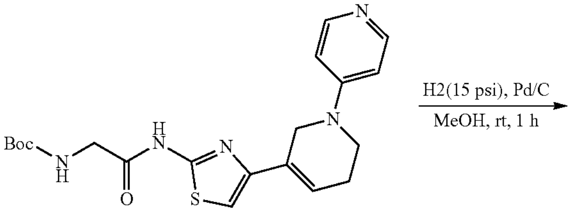

F

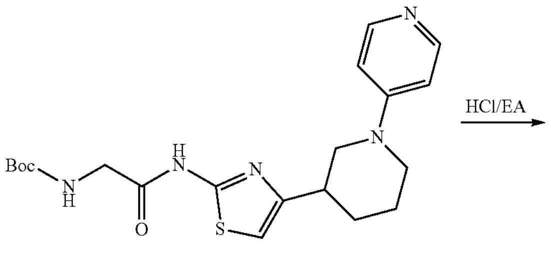

G

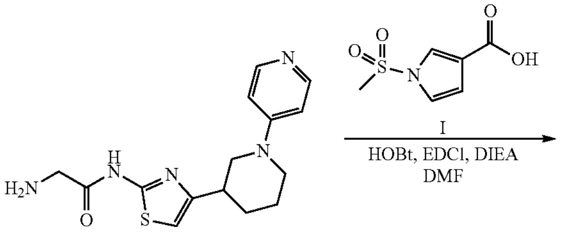

H

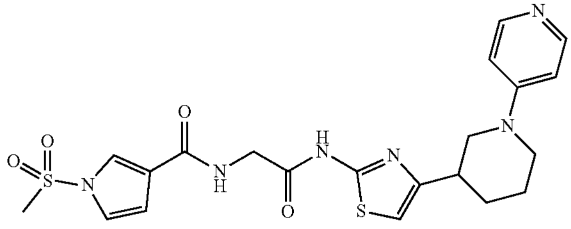

Compound 111

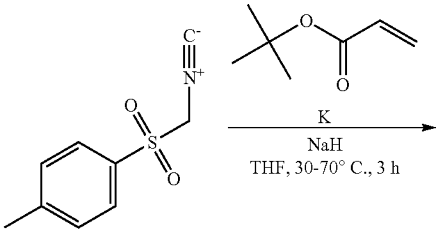

J

-continued

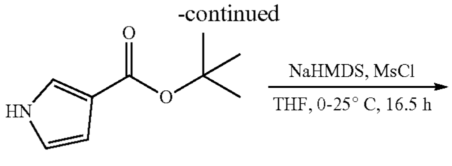

L

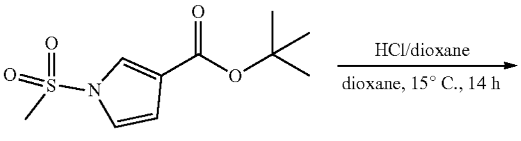

M

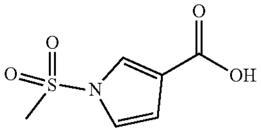

I

Step 1: Preparation of 5-(4,4,5,5-tetramethyl-1,3,2-dioxaborolan-2-yl)-1,2,3,6-tetrahydropyridine (Intermediate B)

B

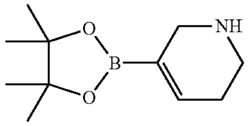

To a mixture of tert-butyl 3-(4,4,5,5-tetramethyl-1,3,2-dioxaborolan-2-yl)-5,6-dihydropyridine-1(2H)-carboxylate (1 g, 3.23 mmol) in DCM (10 mL) was added TFA (15.40 g, 135.06 mmol, 10.00 mL) in one portion at 25° C. The mixture was stirred at 25° C. for 1 hour. The mixture was concentrated in vacuum to give Intermediate B (1.3 g, crude, TFA salt) as colorless oil, which was used for the next step without purification. $^1$H NMR (400 MHz, DMSO-$d_6$) δ 8.72 (br s, 2H), 6.58-6.57 (m, 1H), 3.58-3.58 (m, 2H), 3.16-3.14 (m, 2H), 2.35-2.33 (m, 2H), 1.21 (s, 12H).

Step 2: Preparation of 5-(4,4,5,5-tetramethyl-1,3,2-dioxaborolan-2-yl)-3,6-dihydro-2H-1,4'-bipyridine (Intermediate D)

D

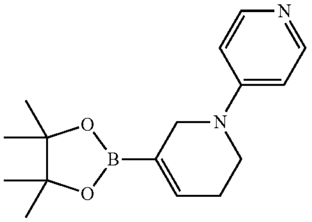

To a mixture of 4-fluoropyridine (150 mg, 1.12 mmol, HCl salt) and Intermediate B (362.91 mg, 1.12 mmol, TFA salt) in dioxane (10 mL) was added $Cs_2CO_3$ (1.10 g, 3.37 mmol) in one portion. The mixture was stirred at 120° C. for 12 h. The mixture was poured into ice-water (20 mL) and extracted with EtOAc (20 mL). The combined organic phase was washed with brine (10 mL), dried with anhydrous $Na_2SO_4$, filtered and concentrated in vacuum to give Intermediate D (300 mg, crude) as yellow oil. LCMS (ESI) m/z $[M+H]^+$=287.3.

Step 3: Preparation of tert-butyl (2-((4-(5,6-dihydro-2H-[1,4'-bipyridin]-3-yl)thiazol-2-yl)amino)-2-oxoethyl)carbamate (Intermediate F)

F

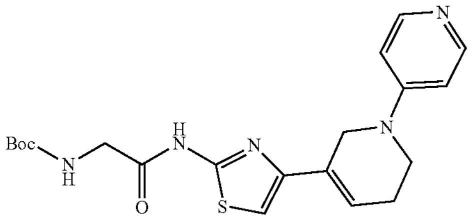

To a mixture of Intermediate D (191.52 mg, 669.23 μmol) and tert-butyl (2-((4-bromothiazol-2-yl)amino)-2-oxoethyl) carbamate [prepared according to the method in Example 6] (150 mg, 446.16 μmol) in dioxane (10 mL) and $H_2O$ (2 mL) was added $K_3PO_4$ (189.41 mg, 892.31 μmol) and [1,1'-bis (di-tert-butylphosphino)ferrocene]dichloropalladium(II) (29.08 mg, 44.62 μmol) in one portion at 25° C. under $N_2$. The mixture was stirred at 75° C. under $N_2$ for 12 h. The mixture was poured into water (40 mL) and stirred for 5 min. The aqueous phase was extracted with EtOAc (30 mL×3). The combined organic phase was washed with brine (10 mL), dried over anhydrous $Na_2SO_4$, filtered and concentrated in vacuum. The residue was purified by reverse phase column (FA) to give Intermediate F (30 mg, 72.20 μmol, 16.18% yield) as light yellow solid. LCMS (ESI) m/z $[M+H]^+$=416.1; $^1H$ NMR (400 MHz, Methanol-$d_4$) δ 8.15-8.13 (m, 2H), 7.09 (s, 1H), 6.95-6.90 (m, 2H), 6.76 (s, 1H), 4.24 (d, J=2.0 Hz, 2H), 3.96 (s, 2H), 3.65-3.62 (m, 2H), 2.54-2.46 (m, 2H), 1.48 (s, 9H).

Step 4: Preparation of tert-butyl (2-oxo-2-((4-(1-(pyridin-4-yl)piperidin-3-yl)thiazol-2-yl)amino) ethyl)carbamate (Intermediate G)

G

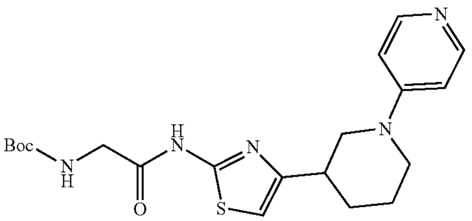

To a solution of Intermediate F (55 mg, 132.37 μmol) in MeOH (5 mL) was added Pd/C (30 mg, 10% purity) under $N_2$. The suspension was degassed under vacuum and purged with $H_2$ several times. The mixture was stirred under $H_2$ (15 psi) at 25° C. for 1 hours. The reaction mixture was filtered and the filter was concentrated in vacuum to give Intermediate G (50 mg, 119.75 μmol, 90.47% yield) as yellow oil, which was used for the next step directly without purification. LCMS (ESI) m/z $[M+H]^+$=418.0.

Step 5: Preparation of 2-amino-N-(4-(1-(pyridin-4-yl)piperidin-3-yl)thiazol-2-yl)acetamide (Intermediate H)

H

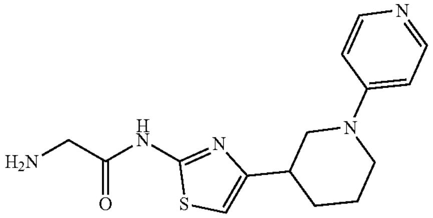

To a solution of Intermediate G (50 mg, 119.75 μmol) in EtOAc (0.5 mL) was added HCl/EtOAc (4 M, 149.69 μL) in one portion at 25° C. The mixture was stirred at 25° C. for 10 min. The mixture was concentrated to give Intermediate H (50 mg, crude, HCl salt) as light-yellow solid. LCMS (ESI) m/z $[M+H]^+$=318.3.

Step 6: Preparation of tert-butyl 1H-pyrrole-3-carboxylate (Intermediate L)

L

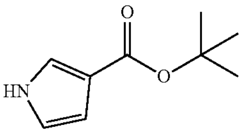

To a mixture of tert-butyl prop-2-enoate (69.42 g, 541.65 mmol, 78.62 mL) and 1-(isocyanomethylsulfonyl)-4-methylbenzene (105.75 g, 541.65 mmol) in THF (1300 mL) was added NaH (25.97 g, 649.37 mmol, 60% purity) slowly at 30° C. during 1 h. The reaction mixture was heated to 70° C. and stirred at 70° C. for 2 h. The reaction mixture was poured into saturated $NH_4Cl$ aqueous solution (1500 mL) and extracted with EA (3×800 mL). The combined organic phase was washed with brine (2×500 mL), dried over anhydrous $Na_2SO_4$ filtered and concentrated under reduced pressure to afford a residue. The residue was purified by silica gel column chromatography (Petroleum ether/EtOAc=20:1-3:1) (TLC:PE/EA=3/1, Rf=0.6) to afford intermediate L (41.5 g, 235.70 mmol, 43% yield) as yellow solid. LCMS (ESI) m/z $[M+Na]^+$=180.4; $^1H$ NMR (400 MHz, $CDCl_3$) δ 8.36 (br s, 1H), 7.35-7.25 (m, 1H), 6.71-6.62 (m, 1H), 6.59-6.49 (m, 1H), 1.48 (s, 9H).

Step 7: Preparation of tert-butyl 1-methylsulfonylpyrrole-3-carboxylate (Intermediate M)

M

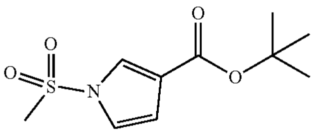

To a solution of intermediate L (40.5 g, 242.22 mmol) in THF (1500 mL) was added NaHMDS (1 M, 484.44 mL) slowly at 0° C. under $N_2$. The reaction mixture was stirred at 0° C. for 30 min under $N_2$. Then to the reaction mixture was added methanesulfonyl chloride (41.62 g, 363.33 mmol, 28.12 mL) slowly at 0° C. under $N_2$. The reaction mixture was warmed to 30° C. and stirred at 30° C. for 16 h under $N_2$. The reaction mixture was poured into saturated $NH_4Cl$ aqueous solution (1500 mL) slowly and extracted with EA (3×1000 mL). The combined organic layers were washed with brine (2×600 mL), dried over anhydrous $Na_2SO_4$, filtered and concentrated under reduced pressure to afford a residue. The residue was purified by silica gel chromatography (PE/EA=10/1) (TLC:PE/EA=3/1, Rf=0.55) to afford a yellow solid. The yellow solid was triturated with MTBE (100 mL) at 20° C. for 20 min, filtered and dried in vacuum to afford intermediate M (25.7 g, 104.77 mmol, 43% yield) as white solid. $^1$H NMR (400 MHz, $CDCl_3$) δ 7.66-7.64 (m, 1H), 7.10-7.08 (m, 1H), 6.73-6.71 (m, 1H), 3.21 (s, 3H), 1.56 (s, 9H).

Step 8: Preparation of 1-methylsulfonylpyrrole-3-carboxylic acid (Intermediate I)

I

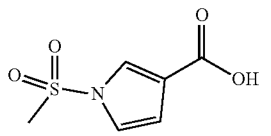

To a mixture of intermediate M (25.7 g, 104.77 mmol) in dioxane (100 mL) was added HCl/dioxane (4 M, 400 mL) at 15° C. The reaction mixture was stirred at 15° C. for 14 hr. The reaction mixture was concentrated under reduced pressure to afford a residue. The residue was triturated with MTBE (150 mL) at 15° C. for 16 h. The mixture was filtered and dried in vacuum to afford intermediate I (18.7 g, 98.84 mmol, 94% yield) as white solid. LCMS (ESI) m/z $[M+H]^+$=189.8; $^1$H NMR (400 MHz, Methanol-$d_4$) δ 7.78-7.77 (m, 1H), 7.25-7.23 (m, 1H), 6.72-6.70 (m, 1H), 3.37 (s, 3H).

Step 9: Preparation of 1-(methylsulfonyl)-N-(2-oxo-2-((4-(1-(pyridin-4-yl)piperidin-3-yl)thiazol-2-yl)amino)ethyl)-1H-pyrrole-3-carboxamide (Compound 111)

Compound 111

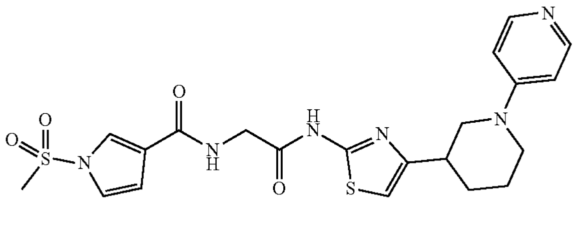

To a mixture of intermediate H (25 mg, 70.65 μmol, HCl salt) and 1-methylsulfonylpyrrole-3-carboxylic acid (13.37 mg, 70.65 μmol) in DMF (2 mL) was added EDCI (20.31 mg, 105.98 μmol), DIEA (45.65 mg, 353.25 μmol, 61.53 μL) and HOBt (14.32 mg, 105.98 μmol) in one portion at 25° C. The mixture was stirred at 25° C. for 12 hours. The reaction solution was concentrated in vacuum and then purified by prep-HPLC (mobile phase: [water (0.1% TFA)-acetonitrile]; B %: 11%-34%) and lyophilized to give Compound 111 (10.12 mg, 16.79 μmol, 23.77% yield, TFA salt) as yellow solid. LCMS (ESI) m/z $[M+H]^+$=489.2; $^1$H NMR (400 MHz, DMSO-$d_6$) δ 12.25 (s, 1H), 8.69-8.67 (m, 1H), 8.22 (d, J=7.4 Hz, 2H), 7.84-7.83 (m, 1H), 7.33-7.29 (m, 1H), 7.22 (d, J=7.4 Hz, 2H), 6.95 (s, 1H), 6.76-6.75 (m, 1H), 4.36-4.28 (m, 1H), 4.21 (d, J=13.4 Hz, 1H), 4.10 (d, J=5.6 Hz, 2H), 3.56 (s, 3H), 3.29-3.21 (m, 2H), 2.97-2.86 (m, 1H), 2.15-2.03 (m, 1H), 1.93-1.81 (m, 2H), 1.60 (d, J=13.2 Hz, 1H).

Example 110. Preparation of N-(2-((4-(2-methyl-1-oxo-1,2-dihydroisoquinolin-7-yl)thiazol-2-yl)amino)-2-oxoethyl)-1-(methylsulfonyl)-1H-pyrrole-3-carboxamide (Compound 112)

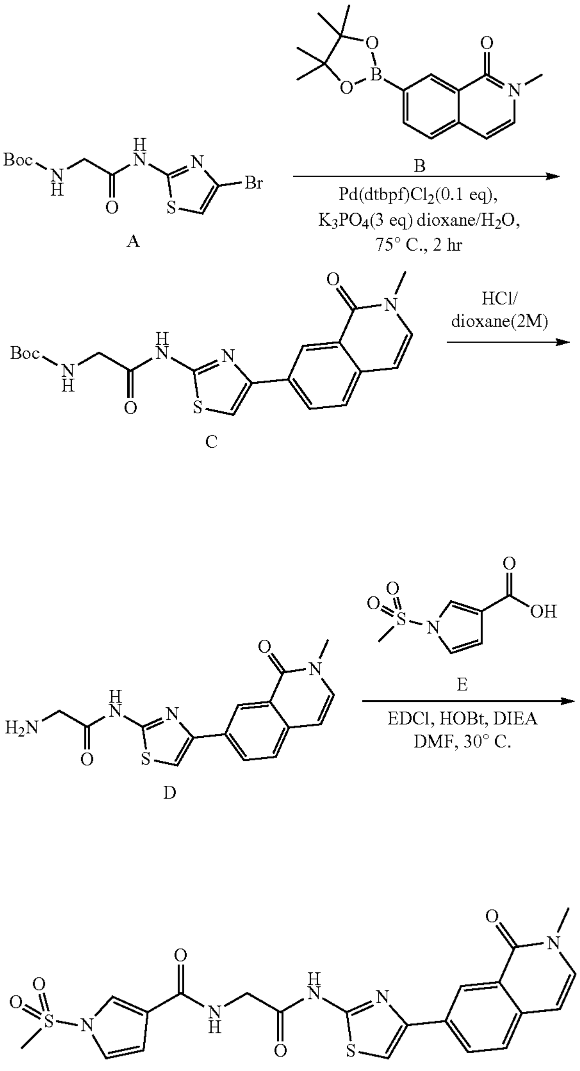

Compound 112

Step 1: Preparation of tert-butyl (2-((4-(2-methyl-1-oxo-1,2-dihydroisoquinolin-7-yl)thiazol-2-yl)amino)-2-oxoethyl)carbamate (Intermediate C)

C

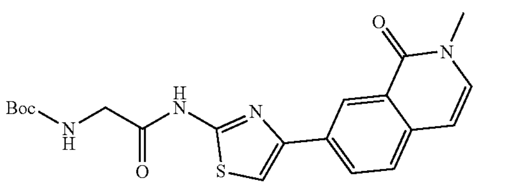

To a mixture of tert-butyl (2-((4-bromothiazol-2-yl)amino)-2-oxoethyl)carbamate [prepared according to the method in Example 6] (100 mg, 297.44 μmol) (prepared according to the method in Example 6) and 2-methyl-7-(4,4,5,5-tetramethyl-1,3,2-dioxaborolan-2-yl)isoquinolin-1(2H)-one (270.37 mg, 594.88 μmol) in dioxane (3 mL) and $H_2O$ (0.75 mL) was added [1,1'-bis(di-tert-butylphosphino)ferrocene]dichloropalladium(II) (19.39 mg, 29.74 μmol) and $K_3PO_4$ (189.41 mg, 892.32 μmol) under $N_2$ at 30° C. The reaction mixture was heated to 75° C. and stirred at 75° C. for 2 hr under $N_2$. The reaction mixture was filtered to afford a residue. The residue was purified by reverse phase column (FA condition) and lyophilized to afford Intermediate C (60 mg, 130.54 μmol, 43.89% yield) as a yellow solid. LCMS (ESI) m/z $[M+H]^+$=415.0; $^1$H NMR (400 MHz, DMSO-$d_6$) δ 12.38 (br s, 1H), 8.81 (s, 1H), 8.22-8.19 (m, 1H), 7.78 (s, 1H), 7.71 (d, J=8.0 Hz, 1H), 7.49 (d, J=7.2 Hz, 1H), 7.17-7.14 (m, 1H), 6.64 (d, J=7.2 Hz, 1H), 3.88 (d, J=6.0 Hz, 2H), 3.53 (s, 3H), 1.41 (s, 9H).

Step 2: Preparation of 2-amino-N-(4-(2-methyl-1-oxo-1,2-dihydroisoquinolin-7-yl)thiazol-2-yl)acetamide (Intermediate D)

D

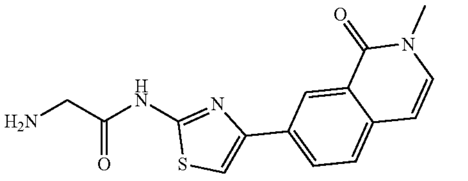

To a mixture in Intermediate C (60 mg, 144.76 μmol) in dioxane (1 mL) was added HCl/dioxane (4 M, 1 mL) at 30° C. The reaction mixture was stirred at 30° C. for 1 h. The reaction mixture was filtered and the solid was dried in vacuum to afford Intermediate D (50 mg, 120.25 μmol, 83.07% yield, HCl salt) as yellow solid. LCMS (ESI) m/z$[M+H]^+$=315.0; $^1$H NMR (400 MHz, DMSO-$d_6$) δ 12.84 (br s, 1H), 8.81 (d, J=1.6 Hz, 1H), 8.36 (br s, 2H), 8.23-8.20 (m, 1H), 7.87 (s, 1H), 7.72 (d, J=8.4 Hz, 1H), 7.50 (d, J=7.6 Hz, 1H), 6.65 (d, J=7.2 Hz, 1H), 3.94-3.92 (m, 2H), 3.53 (s, 3H).

Step 3: Preparation of N-(2-((4-(2-methyl-1-oxo-1,2-dihydroisoquinolin-7-yl)thiazol-2-yl)amino)-2-oxoethyl)-1-(methylsulfonyl)-1H-pyrrole-3-carboxamide (Compound 112)

Compound 112

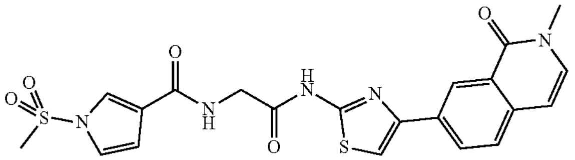

To a mixture of Intermediate D (40 mg, 114.02 μmol, HCl salt) and 1-methylsulfonylpyrrole-3-carboxylic acid [prepared according to the method in Example 4] (21.57 mg, 114.02 μmol) in DMF (1 mL) were added EDCI (32.79 mg, 171.03 μmol), HOBt (23.11 mg, 171.03 μmol) and DIPEA (44.21 mg, 342.05 μmol, 59.58 μL) at 30° C. The reaction mixture was stirred 30° C. for 16 h. The reaction mixture was purified by reverse phase column (FA condition) and lyophilized to afford Compound 112 (11.27 mg, 22.92 μmol, 20.10% yield) as a yellow solid. LCMS (ESI) m/z $[M+H]^+$=486.0. $^1$H NMR (400 MHz, DMSO-$d_6$) δ 12.49 (s, 1H), 8.82 (d, J=1.6 Hz, 1H), 8.69-8.66 (m, 1H), 8.21-8.19 (m, 1H), 7.85-7.84 (m, 1H), 7.77 (s, 1H), 7.70 (d, J=8.4 Hz, 1H), 7.48 (d, J=7.2 Hz, 1H), 7.32-7.30 (m, 1H), 6.78-6.77 (m, 1H), 6.63 (d, J=7.2 Hz, 1H), 4.15 (d, J=6.0 Hz, 2H), 3.57 (s, 3H), 3.52 (s, 3H).

Example 111. Preparation of 1-(methylsulfonyl)-N-(2-oxo-2-((4-(1-(pyridin-4-yl)-1H-pyrazol-3-yl)thiazol-2-yl)amino)ethyl)-1H-pyrrole-3-carboxamide (Compound 113)

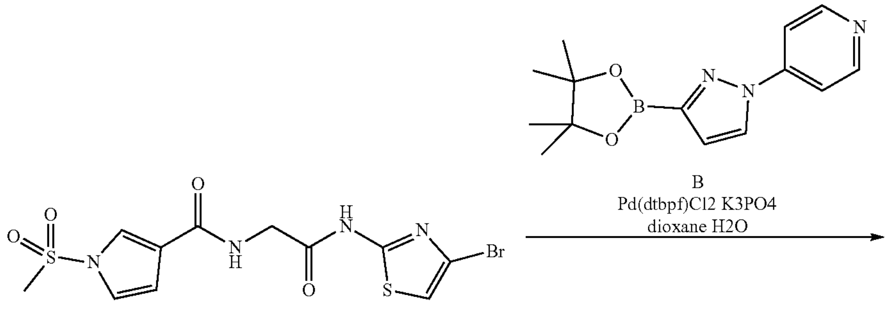

A

-continued

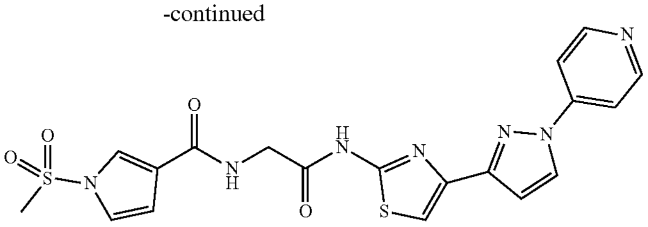

Compound 113

To a solution of N-(2-((4-bromothiazol-2-yl)amino)-2-oxoethyl)-1-(methylsulfonyl)-1H-pyrrole-3-carboxamide [prepared according to the method in Example 6] (80 mg, 196.43 μmol) and 4-(3-(4,4,5,5-tetramethyl-1,3,2-dioxaborolan-2-yl)-1H-pyrazol-1-yl)pyridine (266.29 mg, 982.17 μmol) in dixoane/$H_2O$=4/1 (5 mL) was added $K_3PO_4$ (125.09 mg, 589.30 μmol) and [1,1'-bis(di-tert-butylphosphino)ferrocene]dichloropalladium(II) (25.60 mg, 39.29 μmol). The mixture was stirred at 75° C. under $N_2$ for 4 h. This reaction mixture was diluted with $H_2O$ (10 mL) and extracted with EtOAc (10 mL×2). The combined organic layers were dried over anhydrous $Na_2SO_4$, filtered and concentrated under reduced pressure to give a residue. The residue was purified by reversed phase (0.1% FA condition) and lyophilized to afford Compound 113 (10.17 mg, 18.61 μmol, 9.48% yield, FA salt) as a yellow solid. LCMS (ESI) m/z $[M+H]^+$=472.3; $^1H$ NMR (400 MHz, DMSO-$d_6$) δ 12.85-12.31 (m, 1H), 8.76 (d, J=2.8 Hz, 1H), 8.68-8.66 (m, 3H), 7.91-7.90 (m, 2H), 7.86-7.85 (m, 1H), 7.67 (s, 1H), 7.32 (m, 1H), 6.97 (d, J=2.8 Hz, 1H), 6.78 (m, 1H), 4.15 (d, J=6.0 Hz, 2H), 3.58 (s, 3H).

Example 112. Preparation of 1-(methylsulfonyl)-N-(2-oxo-2-((4-(3-(1-(2,2,2-trifluoroethyl)piperidin-4-yl)phenyl)thiazol-2-yl)amino)ethyl)-1H-pyrrole-3-carboxamide (Compound 114)

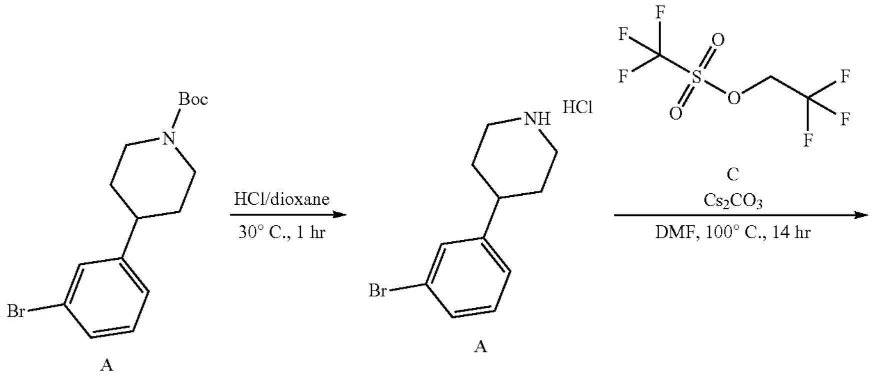

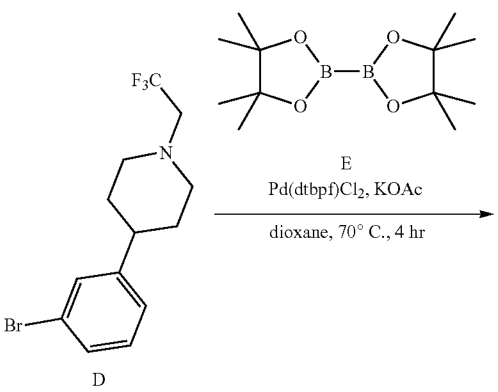

-continued

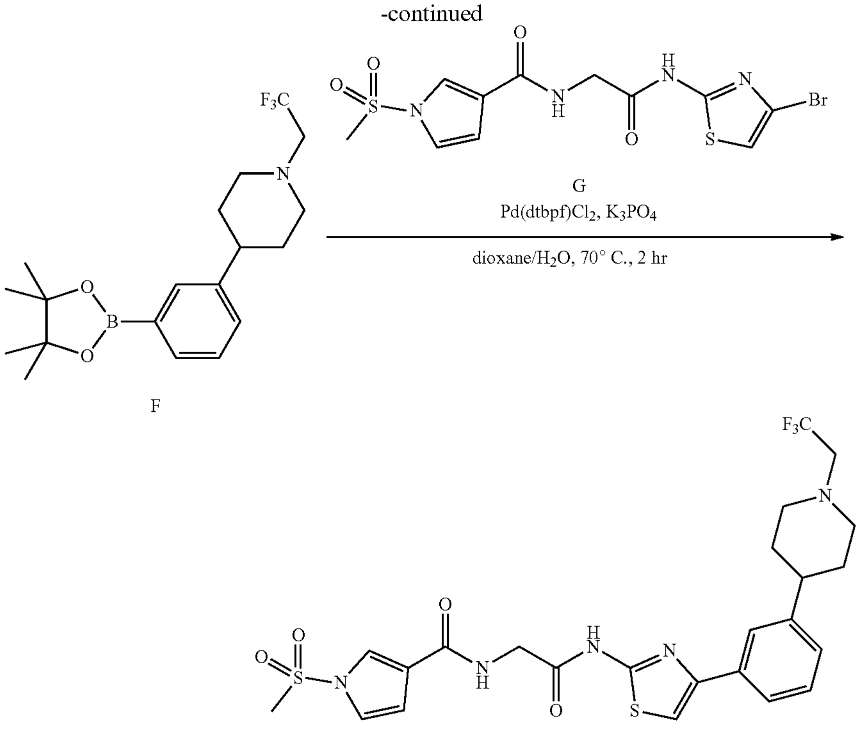

F

Compound 114

Step 1: Preparation of 4-(3-bromophenyl)piperidine (Intermediate B)

B

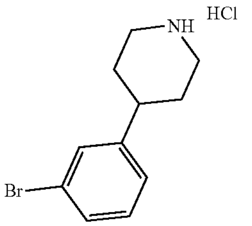

To a solution of Intermediate A (5 g, 14.69 mmol) in EtOAc (30 mL) was added HCl/EtOAc (4 M, 30 mL) at 30° C. The reaction mixture was stirred at 30° C. for 1 h. The reaction mixture was filtered and dried in vacuum to afford Intermediate B (3.9 g, 14.10 mmol, 95.95% yield, HCl salt) as white solid. LCMS (ESI) m/z[M+H]$^+$=240.2.

Step 2: Preparation of 4-(3-bromophenyl)-1-(2,2,2-trifluoroethyl)piperidine (Intermediate D)

D

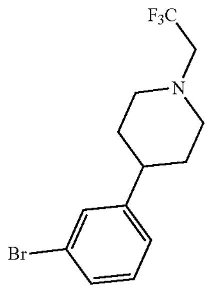

To a mixture of Intermediate B (500 mg, 1.81 mmol, HCl salt) in DMF (5 mL) was added $Cs_2CO_3$ (1.47 g, 4.52 mmol) and 2,2,2-trifluoroethyl trifluoromethanesulfonate (839.12 mg, 3.62 mmol) at 30° C. The reaction mixture was heated to 100° C. and stirred at 100° C. for 14 h. The reaction mixture was poured into water (50 mL), then extracted with EtOAc (50 mL×3), the combined organic phase was washed with brine (50 mL×3) and concentrated under reduced pressure to afford Intermediate D (770 mg, 1.58 mmol, 87.56% yield) as yellow oil. LCMS (ESI) m/z [M+H]$^+$=322.0.

Step 3: Preparation of 4-(3-(4,4,5,5-tetramethyl-1,3,2-dioxaborolan-2-yl)phenyl)-1-(2,2,2-trifluoroethyl)piperidine (Intermediate F)

F

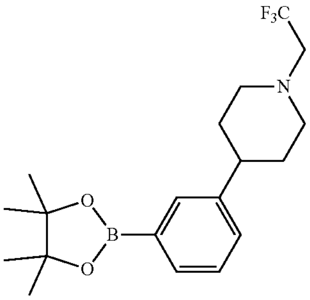

To a mixture of Intermediate D (670 mg, 2.08 mmol) and 4,4,4',4',5,5,5',5'-octamethyl-2,2'-bi(1,3,2-dioxaborolane) (633.73 mg, 2.50 mmol) in dioxane (12 mL) was added KOAc (612.32 mg, 6.24 mmol) and [1,1'-bis(di-tert-butylphosphino)ferrocene]dichloropalladium(II) (135.54 mg, 207.97 μmol) at 30° C. The reaction mixture was heated to 70° C. and stirred at 70° C. for 4 h under $N_2$. The reaction mixture was poured into water (40 mL) and extracted with EtOAc (30 mL×3). The combined organic phase was washed with brine (30 mL), dried over anhydrous $Na_2SO_4$, filtered and concentrated under reduced pressure to afford Intermediate F (1.2 g, crude) as brown oil. LCMS (ESI) m/z $[M+H]^+$=370.2.

Step 4: Preparation of 1-(methylsulfonyl)-N-(2-oxo-2-((4-(3-(1-(2,2,2-trifluoroethyl)piperidin-4-yl)phenyl)thiazol-2-yl)amino)ethyl)-1H-pyrrole-3-carboxamide (Compound 114)

Compound 114

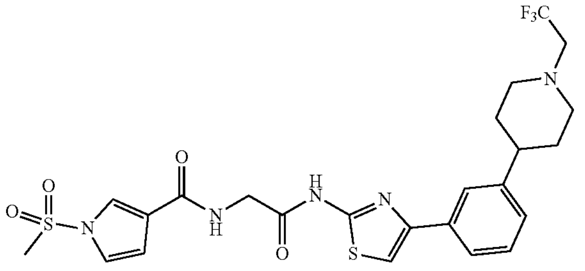

To a mixture of N-(2-((4-bromothiazol-2-yl)amino)-2-oxoethyl)-1-(methylsulfonyl)-1H-pyrrole-3-carboxamide [prepared according to the method in Example 6] (50 mg, 122.77 μmol) and 4-(3-(4,4,5,5-tetramethyl-1,3,2-dioxaborolan-2-yl)phenyl)-1-(2,2,2-trifluoroethyl)piperidine (135.99 mg, 368.31 μmol) in dioxane (1.6 mL) and $H_2O$ (0.4 mL) was added $K_3PO_4$ (78.18 mg, 368.31 μmol) and [1,1'-bis(di-tert-butylphosphino)ferrocene]dichloropalladium(II) (8.00 mg, 12.28 μmol) under $N_2$ at 30° C. The reaction mixture was heated to 70° C. and stirred at 70° C. for 2 h under $N_2$. The reaction mixture was concentrated under reduced pressure to afford a residue. The residue was purified by Prep-HPLC (mobile phase: [water (0.225% FA)-acetonitrile]; B %: 8%-38%) and lyophilized to afford Compound 114 (6.65 mg, 10.27 μmol, 8.36% yield, FA salt) as off-white solid. LCMS (ESI) m/z $[M+H]^+$=570.0; $^1H$ NMR (400 MHz, DMSO-$d_6$) δ 12.37 (br s, 1H), 8.68-8.65 (m, 1H), 8.43 (br s, 1H), 7.83 (, J=7.6 Hz, 2H), 7.72 (br d, J=7.6 Hz, 1H), 7.64 (s, 1H), 7.39-7.28 (m, 2H), 7.21 (d, J=7.6 Hz, 1H), 6.77 (d, J=1.6 Hz, 1H), 4.13 (d, J=6.0 Hz, 2H), 3.56 (s, 3H), 3.24-3.16 (m, 1H), 3.03 (d, J=11.6 Hz, 2H), 2.45-2.42 (m, 2H), 1.82-1.64 (m, 4H).

Example 113. Preparation of N-(2-((4-(3-(2-methyl-1H-imidazol-1-yl)phenyl)thiazol-2-yl)amino)-2-oxoethyl)-1-(methylsulfonyl)-1H-pyrrole-3-carboxamide (Compound 115)

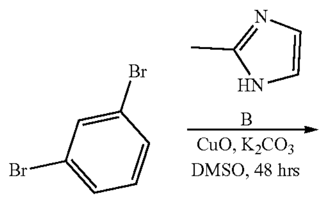

A

-continued

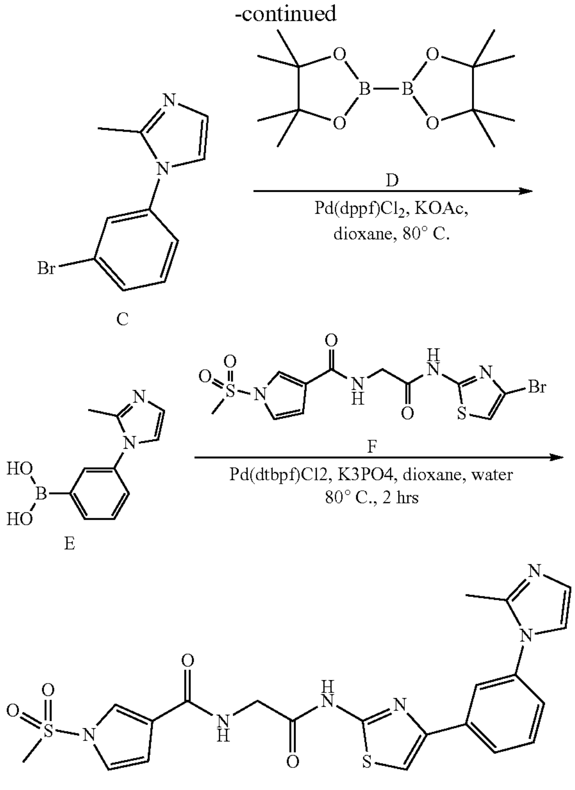

Compound 115

Step 1: Preparation of 1-(3-bromophenyl)-2-methyl-1H-imidazole (Intermediate C)

C

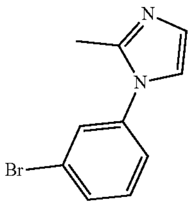

To a solution of 1,3-dibromobenzene (1.5 g, 6.36 mmol, 765.31 μL), 2-methyl-1H-imidazole (522.06 mg, 6.36 mmol) and CuO (151.74 mg, 1.91 mmol, 24.01 μL) in DMSO (15 mL) was added $K_2CO_3$ (2.11 g, 15.26 mmol), the mixture was stirred at 145° C. for 48 h. The reaction mixture was diluted with water (50 mL) and extracted with EtOAc (50 mL×3). The combined organic layers were washed with brine (50 mL), dried over $Na_2SO_4$, filtered and concentrated under reduced pressure to give a residue. The residue was purified column chromatography ($SiO_2$, Petroleum ether/EtOAc=1:1) and concentrated under reduced pressure to give Intermediate C (850 mg, 3.47 mmol, 54.52% yield) as light yellow oil. LCMS (ESI) m/z $[M+H]^+$=237.0; $^1H$ NMR (400 MHz, DMSO-$d_6$) δ 7.72-7.70 (m, 1H), 7.68-7.59 (m, 1H), 7.51-7.44 (m, 2H), 7.32 (s, 1H), 6.91 (s, 1H), 2.29 (s, 3H).

Step 2: Preparation of (3-(2-methyl-1H-imidazol-1-yl)phenyl)boronic acid (Intermediate E)

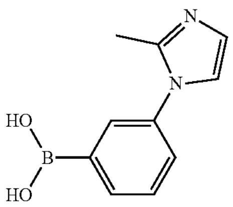

E

To a solution of Intermediate C (500 mg, 2.11 mmol), 4,4,5,5-tetramethyl-2-(4,4,5,5-tetramethyl-1,3,2-dioxaborolan-2-yl)-1,3,2-dioxaborolane (1.61 g, 6.33 mmol) and $Pd(dppf)Cl_2$ (154.31 mg, 210.89 μmol) in dioxane (10 mL) was added KOAc (620.90 mg, 6.33 mmol) under $N_2$, the mixture was stirred at 80° C. for 2 h. The reaction mixture was concentrated under reduced pressure to give a residue. The residue was purified by column chromatography ($SiO_2$, EtOA/MeOH=20:1) and concentrated under reduced pressure to give Intermediate E (150 mg, 542.03 μmol, 25.70% yield) as light yellow oil. LCMS (ESI) m/z $[M+H]^+$=203.3.

Step 3: Preparation of N-(2-((4-(3-(2-methyl-1H-imidazol-1-yl)phenyl)thiazol-2-yl)amino)-2-oxo-ethyl)-1-(methylsulfonyl)-1H-pyrrole-3-carboxamide (Compound 115)

Compound 115

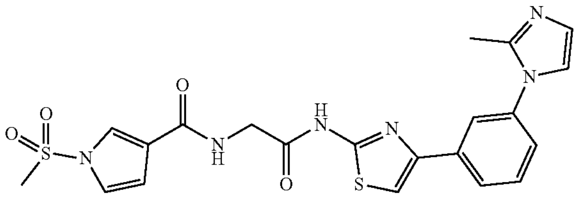

To a solution of N-[2-[(4-bromothiazol-2-yl)amino]-2-oxo-ethyl]-1-methylsulfonyl-pyrrole-3-carboxamide [prepared according to the method in Example 6] (100 mg, 245.54 μmol), Intermediate E (135.90 mg, 491.08 μmol) and 1,1'-bis(di-tert-butylphosphino)ferrocene]dichloropalladium(II) (16.00 mg, 24.55 μmol) in dioxane (2 mL) and water (0.5 mL) was added $K_3PO_4$ (156.36 mg, 736.62 μmol) under $N_2$, the mixture was stirred at 80° C. for 1 h. The reaction mixture was concentrated under reduced pressure to give a residue. The residue was purified by reverse phase (FA) and lyophilized to give Compound 115 (59.73 mg, 112.58 μmol, 45.85% yield, FA salt) as a brown solid. LCMS (ESI) m/z $[M+H]^+$=485.2; $^1H$ NMR (400 MHz, Methanol-$d_4$) δ 8.06 (d, J=8.4 Hz, 1H), 7.98 (s, 1H), 7.83-7.82 (m, 1H), 7.62-7.56 (m, 2H), 7.38-7.34 (m, 2H), 7.28-7.26 (m, 1H), 7.14 (s, 1H), 6.81-6.79 (m, 1H), 4.25 (s, 2H), 3.37 (s, 3H), 2.42 (s, 3H).

Example 114. Preparation of N-(2-((4-(3-(methyl(phenyl)carbamoyl)phenyl)thiazol-2-yl)amino)-2-oxoethyl)-1-(methylsulfonyl)-1H-pyrrole-3-carboxamide (Compound 116)

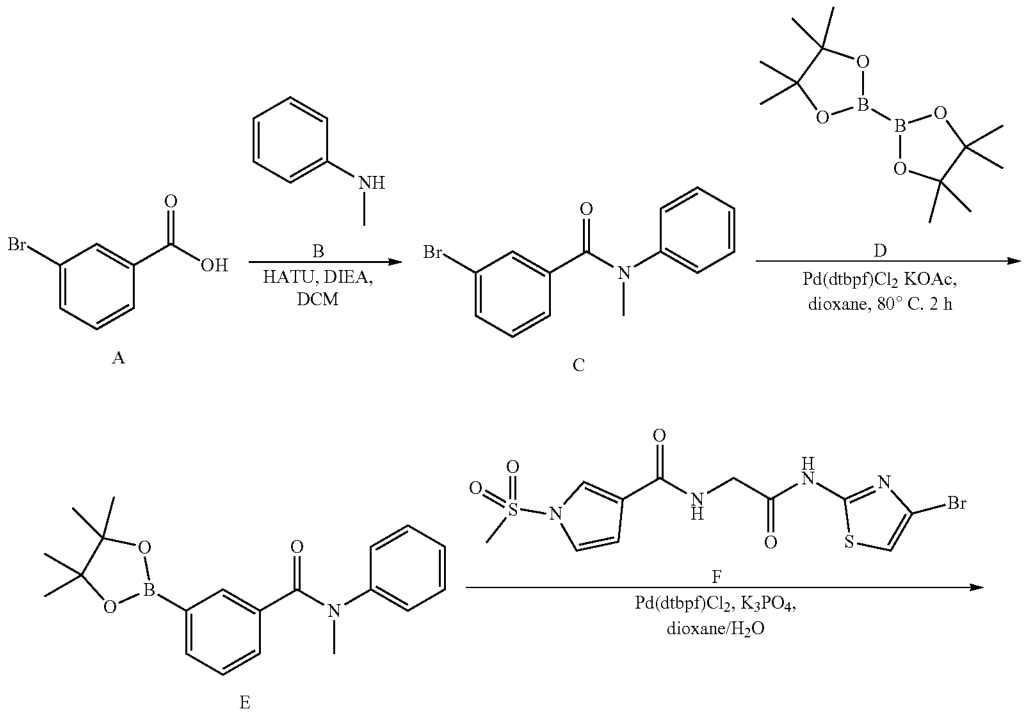

-continued

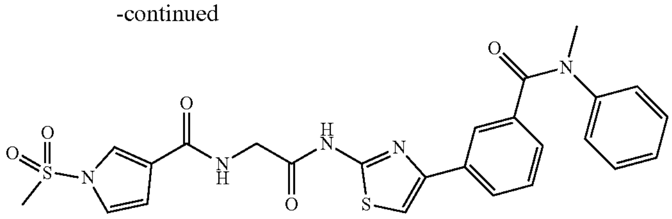

Compound 116

Step 1: Preparation of 3-bromo-N-methyl-N-phenylbenzamide (Intermediate C)

C

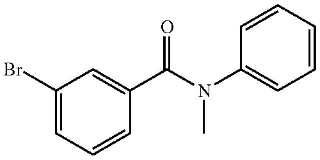

To a mixture of 3-bromobenzoic acid (300 mg, 1.49 mmol) in DCM (1 mL) was added HATU (851.19 mg, 2.24 mmol) and DIPEA (578.65 mg, 4.48 mmol, 779.85 μL). The mixture was stirred at 30° C. for 15 min, then N-methylaniline (191.90 mg, 1.79 mmol, 194.43 μL) was added and stirred at 30° C. for 1 hour. The reaction mixture was poured into water (50.0 mL) and extracted with EtOAc (50.0 mL×3). The combined organics were washed with water and brine, dried over $Na_2SO_4$, filtered and filtration was evaporated to dryness and give Intermediate C (400 mg, 1.32 mmol, 88.22% yield) as yellow solid, which was used for the next step directly. LCMS (ESI) m/z $[M+H]^+$=290.0.

Step 2: Preparation of N-methyl-N-phenyl-3-(4,4,5,5-tetramethyl-1,3,2-dioxaborolan-2-yl)benzamide (Intermediate E)

E

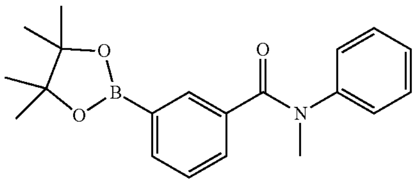

Intermediate C (200 mg, 689.29 μmol), 4,4,5,5-tetramethyl-2-(4,4,5,5-tetramethyl-1,3,2-dioxaborolan-2-yl)-1,3,2-dioxaborolane (192.54 mg, 758.22 μmol), [1,1'-bis(di-tert-butylphosphino)ferrocene]dichloropalladium(II) (44.92 mg, 68.93 μmol) and KOAc (135.30 mg, 1.38 mmol) were taken up in dioxane (2 mL), the mixture was purged with $N_2$ three times. Then the resulting mixture was stirred at 80° C. for 2 h. The reaction mixture was filtered and filtration was evaporated to dryness and give Intermediate E (220 mg, crude) as black oil, which was used for the next step directly. LCMS (ESI) m/z $[M+H]^+$=338.1.

Step 3: Preparation of N-(2-((4-(3-(methyl(phenyl)carbamoyl)phenyl)thiazol-2-yl)amino)-2-oxoethyl)-1-(methylsulfonyl)-1H-pyrrole-3-carboxamide (Compound 116)

Compound 116

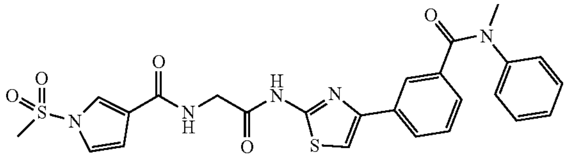

N-[2-[(4-bromothiazol-2-yl)amino]-2-oxo-ethyl]-1-methylsulfonyl-pyrrole-3-carboxamide (prepared according to the method in Example 6) (50 mg, 122.77 μmol), Intermediate E (82.80 mg, 245.54 μmol), [1,1'-bis(di-tert-butylphosphino)ferrocene]dichloropalladium(II) (8.00 mg, 12.28 μmol) and $K_3PO_4$ (78.18 mg, 368.31 μmol) were taken up in dioxane (1 mL) and $H_2O$ (0.2 mL), the mixture was purged with $N_2$ three times. Then the resulting mixture was stirred at 80° C. for 2 h. The reaction mixture was filtered and filtration was evaporated to dryness. The residue was purified by Prep-HPLC (mobile phase: [water (0.225% FA)-acetonitrile]; B %: 35%-65%) and lyophilized to give Compound 116 (15.32 mg, 28.21 μmol, 22.98% yield) as yellow solid. LCMS (ESI) m/z $[M+H]^+$=538.0; $^1H$ NMR (400 MHz, Methanol-$d_4$) δ 7.87 (s, 1H), 7.84-7.80 (m, 2H), 7.29-7.26 (m, 4H), 7.24-7.16 (m, 5H), 6.81-6.80 (m, 1H), 4.25 (s, 2H), 3.50 (s, 3H), 3.38 (s, 3H).

Example 115. Preparation of 1-(methylsulfonyl)-N-(2-oxo-2-((4-(3-(pyridin-4-ylcarbamoyl)phenyl)thiazol-2-yl)amino)ethyl)-1H-pyrrole-3-carboxamide (Compound 117)

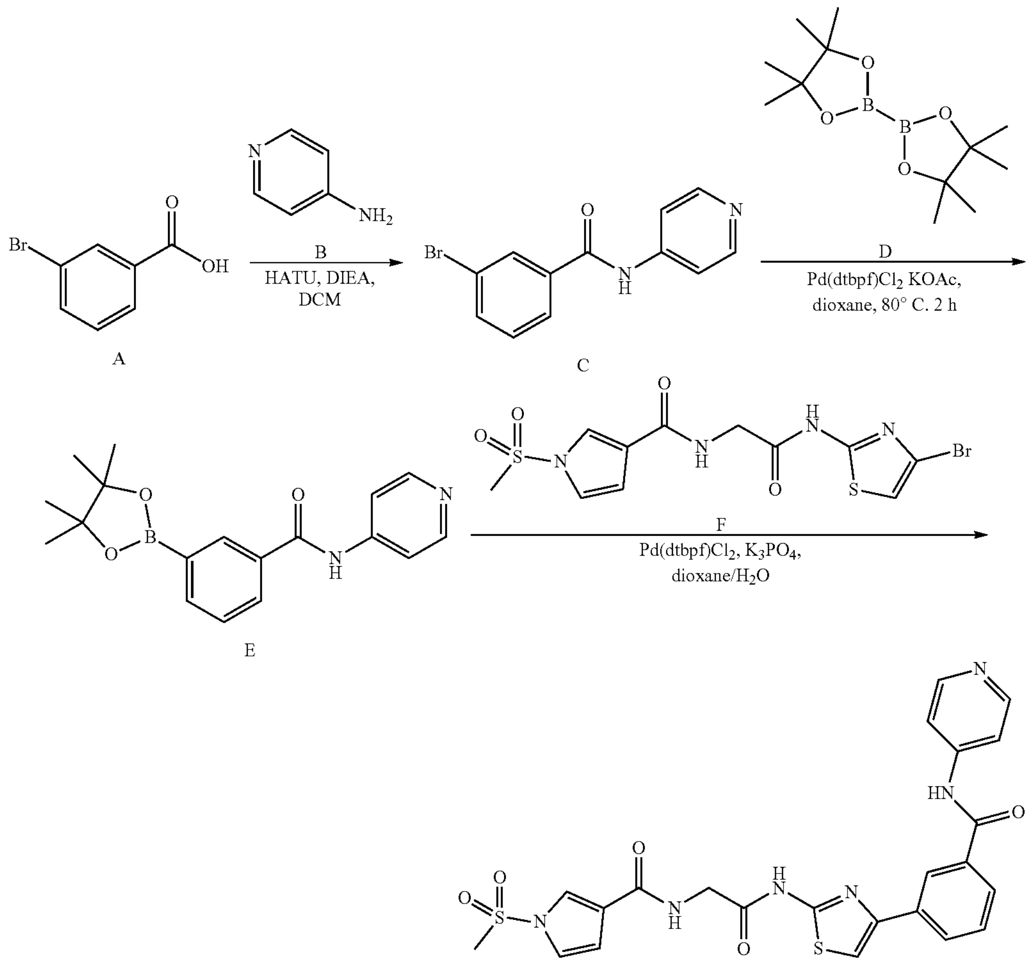

Compound 117

Step 1: Preparation of 3-bromo-N-(pyridin-4-yl)benzamide (Intermediate C)

C

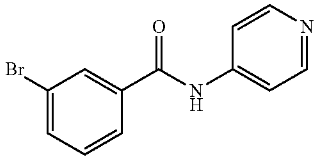

To a mixture of 3-bromobenzoic acid (300 mg, 1.49 mmol) in DCM (3 mL) was added HATU (851.19 mg, 2.24 mmol) and DIPEA (578.65 mg, 4.48 mmol, 779.85 μL). The mixture was stirred at 30° C. for 15 min, then pyridin-4-amine (140.46 mg, 1.49 mmol, 250.82 μL) was added and stirred at 30° C. for 1 hours. The reaction mixture was poured into water (50.0 mL) and extracted with EtOAc (50.0 mL×3). The combined organics were washed with water and brine, dried over $Na_2SO_4$, filtered and filtration was evaporated to dryness to give Intermediate C (410 mg, crude) as yellow solid, which was used for the next step directly. LCMS (ESI) m/z $[M+H]^+$=279.1.

Step 2: Preparation of N-(pyridin-4-yl)-3-(4,4,5,5-tetramethyl-1,3,2-dioxaborolan-2-yl)benzamide (Intermediate E)

E

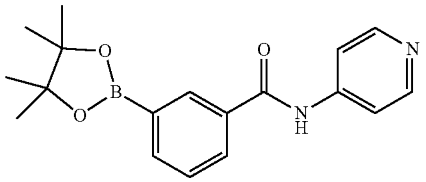

Intermediate C (400 mg, 1.44 mmol), 4,4,5,5-tetramethyl-2-(4,4,5,5-tetramethyl-1,3,2-dioxaborolan-2-yl)-1,3,2-dioxaborolane (733.09 mg, 2.89 mmol), [1,1'-bis(di-tert-butylphosphino)ferrocene]dichloropalladium(II) (94.08 mg, 144.34 μmol) and KOAc (424.98 mg, 4.33 mmol) were taken up in dioxane (5 mL), the mixture was purged with $N_2$ three times. Then the resulting mixture was stirred at 80° C. for 2 h. The reaction mixture was filtered and filtration was evaporated to dryness to give Intermediate E (400 mg, crude) as black oil, which was used for the next step directly. LCMS (ESI) m/z $[M+H]^+$=325.1.

Step 3: Preparation of 1-(methylsulfonyl)-N-(2-oxo-2-((4-(3-(pyridin-4-ylcarbamoyl)phenyl)thiazol-2-yl)amino)ethyl)-1H-pyrrole-3-carboxamide (Compound 117)

Compound 117

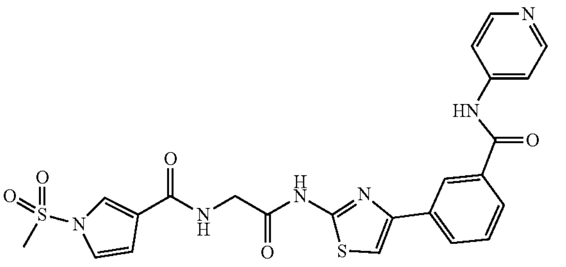

N-[2-[(4-bromothiazol-2-yl)amino]-2-oxo-ethyl]-1-methylsulfonyl-pyrrole-3-carboxamide (prepared according to the method in Example 6) (50 mg, 122.77 μmol), Intermediate E (79.60 mg, 245.54 μmol), [1,1'-bis(di-tert-butylphosphino)ferrocene]dichloropalladium(II) (8.00 mg, 12.28 μmol) and $K_3PO_4$ (78.18 mg, 368.31 μmol) were taken up in dioxane (1 mL) and $H_2O$ (0.2 mL), the mixture was purged with $N_2$ three times. Then the resulting mixture was stirred at 80° C. for 2 h. The reaction mixture was filtered and filtrate was evaporated to dryness. The residue was purified by Prep-HPLC (mobile phase: [water (0.075% TFA)-acetonitrile]; B %: 12%-42%) and lyophilized to give Compound 117 (2.01 mg, 3.15 μmol, 2.56% yield, TFA salt) as white solid. LCMS (ESI) m/z $[M+H]^+$=525.0; $^1$H NMR (400 MHz, Methanol-$d_4$) δ 8.66 (d, J=7.2 Hz, 2H), 8.57-8.56 (m, 1H), 8.36 (d, J=7.2 Hz, 2H), 8.22 (d, J=7.6 Hz, 1H), 7.95 (d, J=8.0 Hz, 1H), 7.85-7.84 (m, 1H), 7.64-7.60 (m, 1H), 7.58 (s, 1H), 7.29-7.28 (m, 1H), 6.82-6.81 (m, 1H), 4.27 (s, 2H), 3.39-3.37 (m, 3H).

Example 116. Preparation of 1-(tert-butyl)-N-(2-((4-(3-(((1-methylazetidin-3-yl)oxy)methyl)phenyl)thiazol-2-yl)amino)-2-oxoethyl)-1H-pyrrole-3-carboxamide (Compound 118)

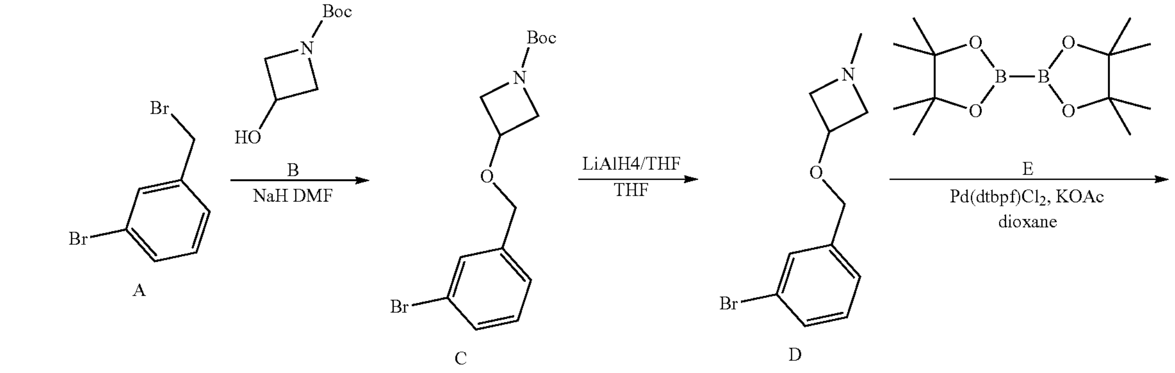

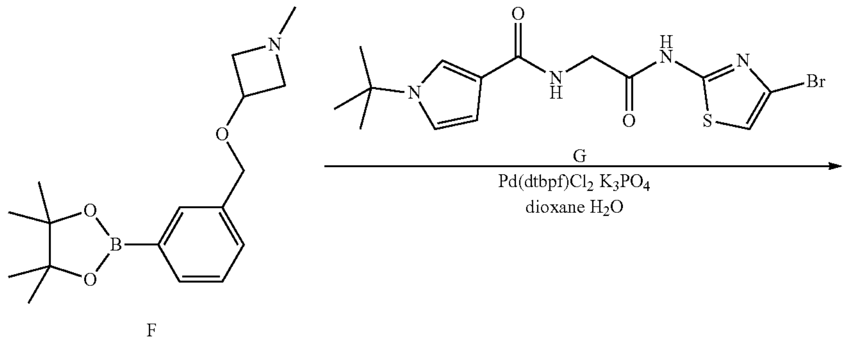

-continued

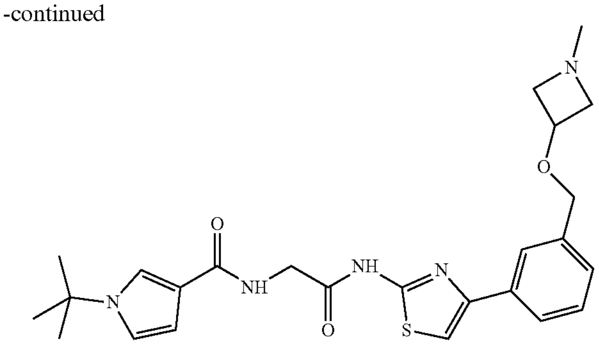

Compound 118

Step 1: Preparation of tert-butyl 3-((3-bromobenzyl) oxy)azetidine-1-carboxylate (Intermediate C)

C

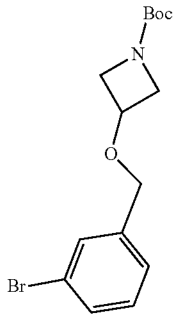

To a solution of 1-(tert-Butoxycarbonyl)-3-hydroxyazetidine (3 g, 17.32 mmol) in THF (50 mL) was added NaH (1.39 g, 34.64 mmol, 60% purity) at 0° C. and stirred for 0.5 h, then 1-bromo-3-(bromomethyl)benzene (4.33 g, 17.32 mmol) was added at 0° C. The mixture was stirred at 30° C. for 4 h. The reaction mixture was quenched by aq. $NH_4Cl$ (50 mL) at 0° C. and extracted with EtOAc (50 mL×2). The combined organic layers were dried over anhydrous $Na_2SO_4$, filtered and concentrated under reduced pressure to afford the residue. The residue was purified by flash column chromatography ($SiO_2$, Petroleum ether/EtOAc=1:0 to 1:1) and concentrated to afford Intermediate C (4 g, 11.69 mmol, 67.48% yield) as colorless oil. LCMS (ESI) m/z $[M+H-56]^+$=286.0; $^1H$ NMR (400 MHz, $CDCl_3$) δ 7.51 (s, 1H), 7.47-7.46 (m, 1H), 7.45-7.24 (m, 2H), 4.43 (s, 2H), 4.32-4.31 (m, 1H), 4.11-4.07 (m, 2H), 3.90-3.88 (m, 2H), 1.45 (s, 9H).

Step 2: Preparation of 3-((3-bromobenzyl)oxy)-1-methylazetidine (Intermediate D)

D

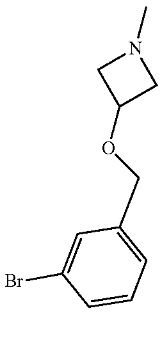

To a solution of Intermediate C (500 mg, 1.46 mmol) in THF (5 mL) was added $LiAlH_4$/THF (1 M, 4.38 mL) at 0° C. and stirred at 80° C. for 2 h. This reaction mixture was quenched by addition $H_2O$ (0.17 mL), and then diluted with 15% NaOH solution (0.51 mL). The reaction mixture was filtered and the filtrate was concentrated under reduced pressure to give Intermediate D (290 mg, 1.13 mmol, 77.49% yield) as colorless oil, which was used for the next step directly. LCMS (ESI) m/z $[M+H]^+$=256.0; $^1H$ NMR (400 MHz, $CDCl_3$) δ 7.22 (m, 4H), 4.44-4.40 (m, 2H), 4.18-4.15 (m, 1H), 3.64-3.61 (m, 2H), 2.94-2.90 (m, 2H), 2.37-2.36 (m, 3H).

Step 3: Preparation of 1-methyl-3-((3-(4,4,5,5-tetramethyl-1,3,2-dioxaborolan-2-yl)benzyl)oxy)azetidine (Intermediate F)

F

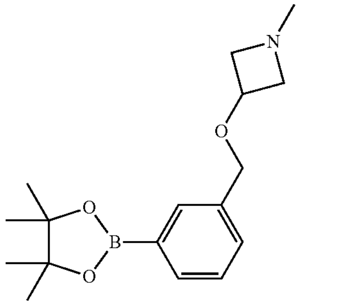

To a solution of Intermediate D (290 mg, 1.13 mmol) and 4,4,5,5-tetramethyl-2-(4,4,5,5-tetramethyl-1,3,2-dioxaborolan-2-yl)-1,3,2-dioxaborolane (345.01 mg, 1.36 mmol) in dioxane (3 mL) was added KOAc (222.23 mg, 2.26 mmol) and [1,1'-bis(di-tert-butylphosphino)ferrocene]dichloropalladium(II) (73.79 mg, 113.22 μmol). The mixture was stirred at 80° C. under $N_2$ for 2 h. The reaction mixture was diluted with $H_2O$ (10 mL) and extracted with EtOAc (10 mL×2). The combined organic layers were dried over anhydrous $Na_2SO_4$, filtered and concentrated under reduced pressure to afford Intermediate F (300 mg, crude) as yellow oil, which was used directly for the next step. LCMS (ESI) m/z $[M+H]^+$=304.2.

Step 4: Preparation of 1-(tert-butyl)-N-(2-((4-(3-(((1-methylazetidin-3-yl)oxy)methyl)phenyl)thiazol-2-yl)amino)-2-oxoethyl)-1H-pyrrole-3-carboxamide (Compound 118)

Compound 118

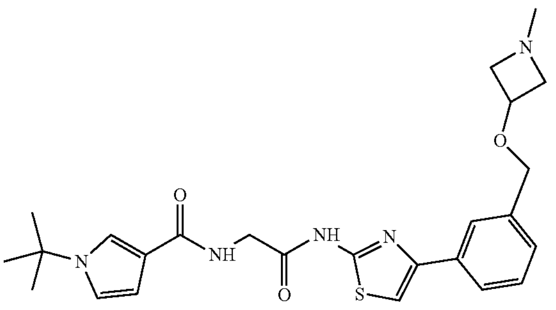

To a solution of N-[2-[(4-bromothiazol-2-yl)amino]-2-oxo-ethyl]-1-tert-butyl-pyrrole-3-carboxamide (prepared according to the method in Example 7) (100 mg, 259.55 μmol) and Intermediate F (157.39 mg, 519.10 μmol) in dioxane/$H_2O$=(4/1, 2 mL) was added $K_3PO_4$ (165.29 mg, 778.66 μmol) and [1,1'-bis(di-tert-butylphosphino)ferrocene]dichloropalladium(II) (33.83 mg, 51.91 μmol). The mixture was stirred at 80° C. under $N_2$ for 2 h. The reaction mixture were diluted with $H_2O$ (5 mL) and extracted with EtOAc (5 mL×2). The combined organic layers were dried over anhydrous $Na_2SO_4$, filtered and concentrated under reduced pressure to give a residue. The residue was purified by reversed phase (0.1% FA condition) and lyophilized to afford the crude. Then the crude was re-purified by Prep-TLC (DCM/MeOH/$NH_3$·$H_2O$=10/1/1) and concentrated to afford Compound 118 (11.01 mg, 22.14 μmol, 8.53% yield) as a white solid. LCMS (ESI) m/z $[M+H]^+$=482.1; $^1H$ NMR (400 MHz, Methanol-$d_4$) δ 7.88 (s, 1H), 7.81 (d, J=7.6 Hz, 1H), 7.58-7.57 (m, 1H), 7.38-7.28 (m, 2H), 7.28 (d, J=7.6 Hz, 1H), 6.95-6.94 (m, 1H), 6.57-6.56 (m, 1H), 4.49 (s, 2H), 4.24-4.20 (m, 4H), 3.65-3.61 (m, 2H), 3.12-3.09 (m, 2H), 2.38 (s, 3H), 1.55 (s, 9H).

Example 117. Preparation of 1-(tert-butyl)-N-(2-((4-(3-(((1-methyl-1H-pyrazol-3-yl)oxy)methyl)phenyl)thiazol-2-yl)amino)-2-oxoethyl)-1H-pyrrole-3-carboxamide (Compound 119)

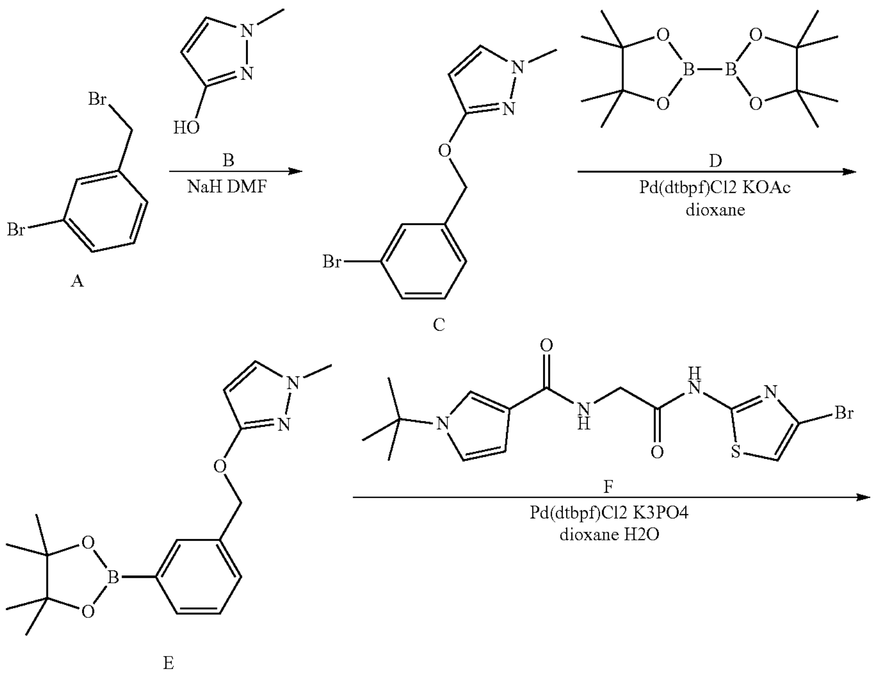

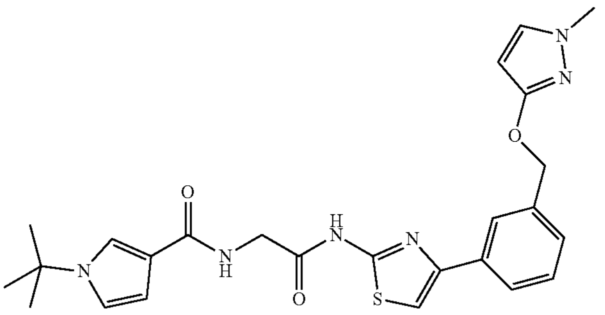

Compound 119

Step 1: Preparation of 3-((3-bromobenzyl)oxy)-1-methyl-1H-pyrazole (Intermediate C)

C

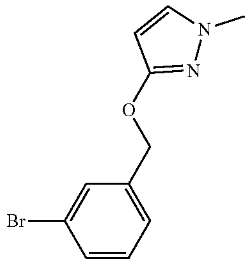

The solution of 1-methylpyrazol-3-ol (500 mg, 5.10 mmol) in anhydrous DMF (10 mL) was added NaH (407.70 mg, 10.19 mmol, 429.15 μL, 60% purity) at 0° C., after stirred for 30 minutes then added 1-bromo-3-(bromomethyl) benzene (1.27 g, 5.10 mmol). The reaction mixture was warmed to 25° C. and stirred for 16 hours. The reaction mixture was poured into saturation $NH_4Cl$ (60 mL) with stirring, then extracted with EtOAc (20 mL×3), the combined organic layers were dried over anhydrous $Na_2SO_4$, concentrated to afford a yellow oil. The yellow oil was purified by reversed phase HPLC (FA) and extraction to afford Intermediate C (120 mg, 426.77 μmol, 8.37% yield) as a yellow oil. LCMS (ESI) m/z $[M+H]^+$=269.0. 1H NMR (400 MHz, $CDCl_3$) δ 7.61 (s, 1H), 7.51-7.48 (m, 1H), 7.48 (d, J=2.4 Hz, 1H), 7.41 (s, 1H), 7.37-7.30 (m, 1H), 5.68 (d, J=2.4 Hz, 1H), 5.11 (s, 2H), 3.66 (s, 3H).

Step 2: Preparation of 1-methyl-3-((3-(4,4,5,5-tetramethyl-1,3,2-dioxaborolan-2-yl)benzyl)oxy)-1H-pyrazole (Intermediate E)

E

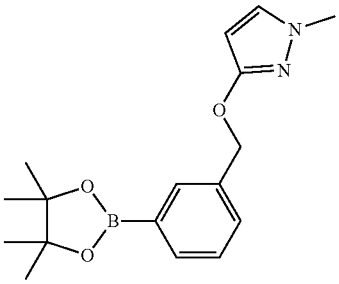

A mixture of Intermediate C (110 mg, 411.80 μmol), 4,4,5,5-tetramethyl-2-(4,4,5,5-tetramethyl-1,3,2-dioxaborolan-2-yl)-1,3,2-dioxaborolane (156.86 mg, 617.70 μmol), [1,1'-bis(di-tert-butylphosphino)ferrocene]dichloropalladium(II) (53.68 mg, 82.36 μmol), KOAc (121.24 mg, 1.24 mmol) in dioxane (3 mL) was degassed and purged with $N_2$ for 3 times, and then the mixture was stirred at 75° C. for 2 h under $N_2$ atmosphere. The mixture was cooled to 25° C. and concentrated in reduced pressure at 40° C. The residue was poured into ice-water (10 mL). The aqueous phase was extracted with EtOAc (10 mL×3). The combined organic phase was washed with brine (10 mL), dried with anhydrous $Na_2SO_4$, filtered and concentrated in vacuum to afford Intermediate E (120 mg, crude) as black oil which was used to next step directly. LCMS (ESI) m/z $[M+H]^+$=315.4.

Step 3: Preparation of 1-(tert-butyl)-N-(2-((4-(3-(((1-methyl-1H-pyrazol-3-yl)oxy)methyl)phenyl)thiazol-2-yl)amino)-2-oxoethyl)-1H-pyrrole-3-carboxamide (Compound 119)

Compound 119

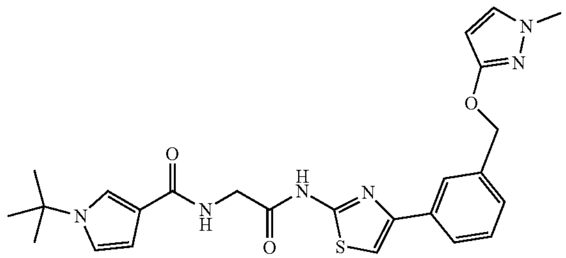

To a mixture of N-[2-[(4-bromothiazol-2-yl)amino]-2-oxo-ethyl]-1-tert-butyl-pyrrole-3-carboxamide (80 mg, 207.64 μmol) [prepared according to the method in Example 7] and Intermediate E (97.86 mg, 311.46 μmol) in dioxane (1.2 mL) and $H_2O$ (0.3 mL) was added [1,1'-bis(di-tert-butylphosphino)ferrocene]dichloropalladium(II) (27.07 mg, 41.53 μmol) and $K_3PO_4$ (132.23 mg, 622.93 μmol) at 25° C. under $N_2$. The reaction mixture was heated to 75° C. and stirred at 75° C. for 2 h. The mixture was cooled to 25° C. and concentrated in reduced pressure. The residue was poured into ice-water (10 mL). The aqueous phase was extracted with EtOAc (10 mL×3). The combined organic phase was washed with brine (10 mL), dried with anhydrous $Na_2SO_4$, filtered and concentrated in vacuum to afford a residue. The residue was purified by reversed phase HPLC (FA) to give a crude product, which was re-purified by Prep-TLC (EA) and concentrated to afford Compound 119 (7.9 mg, 15.88 μmol, 7.65% yield) as white solid. LCMS (ESI) m/z $[M+H]^+$=493.3. $^1H$ NMR (400 MHz, Methanol-$d_4$) δ 8.01-7.93 (m, 1H), 7.86-7.81 (m, 1H), 7.58 (s, 1H), 7.43-7.32 (m, 4H), 6.98-6.92 (m, 1H), 6.57-6.56 (m, 1H), 5.71 (d, J=2.4 Hz, 1H), 5.16 (s, 2H), 4.23 (s, 2H), 3.72 (s, 3H), 1.56 (s, 9H).

Example 118. Preparation of 1-(tert-butyl)-N-(2-((4-(3-methoxyphenyl)thiazol-2-yl)amino)-2-oxoethyl)-1H-pyrrole-3-carboxamide (Compound 120)

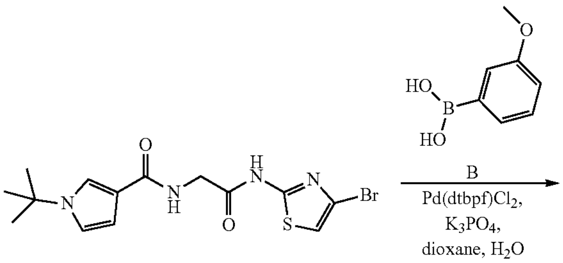

A

-continued

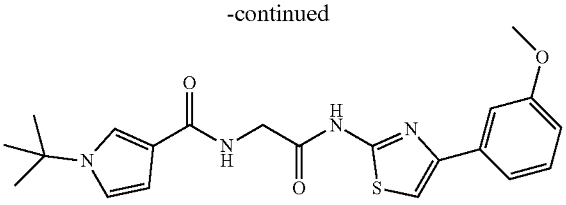

Compound 120

N-[2-[(4-bromothiazol-2-yl)amino]-2-oxo-ethyl]-1-tert-butyl-pyrrole-3-carboxamide [prepared according to the method in Example 7] (75 mg, 194.66 μmol), (3-methoxyphenyl)boronic acid (59.16 mg, 389.33 μmol), [1,1'-bis(di-tert-butylphosphino)ferrocene]dichloropalladium(II) (12.69 mg, 19.47 μmol) and $K_3PO_4$ (123.96 mg, 583.99 μmol) were taken up in dioxane (1 mL) and $H_2O$ (0.2 mL), the mixture was purged with $N_2$ three times. Then the resulting mixture was stirred at 80° C. for 2 h. The reaction mixture was diluted with water (5 mL) and extracted with EtOAc (5 mL×3). The combined organic layers were washed with brine (5 mL), dried over $Na_2SO_4$, filtered and concentrated under reduced pressure to give product. The residue was purified by Prep-HPLC (FA condition) and lyophilized to give Compound 120 (40.28 mg, 97.65 μmol, 50.16% yield) as yellow solid. LCMS (ESI) m/z $[M+H]^+$=413.2; $^1H$ NMR (400 MHz, DMSO-$d_6$) δ 12.30 (br s, 1H), 8.16-8.13 (m, 1H), 7.63 (s, 1H), 7.51-7.45 (m, 3H), 7.35-7.31 (m, 1H), 6.97-6.95 (m, 1H), 6.90-6.88 (m, 1H), 6.47-6.46 (m, 1H), 4.09 (d, J=5.6 Hz, 2H), 3.80 (s, 3H), 1.49 (s, 9H).

Example 119. Preparation of N-(2-((4-(3-methoxyphenyl)thiazol-2-yl)amino)-2-oxoethyl)-1-(methylsulfonyl)-1H-pyrrole-3-carboxamide (Compound 121)

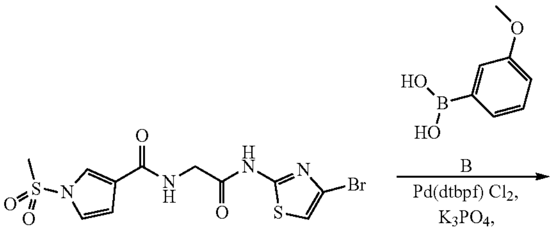

A

-continued

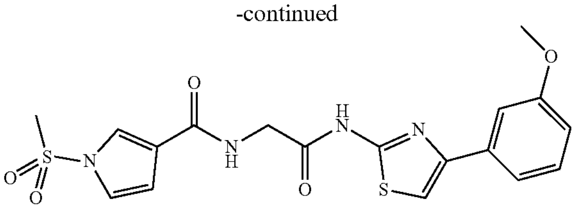

Compound 121

Step 1: Preparation of N-(2-((4-(3-methoxyphenyl)thiazol-2-yl)amino)-2-oxoethyl)-1-(methylsulfonyl)-1H-pyrrole-3-carboxamide (Compound 121)

Compound 121

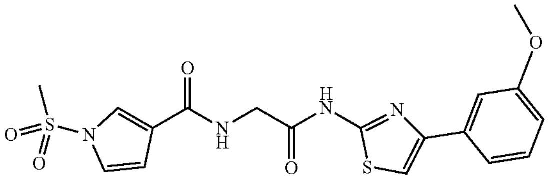

N-[2-[(4-bromothiazol-2-yl)amino]-2-oxo-ethyl]-1-methylsulfonyl-pyrrole-3-carboxamide (prepared according to the method in Example 6) (75 mg, 184.16 μmol), (3-methoxyphenyl)boronic acid (55.97 mg, 368.31 μmol), [1,1'-bis(di-tert-butylphosphino)ferrocene]dichloropalladium(II) (12.00 mg, 18.42 μmol) and $K_3PO_4$ (117.27 mg, 552.47 μmol) were taken up in dioxane (1 mL) and $H_2O$ (0.2 mL), the mixture was purged with $N_2$ three times. Then the resulting mixture was stirred at 80° C. for 2 h. The residue was slurried in MeOH/$H_2O$ (2/1, 5 mL) and stirred for 5 min. The precipitate was collected by filtration and washed with MeOH (3 mL), then dried in vacuum to give Compound 121 (50.31 mg, 115.79 μmol, 62.88% yield) as a yellow solid. LCMS (ESI) m/z $[M+H]^+$=434.9; $^1H$ NMR (400 MHz, DMSO-$d_6$) δ 12.38 (s, 1H), 8.67-8.64 (m, 1H), 7.84 (s, 1H), 7.65 (s, 1H), 7.49-7.45 (m, 2H), 7.35-7.30 (m, 2H), 6.91-6.88 (m, 1H), 6.78-6.77 (m, 1H), 4.14 (br d, J=6.0 Hz, 2H), 3.80 (s, 3H), 3.57 (s, 3H).

Example 120. Preparation of 1-(tert-butyl)-N-(2-((4-(3-(oxetan-3-ylmethoxy)phenyl)thiazol-2-yl)amino)-2-oxoethyl)-1H-pyrrole-3-carboxamide (Compound 122)

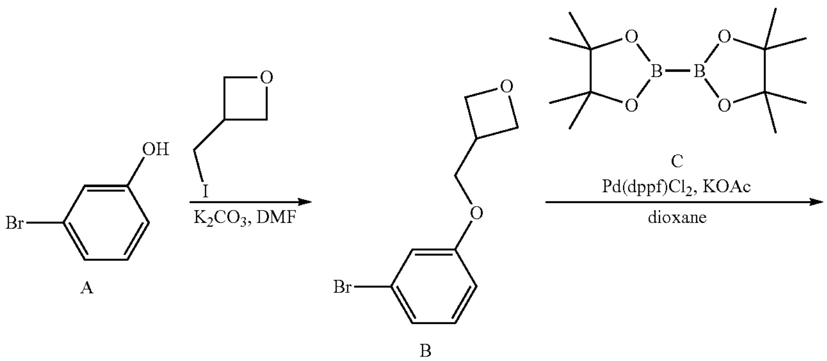

A

B

-continued

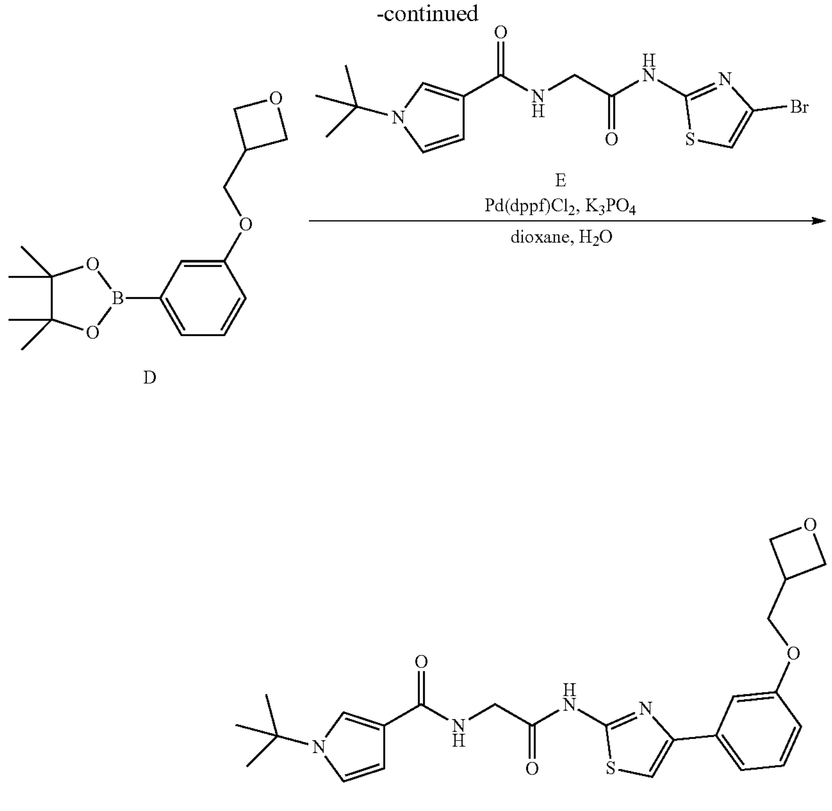

E

D

Compound 122

Step 1: Preparation of 3-((3-bromophenoxy)methyl)oxetane (Intermediate B)

B

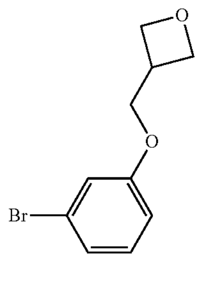

To a solution of 3-bromophenol (300 mg, 1.73 mmol) and 3-(iodomethyl)oxetane (343.34 mg, 1.73 mmol) in DMF (3 mL) was added $K_2CO_3$ (718.96 mg, 5.20 mmol), the mixture was stirred at 30° C. for 2 h. The mixture was diluted with water (20 mL) and extracted with EtOAc (20 mL×3). The combined organic layers were washed with brine (50 mL), dried over $Na_2SO_4$, filtered and concentrated under reduced pressure to give a residue. The residue was purified by reverse phase (FA) and lyophilized to give Intermediate B (300 mg, 1.23 mmol, 71.03% yield) as light yellow oil. LCMS (ESI) m/z $[M+H]^+$=243.0.

Step 2: Preparation of 4,4,5,5-tetramethyl-2-(3-(oxetan-3-ylmethoxy)phenyl)-1,3,2-dioxaborolane (Intermediate D)

D

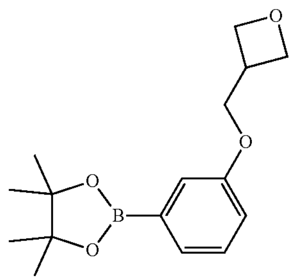

To a solution of Intermediate B (100 mg, 411.36 μmol), 4,4,5,5-tetramethyl-2-(4,4,5,5-tetramethyl-1,3,2-dioxaborolan-2-yl)-1,3,2-dioxaborolane (125.35 mg, 493.63 μmol) and $Pd(dppf)Cl_2$ (60.20 mg, 82.27 μmol) in dioxane (2 mL) was added KOAc (121.12 mg, 1.23 mmol) under $N_2$, the mixture was stirred at 80° C. for 1 h. The reaction mixture was diluted with water 10 mL and extracted with EtOAc (10 mL×3). The combined organic layers were washed with brine (30 mL), dried over $Na_2SO_4$, filtered and concentrated under reduced pressure to give Intermediate D (110 mg, crude) as black brown oil, which was used to the next step without further purification. LCMS (ESI) m/z $[M+H]^+$= 291.3.

Step 3: Preparation of 1-(tert-butyl)-N-(2-((4-(3-(oxetan-3-ylmethoxy)phenyl)thiazol-2-yl)amino)-2-oxoethyl)-1H-pyrrole-3-carboxamide (Compound 122)

Compound 122

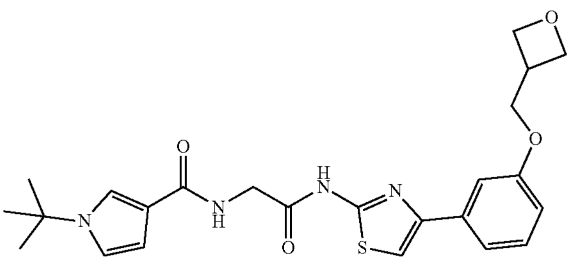

To a solution of N-[2-[(4-bromothiazol-2-yl)amino]-2-oxo-ethyl]-1-tert-butyl-pyrrole-3-carboxamide [prepared according to the method in Example 7] (50 mg, 129.78 μmol), Intermediate D (75.31 mg, 259.55 μmol) and [1,1'-bis(di-tert-butylphosphino)ferrocene]dichloropalladium(II) (8.46 mg, 12.98 μmol) in dioxane (1.2 mL) and water (0.3 mL) was added $K_3PO_4$ (82.64 mg, 389.33 μmol) under $N_2$, the mixture was stirred at 80° C. for 1 h. The reaction mixture was diluted with water (5 mL) and extracted with EtOAc (10 mL×3). The combined organic layers were washed with brine (20 mL), dried over $Na_2SO_4$, filtered and concentrated under reduced pressure to give a residue. The residue was purified by Prep-TLC (EA, Rf=0.4) and concentrated under reduced pressure to give Compound 122 (19.92 mg, 42.44 μmol, 32.70% yield) as a white solid. LCMS (ESI) m/z $[M+H]^+$=469.4; $^1$H NMR (400 MHz, DMSO-$d_6$) δ 12.28 (s, 1H), 8.17-8.14 (m, 1H), 7.66 (s, 1H), 7.50 (br d, J=9.6 Hz, 3H), 7.35-7.31 (m, 1H), 7.96-6.91 (m, 2H), 6.47 (br s, 1H), 4.74-4.71 (m, 2H), 4.46-4.43 (m, 2H), 4.25 (d, J=6.8 Hz, 2H), 4.08 (br d, J=5.6 Hz, 2H), 3.40-3.39 (m, 1H), 1.49 (s, 9H).

Example 121. Preparation of 1-(tert-butyl)-N-(2-((4-(2-methyl-1-oxo-1,2-dihydroisoquinolin-7-yl)thiazol-2-yl)amino)-2-oxoethyl)-1H-pyrrole-3-carboxamide (Compound 123)

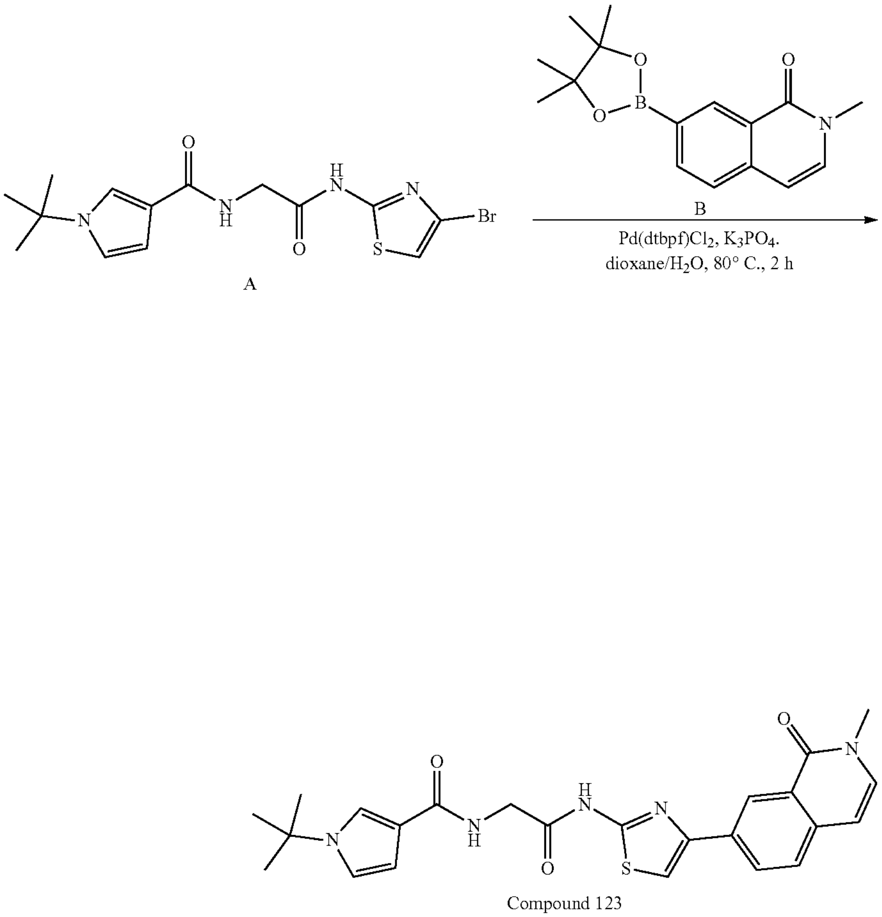

Compound 123

A mixture of N-[2-[(4-bromothiazol-2-yl)amino]-2-oxo-ethyl]-1-tert-butyl-pyrrole-3-carboxamide [prepared according to the method in Example 7] (40 mg, 103.82 μmol), 2-methyl-7-(4,4,5,5-tetramethyl-1,3,2-dioxaborolan-2-yl) isoquinolin-1-one [prepared according to the method in Example 7 (38.49 mg, 134.97 μmol), $K_3PO_4$ (66.11 mg, 311.46 μmol) and [1,1'-bis(di-tert-butylphosphino)ferrocene]dichloropalladium(II) (13.53 mg, 20.76 μmol) in dioxane (2 mL) and $H_2O$ (0.5 mL) was degassed and purged with $N_2$ for 3 times, and then the mixture was stirred at 80° C. for 2 h under $N_2$ atmosphere. Water (20 mL) was added and the reaction mixture was extracted with EtOAc (50 mL×2). The combined organic layers were washed with brine (20 mL), dried over $Na_2SO_4$, filtered and concentrated under reduced pressure to give a residue. The residue was purified by Prep-HPLC (mobile phase: [water (0.1% TFA)-acetonitrile]; B %: 35%-55%) and lyophilized to give Compound 123 (3 mg, 5.19 μmol, 5.00% yield, TFA salt) as a white solid. LCMS (ESI) m/z $[M+H]^+$=464.2. $^1H$ NMR (400 MHz, DMSO-$d_6$) δ 12.42 (s, 1H), 8.81 (d, J=1.6 Hz, 1H), 8.21-8.16 (m, 2H), 7.76 (s, 1H), 7.71 (d, J=8.4 Hz, 1H), 7.52-7.51 (m, 1H), 7.48 (d, J=7.2 Hz, 1H), 6.97-6.96 (m, 1H), 6.64 (d, J=7.2 Hz, 1H), 6.48-6.47 (m, 1H), 4.11 (d, J=5.6 Hz, 2H), 3.53 (s, 3H), 1.50 (s, 9H).

Example 122. Preparation of 1-(tert-butyl)-N-(2-((4-(2-methyl-3-oxo-1,2,3,4-tetrahydroisoquinolin-6-yl)thiazol-2-yl)amino)-2-oxoethyl)-1H-pyrrole-3-carboxamide (Compound 124)

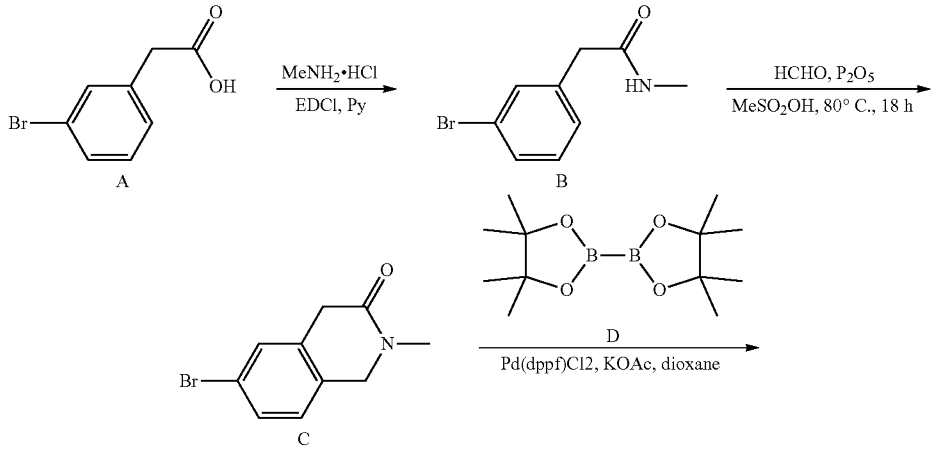

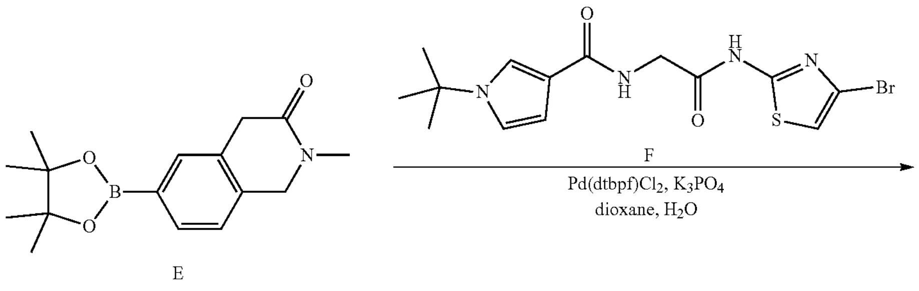

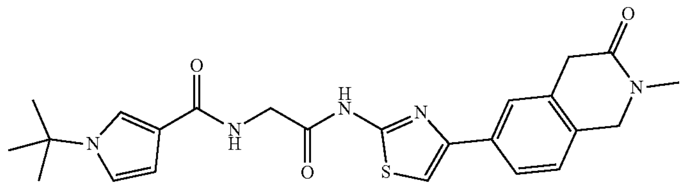

Compound 124

Step 1: Preparation of 2-(3-bromophenyl)-N-methylacetamide (Intermediate B)

B

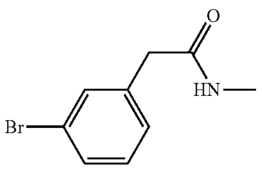

To a mixture of 2-(3-bromophenyl)acetic acid (2 g, 9.30 mmol) in pyridine (10 mL) was added methanamine (1.57 g, 23.25 mmol, HCl salt). The mixture was stirred at 30° C. for 15 min, then EDCI (3.57 g, 18.60 mmol) was added and stirred at 30° C. for 1 hours. The reaction mixture was poured into 100 mL saturated citric acid solution, and extracted with EtOAc (50.0 mL×3). The combined organic layers were washed with water (100 mL) and brine (100 mL), dried over $Na_2SO_4$, filtered and filtration was evaporated to dryness to give Intermediate B (2.1 g, crude) as a yellow solid, which was used for the next step directly. LCMS (ESI) m/z $[M+H]^+$=230.1.

Step 2: Preparation of 6-bromo-2-methyl-1,2-dihydroisoquinolin-3(4H)-one (Intermediate C)

C

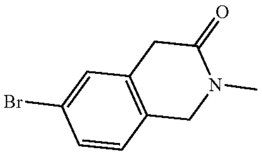

$P_2O_5$ (1.12 g, 7.89 mmol, 487.06 μL) was added into MsOH (12.14 g, 126.27 mmol, 8.99 mL) under $N_2$, the mixture was stirred at 25° C. for 16 h, then Intermediate B (1.8 g, 7.89 mmol) and paraformaldehyde (284.10 mg, 9.47 mmol) was added into the mixture, then heated to 80° C. and stirred for 2 hours. The reaction mixture was adjusted pH=8 with aq. NaOH, and extracted with EtOAc (30.0 mL×3). The combined organic layers were washed with water (50 mL) and brine (50 mL), dried over $Na_2SO_4$, filtered and filtration was evaporated to dryness. The residue was purified by Prep-HPLC (FA condition) and then Prep-TLC ($SiO_2$, PE/EA=1:2) to give Intermediate C (800 mg, 3.33 mmol, 42.22% yield) as yellow solid. LCMS (ESI) m/z $[M+H]^+$=240.1.

Step 3: Preparation of 2-methyl-6-(4,4,5,5-tetramethyl-1,3,2-dioxaborolan-2-yl)-1,2-dihydroisoquinolin-3(4H)-one (Intermediate E)

E

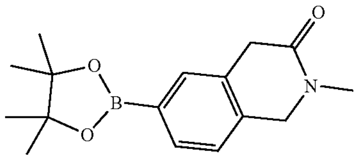

Intermediate C (100 mg, 416.50 μmol), 4,4,5,5-tetramethyl-2-(4,4,5,5-tetramethyl-1,3,2-dioxaborolan-2-yl)-1,3,2-dioxaborolane (116.34 mg, 458.15 μmol), Pd(dppf)$Cl_2$ (30.48 mg, 41.65 μmol) and KOAc (81.75 mg, 833.00 μmol) were taken up in dioxane (0.5 mL), the mixture was purged with $N_2$ three times. Then the resulting mixture was stirred at 80° C. for 2 h. The reaction mixture was diluted with water (5 mL) and extracted with EtOAc (5 mL×3). The combined organic layers were washed with brine (5 mL), dried over $Na_2SO_4$, filtered and concentrated under reduced pressure to give Intermediate E (115 mg, crude) as yellow solid, which was used for the next step directly. LCMS (ESI) m/z $[M+H]^+$=288.3.

Step 4: Preparation of 1-(tert-butyl)-N-(2-((4-(2-methyl-3-oxo-1,2,3,4-tetrahydroisoquinolin-6-yl)thiazol-2-yl)amino)-2-oxoethyl)-1H-pyrrole-3-carboxamide (Compound 124)

Compound 124

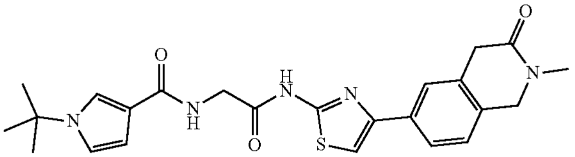

N-[2-[(4-bromothiazol-2-yl)amino]-2-oxo-ethyl]-1-tert-butyl-pyrrole-3-carboxamide [prepared according to the method in Example 7] (100 mg, 259.55 μmol), Intermediate E (111.80 mg, 389.33 μmol), $K_3PO_4$ (110.19 mg, 519.10 μmol) and [1,1'-bis(di-tert-butylphosphino)ferrocene]dichloropalladium(II) (16.92 mg, 25.96 μmol) were taken up in dioxane (1.5 mL) and $H_2O$ (0.3 mL), the mixture was purged with $N_2$ three times. Then the resulting mixture was stirred at 80° C. for 2 h. The reaction mixture was diluted with water (5 mL) and extracted with EtOAc (5 mL×3). The combined organic layers were washed with brine (5 mL), dried over $Na_2SO_4$, filtered and concentrated under reduced pressure to give product. The residue was purified by Prep-HPLC (FA condition) and lyophilized to give Compound 124 (25.22 mg, 52.55 μmol, 20.24% yield) as yellow solid. LCMS (ESI) m/z $[M+H]^+$=466.3. $^1H$ NMR (400 MHz, DMSO-$d_6$) δ 12.30 (br s, 1H), 8.17-8.14 (m, 1H), 7.78-7.72 (m, 2H), 7.59 (s, 1H), 7.51 (s, 1H), 7.31 (d, J=8.0 Hz, 1H), 6.96 (s, 1H), 6.47 (s, 1H), 4.53 (s, 2H), 4.09 (d, J=6.0 Hz, 2H), 3.57 (s, 2H), 2.98 (s, 3H), 1.49 (s, 9H).

Example 123. Preparation of 1-(tert-butyl)-N-(2-oxo-2-((4-(3-(((tetrahydro-2H-pyran-4-yl)oxy)methyl)phenyl)thiazol-2-yl)amino)ethyl)-1H-pyrrole-3-carboxamide (Compound 125)

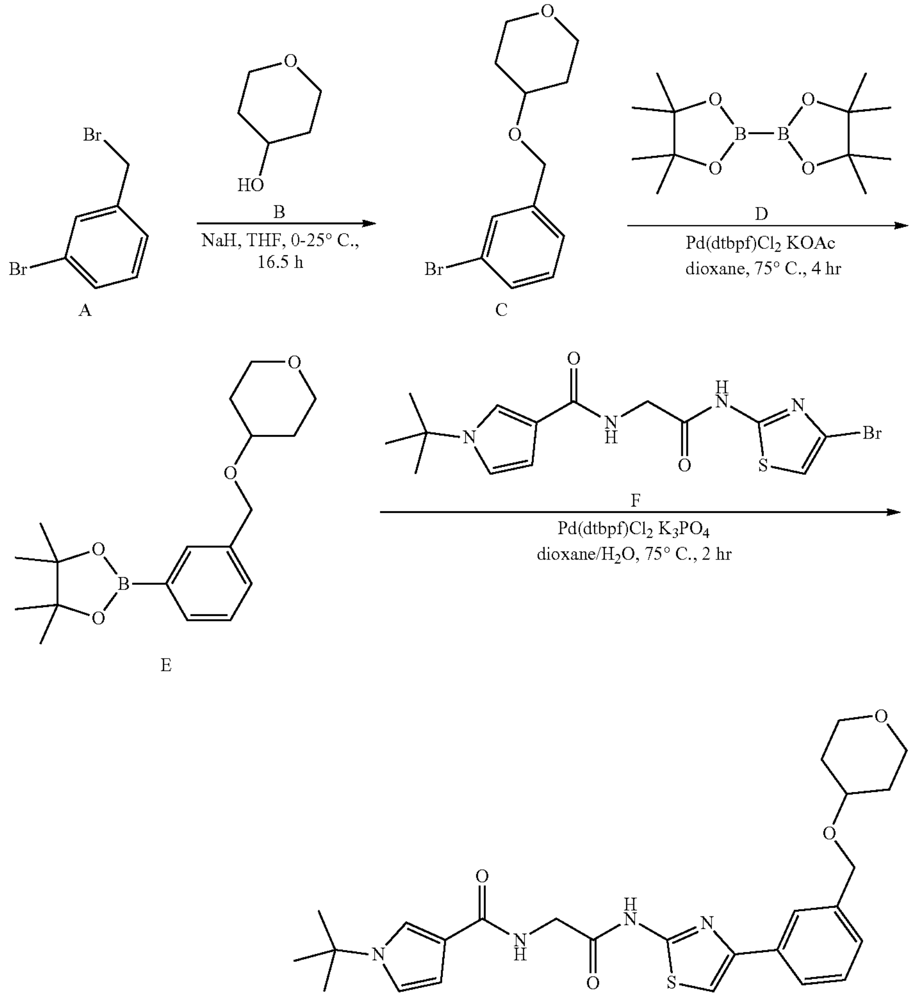

Compound 125

Step 1: Preparation of 4-((3-bromobenzyl)oxy)tetrahydro-2H-pyran (Intermediate C)

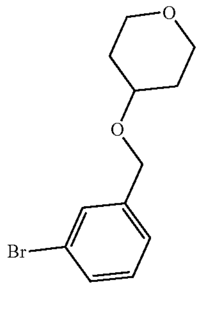

C

To a mixture of tetrahydropyran-4-ol (245.18 mg, 2.40 mmol, 240.38 μL) in THF (5 mL) was added NaH (120.02 mg, 3.00 mmol, 60% purity) slowly at 0° C. The reaction mixture was stirred at 0° C. for 30 min. Then to the reaction mixture was added a solution of 1-bromo-3-(bromomethyl)benzene (500 mg, 2.00 mmol) in THF (1 mL) slowly at 0° C. The reaction mixture was warmed to 25° C. and stirred at 25° C. for 16 h. The reaction mixture was poured into saturated a,q $NH_4Cl$ (20 mL) and extracted with EtOAc (15 mL×3). The combined organic layers were washed with brine (20 mL), dried over anhydrous $Na_2SO_4$, filtered and concentrated under reduced pressure to afford a residue. The residue was purified by silica gel chromatography (PE/EA=20/1-5/1) and concentrated to afford Intermediate C (270 mg, 895.01 μmol, 44.74% yield) as colorless oil. LCMS (ESI) m/z $[M+H]^+$=273.0; $^1H$ NMR (400 MHz, $CDCl_3$) δ 7.52 (s, 1H), 7.42 (d, J=7.6 Hz, 1H), 7.29 (s, 1H), 7.25-7.19 (m, 1H), 4.54 (s, 2H), 4.00-3.95 (m, 2H), 3.62-3.57 (m, 1H), 3.49-3.42 (m, 2H), 1.99-1.90 (m, 2H), 1.73-1.61 (m, 2H).

Step 2: Preparation of 4,4,5,5-tetramethyl-2-(3-(((tetrahydro-2H-pyran-4-yl)oxy)methyl)phenyl)-1,3,2-dioxaborolane (Intermediate E)

E

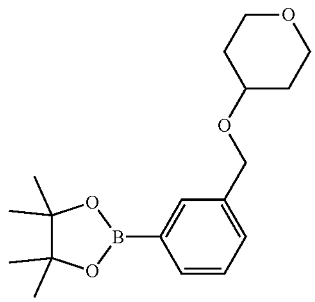

To a mixture of Intermediate C (270 mg, 995.76 μmol) and 4,4,5,5-tetramethyl-2-(4,4,5,5-tetramethyl-1,3,2-dioxaborolan-2-yl)-1,3,2-dioxaborolane (303.43 mg, 1.19 mmol) in dioxane (5 mL) was added KOAc (293.18 mg, 2.99 mmol) and [1,1'-bis(di-tert-butylphosphino)ferrocene]dichloropalladium(II) (64.90 mg, 99.58 μmol) at 25° C. under $N_2$. The reaction mixture was heated to 75° C. and stirred at 75° C. for 4 h under $N_2$. The reaction mixture was filtered and concentrated under reduced pressure to afford Intermediate E (500 mg, crude) as brown oil, which was used for the next step directly.

Step 3: Preparation of 1-(tert-butyl)-N-(2-oxo-2-((4-(3-(((tetrahydro-2H-pyran-4-yl)oxy)methyl)phenyl)thiazol-2-yl)amino)ethyl)-1H-pyrrole-3-carboxamide (Compound 125)

Compound 125

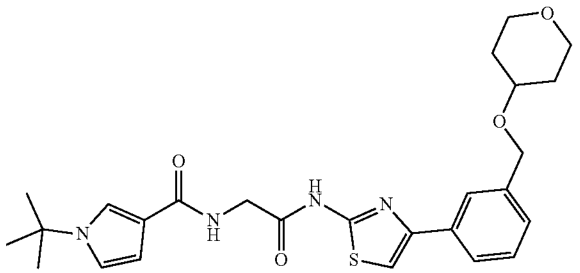

To a mixture of N-[2-[(4-bromothiazol-2-yl)amino]-2-oxo-ethyl]-1-tert-butyl-pyrrole-3-carboxamide [prepared according to the method in Example 6] (50 mg, 129.78 μmol) and Intermediate E (123.89 mg, 389.33 μmol) in dioxane (1.2 mL) and $H_2O$ (0.3 mL) was added $K_3PO_4$ (82.64 mg, 389.33 μmol) and [1,1'-bis(di-tert-butylphosphino)ferrocene]dichloropalladium(II) (8.46 mg, 12.98 μmol) at 25° C. under $N_2$. The reaction mixture was heated to 75° C. and stirred at 75° C. for 2 h under $N_2$. The reaction mixture was filtered and the filtrated was concentrated under reduced pressure to afford a residue. The residue was purified by reverse phase column (FA condition) and lyophilized to afford Compound 125 (5.46 mg, 10.99 μmol, 8.47% yield) as white solid. LCMS (ESI) m/z $[M+H]^+$=497.1; $^1H$ NMR (400 MHz, Methanol-$d_4$) δ 7.91 (s, 1H), 7.81 (d, J=7.6 Hz, 1H), 7.58-7.57 (m, 1H), 7.42-7.34 (m, 2H), 7.33-7.27 (m, 1H), 6.96-6.94 (m, 1H), 6.58-6.56 (m, 1H), 4.62 (s, 2H), 4.23 (s, 2H), 3.96-3.90 (m, 2H), 3.70-3.66 (m, 1H), 3.50-3.43 (m, 2H), 2.03-1.92 (m, 2H), 1.67-1.53 (m, 11H).

Example 124. Preparation of 1-(tert-butyl)-N-(2-oxo-2-((4-(3-(1-((tetrahydro-2H-pyran-4-yl)oxy)ethyl)phenyl)thiazol-2-yl)amino)ethyl)-1H-pyrrole-3-carboxamide (Compound 126)

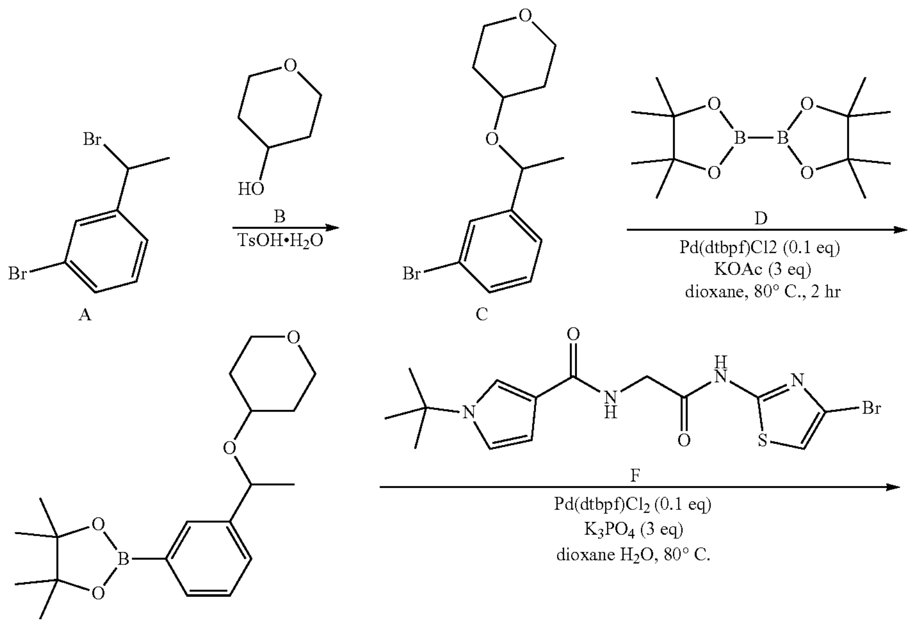

-continued

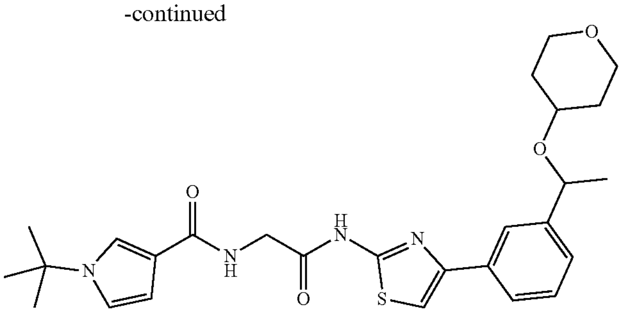

Compound 126

Step 1: Preparation of 4-(1-(3-bromophenyl)ethoxy) tetrahydro-2H-pyran (Intermediate C)

C

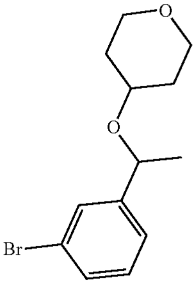

To a mixture of tetrahydropyran-4-ol (0.5 g, 4.90 mmol, 490.20 μL) and 1-(3-bromophenyl)ethanol (984.32 mg, 4.90 mmol) was added TsOH·$H_2O$ (93.13 mg, 489.57 μmol) at 20° C. The mixture was stirred at 120° C. for 3 h. The reaction mixture was cooled to 20° C. and purified by column chromatography ($SiO_2$, Petroleum ether/EtOAc=5/1) and concentrated to give Intermediate C (0.7 g, 2.45 mmol, 50.14% yield) as yellow oil. $^1H$ NMR (400 MHz, $CDCl_3$) δ 7.50 (s, 1H), 7.42 (br d, J=7.6 Hz, 1H), 7.28-7.21 (m, 2H), 4.58-4.56 (m, 1H), 3.95-3.93 (m, 2H), 3.50-3.29 (m, 3H), 2.00-1.86 (m, 1H), 1.79-1.70 (m, 1H), 1.68-1.58 (m, 2H) 1.44-1.42 (m, 3H).

Step 2: Preparation of 4,4,5,5-tetramethyl-2-(3-(1-((tetrahydro-2H-pyran-4-yl)oxy)ethyl)phenyl)-1,3,2-dioxaborolane (Intermediate E)

E

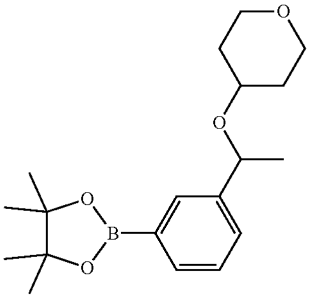

A mixture of Intermediate C (300 mg, 1.05 mmol), 4,4,5,5-tetramethyl-2-(4,4,5,5-tetramethyl-1,3,2-dioxaborolan-2-yl)-1,3,2-dioxaborolane (320.57 mg, 1.26 mmol), KOAc (206.48 mg, 2.10 mmol), Pd(dppf)$Cl_2$ (76.97 mg, 105.20 μmol) in dioxane (5 mL) was degassed and purged with $N_2$ for 3 times, and then the mixture was stirred at 80° C. for 3 h under $N_2$ atmosphere. The reaction mixture was concentrated under reduced pressure to remove solvent. The residue was diluted with water (30 mL) and extracted with EtOAc (15 mL×3). The combined organic layers were washed with water (10 mL×3), dried over $Na_2SO_4$, filtered and concentrated under reduced pressure to give Intermediate E (0.4 g, crude) as brown oil and which was used in next step without further purification.

Step 3: Preparation of 1-(tert-butyl)-N-(2-oxo-2-((4-(3-(1-((tetrahydro-2H-pyran-4-yl)oxy)ethyl)phenyl) thiazol-2-yl)amino)ethyl)-1H-pyrrole-3-carboxamide (Compound 126)

Compound 126

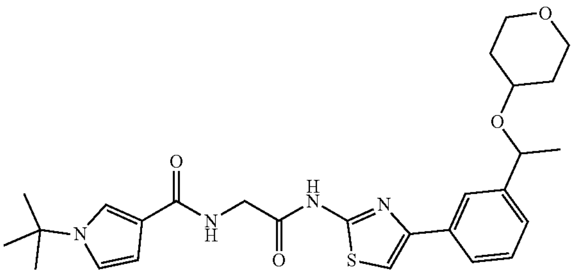

A mixture of Intermediate E (170 mg, 511.68 μmol), N-[2-[(4-bromothiazol-2-yl)amino]-2-oxo-ethyl]-1-tert-butyl-pyrrole-3-carboxamide [prepared according to the method in Example 7] (98.57 mg, 255.84 μmol), $K_3PO_4$ (325.84 mg, 1.54 mmol), [1,1'-bis(di-tert-butylphosphino) ferrocene]dichloropalladium(II) (66.70 mg, 102.34 μmol) in dioxane (3 mL) and $H_2O$ (1 mL) was degassed and purged with $N_2$ for 3 times, and then the mixture was stirred at 80° C. for 3 hr under $N_2$ atmosphere. The reaction mixture was concentrated under reduced pressure to give a residue. The residue was purified by column chromatography ($SiO_2$, Petroleum ether/EtOAc=1/1) and concentrated to afford Compound 126 (80 mg, 156.66 μmol, 30.62% yield) as yellow solid. LCMS (ESI) m/z $[M+H]^+$=511.1; $^1H$ NMR (400 MHz, DMSO-$d_6$) δ 12.31 (br s, 1H), 8.18-8.16 (m, 1H), 7.90 (s, 1H), 7.79 (d, J=8.0 Hz, 1H), 7.62 (s, 1H), 7.53-7.51 (m, 1H), 7.41 (d, J=7.8 Hz, 1H), 7.30 (d, J=7.8 Hz, 1H), 6.98 (m, 1H), 6.48 (dd, J=2.8 Hz, 1.6 Hz, 1H), 4.71-4.70 (m, 1H), 4.11-4.10 (m, 2H), 3.83-3.72 (m, 2H), 3.42-3.37 (m, 2H), 3.26-3.25 (m, 1H), 1.93-1.91 (m, 1H), 1.68-1.66 (m, 1H), 1.50 (s, 9H), 1.46-1.39 (m, 2H), 1.38-1.36 (m, 3H).

Example 125. Preparation of 1-(tert-butyl)-N-(2-((4-(3-(((1-methylpiperidin-4-yl)oxy)methyl)phenyl)thiazol-2-yl)amino)-2-oxoethyl)-1H-pyrrole-3-carboxamide (Compound 127)
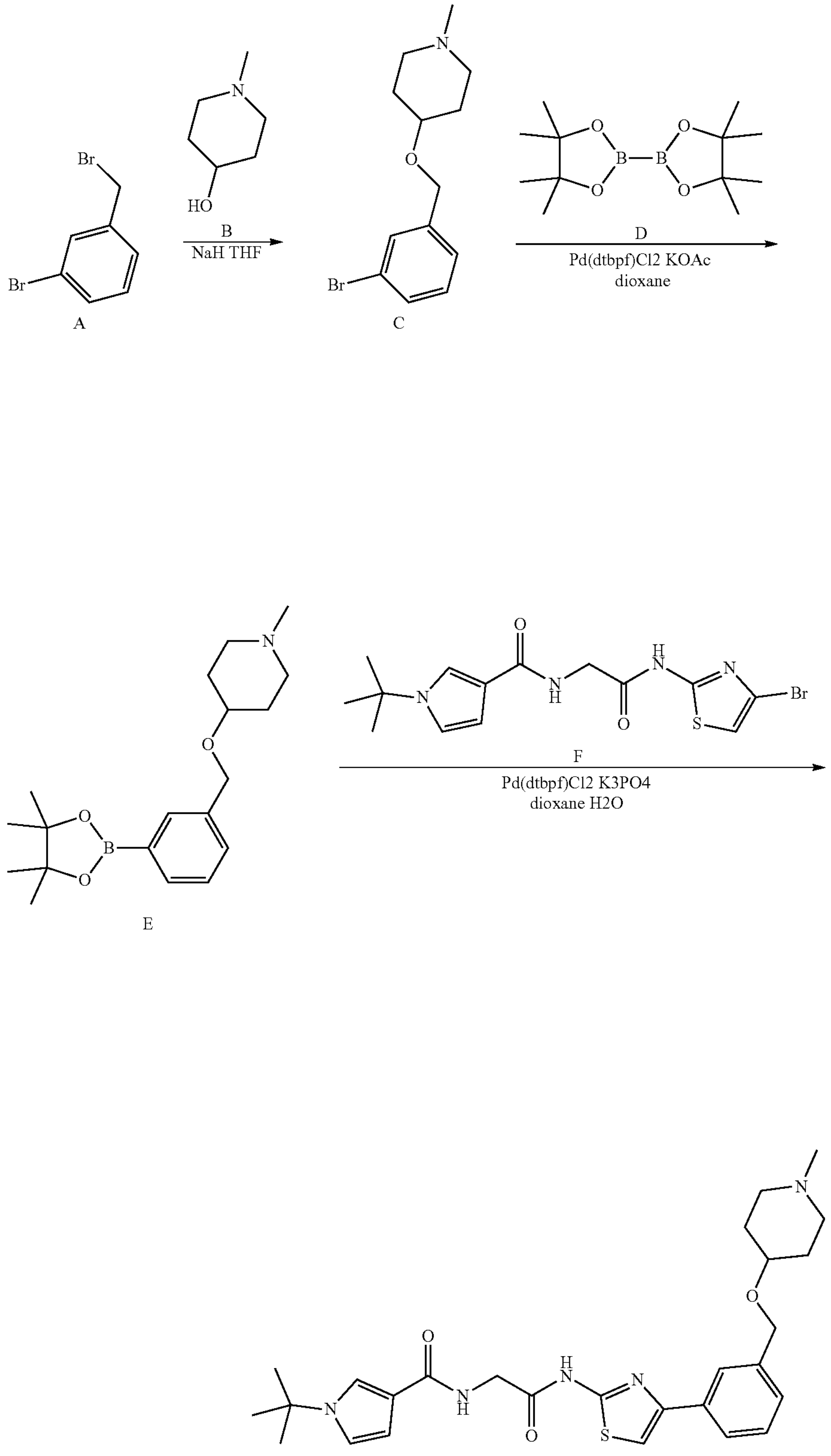
Compound 127

Step 1: Preparation of 4-((3-bromobenzyl)oxy)-1-methylpiperidine (Intermediate C)

C

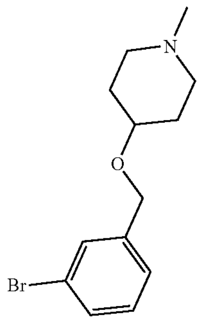

To a solution of 1-methylpiperidin-4-ol (691.23 mg, 6.00 mmol, 701.76 μL) in THF (10 mL) was added NaH (320.06 mg, 8.00 mmol, 60% purity) at 0° C. and stirred for 0.5 h, then 1-bromo-3-(bromomethyl)benzene (1 g, 4.00 mmol) was added to the mixture at 0° C. The mixture was stirred at 30° C. for 4 h. The reaction mixture was diluted with aq. $NH_4Cl$ (20 mL) at 0° C. and extracted with EtOAc (20 mL×2). The combined organic layers were dried over anhydrous $Na_2SO_4$, filtered and concentrated under reduced pressure to afford the residue. The residue was purified by reversed phase (0.1% FA condition), concentrated to remove the acetonitrile. The solution was extracted with EtOAc (20 mL×2), the organic layers were dried over anhydrous $Na_2SO_4$, filtered and concentrated to afford Intermediate C (350 mg, 1.23 mmol, 30.78% yield) as a colorless oil. LCMS (ESI) m/z $[M+H]^+$=286.0.

Step 2: Preparation of 1-methyl-4-((3-(4,4,5,5-tetramethyl-1,3,2-dioxaborolan-2-yl)benzyl)oxy)piperidine (Intermediate E)

E

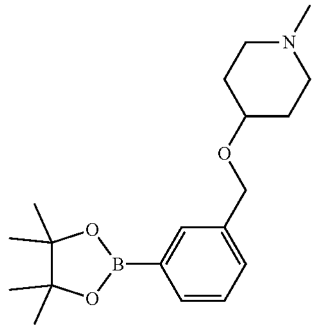

To a solution of Intermediate C (350 mg, 1.23 mmol) and 4,4,5,5-tetramethyl-2-(4,4,5,5-tetramethyl-1,3,2-dioxaborolan-2-yl)-1,3,2-dioxaborolane (375.29 mg, 1.48 mmol) in dioxane (5 mL) was added KOAc (241.73 mg, 2.46 mmol) and [1,1'-bis(di-tert-butylphosphino)ferrocene]dichloropalladium(II) (80.27 mg, 123.16 μmol). The mixture was stirred at 80° C. under $N_2$ for 2 h. The reaction mixture was diluted with $H_2O$ (10 mL) and extracted with EtOAc (10 mL×2). The combined organic layers were dried over anhydrous $Na_2SO_4$, filtered and concentrated under reduced pressure to afford Intermediate E (570 mg, crude) as yellow oil, which was used directly for the next step. LCMS (ESI) m/z $[M+H]^+$=332.0.

Step 3: Preparation of 1-(tert-butyl)-N-(2-((4-(3-(((1-methylpiperidin-4-yl)oxy)methyl)phenyl)thiazol-2-yl)amino)-2-oxoethyl)-1H-pyrrole-3-carboxamide (Compound 127)

Compound 127

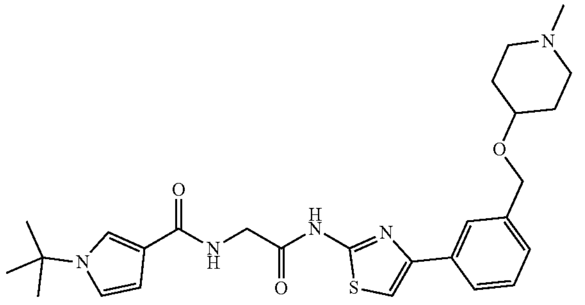

To a solution of N-[2-[(4-bromothiazol-2-yl)amino]-2-oxo-ethyl]-1-tert-butyl-pyrrole-3-carboxamide [prepared according to the method in Example 7] (80 mg, 207.64 μmol) and Intermediate E (206.35 mg, 622.93 μmol) in dioxane/$H_2O$=(4/1, 2 mL) was added $K_3PO_4$ (132.23 mg, 622.93 μmol) and [1,1'-bis(di-tert-butylphosphino)ferrocene]dichloropalladium(II) (27.07 mg, 41.53 μmol). The mixture was stirred at 80° C. under $N_2$ for 2 h. The reaction mixture was diluted with $H_2O$ (20 mL) and extracted with EtOAc (20 mL×2). The combined organic layers were dried over anhydrous $Na_2SO_4$, filtered and concentrated under reduced pressure to give a residue. The residue was purified by reversed phase (0.1% FA condition) and concentrated to remove the acetonitrile, then extracted with EtOAc (20 mL×2). The combined organic layers were dried over anhydrous $Na_2SO_4$, filtered and concentrated under reduced pressure to give the crude product. The crude product was purified by Prep-TLC (DCM/MeOH=10/1, Rf=0.1) and concentrated to afford Compound 127 (17.44 mg, 34.15 μmol, 16.45% yield) as a white solid. LCMS (ESI) m/z $[M+H]^+$=510.5; $^1H$ NMR (400 MHz, Methanol-$d_4$) δ 7.88 (s, 1H), 7.81-7.79 (m, 1H), 7.57-7.56 (m, 1H), 7.37-7.35 (m, 2H), 7.35-7.30 (m, 1H), 6.93-6.64 (m, 1H), 6.57-6.56 (m, 1H), 4.59 (s, 2H), 4.22 (s, 2H), 3.71-3.69 (m, 1H), 3.20-3.14 (m, 2H), 2.92 (br s, 2H), 2.67 (s, 3H), 2.05-1.93 (m, 4H), 1.54 (s, 9H).

Example 126. Preparation of 1-(tert-butyl)-N-(2-((4-(3-(((3,3-difluoro-1-methylpiperidin-4-yl)oxy)methyl)phenyl)thiazol-2-yl)amino)-2-oxoethyl)-1H-pyrrole-3-carboxamide (Compound 128)
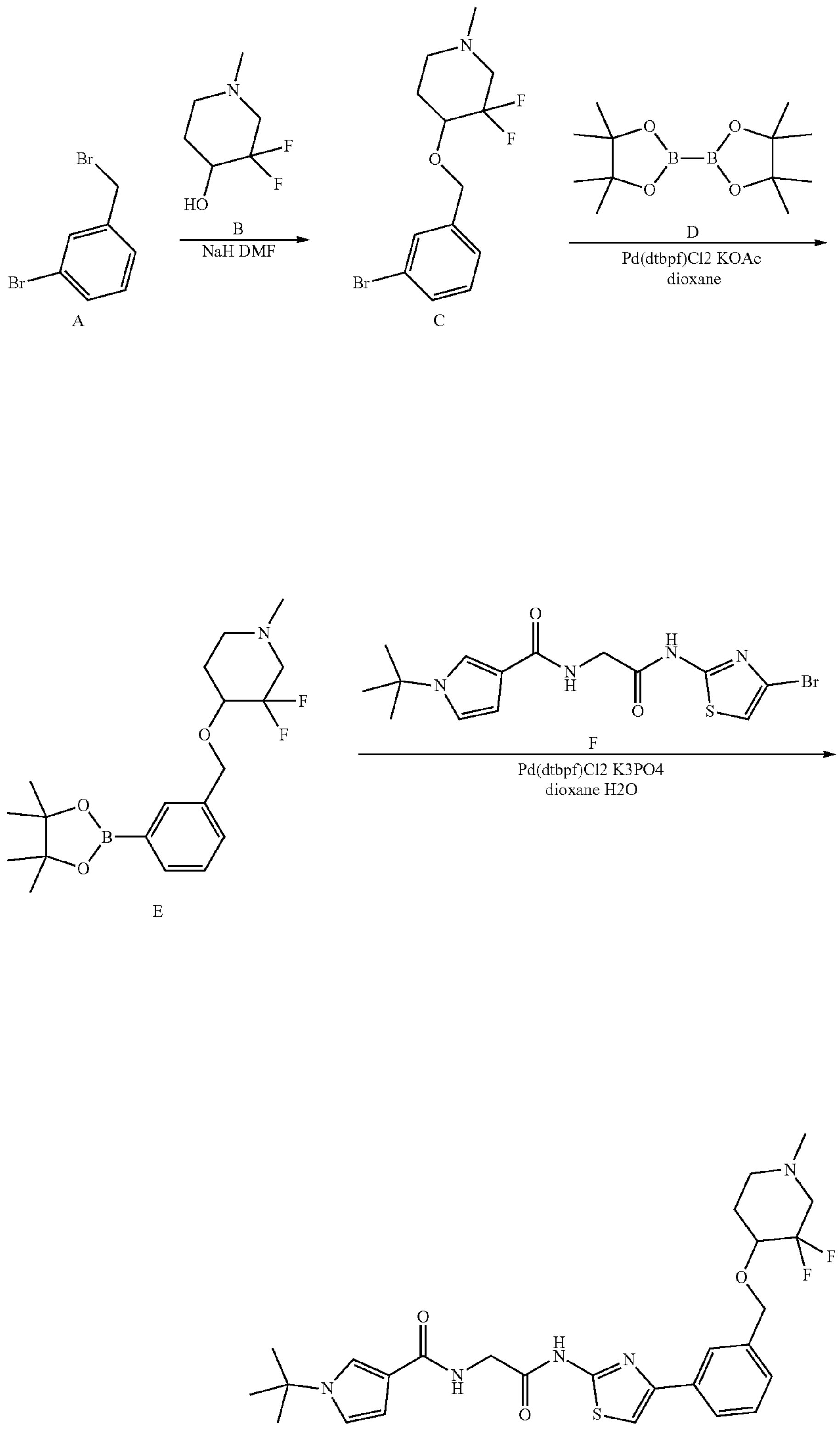
Compound 128

Step 1: Preparation of 4-((3-bromobenzyl)oxy)-3,3-difluoro-1-methylpiperidine (Intermediate C)

C

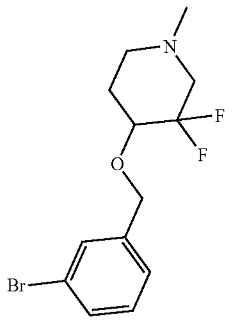

The solution of 3,3-difluoro-1-methyl-piperidin-4-ol (500 mg, 3.31 mmol) in DMF (3 mL) was added NaH (264.61 mg, 6.62 mmol, 60% purity) at 0° C. After stirred at 0° C. for 15 minutes, a solution of 1-bromo-3-(bromomethyl) benzene (826.74 mg, 3.31 mmol) in DMF (2 mL) was added dropwise at 0° C. The reaction mixture was warmed to 25° C. and stirred at 25° C. for 14 hours. The reaction mixture was quenched with saturated $NH_4Cl$ (40 mL) and extracted with EtOAc (20 mL×2), the combined organic layers was dried over anhydrous $Na_2SO_4$ and concentrated to afford a yellow oil. The oil was purified by flash silica gel chromatography (Eluent of 0-60% Ethyl acetate/Petroleum ether gradient) concentrated to afford Intermediate C (800 mg, 2.49 mmol, 75.17% yield) as yellow oil. LCMS (ESI) m/z $[M+H]^+$=320.0; $^1H$ NMR (400 MHz, Methanol-$d_4$) δ 7.52 (s, 1H), 7.44-7.42 (m, 1H), 7.35-7.29 (m, 1H), 7.29-7.23 (m, 1H), 4.74-4.62 (m, 2H), 3.77-3.62 (m, 1H), 2.88-2.73 (m, 1H), 2.71-2.54 (m, 2H), 2.46-2.36 (m, 1H), 2.31 (s, 3H), 1.98-1.87 (m, 2H).

Step 2: Preparation of 3,3-difluoro-1-methyl-4-((3-(4,4,5,5-tetramethyl-1,3,2-dioxaborolan-2-yl)benzyl)oxy)piperidine (Intermediate E)

E

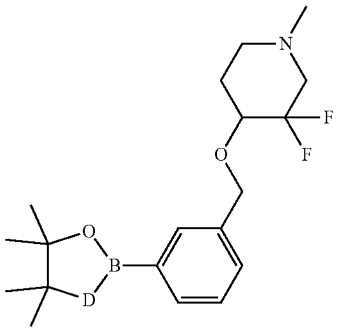

The solution of Intermediate C (400 mg, 1.25 mmol), 4,4,5,5-tetramethyl-2-(4,4,5,5-tetramethyl-1,3,2-dioxaborolan-2-yl)-1,3,2-dioxaborolane (634.51 mg, 2.50 mmol) and KOAc (367.84 mg, 3.75 mmol) in dioxane (4 mL) was added [1,1'-bis(di-tert-butylphosphino)ferrocene]dichloropalladium(II) (81.42 mg, 124.93 μmol) at 25° C. under $N_2$. The reaction mixture was stirred at 80° C. under $N_2$ for 3 hours. The reaction mixture was poured into water (10 mL) and extracted with EtOAc (10 mL×2), the combined organic layers was dried over anhydrous $Na_2SO_4$ and concentrated to afford Intermediate E (800 mg, crude) as a black brown oil, which was used to the next step without further purification. LCMS (ESI) m/z $[M+H]^+$=368.2.

Step 3: Preparation of 1-(tert-butyl)-N-(2-((4-(3-(((3,3-difluoro-1-methylpiperidin-4-yl)oxy)methyl) phenyl)thiazol-2-yl)amino)-2-oxoethyl)-1H-pyrrole-3-carboxamide (Compound 128)

Compound 128

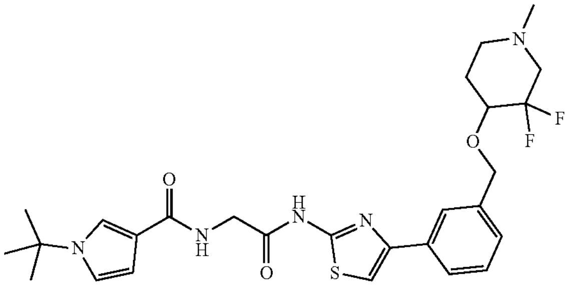

The solution of N-[2-[(4-bromothiazol-2-yl)amino]-2-oxo-ethyl]-1-tert-butyl-pyrrole-3-carboxamide [prepared according to the method in Example 7] (50 mg, 129.78 μmol), Intermediate E (95.32 mg, 259.55 μmol) and $K_3PO_4$ (82.64 mg, 389.33 μmol) in dioxane (0.8 mL) and $H_2O$ (0.2 mL) was added [1,1'-bis(di-tert-butylphosphino)ferrocene] dichloropalladium(II) (8.46 mg, 12.98 μmol) at 25° C. under $N_2$. The reaction mixture was stirred at 80° C. under $N_2$ for 4 hours. The reaction mixture was diluted with water (5 mL), and extracted with EtOAc (5 mL×3). The combined organic layers were concentrated to afford brown oil. The oil was dissolved with DMSO (1 mL) and purified by reversed-phase HPLC (FA), concentrated and lyophilized to afford a brown solid. The solid was dissolved with MeOH (1 mL) and purified by Prep-HPLC (mobile phase: [water (0.05% ammonia hydroxide v/v)-acetonitrile]; B %: 37%-67%), concentrated and lyophilized to afford Compound 128 (14.18 mg, 25.78 μmol, 19.87% yield) as a white solid. LCMS (ESI) m/z $[M+H]^+$=546.4; $^1H$ NMR (400 MHz, Methanol-$d_4$) δ 7.90 (s, 1H), 7.83 (d, J=7.6 Hz, 1H), 7.58-7.57 (m, 1H), 7.41-7.36 (m, 2H), 7.33-7.29 (m, 1H), 6.97-6.93 (m, 1H), 6.57-6.56 (m, 1H), 4.76-4.71 (m, 2H), 4.23 (s, 2H), 3.72-3.70 (m, 1H), 2.89-2.75 (m, 1H), 2.71-2.54 (m, 2H), 2.45-2.35 (m, 1H), 2.31 (s, 3H), 1.98-1.88 (m, 2H), 1.57 (s, 9H).

Example 127. Preparation of 1-(tert-butyl)-N-(2-oxo-2-((4-(3-(((tetrahydrofuran-3-yl)oxy)methyl)phenyl)thiazol-2-yl)amino)ethyl)-1H-pyrrole-3-carboxamide (Compound 129)
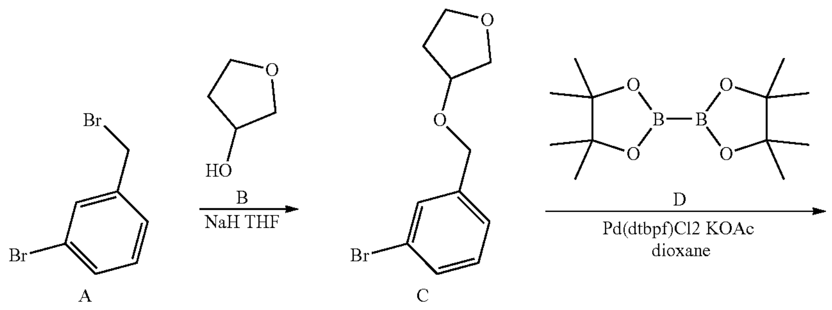
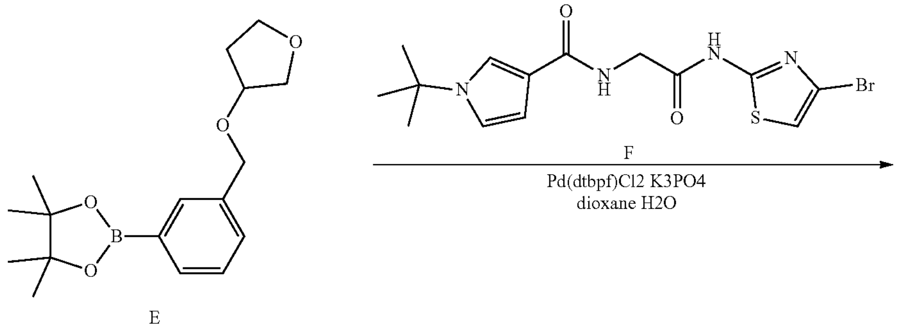
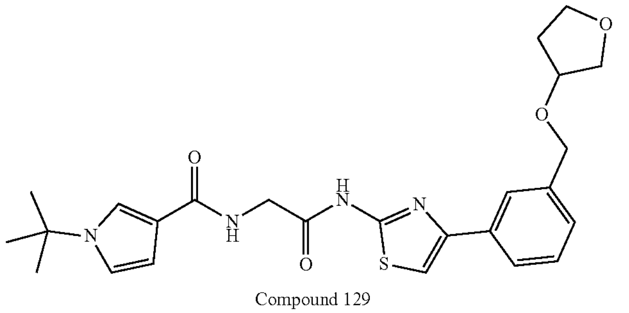
Compound 129

Step 1: Preparation of 3-((3-bromobenzyl)oxy)tetrahydrofuran (Intermediate C)

C

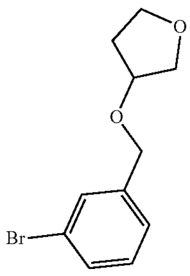

To a solution of tetrahydrofuran-3-ol (1 g, 11.35 mmol, 917.43 μL) in anhydrous THF (7 mL) was added NaH (907.92 mg, 22.70 mmol, 60% purity) at 0° C., after stirred for 15 minutes, a solution of 1-bromo-3-(bromomethyl) benzene (2.84 g, 11.35 mmol) in THF (3 mL) was added dropwise at 0° C. The reaction mixture was warmed to 25° C. and stirred for 3 hours. The reaction mixture was poured into saturation $NH_4Cl$ (60 mL) with stirring, then extracted with EtOAc (20 mL×3), the combined organic layers were dried over anhydrous $Na_2SO_4$, concentrated to afford yellow oil. The oil was dissolved with DCM (5 mL), then purified by flash silica gel chromatography (Eluent of 0-40% Ethyl acetate/Petroleum ether gradient) and concentrated to give Intermediate C (2.5 g, 9.68 mmol, 85.31% yield) as light yellow oil. $^1H$ NMR (400 MHz, DMSO-$d_6$) δ 7.53-7.50 (m, 1H), 7.50-7.45 (m, 1H), 7.35-7.28 (m, 2H), 4.52-4.42 (m, 2H), 4.23-4.17 (m, 1H), 3.74-3.71 (m, 2H), 3.70-3.64 (m, 2H), 1.97-1.91 (m, 2H).

Step 2: Preparation of 4,4,5,5-tetramethyl-2-(3-(((tetrahydrofuran-3-yl)oxy)methyl)phenyl)-1,3,2-dioxaborolane (Intermediate E)

E

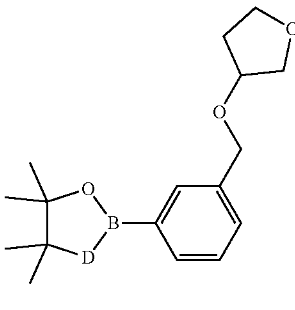

The solution of Intermediate C (500 mg, 1.94 mmol), 4,4,5,5-tetramethyl-2-(4,4,5,5-tetramethyl-1,3,2-dioxaborolan-2-yl)-1,3,2-dioxaborolane (592.57 mg, 2.33 mmol) and KOAc (572.54 mg, 5.83 mmol) in dioxane (1 mL) was added [1,1'-bis(di-tert-butylphosphino)ferrocene]dichloropalladium(II) (126.74 mg, 194.46 μmol) at 25° C. under $N_2$. The reaction mixture was stirred at 80° C. under $N_2$ for 4 hours. The reaction mixture was filtered and the filtrate was concentrated to afford Intermediate E (1.50 g, crude) as brown oil, which was used to the next step without further purification.

Step 3: Preparation of 1-(tert-butyl)-N-(2-oxo-2-((4-(3-(((tetrahydrofuran-3-yl)oxy)methyl)phenyl)thiazol-2-yl)amino)ethyl)-1H-pyrrole-3-carboxamide (Compound 129)

Compound 129

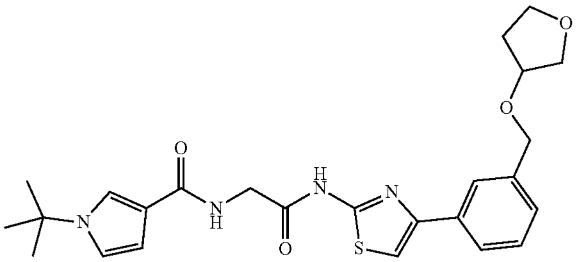

The solution of N-[2-[(4-bromothiazol-2-yl)amino]-2-oxo-ethyl]-1-tert-butyl-pyrrole-3-carboxamide [prepared according to the method in Example 7] (50 mg, 129.78 μmol), Intermediate E (78.95 mg, 259.55 μmol) and $K_3PO_4$ (82.64 mg, 389.33 μmol) in dioxane (0.8 mL) and $H_2O$ (0.2 mL) was added [1,1'-bis(di-tert-butylphosphino)ferrocene] dichloropalladium(II) (8.46 mg, 12.98 μmol) at 25° C. under $N_2$. The reaction mixture was stirred at 75° C. under $N_2$ for 16 hours. The reaction mixture was concentrated to afford brown oil. The oil was dissolved with DMSO (2 mL) and purified by Prep-HPLC (FA), concentrated and extracted with EtOAc (20 mL×2), the combined organic layers was dried over anhydrous $Na_2SO_4$ and concentrated to afford a yellow oil. The oil was dissolved with EtOAc (1 mL) and re-purified by Prep-TLC (EA, Rf=0.3), concentrated to afford a yellow oil. The oil was dissolved with MeOH (0.5 mL) and diluted with $H_2O$ (20 mL) then lyophilized to give Compound 129 (24.67 mg, 51.12 μmol, 39.39% yield) as a yellow gum. LCMS (ESI) m/z $[M+H]^+$=483.4; $^1H$ NMR (400 MHz, DMSO-$d_6$) δ 12.41-12.23 (m, 1H), 8.17-8.15 (m, 1H), 7.87 (s, 1H), 7.81 (d, J=7.8 Hz, 1H), 7.61 (s, 1H), 7.52-7.50 (m, 1H), 7.40-7.38 (m, 1H), 7.28 (d, J=7.5 Hz, 1H), 6.97-6.95 (m, 1H), 6.47-6.46 (m, 1H), 4.56-4.46 (m, 2H), 4.26-4.19 (m, 1H), 4.08 (d, J=6.0 Hz, 2H), 3.80-3.73 (m, 2H), 3.72-3.65 (m, 2H), 2.01-1.93 (m, 2H), 1.49 (s, 9H).

Example 128. Preparation of N-(2-((4-(2-methyl-1,2,3,4-tetrahydroisoquinolin-6-yl)thiazol-2-yl)amino)-2-oxoethyl)-1-(methylsulfonyl)-1H-pyrrole-3-carboxamide (Compound 130)
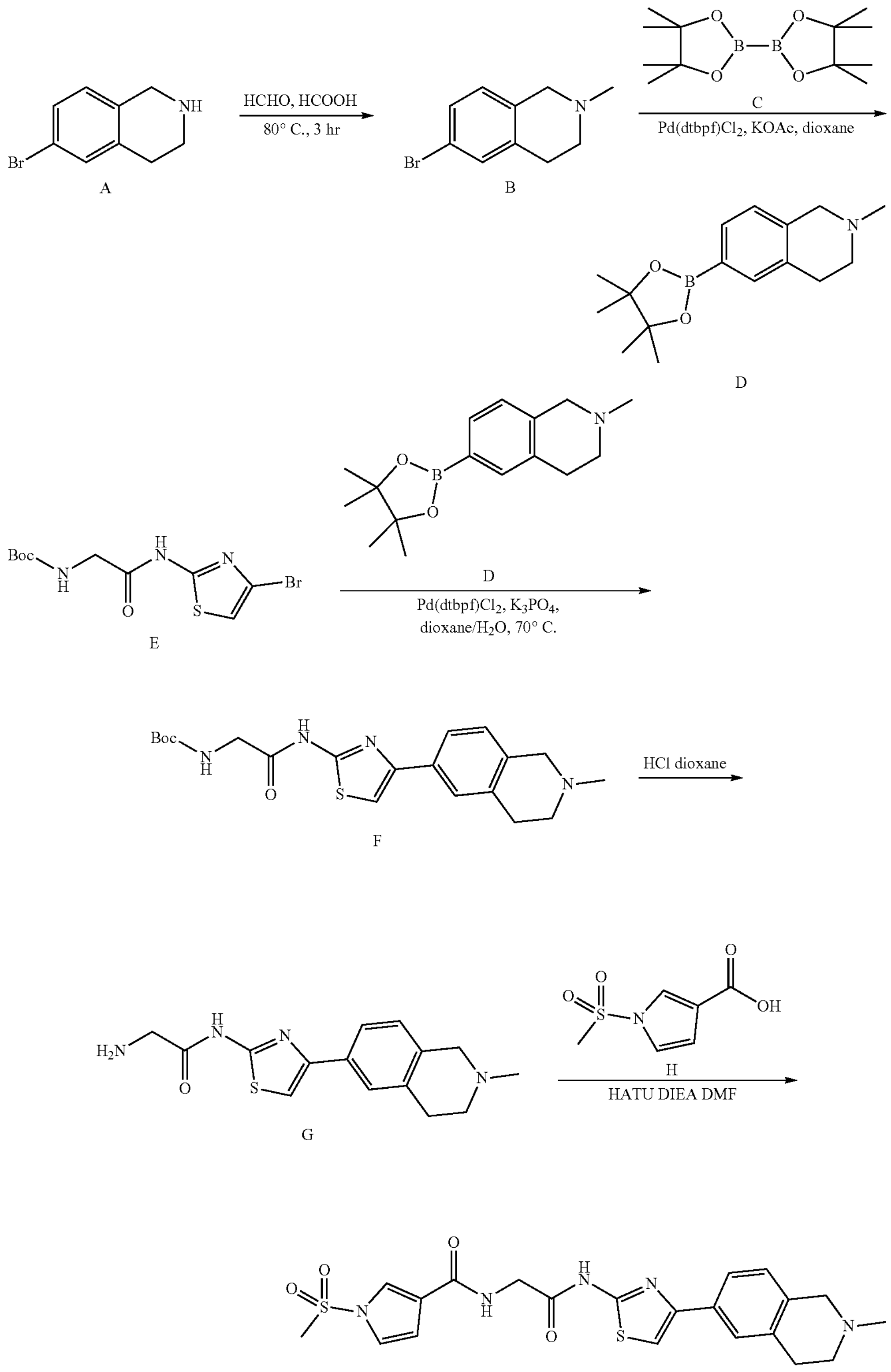
Compound 130

Step 1: Preparation of 6-bromo-2-methyl-3,4-dihydro-1H-isoquinoline (Intermediate B)

B

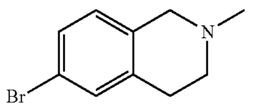

To the solution of 6-bromo-1,2,3,4-tetrahydroisoquinoline (500 mg, 2.36 mmol) in HCOOH (5 mL) was added 37% of aq. HCHO (1.91 g, 23.58 mmol) at 25° C. The reaction mixture was stirred at 80° C. for 3 hours. The reaction mixture was added NaOH (1 M) to adjust pH to 10, then extracted with EtOAc (20 mL×2), concentrated to afford intermediate B (400 mg, 1.64 mmol, 69.51% yield) as yellow oil. LCMS (ESI) m/z [M]+=226.1/228.1. $^1$H NMR (400 MHz, $CDCl_3$) δ 7.26-7.24 (m, 1H), 7.23 (d, J=2.0 Hz, 1H), 6.90 (d, J=8.0 Hz, 1H), 3.52 (s, H), 2.94-2.87 (m, 2H), 2.67-2.65 (m, 2H), 2.46 (s, 3H).

Step 2: Preparation of (S)-tert-butyl (3,3-dimethyl-1-oxo-1-((4-(3-(pyridin-4-yl)phenyl)thiazol-2-yl)amino)butan-2-yl)carbamate (Intermediate D)

D

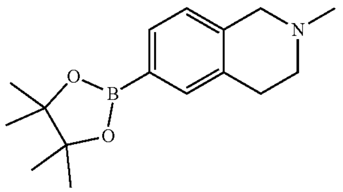

The solution of intermediate B (400 mg, 1.77 mmol), 4,4,5,5-tetramethyl-2-(4,4,5,5-tetramethyl-1,3,2-dioxaborolan-2-yl)-1,3,2-dioxaborolane (898.45 mg, 3.54 mmol) and KOAc (520.85 mg, 5.31 mmol) in dioxane (4 mL) added [1,1'-bis(di-tert-butylphosphino)ferrocene]dichloropalladium(II) (115.30 mg, 176.90 μmol) at 25° C. under $N_2$. The reaction mixture was stirred at 80° C. under $N_2$ for 2 hours. The reaction mixture was poured into water (20 mL). The mixture was extracted with EA (20 mL×3), concentrated to afford intermediate D (900 mg, crude) as a black brown oil, which was used for the next step directly. LCMS (ESI) m/z $[M+H]^+$=274.2.

Step 3: Preparation of (S)-tert-butyl (3,3-dimethyl-1-oxo-1-((4-(3-(pyridin-4-yl)phenyl)thiazol-2-yl)amino)butan-2-yl)carbamate (Intermediate F)

F

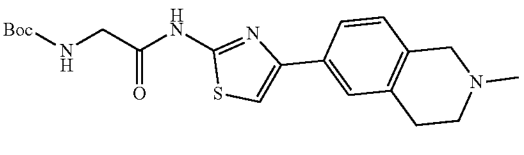

The solution of tert-butyl (2-((4-bromothiazol-2-yl)amino)-2-oxoethyl)carbamate [prepared according to the method in Example 6] (147.69 mg, 439.27 μmol), intermediate D (400 mg, 878.55 μmol) and $K_3PO_4$ (279.73 mg, 1.32 mmol) in dioxane (1.6 mL) and $H_2O$ (0.4 mL) was added [1,1'-bis(di-tert-butylphosphino)ferrocene]dichloropalladium(II) (28.63 mg, 43.93 μmol) at 25° C. under $N_2$. The reaction mixture was stirred at 80° C. under $N_2$ for 16 hours. The reaction mixture was poured into water (20 mL), then extracted with EtOAc (20 mL×3), the combined organic layers were concentrated to afford a black brown residue. The residue was dissolved with MeOH (3 mL) and purified by reversed-phase HPLC (FA), concentrated, then added NaOH (1M) to adjust pH to 10, extracted with EtOAc (20 mL×2), concentrated to afford Intermediate F (40 mg, 98.14 μmol, 22.34% yield) as yellow solid. LCMS (ESI) m/z $[M+H]^+$=403.2.

Step 4: Preparation of 2-amino-N-(4-(2-methyl-1,2,3,4-tetrahydroisoquinolin-6-yl)thiazol-2-yl)acetamide (Intermediate G)

G

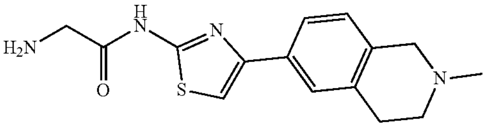

The solution of Intermediate F (40 mg, 99.38 μmol) in HCl/dioxane (0.5 mL) was stirred at 25° C. for 1 hour. The reaction mixture was concentrated to afford Intermediate G (20 mg, 54.18 μmol, 54.52% yield, HCl salt) as yellow solid. LCMS (ESI) m/z $[M+H]^+$=303.0.

Step 5: Preparation of N-(2-((4-(2-methyl-1,2,3,4-tetrahydroisoquinolin-6-yl)thiazol-2-yl)amino)-2-oxoethyl)-1-(methylsulfonyl)-1H-pyrrole-3-carboxamide (Compound 130)

Compound 130

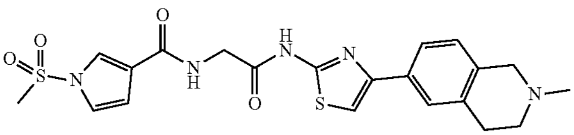

The solution of 1-methylsulfonylpyrrole-3-carboxylic acid [prepared according to the method in Example 4] (13.40 mg, 70.83 μmol), HATU (33.66 mg, 88.53 μmol) and DIEA (22.88 mg, 177.07 μmol, 30.84 μL) in DMF (0.5 mL) was stirred at 25° C. for 5 minutes, then Intermediate D (20 mg, 59.02 μmol, HCl salt) was added at 25° C. The reaction mixture was stirred at 25° C. for 16 hours. The reaction mixture was diluted with water (5 mL), then extracted with EtOAc (5 mL×2). The combined organic layers were concentrated to afford a yellow liquid. The liquid was diluted with MeOH (2 mL), then purified by reversed-phase HPLC (FA), lyophilized to afford Compound 130 (3.56 mg, 7.26 μmol, 12.30% yield, FA salt) as yellow solid. LCMS (ESI) m/z $[M+H]^+$=474.1; $^1$H NMR (400 MHz, DMSO-$d_6$) δ

12.53-12.21 (m, 1H), 8.67-8.66 (m, 1H), 8.26 (s, 1H), 7.84-7.83 (m, 1H), 7.65 (s, 1H), 7.53 (s, 1H), 7.31-7.30 (m, 1H), 7.09 (d, J=8.0 Hz, 1H), 6.77-6.76 (m, 1H), 4.13 (d, J=6.0 Hz, 2H), 3.57 (s, 3H), 3.50 (br s, 2H), 2.86 (d, J=6.0 Hz, 2H), 2.62 (br s, 2H), 2.35 (s, 3H).

Example 129. Preparation of 1-(tert-butyl)-N-(2-((4-(1-methyl-1H-indazol-6-yl)thiazol-2-yl)amino)-2-oxoethyl)-1H-pyrrole-3-carboxamide (Compound 131)

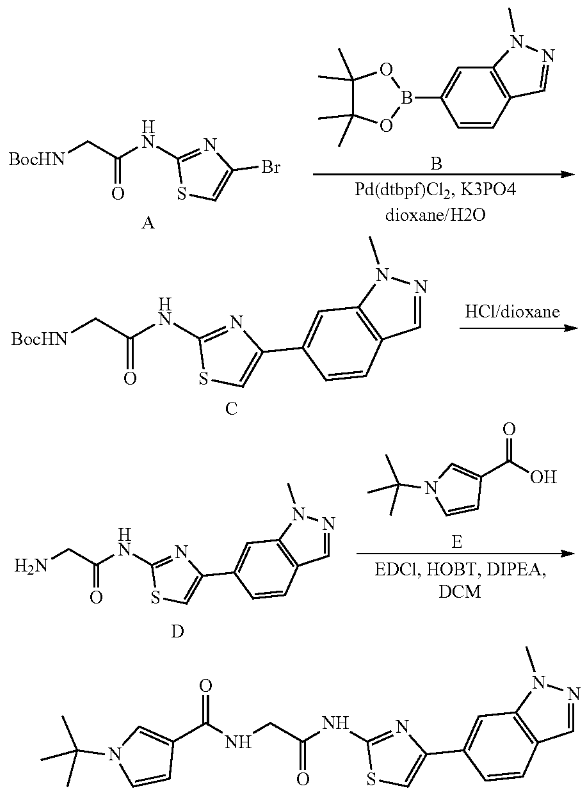

Compound 131

Step 1: Preparation of tert-butyl (2-((4-(1-methyl-1H-indazol-6-yl)thiazol-2-yl)amino)-2-oxoethyl) carbamate (Intermediate C)

C

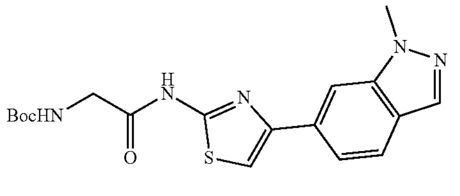

To a mixture of tert-butyl N-[2-[(4-bromothiazol-2-yl) amino]-2-oxo-ethyl]carbamate (Prepared according to the method in Example 6) (300 mg, 892.31 μmol), 1-methyl-6-(4,4,5,5-tetramethyl-1,3,2-dioxaborolan-2-yl)indazole (345.49 mg, 1.34 mmol), $K_3PO_4$ (757.63 mg, 3.57 mmol) in dioxane (5 mL)/$H_2O$ (1 mL) was added [1,1'-bis(di-tert-butylphosphino)ferrocene]dichloropalladium(II) (58.16 mg, 89.23 μmol), the mixture was stirred under $N_2$ at 85° C. for 2 h. The reaction mixture was diluted with water (15 mL) and extracted with EtOAc (25 mL×2). The combined organic layers were washed with brine (10 mL×2), dried over $Na_2SO_4$, filtered and concentrated under reduced pressure to give a residue. The residue was purified by reversed phase (0.1% FA condition), the fraction was lyophilized to give Intermediate C (266 mg, 679.67 μmol, 76.17% yield) as black brown oil. LCMS (ESI) m/z $[M+H]^+$=388.2.

Step 2: Preparation of 2-amino-N-(4-(1-methyl-1H-indazol-6-yl)thiazol-2-yl)acetamide (Intermediate D)

D

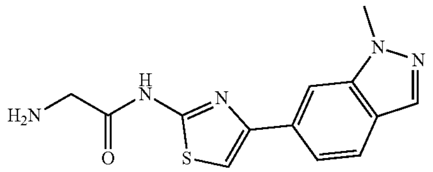

A solution of Intermediate C (260 mg, 671.05 μmol) in HCl/dioxane (3 mL) was stirred at 25° C. for 2 hr. The reaction mixture was concentrated under vacuum to give Intermediate D (210 mg, crude, HCl salt) as a gray solid, which was used to next step without further purification. LCMS (ESI) m/z: $[M+H]^+$=287.9.

Step 3: Preparation of 1-(tert-butyl)-N-(2-((4-(1-methyl-1H-indazol-6-yl)thiazol-2-yl)amino)-2-oxo-ethyl)-1H-pyrrole-3-carboxamide_(Compound 131)

Compound 131

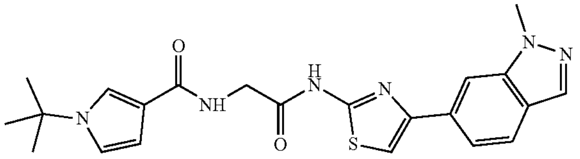

To a mixture of 1-tert-butylpyrrole-3-carboxylic acid [prepared according to the method in Example 34] (92.95 mg, 555.90 μmol), EDCI (213.13 mg, 1.11 mmol), DIEA (239.49 mg, 1.85 mmol, 322.76 μL) and HOBt (60.09 mg, 444.72 μmol) in DCM (4 mL) was added Intermediate D (120 mg, 370.60 μmol, HCl salt), the reaction mixture was stirred at 25° C. for 2 hr. The reaction mixture was concentrated under vacuum to give residue. The residue was purified by Prep-HPLC (mobile phase: [water (0.1% TFA)-acetonitrile]; B %: 38%-68%), fraction was lyophilized to give Compound 131 (32.94 mg, 75.46 μmol, 20.36% yield) as a white solid. LCMS (ESI) m/z $[M+H]^+$=437.1; $^1H$ NMR (400 MHz, Methanol-$d_4$) δ 8.10 (s, 1H), 7.98 (m, 1H), 7.77-7.71 (m, 2H), 7.59-7.52 (m, 2H), 6.97-6.95 (m, 1H), 6.59-6.57 (m, 1H), 4.25 (s, 2H), 4.09 (s, 3H), 1.57 (s, 9H).

Example 130. Preparation of N-(2-((4-(1-methyl-1H-indazol-6-yl)thiazol-2-yl)amino)-2-oxoethyl)-1-(methylsulfonyl)-1H-pyrrole-3-carboxamide (Compound 132)

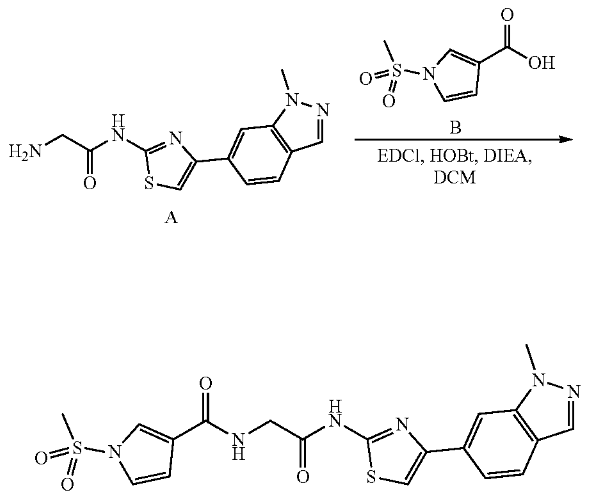

Compound 132

To a solution of 1-methylsulfonylpyrrole-3-carboxylic acid [prepared according to the method in Example 4] (35.06 mg, 185.30 μmol), HATU (88.07 mg, 231.62 μmol) and DIEA (99.79 mg, 772.08 μmol, 134.48 μL) in DCM (2 mL) was added 2-amino-N-[4-(1-methylindazol-6-yl)thiazol-2-yl]acetamide [prepared according to the method in Example 129] (50 mg, 154.42 μmol, HCl salt). The mixture was stirred at 25° C. for 2 h. The reaction mixture was concentrated under vacuum to give residue. The residue was purified by Prep-HPLC (mobile phase: [water (0.1% TFA)-acetonitrile]; B %: 27%-57%). The fraction was lyophilized to give Compound 132 (38.97 mg, 84.99 μmol, 55.04% yield) as an off-white solid. LCMS (ESI) m/z $[M+H]^+$ =458.9; $^1H$ NMR (400 MHz, DMSO-$d_6$) δ 12.43 (s, 1H), 8.70-8.67 (m, 1H), 8.11-8.03 (m, 2H), 7.85-7.78 (m, 2H), 7.74-7.69 (m, 2H), 7.32-7.31 (m, 1H), 6.78-6.77 (m, 1H), 4.16-4.07 (m, 5H), 3.57 (s, 3H).

Example 131. Preparation of 1-(tert-butyl)-N-(2-((4-(1-methyl-2-oxo-1,2-dihydroquinolin-7-yl)thiazol-2-yl)amino)-2-oxoethyl)-1H-pyrrole-3-carboxamide (Compound 133)

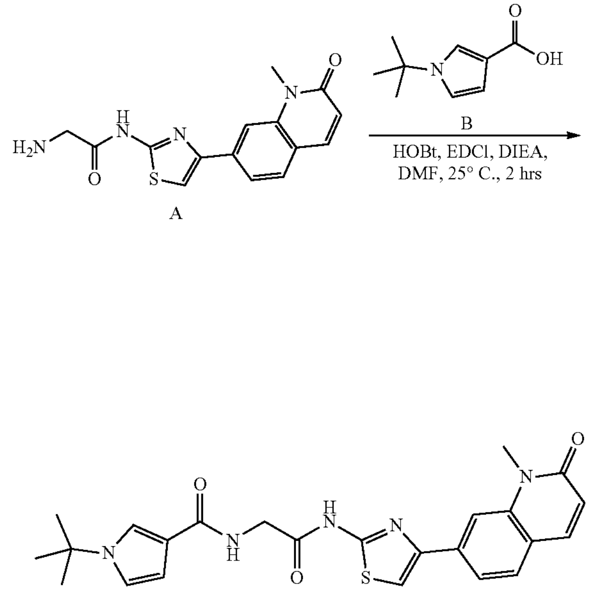

Compound 133

To a solution of 1-tert-butylpyrrole-3-carboxylic acid [prepared according to the method in Example 34] (28.60 mg, 171.05 μmol) in DMF (0.6 mL) was added DIEA (55.26 mg, 427.57 μmol, 74.47 μL), EDCI (40.98 mg, 213.77 μmol), HOBt (28.89 mg, 213.81 μmol) and 2-amino-N-[4-(1-methyl-2-oxo-7-quinolyl)thiazol-2-yl]acetamide (50 mg, 101.48 μmol, HCl salt) (prepared according to the method in Example 12). The mixture was stirred at 25° C. for 14 h. The reaction mixture was diluted with $H_2O$ (5 mL) and extracted with EtOAc (5 mL×3). The combined organic layers were washed with saturated brine (5 mL×3), dried over anhydrous $Na_2SO_4$, filtered and concentrated under reduced pressure to give a residue. The residue was purified by reversed-phase HPLC (basic condition) and lyophilized to give Compound 133 (11.30 mg, 24.38 μmol, 24.02% yield) as yellow solid. LCMS (ESI) m/z $[M+H]^+$=464.0; $^1H$ NMR (400 MHz, DMSO-$d_6$) δ 8.10 (s, 1H), 8.00 (s, 1H), 7.90 (d, J=9.2 Hz, 1H), 7.87-7.72 (m, 3H), 7.52 (s, 1H), 6.97 (s, 1H), 6.60 (d, J=9.2 Hz, 1H), 6.50-6.45 (m, 1H), 4.07 (d, J=6.0 Hz, 2H), 3.68 (s, 3H), 1.49 (s, 9H).

Example 132. Preparation of 1-(tert-butyl)-N-(2-((4-(1,3-dimethyl-2-oxo-1,2,3,4-tetrahydroquinazolin-7-yl)thiazol-2-yl)amino)-2-oxoethyl)-1H-pyrrole-3-carboxamide (Compound 134)

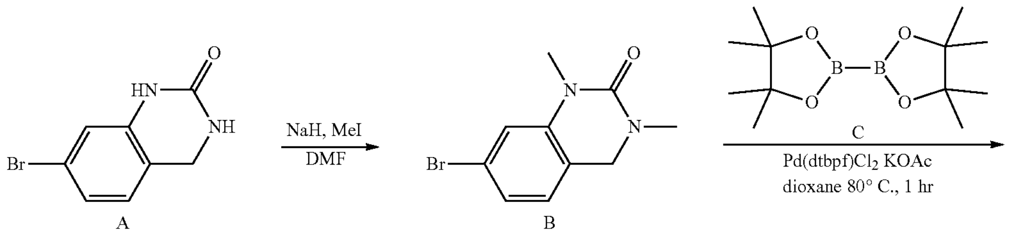

-continued

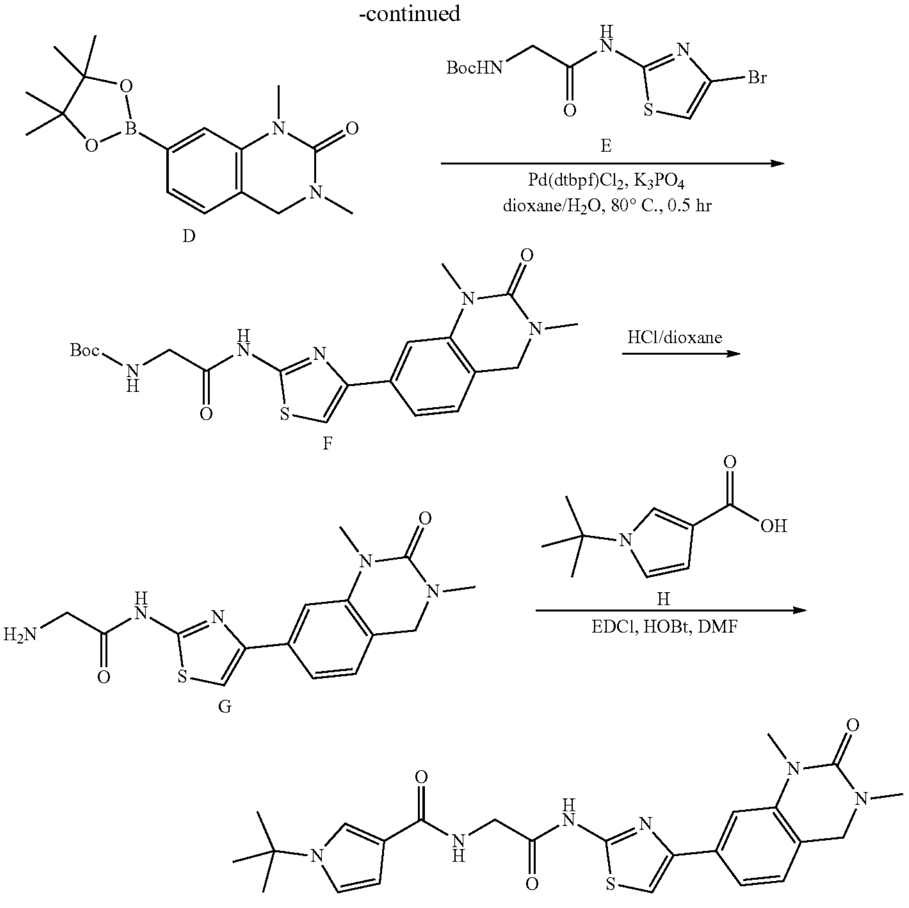

Compound 134

Step 1: Preparation of 7-bromo-1,3-dimethyl-3,4-dihydroquinazolin-2(1H)-one (Intermediate B)

B

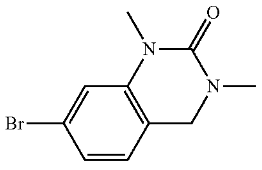

To a solution of 7-bromo-3,4-dihydro-1H-quinazolin-2-one (180 mg, 792.75 μmol) in DMF (3 mL) was added NaH (95.12 mg, 2.38 mmol, 60% purity) at 0° C. The mixture was stirred at 25° C. for 10 min. Then MeI (337.57 mg, 2.38 mmol, 148.06 μL) was added. The mixture was stirred at 25° C. for 0.5 h. The mixture was poured into $H_2O$ (10 mL) and extracted with EtOAc (10 mLx3). The combined organic layer was washed with brine (20 mL), dried over $Na_2SO_4$, filtered and concentrated. The residue was purified by flash silica gel chromatography (Eluent of 0-30% Ethyl acetate/Petroleum ether gradient) and concentrated in vacuum to give Intermediate B (150 mg, 587.98 μmol, 74.17% yield) as yellow oil. LCMS (ESI) m/z $[M+H]^+$=257.0; $^1$H NMR (400 MHz, $CDCl_3$) δ 7.10-7.02 (m, 1H), 6.96-6.82 (m, 2H), 4.27 (d, J=1.6 Hz, 2H), 3.24 (d, J=2.8 Hz, 3H), 3.09-2.92 (m, 3H).

Step 2: Preparation of 1,3-dimethyl-7-(4,4,5,5-tetramethyl-1,3,2-dioxaborolan-2-yl)-3,4-dihydroquinazolin-2(1H)-one (Intermediate D)

D

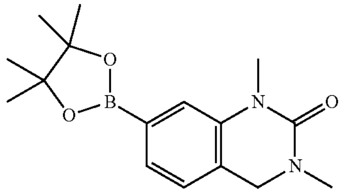

A mixture of Intermediate B (130 mg, 509.58 μmol), 4,4,5,5-tetramethyl-2-(4,4,5,5-tetramethyl-1,3,2-dioxaborolan-2-yl)-1,3,2-dioxaborolane (258.80 mg, 1.02 mmol), potassium acetate (150.03 mg, 1.53 mmol) and [1,1'-bis(di-tert-butylphosphino)ferrocene]dichloropalladium(II) (33.21 mg, 50.96 μmol) in dioxane (3 mL) was degassed and purged with $N_2$ for 3 times, and then the mixture was stirred at 80° C. for 1 hr under $N_2$ atmosphere. The mixture was poured into water (3 mL) and extracted with EtOAc (10 mLx3). The combined organic layer was washed with brine (5 mL), dried over $Na_2SO_4$, filtered and concentrated. The residue was purified by flash silica gel chromatography (Eluent of 0-35% Ethyl acetate/Petroleum ether gradient)

and concentrated in vacuum to give Intermediate D (140 mg, 463.31 μmol, 90.92% yield) as a yellow oil. LCMS (ESI) m/z $[M+H]^+$=303.2.

Step 3: Preparation of tert-butyl (2-((4-(1,3-dimethyl-2-oxo-1,2,3,4-tetrahydroquinazolin-7-yl)thiazol-2-yl)amino)-2-oxoethyl)carbamate (Intermediate F)

F

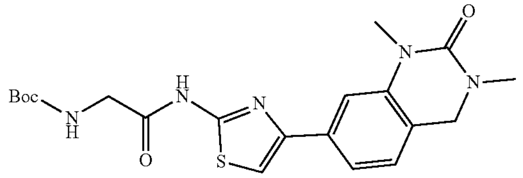

A mixture of tert-butyl N-[2-[(4-bromothiazol-2-yl)amino]-2-oxo-ethyl]carbamate [Prepared according to the method in Example 6] (100 mg, 297.44 μmol), Intermediate D (134.82 mg, 446.16 μmol), [1,1'-bis(di-tert-butylphosphino)ferrocene]dichloropalladium(II) (19.39 mg, 29.74 μmol), $K_3PO_4$ (189.41 mg, 892.32 μmol) in dioxane (3 mL) and $H_2O$ (1 mL) was degassed and purged with $N_2$ for 3 times, and then the mixture was stirred at 80° C. for 0.5 h under $N_2$ atmosphere. The reaction mixture was poured into $H_2O$ (10 mL) and extracted with (15 mL×3). The combined organic layer was washed with brine (5 mL), dried over $Na_2SO_4$, filtered and concentrated. The residue was purified by flash silica gel chromatography (Eluent of 0-30% Ethyl acetate/Petroleum ether gradient) and concentrated in vacuum to give Intermediate F (50 mg, 115.87 μmol, 38.96% yield) as a white solid. LCMS (ESI) m/z $[M+H]^+$=432.1.

Step 4: Preparation of 2-amino-N-(4-(1,3-dimethyl-2-oxo-1,2,3,4-tetrahydroquinazolin-7-yl)thiazol-2-yl)acetamide (Intermediate G)

G

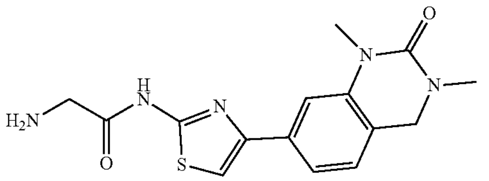

A solution of Intermediate F (50 mg, 115.87 μmol) in HCl/dioxane (4 M, 1 mL) was stirred at 25° C. for 0.5 h. The reaction mixture was concentrated under vacuum. The residue was washed with EtOAc (5 mL) and filtered and dried in vacuum to give Intermediate G (40 mg, 108.74 μmol, 93.84% yield, HCl salt) as a light yellow solid, which was used for the next step without purification. LCMS (ESI) m/z $[M+H]^+$=332.1.

Step 5: Preparation of 1-(tert-butyl)-N-(2-((4-(1,3-dimethyl-2-oxo-1,2,3,4-tetrahydroquinazolin-7-yl)thiazol-2-yl)amino)-2-oxoethyl)-1H-pyrrole-3-carboxamide (Compound 134)

Compound 134

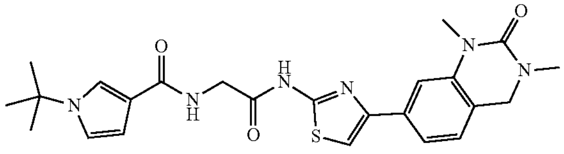

To a solution of Intermediate G (40 mg, 108.74 μmol, HCl salt) and 1-tert-butylpyrrole-3-carboxylic acid [prepared according to the method in Example 34] (21.82 mg, 130.49 μmol) in DMF (3 mL) was added EDCI (31.27 mg, 163.11 μmol), HOBt (22.04 mg, 163.11 μmol) and DIEA (70.27 mg, 543.70 μmol, 94.70 μL). The mixture was stirred at 25° C. for 1 h. The reaction mixture was poured into $H_2O$ (30 mL) and stirred, the mixture was filtered. The solid was purified by Prep-HPLC (mobile phase: [water (0.225% FA)-acetonitrile]; B %: 32%-62%) and lyophilized to give Compound 134 (25.19 mg, 52.42 μmol, 48.20% yield) as a white solid. LCMS (ESI) m/z $[M+H]^+$=481.2; $^1H$ NMR (400 MHz, DMSO-$d_6$) δ 12.59-12.13 (m, 1H), 8.18-8.16 (m, 1H), 7.67 (s, 1H), 7.55-7.49 (m, 2H), 7.42 (d, J=1.2 Hz, 1H), 7.20 (d, J=7.8 Hz, 1H), 6.98-6.97 (m, 1H), 6.48-6.47 (m, 1H), 4.39 (s, 2H), 4.08 (d, J=6.0 Hz, 2H), 3.26 (s, 3H), 2.91 (s, 3H), 1.49 (s, 9H).

Example 133. Preparation of (S)-1-(tert-butyl)-N-(2-oxo-2-((4-(3-(((tetrahydrofuran-3-yl)oxy)methyl)phenyl)thiazol-2-yl)amino)ethyl)-1H-pyrrole-3-carboxamide (Compound 135) and (R)-1-(tert-butyl)-N-(2-oxo-2-((4-(3-(((tetrahydrofuran-3-yl)oxy)methyl)phenyl)thiazol-2-yl)amino)ethyl)-1H-pyrrole-3-carboxamide (Compound 136)

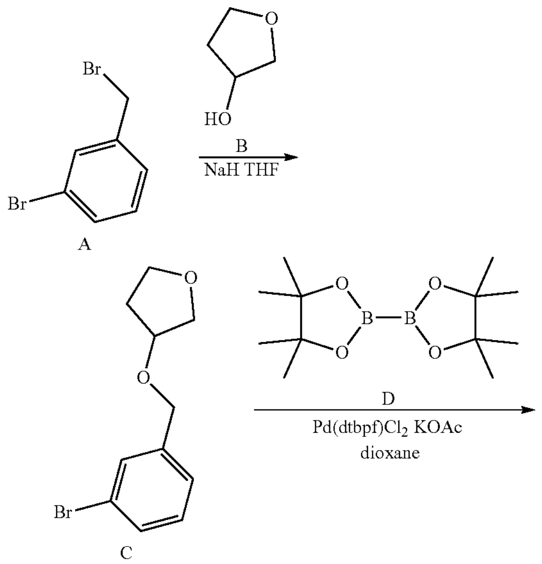

-continued

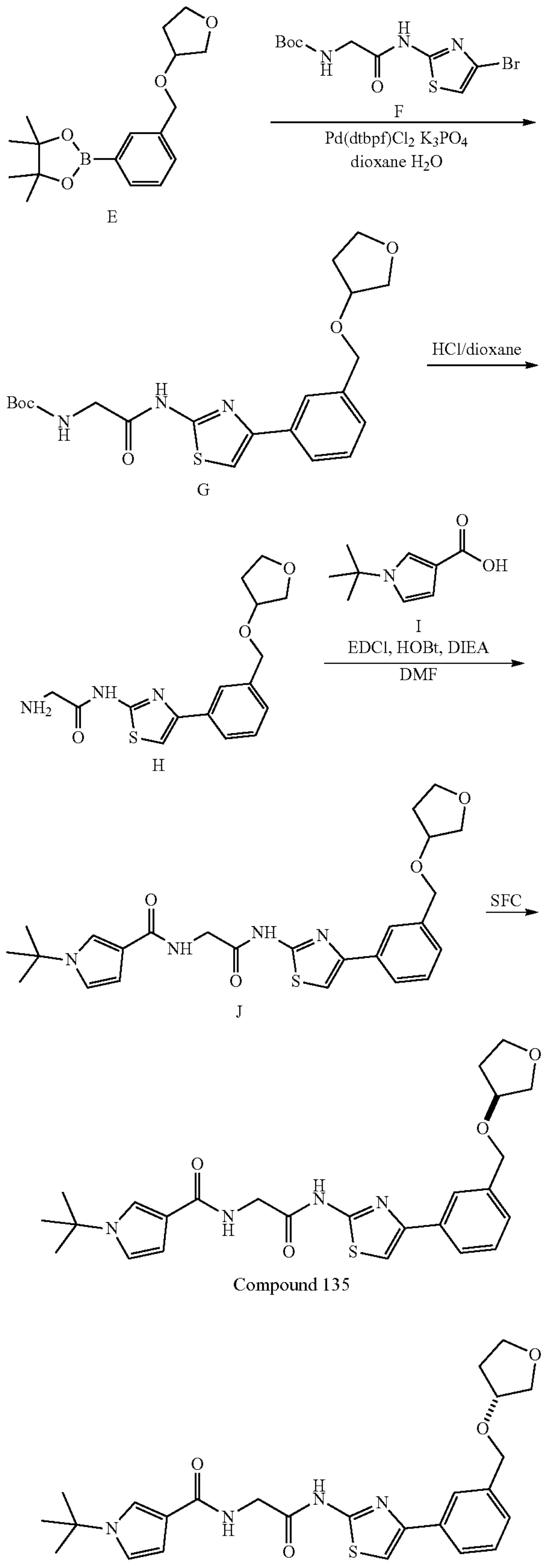

E

F

G

H

I

J

Compound 135

Compound 136

Step 1: Preparation of 3-((3-bromobenzyl)oxy)tetrahydrofuran (Intermediate C)

C

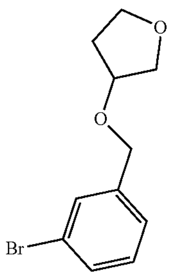

To a solution of tetrahydrofuran-3-ol (2 g, 22.70 mmol, 1.83 mL) in anhydrous THF (15 mL) was added NaH (1.82 g, 45.40 mmol, 60% purity) at 0° C., after stirred for 0.5 hour, a solution of 1-bromo-3-(bromomethyl)benzene (5.67 g, 22.70 mmol) in anhydrous THF (5 mL) was added dropwise at 0° C. The reaction mixture was warmed to 25° C. and stirred for 3 hours. The reaction mixture was poured into saturation $NH_4Cl$ (80 mL) with stirring, then extracted with EtOAc (30 mL×3), the combined organic layers were dried over anhydrous $Na_2SO_4$, concentrated to afford a yellow oil. The oil was dissolved with DCM (5 mL), then purified by flash silica gel chromatography (Eluent of 0-40% Ethyl acetate/Petroleum ether gradient), concentrated to afford Intermediate C (5.00 g, 17.50 mmol, 77.10% yield) as a light yellow oil. $^1$H NMR (400 MHz, DMSO-$d_6$) δ 7.51 (s, 1H), 7.47-7.46 (m, 1H), 7.35-7.28 (m, 2H), 4.51-4.42 (m, 2H), 4.22-4.17 (m, 1H), 3.79-3.73 (m, 1H), 3.73-3.70 (m, 1H), 3.70-3.64 (m, 2H), 1.98-1.91 (m, 2H).

Step 2: Preparation of 4,4,5,5-tetramethyl-2-(3-(((tetrahydrofuran-3-yl)oxy)methyl)phenyl)-1,3,2-dioxaborolane (Intermediate E)

E

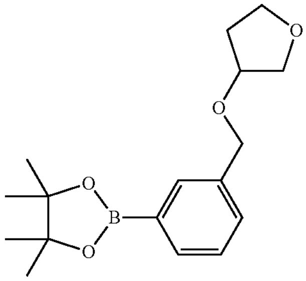

The solution of Intermediate C (2.5 g, 9.72 mmol), 4,4,5,5-tetramethyl-2-(4,4,5,5-tetramethyl-1,3,2-dioxaborolan-2-yl)-1,3,2-dioxaborolane (2.96 g, 11.67 mmol) and KOAc (2.86 g, 29.17 mmol) in dioxane (3 mL) was added [1,1'-bis(di-tert-butylphosphino)ferrocene]dichloropalladium(II) (633.69 mg, 972.29 μmol) at 25° C. under $N_2$. The reaction mixture was stirred at 80° C. under $N_2$ for 3 hours. The reaction mixture was diluted with water (10 mL) and extracted with EtOAc (40 mL), the combined organic layers was dried over anhydrous $Na_2SO_4$ and concentrated to afford Intermediate E (4 g, crude) as a brown oil, which was used to the next step without further purification.

Step 3: Preparation of tert-butyl (2-oxo-2-((4-(3-(((tetrahydrofuran-3-yl)oxy)methyl)phenyl)thiazol-2-yl)amino)ethyl)carbamate (Intermediate G)

G

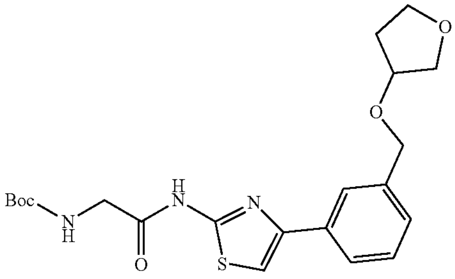

To a solution of tert-butyl N-[2-[(4-bromothiazol-2-yl)amino]-2-oxo-ethyl]carbamate [Prepared according to the method in Example 6] (800 mg, 2.38 mmol), Intermediate E (868.58 mg, 2.86 mmol) and $K_3PO_4$ (1.52 g, 7.14 mmol) in dioxane (8 mL) in dioxane (8 mL) and $H_2O$ (2 mL) was added [1,1'-bis(di-tert-butylphosphino)ferrocene]dichloropalladium(II) (155.08 mg, 237.95 μmol) at 25° C. under $N_2$. The reaction mixture was stirred at 80° C. for 16 hours. The reaction mixture was poured into water (20 mL) and extracted with EtOAc (15 mL×3), the combined organic layers was dried over anhydrous $Na_2SO_4$ and concentrated to afford a brown oil. The oil was purified by flash silica gel chromatography (Eluent of 0-70% Ethyl acetate/Petroleum ether gradient) and concentrated to afford Intermediate G (600 mg, 1.37 mmol, 57.54% yield) as yellow oil. LCMS (ESI) m/z $[M+H]^+$=434.2; $^1$H NMR (400 MHz, DMSO-$d_6$) δ 12.29 (s, 1H), 7.87 (s, 1H), 7.80 (d, J=8.0 Hz, 1H), 7.63 (s, 1H), 7.40-7.38 (m, 1H), 7.28 (d, J=7.6 Hz, 1H), 7.16-7.14 (m, 1H), 4.54-4.47 (m, 2H), 4.25-4.20 (m, 1H), 3.93 (s, 1H), 3.88-3.82 (m, 2H), 3.80-3.73 (m, 2H), 3.72-3.64 (m, 2H), 1.97-1.94 (m, 1H), 1.40 (s, 9H).

Step 4: Preparation of 2-amino-N-(4-(3-(((tetrahydrofuran-3-yl)oxy)methyl)phenyl)thiazol-2-yl)acetamide (Intermediate H)

H

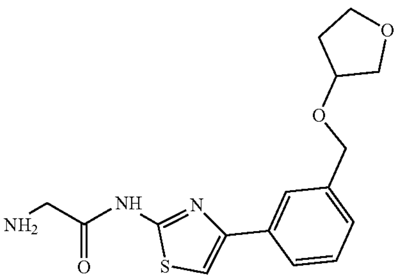

To a solution of Intermediate G (600 mg, 1.38 mmol) in dioxane (3 mL) was added HCl/dioxane (3 mL) and the solution was stirred at 25° C. for 2 hours. The reaction mixture was filtered and the solid was dried in vacuum to give Intermediate H (420 mg, 1.06 mmol, 76.36% yield, HCl salt) as a yellow solid, which was used to the next step without further purification. LCMS (ESI) m/z $[M+H]^+$=334.3; $^1$H NMR (400 MHz, $D_2O$) δ 7.77-7.72 (m, 2H), 7.47-7.41 (m, 2H), 7.38-7.33 (m, 1H), 4.55-4.54 (m, 1H), 4.56 (s, 1H), 4.39-4.34 (m, 1H), 4.09 (s, 2H), 3.92-3.86 (m, 2H), 3.86-3.77 (m, 1H), 3.74-3.68 (m, 1H), 2.12-2.01 (m, 2H).

Step 5: Preparation of 1-(tert-butyl)-N-(2-oxo-2-((4-(3-(((tetrahydrofuran-3-yl)oxy)methyl)phenyl)thiazol-2-yl)amino)ethyl)-1H-pyrrole-3-carboxamide (Intermediate J)

J

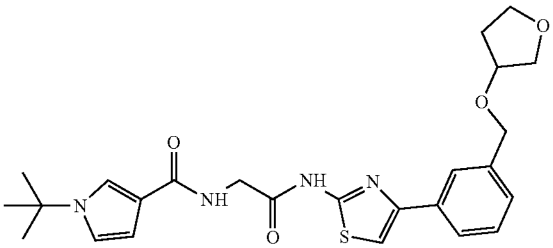

To a solution of 1-tert-butylpyrrole-3-carboxylic acid [prepared according to the method in Example 34] (189.87 mg, 1.14 mmol), EDCI (326.53 mg, 1.70 mmol), HOBt (230.16 mg, 1.70 mmol) and DIEA (440.28 mg, 3.41 mmol, 593.38 μL) in DMF (4 mL) was stirred at 25° C. for 5 minutes, then Intermediate H (420 mg, 1.14 mmol, HCl salt) was added at 25° C. The reaction mixture was stirred at 25° C. for 16 hours. The reaction mixture was diluted with water (5 mL), and extracted with EtOAc (5 mL×3), then concentrated to afford a brown oil. The oil was diluted with DCM (3 mL) and purified by flash silica gel chromatography (Eluent of 0-80% Ethyl acetate/Petroleum ether gradient) and concentrated to afford Intermediate J (250 mg, 513.16 μmol, 45.19% yield) as yellow oil. LCMS (ESI) m/z $[M+H]^+$=483.3; $^1$H NMR (400 MHz, Methanol-$d_4$) δ 7.90 (s, 1H), 7.81 (d, J=8.0 Hz, 1H), 7.58-7.57 (m, 1H), 7.41-7.35 (m, 2H), 7.31-7.27 (m, 1H), 6.97-6.93 (m, 1H), 6.57-6.56 (m, 1H), 4.61-4.52 (m, 2H), 4.29-4.28 (m, 1H), 4.23 (s, 2H), 3.95-3.86 (m, 2H), 3.85-3.75 (m, 2H), 2.11-2.01 (m, 2H), 1.57 (s, 9H); 49.894%.

Step 6: Preparation of (S)-1-(tert-butyl)-N-(2-oxo-2-((4-(3-(((tetrahydrofuran-3-yl)oxy)methyl)phenyl)thiazol-2-yl)amino)ethyl)-1H-pyrrole-3-carboxamide (Compound 135) and (R)-1-(tert-butyl)-N-(2-oxo-2-((4-(3-(((tetrahydrofuran-3-yl)oxy)methyl)phenyl)thiazol-2-yl)amino)ethyl)-1H-pyrrole-3-carboxamide (Compound 136)

Compound 135

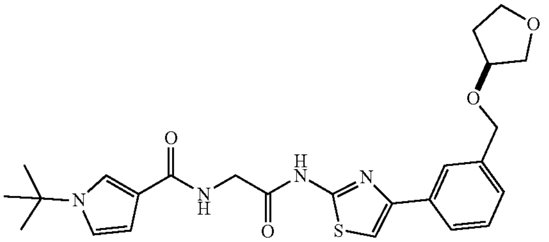

+

-continued

Compound 136

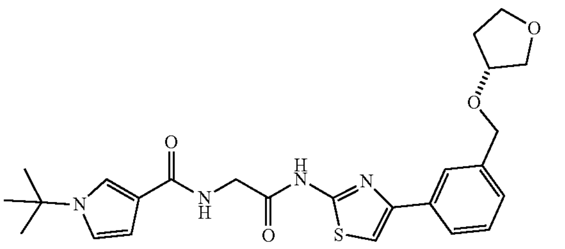

Intermediate J (250 mg, 518.03 μmol) was separated by chiral SFC to afford Compound 135 (64.86 mg, 128.96 μmol, 24.89% yield) as off-white solid and Compound 136 (58.57 mg, 115.25 μmol, 22.25% yield) as off-white solid.

Compound 135: LCMS (ESI) m/z $[M+H]^+$=483.2; $^1H$ NMR (400 MHz, Methanol-$d_4$) δ 7.90 (s, 1H), 7.81 (d, J=7.6

Hz, 1H), 7.58-7.57 (m, 1H), 7.41-7.35 (m, 2H), 7.31-7.26 (m, 1H), 6.95-6.94 (m, 1H), 6.59-6.55 (m, 1H), 4.60-4.53 (m, 2H), 4.29-4.28 (m, 1H), 4.23 (s, 2H), 3.95-3.85 (m, 2H), 3.84-3.76 (m, 2H), 2.11-2.01 (m, 2H), 1.57 (s, 9H); ee %=100%.

Compound 136: LCMS (ESI) m/z $[M+H]^+$=483.1; $^1H$ NMR (400 MHz, Methanol-$d_4$) δ 7.89 (s, 1H), 7.81 (d, J=7.6 Hz, 1H), 7.58-7.57 (m, 1H), 7.40-7.33 (m, 2H), 7.31-7.26 (m, 1H), 6.95-6.94 (m, 1H), 6.57-6.55 (m, 1H), 4.60-4.52 (m, 2H), 4.29-4.28 (m, 1H), 4.23 (s, 2H), 3.94-3.85 (m, 2H), 3.84-3.75 (m, 2H), 2.11-2.00 (m, 2H), 1.56 (s, 9H); ee %=96.29%.

Example 134. Preparation of N-(2-((4-(2-methyl-1-oxo-1,2,3,4-tetrahydroisoquinolin-7-yl)thiazol-2-yl)amino)-2-oxoethyl)-1-(methylsulfonyl)-1H-pyrrole-3-carboxamide (Compound 137)

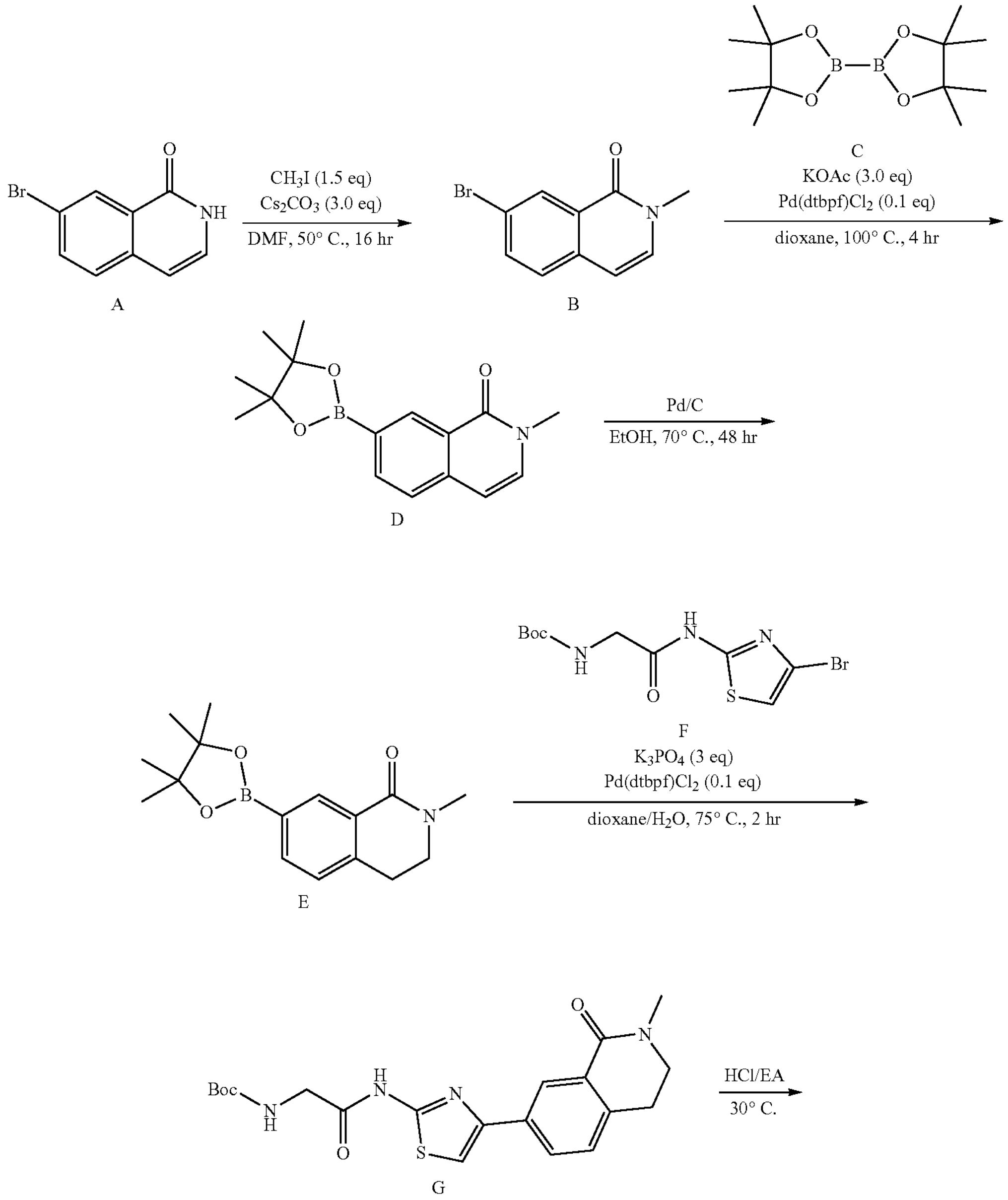

-continued

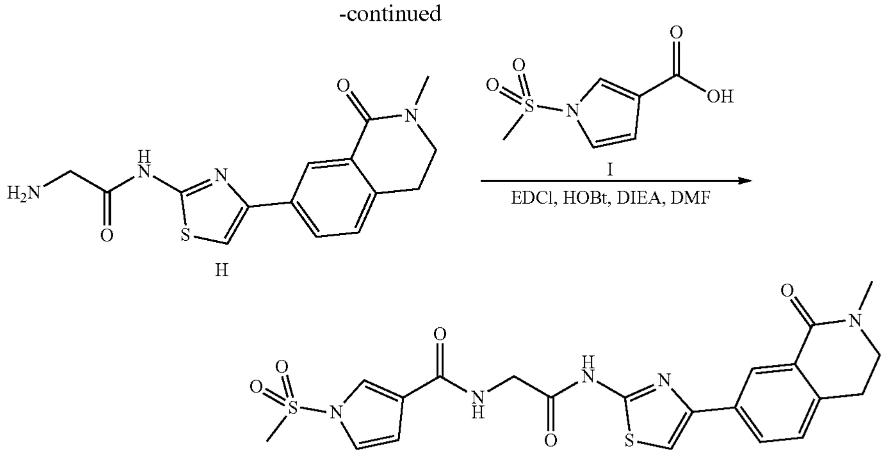

Compound 137

Step 1: Preparation of 7-bromo-2-methylisoquinolin-1(2H)-one (Intermediate B)

B

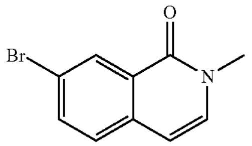

To a mixture of 7-bromoisoquinolin-1(2H)-one (1 g, 4.46 mmol) in DMF (25 mL) was added $Cs_2CO_3$ (2.18 g, 6.69 mmol) and MeI (950.26 mg, 6.69 mmol, 416.78 μL) in one portion at 30° C. under $N_2$. The reaction mixture was stirred at 50° C. for 16 h. The mixture was poured into water (150 mL). The aqueous phase was extracted with EtOAc (75 mL×3). The combined organic phase was washed with brine (50 mL×2), dried over anhydrous $Na_2SO_4$, filtered and concentrated in vacuum to afford Intermediate B (1.05 g, 4.24 mmol, 94.97% yield) as yellow solid. LCMS (ESI) m/z $[M+H]^+$=240.0; $^1H$ NMR (400 MHz, $CDCl_3$) δ 8.58 (d, J=2.0 Hz, 1H), 7.73-7.70 (m, 1H), 7.39 (d, J=8.4 Hz, 1H), 7.10 (d, J=7.6 Hz, 1H), 6.46 (d, J=7.6 Hz, 1H), 3.61 (s, 3H).

Step 2: Preparation of 2-methyl-7-(4,4,5,5-tetramethyl-1,3,2-dioxaborolan-2-yl)isoquinolin-1(2H)-one (Intermediate D)

D

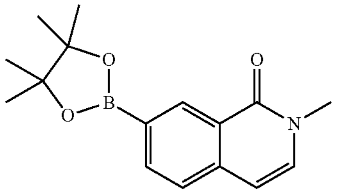

To a mixture of Intermediate B (1.05 g, 4.41 mmol) and 4,4,4',4',5,5,5',5'-octamethyl-2,2'-bi(1,3,2-dioxaborolane) (1.34 g, 5.29 mmol) in dioxane (25 mL) was added KOAc (1.30 g, 13.23 mmol) and [1,1'-bis(di-tert-butylphosphino)ferrocene]dichloropalladium(II) (287.44 mg, 441.03 μmol) at 30° C. under $N_2$. The reaction mixture was heated to 100° C. and stirred at 100° C. for 4 h under $N_2$. The reaction mixture was concentrated in vacuum to afford a residue. The residue was purified by silica gel column chromatography (Petroleum ether/EtOAc=3/1 to 1/1) to afford Intermediate D (2 g, crude) as yellow oil. LCMS (ESI) m/z $[M+H]^+$=286.1; $^1H$ NMR (400 MHz, $CDCl_3$) δ 8.91 (br s, 1H), 8.01 (d, J=7.6 Hz, 1H), 7.49-7.47 (m, 1H), 7.10-7.09 (m, 1H), 6.48-6.46 (m, 1H), 3.61 (s, 3H), 1.60 (s, 12H).

Step 3: Preparation of 2-methyl-7-(4,4,5,5-tetramethyl-1,3,2-dioxaborolan-2-yl)-3,4-dihydroisoquinolin-1(2H)-one (Intermediate E)

E

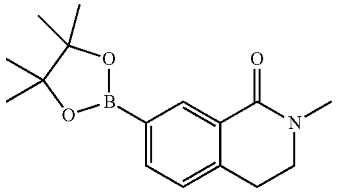

To the solution of Intermediate D (1 g, 2.46 mmol) in EtOH (200 mL) was added Pd/C (250 mg, 10% purity) at 30° C. The reaction mixture was heated to 50° C. and stirred at 50° C. under $H_2$ (15 psi) for 15 h. The reaction mixture was filtered and concentrated under reduced pressure to afford Intermediate E (900 mg, crude) as yellow oil, which was used for the next step directly. LCMS (ESI) m/z $[M+H]^+$=288.1; $^1H$ NMR (400 MHz, $CDCl_3$) δ 8.53 (s, 1H), 7.84-7.82 (m, 1H), 7.17 (d, J=7.6 Hz, 1H), 3.57-3.54 (m, 2H), 3.16 (s, 3H), 3.02-3.00 (m, 2H), 1.34 (s, 12H).

Step 4: Preparation of tert-butyl (2-((4-(2-methyl-1-oxo-1,2,3,4-tetrahydroisoquinolin-7-yl)thiazol-2-yl) amino)-2-oxoethyl)carbamate (Intermediate G)

G

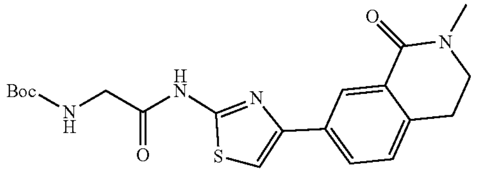

To a mixture of tert-butyl N-[2-[(4-bromothiazol-2-yl) amino]-2-oxo-ethyl]carbamate [prepared according to the method in Example 6] (100 mg, 297.44 μmol) and 2-methyl-7-(4,4,5,5-tetramethyl-1,3,2-dioxaborolan-2-yl)-3,4-dihydroisoquinolin-1(2H)-one [prepared according to the method in Example 7](211.08 mg, 594.88 μmol) in dioxane (3 mL) and $H_2O$ (0.75 mL) was added [1,1'-bis(di-tert-butylphosphino)ferrocene]dichloropalladium(II) (19.39 mg, 29.74 μmol) and $K_3PO_4$ (189.41 mg, 892.32 μmol) under $N_2$ at 30° C. The reaction mixture was heated to 75° C. and stirred at 75° C. for 2 h under $N_2$. The reaction mixture was concentrated under reduced pressure to afford a residue. The residue was purified by reverse phase column (FA condition) and lyophilized to afford Intermediate G (140 mg, 265.35 μmol, 89.21% yield) as a yellow solid. LCMS (ESI) m/z $[M+H]^+$=417.1; $^1H$ NMR (400 MHz, DMSO-$d_6$) δ 12.34 (br s, 1H), 8.45 (s, 1H), 7.97 (d, J=7.2 Hz, 1H), 7.65 (s, 1H), 7.34 (d, J=7.6 Hz, 1H), 7.14 (br s, 1H), 3.86 (d, J=5.6 Hz, 2H), 3.58-3.55 (m, 2H), 3.04 (s, 3H), 3.02-2.98 (m, 2H), 1.39 (s, 9H).

Step 5: Preparation of 2-amino-N-(4-(2-methyl-1-oxo-1,2,3,4-tetrahydroisoquinolin-7-yl)thiazol-2-yl) acetamide (Intermediate H)

H

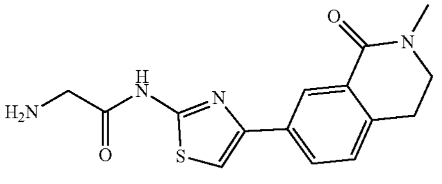

To a mixture of Intermediate G (140 mg, 336.14 μmol) in EtOAc (2 mL) was added HCl/EtOAc (4 M, 2 mL) at 30° C. The reaction mixture was stirred as 30° C. for 1 h and then filtered. The solid was dried in vacuum to give Intermediate H (80 mg, 218.01 μmol, 64.86% yield, HCl salt) as yellow solid. LCMS (ESI) m/z $[M+H]^+$=317.1; $^1H$ NMR (400 MHz, DMSO-$d_6$) δ 12.78 (br s, 1H), 8.46 (d, J=2.0 Hz, 1H), 8.31 (br s, 2H), 7.99-7.97 (m, 1H), 7.76 (s, 1H), 7.36 (d, J=8.4 Hz, 1H), 3.93-3.90 (m, 2H), 3.59-3.56 (m, 2H), 3.05 (s, 3H), 3.02-2.99 (m, 2H).

Step 6: Preparation of N-(2-((4-(2-methyl-1-oxo-1,2,3,4-tetrahydroisoquinolin-7-yl)thiazol-2-yl) amino)-2-oxoethyl)-1-(methylsulfonyl)-1H-pyrrole-3-carboxamide (Compound 137)

Compound 137

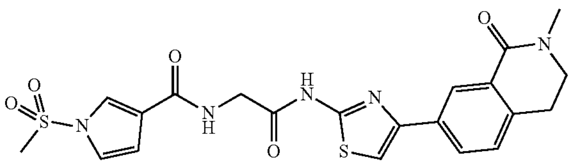

To a mixture Intermediate H (50 mg, 158.04 μmol, HCl salt) and 1-methylsulfonylpyrrole-3-carboxylic acid [prepared according to the method in Example 4] (29.90 mg, 158.04 μmol) in DMF (1 mL) were added EDCI (45.44 mg, 237.06 μmol), HOBt (32.03 mg, 237.06 μmol) and DIPEA (61.27 mg, 474.12 μmol, 82.58 μL) at 30° C. The reaction mixture was stirred 30° C. for 16 h. The reaction mixture was purified by reverse phase column (FA condition) and lyophilized to afford Compound 137 (13.11 mg, 26.89 μmol, 17.01% yield) as yellow solid. LCMS (ESI) m/z $[M+H]^+$=488.0; $^1H$ NMR (400 MHz, DMSO-$d_6$) δ 12.44 (br s, 1H), 8.68-8.65 (m, 1H), 8.46 (d, J=2.0 Hz, 1H), 7.98-7.95 (m, 1H), 7.84-7.83 (m, 1H), 7.66 (s, 1H), 7.35 (d, J=8.0 Hz, 1H), 7.32-7.30 (m, 1H), 4.14 (d, J=6.0 Hz, 2H), 3.58-3.53 (m, 5H), 3.04 (s, 3H), 3.01-2.98 (m, 2H).

Example 135. Preparation of N-(2-((4-(3-(4-amino-tetrahydro-2H-pyran-4-yl)phenyl)thiazol-2-yl) amino)-2-oxoethyl)-1-(methylsulfonyl)-1H-pyrrole-3-carboxamide (Compound 138)

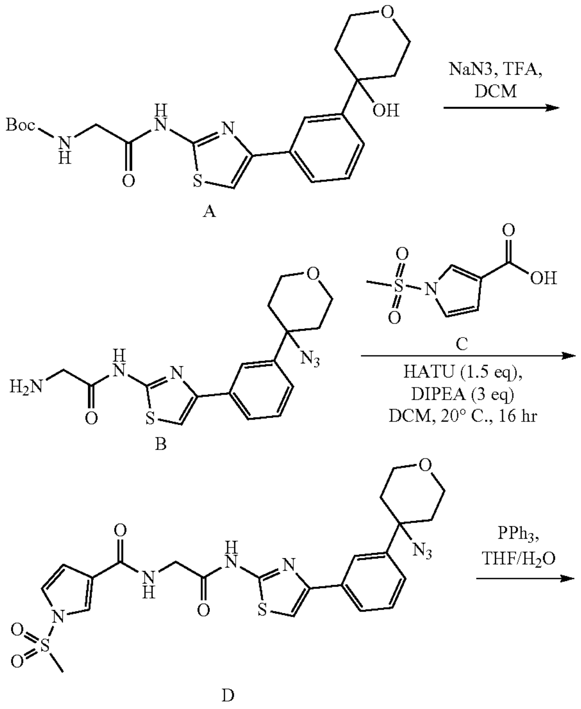

-continued

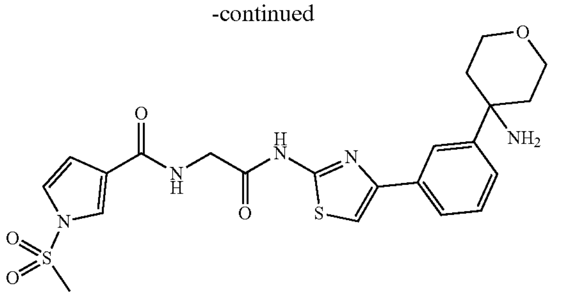

Compound 138

Step 1: Preparation of 2-amino-N-(4-(3-(4-azidotetrahydro-2H-pyran-4-yl)phenyl)thiazol-2-yl)acetamide (Intermediate B)

B

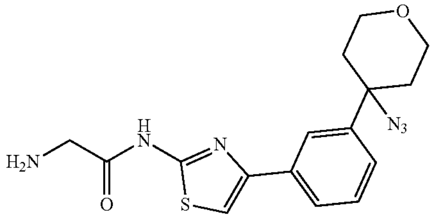

To a solution of tert-butyl N-[2-[[4-[3-(4-hydroxytetrahydropyran-4-yl)phenyl]thiazol-2-yl]amino]-2-oxo-ethyl]carbamate [prepared according to the method in Example 138] (30 mg, 69.20 μmol) in DCM (4 mL) was added $NaN_3$ (9.00 mg, 138.40 μmol) at 0° C. Then TFA (1.54 g, 13.51 mmol, 1 mL) was added dropwise at 0° C. The mixture was stirred at 20° C. for 16 h. Water (5 mL) and sat $NH_4OH$ solution (10 mL) was added. The resulting mixture was filtered and the filtration cake was washed with water (1 mL) and dried in vacuum to give Intermediate B (22 mg, crude) as yellow solid, which was used in next step without further purification. LCMS (ESI) m/z $[M+H]^+$=359.0.

Step 2: Preparation of N-(2-((4-(3-(4-azidotetrahydro-2H-pyran-4-yl)phenyl)thiazol-2-yl)amino)-2-oxoethyl)-1-(methylsulfonyl)-1H-pyrrole-3-carboxamide (Intermediate D)

D

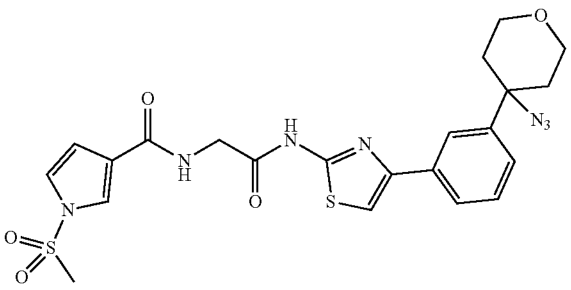

To a solution of 1-methylsulfonylpyrrole-3-carboxylic acid [prepared according to the method in Example 4] (10.57 mg, 55.87 μmol) in DCM (3 mL) was added DIPEA (21.66 mg, 167.62 μmol, 29.20 μL) and HATU (25.49 mg, 67.05 μmol). The reaction mixture was stirred at 20° C. for 10 min. Intermediate B (20.03 mg, 55.87 μmol) was added and the mixture was stirred at 20° C. for 16 h. The reaction mixture was poured into water (10 mL) and the resulting mixture was extracted with EtOAc (15 mL×2). The combined organic phases were washed with water (10 mL), dried over $Na_2SO_4$ and concentrated to give Intermediate D (23 mg, crude) as yellow oil. The crude product was used in next step without further purification. LCMS (ESI) m/z $[M+H]^+$=530.1.

Step 3: Preparation of N-(2-((4-(3-(4-aminotetrahydro-2H-pyran-4-yl)phenyl)thiazol-2-yl)amino)-2-oxoethyl)-1-(methylsulfonyl)-1H-pyrrole-3-carboxamide (Compound 138)

Compound 138

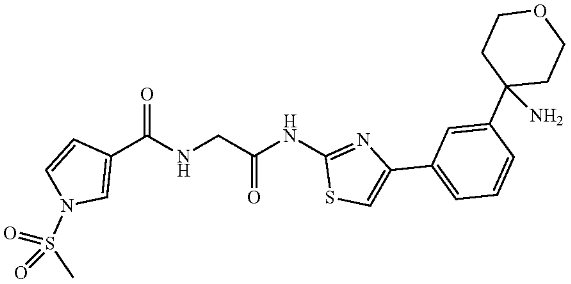

To a solution of Intermediate D (20 mg, 37.76 μmol) in THF (2 mL) and $H_2O$ (0.2 mL) was added $PPh_3$ (19.81 mg, 75.53 μmol). The reaction mixture was stirred at 20° C. for 16 h. Then the reaction mixture was stirred at 50° C. for 16 h. The reaction mixture was concentrated to dryness to give a residue. The residue was added into HCl/dioxane (4M, 0.5 mL) and EtOAc (5 mL) to form HCl salt. The mixture was filtered and the filtration cake was washed with EtOAc (5 mL) to give the crude product (10 mg, yellow oil). The crude product was purified by Prep-HPLC (mobile phase: [water (0.1% TFA)-acetonitrile]; B %: 15%-45%) and lyophilized to afford title compound (4.45 mg, 7.21 μmol, 19.08% yield, TFA salt) as yellow solid. LCMS (ESI) m/z $[M+H]^+$=504.1; $^1H$ NMR (400 MHz, Methanol-$d_4$) δ 8.18 (s, 1H), 8.06-7.96 (m, 1H), 7.87-7.85 (m, 1H), 7.62-7.56 (m, 2H), 7.53 (s, 1H), 7.30 (dd, J=3.2 Hz, 1.6 Hz, 1H), 6.83 (dd, J=3.2 Hz, 1.6 Hz, 1H), 4.28 (s, 2H), 3.98-3.96 (m, 2H), 3.64-3.53 (m, 2H), 3.40 (s, 3H), 2.67-2.65 (m, 2H), 2.19-2.17 (m, 2H).

Example 136. Preparation of N-(2-((4-(3-(2-hydroxypropan-2-yl)phenyl)thiazol-2-yl)amino)-2-oxoethyl)-1-(methylsulfonyl)-1H-pyrrole-3-carboxamide (Compound 139)

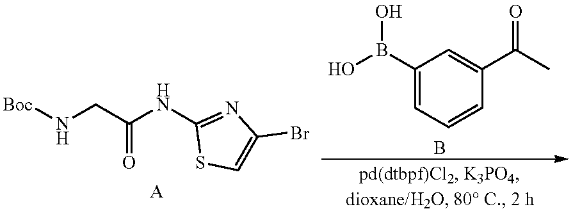

-continued

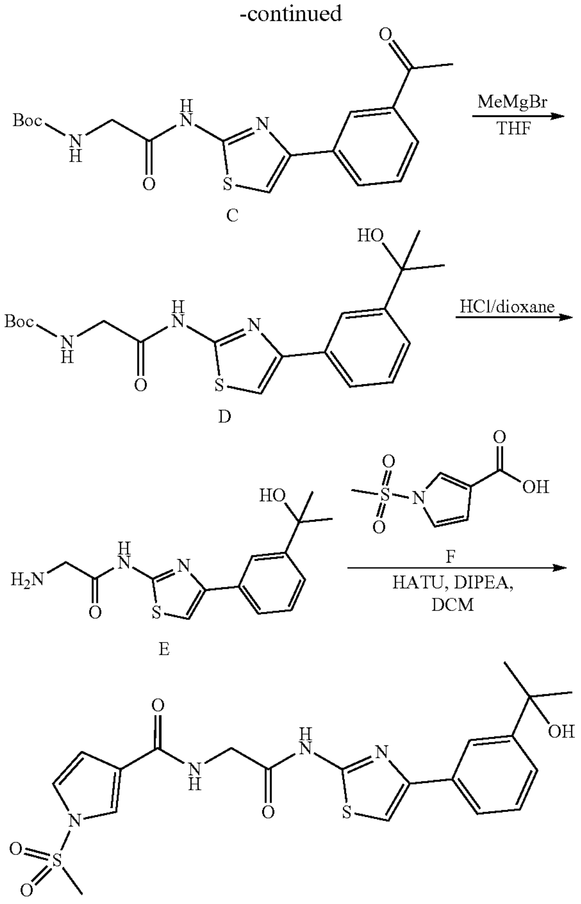

C

D

E

Compound 139

Step 1: Preparation of tert-butyl (2-((4-(3-acetylphenyl)thiazol-2-yl)amino)-2-oxoethyl)carbamate (Intermediate C)

C

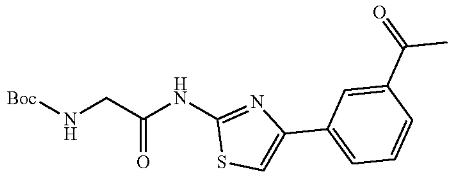

To a mixture of tert-butyl N-[2-[(4-bromothiazol-2-yl)amino]-2-oxo-ethyl]carbamate [prepared according to the method in Example 6] (300 mg, 892.31 μmol), (3-acetylphenyl)boronic acid (438.93 mg, 2.68 mmol), [1,1'-bis(di-tert-butylphosphino)ferrocene]dichloropalladium(II) (116.31 mg, 178.46 μmol) in dioxane (3 mL) and $H_2O$ (0.5 mL) was added $K_3PO_4$ (568.22 mg, 2.68 mmol) under $N_2$. Then the resulting mixture was stirred at 80° C. for 2 h. EtOAc (30 mL) and water (10 mL) were added. The mixture was extracted with EtOAc (50 mL). The organic layer was concentrated in vacuum. The residue was purified by column chromatography ($SiO_2$, PE/EA=5/1 to 2/1) and concentrated in vacuum to give Intermediate C (280 mg, 738.33 μmol, 82.74% yield) as yellow solid. LCMS (ESI) m/z $[M+H]^+$=376.2.

Step 2: Preparation of tert-butyl (2-((4-(3-(2-hydroxypropan-2-yl)phenyl)thiazol-2-yl)amino)-2-oxoethyl)carbamate (Intermediate D)

D

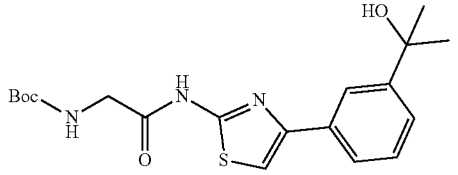

To a solution of Intermediate C (120 mg, 319.62 μmol) in THF (1.5 mL) was added MeMgBr (3 M, 639.25 μL) at 0° C. under $N_2$. The mixture was stirred at 30° C. for 2 h. The reaction mixture was quenched by addition $NH_4Cl$ solution (50 mL) at 0° C., and then extracted with EtOAc (30 mL×2). The combined organic layers were washed with brine (40 mL), dried over $Na_2SO_4$, filtered and concentrated under reduced pressure to give Intermediate D (120 mg, crude) as yellow solid. LCMS (ESI) m/z[M+H]$^+$=392.2.

Step 3: Preparation of 2-amino-N-(4-(3-(2-hydroxypropan-2-yl)phenyl)thiazol-2-yl)acetamide (Intermediate E)

E

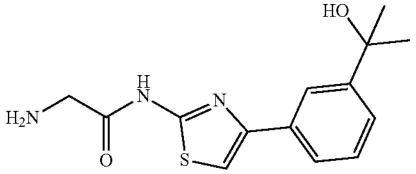

Intermediate D (50 mg, 127.72 μmol) was dissolved in HCl/dioxane (1 mL). The mixture was stirred at 30° C. for 1 h. The reaction mixture was evaporated to dryness. The residue was purified by Prep-HPLC (FA condition) and lyophilized to give Intermediate E (40 mg, 115.00 μmol, 90.04% yield, FA salt) as white solid. LCMS (ESI) m/z $[M+H]^+$=292.1.

Step 4: Preparation of N-(2-((4-(3-(2-hydroxypropan-2-yl)phenyl)thiazol-2-yl)amino)-2-oxoethyl)-1-(methylsulfonyl)-1H-pyrrole-3-carboxamide (Compound 139)

Compound 139

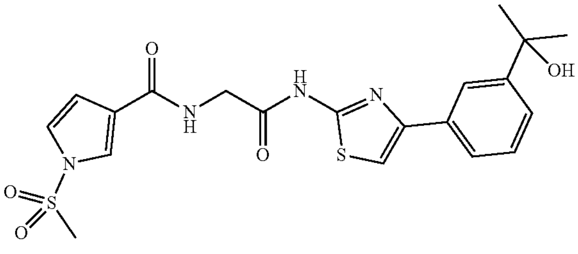

To a mixture of 1-methylsulfonylpyrrole-3-carboxylic acid [prepared according to the method in Example 4] (22.43 mg, 118.56 μmol) in DCM (1 mL) was added HATU (67.62 mg, 177.83 μmol) and DIPEA (61.29 mg, 474.22 μmol, 82.60 μL). The mixture was stirred at 30° C. for 15 min, then Intermediate E (40 mg, 118.56 μmol, FA salt) was added and stirred at 30° C. for 1 hours. The reaction mixture was poured into water (30.0 mL) and extracted with EtOAc (30.0 mL×3). The combined organics were washed with water and brine, dried over $Na_2SO_4$, filtered and filtration was evaporated to dryness. The residue was purified by Prep-TLC ($SiO_2$, DCM:MeOH=10:1) to give Compound 139 (53.83 mg, 115.21 μmol, 97.18% yield) as white solid. LCMS (ESI) m/z $[M+H]^+$=463.1; $^1H$ NMR (400 MHz, Methanol) δ 8.06-8.05 (m, 1H), 7.84-7.83 (m, 1H), 7.74 (d, J=7.6 Hz, 1H), 7.45-7.43 (m, 1H), 7.37-7.32 (m, 2H), 7.28-7.27 (m, 1H), 6.81-6.80 (m, 1H), 4.25 (s, 2H), 3.38 (s, 3H), 1.56 (s, 6H).

Example 137. Preparation of N-(2-((4-(3-(tert-butyl)phenyl)thiazol-2-yl)amino)-2-oxoethyl)-1-(methylsulfonyl)-1H-pyrrole-3-carboxamide (Compound 140)

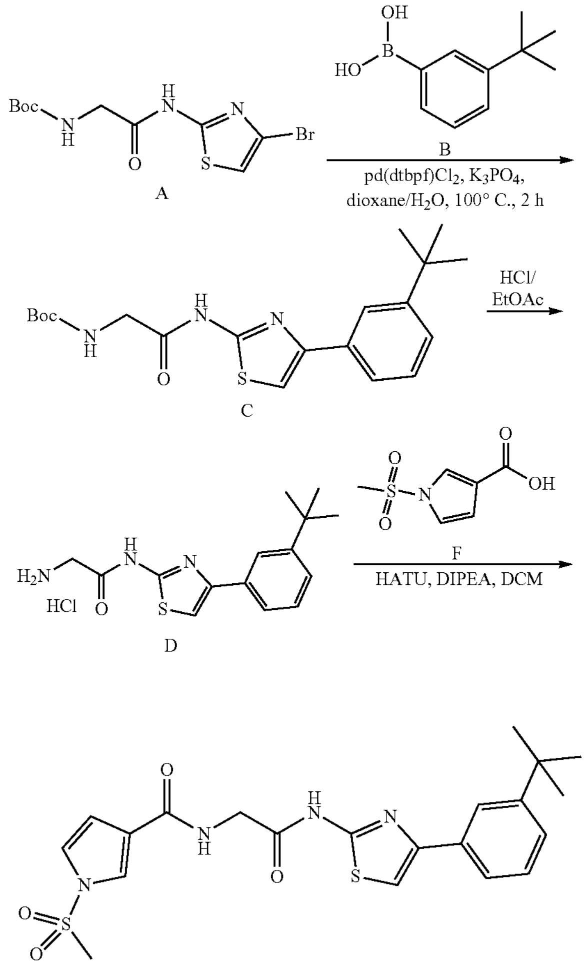

Compound 140

Step 1: Preparation of tert-butyl methyl(2-oxo-2-((4-(3-(pyridin-4-yl)phenyl)thiazol-2-yl)amino)ethyl)carbamate (Intermediate C)

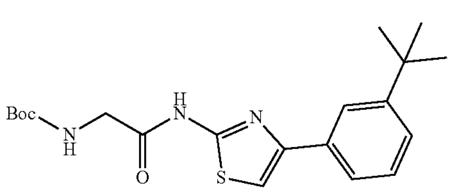

C

To a solution of tert-butyl N-[2-[(4-bromothiazol-2-yl)amino]-2-oxo-ethyl]carbamate [Prepared according to the method in Example 6] (200 mg, 594.88 μmol), (3-(tert-butyl)phenyl)boronic acid (317.73 mg, 1.78 mmol) and [1,1'-bis(di-tert-butylphosphino)ferrocene]dichloropalladium(II) (38.77 mg, 59.49 μmol) in dioxane (2 mL) and water (0.5 mL) was added $K_3PO_4$ (378.82 mg, 1.78 mmol) under $N_2$, the mixture was stirred at 100° C. for 2 h. The reaction mixture was concentrated under reduced pressure to give a residue. The residue was purified by column chromatography ($SiO_2$, Petroleum ether/EtOAc=5/1) and concentrated under reduced pressure to give Intermediate C (150 mg, 364.69 μmol, 61.31% yield) as a white solid. LCMS (ESI) m/z $[M+H]^+$=390.1; $^1H$ NMR (400 MHz, DMSO-$d_6$) δ 12.25 (s, 1H), 7.93 (s, 1H), 7.69-7.62 (m, 2H), 7.37-7.34 (m, 2H), 7.15-7.12 (m, 1H), 3.86 (d, J=6.0 Hz, 2H), 1.40 (s, 9H), 1.32 (s, 9H).

Step 2: Preparation of 2-amino-N-(4-(3-(tert-butyl)phenyl)thiazol-2-yl)acetamide (Intermediate D)

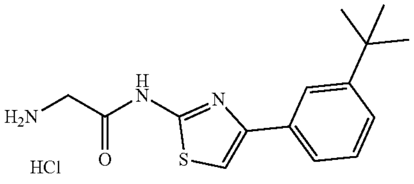

D

To a solution of Intermediate C (150 mg, 385.10 μmol) in EtOAc (2 mL) was added 4 M HCl/EtOAc (2 mL), the mixture was stirred at 30° C. for 2 h. The reaction mixture was concentrated under reduced pressure to give a residue. The residue was triturated with EtOAc (5.0 mL) and MTBE (5.0 mL), filtered and dried in vacuum to give Intermediate D (200 mg, crude, HCl salt) as a white solid. LCMS (ESI) m/z $[M+H]^+$=290.2; $^1H$ NMR (400 MHz, DMSO-$d_6$) δ 12.71 (br s, 1H), 8.43 (br s, 3H), 7.93 (s, 1H), 7.71-7.67 (m, 2H), 7.39-7.34 (m, 2H), 3.93-3.88 (m, 2H), 1.32 (s, 9H).

Step 3: Preparation of N-(2-((4-(3-(tert-butyl)phenyl)thiazol-2-yl)amino)-2-oxoethyl)-1-(methylsulfonyl)-1H-pyrrole-3-carboxamide (Compound 140)

Compound 140

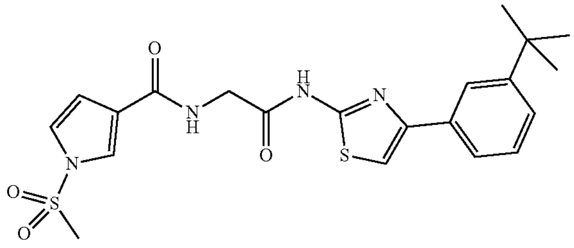

To a solution of 1-methylsulfonylpyrrole-3-carboxylic acid [prepared according to the method in Example 4] (29.03 mg, 153.44 μmol), HATU (70.01 mg, 184.13 μmol) and DIEA (99.16 mg, 767.21 μmol, 133.63 μL) in DCM (1 mL) was added Intermediate D (50 mg, 153.44 μmol, HCl salt), the mixture was stirred at 30° C. for 2 h. The reaction mixture was concentrated under reduced pressure to give a residue. The residue was purified by Prep-HPLC (mobile phase: [water (0.1% TFA)-acetonitrile]; B %: 48%-78%) and lyophilized to give Compound 140 (37.50 mg, 80.61 μmol, 52.53% yield) as a white solid. LCMS (ESI) m/z $[M+H]^+$=461.1; $^1H$ NMR (400 MHz, DMSO-$d_6$) δ 12.38 (s, 1H), 8.67-8.64 (m, 1H), 7.93-7.92 (m, 1H), 7.84-7.83 (m, 1H), 7.70-7.66 (m, 1H), 7.62 (s, 1H), 7.37-7.34 (m, 2H), 7.31-7.30 (m, 1H), 6.78-6.76 (m, 1H), 4.13 (d, J=6.0 Hz, 2H), 3.57 (s, 3H), 1.32 (s, 9H).

Example 138. Preparation of N-(2-((4-(3-(4-hydroxytetrahydro-2H-pyran-4-yl)phenyl)thiazol-2-yl)amino)-2-oxoethyl)-1-(methylsulfonyl)-1H-pyrrole-3-carboxamide (Compound 141)

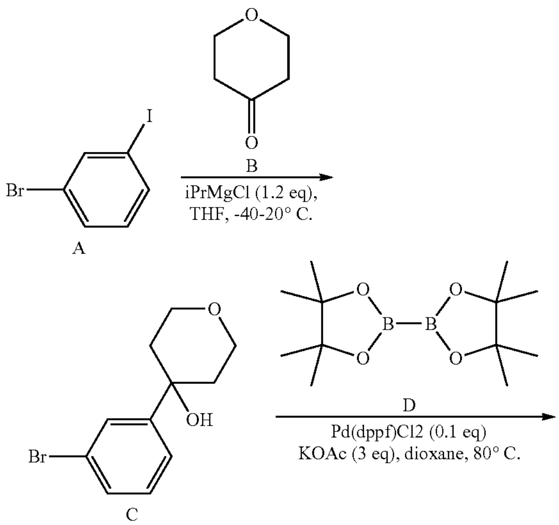

-continued

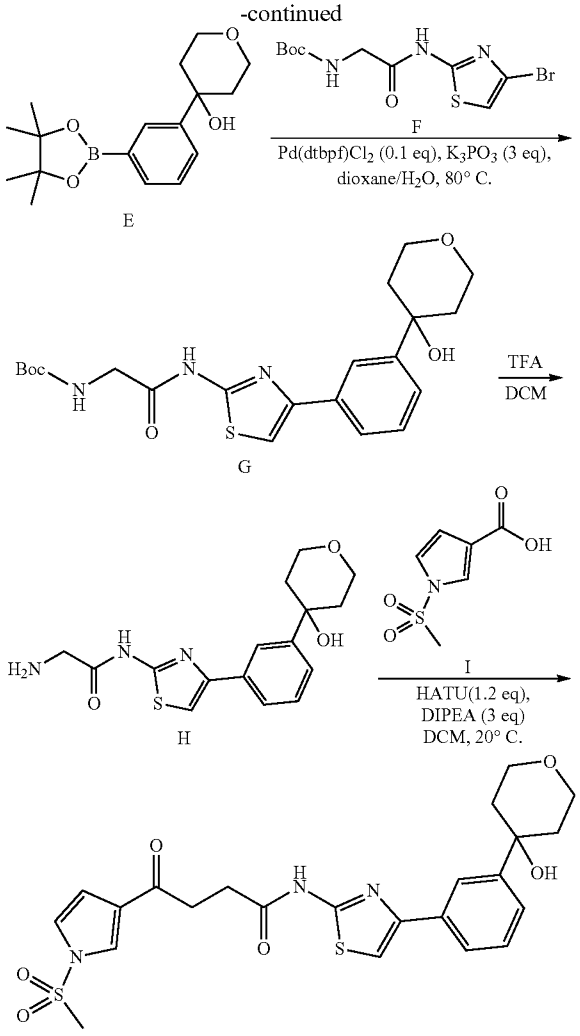

Compound 141

Step 1: Preparation of 4-(3-bromophenyl)tetrahydro-2H-pyran-4-ol (Intermediate C)

C

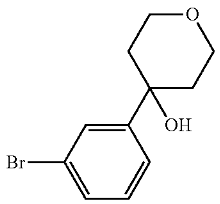

To a solution of 1-bromo-3-iodo-benzene (0.566 g, 2.00 mmol, 254.95 μL) in THF (6 mL) was added isopropylmagnesiumchloride (2 M, 1.20 mL) at −10° C. under $N_2$ protection. The mixture was stirred at −10° C. for 30 min. Tetrahydropyran-4-one (200.30 mg, 2.00 mmol, 183.76 μL) was added. The mixture was stirred while warming up to 20° C. for 1 h. The reaction mixture was quenched by adding water (10 mL) and the resulting mixture was extracted with EtOAc (15 mL×2). The combined organic phases were washed with water (10 mL), dried over $Na_2SO_4$ and concentrated to give Intermediate C (0.52 g, crude) as yellow oil, which was used in next step without further purification. $^1H$ NMR (400 MHz, $CDCl_3$) δ 7.68 (m, 1H), 7.45-7.39 (m, 2H), 7.26-7.22 (m, 1H), 3.97-3.84 (m, 4H), 2.22-2.10 (m, 2H), 1.68-1.66 (m, 2H).

Step 2: Preparation of 4-(3-(4,4,5,5-tetramethyl-1,3,2-dioxaborolan-2-yl)phenyl)tetrahydro-2H-pyran-4-ol (Intermediate E)

E

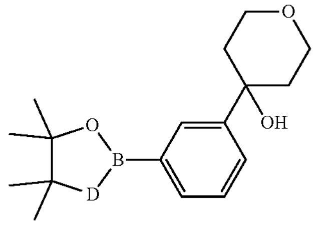

A mixture of Intermediate C (0.5 g, 1.94 mmol), 4,4,5,5-tetramethyl-2-(4,4,5,5-tetramethyl-1,3,2-dioxaborolan-2-yl)-1,3,2-dioxaborolane (592.56 mg, 2.33 mmol), Pd(dppf)$Cl_2$ (142.29 mg, 194.46 μmol) and KOAc (572.53 mg, 5.83 mmol) in dioxane (10 mL) was degassed and purged with $N_2$ for 3 times, and then the mixture was stirred at 80° C. for 16 h under $N_2$ atmosphere. The reaction mixture was quenched by adding water (10 mL) and the resulting mixture was extracted with EtOAc (15 mL×2). The combined organic phases were washed with water (10 mL), dried over $Na_2SO_4$ and concentrated to give Intermediate E (0.55 g, crude) as yellow oil. The crude product was used in next step without further purification. $^1H$ NMR (400 MHz, $CDCl_3$) δ 7.76 (d, J=7.2 Hz, 1H), 7.65-7.60 (m, 1H), 7.45-7.37 (m, 2H), 4.02-3.86 (m, 4H), 2.26-2.24 (m, 2H), 1.77-1.69 (m, 2H), 1.37 (s, 12H).

Step 3: Preparation of tert-butyl (2-((4-(3-(4-hydroxytetrahydro-2H-pyran-4-yl)phenyl)thiazol-2-yl)amino)-2-oxoethyl)carbamate (Intermediate G)

G

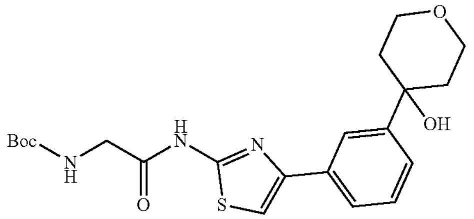

A mixture of tert-butyl N-[2-[(4-bromothiazol-2-yl)amino]-2-oxo-ethyl]carbamate [prepared according to the method in Example 6]carbamate (200 mg, 594.88 μmol), Intermediate E (542.86 mg, 1.78 mmol), $K_3PO_4$ (378.82 mg, 1.78 mmol) and [1,1'-bis(di-tert-butylphosphino)ferrocene] dichloropalladium(II) (38.77 mg, 59.49 μmol) in dioxane (6 mL) and $H_2O$ (2 mL) was degassed and purged with $N_2$ for 3 times, and then the mixture was stirred at 80° C. for 2 h under $N_2$ atmosphere. The reaction mixture was concentrated to dryness to give a residue. The residue was purified by column chromatography ($SiO_2$, Petroleum ether/EtOAc=1/1) and concentrated in vacuum to give Intermediate G (230 mg, 530.54 μmol, 89.19% yield) as yellow oil. LCMS (ESI) m/z $[M+H]^+$=434.0.

Step 4: Preparation of 2-amino-N-(4-(3-(4-hydroxytetrahydro-2H-pyran-4-yl)phenyl)thiazol-2-yl)acetamide (Intermediate H)

H

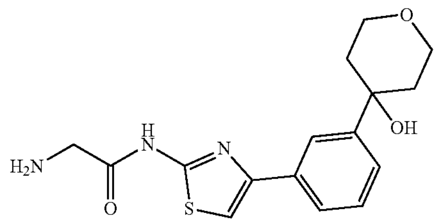

To a solution of Intermediate G (25 mg, 57.67 μmol) in DCM (1 mL) was added TFA (770.00 mg, 6.75 mmol, 0.5 mL). The mixture was stirred at 20° C. for 1 h. The reaction mixture was concentrated to dryness to give Intermediate H (26 mg, crude, TFA salt) as yellow solid, which was used in next step without further purification.

Step 5: Preparation of N-(2-((4-(3-(4-hydroxytetrahydro-2H-pyran-4-yl)phenyl)thiazol-2-yl)amino)-2-oxoethyl)-1-(methylsulfonyl)-1H-pyrrole-3-carboxamide (Compound 141)

Compound 141

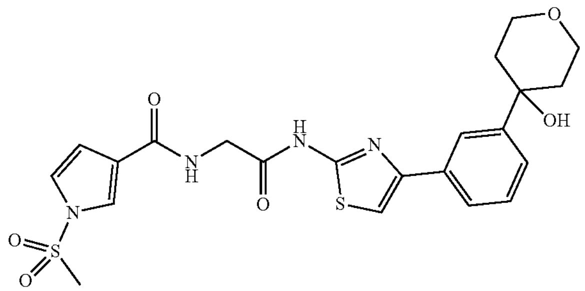

To a solution of 1-methylsulfonylpyrrole-3-carboxylic acid [prepared according to the method in Example 4] (10.57 mg, 55.87 μmol) in DCM (3 mL) was added DIPEA (21.66 mg, 167.62 μmol, 29.20 μL) and HATU (25.49 mg, 67.05 μmol). The reaction mixture was stirred at 20° C. for 10 min. Then Intermediate H (25 mg, 55.87 μmol, TFA salt) was added and the mixture was stirred at 20° C. for 16 h. The reaction mixture was concentrated to dryness to give a residue. The residue was purified by Prep-HPLC (mobile phase: [water (0.1% TFA)-acetonitrile]; B %: 24%-54%) and lyophilized to give Compound 141 (3.39 mg, 6.72 μmol, 12.02% yield) as white solid. LCMS (ESI) m/z $[M+H]^+$=505.1; $^1H$ NMR (400 MHz, DMSO-$d_6$) δ 12.42 (s, 1H), 8.69-6.87 (m, 1H), 8.08 (s, 1H), 7.87-7.83 (m, 1H), 7.76 (d, J=7.6 Hz, 1H), 7.64 (s, 1H), 7.49-7.44 (m, 1H), 7.42-7.36 (m, 1H), 7.34-7.30 (m, 1H), 6.79-6.77 (m, 1H), 4.15-4.13 (m, 2H), 3.85-3.72 (m, 4H), 3.58 (s, 3H), 2.05-1.98 (m, 2H), 1.57 (m, 2H).

Example 139. Preparation of 1-(methylsulfonyl)-N-(2-oxo-2-((6-(3-(pyridin-4-yl)phenyl)pyridin-2-yl)amino)ethyl)-1H-pyrrole-3-carboxamide (Compound 156)

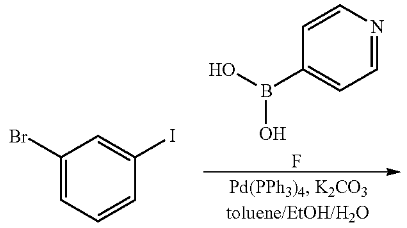

E

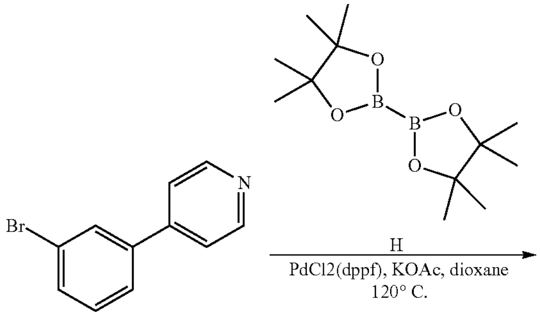

G

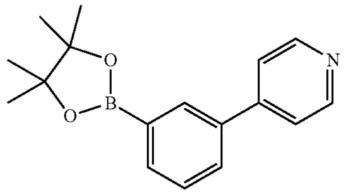

D

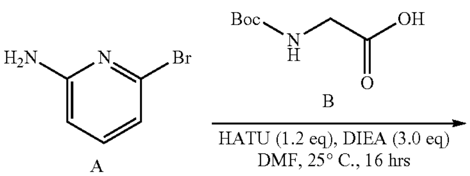

A

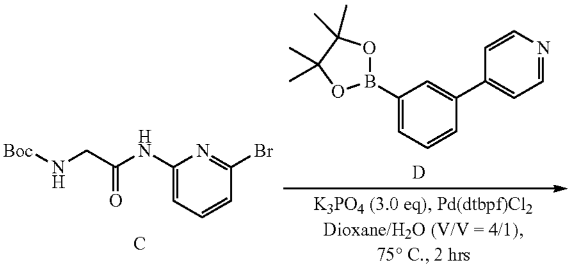

C

-continued

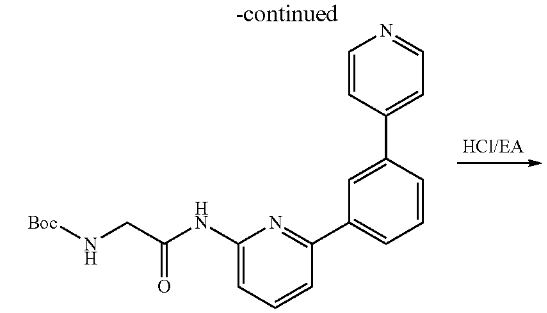

I

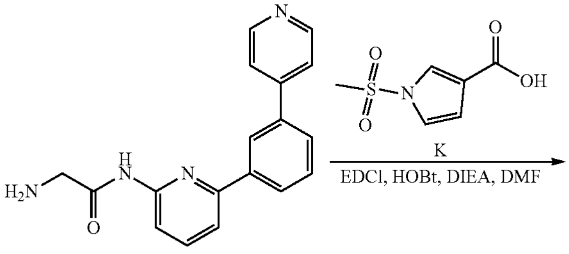

J

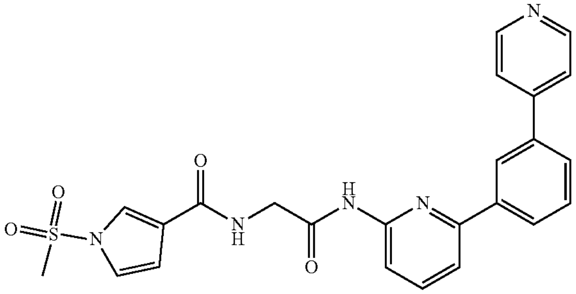

Compound 156

Step 1: Preparation of tert-butyl (2-((6-bromopyridin-2-yl)amino)-2-oxoethyl)carbamate (Intermediate C)

C

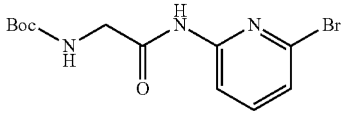

To a solution of 2-(tert-butoxycarbonylamino)acetic acid (5 g, 28.54 mmol) in DMF (50 mL) was added HATU (13.02 g, 34.25 mmol), DIPEA (11.07 g, 85.63 mmol, 14.91 mL) at 0° C. and stirred for 0.5 hour. Then 6-bromopyridin-2-amine (4.94 g, 28.54 mmol) was added to the mixture and stirred at 25° C. for 2.5 h. The reaction mixture was diluted with water (100 mL) and extracted with EA (100 mL×2). The combined organic phase was washed with saturated brines (200 mL×2) and dried over anhydrous $Na_2SO_4$, filtered and concentrated to afford the crude product. The crude product was purified by reversed phase column chromatography (0.1% FA) and lyophilized to give Intermediate C (2.83 g, 8.16 mmol, 28.34% yield) as brown solid. LCMS (ESI) m/z $[M+H]^+$=331.8; $^1H$ NMR (400 MHz, $CDCl_3$) δ 8.63 (br s, 1H), 8.19 (d, J=8.4 Hz, 1H), 7.58 (m, 1H), 7.24 (d, J=7.6 Hz, 1H), 5.19 (br s, 1H), 4.01 (br d, J=5.6 Hz, 2H), 1.4 (s, 9H).

Step 2: Preparation of 4-(3-bromophenyl)pyridine (Intermediate G)

G

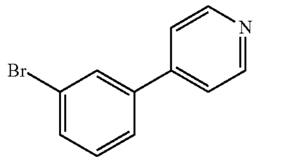

To a mixture of 1-bromo-3-iodo-benzene (5.1 g, 18.03 mmol, 2.30 mL) and 4-pyridylboronic acid (2.22 g, 18.03 mmol) in toluene (50 mL), EtOH (25 mL) and $H_2O$ (25 mL) was added $K_2CO_3$ (6.23 g, 45.07 mmol) and $Pd(PPh_3)_4$ (2.08 g, 1.80 mmol) under $N_2$. The reaction mixture was stirred at 80° C. for 17 h under $N_2$. The reaction mixture was poured into water (100 mL), then extracted by EA (100 mL×3). The combined organic layer was washed with brine, dried over anhydrous sodium sulfate, filtered and concentrated to give residue. The residue was purified by flash silica gel chromatography (Eluent of 0-50% Ethyl acetate/Petroleum ether gradient) to afford Intermediate G (1.33 g, 3.81 mmol, 21.12% yield) as yellow oil. LCMS (ESI) m/z $[M+H]^+$=234.0; $^1H$ NMR (400 MHz, $CDCl_3$) δ 8.73-8.64 (m, 2H), 7.79-7.78 (m, 1H), 7.61-7.54 (m, 2H), 7.50-7.46 (m, 2H), 7.39-7.38 (m, 1H).

Step 3: Preparation of 4-(3-(4,4,5,5-tetramethyl-1,3,2-dioxaborolan-2-yl)phenyl)pyridine (Intermediate D)

D

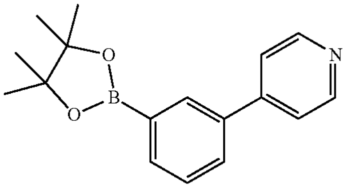

To a solution of Intermediate G (1.33 g, 5.68 mmol) in dioxane (13 mL) was added 4,4,5,5-tetramethyl-2-(4,4,5,5-tetramethyl-1,3,2-dioxaborolan-2-yl)-1,3,2-dioxaborolane (2.89 g, 11.36 mmol), potassium acetate (1.67 g, 17.04 mmol) and $Pd(dppf)Cl_2$ (415.72 mg, 568.15 μmol). The reaction mixture was stirred and refluxed at 120° C. for 17 h under $N_2$ atmosphere. The reaction mixture was concentrated to afford residue. The residue was purified by flash silica gel chromatography (Eluent of 30-80% Ethyl acetate/Petroleum ether gradient) to give Intermediate D (1.7 g, 5.44 mmol, 95.78% yield) as black brown oil. LCMS (ESI) m/z $[M+H]^+$=282.1. $^1H$ NMR (400 MHz, $CDCl_3$) δ 8.66 (d, J=4.8 Hz, 2H), 8.09 (s, 1H), 7.89-7.88 (m, 1H), 7.76-7.71 (m, 1H), 7.59-7.56 (m, 2H), 7.53-7.48 (m, 1H), 1.38 (s, 12H).

Step 4: Preparation of tert-butyl (2-oxo-2-((6-(3-(pyridin-4-yl)phenyl)pyridin-2-yl)amino)ethyl)carbamate (Intermediate I)

I

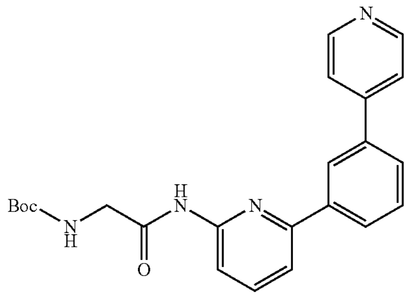

To a solution of Intermediate C (1 g, 3.03 mmol) in dioxane/$H_2O$ (V/=411) (20 mL) were added Intermediate D (1.28 g, 4.54 mmol), $K_3PO_4$ (1.93 g, 9.09 mmol) and [1,1'-bis(di-tert-butylphosphino)ferrocene]dichloropalladium(II) (197.39 mg, 302.87 μmol) under $N_2$ atmosphere at 25° C. Then the mixture was stirred at 60° C. for 2 h. The reaction mixture was diluted with water (40 mL) and extracted with EA (20 mL×3). The combined organic phase was dried over anhydrous $Na_2SO_4$, filtered and concentrated. The residue was purified by flash silica gel chromatography (Eluent of 0-100% Ethyl acetate/Petroleum ether gradient) to afford Intermediate I (700 mg, 1.73 mmol, 57.14% yield, 100% purity) as a yellow solid. LCMS (ESI) m/z $[M+H]^+$=405.1; $^1H$ NMR (400 MHz, $CDCl_3$) δ 8.78-8.72 (m, 3H), 8.27 (s, 1H), 8.17 (m, 1H), 8.00 (d, J=8.0 Hz, 1H), 7.82 (m, 1H), 7.68 (m, 1H), 7.61-7.55 (m, 4H), 5.27 (br s, 1H), 4.04 (br s, 2H), 1.49 (s, 9H).

Step 5: Preparation of 2-amino-N-(6-(3-(pyridin-4-yl)phenyl)pyridin-2-yl)acetamide (Intermediate J)

J

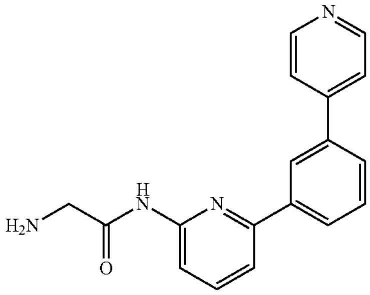

Intermediate I (700 mg, 1.73 mmol) was added to HCl/dioxane (10 mL) and stirred at 25° C. for 2 h. The reaction mixture was filtered and solid was collected. The crude product was triturated with EtOAc (10 mL) for 10 mins. The solid was filtered and dried under reduce pressure to give Intermediate J (740 mg, crude, HCl salt) as a white solid. LCMS (ESI) m/z $[M+H]^+$=305.1; $^1H$ NMR (400 MHz, DMSO-$d_6$) δ 11.13 (s, 1H), 9.04 (d, J=6.4 Hz, 2H), 8.65 (s, 1H), 8.56 (d, J=6.8 Hz, 2H), 8.48 (br s, 3H), 8.34 (d, J=8.0 Hz, 1H), 8.11-8.10 (m, 1H), 7.99-7.97 (m, 3H), 7.76 (m, 1H), 3.89 (br s, 2H).

Step 6: Preparation of 1-(methylsulfonyl)-N-(2-oxo-2-((6-(3-(pyridin-4-yl)phenyl)pyridin-2-yl)amino)ethyl)-1H-pyrrole-3-carboxamide (Compound 156)

Compound 156

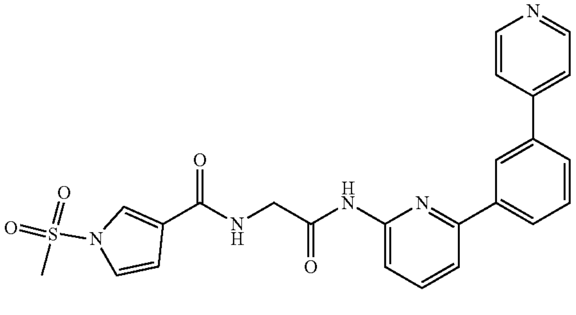

To a solution of 1-(methylsulfonyl)-1H-pyrrole-3-carboxylic acid [prepared according to the method in Example 4] (20 mg, 105.71 μmol) and Intermediate J (36.03 mg, 105.71 μmol, HCl salt) in DMF (1 mL) was added EDCI (40.53 mg, 211.43 μmol), HOBt (28.57 mg, 211.43 μmol) and DIEA (68.31 mg, 528.57 μmol, 92.07 μL) at 25° C. The mixture was stirred at 25-30° C. for 16 h. The reaction mixture was purified directly without work-up. The reaction mixture was purified by reversed phase HPLC (0.1% $NH_3 \cdot H_2O$) and lyophilized to give Compound 156 (16.64 mg, 34.88 μmol, 32.99% yield) as a white solid. LCMS (ESI) m/z $[M+H]^+$= 476.3. $^1$H NMR (400 MHz, DMSO-$d_6$) δ 10.60 (s, 1H), 8.69-8.66 (m, 2H), 8.61-8.60 (m, 1H), 8.48 (s, 1H), 8.19 (d, J=8.0 Hz, 1H), 8.05 (br d, J=8.0 Hz, 1H), 7.95-7.80 (m, 7H), 7.70-7.64 (m, 1H), 7.33-7.29 (m, 1H), 6.79-6.78 (m, 1H), 4.15-4.14 (m, 2H), 3.57 (s, 3H).

Example 140. Preparation of Compounds of the Invention

The compounds in Table 2 and 2a below were synthesized starting from the appropriate common intermediate ([tert-butyl N-[2-[[4-(3-bromophenyl)thiazol-2-yl]amino]-2-oxo-ethyl]carbamate]) and utilizing the synthetic protocol described in Example 10 following Scheme 1 below.

Scheme 1

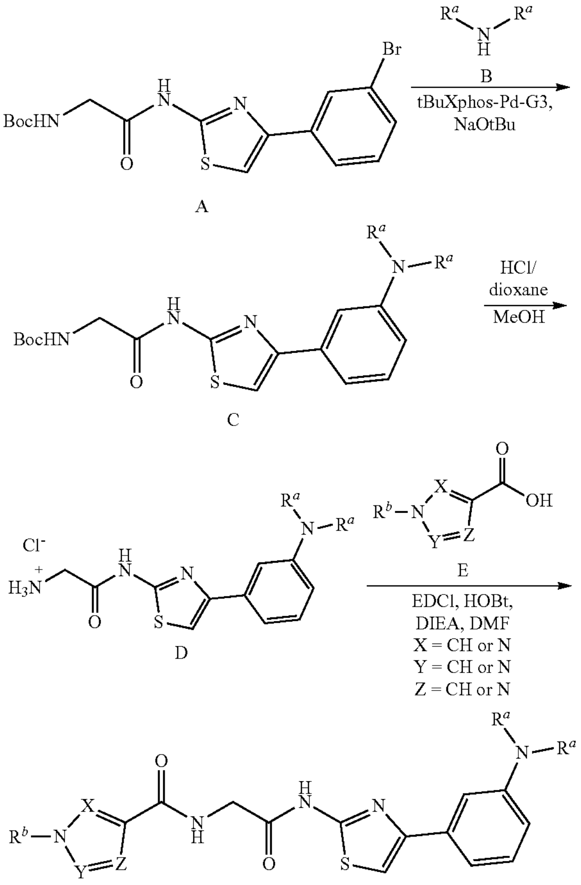

TABLE 2

| Compound # | LC-MS data(m/z) | $^1$H NMR |
|---|---|---|
| 157 | 530.0 | $^1$H NMR (400 MHz, DMSO-$d_6$) δ 12.39 (s, 1H), 8.69-8.65 (m, 1H), 7.89-7.80 (m, 1H), 7.56 (s, 1H), 7.38-7.29 (m, 1H), 7.27-7.17 (m, 2H), 7.00 (s, 1H), 6.79-6.77 (m, 1H), 6.48-6.37 (m, 1H), 4.60 (s, 2H), 4.13 (d, J = 5.6 Hz, 2H), 3.96-3.89 (m, 4H), 3.57 (s, 3H), 1.33 (s, 6H) |
| 158 | 533.9 | $^1$H NMR (400 MHz, DMSO-$d_6$) δ 12.57-12.10 (m, 1H), 8.69-8.66 (m, 1H), 7.86-7.84 (m, 1H), 7.61 (s, 1H), 7.48 (s, 1H), 7.33-7.31 (m, 1H), 7.30-7.21 (m, 2H), 6.92-6.90 (m, 1H), 6.79-6.77 (m, 1H), 4.56 (s, 1H), 4.14 (d, J = 6.0 Hz, 2H), 3.98 (d, J = 2.0 Hz, 1H), 3.58 (s, 3H), 3.35 (s, 3H), 3.30-3.13 (m, 5H), 1.87-1.60 (m, 2H) |
| 159 | 554.3 | $^1$H NMR (400 MHz, Methanol-$d_4$) δ 7.84-7.83 (m, 1H), 7.56 (s, 1H), 7.37-7.35 (m, 2H), 7.28-7.26(m, 2H), 6.96-6.82 (m, 1H), 6.81-6.80(m, 1H), 4.25 (s, 2H), 3.89-3.88 (m, 1H), 3.56-3.54 (m, 2H), 3.53 (s, 3H), 3.38 (s, 3H), 3.22-3.20(m, 1H), 2.83-2.66 (m, 1H), 2.63-2.60 (m, 1H), 2.04-2.00 (m, 1H), 1.71-1.70 (m, 1H) |
| 160 | 518.4 | $^1$H NMR (400 MHz, $CDCl_3$) δ 11.21 (br s, 1H), 7.71-7.70 (m, 1H), 7.38-7.32 (m, 1H), 7.28-7.27 (m, 1H), 7.23-7.21 (m, 1H), 7.17 (s, 1H), 7.05-7.04 (m, 1H), 6.86-6.85 (m, 1H), 6.34-6.33 (m, 1H), 6.29-6.28 (m, 1H), 4.01-3.93 (m, 2H), 3.92-3.79 (m, 3H), 3.73-3.62 (m, 1H), 3.29 (s, 3H), 3.18-3.16 (m, 1H), 2.78-2.75 (m, 1H), 1.26 (d, J = 6.4 Hz, 3H), 1.11 (d, J = 6.4 Hz, 3H) |
| 161 | 518.1 | $^1$H NMR (400 MHz, DMSO-$d_6$) δ 12.21 (s, 1H), 8.68 (d, J = 5.6 Hz, 1H), 7.90-7.81 (m, 1H), 7.62 (s, 1H), 7.48 (s, 1H), 7.36-7.19 (m, 3H), 6.95-6.87 (m, 1H), 6.81-6.75 (m, 1H), 4.14 (d, J = 6.0 Hz, 2H), 3.72-3.65 (m, 1H), 3.58 (s, 3H), 3.49-3.43 (m, 1H), 3.43-3.34 (m, 4H), 2.90-2.77 (m, 1H), |

TABLE 2-continued

| Compound # | LC-MS data(m/z) | $^1$H NMR |
|---|---|---|
| | | 2.76-2.67 (m, 1H), 2.06-1.96 (m, 1H), 1.85-1.74 (m, 1H), 1.64-1.48 (m, 1H), 1.41-1.28 (m, 1H) |
| 162 | 507.2 | $^1$H NMR (400 MHz, DMSO-$d_6$) δ 12.35 (s, 1H), 8.39-8.38 (m, 1H), 7.69-7.68 (m, 1H), 7.62 (s, 1H), 7.45 (s, 1H), 7.37-7.31 (m, 1H), 7.30-7.22 (m, 1H), 7.16-7.15 (m, 1H), 6.95-6.92 (m, 1H), 6.62-6.61 (m, 1H), 4.12 (d, J = 6.0 Hz, 2H), 3.74-3.70 (m, 2H), 3.67-3.57 (m, 2H), 2.32-2.29 (m, 2H), 1.96 (s, 6H), 1.18 (d, J = 6.0 Hz, 6H) |
| 163 | 505.1 | $^1$H NMR (400 MHz, DMSO-$d_6$) δ 12.34 (s, 1H), 8.37 (d, J = 6.0 Hz, 1H), 7.65-7.56 (m, 2H), 7.44 (s, 1H), 7.37-7.20 (m, 2H), 7.11-7.04 (m, 1H), 6.94-6.91 (m, 1H), 6.56-6.55 (m, 1H), 4.10 (d, J = 6.0 Hz, 2H), 3.73-3.71(m, 2H), 3.63-3.60 (m, 2H), 2.28-2.25 (m, 2H), 1.86-1.70 (m, 4H), 1.17 (d, J = 6.0 Hz, 6H) |
| 169 | 572.1 | $^1$H NMR (400 MHz, DMSO-$d_6$) δ 12.35 (s, 1H), 8.65 (t, J = 5.8 Hz, 1H), 7.84 (t, J = 2.0 Hz, 1H), 7.60 (s, 1H), 7.31 (dd, J = 3.3, 2.3 Hz, 1H), 7.29-7.18 (m, 2H), 7.15 (d, J = 2.5 Hz, 1H), 6.77 (dd, J = 3.3, 1.6 Hz, 1H), 6.58 (dt, J = 7.1, 2.4 Hz, 1H), 5.36 (t, J = 5.6 Hz, 1H), 4.13 (d, J = 5.8 Hz, 2H), 3.69-3.58 (m, 2H), 3.57 (s, 3H), 3.49-3.35 (m, 4H), 2.25-2.09 (m, 2H) |
| 170 | 530.4 | $^1$H NMR (400 MHz, DMSO-$d_6$) δ 12.37 (s, 1H), 8.65 (t, J = 5.8 Hz, 1H), 7.84 (t, J = 2.0 Hz, 1H), 7.55 (s, 1H), 7.31 (t, J = 2.8 Hz, 1H), 7.21 (d, J = 4.7 Hz, 2H), 7.03-6.90 (m, 1H), 6.77 (dd, J = 3.3, 1.6 Hz, 1H), 6.41 (td, J = 4.5, 2.4 Hz, 1H), 4.13 (d, J = 5.8 Hz, 2H), 3.79 (d, J = 7.6 Hz, 2H), 3.64 (d, J = 7.6 Hz, 2H), 3.59 (t, J = 5.1 Hz, 2H), 3.57 (s, 3H), 1.82-1.73 (m, 2H), 1.70-1.59 (m, 2H), 1.54-1.39 (m, 2H) |
| 171 | 530.3 | $^1$H NMR (400 MHz, DMSO-$d_6$) δ 12.39 (s, 1H), 8.67 (t, J = 5.9 Hz, 1H), 7.85 (t, J = 2.0 Hz, 1H), 7.54 (s, 1H), 7.31 (dd, J = 3.3, 2.3 Hz, 1H), 7.22-7.13 (m, 2H), 6.99-6.92 (m, 1H), 6.78 (dd, J = 3.4, 1.6 Hz, 1H), 6.44-6.30 (m, 1H), 4.13 (d, J = 5.8 Hz, 2H), 3.65 (s, 2H), 3.61 (d, J = 7.1 Hz, 2H), 3.57 (s, 3H), 3.54 (t, J = 5.1 Hz, 2H), 3.49 (d, J = 7.1 Hz, 2H), 1.81 (t, J = 6.0 Hz, 2H), 1.58-1.47 (m, 2H) |
| 172 | 526.4 | $^1$H NMR (400 MHz, DMSO-$d_6$) δ 12.40 (s, 1H), 8.65 (t, J = 5.8 Hz, 1H), 7.90-7.79 (m, 2H), 7.58 (s, 1H), 7.46 (d, J = 1.3 Hz, 1H), 7.34-7.21 (m, 3H), 7.05 (d, J = 2.0 Hz, 1H), 6.98 (s, 1H), 6.77 (dd, J = 3.3, 1.6 Hz, 1H), 6.50 (dt, J = 7.3, 2.0 Hz, 1H), 5.28 (ddd, J = 13.0, 7.5, 5.5 Hz, 1H), 4.34 (t, J = 7.7 Hz, 2H), 4.13 (d, J = 5.8 Hz, 2H), 4.01 (dd, J = 7.9, 5.4 Hz, 2H), 3.57 (s, 3H) |
| 173 | 559.4 | $^1$H NMR (400 MHz, DMSO-$d_6$) δ 12.37 (s, 1H), 8.66 (t, J = 5.9 Hz, 1H), 7.84 (t, J = 2.0 Hz, 1H), 7.55 (s, 1H), 7.31 (dd, J = 3.3, 2.3 Hz, 1H), 7.19 (d, J = 4.9 Hz, 2H), 7.00-6.89 (m, 1H), 6.77 (dd, J = 3.3, 1.6 Hz, 1H), 6.37 (td, J = 4.6, 2.4 Hz, 1H), 4.13 (d, J = 5.8 Hz, 2H), 3.96 (t, J = 7.4 Hz, 2H), 3.61-3.52 (m, 7H), 3.48 (dd, J = 7.1, 5.7 Hz, 2H), 2.92 (tq, J = 13.3, 7.0, 6.5 Hz, 1H), 2.57 (d, J = 7.4 Hz, 2H), 2.37 (t, J = 4.6 Hz, 4H) |
| 174 | 526.6 | $^1$H NMR (400 MHz, DMSO-$d_6$) δ 12.39 (s, 1H), 8.65 (t, J = 5.9 Hz, 1H), 7.93 (d, J = 2.3 Hz, 1H), 7.84 (t, J = 2.0 Hz, 1H), 7.58 (s, 1H), 7.54 (d, J = 1.8 Hz, 1H), 7.32-7.29 (m, 1H), 7.29-7.22 (m, 2H), 7.07-7.02 (m, 1H), 6.77 (dd, J = 3.3, 1.6 Hz, 1H), 6.49 (dt, J = 7.0, 2.2 Hz, 1H), 6.31 (t, J = 2.1 Hz, 1H), 5.49-5.30 (m, 1H), 4.36 (t, J = 7.6 Hz, 2H), 4.13 (dt, J = 7.5, 4.0 Hz, 4H), 3.57 (s, 3H) |
| 176 | 544.2 | $^1$H NMR (400 MHz, DMSO-$d_6$) δ 12.38 (s, 1H), 8.66 (t, J = 5.9 Hz, 1H), 7.93 (d, J = 8.4 Hz, 1H), 7.79 (dt, J = 41.2, 2.0 Hz, 1H), 7.65 (d, J = 8.2 Hz, 1H), 7.59 (s, 1H), 7.51-7.34 (m, 1H), 7.33-7.22 (m, 3H), 7.02 (dt, J = 6.7, 1.9 Hz, 1H), 6.70 (ddd, J = 55.1, 3.3, 1.6 Hz, 1H), 6.49 (dt, J = 7.5, 1.8 Hz, 1H), 4.15 (dd, J = 14.0, 7.4 Hz, 3H), 3.85 (d, J = 8.9 Hz, 1H), 3.59 (d, J = 12.3 Hz, 3H) |
| 177 | 490.2 | $^1$H NMR (400 MHz, DMSO-$d_6$) δ 12.36 (s, 1H), 8.65 (t, J = 5.9 Hz, 1H), 7.84 (t, J = 2.0 Hz, 1H), 7.54 (s, 1H), 7.31 (dd, J = 3.3, 2.3 Hz, 1H), 7.20 (t, J = 7.8 Hz, 1H), 7.14-7.08 (m, 1H), 7.05 (t, J = 2.0 Hz, 1H), 6.77 (dd, J = 3.4, 1.6 Hz, 1H), 6.48 (dd, J = 8.2, 2.4 Hz, 1H), 4.42 (dt, J = 5.2, 2.4 Hz, 1H), 4.13 (d, J = 5.8 Hz, 2H), 3.57 (s, 3H), 3.45 (dd, J = 10.0, 4.9 Hz, 1H), 3.41-3.26 (m, 2H), 3.14-3.07 (m, 1H), 2.16-2.00 (m, 1H), 1.92 (tt, J = 8.3, 3.5 Hz, 1H) |
| 178 | 490.2 | $^1$H NMR (400 MHz, DMSO-$d_6$) δ 12.36 (s, 1H), 8.65 (t, J = 5.9 Hz, 1H), 7.84 (t, J = 2.0 Hz, 1H), 7.54 (s, 1H), 7.31 (t, J = 2.8 Hz, 1H), 7.20 (t, J = 7.8 Hz, 1H), 7.12 (d, J = 7.6 Hz, 1H), 7.05 (t, J = 2.0 Hz, 1H), 6.77 (dd, J = 3.4, 1.6 Hz, 1H), 6.48 (dd, J = 8.2, 2.5 Hz, 1H), 4.46-4.38 (m, 1H), 4.13 (d, J = 5.8 Hz, 2H), 3.57 (s, 3H), 3.45 (dd, J = 10.0, 4.9 Hz, 1H), 3.41-3.26 (m, 2H), 3.14-3.06 (m, 1H), 2.12-2.00 (m, 1H), 1.96-1.86 (m, 1H) |
| 179 | 490.2 | $^1$H NMR (400 MHz, DMSO-$d_6$) δ 12.37 (s, 1H), 8.65 (t, J = 5.9 Hz, 1H), 7.84 (t, J = 2.0 Hz, 1H), 7.55 (s, 1H), 7.31 (dd, J = 3.3, 2.3 Hz, 1H), 7.20 (d, J = 4.9 Hz, 2H), 7.00-6.91 (m, 1H), 6.77 (dd, J = 3.3, 1.6 Hz, 1H), 6.44-6.34 (m, 1H), 5.50 (s, 1H), 4.13 (d, J = 5.8 Hz, 2H), 3.78 (d, J = 7.1 Hz, 2H), 3.63 (d, J = 7.2 Hz, 2H), 3.57 (s, 3H), 1.47 (s, 3H) |
| 184 | 534.1 | $^1$H NMR (400 MHz, DMSO-$d_6$) δ 12.38 (s, 1H), 8.65 (d, J = 6.0 Hz, 1H), 7.84 (d, J = 2.0 Hz, 1H), 7.56 (s, 1H), 7.31-7.30 (m, 1H), 7.25-7.19 (m, 2H), 6.97 (d, J = 1.2 Hz, 1H), 6.77-6.76 (m, 1H), 6.44-6.37 (m, 1H), 4.50-4.38 (m, 1H), 4.19-4.02 (m, 4H), 3.63-3.59 (m, 2H), 3.57 (s, 3H), 3.56-3.53 (m, 2H), 3.49-3.44 (m, 2H), 3.26 (s, 3H) |

TABLE 2-continued

| Compound # | LC-MS data(m/z) | $^1$H NMR |
|---|---|---|
| 185 | 452.0 | $^1$H NMR (400 MHz, DMSO-d$_6$) δ 12.32 (s, 1H), 8.25-8.21 (m, 1H), 7.58-7.54 (m, 2H), 7.22-7.19 (m, 2H), 7.02-7.01 (m, 1H), 6.95 (d, J = 1.2 Hz, 1H), 6.58-6.56 (m, 1H), 6.39-6.36 (m, 1H), 4.85 (d, J = 6.8 Hz, 2H), 4.63 (d, J = 6.8 Hz, 2H), 4.10 (d, J = 5.6 Hz, 2H), 3.86-3.82 (m, 4H), 2.35-2.30 (m, 2H), 1.80 (s, 3H) |
| 186 | 438.0 | $^1$H NMR (400 MHz, DMSO-d$_6$) δ 12.30 (s, 1H), 8.17-8.13 (m, 1H), 7.54-7.52 (m, 2H), 7.21-7.19 (m, 2H), 6.98-6.94 (m, 2H), 6.49-6.47 (m, 1H), 6.39-6.35 (m, 1H), 4.09 (d, J = 5.6 Hz, 2H), 3.86-3.82 (m, 4H), 2.35-2.30 (m, 2H), 1.50 (s, 9H) |
| 187 | 516.2 | $^1$H NMR (400 MHz, DMSO-d$_6$) δ 12.34 (s, 1H), 8.67-8.64 (m, 1H), 7.84-7.83 (m, 1H), 7.58 (s, 1H), 7.43-7.42 (m, 1H), 7.31-7.30 (m, 1H), 7.27-7.20 (m, 2H), 6.88-6.86 (m, 1H), 6.77-6.76 (m, 1H), 4.13-4.12 (m, 2H), 3.57 (s, 3H), 3.20-3.16 (m, 2H), 2.85-2.81 (m, 2H), 2.01-1.97 (m, 2H), 1.41-1.38 (m, 2H), 0.99 (d, J = 6.8 Hz, 6H) |
| 192 | 513.2 | $^1$H NMR (400 MHz, DMSO-d$_6$) δ 12.36 (s, 1H), 8.32 (d, J = 6.0 Hz, 1H), 7.88 (d, J = 2.4 Hz, 1H), 7.62 (s, 1H), 7.45 (s, 1H), 7.36-7.31 (m, 1H), 7.30-7.24 (m, 1H), 6.97-6.91 (m, 1H), 6.63 (d, J = 2.4 Hz, 1H), 5.03 (d, J = 6.0 Hz, 1H), 4.17 (d, J = 6.0 Hz, 2H), 3.77-3.68 (m, 2H), 3.66-3.59 (m, 4H), 2.33-2.23 (m, 2H), 1.52 (s, 6H), 1.18 (d, J = 6.0 Hz, 6H) |
| 193 | 562.5 | $^1$H NMR (400 MHz, DMSO-d$_6$) δ 12.39 (s, 1H), 8.69-8.66 (m, 1H), 7.81 (d, J = 2.0 Hz, 1H), 7.62 (s, 1H), 7.44 (s, 1H), 7.31-7.30 (m, 1H), 7.29-7.22 (m, 2H), 6.93 (d, J = 8.0 Hz, 1H), 6.75-6.74 (m, 1H), 4.13 (d, J = 5.6 Hz, 2H), 3.99-3.96 (m, 2H), 3.71-3.70 (m, 2H), 3.63-3.59 (m, 4H), 3.15 (s, 3H), 2.28-2.25 (m, 2H), 1.17 (d, J = 6.4 Hz, 6H) |
| 194 | 532.2 | $^1$H NMR (400 MHz, Methanol-d$_4$) δ 7.92 (s, 1H), 7.84-7.83 (m, 1H), 7.76 (d, J = 7.2 Hz, 1H), 7.50-7.47 (m, 2H), 7.32-7.27 (m, 2H), 6.81-6.80 (m, 1H), 4.26 (s, 2H), 3.77-3.74 (m, 1H), 3.57-3.54 (m, 1H), 3.46 (d, J = 12.7 Hz, 1H), 3.39 (s, 3H), 3.37-3.34 (m, 1H), 3.07 (d, J = 12.8 Hz, 1H), 2.10 (s, 1H), 2.00-1.93 (m, 1H), 1.13 (d, J = 10.8 Hz, 6H) |
| 198 | 534.3 | $^1$H NMR (400 MHz, DMSO-d$_6$) δ 12.36 (s, 1H), 8.65 (t, J = 5.9 Hz, 1H), 7.84 (t, J = 2.0 Hz, 1H), 7.56 (s, 1H), 7.31 (dd, J = 3.3, 2.3 Hz, 1H), 7.21 (t, J = 7.8 Hz, 1H), 7.19-7.14 (m, 1H), 7.06 (t, J = 1.9 Hz, 1H), 6.77 (dd, J = 3.3, 1.7 Hz, 1H), 6.52 (ddd, J = 7.9, 2.6, 1.2 Hz, 1H), 4.14 (d, J = 5.8 Hz, 2H), 3.99 (dd, J = 4.0, 1.9 Hz, 2H), 3.57 (s, 3H), 3.47 (dd, J = 10.7, 4.5 Hz, 2H), 3.38-3.24 (m, 8H) |
| 199 | 534.3 | $^1$H NMR (400 MHz, DMSO-d$_6$) δ 12.35 (s, 1H), 8.66 (t, J = 5.9 Hz, 1H), 7.84 (t, J = 2.0 Hz, 1H), 7.56 (s, 1H), 7.31 (dd, J = 3.3, 2.3 Hz, 1H), 7.20 (t, J = 7.8 Hz, 1H), 7.14 (dt, J = 7.6, 1.3 Hz, 1H), 7.03 (t, J = 2.0 Hz, 1H), 6.77 (dd, J = 3.3, 1.6 Hz, 1H), 6.48 (ddd, J = 8.1, 2.6, 1.1 Hz, 1H), 4.13 (d, J = 5.8 Hz, 2H), 4.05 (t, J = 4.2 Hz, 2H), 3.57 (s, 3H), 3.47 (dd, J = 9.6, 5.1 Hz, 2H), 3.36 (s, 6H), 3.27 (dd, J = 9.7, 4.1 Hz, 2H) |
| 200 | 518.4 | $^1$H NMR (400 MHz, DMSO-d$_6$) δ 12.36 (s, 1H), 8.65 (t, J = 5.9 Hz, 1H), 7.84 (t, J = 1.9 Hz, 1H), 7.55 (s, 1H), 7.31 (dd, J = 3.3, 2.3 Hz, 1H), 7.19 (t, J = 7.8 Hz, 1H), 7.16-7.11 (m, 1H), 7.09 (t, J = 2.0 Hz, 1H), 6.77 (dd, J = 3.3, 1.6 Hz, 1H), 6.53-6.46 (m, 1H), 4.13 (d, J = 5.8 Hz, 2H), 3.57 (s, 3H), 3.45-3.24 (m, 8H), 3.04 (dd, J = 9.4, 6.6 Hz, 1H), 2.59 (p, J = 7.2 Hz, 1H), 2.16-2.01 (m, 1H), 1.73 (dq, J = 12.3, 7.8 Hz, 1H) |
| 201 | 518.3 | $^1$H NMR (400 MHz, DMSO-d$_6$) δ 12.36 (s, 1H), 8.65 (t, J = 5.9 Hz, 1H), 7.84 (t, J = 2.0 Hz, 1H), 7.55 (s, 1H), 7.31 (dd, J = 3.3, 2.3 Hz, 1H), 7.19 (t, J = 7.8 Hz, 1H), 7.16-7.10 (m, 1H), 7.09 (t, J = 2.0 Hz, 1H), 6.77 (dd, J = 3.3, 1.7 Hz, 1H), 6.54-6.44 (m, 1H), 4.13 (d, J = 5.8 Hz, 2H), 3.57 (s, 3H), 3.46-3.23 (m, 8H), 3.04 (dd, J = 9.4, 6.6 Hz, 1H), 2.58 (dq, J = 14.3, 7.1 Hz, 1H), 2.08 (dtd, J = 11.9, 7.2, 4.5 Hz, 1H), 1.73 (dq, J = 12.2, 7.8 Hz, 1H) |
| 202 | 530.4 | $^1$H NMR (400 MHz, DMSO-d$_6$) δ 12.32 (s, 1H), 8.63 (s, 1H), 7.82 (t, J = 2.0 Hz, 1H), 7.57 (s, 1H), 7.45 (t, J = 2.1 Hz, 1H), 7.32-7.25 (m, 2H), 7.22 (t, J = 7.8 Hz, 1H), 6.89 (ddd, J = 8.2, 2.7, 1.1 Hz, 1H), 6.75 (dd, J = 3.3, 1.7 Hz, 1H), 4.34 (s, 4H), 4.12 (d, J = 5.8 Hz, 2H), 3.55 (s, 3H), 3.15-3.07 (m, 4H), 1.92-1.85 (m, 4H) |
| 203 | 545.9 | $^1$H NMR (400 MHz, DMSO-d$_6$) δ 12.39 (s, 1H), 8.70-8.69 (m, 1H), 7.84-7.84 (m, 1H), 7.63 (s, 1H), 7.40 (s, 1H), 7.34-7.23 (m, 3H), 6.89 (d, J = 8.0 Hz, 1H), 6.78-6.77 (m, 1H), 4.13-4.14 (m, 2H), 3.58 (s, 3H), 3.05 (s, 4H), 1.24 (s, 12H) |
| 204 | 530.1 | $^1$H NMR (400 MHz, DMSO-d$_6$) δ 12.01 (br s, 1H), 8.71-8.67 (m, 1H),, 7.85-7.84 (m, 1H), 7.64 (s, 1H), 7.54 (s, 1H), 7.38-7.23 (m, 3H), 6.98-6.95 (m, 1H), 6.78-6.76 (m, 1H), 4.38-4.29 (m, 4H), 4.13 (d, J = 5.6 Hz, 2H), 3.57 (s, 3H), 3.33 (s, 2H), 3.08-2.98 (m, 2H), 1.82-1.73 (m, 2H), 1.64-1.53 (m, 2H) |
| 207 | 486.1 | $^1$H NMR (400 MHz, DMSO-d$_6$) δ 12.37 (s, 1H), 8.67-8.64 (m, 1H), 7.84-7.83 (m, 1H), 7.54 (s, 1H), 7.30-7.29 (m, 1H), 7.17-7.15 (m, 2H), 7.05 (s, 1H), 6.77-6.76 (m, 1H), 6.51 (d, J = 7.6 Hz, 1H), 4.13 (d, J = 5.6 Hz, 2H), 3.57 (s, 3H), 3.52 (d, J = 9.2 Hz, 2H), 3.20 (d, J = 8.4 Hz, 2H), 1.70 (d, J = 3.6 Hz, 2H), 0.74-0.69 (m, 1H), 0.28-0.26 (m, 1H) |
| 209 | 518.2 | $^1$H NMR (400 MHz, DMSO-d$_6$) δ 12.40 (br s, 1H), 8.72-8.69 (m, 1H), 7.83-7.61 (m, 1H), 7.61 (s, 1H), 7.47 (s, 1H), 7.34-7.20 (m, 3H), 6.90-6.79 (m, 1H), 6.79-6.78 (m, 1H), 4.14 (d, J = 5.6 Hz, 2H), 3.78-3.56 (m, 5H), 2.95-2.82 (m, 2H), 1.93-1.76 (m, 2H), 1.57-1.43 (m, 2H), 1.13-1.10 (m, 3H) |

TABLE 2-continued

| Compound # | LC-MS data(m/z) | $^1$H NMR |
|---|---|---|
| 210 | 504.1 | $^1$H NMR (400 MHz, DMSO-$d_6$) δ 12.35 (br s, 1H), 8.68-8.65 (m, 1H), 7.86-7.84 (m, 1H), 7.58 (s, 1H), 7.33-7.31 (m, 1H), 7.26 (s, 1H), 7.23-7.19 (m, 1H), 7.17-7.12 (m, 1H), 6.80-6.76 (m, 1H), 6.73-6.71 (m, 1H), 4.14 (d, J = 6.0 Hz, 2H), 3.77-3.73 (m, 2H), 3.64-3.57 (m, 9H), 1.96-1.90 (m, 2H) |
| 212 | 476.0 | $^1$H NMR (400 MHz, DMSO-$d_6$) δ 8.69-8.66 (m, 1H), 7.84 (s, 1H), 7.56 (s, 1H), 7.31-7.30 (m, 1H), 7.20 (d, J = 4.8 Hz, 2H), 6.96 (s, 1H), 6.77-6.76 (m, 1H), 6.44-6.34 (m, 1H), 5.72-5.57 (m, 1H), 4.58 (d, J = 4.0 Hz, 1H), 4.13-4.08 (m, 4H), 3.57 (s, 3H), 3.52-3.50 (m, 2H) |
| 214 | 502.0 | $^1$H NMR (400 MHz, DMSO-$d_6$) δ 12.41-12.35 (m, 1H), 8.74-8.67 (m, 1H), 7.84 (s, 1H), 7.57 (d, J = 2.4 Hz, 1H), 7.31 (d, J = 2.4 Hz, 1H), 7.21-7.16 (m, 2H), 7.11 (s, 1H), 6.77 (d, J = 1.6 Hz, 1H), 6.60-6.58 (m, 1H), 4.63-4.58 (m, 2H), 4.13 (d, J = 4.0 Hz, 2H), 3.77 (d, J = 6.8 Hz, 1H), 3.68 (d, J = 5.6 Hz, 1H), 3.57 (d, J = 2.0 Hz, 3H), 3.53 (d, J = 10.0 Hz, 1H), 3.00 (d, J = 9.2 Hz, 1H), 1.95-1.85 (m, 2H) |
| 215 | 504.2 | $^1$H NMR (400 MHz, Methanol-$d_4$) δ = 8.29 (s, 1H), 7.84-7.83 (m 1H), 7.54 (s, 1H), 7.35-7.33 (m, 2H), 7.28-7.23 (m, 2H), 6.94-6.92 (m, 1H), 6.81-6.80 (m, 1H), 4.25 (s, 2H), 3.83-3.75 (m, 1H), 3.65-3.61 (m, 1H), 3.49-3.46 (m, 1H), 3.38 (s, 3H), 2.82-2.76 (m, 1H), 2.70-2.65 (m, 1H), 2.03-1.98 (m, 1H), 1.93-1.85 (m, 1H), 1.74-1.63 (m, 1H), 1.47-1.37 (m, 1H) |
| 216 | 513.1 | $^1$H NMR (400 MHz, DMSO-$d_6$) δ 12.38 (br s, 1H), 8.68-8.67 (m, 1H), 7.84-7.83 (m, 1H), 7.62 (s, 1H), 7.50-7.46 (m, 1H), 7.36-7.32 (m, 1H), 7.31-7.31 (m, 1H), 7.29-7.24 (m, 1H), 6.93-6.92 (m, 1H), 6.77-6.77 (m, 1H), 4.13 (d, J = 6.0 Hz, 2H), 3.57 (s, 3H), 3.43-3.39 (m, 2H), 3.12-3.02 (m, 3H), 2.06-1.97 (m, 2H), 1.89-1.79 (m, 2H) |
| 220 | 517.3 | $^1$H NMR (400 MHz, DMSO-$d_6$) δ 12.40 (s, 1H), 8.68-8.67(m, 1H), 7.85-7.84 (m, 1H), 7.66 (s, 1H), 7.46 (s, 1H), 7.39-7.24 (m, 3H), 6.93-6.78 (m, 1H), 6.77-6.76 (m, 1H), 4.13 (d, J = 6.0 Hz, 2H), 3.81 (s, 2H), 3.57 (s, 3H), 3.55-3.51 (m, 2H), 3.48-3.43 (m, 2H), 2.91 (s, 3H) |
| 221 | 546.9 | $^1$H NMR (400 MHz, DMSO-$d_6$) δ 12.51-12.21 (m, 1H), 8.68-8.61 (m, 1H), 7.81-7.80 (m, 1H), 7.61 (s, 1H), 7.44 (s, 1H), 7.34-7.32 (m, 1H), 7.28-7.24 (m, 2H), 6.94-6.91 (m, 1H), 6.75-6.74 (m, 1H), 4.13 (d, J = 5.6 Hz, 2H), 3.74-3.69 (m, 2H), 3.63-3.60 (m, 2H), 2.79 (s, 6H), 2.28-2.26 (m, 2H), 1.17 (d, J = 6.4 Hz, 6H) |
| 222 | 530.0 | $^1$H NMR (400 MHz, DMSO-$d_6$) δ 12.41 (s, 1H), 8.69-6.67 (m, 1H), 7.84-7.83 (m, 1H), 7.55 (s, 1H), 7.31-7.30 (m, 1H), 7.20-7.18 (m, 2H), 6.92 (s, 1H), 6.77-6.76 (m, 1H), 6.36-6.35 (m, 1H), 4.13 (d, J = 6.0 Hz, 2H), 3.82-3.77 (m, 5H), 3.57 (s, 3H), 3.12 (s, 3H), 2.52 (s, 2H), 2.08-2.03 (m, 2H) |
| 223 | 516.3 | $^1$H NMR (400 MHz, DMSO-$d_6$) δ 12.37 (s, 1H), 8.65 (t, J = 5.9 Hz, 1H), 7.84 (t, J = 2.0 Hz, 1H), 7.55 (s, 1H), 7.31 (dd, J = 3.3, 2.3 Hz, 1H), 7.21 (d, J = 6.8 Hz, 2H), 7.16 (d, J = 2.5 Hz, 1H), 6.77 (dd, J = 3.3, 1.6 Hz, 1H), 6.60 (dt, J = 7.0, 2.4 Hz, 1H), 4.13 (d, J = 5.8 Hz, 2H), 3.86 (dd, J = 8.7, 6.5 Hz, 2H), 3.61-3.51 (m, 5H), 3.40 (dd, J = 9.5, 7.3 Hz, 2H), 3.20 (dd, J = 9.6, 2.7 Hz, 2H), 3.02 (h, J = 3.6 Hz, 2H) |
| 224 | 504.2 | $^1$H NMR (400 MHz, DMSO-$d_6$) δ 12.36 (s, 1H), 8.66 (t, J = 5.9 Hz, 1H), 7.85 (t, J = 2.0 Hz, 1H), 7.55 (s, 1H), 7.31 (dd, J = 3.3, 2.3 Hz, 1H), 7.20 (t, J = 7.8 Hz, 1H), 7.14 (dt, J = 7.6, 1.3 Hz, 1H), 7.07 (t, J = 2.0 Hz, 1H), 6.78 (dd, J = 3.3, 1.7 Hz, 1H), 6.51 (ddd, J = 8.1, 2.6, 1.1 Hz, 1H), 4.14 (d, J = 5.8 Hz, 2H), 4.12-4.07 (m, 1H), 3.57 (s, 3H), 3.46 (dd, J = 10.5, 5.0 Hz, 1H), 3.36-3.23 (m, 6H), 2.09 (td, J = 8.1, 4.9 Hz, 2H) |
| 225 | 510.1 | $^1$H NMR (400 MHz, DMSO-$d_6$) δ 12.37 (s, 1H), 8.66 (t, J = 5.9 Hz, 1H), 7.84 (t, J = 2.0 Hz, 1H), 7.61 (s, 1H), 7.31 (dd, J = 3.3, 2.3 Hz, 1H), 7.28-7.23 (m, 2H), 7.12 (t, J = 1.7 Hz, 1H), 6.77 (dd, J = 3.3, 1.6 Hz, 1H), 6.59 (td, J = 4.6, 2.5 Hz, 1H), 4.13 (d, J = 5.8 Hz, 2H), 3.74 (t, J = 13.4 Hz, 2H), 3.57 (s, 3H), 3.52 (t, J = 7.2 Hz, 2H), 2.64-2.52 (m, 2H) |
| 227 | 545.2 | $^1$H NMR (400 MHz, DMSO-$d_6$) δ 12.42-12.35 (m, 1H), 8.67-8.66 (m, 1H), 7.85-7.84 (m, 1H), 7.56 (s, 1H), 7.32-7.30 (m, 1H), 7.22 (d, J = 4.8 Hz, 2H), 6.97 (s, 1H), 6.78-6.77 (m, 1H), 6.42-6.40 (m, 1H), 4.14 (d, J = 5.6 Hz, 2H), 3.94-3.93 (m, 2H), 3.63 (d, J = 1.6 Hz, 2H), 3.62-3.59 (m, 5H), 3.58 (s, 3H), 2.36 (s, 4H) |
| 228 | 532.2 | $^1$H NMR (400 MHz, DMSO-$d_6$) δ 7.77-7.76 (m, 1H), 7.51 (s, 1H), 7.39 (s, 1H), 7.33-7.24 (m, 3H), 6.92-6.91 (m, 1H), 6.77-6.76 (m, 1H), 4.12-4.11 (m, 2H), 3.78-3.65 (m, 2H), 3.63-3.51 (m, 4H), 2.27-2.24 (m, 2H), 1.16-1.08 (m, 9H) |
| 229 | 496.2 | $^1$H NMR (400 MHz, Methanol-$d_4$) δ 7.67 (s, 1H), 7.54 (s, 1H), 7.38 (d, J = 4.0 Hz, 2H), 7.30-7.26 (m, 1H), 7.07 (d, J = 2.4 Hz, 1H), 6.94 (d, J = 8.0 Hz, 1H), 6.68-6.66 (m, 1H), 5.39-5.34 (m, 1H), 5.10 (d, J = 3.2 Hz, 2H), 4.88 (s, 2H), 4.25 (s, 2H), 3.86-3.81 (m, 2H), 3.59 (d, J = 12.0 Hz, 2H), 2.40-2.34 (m, 2H), 1.26-1.24 (m, 6H) |
| 230 | 502.1 | $^1$H NMR (400 MHz, DMSO-$d_6$) δ 12.38 (s, 1H), 8.68-8.65 (m, 1H), 7.85-7.84 (m, 1H), 7.59 (s, 1H), 7.32-7.22 (m, 3H), 6.78-6.77 (m, 1H), 6.73-6.70 (m, 1H), 4.75 (d, J = 6.6 Hz, 2H), 4.14 (d, J = 5.8 Hz, 2H), 3.61 (s, 5H), 3.45 (d, J = 11.2 Hz, 2H), 3.19-3.08 (m, 1H), 2.53 (d, J = 1.6 Hz, 2H) |
| 231 | 474.0 | $^1$H NMR (400 MHz, DMSO-$d_6$) δ 12.36 (s, 1H), 8.67-8.64 (m, 1H), 7.84-7.83 (m, 1H), 7.53 (s, 1H), 7.31-7.30 (m, 1H), 7.21-7.17 (m, 1H), 7.12-7.07 (m, 2H), 6.77-6.76 (m, 1H), 6.51-6.49 (m, 1H), 4.12 (d, J = 6.0 Hz, 2H), 3.56 (s, 3H), 3.28-3.24 (m, 4H), 1.99-1.95 (m, 4H) |

TABLE 2-continued

| Compound # | LC-MS data(m/z) | $^1H$ NMR |
|---|---|---|
| 232 | 502.3 | $^1H$ NMR (400 MHz, DMSO-$d_6$) δ 12.28-12.22 (m, 1H), 8.67-8.66 (m, 1H), 7.84-7.83 (m, 1H), 7.58 (s, 1H), 7.45 (s, 1H), 7.30-7.26 (m, 1H), 7.23-7.21 (m, 2H), 6.77 (m, 1H), 6.77-6.76 (m, 1H), 4.14 (d, J = 5.6 Hz, 2H), 3.66-3.60 (m, 2H), 3.57 (s, 3H), 2.66-2.62 (m, 1H), 2.36-2.30 (m, 1H), 1.74-1.69 (m, 4H), 1.02-0.94 (m, 1H), 0.94 (d, J = 6.4 Hz, 3H) |
| 233 | 460.2 | $^1H$ NMR (400 MHz, DMSO-$d_6$) δ 12.35 (s, 1H), 8.66-8.63 (m, 1H), 7.84-7.83 (m, 1H), 7.54 (s, 1H), 7.31-7.30 (m, 1H), 7.20-7.19 (m, 2H), 6.94 (d, J = 0.8 Hz, 1H), 6.77-6.76 (m, 1H), 6.38-6.35 (m, 1H), 4.12 (d, J = 6.0 Hz, 2H), 3.84-3.81 (m, 4H), 3.58 (s, 3H), 2.35-2.28 (m, 2H) |
| 234 | 540.2 | $^1H$ NMR (400 MHz, DMSO-$d_6$) δ 12.37-12.32 (m, 1H), 8.70-8.69 (m, 1H), 7.86-7.85 (m, 1H), 7.62 (s, 1H), 7.53 (s, 1H), 7.31-7.28 (m, 4H), 7.27-7.26 (m, 1H), 6.79-6.78 (m, 1H), 4.25 (s, 2H), 4.14 (d, J = 5.6 Hz, 2H), 3.71-3.67 (m, 3H), 3.67-3.62 (m, 2H), 3.58 (s, 3H), 2.79-2.77 (m, 2H) |
| 235 | 510.1 | $^1H$ NMR (400 MHz, Methanol-$d_4$) δ 7.54 (d, J = 10.4 Hz, 2H), 7.40-7.33 (m, 2H), 7.30-7.23 (m, 1H), 6.98 (d, J = 1.6 Hz, 1H), 6.93 (d, J = 8.0 Hz, 1H), 6.66 (d, J = 1.2 Hz, 1H), 4.97 (d, J = 6.4 Hz, 2H), 4.71 (d, J = 6.4 Hz, 2H), 4.23 (s, 2H), 3.88-3.75 (m, 2H), 3.57 (d, J = 11.6 Hz, 2H), 2.38-2.32 (m, 2H), 1.88 (s, 3H), 1.24 (d, J = 6.0 Hz, 6H) |
| 238 | 502.3 | $^1H$ NMR (400 MHz, DMSO-$d_6$) δ 12.83-11.71 (m, 1H), 8.68-8.65 (m, 1H), 7.85 (s, 1H), 7.59 (s, 1H), 7.46 (s, 1H), 7.33-7.30 (m, 1H), 7.30-7.20 (m, 2H), 6.89 (d, J = 7.2 Hz, 1H), 6.78-6.77(m, 1H), 4.14 (d, J = 6.0 Hz, 2H), 3.66-3.61 (m, 2H), 3.57 (s, 3H), 2.66-2.60 (m, 1H), 2.36-2.30 (m, 1H), 1.79-1.66 (m, 3H), 1.63-1.53 (m, 1H), 1.06-1.02 (m, 1H), 0.93 (d, J = 6.4 Hz, 3H) |
| 239 | 504.0 | $^1H$ NMR (400 MHz, DMSO-$d_6$) δ 12.35 (s, 1H), 8.67-8.64 (m, 1H), 7.84-7.83 (m, 1H), 7.59 (s, 1H), 7.41 (s, 1H), 7.31-7.30 (m, 2H), 7.30-7.26 (m, 1H), 6.77 (d, J = 2.0 Hz, 1H), 6.77-6.76 (m, 1H), 4.14 (d, J = 5.6 Hz, 2H), 3.94-3.89 (m, 2H), 3.73-3.70 (m, 2H), 3.60-3.57 (m, 4H), 3.18 (d, J = 12.0 Hz, 1H), 3.04-3.02 (m, 1H), 1.01 (d, J = 6.4 Hz, 3H) |
| 241 | 524.3 | $^1H$ NMR (400 MHz, DMSO-$d_6$) δ 12.50-12.21 (m, 1H), 8.72-8.60 (m, 1H), 7.88-7.81 (m, 1H), 7.64 (s, 1H), 7.55-7.49 (m, 1H), 7.41-7.24 (m, 3H), 7.02-6.94 (m, 1H), 6.85-6.73 (m, 1H), 4.17-4.10 (m, 2H), 3.58 (s, 3H), 3.39 (s, 4H), 2.15-2.04 (m, 4H) |
| 242 | 488.2 | $^1H$ NMR (400 MHz, DMSO-$d_6$) δ 12.35 (br s, 1H), 8.67-8.66 (m, 1H), 7.84-7.83 (m, 1H), 7.59 (s, 1H), 7.46 (s, 1H), 7.34-7.30 (m, 1H), 7.30-7.19 (m, 2H), 6.88-6.88 (m, 1H), 6.78-6.77 (m, 1H), 4.13 (d, J = 6.0 Hz, 2H), 3.57 (s, 3H), 3.21-3.14 (m, 4H), 1.69-1.60 (m, 4H), 1.59-1.49 (m, 2H) |
| 243 | 518.3 | $^1H$ NMR (400 MHz, D2O + DMSO-$d_6$) δ 7.97 (br s, 1H), 7.90 (br d, J = 7.6 Hz, 1H), 7.79 (s, 1H), 7.69 (s, 1H), 7.58 (br t, J = 8.0 Hz, 1H), 7.49-7.46 (m, 1H), 7.29 (br s, 1H), 6.75 (br d, J = 1.2 Hz, 1H), 4.11 (br s, 2H), 3.65-3.60 (m, 2H), 3.46-3.43 (m, 5H), 1.93-1.78 (m, 4H), 1.24 (s, 3H) |
| 244 | 532.4 | $^1H$ NMR (400 MHz, Methanol-$d_4$) δ 8.20 (br s, 1H), 7.85-7.83 (m, 1H), 7.55 (s, 1H), 7.35-7.32 (m, 2H), 7.28-7.25 (m, 2H), 6.94-6.92 (m, 1H), 6.81-6.80 (m, 1H), 4.25 (s, 2H), 3.72-3.69 (m, 1H), 3.61 (d, J = 12.0 Hz, 1H), 3.38 (s, 3H), 3.37-3.33 (m, 5H), 2.74-2.71 (m, 1H), 2.55-2.52 (m, 1H), 2.06-1.95 (m, 1H), 1.82-1.79 (m, 2H), 1.73-1.70 (m, 1H), 1.20-1.17 (m, 1H) |
| 245 | 480.4 | $^1H$ NMR (400 MHz, DMSO-$d_6$) δ 12.31 (s, 1H), 8.16-8.13 (m, 1H), 7.54 (s, 1H), 7.51-7.50 (m, 1H), 7.21-7.18 (m, 2H), 6.97-6.96 (m, 2H), 6.47-6.46 (m, 1H), 6.41-6.38 (m, 1H), 4.73 (s, 4H), 4.08 (d, J = 6.0 Hz, 2H), 4.00 (s, 4H), 1.49 (s, 9H) |
| 246 | 490.2 | $^1H$ NMR (400 MHz, DMSO-$d_6$) δ 12.38 (s, 1H), 8.66-8.64 (m, 1H), 7.84 (s, 1H), 7.55 (s, 1H), 7.34-7.29 (m, 1H), 7.22 (d, J = 4.8 Hz, 2H), 6.97 (s, 1H), 6.80-6.73 (m, 1H), 6.45-6.36 (m, 1H), 4.33-4.33 (m, 1H), 4.13 (d, J = 5.6 Hz, 2H), 4.08-4.06 (m, 2H), 3.62-3.61 (m, 2H), 3.57 (s, 3H), 3.26 (s, 3H) |
| 226 | 504.4 | $^1H$ NMR (400 MHz, DMSO-$d_6$) δ 12.36 (s, 1H), 8.65 (t, J = 5.9 Hz, 1H), 7.85 (t, J = 2.0 Hz, 1H), 7.55 (s, 1H), 7.31 (t, J = 2.8 Hz, 1H), 7.20 (t, J = 7.8 Hz, 1H), 7.14 (d, J = 7.6 Hz, 1H), 7.07 (t, J = 2.0 Hz, 1H), 6.78 (dd, J = 3.3, 1.7 Hz, 1H), 6.51 (dd, J = 8.0, 2.5 Hz, 1H), 4.20-4.04 (m, 3H), 3.57 (s, 3H), 3.46 (dd, J = 10.5, 5.0 Hz, 1H), 3.36-3.24 (m, 6H), 2.09 (td, J = 8.2, 5.0 Hz, 2H) |
| 427 | 504.2 | $^1H$ NMR (400 MHz, DMSO + $D_2O$) δ 7.80-7.79 (m, 1H), 7.49 (s, 1H), 7.29-7.28 (m, 1H), 7.22-7.14 (m, 2H), 6.90 (s, 1H), 6.75-6.74 (m, 1H), 6.36-6.35 (m, 1H), 4.11 (s, 2H), 3.87 (s, 2H), 3.58-3.45 (m, 7H), 3.25 (s, 3H), 2.94-2.86 (m, 1H) |
| 445 | 516.4 | $^1H$ NMR (400 MHz, DMSO-$d_6$) δ 8.66-8.64 (m, 1H), 7.84 (s, 1H), 7.58 (s, 1H), 7.36 (s, 1H), 7.32-7.24 (m, 3H), 6.82-6.79 (m, 1H), 6.77-6.76 (m, 1H), 4.46 (s, 2H), 4.13 (d, J = 5.6 Hz, 2H), 3.57 (s, 3H), 3.44 (d, J = 11.2 Hz, 2H), 2.86-2.83 (m, 2H), 1.85 (s, 4H) |
| 446 | 540.2 | $^1H$ NMR (400 MHz, DMSO-$d_6$) δ 12.39-12.38 (m, 1H), 8.69-8.68 (m, 1H), 7.86-7.85 (m, 1H), 7.61 (s, 1H), 7.52 (s, 1H), 7.49 (s, 1H), 7.34-7.20 (m, 3H), 6.96-6.95 (m, 1H), 6.79-6.78 (m, 1H), 4.27 (s, 2H), 4.15 (d, J = 5.6 Hz, 2H), 3.77 (s, 3H), 3.63-3.61 (m, 2H), 3.58 (s, 3H), 2.73-2.71 (m, 2H) |
| 449 | 505.9 | $^1H$ NMR (400 MHz, DMSO-$d_6$) δ 12.36 (s, 1H), 8.68-8.66 (m, 1H), 7.84-7.83 (m, 1H), 7.61 (s, 1H), 7.49 (s, 1H), 7.31-7.30 (m, 2H), 7.27-7.25 (m, |

TABLE 2-continued

| Compound # | LC-MS data(m/z) | $^1$H NMR |
|---|---|---|
| | | 1H), 6.92-6.77 (m, 1H), 6.77-6.77 (m, 1H), 4.92-4.89 (m, 1H), 4.13 (d, J = 6.0 Hz, 2H), 3.57 (s, 3H), 3.40-3.38 (m, 2H), 3.19-3.16 (m, 2H), 2.00-1.83 (m, 2H), 1.82-1.79 (m, 2H) |
| 450 | 520.1 | $^1$H NMR (400 MHz, DMSO-d$_6$) δ 12.39 (s, 1H), 8.67-8.66 m, 1H), 7.84-7.83 (m, 1H), 7.60 (s, 1H), 7.47 (s, 1H), 7.37-7.33 (m, 1H), 7.31-7.31 (m, 1H), 7.30-7.25 (m, 1H), 6.93-6.92 (m, 1H), 6.77-6.77 (m, 1H), 4.82-4.81 (m, 1H), 4.13 (d, J = 6.0 Hz, 2H), 3.97-3.95 (m, 1H), 3.71-3.62 (m, 2H), 3.57 (s, 3H), 3.56-3.50 (m, 2H), 3.48-3.38 (m, 1H), 2.71-2.71 (m, 1H), 2.48-2.43 (m, 1H) |
| 451 | 545.2 | $^1$H NMR (400 MHz, DMSO-d$_6$) δ 12.39 (s, 1H), 8.71-8.68 (m, 1H), 7.85 (d, J = 1.6 Hz, 1H), 7.67-7.62 (m, 1H), 7.51 (s, 1H), 7.47-7.40 (m, 1H), 7.38-7.31 (m, 2H), 7.04-7.00 (m, 1H), 6.79-6.77 (m, 1H), 4.88-4.73 (m, 4H), 4.56-4.42 (m, 1H), 4.14 (d, J = 5.6 Hz, 2H), 4.04-3.87 (m, 2H), 3.58 (s, 3H), 3.28-3.15 (m, 2H), 3.13-3.00 (m, 4H) |
| 452 | 520.1 | $^1$H NMR (400 MHz, DMSO-d$_6$) δ 12.38-12.37 (m, 1H), 8.68-8.67 (m, 1H), 7.85 (s, 1H), 7.61 (s, 1H), 7.48 (s, 1H), 7.38-7.25 (m, 3H), 6.96-6.89 (m, 1H), 6.78-6.77 (m, 1H), 4.83-4.77 (m, 1H), 4.14 (m, 2H), 4.02-3.93 (m, 1H), 3.68 (m, 2H), 3.60-3.53 (m, 5H), 3.48-3.43 (m, 1H), 2.72-2.71 (m, 1H), 2.48-2.33 (m, 1H) |
| 468 | 516.0 | $^1$H NMR (400 MHz, DMSO-d$_6$) δ 12.37 (s, 1H), 8.68-8.65 (m, 1H), 7.84-7.83 (m, 1H), 7.53 (s, 1H), 7.31-7.30 (m, 1H), 7.18-7.14 (m, 1H), 7.08-7.05 (m, 2H), 6.77-6.76 (m, 1H), 6.50-6.48 (m, 1H), 4.78 (d, J = 3.2 Hz, 1H), 4.25-4.22 (m, 1H), 4.13 (d, J = 5.6 Hz, 2H), 4.05 (s, 1H), 3.57 (s, 3H), 3.43 (d, J = 8.4 Hz, 1H), 3.27-3.25 (m, 1H), 2.52 (d, J = 2.0 Hz, 1H), 1.94-1.88 (m, 1H), 1.76 (d, J = 9.6 Hz, 1H), 1.60 (d, J = 9.6 Hz, 1H), 1.22-1.17 (m, 1H) |
| 471 | 518.3 | $^1$H NMR (400 MHz, CDCl$_3$) δδ 10.67 (br s, 1H), 7.75-7.74 (m, 1H), 7.59-7.58 (m, 1H), 7.56-7.51 (m, 1H), 7.36-7.35 (m, 1H), 7.17 (s, 1H), 7.15-7.14 (m, 1H), 7.11-7.06 (m, 1H), 6.85-6.84 (m, 1H), 6.65-6.64 (m, 1H), 4.31 (d, J = 5.2 Hz, 2H), 3.92-3.90 (m, 1H), 3.88-3.81 (m, 1H), 3.42-3.39 (m, 1H), 3.25 (s, 3H), 3.19-3.12 (m, 1H), 3.11-3.08 (m, 1H), 2.65-2.63 (m, 1H), 1.18 (d, J = 6.4 Hz, 3H), 0.89 (d, J = 6.4 Hz, 3H) |
| 476 | 447.3 | $^1$H NMR (400 MHz, DMSO-d$_6$) δ 12.34 (s, 1H), 8.35-8.32 (m, 1H), 7.60-7.59 (m, 1H), 7.54 (s, 1H), 7.22-7.18 (m, 2H), 7.09-7.06 (m, 1H), 6.94 (d, J = 1.2 Hz, 1H), 6.56-6.55 (m, 1H), 6.39-6.34 (m, 1H), 4.10 (d, J = 6.0 Hz, 2H), 3.85-3.81 (m, 4H), 2.36-2.28 (m, 2H), 1.84-1.72 (m, 4H) |
| 500 | 516.1 | $^1$H NMR (400 MHz, DMSO-d$_6$) δ 12.35 (br s, 1H), 8.67-8.64 (m, 1H), 7.84-7.83 (m, 1H), 7.52 (s, 1H), 7.31-7.30 (m, 1H), 7.17-7.08 (m, 2H), 7.01 (s, 1H), 6.77-6.76 (m, 1H), 6.48-6.46 (m, 1H), 4.83 (d, J = 4.0 Hz, 1H), 4.15-4.12 (m, 3H), 3.72 (s, 1H), 3.57 (s, 3H), 3.39-3.35 (m, 1H), 2.53 (s, 1H), 2.41 (s, 1H), 1.93-1.83 (m, 2H) 1.60 (d, J = 8.8 Hz, 1H), 1.37 (d, J = 13.2 Hz, 1H) |
| 538 | 516.1 | $^1$H NMR (400 MHz, DMSO-d$_6$) δ 12.41 (s, 1H), 8.70-8.69 (m, 1H), 7.85-7.84 (m, 1H), 7.57 (s, 1H), 7.37-7.30 (m, 1H), 7.21 (d, J = 4.8 Hz, 2H), 6.96 (s, 1H), 6.78-6.77 (m, 1H), 4.73-4.71 (m, 2H), 4.35-4.32 (m, 2H), 4.13 (d, J = 5.6 Hz, 2H), 3.97-3.96 (m, 2H), 3.58 (s, 3H), 1.18-1.11 (m, 4H) |
| 542 | 510.3 | $^1$H NMR (400 MHz, DMSO-d$_6$) δ 12.37 (s, 1H), 8.65 (t, J = 5.9 Hz, 1H), 7.84 (t, J = 2.0 Hz, 1H), 7.56 (s, 1H), 7.31 (dd, J = 3.3, 2.3 Hz, 1H), 7.28-7.17 (m, 2H), 7.02-6.91 (m, 1H), 6.77 (dd, J = 3.3, 1.7 Hz, 1H), 6.43 (dt, J = 6.6, 2.3 Hz, 1H), 4.13 (d, J = 5.8 Hz, 2H), 3.97 (t, J = 8.0 Hz, 2H), 3.79 (dd, J = 7.6, 5.5 Hz, 2H), 3.57 (s, 3H), 3.40-3.08 (m, 2H) |
| 543 | 538.3 | $^1$H NMR (400 MHz, DMSO-d$_6$) δ 12.37 (s, 1H), 8.66 (t, J = 5.9 Hz, 1H), 7.84 (t, J = 2.0 Hz, 1H), 7.60 (s, 1H), 7.48 (t, J = 2.0 Hz, 1H), 7.33-7.28 (m, 2H), 7.25 (t, J = 7.8 Hz, 1H), 6.92 (ddd, J = 8.1, 2.7, 1.1 Hz, 1H), 6.77 (dd, J = 3.3, 1.7 Hz, 1H), 5.96 (td, J = 56.7, 4.5 Hz, 2H), 4.13 (d, J = 5.8 Hz, 2H), 3.86-3.76 (m, 2H), 3.57 (s, 3H), 2.73 (td, J = 12.4, 2.5 Hz, 2H), 2.10-1.90 (m, 1H), 1.79 (d, J = 12.3 Hz, 2H), 1.49 (qd, J = 12.4, 4.1 Hz, 2H) |
| 601 | 463.2 | $^1$H NMR (400 MHz, DMSO-d$_6$) δ 12.32 (s, 1H), 8.42-8.40 (m,, 1H), 7.76-7.75(m, 1H), 7.61 (s, 1H), 7.54 (s, 1H), 7.22-7.19 (m, 2H), 6.94-6.94 (m, 1H), 6.70-6.68 (m, 1H), 6.37-6.35 (m, 1H), 5.23 (d, J = 8.0 Hz, 2H), 5.05 (d, J = 8.4 Hz, 2H), 4.12 (d, J = 6.0 Hz, 2H), 3.84-3.81 (m, 4H), 2.35-2.28 (m, 2H) |
| 777 | 497.4 | $^1$H NMR (400 MHz, CDCl$_3$) δ 10.17-9.77 (m, 1H), 7.62-7.57 (m, 2H), 7.42 (d, J = 1.2 Hz, 1H), 7.31 (s, 1H), 7.15 (s, 1H), 6.91-6.87 (m, 2H), 4.39 (d, J = 6.0 Hz, 2H), 3.89-3.79 (m, 2H), 3.54 (d, J = 10.8 Hz, 2H), 2.50-2.45 (m, 2H), 1.64 (s, 9H), 1.30 (s, 3H), 1.29 (s, 3H) |
| 814 | 448.1 | $^1$H NMR (400 MHz, DMSO-d$_6$) δ 12.40 (s, 1H), 8.61-8.57 (m, 1H), 8.17 (d, J = 2.4 Hz, 1H), 7.56 (s, 1H), 7.23-7.17 (m, 2H), 6.95 (s, 1H), 6.75 (d, J = 2.4 Hz, 1H), 6.40-6.35 (m, 1H), 4.15-4.14 (m, 2H), 3.84-3.83 (m, 4H), 2.53-2.52 (m, 2H), 2.00-1.90 (m, 4H) |

TABLE 2a

| Compound # | LC-MS data(m/z) |
|---|---|
| 168 | 522.2 |
| 175 | 503.2 |
| 180 | 522.3 |

Example 141. Preparation of Compounds of the Invention

The compounds in Table 3 and Table 3a below were synthesized starting from the appropriate common intermediate ([tert-butyl N-[2-[[4-(3-bromophenyl)thiazol-2-yl] amino]-2-oxo-ethyl]carbamate]) and utilizing the synthetic protocol described in Example 10 including a chiral SEC separation following Scheme 2 below.

Scheme 2

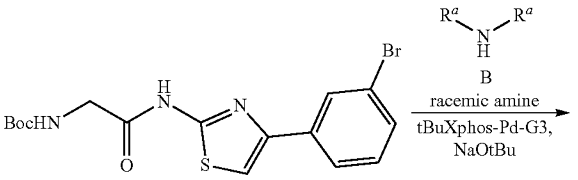

A

-continued

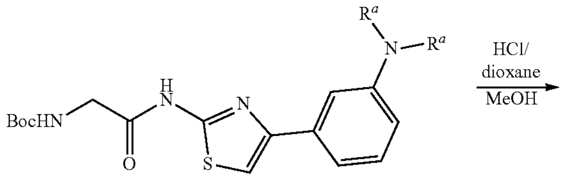

C

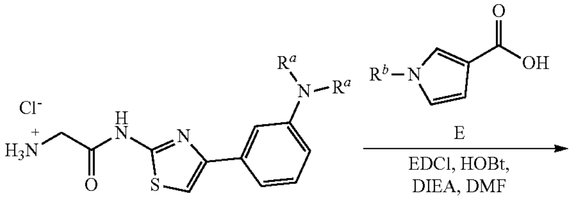

D

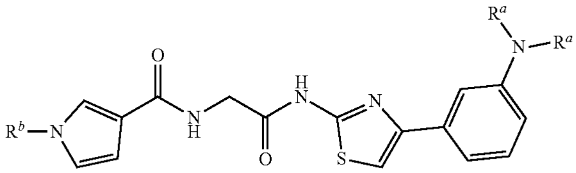

TABLE 3

| Compound # | LC-MS data(m/z) | $^1$H NMR |
|---|---|---|
| 164 | 532.2 | $^1$H NMR (400 MHz, Methanol-$d_4$) δ = 7.84-7.83(m, 1H), 7.51-7.50 (m, 1H), 7.33 (s, 1H), 7.28-7.27 (m, 2H), 7.24-7.20 (m, 1H), 6.89-6.87 (m, 1H), 6.81-6.80 (m, 1H), 4.25 (s, 2H), 3.58-3.55 (m, 1H), 3.39-3.36 (m, 4H), 3.27-3.24 (m, 1H), 2.86-2.85 (m, 1H), 2.58 (d, J = 12.4 Hz, 1H), 1.85-1.81 (m, 2H), 1.03 (d, J = 2.8 Hz, 6H) |
| 165 | 532.2 | $^1$H NMR (400 MHz, Methanol-$d_4$) δ = 7.84-7.83(m, 1H), 7.51-7.50 (m, 1H), 7.33 (s, 1H), 7.28-7.27 (m, 2H), 7.24-7.20 (m, 1H), 6.89-6.87 (m, 1H), 6.81-6.80 (m, 1H), 4.25 (s, 2H), 3.59-3.55 (m, 1H), 3.39-3.36 (m, 4H), 3.27-3.24 (m, 1H), 2.86-2.85 (m, 1H), 2.58 (d, J = 12.4 Hz, 1H), 1.86-1.81 (m, 2H), 1.03 (d, J = 2.8 Hz, 6H) |
| 188 | 518.3 | $^1$H NMR (400 MHz, DMSO-$d_6$) δ 12.58-12.09 (m, 1H), 8.68-8.68 (m, 1H), 7.88-7.82 (m, 1H), 7.59 (s, 1H), 7.46 (s, 1H), 7.32-7.31 (m, 1H), 7.29-7.20 (m, 2H), 6.95-6.86 (m, 1H), 6.79-6.78 (m, 1H), 4.66-4.35 (m, 1H), 4.14 (d, J = 6.0 Hz, 2H), 3.74-3.71 (m, 1H), 3.58 (s, 3H), 3.23-3.12 (m, 3H), 2.95-2.87 (m, 1H), 1.85-1.84 (m, 1H), 1.78-1.67 (m, 2H), 0.95 (d, J = 7.2 Hz, 3H) |
| 190 | 522.3 | $^1$H NMR (400 MHz, DMSO-$d_6$) δ 12.38 (br s, 1H), 8.70-8.67 (m, 1H), 7.84-7.83 (m, 1H), 7.64 (s, 1H), 7.49 (s, 1H), 7.32-7.30 (m, 2H), 7.27-7.25 (m, 1H), 6.95-6.93 (m, 1H), 6.78-6.77 (m, 1H), 5.31 (d, J = 4.8 Hz, 1H), 4.49-4.33 (m, 1H), 4.13 (d, J = 6.0 Hz, 2H), 3.85-3.76 (m, 1H), 3.68-3.62 (m, 1H), 3.57 (s, 3H), 3.53-2.51 (m, 1H), 2.98-2.85 (m, 2H), 1.98-1.92 (m, 1H), 1.60-1.50 (m, 1H) |
| 191 | 522.3 | $^1$H NMR (400 MHz, DMSO-$d_6$) δ 12.38 (br s, 1H), 8.70-8.68 (m, 1H), 7.84-7.83 (m, 1H), 7.62 (s, 1H), 7.47 (s, 1H), 7.32-7.29 (m, 2H), 7.26-7.22 (m, 1H), 6.92-6.89 (m, 1H), 6.77-6.76 (m, 1H), 5.10 (d, J = 4.4 Hz, 1H), 4.77-4.64 (m, 1H), 4.13 (d, J = 5.6 Hz, 2H), 3.83-3.76 (m, 1H), 3.72-3.66 (m, 1H), 3.56 (m, 3H), 3.49-3.45 (m, 1H), 3.23-3.13 (m, 1H), 3.01-2.96 (m, 1H), 1.87-1.79 (m, 1H), 1.76-1.71 (m, 1H) |
| 195 | 522.2 | $^1$H NMR (400 MHz, DMSO-$d_6$) δ 12.39 (s, 1H), 8.70-8.88 (m, 1H), 7.84-7.83 (m, 1H), 7.64 (s, 1H), 7.49 (s, 1H), 7.32-7.30 (m, 2H), 7.27-7.25 (m, 1H), 6.93-6.92 (m, 1H), 6.78-6.77 (m, 1H), 5.31 (d, J = 4.8 Hz, 1H), 4.47-4.33 (m, 1H), 4.13 (d, J = 6.0 Hz, 2H), 3.88-3.78 (m, 1H), 3.68-3.62 (m, 1H), 3.57 (s, 3H), 3.53-3.51 (m, 1H), 2.98-2.85 (m, 2H), 1.98-1.92 (m, 1H), 1.60-1.50 (m, 1H) |
| 196 | 522.2 | $^1$H NMR (400 MHz, DMSO-$d_6$) δ 12.45-12.34 (m, 1H), 8.69-8.68 (m, 1H), 7.84-7.83 (m, 1H), 7.64-7.61 (s, 1H), 7.47 (s, 1H), 7.32-7.28 (m, 2H), 7.25-7.22 (m, 1H), 6.92-6.89 (m, 1H), 6.77-6.76 (m, 1H), 5.10 (d, J = 4.8 Hz, 1H), 4.77-4.64 (m, 1H), 4.13 (d, J = 6.0 Hz, 2H), 3.84-3.76 (m, 1H), 3.72-3.57 (m, 1H), 3.50 (s, 3H), 3.49-3.45 (m, 1H), 3.23-3.13 (m, 1H), 3.01-2.96 (m, 1H), 1.87-1.79 (m, 1H), 1.75-1.71 (m, 1H) |

TABLE 3-continued

| Compound # | LC-MS data(m/z) | $^1$H NMR |
|---|---|---|
| 197 | 513.3 | $^1$H NMR (400 MHz, DMSO-$d_6$) δ 12.35 (br s, 1H), 8.67-8.64 (m, 1H), 7.84 (s, 1H), 7.63 (s, 1H), 7.49 (s, 1H), 7.35-7.31 (m, 1H), 7.30-7.27 (m, 2H), 6.95-6.93 (m, 1H), 6.78-6.77 (m, 1H), 4.14 (d, J = 6.0 Hz, 2H), 3.57 (s, 3H), 3.42-3.41 (m, 2H), 3.23-3.22 (m, 1H), 3.17-3.13 (m, 2H), 1.89-1.83 (m, 3H), 1.81-1.79 (m, 1H) |
| 205 | 518.2 | $^1$H NMR (400 MHz, Methanol-$d_4$) δ 8.24 (s, 1H), 7.84-7.83 (m, 1H), 7.54 (s, 1H), 7.34-7.32 (m, 2H), 7.27-7.24 (m, 2H), 6.95-6.93 (m, 1H), 6.81-6.80 (m, 1H), 4.25 (s, 2H), 3.37 (s, 3H), 3.29-3.26 (m, 1H), 3.15 (d, J = 12.0 Hz, 1H), 3.00-2.90 (m, 2H), 1.96-1.93 (m, 1H), 1.68-1.57 (m, 3H), 1.28 (s, 3H) |
| 206 | 518.2 | $^1$H NMR (400 MHz, Methanol-$d_4$) δ 8.29 (s, 1H), 7.84-7.83 (m, 1H), 7.54 (s, 1H), 7.33-7.32 (m, 2H), 7.27-7.24 (m, 2H), 6.95-6.93 (m, 1H), 6.81-6.80 (m, 1H), 4.25 (s, 2H), 3.37 (s, 3H), 3.29-3.26 (m, 1H), 3.15 (d, J = 12.0 Hz, 1H), 3.00-2.90 (m, 2H), 1.96-1.72 (m, 1H), 1.68-1.57 (m, 3H), 1.28 (s, 3H) |
| 208 | 506.1 | $^1$H NMR (400 MHz, DMSO-$d_6$) δ 12.38 (br s, 1H), 8.68 (s, 1H), 7.84 (s, 1H), 7.62 (s, 1H), 7.48 (s, 1H), 7.31 (s, 2H), 7.31-7.23 (m, 1H), 6.92 (d, J = 7.2 Hz, 1H), 6.77 (s, 1H), 4.87-4.75 (m, 1H), 4.14 (d, J = 4.8 Hz, 2H), 3.57 (s, 3H), 3.49-3.40 (m, 2H), 3.18 (s, 2H), 1.95-1.82 (m, 2H), 1.86-1.72 (m, 1H), 1.62-1.61 (m, 1H) |
| 211 | 513.2 | $^1$H NMR (400 MHz, DMSO-$d_6$) δ 12.39 (br s, 1H), 8.70-8.67 (m, 1H), 7.84 (s, 1H), 7.64 (s, 1H), 7.49 (s, 1H), 7.35-7.32 (m, 1H), 7.31-7.27 (m, 2H), 6.95-6.94 (m, 1H), 6.78-6.77 (m, 1H), 4.13 (d, J = 5.6 Hz, 2H), 3.57 (s, 3H), 3.42 (d, J = 5.2 Hz, 2H), 3.22-3.21 (m, 1H), 3.17-3.13 (m, 2H), 1.88-1.84 (m, 3H), 1.81-1.65 (m, 1H) |
| 213 | 506.0 | $^1$H NMR (400 MHz, DMSO-$d_6$ + $D_2O$) δ 7.80 (s, 1H), 7.53 (s, 1H), 7.43 (s, 1H), 7.29-7.24 (m, 3H), 6.89 (d, J = 6.4 Hz, 1H), 6.75 (s, 1H), 4.85-4.72 (m, 1H), 4.10 (s, 2H), 3.49 (s, 3H), 3.36 (d, J = 18.0 Hz, 2H), 3.21 (s, 1H), 3.09 (s, 1H), 1.90-1.74 (m, 3H), 1.59 (d, J = 11.2 Hz, 1H) |
| 219 | 518.3 | $^1$H NMR (400 MHz, DMSO-$d_6$) δ 12.36 (br s, 1H), 8.68-8.67 (m 1H), 7.86-7.85 (m, 1H), 7.59 (s, 1H), 7.46 (s, 1H), 7.35-7.30 (m, 1H), 7.29-7.18 (m, 2H), 6.90 (d, J = 8.0 Hz, 1H), 6.79-6.78 (m, 1H), 4.54 (d, J = 3.2 Hz, 1H), 4.14 (d, J = 6.0 Hz, 2H), 3.72 (d, J = 3.2 Hz, 1H), 3.58 (s, 3H), 3.24-3.11 (m, 3H), 2.91-2.90 (m, 1H), 1.85-1.84 (m, 1H), 1.77-1.63 (m, 2H), 0.95 (d, J = 7.2 Hz, 3H) |
| 236 | 518.3 | $^1$H NMR (400 MHz, DMSO-$d_6$) δ 12.36 (br s, 1H), 8.68-8.67 (m, 1H), 7.86-7.85 (m, 1H), 7.62 (s, 1H), 7.46 (s, 1H), 7.38-7.24 (m, 3H), 6.95-6.94 (m, 1H), 6.79-6.78 (m, 1H), 4.14 (d, J = 5.6 Hz, 2H), 3.99-3.98 (m, 1H), 3.68-3.53 (m, 6H), 3.47-3.46 (m, 1H), 2.75-2.67 (m, 1H), 2.45-2.37 (m, 1H), 1.60-1.47 (m, 2H), 0.97 (m, 3H) |
| 237 | 518.3 | $^1$H NMR (400 MHz, DMSO-$d_6$) δ 12.36 (br s, 1H), 8.68-8.67 (m, 1H), 7.85 (s, 1H), 7.62 (s, 1H), 7.46 (s, 1H), 7.38-7.24 (m, 3H), 6.95-6.94 (m, 1H), 6.79-6.78 (m, 1H), 4.14 (d, J = 5.6 Hz, 2H), 3.99-3.98 (m, 1H), 3.68-3.52 (m, 6H), 3.47-3.46 (m, 1H), 2.72-2.71 (m, 1H), 2.45-2.36 (m, 1H), 1.60-1.47 (m, 2H), 0.97 (m, 3H) |
| 552 | 539.0 | $^1$H NMR (400 MHz, DMSO-$d_6$) δ 8.68-8.65 (m, 1H), 8.21 (s, 1H), 7.84 (s, 1H), 7.66 (s, 1H), 7.49 (s, 1H), 7.37-7.33 (m, 1H), 7.32-7.30 (m, 1H), 7.29-7.24 (m, 1H), 6.95 (d, J = 6.4 Hz, 1H), 6.79-6.75 (m, 1H), 4.13 (d, J = 5.6 Hz, 2H), 3.90-3.80 (m, 1H), 3.65-3.53 (m, 5H), 3.22-3.16 (m, 1H), 3.05-2.99 (m, 1H), 1.96-1.86 (m, 1H), 1.62 (d, J = 12.0 Hz, 1H) |
| 558 | 539.0 | $^1$H NMR (400 MHz, DMSO-$d_6$) δ 12.94-11.86 (m, 1H), 8.70-8.61 (m, 1H), 8.14 (s, 1H), 7.83-7.82 (m, 1H), 7.64 (s, 1H), 7.46 (s, 1H), 7.36-7.19 (m, 3H), 6.93-6.92 (m, 1H), 6.75-6.74 (m, 1H), 4.11 (d, J = 6.0 Hz, 2H), 3.89-3.77 (m, 1H), 3.65-3.48 (m, 5H), 3.19-3.13 (m, 1H), 3.04-2.97 (m, 1H), 1.97-1.79 (m, 1H), 1.67-1.48 (m, 1H) |
| 582 | 521.4 | $^1$H NMR (400 MHz, DMSO-$d_6$) δ 12.34 (s, 1H), 8.43-8.41 (m, 1H), 7.76-7.75 (m, 1H), 7.61 (s, 1H), 7.44 (s, 1H), 7.32-7.30 (m, 1H), 7.28-7.26 (m, 1H), 7.23-7.21 (m, 1H), 6.93-6.92 (m, 1H), 6.69-6.68 (m, 1H), 5.23 (d, J = 8.0 Hz, 2H), 5.05 (d, J = 7.6 Hz, 2H), 4.13 (d, J = 6.0 Hz, 2H), 3.73-3.69 (m, 2H), 3.63 (d, J = 10.8 Hz, 2H), 2.31-2.25 (m, 2H), 1.18 (d, J = 6.0 Hz, 6H) |
| 423 | 518.1 | $^1$H NMR (400 MHz, DMSO-$d_6$) δ 12.38-12.31 (m, 1H), 8.68-8.65 (m, 1H), 8.33 (s, 1H), 7.84-7.83 (m, 1H), 7.59 (s, 1H), 7.44 (s, 1H), 7.31-7.30 (m, 1H), 7.28-7.20 (m, 2H), 6.90-6.88 (m, 1H), 6.77-6.76 (m, 1H), 4.65-4.62 (m, 1H), 4.13-4.12 (d, J = 6.0 Hz, 2H), 3.72-3.62 (m, 3H), 3.57 (s, 3H), 3.13-3.07 (m, 1H), 2.77-2.70 (m, 1H), 2.43-2.37 (m, 1H), 1.88-1.84 (m, 1H), 1.56-1.43 (m, 2H), 0.98-0.96 (d, J = 6.4 Hz, 3H) |

TABLE 3a
| Compound # | LC-MS data(m/z) |
|---|---|
| 585 | 524.3 |
| 586 | 524.3 |
Example 142. Preparation of N-[2-[[4-[3-[(3S,4S)-4-hydroxy-3-methyl-1-piperidyl]phenyl]thiazol-2-yl]amino]-2-oxo-ethyl]-1-methylsulfonyl-pyrrole-3-carboxamide (Compound 183) and N-[2-[[4-[3-[(3R,4R)-4-hydroxy-3-methyl-1-piperidyl]phenyl]thiazol-2-yl]amino]-2-oxo-ethyl]-1-methylsulfonyl-pyrrole-3-carboxamide (Compound 182)
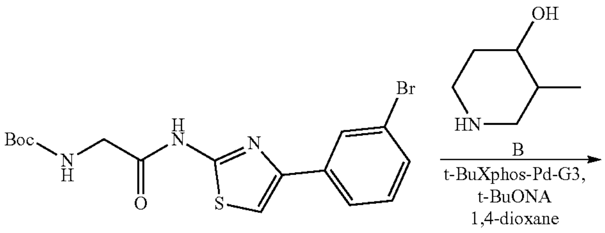
A
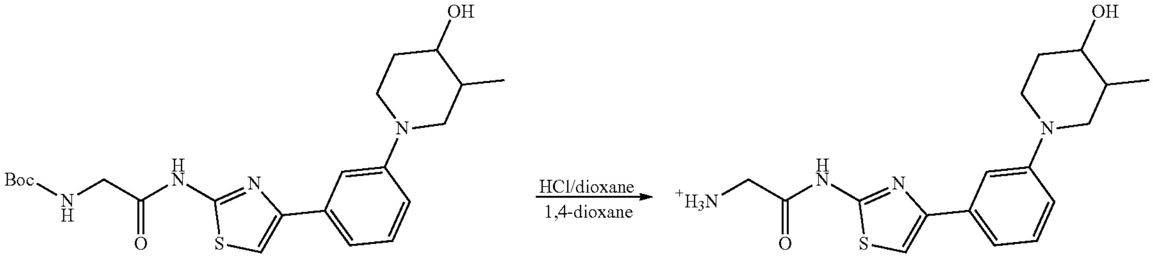
C D
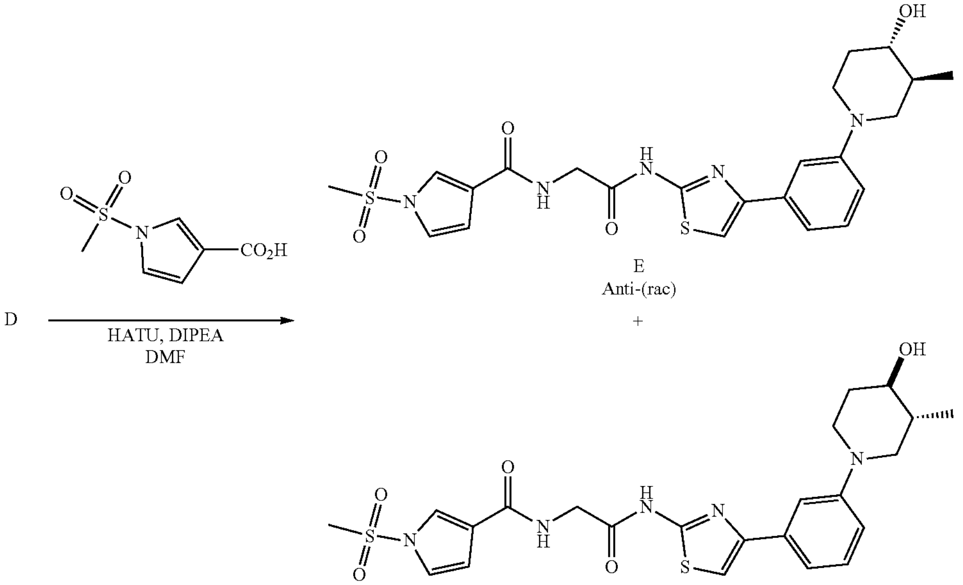
E
Anti-(rac)
+
F
Syn-(rac)
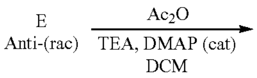

-continued

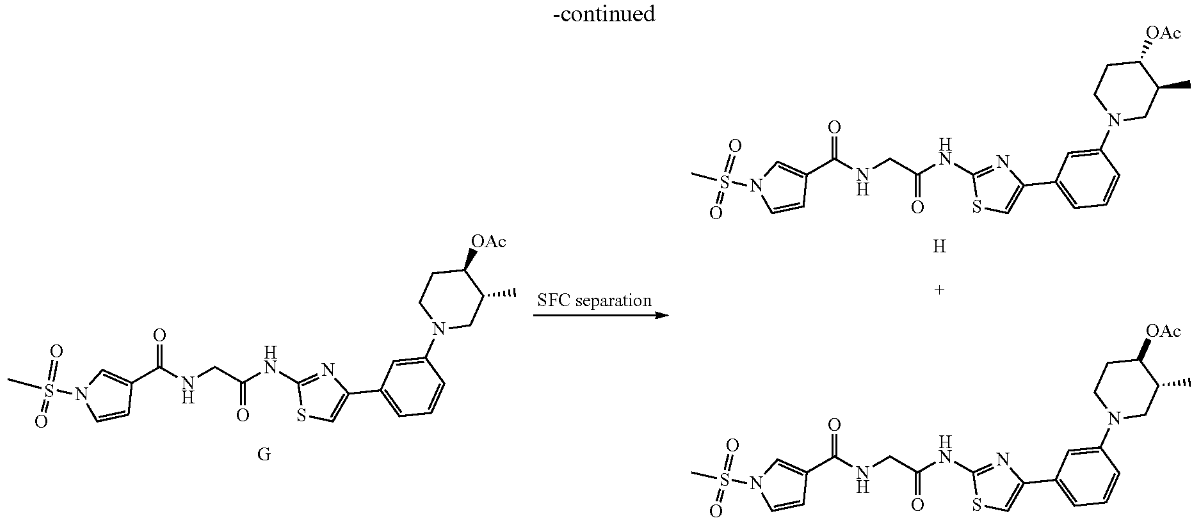

G

H

+

I

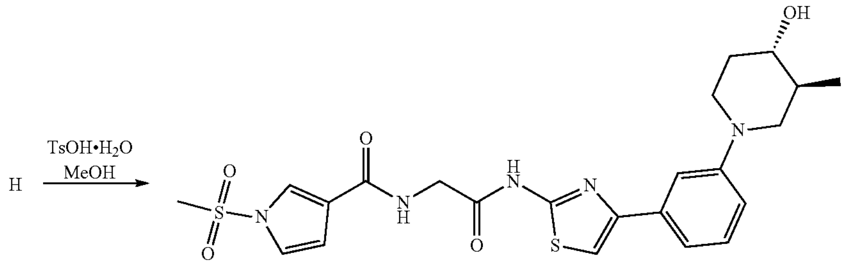

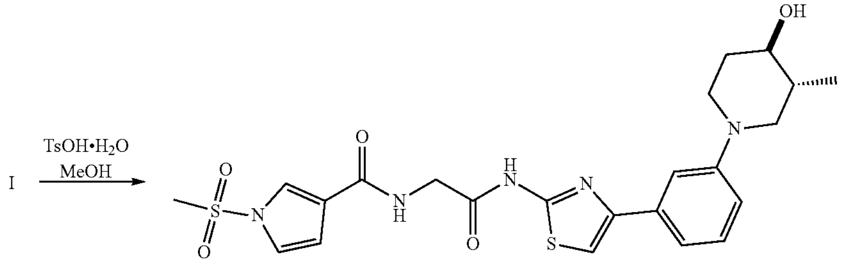

Step 1: Preparation of tert-butyl N-[2-[[4-[3-(4-hydroxy-3-methyl-1-piperidyl)phenyl]thiazol-2-yl]amino]-2-oxo-ethyl]carbamate (Intermediate C)

C

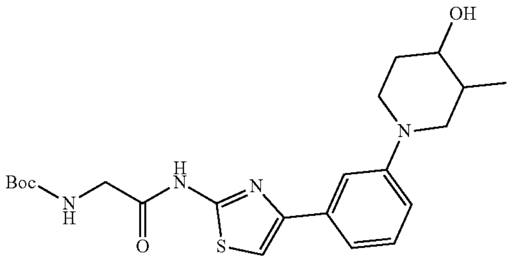

To a solution of tert-butyl N-[2-[[4-(3-bromophenyl)thiazol-2-yl]amino]-2-oxo-ethyl]carbamate (1.20 g, 2.91 mmol) in 1,4-dioxane (12 mL) was added 3-methylpiperidin-4-ol hydrochloride salt (1.32 g, 8.73 mmol) and t-BuONa (1.96 g, 20.37 mmol). After stirring for 10 min t-BuXphos-Pd (gen 3) (0.231 g, 0.291 mmol) was added to the mixture and the mixture was heated to 60° C. for 1 h. The reaction mixture was cooled to room temperature, diluted with water (30 mL) and extracted with ethyl acetate (20 mL×3). The combined organic layers were dried over anhydrous $Na_2SO_4$, filtered and concentrated in vacuo. The residue was purified by flash silica gel chromatography petroleum ether/ethyl acetate 1:0 to 7:1) to give Intermediate C (0.600 g, 1.21 mmol, 41.55% yield, 90% purity) as a yellow solid. LCMS (ESI) m/z: $[M+H]^+$=447.1; $^1H$ NMR (400 MHz, $CDCl_3$) δ 10.19-9.81 (m, 1H), 7.45-7.38 (m, 1H), 7.32-7.28 (m, 1H), 7.26-7.22 (m, 1H), 7.15-7.11 (m, 1H), 6.95-6.88 (m, 1H), 5.20-5.02 (m, 1H), 4.04-3.89 (m, 3H), 3.79-3.61 (m, 1H), 3.40-3.15 (m, 2H), 3.02-2.80 (m, 1H), 2.54-2.45 (m, 1H), 1.84 (s, 2H), 1.63-1.55 (m, 2H), 1.52-1.46 (m, 9H), 1.13-1.00 (m, 3H).

Step 2: Preparation of 2-amino-N-[4-[3-(4-hydroxy-3-methyl-1-piperidyl)phenyl]thiazol-2-yl]acetamide (Intermediate D)

D

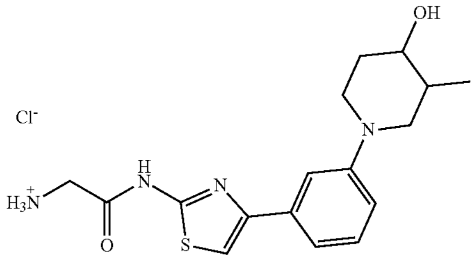

To a cooled (10° C.) solution of Intermediate C (0.660 g, 1.48 mmol) in 1,4-dioxane (2 mL) was added a solution of 4 M HCl in 1,4-dioxane (6 mL). The mixture was warmed to room temperature and stirred. After 1 h, the mixture was concentrated in vacuo to give Intermediate D (0.700 g) as a yellow solid. LCMS (ESI) m/z: $[M+H]^+=347.1$.

Step 3: Preparation of N-(2-((4-(3-((3R,4R)-4-hydroxy-3-methylpiperidin-1-yl)phenyl)thiazol-2-yl)amino)-2-oxoethyl)-1-(methylsulfonyl)-1H-pyrrole-3-carboxamide and N-(2-((4-(3-((3S,4R)-4-hydroxy-3-methylpiperidin-1-yl)phenyl)thiazol-2-yl)amino)-2-oxoethyl)-1-(methylsulfonyl)-1H-pyrrole-3-carboxamide (Intermediate E and F)

E

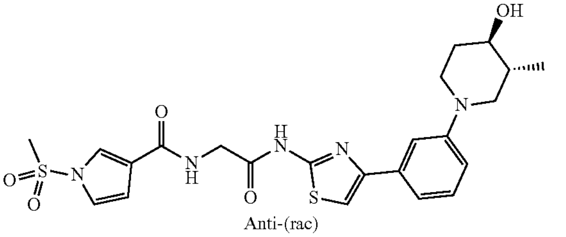

Anti-(rac)

+

F

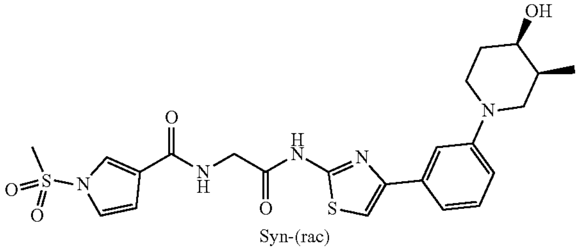

Syn-(rac)

To a cooled solution (10° C.) of Intermediate D (0.700 g, 1.83 mmol), 1-methylsulfonylpyrrole-3-carboxylic acid (0.346 g, 1.83 mmol), EDCI (0.526 g, 2.74 mmol) and HOBt (0.371 g, 2.74 mmol) in DMF (7 mL) was added DIPEA (0.955 mL, 5.48 mmol). The mixture was stirred at 20° C. for 16 h and subsequently diluted with water (20 mL). The resulting mixture was extracted with ethyl acetate (20 mL×3). The combined organic layers were dried over anhydrous $Na_2SO_4$, filtered and concentrated in vacuo. The resultant solids were purified by Prep-HPLC (mobile phase: [water (0.225% FA)-acetonitrile]; B %: 10%-40%) and lyophilized to give racemic anti-isomer Intermediate E (0.190 g, 0.337 mmol, 18.44% yield, 100% purity) as a white solid and racemic syn-isomer Intermediate F (0.130 g, 0.231 mmol, 12.62% yield, 100% purity) as a white solid.

Step 4: Preparation of anti-rac-3-methyl-1-(3-(2-(2-(1-(methylsulfonyl)-1H-pyrrole-3-carboxamido)acetamido)thiazol-4-yl)phenyl)piperidin-4-yl acetate (Intermediate G)

G

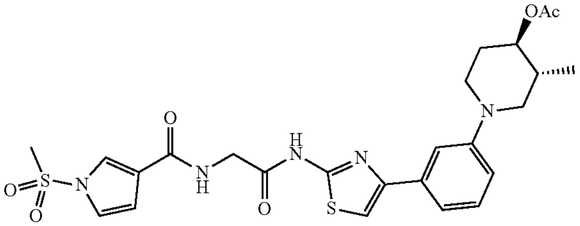

To a solution of racemic anti-isomer Intermediate E (0.100 g, 0.193 mmol) in dichloromethane (1 mL) was added acetic anhydride (0.077 mL, 0.773 mmol), DMAP (0.047 g, 0.386 mmol) and triethylamine (0.054 mL, 0.386 mmol). After 2 h, the reaction mixture was diluted with water (2 mL) and extracted with dichloromethane (2 mL×2), the combined organic layers were concentrated to afford a yellow oil. The oil was dissolved with dichloromethane and purified by flash silica gel chromatography (petroleum ether/ethyl acetate=1:0 to 2:5) and concentrated to give Intermediate G (0.065 g, 0.107 mmol, 55.47% yield, 92.3% purity) as a yellow solid. LCMS (ESI) m/z: $[M+H]^+=560.1$; $^1H$ NMR (400 MHz, DMSO-$d_6$) δ 12.36 (s, 1H), 8.67-8.64 (m, 1H), 7.85-7.84 (m, 1H), 7.61 (s, 1H), 7.47 (s, 1H), 7.32-7.30 (m, 2H), 7.29-7.25 (m, 1H), 6.94-6.92 (m, 1H), 6.78-6.77 (m, 1H), 4.54-4.52 (m, 1H), 4.14 (d, J=6.0 Hz, 2H), 3.75-3.70 (m, 2H), 3.57 (s, 3H), 2.89-2.86 (m, 1H), 2.56 (s, 1H), 2.05 (s, 3H), 2.03-2.01 (m, 1H), 1.99-1.87 (m, 1H), 1.66-1.62 (m, 1H), 0.94 (d, J=6.4 Hz, 3H).

Step 5: Preparation of [(3S,4S)-3-methyl-1-[3-[2-[[2-[(1-methylsulfonylpyrrole-3-carbonyl)amino]acetyl]amino]thiazol-4-yl]phenyl]-4-piperidyl]acetate and [(3R,4R)-3-methyl-1-[3-[2-[[2-[(1-methylsulfonylpyrrole-3-carbonyl)amino]acetyl]amino]thiazol-4-yl]phenyl]-4-piperidyl]acetate (Intermediate H and I)

H

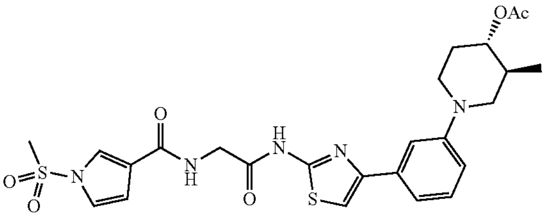

+

-continued

I

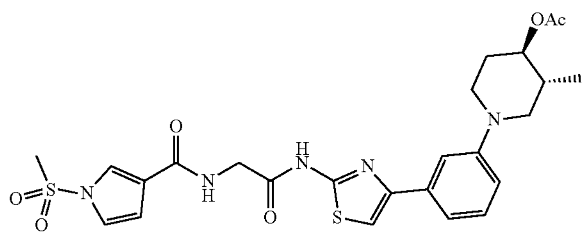

Intermediate G (64.87 mg, 115.92 umol) was separated by chiral SFC. It was concentrated to give Intermediate H (15 mg, 24.45 umol, 21.09% yield, 91.2% purity) as a brown solid and Intermediate 1 (10 mg, 17.42 umol, 15.0% yield, 97.5% purity) as a brown solid.

Intermediate H: LCMS (ESI) m/z: $[M+H]^+$=560.1; $^1H$ NMR (400 MHz, DMSO-$d_6$) δ 12.36 (br s, 1H), 8.67-8.64 (m, 1H), 7.84 (s, 1H), 7.60 (s, 1H), 7.47 (s, 1H), 7.31-7.30 (m, 2H), 7.26-7.24 (m, 1H), 6.93 (d, J=7.2 Hz, 1H), 6.77 (d, J=1.2 Hz, 1H), 4.53-4.51 (m, 1H), 4.14 (d, J=6.0 Hz, 2H), 3.74-3.69 (m, 2H), 3.56 (s, 3H), 2.88-2.82 (m, 1H), 2.57-2.50 (m, 1H), 2.06-2.04 (m, 3H), 2.01-1.96 (m, 1H), 1.85-1.80 (m, 1H), 1.61-1.60 (m, 1H), 0.93 (d, J=6.8 Hz, 3H); ee %=100%.

Intermediate I: LCMS (ESI) m/z: $[M+H]^+$=560.1.; $^1H$ NMR (400 MHz, DMSO-$d_6$) δ 12.35 (br s, 1H), 8.67-8.64 (m, 1H), 7.84-7.80 (m, 1H), 7.60 (s, 1H), 7.46 (s, 1H), 7.31-7.29 (m, 2H), 7.26-7.24 (m, 1H), 6.90 (d, J=8.0 Hz, 1H), 6.77-6.76 (m, 1H), 4.52-4.51 (m, 1H), 4.13 (d, J=5.2 Hz, 2H), 3.73 (d, J=11.2 Hz, 2H), 3.56 (s, 3H), 2.85-2.82 (m, 1H), 2.60 (s, 1H), 2.04 (s, 3H), 1.99-1.97 (m, 1H), 1.86-1.82 (m, 1H), 1.60-1.57 (m, 1H), 0.93 (d, J=6.4 Hz, 3H); ee %=98.16%.

Step 6: Preparation of N-[2-[[4-[3-[(3S,4S)-4-hydroxy-3-methyl-1-piperidyl]phenyl]thiazol-2-yl]amino]-2-oxo-ethyl]-1-methylsulfonyl-pyrrole-3-carboxamide (Compound 183)

Compound 183

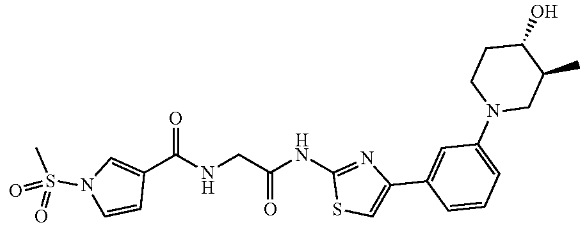

To a solution of Intermediate H (0.015 g, 0.027 mmol) in MeOH (0.2 mL) was added TsOH·$H_2O$ (0.015 g, 0.080 mmol). The reaction mixture was stirred at 40° C. for 16 h. The reaction mixture was subsequently diluted with water (5 mL) and extracted with ethyl acetate (3 mL×3). The combined organic layers were concentrated to afford a yellow residue. The residue was purified by prep-HPLC (mobile phase: [water (0.225% FA)-acetonitrile]; B %: 9%-39%). The appropriate fractions were lyophilized to give Compound 183 (0.001 g, 0.003 mmol, 9.88% yield, 100% purity) as an off-white solid. LCMS (ESI) m/z: $[M+H]^+$=518.4; $^1H$ NMR (400 MHz, Methanol-$d_4$) δ 7.84-7.83 (m, 1H), 7.56-7.55 (m, 1H), 7.35-7.32 (m, 2H), 7.28-7.24 (m, 2H), 6.95-6.92 (m, 1H), 6.81-6.80 (m, 1H), 4.25 (s, 2H), 3.75-3.72 (m, 1H), 3.67-3.63 (m, 1H), 3.37 (s, 3H), 3.31-3.19 (m, 1H), 2.81-2.80 (m, 1H), 2.48-2.42 (m, 1H), 2.01-1.97 (m, 1H), 1.72-1.62 (m, 2H), 1.07 (d, J=6.8 Hz, 3H); ee %=98.61%.

Step 7: Preparation of N-[2-[[4-[3-[(3R,4R)-4-hydroxy-3-methyl-1-piperidyl]phenyl]thiazol-2-yl]amino]-2-oxo-ethyl]-1-methylsulfonyl-pyrrole-3-carboxamide (Compound 182)

Compound 182

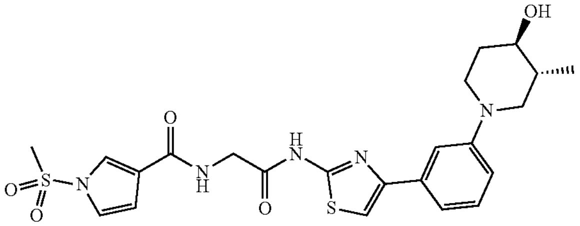

Compound 182 was synthesized using a similar procedure outlined above. The following quantities of reagents were used: Intermediate I (0.010 g, 0.018 mmol), MeOH (0.2 mL), and TsOH·$H_2O$ (0.010 g, 0.054 mmol). Compound 182 (1.17 mg, 2.26 umol, 12.65% yield, 100% purity) was isolated as an off-white solid. LCMS (ESI) m/z: $[M+H]^+$=518.4; $^1H$ NMR (400 MHz, Methanol-$d_4$) δ 7.84-7.83 (m, 1H), 7.55-7.54 (m, 1H), 7.35-7.32 (m, 2H), 7.28-7.24 (m, 2H), 6.95-6.93 (m, 1H), 6.81-6.80 (m, 1H), 4.25 (s, 2H), 3.75-3.72 (m, 1H), 3.68-6.64 (m, 1H), 3.37 (s, 3H), 3.23-3.22 (m, 1H), 2.81-2.80 (m, 1H), 2.48-2.42 (m, 1H), 2.01-1.97 (m, 1H), 1.70-1.65 (m, 2H), 1.07 (d, J=6.4 Hz, 3H); ee %=98.14%.

Example 143. Preparation of 1-(1-hydroxy-2-methylpropan-2-yl)-1H-pyrazole-3-carboxylic acid

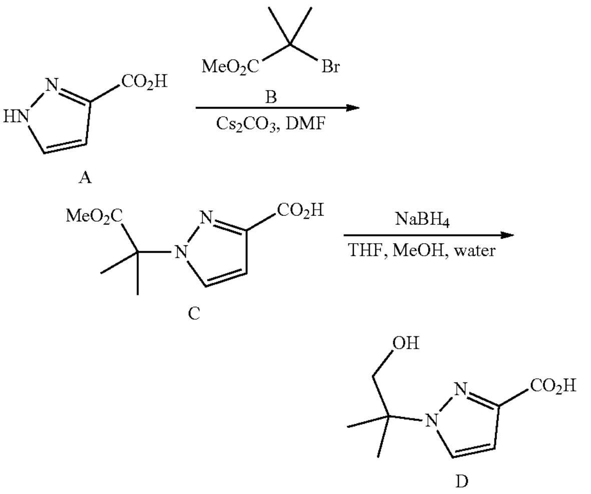

Step 1: Preparation of 1-(2-methoxy-1,1-dimethyl-2-oxo-ethyl)pyrazole-3-carboxylic acid (Intermediate C)

C

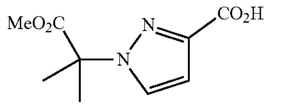

To a solution of methyl 2-bromo-2-methyl-propanoate (5.77 mL, 44.61 mmol) and 1H-pyrazole-3-carboxylic acid (5.00 g, 44.61 mmol) in DMF (50 mL) was added $Cs_2CO_3$ (29.07 g, 89.22 mmol). The mixture was stirred at 60° C. for 1 h. The mixture was diluted with water (100 mL) and extracted with EtOAc (100 mL). The aqueous phase was acidified to pH ~3-4 with 4 M aqueous HCl solution and subsequently extracted with dichloromethane (100 mL×2). The organic layer was concentrated under vacuum. The resulting oil was purified by reversed-phase prep HPLC (mobile phase: [water (0.225% FA)-ACN]; B %: 5%-35%) and lyophilized to give Intermediate C (2.30 g, 9.32 mmol, 20.90% yield, 86.0% purity) as a yellow oil. LCMS (ESI) m/z: $[M+H]^+$=213.1; $^1H$ NMR (400 MHz, DMSO-$d_6$) δ 12.69 (s, 1H), 8.02 (d, J=2.4 Hz, 1H), 6.73 (d, J=2.4 Hz, 1H), 5.75 (s, 1H), 3.64 (s, 3H), 1.80 (s, 6H).

Step 2: Preparation of 1-(1-hydroxy-2-methylpropan-2-yl)-1H-pyrazole-3-carboxylic acid (Intermediate D)

D

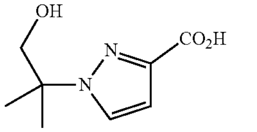

To a solution of Intermediate C (0.200 g, 0.943 mmol) in a mixture of THF (1.2 mL), MeOH (0.4 mL), and water (0.4 mL) was added $NaBH_4$ (0.071 g, 1.88 mmol). After stirring for 1 h, the mixture was quenched with saturated aqueous $NH_4Cl$ (10 mL) and concentrated. The crude product was purified by reverse-phase HPLC (0.1% FA) and concentrated to give Intermediate D (0.060 g, 0.313 mmol, 33.18% yield, 96.0% purity) as a yellow gum. LCMS (ESI) m/z: $[M+H]^+$=185.1.

Example 144. Preparation of 1-methyl-4,5,6,7-tetrahydropyrazolo[4,3-c]pyridine and 2-methyl-4,5,6,7-tetrahydro-2H-pyrazolo[4,3-c]pyridine

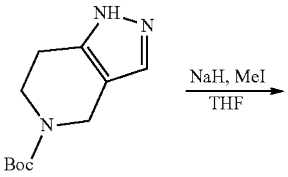

A

-continued

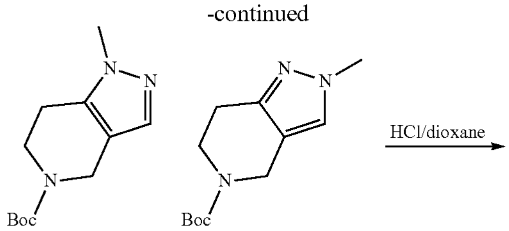

B B'

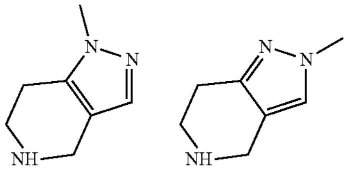

C C'

1-methyl-4,5,6,7-tetrahydropyrazolo[4,3-c]pyridine and 2-methyl-4,5,6,7-tetrahydro-2H-pyrazolo[4,3-c]pyridine were prepared according to the method described in WO2015200677 A2. 1-methyl-4,5,6,7-tetrahydropyrazolo[4,3-c]pyridine and 2-methyl-4,5,6,7-tetrahydro-2H-pyrazolo[4,3-c]pyridine were isolated as an inseparable mixture (405 mg, crude, HCl) as a yellow solid which was used without further purification. LCMS (ESI) m/z: $[M+H]^+$=138.0.

Example 145. Preparation of Compounds of the Invention

The compounds in Table 4 below were synthesized starting from the appropriate starting carboxylic acid, protected (chiral or achiral) amino acid, amine, and heterocyclic carboxylic acid according to Scheme 3 below and following protocol established in Example 10.

Scheme 3

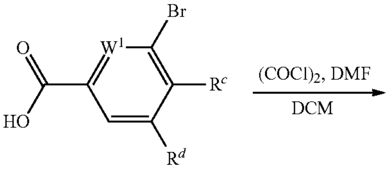

A $W^1$ = N or CN

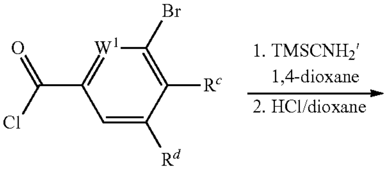

B

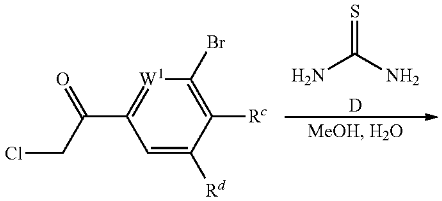

C

-continued

-continued

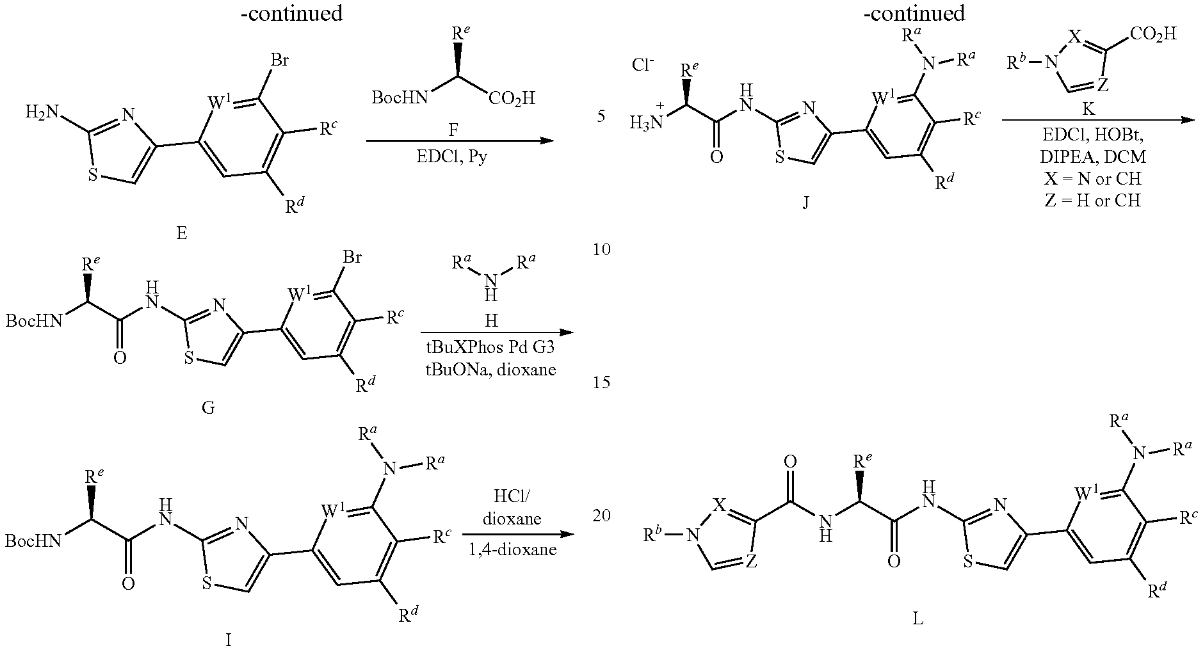

TABLE 4

| Compound # | LC-MS data(m/z) | $^1$H NMR |
|---|---|---|
| 166 | 483.5 | $^1$H NMR (400 MHz, Methanol-d$_4$) δ 7.71-7.64 (m, 1H), 7.63-7.52 (m, 2H), 7.37-7.30 (m, 1H), 7.00-6.91 (m, 1H), 6.71-6.64 (m, 1H), 6.61-6.55 (m, 1H), 4.51-4.40 (m, 1H), 4.24 (s, 2H), 4.08-3.93 (m, 2H), 3.87-3.72 (m, 2H), 3.69-3.58 (m, 1H), 3.28-3.16 (m, 1H), 1.58 (s, 9H), 1.27-1.21 (m, 3H) |
| 240 | 532.3 | $^1$HNMR (400 MHz, DMSO-d$_6$) δ 12.40 (m, 1H), 8.49-8.45 (m, 1H), 7.94-7.93 (m, 1H), 7.60 (s, 1H), 7.45 (s, 1H), 7.34-7.26 (m, 3H), 6.93-6.91 (m, 1H), 6.78-6.77 (m, 1H), 4.68-4.61 (m, 1H), 3.73-3.69 (m, 2H), 3.63-3.60 (m, 2H), 3.56 (s, 3H), 2.32-2.25 (m, 2H), 1.41 (d, J = 7.2 Hz, 3H), 1.17 (d, J = 6.0 Hz, 6H) |
| 364 | 474.2 | $^1$H NMR (400 MHz, DMSO-d$_6$) δ 12.36 (br s, 1H), 8.47 (d, J = 6.8 Hz, 1H), 7.94-7.93 (m, 1H), 7.54 (s, 1H), 7.29-7.28 (m, 1H), 7.20-7.19 (m, 2H), 6.94 (d, J = 1.2 Hz, 1H), 6.78-6.77 (m, 1H), 6.38-6.36 (m, 1H), 4.67-4.60 (m, 1H), 3.84-3.81 (m, 4H), 3.55 (s, 3H), 2.35-2.28 (m, 2H), 1.42 (d, J = 7.2 Hz, 3H) |
| 365 | 490.2 | $^1$H NMR (400 MHz, DMSO-d$_6$) δ 12.35 (br s, 1H), 8.47 (d, J = 6.4 Hz, 1H), 7.94 (s, 1H), 7.55 (s, 1H), 7.29-7.28 (m, 1H), 7.20 (d, J = 4.4 Hz, 2H), 6.96 (s, 1H), 6.78 (d, J = 1.6 Hz, 1H), 6.40-6.37 (m, 1H), 5.60 (s, 1H), 4.67-4.62 (m, 1H), 4.58-4.57 (m, 1H), 4.11-4.08 (m, 2H), 3.55 (s, 3H), 3.54-3.51 (m, 2H), 1.42 (d, J = 7.2 Hz, 3H) |
| 366 | 504.1 | $^1$H NMR (400 MHz, DMSO-d$_6$) δ 12.50-12.48 (m, 1H), 8.47 (d, J = 7.2 Hz, 1H), 7.98-7.97 (m, 1H), 7.55 (s, 1H), 7.29-7.28 (m, 1H), 7.20 (d, J = 4.8 Hz, 2H), 6.94 (s, 1H), 6.79-6.78 (m, 1H), 6.38-6.35 (m, 1H), 4.94-4.89 (m, 1H), 3.85-3.81 (m, 4H), 3.72-3.69 (m, 2H), 3.56 (s, 3H), 2.33-2.30 (m, 2H) |
| 367 | 534.3 | $^1$H NMR (400 MHz, DMSO-d$_6$) δ 12.49 (s, 1H), 8.48 (d, J = 7.2 Hz, 1H), 7.98-7.97 (m, 1H), 7.56 (s, 1H), 7.29-7.28 (m, 1H), 7.22-7.18 (m, 2H), 6.97 (d, J = 0.8 Hz, 1H), 6.79-6.78 (m, 1H), 6.41-6.39 (m, 1H), 4.94-4.89 (m, 1H), 4.36-4.30 (m, 1H), 4.09-4.06 (m, 2H), 3.75-3.67 (m, 2H), 3.63-3.60 (m, 2H), 3.56 (s, 3H), 3.25 (s, 3H) |
| 369 | 548.2 | $^1$H NMR (400 MHz, DMSO-d$_6$) δ 12.46 (br s, 1H), 8.48 (d, J = 7.6 Hz, 1H), 7.98 (s, 1H), 7.60 (s, 1H), 7.47 (s, 1H), 7.29-7.21 (m, 3H), 6.90 (d, J = 8.0 Hz, 1H), 6.79 (d, J = 1.2 Hz, 1H), 4.95-4.90 (m, 1H), 4.67 (d, J = 3.6 Hz, 1H), 3.75-3.68 (m, 2H), 3.67-3.59 (m, 2H), 3.56 (s, 4H), 3.31-3.29 (m, 3H), 2.90-2.85 (m, 2H), 1.85-1.82 (m, 2H), 1.53-1.44 (m, 2H) |
| 370 | 517.9 | $^1$H NMR (400 MHz, DMSO-d$_6$) δ 12.62-12.01 (m, 1H), 8.47 (d, J = 6.8 Hz, 1H), 7.94-7.93 (m, 1H), 7.59 (s, 1H), 7.46 (s, 1H), 7.30-7.20 (m, 3H), 6.90-6.88 (m, 1H), 6.78-6.77 (m, 1H), 4.67-4.60 (m, 2H), 3.65-3.55 (m, 6H), 2.91-2.84 (m, 2H), 1.85-1.81 (m, 2H), 1.52-1.45 (m, 2H), 1.42 (d, J = 7.2 Hz, 3H) |
| 371 | 562.1 | $^1$H NMR (400 MHz, DMSO-d$_6$) δ 8.51 (d, J = 7.2 Hz, 1H), 8.01-7.97 (m, 1H), 7.63 (s, 1H), 7.46 (s, 1H), 7.35-7.25 (m, 3H), 6.95-6.92 (m, 1H), 6.80-6.79 (m, 1H), 4.95-4.90 (m, 1H), 3.75-3.69 (m, 4H), 3.63 (d, J = 10.4 Hz, 2H), 3.57 (s, 3H), 3.31 (s, 3H), 2.29-2.26 (m, 2H), 1.18 (s, 3H), 1.17 (s, 3H) |

TABLE 4-continued

| Compound # | LC-MS data(m/z) | $^1$H NMR |
|---|---|---|
| 372 | 548.1 | $^1$H NMR (400 MHz, Methanol-$d_4$) δ 7.92-7.91 (m, 1H), 7.57-7.53 (m, 1H), 7.39-7.37 (m, 2H), 7.28-7.27 (m, 2H), 6.93-6.88 (m, 1H), 6.85-6.84 (m, 1H), 4.98-4.95 (m, 1H), 4.01-3.99 (m, 1H), 3.91-3.79 (m, 4H), 3.64-3.49 (m, 2H), 3.46 (s, 3H), 3.39 (s, 3H), 2.79-2.76 (m, 1H), 2.45-2.43(m, 1H), 1.25 (d, J = 6.4 Hz, 3H) |
| 373 | 548.1 | $^1$H NMR (400 MHz, DMSO-$d_6$) δ 12.71-12.28 (m, 1H), 8.48 (d, J = 7.2 Hz, 1H), 7.99-7.98 (m, 1H), 7.62 (s, 1H), 7.46 (s, 1H), 7.39-7.32 (m, 1H), 7.32-7.22 (m, 2H), 6.92-6.91(m, 1H), 6.80-6.78 (m, 1H), 4.95-4.90 (m, 1H), 3.95-3.92 (m, 1H), 3.77-3.59 (m, 5H), 3.56 (s, 3H), 3.54-3.48 (m, 1H), 3.31 (s, 3H), 2.70-2.65 (m, 1H), 2.39-2.31 (m, 1H), 1.17 (d, J = 6.0 Hz, 3H) |
| 380 | 598.2 | $^1$H NMR (400 MHz, DMSO-$d_6$) δ 12.57 (s, 1H), 8.53 (d, J = 7.2 Hz, 1H), 8.03-7.92 (m, 1H), 7.77 (s, 1H), 7.53 (d, J = 5.6 Hz, 1H), 7.38 (d, J = 7.3 Hz, 1H), 7.30 (d, J = 1.2 Hz, 1H), 6.79 (d, 3.2 Hz, 1H), 4.99-4.86 (m, 1H), 3.84-3.66 (m, 4H), 3.58 (s, 3H), 3.31 (s, 3H), 2.45 (d, J = 10.8 Hz, 4H), 1.15 (d, J = 6.4 Hz, 6H) |
| 384 | 554.1 | $^1$H NMR (400 MHz, DMSO-$d_6$) δ 12.41 (s, 1H), 8.67 (d, J = 5.6 Hz, 1H), 7.85 (d, J = 2.0 Hz, 1H), 7.75 (s, 1H), 7.57-7.46 (m, 1H), 7.40-7.26 (m, 2H), 6.78 (d, J = 3.2 Hz, 1H), 4.14 (d, J = 6.0 Hz, 2H), 3.77 (d, J = 6.4 Hz, 2H), 3.58 (s, 3H), 2.48-2.41 (m, 4H), 1.16 (d, J = 6.4 Hz, 6H) |
| 385 | 505.5 | $^1$H NMR (400 MHz, DMSO-$d_6$) δ 12.35 (br s, 1H), 8.67-8.66 (m, 1H), 7.84-7.84 (m, 1H), 7.70 (s, 1H), 7.70-7.62 (m, 1H), 7.31-7.30(m, 1H), 7.25 (d, J = 7.2 Hz, 1H), 6.77-6.77 (m, 1H), 6.73 (d, J = 8.4 Hz, 1H), 4.48-4.39(m, 1H), 4.13 (d, J = 5.6 Hz, 2H), 3.98-3.94 (m, 2H), 3.75-3.72 (m, 1H), 3.66-3.66 (m, 1H), 3.56 (s, 3H), 3.56-3.50 (m, 1H), 3.08-3.07 (m, 1H), 1.15 (d, J = 6.8 Hz, 3H) |
| 767 | 533.4 | $^1$H NMR (400 MHz, DMSO-$d_6$) δ 12.34 (s, 1H), 8.47 (d, J = 6.6 Hz, 1H), 7.94 (t, J = 2.0 Hz, 1H), 7.77 (s, 1H), 7.62 (dd, J = 8.5, 7.3 Hz, 1H), 7.29 (dd, J = 3.3, 2.3 Hz, 1H), 7.26 (d, J = 7.3 Hz, 1H), 6.82-6.76 (m, 2H), 4.64 (p, J = 7.0 Hz, 1H), 4.25 (dd, J = 13.0, 2.4 Hz, 2H), 3.69-3.58 (m, 2H), 3.56 (s, 3H), 2.42 (dd, J = 12.8, 10.5 Hz, 2H), 1.42 (d, J = 7.2 Hz, 3H), 1.18 (d, J = 6.2 Hz, 6H). |
| 768 | 533.4 | $^1$H NMR (400 MHz, DMSO-$d_6$) δ 12.34 (s, 1H), 8.47 (d, J = 6.6 Hz, 1H), 7.94 (t, J = 2.0 Hz, 1H), 7.77 (s, 1H), 7.62 (dd, J = 8.5, 7.4 Hz, 1H), 7.29 (dd, J = 3.3, 2.3 Hz, 1H), 7.26 (d, J = 7.3 Hz, 1H), 6.82-6.74 (m, 2H), 4.64 (p, J = 7.1 Hz, 1H), 4.25 (dd, J = 12.8, 2.4 Hz, 2H), 3.63 (dqd, J = 12.6, 6.0, 2.3 Hz, 2H), 3.56 (s, 3H), 2.42 (dd, J = 12.8, 10.5 Hz, 2H), 1.42 (d, J = 7.2 Hz, 3H), 1.18 (d, J = 6.2 Hz, 6H). |
| 769 | 511.4 | $^1$H NMR (400 MHz, DMSO-$d_6$) δ 7.95 (d, J = 6.7 Hz, 1H), 7.76 (s, 1H), 7.62 (dd, J = 8.5, 7.3 Hz, 1H), 7.58 (t, J = 2.1 Hz, 1H), 7.26 (d, J = 7.3 Hz, 1H), 6.95 (t, J = 2.7 Hz, 1H), 6.79 (d, J = 8.6 Hz, 1H), 6.50 (dd, J = 3.0, 1.8 Hz, 1H), 4.63 (p, J = 7.1 Hz, 1H), 4.25 (dd, J = 13.1, 2.4 Hz, 2H), 3.72-3.56 (m, 2H), 2.41 (dd, J = 12.8, 10.5 Hz, 2H), 1.49 (s, 9H), 1.41 (d, J = 7.2 Hz, 3H), 1.18 (d, J = 6.2 Hz, 6H). |
| 770 | 541.4 | $^1$H NMR (400 MHz, DMSO-$d_6$) δ 12.36 (s, 1H), 7.91 (d, J = 7.5 Hz, 1H), 7.77 (s, 1H), 7.65-7.57 (m, 2H), 7.26 (d, J = 7.3 Hz, 1H), 6.96 (t, J = 2.7 Hz, 1H), 6.79 (d, J = 8.6 Hz, 1H), 6.50 (dd, J = 3.0, 1.8 Hz, 1H), 4.91 (q, J = 6.6 Hz, 1H), 4.30-4.19 (m, 2H), 3.76-3.68 (m, 2H), 3.68-3.54 (m, 2H), 3.31 (s, 3H), 2.42 (dd, J = 12.8, 10.5 Hz, 2H), 1.49 (s, 9H), 1.18 (d, J = 6.2 Hz, 6H). |

Example 146. Preparation of N-[2-[[4-[3-[(cis)-2,6-dimethylmorpholin-4-yl]phenyl]-5-fluoro-thiazol-2-yl]amino]-2-oxo-ethyl]-1-methylsulfonyl-pyrrole-3-carboxamide (Compound 181)

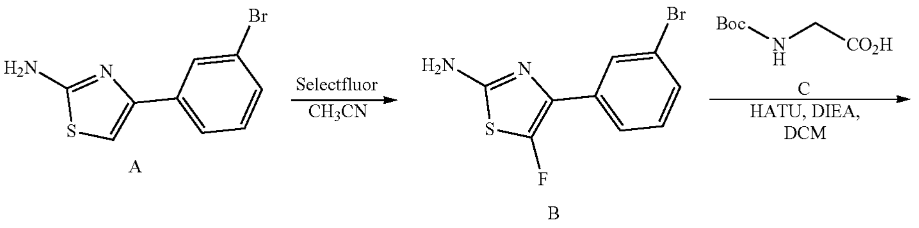

-continued
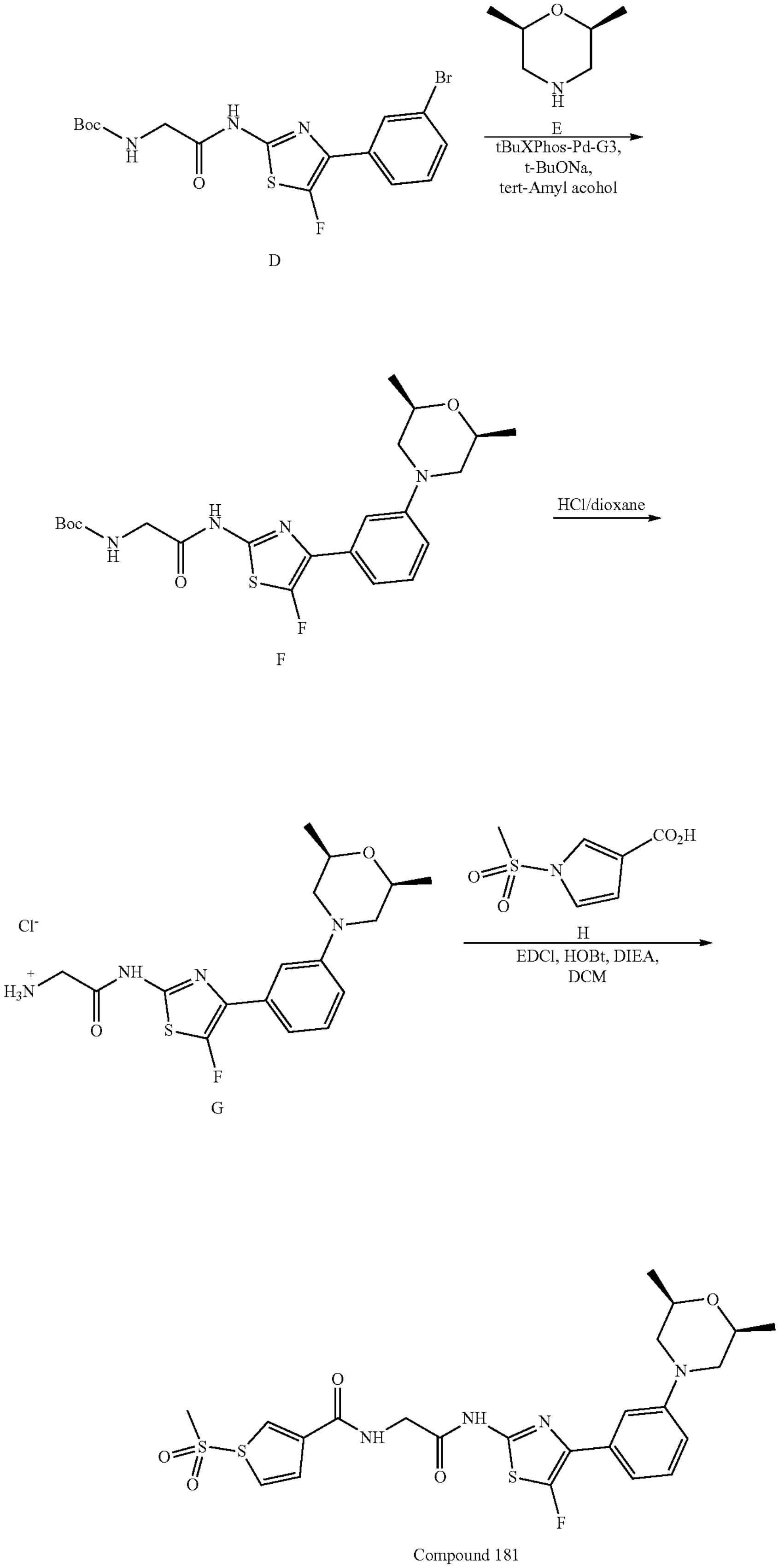
Compound 181

Step 1: Preparation of 4-(3-bromophenyl)-5-fluoro-thiazol-2-amine (Intermediate B)

B

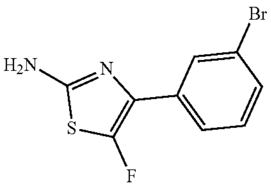

To a cooled (0° C.) solution of 4-(3-bromophenyl)thiazol-2-amine (2.00 g, 7.84 mmol) in acetonitrile (40 mL) was added Selectfluor™ (3.05 g, 8.62 mmol). The mixture was stirred at 30° C. for 16 h and subsequently concentrated to give a residue. The residue was purified by column chromatography (petroleum ether/ethyl acetate=10:1-3:1). The solution was concentrated to give Intermediate B (0.900 g, 3.08 mmol, 39.2% yield, 93.3% purity) as a brown solid. LCMS (ESI) m/z: [$Br^{81}$ M+H]$^+$=274.8.

Step 2: Preparation of tert-butyl N-[2-[[4-(3-bromophenyl)-5-fluoro-thiazol-2-yl]amino]-2-oxo-ethyl] carbamate (Intermediate D)

D

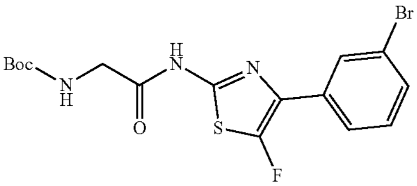

To a solution of Intermediate B (0.800 g, 2.93 mmol) and 2-N-Boc-glycine (0.564 g, 3.22 mmol) in dichloromethane (8 mL) was added HATU (1.34 g, 3.51 mmol) and DIEA (2.55 mL, 14.65 mmol,). The mixture was stirred at 30° C. for 16 h and subsequently concentrated to give a residue. The crude product was purified by reversed-phase HPLC (0.1% FA) to give Intermediate D (0.600 g, 1.35 mmol, 46.2% yield, 97.0% purity) as a yellow solid. LCMS (ESI) m/z: [$Br^{81}$M+H]$^+$=432.1.

Step 3: Preparation of tert-butyl N-[2-[[4-[3-[(cis)-2,6-dimethylmorpholin-4-yl]phenyl]-5-fluoro-thiazol-2-yl]amino]-2-oxo-ethyl]carbamate (Intermediate F)

F

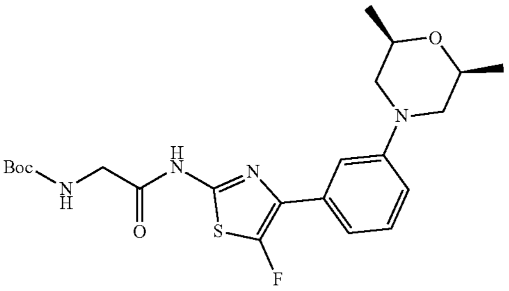

To a solution of Intermediate D (0.300 g, 0.697 mmol) and cis-2,6-dimethylmorpholine (0.161 g, 1.39 mmol) in 2-methylbutan-2-ol (3 mL) was added t-BuXphos-Pd (gen 3) (0.055 g, 0.070 mmol) and t-BuONa (0.134 g, 1.39 mmol). The mixture was stirred at 60° C. under $N_2$ (g). After 4 h, the reaction mixture was cooled to room temperature and poured into water (5 mL) and extracted with ethyl acetate (5 mL×3). The combined organic layers were washed with brine (10 mL), dried over $Na_2SO_4$, filtered and concentrated to give a residue. The residue was purified by prep-TLC ($SiO_2$, dichloromethane:MeOH=10:1). The resulting solid was triturated with dichloromethane: MeOH=10:1 (20 mL), the suspension was filtered and the filtrate was concentrated to give Intermediate F (0.120 g, 0.254 mmol, 36.41% yield, 98.3% purity) as a white solid. LCMS (ESI) m/z: [M+H]$^+$=465.3.

Step 4: Preparation of 2-((4-(3-((cis)-2,6-dimethylmorpholino)phenyl)-5-fluorothiazol-2-yl)amino)-2-oxoethan-1-aminium chloride (Intermediate G)

G

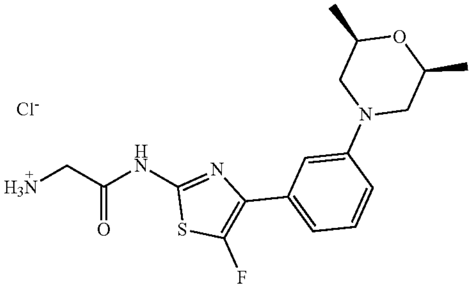

A mixture of Intermediate F (0.120 g, 0.258 mmol) in 4 M HCl in 1,4-dioxane (1.5 mL) was stirred at 30° C. for 2 h. The reaction mixture was subsequently concentrated to give a residue. The residue was triturated with MTBE (5 mL), the suspension was filtered, and the filter cake was dried in vacuum to give Intermediate G (0.090 g, 0.222 mmol, 85.91% yield, 98.85% purity, HCl) as a yellow solid. LCMS (ESI) m/z: [M+H]$^+$=365.2.

Step 5: Preparation of N-[2-[[4-[3-[(cis)-2,6-dimethylmorpholin-4-yl]phenyl]-5-fluoro-thiazol-2-yl] amino]-2-oxo-ethyl]-1-methylsulfonyl-pyrrole-3-carboxamide (Compound 181)

Compound 181

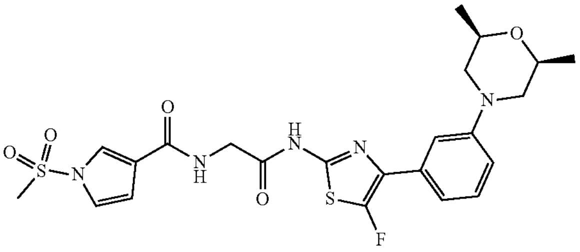

To a solution of Intermediate G (0.090, 0.225 mmol) and 1-methylsulfonylpyrrole-3-carboxylic acid (0.056 g, 0.296 mmol) in dichloromethane (2 mL) was added EDCI (0.057 g, 0.296 mmol), HOBt (0.040 g, 0.296 mmol) and DIEA (0.215 mL, 1.23 mmol). The resulting mixture was stirred at 30° C. for 16 h and subsequently concentrated to give a solid. The solid was purified by reversed-phase HPLC (0.1% FA) and the appropriate fractions were lyophilized to give Compound 181 (0.057 g, 0.104 mmol, 42.5% yield, 99.0% purity) as a white solid. LCMS (ESI) m/z: $[M+H]^+$=536.2; $^1H$ NMR (400 MHz, DMSO-$d_6$) δ 12.45 (br s, 1H), 8.68-8.65 (m, 1H), 7.84-7.83 (m, 1H), 7.34-7.30 (m, 3H), 7.30-7.21 (m, 1H), 6.99-6.95 (m, 1H), 6.77-6.75 (m, 1H), 4.12-4.08 (m, 2H), 3.73-3.67 (m, 2H), 3.58-3.56 (m, 5H), 2.32-2.26 (m, 2H), 1.17 (d, J=6.4 Hz, 6H).

Example 147. Preparation 1-(3-methyloxetan-3-yl)pyrrole-3-carboxylic acid

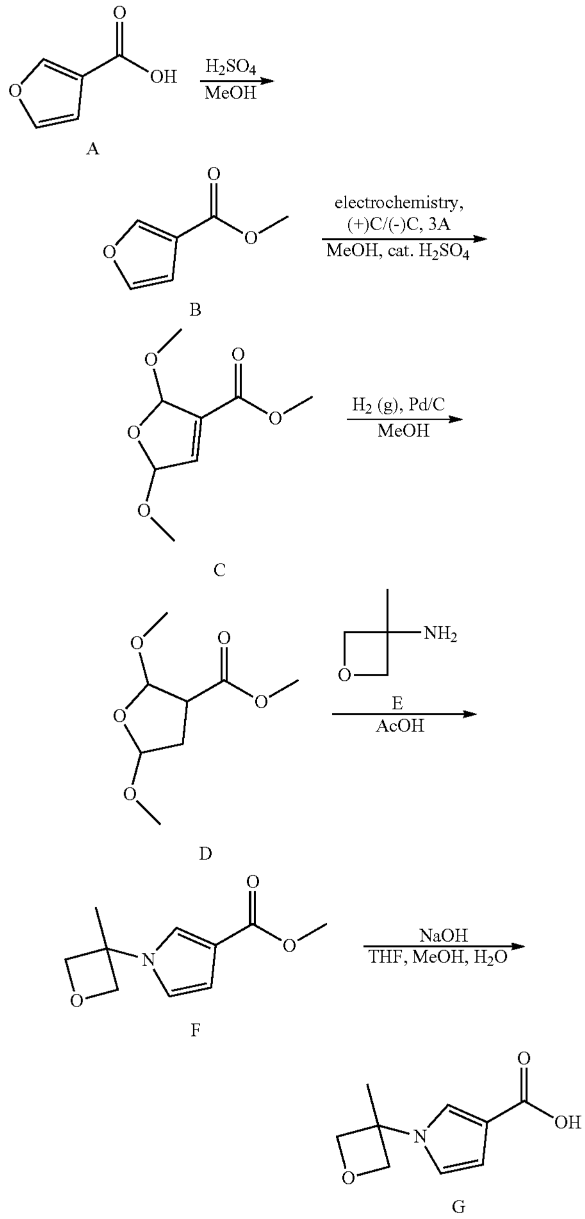

Step 1: Preparation of methyl furan-3-carboxylate (Intermediate B)

B

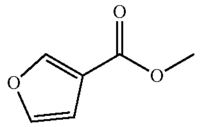

To a solution of furan-3-carboxylic acid (170 g, 1.52 mol) in MeOH (1200 mL) was carefully added concentrated $H_2SO_4$ (60 mL). The mixture was stirred at 80° C. for 1 h, then cooled to room temperature. The reaction mixture was concentrated under reduced pressure to remove the solvent. The residue was poured into saturated aqueous $NaHCO_3$ (1000 mL) and extracted with MTBE (300 mL×3). The combined organic layers were washed with brine (200 mL), dried over $Na_2SO_4$, filtered and concentrated under reduced pressure to give Intermediate B (170 g, 1.35 mol, 88.88% yield) as a yellow oil, which was used into the next step without further purification. $^1H$ NMR (400 MHz, $CDCl_3$) δ 8.02 (d, J=0.8 Hz, 1H), 7.43-7.42 (m, 1H), 6.75 (d, J=1.6 Hz, 1H), 3.84 (s, 3H).

Step 2: Preparation of methyl 2,5-dimethoxy-2,5-dihydrofuran-3-carboxylate (Intermediate C)

C

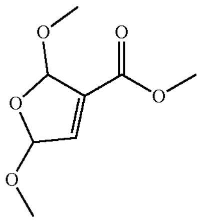

To a solution of Intermediate B (50.00 g, 396.48 mmol) in MeOH (3.6 L) was added $H_2SO_4$ (40 mL). The mixture was electrolyzed with a current density of 3 A using an isostatic graphite anode and a graphite cathode and stirred at −10° C. After stirring for 16 h, the reaction mixture was neutralized to pH~7 with saturated aqueous $NaHCO_3$ and filtered. The filtrate was partially concentrated in vacuo to remove MeOH and resultant aqueous layer was extracted with ethyl acetate (3×300 mL). The combined organic layers were washed with brine (300 mL), dried over $Na_2SO_4$, filtered and concentrated under reduced pressure to give Intermediate C (65.00 g, 345.42 mmol, 87.12% yield) as a yellow oil, which was used into the next step without further purification. $^1H$ NMR (400 MHz, DMSO-$d_6$) δ 7.03-6.89 (m, 1H), 5.99-5.96 (m, 1H), 5.74-5.62 (m, 1H), 3.76-3.71 (m, 3H), 3.31 (d, J=1.6 Hz, 4H), 3.27-3.26 (m, 2H).

Step 3: Preparation of methyl 2,5-dimethoxytetrahydrofuran-3-carboxylate (Intermediate D)

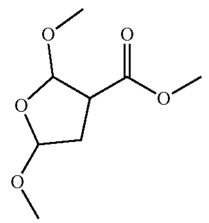

D

To a mixture of Intermediate C (35.00 g, 185.99 mmol) in MeOH (400 mL) was added 10% Pd/C (3.5 g). The mixture was degassed and purged with $H_2$ (g) (3×) and the mixture was subsequently was stirred at 25° C. for 16 h under a balloon of $H_2$ (g). The mixture was filtered and concentrated to afford Intermediate D (35.00 g) as a yellow oil which was used directly in the next step.

Step 4: Preparation of methyl 1-(3-methyloxetan-3-yl)pyrrole-3-carboxylate (Intermediate F)

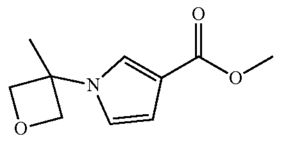

F

To a solution of Intermediate D (35.00 g, 184.02 mmol) in AcOH (240 mL) was added dropwise 3-methyloxetan-3-amine (20.00 g, 229.57 mmol). The mixture was stirred at 90° C. After stirring for 16 h, the reaction mixture was concentrated to remove excess AcOH. The resultant acidic residue was diluted with water (500 mL), basified to (pH~8) with aqueous saturated $NaHCO_3$, and extracted with ethyl acetate (500 mL×2). The combined organic layers were dried over anhydrous $Na_2SO_4$, filtered and concentrated under reduced pressure to give a oil. The oil was purified by column chromatography (petroleum ether/ethyl acetate=1/0 to 1/1) to afford Intermediate F (24.00 g) as a yellow oil. LCMS (ESI) m/z: $[M+H]^+$=196.2.; $^1$H NMR (400 MHz, $CDCl_3$) δ 7.47-7.45 (m, 1H), 6.85-6.83 (m, 1H), 6.69-6.67 (m, 1H), 5.00-4.97 (m, 2H), 4.71-4.68 (m, 2H), 3.84-3.81 (m, 3H), 1.93 (d, J=6.0 Hz, 3H).

Step 5: Preparation of 1-(3-methyloxetan-3-yl)pyrrole-3-carboxylic acid (Intermediate G)

G

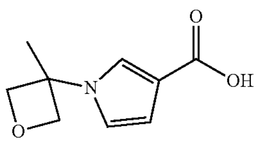

To a solution of Intermediate F (24.00 g, 122.94 mmol) in a mixture 1:1 MeOH/THF (150 mL) was added 4 M NaOH (4 M, 153.69 mL). The mixture was stirred at 80° C. After stirring for 16 h, the reaction mixture was partially concentrated to remove the THF and MeOH. The mixture was diluted with $H_2O$ (200 mL) and extracted with ethyl acetate (500 mL). The aqueous layer was acidified (pH~5) with saturated aqueous citric acid until solids precipitated. The solids were filtered to afford Intermediate G (12.00 g, 66.23 mmol, 53.87% yield) as a white solid. LCMS (ESI) m/z: $[M+H]^+$=182.1; $^1$H NMR (400 MHz, Methanol-$d_4$) δ 7.52-7.51 (m, 1H), 6.93-6.91 (m, 1H), 6.59-6.58 (m, 1H), 4.96 (d, J=6.4 Hz, 2H), 4.70 (d, J=6.8 Hz, 2H), 1.85 (s, 3H).

Example 148. Preparation of Compounds of the Invention

The compounds in Table 5 below were synthesized starting from the common starting material, 2-amino-N-(4-bromothiazol-2-yl)acetamide, the appropriate heterocyclic carboxylic acid, and boronate ester or boronic acid following the Scheme 4 below. Where appropriate SFC purification was used to separate enantiomers.

Scheme 4

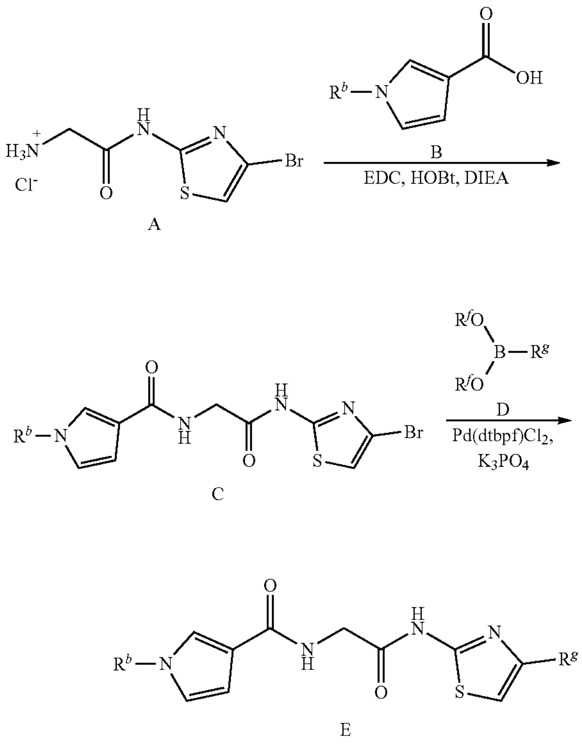

TABLE 5

| Compound # | LC-MS data(m/z) | $^1$H NMR |
|---|---|---|
| 277 | 512.1 | $^1$H NMR (400 MHz, DMSO-$d_6$) δ 12.46 (m, 1H), 8.68-8.66 (m, 1H), 8.40 (s, 1H), 8.25 (s, 1H), 7.90-7.88 (m, 1H), 7.85 (s, 1H), 7.78-7.76 (m, 1H), 7.81-7.73 (m, 1H), 7.56-7.45 (m, 1H), 7.31 (s, 1H), 6.78 (s, 1H), 4.23-4.06 (m, 3H), 3.57 (s, 3H), 1.47-1.30 (m, 2H), 1.22-1.14 (m, 2H) |
| 247 | 419.1 | $^1$H NMR (400 MHz, DMSO-$d_6$) δ 12.39 (s, 1H), 8.68 (s, 1H), 7.85 (s, 1H), 7.78-7.66 (m, 2H), 7.60 (s, 1H), 7.32 (s, 2H), 7.15-7.14 (m, 1H), 6.78 (s, 1H), 4.14-4.13 (m, 2H), 3.58 (s, 3H), 2.36 (s, 3H) |
| 248 | 455.1 | $^1$H NMR (400 MHz, DMSO-$d_6$) δ 12.61-12.19 (m, 1H), 8.64-8.63 (m, 1H), 8.18-8.01 (m, 2H), 7.85 (s, 1H), 7.72 (s, 1H), 7.64-7.47 (m, 2H), 7.32 (s, 1H), 7.26-6.92 (m, 1H), 6.78 (s, 1H), 4.13-4.12 (m, 2H), 3.58 (s, 3H) |
| 249 | 461.1 | $^1$H NMR (400 MHz, DMSO-$d_6$) δ 12.33 (s, 1H), 8.66 (d, J = 6.0 Hz, 1H), 7.87-7.81 (m, 1H), 7.54 (s, 1H), 7.41-7.35 (m, 1H), 7.34-7.27 (m, 1H), 7.26-7.19 (m, 2H), 6.81-6.73 (m, 1H), 5.01-4.87 (m, 1H), 4.13 (d, J = 6.0 Hz, 2H), 3.57 (s, 4H), 2.82-2.73 (m, 1H), 1.40 (d, J = 6.0 Hz, 3H) |
| 250 | 504.2 | $^1$H NMR (400 MHz, DMSO-$d_6$) δ 12.34 (br s, 1H), 8.68-8.65 (m, 1H), 7.85-7.84 (m, 1H), 7.49 (s, 1H), 7.32-7.31 (m, 1H), 7.17-7.11 (m, 1H), 7.08-7.03 (m, 1H), 7.02 (s, 1H), 6.78-6.77 (m, 1H), 4.13 (d, J = 6.0 Hz, 2H), 3.59-3.55 (m, 5H), 3.43-3.40 (m, 2H), 3.30 (s, 3H), 3.29-3.25 (m, 2H), 2.92-2.88 (m, 2H) |
| 252 | 505.2 | $^1$H NMR (400 MHz, DMSO-$d_6$) δ 12.36 (s, 1H), 8.70-8.67 (d, J = 6.0 Hz, 1H), 7.85-7.84 (d, J = 2.0 Hz, 1H), 7.66 (s, 1H), 7.49-7.48 (m, 1H), 7.35-7.31 (m, 3H), 6.81-6.77 (m, 2H), 4.92-4.86 (m, 1H), 4.15-4.14 (d, J = 5.6 Hz, 2H), 4.10-4.06 (m, 1H), 3.58 (s, 3H), 3.19 (s, 3H), 2.44-2.43 (m, 2H), 2.34-2.28 (m, 2H) |
| 253 | 463.1 | $^1$H NMR (400 MHz, DMSO-$d_6$) δ 12.45 (s, 1H), 8.71-8.70 (m, 1H),, 8.09 (d, J = 2.0 Hz, 1H), 8.00 (s, 1H), 7.85 (s, 1H), 7.80 (s, 1H), 7.67 (d, J = 11.2 Hz, 1H), 7.35-7.28 (m, 1H), 7.10 (d, J = 1.2 Hz, 1H), 6.83-6.74 (m, 1H), 4.15 (d, J = 6.0 Hz, 2H), 3.57 (s, 3H) |
| 254 | 505.2 | $^1$H NMR (400 MHz, DMSO-$d_6$) δ 12.36 (s, 1H), 8.70-8.67 (d, J = 6.0 Hz, 1H), 7.86-7.85 (d, J = 2.0 Hz, 1H), 7.66 (s, 1H), 7.49-7.47 (d, J = 8.0 Hz, 1H), 7.37-7.31 (m, 3H), 6.84-6.81 (m, 1H), 6.79-6.77 (m, 1H), 4.47-4.40 (m, 1H), 4.15-4.14 (d, J = 5.6 Hz, 2H), 3.68-3.64 (d, J = 6.8 Hz, 1H), 3.58 (s, 3H), 3.17 (s, 3H), 2.91-2.86 (m, 2H), 1.95-1.89 (m, 2H) |
| 255 | 465.1 | $^1$H NMR (400 MHz, DMSO-$d_6$) δ 12.37 (s, 1H), 8.68 (s, 1H), 7.84 (s, 1H), 7.69 (s, 1H), 7.39-7.09 (m, 3H), 6.77 (s, 1H), 4.64 (s, 2H), 4.13 (s, 2H), 3.58-3.58 (m, 3H), 3.27-3.24 (m, 2H) |
| 256 | 477.2 | $^1$H NMR (400 MHz, DMSO-$d_6$) δ 12.42 (s, 1H), 8.68-8.66 (m, 1H), 8.02 (s, 1H), 7.89-7.83 (m, 2H), 7.72 (s, 1H), 7.50-7.43 (m, 2H), 7.31-7.30 (m, 1H), 6.77-6.76 (m, 1H), 4.14 (d, J = 5.6 Hz, 2H), 3.57 (s, 3H), 2.64-2.55 (m, 4H), 2.07-2.03 (m, 1H), 1.73-1.71 (m, 1H) |
| 257 | 532.0 | $^1$H NMR (400 MHz, Methanol-$d_4$) δ 7.86-7.80 (m, 1H), 7.58-7.53 (m, 1H), 7.38-7.30 (m, 2H), 7.29-7.21 (m, 2H), 6.96-6.91 (m, 1H), 6.82-6.79 (m, 1H), 4.25 (s, 2H), 3.38 (s, 3H), 3.37-3.32 (m, 2H), 3.27 (s, 3H), 2.97-2.88 (m, 1H), 2.83 (d, J = 11.6 Hz, 1H), 2.00-1.78 (m, 2H), 1.72-1.47 (m, 2H), 1.24 (s, 3H) |
| 258 | 532.0 | $^1$H NMR (400 MHz, Methanol-$d_4$) δ 7.85-7.82 (m, 1H), 7.58-7.53 (m, 1H), 7.36-7.31 (m, 2H), 7.29-7.21 (m, 2H), 6.96-6.90 (m, 1H), 6.82-6.79 (m, 1H), 4.25 (s, 2H), 3.38 (s, 3H), 3.38-3.33 (m, 2H), 3.27 (s, 3H), 2.99-2.88 (m, 1H), 2.83 (d, J = 12.4 Hz, 1H), 1.98-1.78 (m, 2H), 1.74-1.47 (m, 2H), 1.24 (s, 3H) |
| 259 | 490 | $^1$H NMR (400 MHz, DMSO-$d_6$) δ 12.41-12.38 (m, 1H), 8.67 (s, 1H), 7.85 (s, 1H), 7.62 (s, 1H), 7.46 (s, 1H), 7.39 (d, J = 6.8 Hz, 1H), 7.32 (s, 1H), 7.24 (d, J = 7.6 Hz, 1H), 6.78 (d, J = 0.8 Hz, 1H), 4.52 (s, 2H), 4.14 (d, J = 5.6 Hz, 2H), 3.77 (s, 2H), 3.58 (s, 3H), 3.00 (s, 2H), 2.94 (s, 3H) |
| 260 | 494.9 | $^1$H NMR (400 MHz, DMSO-$d_6$) δ 12.48-12.37 (m, 1H), 8.73-8.66 (m, 1H), 7.86-7.83 (m, 1H), 7.82-7.79 (m, 1H), 7.59-7.56 (m, 1H), 7.54-7.51 (m, 1H), 7.34-7.30 (m, 1H), 7.11-7.08 (m, 1H), 6.79-6.75 (m, 1H), 4.18-4.11 (m, 2H), 3.99-3.92 (m, 1H), 3.61-3.55 (m, 3H), 2.08-2.07 (m, 1H), 0.87-0.79 (m, 2H), 0.74-0.68 (m, 2H) |
| 263 | 438.2 | $^1$H NMR (400 MHz, DMSO-$d_6$) δ 12.27 (s, 1H), 8.18-8.15 (d, J = 6.0 Hz, 1H), 7.53-7.52 (d, J = 2.0 Hz, 1H), 7.49 (s, 1H), 7.18-7.16 (d, J = 1.6 Hz, 1H), 7.08-7.06 (d, J = 8.0 Hz, 1H), 7.02 (s, 1H), 6.98-6.97 (d, J = 2.4 Hz, 1H), 6.49-6.48 (m, 1H), 4.10-4.08 (d, J = 6.0 Hz, 2H), 3.31-3.26 (d, J = 8.0 Hz, 2H), 2.90-2.86 (d, J = 8.0 Hz, 2H), 2.74 (s, 3H), 1.50 (s, 9H) |
| 264 | 465.1 | $^1$H NMR (400 MHz, DMSO-$d_6$) δ 12.40 (br s, 1H), 8.68 (s, 1H), 7.85 (s, 1H), 7.49-7.42 (m, 2H), 7.32 (s, 1H), 7.13 (d, J = 8.0 Hz, 1H), 6.78 (s, 1H), 4.69 (d, J = 8.4 Hz, 2H), 4.15 (d, J = 4.4 Hz, 2H), 3.58 (s, 3H), 3.32 (s, 2H).. |
| 265 | 460.9 | $^1$H NMR (400 MHz, DMSO-$d_6$) δ 12.44-12.35 (m, 1H), 8.70-8.67 (m, 1H), 7.85-7.84 (m, 1H), 7.64 (s, 1H), 7.59-7.56 (m, 1H), 7.50 (d, J = 7.6 Hz, 1H), 7.36-7.31 (m, 2H), 7.01-6.99 (m, 1H), 6.78-6.76 (m, 1H), 4.14 (d, J = 6.0 Hz, 2H), 3.90-3.86 (m, 1H), 3.57 (s, 3H), 0.83-0.78 (m, 2H), 0.72-0.66 (m, 2H) |
| 266 | 453.3 | $^1$H NMR (400 MHz, DMSO-$d_6$) δ 12.53-12.15 (m, 1H), 8.70-8.67 (m, 1H), 7.84-7.83 (m, 1H), 7.70-7.64 (m, 3H), 7.44-7.40 (m, 1H), 7.32-7.30 (m, 1H), 7.07-7.04 (m, 1H), 6.77-6.76 (m, 1H), 5.97-5.83 (m, 2H), 4.13 (d, J = 5.6 Hz, 2H), 3.57 (s, 3H) |

TABLE 5-continued

| Compound # | LC-MS data(m/z) | $^1$H NMR |
|---|---|---|
| 267 | 558.5 | $^1$H NMR (400 MHz, DMSO-$d_6$) δ 12.35 (s, 1H), 8.69-8.66 (m, 1H), 7.84-7.83 (m, 1H), 7.61 (s, 1H), 7.32-7.30 (m, 1H), 7.21 (s, 1H), 7.02 (s, 1H), 6.77-6.76 (m, 1H), 6.67 (s, 1H), 4.11 (d, J = 6.0 Hz, 2H), 3.72-3.68 (m, 2H), 3.62-3.57 (m, 5H), 2.28-2.23 (m, 2H), 1.93-1.88 (m, 1H), 1.16 (d, J = 6.4 Hz, 6H), 0.95-0.90 (m, 2H), 0.72-0.68 (m, 2H) |
| 270 | 460.2 | $^1$H NMR (400 MHz, Methanol-$d_4$) δ 7.74-7.73 (d, J = 2.0 Hz, 1H), 7.18-7.17 (m, 2H), 7.14-7.12 (d, J = 2.0 Hz, 1H), 6.99-6.98 (m, 2H), 6.72-6.70 (m, 1H), 4.15 (s, 2H), 3.39-3.37 (m, 1H), 3.28 (s, 3H), 3.04-3.03 (m, 1H), 2.85-2.81 (d, J = 8.0 Hz, 2H), 2.69 (s, 3H) |
| 272 | 412.2 | $^1$H NMR (400 MHz, DMSO-$d_6$) δ 12.39-12.11 (m, 1H), 8.27-8.08 (m, 1H), 7.60-7.39 (m, 2H), 7.17-7.03 (m, 3H), 6.99-6.94 (m, 1H), 6.53-6.45 (m, 2H), 5.76-5.66 (m, 1H), 4.08 (d, J = 6.0 Hz, 2H), 2.78-2.65 (m, 3H), 1.49 (s, 9H) |
| 273 | 488.2 | $^1$H NMR (400 MHz, DMSO-$d_6$) δ 12.35 (br s, 1H), 8.70-8.60 (m, 1H), 7.86-7.80 (m, 1H), 7.51 (s, 1H), 7.42 (d, J = 1.6 Hz, 1H), 7.33-7.28 (m, 1H), 7.35-7.26 (m, 1H), 7.11-7.09 (m, 1H), 6.78-6.72 (m, 1H), 4.12 (d, J = 6.0 Hz, 2H), 3.57-3.55 (m, 3H), 2.92-2.81 (m, 5H), 2.72-2.69 (m, 2H), 1.73-1.69 (m, 2H), 1.55-1.49 (m, 2H) |
| 274 | 505.2 | $^1$H NMR (400 MHz, DMSO-$d_6$) δ 12.68-12.09 (m, 1H), 8.69-8.68 (m, 1H), 7.85-7.84 (m, 1H), 7.66 (s, 1H), 7.52-7.45 (m, 2H), 7.36-7.28 (m, 2H), 6.93-6.91 (m, 1H), 6.78-6.77 (m, 1H), 4.43-4.41 (m, 1H), 4.13 (d, J = 6.0 Hz, 2H), 3.86-3.83 (m, 1H), 3.71-3.61 (m, 1H), 3.60-3.55 (m, 3H), 3.54-3.44 (m, 2H), 2.11-1.98 (m, 1H), 1.86-1.65 (m, 2H), 1.59-1.51 (m, 1H) |
| 275 | 522 | $^1$H NMR (400 MHz, DMSO-$d_6$) δ 12.46 (s, 1H), 9.27 (s, 1H), 8.67 (s, 1H), 8.57 (s, 1H), 8.50-8.18 (m, 1H), 7.94-7.92 (m, 1H), 7.89-7.80 (m, 2H), 7.74 (s, 1H), 7.58-7.56 (m, 1H), 7.31 (s, 1H), 6.78 (s, 1H), 4.15-4.14 (m, 2H), 3.57 (s, 3H) |
| 276 | 489.2 | $^1$H NMR (400 MHz, DMSO-$d_6$) δ 12.41-12.34 (m, 1H), 8.64-8.62 (m, 1H), 7.94 (d, J = 7.2 Hz, 1H), 7.85 (d, J = 2.0 Hz, 2H), 7.79-7.77 (m, 1H), 7.58-7.53 (m, 1H), 7.30 (s, 2H), 6.77 (s, 1H), 4.12-4.11 (m, 2H), 3.56 (s, 3H) |
| 278 | 522.1 | $^1$H NMR (400 MHz, DMSO-$d_6$) δ 12.41 (s, 1H), 8.68-8.67 (m, 1H), 8.42-8.12 (m, 2H), 8.12-8.05 (m, 2H), 7.84 (s, 1H), 7.78 (s, 1H), 7.65-7.63 (m, 1H), 7.53-7.51 (m, 1H), 7.31-7.30 (m, 1H), 6.77 (s, 1H), 4.15-4.13 (m, 2H), 3.57 (s, 3H) |
| 279 | 505.2 | $^1$H NMR (400 MHz, DMSO-$d_6$) δ 12.35 (s, 1H), 8.66-8.64 (m, 1H), 7.84-7.83 (m, 1H), 7.66 (s, 1H), 7.53-7.42 (m, 2H), 7.39-7.25 (m, 2H), 7.02-6.86 (m, 1H), 6.78-6.77 (m, 1H), 4.71-4.52 (m, 1H), 4.13 (d, J = 6.0 Hz, 2H), 3.89-3.83 (m, 2H), 3.57 (s, 3H), 3.54-3.46 (m, 2H), 2.04-1.92 (m, 2H), 1.68-1.52 (m, 2H) |
| 280 | 434.2 | $^1$H NMR (400 MHz, DMSO-$d_6$) δ 12.38 (s, 1H), 8.69-8.68 (m, 1H), 7.85-7.84 (m, 1H), 7.47 (s, 1H), 7.32-7.31 (m, 1H), 7.16-7.03 (m, 3H), 6.78-6.77 (m, 1H), 6.55-6.44 (m, 1H), 5.73-5.71 (m, 1H), 4.13 (d, J = 6.0 Hz, 2H), 3.58 (s, 3H), 2.7 (d, J = 5.2 Hz, 3H) |
| 281 | 463 | $^1$H NMR (400 MHz, DMSO-$d_6$) δ 12.39 (s, 1H), 8.70 (d, J = 5.6 Hz, 1H), 7.87-7.81 (m, 1H), 7.67 (s, 1H), 7.49-7.41 (m, 2H), 7.36-7.27 (m, 2H), 6.88 (d, J = 1.6, Hz, 1H), 6.78 (d, J = 3.2 Hz, 1H), 4.67 (d, J = 6.0 Hz, 1H), 4.14 (d, J = 6.0 Hz, 2H), 3.59 (s, 3H), 1.30 (d, J = 6.0 Hz, 6H) |
| 282 | 476 | $^1$H NMR (400 MHz, Methanol-$d_4$) δ 7.87-7.85 (m, 1H), 7.31-7.28 (m, 2H), 7.20 (s, 1H), 7.17-7.14 (m, 1H), 6.84-6.82 (m, 1H), 6.71 (d, J = 8.4 Hz, 1H), 4.32-4.29 (m, 2H), 4.26 (s, 2H), 3.40 (s, 3H), 3.30-3.27 (m, 2H), 2.95 (s, 3H) |
| 283 | 454 | $^1$H NMR (400 MHz, Methanol-$d_4$) δ 7.61-7.59 (m, 1H), 7.28 (d, J = 2.0 Hz, 1H), 7.19 (s, 1H), 7.16-7.13 (m, 1H), 6.99-6.96 (m, 1H), 6.71 (d, J = 8.4 Hz, 1H), 6.60-6.58 (m, 1H), 4.32-4.29 (m, 2H), 4.24 (s, 2H), 3.30-3.26 (m, 2H), 2.94 (s, 3H), 1.58 (s, 9H) |
| 284 | 475.1 | $^1$H NMR (400 MHz, DMSO-$d_6$) δ 12.38 (s, 1H), 8.69 (d, J = 6.0 Hz, 1H), 7.86-7.83 (m, 1H), 7.65 (s, 1H), 7.46 (d, J = 8.0 Hz, 1H), 7.36-7.28 (m, 3H), 6.82-6.76 (m, 2H), 4.73 (d, J = 7.2 Hz, 1H), 4.13 (d, J = 6.0 Hz, 2H), 3.58 (s, 3H), 2.48-2.41 (m, 2H), 2.13-2.00 (m, 2H), 1.78-1.74 (m, 1H), 1.72-1.61 (m, 1H) |
| 285 | 471.1 | $^1$H NMR (400 MHz, DMSO-$d_6$) δ 12.46-12.41 (m, 1H), 8.69-8.68 (m, 1H), 7.85 (s, 1H), 7.785-7.78 (m, 1H), 7.75 (s, 1H), 7.70 (s, 1H), 7.53-7.08 (m, 4H), 6.78-6.77 (m, 1H), 4.15-4.14 (m, 2H), 3.57-3.32 (m, 3H) |
| 286 | 449 | $^1$H NMR (400 MHz, DMSO-$d_6$) δ 12.40 (1H), 8.70 (d, J = 6.0 Hz, 1H), 7.87-7.81 (m, 1H), 7.67 (s, 1H), 7.52-7.42 (m, 2H), 7.38-7.27 (m, 2H), 6.89 (d, J = 2.4 Hz, 1H), 6.78 (d, J = 1.6 Hz, 1H), 4.14 (d, J = 6.0 Hz, 2H), 4.08 (d, J = 6.8 Hz, 2H), 3.58 (s, 3H), 1.36 (d, J = 6.8 Hz, 3H) |
| 287 | 448.2 | $^1$H NMR (400 MHz, DMSO-$d_6$) δ 12.39 (s, 1H), 8.70-8.67 (d, J = 6.0 Hz, 1H), 7.85-7.84 (d, J = 2.0 Hz, 1H), 7.58 (s, 1H), 7.33-7.31 (m, 1H), 7.26-7.18 (m, 3H), 8.79-6.77 (m, 1H), 6.71-6.69 (m, 1H), 4.14-4.13 (d, J = 5.6 Hz, 2H), 3.58 (s, 3H), 2.95 (s, 6H) |
| 288 | 426.3 | $^1$H NMR (400 MHz, DMSO-$d_6$) δ 12.276 (s, 1H), 8.17-8.14 (d, J = 6.0 Hz, 1H), 7.558 (s, 1H), 7.53-7.52 (d, J = 2.0 Hz, 1H), 7.26-7.18 (m, 3H), 6.98-6.97 (d, J = 2.8 Hz, 1H), 6.71-6.69 (m, 1H), 6.48-6.47(m, 1H), 4.11-4.10 (d, J = 6.0 Hz, 2H), 2.95 (s, 6H), 1.50 (s, 9H) |

TABLE 5-continued

| Compound # | LC-MS data(m/z) | $^1$H NMR |
|---|---|---|
| 289 | 522.1 | $^1$H NMR (400 MHz, DMSO-$d_6$) δ 12.50 (s, 1H), 8.77 (s, 1H), 8.69-8.68 (m, 1H), 8.53 (s, 1H), 8.39-8.06 (m, 1H), 8.01-7.99 (m, 1H), 7.92-7.90 (m, 1H), 7.87-7.83 (m, 1H), 7.80 (s, 1H), 7.62-7.60 (m, 1H), 7.35-7.29 (m, 1H), 6.79-6.78 (m, 1H), 4.16-4.12 (m, 2H), 3.58 (s, 3H) |
| 290 | 521.3 | $^1$H NMR (400 MHz, Methanol-$d_4$) δ 8.55 (s, 1H), 7.84-7.83 (m, 1H), 7.57-7.56 (m, 1H), 7.43-7.40 (m, 1H), 7.39-7.38 (m, 1H), 7.31-7.28 (m, 2H), 7.00-6.93 (m, 1H), 6.81-6.80 (m, 1H), 4.72-4.55 (m, 2H), 4.29-4.25 (m, 2H), 4.17-4.07 (m, 1H), 3.85-3.72 (m, 1H), 3.38 (s, 3H), 2.91-2.81 (m, 2H), 2.22-2.08 (m, 1H), 1.86-1.69 (m, 1H) |
| 291 | 547.3 | $^1$H NMR (400 MHz, DMSO-$d_6$) δ 12.34 (br s, 1H), 8.67 (d, J = 6.0 Hz, 1H), 7.84 (d, J = 2.0 Hz, 1H), 7.67 (s, 1H), 7.51-7.45 (m, 2H), 7.36-7.29 (m, 2H), 6.96-6.89 (m, 1H), 6.77 (d, J = 1.6 Hz, 1H), 4.19-4.10 (m, 4H), 3.68 (d, J = 6.8, Hz, 2H), 3.57 (s, 3H), 2.32-2.27 (m, 1H), 1.68 (d, J = 14.0 Hz, 2H), 1.41-1.30 (m, 2H), 1.06 (d, J = 6.0 Hz, 6H) |
| 292 | 547.1 | $^1$H NMR (400 MHz, DMSO-$d_6$) δ 12.37 (s, 1H), 8.67 (d, J = 5.9 Hz, 1H), 7.86-7.83 (m, 1H), 7.66 (s, 1H), 7.49-7.44 (m, 2H), 7.34-7.30 (m, 2H), 6.89 (d, J = 8.0 Hz, 1H), 6.78 (d, J = 1.6 Hz, 1H), 4.14 (d, J = 6.0 Hz, 2H), 3.85 (d, J = 6.0 Hz, 2H), 3.57 (s, 3H), 3.51-3.42 (m, 2H), 2.07 (s, 1H), 1.74 (d, J = 13.6 Hz, 2H), 1.12 (d, J = 6.0 Hz, 6H), 0.93 (d, J = 11.6 Hz, 2H) |
| 293 | 536.1 | $^1$H NMR (400 MHz, DMSO-$d_6$) δ 12.38 (s, 1H), 8.68-8.66 (m, 1H), 7.84-7.83 (m, 1H), 7.62 (s, 1H), 7.52-7.47 (m, 2H), 7.31-7.30 (m, 1H), 7.19-7.18 (m, 1H), 6.77-6.76 (m, 1H), 4.13 (d, J = 6.0 Hz, 2H), 3.79-3.74 (m, 2H), 3.57 (s, 3H), 3.28 (s, 2H), 2.42-2.39 (m, 2H), 1.14 (d, J = 6.0 Hz, 6H) |
| 294 | 536.1 | $^1$H NMR (400 MHz, DMSO-$d_6$) δ 12.42 (s, 1H), 8.70-8.67 (m, 1H), 7.84 (d, J = 1.6 Hz, 1H), 7.63-7.59 (m, 1H), 7.52 (s, 1H), 7.32-7.30 (m, 1H), 7.20-7.16 (m, 1H), 7.04-7.00 (m, 1H), 6.77-6.76 (m, 1H), 4.14 (d, J = 5.6 Hz, 2H), 3.79-3.76 (m, 2H), 3.57 (s, 3H), 3.26 (d, J = 11.2 Hz, 2H), 2.42-2.36 (m, 2H), 1.13 (d, J = 6.4 Hz, 6H) |
| 295 | 536.2 | $^1$H NMR (400 MHz, DMSO-$d_6$) δ 12.38-12.34 (m, 1H), 8.67-8.64 (m, 1H), 7.84-7.83 (m, 1H), 7.73 (s, 1H), 7.31-7.28 (m, 2H), 7.08 (d, J = 9.6 Hz, 1H), 6.80-6.68 (m, 2H), 4.13 (d, J = 6.0 Hz, 2H), 3.71-3.65 (m, 4H), 3.57 (s, 3H), 2.33-2.32 (m, 2H), 1.17 (d, J = 6.0 Hz, 6H) |
| 297 | 536.3 | $^1$H NMR (400 MHz, DMSO-$d_6$) δ 12.38 (br s, 1H), 8.68-8.64 (m, 1H), 7.89-7.81 (m, 1H), 7.55-7.47 (m, 2H), 7.32-7.30 (m, 1H), 7.20-7.15 (m, 1H), 7.00-6.96 (m, 1H), 6.78-6.76 (m, 1H), 4.14 (d, J = 5.6 Hz, 2H), 3.77-3.67 (m, 2H), 3.57 (s, 3H), 3.51 (d, J = 10.4 Hz, 2H), 2.30-2.24 (m, 2H), 1.17 (d, J = 6.0 Hz, 6H) |
| 298 | 459 | $^1$H NMR (400 MHz, DMSO-$d_6$) δ 12.39 (s, 1H), 8.71-8.62 (m, 1H), 7.85-7.84 (m, 1H), 7.77 (s, 1H), 7.73-7.69 (m, 1H), 7.62 (s, 1H), 7.36-7.30 (m, 2H), 7.18 (d, J = 7.6 Hz, 1H), 6.78-6.77 (m, 1H), 4.14 (d, J = 6.0 Hz, 2H), 3.61-3.53 (m, 4H), 2.36-2.29 (m, 2H), 2.15-2.00 (m, 2H), 2.06-1.96 (m, 1H), 1.87-1.80 (m, 1H) |
| 299 | 497.3 | $^1$H NMR (400 MHz, Methanol-$d_4$) δ 8.08 (d, J = 5.6 Hz, 1H), 7.68 (s, 1H), 7.59-7.57 (m, 1H), 7.36 (s, 1H), 7.19-7.18 (m, 1H), 6.95-6.94 (m, 1H), 6.57-6.56 (m, 1H), 4.22 (s, 2H), 4.11-4.07 (m, 2H), 3.75-3.72 (m, 2H), 2.55-2.50 (m, 2H), 1.56 (s, 9H), 1.25 (d, J = 6.4 Hz, 6H) |
| 300 | 517.1 | $^1$H NMR (400 MHz, DMSO-$d_6$) δ 12.38 (s, 1H), 8.69-8.66 (m, 1H), 7.85-7.84 (m, 1H), 7.69 (s, 1H), 7.57-7.47 (m, 2H), 7.39-7.30 (m, 2H), 6.94-6.92 (m, 1H), 6.78-6.77 (m, 1H), 4.28-4.25 (m, 2H), 4.14 (d, J = 5.6 Hz, 2H), 3.58 (s, 3H), 2.83-2.80 (m, 2H) |
| 301 | 479.2 | $^1$H NMR (400 MHz, DMSO-$d_6$) δ 12.37 (s, 1H), 8.69-8.67 (m, 1H), 7.85-7.84 (m, 1H), 7.67 (s, 1H), 7.53-7.43 (m, 2H), 7.38-7.23 (m, 2H), 6.92-6.89 (m, 1H), 6.78-6.77 (m, 1H), 4.21-4.09 (m, 4H), 3.72-3.66 (m, 2H), 3.58 (s, 3H), 3.33 (s, 3H) |
| 307 | 489.3 | $^1$H NMR (400 MHz, DMSO-$d_6$) δ 12.37 (br s, 1H), 8.68 (m, 1H), 7.85 (m, 1H), 7.67 (s, 1H), 7.51-7.44 (m, 2H), 7.36-7.30 (m, 2H), 6.93-6.86 (m, 1H), 6.78 (m, 1H), 4.15 (d, J = 6.0 Hz, 2H), 4.00 (d, J = 6.8 Hz, 2H), 3.58 (s, 3H), 2.80-2.70 (m, 1H), 2.13-2.05 (m, 2H), 1.97-1.81 (m, 4H) |
| 308 | 425.1 | $^1$H NMR (400 MHz, DMSO-$d_6$) δ 12.27 (s, 1H), 8.18-8.15 (m, 1H), 7.55-7.52 (m, 2H), 7.41-7.39 (m, 1H), 7.31-7.21 (m, 2H), 6.99-6.97 (m, 1H), 6.48 (s, 1H), 4.57-4.53 (m, 2H), 4.09 (d, J = 5.6 Hz, 2H), 3.21-3017 (m, 2H), 1.49 (s, 9H) |
| 309 | 447 | $^1$H NMR (400 MHz, DMSO-$d_6$) δ 12.35 (br s, 1H), 8.71-8.68 (m, 1H), 7.85 (s, 1H), 7.55 (s, 1H), 7.40 (d, J = 7.6 Hz, 1H), 7.39-7.25 (m, 3H), 6.78 (s, 1H), 4.57-4.53 (m, 2H), 4.14 (d, J = 5.2 Hz, 2H), 3.57 (s, 3H), 3.21-3.16 (m, 2H) |
| 425 | 464.0 | $^1$H NMR (400 MHz, Methanol-$d_4$) δ 8.34 (s, 1H), 7.98 (d, J = 7.8 Hz, 1H), 7.72 (d, J = 8.0 Hz, 1H), 7.58-7.57 (m, 1H), 7.51-7.47 (m, 2H), 6.95-6.94 (m, 1H), 6.59-6.57 (m, 2H), 4.24 (s, 2H), 2.49 (s, 3H), 1.56 (s, 9H) |
| 455 | 479.0 | $^1$H NMR (400 MHz, DMSO-$d_6$) δ 12.40 (s, 1H), 8.69-8.66 (m, 1H), 7.84 (s, 1H), 7.76 (s, 1H), 7.42 (s, 1H), 7.31 (s, 2H), 6.89 (d, J = 10.4 Hz, 1H), 6.77 (s, 1H), 4.14 (d, J = 5.6 Hz, 2H), 3.93 (s, 1H), 3.57 (s, 3H), 0.82 (d, J = 6.0 Hz, 2H), 0.70 (s, 2H) |
| 457 | 479.2 | $^1$H NMR (400 MHz, DMSO-$d_6$) δ 12.44-12.39 (m, 1H), 8.68-8.65 (m, 1H), 7.84-7.83 (m, 1H), 7.60-7.56 (m, 1H), 7.51 (d, J = 2.0 Hz, 1H), 7.40-7.36 (m, 1H), 7.31-7.30(m, 1H), 7.25-7.19 (m, 1H), 6.77-6.76(m, 1H), 4.13 (d, J = 6.0 Hz, 2H), 4.00-3.95 (m, 1H), 3.57 (s, 3H), 0.84-0.71 (m, 4H) |

TABLE 5-continued

| Compound # | LC-MS data(m/z) | $^1$H NMR |
|---|---|---|
| 463 | 473.0 | $^1$H NMR (400 MHz, DMSO-$d_6$) δ 12.56-12.38 (m, 1H), 8.69 (s, 1H), 8.29-8.15 (m, 2H), 7.87-7.86 (m, 2H), 7.70 (s, 2H), 7.32 (s, 1H), 6.78 (s, 1H), 4.15-4.14 (m, 2H), 3.58 (s, 3H) |
| 467 | 516.1 | $^1$H NMR (400 MHz, DMSO-$d_6$) δ 12.36-12.32 (m, 1H), 8.67-8.64 (m, 1H), 7.84-7.83 (m, 1H), 7.48 (s, 1H), 7.31-7.30 (m, 1H), 7.16-7.13 (m, 1H), 7.06-7.04 (m, 2H), 6.77-6.76 (m, 1H), 4.33-4.28 (m, 1H), 4.13 (d, J = 6.0 Hz, 2H), 3.92-3.86 (m, 1H), 3.79 (d, J = 6.0 Hz, 2H), 3.71-3.66 (m, 1H), 3.57 (s, 3H), 3.44-3.36 (m, 2H), 2.89-2.85 (m, 2H), 2.20-2.11 (m, 1H), 1.96-1.88 (m, 1H) |
| 472 | 495.1 | $^1$H NMR (400 MHz, DMSO-$d_6$) δ 12.41 (s, 1H), 8.69-8.68 (m, 1H), 7.85-7.83 (m, 2H), 7.78 (d, J = 7.6 Hz, 1H), 7.68 (s, 1H), 7.41-7.40 (m, 1H), 7.34-7.31 (m, 1H), 7.28 (d, J = 7.6 Hz, 1H), 6.78-6.77 (m, 1H), 4.15-4.13 (m, 2H), 3.58 (s, 3H), 3.51-3.43 (m, 1H), 3.13-2.97 (m, 2H), 2.85-2.68 (m, 2H) |
| 478 | 490.1 | $^1$H NMR (400 MHz, DMSO-$d_6$) δ 12.33 (s, 1H), 8.68-8.64 (m, 1H), 7.85-7.83 (m, 1H), 7.40 (s, 1H), 7.32-7.30 (m, 1H), 7.13 (d, J = 1.6 Hz, 1H), 7.11-7.07 (m, 1H), 6.78-6.76 (m, 1H), 6.71 (d, J = 8.4 Hz, 1H), 4.12 (d, J = 6.0 Hz, 3H), 4.05-4.01 (m, 1H), 3.57 (s, 3H), 3.46-3.43 (m, 1H), 2.87 (s, 3H), 1.10 (d, J = 6.4 Hz, 3H) |
| 479 | 489.0 | $^1$H NMR (400 MHz, DMSO-$d_6$) δ 12.41 (s, 1H), 8.68 (d, J = 6.0 Hz, 1H), 7.85 (d, J = 2.0 Hz, 1H), 7.81 (s, 1H), 7.75-7.69 (m, 1H), 7.64 (s, 1H), 7.41-7.34 (m, 1H), 7.34-7.31 (m, 1H), 7.22-7.15 (m, 1H), 6.79-6.77 (m, 1H), 4.14 (d, J = 6.0 Hz, 2H), 3.92-3.78 (m, 1H), 3.58 (s, 3H), 3.19 (s, 3H), 3.11-2.98 (m, 1H), 2.69-2.65 (m, 2H), 2.00-1.80 (m, 2H) |
| 480 | 489.0 | $^1$H NMR (400 MHz, DMSO-$d_6$) δ 12.39 (s, 1H), 8.68 (d, J = 5.6 Hz, 1H), 7.93-7.79 (m, 3H), 7.57 (s, 1H), 7.38-7.24 (m, 3H), 6.79-6.77 (m, 1H), 4.14 (d, J = 6.0 Hz, 2H), 3.85 (d, J = 6.8 Hz, 1H), 3.58 (s, 3H), 3.18 (s, 3H), 3.09-2.96 (m, 1H), 2.69-2.62 (m, 2H), 1.97-1.80 (m, 2H) |
| 486 | 516.1 | $^1$H NMR (400 MHz, Methanol-$d_4$) δ 8.56 (s, 1H), 7.85-7.84 (m, 1H), 7.33-7.27 (m, 2H), 7.22-7.21 (m, 1H), 7.13 (s, 1H), 7.08 (d, J = 7.6 Hz, 1H), 6.82-6.81 (m, 1H), 4.90-4.89 (m, 2H), 4.65-4.46 (m, 4H), 4.27 (s, 2H), 3.44 (s, 2H), 3.39 (s, 3H), 3.29-3.28 (m, 1H), 2.94-2.92 (m, 2H) |
| 487 | 510.0 | $^1$H NMR (400 MHz, DMSO-$d_6$) δ 12.34 (s, 1H), 8.66 (m, 1H), 7.85 (m, 1H), 7.51 (s, 1H), 7.34-7.29(m, 1H), 7.23-7.18 (m, 1H), 7.14-7.07 (m, 2H), 6.78 (m, 1H), 6.44-6.11 (m, 1H), 4.13 (d, J = 6.0 Hz, 2H), 3.57 (s, 3H), 3.54 (d, J = 4.8 Hz, 2H), 3.49 (s, 2H), 2.97 (m, 2H) |
| 489 | 461.9 | $^1$H NMR (400 MHz, DMSO-$d_6$) δ 12.47 (s, 1H), 8.71-8.67 (m, 1H), 8.24 (d, J = 5.6 Hz, 1H), 7.98 (s, 1H), 7.85-7.84 (m, 1H), 7.51-7.49 (m, 1H), 7.33-7.31 (m, 2H), 6.78-6.77 (m, 1H), 4.25-4.21 (m, 1H), 4.15 (d, J = 6.0 Hz, 2H), 3.58 (s, 3H), 0.80-0.74 (m, 2H), 0.73-0.70 (m, 2H) |
| 492 | 465.2 | $^1$H NMR (400 MHz, DMSO-$d_6$) δ 12.47 (s, 1H), 8.81-8.80 (d, J = 1.6 Hz, 1H), 8.47-8.37 (m, 2H), 8.20-8.17 (m, 1H), 8.03-7.95 (m, 2H), 7.52-7.51 (m, 1H), 6.97-6.96 (m, 1H), 6.48-6.47 (m, 1H), 4.11-4.10 (d, J = 5.6 Hz, 2H), 3.74 (s, 3H), 1.49 (s, 9H) |
| 494 | 465.2 | $^1$H NMR (400 MHz, DMSO-$d_6$) δ 12.43 (s, 1H), 8.72-8.71 (d, J = 2.0 Hz, 1H), 8.46-8.29 (m, 2H), 8.25-8.14 (m, 1H), 7.82 (s, 1H), 7.72-7.70 (d, J = 8.4 Hz, 1H), 7.52 (s, 1H), 6.97-6.96 (m, 1H), 6.48-6.48(m, 1H), 4.11-4.09 (d, J = 5.6 Hz, 2H), 3.55-3.48 (m, 3H), 1.49 (s, 9H) |
| 501 | 507.1 | $^1$H NMR (400 MHz, DMSO-$d_6$) δ 12.81-12.22 (m, 1H), 8.70-8.67 (m, 1H), 8.06-8.02 (m, 1H), 7.84 (s, 1H), 7.66 (d, J = 1.2 Hz, 1H), 7.57-7.53 (m, 1H), 7.44-7.42 (m, 1H), 7.31 (s, 1H), 6.77 (s, 1H), 4.14 (d, J = 5.6 Hz, 2H), 3.57 (s, 3H) |
| 507 | 493.2 | $^1$H NMR (400 MHz, DMSO-$d_6$) δ 12.46-12.39 (m, 1H), 8.71-8.65 (m, 1H), 7.86-7.84 (m, 1H), 7.56-7.51 (m, 2H), 7.31-7.30 (m, 1H), 7.18-7.14 (m, 1H), 7.00-6.96 (m, 1H), 6.77-6.76 (m, 1H), 4.79-4.75 (m, 1H), 4.13 (d, J = 6.0 Hz, 2H), 3.57 (s, 3H), 2.12-2.05 (m, 2H), 1.85-1.75 (m, 1H), 1.70-1.61 (m, 1H), 1.23-1.12 (m, 2H) |
| 508 | 479.1 | $^1$H NMR (400 MHz, DMSO-$d_6$) δ 12.31 (br s, 1H), 8.69-6.66 (m, 1H), 7.89-7.88 (m, 1H), 7.86-7.85 (m, 1H), 7.63 (s, 1H), 7.52-7.48 (m, 1H), 7.34-7.30 (m, 1H), 7.28-7.26 (m, 1H), 6.78-6.77 (m, 1H), 4.14-4.13 (m, 2H), 4.03-.00 (m, 1H), 3.58 (s, 3H), 0.91-0.80 (m, 2H), 0.79-0.72 (m, 2H) |
| 517 | 460.9 | $^1$H NMR (400 MHz, DMSO-$d_6$) δ 12.31 (s, 1H), 8.69-8.61 (m, 1H), 7.87-7.81 (m, 1H), 7.54 (s, 1H), 7.41-7.35 (m, 1H), 7.34-7.28 (m, 1H), 7.26-7.19 (m, 2H), 6.79-6.71 (m, 1H), 5.03-4.84 (m, 1H), 4.13 (d, J = 6.0 Hz, 2H), 3.57 (s, 3H), 3.46-3.40 (m, 1H), 2.81-2.72 (m, 1H), 1.39 (d, J = 6.0 Hz, 3H) |
| 527 | 460.9 | $^1$H NMR (400 MHz, DMSO-$d_6$) δ 12.35 (s, 1H), 8.70-8.63 (m, 1H), 7.88-7.81 (m, 1H), 7.55 (s, 1H), 7.42-7.35 (m, 1H), 7.35-7.29 (m, 1H), 7.26-7.19 (m, 2H), 6.81-6.75 (m, 1H), 5.01-4.87 (m, 1H), 4.20-4.08 (m, 2H), 3.57 (s, 3H), 3.33-3.27 (m, 1H), 2.81-2.72 (m, 1H), 1.40 (d, J = 6.4 Hz, 3H) |
| 530 | 489.1 | $^1$H NMR (400 MHz, DMSO-$d_6$) δ 12.38 (br s, 1H), 8.68-8.66 (m, 1H), 7.84-7.83 (m, 1H), 7.80 (s, 1H), 7.71 (d, J = 7.6 Hz, 1H), 7.64 (s, 1H), 7.37-7.36 (m, 1H), 7.31-7.30 (m, 1H), 7.23 (d, J = 7.6 Hz, 1H), 6.77-6.76 (m, 1H), 4.14 (d, J = 6.0 Hz, 2H), 4.09-4.02 (m, 1H), 3.63-3.53 (m, 4H), 3.22-3.15 (m, 3H), 2.44-2.29 (m, 4H) |

TABLE 5-continued

| Compound # | LC-MS data(m/z) | $^1$H NMR |
|---|---|---|
| 531 | 489.1 | $^1$H NMR (400 MHz, DMSO-$d_6$) δ 12.27 (br s, 1H), 8.70-8.67 (m, 1H), 7.88-7.81 (m, 3H), 7.57 (s, 1H), 7.36-7.30 (m, 3H), 6.78-6.77 (m, 1H), 4.14 (d, J = 5.6 Hz, 2H), 4.10-4.02 (m, 1H), 3.59-3.51 (m, 4H), 3.19 (s, 3H), 2.41-2.29 (m, 4H) |
| 544 | 465.1 | $^1$H NMR (400 MHz, DMSO-$d_6$) δ 12.35 (s, 1H), 8.68-8.66 (m, 1H), 7.84-7.83 (m, 1H), 7.66-7.46 (m, 3H), 7.38-7.24 (m, 1H), 6.77-6.76 (m, 1H), 4.69-4.65 (m, 2H), 4.12 (d, J = 6.0 Hz, 2H), 3.57 (s, 3H), 3.31-3.26 (m, 2H) |
| 546 | 494.1 | $^1$H NMR (400 MHz, DMSO-$d_6$) δ 12.35 (s, 1H), 8.67-8.64 (m, 1H), 7.84 (s, 1H), 7.53 (s, 1H), 7.31 (s, 1H), 7.06-7.03 (m, 2H), 6.77-6.76 (m, 1H), 4.30 (s, 2H), 4.12 (d, J = 5.6 Hz, 2H), 3.57 (s, 3H), 3.32-3.29 (m, 2H), 2.92 (s, 3H) |
| 565 | 477.9 | $^1$H NMR (400 MHz, DMSO-$d_6$) δ 12.45-12.08 (m, 1H), 8.66 (d, J = 6.0 Hz, 1H), 7.84 (d, J = 2.0 Hz, 1H), 7.72 (d, J = 8.0 Hz, 1H), 7.31-7.30 (m, 1H), 7.17 (d, J = 2.4 Hz, 1H), 6.77-6.76 (m, 1H), 6.41 (d, J = 8.4 Hz, 1H), 4.12 (d, J = 6.0 Hz, 2H), 3.57 (s, 3H), 3.45-3.38 (m, 2H), 2.99 (d, J = 8.4 Hz, 2H), 2.76 (s, 3H) |
| 566 | 487.9 | $^1$H NMR (400 MHz, DMSO-$d_6$) δ 12.35 (s, 1H), 8.69-8.63 (m, 1H), 7.85 (s, 1H), 7.57-7.39 (m, 1H), 7.32 (s, 1H), 7.17-6.96 (m, 2H), 6.91-6.70 (m, 2H), 4.13 (d, J = 4.4 Hz, 2H), 3.58 (s, 3H), 2.78 (s, 2H), 2.65 (s, 3H), 1.19 (s, 6H) |
| 569 | 478.0 | $^1$H NMR (400 MHz, DMSO-$d_6$) δ 12.38 (s, 1H), 8.68 (d, J = 6.0 Hz, 1H), 7.85 (d, J = 2.0 Hz, 1H), 7.63 (s, 1H), 7.33-7.31 (m, 1H), 7.01-6.92 (m, 1H), 6.88 (s, 1H), 6.78-6.77 (m, 1H), 4.13 (d, J = 5.6 Hz, 2H), 3.58 (s, 3H), 3.42-3.37 (m, 2H), 2.94 (d, J = 8.4 Hz, 2H), 2.77 (s, 3H) |
| 574 | 449.0 | $^1$H NMR (400 MHz, DMSO-$d_6$) δ 12.35 (br s, 1H), 8.69-8.66 (m, 1H), 7.85-7.84 (m, 1H), 7.50 (s, 1H), 7.47-7.42 (m, 2H), 7.32-7.31 (m, 1H), 6.97 (d, J = 8.4 Hz, 1H), 6.78-6.77 (m, 1H), 6.06 (s, 2H), 4.13 (d, J = 5.6 Hz, 2H), 3.61 (s, 3H) |
| 607 | 483.0 | $^1$H NMR (400 MHz, DMSO-$d_6$) δ 12.36 (s, 1H), 8.68-8.65 (m, 1H), 7.84-7.83 (m, 1H), 7.49 (s, 1H), 7.32-7.29 (m, 2H), 7.17 (s, 1H), 6.77-6.76 (m, 1H), 6.12 (s, 2H), 4.12 (d, J = 5.6 Hz, 2H), 3.57 (s, 3H) |
| 616 | 467.1 | $^1$H NMR (400 MHz, DMSO-$d_6$) δ 12.37 (s, 1H), 8.70-8.64 (m, 1H), 7.84-7.83 (m, 1H), 7.62 (s, 1H), 7.42-7.27 (m, 3H), 6.77-6.76 (m, 1H), 6.16 (s, 2H), 4.13 (d, J = 5.6 Hz, 2H), 3.57 (s, 3H) |
| 619 | 447.1 | $^1$H NMR (400 MHz, DMSO-$d_6$) δ 12.31 (s, 1H), 8.67-8.65 (m, 1H), 7.84 (s, 1H), 7.75 (s, 1H), 7.71-7.56 (m, 1H), 7.40 (s, 1H), 7.31-7.30 (m, 1H), 6.90-6.62 (m, 2H), 4.58-4.53 (m, 2H), 4.13 (d, J = 5.6 Hz, 2H), 3.57 (s, 3H), 3.24-3.19 (m, 2H) |
| 658 | 460.0 | $^1$H NMR (400 MHz, DMSO-$d_6$) δ 12.27 (s, 1H), 8.66 (d, J = 6.0 Hz, 1H), 7.85 (d, J = 2.0 Hz, 1H), 7.68-7.49 (m, 2H), 7.38-7.29 (m, 1H), 7.27 (s, 1H), 6.78-6.77 (m, 1H), 6.53 (d, J = 8.0 Hz, 1H), 4.13 (d, J = 6.0 Hz, 2H), 3.58 (s, 3H), 3.31-3.27 (m, 2H), 2.92 (d, J = 8.0 Hz, 2H), 2.74 (s, 3H) |
| 685 | 497.2 | $^1$H NMR (400 MHz, DMSO-$d_6$) δ 12.36 (s, 1H), 8.54 (d, J = 1.6 Hz, 1H), 8.28 (d, J = 2.8 Hz, 1H), 8.17 (d, J = 6.0 Hz, 1H), 7.79 (s, 1H), 7.75-7.66 (m, 1H), 7.51 (d, J = 2.0 Hz, 1H), 6.97 (d, J = 2.8 Hz, 1H), 6.48-6.46 (m, 1H), 4.09 (d, J = 6.0 Hz, 2H), 3.76-3.68 (m, 4H), 2.38-2.33 (m, 2H), 1.49 (s, 9H), 1.18 (d, J = 6.0 Hz, 6H) |
| 686 | 519.2 | $^1$H NMR (400 MHz, DMSO-$d_6$) δ 12.42 (s, 1H), 8.67 (d, J = 6.0 Hz, 1H), 8.55 (d, J = 1.6 Hz, 1H), 8.29 (d, J = 2.8 Hz, 1H), 7.87-7.82 (m, 1H), 7.80 (s, 1H), 7.73-7.67 (m, 1H), 7.32-7.30 (m, 1H), 6.78-6.76 (m, 1H), 4.13 (d, J = 6.0 Hz, 2H), 3.75-3.68 (m, 4H), 3.57 (s, 3H), 2.68-2.66 (m, 1H), 2.39-2.33 (m, 2H), 1.18 (d, J = 6.0 Hz, 6H) |
| 700 | 478.2 | $^1$H NMR (400 MHz, DMSO-$d_6$) δ 12.01 (s, 1H), 8.69-8.57 (m, 1H), 7.85-7.84 (m, 1H), 7.48-7.34 (m, 3H), 7.33-7.29 (m, 1H), 6.78-6.77 (m, 1H), 4.11 (d, J = 5.6 Hz, 2H), 3.58 (s, 3H), 3.31-3.27 (m, 2H), 3.00-2.96 (m, 2H), 2.90 (d, J = 1.2 Hz, 3H) |
| 701 | 453.1 | $^1$H NMR (400 MHz, DMSO-$d_6$) δ 12.43-12.40 (m, 1H), 8.70-8.65 (m, 1H), 7.86-7.77 (m, 2H), 7.34-7.27 (m, 3H), 6.82-6.74 (m, 2H), 4.15-4.12 (m, 2H), 3.83-3.81 (m, 3H), 3.57 (s, 3H) |
| 711 | 453.0 | $^1$H NMR (400 MHz, DMSO-$d_6$) δ 12.67-12.19 (m, 1H), 8.68 (s, 1H), 7.84 (s, 1H), 7.65-7.47 (m, 2H), 7.31 (s, 1H), 7.26-7.08 (m, 2H), 6.77 (s, 1H), 4.14-4.13 (m, 2H), 3.87 (s, 3H), 3.57 (s, 3H) |
| 715 | 448.1 | $^1$H NMR (400 MHz, DMSO-$d_6$) δ 12.48 (br s, 1H), 8.71-8.68 (m, 1H), 8.22 (s, 1H), 8.06 (d, J = 8.8 Hz, 1H), 7.99 (s, 1H), 7.85-7.81 (m, 2H), 7.32 (s, 1H), 6.78 (d, J = 0.8 Hz, 1H), 4.16 (d, J = 5.6 Hz, 2H), 3.58 (s, 3H) |
| 717 | 487.3 | $^1$H NMR (400 MHz, DMSO-$d_6$) δ 8.64 (t, J = 5.7 Hz, 1H), 7.84 (t, J = 2.0 Hz, 1H), 7.67 (dt, J = 7.7, 1.4 Hz, 1H), 7.62 (dd, J = 4.0, 2.2 Hz, 2H), 7.34-7.26 (m, 2H), 7.07 (dt, J = 7.8, 1.5 Hz, 1H), 6.77 (dd, J = 3.3, 1.7 Hz, 1H), 4.13 (d, J = 5.8 Hz, 2H), 3.91 (d, J = 8.4 Hz, 2H), 3.77-3.69 (m, 2H), 3.57 (s, 3H), 1.99 (dt, J = 2.7, 1.2 Hz, 2H), 1.79 (t, J = 3.6 Hz, 1H) |
| 718 | 453.0 | $^1$H NMR (400 MHz, DMSO-$d_6$) δ 12.42 (s, 1H), 8.69-8.66 (m, 1H), 7.85 (s, 1H), 7.71-7.61 (m, 2H), 7.48-7.47 (m, 1H), 7.36-7.20 (m, 2H), 6.78-6.77 (m, 1H), 4.14-4.13 (m, 2H), 3.91 (s, 3H), 3.58 (s, 3H) |

TABLE 5-continued

| Compound # | LC-MS data(m/z) | $^1$H NMR |
|---|---|---|
| 719 | 499.1 | $^1$H NMR (400 MHz, DMSO-$d_6$) δ 12.48-12.39 (m, 1H), 8.75-8.65 (m, 1H), 7.98-7.94 (m, 1H), 7.92-7.87 (m, 2H), 7.86-7.83 (m, 1H), 7.34-7.30 (m, 1H), 6.80-6.76 (m, 1H), 4.17-4.11 (m, 2H), 3.59-3.56 (m, 3H), 3.13-3.05 (m, 2H), 2.76-2.68 (m, 2H) |
| 720 | 481.2 | $^1$H NMR (400 MHz, DMSO-$d_6$) δ 12.53-11.94 (m, 1H), 8.71-8.65 (m, 1H), 8.09-8.02 (m, 2H), 7.86-7.82 (m, 1H), 7.75 (s, 1H), 7.46 (d, J = 8.4 Hz, 1H), 7.33-7.29 (m, 1H), 6.80-6.72 (m, 1H), 4.13 (d, J = 5.6 Hz, 2H), 3.57 (s, 3H), 3.06 (s, 2H), 2.65-2.56 (m, 2H) |
| 729 | 483.0 | $^1$H NMR (400 MHz, DMSO-$d_6$ + $D_2O$) δ 7.83 (d, J = 2.0 Hz, 1H), 7.54 (d, J = 2.4 Hz, 1H), 7.32-7.31 (m, 1H), 7.24-7.21 (m, 1H), 6.77-6.76 (m, 1H), 4.76 (d, J = 8.8 Hz, 2H), 4.13 (s, 2H), 3.54 (s, 3H), 3.32 (d, J = 8.8 Hz, 2H) |

Example 149. Preparation of Compounds of the Invention

The compounds in Table 6 below were synthesized starting from the appropriate common intermediate (tert-butyl (2-((4-bromothiazol-2-yl)amino)-2-oxoethyl)carbamate), the corresponding boronate ester, and heterocyclic carboxylic acid utilizing the synthetic protocols described in Example 12. Where appropriate SEC purification was used to separate enantiomers.

TABLE 6

| Compound # | LC-MS data(m/z) | $^1$H NMR |
|---|---|---|
| 268 | 528.2 | $^1$H NMR (400 MHz, DMSO-$d_6$) δ 12.37 (s, 1H), 8.29-8.26 (m, 1H), 7.65-7.59 (m, 1H), 7.57-7.56 (m, 1H), 7.52 (d, J = 2.4 Hz, 1H), 7.21-7.27 (m, 1H), 7.05-6.99 (m, 2H), 6.57-6.56 (m, 1H), 4.84 (d, J = 6.8 Hz, 2H), 4.62 (d, J = 6.8 Hz, 2H), 4.10 (d, J = 6.0 Hz, 2H), 3.82-3.73 (m, 2H), 3.31-3.25 (m, 2H), 2.42-2.37 (m, 2H), 1.79 (s, 3H), 1.14 (s, 3H), 1.12 (s, 3H) |
| 269 | 514.2 | $^1$H NMR (400 MHz, DMSO-$d_6$) δ 12.34 (s, 1H), 8.20-8.17 (m, 1H), 7.67-7.57 (m, 1H), 7.52 (d, J = 2.0 Hz, 2H), 7.20-7.16 (m, 1H), 7.05-6.99 (m, 1H), 6.98-6.96 (m, 1H), 6.48-6.47 (m, 1H), 4.09 (d, J = 6.0 Hz, 2H), 3.82-3.73 (m, 2H), 3.26 (d, J = 11.2 Hz, 2H), 2.42-2.37 (m, 2H), 1.49 (s, 9H), 1.14 (s, 3H), 1.12 (s, 3H) |
| 271 | 439.3 | $^1$H NMR (400 MHz, DMSO-$d_6$) δ 12.21 (s, 1H), 8.24 (s, 1H), 7.57-7.56 (m, 2H), 7.41-7.39 (m, 1H), 7.28-7.26 (m, 2H), 7.02 (s, 1H), 6.57 (s, 1H), 4.86-4.84 (d, J = 6.0 Hz, 2H), 4.64-4.62 (d, J = 6.0 Hz, 2H), 4.58-4.54 (d, J = 8.0 Hz, 2H), 4.11-4.10 (d, J = 4.0 Hz, 2H), 3.21-3.17 (d, J = 8.0 Hz, 2H), 1.80 (s, 3H) |
| 296 | 486.2 | $^1$H NMR (400 MHz, DMSO-$d_6$) δ 12.45-12.41 (m, 1H), 8.69-8.66 (m, 1H), 8.38 (s, 1H), 8.01 (d, J = 8.0 Hz, 1H), 7.84-7.77 (m, 3H), 7.61-7.57 (m, 1H), 7.32-7.30 (m, 1H), 6.92 (s, 1H), 6.78-6.77 (m, 1H), 4.15 (d, J = 6.0 Hz, 2H), 3.57 (s, 3H), 2.31 (s, 3H) |
| 302 | 493.2 | $^1$H NMR (400 MHz, DMSO-$d_6$) δ 12.83-12.00 (m, 1H), 8.70 (d, J = 5.2 Hz, 1H), 7.85 (s, 1H), 7.66 (d, J = 1.6 Hz, 1H), 7.48 (s, 2H), 7.39-7.26 (m, 2H), 6.90 (br d, J = 8.2 Hz, 1H), 6.78 (d, J = 1.6 Hz, 1H), 4.85-4.47 (m, 1H), 4.14 (d, J = 4.8 Hz, 2H), 3.76 (s, 2H), 3.57 (d, J = 1.2 Hz, 3H), 1.23 (s, 6H) |
| 305 | 452.1 | $^1$H NMR (400 MHz, DMSO-$d_6$) δ 12.31-12.17 (m, 1H), 8.13-5.15 (m, 1H), 7.51-7.50 (m, 1H), 7.45 (s, 1H), 7.08 (s, 1H), 7.05-7.054(m, 1H), 6.96-6.95 (m, 1H), 6.91 (d, J = 7.6 Hz, 1H), 6.47-6.46 (m, 1H), 4.07 (d, J = 6.0 Hz, 2H), 3.21 (d, J = 6.0 Hz, 2H), 2.88 (s, 3H), 2.70 (d, J = 6.0 Hz, 2H), 1.93-1.86 (m, 2H), 1.49 (s, 9H) |
| 306 | 474.0 | $^1$H NMR (400 MHz, DMSO-$d_6$) δ 12.32 (br s, 1H), 8.64-8.62 (m, 1H), 7.83-7.83 (m, 1H), 7.46 (s, 1H), 7.34-7.27 (m, 1H), 7.08 (s, 1H), 7.05 (d, J = 7.8 Hz, 1H), 6.91 (d, J = 7.6 Hz, 1H), 6.77-6.76 (m, 1H), 4.12 (d, J = 6.0 Hz, 2H), 3.56 (s, 3H), 3.22-3.19 (m, 2H), 2.88 (s, 3H), 2.70 (d, J = 6.4 Hz, 2H), 1.94-1.85 (m, 2H) |
| 431 | 488.0 | $^1$H NMR (400 MHz, DMSO-$d_6$ + $D_2O$) δ 7.80 (s, 1H), 7.61 (s, 1H), 7.56-7.51 (m, 2H), 7.30-7.29 (m, 1H), 7.26 (d, J = 7.6 Hz, 1H), 6.76 (d, J = 1.6 Hz, 1H), 4.11 (s, 2H), 3.50 (s, 3H), 3.29 (s, 3H), 2.88-2.83 (m, 2H), 2.55 (s, 2H) |
| 469 | 488.2 | $^1$H NMR (400 MHz, DMSO-$d_6$) δ 12.33 (s, 1H), 8.67-8.66 (m, 1H), 7.85-7.84 (m, 1H), 7.47 (s, 1H), 7.32-7.30 (m, 1H), 7.10-7.08 (m, 1H), 7.06-7.03 (m, 1H), 6.96 (s, 1H), 6.78-6.77 (m, 1H), 4.13 (d, J = 5.6 Hz, 2H), 3.89-3.84 (m, 1H), 3.57 (s, 3H), 3.31-3.29 (m, 2H), 2.88-2.84 (m, 2H), 1.12 (d, J = 6.8 Hz, 6H) |

TABLE 6-continued

| Compound # | LC-MS data(m/z) | $^1$H NMR |
|---|---|---|
| 475 | 473.2 | $^1$H NMR (400 MHz, DMSO-d$_6$) δ 12.46 (s, 1H), 8.82 (d, J = 1.6 Hz, 1H), 8.38-8.35 (m, 1H), 8.22-8.19 (m, 1H), 7.78 (s, 1H), 7.71 (d, J = 8.0 Hz, 1H), 7.61-7.60 (m, 1H), 7.49 (d, J = 7.2 Hz, 1H), 7.08-7.07 (m, 1H), 6.64 (d, J = 7.2 Hz, 1H), 6.57-6.56 (m, 1H), 4.12 (d, J = 5.6 Hz, 2H), 3.53 (s, 3H), 1.84-1.73 (m, 4H) |
| 483 | 495.2 | $^1$H NMR (400 MHz, DMSO-d$_6$) δ 12.38 (s, 1H), 8.69-8.67 (m, 1H), 7.84-7.81 (m, 1H), 7.68 (s, 1H), 7.52-7.50 (m, 2H), 7.37-7.35 (m, 1H), 7.32-7.31 (m, 1H), 6.97-6.91 (m, 1H), 6.78-6.77 (m, 1H), 4.14 (d, J = 5.6 Hz, 2H), 4.08 (d, J = 20.0 Hz, 2H), 3.57 (s, 3H), 1.48 (s, 3H), 1.42 (s, 3H) |
| 484 | 487.3 | $^1$H NMR (400 MHz, DMSO-d$_6$) δ 12.32 (s, 1H), 8.26-8.23 (m, 1H), 7.67 (s, 1H), 7.57-7.56 (m, 1H), 7.50-7.47 (m, 2H), 7.39-7.34 (m, 1H), 7.02-7.01 (m, 1H), 6.96-6.94 (m, 1H), 6.57-6.56 (m, 1H), 4.85 (d, J = 6.8 Hz, 2H), 4.63 (d, J = 6.8 Hz, 2H), 4.12 (d, J = 6.0 Hz, 2H), 4.08 (d, J = 19.6 Hz, 2H), 1.79 (s, 3H), 1.48 (s, 3H), 1.42 (s, 3H) |
| 499 | 478.2 | $^1$H NMR (400 MHz, DMSO-d$_6$) δ 8.67 (d, J = 4.8 Hz, 1H), 7.84 (d, J = 1.6 Hz, 1H), 7.45 (s, 1H), 7.34-7.30 (m, 2H), 7.07-7.05(m, 1H), 6.77 (d, J = 1.6 Hz, 1H), 6.53-6.50 (m, 1H), 4.13 (d, J = 4.8 Hz, 2H), 3.95-3.92 (m, 4H), 3.57 (d, J = 1.2 Hz, 3H), 2.31-2.28 (m, 2H) |
| 502 | 509.1 | $^1$H NMR (400 MHz, DMSO-d$_6$) δ 12.39 (s, 1H), 8.69-8.67 (m, 1H), 7.84-7.83 (m, 1H), 7.69 (s, 1H), 7.54-7.52 (m, 2H), 7.37-7.36 (m, 1H), 7.32-7.31 (m, 1H), 6.98-6.94 (m, 1H), 6.77-6.76 (m, 1H), 4.78-4.69 (m, 4H), 4.50 (s, 1H), 4.44 (s, 1H), 4.14 (d, J = 6.0 Hz, 2H), 3.57 (s, 3H) |
| 509 | 487.1 | $^1$H NMR (400 MHz, DMSO-d$_6$) δ 12.30 (s, 1H), 8.19-8.17 (m, 1H), 7.68 (s, 1H), 7.55-7.51 (m, 3H), 7.37-7.35 (m, 1H), 6.98-6.95 (m, 2H), 6.48-6.47(m, 1H), 4.77-4.68 (m, 4H), 4.51-4.45 (m, 2H), 4.10 (d, J = 6.0 Hz, 2H), 1.50 (s, 9H) |
| 510 | 470.0 | $^1$H NMR (400 MHz, DMSO-d$_6$) δ 12.33-12.22 (m, 1H), 8.24-8.22 (m, 1H), 7.56-7.55 (m, 1H), 7.52 (s, 1H), 7.21-7.19 (m, 1H), 7.09-7.00 (m, 3H), 6.56-6.55 (m, 1H), 4.84 (d, J = 6.4 Hz, 2H), 4.63 (d, J = 6.8 Hz, 2H), 4.10 (d, J = 5.6 Hz, 2H), 3.95-3.91 (m, 4H), 2.32-2.26 (m, 2H), 1.78 (s, 3H) |
| 511 | 478.0 | $^1$H NMR (400 MHz, DMSO-d$_6$) δ 13.10-10.81 (m, 1H), 8.67-8.66 (m, 1H), 7.84-7.83 (m, 1H), 7.54 (s, 1H), 7.31-7.30 (m, 1H), 7.22-7.20 (m, 1H), 7.06-7.01 (m, 2H), 6.77-6.76 (m, 1H), 4.13 (d, J = 5.6 Hz, 2H), 3.92-3.91 (m, 4H), 3.57 (s, 3H), 2.33-2.26 (m, 2H) |
| 516 | 465.1 | $^1$H NMR (400 MHz, DMSO-d$_6$) δ 12.33 (s, 1H), 8.35-8.34 (m, 1H), 7.59-7.58 (m, 1H), 7.53 (s, 1H), 7.21-7.20 (m, 1H), 7.09-7.01 (m, 3H), 6.55-6.55 (m, 1H), 4.10 (d, J = 6.0 Hz, 2H), 3.95-3.91 (m, 4H), 2.32-2.28 (m, 2H), 1.84-1.73 (m, 4H) |
| 518 | 477.9 | 1H NMR (400 MHz, DMSO-d$_6$) δ 8.67-8.64 (m, 1H), 7.84-7.83 (m, 1H), 7.67 (s, 1H), 7.34-7.29 (m, 1H), 6.96 (d, J = 10.0 Hz, 1H), 6.77 (d, J = 1.2 Hz, 2H), 6.17-6.13 (m, 1H), 4.13 (d, J = 6.0 Hz, 2H), 3.87-3.84 (m, 4H), 3.57 (s, 3H), 2.36-2.29 (m, 2H) |
| 519 | 470.0 | $^1$H NMR (400 MHz, DMSO-d$_6$) δ 8.25-8.22 (m, 1H), 7.66 (s, 1H), 7.56-7.55 (m, 1H), 7.01-7.00 (m, 1H), 6.96 (d, J = 10.4 Hz, 1H), 6.77 (d, J = 1.6 Hz, 1H), 6.56-6.55 (m, 1H), 6.16-6.14 (m, 1H), 4.84 (d, J = 6.4 Hz, 2H), 4.62 (d, J = 6.8 Hz, 2H), 4.10 (d, J = 6.0 Hz, 2H), 3.87-3.84 (m, 4H), 2.36-2.29 (m, 2H), 1.79 (s, 3H) |
| 521 | 465.0 | $^1$H NMR (400 MHz, DMSO-d$_6$) δ 12.55-12.17 (m, 1H), 8.36-8.33 (m, 1H), 7.66 (s, 1H), 7.59-7.58 (m, 1H), 7.07-7.06 (m, 1H), 6.96 (d, J = 9.6 Hz, 1H), 6.77 (s, 1H), 6.55-6.54 (m, 1H), 6.17-6.13 (m, 1H), 4.09 (d, J = 6.0 Hz, 2H), 3.87-3.83 (m, 4H), 2.36-2.28 (m, 2H), 1.85-1.79 (m, 2H), 1.78-1.70 (m, 2H) |
| 524 | 465.1 | $^1$H NMR (400 MHz, DMSO-d$_6$) δ 12.34 (s, 1H), 8.37-8.35 (m, 1H), 7.60-7.59 (m, 1H), 7.44 (d, J = 2.4 Hz, 1H), 7.36-7.32 (m, 1H), 7.07-7.06 (m, 2H), 6.56-6.55 (m, 1H), 6.54-6.51 (m, 1H), 4.10 (d, J = 6.0 Hz, 2H), 3.95-3.92 (m, 4H), 2.32-2.29 (m, 2H), 1.82-1.80 (m, 2H), 1.76-1.74 (m, 2H) |
| 525 | 470.1 | $^1$H NMR (400 MHz, DMSO-d$_6$) δ 12.33 (s, 1H), 8.26-8.24 (m, 1H), 7.56-7.54 (m, 1H), 7.44 (d, J = 2.4 Hz, 1H), 7.32-7.30 (m, 1H), 7.07-7.06 (m, 1H), 7.01-7.00 (m, 1H), 6.56-6.55 (m, 1H), 6.54-6.49 (m, 1H), 4.84 (d, J = 6.4 Hz, 2H), 4.62 (d, J = 6.8 Hz, 2H), 4.10 (d, J = 6.0 Hz, 2H), 3.95-3.92 (m, 4H), 2.31-2.26 (m, 2H), 1.78 (s, 3H) |
| 528 | 496.1 | $^1$H NMR (400 MHz, DMSO-d$_6$) δ 12.34 (s, 1H), 8.37-8.36 (m, 1H), 7.68 (s, 1H), 7.60-7.59 (m, 1H), 7.53-7.52 (m, 2H), 7.37-7.36 (m, 1H), 7.08-7.06 (m, 1H), 6.97-6.96 (m, 1H), 6.56-6.55 (m, 1H), 4.78-4.74 (m, 2H), 4.73-4.69 (m, 2H), 4.50-4.45 (m, 2H), 4.11 (d, J = 6.0 Hz, 2H), 1.84-1.79 (m, 2H), 1.76-1.72 (m, 2H) |
| 547 | 457.1 | $^1$H NMR (400 MHz, DMSO-d$_6$) δ 12.35 (s, 1H), 8.19-8.17 (m, 1H), 7.60-7.56 (m, 1H), 7.51-7.50 (m, 2H), 7.40-7.36 (m, 1H), 7.25-7.21 (m, 1H), 6.97-6.96 (m, 1H), 6.47-6.46 (m, 1H), 4.09 (d, J = 5.6 Hz, 2H), 3.00-2.95 (m, 1H), 1.48 (s, 9H), 0.84-0.78 (m, 2H), 0.77-0.71 (m, 2H) |
| 548 | 471.1 | $^1$H NMR (400 MHz, DMSO-d$_6$) δ 12.38 (s, 1H), 8.28-8.25 (m, 1H), 7.60-7.55 (m, 2H), 7.51 (d, J = 2.4 Hz, 1H), 7.41-7.36 (m, 1H), 7.25-7.21 (m, 1H), 7.02-7.00 (m, 1H), 6.56-6.55 (m, 1H), 4.84 (d, J = 6.4 Hz, 2H), 4.62 (d, J = 7.2 Hz, 2H), 4.11 (d, J = 6.0 Hz, 2H), 4.00-3.95 (m, 1H), 1.78 (s, 3H), 0.84-0.78 (m, 2H), 0.77-0.71 (m, 2H) |

TABLE 6-continued

| Compound # | LC-MS data(m/z) | $^1$H NMR |
|---|---|---|
| 553 | 475.9 | $^1$H NMR (400 MHz, DMSO-$d_6$) δ 12.41 (br s, 1H), 8.37-8.36 (m, 1H), 7.94 (d, J = 8.0 Hz, 1H), 7.86 (s, 1H), 7.81 (s, 1H), 7.61-7.55 (m, 2H), 7.36-7.29 (m, 1H), 7.09-7.06 (m, 1H), 6.56-6.54 (m, 1H), 4.10 (d, J = 6.0 Hz, 2H), 1.85-1.78 (m, 2H), 1.78-1.72 (m, 2H) |
| 555 | 465.9 | $^1$H NMR (400 MHz, DMSO-$d_6$) δ 12.37 (s, 1H), 8.38-8.35 (m, 1H), 7.76 (s, 1H), 7.60-7.59 (m, 1H), 7.42 (d, J = 1.6 Hz, 1H), 7.36-7.27 (m, 1H), 7.07-7.06 (m, 1H), 6.90-6.86 (m, 1H), 6.55-6.54 (m, 1H), 4.10 (d, J = 6.0 Hz, 2H), 3.95-3.91 (m, 1H), 1.85-1.78 (m, 2H), 1.78-1.71 (m, 2H), 0.86-0.79 (m, 2H), 0.73-0.67 (m, 2H) |
| 556 | 466.1 | $^1$H NMR (400 MHz, DMSO-$d_6$) δ 12.37 (s, 1H), 8.37-8.34 (m, 1H), 7.60-7.56 (m, 2H), 7.50 (d, J = 2.0 Hz, 1H), 7.40-7.36 (m, 1H), 7.25-7.21 (m, 1H), 7.07-7.06 (m, 1H), 6.56-6.55 (m, 1H), 4.11 (d, J = 5.6 Hz, 2H), 4.00-3.95 (m, 1H), 1.84-1.79 (m, 2H), 1.77-1.72 (m, 2H), 0.84-0.78 (m, 2H), 0.77-0.71 (m, 2H) |
| 571 | 454.3 | $^1$H NMR (400 MHz, DMSO-$d_6$) δ 8.41-8.31 (m, 1H), 7.72-7.64 (m, 2H), 7.28-7.11 (m, 3H), 6.63-6.58 (m, 1H), 4.70-4.59 (m, 2H), 4.15-4.07 (m, 2H), 3.26-3.19 (m, 2H), 1.99-1.92 (m, 6H) |
| 575 | 481.1 | $^1$H NMR (400 MHz, DMSO-$d_6$) δ 12.41 (br s, 1H), 8.69-8.68 (m, 1H), 7.84-7.82 (m, 1H), 7.82-7.80 (m, 2H), 7.67 (s, 1H), 7.41-7.32 (m, 1H), 7.32-7.31 (m, 1H), 7.25 (d, J = 7.6 Hz, 1H), 6.78-6.77 (m, 1H), 4.14 (d, J = 5.6 Hz, 2H), 3.57 (s, 3H), 3.09-3.02 (m, 1H), 2.03-1.96 (m, 2H) |
| 576 | 481.1 | $^1$H NMR (400 MHz, DMSO-$d_6$) δ 12.41 (br s, 1H), 8.69-8.66 (m, 1H), 7.84-7.82 (m, 1H), 7.82-7.80 (m, 2H), 7.67 (s, 1H), 7.40-7.32 (m, 1H), 7.31-7.30 (m, 1H), 7.24 (d, J = 7.6 Hz, 1H), 6.78-6.76 (m, 1H), 4.14 (d, J = 6.0 (Hz, 2H), 3.57 (s, 3H), 3.08-3.02 (m, 1H), 2.03-1.95 (m, 2H) |
| 590 | 465.1 | $^1$H NMR (400 MHz, DMSO-$d_6$) δ 12.28 (s, 1H), 8.39-8.26 (m, 1H), 7.71-7.65 (m, 1H), 7.40 (s, 1H), 7.20 (d, J = 2.0 Hz, 1H), 7.16-7.14 (m, 1H), 7.13-7.09 (m, 1H), 6.69 (d, J = 8.0 Hz, 1H), 6.63-6.58 (m, 1H), 4.29-4.21 (m, 2H), 4.10 (d, J = 6.0 Hz, 2H), 3.28-3.22 (m, 2H), 2.88 (s, 3H), 1.98-1.90 (m, 6H) |
| 722 | 464.2 | $^1$H NMR (400 MHz, DMSO-$d_6$) δ 12.49 (s, 1H), 8.73-8.69 (m, 1H), 8.33-8.32 (m, 1H), 8.28-8.27 (m, 1H), 8.05-7.98 (m, 2H), 7.85-7.83 (m, 1H), 7.32-7.30 (m, 1H), 6.78-6.76 (m, 1H), 4.14 (d, J = 5.6 Hz, 2H), 3.58 (s, 3H) |
| 784 | 465.9 | $^1$H NMR (400 MHz, DMSO-$d_6$) δ 12.32 (s, 1H), 8.40-8.33 (m, 1H), 8.13 (d, J = 1.6 Hz, 1H), 8.09 (d, J = 1.6 Hz, 1H), 7.41 (s, 1H), 7.20 (d, J = 2.0 Hz, 1H), 7.14-7.10 (m, 1H), 6.69 (d, J = 8.4 Hz, 1H), 4.29-4.21 (m, 2H), 4.15 (d, J = 6.0 Hz, 2H), 3.28-3.22 (m, 2H), 2.88 (s, 3H), 2.02 (s, 6H) |
| 785 | 455.1 | $^1$H NMR (400 MHz, DMSO-$d_6$) δ 12.44-11.82 (m, 1H), 8.37-8.34 (m, 1H), 8.12-8.08 (m, 2H), 7.68 (s, 1H), 7.26-7.11 (m, 2H), 4.66-4.61 (m, 2H), 4.16 (d, J = 6.0 Hz, 2H), 3.26-3.21 (m, 2H), 2.02 (s, 6H) |
| 787 | 466.0 | $^1$H NMR (400 MHz, DMSO-$d_6$) δ 12.51-12.13 (m, 1H), 8.52-8.43 (m, 1H), 8.16 (d, J = 2.4 Hz, 1H), 7.42 (s, 1H), 7.20 (d, J = 1.6 Hz, 1H), 7.15-7.09 (m, 1H), 6.80 (d, J = 2.4 Hz, 1H), 6.70 (d, J = 8.0 Hz, 1H), 4.29-4.21 (m, 2H), 4.17 (d, J = 6.0 Hz, 2H), 3.27-3.24 (m, 2H), 2.88 (s, 3H), 2.04 (s, 6H) |
| 788 | 452.9 | $^1$H NMR (400 MHz, DMSO-$d_6$) δ 12.37 (s, 1H), 8.39-8.31 (m, 1H), 8.14 (d, J = 1.6 Hz, 1H), 8.04 (d, J = 1.6 Hz, 1H), 7.69 (s, 1H), 7.27-7.13 (m, 2H), 4.67-4.61 (m, 2H), 4.15 (d, J = 6.0 Hz, 2H), 3.28-3.20 (m, 2H), 1.93-1.77 (m, 4H) |
| 791 | 455.1 | $^1$H NMR (400 MHz, DMSO-$d_6$) δ 12.96-11.77 (m, 1H), 8.48 (s, 1H), 8.16 (d, J = 2.4 Hz, 1H), 7.68 (s, 1H), 7.32-7.10 (m, 2H), 6.79 (d, J = 2.6 Hz, 1H), 4.64 (d, J = 8.8 Hz, 2H), 4.16 (d, J = 6.0 Hz, 2H), 3.26-3.19 (m, 2H), 2.04 (s, 6H) |
| 794 | 477.1 | $^1$H NMR (400 MHz, DMSO-$d_6$) δ 12.46 (d, J = 0.8 Hz, 1H), 8.64-8.61 (m, 1H), 8.17 (d, J = 2.4 Hz, 1H), 7.94 (d, J = 8.0 Hz, 1H), 7.88-7.82 (m, 2H), 7.59-7.55 (m, 1H), 7.33-7.31 (m, 1H), 6.75 (d, J = 2.4 Hz, 1H), 4.15 (d, J = 6.0 Hz, 2H), 1.99-1.95 (m, 2H), 1.91-1.88 (m, 2H) |
| 796 | 467.1 | $^1$H NMR (400 MHz, DMSO-$d_6$) δ 12.41 (s, 1H), 8.62-8.59 (m, 1H), 8.16 (d, J = 2.8 Hz, 1H), 7.77 (s, 1H), 7.49-7.36 (m, 1H), 7.34-7.28 (m, 1H), 6.90-6.86 (m, 1H), 6.75 (d, J = 2.4 Hz, 1H), 4.16 (d, J = 6.0 Hz, 2H), 3.95-3.89 (m, 1H), 1.99-1.86 (m, 4H), 0.86-0.78 (m, 2H), 0.75-0.66 (m, 2H) |
| 803 | 453.1 | $^1$H NMR (400 MHz, DMSO-$d_6$) δ 12.39 (s, 1H), 8.60 (d, J = 6.0 Hz, 1H), 8.16 (d, J = 2.4 Hz, 1H), 7.70 (s, 1H), 7.27-7.11 (m, 2H), 6.74 (d, J = 2.4 Hz, 1H), 4.64 (d, J = 8.8 Hz, 2H), 4.15 (d, J = 6.0 Hz, 2H), 3.24 (d, J = 8.4 Hz, 2H), 2.02-1.83 (m, 4H) |
| 811 | 464.1 | $^1$H NMR (400 MHz, DMSO-$d_6$) δ 12.35 (s, 1H), 8.66-8.53 (m, 1H), 8.17 (d, J = 2.4 Hz, 1H), 7.41 (s, 1H), 7.21 (d, J = 2.0 Hz, 1H), 7.15-7.10 (m, 1H), 6.75 (d, J = 2.4 Hz, 1H), 6.70 (d, J = 8.0 Hz, 1H), 4.29-4.22 (m, 2H), 4.15 (d, J = 6.0 Hz, 2H), 3.29-3.23 (m, 2H), 2.89 (s, 3H), 2.00-1.88 (m, 4H) |

Example 150. Preparation of cis-4-[3-fluoro-5-(4,4,5,5-tetramethyl-1,3,2-dioxaborolan-2-yl)phenyl]-2,6-dimethyl-morpholine

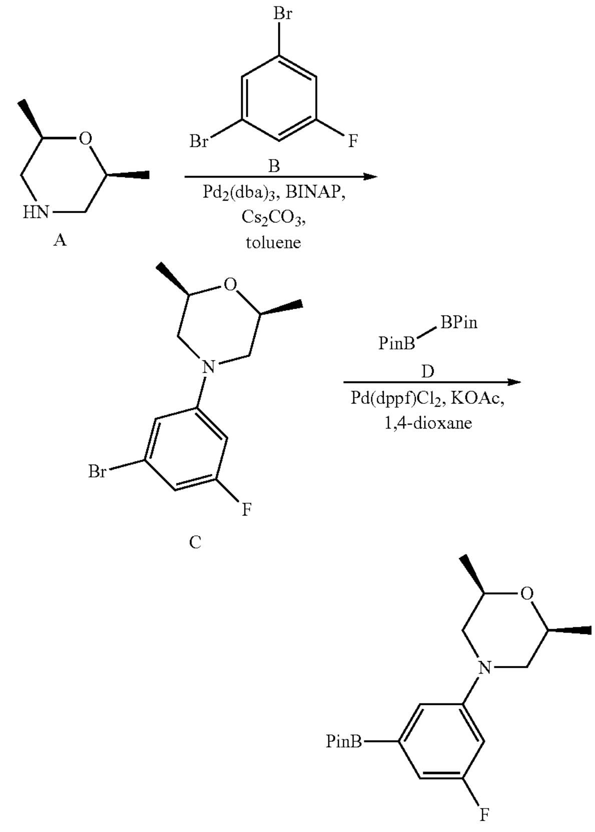

A

C

E

Step 1: Preparation of cis-4-(3-bromo-5-fluoro-phenyl)-2,6-dimethyl-morpholine (Intermediate C)

C

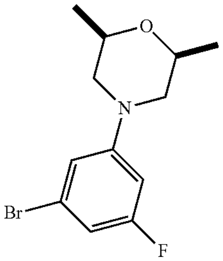

A mixture of 1,3-dibromo-5-fluoro-benzene (6 g, 23.63 mmol, 2.97 mL), cis-2,6-dimethylmorpholine (2.72 g, 23.63 mmol), $Pd_2(dba)_3$ (2.16 g, 2.36 mmol), BINAP (2.94 g, 4.73 mmol), $Cs_2CO_3$ (23.10 g, 70.90 mmol) in toluene (60 mL) was stirred at 80° C. under $N_2$ for 16 h. The reaction mixture was diluted with water (50 mL) and extracted with EA (50 mL*3). The combined organic layers were dried over $Na_2SO_4$, filtered and concentrated under reduced pressure to give a residue. The residue was purified by column chromatography (Petroleum ether/Ethyl acetate=100/1 to 5/1). The solution was concentrated under reduced pressure to give Intermediate C (4 g, 13.59 mmol, 57.5% yield, 97.9% purity) as a yellow oil. LCMS (ESI) m/z: $[^{81}Br\ M+H]^+$=289.7.

Step 2: Preparation of cis-4-[3-fluoro-5-(4,4,5,5-tetramethyl-1,3,2-dioxaborolan-2-yl)phenyl]-2,6-dimethyl-morpholine (Intermediate E)

E

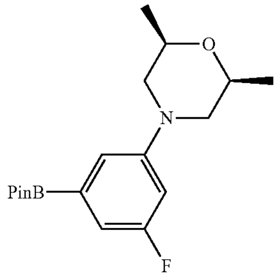

The general protocol for borylation of Ar—Br or HetAr—Br was followed for the synthesis of cis-4-[3-fluoro-5-(4,4,5,5-tetramethyl-1,3,2-dioxaborolan-2-yl)phenyl]-2,6-dimethyl-morpholine. The following quantities of Intermediate C (5 g, 17.35 mmol), 4,4,5,5-tetramethyl-2-(4,4,5,5-tetramethyl-1,3,2-dioxaborolan-2-yl)-1,3,2-dioxaborolane (6.87 g, 27.05 mmol) 1,4-dioxane (50 mL), $Pd(dppf)Cl_2$ (1.52 g, 2.08 mmol), and KOAc (6.13 g, 62.46 mmol) was used to yield Intermediate E (5.3 g, 15.62 mmol, 90.0% yield, 98.8% purity) as a yellow oil. LCMS (ESI) m/z: $[M+H]^+$=336.1; $^1H$ NMR (400 MHz, Methanol-$d_4$) δ 7.10 (d, J=2.4 Hz, 1H), 6.84-6.82 (m, 1H), 6.79-6.75 (m, 1H), 3.79-3.72 (m, 2H), 3.54 (d, J=11.6 Hz, 2H), 2.35-2.30 (m, 2H), 1.34 (s, 12H), 1.23 (d, J=6.4 Hz, 6H).

Example 151. Preparation of 4,4,5,5-tetramethyl-2-(2-methyl-2,3-dihydrobenzofuran-6-yl)-1,3,2-dioxaborolane

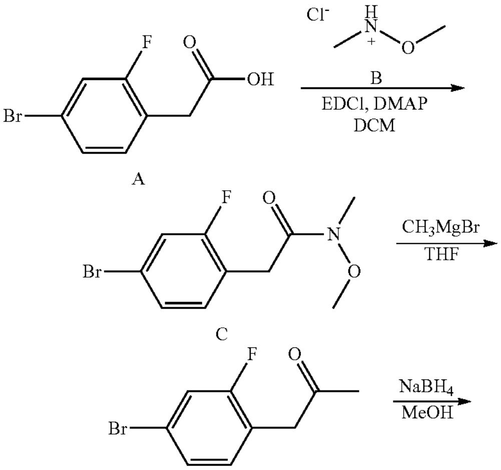

A

C

D

-continued

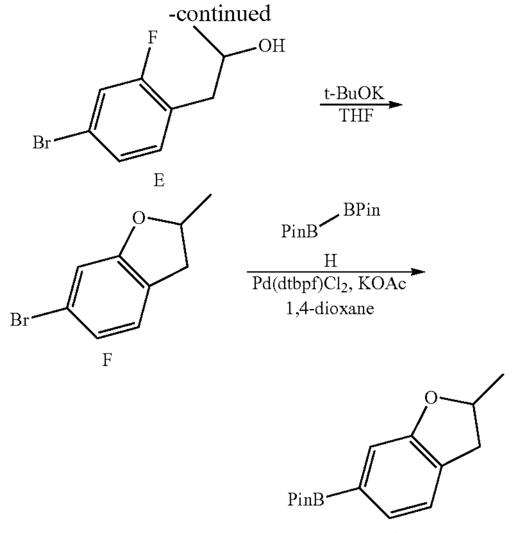

E

F

G

Step 1: Preparation of 2-(4-bromo-2-fluorophenyl)-N-methoxy-N-methylacetamide (Intermediate C)

C

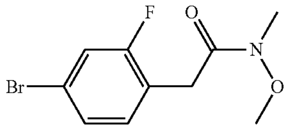

A mixture of 2-(4-bromo-2-fluoro-phenyl)acetic acid (9.00 g, 38.62 mmol), N-methoxymethanamine hydrochloride (11.30 g, 115.86 mmol), EDCI (11.11 g, 57.93 mmol) and DMAP (7.08 g, 57.93 mmol) in dichloromethane (180 mL) was stirred. After stirring for 12 h, the reaction mixture was diluted with water (100 mL) and the aqueous layer was extracted with ethyl acetate (30 mL×2). The combined organic layers were dried over $Na_2SO_4$ and concentrated. The residue was purified by flash silica gel chromatography (petroleum ether/ethyl acetate=0/1 to 1/0) and concentrated under vacuum to give Intermediate C (10.00 g, 28.97 mmol, 75.0% yield, 80.0% purity) as a colorless oil. $^1$H NMR (400 MHz, DMSO-$d_6$) δ 7.55-7.49 (m, 1H), 7.40-7.35 (m, 1H), 7.32-7.24 (m, 1H), 3.79 (s, 2H), 3.72 (s, 3H), 3.12 (s, 3H).

Step 2: Preparation of 1-(4-bromo-2-fluoro-phenyl)propan-2-one (Intermediate D)

D

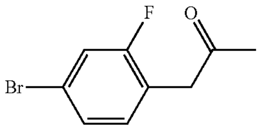

To a cooled (0° C.) solution of Intermediate C (10.00 g, 36.22 mmol) in THF (100 mL) was added dropwise a 3 M solution of bromo(methyl)magnesium (60.36 mL). After stirring for 1.5 h, the reaction mixture was quenched with a mixture of MeOH (10.0 mL) and 1 M HCl solution (100 mL). The mixture was extracted with ethyl acetate (100 mL×3), the organic layer was concentrated. The residue was purified by flash silica gel chromatography (petroleum ether/ethyl acetate=0/1 to 1/3) to give Intermediate D (3.40 g, 14.71 mmol, 40.6% yield) as a yellow oil. $^1$H NMR (400 MHz, $CDCl_3$) δ 7.32-7.22 (m, 2H), 7.06 (d, J=8.0 Hz, 1H), 3.71 (s, 2H), 2.23 (s, 3H).

Step 3: Preparation of 1-(4-bromo-2-fluoro-phenyl)propan-2-ol (Intermediate E)

E

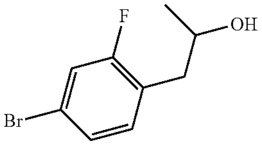

To a solution of Intermediate D (3.40 g, 14.71 mmol) in MeOH (34 mL) was added $NaBH_4$ (1.11 g, 29.43 mmol). The mixture was stirred at 20° C. for 0.5 h and subsequently quenched with saturated aqueous $NH_4Cl$ (20 mL) and extracted with ethyl acetate (20 mL×2). The organic layer was concentrated under vacuum to give Intermediate E (2.90 g, 9.95 mmol, 67.7% yield, 80.0% purity) as a yellow oil. $^1$H NMR (400 MHz, $CDCl_3$) δ 7.26-7.20 (m, 2H), 7.15-7.09 (m, 1H), 4.10-3.99 (m, 1H), 2.83-2.67 (m, 2H), 1.24 (d, J=6.4 Hz, 3H).

Step 4: Preparation of 6-bromo-2-methyl-2,3-dihydrobenzofuran (Intermediate F)

F

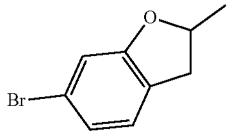

A mixture of Intermediate E (2.90 g, 12.44 mmol) and t-BuOK (4.19 g, 37.33 mmol) in THF (60 mL) was heated at 60° C. for 1 h. The mixture cooled to room temperature and diluted with water (40 mL) and extracted with EtOAc (10 mL×4). The organic layer was concentrated under vacuum. The residue was purified by flash silica gel chromatography (Eluent of 0-40% Ethyl acetate/Petroleum ether gradient) and concentrated under vacuum to give Intermediate F (1.89 g, 7.98 mmol, 64.2% yield, 90.0% purity) as a yellow oil. $^1$H NMR (400 MHz, DMSO-$d_6$) δ 7.14 (d, J=8.0 Hz, 1H), 7.02-6.91 (m, 2H), 5.03-4.89 (m, 1H), 3.29-3.22 (m, 1H), 2.77-2.69 (m, 1H), 1.38 (d, J=6.4 Hz, 3H).

Step 5: Preparation of 4,4,5,5-tetramethyl-2-(2-methyl-2,3-dihydrobenzofuran-6-yl)-1,3,2-dioxaborolane (Intermediate G)

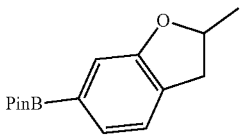

G

To a solution of Intermediate F (0.600 g, 2.82 mmol) and 4,4,5,5-tetramethyl-2-(4,4,5,5-tetramethyl-1,3,2-dioxaborolan-2-yl)-1,3,2-dioxaborolane (0.787 g, 3.10 mmol) in 1,4-dioxane (6 mL) was added Pd(dtbf)$Cl_2$ (0.184 g, 0.282 mmol) and KOAc (0.691 g, 7.04 mmol). The mixture was stirred at 80° C. for 1 h. The reaction mixture was subsequently cooled to ambient temperatures and filtered and the filtrate was concentrated under reduced vacuum to get a residue. The residue was purified by flash silica gel chromatography (petroleum ether/ethyl acetate=0/1 to 1/3) to give Intermediate G (0.400 g) as a yellow solid. LCMS (ESI) m/z: $[M+H]^+$=261.1.

Example 152. Preparation of 2-(4-fluoro-2,3-dihydrobenzofuran-6-yl)-4,4,5,5-tetramethyl-1,3,2-dioxaborolane

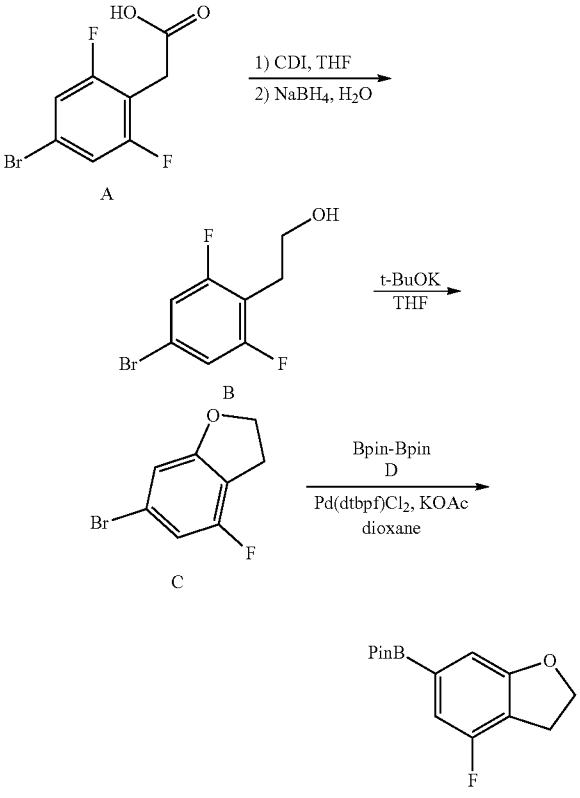

A

B

C

E

Step 1: Preparation of 2-(4-bromo-2,6-difluoro-phenyl)ethanol (Intermediate B)

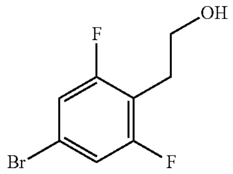

B

To a solution of 2-(4-bromo-2,6-difluoro-phenyl)acetic acid (1.00 g, 3.98 mmol) in THF (10 mL) was added CDI (0.969 g, 5.98 mmol). The mixture was stirred at 15° C. for 12 h Followed addition of a solution of $NaBH_4$ (0.301 g, 7.97 mmol) in water (10 mL) dropwise. The mixture was stirred for an additional 1 h. The mixture was diluted with water (10 mL) and extracted with ethyl acetate (20 mL×2). The organic layer was concentrated in vacuo. The residue was purified by flash silica gel chromatography (petroleum ether/ethyl acetate=0/1 to 1/9) to give Intermediate B (0.890 g, 3.57 mmol, 89.54% yield, 95.0% purity) as a yellow oil. $^1H$ NMR (400 MHz, DMSO-$d_6$) δ 7.45-7.32 (m, 2H), 4.81 (d, J=5.6 Hz, 1H), 3.613.48 (m, 2H), 2.73 (d, J=6.8 Hz, 2H).

Step 2: Preparation of 6-bromo-4-fluoro-2,3-dihydrobenzofuran (Intermediate C)

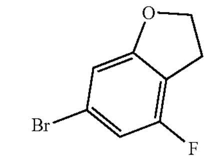

C

A mixture of Intermediate B (0.840 g, 3.54 mmol) and t-BuOK (1.19 g, 10.63 mmol) in THF (20 mL) was stirred at 60° C. for 1 h. The reaction mixture was diluted with water (10 mL) and extracted with EtOAc (10 mL×3). The combined organic layers were concentrated under vacuum. The residue was purified by flash silica gel chromatography (petroleum ether/ethyl acetate=0/1 to 2/5) and concentrated under vacuum to give Intermediate C (520 mg, 1.92 mmol, 54.1% yield, 80.0% purity) as a yellow oil. $^1H$ NMR (400 MHz, DMSO-$d_6$) δ 7.01-6.93 (m, 1H), 6.89 (d, J=1.2 Hz, 1H), 4.64 (d, J=8.8 Hz, 2H), 3.18 (d, J=8.8 Hz, 2H).

Step 3: Preparation of 2-(4-fluoro-2,3-dihydrobenzofuran-6-yl)-4,4,5,5-tetramethyl-1,3,2-dioxaborolane (Intermediate E)

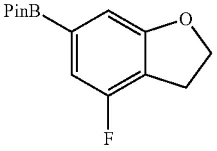

E

To a solution of Intermediate C (0.470 g, 2.17 mmol) and 4,4,5,5-tetramethyl-2-(4,4,5,5-tetramethyl-1,3,2-dioxaborolan-2-yl)-1,3,2-dioxaborolane (0.605 g, 2.38 mmol) in 1,4-dioxane (5 mL) was added Pd(dtbf)$Cl_2$ (0.141 g, 0.217 mmol) and KOAc (0.531 g, 5.41 mmol). The mixture was stirred at 80° C. for 1 h and subsequently diluted with EtOAc (50 mL) and filtered. The filtrate was concentrated under vacuum to give Intermediate E (0.550 g) as a brown solid that was used without further purification. LCMS (ESI) m/z: $[M+H]^+$=265.1.

Example 153. Preparation of 2-[3-(1-fluorocyclobutyl)phenyl]-4,4,5,5-tetramethyl-1,3,2-dioxaborolane

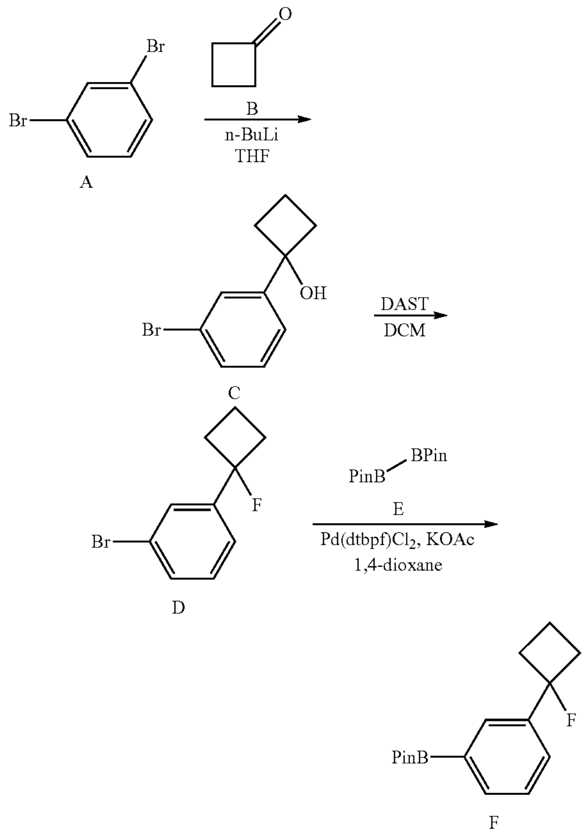

Step 1: Preparation of 1-(3-bromophenyl)cyclobutanol (Intermediate C)

C

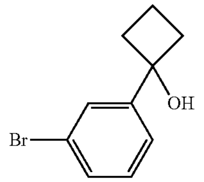

To a cooled (−70° C.) solution of 1,3-dibromobenzene (1.53 mL, 12.72 mmol) in THF (30 mL) was added a solution of 2.5 M n-BuLi (5.09 mL). After 30 min, acyclobutanone (0.855 mL, 11.45 mmol) was added and the mixture was stirred at −70° C. for an additional 2 h. The reaction mixture was quenched with saturated aqueous $NH_4Cl$ (100 mL) and allowed to warm to room temperature. The mixture was extracted with MTBE (50 mL×3), dried over $Na_2SO_4$, filtered and concentrated. The residue was purified by column chromatography ($SiO_2$, petroleum ether/ethyl acetate=20/1 to 5/1), the solution was concentrated to give Intermediate C (1.40 g, 6.16 mmol, 48.48% yield) as a yellow oil. $^1H$ NMR (400 MHz, $CDCl_3$) δ 7.52-7.52 (m, 1H), 7.31-7.27 (m, 2H), 7.13-7.09 (m, 1H), 2.43-2.37 (m, 2H), 2.26-2.19 (m, 2H), 1.96-1.87 (m, 1H), 1.64-1.56 (m, 1H).

Step 2: Preparation of 1-bromo-3-(1-fluorocyclobutyl)benzene (Intermediate D)

D

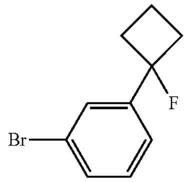

To a cooled (0° C.) solution of Intermediate C (0.800 g, 3.52 mmol) in DCM (8 mL) was added DAST (0.465 mL, 3.52 mmol). After 30 min, saturated aqueous $NaHCO_3$ was added and the mixture was extracted with DCM (5 mL×3), the combined organic layers were washed with brine (10 mL), dried over $Na_2SO_4$, filtered and concentrated to give a residue. The residue was purified by column chromatography (petroleum ether/ethyl acetate=1:0), the solution was concentrated to give Intermediate D (0.650 g, 2.84 mmol, 80.54% yield) as a yellow oil. $^1H$ NMR (400 MHz, $CDCl_3$) δ 7.53 (s, 1H), 7.40-7.29 (m, 2H), 7.22-7.15 (m, 1H), 2.65-2.52 (m, 2H), 2.51-2.39 (m, 2H), 2.08-1.98 (m, 1H), 1.75-1.61 (m, 1H).

Step 3: Preparation of 2-[3-(1-fluorocyclobutyl)phenyl]-4,4,5,5-tetramethyl-1,3,2-dioxaborolane (Intermediate E)

F

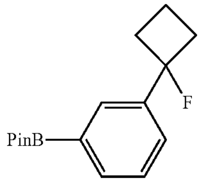

To a solution of Intermediate D (0.300 g, 1.31 mmol) in 1,4-dioxane (3 mL) was added 4,4,5,5-tetramethyl-2-(4,4,5,5-tetramethyl-1,3,2-dioxaborolan-2-yl)-1,3,2-dioxaborolane (0.400 g, 1.57 mmol), Pd(dtbf)$Cl_2$ (0.083 g, 0.131 mmol) and KOAc (0.386 g, 3.93 mmol), the mixture was stirred at 80° C. for 2 h. To the mixture was added silica gel (1 g) and MTBE (20 mL), the solution was filtered and the filtrate was concentrated to give Intermediate F (0.360 g) as a brown oil.

Example 154. Preparation of (7-fluoro-2,3-dihydrobenzofuran-6-yl)boronic acid

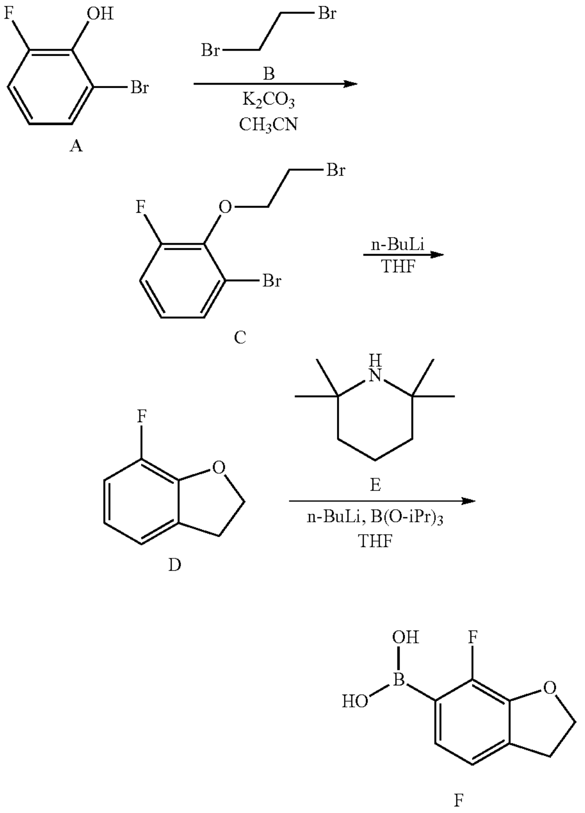

Step 1: Preparation of 1-bromo-2-(2-bromoethoxy)-3-fluoro-benzene (Intermediate C)

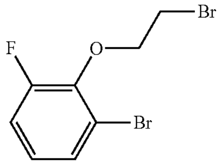
C

To a solution of 2-bromo-6-fluoro-phenol (2.00 g, 10.47 mmol) and 1,2-dibromoethane (1.58 mL, 20.94 mmol) in acetonitrile (20 mL) was added $K_2CO_3$ (1.45 g, 10.47 mmol). The mixture was stirred at 60° C. After 16 h, the mixture was concentrated and diluted with water (30 mL). The mixture was extracted with ethyl acetate (30 mL×3) and the combined organic layers were dried over $Na_2SO_4$, filtered, and concentrated under vacuum. The residue was purified by flash silica gel chromatography (petroleum ether/ethyl acetate=1:0 to 1:3) give Intermediate C (2.90 g, 7.79 mmol, 74.4% yield, 80.0% purity) as a colourless oil. $^1H$ NMR (400 MHz, $CDCl_3$) δ 7.40-7.30 (m, 1H), 7.12-7.04 (m, 1H), 7.01-6.88 (m, 1H), 4.39 (d, J=6.8 Hz, 2H), 3.67 (d, J=6.8 Hz, 2H).

Step 2: Preparation of 7-fluoro-2,3-dihydrobenzofuran (Intermediate D)

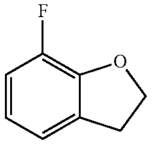
D

To a cooled (−65° C.) solution of Intermediate C (2.40 g, 8.06 mmol) in THF (60 mL) was added a solution of 2.5 M n-BuLi (3.87 mL). The mixture was stirred at for 1 h and subsequently quenched with water (3 mL) and warmed to room temperature. The aqueous layers were extracted with EtOAc (30 mL*3). The combined organic layers were dried over $Na_2SO_4$, filtered and concentrated. The residue was purified by flash silica gel chromatography (petroleum ether/ethyl acetate=1:0 to 1:3) to give Intermediate D (0.800 g, 4.63 mmol, 57.5% yield, 80.0% purity) as a colorless oil. $^1H$ NMR (400 MHz, DMSO-$d_6$) δ 7.09-7.04 (m, 1H), 7.03-6.95 (m, 1H), 6.86-6.75 (m, 1H), 4.62 (d, J=8.8 Hz, 2H), 3.24 (d, J=8.8 Hz, 2H).

Step 3: Preparation of (7-fluoro-2,3-dihydrobenzofuran-6-yl)boronic acid (Intermediate F)

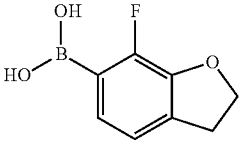
F

To a cooled (−75° C.) solution of 2,2,6,6-tetramethylpiperidine (0.232 mL, 1.37 mmol) in THF (0.5 mL) was added a 2.5 M solution n-BuLi (0.57 mL). The mixture was stirred for 30 min, followed by addition of triisopropyl borate (0.330 mL, 1.43 mmol). The reaction mixture was stirred for an additional 30 min, followed by addition of a solution of Intermediate D (0.180 g, 1.30 mmol) in THF (0.5 mL). The mixture was stirred at −75° C. for 3 h under $N_2$. After 3 h, the reaction mixture was quenched with 1 M HCl (1 mL) and MeOH (2 mL). The resulting solution was warmed to room temperature and concentrated under vacuum. The mixture was purified by reversed phase-HPLC (0.1% formic acid) to give Intermediate F (0.040 g, 0.118 mmol, 9.1% yield, 53.7% purity) as a yellow solid. LCMS (ESI) m/z: $[M+H]^+$=183.1.

Example 155. Preparation of 2-[3-(fluoromethoxy)phenyl]-4,4,5,5-tetramethyl-1,3,2-dioxaborolane

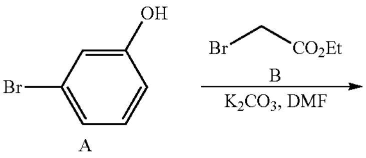

-continued

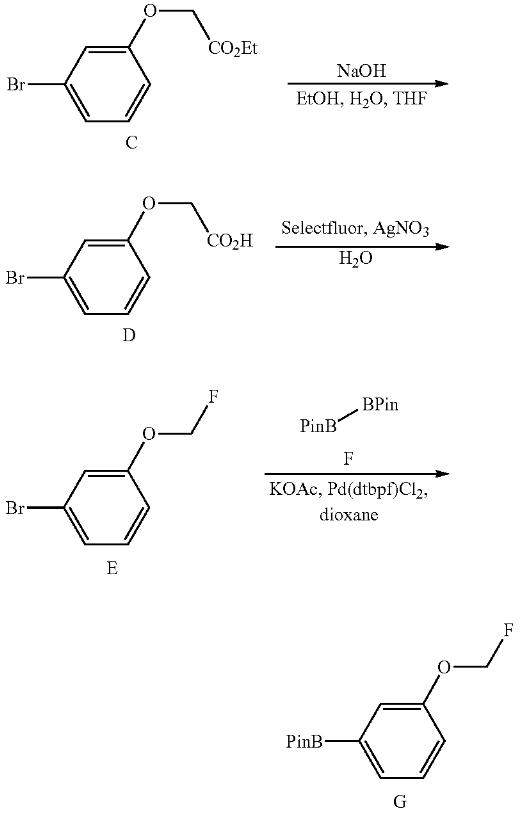

Step 1: Preparation of ethyl 2-(3-bromophenoxy)acetate (Intermediate C)

C

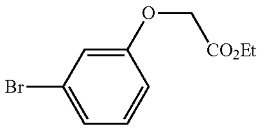

To a solution of 3-bromophenol (1.00 g, 5.78 mmol) and ethyl 2-bromoacetate (0.956 mL, 8.67 mmol) in DMF (10 mL) was added $K_2CO_3$ (1.60 g, 11.56 mmol). The reaction mixture was subsequently heated at 80° C. After 16 h, the mixture was cooled to room temperature and poured over water (50 mL) and extracted with ethyl acetate (50 mL×3). The combined organic layers were washed with brine (50 mL), dried over $Na_2SO_4$, filtered and concentrated. The residue was purified by column chromatography (petroleum ether/ethyl acetate=200/1 to 50/1) and concentrated to give Intermediate C (1.50 g, 5.79 mmol, 100.00% yield, 100% purity) as a colorless oil. LCMS (ESI) m/z: $[M+H]^+$=260.9.; $^1$H NMR (400 MHz, $CDCl_3$) δ 7.18-7.12 (m, 2H), 7.08-7.07 (m, 1H), 6.87-6.84 (m, 1H), 4.61 (s, 2H), 4.31-4.26 (m, 2H), 1.32-1.29 (m, 3H).

Step 2: Preparation of 2-(3-bromophenoxy)acetic acid (Intermediate D)

D

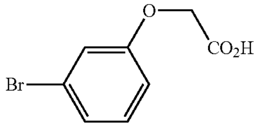

To a mixture of Intermediate C (1.50 g, 5.79 mmol) in a mixture of EtOH (6 mL), THF (6 mL) and $H_2O$ (3 mL) was added NaOH (694.67 mg, 17.37 mmol). After stirring for 1 h, the reaction mixture was acidified to pH~4-5 with 1 M HCl. The aqueous layer was extracted with ethyl acetate (30 mL×3). The combined organics were washed with brine (30 mL), dried over $Na_2SO_4$, filtered and filtration was evaporated to dryness to give Intermediate D (1.30 g) as a white solid. $^1$H NMR (400 MHz, DMSO-$d_6$) δ 13.05 (s, 1H), 7.26-7.22 (m, 1H), 7.15-7.12 (m, 2H), 6.95-6.92 (m, 1H), 4.72 (s, 2H).

Step 3: Preparation of 1-bromo-3-(fluoromethoxy)benzene (Intermediate E)

E

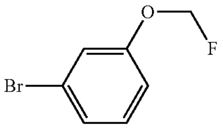

To a mixture of Intermediate D (400 mg, 1.73 mmol), Selectfluor (1.23 g, 3.46 mmol) and $AgNO_3$ (0.059 g, 0.346 mmol) was added $H_2O$ (15 mL) under $N_2$. The mixture was heated at 55° C. After 10 h, the mixture was cooled to ambient temperatures and poured over water (30 mL) and extracted with dichloromethane (30 mL×3). The combined organics were washed with brine (20 mL), dried over $Na_2SO_4$, filtered and concentrated to give Intermediate E (0.290 g, 1.41 mmol, 81.70% yield) as a yellow solid. $^1$H NMR (400 MHz, DMSO-$d_6$) δ 7.36-7.30 (m, 3H), 7.15-7.12 (m, 1H), 5.95 (s, 1H), 5.82 (s, 1H).

Step 4: Preparation of 2-[3-(fluoromethoxy)phenyl]-4,4,5,5-tetramethyl-1,3,2-dioxaborolane (Intermediate G)

G

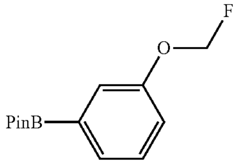

To a mixture of Intermediate E (0.100 g, 0.488 mmol), 4,4,5,5-tetramethyl-2-(4,4,5,5-tetramethyl-1,3,2-dioxaborolan-2-yl)-1,3,2-dioxaborolane (0.130 g, 0.512 mmol) in 1,4-dioxane (1 mL) was added Pd(dtbf)$Cl_2$ (0.032 g, 0.049 mmol) and KOAc (0.096 g, 0.976 mmol). The resulting mixture was stirred at 80° C. After 2 h, the reaction mixture was cooled to ambient temperatures and poured into water (20 mL) and extracted with ethyl acetate (20 mL×3). The combined organic layers were washed with brine (20 mL), dried over $Na_2SO_4$, filtered and concentrated to give Intermediate G (0.111 g) as a yellow solid. LCMS (ESI) m/z: $[M+H]^+$=368.3.

Example 156. Preparation of cis-4-[3-cyclopropyl-5-(4,4,5,5-tetramethyl-1,3,2-dioxaborolan-2-yl)phenyl]-2,6-dimethyl-morpholine

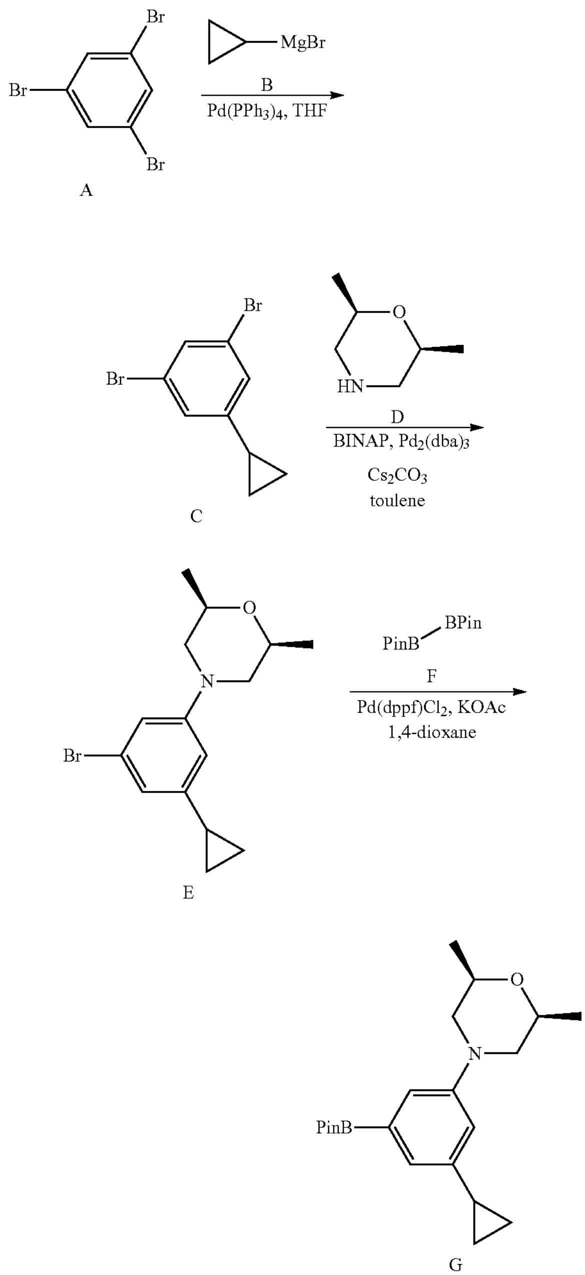

A C E G

Step 1: Preparation of 1,3-dibromo-5-cyclopropyl-benzene (Intermediate C)

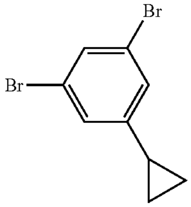

C

To a cooled (0° C.) solution of 1,3,5-tribromobenzene (8.00 g, 25.41 mmol) and $Pd(PPh_3)_4$ (1.47 g, 1.27 mmol) in THF (16 mL) was added a solution of 0.5 M bromo (cyclopropyl)magnesium (50.83 mL). The reaction mixture was warmed to 70° C. After 4 h, the mixture was cooled to ambient temperatures and quenched by saturated aqueous $NH_4Cl$ (100 mL). The resulting mixture as extracted with ethyl acetate (100 mL×2). The combined organic layers were washed with brine (200 mL), dried over $Na_2SO_4$, filtered and concentrated. The residue was purified by column chromatography (petroleum ether) and concentrated under reduced pressure to give Intermediate C (5.00) as a white solid. $^1H$ NMR (400 MHz, $CDCl_3$) δ 7.64 (s, 1H), 7.15 (d, J=1.6 Hz, 2H), 1.90-1.80 (m, 1H), 1.07-0.99 (m, 2H), 0.75-0.69 (m, 2H).

Step 2: Preparation of cis-4-(3-bromo-5-cyclopropylphenyl)-2,6-dimethylmorpholine (Intermediate E)

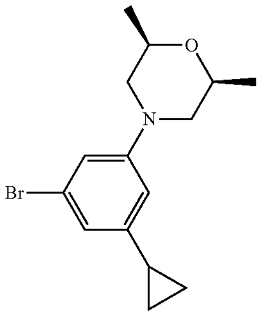

E

To a solution of Intermediate C (2.50 g, 9.06 mmol), cis-2,6-dimethylmorpholine (0.521 g, 4.53 mmol), BINAP (0.564 g 0.906 mmol) and $Cs_2CO_3$ (4.43 g, 13.59 mmol) in toluene (20 mL) was added $Pd_2(dba)_3$ (0.415 g, 0.453 mmol). The reaction mixture was heated at 80° C. After 12 h, the solution was cooled to room temperature and concentrated. The residue was purified by column chromatography (petroleum ether/ethyl acetate=5:1) to give Intermediate E (0.300 g 0.851 mmol, 18.8% yield, 88.0% purity) as a light yellow oil. LCMS (ESI) m/z: $[M+H]^+$=310.1.

Step 3: Preparation of cis-4-[3-cyclopropyl-5-(4,4,5,5-tetramethyl-1,3,2-dioxaborolan-2-yl)phenyl]-2,6-dimethyl-morpholine (Intermediate G)

G

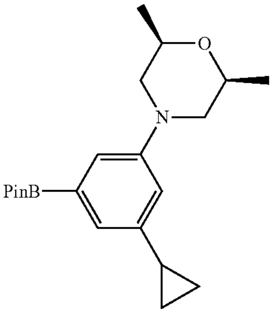

To a solution of Intermediate E (0.200 g, 0.645 mmol), 4,4,5,5-tetramethyl-2-(4,4,5,5-tetramethyl-1,3,2-dioxaborolan-2-yl)-1,3,2-dioxaborolane (0.181 g, 0.710 mmol) in 1,4-dioxane (2 mL) was added and Pd(dppf)$Cl_2$ (0.047 g, 0.064 mmol) and KOAc (0.190 g, 1.93 mmol). The reaction mixture was subsequently heated at 80° C. After 1 h, the reaction mixture was cooled to room temperature and reduced pressure. The residue was purified by column chromatography (petroleum ether/ethyl acetate=10:1) to give Intermediate G (0.200 g, crude) as a light yellow oil. LCMS (ESI) m/z: $[M+H]^+$=358.4.

Example 157. Preparation of 1-methyl-8-(4,4,5,5-tetramethyl-1,3,2-dioxaborolan-2-yl)-2,3,4,5-tetrahydro-1-benzazepine

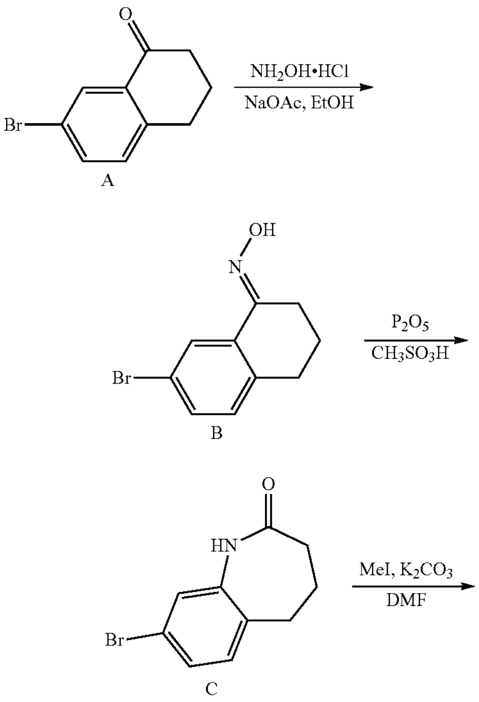

-continued

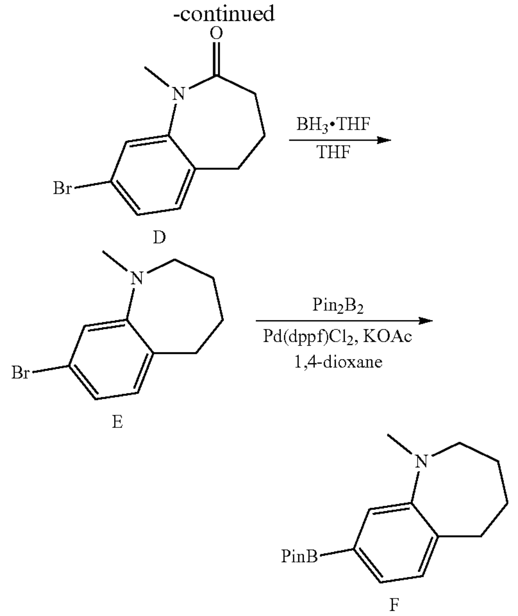

Step 1: Preparation of 7-bromotetralin-1-one oxime (Intermediate B)

B

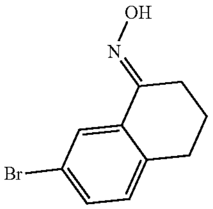

To a solution of 7-bromotetralin-1-one (4.00 g, 17.77 mmol) and $NH_2OH{\cdot}HCl$ (2.47 g, 35.54 mmol) in EtOH (40 mL) was added NaOAc (2.92 g, 35.54 mmol) and mixture was stirred at 70° C. After 2 h, the mixture was cooled to ambient temperatures, partially concentrated, and partitioned between water (40 mL) and ethyl acetate (50 mL). The organic layer was separated and evaporated to give Intermediate B (4.00 g, 15.49 mmol, 87.2% yield, 93.0% purity) as a yellow solid. LCMS (ESI) m/z: $[M+H]^+$=240.0.

Step 2: Preparation of 8-bromo-1,3,4,5-tetrahydro-1-benzazepin-2-one (Intermediate C)

C

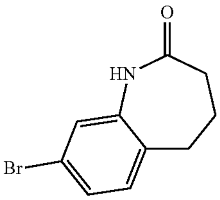

A solution of $P_2O_5$ (4.00 g, 28.18 mmol) in $CH_3SO_3H$ (40 mL) was stirred at 90° C. for 1 h. The mixture was cooled to 50° C. and Intermediate B (4.00 g, 16.66 mmol) was added in portions as 4 batches. The mixture was heated at 80° C. After 12 h, the mixture was cooled to room temperature and slowly poured into ice-water (200 mL) and extracted with ethyl acetate (50 mL). The organic layer was separated, dried over $Na_2SO_4$ and evaporated. The residue was purified by flash silica gel chromatography (petroleum ether ethyl acetate=10/1 to 1/1) and the resulting solution was evaporated to afford a brown solids. The solids were triturated with (petroleum ether ethyl acetate=1/1, 10 mL) and filtered. The solids were dried under vacuum to give Intermediate C (0.800 g, 3.33 mmol, 20.0% yield) as a pure solid. $^1H$ NMR (400 MHz, DMSO-$d_6$) δ 9.60 (s, 1H), 7.29-7.19 (m, 2H), 7.14 (d, J=2.0 Hz, 1H), 2.66 (d, J=7.2 Hz, 2H), 2.20-2.04 (m, 4H).

Step 3: Preparation of 8-bromo-1-methyl-4,5-dihydro-3H-1-benzazepin-2-one (Intermediate D)

D

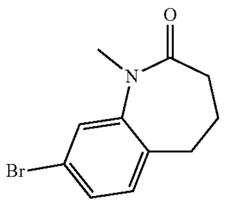

To a mixture of Intermediate C (0.150 g, 0.625 mmol) and $K_2CO_3$ (0.259 g, 1.87 mmol) in DMF (3 mL) was added MeI (0.078 mL, 1.25 mmol,). After 5 h, to the mixture was added water (5 mL) and extracted with ethyl acetate (5 mL×3). The combined organic layer was washed with brine (10 mL), dried over $Na_2SO_4$, filtered and concentrated. The residue was purified by column chromatography (petroleum ether/ethyl acetate=10/1 to 5/1) to give Intermediate D (0.090 g, 0.354 mmol, 56.7% yield) as a white solid. LCMS (ESI) m/z: $[M+H]^+$=254.0; $^1H$ NMR (400 MHz, $CDCl_3$) δ 7.33-7.32 (m, 1H), 7.31-7.27 (m, 1H), 7.08-7.06 (m, 1H), 3.34 (s, 3H), 2.70-2.66 (m, 2H), 2.37-2.27 (m, 2H), 2.22-2.10 (m, 2H).

Step 4: Preparation of 8-bromo-1-methyl-2,3,4,5-tetrahydro-1-benzazepine (Intermediate E)

E

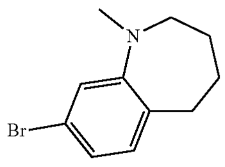

To a cooled (10° C.) mixture of Intermediate D (0.090 g, 0.354 mmol) in THF (3 mL) was added a 1 M solution of $BH_3$·THF (1.06 mL). The mixture was heated to 70° C. After 2 h, the mixture was cooled to ambient temperatures and MeOH slowly added until effervescence ceased. The mixture was concentrated and purified by prep-TLC (petroleum ether/ethyl acetate=5:1) to give Intermediate E (0.050 g, 0.202 mool, 57.0% yield, 97.0% purity) as a colorless oil. LCMS (ESI) m/z: $[M+H]^+$=240.0; $^1H$ NMR (400 MHz, $CDCl_3$) δ 7.02-7.00 (m, 1H), 6.97-6.93 (m, 2H), 2.96-2.90 (m, 2H), 2.86 (s, 3H), 2.77-2.70 (m, 2H), 1.81-1.71 (m, 2H), 1.64-1.57 (m, 2H).

Step 5: Preparation of 1-methyl-8-(4,4,5,5-tetramethyl-1,3,2-dioxaborolan-2-yl)-2,3,4,5-tetrahydro-1-benzazepine (Intermediate F)

F

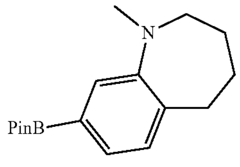

To a solution of Intermediate E (0.050 g, 0.208 mmol) and 4,4,5,5-tetramethyl-2-(4,4,5,5-tetramethyl-1,3,2-dioxaborolan-2-yl)-1,3,2-dioxaborolane (0.063 g, 0.250 mmol) in 1,4-dioxane (1 mL) was added KOAc (0.041 g, 0.416 mmol) and $Pd(dppf)Cl_2$ (0.077 g, 0.104 mmol). The mixture was heated at 80° C. After 2 h, to the mixture was added water (5 mL) and extracted with ethyl acetate (5 mL×3). The combined organic layers were washed with brine (10 mL), dried over $Na_2SO_4$, filtered and concentrated. The residue was purified by prep-TLC (petroleum ether/ethyl acetate=5:1) to give Intermediate F (0.040 g, 0.134 mmol, 64.2% yield, 96.0% purity) as a white solid. LCMS (ESI) m/z: $[M+H]^+$=288.1.

Example 158. Preparation of 2-(difluoromethyl)-4-[3-(4,4,5,5-tetramethyl-1,3,2-dioxaborolan-2-yl)phenyl]triazole

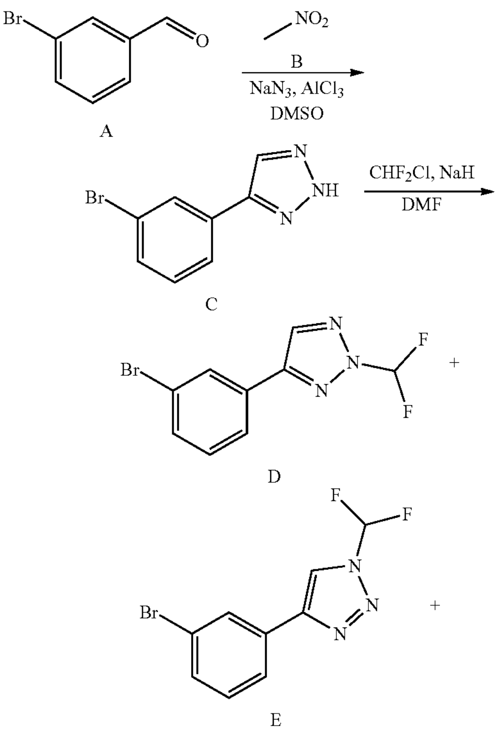

-continued

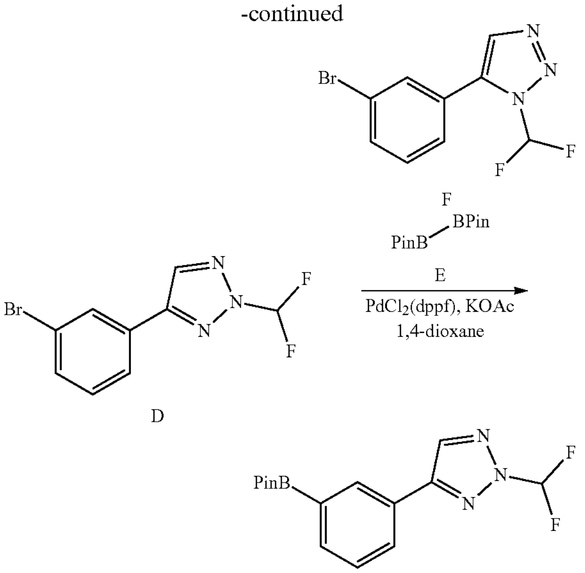

D

G

Step 1: Preparation of 4-(3-bromophenyl)-2H-triazole (Intermediate C)

C

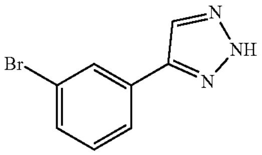

To a cooled (10° C.) mixture of 3-bromobenzaldehyde (3.14 mL, 27.02 mmol), nitromethane (2.19 mL, 40.54 mmol), sodium azide (2.11 g, 32.43 mmol) in DMSO (60 mL) was added $AlCl_3$ (0.360 g, 2.70 mmol). The reaction mixture was subsequently heated at 70° C. After 8 h, water (100 mL) was added to the mixture and extracted with ethyl acetate (50 mL×3). The combined organic layer was washed with brine (50 mL), dried over $Na_2SO_4$, filtered and concentrated The solids were purified by flash chromatography (petroleum ether/ethyl acetate=10:1-5:1) to give Intermediate C (2.60 g, 11.02 mmol, 40.8% yield, 95.0% purity) as a white solid. LCMS (ESI) m/z: [$^{79}$Br M+H]$^+$=224.0.; $^1$H NMR (400 MHz, $CDCl_3$) δ 8.01-8.00 (m, 1H), 7.98 (s, 1H), 7.77-7.75 (m, 1H), 7.54-7.50 (m, 1H), 7.37-7.30 (m, 1H).

Step 2: Preparation of 4-(3-bromophenyl)-2-(difluoromethyl)triazole (Intermediate D)

D

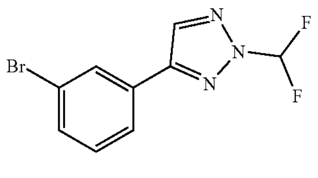

To a cooled (10° C.) mixture of Intermediate C (0.800 g, 3.57 mmol) in DMF (10 mL) was added NaH (0.286 g, 7.14 mmol, 60.0% purity). The mixture was stirred at 10° C. for 0.5 h, followed by bubbling of chloro(difluoro)methane (g) into to the mixture for 30 min. The reaction mixture was quenched with saturated aqueous $NH_4Cl$ (10 mL) and extracted with ethyl acetate (10 mL×3). The combined organic layers were washed with brine (15 mL), dried over $Na_2SO_4$, filtered and concentrated. The residue was purified by column chromatography (petroleum ether/ethyl acetate=10/1 to 5/1) to give Intermediate D (0.170 g, 0.620 mmol, 17.37% yield) as a colorless oil. LCMS (ESI) m/z: [M+H]$^+$=276.0.

In addition to Intermediate D, Intermediate E (0.180 g, 0.657 mmol, 18.39% yield) was isolated as a white solid and Intermediate F (0.170 g, 0.620 mmol, 17.37% yield) was isolated as a colorless oil were also isolated 4-(3-bromophenyl)-1-(difluoromethyl)-1H-1,2,3-triazole (Intermediate E): $^1$H NMR (400 MHz, $CDCl_3$) δ 8.19 (s, 1H), 8.05-8.04 (m, 1H), 7.85-7.78 (m, 1H), 7.77-7.44 (m, 2H), 7.39-7.30 (m, 1H).

5-(3-bromophenyl)-1-(difluoromethyl)-1H-1,2,3-triazole (Intermediate F): $^1$H NMR (400 MHz, $CDCl_3$) δ 7.81 (s, 1H), 7.79-7.62 (m, 3H), 7.52-7.47 (m, 1H), 7.43-7.36 (m, 1H).

Step 3: Preparation of 2-(difluoromethyl)-4-[3-(4,4,5,5-tetramethyl-1,3,2-dioxaborolan-2-yl)phenyl]triazole (Intermediate F)

G

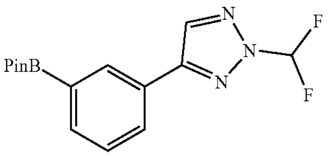

To a solution of Intermediate D (0.070 g, 0.255 mmol) and 4,4,5,5-tetramethyl-2-(4,4,5,5-tetramethyl-1,3,2-dioxaborolan-2-yl)-1,3,2-dioxaborolane (0.130 g, 0.511 mmol) in 1,4-dioxane (2 mL) was added KOAc (0.063 g, 0.639 mmol) and Pd(dppf)$Cl_2$ (0.093 g, 0.128 mmol). The mixture was heated at 80° C. After 2 h, the mixture was extracted with ethyl acetate (10 mL×3). The combined organic layers were washed with brine (10 mL), dried over $Na_2SO_4$, filtered and concentrated. The crude product was purified by flash chromatography (petroleum ether/ethyl acetate=10:1-5:1) to give Intermediate G (0.080 g, 0.249 mmol, 97.54% yield) as a colorless oil. LCMS (ESI) m/z: [M+H]$^+$=322.2.; $^1$H NMR (400 MHz, $CDCl_3$) δ 8.25 (s, 1H), 8.14 (s, 1H), 7.99-7.96 (m, 1H), 7.88-7.86 (m, 1H), 7.56-7.37 (m, 2H), 1.38 (s, 12H).

Example 159. Preparation of 2-cyclopropyl-4-[3-(4,4,5,5-tetramethyl-1,3,2-dioxaborolan-2-yl)phenyl]triazole

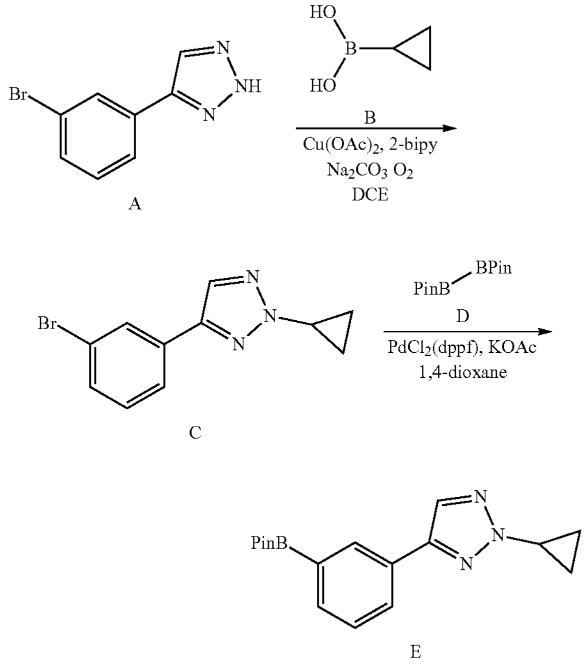

Step 1: Preparation of 4-(3-bromophenyl)-2-cyclopropyl-triazole (Intermediate C)

C

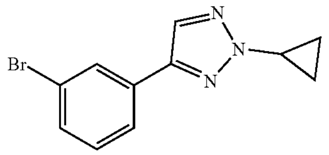

To a mixture of 4-(3-bromophenyl)-2H-triazole (0.500 g, 2.23 mmol) in 1,2-dichloroethane (6 mL) was added cyclopropylboronic acid (0.383 g, 4.46 mmol), $Cu(OAc)_2$ (0.405 g, 2.23 mmol), 2-(2-pyridyl)pyridine (0.349 g, 2.23 mmol), $Na_2CO_3$ (0.473 g, 4.46 mmol) at 10° C., after addition, the mixture was stirred at 60° C. for 1 h under $O_2$ (15 psi) atmosphere. The mixture was filtered off and the filtrate was concentrated to get the crude product. The residue was purified by column chromatography (petroleum ether/ethyl acetate=10/1 to 5/1) to give Intermediate C (0.250 g, 0.909 mmol, 40.7% yield, 96.0% purity) as a colorless oil. LCMS (ESI) m/z: [$^{79}$Br M+H]$^+$=264.0; $^1$H NMR (400 MHz, $CDCl_3$) δ 7.92-7.90 (m, 1H), 7.78-7.72 (m, 1H), 7.66-7.64 (m, 1H), 7.42-7.41 (m, 1H), 7.25-7.23 (m, 1H), 4.05-3.97 (m, 1H), 1.42-1.33 (m, 2H), 1.15-1.05 (m, 2H).

Step 2: Preparation of 2-cyclopropyl-4-[3-(4,4,5,5-tetramethyl-1,3,2-dioxaborolan-2-yl)phenyl]triazole (Intermediate E)

E

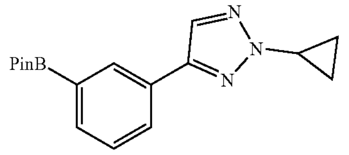

To a solution of Intermediate C (0.200 g, 0.757 mmol) and 4,4,5,5-tetramethyl-2-(4,4,5,5-tetramethyl-1,3,2-dioxaborolan-2-yl)-1,3,2-dioxaborolane (0.385 g, 1.51 mmol) in 1,4-dioxane (1 mL) was added KOAc (0.149 g, 1.51 mmol) and $Pd(dppf)Cl_2$ (0.277 g, 0.379 mmol). The mixture was heated at 80° C. After 2 h, the reaction mixture was cooled to room temperature and water (10 mL) was added. The mixture was extracted with ethyl acetate (10 mL×3). The combined organic layers were washed with brine (15 mL), dried over $Na_2SO_4$, filtered and concentrated. The crude product was purified by flash chromatography (petroleum ether/ethyl acetate=10:1-5:1) to give Intermediate E (0.180 g, 0.578 mmol, 76.39% yield) as a white solid. LCMS (ESI) m/z: [M+H]$^+$=312.2.; $^1$H NMR (400 MHz, $CDCl_3$) δ 8.18 (s, 1H), 7.91-7.89 (m, 1H), 7.85 (s, 1H), 7.81-7.76 (m, 1H), 7.47-7.41 (m, 1H), 4.06-4.00 (m, 1H), 1.43-1.39 (m, 2H), 1.37 (s, 12H), 1.17-1.09 (m, 2H).

Example 160. Preparation of cis-2,6-dimethyl-4-(4-(4,4,5,5-tetramethyl-1,3,2-dioxaborolan-2-yl)pyridin-2-yl)morpholine

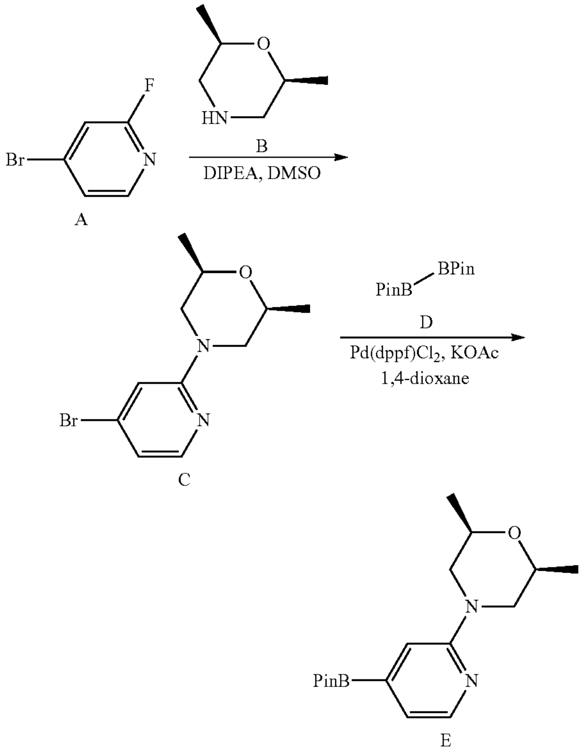

Step 1: Preparation of cis-4-(4-bromopyridin-2-yl)-2,6-dimethylmorpholine (Intermediate C)

C

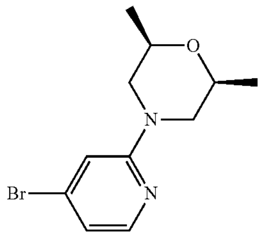

To a solution of 4-bromo-2-fluoro-pyridine (0.500 g, 2.84 mmol) in DMSO (5 mL) was added DIEA (2.47 mL, 14.21 mmol) and cis-2,6-dimethylmorpholine (0.655 g, 5.68 mmol). The mixture was heated at 120° C. for 12 h and subsequently diluted with water (30 mL). The mixture was extracted with ethyl acetate (10 mL×3). The combined the organic layers were washed with saturated aqueous $NH_4Cl$ (20 mL), brine (20 mL), dried over $Na_2SO_4$, filtered and concentrated. The residue was purified by column chromatography (petroleum ether/ethyl acetate=15/1 to 8:1) to get Intermediate C (0.500 g, 1.75 mmol, 61.66% yield) as a yellow oil.; LCMS (ESI) m/z: $[M+H]^+$=273.0.; $^1H$ NMR (400 MHz, $CDCl_3$) δ 7.99 (d, J=5.6 Hz, 1H), 6.79-6.75 (m, 2H), 4.03-4.00 (m, 2H), 3.71-3.68 (m, 2H), 2.56-2.50 (m, 2H), 1.27-1.26 (m, 6H).

Step 2: Preparation of cis-2,6-dimethyl-4-(4-(4,4,5,5-tetramethyl-1,3,2-dioxaborolan-2-yl)pyridin-2-yl)morpholine (Intermediate E)

E

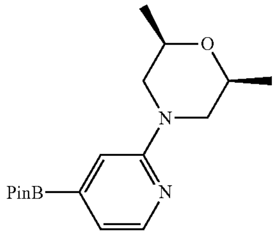

A solution of Intermediate C (0.200 g, 0.738 mmol), 4,4,5,5-tetramethyl-2-(4,4,5,5-tetramethyl-1,3,2-dioxaborolan-2-yl)-1,3,2-dioxaborolane (0.225 g, 0.885 mmol) in 1,4-dioxane (3 mL) was added KOAc (217.17 mg, 2.21 mmol) and Pd(dppf)$Cl_2$ (53.97 mg, 73.76 umol). The mixture was heated at 80° C. After 2 h, the reaction was diluted with water (15 mL) and extracted with ethyl acetate (5 mL×3). The combined the organic layers were washed with brine (10 mL), dried over $Na_2SO_4$, filtered and concentrated to yield Intermediate E (0.200 g, 0.629 mmol, 85.21% yield) as a brown oil which was used directly without further purification. $^1H$ NMR (400 MHz, $CDCl_3$) δ 8.22-8.21 (m, 1H), 7.01 (s, 1H), 6.98 (d, J=4.8 Hz, 1H), 4.12-4.08 (m, 2H), 3.73-3.72 (m, 2H), 2.55-2.49 (m, 2H), 1.35 (s, 12H), 1.29 (m, 3H), 1.28-1.27 (m, 3H).

Example 161. Preparation of 2-methyl-1-(3-(4,4,5,5-tetramethyl-1,3,2-dioxaborolan-2-yl)phenoxy)propan-2-ol

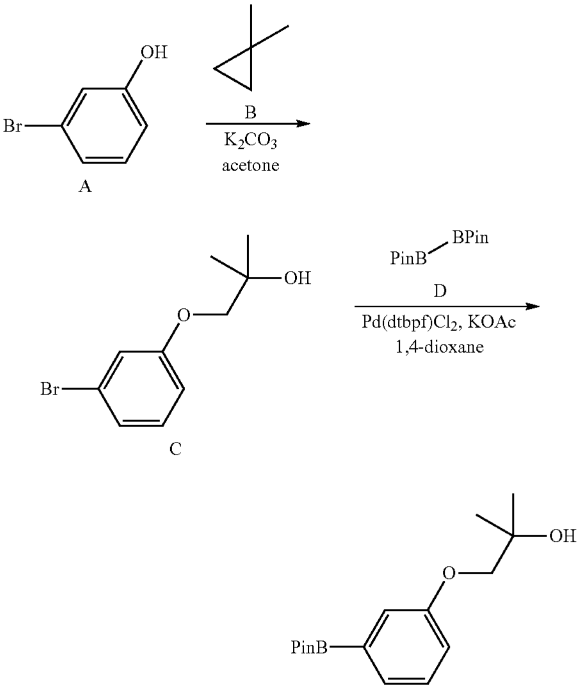

Step 1: Preparation of 1-(3-bromophenoxy)-2-methylpropan-2-ol (Intermediate C)

C

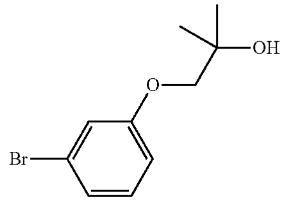

To a cooled (0° C.) of 3-bromophenol (1.00 g, 5.78 mmol) in acetone (10 mL) was added $K_2CO_3$ (0.959 g, 6.94 mmol) and 2,2-dimethyloxirane (1.54 mL, 17.34 mmol) The mixture was heated at 60° C. After stirring for 16 h, the reaction mixture was concentrated. The residue was diluted with water (10 mL) and extracted with ethyl acetate (15 mL×3). The combined organic layers were washed with brine (10 mL), dried over $Na_2SO_4$, filtered and concentrated. The residue was purified by reverse phase column and lyophilized to give Intermediate C (0.400 g, 1.63 mmol, 28.23% yield) as yellow oil.; LCMS (ESI) m/z: $[M-OH]^+$=227.0.; $^1H$ NMR (400 MHz, $CDCl_3$) δ 7.20-7.04 (m, 3H), 6.92-6.80 (m, 1H), 3.77 (s, 2H), 1.34 (s, 6H).

Step 2: Preparation of 2-methyl-1-(3-(4,4,5,5-tetramethyl-1,3,2-dioxaborolan-2-yl)phenoxy)propan-2-ol (Intermediate E)

E

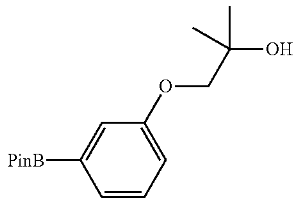

To a solution of Intermediate C (0.200 g, 0.816 mmol), 4,4,5,5-tetramethyl-2-(4,4,5,5-tetramethyl-1,3,2-dioxaborolan-2-yl)-1,3,2-dioxaborolane (0.311 g, 1.22 mmol) in 1,4-dioxane (3 mL) was added KOAc (0.240 g, 2.45 mmol) and $Pd(dtbf)Cl_2$ (0.053 g, 0.082 mmol). The mixture was heated at 70° C. After 1 h, the reaction mixture was cooled to room temperature, poured into water (10 mL), and extracted with ethyl acetate (5 mL×2). The organic layer was washed with brine (10 mL), dried over $Na_2SO_4$ and concentrated to give Intermediate E (0.200 g, 0.448 mmol, 54.95% yield) as yellow solid which was used for next step without further purification. LCMS (ESI) m/z: $[M-OH]^+$=275.1.

Example 162. Preparation of 2-(4-fluorobenzofuran-6-yl)-4,4,5,5-tetramethyl-1,3,2-dioxaborolane

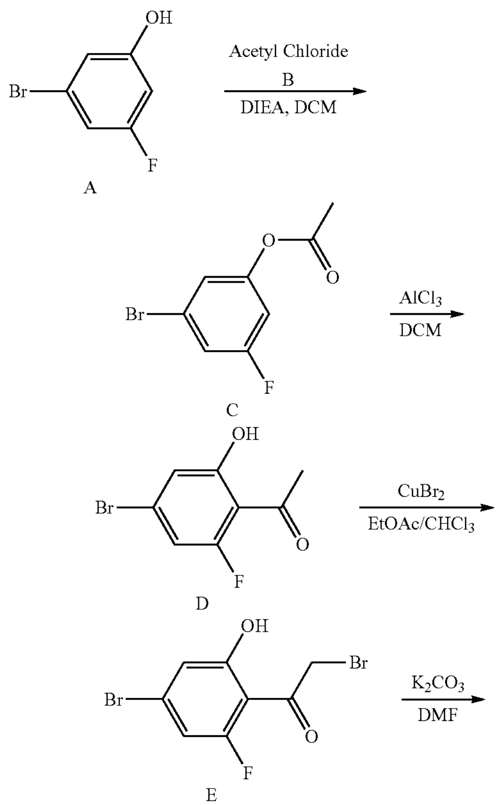

-continued

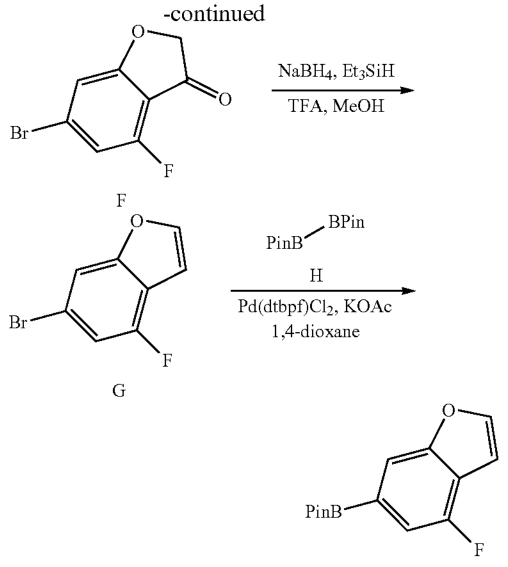

I

Step 1: Preparation of 3-bromo-5-fluorophenyl acetate (Intermediate C)

C

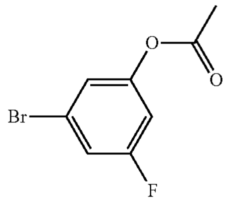

To a solution of 3-bromo-5-fluoro-phenol (15.00 g, 78.53 mmol) in dichloromethane (50 mL) was added DIEA (41.04 mL, 235.60 mmol) and acetyl chloride (8.41 mL, 117.80 mmol). After 30 min, saturated aqueous $NaHCO_3$ (10 mL) was added and the mixture was extracted with dichloromethane (100 mL×2). The combined organic layers were washed with brine (50 mL), dried over $Na_2SO_4$, filtered and concentrated. The residue was purified by $SiO_2$ column (petroleum ether/ethyl acetate=50:1 to 10:1) to give Intermediate C (16.00 g, 68.66 mmol, 87.43% yield) as a white oil.; $^1H$ NMR (400 MHz, $CDCl_3$) δ 7.17-7.09 (m, 2H), 6.86-6.83 (m, 1H), 2.31-2.27 (m, 3H).

Step 2: Preparation of 1-(4-bromo-2-fluoro-6-hydroxy-phenyl)ethenone (Intermediate D)

D

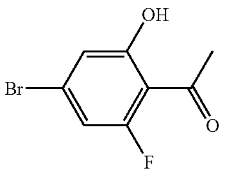

To a cooled (0° C.) solution of Intermediate C (14.00 g, 60.08 mmol) in dichloromethane (100 mL) was added $AlCl_3$ (24.03 g, 180.23 mmol, 9.85 mL). The reaction mixture was stirred 30 min and subsequently concentrated in vacuo. The resulting semi-solid residue was heated at 140° C. After 3 h, water (50 mL) was added to the mixture and extracted with ethyl acetate (100 mL×2). The combined organic phases were washed with brine (50 mL), dried over $Na_2SO_4$, filtered and concentrated. The residue was purified by $SiO_2$ column (petroleum ether/ethyl acetate=50:1 to 10:1) to give Intermediate D (7.00 g, 30.04 mmol, 50.00% yield) as a yellow solid. $^1H$ NMR (400 MHz, $CDCl_3$) δ 12.89 (s, 1H), 7.23-7.00 (m, 1H), 6.85-6.78 (m, 1H), 2.68 (d, J=7.2 Hz, 3H).

Step 3: Preparation of 2-bromo-1-(4-bromo-2-fluoro-6-hydroxy-phenyl)ethenone (Intermediate E)

E

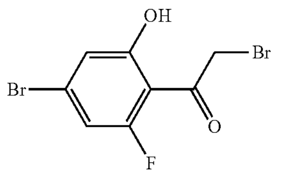

To a solution of Intermediate D (5.00 g, 21.46 mmol) and $CuBr_2$ (9.58 g, 42.91 mmol, 2.01 mL) in ethyl acetate (50 mL) and $CHCl_3$ (50 mL) was heated at 60° C. for 16 h. The mixture was cooled to room temperature, filtered and the filtrate was concentrated in vacuum to give Intermediate E (6.50 g) as a yellow solids which was used for the next step without further purification. $^1H$ NMR (400 MHz, $CDCl_3$) δ 12.28 (s, 1H), 7.08-7.04 (m, 1H), 6.89-6.86 (m, 1H), 4.53 (d, J=3.6 Hz, 2H).

Step 4: Preparation of 6-bromo-4-fluoro-benzofuran-3-one (Intermediate F)

F

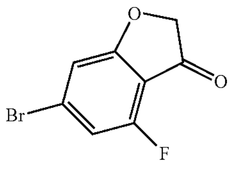

To a solution of Intermediate E (6.50 g, 20.84 mmol) in DMF (120 mL) was added $K_2CO_3$ (4.32 g, 31.26 mmol). The resulting suspension was stirred for 30 min, followed by addition of water (30 mL). The biphasic mixture mixture was extracted with ethyl acetate (50 mL×2). The combined organic phases were washed with brine (30 mL), dried over $Na_2SO_4$, filtered and concentrated. The residue was purified by $SiO_2$ column (petroleum ether/ethyl acetate=50:1 to 5:1) to give Intermediate F (2.00 g, 8.66 mmol, 41.55% yield) as a yellow solid. $^1H$ NMR (400 MHz, $CDCl_3$) δ 7.16 (d, J=0.8 Hz, 1H), 6.93 (d, J=8.0 Hz, 1H), 4.67 (s, 2H).

Step 5: Preparation of 6-bromo-4-fluoro-benzofuran (Intermediate G)

G

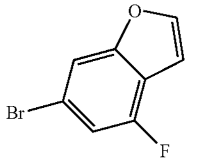

To a cooled (0° C.) solution of Intermediate F (0.300 g, 1.30 mmol) in MeOH (3.0 mL) was added $NaBH_4$ (98.26 mg, 2.60 mmol). After stirring for 1 h, the reaction mixture was quenched with saturated aqueous $NH_4Cl$ (3 mL) and extracted with EtOAc (10 mL×2). The combined organic layers were concentrated under vacuum to give intermediate secondary alcohol (0.300 g) as a yellow solid.

To a solution of alcohol (0.300 g) in TFA (3.0 mL) was added $Et_3SiH$ (0.415 mL, 2.60 mmol). The solution was heated at 60° C. for 2 h. The mixture was quenched with water (2 mL) and extracted with EtOAc (2 mL×2). The combined organic layers were concentrated under vacuum. The residue was purified by flash silica gel chromatography (petroleum ether/ethyl acetate=10:1) to give Intermediate G (0.090 g, 0.377 mmol, 29.0% yield, 90.0% purity) as a yellow oil. $^1H$ NMR (400 MHz, DMSO-$d_6$) δ 8.11 (d, J=2.0 Hz, 1H), 7.86-7.85 (m, 1H), 7.44-7.40 (m, 1H), 7.13-7.12 (m, 1H).

Step 6: Preparation of 2-(4-fluorobenzofuran-6-yl)-4,4,5,5-tetramethyl-1,3,2-dioxaborolane (Intermediate I)

I

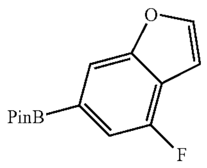

To a solution of Intermediate G (0.070 g, 0.326 mmol) and 4,4,5,5-tetramethyl-2-(4,4,5,5-tetramethyl-1,3,2-dioxaborolan-2-yl)-1,3,2-dioxaborolane (0.091 g, 0.358 mmol) in 1,4-dioxane (0.5 mL) was added Pd(dtbf)$Cl_2$ (0.021 g, 0.033 mmol) and KOAc (0.080 g, 0.814 mmol). The mixture was heated at 80° C. After 1 h, the mixture was cooled to ambient temperatures, diluted with ethyl acetate (50 mL) and filtered. The filtrate was concentrated to give Intermediate I (0.080 g) as a brown solid. LCMS (ESI) m/z: $[M+H]^+$=263.1.

Example 163. Preparation of 1-methylsulfonyl-N-[2-oxo-2-[[4-[3-[[(3R)-tetrahydrofuran-3-yl]methoxy]phenyl]thiazol-2-yl]amino]ethyl]pyrrole-3-carboxamide (Compound 304) and 1-methylsulfonyl-N-[2-oxo-2-[[4-[3-[[(3S)-tetrahydrofuran-3-yl]methoxy]phenyl]thiazol-2-yl]amino]ethyl]pyrrole-3-carboxamide (Compound 303)
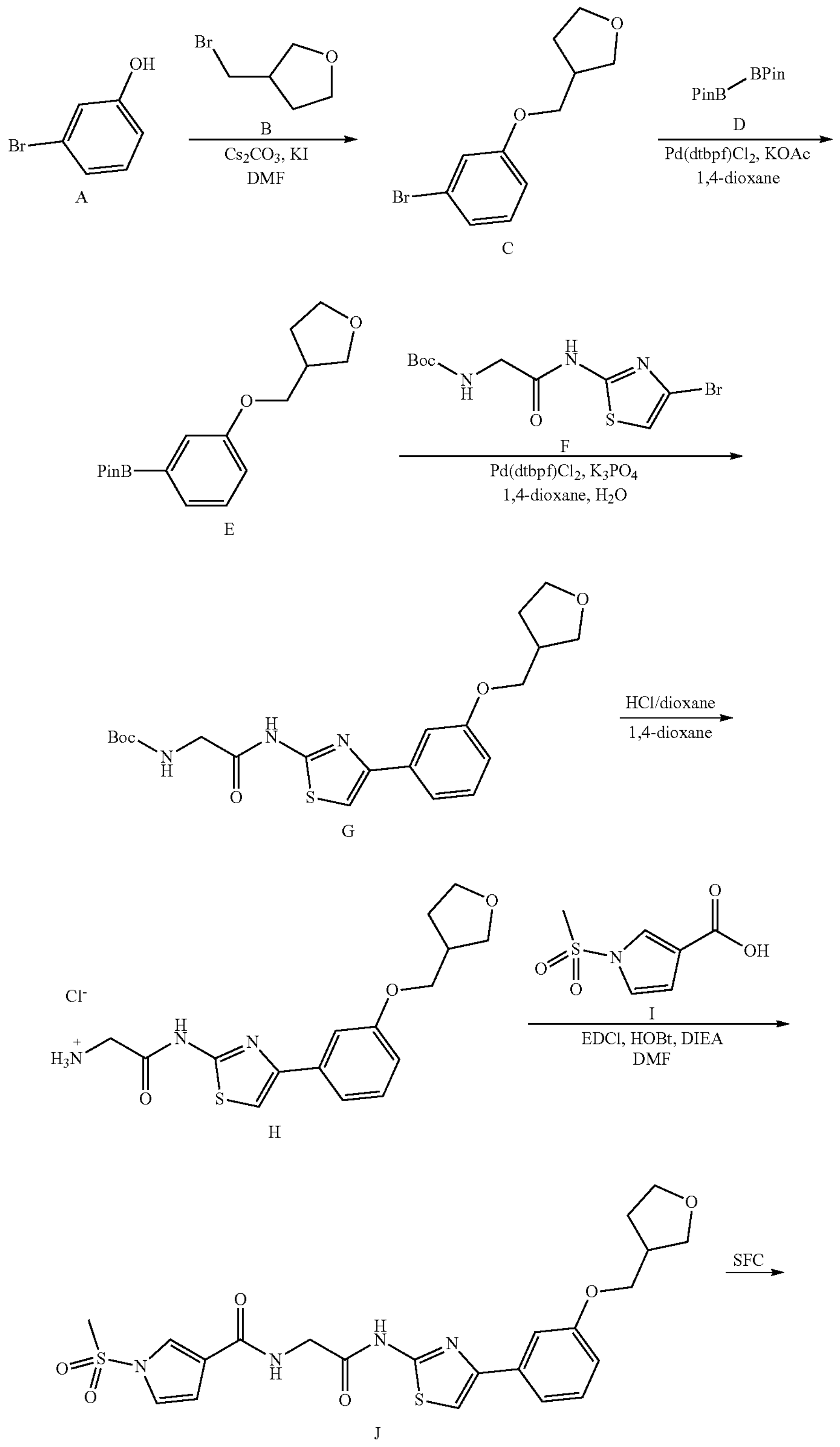

-continued

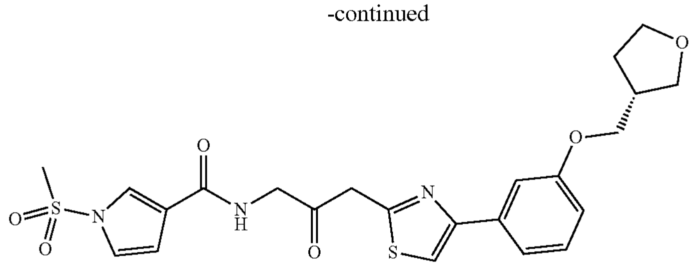

+

Compound 304

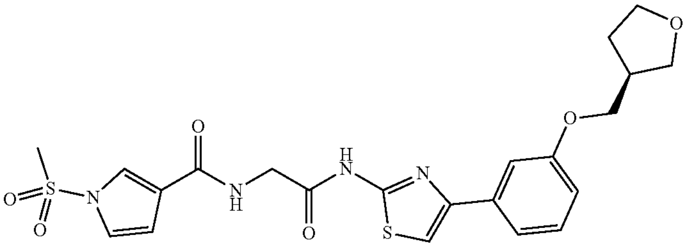

Compound 303

Step 1: Preparation of 3-[(3-bromophenoxy)methyl]tetrahydrofuran (Intermediate C)

C

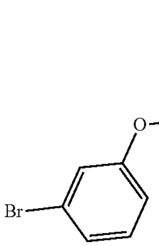

To a solution of 3-bromophenol (0.700 g, 4.05 mmol), 3-(bromomethyl)tetrahydrofuran (0.734 g, 4.45 mmol), and $Cs_2CO_3$ (2.64 g, 8.09 mmol) in DMF (10 mL) was added KI (0.269 g, 1.62 mmol). The mixture was stirred at 70° C. After 16 h, the reaction mixture was poured into water (10 mL) and extracted with ethyl acetate (10 mL×2). The combined organic layers were washed with brine (10 mL) and dried over $Na_2SO_4$ and concentrated. The crude product was purified by reverse phase HPLC to give Intermediate C (0.350 g, 1.30 mmol, 32.13% yield, 95.5% purity) as a colorless oil by extraction. LCMS (ESI) m/z: [$^{79}$Br M+H]$^+$=257.0.

Step 2: Preparation of 4,4,5,5-tetramethyl-2-[3-(tetrahydrofuran-3-ylmethoxy)phenyl]-1,3,2-dioxaborolane (Intermediate E)

E

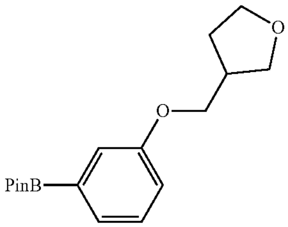

To a solution of Intermediate C (0.350 g, 1.36 mmol) and 4,4,5,5-tetramethyl-2-(4,4,5,5-tetramethyl-1,3,2-dioxaborolan-2-yl)-1,3,2-dioxaborolane (0.691 g, 2.72 mmol) in 1,4-dioxane (5 mL) was added KOAc (0.401 g, 4.08 mmol) and Pd(dtbf)$Cl_2$ (0.089 g, 0.136 mmol). The mixture was stirred at 70° C. After 1 h, the reaction mixture was concentrated to give Intermediate E (0.350 g, 0.833 mmol, 61.20% yield, 72.4% purity) as a yellow oil which was used for next step without further purification. LCMS (ESI) m/z: [M+H]$^+$=305.1.

Step 3: Preparation of tert-butyl N-[2-oxo-2-[[4-[3-(tetrahydrofuran-3-ylmethoxy)phenyl]thiazol-2-yl]amino]ethyl]carbamate (Intermediate G)

G

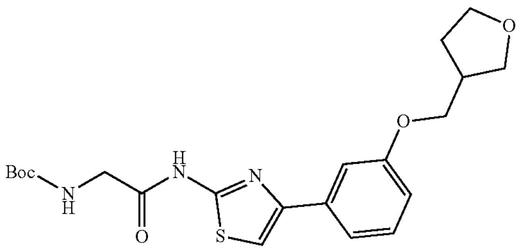

To a solution of tert-butyl N-[2-[(4-bromothiazol-2-yl)amino]-2-oxo-ethyl]carbamate (0.250 g, 0.744 mmol), Intermediate E (0.339 g, 1.12 mmol), $K_3PO_4$ (0.474 g, 2.23 mmol) in 1,4-dioxane (0.5 mL) and $H_2O$ (0.1 mL) was added Pd(dtbpf)$Cl_2$ (0.048 g, 0.074 mmol). Then the mixture was stirred at 70° C. After 1 h, the reaction mixture was cooled to ambient temperatures and concentrated. The crude product was purified by reverse phase HPLC to give Intermediate G (0.220 g, 0.448 mmol, 60.19% yield, 88.2% purity) as a colorless oil. LCMS (ESI) m/z: $[M+H]^+$=434.0.

Step 4: Preparation of 2-oxo-2-((4-(3-((tetrahydrofuran-3-yl)methoxy)phenyl)thiazol-2-yl)amino)ethan-1-aminium chloride (Intermediate H)

H

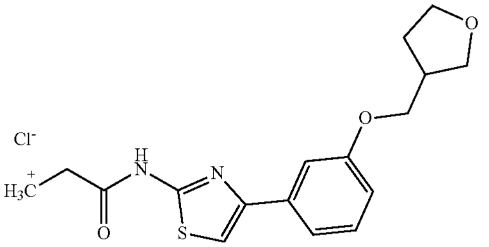

A solution of Intermediate G (0.210 g, 0.484 mmol) in HCl/dioxane (3 mL, 4 M) was stirred at 25° C. for 1 h. The reaction mixture was concentrated to give Intermediate H (150 mg, 361.75 umol, 74.68% yield, 89.2% purity, HCl) as a white solid which was used for next step without further purification. LCMS (ESI) m/z: $[M+H]^+$=334.1.

Step 5: Preparation of 1-methylsulfonyl-N-[2-oxo-2-[[4-[3-(tetrahydrofuran-3-ylmethoxy)phenyl]thiazol-2-yl]amino]ethyl]pyrrole-3-carboxamide (Intermediate J)

J

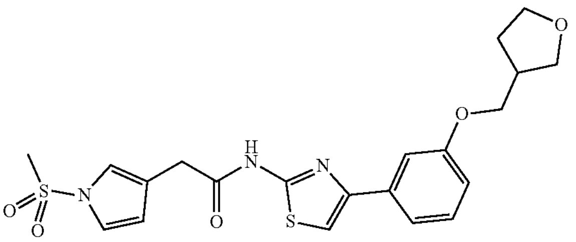

To a solution of Intermediate H (0.150 g, 0.406 mmol), 1-methylsulfonylpyrrole-3-carboxylic acid (0.084 g, 0.446 mmol), EDCI (0.155 g, 0.811 mmol), HOBt (0.110 g, 0.811 mmol) in DMF (2 mL) was added DIEA (0.350 mL, 2.03 mmol). The mixture was stirred at 25° C. for 1 h and subsequently concentrated. The crude product was purified by reverse phase HPLC column and lyophilized to give Intermediate J (0.100 g, 0.198 mmol, 48.87% yield, 100% purity) as a white solid. LCMS (ESI) m/z: $[M+H]^+$=505.2.

Step 6: Preparation of 1-methylsulfonyl-N-[2-oxo-2-[[4-[3-[[(3R)-tetrahydrofuran-3-yl]methoxy]phenyl]thiazol-2-yl]amino]ethyl]pyrrole-3-carboxamide (Compound 304) and 1-methylsulfonyl-N-[2-oxo-2-[[4-[3-[[(3S)-tetrahydrofuran-3-yl]methoxy]phenyl]thiazol-2-yl]amino]ethyl]pyrrole-3-carboxamide (Compound 303)

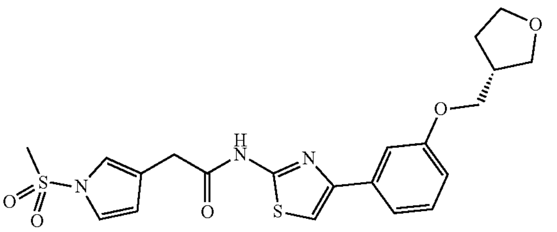

+

Compound 304

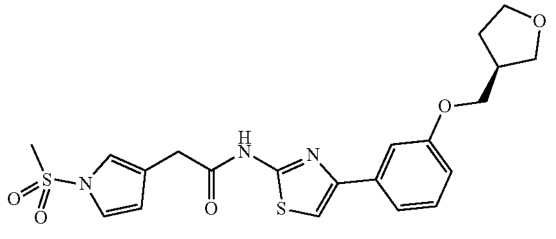

Compound 303

The Intermediate J (0.100 g, 0.198 mmol) was purified by SFC and lyophilized to give Compound 304 (0.021 g, 0.041 mmol, 20.73% yield, 100% purity) as a white solid and Compound 303 (0.026 g, 0.051 mmol, 25.86% yield, 100% purity) as a white solid.

Compound 304: LCMS (ESI) m/z: $[M+H]^+$=505.3; $^1$H NMR (400 MHz, DMSO-$d_6$) δ 12.40 (br s, 1H), 8.68-8.66 (m, 1H), 7.86-7.84 (m, 1H), 7.66 (s, 1H), 7.55-7.44 (m, 2H), 7.40-7.29 (m, 2H), 6.92-6.90 (m, 1H), 6.79-6.77 (m, 1H), 4.14 (d, J=6.0 Hz, 2H), 4.04-3.90 (m, 2H), 3.86-3.74 (m, 2H), 3.71-3.64 (m, 1H), 3.61-3.53 (m, 4H), 2.70-2.65 (m, 1H), 2.12-1.99 (m, 1H), 1.69-1.67 (m, 1H); ee %=100%.

Compound 303: LCMS (ESI) m/z: $[M+H]^+$=505.2; $^1$H NMR (400 MHz, DMSO-$d_6$) δ 12.36 (br s, 1H), 8.68-8.66 (m, 1H), 7.86-7.84 (m, 1H), 7.66 (s, 1H), 7.54-7.44 (m, 2H), 7.37-7.27 (m, 2H), 6.92-6.90 (m, 1H), 6.79-6.77 (m, 1H), 4.14 (d, J=6.0 Hz, 2H), 4.03-3.91 (m, 2H), 3.85-3.76 (m, 2H), 3.71-3.65 (m, 1H), 3.60-3.54 (m, 4H), 2.70-2.67 (m, 1H), 2.11-1.97 (m, 1H), 1.76-1.63 (m, 1H); ee %=96.33%.

Example 164. Preparation of 1-(tert-butyl)-N-(2-((4-(6-(cis-2,6-dimethylmorpholino)pyridin-2-yl)thiazol-2-yl)amino)-2-oxoethyl)-1H-pyrrole-3-carboxamide (Compound 320)

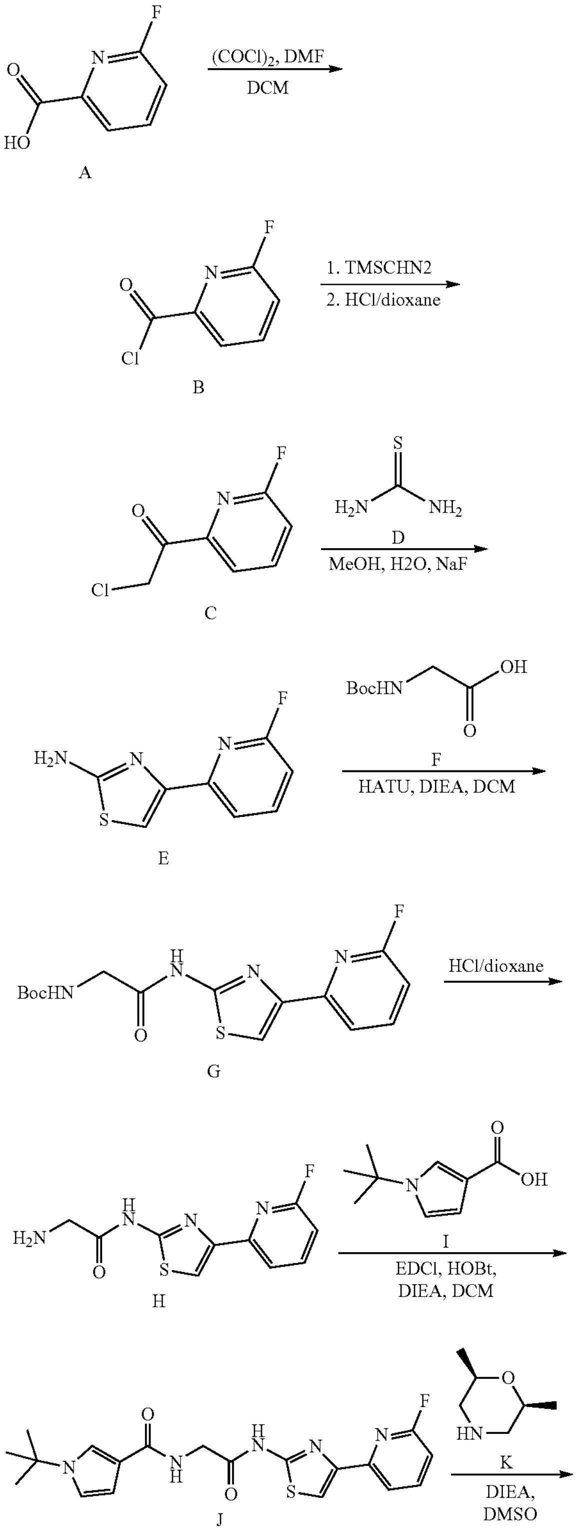

-continued

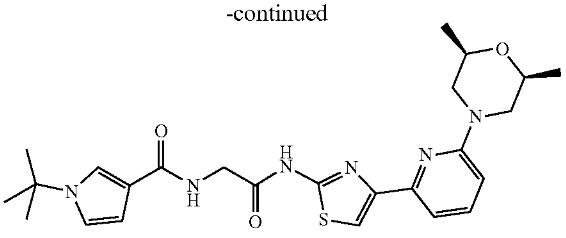

Compound 320

Step 1: Preparation of 6-fluoropyridine-2-carbonyl chloride (Intermediate B)

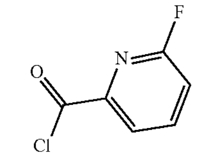

B

To a cooled (0° C.) solution of 6-fluoropyridine-2-carboxylic acid (50.00 g, 354.36 mmol) in dichloromethane (500 mL) and N,N-dimethylformamide (0.26 mL, 3.54 mmol) was added oxalyl chloride (155.10 mL, 1.77 mol). After complete addition of oxalyl chloride, the reaction mixture was warmed to room temperature and stirred for an additional 0.5 h. The mixture was concentrated under vacuum to give intermediate B (56.50 g) as a white solid, which was used to next step without further purification.

Step 2: Preparation of 2-chloro-1-(6-fluoro-2-pyridyl)ethenone (Intermediate C)

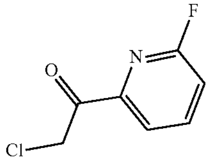

C

To a cooled (0° C.) mixture of intermediate B (56.00 g, 351.00 mmol) in 1,4-dioxane (800 mL) was added in a dropwise manner a solution of 2 M trimethylsilyl diazomethane in hexanes (351 mL). The resulting reaction mixture was stirred at 25° C. for 10 h. The reaction mixture was subsequently quenched with a solution of 4 M HCl in 1,4-dioxane (500 mL). After stirring for 2 h, the reaction solution was concentrated under vacuum to give an oil. The residue was diluted with saturated aqueous $NaHCO_3$ (500 mL) and extracted with ethyl acetate (200 mL×3). The combined organic layers were washed with brine (300 mL×2), dried over $Na_2SO_4$, filtered and concentrated under reduced pressure to give intermediate C (35.50 g) as a white solid, which was used to next step directly. LCMS (ESI) m/z: $[M+H]^+$=173.8.

Step 3: Preparation of 4-(6-fluoro-2-pyridyl)thiazol-2-amine (Intermediate E)

E

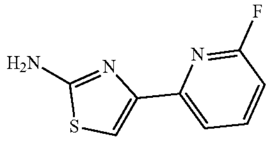

To a solution of intermediate C (35.50 g, 204.53 mmol) and thiourea (14.01 g, 184.07 mmol) in a mixture of MeOH (250 mL) and $H_2O$ (250 mL) at room temperature was added NaF (3.56 g, 84.82 mmol). After stirring for 0.5 h, the reaction mixture was partially concentrated under vacuum to remove MeOH, and the resulting solution was acidified to pH~3 with aqueous 2 M HCl. After 15 min, the solution was extracted with ethyl acetate (200 mL×3), the organic layers were discarded and the aqueous phase was alkalized with $NaHCO_3$ (500 mL) and stirred for 30 min, then extracted with ethyl acetate (325 mL*3), the combined organic layers were washed with brine (225 mL*3), dried over $Na_2SO_4$, filtered and concentrated under reduced pressure. The residue was triturated with petroleum ether (300 mL) and stirred at 25° C. for 10 min and filtered. The resultant solids were dried under vacuum to give intermediate E (28.00 g, 143.43 mmol, 70.13% yield, 100% purity) as a white solid. LCMS (ESI) m/z: $[M+H]^+$=195.8; $^1H$ NMR (400 MHz, DMSO-$d_6$) δ 8.00-7.96 (m, 1H), 7.72 (d, J=7.2 Hz, 1H), 7.24 (s, 1H), 7.16 (s, 2H), 7.02 (d, J=8.0 Hz, 1H).

Step 4: Preparation of tert-butyl N-[2-[[4-(6-fluoro-2-pyridyl)thiazol-2-yl]amino]-2-oxo-ethyl]carbamate (Intermediate G)

G

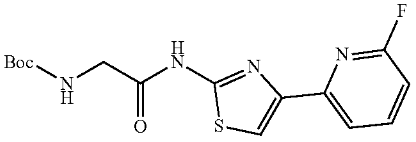

To a solution of N-Boc-glycine (5.92 g, 33.81 mmol), HATU (12.86 g, 33.81 mmol), and DIEA (15.89 g, 122.94 mmol, 21.41 mL) in dichloromethane (100 mL) was added intermediate E (6.00 g, 30.74 mmol). After stirring for 2 h, the reaction mixture was concentrated and subsequently diluted with water (100 mL) and extracted with ethyl acetate (60 mL×4). The combined organic layers were washed with brine (100 mL×2), dried over $Na_2SO_4$, filtered and concentrated under reduced pressure to give a residue. The residue was triturated with a 1:1 mixture of petroleum ether and MeOH (40 mL). After stirring at 25° C. for 20 min, the suspension was filtered, the filter cake was washed with MTBE (20 mL), and dried in vacuo to give intermediate G (7.70 g, 21.63 mmol, 70.4% yield, 99.0% purity) as a white solid. LCMS (ESI) m/z: $[M+H]^+$=353.1.

Step 5: Preparation of 2-((4-(6-fluoropyridin-2-yl)thiazol-2-yl)amino)-2-oxoethan-1-aminium chloride (Intermediate H)

H

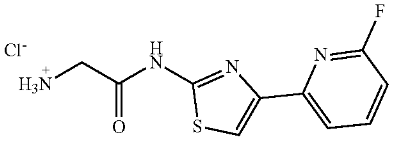

A solution of intermediate G (5.40 g, 15.32 mmol) in 4 M HCl in 1,4-dioxane (35 mL) was stirred at 25° C. for 1.5 h. The mixture was concentrated under vacuum to give intermediate H (4.42 g) as a white solid, which was used to next step directly without further purification. LCMS (ESI) m/z: $[M+H]^+$=252.9.

Step 6: Preparation of 1-tert-butyl-N-[2-[[4-(6-fluoro-2-pyridyl)thiazol-2-yl]amino]-2-oxo-ethyl]pyrrol e-3-carboxamide (Intermediate J)

J

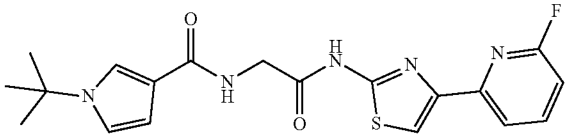

To a solution of intermediate H (3.00 g, 10.39 mmol), 1-tert-butylpyrrole-3-carboxylic acid (1.74 g, 10.39 mmol) and DIEA (6.71 g, 51.95 mmol, 9.05 mL) in dichloromethane (40 mL) was sequentially added HOBt (1.68 g, 12.47 mmol) and EDCI (2.39 g, 12.47 mmol). After stirring for 4 h, the mixture was concentrated under vacuum. The residue was diluted with water (250 mL) and extracted with ethyl acetate (200 mL×3). The combined organic layers were washed with brine (300 mL×3), dried over $Na_2SO_4$, filtered and concentrated under reduced pressure. The resulting solids were triturated with a 1:1 mixture of MTBE/ethyl acetate (400 mL) and after 30 min, the suspension was filtered. The solids were washed with MTBE (85 mL×3) and then dried under vacuum to give intermediate J (3.10 g, 7.64 mmol, 73.6% yield, 99.0% purity) as a white solid. LCMS (ESI) m/z: $[M+H]^+$=402.3; $^1H$ NMR (400 MHz, DMSO-$d_6$) δ 12.40 (s, 1H), 8.18-8.15 (m, 1H), 8.09-8.08 (m, 1H), 7.87-7.83 (m, 2H), 7.52 (s, 1H), 7.11 (d, J=8.0 Hz, 1H), 6.97 (m, 1H), 6.47 (s, 1H), 4.10 (d, J=5.6 Hz, 2H), 1.49 (s, 9H).

Step 7: Preparation of 1-(tert-butyl)-N-(2-((4-(6-(cis-2,6-dimethylmorpholino)pyridin-2-yl)thiazol-2-yl)amino)-2-oxoethyl)-1H-pyrrole-3-carboxamide (Compound 320)

Compound 320

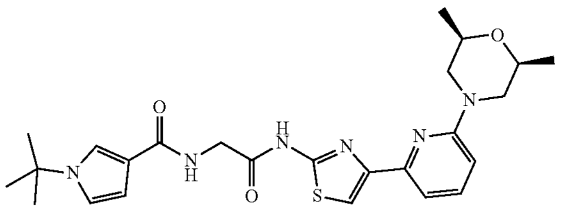

To a solution of intermediate J (0.100 g, 0.249 mmol) in DMSO (1 mL) was added DIEA (0.130 mL, 0.747 mmol) and cis-2,6-dimethylmorpholine (0.057 g, 0.498 mmol) and the mixture was stirred at 120° C. After 12 h, the solution was cooled to room temperature and reaction mixture was diluted with MeOH (3 mL). The residue was purified by prep-HPLC (mobile phase: [water (0.075% TFA)-ACN]; B %: 30%-60%). The appropriate fractions were collected and lyophilized to give Compound 320 (0.079 g, 0.129 mmol, 51.94% yield, 100% purity) as a white solid. LCMS (ESI) m/z: $[M+H]^+$=497.5; $^1$H NMR (400 MHz, DMSO-$d_6$) δ 12.27 (s, 1H), 8.17-8.14 (m, 1H), 7.75 (s, 1H), 7.63-7.59 (m, 1H), 7.51 (s, 1H), 7.25 (d, J=7.2 Hz, 1H), 6.96 (s, 1H), 6.79 (d, J=8.8 Hz, 1H), 6.47 (s, 1H), 4.24 (d, J=12.4 Hz, 2H), 4.08 (d, J=5.6 Hz, 2H), 3.64-3.61 (m, 2H), 2.44-2.38 (m, 2H), 1.49 (s, 9H), 1.18 (d, J=5.6 Hz, 6H).

Example 165. Preparation of Compounds of the Invention

The following compounds in Table 7 were synthesized starting from the appropriate common intermediate ([1-tert-butyl-N-[2-[[4-(6-fluoro-2-pyridyl)thiazol-2-yl]amino]-2-oxo-ethyl]pyrrole-3-carboxamide]), the requisite amine, and utilizing the general synthetic protocols described in example 164. Where appropriate SEC purification was used to separate enantiomers.

TABLE 7

| Compound # | LC-MS data(m/z) | $^1$H NMR |
|---|---|---|
| 310 | 513.1 | $^1$H NMR (400 MHz, DMSO-$d_6$) δ 12.29 (s, 1H), 8.19-8.16 (m, 1H), 7.69 (s, 1H), 7.69-7.52 (m, 1H), 7.52-7.52 (m, 1H), 7.21 (d, J = 7.2 Hz, 1H), 6.97-6.96 (m, 1H), 6.83 (d, J = 8.4 Hz, 1H), 6.48-6.47 (m, 1H), 4.93 (d, J = 4.4 Hz, 1H), 4.25-4.22(m, 1H), 4.09 (d, J = 6.0 Hz, 2H), 4.03-3.89 (m, 1H), 3.56-3.45 (m, 1H), 3.40 (s, 3H), 3.16-3.00(m, 3H), 1.87-1.82 (m, 1H), 1.49 (s, 9H), 1.40-1.38 (m, 1H) |
| 311 | 497.2 | $^1$H NMR (400 MHz, DMSO-$d_6$) δ 12.28 (s, 1H), 8.23-8.13 (m, 1H), 7.61-7.55 (m, 1H), 7.52 (d, J = 2.0 Hz, 1H), 7.20 (d, J = 7.2 Hz, 1H), 6.97 (d, J = 2.8 Hz, 1H), 6.80 (d, J = 8.8 Hz, 1H), 6.53-5.45 (m, 1H), 4.22-4.12 (m, 1H), 4.09 (d, J = 6.0 Hz, 2H), 3.89-6.83 (m, 1H), 3.30-3.12 (m, 4H), 2.55-2.52 (m, 2H), 2.04-1.93 (m, 1H), 1.81-1.69 (m, 1H), 1.53-1.44 (m, 11H) |
| 312 | 497.3 | $^1$H NMR (400 MHz, DMSO-$d_6$) δ 12.27 (s, 1H), 8.17 (d, J = 6.0 Hz, 1H), 7.69 (s, 1H), 7.61-7.55 (m, 1H), 7.52 (d, J = 2.0 Hz, 1H), 7.20 (d, J = 7.2 Hz, 1H), 6.97 (d, J = 2.8 Hz, 1H), 6.80 (d, J = 8.8 Hz, 1H), 6.53-6.45 (m, 1H), 4.20-4.13 (m, 1H), 4.09 (d, J = 6.0 Hz, 2H), 3.90-3.83 (m, 1H), 3.30-3.12 (m, 4H), 2.53 (d, J = 2.0 Hz, 2H), 2.02-1.93 (m, 1H), 1.82-1.73 (m, 1H), 1.56-1.48 (m, 11H) |
| 314 | 483.3 | $^1$H NMR (400 MHz, DMSO-$d_6$) δ 12.29-12.23 (m, 1H), 8.18-8.15 (m, 1H), 7.69 (s, 1H), 7.60-7.56 (m, 1H), 7.52-7.51 (m, 1H), 7.20 (d, J = 7.2 Hz, 1H), 6.98-6.96 (m, 1H), 6.79 (d, J = 8.4 Hz, 1H), 6.48-6.47 (m, 1H), 4.68 (d, J = 4.4 Hz, 1H), 4.12-4.08 (m, 4H), 3.73-3.68 (m, 1H), 3.15-3.08 (m, 2H), 1.84-1.79 (m, 2H), 1.49 (s, 9H), 1.43-1.34 (m, 2H) |
| 315 | 439.2 | $^1$H NMR (400 MHz, Methanol-$d_4$) δ 7.63-7.53 (m, 3H), 7.30 (d, J = 7.2 Hz, 1H), 6.95-6.94 (m, 1H), 6.57-6.56 (m, 1H), 6.32 (d, J = 8.0 Hz, 1H), 4.22 (s, 2H), 4.08-4.04 (m, 4H), 2.44-2.36 (m, 2H), 1.56 (s, 9H) |
| 317 | 524.4 | $^1$H NMR (400 MHz, DMSO-$d_6$ + $D_2O$) δ 8.25-8.22 (m, 1H), 7.65 (s, 1H), 7.60-7.58 (m, 1H), 7.51-7.49 (m, 1H), 7.24 (d, J = 7.2 Hz, 1H), 6.97-6.95 (m, 1H), 6.48-6.46 (m, 1H), 6.36 (d, J = 8.0 Hz, 1H), 4.09-4.03 (m, 2H), 4.03-4.01 (m, 2H), 3.80-3.78 (m, 2H), 3.58 (d, J = 4.0 Hz, 4H), 3.27-3.25 (m, 1H), 2.35-2.33 (m, 4H), 1.47 (s, 9H) |
| 318 | 511.2 | $^1$H NMR (400 MHz, Methanol-$d_4$) δ 7.66 (s, 1H), 7.58-7.57 (m, 1H), 7.56-7.52 (m, 1H), 7.27 (d, J = 7.2 Hz, 1H), 6.96-6.94 (m, 1H), 6.71 (d, J = 8.4 Hz, 1H), 6.58-6.57 (m, 1H), 4.35-4.31 (m, 1H), 4.28-4.20 (m, 3H), 3.36 (s, 3H), 3.34 (d, J = 6.4 Hz, 2H), 3.05-2.94 (m, 1H), 2.80-2.74 (m, 1H), 1.96-1.80 (m, 2H), 1.79-1.74 (m, 1H), 1.69-1.60 (m, 1H), 1.56 (s, 9H), 1.39-1.25 (m, 1H) |
| 319 | 511.5 | $^1$H NMR (400 MHz, DMSO-$d_6$) δ 12.28 (s, 1H), 8.17-8.15 (m, 1H), 7.66 (s, 1H), 7.59-7.55 (m, 1H), 7.51 (s, 1H), 7.18 (d, J = 7.2 Hz, 1H), 6.97 (d, J = 2.4 Hz, 1H), 6.74 (d, J = 8.8 Hz, 1H), 6.47 (s, 1H), 4.26 (d, J = 8.4 Hz, 2H), 4.08 (d, J = 4.4 Hz, 2H), 3.26 (s, 3H), 2.98-2.90 (m, 2H), 2.77-2.57 (m, 3H), 1.78-1.73 (m, 2H), 1.72-1.64 (m, 1H), 1.49 (s, 9H), 1.29-1.17 (m, 1H) |
| 422 | 497.4 | $^1$H NMR (400 MHz, DMSO-$d_6$) δ 12.26 (br s, 1H), 8.17-8.14 (m, 1H), 7.76 (s, 1H), 7.62-7.58 (m, 1H), 7.51 (d, J = 1.6 Hz, 1H), 7.22 (d, J = 7.2 Hz, 1H), 6.97-6.95 (m, 1H), 6.77 (d, J = 8.4 Hz, 1H), 6.47-6.46 (m, 1H), 4.09-4.02 (m, 4H), 3.69-3.65 (m, 2H), 3.29-3.24 (m, 2H), 1.49 (s, 9H), 1.17 (d, J = 6.4 Hz, 6H) |

TABLE 7-continued

| Compound # | LC-MS data(m/z) | $^1H$ NMR |
|---|---|---|
| 424 | 497.2 | $^1H$ NMR (400 MHz, DMSO-$d_6$) δ 12.28-12.20 (m, 1H), 8.44 (s, 1H), 8.17-8.15 (m, 1H), 7.73 (s, 1H), 7.61-7.59 (m, 1H), 7.52-7.50 (m, 1H), 7.23 (d, J = 7.6 Hz, 1H), 6.97-6.95 (m, 1H), 6.77 (d, J = 8.4 Hz, 1H), 6.47-6.46(m, 1H), 4.08 (d, J = 6.0 Hz, 2H), 4.04 (d, J = 3.2 Hz, 2H), 3.69-3.65 (m, 2H), 3.27 (s, 2H), 1.49 (s, 9H), 1.18 (d, J = 6.0 Hz, 6H) |
| 428 | 497.4 | $^1H$ NMR (400 MHz, DMSO-$d_6$) δ 12.39-12.15 (m, 1H), 8.14 (s, 1H), 7.72 (s, 1H), 7.64-7.59 (m, 1H), 7.53-7.51 (m, 1H), 7.24 (d, J = 7.2 Hz, 1H), 6.99-6.97 (m, 1H), 6.79 (d, J = 7.6 Hz, 1H), 6.49-6.47 (m, 1H), 4.07 (d, J = 5.6 Hz, 2H), 3.75-3.72 (m, 2H), 3.56-3.52 (m, 2H), 3.41 (s, 2H), 1.50 (s, 9H), 1.22 (s, 6H) |
| 429 | 483.3 | $^1H$ NMR (400 MHz, DMSO-$d_6$) δ 12.48-12.12 (m, 1H), 8.18-8.14 (m, 1H), 7.74 (s, 1H), 7.66-7.61 (m, 1H), 7.53-7.51 (m, 1H), 7.27 (d, J = 7.6 Hz, 1H), 6.99-6.97 (m, 1H), 6.80 (d, J = 8.4 Hz, 1H), 6.49-6.47 (m, 1H), 4.25 (d, J = 12.4 Hz, 1H), 4.16 (d, J = 12.8 Hz, 1H), 4.08 (d, J = 6.0 Hz, 2H), 3.96-3.91 (m, 1H), 3.61-3.54 (m, 2H), 2.87-2.79 (m, 2H), 1.50 (s, 9H), 1.19 (d, J = 6.0 Hz, 3H) |
| 440 | 524.5 | $^1H$ NMR (400 MHz, Methanol-$d_4$) δ 7.69 (s, 1H), 7.64-7.55 (m, 2H), 7.37 (d, J = 7.2 Hz, 1H), 6.98-6.96 (m, 1H), 6.81-6.69 (m, 1H), 6.64-6.51 (m, 1H), 4.80-4.63 (m, 4H), 4.24 (s, 2H), 3.78-3.65 (m, 4H), 3.63-3.52 (m, 1H), 2.59-2.46 (m, 4H), 1.58 (s, 9H) |
| 620 | 495.2 | $^1H$ NMR (400 MHz, DMSO-$d_6$) δ 12.40-12.02 (m, 1H), 8.17-8.16 (m, 1H), 7.69 (s, 1H), 7.59-7.57 (m, 1H), 7.52-7.51 (m, 1H), 7.19-7.17 (m, 1H), 6.97-6.96 (m, 1H), 6.47-6.46 (m, 1H), 6.42-6.40 (m, 1H), 4.61-4.60 (m, 2H), 4.55-4.53 (m, 2H), 4.09-4.07 (m, 2H), 3.72 (s, 2H), 3.49-3.43 (m, 2H), 2.28-2.24 (m, 2H), 1.49 (s, 9H) |
| 623 | 496.2 | $^1H$ NMR (400 MHz, DMSO-$d_6$) δ 12.32-12.19 (m, 1H), 8.18-8.16 (m, 1H), 7.69 (s, 1H), 7.58-7.49 (m, 2H), 7.18-7.16 (m, 1H), 6.97-6.96 (m, 1H), 6.47-6.45 (m, 1H), 6.42-6.41 (m, 1H), 4.08-4.75 (m, 2H), 3.80-3.71 (m, 1H), 3.69-3.60 (m, 1H), 3.41-3.35 (m, 1H), 3.18-3.10 (m, 1H), 2.82-2.72 (m, 1H), 2.25-2.12 (m, 7H), 1.87-1.74 (m, 1H), 1.49 (s, 9H) |
| 624 | 523.3 | $^1H$ NMR (400 MHz, DMSO-$d_6$) δ 12.27 (br s, 1H), 8.21-8.19 (m, 1H), 7.71 (s, 1H), 7.58-7.50 (m, 2H), 7.17 (d, J = 7.2 Hz, 1H), 6.98-6.97 (m, 1H), 6.50-6.39 (m, 2H), 4.09 (d, J = 6.0 Hz, 2H), 3.63 (d, J = 5.2 Hz, 2H), 3.53-3.50 (m, 2H), 3.39 (s, 2H), 1.92-1.88 (m, 2H), 1.56 (s, 2H), 1.51-1.48 (m, 9H), 1.06-0.96 (m, 4H) |
| 625 | 453.2 | $^1HNMR$ (400 MHz, DMSO-$d_6$) δ 12.27 (br s, 1H), 8.20-8.18 (m, 1H), 7.63 (s, 1H), 7.63-7.57 (m, 1H), 7.53-7.52 (m 1H), 7.23 (d, J = 7.2 Hz, 1H), 6.98-6.97 (m, 1H), 6.48-6.47 (m, 1H), 6.31 (d, J = 8.0 Hz, 1H), 4.17-4.06 (m, 4H), 3.57-3.55 (m, 2H), 2.80-2.79 (m, 1H), 1.52-1.47 (m, 9H), 1.26 (d, J = 6.8 Hz, 3H) |
| 626 | 523.2 | $^1H$ NMR (400 MHz, $CDCl_3$) δ 7.67 (s, 1H), 7.56-7.50 (m, 2H), 7.30 (d, J = 7.6 Hz, 1H), 6.88-6.80 (m, 1H), 6.63 (d, J = 8.4 Hz, 1H), 6.49-6.41 (m, 2H), 4.34 (d, J = 6.0 Hz, 2H), 3.96-3.87 (m, 2H), 3.72-3.54 (m, 6H), 1.87-1.79 (m, 2H), 1.74-1.67 (m, 4H), 1.56 (s, 9H) |
| 627 | 546.3 | $^1H$ NMR (400 MHz, DMSO-$d_6$) δ 12.37-12.29 (m, 1H), 8.58-8.57 (m, 1H), 8.39 (s, 1H), 8.20-8.19 (m, 1H), 7.76 (s, 1H), 7.71-7.56 (m, 1H), 7.52-7.51 (m, 1H), 7.40-7.39 (m, 1H), 7.34-7.31 (m, 1H), 7.29 (d, J = 7.2 Hz, 1H), 6.97-6.88 (m, 1H), 6.88 (d, J = 8.8 Hz, 1H), 6.47 (m, 1H), 4.09 (d, J = 5.6 Hz, 2H), 3.73 (s, 8H), 1.48 (s, 9H) |
| 628 | 525.3 | $^1H$ NMR (400 MHz, DMSO-$d_6$) δ 12.32-12.25 (m, 1H), 8.37 (d, J = 4.4 Hz, 1H), 8.20-8.17 (m, 1H), 7.68 (s, 1H), 7.57-7.52 (m, 1H), 7.52-7.51 (m, 1H), 7.20 (d, J = 7.6 Hz, 1H), 6.97-6.96 (m, 1H), 6.80 (d, J = 8.8 Hz, 1H), 6.47-6.46 (m, 1H), 5.23-5.06 (m, 1H), 4.08 (d, J = 6.0 Hz, 2H), 3.54-3.50 (m, 4H), 2.35-2.32 (m, 2H), 1.93-1.91 (m, 2H), 1.63-1.60 (m, 2H), 1.56-1.53 (m, 2H), 1.48 (s, 9H) |
| 629 | 572.2 | $^1H$ NMR (400 MHz, DMSO-$d_6$) δ 12.31 (br s, 1H), 8.38-8.36 (m, 1H), 8.25-8.20 (m, 1H), 7.66-7.64 (m, 1H), 7.64-7.52 (m, 1H), 7.52-7.48 (m, 1H), 7.26-7.22 (m, 1H), 7.00-6.95 (m, 1H), 6.51-6.45 (m, 1H), 6.40-6.34 (m, 1H), 4.17-4.02 (m, 4H), 3.85-3.75 (m, 2H), 3.61-3.51 (m, 1H), 3.19-3.06 (m, 4H), 2.90-2.77 (m, 4H), 1.52-1.46 (m, 9H) |
| 630 | 549.2 | $^1H$ NMR (400 MHz, DMSO-$d_6$) δ 12.31 (br s, 1H), 8.21-8.19 (m, 1H), 8.19-8.14 (m, 1H), 7.76-7.69 (m, 1H), 7.67-7.57 (m, 1H), 7.55-7.48 (m, 1H), 7.29-7.19 (m, 1H), 7.01-6.94 (m, 1H), 6.90-6.81 (m, 1H), 6.55-6.41 (m, 1H), 4.45-4.30 (m, 2H), 4.18-3.99 (m, 2H), 3.28-3.21 (m, 1H), 3.17-3.03 (m, 2H), 2.48-2.44 (m, 3H), 2.14-1.98 (m, 2H), 1.81-1.62 (m, 2H), 1.49 (s, 9H) |
| 631 | 523.2 | $^1H$ NMR (400 MHz, $CDCl_3$) δ 10.02-9.90 (m, 1H), 7.70 (s, 1H), 7.54-7.52 (m, 1H), 7.49-7.47 (m, 1H), 7.23 (d, J = 7.6 Hz, 1H), 6.84-6.83 (m, 1H), 6.42-6.41 (m, 1H), 6.40-6.36 (m, 1H), 6.31 (d, J = 8.4 Hz, 1H), 4.33 (d, J = 6.0 Hz, 2H), 3.82 (d, J = 10.8 Hz, 1H), 3.74-3.72 (m, 2H), 3.60-3.58 (m, 2H), 3.43 (d, J = 11.6 Hz, 1H), 2.29-2.26 (m, 1H), 1.96-1.91 (m, 1H), 1.78-1.67 (m, 4H), 1.64-1.60 (m, 2H), 1.57 (s, 9H) |
| 632 | 516.3 | $^1H$ NMR (400 MHz, DMSO-$d_6$) δ 12.29 (br s, 1H), 8.49 (s, 1H), 8.32 (d, J = 4.8 Hz, 1H), 8.27 (s, 1H), 8.19-8.16 (m, 1H), 7.82 (s, 1H), 7.67-7.63 (m, 1H), 7.52-7.51 (m, 1H), 7.26-7.20 (m, 2H), 6.97-6.88 (m, 2H), 6.47-6.46 (m, 1H), 4.81 (s, 2H), 4.08 (d, J = 6.0 Hz, 2H), 3.93-3.90 (m, 2H), 2.93-2.90 (m, 2H), 1.49 (s, 9H) |

TABLE 7-continued

| Compound # | LC-MS data(m/z) | $^1$H NMR |
|---|---|---|
| 633 | 519.3 | $^1$H NMR (400 MHz, DMSO-$d_6$) δ 12.28 (br s, 1H), 8.15-8.14 (m, 1H), 8.14 (s, 1H), 7.69 (s, 1H), 7.61-7.51 (m, 2H), 7.20 (d, J = 7.2 Hz, 1H), 7.00-6.61 (m, 2H), 6.47-6.44 (m, 2H), 4.95 (br s, 1H), 4.09-4.04 (m, 2H), 3.71-3.56 (m, 3H), 3.51-3.44 (m, 1H), 2.29-2.13 (m, 2H), 1.49 (s, 9H) |
| 634 | 479.3 | $^1$H NMR (400 MHz, DMSO-$d_6$) δ 12.28 (br s, 1H), 8.31 (s, 1H), 8.19-8.16 (m, 1H), 7.65 (s, 1H), 7.57-7.51 (m, 2H), 7.16 (d, J = 7.2 Hz, 1H), 6.97-6.96 (m, 1H), 6.47-6.47 (m, 1H), 6.38 (d, J = 8.4 Hz, 1H), 4.08 (d, J = 5.6 Hz, 2H), 3.61-3.58 (m, 2H), 3.38 (br s, 2H), 1.92-1.89 (m, 2H), 1.48 (s, 9H), 0.66-0.60 (m, 4H) |
| 635 | 570.3 | $^1$H NMR (400 MHz, DMSO-$d_6$) δ 12.31-12.24 (m, 1H), 8.34 (d, J = 3.6 Hz, 1H), 8.18-8.15 (m, 1H), 7.69 (s, 1H), 7.59-7.55 (m, 1H), 7.51-7.50 (m, 1H), 7.23-7.13 (m, 1H), 6.96-6.95 (m, 1H), 6.81 (d, J = 8.8 Hz, 1H), 6.47-6.46 (m, 1H), 5.15-5.03 (m, 1H), 4.75-4.68 (m, 1H), 4.57-4.52 (m, 1H), 4.08 (d, J = 6.0 Hz, 2H), 3.58-3.56 (m, 4H), 3.05-3.02 (m, 1H), 2.97-2.89 (m, 1H), 2.86-2.80 (m, 1H), 2.58-2.56 (m, 4H), 1.81-1.75 (m, 2H), 1.48 (s, 9H) |
| 636 | 536.2 | $^1$H NMR (400 MHz, DMSO-$d_6$) δ 12.29-12.25 (m, 1H), 8.25 (br s, 1H), 8.18-8.16 (m, 1H), 7.66-7.65 (m, 1H), 7.59-7.55 (m, 1H), 7.52-7.51 (m, 1H), 7.19 (d, J = 7.2 Hz, 1H), 6.97-6.96 (m, 1H), 6.78 (d, J = 8.4 Hz, 1H), 6.47-6.46 (m, 1H), 4.52-4.49 (m, 1H), 4.17 (d, J = 12.4 Hz, 1H), 4.08 (d, J = 6.0 Hz, 2H), 2.93-2.87 (m, 1H), 2.85-2.80 (m, 1H), 2.63-2.62 (m, 3H), 2.28-1.94 (m, 3H), 1.68-1.64 (m, 5H), 1.49-1.42 (m, 11H) |
| 637 | 519.2 | $^1$H NMR (400 MHz, Methanol-$d_4$) δ 8.46-8.41 (m, 1H), 7.71 (s, 1H), 7.61-7.56 (m, 2H), 7.41 (s, 1H), 7.32 (d, J = 7.2 Hz, 1H), 6.98-6.93 (m, 1H), 6.80 (d, J = 8.4 Hz, 1H), 6.59-6.55 (m, 1H), 4.65 (s, 2H), 4.23 (s, 2H), 4.06-3.99 (m, 2H), 3.83 (s, 3H), 2.87-2.77 (m, 2H), 1.57 (s, 9H) |
| 638 | 524.2 | $^1$H NMR (400 MHz, DMSO-$d_6$) δ 12.36-12.24 (m, 1H), 8.31-8.26 (m, 1H), 8.22-8.15 (m, 1H), 7.75 (s, 1H), 7.66-7.58 (m, 1H), 7.52-7.49 (m, 1H), 7.24 (d, J = 7.2 Hz, 1H), 7.01-6.95 (m, 1H), 6.80 (d, J = 8.0 Hz, 1H), 6.48-6.45 (m, 1H), 4.35-4.26 (m, 1H), 4.21-4.20 (m, 1H), 4.08 (d, J = 6.0 Hz, 2H), 3.83-3.73 (m, 2H), 3.60-3.49 (m, 1H), 3.18-3.16 (m, 1H), 2.94-2.88 (m, 1H), 2.88-2.78 (m, 2H), 2.39-2.38 (m, 1H), 2.26-2.14 (m, 3H), 1.49 (s, 9H) |
| 639 | 524.2 | $^1$H NMR (400 MHz, DMSO-$d_6$) δ 12.41-12.23 (m, 1H), 8.44-8.34 (m, 1H), 8.23-8.16 (m, 1H), 7.74 (s, 1H), 7.64-7.52 (m, 1H), 7.51-7.49 (m, 1H), 7.27 (d, J = 7.2 Hz, 1H), 7.00-6.94 (m, 1H), 6.82 (d, J = 8.0 Hz, 1H), 6.47-6.46 (m, 1H), 4.11-4.05 (m, 2H), 3.64-3.53 (m, 8H), 2.38 (d, J = 7.2 Hz, 2H), 1.49 (s, 9H), 1.01-0.99 (m, 3H) |
| 640 | 539.2 | $^1$H NMR (400 MHz, DMSO-$d_6$) δ 12.43-12.18 (m, 1H), 8.44-8.38 (m, 1H), 8.24-8.14 (m, 1H), 7.73 (s, 1H), 7.67-7.60 (m, 1H), 7.54-7.49 (m, 1H), 7.26 (d, J = 7.2 Hz, 1H), 7.00-6.94 (m, 1H), 6.81 (d, J = 8.8 Hz, 1H), 6.47-6.46 (m, 1H), 4.08 (d, J = 6.4 Hz, 2H), 3.58-3.57 (m, 4H), 3.26-3.20 (m, 4H), 2.79 (s, 6H), 1.49 (s, 9H) |
| 641 | 550.5 | $^1$H NMR (400 MHz, DMSO-$d_6$) δ 12.28 (s, 1H), 8.41 (s, 1H), 8.18-8.17 (m, 1H), 7.71 (s, 1H), 7.56-7.54 (m, 1H), 7.51-7.50 (m, 1H), 7.18 (d, J = 7.6 Hz, 1H), 6.97-6.96 (m, 1H), 6.82 (d, J = 8.4 Hz, 1H), 6.46-6.43 (m, 1H), 4.50-4.42 (m, 2H), 4.08 (d, J = 6.0 Hz, 2H), 3.50-3.47 (m, 1H), 3.10-3.06 (m, 1H), 2.83 (s, 3H), 2.83-2.76 (m, 1H), 2.20-2.17 (m, 3H), 2.05 (d, J = 9.2 Hz, 1H), 1.89-1.75 (m, 1H), 1.60-1.55 (m, 2H), 1.49 (s, 9H) |
| 642 | 511.5 | $^1$H NMR (400 MHz, DMSO-$d_6$) δ 12.28 (s, 1H), 8.38 (s, 1H), 8.18-8.15 (m, 1H), 7.69 (s, 1H), 7.60-7.56 (m, 1H), 7.51 (s, 1H), 7.20 (d, J = 7.6 Hz, 1H), 6.96 (s, 1H), 6.80 (d, J = 8.4 Hz, 1H), 6.47 (s, 1H), 4.08 (d, J = 5.6 Hz, 5H), 3.50-3.47 (m, 2H), 3.17-3.12 (m, 1H), 1.91 (d, J = 10.0 Hz, 2H), 1.49 (s, 9H), 1.43 (d, J = 9.2 Hz, 3H), 1.13-1.10 (m, 3H) |
| 643 | 550.4 | $^1$H NMR (400 MHz, DMSO-$d_6$) δ 12.35-12.24 (m, 1H), 8.42 (s, 1H), 8.18-8.17 (m, 1H), 7.72 (s, 1H), 7.61-7.61 (m, 1H), 7.52-7.51 (m, 1H), 7.24 (d, J = 7.2 Hz, 1H), 6.97-6.96 (m, 1H), 6.85 (d, J = 8.4 Hz, 1H), 6.47-6.47 (m, 1H), 4.56 (br d, J = 14.0 Hz, 1H), 4.45 (br d, J = 13.6 Hz, 1H), 4.08 (d, J = 6.0 Hz, 2H), 3.19-3.11 (m, 1H), 2.86-2.79 (m, 4H), 2.62-2.56 (m, 1H), 2.37-2.32 (m, 2H), 2.29-2.25 (m, 1H), 1.78-1.74 (m, 1H), 1.67-1.58 (m, 1H), 1.53-1.49 (m, 10H), 1.41-1.33 (m, 1H) |
| 644 | 481.3 | $^1$H NMR (400 MHz, DMSO-$d_6$) δ 8.18 (d, J = 6.0 Hz, 1H), 7.65 (s, 1H), 7.60 (d, J = 8.0 Hz, 1H), 7.52 (d, J = 2.0 Hz, 1H), 7.26 (d, J = 7.2 Hz, 1H), 6.98 (d, J = 2.4 Hz, 1H), 6.48-6.47 (m, 1H), 6.40-6.31 (m, 1H), 4.74 (s, 4H), 4.15 (s, 4H), 4.08 (d, J = 6.0 Hz, 2H), 1.50 (s, 9H) |
| 645 | 537.5 | $^1$H NMR (400 MHz, DMSO-$d_6$) δ 12.38-12.14 (m, 1H), 8.23-8.12 (m, 1H), 7.71 (s, 1H), 7.61-7.43 (m, 2H), 7.15 (d, J = 6.8 Hz, 1H), 7.00-6.94 (m, 1H), 6.81 (d, J = 8.8 Hz, 1H), 6.49-6.47 (m, 1H), 4.09 (d, J = 5.6 Hz, 2H), 3.68-3.52 (m, 8H), 1.67-1.52 (m, 4H), 1.50 (s, 9H), 1.47-1.32 (m, 4H) |
| 646 | 475.2 | $^1$H NMR (400 MHz, DMSO-$d_6$) δ 12.58-12.08 (m, 1H), 8.23-8.15 (m, 1H), 7.79-7.36 (m, 4H), 6.98 (d, J = 2.8 Hz, 1H), 6.56 (d, J = 8.4 Hz, 1H), 6.48-6.47 (m, 1H), 4.44 (d, J = 12.4 Hz, 4H), 4.09 (d, J = 5.6 Hz, 2H), 1.50 (s, 9H) |
| 647 | 471.2 | $^1$HNMR (400 MHz, DMSO-$d_6$) δ 12.28 (br s, 1H), 8.19-8.17 (m, 1H), 7.71 (s, 1H), 7.60-7.59 (m, 1H), 7.54-7.51 (m, 1H), 7.22 (d, J = 7.2 Hz, 1H), 6.98-6.97 (m, 1H), 6.52-6.41 (m, 2H), 5.58-5.35 (m, 1H), 4.09 (d, J = 6.0 Hz, 2H), 3.78-3.67 (m, 2H), 3.49-3.49 (m, 2H), 2.30-2.14 (m, 2H), 1.50 (s, 9H) |

TABLE 7-continued

| Compound # | LC-MS data(m/z) | $^1$H NMR |
|---|---|---|
| 648 | 495.2 | $^1$H NMR (400 MHz, DMSO-$d_6$) δ 12.30 (br s, 1H), 8.20-8.18 (m, 1H), 7.71 (s, 1H), 7.61-7.60 (m, 1H), 7.52-7.51 (m, 1H), 7.26 (d, J = 7.2 Hz, 1H), 6.98-6.97 (m, 1H), 6.68 (d, J = 8.4 Hz, 1H), 6.49-6.48 (m, 1H), 4.46 (s, 2H), 4.09 (d, J = 6.0 Hz, 2H), 3.94 (d, J = 12.0 Hz, 2H), 2.99-2.96 (m, 2H), 1.88-1.71 (m, 4H), 1.50 (s, 9H) |
| 649 | 509.3 | $^1$HNMR (400 MHz, DMSO-$d_6$) δ 12.30 (br s, 1H), 8.20-8.19 (m, 1H), 7.71 (s, 1H), 7.62-7.51 (m, 2H), 7.21 (d, J = 7.2 Hz, 1H), 6.98-6.97 (m, 1H), 6.54-6.45 (m, 2H), 4.67-4.64 (m, 1H), 4.09 (d, J = 6.0 Hz, 2H), 3.87-3.86 (m, 1H), 3.67-3.63 (m, 1H), 3.53 (d, J = 4.4 Hz, 1H), 3.51-3.47 (m, 2H), 3.44 (s, 2H), 2.99-2.91 (m, 1H), 1.50 (s, 9H), 1.06 (d, J = 6.8 Hz, 3H) |
| 650 | 509.3 | $^1$HNMR (400 MHz, DMSO-$d_6$) δ 12.30 (br s, 1H), 8.20-8.19 (m, 1H), 7.70 (s, 1H), 7.64-7.57 (m, 1H), 7.52-7.51(m, 1H), 7.22 (d, J = 7.2 Hz, 1H), 6.98-6.97 (m 1H), 6.84 (d, J = 8.4 Hz, 1H), 6.49-6.47 (m, 1H), 4.87-4.84 (m, 1H), 4.51 (d, J = 12.4 Hz, 1H), 4.09 (d, J = 6.0 Hz, 2H), 3.90-3.80 (m, 2H), 2.98-2.91 (m, 1H), 2.76-2.68 (m, 2H), 2.12-1.93 (m, 2H), 1.62-1.53 (m, 2H), 1.50 (s, 9H), 1.41-1.30 (m, 1H) |
| 653 | 509.3 | $^1$H NMR (400 MHz, DMSO-$d_6$) δ 12.34-12.18 (m, 1H), 8.17-8.14 (m, 1H), 7.73 (s, 1H), 7.60-7.58 (m, 1H), 7.51-7.50 (m, 1H), 7.23-7.21 (m, 1H), 6.97-6.96 (m, 1H), 6.88-6.86 (m, 1H), 6.47-6.46 (m, 1H), 4.35-4.24 (m, 4H), 4.08-4.07 (m, 2H), 3.79 (s, 2H), 3.51-3.43 (m, 2H), 1.90-1.81 (m, 2H), 1.49 (s, 11H) |
| 654 | 467.2 | $^1$H NMR (400 MHz, DMSO-$d_6$) δ 12.26 (s, 1H), 8.19-8.16 (m, 1H), 7.67 (s, 1H), 7.61-7.49 (m, 2H), 7.16 (d, J = 7.2 Hz, 1H), 6.98-6.97 (m, 1H), 6.49-6.48 (m, 1H), 6.39 (d, J = 8.4 Hz, 1H), 4.09 (d, J = 6.0 Hz, 2H), 3.70-3.66 (m, 1H), 3.00-2.96 (m, 1H), 2.41-2.30 (m, 3H), 2.14-2.08 (m, 1H), 1.63-1.57 (m, 1H), 1.50 (s, 9H), 1.10 (d, J = 6.4 Hz, 3H) |
| 656 | 545.3 | $^1$H NMR (400 MHz, DMSO-$d_6$) δ 12.61-11.98 (m, 1H), 8.19-8.17 (m, 1H), 7.73 (s, 1H), 7.73-7.63 (m, 1H), 7.52-7.51 (m, 1H), 7.25 (d, J = 7.2 Hz, 1H), 6.97-6.87 (m, 1H), 6.86 (d, J = 8.8 Hz, 1H), 6.48-6.47 (m, 1H), 4.58 (d, J = 13.2 Hz, 2H), 4.09 (d, J = 6.0 Hz, 2H), 2.95 (s, 3H), 2.91 (s, 1H), 2.53 (s, 2H), 2.11-2.05 (m, 2H), 1.62-1.56 (m, 2H), 1.50 (s, 9H) |
| 659 | 523.3 | $^1$H NMR (400 MHz, DMSO-$d_6$) δ 12.30 (s, 1H), 8.19 (d, J = 5.6 Hz, 1H), 7.72 (s, 1H), 7.61 (d, J = 7.6 Hz, 1H), 7.52 (d, J = 2.0 Hz, 1H), 7.22 (d, J = 7.6 Hz, 1H), 6.97 (d, J = 2.8 Hz, 1H), 6.83 (d, J = 8.4 Hz, 1H), 6.49-6.48 (m, 1H), 4.57-4.43 (m, 1H), 4.29 (d, J = 12.4 Hz, 1H), 4.09 (d, J = 5.6 Hz, 2H), 3.55-3.26 (m, 2H), 3.20-3.03 (m, 1H), 2.89-2.82 (m, 1H), 1.83 (d, J = 8.6 Hz, 1H), 1.80-1.72 (m, 1H), 1.59 (d, J = 3.2 Hz, 2H), 1.49 (s, 9H), 1.45-1.42 (m, 1H), 1.36-1.30 (m, 1H), 1.27-1.16 (m, 1H) |
| 660 | 571.4 | $^1$H NMR (400 MHz, DMSO-$d_6$) δ 12.27 (s, 1H), 8.20-8.14 (m, 1H), 8.13-8.08 (m, 2H), 7.68 (s, 1H), 7.61-7.55 (m, 1H), 7.52-7.51 (m, 1H), 7.21-7.17 (m, 1H), 6.97-6.96 (m, 1H), 6.56-6.50 (m, 2H), 6.49-6.46 (m, 1H), 6.46-6.42 (m, 1H), 4.08-4.07 (m, 2H), 3.76-3.75 (m, 2H), 3.69-3.57 (m, 2H), 3.50-3.40 (m, 3H), 3.23-3.13 (m, 3H), 1.49 (s, 9H) |
| 661 | 531.3 | $^1$H NMR (400 MHz, DMSO-$d_6$) δ 12.29 (s, 1H), 8.18 (d, J = 5.6 Hz, 1H), 7.74 (s, 1H), 7.68-7.58 (m, 1H), 7.52 (d, J = 2.0 Hz, 1H), 7.27 (d, J = 7.2 Hz, 1H), 6.97 (d, J = 2.4 Hz, 1H), 6.58 (d, J = 8.0 Hz, 1H), 6.49-6.47 (m, 1H), 5.06-4.94 (m, 1H), 4.15-3.95 (m, 4H), 3.92-3.79 (m, 2H), 3.65-3.44 (m, 3H), 1.50 (s, 9H) |
| 662 | 509.1 | $^1$H NMR (400 MHz, DMSO-$d_6$) δ 12.29 (s, 1H), 8.19-8.17 (m, 1H), 7.72 (s, 1H), 7.61-7.59 (m, 1H), 7.52 (d, J = 2.0 Hz, 1H), 7.23 (d, J = 7.2 Hz, 1H), 6.97-6.96 (m, 1H), 6.83 (d, J = 8.4 Hz, 1H), 6.54-6.42 (m, 1H), 4.74-4.71 (m, 1H), 4.64-4.50 (m, 1H), 4.09 (d, J = 5.6 Hz, 2H), 3.94-3.91 (m, 2H), 3.26-3.18 (m, 2H), 2.89-2.75 (m, 1H), 2.66 (d, J = 11.2 Hz, 1H), 1.95-1.91 (m, 1H), 1.86-1.62 (m, 2H), 1.59-1.43 (m, 9H), 1.40-1.28 (m, 1H) |
| 663 | 526.2 | $^1$H NMR (400 MHz, Methanol-$d_4$) δ 8.56-8.48 (m, 1H), 7.71 (s, 1H), 7.64-7.60 (m, 1H), 7.58-7.57 (m, 1H), 7.39 (d, J = 7.2 Hz, 1H), 6.96-6.94 (m, 1H), 6.76 (d, J = 8.4 Hz, 1H), 6.57-6.56 (m, 1H), 4.39 (br d, J = 12.0 Hz, 1H), 4.22 (s, 2H), 4.16-4.07 (m, 2H), 3.96-3.91 (m, 1H), 3.80-3.74 (m, 1H), 3.16-3.06 (m, 2H), 3.04-2.97 (m, 1H), 2.76 (s, 6H), 2.70-2.64 (m, 1H), 1.56 (s, 9H) |
| 664 | 489.2 | $^1$H NMR (400 MHz, DMSO-$d_6$) δ 12.32-12.24 (m, 1H), 8.19-8.10 (m, 1H), 7.77-7.72 (m, 1H), 7.66-7.60 (m, 1H), 7.53-7.49 (m, 1H), 7.28-7.24 (m, 1H), 6.99-6.95 (m, 1H), 6.52-6.45 (m, 2H), 5.56-5.47 (m, 1H), 5.42-5.34 (m, 1H), 4.12-4.03 (m, 2H), 3.93-3.83 (m, 2H), 3.71-3.62 (m, 2H), 1.54-1.42 (m, 9H) |
| 665 | 546.1 | $^1$H NMR (400 MHz, DMSO-$d_6$) δ 8.55-8.44 (m, 1H), 8.23-8.13 (m, 1H), 7.75 (s, 1H), 7.71-7.61 (m, 1H), 7.52-7.51 (m, 1H), 7.29 (d, J = 7.6 Hz, 1H), 6.98-6.87 (m, 1H), 6.86 (d, J = 8.4 Hz, 1H), 6.48-6.47 (m, 1H), 4.09 (d, J = 5.6 Hz, 2H), 3.76-3.66 (m, 4H), 3.26-3.21 (m, 4H), 2.92 (s, 3H), 1.50 (s, 9H) |
| 667 | 531.2 | $^1$H NMR (400 MHz, DMSO-$d_6$) δ 12.43-12.01 (m, 1H), 8.45 (s, 1H), 8.20-8.16 (m, 1H), 7.75 (s, 1H), 7.62-7.60 (m, 1H), 7.53-7.52 (m, 1H), 7.25-7.23 (m, 1H), 6.98-6.97 (m, 1H), 6.52-6.50 (m, 1H), 6.49-6.48 (m, 1H), 4.10-4.08 (m, 2H), 3.90-3.82 (m, 2H), 3.68-3.60 (m, 1H), 3.56-3.48 (m, 1H), 3.27-3.26 (m, 1H), 3.08 (s, 3H), 2.43-2.41 (m, 2H), 1.50 (s, 9H) |

TABLE 7-continued

| Compound # | LC-MS data(m/z) | $^1$H NMR |
|---|---|---|
| 668 | 509.2 | $^1$H NMR (400 MHz, Methanol-d$_4$) δ 7.69 (s, 1H), 7.58-7.53 (m, 2H), 7.30 (d, J = 7.2 Hz, 1H), 6.95-6.94 (m, 1H), 6.80 (d, J = 8.8 Hz, 1H), 6.57-6.56 (m, 1H), 4.65-4.63 (m, 1H), 4.58-4.53 (m, 1H), 4.22 (s, 2H), 3.99 (d, J = 12.8 Hz, 1H), 3.65 (d, J = 13.2 Hz, 1H), 3.62-3.58 (m, 1H), 3.48-3.46 (m, 1H), 2.52-2.41 (m, 2H), 1.99-1.97 (m, 2H), 1.94-1.91 (m, 1H), 1.68-1.64 (m, 1H), 1.56 (s, 9H) |
| 669 | 523.3 | $^1$HNMR (400 MHz, DMSO-d$_6$) δ 12.36-12.13 (m, 1H), 8.49-8.40 (m, 1H), 8.22-8.14 (m, 1H), 7.70-7.65 (m, 1H), 7.61-7.55 (m, 1H), 7.55-7.50 (m, 1H), 7.22-7.17 (m, 1H), 6.99-6.95 (m, 1H), 6.82-6.77 (m, 1H), 6.50-6.45 (m, 1H), 4.12-4.06 (m, 2H), 3.90-3.81 (m, 1H), 3.79-3.71 (m, 1H), 3.69-3.47 (m, 6H), 1.84-1.72 (m, 1H), 1.69-1.55 (m, 5H), 1.52-1.45 (m, 9H) |
| 670 | 496.2 | $^1$H NMR (400 MHz, DMSO-d$_6$) δ 12.27 (s, 1H), 8.21-8.13 (m, 1H), 7.70 (s, 1H), 7.60-7.50 (m, 2H), 7.17 (d, J = 7.2 Hz, 1H), 7.01-6.93 (m, 1H), 6.52-6.38 (m, 2H), 4.08 (d, J = 6.0 Hz, 2H), 3.80-3.71 (m, 1H), 3.69-3.62 (m, 1H), 3.37-3.36 (m, 1H), 3.19-3.11 (m, 1H), 2.81-2.73 (m, 1H), 2.22 (s, 6H), 2.18-2.11 (m, 1H), 1.88-1.74 (m, 1H), 1.49 (s, 9H) |
| 671 | 509.1 | $^1$H NMR (400 MHz, DMSO-d$_6$) δ 12.18 (s, 1H), 8.41 (s, 1H), 8.21-8.14 (m, 1H), 7.68 (s, 1H), 7.59-7.46 (m, 2H), 7.17 (d, J = 7.2 Hz, 1H), 7.03-6.94 (m, 1H), 6.51-6.43 (m, 1H), 6.41 (d, J = 8.4 Hz, 1H), 4.08 (d, J = 6.0 Hz, 2H), 3.85-3.79 (m, 2H), 3.64-3.57 (m, 2H), 3.56-3.50 (m, 2H), 3.49-3.43 (m, 2H), 2.05-1.84 (m, 4H), 1.49 (s, 9H) |
| 672 | 478.2 | $^1$HNMR (400 MHz, DMSO-d$_6$) δ 12.15 (br s, 1H), 8.17-8.14 (m, 1H), 7.72 (s, 1H), 7.62-7.60 (m, 1H), 7.52-7.50 (m, 1H), 7.24 (d, J = 7.2 Hz, 1H), 6.98-6.96 (m, 1H), 6.57-6.43 (m, 2H), 4.08 (d, J = 6.0 Hz, 2H), 3.86-3.72 (m, 2H), 3.61-3.47 (m, 3H), 2.42-2.25 (m, 2H), 1.50 (s, 9H) |
| 673 | 467.2 | $^1$HNMR (400 MHz, DMSO-d$_6$) δ 12.28 (br s, 1H), 8.20-8.18 (m, 1H), 7.67 (s, 1H), 7.59-7.49 (m, 2H), 7.16 (d, J = 7.2 Hz, 1H), 6.98-6.97 (m, 1H), 6.49-6.48 (m, 1H), 6.39 (d, J = 8.4 Hz, 1H), 4.09 (d, J = 6.0 Hz, 2H), 3.68-3.67 (m, 1H), 3.60-3.55 (m, 1H), 3.39 (s, 1H), 2.98-2.96 (m, 1H), 2.38-2.31 (m, 1H), 2.14-2.04 (m, 1H), 1.62-1.59 (m, 1H), 1.50 (s, 9H), 1.10 (d, J = 6.8 Hz, 3H) |
| 674 | 495.2 | $^1$H NMR (400 MHz, DMSO-d$_6$) δ 12.34 (s, 1H), 8.20-8.17 (m, 1H), 7.68 (s, 1H), 7.68-7.58 (m, 1H), 7.52-7.51 (m, 1H), 7.22 (d, J = 7.2 Hz, 1H), 6.98-6.97 (m, 1H), 6.52-6.41 (m, 2H), 4.09 (d, J = 5.6 Hz, 2H), 3.88-3.85 (m, 2H), 3.68-3.53 (m, 6H), 3.03 (d, J = 2.8 Hz, 2H), 1.50 (s, 9H) |
| 675 | 471.2 | $^1$H NMR (400 MHz, DMSO-d$_6$) δ 12.28-12.24 (m, 1H), 8.14-8.12 (m, 1H), 7.69 (s, 1H), 7.68-7.60 (m, 1H), 7.52-7.51 (m, 1H), 7.22 (d, J = 7.2 Hz, 1H), 6.97-6.96 (m, 1H), 6.52-6.43 (m, 2H), 5.59-5.35 (m, 1H), 4.08 (d, J = 5.6 Hz, 2H), 3.90-3.75 (m, 1H), 3.74-3.56 (m, 2H), 3.48-3.46 (m, 1H), 2.37-2.19 (m, 2H), 1.50 (s, 9H) |
| 676 | 509.3 | $^1$H NMR (400 MHz, DMSO-d$_6$) δ 12.44-12.12 (m, 1H), 8.11 (s, 1H), 7.68 (s, 1H), 7.60-7.59 (m, 1H), 7.53-7.52 (m, 1H), 7.23 (d, J = 7.2 Hz, 1H), 6.97-6.84 (m, 1H), 6.83 (d, J = 8.4 Hz, 1H), 6.48-6.47 (m, 1H), 4.77-4.74 (m, 1H), 4.59 (d, J = 13.2 Hz, 1H), 4.07 (d, J = 6.0 Hz, 2H), 3.89-3.78 (m, 2H), 3.22-3.15 (m, 1H), 2.83-2.73 (m, 1H), 2.70-2.64 (m, 1H), 2.10-1.98 (m, 2H), 1.70-1.57 (m, 1H), 1.50 (s, 9H), 1.48-1.15 (m, 2H) |
| 677 | 489.4 | $^1$H NMR (400 MHz, DMSO-d$_6$) δ 12.47-12.00 (m, 1H), 8.15-8.14 (m, 1H), 7.73 (s, 1H), 7.67-7.59 (m, 1H), 7.52-7.51 (m, 1H), 7.26 (d, J = 7.2 Hz, 1H), 6.97-6.96 (m, 1H), 6.53 (d, J = 8.4 Hz, 1H), 6.47-6.46 (m, 1H), 5.67-5.34 (m, 2H), 4.08 (d, J = 5.6 Hz, 2H), 3.97-3.67 (m, 4H), 1.49 (s, 9H) |
| 678 | 559.2 | $^1$H NMR (400 MHz, DMSO-d$_6$) δ 12.40-12.23 (m, 1H), 8.22-8.16 (m, 2H), 8.07 (d, J = 6.0 Hz, 1H), 7.74 (s, 1H), 7.68-7.63 (m, 1H), 7.52-7.51(m, 1H), 7.28 (d, J = 7.6 Hz, 1H), 6.97-6.96 (m, 1H), 6.86 (d, J = 8.0 Hz, 1H), 6.79 (s, 1H), 6.79-6.73 (m, 1H), 6.47-6.46 (m, 1H), 4.09 (d, J = 5.6 Hz, 2H), 3.74-3.68 (m, 4H), 3.47 (s, 4H), 2.35 (s, 3H), 1.49 (s, 9H) |
| 679 | 489.3 | $^1$H NMR (400 MHz, DMSO-d$_6$) δ 12.35-12.23 (m, 1H), 8.19-8.07 (m, 1H), 7.76-7.70 (m, 1H), 7.68-7.60 (m, 1H), 7.55-7.49 (m, 1H), 7.32-7.24 (m, 1H), 6.95 (s, 1H), 6.56-6.43 (m, 2H), 4.09-4.04 (m, 2H), 3.96-3.87 (m, 2H), 3.72-3.63 (m, 2H), 2.61-2.56 (m, 2H), 1.51-1.47 (m, 9H) |
| 680 | 510.3 | $^1$H NMR (400 MHz, DMSO-d$_6$) δ 12.33-12.30 (m, 1H), 9.71-9.60 (m, 1H), 8.24-8.16 (m, 1H), 7.82-7.79 (m, 1H), 7.72-7.62 (m, 1H), 7.54-7.49 (m, 1H), 7.31-7.25 (m, 1H), 7.00-6.95 (m, 1H), 6.87 (d, J = 8.4 Hz, 1H), 6.50-6.44 (m, 1H), 4.12-4.02 (m, 4H), 3.38-3.37 (m, 1H), 3.37-3.25 (m, 2H), 3.13-3.04 (m, 1H), 3.13-3.04 (m, 1H), 2.88 (m, 6H), 2.15-2.04 (m, 1H), 1.90-1.70 (m, 2H), 1.54-1.37 (m, 10H) |
| 681 | 516.1 | $^1$H NMR (400 MHz, DMSO-d$_6$) δ 12.26 (s, 1H), 8.42-8.37 (m, 2H), 8.36 (d, J = 5.2 Hz, 1H), 8.20-8.16 (m, 1H), 7.82 (s, 1H), 7.68-7.64 (m, 1H), 7.54-7.50 (m, 1H), 7.29 (d, J = 5.2 Hz, 1H), 7.26 (d, J = 7.2 Hz, 1H), 6.98-6.95 (m, 1H), 6.90 (d, J = 8.4 Hz, 1H), 6.48-6.44 (m, 1H), 4.80 (s, 2H), 4.09 (d, J = 5.6 Hz, 2H), 3.94 (d, J = 5.6 Hz, 2H), 2.94-2.88 (m, 2H), 1.49 (s, 9H) |
| 682 | 534.2 | $^1$H NMR (400 MHz, DMSO-d$_6$) δ 8.61 (s, 1H), 8.47-8.36 (m, 1H), 8.19-8.17 (m, 1H), 7.97 (s, 1H), 7.74 (s, 1H), 7.64-7.54 (m, 1H), 7.53-7.52 (m, 1H), 7.27-7.25 (m, 1H), 6.98-6.97 (m, 1H), 6.90-6.88 (m, 1H), 6.48-6.47 (m, 1H), 4.67-4.50 (m, 3H), 4.10-4.07 (m, 2H), 3.09-3.01 (m, 2H), 2.14-2.12 (m, 2H), 1.96-1.92 (m, 2H), 1.50 (s, 9H) |

TABLE 7-continued

| Compound # | LC-MS data(m/z) | $^1$H NMR |
|---|---|---|
| 684 | 513.5 | $^1$HNMR (400 MHz, DMSO-$d_6$) δ 12.72-11.73 (m, 1H), 8.46 (s, 1H), 8.21-8.17 (m, 1H), 7.73 (s, 1H), 7.67-7.62 (m, 1H), 7.53-7.51 (m, 1H), 7.28 (d, J = 7.6 Hz, 1H), 6.9 9-6.96 (m, 1H), 6.80 (d, J = 8.8 Hz, 1H), 6.51-6.43 (m, 1H), 4.27-4.05 (m, 4H), 3.99-3.94 (m, 1H), 3.71-3.63 (m, 1H), 3.59-3.55 (m, 1H), 3.47 (d, J = 1.6 Hz, 1H), 3.31 (s, 3H), 2.91-2.83 (m, 1H), 2.68-2.61 (m, 2H), 1.50 (s, 9H) |
| 687 | 457.3 | $^1$H NMR (400 MHz, DMSO-$d_6$) δ 12.22 (s, 1H), 8.18 (s, 1H), 7.68 (s, 1H), 7.66-7.58 (m, 1H), 7.52 (d, J = 2.0 Hz, 1H), 7.31 (s, 1H), 6.97 (d, J = 2.8 Hz, 1H), 6.54-6.34 (m, 2H), 5.68-5.38 (m, 1H), 4.44-4.23 (m, 2H), 4.09 (d, J = 5.6 Hz, 4H), 1.50 (s, 9H) |
| 690 | 471.4 | $^1$HNMR (400 MHz, $CDCl_3$) δ 10.31 (br s, 1H), 7.69 (s, 1H), 7.56-7.52 (m, 1H), 7.52-7.48 (m, 1H), 7.29 (d, J = 7.6 Hz, 1H), 6.83 (m, 1H), 6.55 (m, 1H), 6.46 (m, 1H), 6.34 (d, J = 8.0 Hz, 1H), 5.49-5.29 (m, 1H), 4.38 (d, J = 5.6 Hz, 2H), 3.99-3.56 (m, 4H), 2.47-2.32 (m, 1H), 2.27-2.03 (m, 1H), 1.55 (s, 9H) |
| 694 | 506.4 | $^1$H NMR (400 MHz, Methanol-$d_4$) δ 8.47 (s, 1H), 8.43 (s, 1H), 7.77 (s, 1H), 7.71-7.67 (m, 1H), 7.60-7.55 (m, 1H), 7.46 (d, J = 7.6 Hz, 1H), 6.98-6.90 (m, 2H), 6.60-6.53 (m, 1H), 5.01 (s, 2H), 4.31-4.14 (m, 6H), 1.58-1.55 (m, 9H) |
| 696 | 547.2 | $^1$H NMR (400 MHz, DMSO-$d_6$) δ 8.40 (s, 1H), 8.18-8.16 (m, 1H), 7.70 (s, 1H), 7.61-7.57 (m, 1H), 7.52-7.51 (m, 2H), 7.21 (d, J = 7.2 Hz, 1H), 6.97-6.96 (m, 1H), 6.81 (d, J = 8.4 Hz, 1H), 6.47-6.46 (m, 1H), 6.06 (d, J = 2.4 Hz, 1H), 4.44 (d, J = 13.2 Hz, 2H), 4.08 (d, J = 6.0 Hz, 2H), 3.75 (s, 3H), 2.97-2.92 (m, 2H), 2.82-2.79 (m, 1H), 1.94 (d, J = 10.4 Hz, 2H), 1.63-1.55 (m, 2H), 1.49 (s, 9H) |
| 697 | 533.5 | $^1$H NMR (400 MHz, DMSO-$d_6$) δ 12.30-12.23 (m, 1H), 8.18-8.16 (m, 1H), 7.68 (s, 1H), 7.62-7.58 (m, 1H), 7.52-7.51 (m, 1H), 7.22 (d, J = 7.2 Hz, 1H), 6.99-6.61 (m, 3H), 6.47-6.46 (m, 1H), 4.22-4.17 (m, 2H), 4.08(d, J = 5.6 Hz, 2H), 3.85-3.80 (m, 1H), 3.30-3.28 (m, 2H), 2.02-1.98 (m, 1H), 1.79-1.75 (m, 1H), 1.71-1.63 (m, 1H), 1.56-1.49 (m, 10H) |
| 704 | 549.5 | $^1$H NMR (400 MHz, DMSO-$d_6$) δ 12.25-11.97 (m, 1H), 8.16-8.14 (m, 1H), 7.65 (s, 1H), 7.63-7.59 (m, 1H), 7.51-7.50 (m, 1H), 7.23 (d, J = 7.2 Hz, 1H), 6.97-6.95 (m, 1H), 6.83 (d, J = 8.4 Hz, 1H), 6.48-6.45 (m, 1H), 4.60-4.53 (m, 1H), 4.24 (d, J = 12.8 Hz, 1H), 4.08 (d, J = 6.0 Hz, 2H), 3.19-3.14 (m, 1H), 3.11-2.97 (m, 2H), 2.58 (s, 3H), 2.14-2.04 (m, 1H), 1.86-1.75 (m, 2H), 1.66-1.57 (m, 1H), 1.49 (s, 9H) |
| 706 | 548.3 | $^1$H NMR (400 MHz, Methanol-$d_4$) δ 7.70 (s, 1H), 7.64-7.53 (m, 2H), 7.39-7.26 (m, 3H), 6.98-6.92 (m, 1H), 6.79-6.77 (m, 1H), 6.58-6.57 (m, 1H), 4.23 (s, 2H), 3.82 (s, 3H), 3.74-3.73 (m, 4H), 3.12-2.93 (m, 4H), 1.57 (s, 9H) |
| 709 | 534.2 | $^1$HNMR (400 MHz, DMSO-$d_6$) δ 12.28 (s, 1H), 8.64 (s, 1H), 8.19-8.15 (m, 1H), 8.02 (s, 1H), 7.71 (s, 1H), 7.65-7.60 (m, 1H), 7.52-7.50 (m, 1H), 7.25 (d, J = 7.2 Hz, 1H), 6.98-6.95 (m, 1H), 6.88 (d, J = 8.8 Hz, 1H), 6.48-6.46 (m, 1H), 4.62-4.57 (m, 1H), 4.52-4.44 (m, 1H), 4.21 (br d, J = 12.8 Hz, 1H), 4.08 (d, J = 6.0 Hz, 2H), 3.40 (d, J = 2.8 Hz, 1H), 3.11-3.03 (m, 1H), 2.19-2.10 (m, 2H), 1.85-1.79 (m, 1H), 1.67-1.62 (m, 1H), 1.49 (s, 9H) |
| 724 | 485.4 | $^1$HNMR (400 MHz, DMSO-$d_6$) δ 12.33-12.23 (m, 1H), 8.19-8.16 (m, 1H), 7.70 (s, 1H), 7.59-7.57 (m, 1H), 7.52-7.51 (m, 1H), 7.21 (d, J = 7.2 Hz, 1H), 6.98-6.96 (m, 1H), 6.48-6.44 (m, 1H), 6.44 (d, J = 8.4 Hz, 1H), 5.28-5.13 (m, 1H), 4.10 (d, J = 6.0 Hz, 2H), 3.83-3.67 m, 4H), 3.08-3.03 (m, 1H), 1.49 (s, 9H), 1.16 (d, J = 6.8 Hz, 3H) |
| 727 | 509.1 | $^1$H NMR (400 MHz, DMSO-$d_6$) δ 12.31 (s, 1H), 8.21-8.18 (m, 1H), 7.73 (s, 1H), 7.61-7.59 (m, 1H), 7.52-7.51 (m, 1H), 7.23 (d, J = 7.2 Hz, 1H), 6.98-6.97 (m, 1H), 6.83 (d, J = 8.8 Hz, 1H), 6.48-6.47 (m, 1H), 4.75-4.72 (m, 1H), 4.64-4.47 (m, 1H), 4.09 (d, J = 6.0 Hz, 2H), 3.99-3.83 (m, 2H), 3.33-3.15 (m, 2H), 2.89-2.75 (m, 1H), 2.70-2.59 (m, 1H), 1.94-1.91 (m, 1H), 1.85-1.63 (m, 2H), 1.49 (s, 9H), 1.42-1.29 (m, 1H) |

Example 166. Preparation of Compounds of the Invention

The following compounds in Table 8 below were synthesized starting from the appropriate common intermediate (2-amino-N-(4-(6-fluoropyridin-2-yl)thiazol-2-yl)acetamide hydrochloride), the appropriate heterocyclic carboxylic acid, and amine following the synthetic scheme shown in Scheme 5 below.

Scheme 5

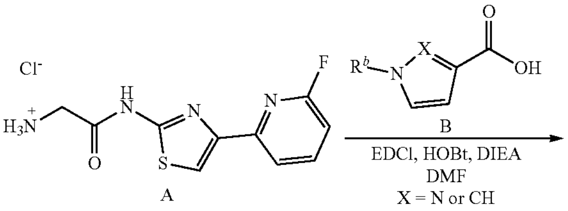

-continued

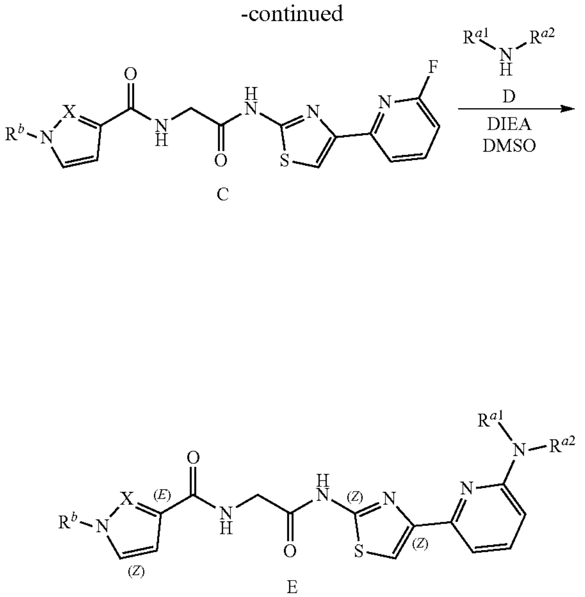

C

E

Example 167. Preparation of Compounds of the Invention

The following compounds in Table 9 below were synthesized starting from the appropriate starting 6-member heterocyclic carboxylic acid, amine, and 5-member heterocyclic carboxylic acid following the synthetic route shown in Scheme 6 below. Where appropriate SFC purification was used to separate enantiomers.

Scheme 6:

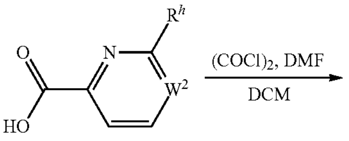

A $W^2$ = N or CH
$R^h$ = F or Cl

TABLE 8

| Compound # | LC-MS data(m/z) | $^1$H NMR |
|---|---|---|
| 313 | 511.3 | $^1$H NMR (400 MHz, DMSO-$d_6$) δ 12.30 (s, 1H), 8.25 (d, J = 6.0 Hz, 1H), 7.70 (s, 1H), 7.62-7.53 (m, 2H), 7.19 (d, J = 7.2 Hz, 1H), 7.04-6.99 (m, 1H), 6.81 (d, J = 8.4 Hz, 1H), 6.57-6.56 (m, 1H), 4.84 (d, J = 6.4 Hz, 2H), 4.62 (d, J = 6.8 Hz, 2H), 4.11 (s, 2H), 3.86-3.83 (m, 1H), 3.31 (s, 3H), 3.30-3.12 (m, 4H), 2.02-1.92 (m, 1H), 1.79 (s, 3H), 1.76 1.73 (m, 1H), 1.53-1.39 (m, 2H) |
| 316 | 511.1 | $^1$H NMR (400 MHz, Methanol-$d_4$) δ 7.67 (s, 1H), 7.62-7.54 (m, 2H), 7.34 (d, J = 7.6 Hz, 1H), 6.98-6.97 (m, 1H), 6.72 (d, J = 8.4 Hz, 1H), 6.68-6.64 (m, 1H), 4.98 (d, J = 6.8 Hz, 2H), 4.72 (d, J = 6.8 Hz, 2H), 4.30-4.20 (m, 4H), 3.79-3.68 (m, 2H), 2.51-2.44 (m, 2H), 1.88 (s, 3H), 1.26 (d, J = 6.4 Hz, 6H) |
| 330 | 511.3 | $^1$H NMR (400 MHz, DMSO-$d_6$) δ 12.31 (s, 1H), 8.26 (d, J = 6.0 Hz, 1H), 7.71 (s, 1H), 7.63-7.55 (m, 2H), 7.20 (d, J = 7.2 Hz, 1H), 7.04-7.00 (m, 1H), 6.82 (d, J = 8.4 Hz, 1H), 6.58-6.57 (m, 1H), 4.85 (d, J = 6.4 Hz, 2H), 4.63 (d, J = 6.8 Hz, 2H), 4.11 (d, J = 6.0 Hz, 2H), 3.89-3.80 (m, 1H), 3.32 (s, 3H), 3.31-3.13 (m, 4H), 1.97 (s, 1H), 1.80 (s, 3H), 1.78-1.68 (m, 1H), 1.56-1.36 (m, 2H) |
| 342 | 519.3 | $^1$H NMR (400 MHz, DMSO-$d_6$) δ 12.34 (br s, 1H), 8.68-8.66 (m, 1H), 7.87-7.83 (m, 1H), 7.76 (s, 1H), 7.62-7.60 (m, 1H), 7.31-7.30 (m, 1H), 7.25 (d, J = 7.2 Hz, 1H), 6.82-6.75 (m, 2H), 4.26-4.24 (m, 2H), 4.13 (d, J = 6.0 Hz, 2H), 3.63-3.61 (m, 2H), 3.57 (s, 3H), 2.44-2.38 (m, 2H), 1.18 (d, J = 6.4 Hz, 6H) |
| 344 | 498.3 | $^1$H NMR (400 MHz, $CDCl_3$) δ 9.84-9.78 (m, 1H), 7.67 (s, 1H), 7.58 (d, J = 2.4 Hz, 1H), 7.57-7.53 (m, 2H), 7.32 (d, J = 7.2 Hz, 1H), 6.87 (d, J = 2.4 Hz, 1H), 6.58 (d, J = 8.4 Hz, 1H), 4.37 (d, J = 6.0 Hz, 2H), 4.16 (d, J = 11.2 Hz, 2H), 3.79-3.71 (m, 2H), 2.58-2.52 (m, 2H), 1.62 (s, 9H), 1.30 (d, J = 6.4 Hz, 6H) |
| 752 | 475.3 | $^1$H NMR (400 MHz, DMSO-$d_6$) δ 12.34 (s, 1H), 8.66 (t, J = 5.9 Hz, 1H), 7.84 (t, J = 2.0 Hz, 1H), 7.67 (s, 1H), 7.55 (dd, J = 8.4, 7.3 Hz, 1H), 7.31 (dd, J = 3.3, 2.3 Hz, 1H), 7.16 (d, J = 7.3 Hz, 1H), 6.77 (dd, J = 3.3, 1.7 Hz, 1H), 6.41 (d, J = 8.4 Hz, 1H), 4.13 (d, J = 5.8 Hz, 2H), 3.57 (s, 3H), 3.50-3.41 (m, 4H), 2.00-1.88 (m, 4H) |
| 753 | 461.2 | $^1$H NMR (400 MHz, DMSO-$d_6$) δ 12.36 (s, 1H), 8.66 (t, J = 5.8 Hz, 1H), 7.84 (t, J = 2.0 Hz, 1H), 7.64 (s, 1H), 7.57 (dd, J = 8.3, 7.4 Hz, 1H), 7.31 (dd, J = 3.3, 2.3 Hz, 1H), 7.23 (dd, J = 7.4, 0.8 Hz, 1H), 6.77 (dd, J = 3.3, 1.7 Hz, 1H), 6.31 (dd, J = 8.2, 0.8 Hz, 1H), 4.13 (d, J = 5.8 Hz, 2H), 3.98 (t, J = 7.4 Hz, 4H), 3.57 (s, 3H), 2.33 (dq, J = 10.7, 7.4 Hz, 2H) |
| 754 | 491.2 | $^1$H NMR (400 MHz, DMSO-$d_6$) δ 12.36 (s, 1H), 8.66 (t, J = 5.9 Hz, 1H), 7.84 (t, J = 2.0 Hz, 1H), 7.73 (s, 1H), 7.64 (dd, J = 8.5, 7.4 Hz, 1H), 7.31 (dd, J = 3.3, 2.3 Hz, 1H), 7.28 (d, J = 7.3 Hz, 1H), 6.83-6.75 (m, 2H), 4.13 (d, J = 5.8 Hz, 2H), 3.73 (dd, J = 5.8, 3.9 Hz, 4H), 3.57 (s, 3H), 3.52 (dd, J = 5.7, 4.0 Hz, 4H) |
| 761 | 489.2 | $^1$H NMR (400 MHz, DMSO-$d_6$) δ 12.34 (s, 1H), 8.67 (s, 1H), 7.84 (t, J = 2.0 Hz, 1H), 7.68 (s, 1H), 7.57 (dd, J = 8.5, 7.3 Hz, 1H), 7.33-7.28 (m, 1H), 7.19 (d, J = 7.3 Hz, 1H), 6.80-6.70 (m, 2H), 4.13 (d, J = 5.8 Hz, 2H), 3.63-3.52 (m, 7H), 1.67-1.52 (m, 6H) |

-continued

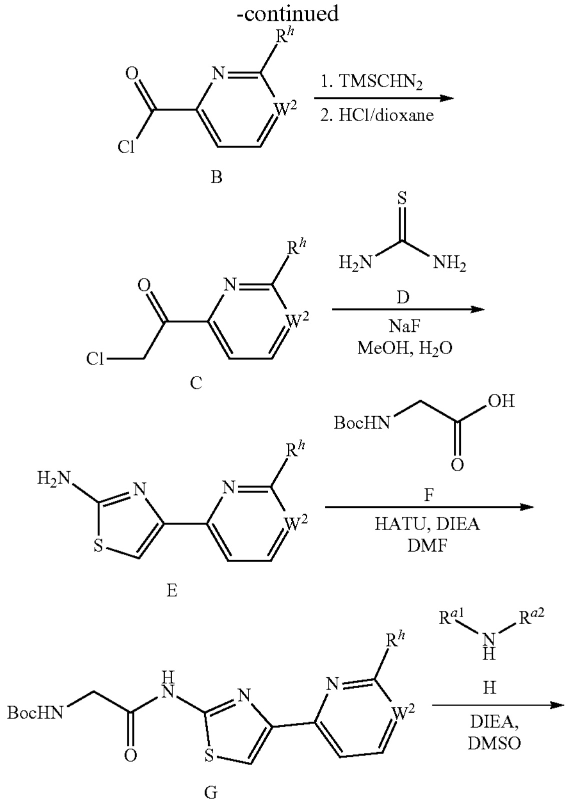

-continued

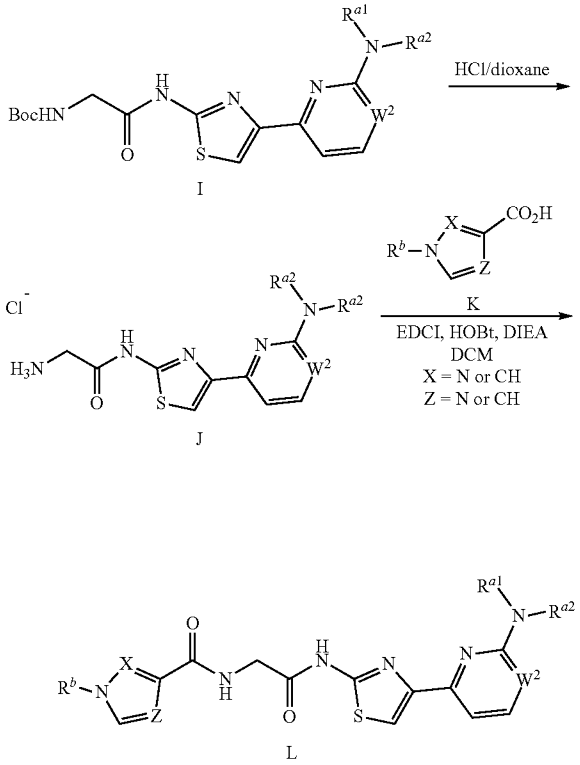

TABLE 9

| Compound # | LC-MS data(m/z) | $^1$H NMR |
|---|---|---|
| 321 | 497.9 | $^1$H NMR (400 MHz, Methanol-d$_4$) δ 8.34 (d, J = 4.8 Hz, 1H), 7.94 (s, 1H), 7.55-7.54 (m, 1H), 7.16 (d, J = 4.8 Hz, 1H), 6.98-6.96 (m, 1H), 6.66-6.64 (m, 1H), 4.97 (d, J = 6.8 Hz, 2H), 4.71 (d, J = 6.8 Hz, 2H), 4.53-4.48 (m, 2H), 4.23 (s, 2H), 3.90-3.84 (m, 1H), 3.34-3.27 (m, 2H), 1.95-1.90 (m, 2H), 1.88 (s, 3H), 1.53-1.45 (m, 2H) |
| 322 | 483.9 | $^1$H NMR (400 MHz, Methanol-d$_4$) δ 8.35 (d, J = 5.2 Hz, 1H), 7.95 (s, 1H), 7.57 (d, J = 2.4 Hz, 1H), 7.17 (d, J = 5.2 Hz, 1H), 6.95 (d, J = 2.8 Hz, 1H), 6.57 (d, J = 1.6 Hz, 1H), 4.57-4.48 (m, 2H), 4.23 (s, 2H), 3.92-3.82 (m, 1H), 3.34 (d, J = 3.2 Hz, 1H), 3.28 (d, J = 2.8 Hz, 1H), 1.98-1.87 (m, 2H), 1.57-1.55 (m, 9H), 1.53-1.43 (m, 2H) |
| 323 | 499.2 | $^1$H NMR (400 MHz, DMSO-d$_6$ + D$_2$O) δ 8.48-8.44 (d, J = 4.8 Hz, 1H), 8.10 (s, 1H), 7.94-7.91 (d, J = 2.4 Hz, 1H), 7.14-7.09 (d, J = 4.8 Hz, 1H), 6.66-6.62 (d, J = 2.4 Hz, 1H), 4.64-4.56 (m, 2H), 4.16 (s, 2H), 3.63-3.53 (m, 2H), 2.58-2.54 (m, 2H), 1.57 (s, 9H), 1.18-1.13 (d, J = 6.4 Hz, 6H) |
| 324 | 511.9 | $^1$H NMR (400 MHz, DMSO-d$_5$) δ 12.47-12.41 (m, 1H), 8.47 (d, J = 4.8 Hz, 1H), 8.25-8.24 (m, 1H), 8.07 (s, 1H), 7.56-7.55 (m, 1H), 7.12 (d, J = 4.8 Hz, 1H), 7.01-7.00 (m, 1H), 6.56-6.55 (m, 1H), 4.84 (d, J = 6.8 Hz, 2H), 4.63-4.60 (m, 4H), 4.10 (d, J = 6.0 Hz, 2H), 3.59-3.54 (m, 2H), 2.57-2.51 (m, 2H), 1.78 (s, 3H), 1.17 (d, J = 6.0 Hz, 6H) |
| 325 | 519.9 | $^1$H NMR (400 MHz, DMSO-d$_6$) δ 12.52 (s, 1H), 8.75-8.72 (m, 1H), 8.52 (d, J = 5.2 Hz, 1H), 8.15 (s, 1H), 7.90-7.89 (m, 1H), 7.37-7.36 (m, 1H), 7.17 (d, J = 4.8 Hz, 1H), 6.83-6.82 (m, 1H), 4.67 (d, J = 12.4 Hz, 2H), 4.19 (d, J = 6.0 Hz, 2H), 3.66-3.62 (m, 5H), 2.63-2.57 (m, 2H), 1.24-1.22 (m, 6H) |
| 326 | 498.0 | $^1$H NMR (400 MHz, DMSO-d$_6$) δ 12.40 (s, 1H), 8.46 (d, J = 5.2 Hz, 1H), 8.20-8.17 (m, 1H), 8.08 (s, 1H), 7.51-7.50 (m, 1H), 7.11 (d, J = 4.8 Hz, 1H), 6.97-6.96 (m, 1H), 6.47-6.46 (m, 1H), 4.61 (d, J = 12.8 Hz, 2H), 4.08 (d, J = 6.0 Hz, 2H), 3.59-3.55 (m, 2H), 2.54 (s, 2H), 1.48 (s, 9H), 1.17 (d, J = 6.4 Hz, 6H). |
| 328 | 496.0 | $^1$H NMR (400 MHz, Methanol-d$_4$) δ 12.36 (s, 1H), 8.39-8.36 (m, 1H), 7.92 (d, J = 2.4 Hz, 1H), 7.77 (s, 1H), 7.64-7.60 (m, 1H), 7.25 (d, J = 7.6 Hz, 1H), 6.80 (d, J = 8.4 Hz, 1H), 6.62 (d, J = 2.4 Hz, 1H), 4.25 (d, J = 12.0 Hz, 2H), 4.14 (d, J = 6.0 Hz, 2H), 3.71-3.56 (m, 2H), 2.44-2.38 (m, 2H), 1.61 (s, 3H), 1.28-1.23 (m, 2H), 1.18 (d, J = 6.4 Hz, 6H), 1.00-0.90 (m, 2H) |

TABLE 9-continued

| Compound # | LC-MS data(m/z) | $^1$H NMR |
|---|---|---|
| 331 | 508.3 | $^1$H NMR (400 MHz, DMSO-$d_6$) δ 12.33 (s, 1H), 8.37 (d, J = 6.0 Hz, 1H), 7.77 (s, 1H), 7.69 (d, J = 2.0 Hz, 1H), 7.63 (d, J = 8.0 Hz, 1H), 7.26 (d, J = 7.2 Hz, 1H), 7.16 (d, J = 2.8 Hz, 1H), 6.80 (d, J = 8.4 Hz, 1H), 6.62-6.61(m, 1H), 4.26 (d, J = 12.8 Hz, 2H), 4.11 (d, J = 6.0 Hz, 2H), 3.68-3.59 (m, 2H), 2.41-2.39 (m, 2H), 1.96 (s, 6H), 1.19 (d, J = 6.4 Hz, 6H) |
| 332 | 549.3 | $^1$H NMR (400 MHz, DMSO-$d_6$) δ 12.32 (s, 1H), 8.38-8.36 (m, 1H), 7.77 (s, 1H), 7.63-7.62 (m, 1H), 7.54-7.53 (m, 1H), 7.26 (d, J = 7.2 Hz, 1H), 7.00-6.99 (m, 1H), 6.80 (d, J = 8.4 Hz, 1H), 6.56-6.55 (m, 1H), 4.26 (d, J = 11.2 Hz, 2H), 4.11 (d, J = 6.0 Hz, 2H), 3.65-3.62 (m, 2H), 2.45-2.42 (m, 2H), 1.60-1.51 (m, 4H), 1.19 (d, J = 6.0 Hz, 6H) |
| 333 | 495.3 | $^1$H NMR (400 MHz, DMSO-$d_6$) δ 12.33 (s, 1H), 8.24-8.23 (m, 1H), 7.76 (s, 1H), 7.63-7.60 (m, 1H), 7.44-7.43 (m, 1H), 7.26 (d, J = 7.2 Hz, 1H), 6.89-6.88 (m, 1H), 6.80 (d, J = 8.4 Hz, 1H), 6.45-6.44 (m, 1H), 4.26 (d, J = 11.6 Hz, 2H), 4.08 (d, J = 6.0 Hz, 2H), 3.70-3.55 (m, 2H), 2.42-2.41(m, 2H), 1.50 (s, 3H), 1.19 (d, J = 6.0 Hz, 6H), 1.10-1.03 (m, 2H), 0.90-0.84 (m, 2H) |
| 334 | 515.3 | $^1$H NMR (400 MHz, DMSO-$d_6$) δ 12.33 (s, 1H), 8.25-8.24 (m, 1H), 7.77 (s, 1H), 7.63-7.60 (m, 1H), 7.55-7.54(m, 1H), 7.26 (d, J = 7.2 Hz, 1H), 7.00-6.99 (m, 1H), 6.80 (d, J = 8.4 Hz, 1H), 6.52-6.51(m, 1H), 4.66-4.42 (m, 2H), 4.26 (d, J = 11.2 Hz, 2H), 4.10 (d, J = 5.6 Hz, 2H), 3.63-3.62 (m, 2H), 2.42-2.41 (m, 2H), 1.52 (d, J = 1.6 Hz, 6H), 1.19 (d, J = 6.0 Hz, 6H) |
| 335 | 512.4 | $^1$H NMR (400 MHz, $CDCl_3$) δ 10.41-10.07 (m, 1H), 7.68 (s, 1H), 7.67-7.63 (m, 1H), 7.57 (d, J = 2.4 Hz, 1H), 7.56-7.50 (m, 1H), 7.30 (d, J = 7.6 Hz, 1H), 7.01 (d, J = 2.4 Hz, 1H), 6.58 (d, J = 8.4 Hz, 1H), 5.17 (d, J = 6.4 Hz, 2H), 4.70 (d, J = 6.8 Hz, 2H), 4.42 (d, J = 6.0 Hz, 2H), 4.20-4.08 (m, 2H), 3.82-3.69 (m, 2H), 2.58-2.52 (m, 2H), 1.98 (s, 3H), 1.29 (d, J = 6.0 Hz, 6H) |
| 336 | 502.9 | $^1$H NMR (400 MHz, DMSO-$d_6$) δ 12.36 (s, 1H), 8.71-8.63 (m, 1H), 7.87-7.81 (m, 1H), 7.69 (s, 1H), 7.61-7.53 (m, 1H), 7.34-7.28 (m, 1H), 7.18 (d, J = 7.2 Hz, 1H), 6.82-6.73 (m, 2H), 4.37-4.21 (m, 2H), 4.13 (d, J = 6.0 Hz, 2H), 3.57 (s, 3H), 2.88-2.69 (m, 2H), 1.86-1.75 (m, 1H), 1.73-1.64 (m, 1H), 1.63-1.54 (m, 1H), 1.53-1.37 (m, 1H), 1.22-1.06 (m, 1H), 0.93 (d, J = 6.8 Hz, 3H) |
| 337 | 497.2 | $^1$H NMR (400 MHz, DMSO-$d_6$) δ 12.32 (br s, 1H), 8.28-8.25 (m, 1H), 7.69 (s, 1H), 7.60-7.56 (m, 2H), 7.20 (d, J = 7.2 Hz, 1H), 7.02-7.01 (m, 1H), 6.80 (d, J = 8.4 Hz, 1H), 6.57-6.56 (m, 1H), 4.84 (d, J = 6.4 Hz, 2H), 4.70 (s, 1H), 4.63 (d, J = 6.8 Hz, 2H), 4.12-4.09 (m, 4H), 3.73-3.68 (m, 1H), 3.14-3.08 (m, 2H), 1.82-1.79 (m, 5H), 1.42-1.33 (m, 2H) |
| 338 | 484.0 | $^1$H NMR (400 MHz, DMSO-$d_6$) δ 12.35 (s, 1H), 8.29-8.26 (m, 1H), 7.93 (d, J = 2.0 Hz, 1H), 7.70 (s, 1H), 7.59-7.55 (m, 1H), 7.19 (d, J = 7.2 Hz, 1H), 6.79 (d, J = 8.8 Hz, 1H), 6.64 (d, J = 2.0 Hz, 1H), 4.67 (d, J = 4.0 Hz, 1H), 4.17 (d, J = 6.0 Hz, 2H), 4.12-4.08 (m, 2H), 3.73-3.67 (m, 1H), 3.14-3.09 (m, 2H), 1.80 (d, J = 9.2 Hz, 2H), 1.57 (s, 9H), 1.41-1.33 (m, 2H) |
| 339 | 507.1 | $^1$H NMR (400 MHz, DMSO-$d_6$) δ 12.36-12.35 (m, 1H), 8.73-8.59 (m, 1H), 7.86-7.83 (m, 1H), 7.74-7.70 (m, 1H), 7.65-7.57 (m, 1H), 7.33-7.29 (m, 1H), 7.25-7.20 (m, 1H), 6.88-6.82 (m, 1H), 6.79-6.75 (m, 1H), 5.01-4.80 (m, 1H), 4.18-4.09 (m, 2H), 3.89-3.78 (m, 2H), 3.59-3.50 (m, 5H), 2.03-1.87 (m, 2H), 1.78-1.66 (m, 2H) |
| 340 | 502.9 | $^1$H NMR (400 MHz, DMSO-$d_6$) δ 12.35 (s, 1H), 8.69-8.65 (m, 1H), 7.86-7.84 (m, 1H), 7.70 (s, 1H), 7.59-7.55 (m, 1H), 7.33-7.31 (m, 1H), 7.19 (d, J = 7.2 Hz, 1H), 6.82-6.76 (m, 2H), 4.37-4.23 (m, 2H), 4.14 (d, J = 6.0 Hz, 2H), 3.58 (s, 3H), 2.87-2.75 (m, 1H), 2.47 (s, 1H), 1.84-1.43 (m, 4H), 1.21-1.09 (m, 1H), 0.94 (d, J = 6.8 Hz, 3H) |
| 341 | 482.9 | $^1$H NMR (400 MHz, DMSO-$d_6$) δ 12.38-12.33 (m, 1H), 8.29-8.27 (m, 1H), 7.73 (s, 1H), 7.64-7.62 (m, 1H), 7.57-7.56 (m, 1H), 7.29 (d, J = 7.2 Hz, 1H), 7.01-7.00 (m, 1H), 6.80 (d, J = 8.4 Hz, 1H), 6.57-6.57 (m, 1H), 4.85 (d, J = 6.4 Hz, 2H), 4.63 (d, J = 6.8 Hz, 2H), 4.11 (d, J = 5.6 Hz, 2H), 3.74-3.71 (m, 4H), 3.53-3.51 (m, 4H), 1.79 (s, 3H) |
| 343 | 497.2 | $^1$H NMR (400 MHz, DMSO-$d_6$) δ 7.91-7.83 (m, 1H), 7.62 (s, 1H), 7.58-7.54 (m, 2H), 7.25 (d, J = 7.2 Hz, 1H), 7.06-7.04 (m, 1H), 6.71-6.69 (m, 1H), 6.52 (s, 1H), 5.38-5.35 (m, 1H), 4.94-4.91 (m, 2H), 4.78-4.72 (m, 2H), 4.22 (d, J = 11.6 Hz, 2H), 3.99-3.92 (m, 2H), 3.68-3.53 (m, 2H), 2.41-2.35 (s, 2H), 1.17 (d, J = 6.0 Hz, 6H) |
| 398 | 525.2 | $^1$H NMR (400 MHz, DMSO-$d_6$) δ 12.28 (s, 1H), 8.25-8.23 (m, 1H), 7.69 (s, 1H), 7.56-7.55 (m, 2H), 7.14 (d, J = 7.2 Hz, 1H), 7.01-7.00 (m, 1H), 6.79 (d, J = 8.4 Hz, 1H), 6.56-6.55 (m, 1H), 4.84 (d, J = 6.4 Hz, 2H), 4.62 (d, J = 6.8 Hz, 2H), 4.19 (d, J = 13.2 Hz, 1H), 4.10 (d, J = 5.6 Hz, 2H), 3.83-3.80 (m, 2H), 3.32-3.30 (m, 1H), 3.09-3.08 (m, 1H), 2.82 (d, J = 13.2 Hz, 1H), 1.79 (s, 3H), 1.75-1.68 (m, 1H), 1.53-1.47 (m, 1H), 0.94 (s, 3H), 0.82 (s, 3H) |
| 458 | 506.3 | $^1$H NMR (400 MHz, DMSO-$d_6$) δ 12.36 (s, 1H), 8.40-8.37 (m, 1H), 7.77 (d, J = 2.0 Hz, 1H), 7.69-7.57 (m, 2H), 7.26 (d, J = 7.2 Hz, 1H), 7.08 (d, J = 2.4 Hz, 1H), 6.81 (d, J = 8.4 Hz, 1H), 6.57-6.56 (m, 1H), 4.26 (d, J = 12.4 Hz, 2H), 4.10 (d, J = 5.2 Hz, 2H), 3.69-3.58 (m, 2H), 2.42 (d, J = 12.0 Hz, 2H), 1.86-1.71 (m, 4H), 1.19 (d, J = 4.8 Hz, 6H) |

TABLE 9-continued

| Compound # | LC-MS data(m/z) | $^{1}$H NMR |
|---|---|---|
| 473 | 448.1 | $^{1}$H NMR (400 MHz, DMSO-$d_6$) δ 12.13 (s, 1H), 8.36-8.38 (m, 1H), 7.63 (s, 1H), 7.60-7.59 (m, 1H), 7.56 (d, J = 8.0 Hz, 1H), 7.23 (d, J = 6.8 Hz, 1H), 7.07-7.06 (m, 1H), 6.56-6.55 (m, 1H), 6.31 (d, J = 8.4 Hz, 1H), 4.10 (d, J = 6.0 Hz, 2H), 3.99-3.95 (m, 4H), 2.34-2.31 (m, 2H), 1.83-1.80 (m, 2H), 1.76-1.74 (m, 2H |
| 535 | 517.1 | $^{1}$H NMR (400 MHz, DMSO-$d_6$) δ 12.32 (d, J = 1.2 Hz, 1H), 8.31-8.30 (m, 1H), 7.77 (s, 1H), 7.64-7.62 (m, 1H), 7.49-7.39 (m, 1H), 7.26 (d, J = 7.2 Hz, 1H), 6.91-6.90 (m, 1H), 6.80 (d, J = 8.4 Hz, 1H), 6.55-6.54 (m, 1H), 4.43-4.31 (m, 1H), 4.26 (d, J = 11.6 Hz, 2H), 4.10 (d, J = 6.0 Hz, 2H), 3.74-3.53 (m, 2H), 2.44-2.37 (m, 2H), 2.32-2.21 (m, 2H), 1.19 (d, J = 6.4 Hz, 6H) |
| 595 | 464.2 | $^{1}$H NMR (400 MHz, DMSO-$d_6$) δ 13.55-10.82 (m, 1H), 8.42-8.41 (m, 1H), 7.76-7.75 (m, 1H), 7.64 (s, 1H), 7.58-7.57 (m, 1H), 7.26-7.20 (m, 2H), 6.69 (d, J = 14.8 Hz, 1H), 6.31 (d, J = 8.0 Hz, 1H), 5.23 (d, J = 8.0 Hz, 2H), 5.04 (d, J = 8.4 Hz, 2H), 4.12 (d, J = 6.0 Hz, 2H), 3.98-3.96(m, 4H), 2.38-2.30 (m, 2H) |
| 602 | 522.3 | $^{1}$H NMR (400 MHz, DMSO-$d_6$) δ 12.34 (s, 1H), 8.43-8.40 (m, 1H), 7.76-7.75 (m, 2H), 7.64-7.60 (m, 1H), 7.26 (d, J = 7.2 Hz, 1H), 7.22-7.21 (m, 1H), 6.80 (d, J = 8.4 Hz, 1H), 6.69-6.68 (m, 1H), 5.23 (d, J = 8.0 Hz, 2H), 5.05 (d, J = 8.0 Hz, 2H), 4.26 (d, J = 11.6 Hz, 2H), 4.12 (d, J = 5.6 Hz, 2H), 3.64-3.60 (m, 2H), 2.44-2.38 (m, 2H), 1.18 (d, J = 6.4 Hz, 6H) |
| 618 | 503.2 | $^{1}$H NMR (400 MHz, DMSO-$d_6$) δ 12.27 (s, 1H), 8.18-8.15 (m, 1H), 7.69 (s, 1H), 7.61-7.58 (m, 1H), 7.52-7.51 (m, 1H), 7.20 (d, J = 7.2 Hz, 1H), 6.97-6.96 (m, 1H), 6.48-6.44 (m, 2H), 6.33-6.03 (m, 1H), 4.08 (d, J = 6.0 Hz, 2H), 3.69-3.63 (m, 1H), 3.62-3.55 (m, 1H), 3.49-3.44 (m, 2H), 2.91-2.81 (m, 1H), 2.20-2.13 (m, 1H), 2.03-1.99 (m, 1H), 1.49 (s, 9H) |
| 683 | 525.0 | $^{1}$H NMR (400 MHz, DMSO-$d_6$) δ 12.36 (br s, 1H), 8.69-8.65 (m, 1H), 7.85-7.83 (m, 1H), 7.69 (s, 1H), 7.61-7.56 (m, 1H), 7.32-7.30 (m, 1H), 7.20 (d, J = 7.2 Hz, 1H), 6.78-6.77 (m, 1H), 6.46 (d, J = 8.0 Hz, 1H), 6.33-6.03 (m, 1H), 4.13 (d, J = 5.6 Hz, 2H), 3.69-3.63 (m, 1H), 3.57 (s, 4H), 3.49-3.44 (m, 2H), 2.92-2.81 (m, 1H), 2.18-2.11 (m, 1H), 2.05-1.99 (m, 1H) |
| 698 | 525.1 | $^{1}$H NMR (400 MHz, DMSO-$d_6$) δ 12.36 (s, 1H), 8.69-8.67 (m, 1H), 7.85-7.83 (m, 1H), 7.69 (s, 1H), 7.61-7.56 (m, 1H), 7.32-7.30 (m, 1H), 7.20 (d, J = 7.2 Hz, 1H), 6.78-6.77 (m, 1H), 6.46 (d, J = 8.4 Hz, 1H), 6.33-6.03 (m, 1H), 4.13 (d, J = 6.0 Hz, 2H), 3.69-3.63 (m, 1H), 3.57 (s, 4H), 3.49-3.44 (m, 2H), 2.87-2.83 (m, 1H), 2.17-2.14 (m, 1H), 2.03-1.99 (m, 1H) |
| 731 | 520.3 | $^{1}$H NMR (400 MHz, DMSO-$d_6$) δ 12.34 (s, 1H), 8.39-8.38 (m, 1H), 7.76 (s, 1H), 7.65-7.60 (m, 2H), 7.25 (d, J = 7.2 Hz, 1H), 7.09-7.06 (m, 1H), 6.80 (d, J = 8.4 Hz, 1H), 6.63-6.61 (m, 1H), 4.25 (d, J = 11.2 Hz, 2H), 4.11 (d, J = 5.6 Hz, 2H), 3.66-3.60 (m, 2H), 2.90-2.85 (m, 2H), 2.84-2.76 (m, 2H), 2.43-2.38 (m, 2H), 2.15-2.13 (m, 1H), 2.06-1.99 (m, 1H), 1.18 (d, J = 6.0 Hz, 6H) |
| 736 | 529.3 | $^{1}$H NMR (400 MHz, DMSO-$d_6$) δ 12.31-12.27 (m, 1H), 8.29-8.28 (m, 1H), 7.76 (s, 1H), 7.64-7.62 (m, 1H), 7.50 (s, 1H), 7.26 (d, J = 7.2 Hz, 1H), 6.96-6.95 (m, 1H), 6.81 (d, J = 8.8 Hz, 1H), 6.60-6.59 (m, 1H), 4.97 (s, 1H), 4.89-4.86 (m, 2H), 4.85 (s, 1H), 4.78 (d, J = 7.2 Hz, 2H), 4.27 (d, J = 11.6 Hz, 2H), 4.11 (d, J = 5.6 Hz, 2H), 3.63-3.61 (m, 2H), 2.44-2.39 (m, 2H), 1.19 (d, J = 6.4 Hz, 6H) |
| 737 | 531.1 | $^{1}$H NMR (400 MHz, DMSO-$d_6$) δ 12.31 (s, 1H), 8.31-8.29 (m, 1H), 7.76 (s, 1H), 7.64-7.62 (m, 1H), 7.45 (s, 1H), 7.26 (d, J = 7.2 Hz, 1H), 6.88-6.87 (m, 1H), 6.80 (d, J = 8.8 Hz, 1H), 6.57-6.46 (m, 1H), 5.98-5.84 (m, 1H), 4.26 (d, J = 12.8 Hz, 2H), 4.09 (d, J = 5.6 Hz, 2H), 3.65-3.61 (m, 2H), 2.42 (s, 2H), 1.32 (s, 4H), 1.20 (s, 3H), 1.18 (s, 3H) |
| 745 | 531.2 | $^{1}$HNMR (400 MHz, DMSO-$d_6$) δ 12.44 (br s, 1H), 8.76-8.74 (m, 1H), 7.91-7.90 (m, 1H), 7.79 (s, 1H), 7.66-7.65 (m, 1H), 7.38-7.37 (m, 1H), 7.28 (d, J = 7.2 Hz, 1H), 6.91-6.82 (m, 2H), 4.79-4.76 (m, 1H), 4.62 (d, J = 13.2 Hz, 1H), 4.19 (d, J = 6.0 Hz, 2H), 3.99-3.96 (m, 2H), 3.63 (s, 3H), 3.35-3.18 (m, 2H), 2.86-2.84 (m, 1H), 2.76-2.66 (m, 1H), 1.99-1.96 (m, 1H), 1.91-1.68 (m, 2H), 1.41-1.38 (m 1H) |
| 746 | 531.3 | $^{1}$HNMR (400 MHz, DMSO-$d_6$) δ 12.42 (br s, 1H), 8.76-8.74 (m, 1H), 7.91-7.89 (m, 1H), 7.79 (s, 1H), 7.66-7.64 (m, 1H), 7.38-7.37 (m, 1H), 7.28 (d, J = 7.2 Hz, 1H), 6.93-6.80 (m, 2H), 4.79-4.77 (m, 1H), 4.62 (d, J = 13.2 Hz, 1H), 4.19 (br d, J = 6.0 Hz, 2H), 3.97-3.76 (m, 2H), 3.63 (s, 3H), 3.35-3.17 (m, 2H), 2.86-2.84 (m, 1H), 2.76-2.64 (m, 1H), 1.98-1.96 (m, 1H), 1.90-1.69 (m, 2H), 1.45-1.36 (m, 1H) |
| 748 | 533.2 | $^{1}$H NMR (400 MHz, DMSO-$d_6$) δ 12.32 (s, 1H), 8.28 (m, 1H), 7.77 (s, 1H), 7.63 (m, 1H), 7.58 (m, 1H), 7.26 (d, J = 7.2 Hz, 1H), 7.02 (m, 1H), 6.80 (d, J = 8.4 Hz, 1H), 6.55 (m, 1H), 6.32-5.97 (m, 1H), 4.26 (d, J = 11.6 Hz, 2H), 4.10 (d, J = 6.0 Hz, 2H), 3.64 (m, 2H), 2.42 (m, 2H), 1.60 (s, 6H), 1.19 (d, J = 6.4 Hz, 6H) |
| 749 | 533.2 | $^{1}$H NMR (400 MHz, DMSO-$d_6$) δ 12.35 (s, 1H), 8.47 (m, 1H), 7.77 (s, 1H), 7.68-7.54 (m, 2H), 7.26 (d, J = 7.2 Hz, 1H), 7.02 (s, 1H), 6.81 (d, J = 8.4 Hz, 1H), 6.63 (m, 1H), 6.46-6.20 (m, 1H), 4.26 (d, J = 11.2 Hz, 2H), 4.11 (d, J = 6.0 Hz, 2H), 3.64 (m, 2H), 2.42 (m, 2H), 1.57-1.42 (m, 3H), 1.28-1.13 (m, 9H) |

TABLE 9-continued

| Compound # | LC-MS data(m/z) | $^{1}$H NMR |
|---|---|---|
| 764 | 531.2 | $^{1}$HNMR (400 MHz, DMSO-d$_6$) δ 12.38 (s, 1H), 8.70-8.68 (m, 1H), 7.85-7.84 (m, 1H), 7.73 (s, 1H), 7.61-7.55 (m, 1H), 7.33-7.31 (m, 1H), 7.24-7.22 (m, 1H), 6.85 (d, J = 8.4 Hz, 1H), 6.79-6.77 (m, 1H), 4.78-4.74 (m, 1H), 4.60-4.58 (m, 1H), 4.14-4.13 (m, 2H), 3.87-3.80 (m, 2H), 3.58 (s, 3H), 3.20-3.17 (m, 1H), 2.84-2.74 (m, 1H), 2.67-2.63 (m, 1H), 2.12-1.97 (m, 2H), 1.72-1.58 (m, 1H), 1.54-1.36 (m, 2H) |
| 766 | 531.2 | $^{1}$HNMR (400 MHz, DMSO-d$_6$) δ 12.38 (s, 1H), 8.70-8.68 (m, 1H), 7.85-7.84 (m, 1H), 7.73 (s, 1H), 7.61-7.55 (m, 1H), 7.33-7.31 (m, 1H), 7.24-7.22 (m, 1H), 6.85 (d, J = 8.4 Hz, 1H), 6.79-6.77 (m, 1H), 4.78-4.74 (m, 1H), 4.60-4.58 (m, 1H), 4.14-4.13 (m, 2H), 3.87-3.80 (m, 2H), 3.58 (s, 3H), 3.20-3.17 (m, 1H), 2.84-2.74 (m, 1H), 2.67-2.63 (m, 1H), 2.12-1.97 (m, 2H), 1.72-1.58 (m, 1H), 1.54-1.36 (m, 2H) |
| 778 | 514.2 | $^{1}$H NMR (400 MHz, Methanol-d$_4$) δ 7.88 (d, J = 4.4 Hz, 2H), 7.68 (s, 1H), 7.60-7.56 (m, 1H), 7.34 (d, J = 7.2 Hz, 1H), 6.72 (d, J = 8.4 Hz, 1H), 4.30 (s, 2H), 4.24 (d, J = 11.6 Hz, 2H), 3.78-3.69 (m, 2H), 3.66 (s, 2H), 2.51-2.45 (m, 2H), 1.59 (s, 6H), 1.27 (s, 3H), 1.25 (s, 3H) |
| 781 | 507.0 | $^{1}$H NMR (400 MHz, CDCl$_3$) δ 10.96-10.60 (m, 1H), 8.11 (m, 1H), 7.79 (d, J = 1.2 Hz, 1H), 7.65 (s, 1H), 7.61 (d, J = 1.2 Hz, 1H), 7.54 (m, 1H), 7.22 (d, J = 7.2 Hz, 1H), 6.58 (d, J = 8.8 Hz, 1H), 4.28 (d, J = 6.4 Hz, 2H), 4.12 (m, 2H), 3.82-3.66 (m, 2H), 2.54 (m, 2H), 1.89-1.81 (m, 2H), 1.81-1.73 (m, 2H), 1.28 (d, J = 6.4 Hz, 6H) |
| 786 | 509.0 | $^{1}$H NMR (400 MHz, CDCl$_3$) δ 10.31-9.72 (m, 1H), 7.75 (d, J = 2.4 Hz, 1H), 7.68 (s, 1H), 7.59 (m, 1H), 7.57-7.51 (m, 1H), 7.30 (d, J = 7.6 Hz, 1H), 7.00 (d, J = 2.4 Hz, 1H), 6.59 (d, J = 8.4 Hz, 1H), 4.40 (d, J = 6.0 Hz, 2H), 4.19-4.10 (m, 2H), 3.81-3.70 (m, 2H), 2.56 (m, 2H), 2.05 (s, 6H), 1.29 (d, J = 6.4 Hz, 6H) |
| 806 | 507.4 | $^{1}$H NMR (400 MHz, DMSO-d$_6$) δ 12.39 (s, 1H), 8.61 (m, 1H), 8.16 (d, J = 2.4 Hz, 1H), 7.77 (s, 1H), 7.62 (m, 1H), 7.25 (d, J = 7.2 Hz, 1H), 6.80 (d, J = 8.4 Hz, 1H), 6.75 (d, J = 2.4 Hz, 1H), 4.25 (m, 2H), 4.15 (d, J = 6.0 Hz, 2H), 3.68-3.55 (m, 2H), 2.41 (m, 2H), 2.00-1.93 (m, 2H), 1.93-1.87 (m, 2H), 1.18 (d, J = 6.0 Hz, 6H) |
| 819 | 509.4 | $^{1}$H NMR (400 MHz, DMSO-d$_6$) δ 12.34 (s, 1H), 8.37-8.34 (m, 1H), 8.12 (d, J = 1.6 Hz, 1H), 8.08 (d, J = 1.6 Hz, 1H), 7.76 (s, 1H), 7.64-7.60 (m, 1H), 7.25 (d, J = 7.2 Hz, 1H), 6.79 (d, J = 8.8 Hz, 1H), 4.25 (d, J = 11.6 Hz, 2H), 4.16 (d, J = 6.0 Hz, 2H), 3.64-3.61 (m, 2H), 2.44-2.38 (m, 2H), 2.02 (s, 6H), 1.18 (s, 3H), 1.17 (s, 3H) |
| 251 | 506.4 | $^{1}$H NMR (400 MHz, DMSO-d$_6$) δ 12.26 (s, 1H), 8.15 (t, J = 5.9 Hz, 1H), 7.75 (s, 1H), 7.62 (dd, J = 8.5, 7.3 Hz, 1H), 7.51 (t, J = 2.1 Hz, 1H), 7.25 (d, J = 7.3 Hz, 1H), 6.96 (t, J = 2.7 Hz, 1H), 6.79 (d, J = 8.5 Hz, 1H), 6.47 (dd, J = 3.0, 1.8 Hz, 1H), 4.25 (dd, J = 13.1, 2.4 Hz, 2H), 4.08 (d, J = 5.9 Hz, 2H), 3.70-3.56 (m, 2H), 2.42 (dd, J = 12.8, 10.5 Hz, 2H), 1.18 (d, J = 6.2 Hz, 6H). |

Example 168. Preparation of 1-(3-methyloxetan-3-yl)-1H-pyrazole-3-carboxylic acid

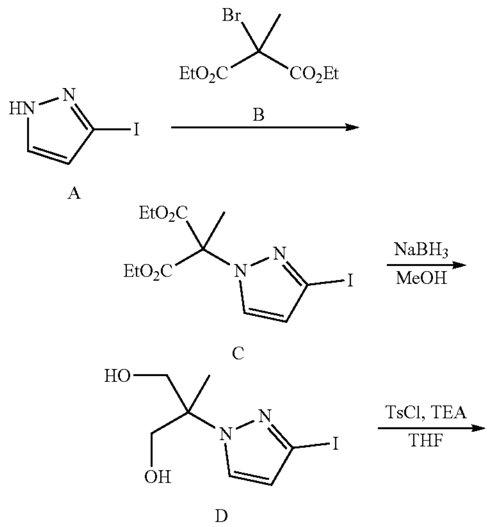

-continued

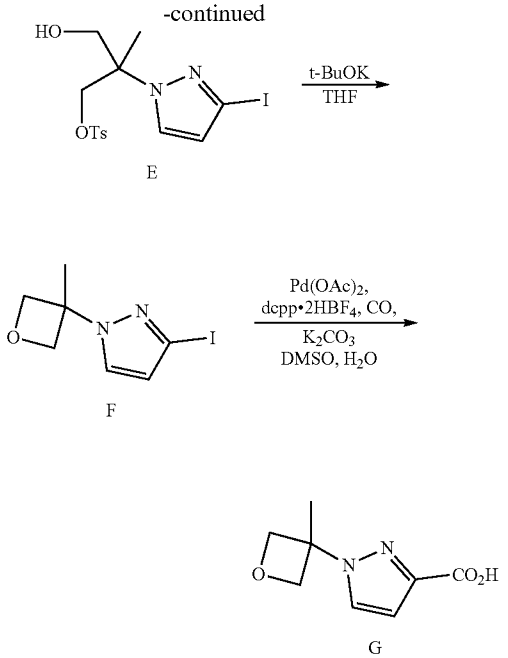

Step 1: Preparation of diethyl 2-(3-iodo-1H-pyrazol-1-yl)-2-methylmalonate (Intermediate C)

C

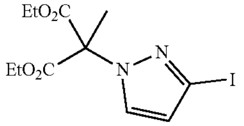

To a solution of 3-iodo-1H-pyrazole (2.00 g, 10.31 mmol) in DMF (20 mL) was added $K_2CO_3$ (2.85 g, 20.62 mmol) and diethyl 2-bromo-2-methylmalonate (3.13 g, 12.37 mmol, 2.35 mL). The mixture was stirred at 80° C. for 1.5 h. The reaction mixture was then treated with $H_2O$ (50 mL), extracted with ethyl acetate (50 mL*3). The organic layer was evaporated to give Intermediate C (4.00 g, 9.62 mmol, 93.3% yield, 88.1% purity) as a yellow oil. LCMS (ESI) m/z: $[M+H]^+$=367.1.; $^1H$ NMR (400 MHz, $CDCl_3$) δ 7.53 (d, J=2.4 Hz, 1H), 6.48 (d, J=2.4 Hz, 1H), 4.29-4.24 (m, 4H), 2.11 (s, 3H), 1.31-1.26 (m, 6H).

Step 2: Preparation of 2-(3-iodo-1H-pyrazol-1-yl)-2-methylpropane-1,3-diol (Intermediate D)

D

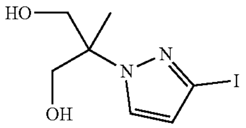

To a solution of Intermediate C (4.00 g, 10.92 mmol) in MeOH (20 mL) was added $NaBH_4$ (0.620 g, 16.39 mmol). The mixture was stirred at 20° C. for 12 h. The reaction mixture was quenched by 1 N HCl (in water) (3 mL) and then concentrated to give a residue. The residue was purified by reversed phased HPLC to give Intermediate D (1.10 g, 3.31 mmol, 30.3% yield, 85.0% purity) as a colorless oil. LCMS (ESI) m/z: $[M+H]^+$=283.0.; $^1H$ NMR (400 MHz, $CDCl_3$) δ 7.43 (d, J=2.4 Hz, 1H), 6.47 (d, J=2.4 Hz, 1H), 4.02-3.95 (m, 2H), 3.94-3.88 (m, 2H), 1.47 (s, 3H).

Step 3: Preparation of 3-hydroxy-2-(3-iodo-1H-pyrazol-1-yl)-2-methylpropyl 4-methylbenzenesulfonate (Intermediate E)

E

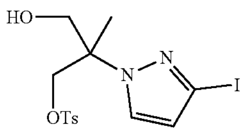

To a solution of Intermediate D (1.00 g, 3.55 mmol) in THF (10.0 mL) was added triethylamine (0.987 mL, 7.09 mmol) and TsCl (0.743 g, 3.90 mmol). The mixture was stirred at 25° C. for 12 h. The reaction mixture was pushed into water (20 mL), and extracted with ethyl acetate (20 mL×3). The organic phase was concentrated to give Intermediate E (1.50 g, 2.06 mmol, 58.2% yield, 60.0% purity) as a yellow oil. LCMS (ESI) m/z: $[M+H]^+$=437.0.

Step 4: Preparation of 3-iodo-1-(3-methyloxetan-3-yl)-1H-pyrazole (Intermediate F)

F

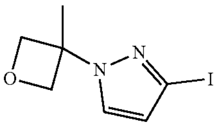

To a solution of Intermediate E (1.50 g, 3.44 mmol) in THF (10 mL) was added potassium; 2-methylpropan-2-olate (1.16 g, 10.31 mmol). The mixture was stirred at 20° C. for 1 h. The reaction mixture was concentrated under vacuum to get a residue. The residue was purified by reversed phased HPLC (FA) to give Intermediate F (0.450 g, 1.70 mmol, 49.56% yield, 100% purity) as a yellow solid. LCMS (ESI) m/z: $[M+H]^+$=265.0.; $^1H$ NMR (400 MHz, $CDCl_3$) δ 7.35 (d, J=2.4 Hz, 1H), 6.49 (d, J=2.4 Hz, 1H), 5.14 (d, J=6.4 Hz, 2H), 4.64 (d, J=6.8 Hz, 2H), 1.93 (s, 3H).

Step 5: Preparation of 1-(3-methyloxetan-3-yl)-1H-pyrazole-3-carboxylic acid (Intermediate G)

G

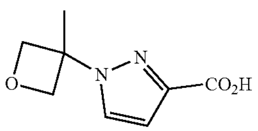

To a mixture of Intermediate F (0.100 g, 0.379 mmol), dicyclohexyl(3-dicyclohexylphosphaniumylpropyl)phosphonium; ditetrafluoroborate (0.023 g, 0.038 mmol) and $K_2CO_3$ (0.079 g, 0.568 mmol) in DMSO (1 mL) and $H_2O$ (0.5 mL) was added $Pd(OAc)_2$ (0.004 g, 0.019 mmol) and the suspension was degassed under vacuum and purged with CO balloon several times. Then the mixture was stirred at 100° C. for 12 h under CO (15 psi). The reaction mixture was filtered and the filtrate was purified by reversed phased HPLC to give Intermediate G (60 mg, 329.35 umol, 86.97% yield, 100% purity) as a white solid. LCMS (ESI) m/z: $[M-H]^+$=181.1; $^1H$ NMR (400 MHz, Methanol-$d_4$) δ 7.86 (d, J=2.4 Hz, 1H), 6.83 (d, J=2.4 Hz, 1H), 5.15 (d, J=6.8 Hz, 2H), 4.70 (d, J=6.8 Hz, 2H), 1.92 (s, 3H).

Example 169. Preparation of 1-(1-methylcyclopropyl)pyrazole-3-carboxylic acid

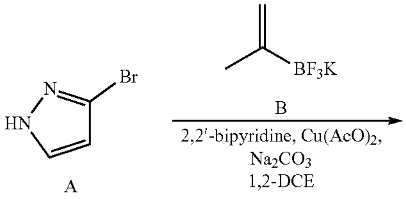

-continued

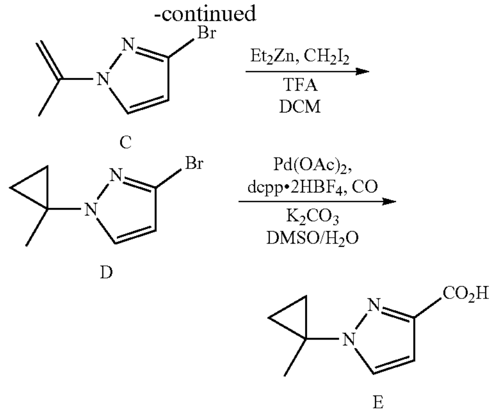

C

D

E

Step 1: Preparation of 3-bromo-1-(prop-1-en-2-yl)-1H-pyrazole (Intermediate C)

C

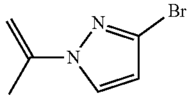

A mixture of $Cu(OAc)_2$ (4.94 g, 27.22 mmol) and 2-(2-pyridyl)pyridine (8.50 g, 54.43 mmol) in 1,2-DCE (40 mL) was stirred at 70° C. for 30 min. To the suspension was added 3-bromo-1H-pyrazole (4.00 g, 27.22 mmol), difluoro (prop-1-en-2-yl-12-fluoraneyl)borane, potassium salt (8.05 g, 54.43 mmol) and $Na_2CO_3$ (2.88 g, 27.22 mmol). The mixture was stirred at 70° C. for 16 h under $O_2$ (15 Psi). The reaction mixture was poured into $H_2O$ (200 mL) and extracted with ethyl acetate (200 mL×3). The combined organic layers were washed with brine (100 mL), dried over $Na_2SO_4$, filtered, and concentrated. The residue was purified by flash silica gel chromatography (ethyl acetate/petroleum ether=0:1 to 1:3) to give Intermediate C (3.30 g, 16.94 mmol, 62.3% yield, 96.0% purity) as a white oil. LCMS (ESI) m/z: $[M+H]^+$=186.9.; $^1H$ NMR (400 MHz, $CDCl_3$) δ 7.56 (d, J=2.8 Hz, 1H), 6.35 (d, J=2.4 Hz, 1H), 5.34 (s, 1H), 4.70 (s, 1H), 2.25 (d, J=0.8 Hz, 3H).

Step 2: Preparation of 3-bromo-1-(1-methylcyclopropyl)-1H-pyrazole (Intermediate D)

D

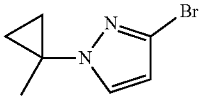

To a cooled (0° C.) solution of TFA (7.92 mL, 106.93 mmol,) in dichloromethane (20 mL) was added dropwise a 1 M solution of $ZnEt_2$ (106.93 mL) under $N_2$ atmosphere at. After 30 min, a solution of $CH_{212}$ (8.63 mL, 106.93 mmol) was added dropwise and stirred for another 30 min. To the mixture was added a solution of Intermediate C (2.00 g, 10.69 mmol) in dichloromethane (5 mL) and the mixture was gradually warmed to room temperature. After stirring for 16 h, the reaction mixture was poured into saturated aqueous $NH_4Cl$ solution (200 mL) and extracted with ethyl acetate (100 mL×3). The combined organic layers were washed with brine (100 mL), dried over $Na_2SO_4$, filtered and concentrated. The residue was purified by flash silica gel chromatography (ethyl acetate/petroleum ether=0:1 to 1:3) to give Intermediate D (0.250 g, 1.24 mmol, 11.63% yield) as a yellow oil. LCMS (ESI) m/z: $[M+H]^+$=201.0.; $^1H$ NMR (400 MHz, $CDCl_3$) δ 7.37 (d, J=2.4 Hz, 1H), 6.21 (d, J=2.0 Hz, 1H), 1.60 (s, 3H), 1.28-1.20 (m, 2H), 0.94-0.86 (m, 2H).

Step 3: Preparation of 1-(1-methylcyclopropyl)pyrazole-3-carboxylic acid (Intermediate E)

E

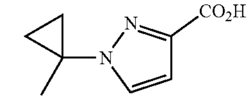

A mixture of Intermediate D (0.250 g, 1.24 mmol), dicyclohexyl(3-dicyclohexyl phosphaniumylpropyl)phosphonium; ditetrafluoroborate (0.228 g, 0.373 mmol), $Pd(OAc)_2$ (0.084 g, 0.373 mmol) and $K_2CO_3$ (0.343 g, 2.49 mmol) was diluted in DMSO (2 mL) and $H_2O$ (1 mL). The mixture was degassed and purged with CO (3×) and stirred at 100° C. for 16 h under CO (15 psi). The reaction mixture was poured into $H_2O$ (10 mL) and extracted with ethyl acetate (20 mL×3). The aqueous phase was acidified to pH~2 with 1 N HCl (5 mL) and extracted with ethyl acetate (30 mL×3). The combined organic layers were washed with brine (20 mL), dried over $Na_2SO_4$, filtered and concentrated to give Intermediate E (0.140 g, 0.804 mmol, 64.65% yield, 95.4% purity) as a yellow oil. LCMS (ESI) m/z: $[M+H]^+$=167.1.

Example 170. Preparation of 1-(1-cyano-1-methyl-ethyl)imidazole-4-carboxylic acid

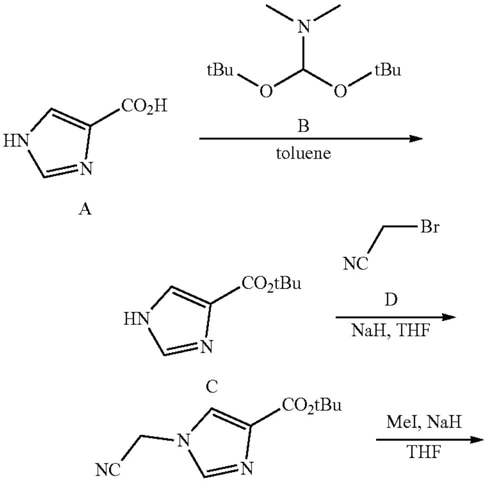

A

C

E

-continued

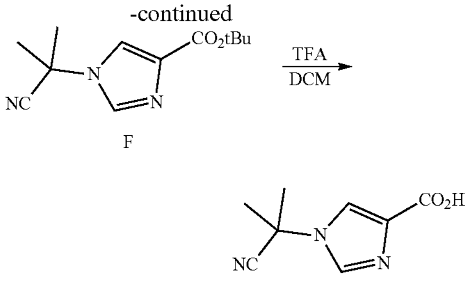

F

G

Step 1: Preparation of tert-butyl 1H-imidazole-4-carboxylate (Intermediate C)

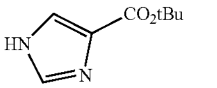

C

A solution of 1H-imidazole-4-carboxylic acid (2.50 g, 22.30 mmol) in toluene (40 mL) was stirred at 80° C. was added 1,1-ditertbutoxy-N,N-dimethyl-methanamine (6.80 g, 33.46 mmol, 8.02 mL). After 3 h, the reaction was diluted with water (250 mL) and extracted with ethyl acetate (100 mL×3). The combined the organic layers were dried over $Na_2SO_4$, filtered and concentrated. The residue was purified by column chromatography (petroleum ether/ethyl acetate=10/1 to 3/1), the fraction was concentrated to give Intermediate C (0.550 g, 3.27 mmol, 14.66% yield) as a yellow solid. $^1H$ NMR (400 MHz, DMSO-$d_6$) δ 12.94-12.51 (m, 1H), 7.80-7.48 (m, 2H), 1.50 (s, 9H).

Step 2: Preparation of tert-butyl 1-(cyanomethyl)imidazole-4-carboxylate (Intermediate E)

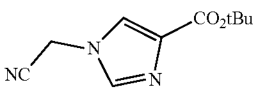

E

To a cooled (15° C.) solution of Intermediate C (0.550 g, 3.27 mmol) in THF (10 mL) was added NaH (0.157 g, 3.92 mmol, 60% purity). After 30 min, 2-bromoacetonitrile (0.262 mL, 3.92 mmol) was added. The mixture was warmed to room temperature and stirred for 2 h. The reaction was diluted with water (200 mL) and extracted with ethyl acetate (50 mL×3). The combined the organic layers were dried over $Na_2SO_4$, filtered and concentrated. The residue was purified by column chromatography ($SiO_2$, petroleum ether/ethyl acetate=10/1 to 3/1) to give Intermediate E (0.520 g, 2.51 mmol, 76.74% yield) as a yellow solid. $^1H$ NMR (400 MHz, $CDCl_3$) δ 7.64-7.61 (m, 2H), 5.03-5.00 (m, 2H), 1.58 (s, 9H).

Step 3: Preparation of tert-butyl 1-(1-cyano-1-methyl-ethyl)imidazole-4-carboxylate (Intermediate F)

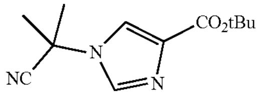

F

To a cooled (0° C.) solution of Intermediate E (0.400 g, 1.93 mmol) in THF (8 mL) was added NaH (0.386 g, 9.65 mmol, 60% purity) in portion. The mixture was stirred at 25° C. for 1 h, followed by addition of MeI (0.721 mL, 11.58 mmol). After 12 h, the reaction was slowly poured into saturated aqueous $NH_4Cl$ (20 mL) and extracted with ethyl acetate (5 mL×3). The combined the organic layers were dried over $Na_2SO_4$, filtered, and concentrated. The residue was purified by column chromatography ($SiO_2$, petroleum ether/ethyl acetate=10/1 to 1/1) to give Intermediate F (0.100 g, 0.397 mmol, 20.54% yield, 93.3% purity) as a yellow solid. LCMS (ESI) m/z: $[M+H]^+$=236.1.; $^1H$ NMR (400 MHz, $CDCl_3$) δ 7.71-7.64 (m, 2H), 1.94 (s, 6H), 1.52 (s, 9H).

Step 4: Preparation of 1-(1-cyano-1-methyl-ethyl) imidazole-4-carboxylic acid (Intermediate G)

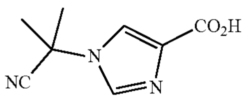

F

To a solution of Intermediate F (0.050 g, 0.213 mmol) in dichloromethane (0.7 mL) was added TEA (0.157 mL, 2.13 mmol) and stirred at for 2 h. The mixture was concentrated to afford Intermediate G (0.034 g, 0.190 mmol, 89.29% yield) as a yellow solid which was used into the next step without further purification. LCMS (ESI) m/z: $[M+H]^+$ =180.0.

Example 171. Preparation of Compounds of the Invention

The following compounds in Table 10 below were synthesized utilizing the general synthetic protocols described in Examples 62 and 63, starting from the appropriate common intermediate (4-bromothiazol-2-amine), the appropriate heterocyclic carboxylic acid, N-Boc amino acid and boronic ester or acid. Where appropriate SEC purification was used to separate enantiomers.

TABLE 10

| Compound # | LC-MS data(m/z) | $^1$H NMR |
|---|---|---|
| 345 | 509.1 | $^1$H NMR (400 MHz, DMSO-$d_6$) δ 12.69 (s, 1H), 8.83 (d, J = 1.6 Hz, 1H), 8.23-8.20 (m, 1H), 8.00-7.93 (m, 2H), 7.82 (s, 1H), 7.72 (d, J = 8.4 Hz, 1H), 7.49 (d, J = 7.2 Hz, 1H), 6.69 (d, J = 2.4 Hz, 1H), 6.64 (d, J = 7.2 Hz, 1H), 4.98-4.94 (m, 1H), 3.89-3.74 (m, 2H), 3.53 (s, 3H), 3.32 (s, 3H), 1.59 (s, 9H) |
| 346 | 523.1 | $^1$H NMR (400 MHz, DMSO-$d_6$) δ 12.69 (s, 1H), 8.83 (s, 1H), 8.22 (d, J = 2.0 Hz, 1H), 8.13 (d, J = 7.6 Hz, 1H), 8.07 (d, J = 2.4 Hz, 1H), 7.82 (s, 1H), 7.72 (d, J = 8.6 Hz, 1H), 7.49 (d, J = 7.2 Hz, 1H), 6.79 (d, J = 2.4 Hz, 1H), 6.64 (d, J = 7.2 Hz, 1H), 5.07 (d, J = 2.4, Hz, 2H), 5.02-4.93 (m, 1H), 4.66 (d, J = 6.4 Hz, 2H), 3.90-3.73 (m, 2H), 3.53 (s, 3H), 3.32-3.32 (m, 3H), 1.89 (s, 3H) |
| 347 | 522.2 | $^1$H NMR (400 MHz, DMSO-$d_6$) δ 12.52 (s, 1H), 8.81 (d, J = 1.6 Hz, 1H), 8.22-8.19 (m, 1H), 7.94 (d, J = 7.6 Hz, 1H), 7.78 (s, 1H), 7.70 (d, J = 8.4 Hz, 1H), 7.63-7.62 (m, 1H), 7.50 (d, J = 7.2 Hz, 1H), 6.97-6.96 (m, 1H), 6.65 (d, J = 7.2 Hz, 1H), 6.51-6.56 (m, 1H), 4.92 (d, J = 7.2 Hz, 1H), 4.03-3.98 (m, 2H), 3.76-3.66 (m, 2H), 3.31 (s, 3H), 1.49 (s, 9H), 1.28-1.25 (m, 3H) |
| 348 | 491.9 | $^1$H NMR (400 MHz, DMSO-$d_6$) δ 12.46-12.36 (m, 1H), 8.81 (s, 1H), 8.21-8.19 (m, 1H), 8.04 (d, J = 6.4 Hz, 1H), 7.76 (s, 1H), 7.70 (d, J = 8.4 Hz, 1H), 7.64 (d, J = 1.6 Hz, 1H), 7.48 (d, J = 7.6 Hz, 1H), 7.01-6.99 (m, 1H), 6.63 (d, J = 7.6 Hz, 1H), 6.60-6.58 (m, 1H), 4.85-4.83 (m, 2H), 4.66-4.61 (m, 3H), 3.52 (s, 3H), 1.79 (s, 3H), 1.42 (d, J = 7.2 Hz, 3H) |
| 351 | 532.3 | $^1$H NMR (400 MHz, DMSO-$d_6$) δ 12.56 (br s, 1H), 8.55-8.41 (m, 2H), 8.04-7.92 (m, 2H), 7.68 (s, 1H), 7.42-7.22 (m, 2H), 6.80 (m, 1H), 4.92 (m, 1H), 3.78-3.68 (m, 2H), 3.61-3.53 (m, 5H), 3.35-3.30 (m, 3H), 3.05 (s, 3H), 3.01 (m, 2H) |
| 368 | 580.2 | $^1$H NMR (400 MHz, DMSO-$d_6$) δ 8.53 (d, J = 7.2 Hz, 1H), 7.99-7.98(m, 1H), 7.64-7.60 (m, 1H), 7.53 (d, J = 2.4 Hz, 1H), 7.30-7.29 (m, 1H), 7.21-7.17 (m, 1H), 7.07-6.98 (m, 1H), 6.80-6.78 (m, 1H), 4.92 (d, J = 6.8 Hz, 1H), 3.80-3.77 (m, 2H), 3.73-3.70 (m, 2H), 3.57 (s, 3H), 3.31 (s, 3H), 3.26 (d, J = 11.6 Hz, 2H), 2.42-2.37 (m, 2H), 1.14 (s, 3H), 1.12 (s, 3H) |
| 430 | 530.2 | $^1$H NMR (400 MHz, DMSO-$d_6$) δ 12.61 (br s, 1H), 8.82 (d, J = 1.6 Hz, 1H), 8.51 (d, J = 7.2 Hz, 1H), 8.20 (d, J = 1.7, 8.3 Hz, 1H), 8.02-7.96 (m, 1H), 7.78 (s, 1H), 7.70 (d, J = 8.4 Hz, 1H), 7.51-7.43 (m, 1H), 7.33-7.26 (m, 1H), 6.80 (d, J = 1.5, 3.2 Hz, 1H), 6.62 (d, J = 7.3 Hz, 1H), 4.94 (d, J = 6.8 Hz, 1H), 3.79-3.68 (m, 2H), 3.57 (s, 3H), 3.52 (s, 3H), 3.32 (s, 3H) |
| 453 | 522.2 | $^1$H NMR (400 MHz, DMSO-$d_6$) δ 12.78-12.34 (m, 1H), 8.82 (d, J = 1.6 Hz, 1H), 8.23-8.20 (m, 1H), 8.02 (d, J = 7.2 Hz, 1H), 7.80 (s, 1H), 7.73-7.68 (m, 2H), 7.49 (d, J = 7.2 Hz, 1H), 7.02-7.00 (m, 1H), 6.64 (d, J = 7.2 Hz, 1H), 6.60-6.59 (m, 1H), 4.97-4.90 (m, 1H), 4.86-4.84 (m, 2H), 4.63 (d, J = 6.8 Hz, 2H), 3.77-3.68 (m, 2H), 3.53 (s, 3H), 3.32 (s, 3H), 1.80 (s, 3H) |
| 456 | 505.0 | $^1$H NMR (400 MHz, DMSO-$d_6$) δ 12.58-12.39 (m, 1H), 8.50 (d, J = 7.2 Hz, 1H), 7.98 (d, J = 2.0 Hz, 1H), 7.65 (s, 1H), 7.60-7.56 (m, 1H), 7.50 (d, J = 8.0 Hz, 1H), 7.34-7.30 (m, 1H), 7.29 (d, J = 2.4 Hz, 1H), 7.00 (d, J = 1.6 Hz, 1H), 6.79 (d, J = 3.2 Hz, 1H), 4.93 (d, J = 6.8 Hz, 1H), 3.89 (d, J = 3.2 Hz, 1H), 3.75-3.67 (m, 2H), 3.56 (s, 3H), 0.85-0.77 (m, 2H), 0.71-0.65 (m, 2H) |
| 459 | 533.0 | $^1$H NMR (400 MHz, DMSO-$d_6$) δ 12.57 (br s, 1H), 8.52 (d, J = 7.2 Hz, 1H), 8.04-7.93 (m, 2H), 7.91-7.79 (m, 2H), 7.58-7.56 (m, 1H), 7.37-7.24 (m, 2H), 6.80-6.79 (m, 1H), 4.95-4.90 (m, 1H), 3.77-3.68 (m, 2H), 3.57 (s, 3H), 3.32(s, 3H) |
| 485 | 522.3 | $^1$H NMR (400 MHz, DMSO-$d_6$) δ 12.52 (s, 1H), 8.69 (s, 1H), 8.09 (s, 1H), 7.94 (d, J = 7.6 Hz, 1H), 7.76 (s, 1H), 7.63-7.62 (m, 1H), 7.52 (d, J = 7.6 Hz, 1H), 6.97-6.96 (m, 1H), 6.67 (d, J = 7.6 Hz, 1H), 6.53-6.50 (m, 1H), 4.95-4.90 (m, 1H), 3.80-3.65 (m, 2H), 3.54 (s, 3H), 3.32 (s, 3H), 2.55 (s, 3H), 1.50 (s, 9H) |
| 493 | 474.2 | $^1$H NMR (400 MHz, DMSO-$d_6$) δ 12.44 (br s, 1H), 8.82 (d, J = 1.6 Hz, 1H), 8.27-8.25 (m, 1H), 8.22-8.20 (m, 1H), 7.78 (s, 1H), 7.71 (d, J = 8.4 Hz, 1H), 7.49 (d, J = 7.2 Hz, 1H), 7.40-7.39 (m, 1H), 6.87-6.79 (m, 1H), 6.64 (d, J = 7.2 Hz, 1H), 6.51-6.50 (m, 1H), 4.11 (d, J = 6.0 Hz, 2H), 3.53 (s, 3H), 2.60 (s, 1H), 2.20 (s, 6H) |
| 504 | 476.1 | $^1$H NMR (400 MHz, DMSO-$d_6$) δ 12.44 (s, 1H), 8.82 (d, J = 2.0 Hz, 1H), 8.26-8.16 (m, 2H), 7.78 (s, 1H), 7.71 (d, J = 8.4 Hz, 1H), 7.49 (d, J = 7.2 Hz, 1H), 7.43 (d, J = 2.0 Hz, 1H), 6.85 (d, J = 2.8 Hz, 1H), 6.64 (d, J = 7.2 Hz, 1H), 6.50-6.49 (m, 1H), 4.11 (d, J = 6.0 Hz, 2H), 3.53 (s, 3H), 2.49-2.41 (m, 2H), 2.24-2.13 (m, 2H), 2.01-1.78 (m, 2H), 1.59 (s, 3H) |
| 513 | 550.9 | $^1$H NMR (400 MHz, Methanol-$d_4$) δ 8.18-8.10 (m, 1H), 7.93-7.88 (m, 1H), 7.57 (d, J = 2.4 Hz, 1H), 7.40-7.34 (m, 1H), 7.33-7.28 (m, 1H), 7.27-7.25 (m, 1H), 6.84-6.83 (m, 1H), 4.97-4.94 (m, 1H), 3.88-3.79 (m, 2H), 3.42 (s, 3H), 3.37 (s, 3H) |
| 526 | 517.2 | $^1$HNMR (400 MHz, DMSO-$d_6$) δ 12.57 (s, 1H), 8.82 (d, J = 1.6 Hz, 1H), 8.23-8.20 (m, 1H), 8.14-8.12 (m, 1H), 7.79 (s, 1H), 7.73-7.70 (m, 2H), 7.48 (d, J = 7.2 Hz, 1H), 7.07-7.06 (m, 1H), 6.64 (d, J = 7.2 Hz, 1H), 6.60-6.57 (m, 1H), 4.94-4.89 (m, 1H), 3.76-3.68 (m, 2H), 3.53 (s, 3H), 3.32 (m, 3H), 1.85-1.73 (m, 4H) |

TABLE 10-continued

| Compound # | LC-MS data(m/z) | $^1$H NMR |
|---|---|---|
| 532 | 487.0 | $^1$HNMR (400 MHz, DMSO-$d_6$) δ 12.44 (s, 1H), 8.82 (d, J = 1.6 Hz, 1H), 8.22-8.15 (m, 2H), 7.78 (s, 1H), 7.72-7.67 (m, 2H), 7.48 (d, J = 7.6 Hz, 1H), 7.07-7.06 (m, 1H), 6.64-6.58 (m, 2H), 4.67-4.60 (m, 1H), 3.53 (s, 3H), 1.85-1.73 (m, 4H), 1.42 (d, J = 7.2 Hz, 3H) |
| 534 | 488.2 | $^1$H NMR (400 MHz, DMSO-$d_6$) δ 12.43 (br s, 1H), 8.82 (d, J = 1.6 Hz, 1H), 8.22-8.20 (m, 1H), 8.07 (d, J = 6.8 Hz, 1H), 7.78 (s, 1H), 7.71 (d, J = 8.4 Hz, 1H), 7.54-7.42 (m, 2H), 6.83-6.82 (m, 1H), 6.64 (d, J = 7.2 Hz, 1H), 6.56-6.48 (m, 1H), 4.65-4.62 (m, 1H), 3.53 (s, 3H), 2.60 (s, 1H), 2.19 (s, 6H), 1.42 (d, J = 7.2 Hz, 3H) |
| 536 | 490.1 | $^1$H NMR (400 MHz, DMSO-$d_6$) δ 12.41 (s, 1H), 8.82 (d, J = 1.6 Hz, 1H), 8.22-8.20 (m, 1H), 8.00 (d, J = 6.8 Hz, 1H), 7.78 (s, 1H), 7.71 (d, J = 8.0 Hz, 1H), 7.53-7.47 (m, 2H), 6.87-6.80 (m, 1H), 6.64 (d, J = 7.2 Hz, 1H), 6.52-6.61 (m, 1H), 4.70-4.57 (m, 1H), 3.53 (s, 3H), 2.48-2.41 (m, 2H), 2.22-2.15 (m, 2H), 1.97-1.82 (m, 2H), 1.59 (s, 3H), 1.42 (d, J = 7.6 Hz, 3H) |
| 537 | 523.1 | $^1$H NMR (400 MHz, DMSO-$d_6$) δ 12.54 (s, 1H), 8.51 (d, J = 7.2 Hz, 1H), 7.98-7.97 (m, 1H), 7.61-7.57 (m, 1H), 7.52 (d, J = 2.0 Hz, 1H), 7.41-7.36 (m, 1H), 7.30-7.28 (m, 1H), 7.25-7.21 (m, 1H), 6.79-6.78 (m, 1H), 4.94-4.89 (m, 1H), 4.00-3.95 (m, 1H), 3.75-3.67 (m, 2H), 3.56 (s, 3H), 3.31 (s, 3H), 0.84-0.78 (m, 2H), 0.77-0.72 (m, 2H) |
| 540 | 522.1 | 1H NMR (400 MHz, DMSO-$d_6$) δ 12.52 (s, 1H), 8.49 (d, J = 7.2 Hz, 1H), 7.98-7.97 (m, 1H), 7.68 (s, 1H), 7.29-7.28 (m, 1H), 7.03-6.92 (m, 1H), 6.79-6.77 (m, 2H), 6.17-6.13 (m, 1H), 4.93-4.88 (m, 1H), 3.87-3.84 (m, 4H), 3.75-3.66 (m, 2H), 3.56 (s, 3H), 3.31 (s, 3H), 2.34-2.31 (m, 2H) |
| 549 | 522.2 | $^1$H NMR (400 MHz, Methanol-$d_4$) δ 7.90-7.89 (m, 1H), 7.28 (s, 1H), 7.25-7.24 (m, 2H), 7.09-7.07 (m, 1H), 6.97-6.94 (m, 1H), 6.83-6.82 (m, 1H), 4.96-4.93 (m, 1H), 3.99-3.95 (m, 4H), 3.84-3.82 (m, 2H), 3.41 (s, 3H), 3.36 (s, 3H), 2.38-2.31 (m, 2H) |
| 551 | 508.0 | $^1$H NMR (400 MHz, Methanol-$d_4$) δ 8.32 (d, J = 8.4 Hz, 1H), 8.17 (d, J = 1.6 Hz, 1H), 8.08-8.02 (m, 1H), 7.68-7.61 (m, 2H), 7.37 (d, J = 7.2 Hz, 1H), 6.99-6.91 (m, 1H), 6.72 (d, J = 7.2 Hz, 1H), 6.63-6.57 (m, 1H), 6.40 (s, 1H), 4.98-4.94 (m, 1H), 3.90-3.78 (m, 2H), 3.62 (s, 3H), 3.43 (s, 3H), 1.57 (s, 9H) |
| 561 | 526.0 | $^1$H NMR (400 MHz, DMSO + $D_2O$) δ 8.81 (s, 1H), 8.37-8.28 (m, 1H), 7.87-7.76 (m, 2H), 7.72-7.65 (m, 1H), 7.63-7.55 (m, 1H), 7.00-6.92 (m, 1H), 6.51 (d, J = 1.6 Hz, 1H), 4.91-4.82 (m, 1H), 3.72-3.66 (m, 2H), 3.51-3.46 (m, 3H), 3.30 (s, 3H), 1.50-1.45 (m, 9H) |
| 563 | 526.1 | $^1$H NMR (400 MHz, DMSO-$d_6$) δ 12.56 (br s, 1H), 8.67 (s, 1H), 8.13-8.09 (m, 1H), 7.95 (d, J = 7.6 Hz, 1H), 7.90 (s, 1H), 7.67-7.56 (m, 2H), 6.97-6.96 (m, 1H), 6.67 (d, J = 7.6 Hz, 1H), 6.51-6.50 (m, 1H), 4.95-4.90 (m, 1H), 3.78-3.66 (m, 2H), 3.55 (s, 3H), 3.32 (s, 3H), 1.50 (s, 9H) |
| 564 | 540.2 | $^1$H NMR (400 MHz, DMSO-$d_6$) δ 12.58 (br s, 1H), 8.68 (s, 1H), 8.13-8.10 (m, 1H), 8.02 (d, J = 7.6 Hz, 1H), 7.90 (s, 1H), 7.69-7.68 (m, 1H), 7.59 (d, J = 7.6 Hz, 1H), 7.01-7.00 (m, 1H), 6.67 (d, J = 7.2 Hz, 1H), 6.60-6.59 (m, 1H), 4.95-4.90 (m, 1H), 4.86-4.84 (m, 2H), 4.63 (d, J = 6.8 Hz, 2H), 3.78-3.67 (m, 2H), 3.55 (s, 3H), 3.32-3.32 (m, 3H), 1.80 (s, 3H) |
| 567 | 522.2 | $^1$H NMR (400 MHz, DMSO-$d_6$) δ 12.41 (s, 1H), 8.81 (d, J = 2.0 Hz, 1H), 8.22-8.19 (m, 1H), 7.94 (d, J = 7.2 Hz, 1H), 7.77 (s, 1H), 7.70 (d, J = 8.4 Hz, 1H), 7.59-7.57 (m, 1H), 7.48 (d, J = 7.2 Hz, 1H), 6.98-6.96 (m, 1H), 6.63 (d, J = 7.2 Hz, 1H), 6.51-6.49 (m, 1H), 4.69-4.63 (m, 1H), 3.52 (s, 3H), 3.47-3.43 (m, 2H), 3.24 (s, 3H), 2.16-1.93 (m, 2H), 1.50-1.48 (m, 9H) |
| 570 | 478.1 | $^1$H NMR (400 MHz, DMSO-$d_6$) δ 12.39 (s, 1H), 8.81 (d, J = 1.6 Hz, 1H), 8.22-8.19 (m, 1H), 7.97 (d, J = 6.8 Hz, 1H), 7.77 (s, 1H), 7.70 (d, J = 8.4 Hz, 1H), 7.59 (t, J = 2.0 Hz, 1H), 7.48 (d, J = 7.2 Hz, 1H), 6.96 (d, J = 2.8 Hz, 1H), 6.63 (d, J = 7.2 Hz, 1H), 6.51-6.49 (m, 1H), 4.67-4.59 (m, 1H), 3.52 (s, 3H), 1.49 (s, 9H), 1.42 (d, J = 7.2 Hz, 3H) |
| 573 | 522.1 | $^1$H NMR (400 MHz, DMSO-$d_6$) δ 12.52 (s, 1H), 8.51 (d, J = 7.2 Hz, 1H), 7.98-7.97 (m, 1H), 7.46 (d, J = 2.0 Hz, 1H), 7.37-7.31 (m, 1H), 7.30-7.28 (m, 1H), 7.07-7.06 (m, 1H), 6.79-6.78 (m, 1H), 6.53-6.51 (m, 1H), 4.94-4.89 (m, 1H), 3.95-3.92 (m, 4H), 3.74-3.68 (m, 2H), 3.56 (s, 3H), 3.30 (s, 3H), 2.31-2.25 (m, 2H) |
| 583 | 544.4 | $^1$H NMR (400 MHz, DMSO-$d_6$) δ 12.57 (s, 1H), 8.84 (d, J = 1.6 Hz, 1H), 8.37-8.34 (m, 1H), 8.21-7.87 (m, 3H), 7.82 (d, J = 8.4 Hz, 1H), 7.63 (d, J = 2.0 Hz, 1H), 7.58 (d, J = 7.6 Hz, 1H), 6.97 (d, J = 2.8 Hz, 1H), 6.86 (d, J = 7.6 Hz, 1H), 6.52-6.51 (m, 1H), 4.95-4.90 (m, 1H), 3.73-3.70 (m, 2H), 3.32 (s, 3H), 1.50 (s, 9H) |
| 584 | 519.2 | $^1$H NMR (400 MHz, DMSO-$d_6$) δ 12.60 (br s, 1H), 8.83 (d, J = 1.6 Hz, 1H), 8.24-8.20 (s, 8.4 Hz, 1H), 8.17 (d, J = 7.6 Hz, 1H), 7.83-7.80 (m, 2H), 7.72 (d, J = 8.4 Hz, 1H), 7.49 (d, J = 7.2 Hz, 1H), 7.16-7.14 (m, 1H), 6.66-6.63 (m, 2H), 4.97-4.91 (m, 1H), 3.77-3.68 (m, 2H), 3.53 (s, 3H), 3.32 (s, 3H), 1.96 (s, 6H) |
| 596 | 493.1 | $^1$H NMR (400 MHz, Methanol-$d_4$) δ 7.92-7.88 (m, 1H), 7.45-7.40 (m, 1H), 7.38 (d, J = 1.6 Hz, 1H), 7.28-7.25 (m, 1H), 7.25-7.22 (m, 1H), 6.87-6.81 (m, 2H), 4.97-4.93 (m, 1H), 5.96 (s, 2H), 3.87-3.78 (m, 2H), 3.43 (s, 3H), 3.38 (s, 3H) |

TABLE 10-continued

| Compound # | LC-MS data(m/z) | $^1$H NMR |
|---|---|---|
| 598 | 525.3 | $^1$H NMR (400 MHz, DMSO-$d_6$) δ 12.52 (s, 1H), 8.51 (d, J = 6.8 Hz, 1H), 7.99-7.98 (m, 1H), 7.82-7.80 (m, 2H), 7.68 (s, 1H), 7.40-7.38 (m, 1H), 7.29-7.25 (m, 1H), 7.25 (d, J = 7.6 Hz, 1H), 6.79-6.78 (m, 1H), 4.95-4.90 (m, 1H), 3.73-3.68 (m, 2H), 3.56 (s, 3H), 3.31 (s, 3H), 3.08-3.05 (m, 1H), 2.03-1.97 (m, 2H) |
| 599 | 525.3 | $^1$H NMR (400 MHz, DMSO-$d_6$) δ 12.52 (br s, 1H), 8.51 (d, J = 7.2 Hz, 1H), 7.99-7.98 (m, 1H), 7.82-7.80 (m, 2H), 7.68 (s, 1H), 7.40-7.38 (m, 1H), 7.30-7.25 (m, 1H), 7.25 (d, J = 7.6 Hz, 1H), 6.79-6.78 (m, 1H), 4.94-4.89 (m, 1H), 3.73-3.68 (m, 2H), 3.56 (s, 3H), 3.31 (s, 3H), 3.08-3.05 (m, 1H), 2.03-1.97 (m, 2H) |
| 603 | 550.3 | $^1$H NMR (400 MHz, DMSO-$d_6$) δ 12.52 (s, 1H), 8.79-8.78 (m, 1H), 8.25-8.24 (m, 1H), 7.95 (d, J = 7.6 Hz, 1H), 7.80 (s, 1H), 7.76 (d, J = 8.4 Hz, 1H), 7.66 (d, J = 7.6 Hz, 1H), 7.63-7.62 (m, 1H), 6.97-6.96 (m, 1H), 6.78 (d, J = 7.6 Hz, 1H), 6.51-6.50 (m, 1H), 5.80-5.67 (m, 1H), 4.99-4.89 (m, 3H), 4.81-4.80 (m, 2H), 3.79-3.64 (m, 2H), 3.32 (s, 3H), 1.50 (s, 9H) |
| 610 | 523.2 | $^1$H NMR (400 MHz, DMSO-$d_6$) δ 12.53 (s, 1H), 8.51 (d, J = 7.2 Hz, 1H), 7.99 (d, J = 2.0 Hz, 1H), 7.79 (s, 1H), 7.44 (s, 1H), 7.37-7.24 (m, 2H), 6.91-6.87 (m, 1H), 6.80-6.79 (m, 1H), 4.95-4.91 (m, 1H), 3.96-3.93 (m, 1H), 3.77-3.65 (m, 2H), 3.57 (s, 3H), 3.32 (s, 3H), 0.89-0.78 (m, 2H), 0.75-0.64 (m, 2H) |
| 617 | 527.0 | $^1$H NMR (400 MHz, DMSO-$d_6$) δ 12.51-12.48 (m, 1H), 8.49 (d, J = 7.2 Hz, 1H), 7.98-7.97 (m, 1H), 7.50 (s, 1H), 7.30-7.28 (m, 2H), 7.17 (s, 1H), 6.79-6.78 (m, 1H), 6.12 (s, 2H), 4.93-4.88 (m, 1H), 3.71-3.68 (m, 2H), 3.56 (s, 3H), 3.30 (s, 3H) |
| 688 | 491.1 | $^1$H NMR (400 MHz, DMSO-$d_6$) δ 12.42 (s, 1H), 8.51-8.49 (m, 1H), 7.99-7.93 (m, 1H), 7.77 (s, 1H), 7.70-7.62 (m, 1H), 7.41 (s, 1H), 7.31-7.29 (m, 1H), 6.85-6.75 (m, 2H), 4.95-4.92 (m, 1H), 4.59-4.54 (m, 2H), 3.78-3.65 (m, 2H), 3.57 (s, 3H), 3.32 (s, 3H), 3.25-3.21 (m, 2H) |
| 695 | 511.1 | $^1$H NMR (400 MHz, DMSO-$d_6$) δ 12.48 (s, 1H), 8.50 (d, J = 7.2 Hz, 1H), 7.98-7.97 (m, 1H), 7.63 (s, 1H), 7.37-7.35 (m, 2H), 7.29-7.28 (m, 1H), 6.79-6.78 (m, 1H), 6.16 (s, 2H), 4.93-4.88 (m, 1H), 3.74-3.66 (m, 2H), 3.56 (s, 3H), 3.30 (s, 3H) |
| 708 | 509.1 | $^1$H NMR (400 MHz, DMSO-$d_6$) δ 12.75-11.97 (m, 1H), 8.51-8.48 (m, 1H), 7.98-7.93 (m, 1H), 7.61-7.57 (m, 3H), 7.29-7.28 (m, 1H), 6.79-6.78 (m, 1H), 4.92-4.88 (m, 1H), 4.68-4.65 (m, 2H), 3.76-3.63 (m, 2H), 3.56 (s, 3H), 3.31 (s, 3H), 3.29 (s, 2H) |
| 710 | 497.0 | $^1$H NMR (400 MHz, DMSO-$d_6$) δ 12.54 (s, 1H), 8.51-8.49 (m, 1H), 7.98-7.97 (m, 1H), 7.60-7.50 (m, 2H), 7.30-7.28 (m, 1H), 7.24-7.18 (m, 1H), 7.18-7.11 (m, 1H), 6.79-6.78 (m, 1H), 4.95-4.90 (m, 1H), 3.87 (s, 3H), 3.75-3.65 (m, 2H), 3.56 (s, 3H), 3.31 (s, 3H) |
| 712 | 474.0 | $^1$H NMR (400 MHz, DMSO-$d_6$) δ 12.56 (s, 1H), 8.52 (d, J = 7.2 Hz, 1H), 8.34-8.33 (m, 1H), 8.24-8.23 (m, 1H), 7.98-7.97 (m, 1H), 7.88-7.97 (s, 1H), 7.79-7.68 (m, 1H), 7.70-7.61 (m, 1H), 7.29 (d, J = 3.2 Hz, 1H), 6.79 (d, J = 3.2 Hz, 1H), 4.97-4.88 (m, 1H), 3.76-3.67 (m, 2H), 3.56 (s, 3H), 3.31 (s, 3H) |
| 713 | 522.1 | $^1$H NMR (400 MHz, DMSO-$d_6$) δ 12.47 (br s, 1H), 8.49 (br d, J = 6.8 Hz, 1H), 7.98-7.97 (m, 1H), 7.62 (s, 1H), 7.29-7.28 (m, 1H), 6.95 (d, J = 10.0 Hz, 1H), 6.87 (s, 1H), 6.79-6.78 (m, 1H), 4.93-4.88 (m, 1H), 3.74-3.66 (m, 2H), 3.56 (s, 3H), 3.38 (s, 2H), 3.30 (br s, 3H), 2.95-2.91 (d, J = 8.0 Hz, 2H), 2.76 (s, 3H) |
| 714 | 492.2 | $^1$H NMR (400 MHz, Methanol-$d_4$) δ 8.15-8.14 (m, 1H), 8.02-7.98 (m, 1H), 7.90-7.89 (m, 1H), 7.69 (s, 1H), 7.48-7.45 (m, 1H), 7.27-7.25 (m, 1H), 6.84-6.83 (m, 1H), 4.96-4.93 (m, 1H), 3.87-3.79 (m, 2H), 3.42 (s, 3H), 3.37 (s, 3H) |
| 716 | 497.0 | $^1$H NMR (400 MHz, DMSO-$d_6$) δ 12.62-12.46 (m, 1H), 8.50-8.49 (m, 1H), 7.99-7.98 (m, 1H), 7.73-7.60 (m, 2H), 7.48-7.47 (m, 1H), 7.32-7.24 (m, 2H), 6.80-6.79 (m, 1H), 4.92-4.91 (m, 1H), 3.91 (s, 3H), 3.76-3.69 (m, 2H), 3.57 (s, 3H), 3.32 (s, 3H) |
| 721 | 507.9 | $^1$H NMR (400 MHz, Methanol-$d_4$) δ 8.30-8.20 (m, 2H), 7.91-7.89 (m, 1H), 7.76-7.66 (m, 2H), 7.29-7.24 (m, 1H), 6.84-6.83 (m, 1H), 4.97-4.93 (m, 1H), 3.88-3.78 (m, 2H), 3.42 (s, 3H), 3.37 (s, 3H) |
| 725 | 563.2 | $^1$H NMR (400 MHz, $CDCl_3$) δ 10.42 (s, 1H), 8.62 (d, J = 1.6 Hz, 1H), 8.27 (d, J = 2.8 Hz, 1H), 7.75 (d, J = 2.0 Hz, 1H), 7.63-7.58 (m, 1H), 7.26 (s, 1H), 7.20-7.18 (m, 1H), 6.84 (d, J = 6.8 Hz, 1H), 6.73-6.71 (m, 1H), 5.06-5.00 (m, 1H), 4.08-4.04 (m, 1H), 3.89-3.82 (m, 2H), 3.72-3.67 (m, 1H), 3.56 (d, J = 10.8 Hz, 2H), 3.51 (s, 3H), 3.25 (s, 3H), 2.53 (d, J = 11.2 Hz, 2H), 1.30 (d, J = 6.4 Hz, 6H) |
| 726 | 497.2 | $^1$H NMR (400 MHz, DMSO-$d_6$) δ 12.79-12.24 (m, 1H), 8.50 (d, J = 7.2 Hz, 1H), 7.98-7.97 (m, 1H), 7.79 (s, 1H), 7.42-7.23 (m, 3H), 6.87-6.72 (m, 2H), 4.94-4.91 (m, 1H), 3.82 (s, 3H), 3.76-3.66 (m, 2H), 3.56 (s, 3H), 3.31 (s, 3H) |
| 728 | 529.2 | $^1$HNMR (400 MHz, $CDCl_3$) δ 10.36 (br s, 1H), 7.78 (d, J = 1.6 Hz, 1H), 7.57-7.47 (m, 2H), 7.20-7.14 (m, 1H), 7.10-7.04 (m, 2H), 6.99 (d, J = 6.8 Hz, 1H), 6.78-6.74 (m, 1H), 5.19-5.06 (m, 1H), 4.06-4.03(m, 1H), 3.76-3.65 (m, 1H), 3.50 (s, 3H), 3.25 (s, 3H) |

TABLE 10-continued

| Compound # | LC-MS data(m/z) | $^1$H NMR |
|---|---|---|
| 732 | 525.0 | $^1$H NMR (400 MHz, DMSO-$d_6$) δ 12.74-12.22 (m, 1H), 8.49 (d, J = 7.2 Hz, 1H), 8.10-8.03 (m, 2H), 8.00-7.95 (m, 1H), 7.75 (s, 1H), 7.46 (d, J = 8.4 Hz, 1H), 7.31-7.26 (m, 1H), 6.80-6.77 (m, 1H), 4.94-4.87 (m, 1H), 3.76-3.66 (m, 2H), 3.55 (s, 3H), 3.05 (s, 2H), 2.65-2.52 (m, 5H) |
| 733 | 543.2 | $^1$H NMR (400 MHz, DMSO-$d_6$) δ 12.53 (s, 1H), 8.51 (d, J = 7.2 Hz, 1H), 7.99-7.98 (m, 2H), 7.95-7.87 (m, 2H), 7.30-7.28 (m, 1H), 6.79-6.78 (m, 1H), 4.94-4.89 (m, 1H), 3.75-3.67 (m, 2H), 3.56 (s, 3H), 3.31 (s, 3H), 3.08 (br s, 2H), 2.70-2.63 (m, 2H) |
| 779 | 474.1 | $^1$H NMR (400 MHz, DMSO-$d_6$) δ 8.81 (d, J = 2.0 Hz, 1H), 8.38-8.35 (m, 1H), 8.21-8.19 (m, 1H), 8.14 (d, J = 1.2 Hz, 1H), 8.04 (d, J = 1.2 Hz, 1H), 7.78 (s, 1H), 7.70 (d, J = 8.4 Hz, 1H), 7.48 (d, J = 7.2 Hz, 1H), 6.63 (d, J = 7.2 Hz, 1H), 4.17 (d, J = 6.0 Hz, 2H), 3.52 (s, 3H), 1.89-1.82 (m, 4H) |
| 782 | 476.1 | $^1$H NMR (400 MHz, DMSO-$d_6$) δ 12.54 (s, 1H), 8.81 (s, 3H), 8.21 (d, J = 8.4 Hz, 1H), 7.80 (s, 1H), 7.71 (d, J = 8.0 Hz, 1H), 7.49 (d, J = 7.2 Hz, 1H), 6.64 (d, J = 7.2 Hz, 1H), 4.19 (d, J = 5.6 Hz, 2H), 3.53 (s, 3H), 2.72 (s, 1H), 2.34 (s, 6H) |
| 792 | 479.2 | $^1$H NMR (400 MHz, DMSO-$d_6$) δ 8.82 (d, J = 1.6 Hz, 1H), 8.24-8.20 (m, 1H), 8.13 (d, J = 7.2 Hz, 1H), 7.95 (d, J = 2.4 Hz, 1H), 7.81 (s, 1H), 7.71 (d, J = 8.4 Hz, 1H), 7.49 (d, J = 7.2 Hz, 1H), 6.68 (d, J = 2.4 Hz, 1H), 6.64 (d, J = 7.2 Hz, 1H), 4.75-4.68 (m, 1H), 3.53 (s, 3H), 1.59 (s, 9H), 1.49 (d, J = 7.2 Hz, 3H) |
| 793 | 474.0 | $^1$H NMR (400 MHz, DMSO-$d_6$) δ 12.53-12.50 (m, 1H), 8.81-8.81 (d, J = 1.2 Hz, 1H), 8.64-8.61 (m, 1H), 8.22-8.18 (m, 2H), 7.78 (s, 1H), 7.70 (d, J = 8.4 Hz, 1H), 7.48 (d, J = 7.2 Hz, 1H), 6.75 (d, J = 2.8 Hz, 1H), 6.63 (d, J = 7.2 Hz, 1H), 4.16 (d, J = 5.6 Hz, 2H), 3.52 (s, 3H), 1.99-1.95 (m, 2H), 1.92-1.90 (m, 2H) |
| 801 | 493.1 | $^1$H NMR (400 MHz, DMSO-$d_6$) δ 12.54 (s, 1H), 8.82 (d, J = 1.6 Hz, 1H), 8.23-8.20 (m, 1H), 8.14 (d, J = 7.2 Hz, 1H), 8.03 (d, J = 1.6 Hz, 1H), 7.97 (d, J = 1.6 Hz, 1H), 7.80 (s, 1H), 7.71 (d, J = 8.4 Hz, 1H), 7.49 (d, J = 7.2 Hz, 1H), 6.64 (d, J = 7.2 Hz, 1H), 4.90 (d, J = 6.8 Hz, 2H), 4.71 (d, J = 7.2 Hz, 1H), 4.64 (d, J = 7.2 Hz, 2H), 3.53 (s, 3H), 1.83 (s, 3H), 1.47 (d, J = 7.2 Hz, 3H) |
| 802 | 520.2 | $^1$H NMR (400 MHz, DMSO-$d_6$) δ 12.68 (s, 1H), 8.82 (d, J = 1.6 Hz, 1H), 8.24-8.20 (m, 1H), 8.16-8.14 (m, 2H), 8.08 (d, J = 8.0 Hz, 1H), 7.82 (s, 1H), 7.71 (d, J = 8.4 Hz, 1H), 7.49 (d, J = 7.2 Hz, 1H), 6.64 (d, J = 7.2 Hz, 1H), 4.96-4.92 (m, 1H), 3.88-3.84 (m, 1H), 3.76-3.72 (m, 1H), 3.53 (s, 3H), 3.31 (s, 3H), 2.03 (s, 6H) |
| 804 | 523.1 | $^1$H NMR (400 MHz, DMSO-$d_6$) δ 12.64 (s, 1H), 8.83 (d, J = 1.6 Hz, 1H), 8.22-8.21 (m, 1H), 8.06-7.98 (m, 3H), 7.82 (s, 1H), 7.71 (d, J = 8.4 Hz, 1H), 7.49 (d, J = 7.2 Hz, 1H), 6.64 (d, J = 7.2 Hz, 1H), 4.94 (d, J = 2.8 Hz, 1H), 4.90 (d, J = 7.2 Hz, 2H), 4.64 (d, J = 7.2 Hz, 2H), 3.91-3.81 (m, 1H), 3.75-3.71 (m, 1H), 3.53 (s, 3H), 3.31 (s, 3H), 1.83 (s, 3H) |
| 805 | 488.1 | $^1$H NMR (400 MHz, DMSO-$d_6$) δ 12.55 (s, 1H), 8.83 (s, 1H), 8.54-8.42 (m, 1H), 8.33-8.08 (m, 2H), 7.81 (s, 1H), 7.77-7.65 (m, 1H), 7.55-7.37 (m, 1H), 6.77 (s, 1H), 6.70-6.49 (m, 1H), 4.78-4.63 (m, 1H), 3.53 (s, 3H), 2.03-1.89 (m, 4H), 1.49 (d, J = 6.4 Hz, 3H) |
| 812 | 518.2 | $^1$H NMR (400 MHz, DMSO-$d_6$) δ 12.68 (s, 1H), 8.83 (s, 1H), 8.27 (d, J = 8.0 Hz, 1H), 8.24-8.20 (m, 1H), 8.18 (d, J = 2.8 Hz, 1H), 7.82 (s, 1H), 7.71 (d, J = 8.0 Hz, 1H), 7.49 (d, J = 7.2 Hz, 1H), 6.79 (d, J = 2.4 Hz, 1H), 6.64 (d, J = 7.2 Hz, 1H), 4.98-4.92 (m, 1H), 3.88-3.83 (m, 1H), 3.80-3.75 (m, 1H), 3.53 (s, 3H), 3.30 (s, 3H), 1.98-1.93 (m, 4H) |
| 816 | 520.1 | $^1$H NMR (400 MHz, DMSO-$d_6$) δ 12.70 (s, 1H), 8.82 (s, 1H), 8.23-8.20 (m, 1H), 8.18 (d, J = 2.4 Hz, 1H), 8.16 (s, 1H), 7.81 (s, 1H), 7.71 (d, J = 8.4 Hz, 1H), 7.48 (d, J = 7.2 Hz, 1H), 6.84 (d, J = 2.8 Hz, 1H), 6.63 (d, J = 7.6 Hz, 1H), 4.97-4.95 (m, 1H), 3.89-3.84 (m, 1H), 3.79-3.75 (m, 1H), 3.53 (s, 3H), 3.31 (s, 3H), 2.05 (s, 6H) |

Example 172. Preparation of Compounds of the Invention

The following compounds in Table 11 were synthesized utilizing the general synthetic protocols described in Example 61 and starting from the appropriate common intermediate (4-(3-(4,4,5,5-tetramethyl-1,3,2-dioxaborolan-2-yl)phenyl)thiazol-2-amine), heteroaryl halide, N-Boc amino acid, and the appropriate heterocyclic carboxylic acid.

TABLE 11

| Compound # | LC-MS data(m/z) | $^1$H NMR |
|---|---|---|
| 352 | 530.1 | $^1$H NMR (400 MHz, DMSO-$d_6$) δ 12.58 (s, 1H), 8.50 (d, J = 7.2 Hz, 1H), 8.42-8.41 (m, 1H), 8.26 (s, 1H), 8.01-7.97 (m, 1H), 7.91-7.88 (m, 1H), 7.79-7.77 (m, 1H), 7.74 (s, 1H), 7.54-7.50 (m, 1H), 7.30-7.29 (m, 1H), 6.81-6.78 (m, 1H), 4.96-4.91 (m, 1H), 4.22 (s, 3H), 3.74-3.71 (m, 2H), 3.57 (s, 3H), 3.32 (s, 3H) |

TABLE 11-continued

| Compound # | LC-MS data(m/z) | $^1$H NMR |
|---|---|---|
| 355 | 499.8 | $^1$H NMR (400 MHz, DMSO-$d_6$) δ 12.44 (br s, 1H), 8.50 (d, J = 6.4 Hz, 1H), 8.42 (d, J = 1.6 Hz, 1H), 8.27 (s, 1H), 7.96 (d, J = 2.0 Hz, 1H), 7.90 (d, J = 8.0 Hz, 1H), 7.79 (d, J = 8.0 Hz, 1H), 7.74 (s, 1H), 7.52 (d, J = 7.6 Hz, 1H), 7.31-7.29 (m, 1H), 6.81-6.79 (m, 1H), 4.70-4.62 (m, 1H), 4.23 (s, 3H), 3.57 (s, 3H), 1.44 (d, J = 7.2 Hz, 3H) |
| 356 | 540.2 | $^1$H NMR (400 MHz, DMSO-$d_6$) δ 12.57 (s, 1H), 8.60 (s, 1H), 8.51 (d, J = 7.6 Hz, 1H), 8.03-7.96 (m, 3H), 7.91-7.83 (m, 1H), 7.77 (s, 1H), 7.63-7.54 (m, 1H), 7.42-7.32 (m, 1H), 7.31-7.29 (m, 1H), 6.81-6.79 (m, 1H), 4.97-4.92 (m, 1H), 3.76-3.71 (m, 2H), 3.57 (s, 3H), 3.33 (s, 3H), 2.62 (d, J = 2.8 Hz, 3H) |
| 568 | 516.0 | $^1$H NMR (400 MHz, DMSO-$d_6$) δ 12.52 (s, 1H), 8.39 (s, 1H), 8.13 (d, J = 7.2 Hz, 1H), 7.85-7.63 (m, 5H), 7.48-7.41 (m, 1H), 7.09-7.03 (m, 1H), 6.73 (d, J = 2.0 Hz, 1H), 6.62-6.53 (m, 1H), 4.95-4.89 (m, 1H), 3.90 (s, 3H), 3.79-3.66 (m, 2H), 3.31 (s, 3H), 1.91-1.68 (m, 4H) |
| 572 | 521.1 | $^1$H NMR (400 MHz, Methanol-$d_4$) δ8.34-8.33 (m, 1H), 7.84-7.80 (m, 1H), 7.73-7.68 (m, 1H), 7.65-7.60 (m, 2H), 7.48-7.40 (m, 2H), 6.98-6.96 (m, 1H), 6.71-6.65 (m, 2H), 5.00-4.94 (m, 3H), 4.74-4.69 (m, 2H), 3.95 (s, 3H), 3.86-3.82 (m, 2H), 3.43 (s, 3H), 1.88 (s, 3H) |
| 588 | 486.1 | $^1$H NMR (400 MHz, DMSO-$d_6$) δ 12.40 (s, 1H), 8.42-8.35 (m, 1H), 8.16 (d, J = 6.8 Hz, 1H), 7.83-7.78 (m, 1H), 7.77-7.74 (m, 1H), 7.74-7.70 (m, 1H), 7.69 (s, 1H), 7.68-7.66 (m, 1H), 7.48-7.40 (m, 1H), 7.09-7.04 (m, 1H), 6.73 (d, J = 2.0 Hz, 1H), 6.61-6.56 (m, 1H), 4.70-4.57 (m, 1H), 3.90 (s, 3H), 1.86-1.79 (m, 2H), 1.78-1.72 (m, 2H), 1.42 (d, J = 7.2 Hz, 3H) |
| 589 | 491.1 | $^1$H NMR (400 MHz, DMSO-$d_6$) δ 12.38 (s, 1H), 8.43-8.35 (m, 1H), 8.05 (d, J = 6.8 Hz, 1H), 7.81 (d, J = 8.0 Hz, 1H), 7.75 (d, J = 2.0 Hz, 1H), 7.72 (d, J = 8.0 Hz, 1H), 7.70-7.67 (m, 1H), 7.66-7.63 (m, 1H), 7.48-7.40 (m, 1H), 7.03-6.98 (m, 1H), 6.73 (d, J = 2.4 Hz, 1H), 6.64-6.55 (m, 1H), 4.87-4.82 (m, 2H), 4.69-4.64 (m, 1H), 4.62 (d, J = 6.8 Hz, 2H), 3.90 (s, 3H), 1.84-1.74 (m, 3H), 1.47-1.36 (m, 3H) |
| 591 | 499.1 | $^1$H NMR (400 MHz, DMSO-$d_6$) δ 12.57-12.41 (m, 1H), 8.55-8.47 (m, 1H), 8.41-8.37 (m, 1H), 7.98-7.94 (m, 1H), 7.85-7.69 (m, 4H), 7.48-7.40 (m, 1H), 7.33-7.28 (m, 1H), 6.82-6.77 (m, 1H), 6.76-6.71 (m, 1H), 4.73-4.61 (m, 1H), 3.90 (s, 3H), 3.57 (s, 3H), 1.50-1.36 (m, 3H) |
| 615 | 519.4 | $^1$H NMR (400 MHz, DMSO + $D_2O$) δ 8.41 (s, 1H), 8.25 (s, 1H), 7.89 (d, J = 8.0 Hz, 1H), 7.82-7.72 (m, 3H), 7.55-7.50 (m, 1H), 7.15-7.12 (m, 1H), 6.66-6.64 (m, 1H), 4.94-4.90 (m, 1H), 4.21 (s, 3H), 3.79-3.66 (m, 2H), 3.31 (s, 3H), 1.95 (s, 6H) |
| 815 | 517.2 | $^1$H NMR (400 MHz, DMSO-$d_6$) δ 13.21-12.05 (m, 1H), 8.39 (s, 1H), 8.26 (d, J = 7.6 Hz, 1H), 8.18 (d, J = 2.8 Hz, 1H), 7.88-7.65 (m, 4H), 7.46-7.42 (m, 1H), 6.78 (d, J = 2.4 Hz, 1H), 6.73 (d, J = 1.6 Hz, 1H), 4.96-4.91 (m, 1H), 3.90 (s, 3H), 3.87-3.81 (m, 1H), 3.79-3.73 (m, 1H), 3.31 (s, 3H), 2.01-1.88 (m, 4H) |
| 462 | 529.4 | $^1$H NMR (400 MHz, $CDCl_3$) δ 8.25 (s, 1H), 7.81-7.79 (m, 1H), 7.72-7.70 (m, 2H), 7.42-7.40 (m, 2H), 7.21-7.12 (m, 2H), 7.15-7.10 (m, 1H), 6.75-6.74 (m, 1H), 6.59 (d, J = 2.0 Hz, 1H), 5.10-5.05 (m, 1H), 4.06-4.03 (m, 1H), 3.98 (s, 3H), 3.72-3.68 (m, 1H), 3.45 (s, 3H), 3.20 (s, 3H) |

Example 173. Preparation of Compounds of the Invention

The following compounds in Table 12 below were synthesized starting from the common starting material, 4-(3-bromophenyl)thiazol-2-amine) and the appropriate chiral N-Boc amino acid, heterocyclic carboxylic acid, and boronate ester including a chiral separation following the synthetic route shown in Scheme 7 below. Where appropriate SEC purification was used to separate enantiomers.

Scheme 7

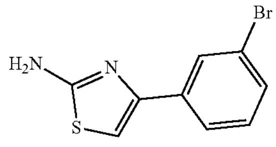

A

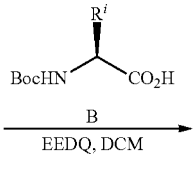

-continued

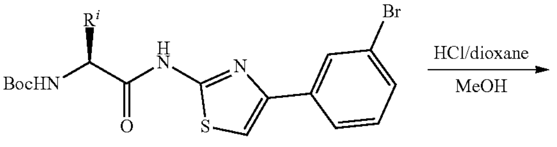

C

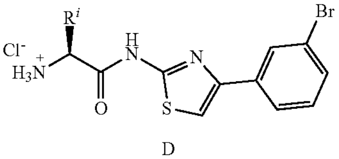

D

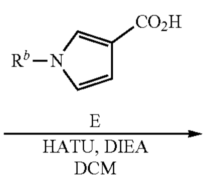

-continued

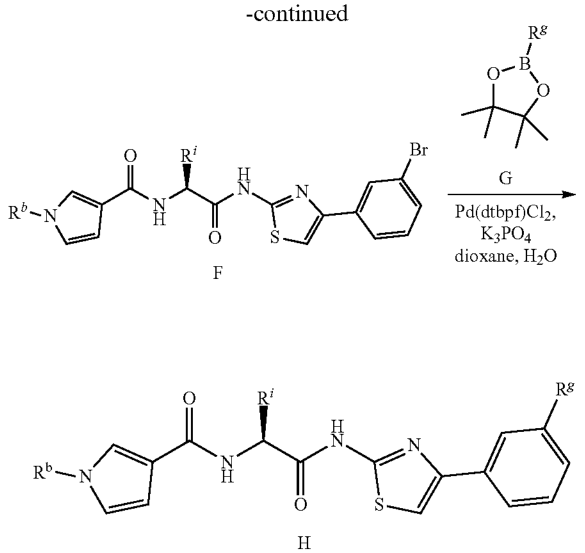

F

G

H

TABLE 12

| Compound # | LC-MS data(m/z) | $^1$H NMR |
|---|---|---|
| 359 | 576.4 | $^1$H NMR (400 MHz, Methanol-d$_4$) δ 8.71 (d, J = 5.2 Hz, 1H), 8.37-8.35 (m, 1H), 8.05-8.03 (m, 1H), 8.02 (d, J = 0.8 Hz, 1H), 7.91-7.89 (m, 2H), 7.75-7.73 (m, 1H), 7.60-7.56 (m, 2H), 7.28-7.26 (m, 1H), 6.94-6.66 (m, 2H), 4.97-4.96 (m, 1H), 3.88-3.80 (m, 2H), 3.43 (s, 3H), 3.37 (s, 3H) |
| 360 | 529.4 | $^1$H NMR (400 MHz, DMSO-d$_6$) δ 12.51 (s, 1H), 8.50 (d, J = 6.8 Hz, 1H), 8.16 (s, 1H), 8.08 (s, 1H), 7.99 (s, 1H), 7.89 (s, 1H), 7.73-7.71 (m, 2H), 7.51 (d, J = 7.6 Hz, 1H), 7.42-7.39 (m, 1H), 7.30-7.29 (m, 1H), 6.80-6.79 (m, 1H), 4.96-4.91 (m, 1H), 3.88 (s, 3H), 3.76-3.68 (m, 2H), 3.57 (s, 3H), 3.32 (s, 3H) |
| 436 | 530.4 | $^1$H NMR (400 MHz, DMSO-d$_6$) δ 12.58 (s, 1H), 8.51 (d, J = 7.2 Hz, 1H), 8.39 (s, 1H), 8.03-7.99 (m, 2H), 7.83 (s, 1H), 7.79 (d, J = 7.6 Hz, 1H), 7.60-7.58 (m, 1H), 7.30-7.29 (m, 1H), 6.93 (s, 1H), 6.80-6.79 (m, 1H), 4.95-4.90 (m, 1H), 3.74-3.71 (m, 2H), 3.57 (s, 3H), 2.54 (s, 3H), 2.31 (s, 3H) |
| 438 | 560.3 | $^1$H NMR (400 MHz, Methanol-d$_4$) δ 8.47-8.39 (m, 1H), 8.31 (s, 1H), 8.04 (d, J = 8.4 Hz, 1H), 7.92-7.90 (m, 1H), 7.81 (s, 1H), 7.73-7.71 (m, 2H), 7.58-7.57 (m, 2H), 7.27-7.26 (m, 1H), 6.85-6.84 (m, 1H), 4.97-4.95 (m, 1H), 3.88-3.80 (m, 2H), 3.43 (s, 3H), 3.38 (s, 3H) |
| 443 | 556.4 | $^1$H NMR (400 MHz, DMSO-d$_6$) δ 12.54 (s, 1H), 8.50 (d, J = 6.8 Hz, 1H), 8.29-8.26 (m, 2H), 8.01-7.98 (m, 2H), 7.85 (s, 1H), 7.73 (d, J = 7.6 Hz, 1H), 7.59-7.55 (m, 1H), 7.37-7.35 (m, 1H), 7.30-7.28 (m, 1H), 7.17 (s, 1H), 6.80-6.78 (m, 1H), 4.95-4.90 (m, 1H), 3.92 (s, 3H), 3.76-3.68 (m, 2H), 3.56 (s, 3H), 3.32 (s, 3H) |
| 444 | 556.4 | $^1$H NMR (400 MHz, DMSO-d6) δ 12.54 (s, 1H), 8.50 (d, J = 6.8 Hz, 1H), 8.29-8.26 (m, 2H), 8.01-7.98 (m, 2H), 7.85 (s, 1H), 7.73 (d, J = 7.6 Hz, 1H), 7.59-7.55 (m, 1H), 7.37-7.35 (m, 1H), 7.30-7.28 (m, 1H), 7.17 (s, 1H), 6.80-6.78 (m, 1H), 4.95-4.90 (m, 1H), 3.92 (s, 3H), 3.76-3.68 (m, 2H), 3.56 (s, 3H), 3.32 (s, 3H) |

Example 174. Preparation of N-[(1S)-2-[[4-[3-(2,6-dimethylpyrimidin-4-yl)phenyl]thiazol-2-yl]amino]-1-(methoxymethyl)-2-oxo-ethyl]-1-methylsulfonyl-pyrrole-3-carboxamide (Compound 358)

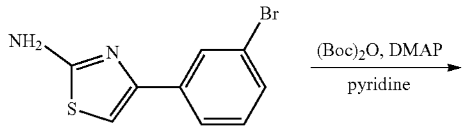

A

-continued

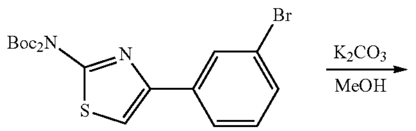

B

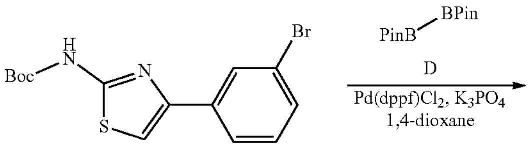

C

-continued

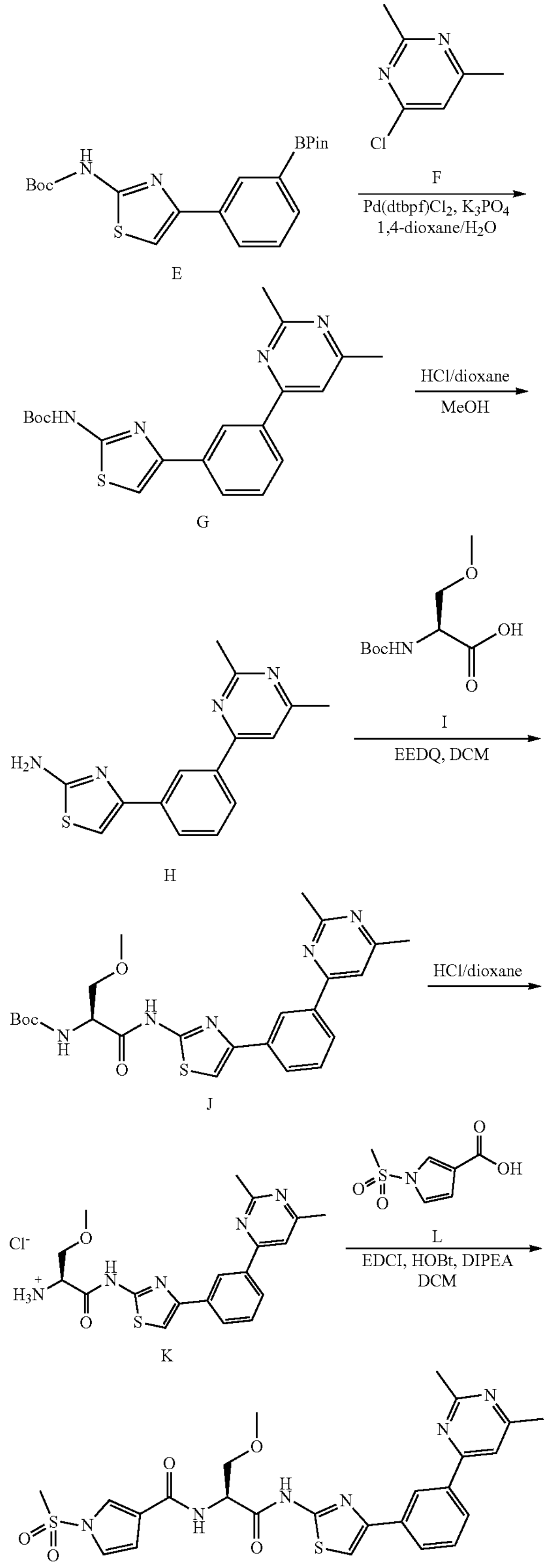

E

G

H

J

K

Compound 358

Step 1: Preparation of tert-butyl N-[4-(3-bromophenyl)thiazol-2-yl]-N-tert-butoxycarbonyl-carbamate (Intermediate B)

B

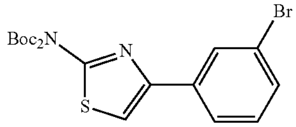

To a solution of 4-(3-bromophenyl)thiazol-2-amine (1.00 g, 3.92 mmol) in pyridine (10 mL) was added $(Boc)_2O$ (1.08 mL, 4.70 mmol). The mixture was stirred at 25° C. for 2 h, followed by addition of additional $(Boc)_2O$ (1.80 mL, 7.84 mmol) and DMAP (0.048 g, 0.392 mmol). After stirring for an additional 2 h, the mixture was diluted with water (10 mL) and extracted with ethyl acetate (30 mL×3). The combined organic layers were washed by saturated citric acid solution (15 mL×3), dried over anhydrous $Na_2SO_4$, and concentrated to afford Intermediate B (1.70 g, 3.73 mmol, 95.25% yield) as a brown solid which was used in the next step without further purification. LCMS (ESI) m/z: $[^{81}Br\ M+H]^+$=457.0.

Step 2: Preparation of tert-butyl N-[4-(3-bromophenyl)thiazol-2-yl]carbamate (Intermediate C)

C

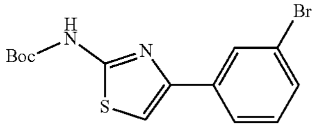

A mixture of Intermediate B (1.60 g, 3.51 mmol), $K_2CO_3$ (0.971 g, 7.03 mmol) in MeOH (16 mL) was stirred for 2 h. The reaction mixture was diluted with water (30 mL) and extracted with ethyl acetate (50 mL×2). The combined organic layers were dried over anhydrous $Na_2SO_4$, filtered and concentrated under reduced pressure to give a residue. The residue was purified by column chromatography ($SiO_2$, petroleum ether/ethyl acetate=50/0 to 10:1) to give Intermediate C (0.950 g, 2.67 mmol, 76.11% yield) as a white solid. LCMS (ESI) m/z: $[^{79}Br\ M+H]^+$=355.0; $^1H$ NMR (400 MHz, DMSO-$d_6$) δ 11.59 (s, 1H), 8.06-8.05 (m, 1H), 7.90-7.86 (m, 1H), 7.71 (s, 1H), 7.51-7.48 (m, 1H), 7.40-7.38 (m, 1H), 1.49 (s, 9H).

Step 3: Preparation of tert-butyl N-[4-[3-(4,4,5,5-tetramethyl-1,3,2-dioxaborolan-2-yl)phenyl]thiazol-2-yl]carbamate (Intermediate E)

E

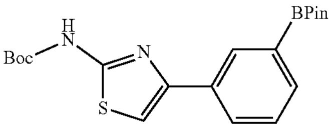

To a solution of 4,4,5,5-tetramethyl-2-(4,4,5,5-tetramethyl-1,3,2-dioxaborolan-2-yl)-1,3,2-dioxaborolane (1.50 g, 5.91 mmol) in 1,4-dioxane (6 mL) was added Intermediate C (0.700 g, 1.97 mmol) and KOAc (0.580 g, 5.91 mmol) and Pd(dppf)$Cl_2$ (144.18 mg, 197.04 umol) under $N_2$ atmosphere. The mixture was subsequently stirred at 80° C. After stirring for 2 h, the reaction mixture was diluted with water (5 mL) and extracted with ethyl acetate (20 mL×2). The combined organic layers were dried over anhydrous $Na_2SO_4$, filtered and concentrated under reduced pressure to give a residue. The residue was purified by column chromatography ($SiO_2$, petroleum ether/ethyl acetate=20/1 to 1:1) to give Intermediate E (2.15 g, 1.34 mmol, 67.8% yield, 25.0% purity by $^1$H NMR) as a white solid. $^1$H NMR (400 MHz, DMSO-$d_6$) δ 8.24 (s, 1H), 7.98-7.96 (m, 1H), 7.63-7.56 (m, 2H), 7.44-7.40 (m, 1H), 1.49 (s, 9H), 1.31 (s, 12H).

Step 4: Preparation of tert-butyl N-[4-[3-(2,6-dimethylpyrimidin-4-yl)phenyl]thiazol-2-yl]carbamate (Intermediate G)

G

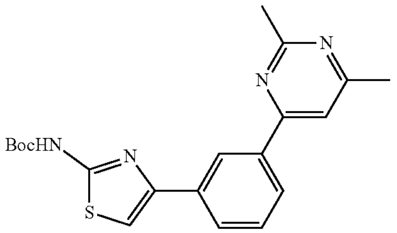

To a solution of 4-chloro-2,6-dimethyl-pyrimidine (0.744 g, 5.22 mmol) in 1,4-dioxane (20 mL) and water (4 mL) was added Intermediate E (2.10 g, 5.22 mmol), $K_3PO_4$ (3.32 g, 15.66 mmol) and Pd(dtbpf)$Cl_2$ (0.340 g, 0.522 mmol) under $N_2$ atmosphere. The mixture was subsequently stirred at 80° C. After 2 h, the reaction mixture was diluted with water (5 mL) and extracted with ethyl acetate (20 mL×2). The combined organic layers were dried over anhydrous $Na_2SO_4$, filtered and concentrated under reduced pressure to give a residue. The resulting residue was purified by column chromatography ($SiO_2$, Petroleum ether/Ethyl acetate=10/1 to 0/1) to afford Intermediate G (0.550 g, 1.44 mmol, 27.55% yield) as a white solid. LCMS (ESI) m/z: $[M+H]^+$=383.4.; $^1$H NMR (400 MHz, DMSO-$d_6$) δ 11.64 (s, 1H), 8.64 (t, J=1.6 Hz, 1H), 8.08 (d, J=7.6 Hz, 1H), 8.02-7.99 (m, 1H), 7.80 (s, 1H), 7.71 (s, 1H), 7.57 (t, J=8.0 Hz, 1H), 2.64 (s, 3H), 1.49 (s, 9H), 1.06 (s, 3H).

Step 5: Preparation of 4-[3-(2,6-dimethylpyrimidin-4-yl)phenyl]thiazol-2-amine (Intermediate H)

H

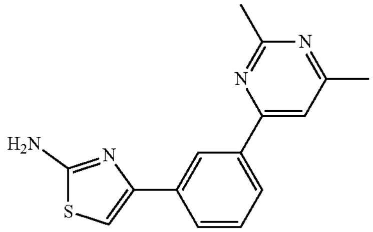

A mixture of Intermediate G (0.500 g, 1.31 mmol) in a 4 M solution of HCl in 1,4-dioxane (10 mL) was stirred at 25° C. for 12 h. To the mixture was added MeOH (5 mL) and stirred at 60° C. After 2 h, the mixture was cooled to ambient temperatures and concentrated. The residue was diluted with water (5 mL), basicified to pH~10 with saturated aqueous $Na_2CO_3$ solution and the aqueous layer was extracted with ethyl acetate (10 mL×2). The combined organic layers were dried with anhydrous $Na_2SO_4$ and concentrated to afford Intermediate H (0.250 g, 0.885 mmol, 67.73% yield) as a white solid which was used into the next step without further purification. LCMS (ESI) m/z: $[M+H]^+$=283.3.

Step 6: Preparation of tert-butyl N-[(1S)-2-[[4-[3-(2,6-dimethylpyrimidin-4-yl)phenyl]thiazol-2-yl]amino]-1-(methoxymethyl)-2-oxoethyl]carbamate (Intermediate J)

J

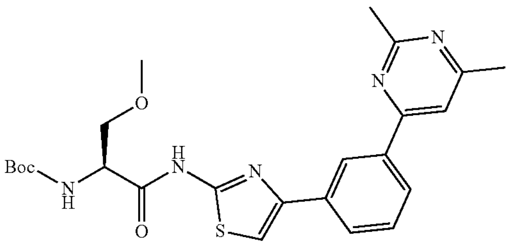

To a solution of (2S)-2-(tert-butoxycarbonylamino)-3-methoxy-propanoic acid (0.252 g, 1.15 mmol) and Intermediate H (0.250 g, 0.885 mmol) in dichloromethane (25 mL) was added EEDQ (0.328 g, 1.33 mmol). After stirring for 12 h, the reaction was diluted with water (2 mL) and acidified to pH~6 with 1 N HCl. The aqueous mixture was extracted with ethyl acetate (30 mL×2). The combined organic layers were washed with saturated aqueous $NaHCO_3$ solution (15 mL×2). Then the combined organic layers were dried with anhydrous $Na_2SO_4$ and concentrated. The residue was purified by column chromatography ($SiO_2$, petroleum ether/ethyl acetate=10/1 to 1/1) to give Intermediate J (0.220 g, 0.437 mmol, 49.3% yield, 96.0% purity) as a white solid. LCMS (ESI) m/z: $[M+H]^+$=484.4; ee %=100%.

Step 7: Preparation of (S)-1-((4-(3-(2,6-dimethylpyrimidin-4-yl)phenyl)thiazol-2-yl)amino)-3-methoxy-1-oxopropan-2-aminium chloride (Intermediate K)

K

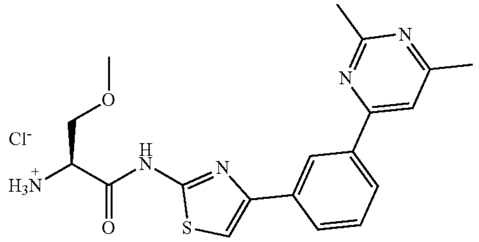

A mixture of Intermediate J (0.100 g, 0.208 mmol) in a solution of 4 M HCl in 1,4-dioxane (2 mL, 4M) was stirred at 25° C. for 0.5 h. The mixture was concentrated to afford Intermediate K (0.087 g) as a white solid which was used into the next step without further purification. LCMS (ESI) m/z: $[M+H]^+$=384.4.

Step 8: Preparation of N-[(1S)-2-[[4-[3-(2,6-dimethylpyrimidin-4-yl)phenyl]thiazol-2-yl]amino]-1-(methoxymethyl)-2-oxo-ethyl]-1-methylsulfonyl-pyrrole-3-carboxamide (Compound 358)

Compound 358

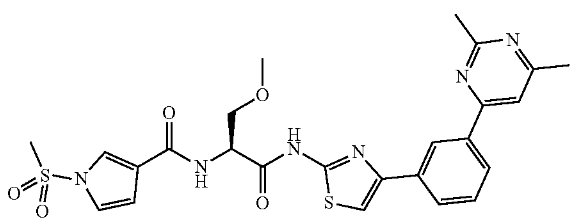

A mixture of 1-methylsulfonylpyrrole-3-carboxylic acid (0.043 g, 0.227 mmol), Intermediate K (0.087 g, 0.227 mmol), HOBt (0.092 g, 0.682 mmol), EDCI (0.131 g, 0.682 mmol), and DIPEA (0.119 mL, 0.682 mmol) in dichloromethane (1 mL) was stirred at 25° C. for 2 h. The reaction mixture was diluted with water (3 mL) and extracted with dichloromethane (3 mL×2). The combined organic layers were dried over anhydrous $Na_2SO_4$, filtered and concentrated under reduced pressure to give a residue. The residue was purified by prep-TLC ($SiO_2$, petroleum ether/ethyl acetate=0:1) to afford Compound 358 (0.024 g, 0.043 mmol, 19.06% yield, 100% purity) as a white solid. LCMS (ESI) m/z: $[M+H]^+$=555.4.; $^1$H NMR (400 MHz, Methanol-$d_4$) δ 8.70-8.69 (m, 1H), 8.08-8.04 (m, 2H), 7.92-7.91 (m, 1H), 7.72 (s, 1H), 7.58-7.56 (m, 2H), 7.27-7.26 (m, 1H), 6.86-6.85 (m, 1H), 4.98-4.95 (m, 1H), 3.89-3.81 (m, 2H), 3.44 (s, 3H), 3.38 (s, 3H), 2.72 (s, 3H), 2.57 (s, 3H).

Example 175. Preparation of N-[(1S)-1-(methoxymethyl)-2-[[4-[3-(2-methylpyrimidin-4-yl)phenyl]thiazol-2-yl]amino]-2-oxo-ethyl]-1-methylsulfonyl-pyrrole-3-carboxamide (Compound 357)

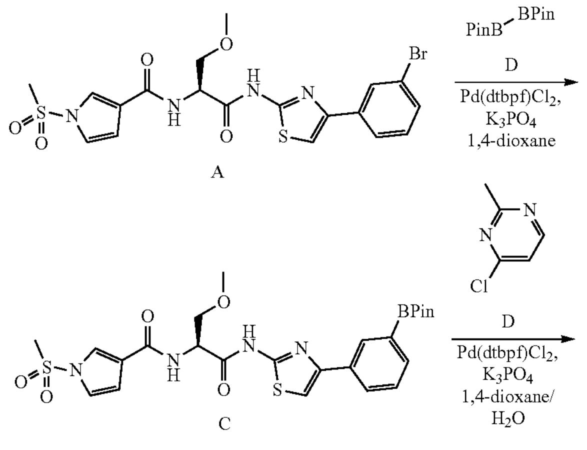

-continued

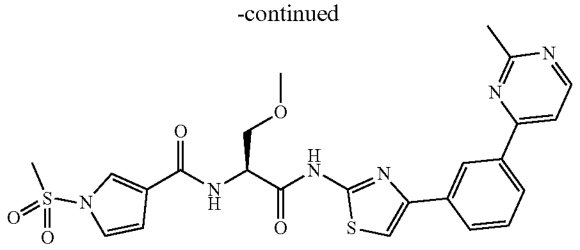

Compound 357

Step 1: Preparation of N-[(1S)-1-(methoxymethyl)-2-oxo-2-[[4-[3-(4,4,5,5-tetramethyl-1,3,2-dioxaborolan-2-yl)phenyl]thiazol-2-yl]amino]ethyl]-1-methylsulfonyl-pyrrole-3-carboxamide (Intermediate C)

C

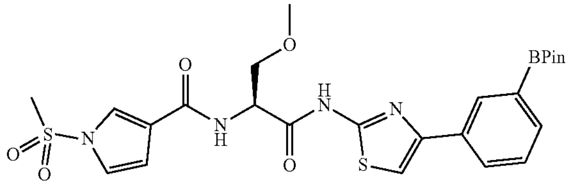

To a solution of 4,4,5,5-tetramethyl-2-(4,4,5,5-tetramethyl-1,3,2-dioxaborolan-2-yl)-1,3,2-dioxaborolane (0.144 g, 0.569 mmol) in 1,4-dioxane (1 mL) was added N-[(1S)-2-[[4-(3-bromophenyl)thiazol-2-yl]amino]-1-(methoxymethyl)-2-oxo-ethyl]-1-methylsulfonyl-pyrrole-3-carboxamide (0.150 g, 0.284 mmol) and $K_3PO_4$ (0.181 g, 0.853 mmol) and Pd(dtbf)$Cl_2$ (0.019 g, 0.028 mmol) under $N_2$ atmosphere. After stirring for 2 h, the mixture was diluted with water (3 mL) and extracted with ethyl acetate (10 mL×3). The combined organic layers were dried over anhydrous $Na_2SO_4$ and concentrated. The residue was purified by column chromatography ($SiO_2$, petroleum ether/ethyl acetate=10/1 to 0/1) to afford Intermediate C (0.070 g, 0.090 mmol, 31.7% yield, 74.0% purity) as a white solid. LCMS (ESI) m/z: $[M+H]^+$=575.1; $^1$H NMR (400 MHz, DMSO-$d_6$) δ 12.56 (s, 1H), 8.49 (d, J=7.6 Hz, 1H), 8.30 (s, 1H), 7.99-7.98 (m, 2H), 7.67 (s, 1H), 7.62 (d, J=7.2 Hz, 1H), 7.45-7.46 (m, 1H), 7.30-7.28 (m, 1H), 6.80-6.79 (m, 1H), 4.95-4.90 (m, 1H), 3.78-3.66 (m, 2H), 3.56 (s, 3H), 1.32 (s, 12H).

Step 2: Preparation of N-[(1S)-1-(methoxymethyl)-2-[[4-[3-(2-methylpyrimidin-4-yl)phenyl]thiazol-2-yl]amino]-2-oxo-ethyl]-1-methylsulfonyl-pyrrole-3-carboxamide (Compound 357)

Compound 357

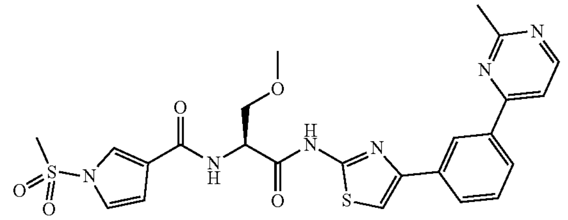

To a solution of 4-bromo-2-methyl-pyrimidine (0.032 g, 0.183 mmol) in 1,4-dioxane (1 mL) and water (0.2 mL) was added Intermediate C (0.070 g, 0.122 mmol), $K_3PO_4$ (0.078 g, 0.366 mmol) and Pd(dtbpf)$Cl_2$ (0.008 g, 0.012 mmol) under $N_2$ atmosphere. The mixture was stirred at 25° C. for 2 h and subsequently diluted with water (3 mL) and extracted with ethyl acetate (10 mL×3). The organic layers were dried over anhydrous $Na_2SO_4$ and concentrated. The residue was purified by prep-TLC ($SiO_2$, petroleum ether/ethyl acetate=0:1) to afford Compound 357 (0.025 g, 0.045 mmol, 37.24% yield, 98% purity) as a white solid. LCMS (ESI) m/z: $[M+H]^+$=541.3; $^1$H NMR (400 MHz, Methanol-$d_4$) δ 8.85-8.84 (m, 2H), 8.21-8.16 (m, 3H), 7.91-7.90 (m, 1H), 7.63-7.60 (m, 2H), 7.27-7.26 (m, 1H), 6.85-6.84 (m, 1H), 4.97-4.94 (m, 1H), 3.88-3.80 (m, 2H), 3.43 (s, 3H), 3.37 (s, 3H), 2.87 (s, 3H); ee %=100%.

Example 176. Preparation of N-[2-[[6-[3-[(cis)-2,6-dimethylmorpholin-4-yl]phenyl]-2-pyridyl]amino]-2-oxo-ethyl]-1-methylsulfonyl-pyrrole-3-carboxamide (Compound 374)

Compound 374

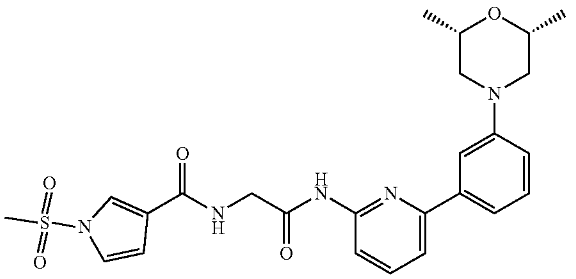

N-[2-[[6-[3-[(cis)-2,6-dimethylmorpholin-4-yl]phenyl]-2-pyridyl]amino]-2-oxo-ethyl]-1-methylsulfonyl-pyrrole-3-carboxamide was synthesized utilizing the general synthetic protocols described in Example 139 and starting from the appropriate common intermediate ((cis)-2,6-dimethyl-4-[3-(4,4,5,5-tetramethyl-1,3,2-dioxaborolan-2-yl)phenyl]morpholine) and heterocyclic carboxylic acid. LCMS (ESI) m/z: $[M+H]^+$=512.1; $^1$H NMR (400 MHz, DMSO-$d_6$) δ 10.51 (s, 1H), 8.63-8.56 (m, 1H), 8.00 (d, J=8.0 Hz, 1H), 7.88-7.81 (m, 2H), 7.68-7.63 (m, 1H), 7.62-7.58 (m, 1H), 7.50-7.46 (m, 1H), 7.36-7.29 (m, 2H), 7.06-6.99 (m, 1H), 6.80-6.75 (m, 1H), 4.14 (d, J=4.8 Hz, 2H), 3.78-3.64 (m, 4H), 3.57 (s, 3H), 2.36-2.27 (m, 2H), 1.18 (d, J=6.0 Hz, 6H).

Example 177. Preparation of Compounds of the Invention

The following compounds in Table 13 below were synthesized utilizing the general synthetic protocols shown in Scheme 8 below from the appropriate amino-thiazole, cis-dimethyl morpholine, chiral N-Boc amino acid and heterocyclic carboxylic acid. Where appropriate SFC purification was used to separate enantiomers.

Scheme 8

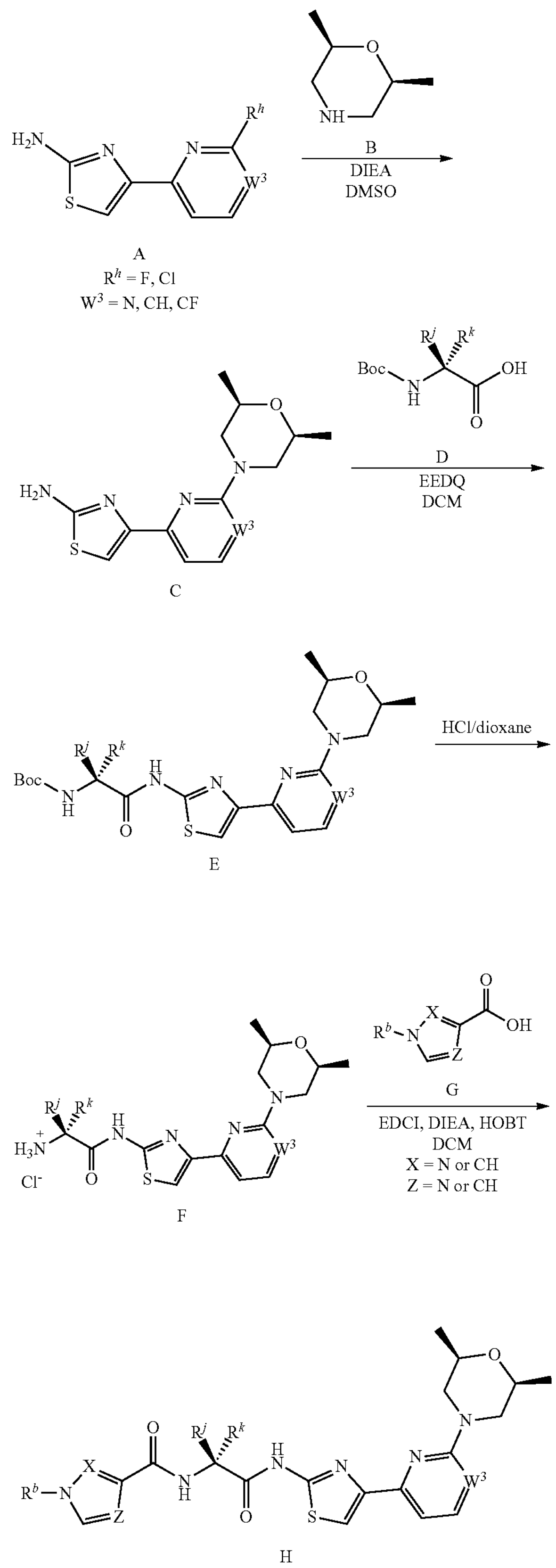

TABLE 13

| Compound # | LC-MS data(m/z) | $^1$H NMR |
|---|---|---|
| 375 | 541.5 | $^1$H NMR (400 MHz, $CDCl_3$) δ 10.85-10.60 (m, 1H), 7.70 (s, 1H), 7.56 (m, 1H), 7.53-7.50 (m, 1H), 7.36 (d, J = 7.6 Hz, 1H), 6.96 (d, J = 7.2 Hz, 1H), 6.87 (m, 1H), 6.62-6.55 (m, 2H), 4.97 (d, J = 6.4 Hz, 2H), 4.95-4.90 (m, 1H), 4.68 (d, J = 6.8 Hz, 2H), 4.47-4.37 (m, 1H), 4.15 (d, J = 12.8 Hz, 2H), 3.90-3.82 (m, 1H), 3.81-3.70 (m, 2H), 3.33 (m, 1H), 2.56 (m, 2H), 1.91 (s, 3H), 1.30 (d, J = 6.4 Hz, 6H) |
| 376 | 573.2 | $^1$H NMR (400 MHz, DMSO-$d_6$) δ 12.42 (s, 1H), 8.01 (d, J = 7.6 Hz, 1H), 7.69(s, 1H), 7.87-7.67 (m, 1H), 7.58-7.55 (m, 1H), 7.41-7.40 (m, 1H), 7.01-7.00 (m, 1H), 6.60-6.59 (m, 1H), 4.86-4.85 (m, 1H), 4.84-4.83 (m, 2H), 4.63 (d, J = 6.8 Hz, 2H), 3.96 (d, J = 12.0 Hz, 2H), 3.73-3.69 (m, 4H), 3.31 (s, 3H), 2.62-2.56 (m, 2H), 1.79 (s, 3H), 1.17 (s, 3H), 1.15 (s, 3H) |
| 377 | 581.2 | $^1$H NMR (400 MHz, DMSO-$d_6$) δ 12.50-12.44 (m, 1H), 8.50 (d, J = 7.2 Hz, 1H), 7.99-7.98 (m, 1H), 7.69 (s, 1H), 7.58-7.55 (m, 1H), 7.41-7.40 (m, 1H), 7.30-7.30 (m, 1H), 6.80-6.79 (m, 1H), 4.95-4.90 (m, 1H), 3.96 (d, J = 12.4 Hz, 2H), 3.75-3.70 (m, 4H), 3.57 (s, 3H), 3.32 (s, 3H), 2.62-2.56 (m, 2H), 1.17 (s, 3H), 1.15 (s, 3H) |
| 378 | 529.2 | $^1$H NMR (400 MHz, DMSO-$d_6$) δ 12.29 (br s, 1H), 8.25-8.24 (m, 1H), 7.67 (s, 1H), 7.27-7.55 (m, 2H), 7.39-7.39 (m, 1H), 7.01-7.00(m, 1H), 6.56-6.55 (m, 1H), 4.84 (d, J = 6.4 Hz, 2H), 4.62 (d, J = 6.8 Hz, 2H), 4.10 (d, J = 6.0 Hz, 2H), 3.95 (d, J = 12.4 Hz, 2H), 3.72-3.70 (m, 2H), 2.61-2.55 (m, 2H), 1.78 (s, 3H), 1.16 (s, 3H), 1.14 (s, 3H) |
| 379 | 537.1 | $^1$H NMR (400 MHz, DMSO-$d_6$) δ 12.27-12.17 (m, 1H), 8.61-8.58(m, 1H), 7.78-7.77 (m, 1H), 7.61 (s, 1H), 7.52-7.47 (m, 1H), 7.33-7.32(m, 1H), 7.25-7.23 (m, 1H), 6.7-6.69(m, 1H), 4.07 (d, J = 6.0 Hz, 2H), 3.88 (d, J = 12.4 Hz, 2H), 3.67-3.65 (m, 2H), 3.50 (s, 3H), 2.55-2.47 (m, 2H), 1.09 (s, 3H), 1.08 (s, 3H) |
| 381 | 542.3 | $^1$H NMR (400 MHz, DMSO-$d_6$) δ 12.51 (s, 1H), 8.47 (d, J = 5.2 Hz, 1H), 8.10 (s, 1H), 7.95 (d, J = 7.6 Hz, 1H), 7.61-7.60 (m, 1H), 7.12 (d, J = 4.8 Hz, 1H), 6.96-6.95 (m, 1H), 6.50-6.49(m, 1H), 4.92-4.87 (m, 1H), 4.62 (d, J = 12.4 Hz, 2H), 3.71-3.68 (m, 2H), 3.57-3.55 (m, 2H), 3.30 (s, 4H), 2.57-2.53 (m, 2H), 1.48 (s, 9H), 1.17 (d, J = 6.0 Hz, 6H) |
| 454 | 555.3 | $^1$H NMR (400 MHz, DMSO-$d_6$) δ 12.45 (s, 1H), 8.03 (d, J = 7.6 Hz, 1H), 7.77 (s, 1H), 7.68-7.67 (m, 1H), 7.65-7.59 (m, 1H), 7.26 (d, J = 7.6 Hz, 1H), 7.01-7.00 (m, 1H), 6.80 (d, J = 8.8 Hz, 1H), 6.59-6.58 (m, 1H), 4.95-4.87 (m, 1H), 4.85-4.83 (m, 2H), 4.62 (d, J = 6.8 Hz, 2H), 4.25 (d, J = 11.6 Hz, 2H), 3.75-3.67 (m, 2H), 3.67-3.59 (m, 2H), 3.30 (s, 3H), 2.41-2.38 (m, 2H), 1.79 (s, 3H), 1.19 (s, 3H), 1.17 (s, 3H) |
| 539 | 525.2 | $^1$H NMR (400 MHz, DMSO-$d_6$) δ 12.29 (s, 1H), 8.05 (d, J = 6.8 Hz, 1H), 7.76 (s, 1H), 7.66-7.58 (m, 2H), 7.26 (d, J = 7.2 Hz, 1H), 7.00-6.99 (m, 1H), 6.79 (d, J = 8.4 Hz, 1H), 6.58-6.57(m, 1H), 4.84-4.82(m, 2H), 4.69-4.57 (m, 3H), 4.25 (d, J = 11.6 Hz, 2H), 3.69-3.56 (m, 2H), 2.41-2.38(m, 2H), 1.79 (s, 3H), 1.41 (d, J = 7.2 Hz, 3H), 1.18 (d, J = 6.0 Hz, 6H) |
| 560 | 520.2 | $^1$H NMR (400 MHz, DMSO-$d_6$) δ 12.31 (s, 1H), 8.16 (d, J = 6.8 Hz, 1H), 7.76 (s, 1H), 7.69-7.58 (m, 2H), 7.26 (d, J = 7.2 Hz, 1H), 7.09-7.02 (m, 1H), 6.79 (d, J = 8.8 Hz, 1H), 6.58-6.57 (m, 1H), 4.63-4.61 (m, 1H), 4.25 (d, J = 11.2 Hz, 2H), 3.68-3.57 (m, 2H), 2.44-2.38 (m, 2H), 1.87-1.71 (m, 4H), 1.41 (d, J = 7.2 Hz, 3H), 1.18 (d, J = 6.4 Hz, 6H) |
| 577 | 550.2 | $^1$H NMR (400 MHz, DMSO-$d_6$) δ 12.43 (s, 1H), 8.13 (d, J = 7.2 Hz, 1H), 7.78 (s, 1H), 7.71-7.70 (m, 1H), 7.64-7.60 (m, 1H), 7.26 (d, J = 7.2 Hz, 1H), 7.06-7.05 (m, 1H), 6.79 (d, J = 8.8 Hz, 1H), 6.58-6.57 (m, 1H), 4.92-4.87 (m, 1H), 4.25 (d, J = 11.6 Hz, 2H), 3.75-3.57 (m, 4H), 3.31 (s, 3H), 2.44-2.38 (m, 2H), 1.85-1.79 (m, 2H), 1.78-1.71 (m, 2H), 1.19 (s, 3H), 1.17 (s, 3H) |
| 587 | 552.3 | $^1$H NMR (400 MHz, DMSO-$d_6$) δ 12.62-12.36 (m, 1H), 8.15 (d, J = 7.6 Hz, 1H), 7.87-7.73 (m, 2H), 7.63-7.61 (m, 1H), 7.27 (d, J = 7.2 Hz, 1H), 7.18-7.11 (m, 1H), 6.80 (d, J = 8.8 Hz, 1H), 6.65-6.64 (m, 1H), 4.96-4.92 (m, 1H), 4.26 (d, J = 11.2 Hz, 2H), 3.77-3.59 (m, 4H), 3.32 (s, 3H), 2.52-2.42 (m, 2H), 1.96 (s, 6H), 1.19 (d, J = 6.4 Hz, 6H) |
| 600 | 536.4 | $^1$H NMR (400 MHz, DMSO-$d_6$) δ 12.32 (s, 1H), 8.23 (d, J = 6.8 Hz, 1H), 7.80-7.79 (m, 1H), 7.75 (s, 1H), 7.61-7.59 (m, 1H), 7.25 (d, J = 7.2 Hz, 1H), 7.20-7.19 (m, 1H), 6.79 (d, J = 8.8 Hz, 1H), 6.71-6.71 (m, 1H), 5.23 (d, J = 7.6 Hz, 2H), 5.04-5.01 (m, 2H), 4.63-4.62 (m, 1H), 4.25 (d, J = 11.2 Hz, 2H), 3.63-3.57 (m, 2H), 2.42-2.37 (m, 2H), 1.41 (d, J = 6.8 Hz, 3H), 1.17 (d, J = 6.0 Hz, 6H) |
| 605 | 526.3 | $^1$H NMR (400 MHz, DMSO-$d_6$) δ 12.63-12.31 (m, 1H), 8.28 (d, J = 7.2 Hz, 1H), 8.05 (d, J = 2.4 Hz, 1H), 7.79 (s, 1H), 7.63-7.62(m, 1H), 7.26 (d, J = 7.2 Hz, 1H), 6.80 (d, J = 8.4 Hz, 1H), 6.76 (d, J = 2.4 Hz, 1H), 5.07-5.06 (m, 2H), 4.72-4.70 (m, 1H), 4.65 (d, J = 7.6 Hz, 2H), 4.26 (d, J = 11.6 Hz, 2H), 3.69-3.59 (m, 2H), 2.45-2.39 (m, 2H), 1.88 (s, 3H), 1.48 (d, J = 7.2 Hz, 3H), 1.19 (d, J = 6.0 Hz, 6H) |
| 666 | 577.1 | $^1$H NMR (400 MHz, DMSO-$d_6$) δ 12.46-12.27 (m, 1H), 8.41 (s, 1H), 8.29 (d, J = 8.0 Hz, 1H), 8.07-8.06 (m, 1H), 7.79 (s, 1H), 7.63-7.62 (m, 1H), 7.32-7.23 (m, 2H), 6.85-6.74 (m, 2H), 4.80-4.79 (m, 1H), 4.26-4.25 (m, 2H), 3.95-3.83 (m, 1H), 3.64-3.63 (m, 2H), 3.58 (s, 3H), 3.29 (s, 3H), 2.42-2.41 (m, 2H), 1.22-1.14 (m, 9H) |

TABLE 13-continued

| Compound # | LC-MS data(m/z) | $^1$H NMR |
|---|---|---|
| 691 | 569.1 | $^1$H NMR (400 MHz, DMSO-$d_6$) δ 12.52-12.47 (m, 1H), 8.50 (d, J = 7.2 Hz, 1H), 7.98 (s, 1H), 7.71 (s, 1H), 7.61-7.56 (m, 1H), 7.30-7.28 (m, 1H), 7.21 (d, J = 6.8 Hz, 1H), 6.79 (d, J = 2.0 Hz, 1H), 6.46 (d, J = 8.4 Hz, 1H), 6.33-6.03 (m, 1H), 4.95-4.90 (m, 1H), 3.73-3.68 (m, 3H), 3.65 (d, J = 8.4 Hz, 2H), 3.56 (s, 4H), 3.49-3.44 (m, 3H), 2.91-2.81 (m, 1H), 2.18-2.13 (m, 1H), 2.05-1.99 (m, 1H) |
| 699 | 569.2 | $^1$H NMR (400 MHz, DMSO-$d_6$) δ 12.50-12.46 (m, 1H), 8.50 (d, J = 7.2 Hz, 1H), 7.99-7.97 (m, 1H), 7.71 (s, 1H), 7.61-7.56 (m, 1H), 7.30-7.26 (m, 1H), 7.21 (d, J = 7.2 Hz, 1H), 6.80-6.78 (m, 1H), 6.46 (d, J = 8.4 Hz, 1H), 6.33-6.03 (m, 1H), 4.95-4.91 (m, 1H), 3.73-3.68 (m, 3H), 3.67-3.63 (m, 2H), 3.56 (s, 4H), 3.49-3.44 (m, 3H), 2.89-2.83 (m, 1H), 2.20-2.11 (m, 1H), 2.05-1.97 (m, 1H) |
| 730 | 564.4 | $^1$H NMR (400 MHz, DMSO-$d_6$) δ 12.44 (s, 1H), 8.16 (d, J = 7.2 Hz, 1H), 7.77 (s, 1H), 7.74-7.72 (m, 1H), 7.65-7.60 (m, 1H), 7.26 (d, J = 7.2 Hz, 1H), 7.08-7.05 (m, 1H), 6.80 (d, J = 8.4 Hz, 1H), 6.66-6.64 (m, 1H), 4.95-4.89 (m, 1H), 4.25 (d, J = 11.2 Hz, 2H), 3.74-3.68 (m, 2H), 3.66-3.60 (m, 2H), 3.31 (s, 3H), 2.90-2.85 (m, 2H), 2.85-2.76 (m, 2H), 2.44-2.38 (m, 2H), 2.19-2.12 (m, 1H), 2.06-1.99 (m, 1H), 1.18 (d, J = 6.4 Hz, 6H) |
| 742 | 545.1 | $^1$H NMR (400 MHz, DMSO-$d_6$) δ 12.17 (s, 1H), 8.75 (s, 1H), 7.91-7.90 (m, 1H), 7.76 (s, 1H), 7.58-7.57 (m, 1H), 7.34-7.30 (m, 1H), 7.25 (d, J = 7.6 Hz, 1H), 6.80-6.75 (m, 2H), 4.25-4.24 (m, 2H), 3.64-3.62 (m, 2H), 3.57 (s, 3H), 2.43-2.40 (m, 2H), 1.56-1.51 (m, 2H), 1.18 (d, J = 6.0 Hz, 8H) |
| 747 | 533.2 | $^1$HNMR (400 MHz, Methanol-$d_4$) δ 7.75-7.65 (m, 2H), 7.63-7.58 (m, 1H), 7.37 (d, J = 7.6 Hz, 1H), 7.30 (s, 1H), 6.77-6.70 (m, 2H), 4.47 (s, 2H), 4.28-4.24 (m, 2H), 3.78-3.72 (m, 2H), 3.45-3.35 (m, 6H), 2.53-2.47 (m, 2H), 1.28 (d, J = 6.4 Hz, 6H) |
| 772 | 575.2 | $^1$H NMR (400 MHz, DMSO-$d_6$) δ 12.47 (s, 1H), 8.50 (d, J = 7.2 Hz, 1H), 7.98-7.97 (m, 1H), 7.74 (s, 1H), 7.64-7.57 (m, 1H), 7.29-7.28 (m, 1H), 7.22 (d, J = 7.6 Hz, 1H), 6.86-6.76 (m, 2H), 4.94-4.91 (m, 1H), 4.74-4.71 (m, 1H), 4.56 (br d, J = 12.6 Hz, 1H), 3.91-3.90 (m, 2H), 3.76-3.65 (m, 2H), 3.56 (s, 3H), 3.32-3.29 (m, 4H), 3.24-3.21 (m, 1H), 2.86-2.73 (m, 1H), 2.68-2.63 (m, 1H), 1.97-1.88 (m, 1H), 1.84-1.65 (m, 2H), 1.41-1.29 (m, 1H) |
| 773 | 575.2 | $^1$HNMR (400 MHz, DMSO-$d_6$) δ 12.48 (s, 1H), 8.50 (d, J = 7.2 Hz, 1H), 7.98-7.97 (m, 1H), 7.74 (s, 1H), 7.62-7.60 (m, 1H), 7.30-7.29 (m, 1H), 7.23 (d, J = 7.2 Hz, 1H), 6.86-6.77 (m, 2H), 4.92 (br d, J = 6.8 Hz, 1H), 4.73-4.70 (m, 1H), 4.56 (br d, J = 13.2 Hz, 1H), 3.91-3.90 (m, 2H), 3.72-3.69 (m, 2H), 3.56 (s, 3H), 3.33-3.29 (m, 4H), 3.23-3.20 (m, 1H), 2.86-2.75 (m, 1H), 2.69-2.60 (m, 1H), 1.97-1.88 (m, 1H), 1.85-1.64 (m, 2H), 1.42-1.29 (m, 1H) |
| 774 | 575.1 | $^1$H NMR (400 MHz, DMSO-$d_6$) δ 12.86-12.11 (m, 1H), 8.51 (d, J = 7.2 Hz, 1H), 7.98-7.97 (m, 1H), 7.74 (s, 1H), 7.60-7.58(m, 1H), 7.33-7.17 (m, 2H), 6.88-6.76 (m, 2H), 4.94-4.91 (m, 1H), 4.77-4.74 (m, 1H), 4.58 (br d, J = 13.6 Hz, 1H), 3.88-3.79 (m, 2H), 3.72-3.71 (m, 2H), 3.56 (s, 3H), 3.31 (s, 3H), 3.18-3.16 (m, 1H), 2.83-2.73 (m, 1H), 2.70-2.60 (m, 1H), 2.11-1.95 (m, 2H), 1.69-1.56 (m, 1H), 1.54-1.35 (m, 2H) |
| 775 | 575.1 | $^1$H NMR (400 MHz, DMSO-$d_6$) δ 12.79-12.23 (m, 1H), 8.51 (d, J = 7.2 Hz, 1H), 7.98-7.97 (m, 1H), 7.74 (s, 1H), 7.61-7.59(m, 1H), 7.29-7.28 (m, 1H), 7.23 (d, J = 7.2 Hz, 1H), 6.84 (d, J = 8.4 Hz, 1H), 6.79-6.78 (m, 1H), 4.92 (br d, J = 6.4 Hz, 1H), 4.76-4.73 (m, 1H), 4.59 (br d, J = 13.2 Hz, 1H), 3.87-3.79 (m, 2H), 3.73-3.71 (m, 2H), 3.56 (s, 3H), 3.31 (s, 3H), 3.22-3.15(m, 1H), 2.83-2.73 (m, 1H), 2.69-2.61 (m, 1H), 2.10-1.98 (m, 2H), 1.69-1.57 (m, 1H), 1.52-1.38 (m, 2H) |
| 783 | 542.2 | $^1$H NMR (400 MHz, DMSO-$d_6$) δ 12.55 (s, 1H), 7.98-7.93 (m, 2H), 7.80 (s, 1H), 7.64-7.60 (m, 1H), 7.26 (d, J = 7.2 Hz, 1H), 6.80 (d, J = 8.8 Hz, 1H), 6.68 (d, J = 2.4 Hz, 1H), 4.97-4.92 (m, 1H), 4.25 (d, J = 11.6 Hz, 2H), 3.88-3.81 (m, 1H), 3.78-3.71 (m, 1H), 3.65-3.60 (m, 2H), 3.30 (s, 3H), 2.44-2.38 (m, 2H), 1.58 (s, 9H), 1.19 (s, 3H), 1.17 (s, 3H) |
| 789 | 542.2 | $^1$H NMR (400 MHz, DMSO-$d_6$) δ 12.55-12.47 (m, 1H), 7.95 (d, J = 8.0 Hz, 1H), 7.91 (s, 2H), 7.79 (s, 1H), 7.64-7.60 (m, 1H), 7.25 (d, J = 7.2 Hz, 1H), 6.80 (d, J = 8.4 Hz, 1H), 4.93-4.89 (m, 1H), 4.25 (d, J = 11.2 Hz, 2H), 3.81-3.79 (m, 1H), 3.72-3.68 (m, 1H), 3.66-3.60 (m, 2H), 3.29 (s, 3H), 2.44-2.38 (m, 2H), 1.53 (s, 9H), 1.19 (s, 3H), 1.17 (s, 3H) |
| 795 | 521.2 | $^1$H NMR (400 MHz, DMSO-$d_6$) δ 12.43-12.37 (m, 1H), 8.46 (d, J = 6.8 Hz, 1H), 8.16 (d, J = 2.0 Hz, 1H), 7.78 (s, 1H), 7.63-7.59 (m, 1H), 7.25 (d, J = 7.6 Hz, 1H), 6.80-6.75 (m, 2H), 4.70-4.66 (m, 1H), 4.25 (d, J = 11.6 Hz, 2H), 3.66-3.58 (m, 2H), 2.44-2.38 (m, 2H), 1.98-1.95 (m, 2H), 1.91-1.88 (m, 2H), 1.46 (d, J = 5.6 Hz, 3H), 1.18 (d, J = 6.0 Hz, 6H) |
| 797 | 526.1 | $^1$H NMR (400 MHz, DMSO-$d_6$) δ 12.55-12.09 (m, 1H), 8.11 (d, J = 7.2 Hz, 1H), 8.02 (d, J = 1.2 Hz, 1H), 7.96 (d, J = 1.2 Hz, 1H), 7.78 (s, 1H), 7.63-7.61 (m, 1H), 7.25 (d, J = 7.6 Hz, 1H), 6.80 (d, J = 8.4 Hz, 1H), 4.88 (d, J = 6.8 Hz, 2H), 4.75-4.60 (m, 3H), 4.25 (d, J = 11.6 Hz, 2H), 3.65-3.60 (m, 2H), 2.43-2.40 (m, 2H), 1.82 (s, 3H), 1.45 (d, J = 7.2 Hz, 3H), 1.18 (d, J = 6.0 Hz, 6H) |
| 799 | 556.2 | $^1$H NMR (400 MHz, DMSO-$d_6$) δ 8.04-7.98 (m, 3H), 7.80 (s, 1H), 7.63-7.62 (m, 1H), 7.26 (d, J = 7.2 Hz, 1H), 6.81 (d, J = 8.8 Hz, 1H), 4.90 (d, J = 6.8 Hz, 3H), 4.64 (d, J = 7.2 Hz, 2H), 4.26-4.25 (m, 2H), 3.87-3.81 (m, 1H), 3.72-3.71 (m, 1H), 3.68-3.58 (m, 2H), 3.30 (s, 3H), 2.42-2.41 (m, 2H), 1.83 (s, 3H), 1.19 (d, J = 6.0 Hz, 6H) |

TABLE 13-continued

| Compound # | LC-MS data(m/z) | $^1$H NMR |
|---|---|---|
| 800 | 556.2 | $^1$H NMR (400 MHz, DMSO-$d_6$) δ 8.12 (d, J = 7.6 Hz, 1H), 8.07 (d, J = 2.4 Hz, 1H), 7.80 (s, 1H), 7.63-7.62 (m, 1H), 7.26 (d, J = 7.2 Hz, 1H), 6.84-6.74 (m, 2H), 5.06-5.05 (m, 2H), 5.00-4.92 (m, 1H), 4.66 (d, J = 6.8 Hz, 2H), 4.26-4.24 (m, 2H), 3.88-3.81 (m, 1H), 3.78-3.73 (m, 1H), 3.68-3.58 (m, 2H), 3.31 (s, 3H), 2.44-2.40 (m, 2H), 1.89 (s, 3H), 1.19 (d, J = 6.0 Hz, 6H) |
| 807 | 551.3 | $^1$H NMR (400 MHz, DMSO-$d_6$) δ 12.91-12.25 (m, 1H), 8.26 (d, J = 7.6 Hz, 1H), 8.18 (d, J = 2.4 Hz, 1H), 7.80 (s, 1H), 7.65-7.61 (m, 1H), 7.26 (d, J = 7.2 Hz, 1H), 6.83-6.75 (m, 2H), 4.99-4.90 (m, 1H), 4.26 (br d, J = 11.6 Hz, 2H), 3.87-3.72 (m, 2H), 3.68-3.57 (m, 2H), 3.31 (s, 3H), 2.45-2.42 (m, 2H), 2.05-1.80 (m, 4H), 1.19 (d, J = 6.4 Hz, 6H) |
| 808 | 553.3 | $^1$H NMR (400 MHz, DMSO-$d_6$) δ 12.96-12.29 (m, 1H), 8.25-8.11 (m, 2H), 7.80 (s, 1H), 7.63-7.61 (m, 1H), 7.26 (d, J = 7.2 Hz, 1H), 6.93-6.75 (m, 2H), 5.06-4.92 (m, 1H), 4.26 (d, J = 11.6 Hz, 2H), 3.89-3.73 (m, 2H), 3.69-3.58 (m, 2H), 3.32 (s, 3H), 2.53-2.05 (m, 2H), 2.05 (s, 6H), 1.19 (d, J = 6.4 Hz, 6H) |
| 809 | 551.3 | $^1$H NMR (400 MHz, DMSO-$d_6$) δ 12.68-12.40 (m, 1H), 8.16 (d, J = 1.2 Hz, 1H), 8.09 (d, J = 1.2 Hz, 1H), 8.04 (d, J = 8.0 Hz, 1H), 7.81 (s, 1H), 7.65-7.61 (m, 1H), 7.26 (d, J = 7.2 Hz, 1H), 6.81 (d, J = 8.4 Hz, 1H), 4.94-4.89 (m, 1H), 4.26 (d, J = 11.2 Hz, 2H), 3.86-3.81 (m, 1H), 3.83-3.64 (m, 1H), 3.64-3.63 (m, 2H), 3.30 (s, 3H), 2.52-2.42 (m, 2H), 1.89-1.84 (m, 4H), 1.19 (d, J = 6.0 Hz, 6H) |
| 810 | 553.3 | $^1$H NMR (400 MHz, DMSO-$d_6$) δ 12.92-12.15 (m, 1H), 8.14 (d, J = 5.2 Hz, 2H), 8.06 (d, J = 8.4 Hz, 1H), 7.80 (s, 1H), 7.65-7.61 (m, 1H), 7.26 (d, J = 7.2 Hz, 1H), 6.80 (d, J = 8.8 Hz, 1H), 4.98-4.88 (m, 1H), 4.26 (d, J = 12.0 Hz, 2H), 3.88-3.81 (m, 1H), 3.75-3.71 (m, 1H), 3.68-3.59 (m, 2H), 3.30 (s, 3H), 2.45-2.39 (m, 2H), 2.03 (s, 6H), 1.19 (d, J = 6.0 Hz, 6H) |

Example 178. Preparation of N-[2-[[4-[3-(3,6-dihydro-2H-pyran-5-yl)phenyl]thiazol-2-yl]amino]-2-oxo-ethyl]-1-methylsulfonyl-pyrrole-3-carboxamide (Compound 396), 1-methylsulfonyl-N-[2-oxo-2-[[4-[3-[(3R)-tetrahydropyran-3-yl]phenyl]thiazol-2-yl]amino]ethyl]pyrrole-3-carboxamide (Compound 420) and 1-methylsulfonyl-N-[2-oxo-2-[[4-[3-[(3S)-tetrahydropyran-3-yl]phenyl]thiazol-2-yl]amino]ethyl]pyrrole-3-carboxamide (Compound 419)

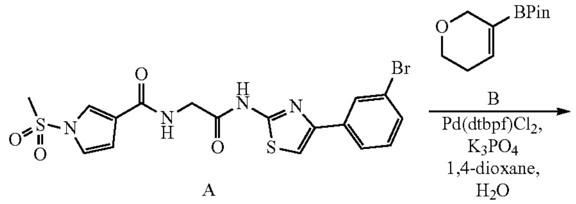

A

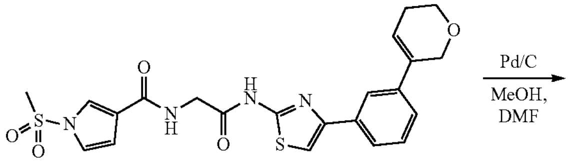

Compound 396

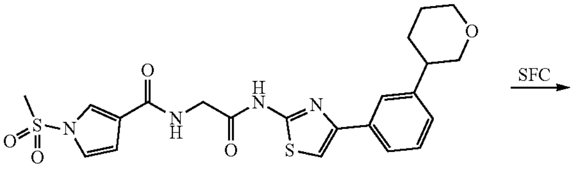

Compound 776

-continued

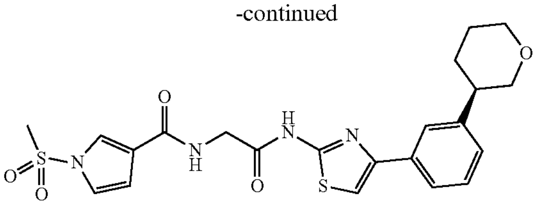

+

Compound 419

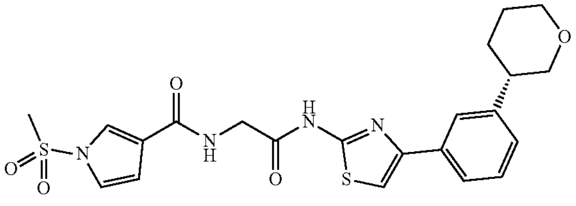

Compound 420

Step 1: Preparation of N-[2-[[4-[3-(3,6-dihydro-2H-pyran-5-yl)phenyl]thiazol-2-yl]amino]-2-oxo-ethyl]-1-methylsulfonyl-pyrrole-3-carboxamide (Compound 396)

Compound 396

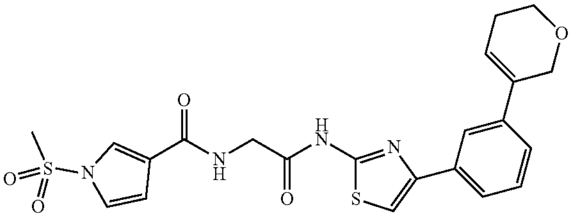

A mixture of N-[2-[[4-(3-bromophenyl)thiazol-2-yl]amino]-2-oxo-ethyl]-1-methylsulfonyl-pyrrole-3-carboxamide (0.500 g, 1.03 mmol), 2-(3,6-dihydro-2H-pyran-5-yl)-4,4,5,5-tetramethyl-1,3,2-dioxaborolane (0.217 g, 1.03 mmol), $K_3PO_4$ (0.659 g, 3.10 mmol) and Pd(dtbpf)$Cl_2$ (0.067 g, 0.103 mol) in 1,4-dioxane (10 mL) and $H_2O$ (1 mL) was degassed and purged with $N_2$ (3×). The resulting mixture was stirred at 70° C. After 12 h, the mixture reaction was cooled to room temperature and water (20 mL) was added slowly until solids precipitated out of solution. The solids were filtered and washed with water. The solids were purified by reversed phase HPLC. Then the solution was extracted with ethyl acetate (20 mL×3), the combined organic layers were dried over anhydrous $Na_2SO_4$, filtered and concentrated under reduced pressure to give Compound 396 (0.250 g, 0.478 mmol, 46.2% yield, 93.0% purity) as a yellow solid. LCMS (ESI) m/z: $[M+H]^+$=487.2; $^1$H NMR (400 MHz, DMSO-$d_6$) δ 12.40 (s, 1H), 8.69-8.67 (m, 1H), 7.89 (s, 1H), 7.86-7.84 (m, 1H), 7.81 (d, J=7.6 Hz, 1H), 7.71 (s, 1H), 7.43-7.38 (m, 1H), 7.35-7.31 (m, 2H), 6.79-6.77 (m, 1H), 6.36-6.35 (m, 1H), 4.48 (d, J=2.0 Hz, 2H), 4.14 (d, J=5.6 Hz, 2H), 3.77-3.75 (m, 2H), 3.58 (s, 3H), 2.31-2.27 (m, 2H).

Step 2: Preparation of 1-methylsulfonyl-N-[2-oxo-2-[[4-(3-tetrahydropyran-3-ylphenyl)thiazol-2-yl]amino]ethyl]pyrrole-3-carboxamide (Compound 776)

Compound 776

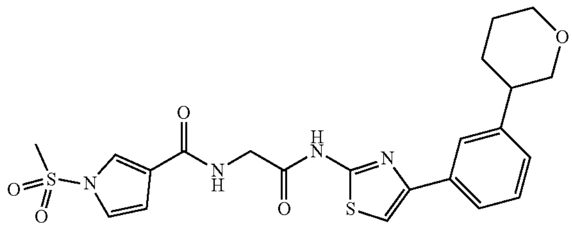

To a solution of N-[2-[[4-[3-(3,6-dihydro-2H-pyran-5-yl)phenyl]thiazol-2-yl]amino]-2-oxo-ethyl]-1-methylsulfonyl-pyrrole-3-carboxamide (0.170 g, 0.349 mmol) in MeOH (3 mL) and DMF (3 mL) was added 10% Pd/C (0.020 g, 0.349 mmol) under $N_2$ (g). The suspension was subjected to three cycles of degassing under vacuum and purging with $H_2$. The mixture was stirred under $H_2$ (15 psi) at 40° C. After 12 h, the reaction mixture was filtered and partially concentrated under reduced pressure to remove MeOH. The crude product was purified by prep reversed phase HPLC concentrated under reduced pressure to remove acetonitrile, and lyophilized to give Compound 776 (0.036 g, 0.073 mmol, 20.88% yield, 99% purity) as a white solid. LCMS (ESI) m/z: $[M+H]^+$=489.1; 1 H NMR (400 MHz, DMSO-$d_6$) δ 12.39 (s, 1H), 8.68-8.66 (m, 1H), 7.86-7.84 (m, 1H), 7.80 (s, 1H), 7.75 (d, J=7.6 Hz, 1H), 7.64 (s, 1H), 7.38-7.36 (m, 1H), 7.33-7.31 (m, 1H), 7.23 (d, J=7.6 Hz, 1H), 6.78 (m, 1H), 4.14 (d, J=5.6 Hz, 2H), 3.92-3.85 (m, 2H), 3.58 (s, 3H), 3.40 (s, 2H), 2.84-2.82 (m, 1H), 2.00-1.96 (m, 1H), 1.81-1.76 (m, 1H), 1.70-1.68 (m, 2H).

Step 3: Preparation of 1-methylsulfonyl-N-[2-oxo-2-[[4-[3-[(3R)-tetrahydropyran-3-yl]phenyl]thiazol-2-yl]amino]ethyl]pyrrole-3-carboxamide (Compound 420) and 1-methylsulfonyl-N-[2-oxo-2-[[4-[3-[(3S)-tetrahydropyran-3-yl]phenyl]thiazol-2-yl]amino]ethyl]pyrrole-3-carboxamide (Compound 419)

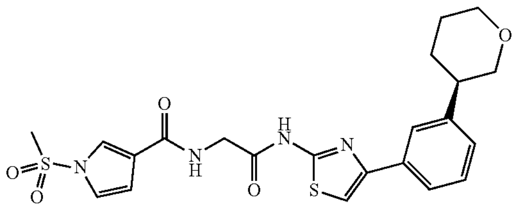

+

Compound 420

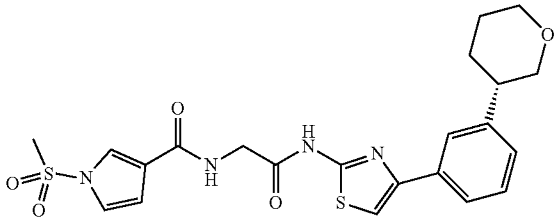

Compound 419

1-methylsulfonyl-N-[2-oxo-2-[[4-(3-tetrahydropyran-3-ylphenyl)thiazol-2-yl]amino]ethyl]pyrrole-3-carboxamide (0.086 g, 0.176 mmol) was purified by SFC separation (mobile phase: [0.1% $NH_4OH$ MeOH]; B %: 70%-70%), followed by re-purification by reversed-phase prep-HPLC to give Compound 420 (0.026 g, 0.054 mmol, 33.53% yield, 100% purity) as a white solid and Compound 419 (0.029 g, 0.059 mmol, 36.73% yield, 100% purity) as a white solid.

Compound 420: LCMS (ESI) m/z: $[M+H]^+$=489.2; $^1$H NMR (400 MHz, DMSO-$d_6$) δ 12.39 (s, 1H), 8.68-8.66 (m, 1H), 7.86-7.84 (m, 1H), 7.81 (s, 1H), 7.75 (d, J=7.6 Hz, 1H), 7.64 (s, 1H), 7.39-7.34 (m, 1H), 7.33-7.31 (m, 1H), 7.23 (d, J=7.6 Hz, 1H), 6.79-6.77 (m, 1H), 4.14 (d, J=6.0 Hz, 2H), 3.91-3.85 (m, 2H), 3.58 (s, 3H), 3.40-3.36 (m, 2H), 2.84-2.82 (m, 1H), 1.98 (d, J=13.6 Hz, 1H), 1.81-1.73 (m, 1H), 1.71-1.65 (m, 2H); ee %=100%.

Compound 419: LCMS (ESI) m/z: $[M+H]^+$=489.2; $^1$H NMR (400 MHz, DMSO-$d_6$) δ 12.38-12.35 (m, 1H), 8.68-8.66 (m, 1H), 7.86-7.84 (m, 1H), 7.81 (s, 1H), 7.75 (d, J=7.6 Hz, 1H), 7.64 (s, 1H), 7.38-7.36 (m, 1H), 7.33-7.31 (m, 1H), 7.23 (d, J=7.6 Hz, 1H), 6.79-6.77 (m, 1H), 4.14 (d, J=5.6 Hz, 2H), 3.92-3.85 (m, 2H), 3.58 (s, 3H), 3.44-3.36 (m, 2H), 2.84-2.82 (m, 1H), 2.00-1.96 (m, 1H), 1.81-1.73 (m, 1H), 1.71-1.68 (m, 2H); ee %=100%.

Example 179. Preparation of Compounds of the Invention

The following compounds in Table 14 below were synthesized utilizing the general synthetic protocols described in Example 178 and starting from the appropriate common intermediate (N-(2-((4-(3-bromophenyl)thiazol-2-yl)amino)-2-oxoethyl)-1-(methylsulfonyl)-1H-pyrrole-3-carboxamide), and the appropriate boronate ester.

TABLE 14

| Compound # | LC-MS data(m/z) | $^1$H NMR |
|---|---|---|
| 388 | 545.1 | $^1$H NMR (400 MHz, DMSO-$d_6$) δ 12.41 (s, 1H), 8.70 (d, J = 5.6 Hz, 1H), 7.89-7.80 (m, 2H), 7.74 (d, J = 7.6 Hz, 1H), 7.66 (s, 1H), 7.37 (d, J = 7.6 Hz, 1H), 7.34-7.30 (m, 1H), 7.25 (d, J = 7.6 Hz, 1H), 6.79-6.77 (m, 1H), 4.14 (d, J = 5.6 Hz, 2H), 3.59 (s, 3H), 3.22-3.10 (m, 1H), 1.74-1.70 (m, 2H), 1.44 (d, J = 12.8 Hz, 2H), 1.32 (s, 6H), 1.17 (s, 6H) |
| 390 | 517.1 | $^1$H NMR (400 MHz, DMSO-$d_6$) δ 12.09 (s, 1H), 8.73-8.58 (m, 1H), 7.85-7.43 (m, 1H), 7.79 (s, 1H), 7.75-7.69 (m, 1H), 7.63 (s, 1H), 7.38-7.29 (m, 2H), 7.22-7.16 (m, 1H), 6.79-6.75 (m, 1H), 4.19-4.08 (m, 2H), 3.57 (s, 5H), 2.93-2.78 (m, 1H), 1.83-1.68 (m, 2H), 1.34-1.21 (m, 2H), 1.15 (s, 6H) |
| 391 | 515.2 | $^1$H NMR (400 MHz, DMSO-$d_6$) δ 8.73-8.61 (m, 1H), 7.99-7.93 (m, 1H), 7.87-7.83 (m, 1H), 7.81-7.76 (m, 1H), 7.70-7.66 (m, 1H), 7.38 (s, 2H), 7.33-7.29 (m, 1H), 6.80-6.74 (m, 1H), 6.24-6.16 (m, 1H), 4.42-4.29 (m, 1H), 4.20-4.10 (m, 2H), 3.81-3.68 (m, 1H), 3.57 (s, 3H), 2.45-2.39 (m, 1H), 2.29-2.17 (m, 1H), 1.27-1.23 (m, 6H) |
| 392 | 489.2 | $^1$H NMR (400 MHz, DMSO-$d_6$) δ 12.43 (s, 1H), 8.70-8.69 (m, 1H), 7.93 (s, 1H), 7.86-7.85 (m, 1H), 7.78 (d, J = 7.6 Hz, 1H), 7.62 (s, 1H), 7.38-7.37 (m, 1H), 7.33-7.32 (m, 1H), 7.26 (d, J = 7.6 Hz, 1H), 6.79-6.78 (m, 1H), 4.38-4.34 (m, 1H), 4.14 (d, J = 6.0 Hz, 2H), 4.05 (d, J = 12.0 Hz, 1H), 3.59-3.55 (m, 4H), 1.90-1.78 (m, 2H), 1.75-1.62 (m, 1H), 1.61-1.52 (m, 2H), 1.51-1.46 (m, 1H) |
| 393 | 489.2 | $^1$H NMR (400 MHz, DMSO-$d_6$) δ 12.41 (s, 1H), 8.68-8.67 (m, 1H), 7.93 (s, 1H), 7.86-7.85 (m, 1H), 7.77 (d, J = 8.0 Hz, 1H), 7.62 (s, 1H), 7.38-7.37 (m, 1H), 7.33-7.32 (m, 1H), 7.26 (d, J = 8.0 Hz, 1H), 6.79-6.78 (m, 1H), 4.38-4.34 (m, 1H), 4.14 (d, J = 6.0 Hz, 2H), 4.08-4.03 (m, 1H), 3.58 (s, 4H), 1.90-1.82 (m, 2H), 1.69-1.62 (m, 1H), 1.60-1.54 (m, 2H), 1.50-1.46 (m, 1H) |
| 399 | 489.2 | $^1$H NMR (400 MHz, DMSO-$d_6$) δ 12.85-11.98 (m, 1H), 8.77-8.60 (m, 1H), 7.91-7.77 (m, 2H), 7.77-7.68 (m, 1H), 7.62(s, 1H), 7.42-7.27 (m, 2H), 7.26-7.15 (m, 1H), 6.78 (s, 1H), 4.23-4.06 (m, 2H), 4.03-3.86 (m, 2H), 3.57 (s, 3H), 3.51-3.44 (m, 2H), 2.89-2.70 (m, 1H), 1.82-1.60 (m, 4H) |
| 400 | 487.2 | $^1$H NMR (400 MHz, DMSO-$d_6$) δ 12.41 (s, 1H), 8.67 (s, 1H), 7.97 (s, 1H), 7.84 (m, 1H), 7.80 (s, 1H), 7.71-7.67 (m, 1H), 7.46-7.38 (m, 2H), 7.31 (m, 1H), 6.77 (m, 1H), 6.31 (br s, 1H), 4.25 (m, 2H), 4.14 (m, 2H), 3.85 (m, 2H), 3.57 (s, 3H), 2.52-2.52 (m, 2H) |
| 411 | 543.1 | $^1$H NMR (400 MHz, DMSO-$d_6$) δ 12.40 (s, 1H), 8.67 (d, J = 6.0 Hz, 1H), 7.96 (s, 1H), 7.85 (d, J = 2.0 Hz, 1H), 7.82-7.78 (m, 1H), 7.70 (s, 1H), 7.49-7.37 (m, 2H), 7.33-7.31 (m, 1H), 6.79-6.77 (m, 1H), 6.24 (s, 1H), 4.15 (d, J = 6.0 Hz, 2H), 3.58 (s, 3H), 2.36 (s, 2H), 1.29 (s, 6H), 1.25 (s, 6H) |

Example 180. Preparation of Compounds of the Invention

The following compounds in Table 15 below were synthesized utilizing the general synthetic protocols described in Example 178 and starting (S)—N-(1-((4-(3-bromophenyl)thiazol-2-yl)amino)-3-methoxy-1-oxopropan-2-yl)-1-(methylsulfonyl)-1H-pyrrole-3-carboxamide, and the appropriate boronate ester.

TABLE 15

| Compound # | LC-MS data(m/z) | $^1$H NMR |
|---|---|---|
| 353 | 589.4 | $^1$H NMR (400 MHz, $CDCl_3$) δ 9.99 (br s, 1H), 7.79-7.71 (m, 2H), 7.67 (d, J = 7.6 Hz, 1H), 7.38 (d, J = 7.2 Hz, 1H), 7.23 (d, J = 7.6 Hz, 1H), 7.21-7.19 (m, 1H), 7.21-7.18 (m, 1H), 6.84 (d, J = 6.4 Hz, 1H), 6.73 (d, J = 1.6, 3.2 Hz, 1H), 5.00 (d, J = 4.0 Hz, 1H), 4.07 (d, J = 5.2 Hz, 1H), 3.68 (d, J = 2.0 Hz, 1H), 3.53 (s, 3H), 3.27 (s, 3H), 3.20-3.10 (m, 1H), 1.80 (d, J = 10.0 Hz, 2H), 1.57-1.53 (m, 1H), 1.44-1.37 (m, 6H), 1.35 (s, 1H), 1.28 (s, 6H) |
| 354 | 587.3 | $^1$H NMR (400 MHz, $CDCl_3$) δ 10.48-9.55 (m, 1H), 7.85 (s, 1H), 7.76 (m, 1H), 7.72-7.68 (m, 1H), 7.43-7.34 (m, 2H), 7.21 (s, 1H), 7.19 (m, 1H), 6.84 (d, J = 6.4 Hz, 1H), 6.72 (m, 1H), 6.11 (s, 1H), 4.99 (m, 1H), 4.07 (m, 1H), 3.66 (m, 1H), 3.51 (s, 3H), 3.26 (s, 3H), 2.40(s, 2H), 1.34 (d, J = 9.2 Hz, 12H) |

Example 181. Preparation of N-(2-((4-(6-((cis)-2,6-dimethyl-3,6-dihydro-2H-pyran-4-yl)pyridin-2-yl)thiazol-2-yl)amino)-2-oxoethyl)-1-(methylsulfonyl)-1H-pyrrole-3-carboxamide (Compound 350)

Compound 350

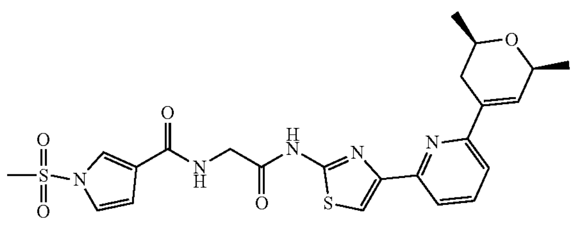

(±)

The following compounds in Table 16 below were synthesized utilizing the general synthetic protocols described in Example 161 from N-(2-((4-(6-bromopyridin-2-yl)thiazol-2-yl)amino)-2-oxoethyl)-1-(methylsulfonyl)-1H-pyrrole-3-carboxamide, and the appropriate boronate ester.

LCMS (ESI) m/z: $[M+H]^+$=516.1; $^1H$ NMR (400 MHz, DMSO-$d_6$) δ 12.14 (s, 1H), 8.69-8.68 (m, 1H), 7.88-7.83 (m, 3H), 7.82-7.78 (m, 1H), 7.51-7.46 (m, 1H), 7.34-7.29 (m, 1H), 6.79-6.76 (m, 1H), 6.76-6.74 (m, 1H), 4.46-4.35 (m, 1H), 4.14 (d, J=6.0 Hz, 2H), 3.77-3.71 (m, 1H), 3.58-3.55 (m, 3H), 2.69-2.66 (m, 1H), 2.26-2.14 (m, 1H), 1.34-1.21 (m, 6H).

Example 182. Preparation of N-(2-((4-(3-((trans)-4-hydroxycyclohexyl)phenyl)thiazol-2-yl)amino)-2-oxoethyl)-1-(methylsulfonyl)-1H-pyrrole-3-carboxamide (Compound 386) and N-(2-((4-(3-((cis)-4-hydroxycyclohexyl)phenyl)thiazol-2-yl)amino)-2-oxoethyl)-1-(methylsulfonyl)-1H-pyrrole-3-carboxamide (Compound 387)

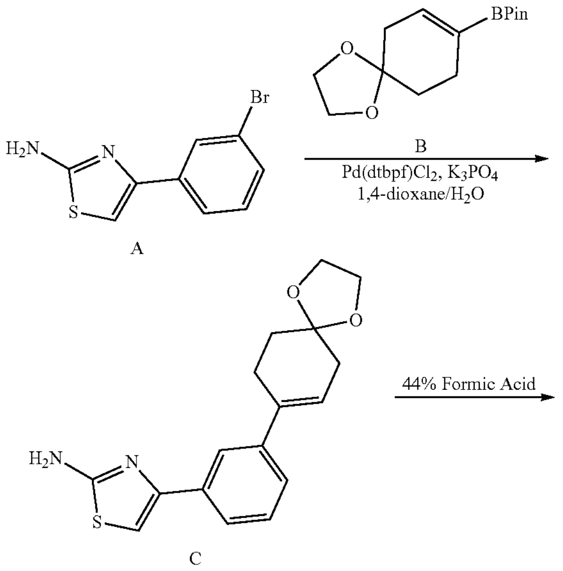

-continued

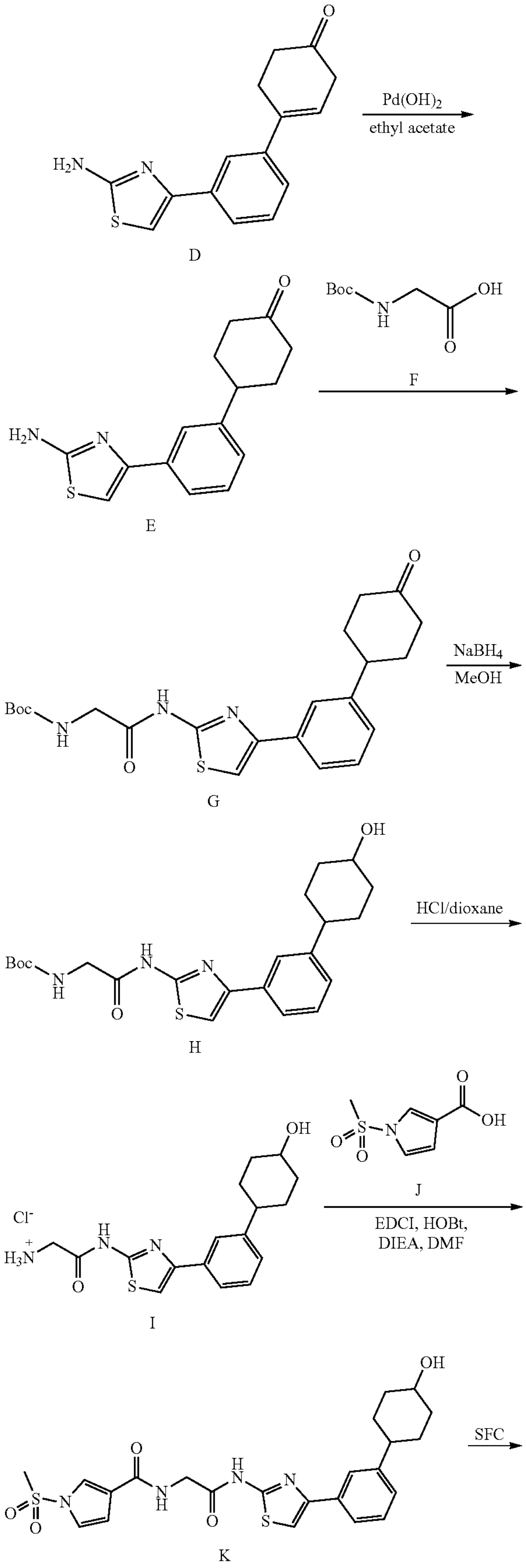

-continued

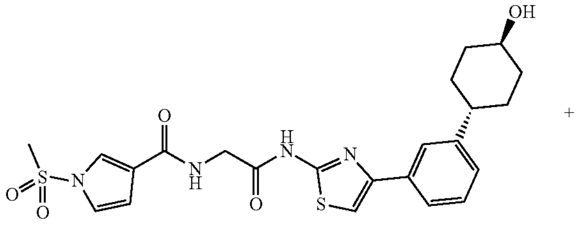

Compound 386

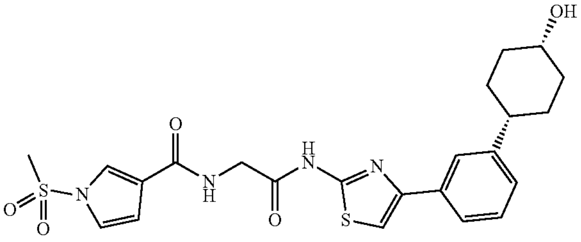

Compound 387

Step 1: Preparation of 4-[3-(1,4-dioxaspiro[4.5]dec-7-en-8-yl)phenyl]thiazol-2-amine (Intermediate C)

C

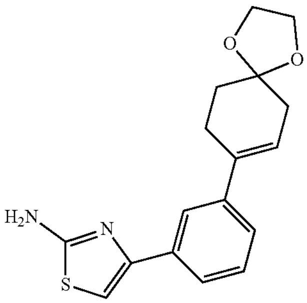

To a solution of 4-(3-bromophenyl)thiazol-2-amine (0.800 g, 3.14 mmol), 2-(1,4-dioxaspiro[4.5]dec-7-en-8-yl)-4,4,5,5-tetramethyl-1,3,2-dioxaborolane (1.25 g, 4.70 mmol), $K_3PO_4$ (2.00 g, 9.41 mmol) in 1,4-dioxane (10 mL) and $H_2O$ (2 mL) was added Pd(dtbpf)$Cl_2$ (0.204 g, 0.314 mmol). The mixture was subsequently stirred at 70° C. After 1 h, the reaction mixture was cooled to ambient temperatures and poured into water (20 mL). The resulting biphasic solution was extracted with ethyl acetate (20 mL×2) and the combined organic layers were washed with brine (20 mL), dried over $Na_2SO_4$ and concentrated. The crude product was purified by column chromatography ($SiO_2$, petroleum ether/ethyl acetate=10:1 to 3:1) to give Intermediate C (0.950 g, 2.95 mmol, 94.1% yield, 97.7% purity) as a white solid. LCMS (ESI) m/z: $[M+H]^+$=315.1.

Step 2: Preparation of 4-[3-(2-aminothiazol-4-yl)phenyl]cyclohex-3-en-1-one (Intermediate D)

D

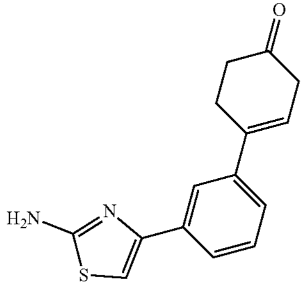

A solution of Intermediate C (0.905 g, 3.02 mmol) in formic acid (10 mL) was stirred at 60° C. for 1 h. The reaction mixture was cooled to ambient temperatures and poured into water (10 mL). The aqueous layer was extracted with ethyl acetate (10 mL×2). The combined organic layers were washed with brine (10 mL), dried over $Na_2SO_4$ and concentrated. The crude product was purified by reverse phase HPLC to give Intermediate D (0.600 g, 2.21 mmol, 73.2% yield, 99.6% purity) as a yellow solid by lyophilization. LCMS (ESI) m/z: $[M+H]^+$=271.1.

Step 3: Preparation of 4-[3-(2-aminothiazol-4-yl)phenyl]cyclohexanone (Intermediate E)

E

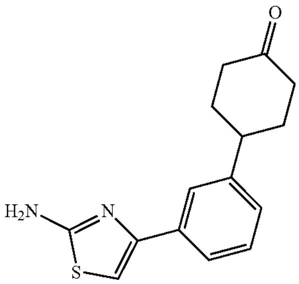

To a solution of Intermediate D (0.600 g, 2.22 mmol) in ethyl acetate (6 mL) was added 20% $Pd(OH)_2$ (0.200 g). The mixture was stirred at 60° C. for 4 d under $H_2$ (50 psi). The reaction mixture was filtered and the filtrate was concentrated to give Intermediate E (0.500 g, 1.72 mmol, 77.67% yield, 93.9% purity) as a yellow solid. LCMS (ESI) m/z: $[M+H]^+$=273.1; $^1H$ NMR (400 MHz, DMSO-$d_6$) δ 7.80 (s, 1H), 7.69 (d, J=7.6 Hz, 1H), 7.35-7.34 (m, 1H), 7.25 (d, J=7.6 Hz, 1H), 7.07 (d, J=7.6 Hz, 3H), 3.12 (d, J=12.0 Hz, 1H), 2.64-2.62 (m 2H), 2.40-2.31 (m, 2H), 2.24-2.11 (m, 2H), 1.96-1.94 (m, 2H).

Step 4: Preparation of tert-butyl N-[2-oxo-2-[[4-[3-(4-oxocyclohexyl)phenyl]thiazol-2-yl]amino]ethyl] carbamate (Intermediate G)

G

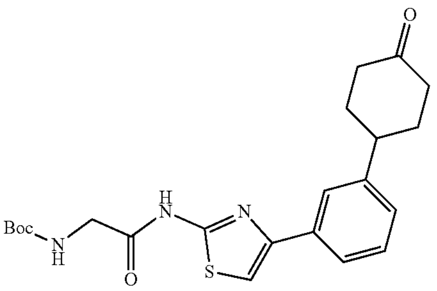

To a solution of Intermediate E (0.470 g, 1.73 mmol), N-Boc-glycine (0.363 g, 2.07 mmol), [chloro(dimethylamino)methylene]-dimethylammonium; hexafluorophosphate (0.726 g, 2.59 mmol) in acetonitrile (5 mL) was added N-methylimidazole (0.413 mL, 5.18 mmol). The mixture was stirred at 25° C. for 16 h and subsequently filtered and concentrated. The crude product was purified by reverse phase HPLC to give Intermediate G (0.400 g, 0.880 mmol, 51.0% yield, 94.5% purity) as a yellow solid by extraction. LCMS (ESI) m/z: $[M+H]^+$=430.1.; $^1$H NMR (400 MHz, $CDCl_3$) δ 10.34-9.56 (m, 1H), 7.64 (s, 1H), 7.58-7.56 (m, 1H), 7.31-7.29 (m, 1H), 7.15 (d, J=7.6 Hz, 1H), 7.08 (s, 1H), 5.11 (s, 1H), 3.97 (s, 2H), 3.07-2.96 (m, 1H), 2.49-2.40 (m, 4H), 2.26-2.14 (m, 2H), 1.99-1.90 (m, 2H), 1.42 (s, 9H).

Step 5: Preparation of tert-butyl N-[2-[[4-[3-(4-hydroxycyclohexyl)phenyl]thiazol-2-yl]amino]-2-oxo-ethyl]carbamate (Intermediate H)

H

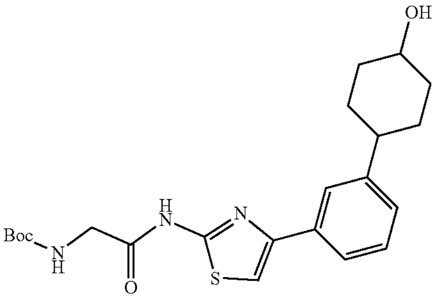

To a solution of Intermediate G (0.390 g, 0.908 mmol) in e (5 mL) was added $NaBH_4$ (0.051 g, 1.36 mmol). After stirring for 1 h at room temperature, the reaction mixture was poured into water (10 mL) and extracted with ethyl acetate (10 mL×2). The combined organic layers were washed with brine (10 mL), dried over $Na_2SO_4$ and concentrated. The crude product was purified by reverse phase HPLC to give Intermediate H (0.300, 0.681 mmol, 75.03% yield, 98.0% purity) as a white solid after lyophilization. LCMS (ESI) m/z: $[M+H]^+$=432.2; $^1$H NMR (400 MHz, DMSO-$d_6$) δ 12.29 (s, 1H), 7.77 (s, 1H), 7.70 (d, J=7.6 Hz, 1H), 7.62 (s, 1H), 7.34-7.30 (m, 1H), 7.18 (d, J=5.6 Hz, 2H), 4.60 (s, 1H), 3.86 (d, J=6.0 Hz, 2H), 3.50-3.43 (m, 1H), 1.94 (d, J=9.6 Hz, 2H), 1.81 (d, J=13.2 Hz, 2H), 1.57-1.48 (m, 2H), 1.46-1.35 (m, 9H), 1.33-1.28 (m, 2H).

Step 6: Preparation of 2-((4-(3-(4-hydroxycyclohexyl)phenyl)thiazol-2-yl)amino)-2-oxoethan-1-aminium chloride (Intermediate I)

I

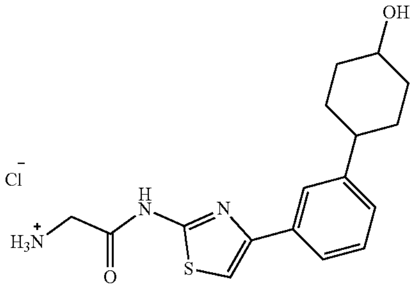

A solution of Intermediate H (0.300 g, 0.695 mmol) in a solution of 4 M HCl 1,4-dioxane (3 mL). After stirring for 1 h at room temperature, the reaction mixture was concentrated to give Intermediate I (0.255 g) as a white solid. LCMS (ESI) m/z: $[M+H]^+$=332.1.

Step 7: Preparation of N-[2-[[4-[3-(4-hydroxycyclohexyl)phenyl]thiazol-2-yl]amino]-2-oxo-ethyl]-1-methylsulfonyl-pyrrole-3-carboxamide (Intermediate K)

K

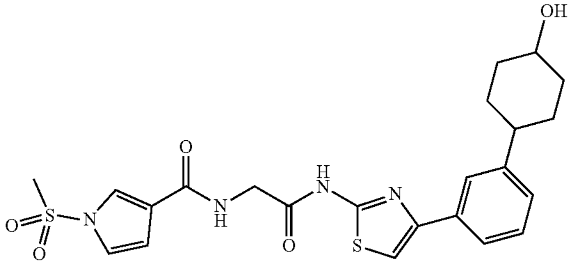

To a solution of Intermediate I (0.250 g, 0.680 mmol), 1-methylsulfonylpyrrole-3-carboxylic acid (0.154 g, 0.815 mmol), EDCI (0.261 g, 1.36 mmol), HOBt (0.184 g, 1.36 mmol) in DMF (0.5 mL) was added DIEA (0.592 mL, 3.40 mmol). After stirring for 1 h at room temperature, the reaction mixture was filtered and the filtrate was purified by reverse phase HPLC to give Intermediate K (0.150 g, 0.276 mmol, 40.58% yield, 92.4% purity) as a white solid after lyophilization. LCMS (ESI) m/z: $[M+H]^+$=503.0.

Step 8: Preparation of N-(2-((4-(3-((trans)-4-hydroxycyclohexyl)phenyl)thiazol-2-yl)amino)-2-oxoethyl)-1-(methylsulfonyl)-1H-pyrrole-3-carboxamide (Compound 386) and N-(2-((4-(3-((cis)-4-hydroxycyclohexyl)phenyl)thiazol-2-yl)amino)-2-oxoethyl)-1-(methylsulfonyl)-1H-pyrrole-3-carboxamide (Compound 387)

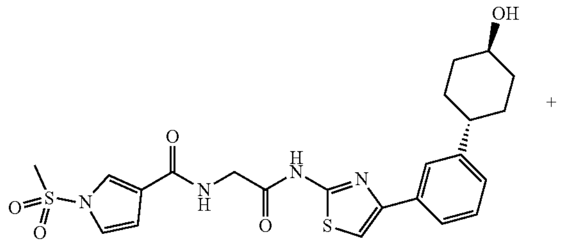

Compound 386

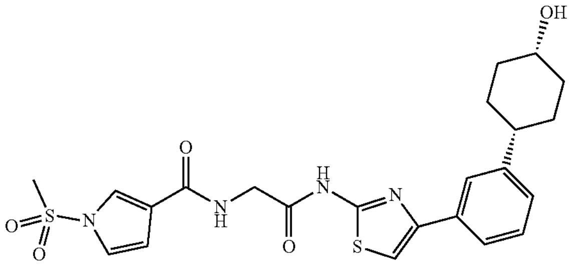

Compound 387

The Intermediate K (150 mg, 298.44 umol) was purified by prep-HPLC (FA) to give Compound 386 (78.31 mg, 155.81 umol, 52.21% yield, 100% purity) as a white solid by lyophilization and Compound 387 (6.52 mg, 12.51 umol, 4.19% yield, 96.4% purity) as a white solid by lyophilization.

Compound 386: LCMS (ESI) m/z: $[M+H]^+=503.3$; $^1H$ NMR (400 MHz, DMSO-$d_6$) δ 12.41 (s, 1H), 8.71-8.70 (m, 1H), 7.86-7.84 (m, 1H), 7.78 (s, 1H), 7.73-7.67 (m, 1H), 7.62 (s, 1H), 7.38-7.29 (m, 2H), 7.18 (d, J=7.6 Hz, 1H), 6.79-6.77 (m, 1H), 4.88-4.36 (m, 1H), 4.15 (d, J=6.0 Hz, 2H), 3.58 (s, 3H), 3.51-3.46 (m, 1H), 2.50-2.45 (m, 1H), 2.02-1.89 (m, 2H), 1.87-1.72 (m, 2H), 1.54-1.52 (m, 2H), 1.39-1.25 (m, 2H).

Compound 387: LCMS (ESI) m/z: $[M+H]^+=503.3$; $^1H$ NMR (400 MHz, DMSO-$d_6$) δ 12.48 (s, 1H), 8.70-8.69 (m, 1H), 7.86-7.85 (m, 2H), 7.70 (d, J=7.6 Hz, 1H), 7.62 (s, 1H), 7.39-7.29 (m, 2H), 7.17 (d, J=7.6 Hz, 1H), 6.78-6.76 (m, 1H), 4.43 (s, 1H), 4.14 (d, J=5.6 Hz, 2H), 3.93 (s, 1H), 3.58 (s, 3H), 2.55 (s, 1H), 1.98-1.71 (m, 4H), 1.63-1.45 (m, 4H).

Example 183. Preparation of 4-(1-(methylsulfonyl)-1H-pyrrol-3-yl)-N-(4-(3-(1-(oxetan-3-yl)-1,2,3,6-tetrahydropyridin-4-yl)phenyl)thiazol-2-yl)-4-oxobutanamide (Compound 389)

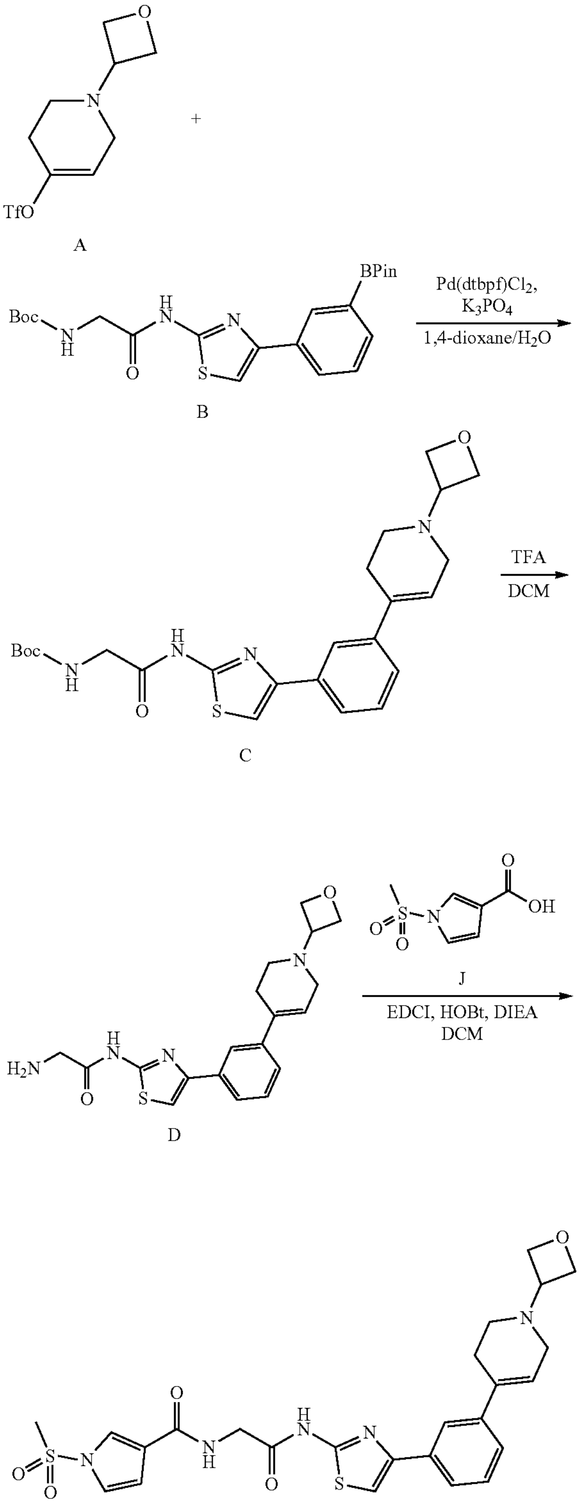

Compound 389

Step 1: Preparation of tert-butyl (2-((4-(3-(1-(oxetan-3-yl)-1,2,3,6-tetrahydropyridin-4-yl)phenyl)thiazol-2-yl)amino)-2-oxoethyl)carbamate (Intermediate C)

C

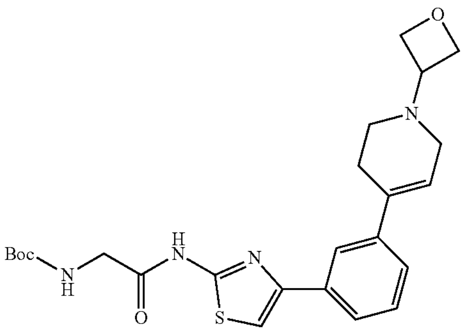

A mixture of 1-(oxetan-3-yl)-1,2,3,6-tetrahydropyridin-4-yl trifluoromethanesulfonate (0.520 g, 1.81 mmol), tert-butyl N-[2-oxo-2-[[4-[3-(4,4,5,5-tetramethyl-1,3,2-dioxaborolan-2-yl)phenyl]thiazol-2-yl]amino]ethyl]carbamate (0.998 g, 2.17 mmol), $Pd(dtbpf)Cl_2$ (0.118 g, 0.181 mmol), and $K_3PO_4$ (1.15 g, 5.43 mmol) in a mixture of 1,4-dioxane (8 mL) and $H_2O$ (2 mL) was degassed and purged with $N_2$ (3×). The mixture was subsequently stirred at 80° C. under a constant stream of $N_2$ atmosphere. After 2 h, the mixture was cooled to room temperature, followed by addition of water (100 mL). The mixture was extracted with ethyl acetate (100 mL×2). The combined organic layers were washed with brine (100 mL), dried over anhydrous $Na_2SO_4$, filtered and the filtrate was concentrated to give solids. The crude product was triturated with MTBE (20 mL), stirred for 10 min, and filtered. The solids were collected to give Intermediate C (0.700 g, 1.46 mmol, 80.5% yield, 98.0% purity) as a white solid. LCMS (ESI) m/z: $[M+H]^+$=471.2.

Step 2: Preparation of 2-((4-(3-(1-(oxetan-3-yl)-1,2,3,6-tetrahydropyridin-4-yl)phenyl)thiazol-2-yl)amino)-2-oxoethan-1-aminium chloride (Intermediate D)

D

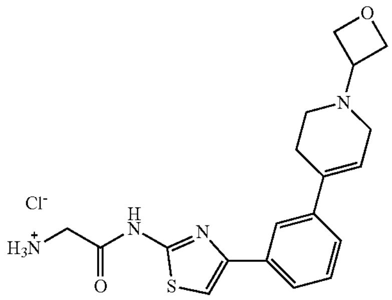

To a cooled (0° C.) solution of Intermediate C (0.080 g, 0.170 mmol) in dichloromethane (2 mL) was added TFA (0.2 mL). After stirring for 2 h, saturated aqueous $NaHCO_3$ (40 mL) was added and the reaction mixture was extracted with dichloromethane (40 mL×3). The combined organic layers were dried over $Na_2SO_4$, filtered and concentrated under reduced pressure to give Intermediate D (0.050 g, 0.135 mmol, 79.39% yield) as a yellow solid which was used into the next step without further purification. LCMS (ESI) m/z: $[M+H]^+$=371.1.

Step 3: Preparation of 4-(1-(methylsulfonyl)-1H-pyrrol-3-yl)-N-(4-(3-(1-(oxetan-3-yl)-1,2,3,6-tetrahydropyridin-4-yl)phenyl)thiazol-2-yl)-4-oxobutanamide (Compound 389)

Compound 389

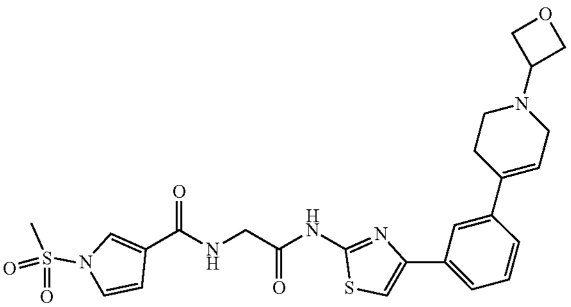

To a solution of 1-methylsulfonylpyrrole-3-carboxylic acid (0.025 g, 0.130 mmol) in dichloromethane (2 mL) was added HOBt (0.022 g, 0.162 mmol), DIEA (0.056 mL, 323.91 umol), EDCI (0.031 g, 0.162 mmol), and Intermediate D (0.040 g, 0.108 mmol) was added. The mixture was stirred at 25° C. for 2 h and subsequently filtered. The filter cake was collected and the solids were triturated with MeOH (4 mL) at 20° C. for 10 min and filtered. The resulting solids were lyophilized to give Compound 389 (0.008 g, 0.015 mmol, 13.5% yield, 98.5% purity) as a white solid. LCMS (ESI) m/z: $[M+H]^+$=542.1; $^1H$ NMR (400 MHz, DMSO-$d_6$) δ 12.39 (s, 1H), 8.67-8.64 (m, 1H), 7.96 (s, 1H), 7.84 (s, 1H), 7.78-7.77 (m, 1H), 7.68 (s, 1H), 7.40 (d, J=4.8 Hz, 2H), 7.31-7.30 (m, 1H), 6.77 (s, 1H), 6.21 (s, 1H), 4.61-4.58 (m, 2H), 4.53-4.50 (m, 2H), 4.14 (d, J=5.6 Hz, 2H), 3.57 (s, 4H), 3.02 (s, 2H), 2.53 (s, 2H), 2.52-2.50 (m, 2H).

Example 184. Preparation of N-(2-((4-(3-(2-oxa-7-azaspiro[3.5]nonan-7-yl)phenyl)thiazol-2-yl)amino)-2-oxoethyl)-1-(tert-butyl)-1H-pyrrole-3-carboxamide (Compound 397)

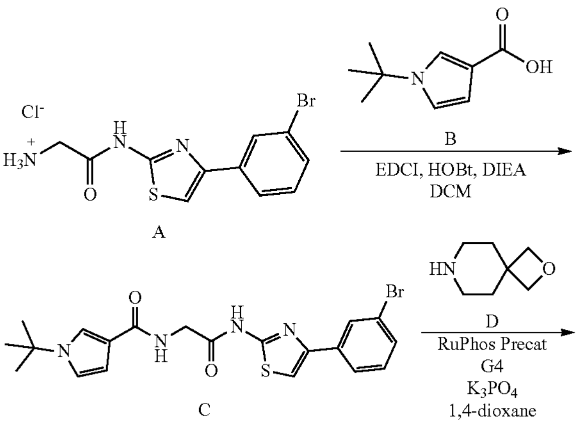

-continued

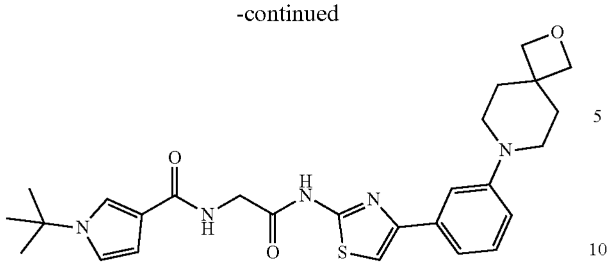

Compound 397

Step 1: Preparation of N-(2-((4-(3-bromophenyl) thiazol-2-yl)amino)-2-oxoethyl)-1-(tert-butyl)-1H-pyrrole-3-carboxamide (Intermediate C)

C

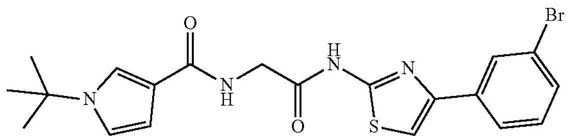

To a solution of 2-amino-N-[4-(3-bromophenyl)thiazol-2-yl]acetamide (2.09 g, 5.98 mmol) in dichloromethane (20 mL) was added EDCI (1.72 g, 8.97 mmol), DIEA (3.86 g, 29.90 mmol, 5.21 mL) and HOBt (1.21 g, 8.97 mmol). The mixture was stirred at 25° C. for 30 min, followed by addition of 1-tert-butylpyrrole-3-carboxylic acid (1.00 g, 5.98 mmol). After 16 h, the mixture was concentrated in reduced pressure. The residue was poured into ice-water (20 mL) and stirred. The aqueous phase was extracted with ethyl acetate (20 mL×3). The combined organic phases were washed with brine (20 mL), dried with anhydrous $Na_2SO_4$, filtered and concentrated. The residue was purified by silica gel column chromatography (petroleum ether/ethyl acetate=1:0 to 0:1)) to afford Intermediate C (1.50 g, 3.25 mmol, 54.36% yield) as yellow solid. LCMS (ESI) m/z: $[M+H]^+$=463.0; $^1$H NMR (400 MHz, DMSO-$d_6$) δ 12.37 (s, 1H), 8.24-8.17 (m, 1H), 8.12 (d, J=1.6 Hz, 1H), 7.95-7.88 (m, 1H), 7.78 (s, 1H), 7.57-7.49 (m, 2H), 7.41 (s, 1H), 6.99-6.97 (m, 1H), 6.48-6.47 (m, 1H), 4.13-4.07 (m, 2H), 1.50 (s, 9H).

Step 2: Preparation of N-(2-((4-(3-(2-oxa-7-azaspiro [3.5]nonan-7-yl)phenyl)thiazol-2-yl)amino)-2-oxo-ethyl)-1-(tert-butyl)-1H-pyrrole-3-carboxamide (Compound 397)

Compound 397

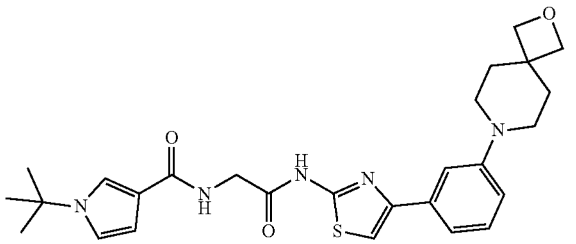

In a sealed tube was suspended tert-butyl N-({[4-(3-bromophenyl)-1,3-thiazol-2-yl]carbamoyl}methyl)carbamate (0.050 g, 0.11 mmol), 2-oxa-7-azaspiro[3.5]nonane (0.018 g, 0.13 mmol), potassium phosphate (0.069 g, 0.32 mmol) and RuPhos Precatalyst G4 (0.011 g, 0.090 mmol) in 1,4-dioxane (1 mL). The reaction mixture was subsequently heated at 90° C. overnight. The reaction was cooled to room temperature and filtered through a pad of Celite. The filtrate was concentrated in vacuo and the crude product was purified via silica gel chromatography (ethyl acetate:heptane=2:3 to 4:5) affording the title compound as a light-yellow powder (12.1 mg, 22%). LCMS (ESI) m/z: $[M+H]^+$= 508.4; $^1$H NMR (400 MHz, DMSO-$d_6$) δ 12.24 (s, 1H), 8.12 (s, 1H), 7.56 (s, 1H), 7.52-7.42 (m, 2H), 7.28 (d, J=7.7 Hz, 1H), 7.22 (t, J=7.8 Hz, 1H), 6.95 (t, J=2.7 Hz, 1H), 6.89 (d, J=9.6 Hz, 1H), 6.45 (dd, J=3.0, 1.7 Hz, 1H), 4.34 (s, 4H), 4.07 (d, J=5.9 Hz, 2H), 3.14-3.08 (m, 4H), 1.91-1.85 (m, 4H), 1.48 (s, 9H).

Example 185. Preparation of Compounds of the Invention

The following compounds in Table 16 below were synthesized starting from the appropriate common intermediate (1-(methylsulfonyl)-N-(2-oxo-2-((4-(3-(4,4,5,5-tetramethyl-1,3,2-dioxaborolan-2-yl)phenyl)thiazol-2-yl)amino) ethyl)-1H-pyrrole-3-carboxamide) utilizing the synthetic protocol described in Example 1.

TABLE 16

| Compound # | LC-MS data(m/z) | $^1$H NMR |
|---|---|---|
| 261 | 486.2 | $^1$H NMR (400 MHz, DMSO-$d_6$) δ 12.49-12.03 (m, 1H), 8.65 (s, 1H), 8.40 (s, 1H), 8.25 (s, 1H), 7.89-7.84 (m, 2H), 7.78-7.71 (m, 2H), 7.55-7.49 (m, 1H), 7.33-7.31 (m, 1H), 6.77 (d, J = 0.9 Hz, 1H), 4.21 (s, 3H), 4.14 (d, J = 2.4 Hz, 2H), 3.56 (s, 3H) |
| 404 | 526.9 | $^1$H NMR (400 MHz, DMSO-$d_6$) δ 12.58-12.41 (m, 1H), 8.82-8.61 (m, 1H), 8.44-8.38 (m, 1H), 7.87-7.80 (m, 2H), 7.74-7.69 (m, 2H), 7.42 (d, J = 2.4 Hz, 1H), 7.35-7.29 (m, 1H), 6.82-6.75 (m, 1H), 6.56 (s, 1H), 4.91-4.81 (m, 2H), 4.25-4.06 (m, 6H), 3.58 (s, 3H) |
| 405 | 511.2 | $^1$H NMR (400 MHz, DMSO-$d_6$) δ 12.58-12.45 (m, 1H), 8.96 (s, 1H), 8.73-8.66 (m, 1H), 8.40-8.31 (m, 1H), 8.08-7.97 (m, 1H), 7.86-7.85 (m, 1H), 7.71 (s, 1H), 7.57 (d, J = 7.8 Hz, 1H), 7.38-7.28 (m, 1H), 7.24 (s, 1H), 6.79-6.78 (m, 1H), 4.16 (d, J = 5.7 Hz, 2H), 3.58 (s, 3H), 2.57-2.53 (m, 6H) |
| 406 | 510.2 | $^1$H NMR (400 MHz, DMSO-$d_6$) δ 12.64-12.33 (m, 1H), 8.74-8.65 (m, 1H), 8.63-8.57 (m, 1H), 8.18-8.13 (m, 1H), 8.04-7.98 (m, 1H), 7.98-7.91 (m, 1H), 7.88-7.83 (m, 1H), 7.78-7.71 (m, 1H), 7.69-7.63 (m, 1H), 7.58-7.49 (m, 1H), 7.36-7.29 (m, 1H), 7.14-7.05 (m, 1H), 6.83-6.74 (m, 1H), 4.22-4.11 (m, 2H), 3.63-3.56 (m, 3H), 2.52 (s, 3H), 2.40-2.35 (m, 3H) |

TABLE 16-continued

| Compound # | LC-MS data(m/z) | $^1$H NMR |
|---|---|---|
| 407 | 496.1 | $^1$H NMR (400 MHz, Methanol-d$_4$) δ 8.48-8.42 (m, 2H), 8.24-8.21 (m, 1H), 8.11 (d, J = 7.6 Hz, 1H), 7.88-7.80 (m, 3H), 7.74-7.67 (m, 1H), 7.62 (s, 1H), 7.30-7.29 (m, 1H), 6.83-6.82 (m, 1H), 4.29 (s, 2H), 3.40 (s, 3H), 2.87 (s, 3H) |
| 409 | 523.2 | $^1$H NMR (400 MHz, DMSO-d$_6$) δ 12.49-12.46 (m, 1H), 8.74-8.65 (m, 3H), 8.11-8.06 (m, 2H), 7.91-7.77 (m, 3H), 7.62-7.61 (m, 1H), 7.33-7.32 (m, 1H), 6.79-6.78 (m, 1H), 4.16-4.15 (m, 2H), 3.58 (s, 3H), 2.32-2.25 (m, 1H), 1.11-1.09 (m, 4H) |
| 410 | 517.1 | $^1$H NMR (400 MHz, DMSO-d$_6$) δ 8.87-8.86 (m, 1H), 8.74-8.73 (m, 1H), 8.69-8.66 (m, 1H), 8.21-8.10 (m, 1H), 8.14-8.12 (m, 2H), 7.85-7.84 (m, 1H), 7.83-7.81 (m, 1H), 7.68-7.61 (m, 1H), 7.32-7.30 (m, 1H), 6.78-6.75 (m, 1H), 4.16-4.14 (m, 2H), 3.57 (s, 3H) |
| 413 | 514.3 | $^1$H NMR (400 MHz, DMSO-d$_6$) δ 12.43 (s, 1H), 8.69-6.68 (m, 1H), 8.53 (d, J = 2.4 Hz, 1H), 8.19 (s, 1H), 8.05-8.00 (m, 1H), 7.86-7.85 (m, 1H), 7.78 (s, 1H), 7.61 (d, J = 4.8 Hz, 2H), 7.55 (d, J = 6.8 Hz, 1H), 7.32-7.31 (m, 1H), 6.79-6.78 (m, 1H), 4.15 (d, J = 6.0 Hz, 2H), 3.58 (s, 3H), 2.54 (s, 3H) |
| 441 | 583.1 | $^1$H NMR (400 MHz, DMSO-d$_6$) δ 12.45 (s, 1H), 8.70-8.68 (m, 1H), 8.30 (s, 1H), 8.26 (d, J = 5.6 Hz, 1H), 8.08 (s, 1H), 8.01 (d, J = 7.6 Hz, 1H), 7.88-7.83 (m, 2H), 7.75 (d, J = 7.6 Hz, 1H), 7.59-7.57 (m, 1H), 7.41-7.36 (m, 1H), 7.34-7.30 (m, 1H), 7.17 (s, 1H), 6.79-6.77 (m, 1H), 4.34-4.32 (m, 2H), 4.16-4.14(m, 2H), 3.58 (s, 3H), 3.46-3.44 (m, 2H), 1.84 (s, 3H) |
| 442 | 541.1 | $^1$H NMR (400 MHz, DMSO-d$_6$) δ 12.44 (s, 1H), 8.71 (s, 1H), 8.33-8.26 (m, 2H), 8.03 (d, J = 7.8 Hz, 3H), 7.85 (d, J = 6.0 Hz, 2H), 7.73 (d, J = 8.4 Hz, 1H), 7.64-7.57 (m, 1H), 7.45 (d, J = 5.2 Hz, 1H), 7.35-7.30 (m, 1H), 7.19 (s, 1H), 6.78 (s, 1H), 4.57-4.47 (m, 2H), 4.16-4.14 (m, 2H), 3.58 (s, 3H), 3.29-3.25 (m, 2H) |
| 447 | 486.3 | $^1$H NMR (400 MHz, DMSO-d$_6$) δ 12.46 (s, 1H), 8.70-8.67 (m, 1H), 8.54 (s, 1H), 8.46 (s, 1H), 7.86-7.84 (m, 2H), 7.75 (d, J = 7.6 Hz, 1H), 7.71 (s, 1H), 7.52-7.48 (m, 1H), 7.32-7.30 (m, 1H), 6.78 (d, J = 0.8 Hz, 1H), 4.14 (d, J = 6.0 Hz, 2H), 4.11 (s, 3H), 3.57 (s, 3H) |

Example 186. Preparation of 2-bromo-6,7-dihydro-4H-pyrazolo[5,1-c][1,4]oxazine

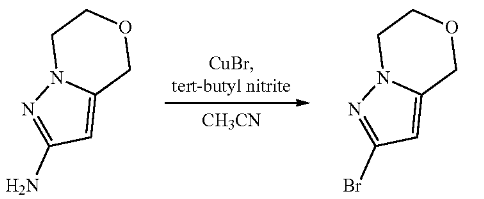

A B

Step 1: Preparation of 2-bromo-6,7-dihydro-4H-pyrazolo[5,1-c][1,4]oxazine (Intermediate B)

B

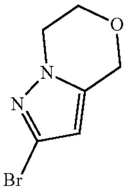

To a cooled (0° C.) solution of 6,7-dihydro-4H-pyrazolo[5,1-c][1,4]oxazin-2-amine (0.150 g, 1.08 mmol) and CuBr (0.155 g, 1.08 mmol) in acetonitrile (1.5 mL) was added tert-butyl nitrite (0.256 mL, 2.16 mmol). The mixture was stirred at 50° C. for 5 h, followed by addition of $H_2O$ (3 mL). The resulting solution was extracted with ethyl acetate (3 mL×2). The combined organic layers were concentrated under reduced pressure. The residue was diluted with MeOH (2 mL) and purified by reversed-phase HPLC (0.1% formic acid) to give Intermediate B (0.050 g, 0.214 mmol, 19.9% yield, 87.0% purity) as a yellow solid. LCMS (ESI) m/z: [$^{81}$Br M+H]$^+$=204.8; $^1$H NMR (400 MHz, DMSO-d$_6$) δ 6.20 (s, 1H), 4.75 (s, 2H), 4.10-4.02 (m, 4H).

Example 187. Preparation of Compounds of the Invention

The following compounds in Table 17 below were synthesized starting from the appropriate common intermediate 1-(tert-butyl)-N-(2-oxo-2-((4-(3-(4,4,5,5-tetramethyl-1,3,2-dioxaborolan-2-yl)phenyl)thiazol-2-yl)amino)ethyl)-1H-pyrrole-3-carboxamide utilizing the synthetic protocol described in Example 8.

TABLE 17

| Compound # | LC-MS data(m/z) | $^1$H NMR |
|---|---|---|
| 402 | 475.3 | $^1$H NMR (400 MHz, DMSO-$d_6$) δ 12.38 (br s, 1H), 9.53 (s, 1H), 8.39 (s, 1H), 8.20 (d, J = 6.0 Hz, 1H), 8.06 (d, J = 7.6 Hz, 1H), 7.97 (d, J = 2.4 Hz, 1H), 7.89-7.82 (m, 2H), 7.67-7.59 (m, 1H), 7.52 (d, J = 2.0 Hz, 1H), 6.97 (d, J = 2.8 Hz, 1H), 6.48 (d, J = 1.6 Hz, 1H), 4.10 (d, J = 6.0 Hz, 2H), 2.71 (s, 3H), 1.49 (s, 9H) |
| 415 | 505.0 | $^1$H NMR (400 MHz, DMSO-$d_6$) δ 12.38 (br s, 1H), 8.42-8.40 (m, 1H), 8.18-8.16 (m, 1H), 7.83-7.81 (m, 1H), 7.76-7.66 (m, 2H), 7.54-7.52 (m, 1H), 7.46-7.44 (m, 1H), 6.98-6.96 (m, 1H), 6.56 (s, 1H), 6.49-6.47 (m, 1H), 4.85 (s, 2H), 4.22-4.15 (m, 2H), 4.15-4.06 (m, 4H), 1.50 (s, 9H) |
| 417 | 474.2 | $^1$H NMR (400 MHz, DMSO-$d_6$) δ 12.39-12.31 (m, 1H), 8.61 (s, 1H), 8.17-8.16 (m, 1H), 8.00 (d, J = 8.0 Hz, 1H), 7.94 (d, J = 8.0 Hz, 1H), 7.80 (d, J = 4.4 Hz, 2H), 7.73 (s, 1H), 7.56-7.50 (m, 2H), 7.26-7.24 (m, 1H), 6.97 (s, 1H), 6.48-6.47 (m, 1H), 4.10 (d, J = 6.0 Hz, 2H), 2.56 (s, 3H), 1.49 (s, 9H) |
| 434 | 520.2 | $^1$H NMR (400 MHz, DMSO-$d_6$) δ 12.32 (s, 1H), 8.33 (s, 1H), 8.20-8.17 (m, 1H), 8.00 (br s, 3H), 7.89-7.79 (m, 3H), 7.67 (s, 1H), 7.56-7.44 (m, 2H), 6.97 (br s, 1H), 6.86 (d, J = 2.0 Hz, 1H), 6.48 (br s, 1H), 4.34 (s, 2H), 4.10 (br d, J = 5.6 Hz, 2H), 1.49 (s, 9H), 1.26 (s, 6H) |

Example 188. Preparation of N-[2-[[4-[3-[2-(azetidin-1-yl)pyrimidin-4-yl]phenyl]thiazol-2-yl]amino]-2-oxo-ethyl]-1-methylsulfonyl-pyrrole-3-carboxamide (Compound 408)

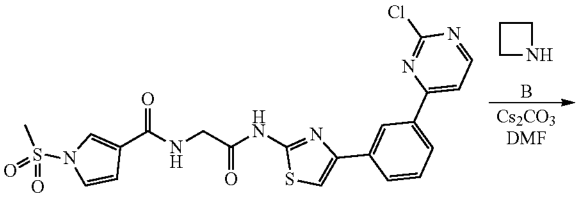

A

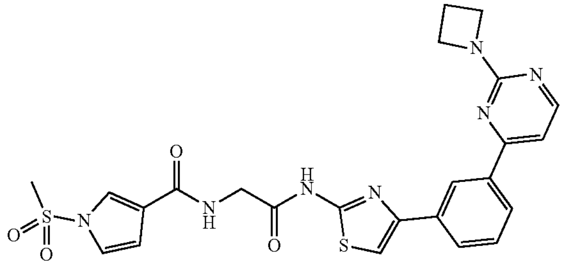

Compound 408

A suspension of N-[2-[[4-[3-(2-chloropyrimidin-4-yl)phenyl]thiazol-2-yl]amino]-2-oxo-ethyl]-1-methylsulfonyl-pyrrole-3-carboxamide (0.020 g, 0.039 mmol), $Cs_2CO_3$ (0.038 g, 0.116 mmol) and azetidine (0.026 mL, 386.86 umol) in DMF (0.5 mL) was stirred at 60° C. After 8 h, the mixture was cooled to ambient temperatures and water (5 mL) was added. The aqueous mixture was extracted with ethyl acetate (5 mL×3). The combined organic phase was dried over anhydrous $Na_2SO_4$, filtered and concentrated. The residue was purified by preparative HPLC and lyophilized to give Compound 408 (0.012 g, 0.020 mmol, 51.33% yield, 100% purity, formic acid salt) as a white solid. LCMS (ESI) m/z: $[M+H]^+$=538.2; $^1$H NMR (400 MHz, DMSO-$d_6$) δ 12.46-12.38 (m, 1H), 8.68-8.67 (m, 1H), 8.57 (s, 1H), 8.43-8.42 (d, J=5.2 Hz, 1H), 8.05-8.02 (m, 2H), 7.85 (s, 1H), 7.77 (s, 1H), 7.58-7.57 (m, 1H), 7.33-7.32 (m, 1H), 7.26-7.25 (d, J=5.2 Hz, 1H), 6.79-6.78 (m, 1H), 4.17-4.11 (m, 6H), 3.58 (s, 2H), 3.60-3.56 (m, 1H), 2.38-2.37 (m, 2H).

Example 189. Preparation of Compounds of the Invention

The following compounds in Table 18 were synthesized utilizing the general synthetic protocols described in Example 57 and starting from the common intermediate, tert-butyl (2-oxo-2-((4-(3-(4,4,5,5-tetramethyl-1,3,2-dioxaborolan-2-yl)phenyl)thiazol-2-yl)amino)ethyl)carbamate, the appropriate aryl halide, and heterocyclic carboxylic acid.

TABLE 18

| Compound # | LC-MS data(m/z) | $^1$H NMR |
|---|---|---|
| 167 | 476.3 | $^1$H NMR (400 MHz, DMSO-$d_6$) δ 12.48 (br s, 1H), 8.79-8.72 (m, 2H), 8.31-8.28 (m, 1H), 8.13-8.06 (m, 2H), 7.94-7.92 (m, 2H), 7.79 (s, 1H), 7.62-7.58 (m, 1H), 6.65 (d, J = 2.4 Hz, 1H), 4.19 (d, J = 6.0 Hz, 2H), 2.71 (s, 3H), 1.57 (s, 9H) |
| 403 | 499.8 | $^1$H NMR (400 MHz, DMSO-$d_6$) δ 12.51 (s, 1H), 8.72 (d, J = 6.0 Hz, 1H), 8.43 (d, J = 1.6 Hz, 1H), 8.28 (s, 1H), 7.93-7.87 (m, 1H), 7.84 (d, J = 2.0 Hz, 1H), 7.80-7.78 (m, 1H), 7.76 (s, 1H), 7.54-7.52 (m, 1H), 7.32-7.30 (m, 1H), 6.80-6.79 (m, 1H), 4.23 (s, 3H), 4.15 (d, J = 6.0 Hz, 2H), 3.72 (q, J = 7.2 Hz, 2H), 1.13 (d, J = 7.2 Hz, 3H) |
| 412 | 511.4 | $^1$H NMR (400 MHz, DMSO-$d_6$) δ 12.47 (s, 1H), 8.70 (s, 2H), 8.10-8.04 (m, 2H), 7.85-7.78 (m, 3H), 7.60-7.59 (m, 1H), 7.32 (s, 1H), 6.78 (s, 1H), 4.16 (d, J = 3.6 Hz, 2H), 3.57 (s, 3H), 2.66 (s, 3H), 2.51 (s, 3H) |
| 416 | 496.9 | $^1$H NMR (400 MHz, DMSO-$d_6$) δ 12.47 (br s, 1H), 8.78 (d, J = 5.2 Hz, 1H), 8.72 (s, 1H), 8.69-8.66 (m, 1H), 8.13-8.06 (m, 2H), 7.92 (d, J = 5.2 Hz, 1H), 7.85-7.84 (m, 1H), 7.79 (s, 1H), 7.63-7.59 (m, 1H), 7.32-7.30 (m, 1H), 6.78-6.77 (m, 1H), 4.15 (d, J = 6.0 Hz, 2H), 3.57 (s, 3H), 2.71 (s, 3H) |

TABLE 18-continued

| Compound # | LC-MS data(m/z) | $^1$H NMR |
|---|---|---|
| 144 | 477.0 | $^1$H NMR (400 MHz, Methanol-$d_4$) δ 8.33 (s, 1H), 7.84 (d, J = 8.0 Hz, 1H), 7.71 (d, J = 7.6 Hz, 1H), 7.62 (d, J = 2.4 Hz, 1H), 7.57-7.56 (m, 1H), 7.46-7.39 (m, 2H), 6.99-6.97 (m, 1H), 6.70-6.64 (m, 2H), 4.99 (d, J = 6.8 Hz, 2H), 4.72 (d, J = 6.4 Hz, 2H), 4.25 (s, 2H), 3.95 (s, 3H), 1.89 (s, 3H) |
| 474 | 472.0 | $^1$H NMR (400 MHz, DMSO-$d_6$) δ 12.42 (s, 1H), 8.38-8.35 (m, 2H), 7.79 (d, J = 8.0 Hz, 1H), 7.75 (d, J = 2.0 Hz, 1H), 7.72 (d, J = 7.6 Hz, 1H), 7.68 (s, 1H), 7.60-7.59 (m, 1H), 7.44-7.08 (m, 1H), 7.08-7.07 (m, 1H), 6.72 (d, J = 2.4 Hz, 1H), 6.56-6.55 (m, 1H), 4.11 (d, J = 5.6 Hz, 2H), 3.89 (s, 3H), 1.84-1.80 (m, 2H), 1.77-1.74 (m, 2H) |
| 529 | 489.1 | $^1$H NMR (400 MHz, DMSO-$d_6$) δ 9.11 (s, 1H), 8.66 (s, 1H), 8.54 (s, 1H), 8.26-8.24 (m, 1H), 8.07-8.01 (m, 2H), 7.79 (s, 1H), 7.61-7.56 (m, 2H), 7.02-7.00 (m, 1H), 6.57-6.56 (m, 1H), 4.84 (d, J = 6.4 Hz, 2H), 4.63 (d, J = 6.8 Hz, 2H), 4.12 (d, J = 4.8 Hz, 2H), 2.60 (s, 3H), 1.79 (s, 3H) |
| 541 | 485.1 | $^1$H NMR (400 MHz, DMSO-$d_6$) δ 12.47 (br s, 1H), 8.69-8.67 (m, 1H), 8.38-8.37 (m, 1H), 7.85-7.84 (m, 1H), 7.84-7.74 (m, 1H), 7.77-7.74 (m, 1H), 7.70-7.69 (m, 1H), 7.69 (s, 1H), 7.54 (d, J = 1.2 Hz, 1H), 7.44-7.43 (m, 1H), 7.32-7.30 (m, 1H), 6.78-6.77 (m, 1H), 6.72 (d, J = 2.0 Hz, 1H), 4.15 (d, J = 5.6 Hz, 2H), 3.90 (s, 3H), 3.57 (s, 3H) |
| 562 | 474.2 | $^1$H NMR (400 MHz, DMSO-$d_6$) δ 12.60-12.29 (m, 1H), 8.44-8.33 (m, 2H), 7.85-7.65 (m, 5H), 7.48-7.40 (m, 1H), 7.19-7.13 (m, 1H), 6.76-6.71 (m, 1H), 6.65-6.60 (m, 1H), 4.18-4.08 (m, 2H), 3.95-3.87 (m, 3H), 2.00-1.91 (m, 6H) |
| 780 | 473.0 | $^1$H NMR (400 MHz, DMSO-$d_6$) δ 12.44 (s, 1H), 8.46-8.39 (m, 2H), 8.14 (d, J = 1.6 Hz, 1H), 8.04 (d, J = 1.2 Hz, 1H), 7.79-7.75 (m, 1H), 7.75 (d, J = 2.4 Hz, 1H), 7.72-7.71 (m, 1H), 7.69 (s, 1H), 7.46-7.44 (m, 1H), 6.73 (d, J = 2.4 Hz, 1H), 4.17 (d, J = 6.0 Hz, 2H), 3.90 (s, 3H), 1.87-1.86 (m, 4H) |
| 790 | 475.0 | $^1$H NMR (400 MHz, DMSO-$d_6$) δ 12.86-12.26 (m, 1H), 8.51-8.49 (m, 1H), 8.39 (s, 1H), 8.16 (d, J = 2.4 Hz, 1H), 7.81 (d, J = 7.6 Hz, 1H), 7.79-7.69 (m, 3H), 7.46-7.44 (m, 1H), 6.80 (d, J = 2.4 Hz, 1H), 6.73 (d, J = 2.4 Hz, 1H), 4.19 (d, J = 6.0 Hz, 2H), 3.90 (s, 3H), 2.05 (s, 6H) |
| 798 | 478.2 | $^1$H NMR (400 MHz, DMSO-$d_6$) δ 12.58-12.39 (m, 1H), 8.52-8.43 (m, 1H), 8.42-8.32 (m, 1H), 8.09-8.02 (m, 1H), 7.84-7.79 (m, 1H), 7.78-7.75 (m, 1H), 7.75-7.71 (m, 1H), 7.71-7.68 (m, 1H), 7.50-7.40 (m, 1H), 6.81-6.68 (m, 2H), 5.10-5.00 (m, 2H), 4.71-4.58 (m, 2H), 4.24-4.13 (m, 2H), 3.96-3.85 (m, 3H), 1.96-1.79 (m, 3H) |
| 813 | 473.0 | $^1$H NMR (400 MHz, DMSO-$d_6$) δ 12.53-12.44 (m, 1H), 8.67-8.56 (m, 1H), 8.44-8.35 (m, 1H), 8.20-8.14 (m, 1H), 7.86-7.78 (m, 1H), 7.78-7.68 (m, 3H), 7.51-7.37 (m, 1H), 6.78-6.71 (m, 2H), 4.22-4.11 (m, 2H), 3.94-3.86 (m, 3H), 2.01-1.88 (m, 4H) |

Example 190. Preparation of N-(2-((4-(3-(3-chloro-6-methylpyridin-2-yl)-4-methylphenyl)thiazol-2-yl)amino)-2-oxoethyl)-1-(methylsulfonyl)-1H-pyrrole-3-carboxamide (Compound 401)

N-(2-((4-(3-(3-chloro-6-methylpyridin-2-yl)-4-methylphenyl)thiazol-2-yl)amino)-2-oxoethyl)-1-(methylsulfonyl)-1H-pyrrole-3-carboxamide was prepared according to Scheme 9 using the appropriate starting materials and utilizing the general synthetic protocol described in Example 57.

Scheme 9

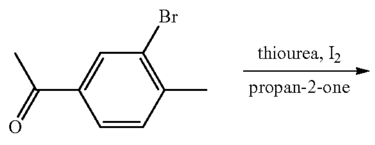

A

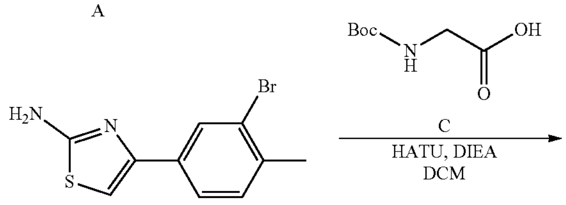

B

-continued

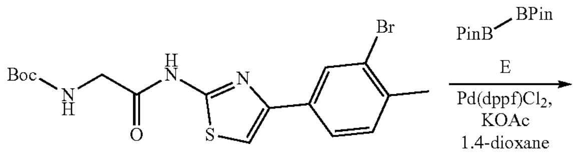

D

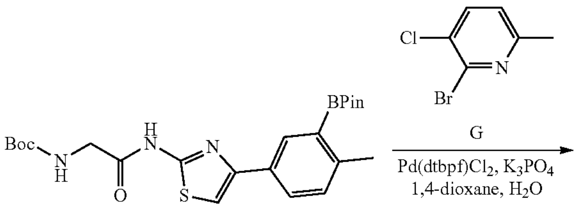

F

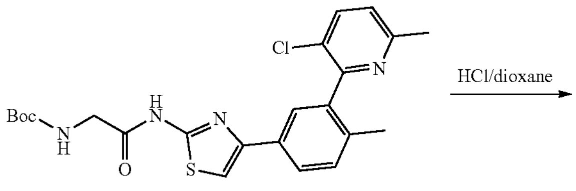

H

-continued

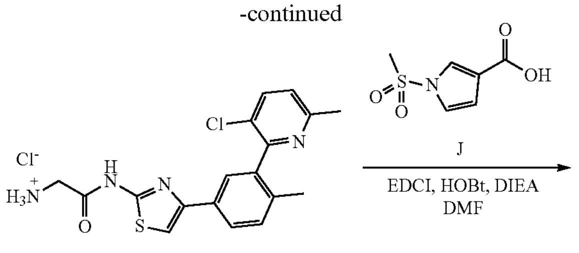

I

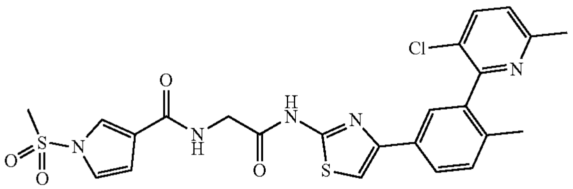

Compound 401

LCMS (ESI) m/z: $[M+H]^+$=544.1; $^1H$ NMR (400 MHz, DMSO-$d_6$) δ 12.38-12.09 (m, 1H), 8.67-8.64 (m, 1H), 7.94 (d, J=8.4 Hz, 1H), 7.88-7.86 (m, 1H), 7.84-7.83 (m, 1H), 7.74 (d, J=1.6 Hz, 1H), 7.63 (s, 1H), 7.38-7.33 (m, 2H), 7.31-7.29 (m, 1H), 6.77-6.76 (m, 1H), 4.12 (d, J=6.0 Hz, 2H), 3.56 (s, 3H), 2.51 (s, 3H), 2.09 (s, 3H).

Example 191. Preparation of Sodium 2-(4-(3-(2-(2-(1-(methylsulfonyl)-1H-pyrrole-3-carboxamido)acetamido)thiazol-4-yl)phenyl)pyridin-2-yl)acetate (Compound 421)

Compound 421

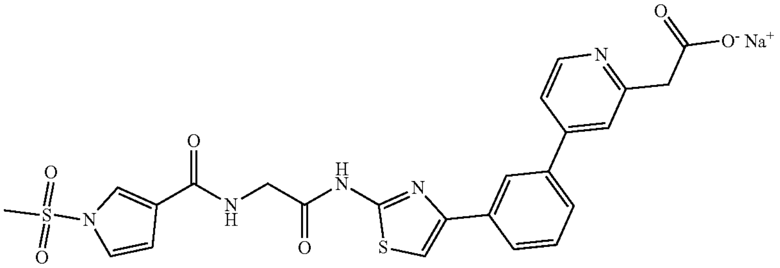

Sodium 2-(4-(3-(2-(2-(1-(methylsulfonyl)-1H-pyrrole-3-carboxamido)acetamido)thiazol-4-yl)phenyl)pyridin-2-yl) acetate was synthesized utilizing the general synthetic protocols described in Example 14 and starting from the common intermediate, 1-(methylsulfonyl)-N-(2-oxo-2-((4-(3-(4,4,5,5-tetramethyl-1,3,2-dioxaborolan-2-yl)phenyl)thiazol-2-yl)amino)ethyl)-1H-pyrrole-3-carboxamide, the appropriate aryl halide.

LCMS (ESI) m/z: $[M+H]^+$=540.3; $^1H$NMR (400 MHz, DMSO-$d_6$) δ 18.43 (d, J=5.2 Hz, 1H), 8.24 (s, 2H), 7.92 (d, J=7.6 Hz, 1H), 7.84-7.82 (m, 1H), 7.65 (s, 1H), 7.59 (d, J=7.6 Hz, 1H), 7.51-7.45 (m, 2H), 7.34-7.27 (m, 2H), 6.79-6.78 (m, 1H), 3.95 (d, J=2.8 Hz, 2H), 3.55 (s, 3H), 3.47 (s, 2H).

Example 192. Preparation of 2-methyl-2-[3-[3-[2-[[2-[(1-methylsulfonylpyrrole-3-carbonyl)amino]acetyl]amino]thiazol-4-yl]phenyl]pyrazol-1-yl]propanoic acid (Compound 217) and N-[2-[[4-[3-[1-[1,1-dimethyl-2-(methylamino)-2-oxo-ethyl]pyrazol-3-yl]phenyl]thiazol-2-yl]amino]-2-oxo-ethyl]-1-methylsulfonyl-pyrrole-3-carboxamide (Compound 414)
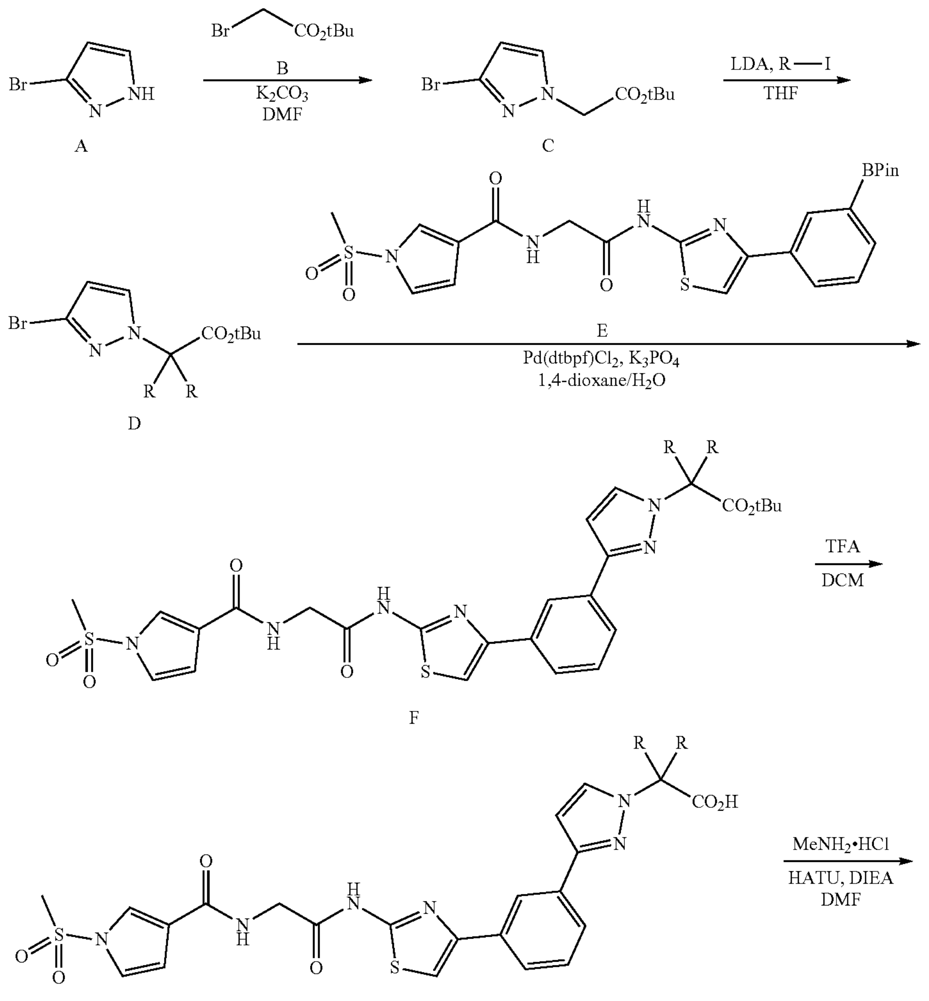
Compound 217
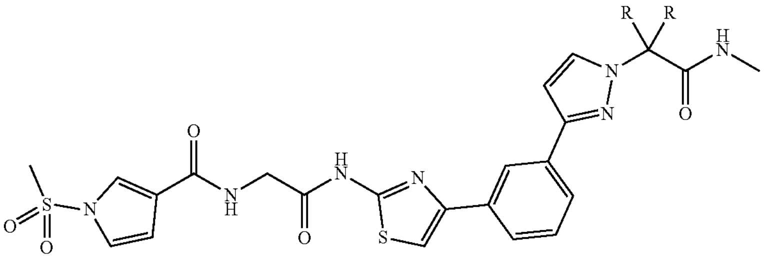
Compound 414

Step 1: Preparation of tert-butyl 2-(3-bromopyrazol-1-yl)acetate (Intermediate C)

C

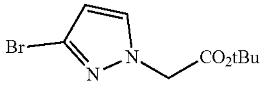

To a solution of 3-bromo-1H-pyrazole (1.00 g, 6.80 mmol) in DMF (10 mL) was added tert-butyl 2-bromoacetate (1.51 mL, 10.21 mmol), $K_2CO_3$ (2.82 g, 20.41 mmol). The reaction was stirred at 50° C. for 3 h, followed by addition of saturated aqueous $NH_4Cl$ (10 mL). The mixture was extracted with ethyl acetate (10 mL×3). The combined organic layers were washed with aqueous brine (10 mL×3), dried over $Na_2SO_4$, filtered and concentrated. The residue was purified by flash silica gel chromatography (ethyl acetate/petroleum ether gradient=0:1 to 1:3) to afford Intermediate C (1.50 g, 5.74 mmol, 84.43% yield, 100% purity) as a colorless oil. LCMS (ESI) m/z: [$^{79}$Br M−56+H]$^+$=205.0; $^1$H NMR (400 MHz, DMSO-d$_6$) δ 7.75 (d, J=2.4 Hz, 1H), 6.41 (d, J=2.4 Hz, 1H), 4.95 (s, 2H), 1.43 (s, 9H).

Step 2: Preparation of tert-butyl 2-(3-bromopyrazol-1-yl)-2-methyl-propanoate (Intermediate D)

D

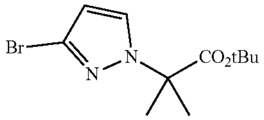

To a cooled (−60° C.) solution of tert-butyl 2-(3-bromopyrazol-1-yl)acetate (0.550 g, 2.11 mmol) in THF (5 mL) was added a 2 M solution of LDA (2 M, 2.63 mL) in THF. The mixture was allowed to gradually warm to ambient temperatures, stirred at 25° C. for 30 min, and cooled again to −60° C. A solution of MeI (0.328 mL, 5.27 mmol) in THF (0.5 mL) was subsequently added and the mixture was allowed to gradually warm to room temperature. After stirring for 1 h, the mixture was quenched by addition saturated aqueous $NH_4Cl$ (5 mL) and extracted with ethyl acetate (5 mL×3). The combined organic layers were washed with brine (5 mL*3), dried over $Na_2SO_4$, and concentrated. The residue was purified by flash silica gel chromatography (ethyl acetate/petroleum ether=0:1 to 1:1) to afford Intermediate D (0.350 g, 1.16 mmol, 55.2% yield, 96.0% purity) as a colorless oil. LCMS (ESI) m/z: [$^{79}$Br M−56+H]$^+$=233.1; $^1$H NMR (400 MHz, DMSO-d$_6$) δ 7.91 (d, J=2.4 Hz, 1H), 6.42 (d, J=2.4 Hz, 1H), 1.71 (s, 6H), 1.34 (s, 9H).

Step 3: Preparation of tert-butyl 2-methyl-2-[3-[3-[2-[[2-[(1-methylsulfonylpyrrole-3-carbonyl)amino]acetyl]amino]thiazol-4-yl]phenyl]pyrazol-1-yl]propanoate (Intermediate F)

F

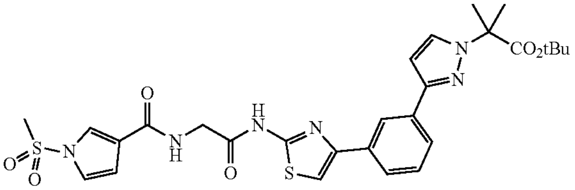

A mixture of 1-methylsulfonyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (0.580 g, 1.09 mmol), Intermediate D (0.350 g, 1.16 mmol), Pd(dtbpf)$Cl_2$ (0.143 g, 0.219 mmol), $K_3PO_4$ (0.696 g, 3.28 mmol) in a mixture of 1,4-dioxane (5 mL) and $H_2O$ (1 mL) was degassed and purged with $N_2$ (3×). The mixture was stirred at 80° C. for 2 h under $N_2$ atmosphere. The mixture was subsequently diluted with water (10 mL) and extracted with ethyl acetate (10 mL×3). The combined organic layers were washed with brine (10 mL). The organic phase was concentrated under reduced pressure. The residue was triturated with a mixture of ethyl acetate (20 mL) and petroleum ether (5 mL) for 10 min and filtered. The resulting solids were dried under reduced pressure to afford Intermediate F (0.500 g, 0.751 mmol, 68.7% yield, 92.0% purity) as a white solid. LCMS (ESI) m/z: [M+H]$^+$=613.5; $^1$H NMR (400 MHz, DMSO-d$_6$) δ 12.43 (br s, 1H), 8.70-8.68 (m, 1H), 8.33 (s, 1H), 7.95 (d, J=2.4 Hz, 1H), 7.87-7.80 (m, 2H), 7.75 (d, J=7.6 Hz, 1H), 7.69 (s, 1H), 7.47-7.45 (m, 1H), 7.33-7.31 (m, 1H), 6.83-6.75 (m, 2H), 4.16 (d, J=5.6 Hz, 2H), 3.58 (s, 3H), 1.79 (s, 6H), 1.35 (s, 9H).

Step 4: Preparation of 2-methyl-2-[3-[3-[2-[[2-[(1-methylsulfonylpyrrole-3-carbonyl)amino]acetyl]amino]thiazol-4-yl]phenyl]pyrazol-1-yl]propanoic acid (Compound 217)

Compound 217

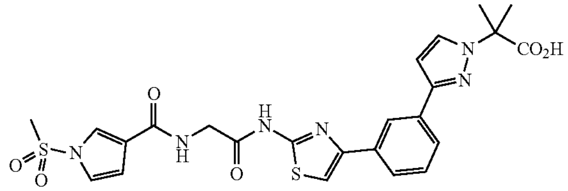

To a solution of Intermediate F (0.500 g, 0.816 mmol) in dichloromethane (10 mL) was added TFA (2.5 mL, 33.77 mmol). After stirring for 16 h, the reaction mixture was concentrated under reduced pressure to remove solvent. The residue was triturated with ethyl acetate (20 mL) and filtered to afford Compound 217 (0.460 g, 0.808 mmol, 99.05% yield, 97.8% purity) as a white solid. LCMS (ESI) m/z: [M+H]$^+$=557.3; $^1$H NMR (400 MHz, DMSO-d$_6$) δ 12.48 (s, 1H), 8.71-8.69 (m, 1H), 8.36 (s, 1H), 7.97 (d, J=2.4 Hz, 1H), 7.88-7.79 (m, 2H), 7.75-7.73 (m, 1H), 7.70 (s, 1H), 7.47-7.45 (m, 1H), 7.33-7.31 (m, 1H), 6.79 (d, J=2.4 Hz, 2H), 4.16-4.14 (m, 2H), 3.58 (s, 3H), 1.81 (s, 6H).

Step 5: Preparation of N-[2-[[4-[3-[1-[1,1-dimethyl-2-(methylamino)-2-oxo-ethyl]pyrazol-3-yl]phenyl]thiazol-2-yl]amino]-2-oxo-ethyl]-1-methylsulfonyl-pyrrole-3-carboxamide (Compound 414)

Compound 414

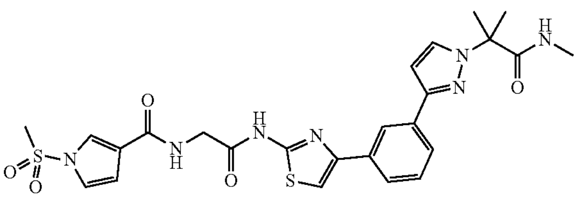

A solution of 2-methyl-2-[3-[3-[2-[[2-[(1-methylsulfonylpyrrole-3-carbonyl)amino]acetyl]amino]thiazol-4-yl]phenyl]pyrazol-1-yl]propanoic acid (0.050 g, 0.089 mmol) in DMF (1 mL) were added DIPEA (0.235 mL, 0.001 mmol) and methylamine hydrochloride (0.061 g, 0.898 mmol). The solution was stirred for 5 min, followed by addition of HATU (0.102 g, 0.269 mmol). After stirring for 16 h, water (3 mL) was slowly added to the mixture and stirred vigorously until precipitates formed. The resulting solids were filtered and purified by prep-HPLC. The resulting solvent was concentrated to remove ACN, then lyophilized to afford Compound 414 (0.008 g, 0.014 mmol, 15.7% yield, 98.0% purity) as a white solid. LCMS (ESI) m/z: $[M+H]^+$=570.4; $^1H$ NMR (400 MHz, DMSO-$d_6$) δ 12.45 (s, 1H), 8.69-8.67 (m 1H), 8.38-8.36 (m, 1H), 7.92 (d, J=2.8 Hz, 1H), 7.87-7.85 (m, 1H), 7.84-7.82 (m, 1H), 7.78-7.74 (m, 1H), 7.70 (s, 1H), 7.48-7.46 (m, 1H), 7.35-7.30 (m, 2H), 6.85-6.74 (m, 2H), 4.15 (d, J=6.0 Hz, 2H), 3.58 (s, 3H), 2.59 (d, J=4.4 Hz, 3H), 1.76 (s, 6H).

Example 193. Preparation of Compounds of the Invention

The following compounds in Table 19 were synthesized starting from the appropriate carboxylic acid and utilizing the general synthetic protocols described in Example 192.

TABLE 19

| Compound # | LC-MS data(m/z) | $^1H$ NMR |
|---|---|---|
| 189 | 556.4 | $^1H$ NMR (400 MHz, DMSO-$d_6$) δ 12.47 (br s, 1H), 8.69-8.67 (m, 1H), 8.39 (s, 1H), 7.87-7.85 (m, 1H), 7.82 (d, J = 7.6 Hz, 1H), 7.74-7.71 (m, 2H), 7.70 (s, 1H), 7.47-7.45 (m, 1H), 7.32 (m, 1H), 6.81-6.74 (m, 2H), 5.18 (s, 2H), 4.15 (d, J = 5.6 Hz, 2H), 3.58 (s, 3H), 3.07 (s, 3H), 2.88 (s, 3H) |
| 218 | 529.3 | $^1H$ NMR (400 MHz, DMSO-$d_6$) δ 12.54 (s, 1H), 8.76-8.69 (m, 1H), 8.51-8.40 (m, 1H), 7.93-7.85 (m, 3H), 7.82-7.78 (m, 1H), 7.77-7.76 (m, 1H), 7.55-7.49 (m, 1H), 7.38 (m, 1H), 6.92-6.73 (m, 1H), 5.08 (s, 2H), 4.29-4.16 (m, 2H), 3.64 (s, 4H), 3.27-3.19 (m, 1H) |
| 418 | 584.5 | $^1H$ NMR (400 MHz, DMSO-$d_6$) δ 12.50 (br s, 1H), 8.68-8.66 (m, 1H), 8.36 (s, 1H), 7.96 (d, J = 2.4 Hz, 1H), 7.88-7.81 (m, 2H), 7.76-7.74 (m, 1H), 7.70 (s, 1H), 7.48-7.46 (m, 1H), 7.33-7.31 (m, 1H), 6.87 (d, J = 2.4 Hz, 1H), 6.79-6.77 (m, 1H), 4.15 (d, J = 5.6 Hz, 2H), 3.58 (s, 3H), 3.01-2.74 (m, 3H), 2.47-2.15 (m, 3H), 1.75 (s, 6H) |
| 435 | 579.1 | $^1H$ NMR (400 MHz, DMSO-$d_6$) δ 12.44 (s, 1H), 8.69 (m, 1H), 8.61 (d, J = 4.8 Hz, 1H), 8.27 (s, 1H), 8.02 (d, J = 7.6 Hz, 1H), 7.88-7.81 (m, 2H), 7.75 (d, J = 8.0 Hz, 1H), 7.66-7.57 (m, 4H), 7.32 (m, 1H), 6.78 (m, 1H), 4.16 (d, J = 6.0 Hz, 2H), 3.58 (s, 3H), 2.62 (d, J = 4.4 Hz, 3H), 1.42-1.39 (m, 2H), 1.29-1.26 (m, 2H) |
| 439 | 593.1 | $^1H$ NMR (400 MHz, DMSO-$d_6$) δ 12.45 (s, 1H), 8.68 (m, 1H), 8.58 (d, J = 5.2 Hz, 1H), 8.21 (s, 1H), 8.02 (d, J = 8.0 Hz, 1H), 7.85 (m, 1H), 7.82 (s, 1H), 7.69 (d, J = 8.0 Hz, 1H), 7.63-7.57 (m, 2H), 7.35 (s, 1H), 7.32 (m, 1H), 6.78 (m, 1H), 4.15 (d, J = 6.0 Hz, 2H), 3.58 (s, 3H), 2.92-2.85 (m, 6H), 1.52-1.49 (m, 2H), 1.37-1.33 (m, 2H) |
| 217 | 557.3 | $^1H$ NMR (400 MHz, DMSO-$d_6$) δ 12.48 (s, 1H), 8.71-8.69 (m, 1H), 8.36 (s, 1H), 7.97 (d, J = 2.4 Hz, 1H), 7.88-7.79 (m, 2H), 7.75-7.73 (m, 1H), 7.70 (s, 1H), 7.47-7.45 (m, 1H), 7.33-7.31 (m, 1H), 6.79 (d, J = 2.4 Hz, 2H), 4.16-4.14 (m, 2H), 3.58 (s, 3H), 1.81 (s, 6H) |

Example 194. Preparation of N-[2-[[4-[6-[(cis)-2,6-dimethyltetrahydropyran-4-yl]-2-pyridyl]thiazol-2-yl]amino]-2-oxo-ethyl]-1-methylsulfonyl-pyrrole-3-carboxamide (Compound 329)

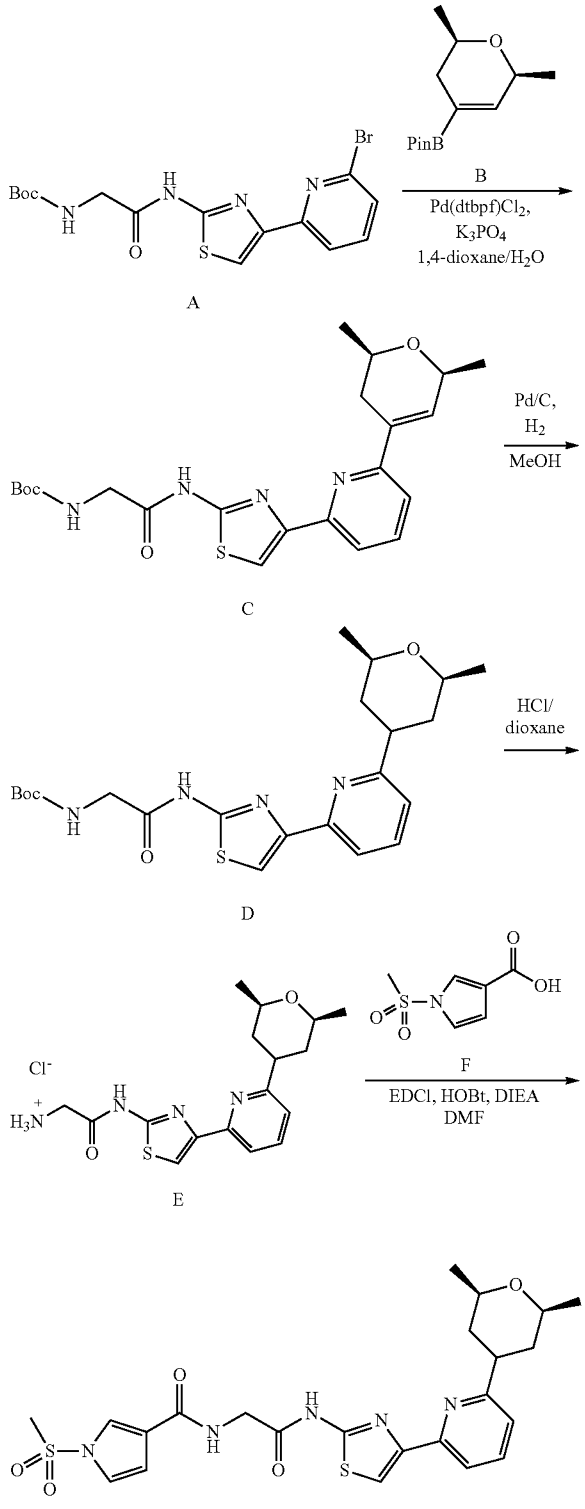

A

C

D

E

Compound 329

Step 1: Preparation of tert-butyl (2-((4-(6-((cis)-2,6-dimethyl-3,6-dihydro-2H-pyran-4-yl)pyridin-2-yl)thiazol-2-yl)amino)-2-oxoethyl)carbamate (intermediate C)

C

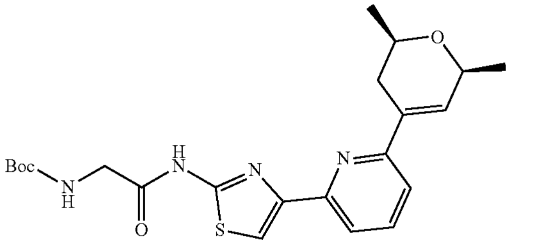

To a solution of 2-cis-2,6-dimethyl-3,6-dihydro-2H-pyran-4-yl)-4,4,5,5-tetramethyl-1,3,2-dioxaborolane (0.277 g, 1.16 mmol), tert-butyl (2-((4-(6-bromopyridin-2-yl)thiazol-2-yl)amino)-2-oxoethyl)carbamate (0.400 g, 0.968 mmol) in a mixture of 1,4-dioxane (4 ml-) and $H_2O$ (1 ml-) was added $K_3PO_4$ (0.411 g, 1.94 mmol), Pd(dtbpf)$Cl_2$ (0.063 g, 0.097 mmol). The mixture was heated to 60° C. and stirred for 1 h. The reaction mixture was subsequently cooled to room temperature and diluted with water (10 mL). The aqueous layer was extracted with ethyl acetate (10 mL×3) and the combined organic layers were dried over $Na_2SO_4$, filtered and concentrated. The crude product was purified by column chromatography ($SiO_2$, petroleum ether/ethyl acetate=100/1 to 1/1) to give Intermediate C (0.400 g, 0.855 mmol, 88.3% yield, 95.0% purity) as a white solid. LCMS (ESI) m/z: $[M+H]^+$=445.2; $^1H$ NMR (400 MHz, $CDCl_3$) δ 10.01-9.67 (m, 1H), 7.85-7.79 (m, 2H), 7.77-7.70 (m, 1H), 7.34 (d, J=7.6 Hz, 1H), 6.68 (s, 1H), 5.22 (s, 1H), 4.50 (d, J=4.0 Hz, 1H), 4.11-4.03 (m, 2H), 2.74-2.63 (m, 1H), 2.47-2.31 (m, 1H), 1.52 (s, 10H), 1.41 (d, J=6.4 Hz, 6H).

Step 2: Preparation of tert-butyl (2-((4-(6-((cis)-2,6-dimethyltetrahydro-2H-pyran-4-yl)pyridin-2-yl)thiazol-2-yl)amino)-2-oxoethyl)carbamate (Intermediate D)

D

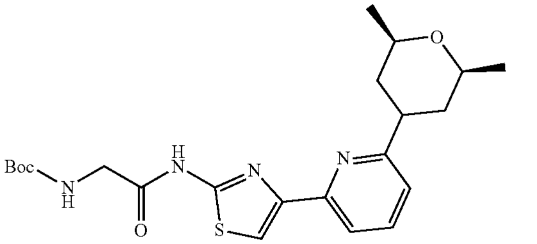

To a solution of Intermediate C (0.050 g, 0.112 mmol) in MeOH (5 mL) was added 10% Pd/C under $N_2$ atmosphere. The suspension was degassed and purged with $H_2$ (3×). The mixture was stirred under $H_2$ (15 Psi) at 25° C. for 12 h and subsequently filtered and concentrated to give Intermediate D (0.050 g) as a brown oil. LCMS (ESI) m/z: $[M+H]^+$=447.2.

Step 3: Preparation of 2-((4-(6-((cis)-2,6-dimethyltetrahydro-2H-pyran-4-yl)pyridin-2-yl)thiazol-2-yl)amino)-2-oxoethan-1-aminium chloride (Intermediate E)

E

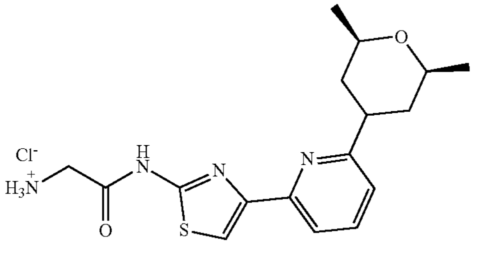

The mixture of Intermediate D (0.020 g, 0.045 mmol) in a solution of 4 M HCl in 1,4-dioxane (0.2 mL) was stirred 30 min at 25° C. The mixture was subsequently concentrated to give Intermediate E (0.017 g) as a white solid. LCMS (ESI) m/z: $[M+H]^+$=347.1.

Step 4: Preparation of N-[2-[[4-[6-[(cis)-2,6-dimethyltetrahydropyran-4-yl]-2-pyridyl]thiazol-2-yl]amino]-2-oxo-ethyl]-1-methylsulfonyl-pyrrole-3-carboxamide (Compound 329)

Compound 329

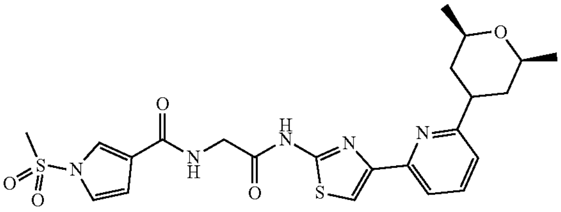

To a solution of Intermediate E (0.015 g, 0.039 mmol), 1-methylsulfonylpyrrole-3-carboxylic acid (0.010 g, 0.051 mmol) in DMF (0.5 mL) was added EDCI (0.015 g, 0.078 mmol), HOBt (0.011 g, 0.078 mmol), and DIEA (0.041 mL, 0.235 mmol,). The mixture was stirred for 1 h and subsequently diluted with MeOH (1 mL). The reaction solution was purified by reversed phase prep-HPLC (mobile phase: [water(0.225% FA)-ACN]; B %: 23%-53%) to give Compound 329 (0.010 g, 0.018 mmol, 46.9% yield, 95.0% purity) as a white solid after lyophilization. LCMS (ESI) m/z: $[M+H]^+$=518.3; $^1$H NMR (400 MHz, DMSO-$d_6$) δ 8.71-8.63 (m, 1H), 7.86-7.75 (m, 4H), 7.37-7.29 (m, 1H), 7.21 (d, J=7.2 Hz, 1H), 6.77 (d, J=3.2 Hz, 1H), 4.14 (d, J=5.6 Hz, 2H), 3.61-3.56 (m, 5H), 3.01 (d, J=12.0 Hz, 1H), 1.87-1.81 (m, 2H), 1.45-1.36 (m, 2H), 1.16 (d, J=6.4 Hz, 6H).

Example 195. Preparation of 1-(3-methyloxetan-3-yl)-N-[2-[[4-[6-(1-methylpyrazol-3-yl)-2-pyridyl]thiazol-2-yl]amino]-2-oxo-ethyl]pyrrole-3-carboxamide (Compound 327)

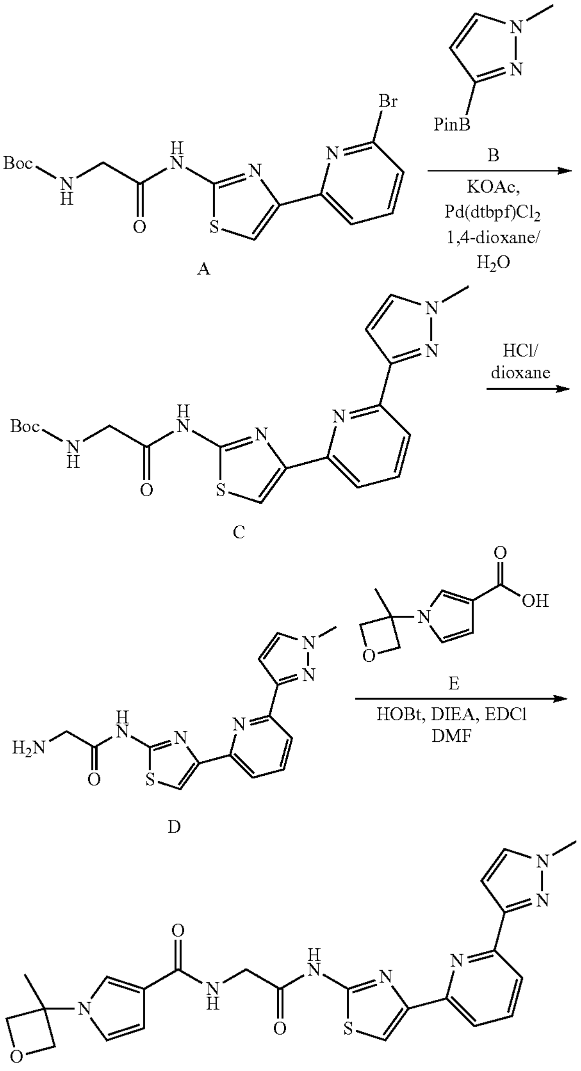

Compound 327

Step 1: Preparation of tert-butyl N-[2-[[4-[6-(1-methylpyrazol-3-yl)-2-pyridyl]thiazol-2-yl]amino]-2-ox o-ethyl]carbamate (Intermediate C)

C

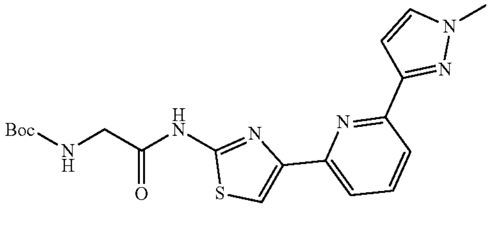

To a mixture of 1-methyl-3-(4,4,5,5-tetramethyl-1,3,2-dioxaborolan-2-yl)pyrazole (0.242 g, 1.16 mmol) and tert-butyl (2-((4-(6-bromopyridin-2-yl)thiazol-2-yl)amino)-2-oxoethyl)carbamate (0.400 g, 0.968 mmol) in a mixture of 1,4-dioxane (4 mL) and water (0.8 mL) was added Pd(dtbpf) $Cl_2$ (0.063 g, 0.097 mmol) and KOAc (0.0285 g, 2.90 mmol) in one portion. The mixture was subsequently stirred at 75° C. After 2 h, the mixture was cooled to room temperature, combined with another batch of equal scale, and added to water (10 mL). The aqueous layer was extracted with ethyl acetate (20 mL×3). The combined organic phases were dried over anhydrous $Na_2SO_4$, filtered and concentrated. The crude product was purified by reversed-phase column to afford Intermediate C (0.300 g, 0.646 mmol, 66.8% yield, 89.3% purity) as a white solid. LCMS (ESI) m/z: $[M+H]^+$= 415.1.

Step 2: Preparation of 2-((4-(6-(1-methyl-1H-pyrazol-3-yl)pyridin-2-yl)thiazol-2-yl)amino)-2-oxo-ethan-1-aminium chloride (Intermediate D)

D

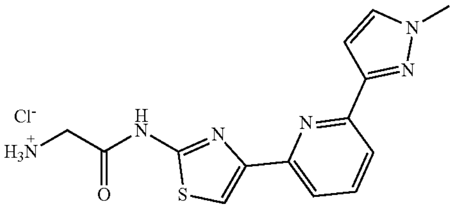

To a solution of Intermediate C (0.300 g, 0.724 mmol) in 1,4-dioxane (2 mL) was added a solution of 4 M HCl in 1,4-dioxane (5.71 mL) at 25° C. After stirring for 15 min, the solution was concentrated to give Intermediate D (0.180 g, 0.513 mmol, 70.89% yield) as a yellow solid, which was used into the next step without further purification. $^1$H NMR (400 MHz, DMSO-$d_6$) δ 13.09-12.54 (m, 1H), 8.51 (s, 2H), 8.04 (s, 1H), 7.97-7.89 (m, 1H), 7.88-7.81 (m, 3H), 6.96 (d, J=2.4 Hz, 1H), 3.99-3.90 (m, 5H).

Step 3: Preparation of 1-(3-methyloxetan-3-yl)-N-[2-[[4-[6-(1-methylpyrazol-3-yl)-2-pyridyl]thiazol-2-yl]amino]-2-oxo-ethyl]pyrrole-3-carboxamide (Compound 327)

Compound 327

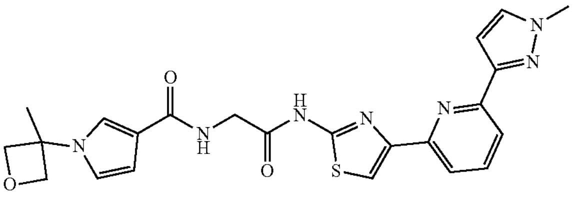

To a solution of Intermediate D (0.080 g, 0.228 mmol), HOBt (0.046 g, 0.342 mmol), EDCI (0.066 g, 0.342 mmol), and 1-(3-methyloxetan-3-yl)pyrrole-3-carboxylic acid (0.050 g, 0.274 mmol) in DMF (4 mL) was added DIEA (0.199 mL, 1.14 mmol). After 3 h, the mixture was combined with another batch of equal scale and added to water (15 mL). The mixture was extracted with ethyl acetate (20 mL×3). The combined organic phase was dried over anhydrous $Na_2SO_4$, filtered and concentrated The residue was purified by reversed-phase HPLC to give Compound 327 (0.072 g, 0.151 mmol, 66.4% yield, 99.7% purity) as a off-white solid after lyopholization. LCMS (ESI) m/z: $[M+H]^+$=478.2; $^1$H NMR (400 MHz, DMSO-$d_6$) δ 12.49-12.19 (m, 1H), 8.29-8.28 (m, 1H), 7.97-7.87 (m, 2H), 7.86-7.78 (m, 3H), 7.57-7.56 (m, 1H), 7.02-7.01 (m, 1H), 6.95 (d, J=2.4 Hz, 1H), 6.58-6.57 (m, 1H), 4.84 (d, J=6.8 Hz, 2H), 4.62 (d, J=6.8 Hz, 2H), 4.12 (d, J=5.6 Hz, 2H), 3.93 (s, 3H), 1.79 (s, 3H).

Example 196. Preparation of N-[2-[[4-[6-(4-methoxy-3-pyridyl)-2-pyridyl]thiazol-2-yl]amino]-2-oxo-ethyl]-1-(3-methyloxetan-3-yl)pyrrole-3-carboxamide (Compound 262)

N-[2-[[4-[6-(4-methoxy-3-pyridyl)-2-pyridyl]thiazol-2-yl]amino]-2-oxo-ethyl]-1-(3-methyloxetan-3-yl)pyrrole-3-carboxamide was synthesized starting from the appropriate common intermediate (tert-butyl (2-((4-(6-bromopyridin-2-yl)thiazol-2-yl)amino)-2-oxoethyl)carbamate) and the corresponding boronic ester utilizing the synthetic protocol described in Example 195.

LCMS (ESI) m/z: $[M+H]^+$=505.0; $^1$H NMR (400 MHz, DMSO-$d_6$) δ 12.42 (s, 1H), 9.19 (s, 1H), 8.82 (d, J=6.8 Hz, 1H), 8.30-8.24 (m, 1H), 8.13 (s, 1H), 8.09-7.98 (m, 3H), 7.96-7.91 (m, 1H), 7.72 (d, J=6.8 Hz, 1H), 7.58-7.54 (m, 1H), 7.03-7.00 (m, 1H), 6.58-6.55 (m, 1H), 4.84 (d, J=6.8 Hz, 2H), 4.63 (d, J=6.8 Hz, 2H), 4.16 (s, 3H), 4.12 (d, J=5.6 Hz, 2H), 1.79 (s, 3H).

Example 197. Preparation of N-(2-((4-(3-((3-methyloxetan-3-yl)ethynyl)phenyl)thiazol-2-yl)amino)-2-oxoethyl)-1-(methylsulfonyl)-1H-pyrrole-3-carboxamide (Compound 361)

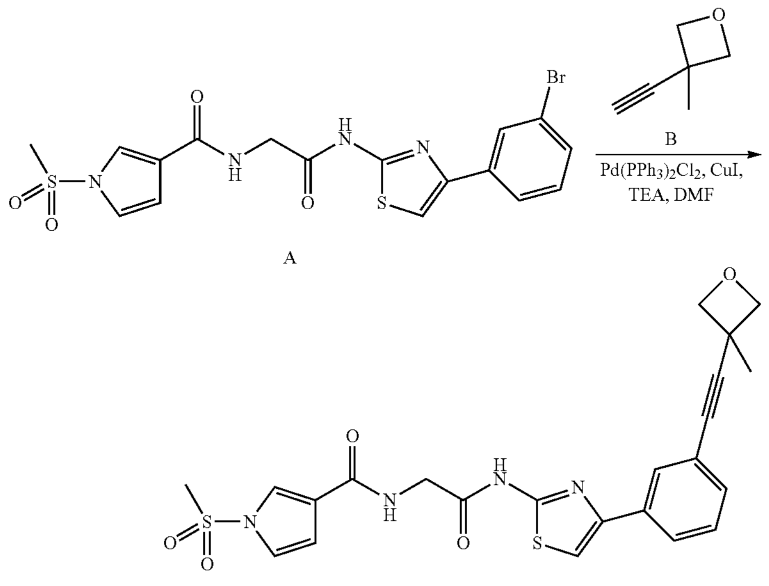

A

Compound 361

To a solution of N-[2-[[4-(3-bromophenyl)thiazol-2-yl]amino]-2-oxo-ethyl]-1-methylsulfonyl-pyrrole-3-carboxamide (0.050 g, 0.103 mmol), CuI (0.002 g, 0.10 mmol), TEA (0.043 mL, 0.310 mmol) in DMF (1 mL) was added $Pd(PPh_3)_2Cl_2$ (0.007 g, 0.010 mmol) and 3-ethynyl-3-methyl-oxetane (0.050 g, 0.0517 mmol). The mixture was stirred at 100° C. for 2 h, subsequently cooled to room temperature and diluted with water (3 mL) and extracted with ethyl acetate (6 mL×2). The combined organic layers were washed with brine (4 mL×2), dried over anhydrous $Na_2SO_4$, filtered and concentrated. The residue was purified by reverse-phase HPLC (0.1% $NH_4OH$) to give Compound 361 (0.046 g, 0.090 mmol, 43.47% yield) as a brown solid. LCMS (ESI) m/z: $[M+H]^+$=499.3; $^1H$ NMR (400 MHz, DMSO-$d_6$) 5=12.26-12.00 (m, 1H), 8.69-8.68 (m, 1H), 7.99 (s, 1H), 7.90 (d, J=7.6 Hz, 1H), 7.85 (s, 1H), 7.75 (s, 1H), 7.48-7.40 (m, 1H), 7.40-7.35 (m, 1H), 7.32-7.31 (m, 1H), 6.77-6.76 (m, 1H), 4.76 (d, J=5.6 Hz, 2H), 4.45 (d, J=5.6 Hz, 2H), 4.14 (d, J=5.6 Hz, 2H), 3.57 (s, 3H), 1.65 (s, 3H).

Example 198. Preparation of Compounds of the Invention

The compounds in Table 20 were synthesized starting from the appropriate common intermediate (N-[2-[[4-(3-bromophenyl)thiazol-2-yl]amino]-2-oxo-ethyl]-1-methylsulfonyl-pyrrole-3-carboxamide) and the corresponding alkyne utilizing the synthetic protocol described in Example 197.

TABLE 20

| Compound # | LC-MS data(m/z) | $^1H$ NMR |
|---|---|---|
| 349 | 485.1 | $^1HNMR$ (400 MHz, DMSO-$d_6$) δ 12.20 (s, 1H), 8.68-8.65 (m, 1H), 7.99 (s, 1H), 7.92-7.89 (m, 1H), 7.84-7.83 (m, 1H), 7.73 (s, 1H), 7.45-7.42 (m, 1H), 7.40-7.37 (m, 1H), 7.31-7.29 (m, 1H), 6.77-6.76 (m, 1H), 4.83-4.80 (m, 2H), 4.64-4.59 (m, 2H), 4.20-4.12 (m, 3H), 3.56 (s, 3H) |
| 363 | 523.2 | $^1H$ NMR (400 MHz, DMSO-$d_6$) δ 12.39 (s, 1H), 8.68-8.66 (m, 1H), 7.98 (s, 1H), 7.91 (d, J = 8.0 Hz, 1H), 7.85-7.83 (m, 1H), 7.76 (s, 1H), 7.43 (d, J = 8.0 Hz, 1H), 7.40-7.36 (m, 1H), 7.32-7.30 (m, 1H), 6.77 (m, 1H), 4.14 (d, J = 5.6 Hz, 2H), 3.57 (s, 3H), 3.33 (s, 3H), 1.49 (s, 6H) |
| 426 | 487.2 | $^1H$ NMR (400 MHz, DMSO-$d_6$) δ 12.36 (m, 1H), 8.68-8.66 (m, 1H), 7.95 (s, 1H), 7.88 (d, J = 8.0 Hz, 1H), 7.86-7.82 (m, 1H), 7.74 (s, 1H), 7.45-7.40 (m, 1H), 7.35-7.29 (m, 2H), 6.77 (m, 1H), 5.47 (s, 1H), 4.14 (d, J = 5.6 Hz, 2H), 3.57 (s, 3H), 1.48 (s, 6H) |

Example 199. Preparation of 1-(tert-butyl)-N-(2-((4-(6-(3-methoxy-3-methylbut-1-yn-1-yl)pyridin-2-yl)thiazol-2-yl)amino)-2-oxoethyl)-1H-pyrrole-3-carboxamide (Compound 362)

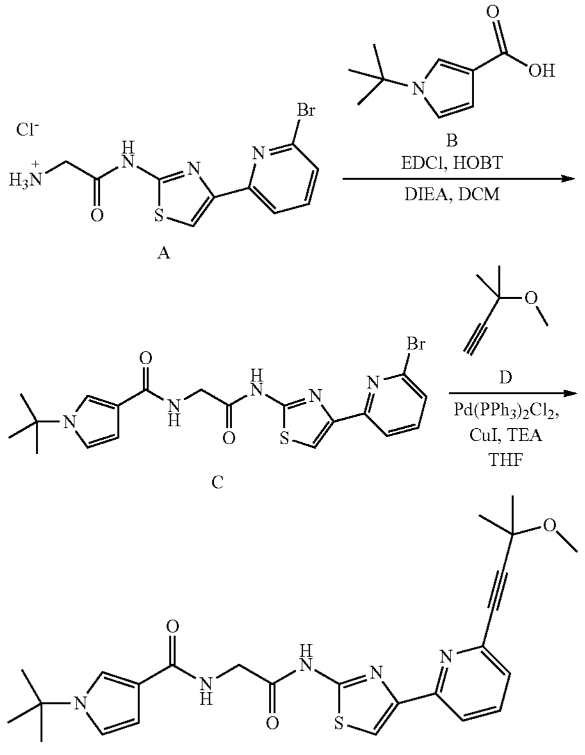

Compound 362

Step 1: Preparation of N-(2-((4-(6-bromopyridin-2-yl)thiazol-2-yl)amino)-2-oxoethyl)-1-(tert-butyl)-1H-pyrrole-3-carboxamide (Intermediate C)

C

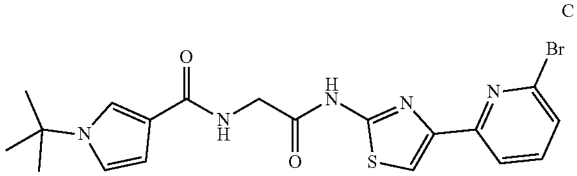 [SMILES: CC(C)(C)n1ccc(C(=O)NCC(=O)Nc2nc(-c3cccc(Br)n3)cs2)c1]

To a solution of 1-tert-butylpyrrole-3-carboxylic acid (0.258 g, 1.54 mmol), EDCI (0.329 g, 1.72 mmol), HOBt (0.232 g, 1.72 mmol), DIEA (1.79 mL, 10.30 mmol) in dichloromethane (12 mL) was added Intermediate A (0.600 g, 1.72 mmol). The reaction mixture was stirred at 25° C. for 2 h and subsequently concentrated. The resulting oil was diluted with water (60 mL) and extracted with ethyl acetate (35 mL×2). The combined organic layers were washed with brine (30 mL×2), dried over $Na_2SO_4$, filtered and concentrated. The resulting solids were triturated with MTBE (20 mL), filtered, and the solids were washed with additional MTBE. The resulting solids were dried to give Intermediate C (0.500 g, 1.06 mmol, 61.76% yield) as a white solid. LCMS (ESI) m/z: $[M+H]^+$=463.9.

Step 2: Preparation 1-(tert-butyl)-N-(2-((4-(6-(3-methoxy-3-methylbut-1-yn-1-yl)pyridin-2-yl)thiazol-2-yl)amino)-2-oxoethyl)-1H-pyrrole-3-carboxamide (Compound 362)

Compound 362

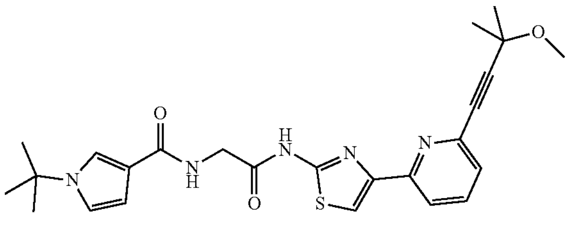

To a mixture of Intermediate C (0.160 g, 0.346 mmol), $Pd(PPh_3)_2Cl_2$ (0.024 g, 0.035 mmol), CuI (0.007 g, 0.035 mmol), TEA (0.145 mL, 1.04 mmol) in DMF (3 mL) was added 3-methoxy-3-methyl-but-1-yne (0.085 mL, 1.73 mmol) under a constant stream of $N_2$ (g). The resulting mixture was stirred at 100° C. After 3 h, the mixture was cooled to ambient temperatures, filtered through a pad of silica with dichloromethane and concentrated. The residue was purified by reversed phase HPLC (mobile phase: [water (0.05% ammonia hydroxide v/v)-ACN]; B %: 38%-58%), to give Compound 362 (0.062 g, 0.124 mmol, 35.86% yield) as a off-white solid after lyophilization. LCMS (ESI) m/z: $[M+H]^+$=480.4; $^1H$ NMR (400 MHz, DMSO-$d_6$) δ 12.53-11.96 (m, 1H), 8.16-8.13 (m, 1H), 7.93-7.87 (m, 2H), 7.81 (s, 1H), 7.52-7.51 (m, 1H), 7.48-7.44 (m, 1H), 6.97-6.95 (m, 1H), 6.49-6.47 (m, 1H), 4.08 (d, J=5.6 Hz, 2H), 3.37-3.35 (m, 3H), 1.51-1.48 (m, 15H).

Example 200. Preparation of 1-tert-butyl-N-[2-[[4-[6-(2-methyltriazol-4-yl)-2-pyridyl]thiazol-2-yl]amino]-2-oxo-ethyl]pyrrole-3-carboxamide (Compound 382)

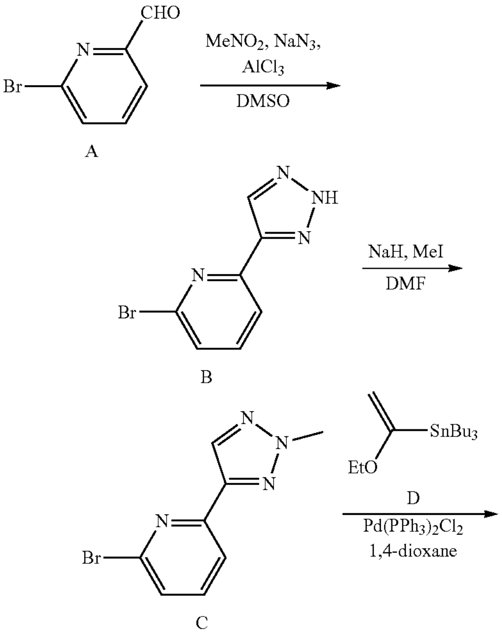

-continued

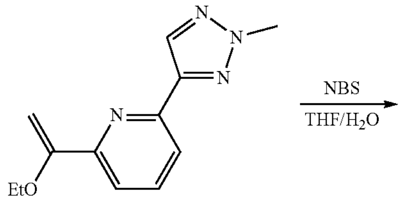

E

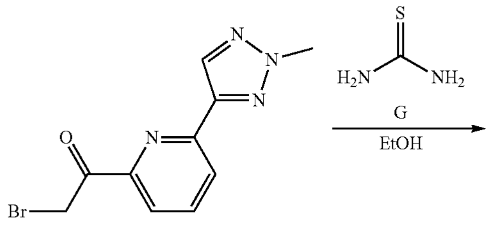

F

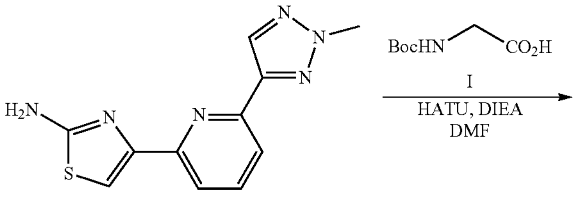

H

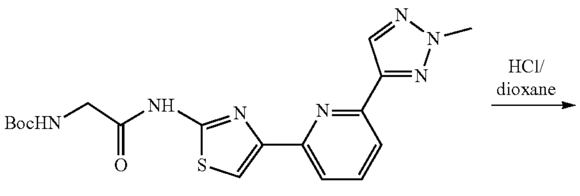

J

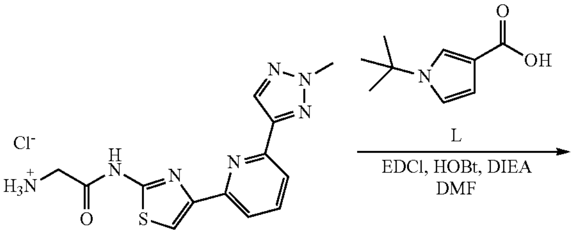

K

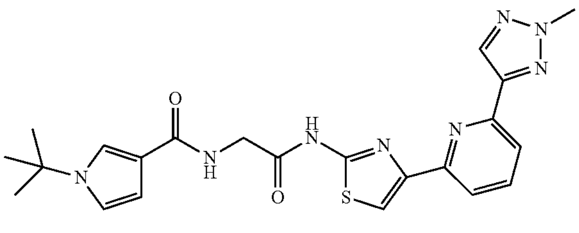

Compound 382

Step 1: Preparation of 2-bromo-6-(2H-triazol-4-yl)pyridine (Intermediate B)

B

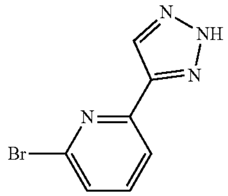

To a solution of 6-bromopyridine-2-carbaldehyde (5.00 g, 26.88 mmol), $NaN_3$ (2.10 g, 32.26 mmol), and nitromethane (2.46 g, 40.32 mmol, 2.18 mL) in DMSO (60 mL) was added $AlCl_3$ (0.358 g, 2.69 mmol, 146.90 uL) in portions at 25° C. After complete addition of $AlCl_3$, the mixture was stirred at 70° C. The reaction was allowed to stir for 12 h and subsequently cooled to ambient temperatures and diluted with water (100 mL). The mixture was extracted with ethyl acetate (50 mL×3). The combined organic layers were dried over $Na_2SO_4$, filtered and concentrated. The residue was purified by flash silica gel chromatography (ethyl acetate/petroleum ether=0:1 to 1:1) to give Intermediate B (2.50 g, 11.11 mmol, 41.33% yield) as a yellow solid. LCMS (ESI) m/z: $[M+H]^+$=225.0; $^1H$ NMR (400 MHz, DMSO-$d_6$) δ 8.03-7.99 (m, 1H), 7.91-7.76 (m, 2H), 7.67-7.55 (m, 2H).

Step 2: Preparation of 2-bromo-6-(2-methyltriazol-4-yl)pyridine (Intermediate C)

C

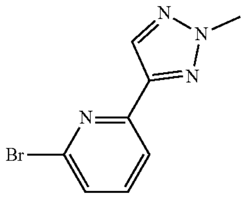

To a solution of Intermediate B (2.20 g, 9.78 mmol) in DMF (20 mL) was added NaH (0.587 g, 14.66 mmol, 60% purity) in portions at 25° C. The mixture was stirred for 30 min, followed by addition of MeI (0.730 mL, 11.73 mmol). After an additional 30 min, the reaction mixture was diluted with water (30 mL) and extracted with ethyl acetate (20 mL×3). The combined organic layers were washed with brine (10 mL×3), dried over $Na_2SO_4$, filtered and concentrated. The residue was purified by flash silica gel chromatography (ethyl acetate/petroleum ether=0:1 to 1:3). The appropriate fractions were collected to give Intermediate C (1.20 g, 5.02 mmol, 51.35% yield) as a white solid. LCMS (ESI) m/z: $[M+H]^+$=239.1.; 1H NMR (400 MHz, $CDCl_3$) δ 8.16 (s, 1H), 7.85 (d, J=7.6 Hz, 1H), 7.63-7.58 (m, 1H), 7.43 (d, J=8.0 Hz, 1H), 4.27 (s, 3H).

Additionally, 2-bromo-6-(1-methyltriazol-4-yl)pyridine (0.700 g, 2.93 mmol, 29.95% yield) was also isolated separately as a white solid.

Step 3: Preparation of 2-(1-ethoxyvinyl)-6-(2-methyltriazol-4-yl)pyridine (Intermediate E)

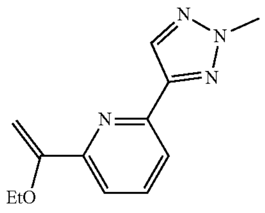

E

A mixture of Intermediate C (1.10 g, 4.60 mmol), tributyl (1-ethoxyvinyl)stannane (4.66 mL, 13.80 mmol), $Pd(PPh_3)_2Cl_2$ (0.323 g, 0.461 mmol) in 1,4-dioxane (10 mL) was stirred at 100° C. for 2 h. The reaction mixture was subsequently cooled to ambient temperatures, diluted with KF (10 mL), and extracted with ethyl acetate (10 mL×3). The combined organic layers were dried over $Na_2SO_4$, filtered and concentrated under reduced pressure to give Intermediate E (1.20 g) as a brown oil. LCMS (ESI) m/z: $[M+H]^+$=231.1.

Step 4: Preparation of 2-bromo-1-[6-(2-methyltriazol-4-yl)-2-pyridyl]ethenone (Intermediate F)

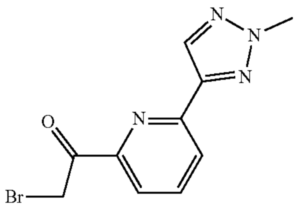

F

A mixture of Intermediate E (1.10 g, 4.78 mmol), NBS (1.70 g, 9.55 mmol) in a mixture of THF (20 mL) and $H_2O$ (1 mL) was stirred at 25° C. After 1 h, the reaction mixture was diluted with water (20 mL) and extracted with ethyl acetate (20 mL×3). The combined organic layers were dried over $Na_2SO_4$, filtered and concentrated. The residue was purified by flash silica gel chromatography (ethyl acetate/petroleum ether=0:1 to 1:3) and concentrated to give Intermediate F (1.00 g, 3.56 mmol, 74.47% yield) as a yellow oil. $^1H$ NMR (400 MHz, $CDCl_3$) δ 8.20 (s, 1H), 8.16-8.13 (m, 1H), 8.06-8.03 (m, 1H), 7.97-7.92 (m, 1H), 4.95 (s, 2H), 4.29 (s, 3H).

Step 5: Preparation of 4-[6-(2-methyltriazol-4-yl)-2-pyridyl]thiazol-2-amine (Intermediate H)

H

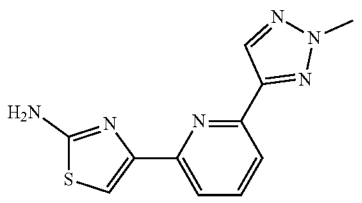

A mixture of Intermediate F (0.900 g, 3.20 mmol), thiourea (0.268 g, 3.52 mmol) in EtOH (10 mL) was stirred at 80° C. After 12 h, the resulting solids were filtered and washed with EtOH to give Intermediate H (0.800 g, 3.10 mmol, 96.74% yield) as a white solid. LCMS (ESI) m/z: $[M+H]^+$=259.1; $^1H$ NMR (400 MHz, DMSO-$d_6$) δ 8.47 (s, 1H), 8.05-7.99 (m, 1H), 7.96-7.92 (m, 1H), 7.88 (d, J=7.6 Hz, 1H), 7.67 (s, 1H), 4.26 (s, 3H).

Step 6: Preparation of tert-butyl N-[2-[[4-[6-(2-methyltriazol-4-yl)-2-pyridyl]thiazol-2-yl]amino]-2-oxo-ethyl]carbamate (Intermediate J)

J

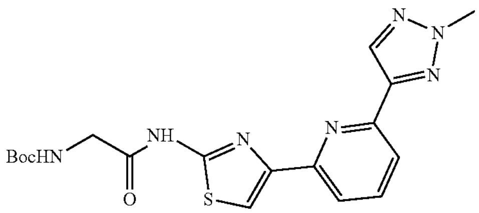

A mixture of Intermediate H (0.200 g, 0.774 mmol), N-Boc-glycine (0.271 g, 1.55 mmol), DIEA (0.405 mL, 2.32 mmol), HATU (0.589 g, 1.55 mmol) in DMF (2 mL) was stirred at 25° C. for 1 h. The reaction mixture was diluted with water (10 mL) and extracted with ethyl acetate (10 mL×3). The combined organic layers were dried over $Na_2SO_4$, filtered, and concentrated. The resulting solids were triturated with ethyl acetate (5 mL), stirred, filtered and dried to give Intermediate J (0.180 g, 0.433 mmol, 55.95% yield) as a white solid. LCMS (ESI) m/z: $[M+H]^+$=416.1; $^1H$ NMR (400 MHz, DMSO-$d_6$) δ 8.39 (s, 1H), 8.04 (s, 1H), 8.02-7.97 (m, 1H), 7.91-7.89 (m, 1H), 7.85-7.82 (m, 1H), 7.21-7.17 (m, 1H), 4.26 (s, 3H), 3.89 (d, J=6.0 Hz, 2H), 1.41 (s, 9H).

Step 7: Preparation of 2-((4-(6-(2-methyl-2H-1,2,3-triazol-4-yl)pyridin-2-yl)thiazol-2-yl)amino)-2-oxoethan-1-aminium chloride (Intermediate K)

K

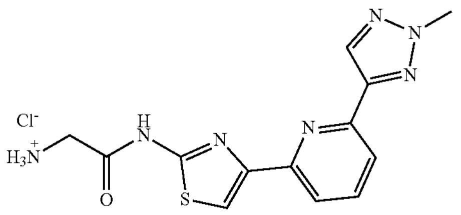

A solution of tert-butyl N-[2-[[4-[6-(2-methyltriazol-4-yl)-2-pyridyl]thiazol-2-yl]amino]-2-oxo-ethyl]carbamate (0.180 g, 0.433 mmol) in 1,4-dioxane (1 mL) was added a solution of 4 M HCl in 1,4-dioxane (1.08 mL). The reaction mixture was stirred at 25° C. for 12 h and subsequently concentrated to give Intermediate K (0.160 g) as a white solid. LCMS (ESI) m/z: $[M+H]^+$=316.1.

Step 8: Preparation of 1-tert-butyl-N-[2-[[4-[6-(2-methyltriazol-4-yl)-2-pyridyl]thiazol-2-yl]amino]-2-oxo-ethyl]pyrrole-3-carboxamide (Compound 382)

Compound 382

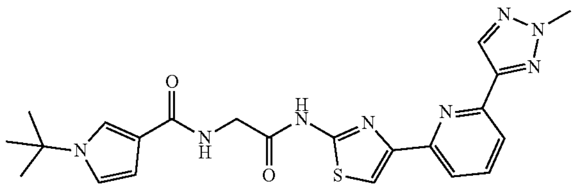

A mixture of Intermediate K (0.160 g, 0.455 mmol), 1-tert-butylpyrrole-3-carboxylic acid (0.114 g, 0.682 mmol), DIEA (0.396 mL, 2.27 mmol), EDCI (0.174 g, 0.910 mmol) and HOBt (0.123 g, 0.910 mmol) in DMF (2 mL) was stirred at 25° C. for 12 h. The reaction mixture was subsequently diluted with water (10 mL) and extracted with ethyl acetate (10 mL×3). The combined organic layers were washed with brine (10 mL×3), dried over $Na_2SO_4$, filtered and concentrated. The resulting solids were triturated with ethyl acetate (5 mL), filtered, and dried to give Compound 382 (0.103 g, 0.216 mmol, 47.46% yield, 97.33% purity) as a white solid. LCMS (ESI) m/z: $[M+H]^+$=465.2; $^1$H NMR (400 MHz, DMSO-$d_6$) δ 12.46-12.24 (m, 1H), 8.39 (s, 1H), 8.22-8.18 (m, 1H), 8.03 (s, 1H), 8.02-7.96 (m, 1H), 7.94-7.89 (m, 1H), 7.85-7.82 (m, 1H), 7.54-7.52 (m, 1H), 6.99-6.97 (m, 1H), 6.50-6.48 (m, 1H), 4.26 (s, 3H), 4.12 (d, J=5.6 Hz, 2H), 1.50 (s, 9H).

Example 201. Preparation of Compounds of the Invention

The following compounds in Table 21 were synthesized starting from utilizing corresponding α-bromo-ketone or α-chloro-ketone, amino acid, and heterocyclic carboxylic acid, and SFC separation if necessary utilizing the synthetic protocol described in Example 200.

TABLE 21

| Compound # | LC-MS data(m/z) | $^1$H NMR |
|---|---|---|
| 383 | 453.0 | $^1$H NMR (400 MHz, DMSO-$d_6$) δ 12.28-12.19 (m, 1H), 8.20-8.16 (m, 1H), 7.61 (s, 1H), 7.55-7.50 (m, 1H), 7.24-7.18 (m, 1H), 7.10-7.04 (m, 1H), 6.99-6.95 (m, 1H), 6.50-6.45 (m, 1H), 4.13-4.04 (m, 2H), 3.11 (s, 3H), 2.75-2.69 (m, 2H), 1.93-1.83 (m, 2H), 1.49 (s, 9H) |
| 394 | 475.1 | $^1$H NMR (400 MHz, DMSO-$d_6$) δ 12.39-12.23 (m, 1H), 8.71-8.64 (m, 1H), 7.87-7.83 (m, 1H), 7.62 (s, 1H), 7.34-7.30 (m, 1H), 7.24-7.19 (m, 1H), 7.09-7.05 (m, 1H), 6.80-6.75 (m, 1H), 4.16-4.10 (m, 2H), 3.56 (s, 3H), 3.39-3.34 (m, 2H), 3.14-3.11 (m, 3H), 2.75-2.69 (m, 2H), 1.93-1.84 (m, 2H) |
| 395 | 440.2 | $^1$H NMR (400 MHz, DMSO-$d_6$) δ 12.28 (br s, 1H), 8.18-8.17 (m, 1H), 7.92-7.81 (m, 1H), 7.75-7.68 (m, 2H), 7.67-7.61 (m, 1H), 7.52-7.51 (m, 1H), 6.97-6.96 (m, 1H), 6.48-6.47 (m, 1H), 6.17 (s, 1H), 4.10 (d, J = 6.0 Hz, 2H), 1.50 (s, 9H), 1.37-1.30 (m, 2H), 1.17-1.07 (m, 2H) |
| 142 | 435.3 | $^1$H NMR (400 MHz, DMSO-$d_6$) δ 9.55 (s, 1H), 9.27 (s, 1H), 8.48 (s, 1H), 8.33-8.31 (m, 1H), 8.17 (d, J = 8.8 Hz, 1H), 7.97 (s, 1H), 7.90 (s, 1H), 7.53-7.51 (m, 1H), 6.98-6.96 (m, 1H), 6.48-6.47 (m, 1H), 4.04 (d, J = 5.6 Hz, 2H), 1.50 (s, 9H) |
| 470 | 479.2 | $^1$H NMR (400 MHz, DMSO-$d_6$) δ 12.42 (s, 1H), 8.39 (s, 1H), 8.30-8.26 (m, 1H), 8.04 (s, 1H), 8.02-7.96 (m, 1H), 7.94-7.89 (m, 1H), 7.85-7.82 (m, 1H), 7.59-7.57 (m, 1H), 7.04-7.01 (m, 1H), 6.59-6.57 (m, 1H), 4.85 (d, J = 6.8 Hz, 2H), 4.63 (d, J = 6.8 Hz, 2H), 4.26 (s, 3H), 4.13 (d, J = 6.0 Hz, 2H), 1.80 (s, 3H) |
| 481 | 474.0 | $^1$H NMR (400 MHz, DMSO-$d_6$) δ 12.36 (s, 1H), 8.21-8.19 (m, 1H), 7.90-7.76 (m, 3H), 7.53-7.52(m, 1H), 7.31-7.29 (m, 1H), 6.98-6.97 (m, 1H), 6.49-6.47 (m, 1H), 4.10 (d, J = 6.0 Hz, 2H), 3.63-3.49 (m, 1H), 3.05-2.86 (m, 4H), 1.50 (s, 9H) |
| 488 | 479.1 | $^1$H NMR (400 MHz, DMSO-$d_6$) δ 12.42-12.33 (m, 1H), 8.39 (s, 1H), 8.04 (s, 1H), 8.02-7.96 (m, 2H), 7.95-7.89 (m, 1H), 7.85-7.82 (m, 1H), 7.61-6.59 (m, 1H), 6.99-6.96 (m, 1H), 6.52-6.50 (m, 1H), 4.68-4.63 (m, 1H), 4.26 (s, 3H), 1.50 (s, 9H), 1.43 (d, J = 7.2 Hz, 3H) |
| 495 | 454.1 | $^1$H NMR (400 MHz, DMSO-$d_6$) δ 12.33 (s, 1H), 12.21 (s, 1H), 8.18 (s, 1H), 7.86-7.67 (m, 3H), 7.52-7.51 (m, 1H), 7.44 (d, J = 8.0 Hz, 1H), 7.02-6.93 (m, 1H), 6.51-6.43 (m, 1H), 4.09 (d, J = 5.2 Hz, 2H), 3.80 (s, 2H), 1.49 (s, 9H), 1.21-1.16 (m, 2H), 0.98-0.90 (m, 2H) |
| 514 | 468.1 | $^1$H NMR (400 MHz, Methanol-$d_4$) δ 7.86-7.82 (m, 2H), 7.75-7.73 (m, 1H), 7.60-7.59 (m, 1H), 7.19 (d, J = 7.6 Hz, 1H), 6.97-6.96 (m, 1H), 6.59-6.58 (m, 1H), 4.38-4.30 (m, 1H), 4.25 (s, 2H), 3.68-3.64 (m, 1H), 3.31 (s, 3H), 2.63-2.60 (m, 2H), 2.46-2.43 (m, 2H), 1.58 (s, 9H) |

TABLE 21-continued

| Compound # | LC-MS data(m/z) | $^1$H NMR |
|---|---|---|
| 515 | 468.1 | $^1$H NMR (400 MHz, Methanol-$d_4$) δ 7.86-7.84 (m, 2H), 7.76-7.72 (m, 1H), 7.60-7.59 (m, 1H), 7.20 (d, J = 7.6 Hz, 1H), 6.97-6.96 (m, 1H), 6.60-6.59 (m, 1H), 4.25 (s, 2H), 3.99-3.94 (m, 1H), 3.32 (s, 3H), 3.20-3.19 (m, 1H), 2.73-2.68 (m, 2H), 2.29-2.26 (m, 2H), 1.58 (s, 9H) |
| 545 | 523.0 | $^1$H NMR (400 MHz, DMSO-$d_6$) δ 12.53 (br s, 1H), 8.50 (d, J = 7.2 Hz, 1H), 7.98-7.97 (m, 1H), 7.90-7.88 (m, 1H), 7.64 (s, 1H), 7.50-7.49 (m, 1H), 7.31-7.22 (m, 2H), 6.79-6.78 (m, 1H), 4.95-4.92 (m, 1H), 4.03-4.00 (m, 1H), 3.78-3.65 (m, 2H), 3.56 (s, 3H), 3.31 (s, 3H), 0.88-0.73 (m, 4H) |
| 593 | 551.1 | $^1$H NMR (400 MHz, DMSO-$d_6$) δ 12.59 (s, 1H), 8.51 (d, J = 7.2 Hz, 1H), 7.99-7.95 (m, 2H), 7.84-7.81 (m, 1H), 7.76 (s, 1H), 7.36 (d, J = 9.2 Hz, 1H), 7.31-7.28 (m, 1H), 6.80-6.78 (m, 1H), 4.95-4.89 (m, 1H), 3.74-3.68 (m, 2H), 3.56 (s, 3H), 3.31 (s, 3H) |
| 611 | 509.2 | $^1$H NMR (400 MHz, DMSO-$d_6$) δ 13.37-11.77 (s, 1H), 9.47 (d, J = 2.4 Hz, 1H), 8.98 (d, J = 2.0 Hz, 1H), 8.00 (s, 1H), 7.96 (d, J = 7.2 Hz, 1H), 7.76 (d, J = 7.6 Hz, 1H), 7.64-7.63 (m, 1H), 6.98-6.97 (m, 1H), 6.73 (d, J = 7.6 Hz, 1H), 6.52-6.51 (m, 1H), 4.95-4.90 (m, 1H), 3.77-3.69 (m, 2H), 3.55 (s, 3H), 3.32 (s, 3H), 1.50 (s, 9H) |
| 612 | 497.1 | $^1$H NMR (400 MHz, DMSO-$d_6$) δ 12.46 (s, 1H), 8.71-8.88 (m, 1H), 7.84 (s, 1H), 7.74-7.71 (m, 1H), 7.53 (d, J = 2.0 Hz, 1H), 7.32-7.27 (m, 2H), 6.77 (d, J = 1.6 Hz, 1H), 4.23 (s, 1H), 4.14 (d, J = 5.6 Hz, 2H), 3.57 (s, 3H), 0.81 (s, 2H), 0.70-0.62 (m, 2H) |
| 613 | 541.1 | $^1$H NMR (400 MHz, $CDCl_3$) δ 10.26 (br s, 1H), 7.77-7.76 (m, 1H), 7.73-7.67 (m, 1H), 7.36 (d, J = 2.4 Hz, 1H), 7.16-7.15 (m, 1H), 6.99-6.92 (m, 2H), 6.73-6.72 (m, 1H), 5.07-5.03 (m, 1H), 4.26-4.23 (m, 1H), 4.05-4.01 (m, 1H), 3.70-3.66 (m, 1H), 3.48 (s, 3H), 3.24 (s, 3H), 0.94-0.90 (m, 2H), 0.65-0.60 (m, 2H) |
| 693 | 520.0 | $^1$H NMR (400 MHz, DMSO-$d_6$) δ 12.47 (s, 1H), 8.68 (d, J = 6.0 Hz, 1H), 8.38 (s, 1H), 8.28 (s, 1H), 7.89 (s, 1H), 7.84 (d, J = 2.0 Hz, 1H), 7.32-7.30 (m, 1H), 6.78-6.76 (m, 1H), 4.33 (d, J = 11.6 Hz, 2H), 4.14 (d, J = 6.0 Hz, 2H), 3.67-3.57 (m, 2H), 3.57 (s, 3H), 2.54 (s, 2H), 1.18 (d, J = 6.0 Hz, 6H) |
| 705 | 498.1 | $^1$H NMR (400 MHz, DMSO-$d_6$) δ 12.41 (s, 1H), 8.39 (s, 1H), 8.29 (s, 1H), 8.18 (d, J = 6.0 Hz, 1H), 7.89 (s, 1H), 7.52 (d, J = 2.0 Hz, 1H), 6.98 (t, J = 2.8 Hz, 1H), 6.49-6.47 (m, 1H), 4.33 (d, J = 11.6 Hz, 2H), 4.09 (d, J = 6.0 Hz, 2H), 3.68-3.62 (m, 2H), 2.53 (s, 2H), 1.50 (s, 9H), 1.19 (d, J = 6.0 Hz, 6H) |
| 707 | 564.1 | $^1$H NMR (400 MHz, DMSO-$d_6$) δ 12.58 (s, 1H), 8.51 (d, J = 7.2 Hz, 1H), 8.39 (s, 1H), 8.29 (s, 1H), 7.98 (d, J = 2.0 Hz, 1H), 7.91 (s, 1H), 7.31-7.28 (m, 1H), 6.80-6.78 (m, 1H), 4.95-4.87 (m, 1H), 4.33 (d, J = 11.6 Hz, 2H), 3.74-3.69 (m, 2H), 3.67-3.62 (m, 2H), 3.57 (s, 3H), 3.31 (s, 3H), 2.52 (s, 2H), 1.18 (d, J = 6.4 Hz, 6H) |
| 723 | 597.1 | $^1$H NMR (400 MHz, DMSO-$d_6$) δ 12.54 (s, 1H), 8.54 (d, J = 6.8 Hz, 1H), 8.03-7.96 (m, 1H), 7.89 (s, 1H), 7.32-7.27 (m, 1H), 7.21 (d, J = 1.6 Hz, 1H), 6.92 (d, J = 1.6 Hz, 1H), 6.82-6.75 (m, 1H), 4.95-4.82 (m, 1H), 4.30 (d, J = 12.4 Hz, 2H), 3.76-3.68 (m, 2H), 3.64-3.54 (m, 5H), 3.31 (s, 3H), 2.46 (s, 2H), 1.17 (d, J = 6.0 Hz, 6H) |
| 734 | 577.2 | $^1$H NMR (400 MHz, Methanol-$d_4$) δ 7.90-7.89 (m, 1H), 7.66 (s, 1H), 7.26-7.25 (m, 1H), 7.22 (s, 1H), 6.83-6.82 (m, 1H), 6.56 (s, 1H), 4.97-4.94 (m, 1H), 4.21 (d, J = 11.2 Hz, 2H), 3.84-3.81 (m, 2H), 3.72-3.71 (m, 2H), 3.42 (s, 3H), 3.37 (s, 3H), 2.48-2.30 (m, 2H), 2.31 (s, 3H), 1.25 (d, J = 6.4 Hz, 6H) |
| 740 | 566.2 | $^1$H NMR (400 MHz, DMSO-$d_6$) δ 12.40 (s, 1H), 8.14 (d, J = 7.2 Hz, 1H), 7.80-7.79 (m, 1H), 7.74 (s, 1H), 7.14-7.13 (m, 2H), 6.64-6.63 (m, 2H), 4.94-4.89 (m, 1H), 4.25-4.22 (m, 2H), 3.72-3.69 (m, 2H), 3.63-3.60 (m, 2H), 3.30 (s, 3H), 2.42-2.36 (m, 2H), 2.28 (s, 3H), 1.95 (s, 6H), 1.18 (d, J = 6.4 Hz, 6H) |
| 817 | 567.2 | $^1$H NMR (400 MHz, $CDCl_3$) δ 9.89 (s, 1H), 7.77 (d, J = 1.6 Hz, 1H), 7.72-7.69 (m, 2H), 7.19 (s, 1H), 6.96 (d, J = 2.4 Hz, 1H), 6.42 (s, 1H), 5.03-5.00 (m, 1H), 4.15 (d, J = 11.6 Hz, 2H), 4.08-4.05 (m, 1H), 3.76-3.73 (m, 3H), 3.51 (s, 3H), 2.57-2.51 (m, 2H), 2.32 (s, 3H), 2.07 (s, 6H), 1.30 (s, 3H), 1.29 (s, 3H) |
| 818 | 567.3 | $^1$H NMR (400 MHz, Methanol-$d_4$) δ 8.06-8.03 (m, 2H), 7.66 (s, 1H), 7.22 (s, 1H), 6.56 (s, 1H), 4.95-4.93 (m, 1H), 4.22 (d, J = 11.6 Hz, 2H), 3.90-3.89 (m, 1H), 3.85-3.78 (m, 1H), 3.73-3.71 (m, 2H), 3.42 (s, 3H), 2.48-2.42 (m, 2H), 2.31 (s, 3H), 2.05 (s, 6H), 1.25 (d, J = 6.0 Hz, 6H) |

Example 202. Preparation of Compounds of the Invention

The compounds in Table 22 below were synthesized starting from the appropriate common intermediate ([tert-butyl N-[2-[[4-(3-bromophenyl)thiazol-2-yl]amino]-2-oxo-ethyl]carbamate]) and utilizing the synthetic protocol described in Example 10 following Scheme 10 below.

Scheme 10

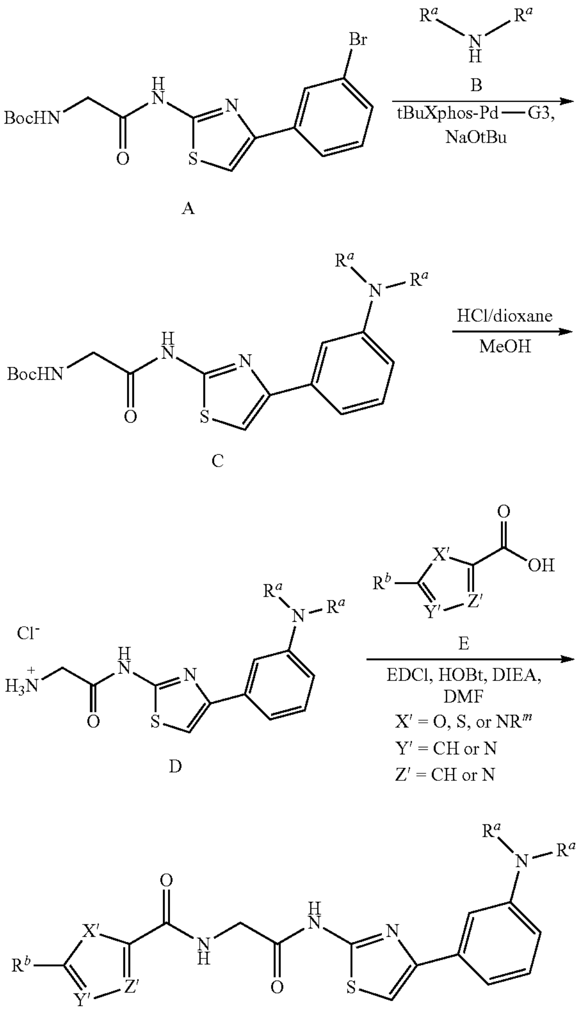

TABLE 22

| Compound # | LC-MS data(m/z) | $^1$H NMR |
|---|---|---|
| 820 | 456.2 | $^1$H NMR (400 MHz, DMSO-d$_6$) δ 12.53-12.33 (m, 1H), 9.00-8.86 (m, 1H), 7.84-7.81 (m, 1H), 7.57-7.53 (m, 1H), 7.22-7.17 (m, 2H), 6.96-6.92 (m, 1H), 6.39-6.34 (m, 1H), 4.20-4.14 (m, 2H), 3.86-3.79 (m, 4H), 2.33-2.32 (m, 2H), 1.39 (s, 9H) |
| 823 | 498.3 | $^1$H NMR (400 MHz, DMSO-d$_6$) δ 12.37 (s, 1H), 9.01 (t, J = 6.0 Hz, 1H), 7.58 (s, 1H), 7.43 (t, J = 2.0 Hz, 1H), 7.31 (dt, J = 7.6, 1.3 Hz, 1H), 7.24 (t, J = 7.9 Hz, 1H), 7.11 (s, 1H), 6.96-6.82 (m, 1H), 4.14 (d, J = 6.0 Hz, 2H), 3.70 (dqd, J = 12.5, 6.0, 2.1 Hz, 2H), 3.65-3.54 (m, 2H), 2.27 (dd, J = 11.9, 10.3 Hz, 2H), 1.30 (s, 9H), 1.16 (d, J = 6.2 Hz, 6H) |

Example 203. Preparation of Compounds of the Invention

The following compounds in Table 23 below were synthesized starting from the appropriate starting 6-member heterocyclic carboxylic acid, amine, and 5-member heterocyclic carboxylic acid following the synthetic route shown in Scheme 11 below. Where appropriate SFC purification was used to separate enantiomers.

Scheme 11

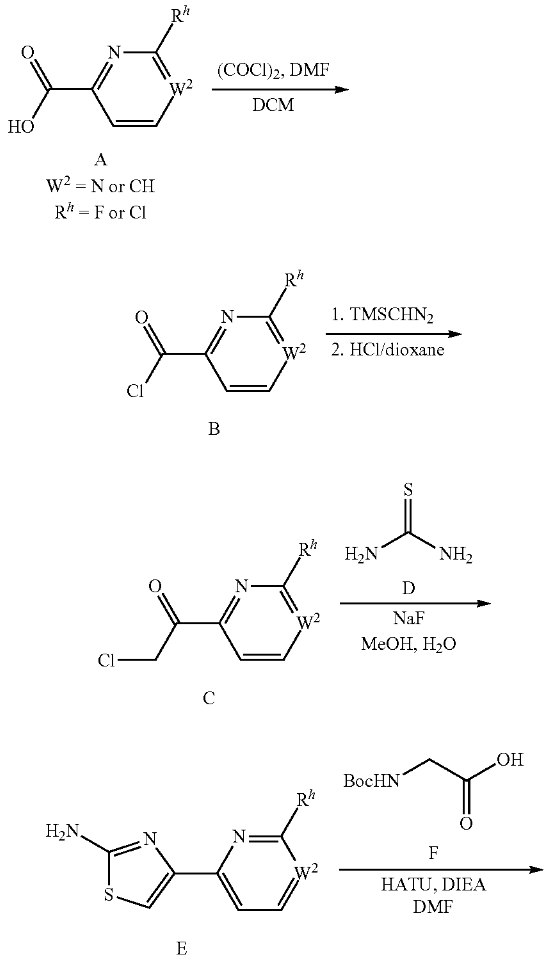

-continued

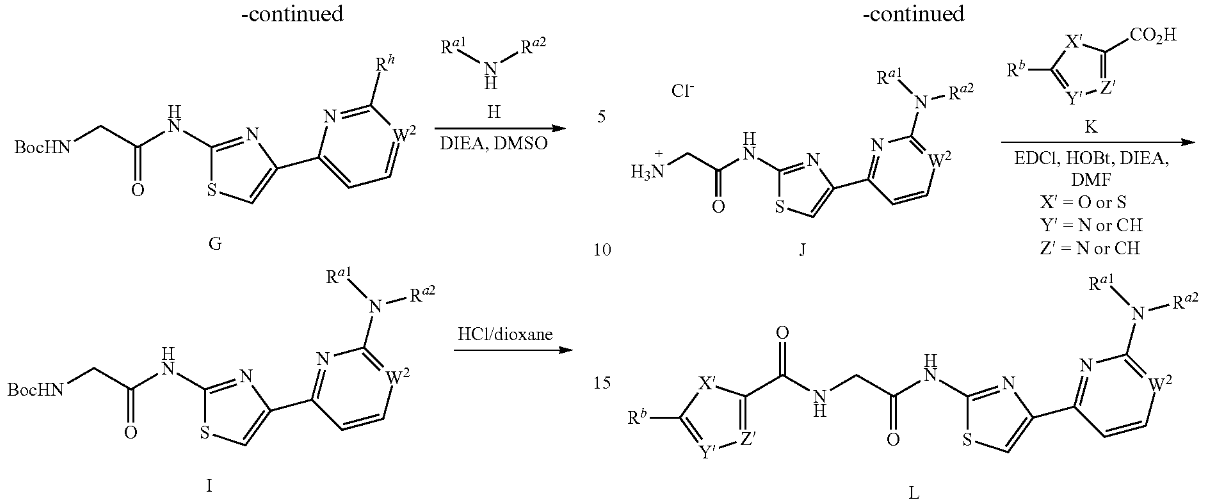

G J I L

TABLE 23

| Compound # | LC-MS data(m/z) | ¹H NMR |
|---|---|---|
| 822 | 515.2 | ¹H NMR (400 MHz, DMSO-$d_6$) δ 12.43 (br d, J = 2.4 Hz, 1H), 9.00-8.97 (m, 1H), 7.83 (s, 1H), 7.77 (s, 1H), 7.63-7.60 (m, 1H), 7.25 (d, J = 7.2 Hz, 1H), 6.80 (d, J = 8.8 Hz, 1H), 4.26 (d, J = 11.6 Hz, 2H), 4.19 (d, J = 6.4 Hz, 2H), 3.64-3.60 (m, 2H), 2.43-2.38 (m, 2H), 1.39 (s, 9H), 1.18 (d, J = 6.4 Hz, 6H) |
| 824 | 473.1 | ¹H NMR (400 MHz, DMSO-$d_6$) δ 8.89 (t, J = 6.0 Hz, 1H), 7.76 (s, 1H), 7.62 (dd, J = 8.5, 7.4 Hz, 1H), 7.25 (d, J = 7.3 Hz, 1H), 6.79 (d, J = 8.5 Hz, 1H), 6.61 (s, 1H), 4.25 (dd, J = 13.0, 2.3 Hz, 2H), 4.13 (d, J = 6.0 Hz, 2H), 3.98 (s, 3H), 3.63 (dqd, J = 12.6, 6.2, 2.3 Hz, 2H), 2.41 (dd, J = 12.8, 10.5 Hz, 2H), 1.18 (d, J = 6.2 Hz, 6H) |
| 826 | 513.2 | ¹HNMR (400 MHz, Methanol-$d_4$) δ 7.69 (s, 1H), 7.62-7.55 (m, 1H), 7.35 (d, J = 7.2 Hz, 1H), 7.24 (s, 1H), 6.73 (d, J = 8.4 Hz, 1H), 4.98 (d, J = 6.0 Hz, 2H), 4.60 (d, J = 6.0 Hz, 2H), 4.33 (s, 2H), 4.28-4.20 (m, 2H), 3.79-3.67 (m, 2H), 2.53-2.42 (m, 2H), 1.79 (s, 3H), 1.26 (d, J = 6.4 Hz, 6H) |
| 827 | 499.3 | ¹H NMR (400 MHz, DMSO-$d_6$) δ 9.03 (t, J = 6.0 Hz, 1H), 7.77 (s, 1H), 7.62 (dd, J = 8.5, 7.3 Hz, 1H), 7.25 (d, J = 7.3 Hz, 1H), 7.13 (s, 1H), 6.79 (d, J = 8.5 Hz, 1H), 4.32-4.20 (m, 2H), 4.16 (d, J = 6.0 Hz, 2H), 3.71-3.57 (m, 2H), 2.42 (dd, J = 12.8, 10.5 Hz, 2H), 1.31 (s, 9H), 1.18 (d, J = 6.2 Hz, 6H) |

Example 204. Preparation of Compounds of the Invention

The following compounds in Table 24 were synthesized utilizing the general synthetic protocols described in Example 61 and starting from the appropriate common intermediate (4-(3-(4,4,5,5-tetramethyl-1,3,2-dioxaborolan-2-yl)phenyl)thiazol-2-amine), heteroaryl halide, N-Boc amino acid, and the appropriate heterocyclic carboxylic acid.

TABLE 24

| Compound # | LC-MS data(m/z) | ¹H NMR |
|---|---|---|
| 821 | 510.4 | ¹H NMR (400 MHz, DMSO-$d_6$) δ 12.94-12.36 (m, 1H), 8.79 (d, J = 7.2 Hz, 1H), 8.42 (s, 1H), 8.27 (s, 1H), 7.90 (d, J = 8.0 Hz, 1H), 7.83-7.72 (m, 2H), 7.55-7.50 (m, 1H), 7.16 (s, 1H), 4.99-4.85 (m, 1H), 4.22 (s, 3H), 3.89-3.74 (m, 2H), 3.31 (s, 3H), 1.32 (s, 9H) |

Example 205. Preparation of 1-(2,2-difluorocyclopropyl)-1H-pyrrole-3-carboxylic acid

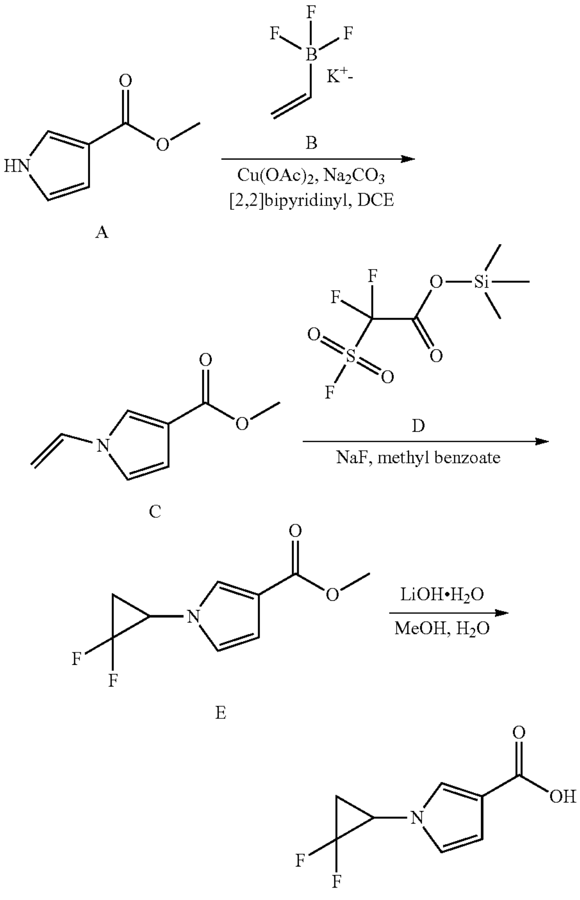

A C E F

Step 1: Preparation of methyl 1-vinyl-1H-pyrrole-3-carboxylate (intermediate C)

C

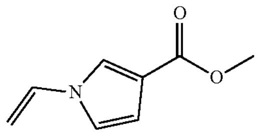

To a solution of methyl 1H-pyrrole-3-carboxylate (2.00 g, 15.98 mmol) and potassium; trifluoro(vinyl)boranuide (4.28 g, 31.97 mmol) in 1,2-dichloro-ethane (60 mL) was added 2-(2-pyridyl)pyridine (2.50 g, 15.98 mmol) and copper(II) acetate (2.90 g, 15.98 mmol), $Na_2CO_3$ (3.39 g, 31.97 mmol) at 25° C. The suspension subjected to three cycles of degassing and purging with $O_2$ (g). The reaction mixture was stirred under an atmosphere of $O_2$ (g) at 70° C. After 1 h, the mixture was cooled to room temperature and washed with water (50 mL). The resultant aqueous layer was extracted with ethyl acetate (3×70 mL) and the organic layer was concentrated. The resulting oil was purified by column chromatography ($SiO_2$, petroleum ether/ethyl acetate=100/1 to 1/1) and concentrated to give Intermediate C (1.2 g, 7.94 mmol, 49.67% yield) as a yellow oil. LCMS (ESI) m/z: $[M+H]^+$=152.1; $^1H$ NMR (400 MHz, $CDCl_3$) δ 7.49 (d, J=1.6 Hz, 1H), 6.89-6.85 (m, 1H), 6.83-6.77 (m, 1H), 6.65-6.64 (m, 1H), 5.26-5.21 (m, 1H), 4.83-4.80 (m, 1H), 3.82 (s, 3H).

Step 2: Preparation of methyl 1-(2,2-difluorocyclopropyl)-1H-pyrrole-3-carboxylate (Intermediate E)

E

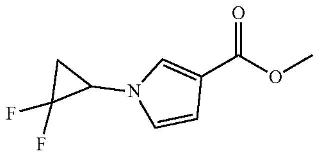

To a solution of Intermediate C (1.20 g, 7.94 mmol) and NaF (0.033 g, 0.793 mmol) in methyl benzoate (12 mL) was added trimethylsilyl 2,2-difluoro-2-fluorosulfonyl-acetate (7.82 mL, 39.69 mmol) in a dropwise manner. The mixture was subsequently heated to 105° C. After 2 h, the mixture was cooled to room temperature and washed with water (10 mL). The resulting aqueous layer was extracted with ethyl acetate (3×30 mL) and concentrated. The resulting oil was purified by column chromatography ($SiO_2$, petroleum ether/ethyl acetate=100/1 to 1/1) and concentrated to give Intermediate E (0.150 g, 0.746 mmol, 9.39% yield) as a yellow oil. LCMS (ESI) m/z: $[M+H]^+$=202.0; $^1H$ NMR (400 MHz, $CDCl_3$) δ 7.37-7.34 (m, 1H), 7.35 (s, 1H), 6.68 (d, J=2.4 Hz, 1H), 6.61-6.60 (m, 1H), 3.93-3.85 (m, 1H), 3.81 (s, 3H), 2.11-1.99 (m, 1H), 1.98-1.87 (m, 1H).

Step 3: Preparation of 1-(2,2-difluorocyclopropyl)-1H-pyrrole-3-carboxylic acid (Intermediate F)

F

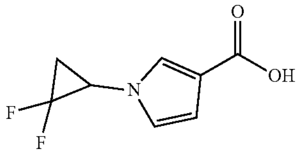

To a solution of Intermediate D (0.100 g, 0.497 mmol) in MeOH (1 mL) and $H_2O$ (1 mL) was added LiOH·$H_2O$ (0.042 g, 0.994 mmol) and the mixture was heated to 50° C. After 12 h, the mixture was cooled to room temperature and the mixture was acidified to pH 5-6 with aqueous 1 M·HCl (0.50 mL). The resulting acidic aqueous layer was extracted with three times with ethyl acetate and concentrated to give Intermediate F (120 mg, crude) as a yellow oil. LCMS (ESI) m/z: $[M+H]^+$=188.0.

Example 206. Preparation of 1-(tert-butyl)-N-(2-((4-(6-(cis-2,6-dimethylmorpholino)pyridin-2-yl)-5-fluorothiazol-2-yl)amino)-2-oxoethyl)-1H-pyrrole-3-carboxamide (Compound 520)

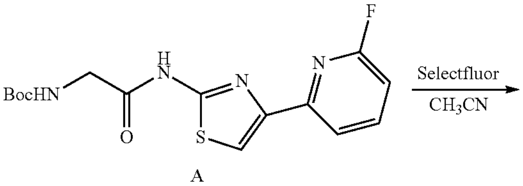

A

-continued

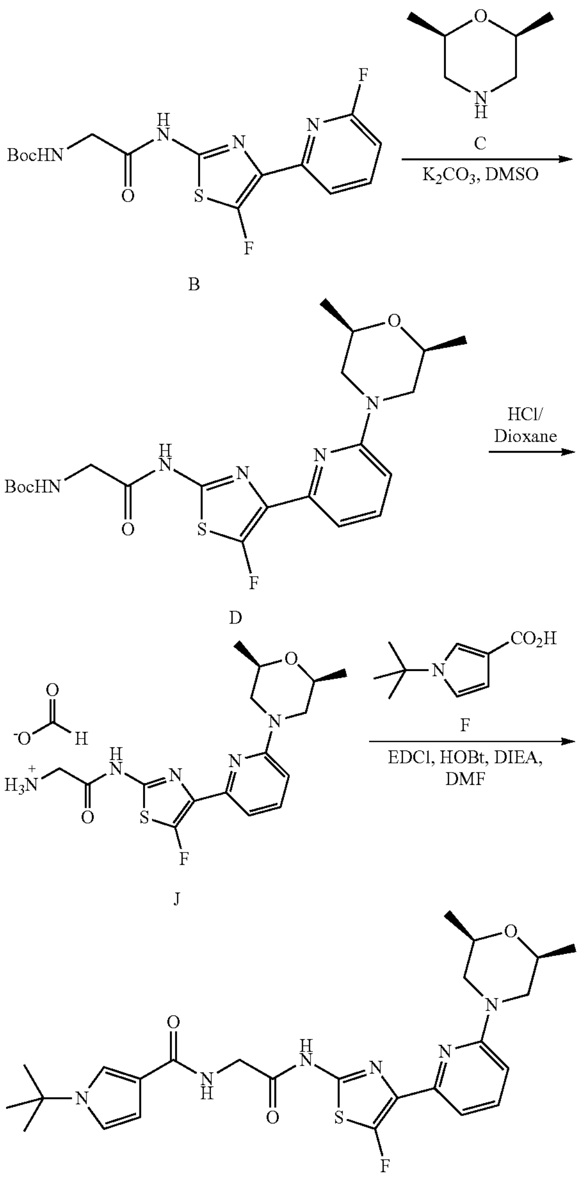

Compound 520

Step 1: Preparation of tert-butyl (2-((5-fluoro-4-(6-fluoropyridin-2-yl)thiazol-2-yl)amino)-2-oxoethyl) carbamate (Intermediate B)

B

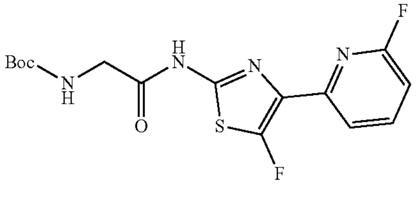

To a mixture of tert-butyl N-[2-[[4-(6-fluoro-2-pyridyl) thiazol-2-yl]amino]-2-oxo-ethyl]carbamate (2.00 g, 5.68 mmol) in $CH_3CN$ (20 mL) was added Selectfluor® (1.81 g, 5.11 mmol) at 0° C. After 24 h, the mixture was diluted with water (50 mL) and extracted with ethyl acetate (50 mL). The organic layer was separated and evaporated. The solids were purified by reversed-phase HPLC (0.1% FA condition). The solution was concentrated to give Intermediate B (0.560 g, 1.51 mmol, 26.64% yield, 100% purity) as white solids. LCMS (ESI) m/z: $[M+H]^+$=371.0; $^1H$ NMR (400 MHz, Methanol-$d_4$) δ 7.87-7.81 (m, 1H), 7.68-7.66 (m, 1H), 6.87-6.84 (m, 1H), 4.14 (s, 2H), 1.54-1.42 (m, 9H).

Step 2: Preparation of tert-butyl (2-((4-(6-(cis-2,6-dimethylmorpholino)pyridin-2-yl)-5-fluorothiazol-2-yl)amino)-2-oxoethyl)carbamate (Intermediate D)

D

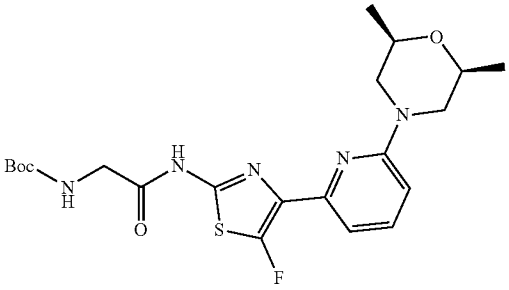

To a mixture of Intermediate B (0.350 g, 0.945 mmol) and cis-2,6-dimethylmorpholine (0.218 g, 1.89 mmol) in DMSO (4 mL) was added $K_2CO_3$ (0.392 g, 2.83 mmol) at 20° C. and the mixture was stirred at 80° C. After 2 h, the mixture was cooled to room temperature and combined with another batch of equal reaction scale. To the mixture was added water (10 mL) and the aqueous layer was extracted with ethyl acetate (3×10 mL). The combined organic layer was washed with brine (20 mL), dried over $Na_2SO_4$, filtered, and concentrated. The resulting oil was purified by column chromatography ($SiO_2$, petroleum ether/ethyl acetate=3/1 to 1/1) to give Intermediate D (0.110 g, 0.163 mmol, 17.25% yield, 69% purity) as a yellow solid. LCMS (ESI) m/z: $[M+H]^+$=466.2.

Step 3: Preparation of 2-((4-(6-(cis-2,6-dimethyl-morpholino)pyridin-2-yl)-5-fluorothiazol-2-yl) amino)-2-oxoethan-1-aminium formate (Intermediate E)

E

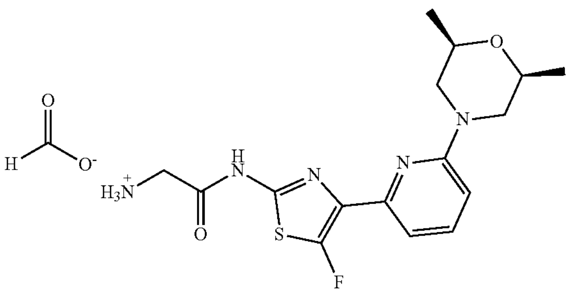

A mixture of Intermediate D (0.110 g, 0.236 mmol) was added a solution of 4 M HCl in 1,4-dioxane (2 mL). The mixture was stirred at 20° C. After 2 h, the mixture was concentrated to get the crude product. The crude product was purified by reversed-phase HPLC (0.1% FA condition). The solution was lyophilized to give Intermediate E (0.025 g, 0.061 mmol, 25.72% yield, 100% purity) as white solids. LCMS (ESI) m/z: $[M+H]^+$=366.1.

Step 4: Preparation of 1-(tert-butyl)-N-(2-((4-(6-(cis-2,6-dimethylmorpholino)pyridin-2-yl)-5-fluoro-thiazol-2-yl)amino)-2-oxoethyl)-1H-pyrrole-3-carboxamide (Compound 520)

Compound 520

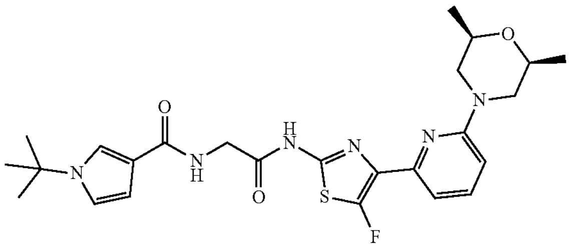

To a mixture of 1-tert-butylpyrrole-3-carboxylic acid (0.011 g, 0.061 mmol) in DMF (1 mL) was added EDCI (0.023 g, 0.122 mmol), HOBt (–0.016 g, 0.122 mmol), DIPEA (0.053 mL, 0.304 mmol). After 10 min, Intermediate E (0.025 g, 0.061 mmol) was added. The mixture was stirred at 20° C. for 15 h, followed by addition of water (5 mL). The reaction mixture was extracted with ethyl acetate (3×5 mL), the combined organic layer was washed with brine (10 mL), dried over $Na_2SO_4$, filtered and concentrated. The solids were purified by pre-HPLC (mobile phase: [water (0.225% FA)-ACN]; B %: 45%-75%), the solution was lyophilized to give Compound 520 (0.002 g, 0.0046 mmol, 7.60% yield, 99% purity) as white solids. LCMS (ESI) m/z: $[M+H]^+$=515.1; $^1H$ NMR (400 MHz, Methanol-$d_4$) δ 7.64-7.56 (m, 2H), 7.20 (d, J=7.6 Hz, 1H), 6.98-6.93 (m, 1H), 6.71 (d, J=8.4 Hz, 1H), 6.57-6.56 (m, 1H), 4.25 (s, 1H), 4.22 (s, 1H), 4.20 (s, 2H), 3.78-3.66 (m, 2H), 2.50-2.44 (m, 2H), 1.57 (s, 9H), 1.24-1.23 (m, 6H).

Example 207. Preparation of N-(2-((4-(6-(cis-2,6-dimethylmorpholino)pyridin-2-yl)thiazol-2-yl)amino)-2-oxoethyl)-1-((S)-3-methyltetrahydrofuran-3-yl)-1H-pyrrole-3-carboxamide and N-(2-((4-(6-(cis-2,6-dimethylmorpholino)pyridin-2-yl)thiazol-2-yl)amino)-2-oxoethyl)-1-((R)-3-methyltetrahydrofuran-3-yl)-1H-pyrrole-3-carboxamide (Compounds 491 and 490)

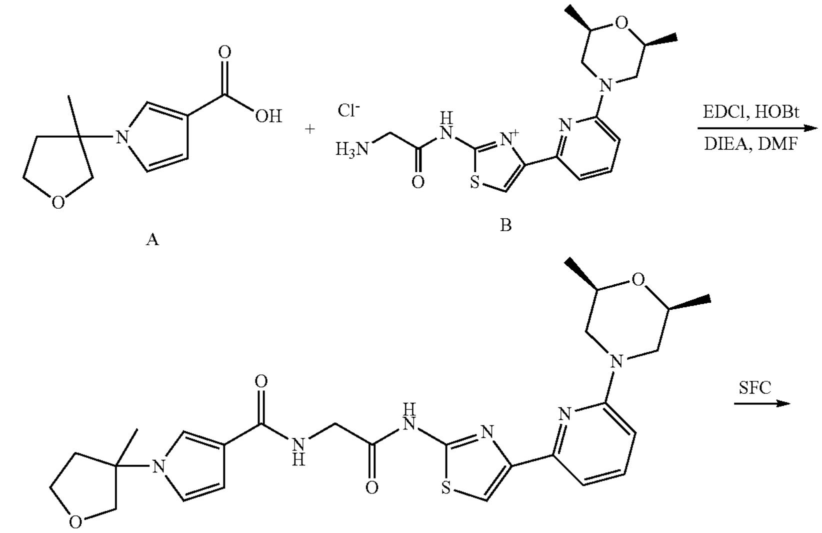

A

B

C

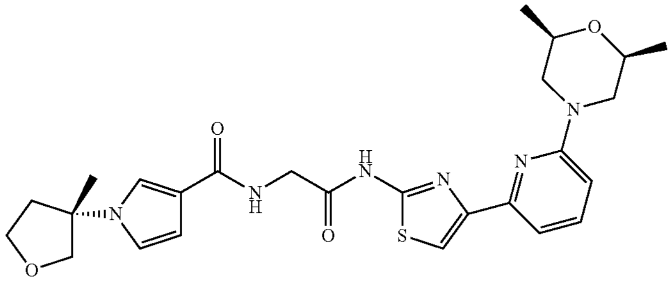

+

Compound 491

-continued

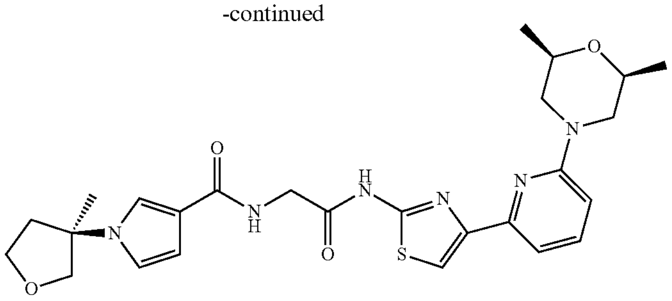

Compound 490

Step 1: Preparation of Intermediate 6 N-[2-[[4-[6-[cis-2,6-dimethylmorpholin-4-yl]-2-pyridyl]thiazol-2-yl]amino]-2-oxo-ethyl]-1-(3-methyltetrahydro-furan-3-yl)pyrrole-3-carboxamide (Intermediate C)

C

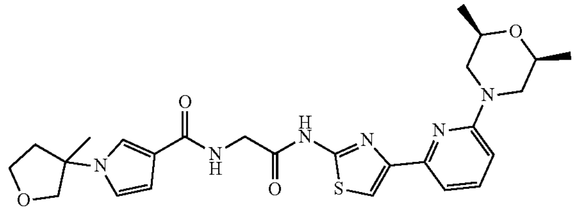

To a solution of Intermediate A (0.200 g, 1.02 mmol) and Intermediate B (0.392 g, 1.13 mmol) in DMF (4 mL) was added EDCI (0.393 g, 2.05 mmol), HOBt (0.277 g, 2.05 mmol), DIEA (0.36 mL, 2.05 mmol) at 25° C. The reaction mixture was stirred for 1 h at 25° C., followed by addition of water (5 mL). The resulting mixture was extracted with ethyl acetate (3×5 mL) and the combined organic layers were concentrated. The residue was purified by prep-HPLC (mobile phase:[water(0.225% FA)-ACN]; B %: 32%-65%) and lyophilized to give Intermediate C (0.250 g, 0.429 mmol, 41.86% yield, 90% purity) as white solids. LCMS (ESI) m/z: $[M+H]^+$=525.2.

Step 2: Preparation of N-(2-((4-(6-((cis-2,6-dimethylmorpholino)pyridin-2-yl)thiazol-2-yl)amino)-2-oxoethyl)-1-((S)-3-methyltetrahydrofuran-3-yl)-1H-pyrrole-3-carboxamide and N-(2-((4-(6-(cis-2,6-dimethylmorpholino)pyridin-2-yl)thiazol-2-yl) amino)-2-oxoethyl)-1-((R)-3-methyltetrahydrofuran-3-yl)-1H-pyrrole-3-carboxamide (Compounds 491 and 490)

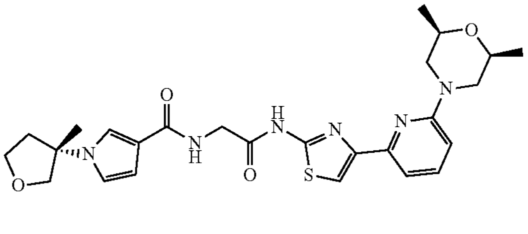

Compound 491

+

-continued

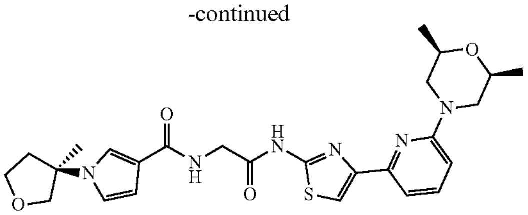

Compound 490

Intermediate C (0.250 g, 0.429 mmol) was separated by SFC to give two peaks. The first peak was concentrated and lyophilized to give Compound 491 (0.080 g, 0.145 mmol, 30.40% yield, 95% purity) as an off-white solids (Rt=2.447 min). The second peak was concentrated and lyophilized to give Compound 490 (0.080 g, 0.145 mmol, 30.40% yield, 95% purity) as off-white solids.

Compound 491: LCMS (ESI) m/z: $[M+H]^+$=525.3; $^1H$ NMR (400 MHz, DMSO-$d_6$) δ 12.29 (s, 1H), 8.23-8.20 (m, 1H), 7.76 (s, 1H), 7.68-7.59 (m, 1H), 7.53-7.52 (m, 1H), 7.26 (d, J=7.2 Hz, 1H), 6.97-6.96 (m, 1H), 6.80 (d, J=8.8 Hz, 1H), 6.51-6.50 (m, 1H), 4.26 (d, J=12.8 Hz, 2H), 4.09 (d, J=6.0 Hz, 2H), 4.00 (d, J=8.8 Hz, 1H), 3.95-3.85 (m, 2H), 3.76 (d, J=9.2 Hz, 1H), 3.69-3.57 (m, 2H), 2.46-2.37 (m, 3H), 2.29-2.15 (m, 1H), 1.59 (s, 3H), 1.19 (d, J=6.0 Hz, 6H).

Compound 490: LCMS (ESI) m/z: $[M+H]^+$=525.3; $^1H$ NMR (400 MHz, DMSO-$d_6$) δ 12.30 (s, 1H), 8.28-8.18 (m, 1H), 7.76 (s, 1H), 7.64-7.60 (m, 1H), 7.53-7.52 (m, 1H), 7.26 (d, J=7.2 Hz, 1H), 6.97-6.96 (m, 1H), 6.80 (d, J=8.4 Hz, 1H), 6.51-6.50 (m, 1H), 4.26 (d, J=11.6 Hz, 2H), 4.09 (d, J=6.0 Hz, 2H), 4.00 (d, J=9.2 Hz, 1H), 3.94-3.87 (m, 2H), 3.76 (d, J=8.4 Hz, 1H), 3.69-3.58 (m, 2H), 2.46-2.37 (m, 3H), 2.29-2.17 (m, 1H), 1.59 (s, 3H), 1.19 (d, J=6.0 Hz, 6H).

Example 208. Preparation of Compounds of the Invention

The compounds in Table 25 were synthesized starting from the appropriate heterocyclic carboxylic acid and the corresponding primary amine hydrochloride utilizing the synthetic protocol described in Example 207 (Compounds 491 and 490).

TABLE 25

| Compound # | LC-MS data(m/z) | $^1$H NMR |
|---|---|---|
| 505 | 466.1 | $^1$H NMR (400 MHz, DMSO-d$_6$) δ 12.32 (s, 1H), 8.21-8.19 (m, 1H), 7.58-7.49 (m, 2H), 7.24-7.15 (m, 2H), 7.01-6.91 (m, 2H), 6.51-6.50 (m, 1H), 6.42-6.33 (m, 1H), 4.09 (d, J = 6.0 Hz, 2H), 4.00 (d, J = 8.8 Hz, 1H), 3.94-3.87 (m, 2H), 3.85-3.83 (m, 4H), 3.76 (d, J = 9.2 Hz, 1H), 2.42-2.34 (m, 2H), 2.33-2.18 (m, 2H), 1.59 (s, 3H) |
| 506 | 466.1 | $^1$H NMR (400 MHz, DMSO-d$_6$) δ 12.32 (s, 1H), 8.2 1-8.20 (m, 1H), 7.66-7.46 (m, 2H), 7.24-7.14 (m, 2H), 6.96-6.95 (m, 2H), 6.51-6.50 (m, 1H), 6.43-6.29 (m, 1H), 4.09 (d, J = 6.0 Hz, 2H), 4.00 (d, J = 9.2 Hz, 1H), 3.93-3.87 (m, 2H), 3.85-3.83 (m, 4H), 3.76 (d, J = 9.2 Hz, 1H), 2.44-2.19 (m, 4H), 1.59 (s, 3H) |
| 621 | 531.2 | $^1$H NMR (400 MHz, DMSO-d$_6$) δ 12.34 (s, 1H), 8.29 (d, J = 6.0 Hz, 1H), 7.77 (s, 1H), 7.64-7.63 (m, 1H), 7.49 (d, J = 2.0 Hz, 1H), 7.26 (d, J = 7.6 Hz, 1H), 6.95 (d, J = 2.4 Hz, 1H), 6.81 (d, J = 8.4 Hz, 1H), 6.54-6.53 (m, 1H), 4.33-4.21 (m, 2H), 4.09 (d, J = 6.0 Hz, 2H), 3.68-3.57 (m, 2H), 2.44-2.41 (m, 2H), 2.31-2.25 (m, 1H), 2.11-2.01 (m, 1H), 1.62 (s, 3H), 1.19 (d, J = 6.0 Hz, 6H) |
| 622 | 531.2 | $^1$H NMR (400 MHz, DMSO-d$_6$) δ 12.34 (s, 1H), 8.29 (d, J = 6.0 Hz, 1H), 7.77 (s, 1H), 7.63-7.62 (m, 1H), 7.49 (d, J = 2.0 Hz, 1H), 7.26 (d, J = 7.6 Hz, 1H), 6.95 (d, J = 2.4 Hz, 1H), 6.81 (d, J = 8.4 Hz, 1H), 6.54-6.53 (m, 1H), 4.26 (d, J = 10.8 Hz, 2H), 4.09 (d, J = 6.0 Hz, 2H), 3.69-3.55 (m, 2H), 2.44-2.38 (m, 2H), 2.32-2.23 (m, 1H), 2.11-1.99 (m, 1H), 1.62 (s, 3H), 1.19 (d, J = 6.0 Hz, 6H) |
| 651 | 472.1 | $^1$H NMR (400 MHz, DMSO-d$_6$) δ 12.34 (s, 1H), 8.26 (d, J = 6.0 Hz, 1H), 7.55 (s, 1H), 7.48 (d, J = 2.0 Hz, 1H), 7.23-7.13 (m, 2H), 6.98-6.89 (m, 2H), 6.54-6.53 (m, 1H), 6.38-6.37 (m, 1H), 4.09 (d, J = 6.0 Hz, 2H), 3.84 (d, J = 7.2 Hz, 4H), 2.34-2.31 (m, 2H), 2.30-2.23 (m, 1H), 2.11-2.00 (m, 1H), 1.63 (s, 3H) |
| 652 | 472.1 | $^1$H NMR (400 MHz, DMSO-d$_6$) δ 12.34 (s, 1H), 8.25 (d, J = 5.2 Hz, 1H), 7.54 (s, 1H), 7.48 (d, J = 1.6 Hz, 1H), 7.20 (d, J = 4.8 Hz, 2H), 6.95 (s, 2H), 6.53-6.52 (m, 1H), 6.37-6.36 (m, 1H), 4.09 (d, J = 6.0 Hz, 2H), 3.84 (d, J = 7.2 Hz, 4H), 2.35-2.31 (m, 2H), 2.30-2.23 (m, 1H), 2.10-2.01 (m, 1H), 1.63 (s, 3H) |

Example 209. Preparation of Compounds of the Invention

The following compounds in Table 26 below were synthesized utilizing the general synthetic protocols shown in Scheme 12 below from the appropriate bromo-pyridine or heteroaryl ketone, amino acid, and heterocyclic carboxylic acid. Where appropriate SEC purification was used to separate enantiomers.

Scheme 12

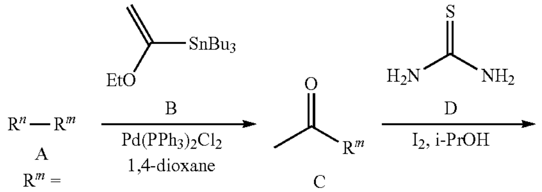

A $R^m$ = substituted heterocycle $R^n$ = Br or Cl

C

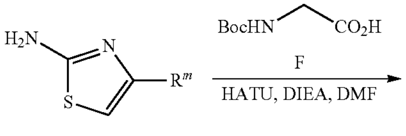

E

-continued

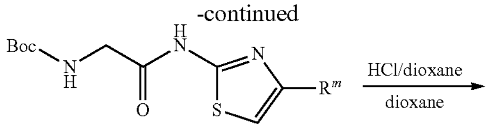

G

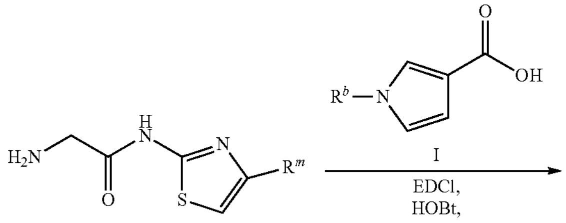

H

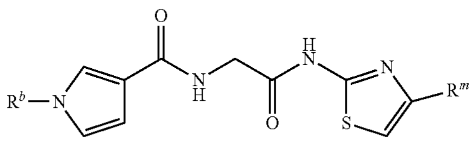

J

TABLE 26

| Compound # | LC-MS data(m/z) | $^1$H NMR |
|---|---|---|
| 147 | 513.3 | $^1$H NMR (400 MHz, DMSO-$d_6$) δ 12.60-12.21 (m, 1H), 8.69-8.68 (m, 1H), 8.59-8.52 (m, 2H), 7.87-7.81 (m, 2H), 7.76 (s, 1H), 7.55 (d, J = 7.2 Hz, 1H), 7.48 (d, J = 6.0 Hz, 2H), 7.31-7.30 (m, 1H), 6.89 (d, J = 8.0 Hz, 1H), 6.77-6.76 (m, 1H), 5.52 (s, 2H), 4.13 (d, J = 6.0 Hz, 2H), 3.57 (s, 3H) |
| 148 | 430.8 | 1H NMR (400 MHz, DMSO-$d_6$) δ 12.54 (s, 1H), 8.75-8.66 (m, 1H), 8.20 (d, J = 1.2 Hz, 1H), 8.15 (s, 1H), 8.04-7.92 (m, 2H), 7.85-7.83 (m, 1H), 7.32-7.30 (m, 1H), 6.78-6.76 (m, 1H), 4.15 (d, J = 5.9 Hz, 2H), 3.57 (s, 3H) |
| 482 | 461.0 | $^1$H NMR (400 MHz, DMSO-$d_6$) δ 12.44-12.12 (m, 1H), 8.74-8.71 (m, 1H), 7.91-7.90 (m, 1H), 7.68 (s, 1H), 7.38-7.35 (m, 2H), 7.16 (d, J = 7.2 Hz, 1H), 6.84-6.83 (m, 1H), 4.18 (d, J = 6.0 Hz, 2H), 3.63 (s, 3H), 3.52-3.48 (m, 2H), 3.01-2.96 (m, 5H) |
| 496 | 477.1 | $^1$H NMR (400 MHz, Methanol-$d_4$) δ 8.01-7.95 (m, 2H), 7.79-7.74 (m, 1H), 7.60-7.56 (m, 1H), 7.06-6.97 (m, 2H), 6.66-6.61 (m, 1H), 4.30-4.20 (m, 2H), 1.84-1.70 (m, 4H) |
| 497 | 490.1 | $^1$H NMR (400 MHz, DMSO-$d_6$) δ 12.49 (s, 1H), 8.70 (s, 1H), 8.11 (s, 1H), 7.99-7.74 (m, 3H), 7.37-7.17 (m, 2H), 6.78 (s, 1H), 4.15 (s, 2H), 3.57 (s, 3H) |
| 498 | 483.0 | $^1$H NMR (400 MHz, DMSO-$d_6$) δ 12.38 (br s, 1H), 8.38-8.37 (m, 1H), 7.91-7.77 (m, 2H), 7.61-7.59 (m, 1H), 7.54 (d, J = 6.8 Hz, 1H), 7.08-7.06 (m, 1H), 6.87-6.79 (m, 1H), 6.57-6.55 (m, 1H), 4.52-4.37 (m, 2H), 4.11 (d, J = 5.6 Hz, 2H), 1.88-1.71 (m, 4H), 1.53-1.38 (m, 6H) |
| 503 | 468.1 | $^1$H NMR (400 MHz, DMSO-$d_6$) δ 12.67-12.12 (m, 1H), 8.20-8.17 (m, 1H), 8.13-8.09 (m, 1H), 7.91 (d, J = 7.6 Hz, 1H), 7.78 (s, 1H), 7.52-7.51 (m, 1H), 7.22 (d, J = 8.0 Hz, 1H), 6.97-6.96 (m, 1H), 6.54-6.40 (m, 1H), 4.10 (d, J = 5.6 Hz, 2H), 1.49 (s, 9H) |
| 512 | 450.0 | $^1$H NMR (400 MHz, Methanol-$d_4$) δ 7.93-7.52 (m, 5H), 6.98-6.94 (m, 1H), 6.88-6.85 (m, 1H), 6.58-6.56 (m, 1H), 4.23 (s, 2H), 1.57 (s, 9H) |
| 522 | 459.0 | $^1$H NMR (400 MHz, DMSO-$d_6$) δ 12.24 (br s, 1H), 8.39-8.36 (m, 1H), 8.28-7.97 (m, 4H), 7.61-7.60 (m, 1H), 7.11-7.06 (m, 1H), 7.03-7.01 (m, 1H), 6.57-6.56 (m, 1H), 4.07 (s, 2H), 1.85-1.75 (m, 4H) |
| 533 | 472.0 | $^1$H NMR (400 MHz, DMSO-$d_6$) δ 12.33 (br s, 1H), 8.72-8.71 (m, 1H), 8.17-7.75(m, 5H), 7.32-7.31 (m, 1H), 7.02 (d, J = 8.4 Hz, 1H), 6.78-6.77 (m, 1H), 4.15 (d, J = 6.0 Hz, 2H), 3.58 (s, 3H) |
| 550 | 440.0 | $^1$H NMR (400 MHz, DMSO-$d_6$) δ 12.43-12.31 (m, 1H), 8.24-8.15 (m, 1H), 7.86-7.75 (m, 2H), 7.61-7.48 (m, 2H), 6.98-6.97 (m, 1H), 6.83 (d, J = 8.0 Hz, 1H), 6.48-6.47 (m, 1H), 4.35-4.26 (m, 1H), 4.10 (d, J = 6.0 Hz, 2H), 1.50 (s, 9H), 0.82-0.80(m, 2H), 0.75-0.69 (m, 2H) |
| 559 | 448.9 | $^1$H NMR (400 MHz, DMSO-$d_6$) δ 12.40 (s, 1H), 8.39-8.38 (m, 1H), 7.85-7.78 (m, 2H), 7.63-7.54 (m, 2H), 7.11-7.05 (m, 1H), 6.83 (d, J = 8.0 Hz, 1H), 6.57-6.56 (m, 1H), 4.33-4.32 (m, 1H), 4.11 (d, J = 6.0 Hz, 2H), 1.88-1.70 (m, 4H), 0.87-0.70 (m, 4H) |
| 597 | 462.0 | $^1$H NMR (400 MHz, DMSO-$d_6$) δ 12.43 (s, 1H), 8.70-8.69 (m, 1H), 7.86-7.85 (m, 1H), 7.84-7.78 (m, 2H), 7.58 (d, J = 7.2 Hz, 1H), 7.32-7.31 (m, 1H), 6.83 (d, J = 8.0 Hz, 1H), 6.78-6.76 (m, 1H), 4.33-4.32 (m, 1H), 4.15 (d, J = 5.6 Hz, 2H), 3.58 (s, 3H), 0.87-0.69 (m, 4H) |
| 604 | 526.3 | $^1$H NMR (400 MHz, Methanol-$d_4$) δ 7.96-7.88 (m, 2H), 7.83-7.74 (m, 2H), 7.30-7.23 (m, 2H), 6.85-6.83 (m, 1H), 4.98-4.94 (m, 1H), 3.89-3.78 (m, 2H), 3.43 (s, 3H), 3.38 (s, 3H), 3.09-2.99 (m, 1H), 2.38-2.30 (m, 1H), 1.95-1.83 (m, 1H) |
| 606 | 526.1 | $^1$H NMR (400 MHz, Methanol-$d_4$) δ 7.90-7.89 (m, 2H), 7.79-7.76 (m, 2H), 7.26-7.25 (m, 2H), 6.83-6.82 (m, 1H), 4.98-4.95 (m, 1H), 3.87-3.79 (m, 2H), 3.41 (s, 3H), 3.36 (s, 3H), 3.05-3.02 (m, 1H), 2.35-2.31 (m, 1H), 1.89-1.86 (m, 1H) |
| 608 | 482.1 | $^1$H NMR (400 MHz, DMSO-$d_6$) δ 12.44 (s, 1H), 8.70-8.66 (m, 1H), 7.91-7.79 (m, 4H), 7.42-7.36 (m, 1H), 7.34-7.28 (m, 1H), 6.78-6.76 (m, 1H), 4.14 (d, J = 5.6 Hz, 2H), 3.57 (s, 3H), 3.27-3.18 (m, 1H), 2.45-2.36 (m, 1H), 2.09-1.95 (m, 1H) |
| 609 | 482.1 | $^1$H NMR (400 MHz, DMSO-$d_6$) δ 12.44 (br s, 1H), 9.70-8.69 (m, 1H), 7.86-7.81 (m, 4H), 7.39-7.38 (m, 1H), 7.32-7.30 (m, 1H), 6.78-6.76 (m, 1H), 4.15 (d, J = 6.0 Hz, 2H), 3.57 (s, 3H), 3.26-3.18 (m, 1H), 2.45-2.41 (m, 1H), 2.04-2.00 (m, 1H) |
| 614 | 480.0 | $^1$H NMR (400 MHz, DMSO-$d_6$) δ 12.67-12.21 (m, 1H), 8.76-8.55 (m, 1H), 7.84 (d, J = 2.0 Hz, 1H), 7.75 (s, 2H), 7.58-7.50 (m, 1H), 7.36-7.26 (m, 1H), 6.81-6.74 (m, 1H), 4.62-4.43 (m, 1H), 4.14 (d, J = 6.0 Hz, 2H), 3.57 (s, 3H), 0.92-0.62 (m, 4H) |

Example 210. Preparation of N-(2-((3'-(cis-2,6-dimethylmorpholino)-2-fluoro-[1,1'-biphenyl]-3-yl)amino)-2-oxoethyl)-1-(methylsulfonyl)-1H-pyrrole-3-carboxamide (Compound 477)

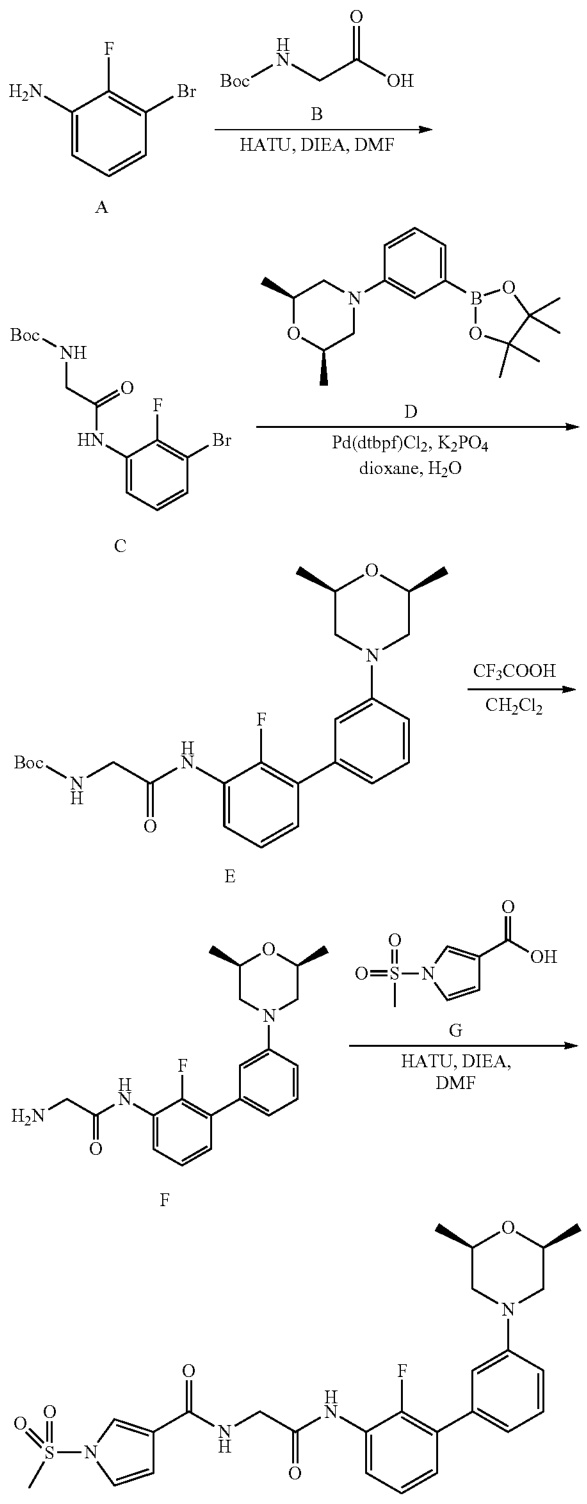

Compound 477

Step 1: Preparation of tert-butyl (2-((3-bromo-2-fluorophenyl)amino)-2-oxoethyl)carbamate (Intermediate C)

C

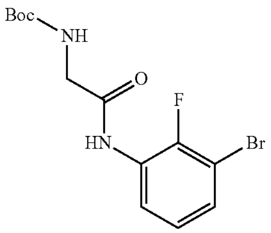

To a solution of 2-(tert-butoxycarbonylamino)acetic acid (553.17 mg, 3.16 mmol) in DCM (6 mL) was added HATU (1.40 g, 3.68 mmol) and DIEA (1.02 g, 7.89 mmol, 1.38 mL). The mixture was stirred at 25° C. for 1 h until the color of mixture turned brown. Then to the mixture was added 3-bromo-2-fluoro-aniline (500.00 mg, 2.63 mmol) and then the reaction mixture was stirred at 25° C. for 2 h. The reaction mixture was combined with another batch. The combined reaction mixture was washed with water (15 mL×1) and extracted with EtOAc (15 mL×3). The combined organic layers were dried with $Na_2SO_4$, filtered and concentrated under vacuum to give a residue. The residue was purified by Silica gel column chromatography (Petroleum ether:Ethyl acetate=1:0-3:1) to give Intermediate C (580 mg, 1.37 mmol, 26.03% yield, 82% purity) as a colorless oil. LCMS (ESI) m/z: $[M-99]^+$=247.0. $^1H$ NMR (400 MHz, DMSO-$d_6$) δ 8.76-8.72 (d, J=2.0 Hz, 1H), 8.21 (s, 2H), 8.14-8.04 (m, 2H), 7.81 (s, 1H), 7.70-7.67 (m, 1H), 7.64-7.56 (d, J=8.0 Hz, 1H), 7.22-7.17 (d, J=6.0 Hz, 1H), 4.52-4.45 (d, J=6.0 Hz, 2H), 3.92-3.84 (m, 2H), 3.17 (s, 3H), 2.72-2.68 (m, 2H), 2.46-2.43 (m, 4H), 1.51 (s, 6H), 1.41 (s, 9H) ppm.

Step 2: Preparation of tert-butyl (2-((3'-(cis-2,6-dimethylmorpholino)-2-fluoro-[1,1'-biphenyl]-3-yl)amino)-2-oxoethyl)carbamate (Intermediate E)

E

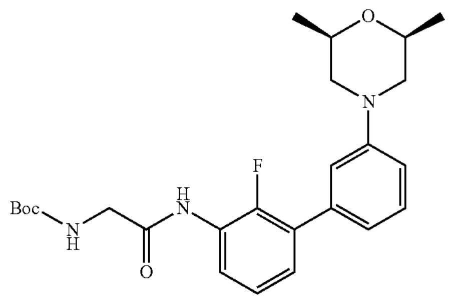

To a solution of Intermediate C (537.91 mg, 1.28 mmol) and cis-2,6-dimethyl-4-[3-(4,4,5,5-tetramethyl-1,3,2-dioxaborolan-2-yl)phenyl]morpholine (270 mg, 851.12 umol) in dioxane (6 mL) and $H_2O$ (0.6 mL) was added [1,1'-bis(di-tert-butylphosphino)ferrocene]dichloropalladium(II) (55.47 mg, 85.11 umol) and $K_3PO_4$ (632.32 mg, 2.98 mmol) under $N_2$ at 25° C. Then the reaction mixture was stirred at 80° C. for 3 h. The reaction mixture was washed with water (15 mL×1) and extracted with EtOAc (20 mL×3). The combined organic layers were dried over $Na_2SO_4$, filtered and concentrated under vacuum to give a residue. The residue was purified by Silica gel column chromatography (Petroleum ether:Ethyl acetate=1:0-5:1) to give Intermediate E (500 mg, crude) as a colorless oil.

LCMS (ESI) m/z: $[M+H]^+$=458.2.

Step 3: Preparation of 2-amino-N-(3'-(cis-2,6-dimethylmorpholino)-2-fluoro-[1,1'-biphenyl]-3-yl)acetamide (Intermediate F)

F

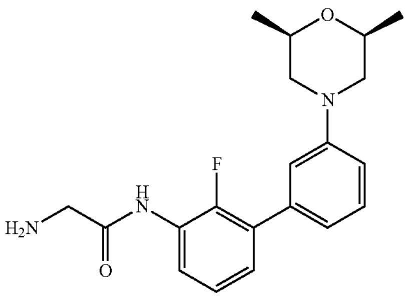

To a solution of Intermediate E (440 mg, 961.67 umol) in $CH_2Cl_2$ (10 mL) was added $CF_3COOH$ (4.62 g, 40.52 mmol, 3.00 mL) at 25° C. Then the reaction mixture was stirred at 25° C. for 3 h. The reaction mixture was combined with another batch. The combined organic layers were quenched with saturated $NaHCO_3$ (10 mL) and $NaHCO_3$solid at 0° C. to pH=8-9. Then the mixture was extracted with EtOAc (50 mL*3). The combined organic layers were dried over $Na_2SO_4$, filtered and concentrated under vacuum to give Intermediate F (240 mg, 598.96 umol, 62.28% yield, 89.2% purity) as a brown oil. LCMS (ESI) m/z: $[M+H]^+$=358.1.

Step 4: Preparation of N-(2-((3'-(cis-2,6-dimethylmorpholino)-2-fluoro-[1,1'-biphenyl]-3-yl)amino)-2-oxoethyl)-1-(methylsulfonyl)-1H-pyrrole-3-carboxamide (Compound 477)

Compound 477

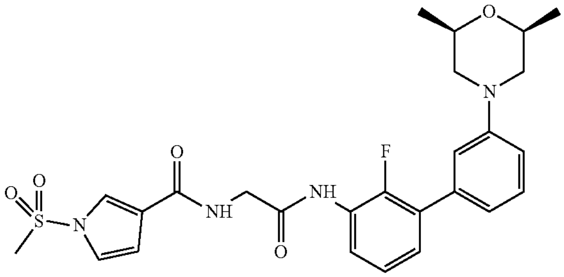

To a solution of 1-methylsulfonylpyrrole-3-carboxylic acid (116.45 mg, 615.52 umol) in DMF (2 mL) was added HATU (297.87 mg, 783.39 umol) and DIEA (216.96 mg, 1.68 mmol, 292.40 uL), then the mixture was stirred at 25° C. for 20 min. Then the mixture was added Intermediate 6 (200 mg, 499.13 umol). The reaction mixture was stirred at 25° C. for 4 h. The reaction mixture was combined with another batch. The combined organic layers were filtered. The filtrate was purified by Prep-HPLC (mobile phase: [water (10 mM $NH_4HCO_3$)-ACN]; B %: 33%-63%) to give a solution of product in $MeCN/H_2O$. Then the solution was lyophilized to give Compound 477 (120 mg, 227.02 umol, 45.48% yield, 100% purity) as a white solid. LCMS (ESI) m/z: $[M+H]^+$=529.2; $^1H$ NMR (400 MHz, DMSO-$d_6$) δ 9.87 (s, 1H), 8.65-8.62 (d, J=6.0 Hz, 1H), 7.92-7.84 (m, 2H), 7.33-7.30 (m, 2H), 7.24-7.22 (m, 2H), 7.05-6.90 (m, 2H), 6.93-6.85 (m, 1H), 6.79-6.78 (m, 1H), 4.11-4.10 (d, J=6.0 Hz, 2H), 3.73-3.68 (m, 2H), 3.66-3.63 (d, J=12 0 Hz, 2H), 3.57 (s, 1H), 2.31-2.26 (m, 2H), 1.17-1.16 (d, J=6.0 Hz, 6H).

Example 211. Preparation of 1-(3-methyloxetan-3-yl)-N-[2-[[4-[6-(6-methylpyrazin-2-yl)-2-pyridyl]thiazol-2-yl]amino]-2-oxo-ethyl]pyrrole-3-carboxamide (Compound 523)

1-(3-methyloxetan-3-yl)-N-[2-[[4-[6-(6-methylpyrazin-2-yl)-2-pyridyl]thiazol-2-yl]amino]-2-oxo-ethyl]pyrrole-3-carboxamide was synthesized starting from tert-butyl N-[2-[[4-(6-bromo-2-pyridyl)thiazol-2-yl]amino]-2-oxo-ethyl]carbamate and the corresponding stannane and heterocyclic carboxylic acid utilizing the synthetic protocol described in Example 82.

TABLE 27

| Compound # | LC-MS data(m/z) | $^1H$ NMR |
|---|---|---|
| 523 | 490.1 | $^1H$ NMR (400 MHz, DMSO-$d_6$) δ 9.57 (s, 1H), 8.64 (s, 1H), 8.29-8.27 (m, 2H), 8.17 (s, 1H), 8.08-8.06 (m, 1H), 8.03-8.02 (m, 1H), 7.57-7.56 (m, 1H), 7.02-7.01 (m, 1H), 6.57-6.56 (m, 1H), 4.85 (d, J = 6.8 Hz, 2H), 4.63 (d, J = 6.8 Hz, 2H), 4.13 (d, J = 6.0 Hz, 2H), 2.61 (s, 3H), 1.79 (s, 3H) |

Example 212. Preparation of 1-(bicyclo[1.1.1]pentan-1-yl)-1H-1,2,4-triazole-3-carboxylic acid

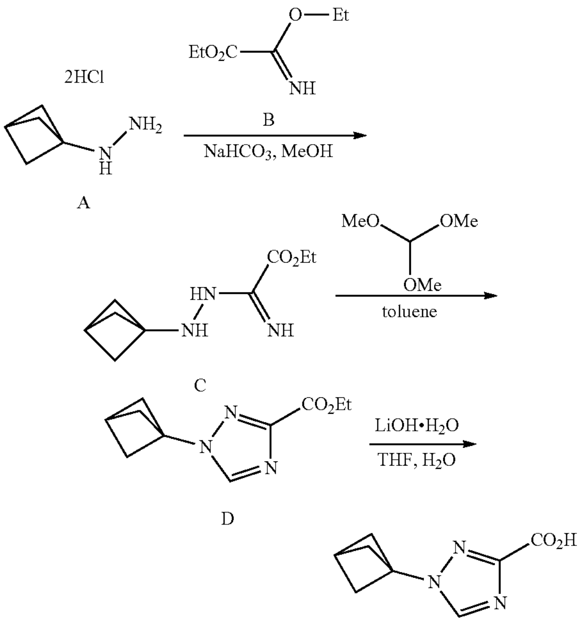

Step 1: Preparation of ethyl 2-(2-(bicyclo[1.1.1]pentan-1-yl)hydrazinyl)-2-iminoacetate (Intermediate C)

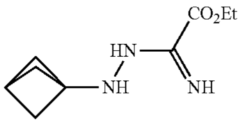

C

To a cooled (0° C.) mixture of 3-bicyclo[1.1.1]pentanylhydrazine bishydrochloride (1.00 g, 7.43 mmol) and ethyl 2-ethoxy-2-imino-acetate (1.19 g, 8.17 mmol) in MeOH (8 mL) was added $NaHCO_3$ (1.87 g, 22.29 mmol). After stirring for 1 h, the mixture was filtered to give Intermediate C (1.20 g) in MeOH solution which was used into the next step directly. LCMS (ESI) m/z: $[M+H]^+$=198.1.

Step 2: Preparation of ethyl 1-(bicyclo[1.1.1]pentan-1-yl)-1H-1,2,4-triazole-3-carboxylate (Intermediate D)

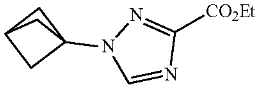

D

A solution of Intermediate C (1.20 g, 6.08 mmol) in MeOH and trimethyl orthoformate (6.67 mL, 60.84 mmol) in toluene (8 mL) was stirred at 100° C. After 1 h, the mixture was cooled to room temperature and concentrated. To the resultant oil was added water (10 mL) and extracted with dichloromethane (3×10 mL). The combined organic layers were washed with brine (10 mL), dried over $Na_2SO_4$, filtered and concentrated. The crude product was purified by reversed-phase HPLC (0.1% FA condition). The appropriate fractions were collected and concentrated until $CH_3CN$ was removed. The aqueous was extracted with dichloromethane (3×10 mL) and the combined organic layer was washed with aqueous saturated $NaHCO_3$, dried over $Na_2SO_4$, filtered and concentrated to give Intermediate D (0.300 g, 1.30 mmol, 21.41% yield, 90% purity) as a brown solid. LCMS (ESI) m/z: $[M+H]^+$=208.1; H NMR (400 MHz, $CDCl_3$) δ 8.13 (s, 1H), 4.52-4.43 (m, 2H), 2.76-2.70 (m, 1H), 2.40 (s, 6H), 1.46-1.41 (m, 3H).

Step 3: Preparation of 1-(bicyclo[1.1.1]pentan-1-yl)-1H-1,2,4-triazole-3-carboxylic acid (Intermediate E)

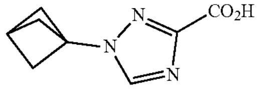

E

A mixture of Intermediate D (0.300 g, 1.45 mmol), $LiOH{\cdot}H_2O$ (0.304 g, 7.24 mmol) in THF (3 mL) and water (0.5 mL) was stirred at room temperature. After 15 h, the mixture was extracted with ethyl acetate (3×5 mL) and the aqueous layer was acidified (pH 3) with aqueous 1 M HCl. The acidic aqueous layer was extracted with ethyl acetate (3×5 mL) and the combined organic layer was washed with brine (10 mL), dried over $Na_2SO_4$, filtered and concentrated to give Intermediate E (0.200 g) as a white solid. LCMS (ESI) m/z: $[M+H]^+$=180.1.

Example 213. Preparation of (S)—N-(1-((4-(3-(4-(difluoromethyl)piperidin-1-yl)phenyl)thiazol-2-yl)amino)-3-methoxy-1-oxopropan-2-yl)-1-(methylsulfonyl)-1H-pyrrole-3-carboxamide (Compound 557)

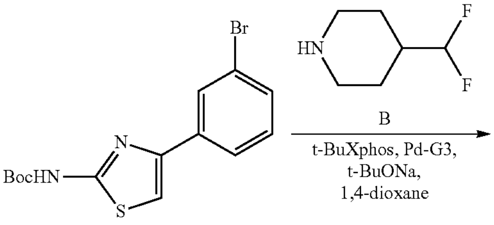

A

-continued

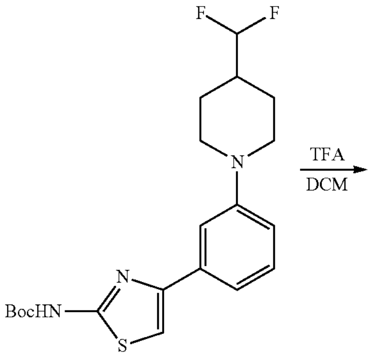

C

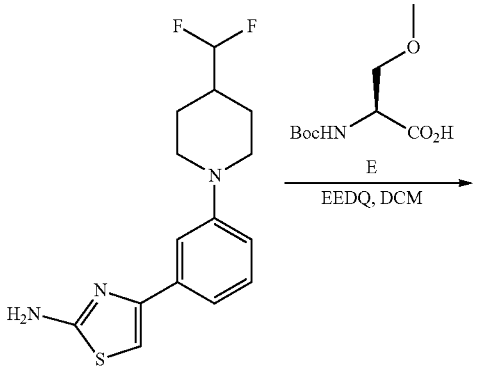

D

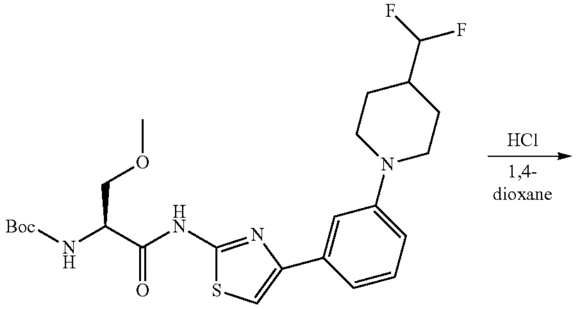

F

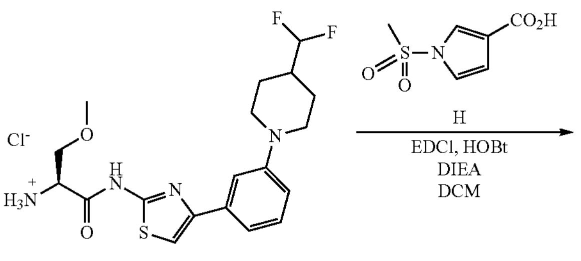

G

-continued

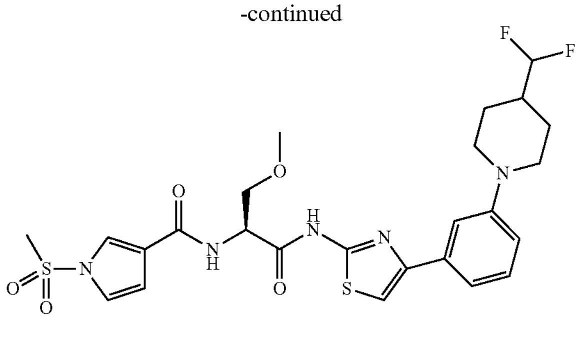

Compound 557

Step 1: Preparation of tert-butyl N-[4-[3-[4-(difluoromethyl)-1-piperidyl]phenyl]thiazol-2-yl]carbamate (Intermediate C)

C

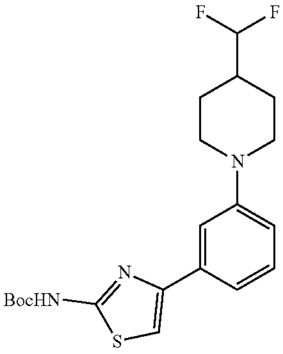

To a solution of tert-butyl N-[4-(3-bromophenyl)thiazol-2-yl]carbamate (0.500 g, 1.41 mmol), 4-(difluoromethyl)piperidine hydrochloride (0.483 g, 2.81 mmol) and t-BuXPhos Pd G3 (0.119 g, 0.150 mmol) in 1,4-dioxane (5 mL) was added t-BuONa (0.541 g, 5.63 mmol) under $N_2$ (g). The mixture was stirred at 70° C. After 3 h, the reaction mixture was cooled to room temperature and diluted with water (50 mL). The biphasic mixture was extracted with ethyl acetate (2×50 mL). The combined organic layers were washed with brine (50 mL), dried over $Na_2SO_4$, filtered and concentrated under reduced pressure. The residue was purified by column chromatography ($SiO_2$, petroleum ether/ethyl acetate=6:1) and concentrated under reduced pressure to give Intermediate C (0.250 g, 0.534 mmol, 37.95% yield, 87.50% purity) as a light yellow solid. LCMS (ESI) m/z: $[M+H]^+$=410.1.

Step 2: Preparation of 4-[3-[4-(difluoromethyl)-1-piperidyl]phenyl]thiazol-2-amine (Intermediate D)

D

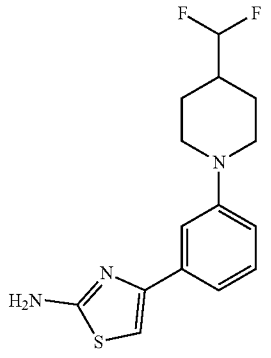

To a solution of Intermediate C (0.240 g, 0.586 mmol) in dichloromethane (2 mL) was added TFA (0.20 mL, 2.70 mmol). The mixture was stirred at 30° C. for 2 hours and concentrated under reduced pressure to give a residue. The residue was diluted with aqueous saturated $NaHCO_3$ (50 mL) and extracted with ethyl acetate (2×50 mL), dried over $Na_2SO_4$, filtered and concentrated under reduced pressure to give Intermediate 8 (0.180 g) as a light yellow oil, which was used to the next step without further purification.

Step 3: Preparation of tert-butyl N-[(1S)-2-[[4-[3-[4-(difluoromethyl)-1-piperidyl]phenyl]thiazol-2-yl]amino]-1-(methoxymethyl)-2-oxoethyl]carbamate (Intermediate F)

F

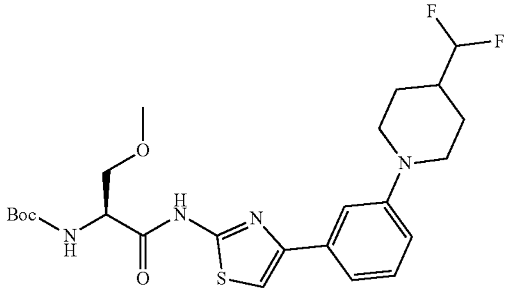

To a solution of Intermediate D (0.180 g, 0.582 mmol) and (2S)-2-(tertbutoxycarbonylamino)-3-methoxy-propanoic acid (0.153 g, 0.698 mmol) in dichloromethane (6 mL) was added EEDQ (0.216 g, 0.873 mmol). The mixture was stirred at 30° C. for 2 h, and the reaction mixture was concentrated under reduced pressure to give a residue. The residue was purified by column chromatography ($SiO_2$, petroleum ether/ethyl acetate=2:1) and concentrated under reduced pressure to give Intermediate F (0.220 g, 0.427 mmol, 73.32% yield, 99% purity) as a light yellow oil. LCMS (ESI) m/z: $[M+H]^+$=511.2.

Step 4: Preparation of (S)-1-((4-(3-(4-(difluoromethyl)piperidin-1-yl)phenyl)thiazol-2-yl)amino)-3-methoxy-1-oxopropan-2-aminium chloride (Intermediate G)

G

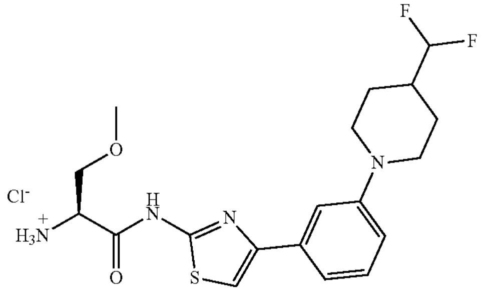

To a solution of Intermediate F (0.220 g, 0.431 mmol) in 1,4-dioxane was added a solution of 4 M HCl in 1,4-dioxane (5 mL). After stirring for 2 h, the reaction mixture was concentrated under reduced pressure to give Intermediate G (0.200 g) as a light yellow oil, which was used to the next step without further purification. LCMS (ESI) m/z: $[M+H]^+$= 410.9.

Step 5: Preparation of (S)—N-(1-((4-(3-(4-(difluoromethyl)piperidin-1-yl)phenyl)thiazol-2-yl)amino)-3-methoxy-1-oxopropan-2-yl)-1-(methylsulfonyl)-1H-pyrrole-3-carboxamide (Compound 557)

Compound 557

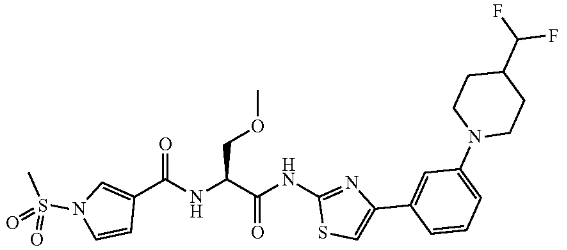

To a solution of Intermediate 11 (0.200 g, 0.447 mmol), 1-methylsulfonylpyrrole-3-carboxylic acid (0.102 g, 0.537 mmol), EDCI (0.129 g, 0.671 mmol) and DIEA (0.40 mL, 2.24 mmol) in dichloromethane (2 mL) was added HOBt (0.091 g, 0.671 mmol). The mixture was stirred at 30° C. for 2 h and subsequently concentrated under reduced pressure to give a residue. The residue was purified by reverse phase (FA) and the appropriated fractions were concentrated under reduced pressure to remove MeCN and lyophilized to give Compound 557 (0.123 g, 0.209 mmol, 46.80% yield, 99.11% purity) as a white solid. LCMS (ESI) m/z: $[M+H]^+$= 582.1; $^1H$ NMR (400 MHz, DMSO-$d_6$) δ 12.51 (s, 1H), 8.52 (d, J=7.2 Hz, 1H), 8.05-7.90 (m, 1H), 7.76-7.60 (m, 2H), 7.49 (d, J=2.0 Hz, 1H), 7.41-7.26 (m, 2H), 7.23-7.04 (m, 1H), 6.79-6.78 (m, 1H), 6.22-5.81 (m, 1H), 4.94-4.91 (m, 1H), 3.82-3.76 (m, 2H), 3.73-3.67 (m, 2H), 3.56 (s, 3H), 3.31 (s, 3H), 3.07-2.89 (m, 2H), 2.12-2.03 (m, 1H), 1.85 (d, J=12.4 Hz, 2H), 1.75-1.49 (m, 2H); ee %=100%.

Example 214. Preparation of Compounds of the Invention

The compounds in Table 28 below were synthesized starting from the appropriate starting material tert-butyl N-[4-(3-bromophenyl)-5-fluoro-thiazol-2-yl]carbamate and amine following the synthetic protocol described in Example 213 (Compound 557).

TABLE 28

| Compound # | LC-MS data(m/z) | $^1$H NMR |
|---|---|---|
| 461 | 522.3 | $^1$H NMR (400 MHz, DMSO-d$_6$) δ 12.67-12.53 (m, 1H), 8.56-8.45 (m, 1H), 8.04-7.96 (m, 1H), 7.31-7.24 (m, 2H), 7.14-7.10 (m, 1H), 6.85-6.83 (m, 1H), 6.80-6.78 (m, 1H), 6.44-6.39 (m, 1H), 4.92-4.84 (m, 1H), 3.87-3.80 (m, 4H), 3.76-3.67 (m, 2H), 3.60-3.56 (m, 3H), 3.32-3.30 (m, 3H), 2.36-2.31 (m, 2H) |

Example 215. Preparation of 1-(1-cyanocyclopropyl)-N-[2-[[4-[3-(cyclopropoxy)phenyl]thiazol-2-yl]amino]-2-oxo-ethyl]pyrrole-3-carboxamide (Compound 554)

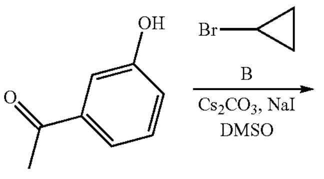

A

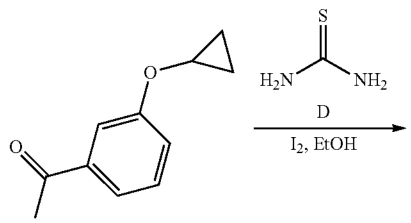

C

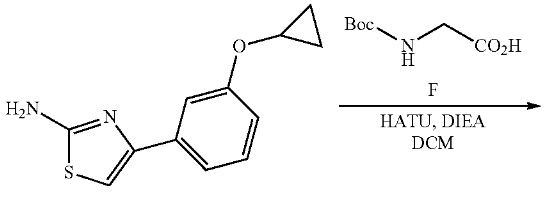

E

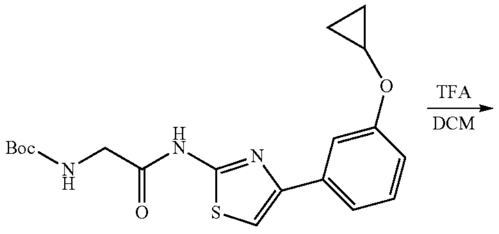

G

-continued

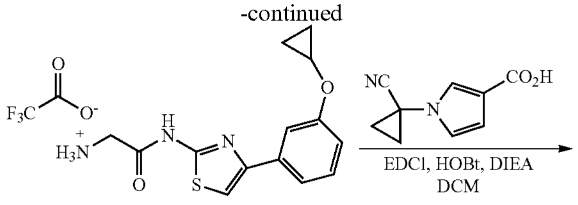

H

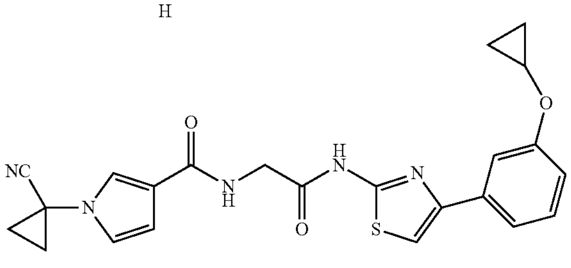

Compound 554

Step 1: Preparation of 1-[3-(cyclopropoxy)phenyl]ethenone (Intermediate C)

C

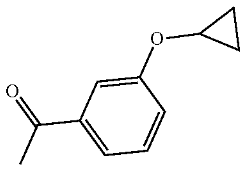

To a solution of 1-(3-hydroxyphenyl)ethanone (20.00 g, 146.90 mmol), NaI (3.30 g, 22.03 mmol), bromocyclopropane (25.89 mL, 323.18 mmol) in DMSO (50 mL) was added $Cs_2CO_3$ (119.66 g, 367.25 mmol). The mixture was stirred at 140° C. After 12 h, the mixture was cooled to room temperature and diluted with water (600 mL). The mixture was extracted with MTBE (200 mL) and the combined organic layers were evaporated. The residue was purified by column chromatography (petroleum ether/ethyl acetate=30/1 to 10/1, $SiO_2$) and evaporated to afford Intermediate 3 (13.00 g, 67.87 mmol, 46.20% yield, 92% purity) as a yellow oil. LCMS (ESI) m/z: $[M+H]^+$=177.1.

Step 2: Preparation of 4-[3-(cyclopropoxy)phenyl]thiazol-2-amine (Intermediate E)

E

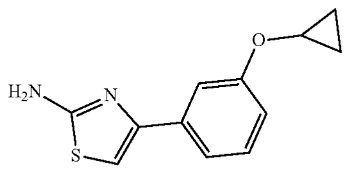

To a solution of Intermediate C (13.00 g, 73.78 mmol) and thiourea (11.23 g, 147.55 mmol) in EtOH (130 mL) was added $I_2$ (18.72 g, 73.78 mmol, 14.86 mL). The reaction mixture was stirred at 80° C. for 10 h and then cooled to room temperature and quenched by addition saturated aqueous $Na_2S_2O_3$ (200 mL). The aqueous mixture was extracted with ethyl acetate (3×200 mL). The combined organic layers were washed with brine (200 mL), dried over $Na_2SO_4$, filtered and concentrated under reduced pressure to give an oil. The oil was purified by flash silica gel chromatography (Eluent of 0-60% Ethyl acetate/Petroleum ether gradient) and concentrated under reduced pressure to afford Intermediate E (12.00 g, 49.07 mmol, 66.52% yield, 95% purity) as red solids. LCMS (ESI) m/z: $[M+H]^+$=232.9; $^1H$ NMR (400 MHz, DMSO-$d_6$) δ 7.51-7.45 (m, 1H), 7.43-7.36 (m, 1H), 7.29-7.27 (m, 1H), 7.05 (s, 2H), 7.01 (s, 1H), 6.95-6.91 (m, 1H), 3.94-3.81 (m, 1H), 0.89-0.55 (m, 4H).

Step 3: Preparation of tert-butyl N-[2-[[4-[3-(cyclopropoxy)phenyl]thiazol-2-yl]amino]-2-oxo-ethyl]carbamate (Intermediate G)

G

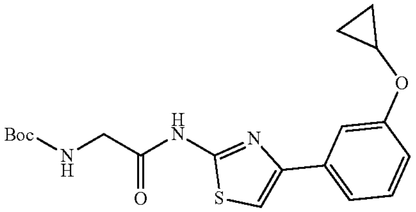

To a mixture of 2-(tert-butoxycarbonylamino)acetic acid (0.452 g, 2.58 mmol) in dichloromethane (5 mL) was added HATU (1.23 g, 3.23 mmol) and N,N-diisopropylethylamine (1.12 mL, 6.46 mmol). To the mixture was added Intermediate E (0.500 g, 2.15 mmol) and stirred at 30° C. After 2 h, the mixture combined with two additional batches (or equal scale) was poured into water (50 mL) and extracted with DCM (3×15 mL). The combined organic layer was washed with aqueous saturated $NaHCO_3$ solution (3×10 mL), aqueous saturated critic acid solution (3×10 mL), brine (10 mL*2), dried over $Na_2SO_4$, filtered and concentrated under vacuum to give Intermediate G (1.50 g) as yellow solids which were used to next step directly without further purification. LCMS (ESI) m/z: $[M+H]^+$=390.1; $^1H$ NMR (400 MHz, DMSO-$d_6$) δ 12.27 (s, 1H), 7.64 (s, 1H), 7.59-7.55 (m, 1H), 7.50 (d, J=7.6 Hz, 1H), 7.36-7.32 (m, 1H), 7.18-7.15 (m, 1H), 7.03-6.98 (m, 1H), 3.93-3.77 (m, 3H), 1.45-1.38 (m, 9H), 0.85-0.77 (m, 2H), 0.72-0.65 (m, 2H).

Step 4: Preparation of 2-((4-(3-cyclopropoxyphenyl)thiazol-2-yl)amino)-2-oxoethan-1-aminium trifluoroacetate(Intermediate I)

H

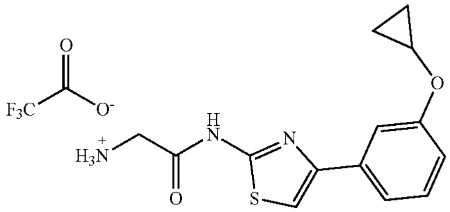

The mixture of Intermediate G (1.50 g, 3.85 mmol) and TFA (3 mL) in dichloromethane (10 mL) was stirred at 25° C. for 2 h. The mixture was subsequently diluted with dichloromethane (30 mL) then concentrated under vacuum. This operation was repeated three additional times. The resulting oil was triturated with MTBE (10 mL) to yield white solids. The solids were filtered and dried under reduced pressure to give Intermediate H (1.20 g) as white solids which was used to next step directly without further purification. LCMS (ESI) m/z: $[M+H]^+$=290.2.

Step 5: Preparation of 1-(1-cyanocyclopropyl)-N-[2-[[4-[3-(cyclopropoxy)phenyl]thiazol-2-yl]amino]-2-oxo-ethyl]pyrrole-3-carboxamide (Compound 554)

Compound 554

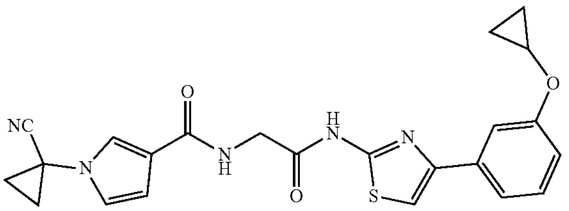

To a mixture of 1-(1-cyanocyclopropyl)pyrrole-3-carboxylic acid (0.131 g, 0.744 mmol) in dichloromethane (3 mL) was added EDCI (0.178 g, 0.930 mmol), HOBt (0.126 g, 0.930 mmol) and N,N-diisoproplyethylamine (0.324 mL, 1.86 mmol). To the mixture was added Intermediate H (0.250 g, 0.620 mmol) and stirred at 30° C. for 2 h. The mixture was poured into water (30 mL) and extracted with dichloromethane (3×10 mL). The combined organic layers were washed with brine (10 mL), dried over $Na_2SO_4$, filtered and concentrated under reduced pressure. The residue was purified by reverse phase flash (FA(0.1%) condition) and lyophilized to give Compound 554 (127.33 mg, 284.53 umol, 45.91% yield, 100% purity) as a white solid. LCMS (ESI) m/z: $[M+H]^+$=448.1; $^1H$ NMR (400 MHz, DMSO-$d_6$) δ 12.35 (s, 1H), 8.38-8.35 (m, 1H), 7.64 (s, 1H), 7.60-7.59 (m, 2H), 7.50 (d, J=7.6 Hz, 1H), 7.37-7.33 (m, 1H), 7.08-7.07 (m, 1H), 7.02-6.99 (m, 1H), 6.56-6.55 (m, 1H), 4.11 (d, J=5.6 Hz, 2H), 3.91-3.86 (m, 1H), 1.86-1.79 (m, 2H), 1.79-1.72 (m, 2H), 0.84-0.78 (m, 2H), 0.72-0.66 (m, 2H).

Example 216. Preparation of Compounds of the Invention

The compounds in Table 29 below were synthesized starting from the appropriate aryl ketone, N-Boc amino acid and heterocyclic carbocylic acid following the synthetic protocol described in Example 215 (Compound 554).

TABLE 29

| Compound # | LC-MS data(m/z) | $^1$H NMR |
|---|---|---|
| 592 | 551.2 | $^1$H NMR (400 MHz, DMSO-$d_6$) δ 12.55 (s, 1H), 8.50 (d, J = 7.2 Hz, 1H), 7.98-7.97 (m, 3H), 7.80 (s, 1H), 7.61-7.59 (m, 1H), 7.30-7.28 (m, 1H), 6.79-6.78 (m, 1H), 4.93-4.88 (m, 1H), 3.74-3.67 (m, 2H), 3.56 (s, 3H), 3.30 (s, 3H) |

Example 217. Preparation of Compounds of the Invention

The compounds in Table 30 below were synthesized starting from 2-amino-N-(4-bromothiazol-2-yl)acetamide, the appropriate heterocyclic carboxylic acid, and boronate ester utilizing the synthetic protocol described in Example 109. Where appropriate SEC purification was used to separate enantiomers.

TABLE 30

| Compound # | LC-MS data(m/z) | $^1$H NMR |
|---|---|---|
| 432 | 467.4 | $^1$H NMR (400 MHz, DMSO-$d_6$) δ 12.37-12.30 (m, 1H), 8.21-8.12 (m, 1H), 7.94-7.88 (m, 1H), 7.80-7.71 (m, 1H), 7.63-7.56 (m, 1H), 7.54-7.47 (m, 1H), 7.40-7.32 (m, 1H), 7.28-7.19 (m, 1H), 7.00-6.93 (m, 1H), 6.52-6.43 (m, 1H), 4.39-4.29(m, 1H), 4.13-4.07 (m, 2H), 4.07-3.99 (m, 1H), 3.58-3.54 (m, 1H), 1.91-1.79 (m, 2H), 1.57 (d, J = 5.1 Hz, 4H), 1.51-1.36 (m, 9H) |
| 578 | 470.2 | $^1$H NMR (400 MHz, Methanol-$d_4$) δ 7.80-7.79 (m, 1H), 7.30-7.23 (m, 1H), 6.82-6.74 (m, 2H), 4.36-4.15 (m, 3H), 4.13-3.93 (m, 1H), 3.69 (s, 3H), 3.38 (s, 3H), 3.11-2.66 (m, 3H), 2.18-2.05 (m, 1H), 1.85-1.65 (m, 2H), 1.64-1.47 (m, 1H) |
| 579 | 470.1 | $^1$H NMR (400 MHz, Methanol-$d_4$) δ 7.86-7.78 (m, 1H), 7.30-7.22 (m, 1H), 6.81-6.77 (m, 2H), 4.30-4.14 (m, 3H), 4.13-3.92 (m 1H), 3.69 (s, 3H), 3.38 (s, 3H), 3.04-2.69 (m, 3H), 2.15-2.05 (m, 1H), 1.85-1.65 (m, 2H), 1.64-1.45 (m, 1H) |
| 580 | 448.2 | $^1$H NMR (400 MHz, Methanol-$d_4$) δ 7.58-7.55 (m, 1H), 6.97-6.92 (m, 1H), 6.77 (s, 1H), 6.58-6.53 (m, 1H), 4.31-4.21 (m, 1H), 4.19 (s, 2H), 4.12-3.95 (m, 1H), 3.69 (s, 3H), 3.03-2.70 (m, 3H), 2.15-2.04 (m, 1H), 1.84-1.65 (m, 2H), 1.59-1.50 (m, 10H) |
| 581 | 448.2 | $^1$H NMR (400 MHz, Methanol-$d_4$) δ 7.58-7.54 (m, 1H), 6.97-6.92 (m, 1H), 6.77 (s, 1H), 6.58-6.54 (m, 1H), 4.30-4.21 (m, 1H), 4.19 (s, 2H), 4.11-3.96 (m, 1H), 3.69 (s, 3H), 3.00-2.72 (m, 3H), 2.15-2.04 (m, 1H), 1.83-1.65 (m, 2H), 1.62-1.52 (m, 10H) |

Example 218. Preparation of Compounds of the Invention

The compounds in Table 31 were synthesized starting from the appropriate common intermediate tert-butyl (4-(3-bromophenyl)thiazol-2-yl)carbamate and the corresponding amino acid and heterocyclic carboxylic acid utilizing the synthetic protocol described in Example 32.

TABLE 31

| Compound # | LC-MS data(m/z) | $^1$H NMR |
|---|---|---|
| 464 | 439.2 | $^1$H NMR (400 MHz, DMSO-$d_6$) δ 12.35 (s, 1H), 8.18-8.15 (m, 1H), 8.00 (s, 1H), 7.81-7.79 (m, 1H), 7.67 (s, 1H), 7.52-7.51 (m, 1H), 7.44-7.40 (m, 1H), 7.34-7.32 (m, 1H), 6.98-6.96 (m, 1H), 6.48-6.47 (m, 1H), 5.00-4.96 (m, 2H), 4.67-4.64 (m, 2H), 4.33-4.26 (m, 1H), 4.09 (d, J = 6.0 Hz, 2H), 1.49 (s, 9H) |

TABLE 31-continued

| Compound # | LC-MS data(m/z) | $^1$H NMR |
|---|---|---|
| 465 | 461.1 | $^1$H NMR (400 MHz, DMSO-$d_6$) δ 12.43 (br s, 1H), 8.71-8.65 (m, 1H), 8.00 (s, 1H), 7.84-7.83 (m, 1H), 7.81-7.78 (m, 1H), 7.67 (s, 1H), 7.43-7.40 (m, 1H), 7.33-7.30 (m, 2H), 6.77-6.76 (m, 1H), 5.00-4.96 (m, 2H), 4.66-4.63 (m, 2H), 4.33-4.25 (m, 1H), 4.13 (d, J = 6.0 Hz, 2H), 3.57 (s, 3H) |
| 466 | 505.1 | 1H NMR (400 MHz, DMSO-$d_6$) δ 12.85-12.33 (m, 1H), 8.51 (d, J = 6.8 Hz, 1H), 8.04-7.96 (m, 2H), 7.85-7.79 (m, 1H), 7.70 (s, 1H), 7.46-7.40 (m, 1H), 7.36-7.28 (m, 2H), 6.80-6.79 (m, 1H), 5.00-4.97 (m, 2H), 4.94-4.89 (m, 1H), 4.67-4.64 (m, 2H), 4.33-4.26 (m, 1H), 3.78-3.67 (m, 2H), 3.57 (s, 3H), 3.32 (s, 3H) |

Example 219. Preparation of Compounds of the Invention

The following compounds in Table 32 were synthesized utilizing the general synthetic protocols described in Example 61 and starting from the appropriate common intermediate 4-(3-bromo-5-fluoro-phenyl)thiazol-2-amine, heteroaryl halide, N-Boc amino acid, and the appropriate heterocyclic carboxylic acid.

TABLE 32

| Compound # | LC-MS data(m/z) | $^1$H NMR |
|---|---|---|
| 738 | 548.2 | $^1$H NMR (400 MHz, DMSO-$d_6$) δ 12.74-12.49 (m, 1H), 8.51 (d, J = 7.2 Hz, 1H), 8.34 (s, 1H), 8.30 (s, 1H), 7.99-7.98 (m, 1H), 7.88 (s, 1H), 7.72 (d, J = 10.0 Hz, 1H), 7.63 (d, J = 9.6 Hz, 1H), 7.32-7.28 (m, 1H), 6.80-6.78 (m, 1H), 4.96-4.90 (m, 1H), 4.23 (s, 3H), 3.75-3.70 (m, 2H), 3.57 (s, 3H), 3.32 (s, 3H) |
| 739 | 537.3 | $^1$H NMR (400 MHz, DMSO-$d_6$) δ 12.58 (s, 1H), 8.34 (s, 1H), 8.30 (s, 1H), 8.17 (d, J = 7.2 Hz, 1H), 7.88 (s, 1H), 7.81 (d, J = 1.6 Hz, 1H), 7.72 (d, J = 10.0 Hz, 1H), 7.63 (d, J = 9.6 Hz, 1H), 7.15-7.14 (m, 1H), 6.65 (d, J = 1.6 Hz, 1H), 4.98-4.91 (m, 1H), 4.23 (s, 3H), 3.74-3.71 (m, 2H), 3.31 (s, 3H), 1.96 (s, 6H) |
| 825 | 528.3 | $^1$H NMR (400 MHz, DMSO-$d_6$) δ 12.69 (s, 1H), 8.78 (d, J = 8.0 Hz, 1H), 8.33 (s, 1H), 8.29-8.28 (m, 1H), 7.87 (s, 1H), 7.73-7.69 (m, 1H), 7.64-7.60 (m, 1H), 7.15 (s, 1H), 4.90-4.88 (m, 1H), 4.22 (s, 3H), 3.85-3.76 (m, 2H), 3.30 (s, 3H), 1.31 (s, 9H) |

Example 220. Preparation of Compounds of the Invention

The following compounds in Table 33 were synthesized utilizing the general synthetic protocols described in Example 5 and starting from the appropriate common intermediate 4-phenylthiazol-2-amine, N-Boc amino acid, and the appropriate heterocyclic carboxylic acid.

TABLE 33

| Compound # | LC-MS data(m/z) | $^1$H NMR |
|---|---|---|
| 594 | 449.0 | $^1$H NMR (400 MHz, DMSO-$d_6$) δ 12.52 (s, 1H), 8.51 (d, J = 7.2 Hz, 1H), 7.99-7.98 (m, 1H), 7.91 (d, J = 7.2 Hz, 2H), 7.64 (s, 1H), 7.47-7.40 (m, 2H), 7.36-7.27 (m, 2H), 6.79-6.78 (m, 1H), 4.95-4.90 (m, 1H), 3.76-3.67 (m, 2H), 3.61-3.52 (m, 3H), 3.31 (s, 3H) |

Example 221. Preparation of Compounds of the Invention

The following compounds in Table 34 were synthesized utilizing the general synthetic protocols described in Example 58 or Example 59 and starting from the appropriate common intermediate 4-(3-bromophenyl)thiazol-2-amine, boronate ester or trifluoroborate, N-Boc amino acid, and the appropriate heterocyclic carboxylic acid.

TABLE 34

| Compound # | LC-MS data(m/z) | $^1H$ NMR |
|---|---|---|
| 153 | 510.2 | $^1H$ NMR (400 MHz, DMSO-$d_6$) δ = 11.99 (br s, 1H), 8.65 (d, J = 6.0 Hz, 2H), 8.27 (br d, J = 7.6 Hz, 2H), 8.98-7.96 (m, 2H), 7.78-7.72 (m, 4H), 7.57-7.53 (m, 1H), 7.30-7.29 (m, 1H), 6.76 (d, J = 1.6 Hz, 1H), 3.55 (s, 3H), 1.51 (s, 6H) |
| 154 | 496.3 | $^1H$ NMR (400 MHz, DMSO-$d_6$) δ 12.43 (s, 1H), 8.68-8.66 (m, 1H), 8.53 (d, J = 5.2 Hz, 1H), 8.28 (s, 1H), 8.00 (d, J = 7.6 Hz, 1H), 7.84-7.82 (m, 2H), 7.73 (d, J = 7.2 Hz, 1H), 7.63 (s, 1H), 7.60-7.56 (m, 1H), 7.54 (d, J = 5.2 Hz, 1H), 7.32-7.30 (m, 1H), 6.77 (s, 1H), 4.15 (d, J = 5.6 Hz, 2H), 3.57 (s, 3H), 2.56 (s, 3H) |
| 155 | 496.1. | $^1H$ NMR (400 MHz, Methanol-$d_4$) δ = 8.64-8.60 (m, 2H), 8.22-8.21(m, 1H), 7.95 (d, J = 7.8 Hz, 1H), 7.73-7.68 (m, 3H), 7.66 (s, 1H), 7.61-7.54 (m, 1H), 7.50 (br s, 1H), 7.28-7.20 (m, 1H), 6.58 (br s, 1H), 4.38 (s, 2H), 3.43 (s, 3H), 3.16 (br s, 3H) |
| 741 | 501.1 | $^1H$ NMR (400 MHz, DMSO-$d_6$) δ 12.42 (s, 1H), 8.68-8.68 (m, 1H), 7.88-7.81 (m, 2H), 7.71 (d, J = 7.6 Hz, 1H), 7.65(s, 1H), 7.38-7.34 (m, 1H), 7.34-7.30 (m, 1H), 7.23 (d, J = 7.6 Hz, 1H), 6.78 (d, J = 3.2 Hz, 1H), 4.14 (d, J = 6.0 Hz, 2H), 4.02 (d, J = 4.8 Hz, 1H), 3.85-3.79 (m, 1H), 3.58 (s, 3H), 3.48 (d, J = 5.2 Hz, 2H), 2.12-2.04 (m, 1H), 2.03-1.96 (m, 1H), 1.38-1.37(m, 1H), 1.04-1.02 (m, 1H), 0.94-0.87 (m, 1H) |

Example 222. Preparation of potassium 3-oxabicyclo[4.1.0]heptan-6-yltrifluoroborate

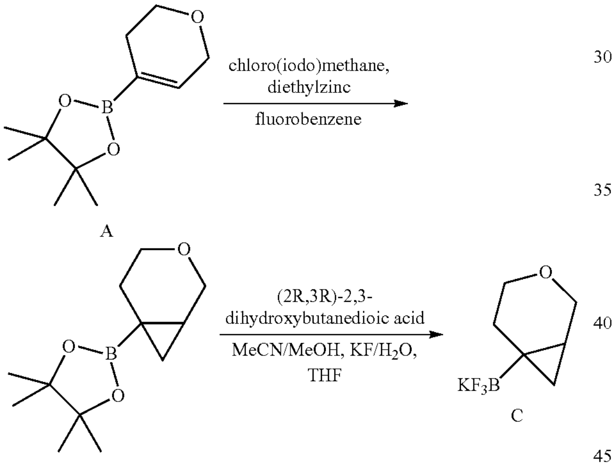

A

B

C

Potassium 3-oxabicyclo[4.1.0]heptan-6-yltrifluoroborate was synthesized according to the protocol described by Hobbs et al. in *J. Med. Chem.* 62(15): 6972-6984 (2019). $^1H$ NMR (400 MHz, $D_2O$) δ 3.97-3.82 (m, 2H), 3.56-3.44 (d, 1H), 3.24-3.20 (m, 1H), 1.80-1.77 (m, 1H), 1.60-1.46 (m, 1H), 0.80-0.70 (m, 11H), 0.51-10.48 (m, 1H), 0.12 (s, 1H).

Example 223. Preparation of Compounds of the Invention

The following compounds in Table 35 were synthesized utilizing the general synthetic protocols described in Example 79 and starting from the appropriate common intermediate of tert-butyl N-[2-[[4-(3-bromophenyl)thiazol-2-yl]amino]-2-oxo-ethyl]carbamate, boronate ester or trifluoroborate, and the appropriate heterocyclic carboxylic acid.

TABLE 35

| Compound # | LC-MS data(m/z) | $^1H$ NMR |
|---|---|---|
| 743 | 501.1 | $^1H$ NMR (400 MHz, DMSO-$d_6$) δ 12.42 (s, 1H), 8.68-8.68 (m, 1H), 7.88-7.81 (m, 2H), 7.71 (d, J = 7.6 Hz, 1H), 7.65(s, 1H), 7.38-7.34 (m, 1H), 7.34-7.30 (m, 1H), 7.23 (d, J = 7.6 Hz, 1H), 6.78 (d, J = 3.2 Hz, 1H), 4.14 (d, J = 6.0 Hz, 2H), 4.02 (d, J = 4.8 Hz, 1H), 3.85-3.79 (m, 1H), 3.58 (s, 3H), 3.48 (d, J = 5.2 Hz, 2H), 2.12-2.04 (m, 1H), 2.03-1.96 (m, 1H), 1.38-1.37(m, 1H), 1.04-1.02 (m, 1H), 0.94-0.87 (m, 1H) |
| 744 | 479.3 | $^1H$ NMR (400 MHz, DMSO-$d_6$) δ 12.50-12.00 (m, 1H), 8.18-8.16 (m, 1H), 7.83 (s, 1H), 7.70 (d, J = 7.6 Hz, 1H), 7.63 (s, 1H), 7.52-7.51 (m, 1H), 7.38-7.30 (m, 1H), 7.23 (d, J = 7.6 Hz, 1H), 6.97-6.96 (m, 1H), 6.51-6.44 (m, 1H), 4.08 (d, J = 6.0 Hz, 2H), 4.01 (d, J = 4.8, 1H), 3.81 (d, J = 11.6 Hz, 1H), 3.50-3.45 (m, 2H), 2.13-1.94 (m, 2H), 1.49 (s, 9H), 1.42-1.33 (m, 1H), 1.03 (d, J = 4.4, 1H), 0.94-0.86 (m, 1H) |

Example 224. Preparation of 1-tert-butyl-N-[2-[[4-[6-[(3S,4R)-3-fluoro-4-methyl-1-piperidyl]-2-pyridyl]thiazol-2-yl]amino]-2-oxo-ethyl]pyrrole-3-carboxamide (Compound 702)

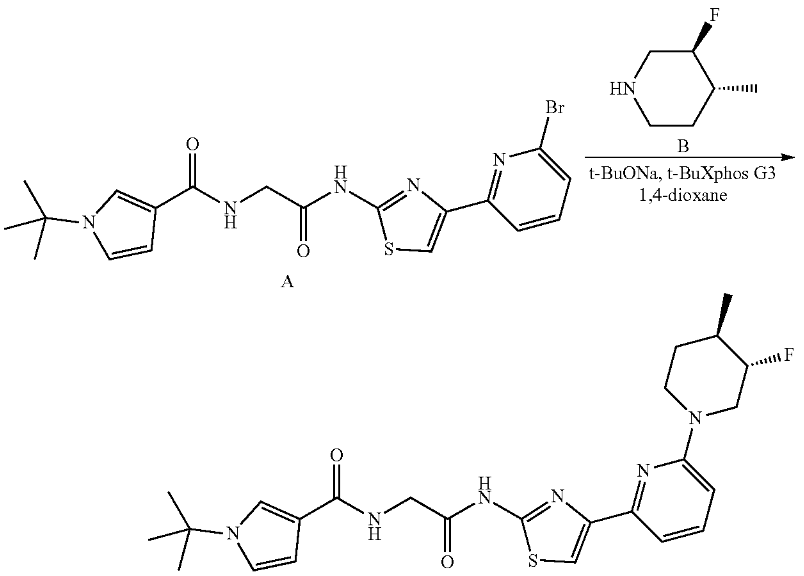

A mixture of N-[2-[[4-(6-bromo-2-pyridyl)thiazol-2-yl]amino]-2-oxo-ethyl]-1-tert-butyl-pyrrole-3-carboxamide (0.040 g, 0.087 mmol), (3S,4R)-3-fluoro-4-methyl-piperidine hydrochloride (0.040 g, 0.260 mmol), [2-(2-aminophenyl)phenyl]-methylsulfonyloxy-palladium; ditert-butyl-[2-(2,4,6-triisopropylphenyl)phenyl]phosphane (0.007 g, 0.009 mmol) and t-BuONa (0.037 g, 0.389 mmol) in 1,4-dioxane (0.4 mL) was degassed and purged with $N_2$ (g) (3 times). The mixture was stirred at 60° C. After 2 h, the reaction mixture was cooled to room temperature and quenched by addition of water (1 mL). The biphasic mixture was extracted with ethyl acetate (3×2 mL). The combined organic layers were concentrated. The oil was initially purified by Prep-TLC (petroleum ether:ethyl acetate=3:1), then subsequently purified by Prep-HPLC (FA (0.1%) condition). The eluent was lyophilized to give Compound 702 (0.002 g, 0.004 mmol, 5.02% yield) as an off-white solid. LCMS (ESI) m/z: $[M+H]^+$=499.4; $^1$HNMR (400 MHz, $CDCl_3$) δ 7.69 (s, 1H), 7.57-7.49 (m, 2H), 7.32 (d, J=7.6 Hz, 1H), 6.83 (m, 1H), 6.62 (d, J=8.4 Hz, 1H), 6.47-6.41 (m, 1H), 4.77-4.62 (m, 2H), 4.37-4.32 (m, 2H), 4.31-4.09 (m, 2H), 2.92-2.82 (m, 2H), 1.86-1.82 (m, 1H), 1.55 (s, 9H), 1.39-1.32 (m, 1H), 1.12 (d, J=6.0 Hz, 3H).

Example 225. Preparation of Compounds of the Invention

The following compounds in Table 36 were synthesized starting from the appropriate common intermediate ([1-tert-butyl-N-[2-[[4-(6-bromo-2-pyridyl)thiazol-2-yl]amino]-2-oxo-ethyl]pyrrole-3-carboxamide]), the requisite amine, and utilizing the general synthetic protocols described in Example 224 (Compound 702).

TABLE 36

| Compound # | LC-MS data(m/z) | $^1$H NMR |
|---|---|---|
| 655 | 520.5 | $^1$H NMR (400 MHz, DMSO-$d_6$) δ 8.07-7.90 (m, 1H), 7.75-7.62 (m, 2H), 7.51-7.50 (m, 1H), 7.33 (d, J = 7.6 Hz, 1H), 7.03-6.92 (m, 2H), 6.46-6.45 (m, 1H), 4.91 (s, 2H), 4.18-4.08 (m, 2H), 4.01 (d, J = 5.2 Hz, 4H), 2.31 (s, 3H), 1.49 (s, 9H) |
| 657 | 505.5 | $^1$H NMR (400 MHz, DMSO-$d_6$) δ 12.51 (s, 1H), 8.18-8.15 (m, 1H), 7.81 (s, 1H), 7.70-7.66 (m, 1H), 7.52-7.51(m, 1H), 7.32 (d, J = 7.6 Hz, 1H), 7.12 (d, J = 1.2 Hz, 1H), 7.01-6.94 (m, 2H), 6.90 (d, J = 1.2 Hz, 1H), 6.47-6.46 (m, 1H), 4.77 (s, 2H), 4.18-4.03 (m, 6H), 1.49 (s, 9H) |
| 689 | 497.4 | $^1$H NMR (400 MHz, DMSO-$d_6$) δ 8.16-8.05 (m, 1H), 7.67-7.61 (m, 1H), 7.59-7.51 (m, 2H), 7.23-7.18 (m, 1H), 6.99-6.95 (m, 1H), 6.49-6.46 (m, 1H), 6.43-6.38 (m, 1H), 4.44-4.39 (m, 1H), 4.31-4.24 (m, 1H), 4.10-3.99 (m, 2H), 3.82-3.73 (m, 2H), 3.46-3.43 (m, 2H), 1.83-1.75 (m, 2H), 1.54-1.44 (m, 9H), 1.18-1.07 (m, 1H) |
| 692 | 506.5 | $^1$HNMR (400 MHz, $CDCl_3$) δ 7.94 (s, 1H), 7.70 (s, 1H), 7.67-7.62 (m, 1H), 7.54 (m, 1H), 7.46 (d, J = 7.2 Hz, 1H), 6.84 (m, 1H), 6.70 (d, J = 8.4 Hz, 1H), 6.49-6.44 (m, 1H), 6.44-6.42 (m, 1H), 4.89 (s, 2H), 4.40-4.32 (m, 4H), 4.31-4.25 (m, 2H), 1.56 (s, 9H) |

TABLE 36-continued

| Compound # | LC-MS data(m/z) | $^1$H NMR |
|---|---|---|
| 703 | 515.3 | $^1$HNMR (400 MHz, $CDCl_3$) δ 7.69 (s, 1H), 7.57-7.52 (m, 2H), 7.34 (d, J = 7.6 Hz, 1H), 6.83 (m, 1H), 6.49-6.45 (m, 1H), 6.45-6.42 (m, 1H), 4.34 (d, J = 5.6 Hz, 2H), 4.18 (d, J = 11.2 Hz, 1H), 3.91 (d, J = 10.8 Hz, 1H), 3.47-3.35 (m, 1H), 3.34-3.24 (m, 2H), 2.98-2.78 (m, 2H), 2.40 (d, J = 12.8 Hz, 1H), 1.56 (s, 9H) |

Example 226. Preparation of 1-(tert-butyl)-N-(2-((4-(3-(5-methyl-4,5,6,7-tetrahydropyrazolo[1,5-a]pyrazin-2-yl)phenyl)thiazol-2-yl)amino)-2-oxoethyl)-1H-pyrrole-3-carboxamide (Compound 143)

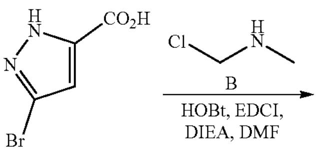

A

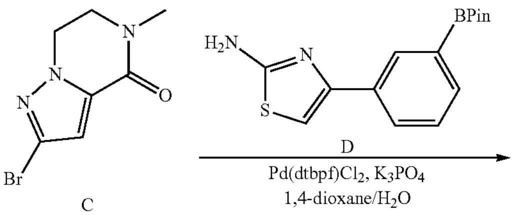

C

D

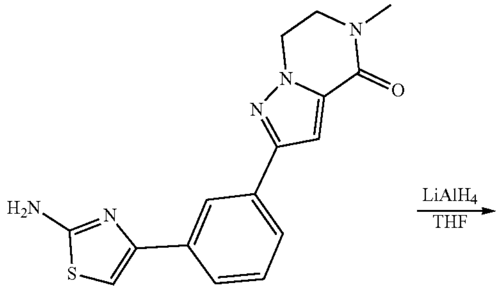

E

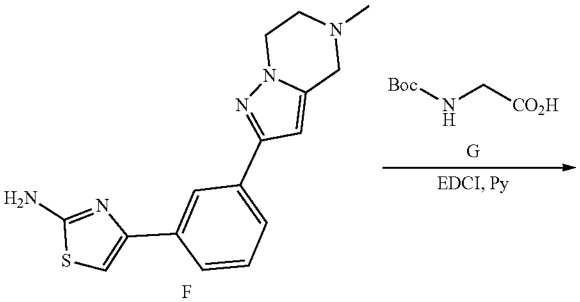

F

-continued

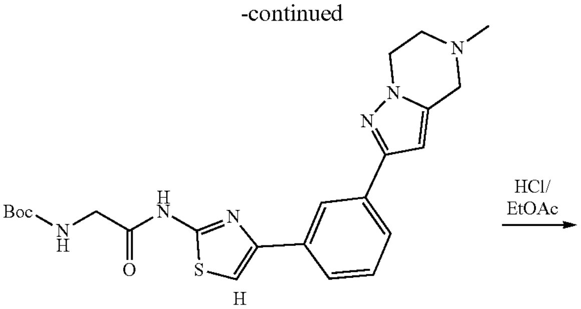

H

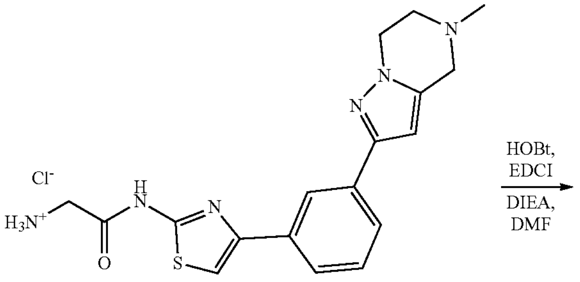

I

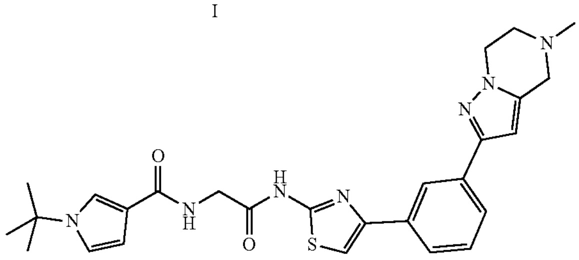

Compound 143

Step 1: Preparation of 2-bromo-5-methyl-6,7-dihydropyrazolo[1,5-a]pyrazin-4(5H)-one (Intermediate C)

C

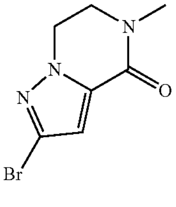

A mixture of 3-bromo-1H-pyrazole-5-carboxylic acid (1.00 g, 5.24 mmol), 2-chloro-N-methyl-ethanamine hydrochloride (1.02 g, 7.85 mmol), N,N-diisopropylethylamine (4.56 mL, 26.18 mmol), EDCI (1.51 g, 7.85 mmol) and HOBt (1.06 g, 7.85 mmol) in DMF (10 mL) was degassed and purged with $N_2$ (g) (3 times). The mixture was stirred at 25° C. for 12 h and subsequently diluted with water (10 mL). The mixture aqueous mixture was extracted with ethyl acetate (3×10 mL). The combined organic layers were washed with brine (3×10 mL), dried over $Na_2SO_4$, filtered and concentrated under reduced pressure. The oil was purified by reversed phase (FA (0.1%) condition) and lyophilized to give Intermediate C (0.510 g, 2.22 mmol, 42.34% yield) as yellow solids. LCMS (ESI) m/z: $[^{81}BrM+H]^+$=232.0; $^1H$ NMR (400 MHz, DMSO-$d_6$) δ 6.84 (s, 1H), 4.41-4.33 (m, 2H), 3.80-3.76 (m, 2H), 3.32 (s, 3H).

Step 2: Preparation of 2-(3-(2-aminothiazol-4-yl)phenyl)-5-methyl-6,7-dihydropyrazolo[1,5-a]pyrazin-4(5H)-one (Intermediate E)

E

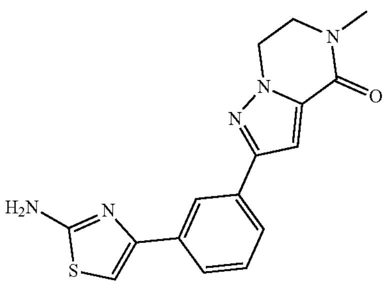

A mixture of Intermediate C (0.500 g, 2.17 mmol), Intermediate D (0.788 g, 2.61 mmol), $K_3PO_4$ (1.38 g, 6.52 mmol), [1,1'-bis(di-tert-butylphosphino)ferrocene]dichloropalladium (0.142 g, 0.217 mmol) in a mixture of 1,4-dioxane (5 mL) and water (0.5 mL). The reaction mixture was subjected to three cycles of degassing and purging with $N_2$ (g) and subsequently stirred at 80° C. After 1 h, the reaction mixture was cooled to room temperature and quenched by addition water (10 mL). The biphasic mixture was extracted with ethyl acetate (3×10 mL). The combined organic layers were washed with brine (3×10 mL), dried over $Na_2SO_4$, filtered and concentrated under reduced pressure. The oil was purified by column chromatography ($SiO_2$, petroleum ether/ethyl acetate=3/1 to 1/3) and concentrated in vacuum to give Intermediate E (0.380 g, 1.17 mmol, 53.74% yield) as yellow solids. LCMS (ESI) m/z: $[M+H]^+$=326.1; $^1H$ NMR (400 MHz, DMSO-$d_6$) δ 8.34 (s, 1H), 7.79-7.69 (m, 2H), 7.43-7.39 (m, 1H), 7.26 (s, 1H), 7.18-7.05 (m, 3H), 4.48-4.40 (m, 2H), 3.87-3.78 (m, 2H), 3.04 (s, 3H).

Step 3: Preparation of 4-(3-(5-methyl-4,5,6,7-tetrahydropyrazolo[1,5-a]pyrazin-2-yl)phenyl)thiazol-2-amine (Intermediate F)

F

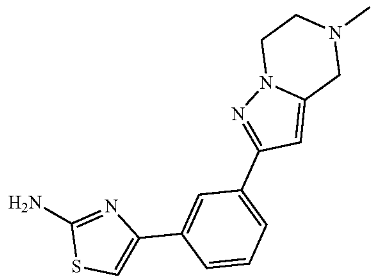

To a cooled (0° C.) solution of Intermediate E (0.100 g, 0.307 mmol) in THF (1 mL) was added $LiAlH_4$ (0.023 g, 0.615 mmol). After 1 h, the reaction mixture was quenched by addition 30% NaOH (0.1 mL), and the resultant solids was filtered off. The filtrate was concentrated under reduced pressure to give Intermediate F (0.100 g) as yellow solids, which was used to next step directly without further purification. LCMS (ESI) m/z: $[M+H]^+$=312.0; $^1H$ NMR (400 MHz, DMSO-$d_6$) δ 8.26-8.24 (m, 1H), 7.73-7.60 (m, 2H), 7.37 (m, 1H), 7.09 (d, J=13.4 Hz, 3H), 6.48 (s, 1H), 4.15-4.13 (m, 2H), 3.61 (s, 2H), 2.88-2.84 (m, 2H), 2.41 (s, 3H).

Step 4: Preparation of tert-butyl (2-((4-(3-(5-methyl-4,5,6,7-tetrahydropyrazolo[1,5-a]pyrazin-2-yl)phenyl)thiazol-2-yl)amino)-2-oxoethyl)carbamate (Intermediate H)

H

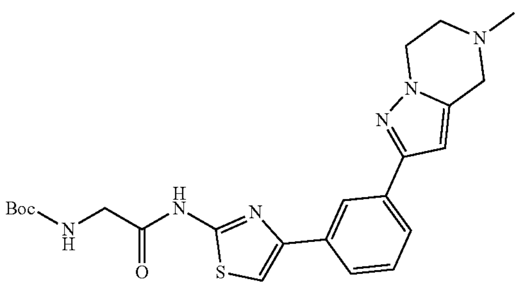

A mixture of Intermediate F (0.080 g, 0.257 mmol), 2-(tert-butoxycarbonylamino)acetic acid (0.540 g, 3.08 mmol) and EDCI (0.246 g, 1.28 mmol) in pyridine (1 mL) was stirred at 60° C. After 24 h, the mixture was cooled to room temperature and poured into water (20 mL). The biphasic solution was extracted with ethyl acetate (3×10 mL). The combined organic layers were washed with brine (3×10 mL), dried over $Na_2SO_4$, filtered and concentrated in vacuum. The residue was purified by reverse phase (FA (0.1%) conditions) and lyophilized to give Intermediate H (0.090 g, 0.169 mmol, 65.73% yield) as yellow solids. LCMS (ESI) m/z: $[M+H]^+$=469.2; $^1H$ NMR (400 MHz, $CDCl_3$) δ 9.93-9.70 (m, 1H), 8.18-8.13 (m, 1H), 7.70-7.62 (m, 2H), 7.39-7.32 (m, 1H), 7.17-7.13 (m, 1H), 6.32-6.19 (m, 1H), 5.20-4.96 (m, 1H), 4.23-4.19 (m, 2H), 4.03-3.93 (m, 2H), 3.67-3.58 (m, 2H), 2.91-2.83 (m, 2H), 2.48-2.41 (m, 3H), 1.42 (s, 9H).

Step 5: Preparation of 2-((4-(3-(5-methyl-4,5,6,7-tetrahydropyrazolo[1,5-a]pyrazin-2-yl)phenyl)thiazol-2-yl)amino)-2-oxoethan-1-aminium chloride (Intermediate I)

I

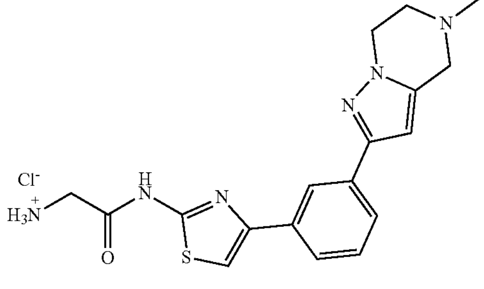

A solution of Intermediate H (0.090 g, 0.192 mmol) in ethyl acetate was added a solution of 4 M HCl in EtOAc (1.5 mL). The reaction mixture was stirred for 30 min and subsequently concentrated in vacuo to give Intermediate H (0.085 g) as light yellow solids, which was used into next step without purification. LCMS (ESI) m/z: $[M+H]^+$=369.2.

Step 6: Preparation of 1-(tert-butyl)-N-(2-((4-(3-(5-methyl-4,5,6,7-tetrahydropyrazolo[1,5-a]pyrazin-2-yl)phenyl)thiazol-2-yl)amino)-2-oxoethyl)-1H-pyrrole-3-carboxamide (Compound 143)

Compound 143

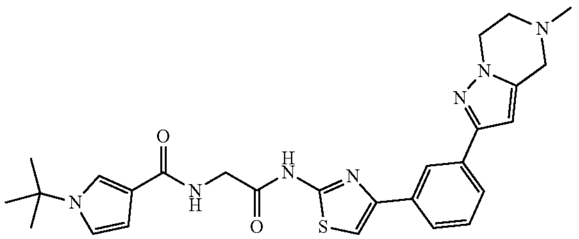

To a solution of 1-tert-butylpyrrole-3-carboxylic acid (0.047 g, 0.278 mmol), EDCI (0.053 g, 0.278 mmol), HOBt (0.038 g, 0.278 mmol) and N,N-diisopropylethylamine (0.161 mL, 0.926 mmol) in DMF (0.7 mL) was added Intermediate H (0.075 g, 0.185 mmol). After stirring for 2 h, the mixture was poured into water (2 mL) and the resulting solids were filtered. The solids were washed with MeOH (1 mL) and further dried. The solids were purified by flash chromatography (Eluent of 20%-100% petroleum ether: ethyl acetate then 0-35% ethyl acetate:MeOH) and concentrated to give Compound 143 (0.019 g, 0.036 mmoll, 19.27% yield) as yellow solids. LCMS (ESI) m/z: $[M+H]^+$=518.3; $^1$H NMR (400 MHz, DMSO-$d_6$) δ 12.58-11.97 (m, 1H), 8.39 (s, 1H), 8.18 (s, 1H), 7.81 (d, J=7.6 Hz, 1H), 7.73-7.66 (m, 2H), 7.53 (s, 1H), 7.48-7.40 (m, 11H), 6.98 (d, J-=2.0 Hz, 12H), 6.56-6.43 (m, 2H), 4.20-4.08 (m, 4H), 3.63 (s, 2H), 2.89-2.87 (m, 2H), 2.42 (s, 3H), 1.50 (s, 9H).

Example 227. Preparation of Compounds of the Invention

The following compounds in Table 37 were synthesized starting from the appropriate common intermediate 2-(3-(2-aminothiazol-4-yl)phenyl)-5-methyl-6,7-dihydropyrazolo [1,5-a]pyrazin-4(5H)-one, the requisite amino acid and heterocycle, and utilizing the general synthetic protocols described in Example 226 (Compound 143).

TABLE 37

| Compound # | LC-MS data(m/z) | $^1$H NMR |
|---|---|---|
| 433 | 554.2 | $^1$H NMR (400 MHz, DMSO-d6) δ 12.49-12.37 (m, 1H), 8.69 (m, 1H), 8.48 (s, 1H), 7.88-7.85 (m, 2H), 7.81 (d, J = 7.6 Hz, 1H), 7.76 (s, 1H), 7.48 (m, 1H), 7.33-7.29 (m, 2H), 6.79 (m, 1H), 4.46 (m, 2H), 4.15 (d, J = 5.6 Hz, 2H), 3.84 (m, 2H), 3.58 (s, 3H), 3.04 (s, 3H) |
| 437 | 532.1 | $^1$H NMR (400 MHz, DMSO-$d_6$) δ 8.48 (s, 1H), 8.18-8.16 (m, 1H), 7.87 (d, J = 8.4 Hz, 1H), 7.81 (d, J = 7.6 Hz, 1H), 7.76 (s, 1H), 7.54-7.52 (m, 1H), 7.49-7.47 (m, 1H), 7.30 (s, 1H), 6.99-6.97 (m, 1H), 6.50-6.48 (m, 1H), 4.47.4.45 (m, 2H), 4.11 (d, J = 5.6 Hz, 2H), 3.86-3.82 (m, 2H), 3.04 (s, 3H), 1.50 (s, 9H) |

Example 228. Preparation of Compounds of the Invention

The following compounds in Table 38 were synthesized starting from the appropriate common intermediate tert-butyl N-({[4-(3-bromophenyl)-1,3-thiazol-2-yl]carbamoyl}methyl)carbamate and appropriate amine utilizing the general synthetic protocols described in Example 184.

TABLE 38

| Compound # | LC-MS data(m/z) | $^1$H NMR |
|---|---|---|
| 448 | 454.2 | $^1$H NMR (400 MHz, Methanol-$d_4$) δ = 7.58 (s, 1H), 7.31 (s, 1H), 7.27-7.16 (m, 2H), 7.05 (s, 1H), 6.95-6.94 (m, 1H), 6.57 (d, J = 2.0 Hz, 1H), 6.46 (d, J = 7.6 Hz, 1H), 4.70-4.64 (m, 1H), 4.22 (s, 2H), 4.22-4.14 (m, 2H), 3.63-3.60 (m, 2H), 1.56 (s, 9H) |

Example 229. Preparation of Compounds of the Invention

The following compounds in Table 39 were synthesized starting from the appropriate common intermediate tert-butyl N-[2-[[4-[6-(1-methylpyrazol-3-yl)-2-pyridyl]thiazol-2-yl]amino]-2-oxo-ethyl]carbamate and appropriate heterocyclic carboxylic acid utilizing the general synthetic protocols described in Example 195.

TABLE 39

| Compound # | LC-MS data(m/z) | $^1$H NMR |
|---|---|---|
| 145 | 464.2 | $^1$H NMR (400 MHz, DMSO-$d_6$) δ 12.36 (s, 1H), 8.19-8.16 (m, 1H), 7.94 (s, 1H), 7.91-7.87 (m, 1H), 7.84 (s, 1H), 7.82 (s, 1H), 7.80 (d, J = 2.4 Hz, 1H), 7.52-7.51 (m, 1H), 6.97-6.96 (m, 1H), 6.95 (d, J = 2.0 Hz, 1H), 6.48-6.47 (m, 1H), 4.10 (d, J = 5.6 Hz, 2H), 3.93 (s, 3H), 1.49 (s, 9H) |

Example 230. Preparation of 1-(methylsulfonyl)-N-(2-oxo-2-((4-(2-(pyridin-4-yl)-1H-imidazol-4-yl)thiazol-2-yl)amino)ethyl)-1H-pyrrole-3-carboxamide (Compound 146)

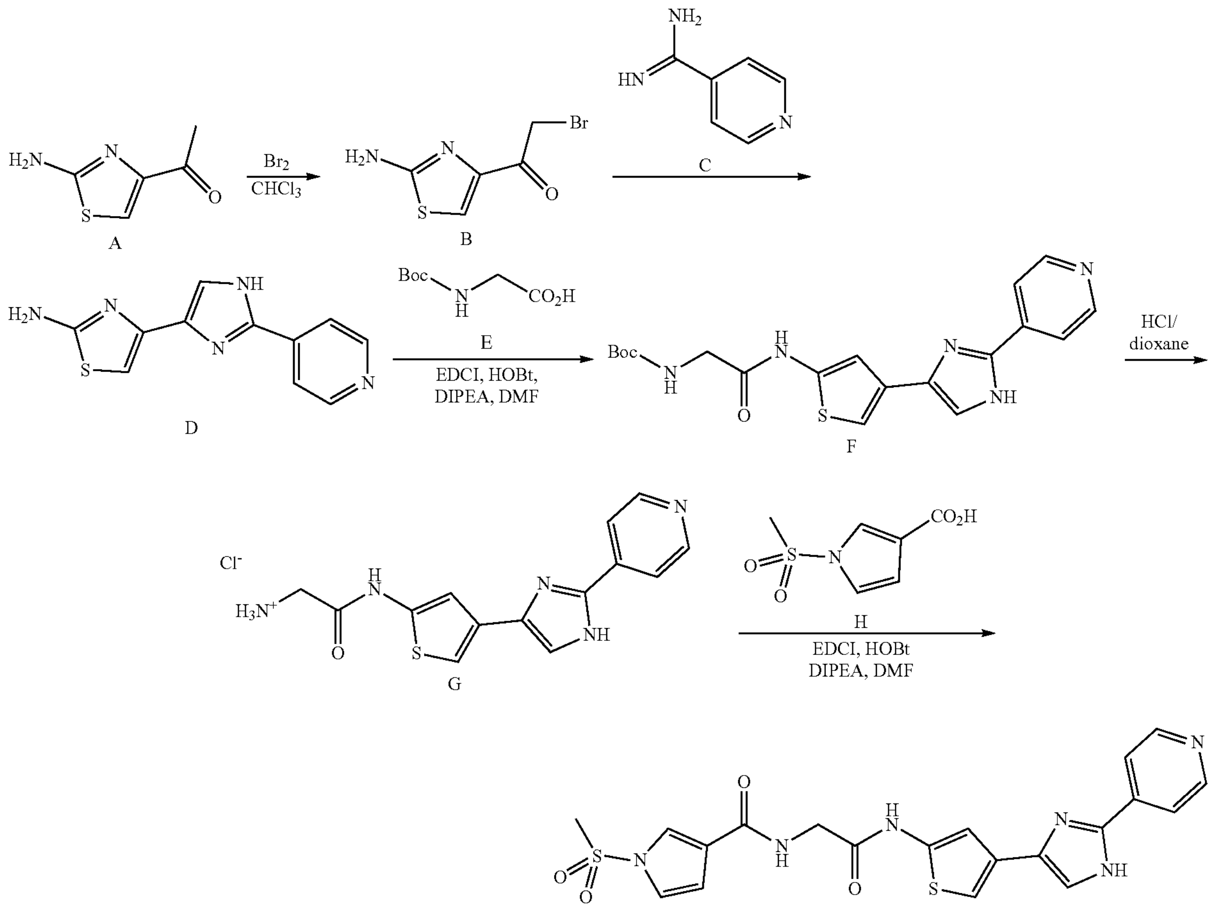

Compound 146

Step 1: Preparation of 1-(2-aminothiazol-4-yl)-2-bromoethanone (Intermediate B)

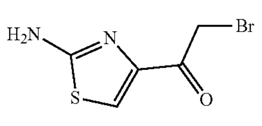

B

To a solution of 1-(2-aminothiazol-4-yl)ethanone (1.50 g, 10.55 mmol) in $CHCl_3$ (15 mL) was added $Br_2$ (0.60 mL, 11.61 mmol). The reaction mixture was stirred at 60° C. After 2 h, the reaction mixture was cooled to room temperature and concentrated under reduced pressure to remove $CHCl_3$. The residue was diluted with water (5 mL) and basified (pH~8) with aqueous saturated $NaHCO_3$. The aqueous mixture was extracted with ethyl acetate (2×15 mL). The combined organic layers were dried over anhydrous $Na_2SO_4$, filtered and concentrated under reduced pressure. The residue was purified by reversed-phase HPLC (0.1% $NH_3 \cdot H_2O$ condition) and lyophilized to give Intermediate B (1.00 g, 4.52 mmol, 42.87% yield) as pink solids. LCMS (ESI) m/z: $[M+H]^+$=223.1; $^1$H NMR (400 MHz, DMSO) δ 7.44 (s, 1H), 2.41 (s, 2H).

Step 2: Preparation of 4-(2-(pyridin-4-yl)-1H-imidazol-4-yl)thiazol-2-amine (Intermediate D)

D

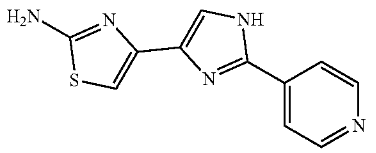

A mixture of Intermediate B (1.00 g, 4.52 mmol), pyridine-4-carboxamidine (0.603 g, 4.98 mmol), $K_2CO_3$ (1.25 g, 9.05 mmol) in THF (10 mL) was stirred at 60° C. After 2 h, the heterogeneous reaction mixture was cooled to room temperature, filtered, and the filtrate was concentrated in vacuo. The residue was purified by reversed-phase HPLC (0.1% $NH_3 \cdot H_2O$) and lyophilized to give Intermediate D (0.220 g, 0.904 mmol, 19.99% yield) as white solids. LCMS (ESI) m/z=$[M+H]^+$=244.2; $^1H$ NMR (400 MHz, DMSO-$d_6$) δ 8.70-8.69 (m, 2H), 8.27 (s, 2H), 8.20-8.19 (m, 2H), 7.40 (s, 3H).

Step 3: Preparation of tert-butyl (2-oxo-2-((4-(2-(pyridin-4-yl)-1H-imidazol-4-yl)thiazol-2-yl)amino)ethyl)carbamate (Intermediate F)

F

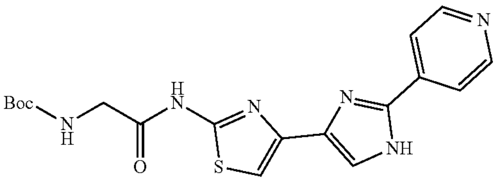

A mixture of Intermediate D (0.200 g, 0.822 mmol), 2-(tertbutoxycarbonylamino) acetic acid (0.216 g, 1.23 mmol), HOBt (0.333 g, 2.47 mmol), EDCI (0.473 g, 2.47 mmol) in DMF (2 mL) was stirred at 25° C. After 2 h, the reaction mixture was diluted with water (2 mL) and extracted with ethyl acetate (2×5 mL). The combined organic layers were washed with brine (2×4 mL), dried over $Na_2SO_4$, filtered and concentrated under reduced pressure to give a residue. The residue was purified by reversed-phase HPLC (0.1% $NH_3 \cdot H_2O$) and lyophilized to give Intermediate F (0.030 g, 0.064 mmol, 7.75% yield) as white solids. LCMS (ESI) m/z=$[M+H]^+$=401.3.

Step 4: Preparation of 2-oxo-2-((4-(2-(pyridin-4-yl)-1H-imidazol-4-yl)thiazol-2-yl)amino)ethan-1-aminium chloride (Intermediate F)

G

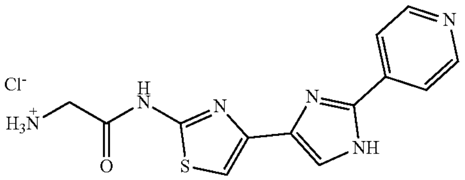

To a solution of Intermediate F (0.010 g, 0.025 mmol) in 1,4-dioxane (0.5 mL) was added a solution of 4 M HCl in 1,4-dioxane (0.062 mL). After 2 h, the mixture was concentrated in vacuo to afford Intermediate G (0.008 g) as white solid, which was used into the next step without further purification. LCMS (ESI) m/z=$[M+H]^+$=301.0.

Step 5: Preparation of 1-(methylsulfonyl)-N-(2-oxo-2-((4-(2-(pyridin-4-yl)-1H-imidazol-4-yl)thiazol-2-yl)amino)ethyl)-1H-pyrrole-3-carboxamide (Compound 146)

Compound 146

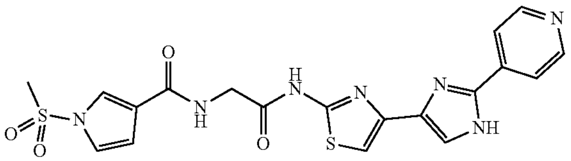

To a solution of Intermediate G (0.007 g, 0.021 mmol), 1-methylsulfonylpyrrole-3-carboxylic acid (0.008 g, 0.042 mmol) in DMF (0.5 mL) was added HOBt (0.008 g, 0.062 mmol), EDCI (0.012 g, 0.062 mmol) and N,N-diisopropylethylamine (0.018 mL, 0.104 mmol). After 2 h, the reaction mixture was diluted with water (3 mL) and the aqueous layer was extracted with ethyl acetate (2×10 mL). The combined organic layers were dried over anhydrous $Na_2SO_4$, filtered and concentrated under reduced pressure to give a residue. The crude product was purified by reversed-phase HPLC (0.1% $NH_3 \cdot H_2O$) and lyophilized to give compound 146 (0.003 g, 0.006 mmol, 27.75% yield) as white solids. LCMS (ESI) m/z=$[M+H]^+$=472.3; $^1H$ NMR (400 MHz, DMSO-$d_6$) δ 8.75-8.73 (m, 2H), 8.68-8.66 (m, 1H), 8.30-8.28 (m, 2H), 7.87-7.85 (m, 1H), 7.33-7.32 (m, 1H), 6.80-6.79 (m, 1H), 5.83-5.82 (m, 2H), 4.17 (d, J=6.0 Hz, 2H), 3.58 (s, 3H).

Example 231. Preparation of Compounds of the Invention

The following compounds in Table 40 were synthesized starting from the appropriate thiourea utilizing the general synthetic protocols described in Example 4.

TABLE 40

| Compound # | LC-MS data(m/z) | $^1$H NMR |
|---|---|---|
| 149 | 483.2 | $^1$H NMR (400 MHz, DMSO-$d_6$) δ 12.49 (br s, 1H), 8.76-8.68 (m, 3H), 8.21-8.16 (m, 2H), 8.10-8.06 (m, 3H), 8.03-7.98 (m, 1H), 7.85-7.83 (m, 1H), 7.32-7.31 (m, 1H), 6.78-6.77 (m, 1H), 4.16 (d, J = 6.0 Hz, 2H), 3.58 (s, 3H) |
| 152 | 496.3 | $^1$H NMR (400 MHz, DMSO-$d_6$) δ 8.85 (d, J = 6.4 Hz, 2H), 8.68-8.66 (m, 1H), 8.45 (s, 1H), 8.21-8.13 (m, 3H), 7.93 (s, 1H), 7.91-7.86 (m, 2H), 7.66-7.65 (m, 1H), 7.33-7.31 (m, 1H), 6.81-6.79 (m, 1H), 4.49 (d, J = 5.6 Hz, 2H), 3.85 (s, 3H), 3.58 (s, 3H) |

Example 232. Preparation of 1-(methylsulfonyl)-N-(2-oxo-2-((4-(3-(2-(pyridin-4-yl)ethyl)phenyl)thiazol-2-yl)amino)ethyl)-1H-pyrrole-3-carboxamide (Compound 151)

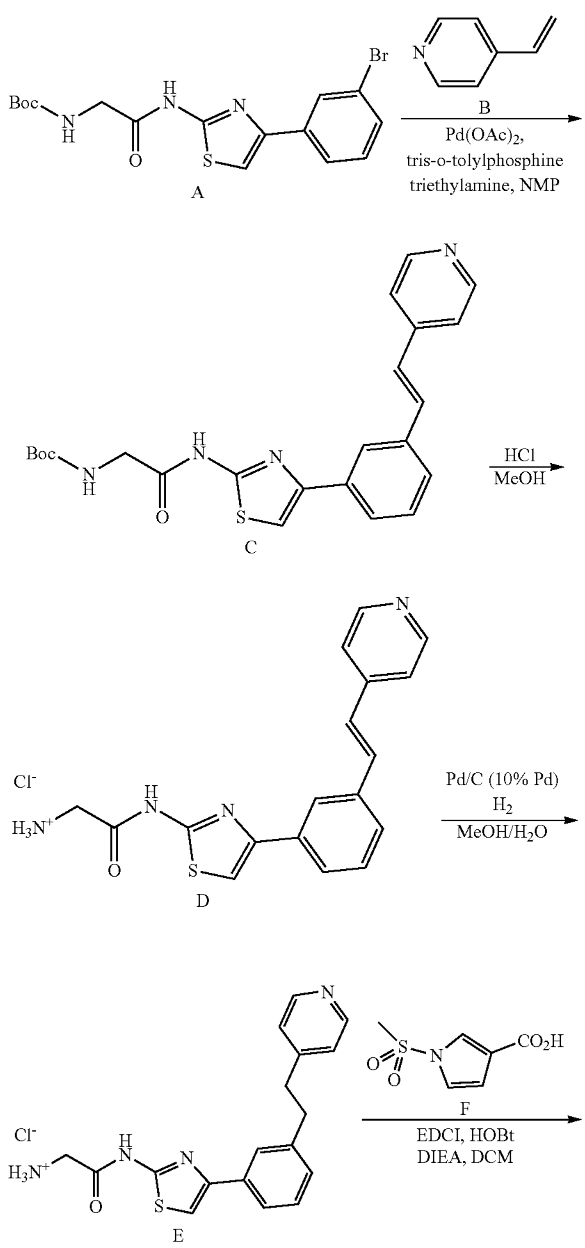

-continued

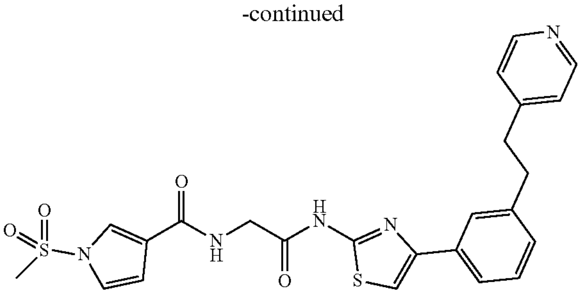

Compound 151

Step 1: Preparation of tert-butyl N-[2-oxo-2-[[4-[3-[(E)-2-(4-pyridyl)vinyl]phenyl]thiazol-2-yl]amino]ethyl]carbamate (Intermediate C)

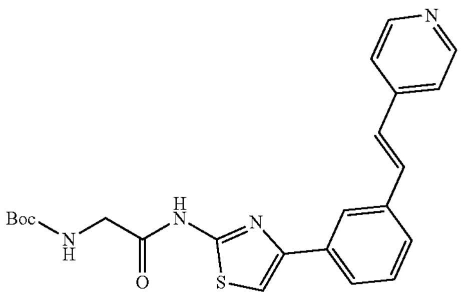

C

A mixture of tert-butyl N-[2-[[4-(3-bromophenyl)thiazol-2-yl]amino]-2-oxo-ethyl]carbamate (0.100 g, 0.243 mmol), 4-vinylpyridine (0.262 mL, 2.43 mmol), $Pd(OAc)_2$ (0.005 g, 0.025 mmol), tris-o-tolylphosphine (0.015 g, 0.049 mmol) and triethylamine (0.101 mL, 0.728 mmol) in NMP (1 mL) was degassed and purged with $N_2$ (g). The mixture was subsequently stirred at 140° C. After 2 h, the reaction mixture cooled to room temperature and poured into water (10 mL). The resulting solids were collected by filtration and sequentially washed with MeOH (3 mL) and ethyl acetate (2 mL), and dried in vacuo to give intermediate C (0.175 g, 0.378 mmol, 77.91% yield) as gray solids. LCMS (ESI) m/z: $[M+H]^+$=437.4.

Step 2: Preparation of (E)-2-oxo-2-((4-(3-(2-(pyridin-4-yl)vinyl)phenyl)thiazol-2-yl)amino)ethan-1-aminium chloride (Intermediate D)

D

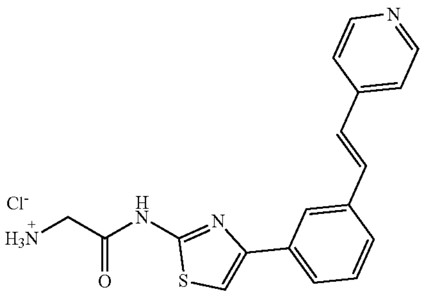

To a solution of Intermediate C (0.170 g, 0.389 mmol) in MeOH (5 mL) was added concentrated HCl (12 M, 1 mL). After stirring at 25° C. for 2 h, the resulting solids were subsequently filtered and the filtrate was concentrated under reduced pressure to give Intermediate D (0.160 g) as yellow solids. LCMS (ESI) m/z: $[M+H]^+=337.3$.

Step 3: Preparation of 2-oxo-2-((4-(3-(2-(pyridin-4-yl)ethyl)phenyl)thiazol-2-yl)amino)ethan-1-aminium chloride (Intermediate E)

E

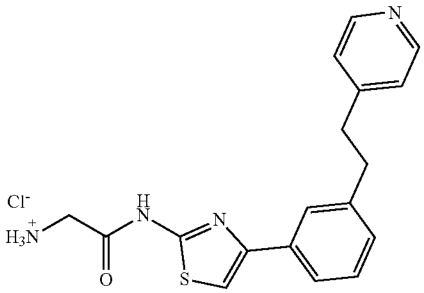

To a solution of Intermediate D (0.080 g, 0.238 mmol) in MeOH (5 mL) and water (1 mL) was added Pd/C (0.050 g, 10% purity) under $N_2$ (g). The suspension was degassed under vacuum and purged with $H_2$ (g) three times. The mixture was stirred under an atmosphere of $H_2$ (g) at 25° C. for 16 h. The reaction mixture was subsequently filtered over Celite® and the filtrate was concentrated under reduced pressure to give Intermediate E (0.050 g) as yellow solids, which was used into the next step without further purification. LCMS (ESI) m/z: $[M+H]^+=339.3$.

Step 4: Preparation of 1-(methylsulfonyl)-N-(2-oxo-2-((4-(3-(2-(pyridin-4-yl)ethyl)phenyl)thiazol-2-yl)amino)ethyl)-1H-pyrrole-3-carboxamide (Compound 151)

Compound 151

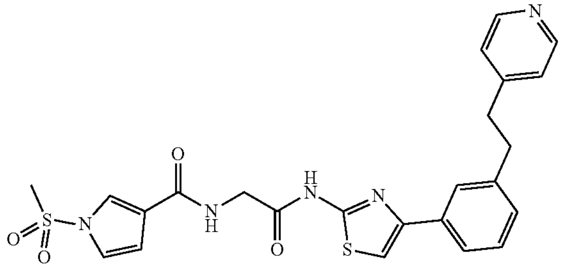

To a solution of intermediate E (0.030 g, 0.080 mmol), N,N-diisopropylethylamine (0.070 mL, 0.400 mmol) and 1-methylsulfonylpyrrole-3-carboxylic acid (0.018 g, 0.096 mmol) in DMF (1 mL) was added EDCI (0.023 g, 0.120 mmol) and HOBt (0.016 g, 0.120 mmol). The mixture was stirred at 25° C. for 4 h and subsequently concentrated under reduced pressure to give a residue. The residue was purified by Prep-HPLC (TFA condition, C18; mobile phase: [water (0.1% TFA)-ACN]; B %: 11%-41%, 10 min) and lyophilized to give Compound 151 (0.024 g, 0.039 mmol, 48.59% yield) as a off-white solid. LCMS (ESI) m/z: $[M+H]^+=510.1$; $^1$H NMR (400 MHz, DMSO-$d_6$) δ 12.38 (s, 1H), 8.75-8.67 (m, 3H), 7.84-7.72 (m, 5H), 7.59 (s, 1H), 7.36-7.31 (m, 2H), 7.20 (d, J=7.6 Hz, 1H), 6.77-6.76 (m, 1H), 4.13 (d, J=6.0 Hz, 2H), 3.57 (s, 3H), 3.21-3.17 (m, 2H), 3.05-3.01 (m, 2H).

Example 233. Preparation of Compounds of the Invention

The following compounds in Table 41 were synthesized starting from the appropriate common (E)-2-oxo-2-((4-(3-(2-(pyridin-4-yl)vinyl)phenyl)thiazol-2-yl)amino)ethan-1-aminium chloride and appropriate heterocyclic carboxylic acid utilizing the general synthetic protocols described in Example 232 (Compound 151).

TABLE 41

| Compound # | LC-MS data(m/z) | $^1$H NMR |
|---|---|---|
| 150 | 508.1 | $^1$H NMR (400 MHz, DMSO-$d_6$) δ 12.43 (s, 1H), 8.71-8.68 (m, 3H), 8.22 (s, 1H), 7.91 (d, J = 7.6 Hz, 3H), 7.85-7.79 (m, 2H), 7.72-7.66 (m, 2H), 7.54-7.43 (m, 2H), 7.32-7.31 (m, 1H), 6.78-6.77 (m, 1H), 4.15 (d, J = 5.6 Hz, 2H), 3.57 (s, 3H) |

Example 234. Preparation of propyl 4-[2-[[2-[(1-methylsulfonylpyrrole-3-carbonyl)amino]acetyl]amino]thiazol-4-yl]piperidine-1-carboxylate (Compound 765)

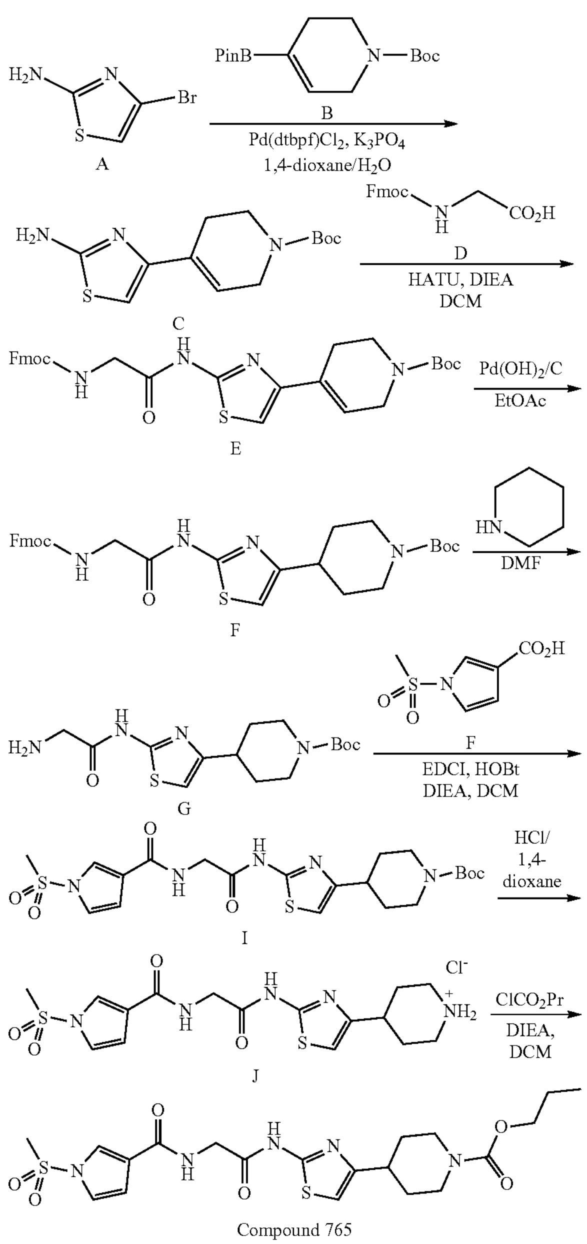

Compound 765

Step 1: Preparation of tert-butyl 4-(2-aminothiazol-4-yl)-3,6-dihydro-2H-pyridine-1-carboxylate (Intermediate C)

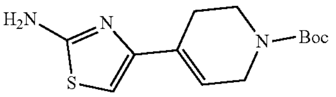

C

To a suspension of 4-bromothiazol-2-amine (5.00 g, 27.93 mmol), tert-butyl 4-(4,4,5,5-tetramethyl-1,3,2-dioxaborolan-2-yl)-3,6-dihydro-2H-pyridine-1-carboxylate (8.64 g, 27.93 mmol) and $K_3PO_4$ (17.78 g, 83.78 mmol) in a mixture of 1,4-dioxane (40 mL) and water (10 mL) was added Pd(dtbpf)$Cl_2$ (1.82 g, 2.79 mmol) at 25° C. under $N_2$ (g). The reaction mixture was stirred at 80° C. under $N_2$ for 12 h. The reaction mixture was cooled to room temperature, diluted with water (200 mL) and extracted with ethyl acetate (3×100 mL). The combined organic layers were concentrated to afford a yellow oil. The oil was dissolved with ethyl acetate (1 mL) and poured into petroleum ether (15 mL) to give brown precipitates. The heterogeneous mixture was filtered and the solids were purified by flash silica gel chromatography (Eluent of 0-60% ethyl acetate/petroleum ether gradient). The eluent was concentrated to give Intermediate 3 (5.10 g, 18.13 mmol, 64.90% yield) as yellow oil.

LCMS (ESI) m/z: $[M+H]^+$=282.2. $^1$HNMR (400 MHz, $CDCl_3$) δ 6.42 (br s, 1H), 6.28 (s, 1H), 5.09 (s, 2H), 4.11-4.06 (m, 2H), 3.60 (d, J=5.2 Hz, 2H), 2.41 (s, 2H), 1.47 (s, 9H).

Step 2: Preparation of tert-butyl 4-[2-[[2-(9H-fluoren-9-ylmethoxycarbonylamino)acetyl]amino]thiazol-4-yl]-3,6-dihydro-2H-pyridine-1-carboxylate (Intermediate E)

E

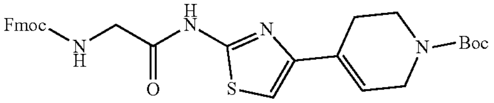

To a mixture of 2-(9H-fluoren-9-ylmethoxycarbonylamino)acetic acid (5.39 g, 18.13 mmol), HATU (10.34 g, 27.19 mmol) and N,N-diisopropylethylamine (7.03 g, 54.38 mmol, 9.47 mL) in dichloromethane (50 mL) was added Intermediate 3 (5.10 g, 18.13 mmol) at 25° C. After 5 h, the reaction mixture was diluted with water (50 mL) and extracted with dichloromethane (2×20 mL). The combined organic layers were concentrated to afford a brown oil. The oil was purified by reverse-phase HPLC (FA (0.1%) conditions). The eluent was concentrated to remove $CH_3CN$ and extracted with ethyl acetate (2×20 mL). The combined organic layers was concentrated to afford yellow solids which were repurified by flash chromatography (eluent of 0-60% ethyl acetate/petroleum ether gradient). The eluent was concentrated to give Intermediate 5 (9.00 g, 14.45 mmol, 79.71% yield) as yellow solids. LCMS (ESI) m/z: $[M+H]^+$=561.5; $^1$HNMR (400 MHz, $CDCl_3$) δ 10.14-9.58 (m, 1H), 7.78-7.76 (m, 2H), 7.60 (d, J=5.6 Hz, 2H), 7.42-7.27 (m, 4H), 6.72 (s, 1H), 6.49-6.45 (m, 1H), 5.58 (s, 1H), 4.51-4.45 (m, 2H), 4.26-4.22 (m, 1H), 4.12-4.10 (m, 2H), 3.64-3.61 (m, 2H), 2.47 (s, 2H), 1.49 (s, 9H).

Step 3: Preparation of tert-butyl 4-[2-[[2-(9H-fluoren-9-ylmethoxycarbonylamino)acetyl]amino]thiazol-4-yl]piperidine-1-carboxylate (Intermediate F)

F

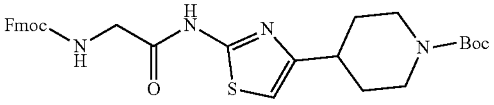

A mixture of Intermediate 5 (9.00 g, 12.84 mmol) and $Pd(OH)_2$ (4.50 g, 6.41 mmol, 20% purity) in ethyl acetate (90 mL) was degassed and purged with $H_2$ (g). The mixture was stirred at 30° C. under $H_2$ (15 psi). After 48 h, the reaction mixture was filtered to over Celite® and the filtrate was concentrated to afford a black oil. The oil was purified by flash chromatography (Eluent of 0-60% ethyl acetate/petroleum ether gradient). The eluent was concentrated to give Intermediate 6 (6.00 g, 10.14 mmol, 78.93% yield) as yellow solids. LCMS (ESI) m/z: $[M+H]^+$=563.2; $^1$HNMR (400 MHz, DMSO-$d_6$) δ 12.11 (s, 1H), 7.90 (d, J=7.6 Hz, 2H), 7.73-7.69 (m, 3H), 7.42-7.40 (m, 2H), 7.35-7.31 (m, 2H), 6.80 (s, 1H), 4.31-4.30 (m, 2H), 4.25 (d, J=6.4 Hz, 1H), 4.00-3.98 (m, 2H), 3.89 (d, J=6.4 Hz, 2H), 2.85-2.76 (m, 3H), 1.89 (d, J=10.8 Hz, 2H), 1.46-1.39 (m, 11H).

Step 4: Preparation of tert-butyl 4-[2-[(2-amino-acetyl)amino]thiazol-4-yl]piperidine-1-carboxylate (Intermediate G)

G

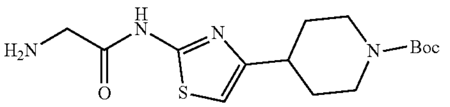

A mixture of Intermediate 6 (4.00 g, 7.11 mmol) in piperidine (4 mL) and DMF (40 mL) was stirred at 25° C. for 1 h. The reaction mixture was poured into water (200 mL) to give light yellow precipitates. The resulting precipitates were filtered and the filtrate was extracted with ethyl acetate (5×50 mL). The combined organic layers were washed with brine (3×100 mL) and concentrated to afford yellow solids. The solids were triturated with MTBE (20 mL) to yield Intermediate 7 (1.251 g, 3.47 mmol, 48.83% yield) as white solids. LCMS (ESI) m/z; $[M+H]^+$=341.2; $^1$HNMR (400 MHz, DMSO-$d_6$) δ 6.78 (s, 1H), 5.24 (s, 2H), 4.00 (d, J=2.8 Hz, 2H), 3.51-3.36 (m, 2H), 2.88-2.71 (m, 3H), 1.88 (d, J=11.2 Hz, 2H), 1.47-1.39 (m, 11H).

Step 5: Preparation of tert-butyl4-[2-[[2-[(1-methyl-sulfonylpyrrole-3-carbonyl)amino]acetyl]amino] thiazol-4-yl]piperidine-1-carboxylate (Intermediate I)

I

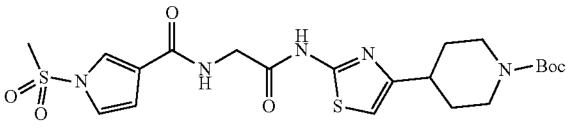

To a solution of 1-methylsulfonylpyrrole-3-carboxylic acid (0.183 g, 0.969 mmol) in dichloromethane (2 mL) was added EDCI (0.253 g, 1.32 mmol), HOBt (0.179 g, 1.32 mmol), N,N-diisopropylethylamine (0.767 mL, 4.41 mmol) and Intermediate 7 (0.300 g, 0.881 mmol). After 2 h, the mixture was diluted with water (20 mL) and extracted with dichloromethane (2×20 mL). The combined organic layers were dried over anhydrous $Na_2SO_4$, filtered and concentrated. The residue was purified by flash (petroleum ether/ethyl acetate=1/0 to 0/1) and concentrated to give Intermediate 9 (0.350 g, 0.662 mmol, 75.13% yield) as white solids. LCMS (ESI) m/z: $[M+H]^+$=512.1; $^1$H NMR (400 MHz, DMSO-$d_6$) δ 12.18 (s, 1H), 8.64-8.62 (m, 1H), 7.87-7.80 (m, 1H), 7.30-7.29 (m, 1H), 6.80 (s, 1H), 6.76-6.75 (m, 1H), 4.08 (d, J=6.0 Hz, 2H), 4.00 (d, J=11.6 Hz, 2H), 3.56 (s, 3H), 2.90-2.72 (m, 3H), 1.89 (d, J=10.8 Hz, 2H), 1.50-1.45 (m, 1H), 1.44-1.42 (m, 1H), 1.40 (s, 9H).

Step 6: Preparation of 1-methylsulfonyl-N-[2-oxo-2-[[4-(4-piperidyl)thiazol-2-yl]amino]ethyl]pyrrole-3-carboxamide (Intermediate J)

J

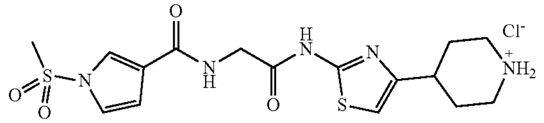

To a solution of Intermediate 9 (0.070 g, 0.137 mmol) in 1,4-dioxane (1 mL) was added a solution of 4 M HCl in 1,4-dioxane (0.244 mL). After 1 h, the reaction mixture was concentrated under reduced pressure to give Intermediate 10 (0.060 g, 0.133 mmol, 96.87% yield) as light yellow solids. LCMS (ESI) m/z: $[M+H]^+$=412.1.

Step 7: Preparation of propyl 4-[2-[[2-[(1-methyl-sulfonylpyrrole-3-carbonyl)amino]acetyl]amino] thiazol-4-yl]piperidine-1-carboxylate (Compound 765)

Compound 765

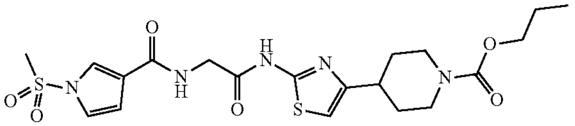

To a solution of Intermediate 10 (0.030 g, 0.067 mmol) and N,N-diisopropylethylamine (0.058 mL, 0.335 mmol) in dichloromethane (1 mL) was added propyl chloroformate (0.008 mL, 0.074 mmol) at 0° C. After 1 h, the reaction was quenched with aqueous saturated $NaHCO_3$ (5 mL) and extracted with dichloromethane (2×5 mL). The combined organic layers were dried over anhydrous $Na_2SO_4$, filtered and concentrated under reduced pressure. The residue was purified prep-HPLC (mobile phase: [water (10 mM $NH_4HCO_3$)-ACN]; B %: 18%-48%). The appropriate fractions were concentrated under reduced pressure to remove $CH_3CN$ and then lyophilized to give Compound 765 (0.005 g, 0.010 mmol, 15.67% yield) as white solids. LCMS (ESI) m/z: $[M+H]^+$=498.2; $^1$H NMR (400 MHz, DMSO-$d_6$) δ 8.68-8.61 (m, 1H), 7.83-7.82 (m, 1H), 7.35-7.26 (m, 1H), 6.80 (s, 1H), 6.76-6.75 (m, 1H), 4.11-3.99 (m, 4H), 3.96-3.93 (m, 2H), 3.56 (s, 3H), 3.01-2.74 (m, 3H), 1.95-1.87 (m, 2H), 1.64-1.38 (m, 4H), 0.91-0.87 (m, 3H).

Example 235. Preparation of Compounds of the Invention

The following compounds in Table 42 were synthesized starting utilizing the general synthetic protocols described in Example 234 (Compound 765) utilizing the common starting material 4-bromothiazol-2-amine and appropriate boronic ester followed by a SFC separation

TABLE 42

| Compound # | LC-MS data(m/z) | $^1$H NMR |
|---|---|---|
| 771 | 498.0 | $^1$H NMR (400 MHz, MeOH-d$_4$) δ 7.82-7.81 (m, 1H), 7.27-7.25 (m, 1H), 6.79-6.77 (m, 2H), 4.29-4.21 (m, 3H), 4.04-4.01 (m, 3H), 3.37 (s, 3H), 2.96-2.94 (m, 2H), 2.79-2.78 (m, 1H), 2.11-2.06 (m, 1H), 1.77-1.50 (m, 5H), 0.97-0.93 (m, 3H) |

Example 236. Preparation of Compounds of the Invention

The following compounds in Table 43 were synthesized utilizing the general synthetic protocols described in Example 6 utilizing the appropriate, N-Boc amino acid, heterocyclic carboxylic acid, and boronic ester followed by a SFC separation

TABLE 43

| Compound # | LC-MS data(m/z) | $^1$H NMR |
|---|---|---|
| 735 | 504.1 | $^1$HNMR (400 MHz, DMSO + D$_2$O) δ 8.00-7.93 (m, 1H), 7.61-7.53 (m, 2H), 7.30-7.29 (m, 1H), 7.25 (s, 1H), 6.80-6.78 (m, 1H), 6.51 (d, J = 8.0 Hz, 1H), 4.88 (d, J = 5.6 Hz, 1H), 3.74-3.70 (m, 2H), 3.52 (s, 3H), 3.31-3.25 (m, 5H), 2.90 (d, J = 8.4 Hz, 2H), 2.71 (s, 3H) |
| 758 | 522.2 | $^1$HNMR (400 MHz, DMSO-d$_6$) δ 12.42 (br s, 1H), 8.50 (d, J = 7.2 Hz, 1H), 8.00-7.99 (m, 1H), 7.50-7.35 (m, 3H), 7.31-7.29 (m, 1H), 6.80-6.79 (m, 1H), 4.91 (br d, J = 6.4 Hz, 1H), 3.77-3.66 (m, 2H), 3.57 (s, 3H), 3.33-3.30 (m, 5H), 2.99-2.98 (m, 2H), 2.91 (d, J = 1.2 Hz, 3H) |
| 759 | 522.2 | $^1$HNMR (400 MHz, DMSO-d$_6$) δ 12.42 (br s, 1H), 8.50 (d, J = 7.2 Hz, 1H), 7.99-7.98 (m, 1H), 7.52-7.36 (m, 3H), 7.31-7.29 (m, 1H), 6.80-6.79 (m, 1H), 4.91-4.89 (m, 1H), 3.79-3.66 (m, 2H), 3.57 (s, 3H), 3.33-3.30 (m, 5H), 2.99-2.98 (m, 2H), 2.91-2.90 (m, 3H) |

Example 237. Preparation of N-[2-[[4-[6-[(4R)-3,3-difluoro-4-(methylamino)-1-piperidyl]-2-pyridyl]thiazol-2-yl]amino]-2-oxo-ethyl]-1-methylsulfonyl-pyrrole-3-carboxamide (Compound 763)

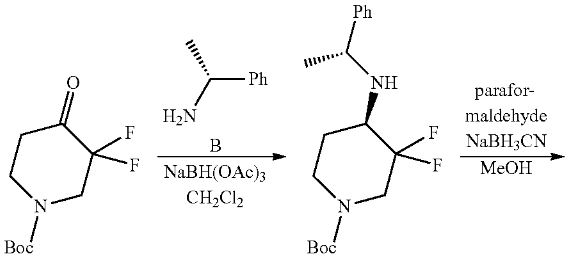

A C

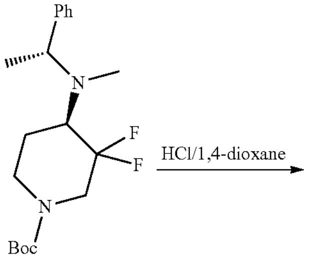

D

-continued

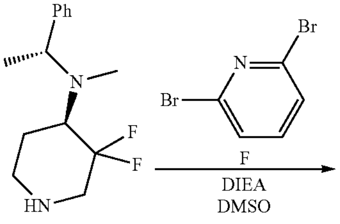

E

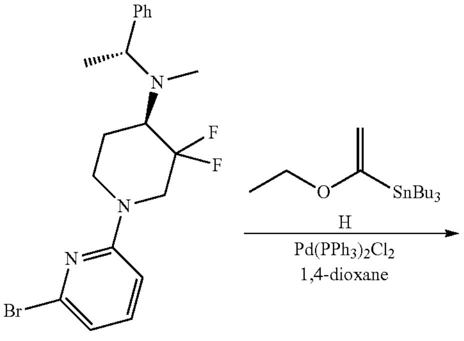

G

-continued
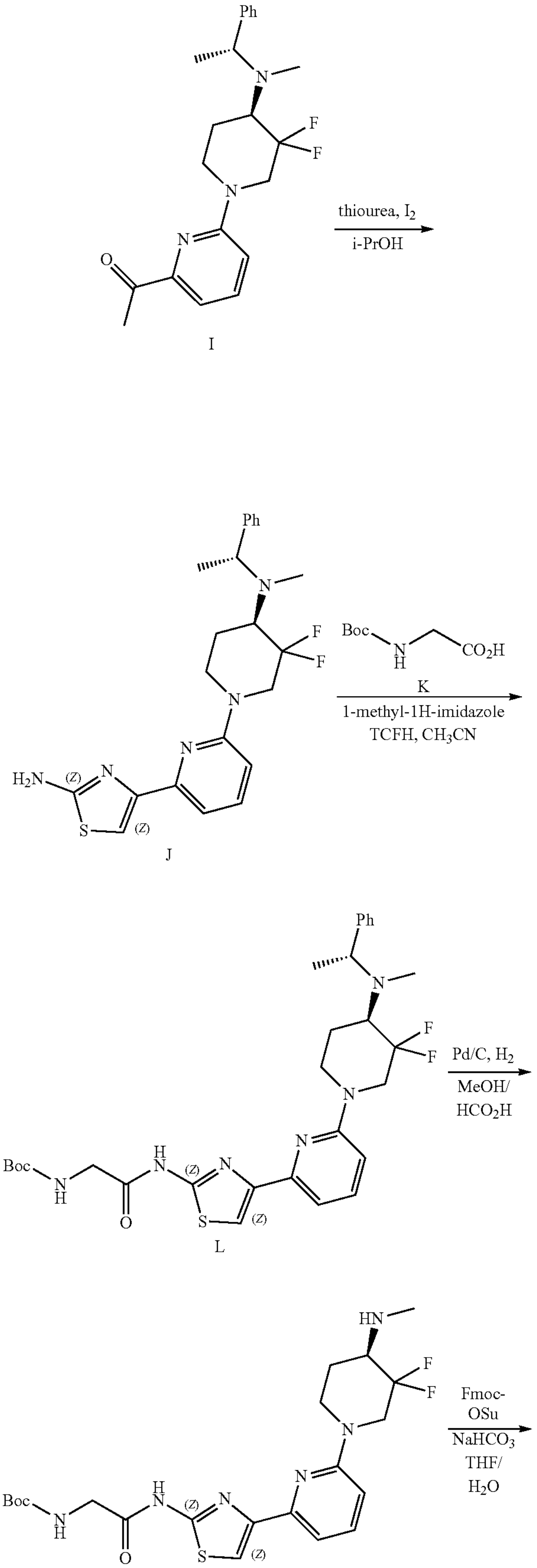
-continued
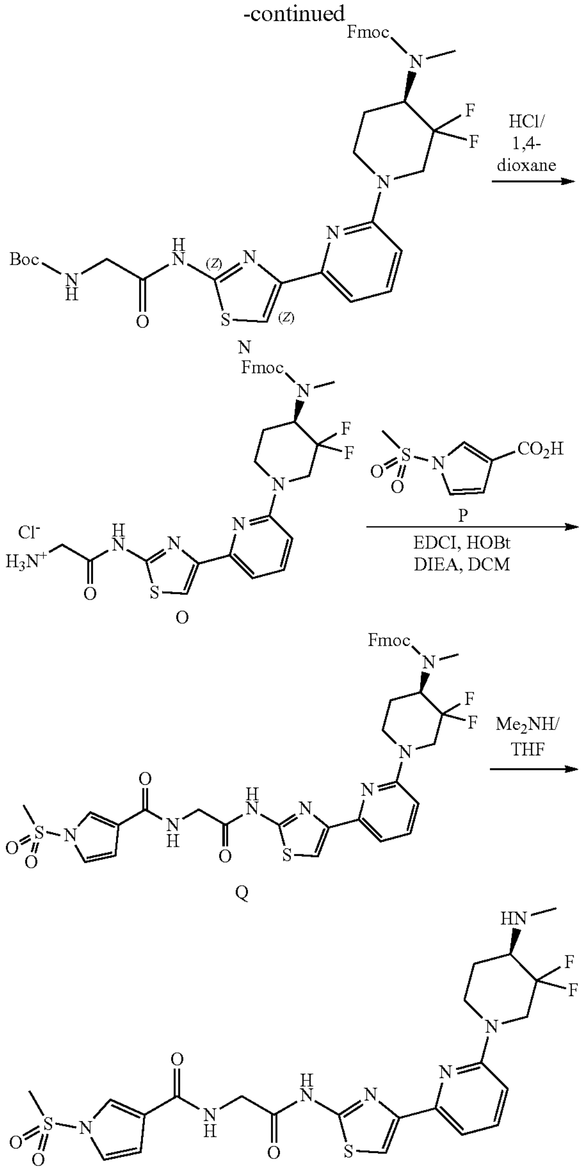
Compound 763
Step 1: Preparation of tert-butyl (4R)-3,3-difluoro-4-[[(1R)-1-phenylethyl]amino]piperidine-1-carboxylate (Intermediate C)
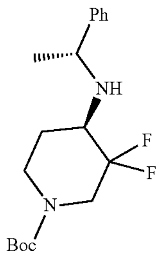
C
To a mixture of tert-butyl 3,3-difluoro-4-oxo-piperidine-1-carboxylate (8.00 g, 34.01 mmol), (1R)-1-phenylethanamine (6.58 mL, 51.01 mmol,) in dichloromethane (160 mL) was added $NaBH(OAc)_3$ (28.83 g, 136.04 mmol). After 12 h, the mixture was concentrated under vacuum to removed excess dichloromethane. The oil was diluted with water (100 mL) and extracted with ethyl acetate (3×80 mL). The combined organic layers were washed with brine (2×100 mL), dried over $Na_2SO_4$, filtered and concentrated under reduced pressure. The residue was purified by column chromatography (petroleum ether/ethyl acetate=100/1 to 3/1) to give Intermediate C (4.30 g, 11.12 mmol, 32.69% yield) as colorless oil. LCMS (ESI) m/z: $[M+H]^+$=341.1.

Step 2: Preparation of tert-butyl (4R)-3,3-difluoro-4-[methyl-[(1R)-1-phenylethyl]amino]piperidine-1-carboxylate (Intermediate D)

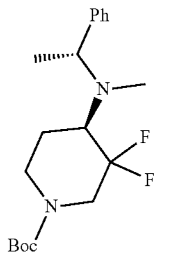

D

To a mixture of Intermediate C (4.00 g, 11.75 mmol), paraformaldehyde (3.53 g, 117.51 mmol) in MeOH (80 mL) was added $NaBH_3CN$ (3.69 g, 58.75 mmol). After 12 h, the mixture was concentrated under vacuum to remove MeOH. The resulting mixture was diluted with water (50 mL) and extracted with ethyl acetate (2×50 mL). The combined organic layers were washed with brine (2×60 mL), dried over $Na_2SO_4$, filtered and concentrated under reduced pressure to give a residue. The residue was purified by column chromatography (petroleum ether/ethyl acetate=100/1 to 10/1) to give Intermediate D (4.10 g, 11.57 mmol, 98.44% yield) as a colorless oil. LCMS (ESI) m/z: $[M+H]^+$=355.1; $^1$HNMR (400 MHz, $CDCl_3$) δ 7.38-7.28 (m, 4H), 7.27-7.21 (m, 1H), 4.27-4.01 (m, 3H), 2.98-2.83 (m, 1H), 2.82-2.49 (m, 2H), 2.46 (d, J=2.8 Hz, 3H), 2.00-1.85 (m, 1H), 1.62-1.52 (m, 1H), 1.45 (s, 9H), 1.40 (d, J=6.8 Hz, 3H).

Step 3: Preparation of (4R)-3,3-difluoro-N-methyl-N-[(1R)-1-phenylethyl]piperidin-4-amine (Intermediate E)

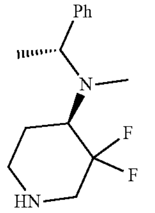

E

To a solution of Intermediate D (4.10 g, 11.57 mmol) in 1,4-dioxane was added a solution of 4 M HCl in 1,4-dioxane (40 mL). The reaction mixture was stirred at 25° C. for 1 h. The mixture was concentrated under vacuum to remove MeOH and the resulting mixture was diluted with aqueous saturated $NaHCO_3$ (50 mL). The aqueous layer was extracted with ethyl acetate (2×50 mL). The combined organic layers were washed with brine (2×60 mL), dried over $Na_2SO_4$, filtered and concentrated under reduced pressure to give Intermediate E (2.70 g) as brown oil.

Step 4: Preparation of (4R)-1-(6-bromo-2-pyridyl)-3,3-difluoro-N-methyl-N-[(1R)-1-phenylethyl]piperidin-4-amine (Intermediate G)

G

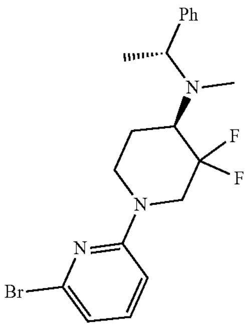

A mixture of Intermediate E (3.10 g, 12.19 mmol), 2,6-dibromopyridine (5.78 g, 24.38 mmol), N.N-diisopropylethylamine (6.37 mL, 36.57 mmol) in DMSO (35 mL) was stirred at 120° C. for 8 h under $N_2$ (g). The reaction mixture was diluted with water (100 mL) and extracted with ethyl acetate (3×100 mL). The combined organic layers were washed with brine (2×150 mL), dried over $Na_2SO_4$, filtered and concentrated under reduced pressure. The residue was purified by column chromatography (petroleum ether/ethyl acetate=50/1 to 3/1) to give Intermediate F (3.50 g, 8.53 mmol, 69.98% yield) as a colorless oil. LCMS (ESI) m/z; $[^{79}BrM+H]^+$=410.0; $^1$HNMR (400 MHz, $CDCl_3$) δ 7.39-7.27 (m, 5H), 7.26-7.22 (m, 1H), 6.77 (d, J=7.6 Hz, 1H), 6.54 (d, J=8.4 Hz, 1H), 4.49-4.32 (m, 2H), 4.08 (m, 1H), 3.08-2.96 (m, 1H), 2.96-2.84 (m, 1H), 2.74 (m, 1H), 2.46 (d, J=2.8 Hz, 3H), 2.02 (m, 1H), 1.66-1.57 (m, 1H), 1.42 (d, J=6.8 Hz, 3H).

Step 5: Preparation of 1-[6-[(4R)-3,3-difluoro-4-[methyl-[(1R)-1-phenylethyl]amino]-1-piperidyl]-2-pyridyl]ethenone (Intermediate H)

I

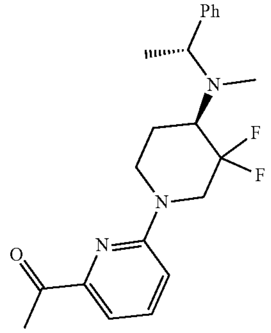

A mixture of Intermediate G (3.00 g, 7.31 mmol), tributyl (1-ethoxyvinyl)stannane (3.70 mL, 10.97 mmol), dichloropalladium; triphenylphosphine (0.513 g, 0.731 mmol) in 1,4-dioxane (30 mL) was degassed and purged with $N_2$ (g) (3 times). The reaction mixture was stirred at 100° C. for 4 h under $N_2$ (g). The reaction mixture was cooled to room temperature and quenched by addition 2 N HCl (40 mL). After stirring for 2 h, the mixture was basified with aqueous saturated $Na_2CO_3$ (40 mL), followed by addition of aqueous saturated KF solution (20 mL). After 1 h, the mixture was filtered and the filtrate was extracted with ethyl acetate (2×50 mL). The combined organic layers were washed with brine (50 mL), dried over $Na_2SO_4$, filtered and concentrated under reduced pressure. The oil was purified by column chromatography (petroleum ether/ethyl acetate=50/1 to 3/1) and concentrated to give Intermediate I (1.70 g, 3.87 mmol, 52.92% yield) as yellow solids. LCMS (ESI) m/z: $[M+H]^+$=374.2.

Step 6: Preparation of 4-[6-[(4R)-3,3-difluoro-4-[methyl-[(1R)-1-phenylethyl]amino]-1-piperidyl]-2-pyridyl]thiazol-2-amine (Intermediate J)

J

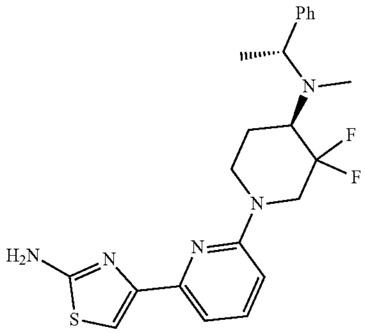

A mixture of Intermediate I (1.60 g, 4.28 mmol), thiourea (0.652 g, 8.57 mmol), 12 (1.09 g, 4.28 mmol) in i-PrOH (16 mL) was degassed and purged with $N_2$ (g) (3 times). The mixture was stirred at 100° C. for 6 h. The reaction mixture was cooled to room temperature and diluted with aqueous saturated $NaHCO_3$ (40 mL). The aqueous layer was extracted with ethyl acetated (3×40 mL). The combined organic layers were washed with brine (2×50 mL), dried over $Na_2SO_4$, filtered and concentrated under reduced pressure. The solids were purified by column chromatography (petroleum ether/ethyl acetate=20/1 to 2/1) and concentrated to give Intermediate J (1.10 g, 2.56 mmol, 59.77% yield) as white solids. LCMS (ESI) m/z: $[M+H]^+$=430.1.

Step 7: Preparation of tert-butyl N-[2-[[4-[6-[(4R)-3,3-difluoro-4-[methyl-[(1R)-1-phenylethyl]amino]-1-piperidyl]-2-pyridyl]thiazol-2-yl]amino]-2-oxo-ethyl]carbamate (Intermediate L)

L

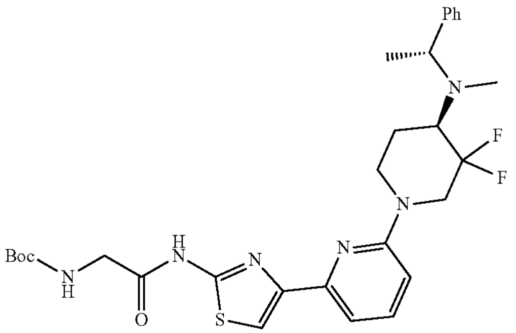

To a mixture of Intermediate J (0.650 g, 1.51 mmol), 2-(tert-butoxycarbonylamino)acetic acid (0.398 g, 2.27 mmol) and 1-methylimidazole (0.362 mL, 4.54 mmol) in $CH_3CN$ (6 mL) was added [chloro(dimethylamino)methylene]-dimethylammonium; hexafluorophosphate (0.637 g, 2.27 mmol) and the mixture was stirred at room temperature. After 4 h, the reaction mixture was diluted with water (50 mL) and extracted with ethyl acetate (2×30 mL). The combined organic layers were washed with brine (2×40 mL), dried over $Na_2SO_4$, filtered and concentrated under reduced pressure to give solids. The solids were triturated with MeOH (30 mL), filtered and dried in the air to give Intermediate L (0.750 g, 1.28 mmol, 84.47% yield) as a white solid. LCMS (ESI) m/z: $[M+H]^+$=587.3.

Step 8: Preparation of tert-butyl N-[2-[[4-[6-[(4R)-3,3-difluoro-4-(methylamino)-1-piperidyl]-2-pyridyl]thiazol-2-yl]amino]-2-oxoethyl]carbamate (Intermediate M)

M

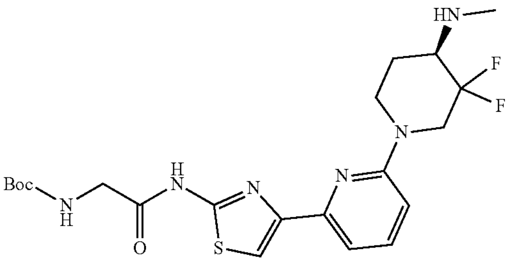

A solution of Intermediate L (0.300 g, 0.511 mmol) in MeOH (30 mL) and formic acid (0.500 mL, 511.34 umol,) was added Pd/C (0.050 g, 0.511 mmol, 10% purity), the mixture was degassed and purged with $H_2$ (g) (3 times). The resulting suspension was stirred at 25° C. under $H_2$ (50 psi). After 12 h, the reaction mixture was purged with $N_2$ (g) and filtered. The filtrate was diluted with sat. $NaHCO_3$ (20 mL) and the resulting solution was partially concentrated to remove MeOH. The aqueous layer was extracted with ethyl acetate (3×30 mL). The combined organic phases were washed with brine (50 mL), dried over $Na_2SO_4$, filtered and concentrated under reduced pressure to give Intermediate M (0.190 g) as white solids. LCMS (ESI) m/z: $[M+H]^+$=483.1.

Step 9: Preparation of 9H-fluoren-9-ylmethyl N-[(4R)-1-[6-[2-[[2-(tert-butoxycarbonylamino) acetyl]amino]thiazol-4-yl]-2-pyridyl]-3,3-difluoro-4-piperidyl]-N-methyl-carbamate (Intermediate N)

N

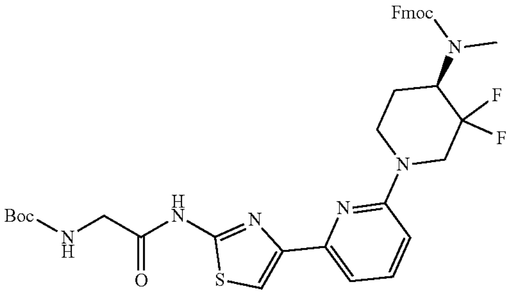

A mixture of Intermediate M (0.190 g, 0.394 mmol), FmocOSu (0.199 g, 0.591 mmol), $NaHCO_3$ (0.099 g, 1.18 mmol) in THF (1.5 mL) and water (1.5 mL) was stirred at 25° C. After 6 h, the reaction mixture was diluted with ethyl acetate (20 mL). The organic layer was washed with water (2×15 mL), brine (15 mL), dried over $Na_2SO_4$, filtered and concentrated in vacuo. The residue was purified by column chromatography (petroleum ether/ethyl acetate=20/1 to 1/1) and concentrated to give Intermediate N (0.120 g, 0.167 mmol, 42.38% yield) as white solids. LCMS (ESI) m/z: $[M+H]^+$=705.3.

Step 10: Preparation of (R)-2-((4-(6-(4-((((9H-fluoren-9-yl)methoxy)carbonyl)(methyl)amino)-3,3-difluoropiperidin-1-yl)pyridin-2-yl)thiazol-2-yl) amino)-2-oxoethan-1-aminium chloride (Intermediate O)

O

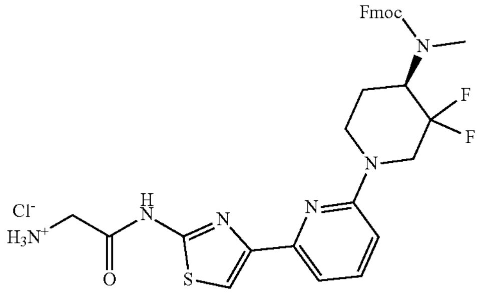

To a mixture of Intermediate N (0.120 g, 0.170 mmol) in 1,4-dioxane was added a solution of 4 M HCl in 1,4-dioxane (15 mL). The mixture was stirred at room temperature for 1 h, and subsequently concentrated under vacuum to give Intermediate O (0.109 g, 0.179 mmol, 100.00% yield) as yellow solids which was used to next step directly. LCMS (ESI) m/z: $[M+H]^+$=605.0.

Step 11: Preparation of Intermediate 16 9H-fluoren-9-ylmethyl N-[(4R)-3,3-difluoro-1-[6-[2-[[2-[(1-methylsulfonylpyrrole-3-carbonyl)amino]acetyl] amino]thiazol-4-yl]-2-pyridyl]-4-piperidyl]-N-methyl-carbamate (Intermediate Q)

Q

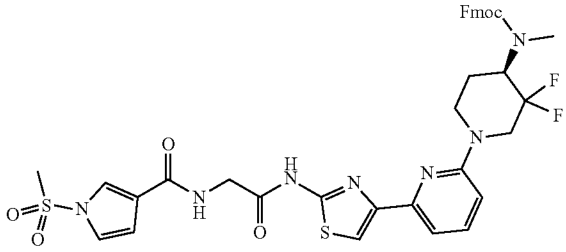

To a solution of Intermediate O (0.109 g, 0.170 mmol), 1-methylsulfonylpyrrole-3-carboxylic acid (0.039 g, 0.204 mmol) and N,N-diisopropylethylamine (0.178 mL, 1.02 mmol) in dichloromethane (2 mL) was added EDCI (0.039 g, 0.204 mmol) and HOBt (0.028 g, 0.204 mmol). The reaction mixture was subsequently stirred at 25° C. After 8 h, the reaction mixture was diluted with water (15 mL), and extracted with ethyl acetate (2×15 mL). The combined organic phases were washed with brine (2×15 mL), dried over $Na_2SO_4$, filtered and concentrated under vacuum to give residue. The residue was purified by column chromatography (petroleum ether/ethyl acetate=50/1 to 1/1) and concentrated to give Intermediate Q (0.080 g, 0.103 mmol, 60.65% yield) as white solids. LCMS (ESI) m/z: $[M+H]^+$=776.3.

Step 12: Preparation of N-[2-[[4-[6-[(4R)-3,3-difluoro-4-(methylamino)-1-piperidyl]-2-pyridyl]thiazol-2-yl]amino]-2-oxo-ethyl]-1-methylsulfonyl-pyrrole-3-carboxamide (Compound 763)

Compound 763

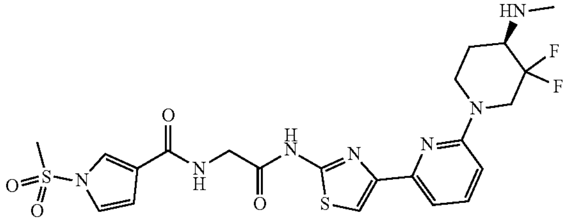

To a solution of Intermediate Q (0.080 g, 0.103 mmol) in THF was added a solution of 2 M dimethylamine in THF (4.00 mL). The reaction mixture was stirred at 25° C. for 8 h and subsequently concentrated under vacuum. The crude product was triturated with MTBE (10 mL), stirred for 30 min, and filtered. The filter cake was dried in the air to give Compound 763 (0.040 g, 0.069 mmol, 66.46% yield) as white solids. LCMS (ESI) m/z: $[M+H]^+$=554.1; $^1H$ NMR (400 MHz, DMSO-$d_6$) δ 12.45-12.26 (m, 1H), 8.68 (m, 1H), 7.84 (m, 1H), 7.76 (s, 1H), 7.62 (m, 1H), 7.31 (m, 1H), 7.26 (d, J=7.2 Hz, 1H), 6.89 (d, J=8.8 Hz, 1H), 6.77 (m, 1H), 4.45-4.29 (m, 1H), 4.13 (d, J=5.6 Hz, 2H), 4.06-3.94 (m, 1H), 3.66-3.56 (m, 4H), 3.31-3.26 (m, 2H), 3.03-2.89 (m, 1H), 2.41 (s, 3H), 2.01-1.92 (m, 1H), 1.64-1.51 (m, 1H).

Example 238. Preparation of Compounds of the Invention

The following compounds in Table 44 were synthesized starting from the appropriate common intermediate tert-butyl 3,3-difluoro-4-oxo-piperidine-1-carboxylate and appropriate 1-phenylethanamine enantiomer utilizing the general synthetic protocols described in Example 237 (Compound 763).

TABLE 44

| Compound # | LC-MS data(m/z) | $^1$H NMR |
|---|---|---|
| 757 | 568.2 | $^1$H NMR (400 MHz, Methanol-$d_4$) δ 7.84 (m, 1H), 7.72 (s, 1H), 7.65 (m, 1H), 7.43 (d, J = 7.6 Hz, 1H), 7.28 (m, 1H), 6.88 (d, J = 8.4 Hz, 1H), 6.81 (m, 1H), 5.11-4.98 (m, 1H), 4.71 (d, J = 14.0 Hz, 1H), 4.26 (s, 2H), 4.19-4.05 (m, 1H), 3.38 (s, 3H), 3.13-3.06 (m, 2H), 3.05 (s, 6H), 2.42 (d, J = 12.8 Hz, 1H), 2.17-2.08 (m, 1H) |
| 760 | 554.1 | $^1$HNMR (400 MHz, DMSO-$d_6$) δ 12.37 (s, 1H), 8.65 (s, 1H), 7.84 (s, 1H), 7.73 (s, 1H), 7.62 (m, 1H), 7.31 (br s, 1H), 7.25 (d, J = 7.6 Hz, 1H), 6.88 (d, J = 8.4 Hz, 1H), 6.77 (s, 1H), 4.31 (d, J = 7.6 Hz, 1H), 4.12 (d, J = 5.6 Hz, 2H), 3.97 (s, 1H), 3.65 (s, 1H), 3.57 (s, 3H), 2.88 (s, 2H), 2.40 (s, 3H), 1.93 (s, 1H), 1.58 (d, J = 9.2 Hz, 1H) |
| 762 | 567.9 | $^1$HNMR (400 MHz, DMSO-$d_6$) δ 12.42-12.35 (m, 1H), 8.69-8.67 (m, 1H), 7.84-7.83 (m, 1H), 7.75 (s, 1H), 7.64-7.60 (m, 1H), 7.31-7.30 (m, 1H), 7.25 (d, J = 7.2 Hz, 1H), 6.90 (d, J = 8.4 Hz, 1H), 6.77-6.76 (m, 1H), 4.74-4.66 (m, 1H), 4.49-4.46 (m, 1H), 4.13 (d, J = 5.6 Hz, 2H), 3.57 (s, 3H), 3.07-2.94 (m, 3H), 2.36 (s, 6H), 1.90-1.73 (m, 2H) |

Example 239. Preparation of 1-methylsulfonyl-N-[2-[[4-[6-(3-oxabicyclo[4.1.0]heptan-6-yl)-2-pyridyl]thiazol-2-yl]amino]-2-oxo-ethyl]pyrrole-3-carboxamide (Compound 750)

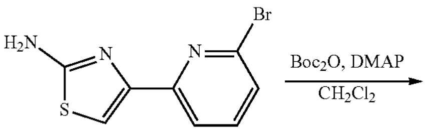

A

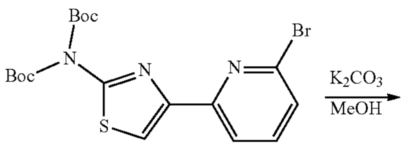

B

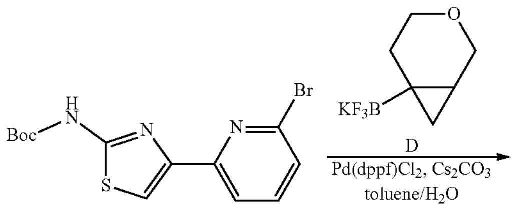

C

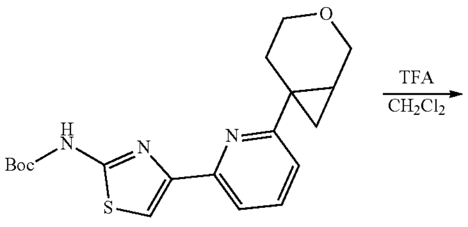

E

-continued

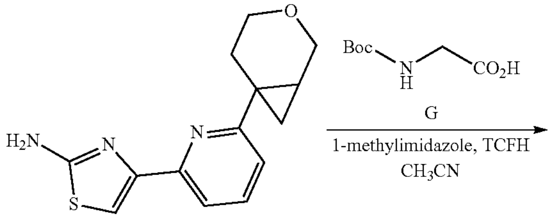

F

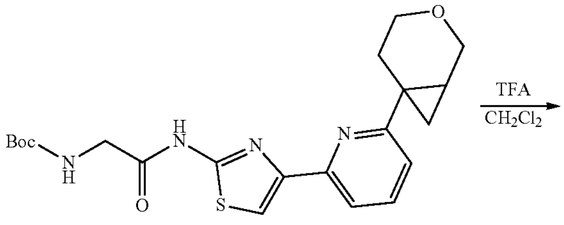

H

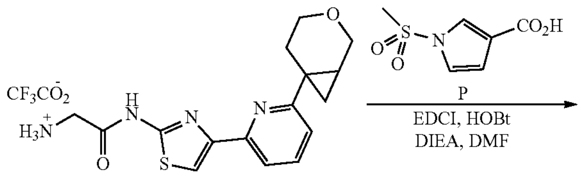

I

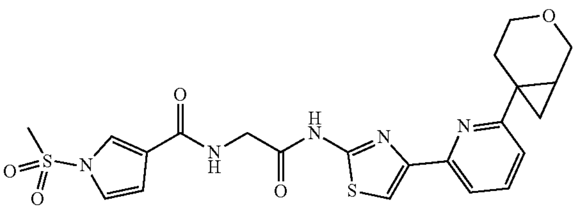

(±)
Compound 750

Step 1: Preparation of tert-butyl N-[4-(6-bromo-2-pyridyl)thiazol-2-yl]-N-tertbutoxycarbonyl-carbamate (Intermediate B)

B

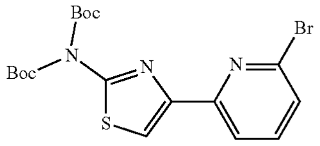

To a solution of 4-(6-bromo-2-pyridyl)thiazol-2-amine (5.00 g, 19.52 mmol) in dichloromethane (50 mL) was added DMAP (0.239 g, 1.95 mmol) and $Boc_2O$ (11.21 mL, 48.80 mmol). The reaction mixture was stirred at 25° C. After 16 h, the mixture was diluted with dichloromethane (100 mL) and washed with $H_2O$ (70 mL). The organic layers were dried over anhydrous $Na_2SO_4$, filtered and concentrated under reduced pressure to give Intermediate B (8.90 g, 19.50 mmol, 99.90% yield) as brown oil. LCMS (ESI) m/z: $[^{79}BrM+H]^+$=456.0.

Step 2: Preparation of tert-butyl N-[4-(6-bromo-2-pyridyl)thiazol-2-yl]carbamate (Intermediate C)

C

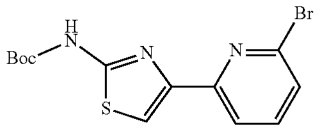

A suspension of Intermediate B (8.90 g, 19.50 mmol) and $K_2CO_3$ (8.09 g, 58.51 mmol) in MeOH (90 mL) was stirred at 40° C. for 2 h. The reaction mixture was cooled to room temperature and filtered to remove the solid and the filtrate was subsequently concentrated in vacuo. The residue was purified by silica gel chromatography (petroleum ether/ethyl acetate=20/1-5/1) to give Intermediate C (5.60 g, 15.27 mmol, 78.30% yield) as white solids. LCMS (ESI) m/z: $[^{79}BrM+H]^+$=356.0; $^1$HNMR (400 MHz, $CDCl_3$) δ 8.19 (s, 1H), 7.87-7.85 (m, 1H), 7.75 (s, 1H), 7.60-7.56 (m, 1H), 7.38-7.36 (m, 1H).

Step 3: Preparation of 9H-fluoren-9-ylmethyl N-[(4S)-1-[6-[2-[(2-aminoacetyl)amino]thiazol-4-yl]-2-pyridyl]-3,3-difluoro-4-piperidyl]-N-methyl-carbamate (Intermediate E)

E

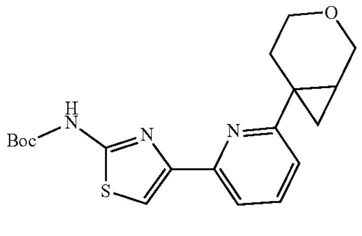

To Intermediate C (0.900 g, 2.53 mmol) and difluoro-[(Z)-3-oxabicyclo [4.1.0]heptan-6-ylboranylidene-fluoranyl]potassium (0.670 g, 3.28 mmol) in a mixture of toluene (9 mL) and water (1.8 mL) was added $Cs_2CO_3$ (1.65 g, 5.05 mmol) and Pd(dppf)$Cl_2$ (0.184 g, 0.253 mmol) at 25° C. The biphasic mixture was subsequently stirred at 110° C. After 16 h, the mixture was cooled to room temperature and poured into water (50 mL). The biphasic mixture was extracted with ethyl acetate (3x30 mL). The combined organic layers were dried over anhydrous $Na_2SO_4$, filtered and concentrated under reduced pressure. The residue was purified by silica gel chromatography (petroleum ether/ethyl acetate=5/1-1/1) (TLC: PE/EA=1/1) to afford Intermediate 5 (0.120 g, 0.305 mmol, 12.08% yield) as yellow solids. LCMS (ESI) m/z: $[M+H]^+$=374.1.

Step 4: Preparation of 4-[6-(3-oxabicyclo[4.1.0]heptan-6-yl)-2-pyridyl]thiazol-2-amine (Intermediate F)

F

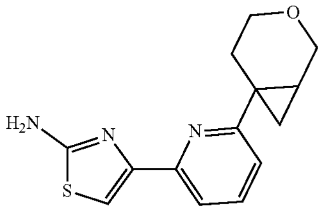

To a cooled (0° C.) solution of Intermediate E (0.220 g, 0.589 mmol) in dichloromethane (3 mL) was added TFA (11.00 mL, 13.51 mmol). The reaction mixture was subsequently warmed to room temperature and stirred for 1 h. The mixture was slowly poured into a solution of aqueous saturated $NaHCO_3$ (30 mL) and extracted with ethyl acetate (3x30 mL). The combined organic layers were dried over anhydrous $Na_2SO_4$, filtered and concentrated under reduced pressure. A subsequent batch on similar scale was prepared under the same conditions. The batches were combined and purified by silica gel chromatography (petroleum ether/ethyl acetate=5/1-1/1) to afford Intermediate F (0.360 g, 1.32 mmol, 89.43% yield) as yellow solids. LCMS (ESI) m/z: $[M+H]^+$=274.0.

Step 5: Preparation of tert-butyl N-[2-[[4-[6-(3-oxabicyclo[4.1.0]heptan-6-yl)-2-pyridyl]thiazol-2-yl]amino]-2-oxo-ethyl]carbamate (Intermediate H)

H

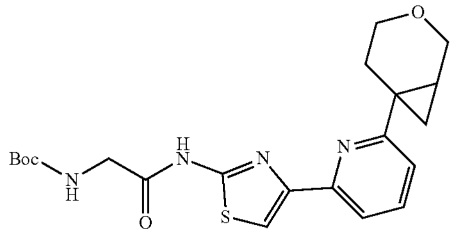

To a solution of 2-(tert-butoxycarbonylamino)acetic acid (0.288 g, 1.65 mmol) and Intermediate F (0.300 g, 1.10 mmol) in $CH_3CN$ (5 mL) was added 1-methylimidazole (0.262 mL, 3.29 mmol) and [chloro(dimethylamino)methylene]-dimethyl-ammonium; hexafluorophosphate (0.462 g, 1.65 mmol) at 30° C. After stirring for 1 h, the mixture was poured into water (30 mL) and extracted with ethyl acetate (3×20 mL). The combined organic layers were dried over anhydrous $Na_2SO_4$, filtered and concentrated under reduced pressure. The residue was purified by flash chromatography (petroleum ether/ethyl acetate=5/1-1/1) to afford Intermediate H (0.480 g, 0.896 mmol, 81.67% yield) as yellow solids. LCMS (ESI) m/z: $[M+H]^+$=431.2; $^1$HNMR (400 MHz, $CDCl_3$) δ 9.58 (s, 1H), 7.75-7.73 (m, 1H), 7.73-7.71 (m, 1H), 7.68-7.64 (m, 1H), 7.15-7.13 (m, 1H), 5.15 (s, 1H), 4.09-4.01 (m, 4H), 3.67-3.51 (m, 1H), 3.50-3.48 (m, 1H), 2.68-2.65 (m, 1H), 2.16-1.85 (m, 1H), 1.85-1.51 (m, 1H), 1.40 (s, 9H), 1.39-1.38 (m, 1H), 1.11-1.08 (m, 1H).

Step 6: Preparation of 2-amino-N-[4-[6-(3-oxabicyclo[4.1.0]heptan-6-yl)-2-pyridyl]thiazol-2-yl]acetamide (Intermediate I)

I

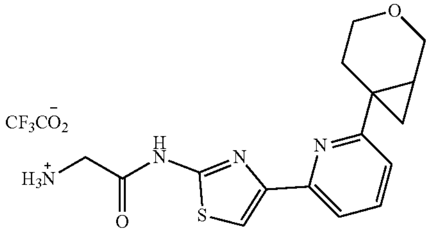

A a cooled (0° C.) solution of Intermediate H (0.480 g, 1.11 mmol) in dichloromethane (4.5 mL) was added TFA (1.50 mL, 20.26 mmol). The mixture was warmed to 30° C. and stirred for 1 h. The reaction mixture was subsequently slowly poured into a solution of aqueous saturated $NaHCO_3$ (40 mL) and extracted with ethyl acetate (4×30 mL*4). The combined organic layers were dried over anhydrous $Na_2SO_4$, filtered and concentrated under reduced pressure to afford Intermediate I (0.360 g, 0.817 mmol, 73.29% yield) as yellow solids. LCMS (ESI) m/z: $[M+H]^+$=331.1.

Step 7: Preparation of 1-methylsulfonyl-N-[2-[[4-[6-(3-oxabicyclo[4.1.0]heptan-6-yl)-2-pyridyl]thiazol-2-yl]amino]-2-oxo-ethyl]pyrrole-3-carboxamide (Compound 750)

Compound 750

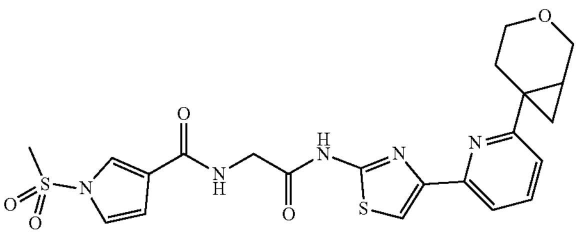

(±)

To a solution of 1-methylsulfonylpyrrole-3-carboxylic acid (0.057 g, 0.303 mmol), Intermediate I (0.100 g, 0.303 mmol), EDCI (0.087 g, 0.454 mmol), HOBt (0.061 g, 0.454 mmol) in DMF (1 mL) was added N,N-diisopropylethylamine (0.158 mL, 0.908 mmol). The reaction mixture was stirred at room temperature. After 1 h, the mixture was poured into water (20 mL) and resulting precipitates were filtered. The solids were triturated with MeOH (15 mL) at room temperature for 10 min and filtered. The filter cake was dried under reduced pressure to afford Compound 750 (0.048 g, 0.092 mmol, 30.28% yield) as off-white solids. LCMS (ESI) m/z: $[M+H]^+$=502.4; $^1$HNMR (400 MHz, DMSO-$d_6$) δ 12.42 (s, 1H), 8.71-8.69 (m, 1H), 7.86-7.85 (m, 1H), 7.80-7.78 (m, 2H), 7.72-7.70 (m, 1H), 7.32-7.29 (m, 1H), 7.29-7.27 (m, 1H), 6.79-6.78 (m, 1H), 4.15-3.95 (m, 2H), 3.95-3.94 (m, 1H), 3.86-3.84 (m, 1H), 3.58-3.57 (m, 4H), 3.57-3.55 (m, 1H), 2.68-2.63 (m, 1H), 1.35-1.34 (m, 1H), 1.34-1.33 (m, 1H), 1.04-1.03 (m, 1H), 1.03-1.02 (m, 1H).

Example 240. Preparation of Compounds of the Invention

The following compounds in Table 45 were synthesized starting utilizing the common intermediate 4-[6-(3-oxabicyclo[4.1.0]heptan-6-yl)-2-pyridyl]thiazol-2-amine utilizing the appropriate, N-Boc amino acid, heterocyclic carboxylic acid, followed by a SFC separation if required following general synthetic protocols described in Example 239 (Compound 750).

TABLE 45

| Compound # | LC-MS data(m/z) | $^1$H NMR |
|---|---|---|
| 751 | 480.3 | $^1$H NMR (400 MHz, DMSO-$d_6$) δ 12.33 (s, 1H), 8.18-8.16 (m, 1H), 7.81-7.77 (m, 2H), 7.74-7.72 (m, 1H), 7.53-7.52 (m, 1H), 7.28-7.26 (m, 1H), 6.97-6.96 (m, 1H), 6.49-6.48 (m, 1H), 4.10 (d, J = 5.2 Hz, 2H), 3.94-3.93 (m, 1H), 3.86-3.83 (m, 1H), 3.56-3.55 (m, 1H), 3.40-3.39 (m, 1H), 2.71-2.62(m, 1H), 2.05-2.02 (m, 2H), 1.83-1.78 (m, 1H), 1.49 (s, 9H), 1.34-1.33 (m, 1H), 1.04-1.01 (m, 1H) |
| 755 | 546.1 | $^1$HNMR (400 MHz, Methanol-$d_4$) δ 7.91-7.90 (m, 1H), 7.82-7.77 (m, 1H), 7.75 (s, 1H), 7.74-7.71 (m, 1H), 7.27-7.25(m, 1H), 7.24 (d, J = 8.0 Hz, 1H), 6.84-6.83 (m, 1H), 4.97-4.94 (m, 1H), 4.04-4.03 (m, 1H), 3.95-3.92 (m, 1H), 3.84-3.81 (m, 2H), 3.65-3.63 (m, 1H), 3.52-3.50 (m, 1H), 3.42 (s, 3H), 3.37 (s, 3H), 2.66-2.62 (m, 1H), 2.13-2.12 (m, 1H), 1.83-1.81 (m, 1H), 1.40-1.36 (m, 1H), 1.05-1.02 (m, 1H) |
| 756 | 546.1 | $^1$HNMR (400 MHz, Methanol-$d_4$) δ 7.91-7.90 (m, 1H), 7.82-7.77 (m, 1H), 7.75 (s, 1H), 7.74-7.71 (m, 1H), 7.26-7.25 (m, 1H), 7.25 (br d, J = 7.2 Hz, 1H), 6.84-6.83 (m, 1H), 4.97-4.94 (m, 1H), 4.04-4.03 (m, 1H), 3.95-3.92 (m, 1H), 3.84-3.81 (m, 2H), 3.65-3.63 (m, 1H), 3.52-3.50 (m, 1H), 3.42 |

TABLE 45-continued

| Compound # | LC-MS data(m/z) | $^1$H NMR |
|---|---|---|
| | | (s, 3H), 3.37 (s, 3H), 2.66-2.62 (m, 1H), 2.13-2.12 (m, 1H), 1.83-1.81 (m, 1H), 1.39-1.36 (m, 1H), 1.04-1.02 (m, 1H) |
| 423 | 518.1 | $^1$H NMR (400 MHz, DMSO-d6) δ = 12.38-12.31 (m, 1H), 8.68-8.65 (m, 1H), 8.33 (s, 1H), 7.84-7.83 (m, 1H), 7.59 (s, 1H), 7.44 (s, 1H), 7.31-7.30 (m, 1H), 7.28-7.20 (m, 2H), 6.90-6.88 (m, 1H), 6.77-6.76 (m, 1H), 4.65-4.62 (m, 1H), 4.13-4.12 (d, J = 6.0 Hz, 2H), 3.72-3.62 (m, 3H), 3.57 (s, 3H), 3.13-3.07 (m, 1H), 2.77-2.70 (m, 1H), 2.43-2.37 (m, 1H), 1.88-1.84 (m, 1H), 1.56-1.43 (m, 2H), 0.98-0.96 (d, J = 6.4 Hz, 3H) ppm |
| 460 | 539.1 | $^1$H NMR (400 MHz, DMSO-d6) δ = 12.37 (s, 1H), 8.70-8.67 (m, 1H), 8.60 (s, 2H), 7.85-7.84 (m, 1H), 7.68-7.67 (m, 1H), 7.50 (s, 1H), 7.40 (d, J = 7.6 Hz, 1H), 7.32-7.29 (m, 2H), 6.98-6.78 (m, 1H), 6.77-6.76 (m, 1H), 4.20-4.17 (m, 1H), 4.14 (d, J = 6.0 Hz, 2H), 3.92 (s, 1H), 3.86 (d, J = 14.0 Hz, 1H), 3.58 (s, 3H), 3.33-3.26 (m, 1H), 3.01-2.98 (m, 1H), 2.11 (s, 1H), 2.13 (s, 1H), 1.86-1.81 (m, 1H) ppm |
| 462 | 529.4 | $^1$H NMR (400 MHz, $CDCl_3$) δ 8.25 (s, 1H), 7.81-7.79 (m, 1H), 7.72-7.70 (m, 2H), 7.42-7.40 (m, 2H), 7.21-7.12 (m, 2H), 7.15-7.10 (m, 1H), 6.75-6.74 (m, 1H), 6.59 (d, J = 2.0 Hz, 1H), 5.10-5.05 (m, 1H), 4.06-4.03 (m, 1H), 3.98 (s, 3H), 3.72-3.68 (m, 1H), 3.45 (s, 3H), 3.20 (s, 3H) |

Example 241. Assay for ATPase Catalytic Activity of BRM and BRG-1

The ATPase catalytic activity of BRM or BRG-1 was measured by the in vitro biochemical assay using ADP-Glo™ (Promega, V9102). The ADP-Glo™ kinase assay is performed in two steps once the reaction is complete. The first step is to deplete any unconsumed ATP in the reaction. The second step is to convert the reaction product ADP to ATP, which will be utilized by the luciferase to generate luminesce and be detected by a luminescence reader, such as Envision.

The assay reaction mixture (10 μL) contains 30 nM of BRM or BRG-1, 20 nM salmon sperm DNA (from Invitrogen, UltraPure™ Salmon Sperm DNA Solution, cat #15632011), and 400 μM of ATP in the ATPase assay buffer, which comprises of 20 mM Tris, pH 8, 20 mM $MgCl_2$, 50 mM NaCl, 0.1% Tween-20, and 1 mM fresh DTT (Pierce™° DTT (Dithiothreitol), cat #20290). The reaction is initiated by the addition of the 2.5 μL ATPase solution to 2.5 μL ATP/DNA solution on low volume white Proxiplate-384 plus plate (PerkinElmer, cat #6008280) and incubates at room temperature for 1 hour. Then following addition of 5 μL of ADP-Glo™ Reagent provided in the kit, the reaction incubates at room temperature for 40 minutes. Then 10 μL of Kinase Detection Reagent provided in the kit is added to convert ADP to ATP, and the reaction incubates at room temperature for 60 minutes. Finally, luminescence measurement is collected with a plate-reading luminometer, such as Envision.

BRM and BRG-1 were synthesized from high five insect cell lines with a purity of greater than 90%. $IP_{50}$ data for compounds 1-827 from the ATPase catalytic activity assay described herein are shown in Table 46 below.

TABLE 46

BRM and BRG1 Inhibition Data for Compounds of the Invention

| Compound No. | BRM $IP_{50}$ (μM)* | BRG1 $IP_{50}$ (μM)* |
|---|---|---|
| 1 | ++++ | ++++ |
| 2 | +++ | +++ |
| 3 | + | + |
| 4 | ++++ | ++++ |
| 5 | +++ | +++ |
| 6 | ++ | ++ |

TABLE 46-continued

BRM and BRG1 Inhibition Data for Compounds of the Invention

| Compound No. | BRM $IP_{50}$ (μM)* | BRG1 $IP_{50}$ (μM)* |
|---|---|---|
| 7 | +++ | +++ |
| 8 | +++ | +++ |
| 9 | ++++ | ++++ |
| 10 | ++++ | ++++ |
| 11 | +++ | +++ |
| 12 | +++ | +++ |
| 13 | +++ | +++ |
| 14 | ++++ | ++++ |
| 15 | ++++ | ++++ |
| 16 | ++++ | ++++ |
| 17 | +++ | +++ |
| 18 | +++ | +++ |
| 19 | +++ | +++ |
| 20 | +++ | +++ |
| 21 | +++ | +++ |
| 22 | ++++ | ++++ |
| 23 | ++++ | ++++ |
| 24 | +++ | +++ |
| 25 | +++ | ++ |
| 26 | +++ | +++ |
| 27 | ++ | + |
| 28 | + | + |
| 29 | + | + |
| 30 | +++ | +++ |
| 31 | + | + |
| 32 | + | + |
| 33 | +++ | +++ |
| 34 | +++ | +++ |
| 34 | +++ | ++ |
| 35 | ++ | ++ |
| 36 | ++ | ++ |
| 37 | + | + |
| 38 | ++ | ++ |
| 39 | + | + |
| 40 | +++ | +++ |
| 41 | ++++ | +++ |
| 42 | +++ | ++ |
| 43 | +++ | +++ |
| 44 | +++ | ++ |
| 45 | ++++ | ++++ |
| 46 | ++++ | ++++ |
| 47 | +++ | +++ |
| 48 | +++ | +++ |
| 49 | ++ | ++ |
| 50 | ++ | ++ |
| 51 | + | + |
| 52 | ++ | + |
| 53 | ++++ | ++++ |
| 54 | ++++ | ++++ |

TABLE 46-continued

BRM and BRG1 Inhibition Data for Compounds of the Invention

| Compound No. | BRM $IP_{50}$ (μM)* | BRG1 $IP_{50}$ (μM)* |
|---|---|---|
| 55 | ++++ | ++++ |
| 56 | +++ | +++ |
| 57 | ++++ | ++++ |
| 58 | +++ | +++ |
| 58 | +++ | +++ |
| 58 | +++ | +++ |
| 59 | ++++ | ++++ |
| 60 | ++++ | ++++ |
| 60 | ++++ | ++++ |
| 60 | ++++ | ++++ |
| 61 | ++++ | ++++ |
| 62 | +++ | +++ |
| 63 | +++ | +++ |
| 64 | +++ | +++ |
| 65 | ++++ | ++++ |
| 66 | +++ | +++ |
| 67 | ++++ | ++++ |
| 68 | ++++ | ++++ |
| 69 | ++++ | ++++ |
| 70 | ++++ | ++++ |
| 70 | ++++ | ++++ |
| 70 | ++++ | ++++ |
| 70 | ++++ | +++ |
| 71 | ++++ | ++++ |
| 71 | +++ | ++++ |
| 72 | ++++ | ++++ |
| 73 | +++ | +++ |
| 74 | + | + |
| 75 | +++ | +++ |
| 76 | +++ | +++ |
| 77 | +++ | +++ |
| 78 | +++ | +++ |
| 79 | ++ | ++ |
| 80 | ++ | ++ |
| 81 | ++++ | ++++ |
| 81 | ++++ | ++++ |
| 82 | ++++ | ++++ |
| 83 | +++ | +++ |
| 84 | ++++ | +++ |
| 84 | ++++ | +++ |
| 85 | ++++ | ++++ |
| 86 | ++++ | ++++ |
| 87 | ++++ | ++++ |
| 88 | ++++ | ++++ |
| 89 | +++ | +++ |
| 90 | ++++ | ++++ |
| 91 | +++ | ++ |
| 92 | +++ | +++ |
| 93 | +++ | +++ |
| 94 | ++++ | ++++ |
| 95 | +++ | +++ |
| 96 | +++ | ++ |
| 97 | ++ | ++ |
| 98 | +++ | +++ |
| 99 | ++++ | +++ |
| 100 | +++ | +++ |
| 101 | ++++ | ++++ |
| 102 | ++ | ++ |
| 103 | ++ | ++ |
| 104 | +++ | +++ |
| 105 | +++ | ++++ |
| 106 | ++++ | ++++ |
| 107 | +++ | +++ |
| 108 | ++++ | +++ |
| 109 | +++ | +++ |
| 110 | +++ | +++ |
| 111 | ++ | ++ |
| 112 | ++++ | ++++ |
| 113 | ++ | ++ |
| 114 | ++ | ++ |
| 115 | ++ | ++ |
| 116 | + | + |
| 117 | +++ | +++ |
| 118 | + | + |
| 119 | +++ | ++ |
| 120 | +++ | ++ |

TABLE 46-continued

BRM and BRG1 Inhibition Data for Compounds of the Invention

| Compound No. | BRM $IP_{50}$ (μM)* | BRG1 $IP_{50}$ (μM)* |
|---|---|---|
| 121 | +++ | +++ |
| 122 | +++ | +++ |
| 123 | ++++ | +++ |
| 124 | +++ | ++ |
| 125 | +++ | +++ |
| 126 | +++ | ++ |
| 127 | ++ | ++ |
| 128 | ++ | ++ |
| 129 | +++ | +++ |
| 130 | ++ | ++ |
| 131 | +++ | ++ |
| 132 | +++ | +++ |
| 133 | ++ | ++ |
| 134 | +++ | ++ |
| 135 | +++ | +++ |
| 136 | +++ | +++ |
| 137 | +++ | ++++ |
| 138 | + | + |
| 139 | ++ | ++ |
| 140 | ++ | ++ |
| 141 | ++ | ++ |
| 142 | ++ | ++ |
| 143 | ++ | ++ |
| 144 | +++ | +++ |
| 145 | +++ | +++ |
| 146 | + | + |
| 147 | ++++ | +++ |
| 148 | ++ | ++ |
| 149 | ++++ | ++++ |
| 150 | ++++ | ++++ |
| 151 | ++++ | ++++ |
| 152 | ++ | ++ |
| 153 | ++ | ++ |
| 154 | ++++ | ++++ |
| 155 | ++ | ++ |
| 156 | +++ | +++ |
| 157 | ++ | ++ |
| 158 | +++ | +++ |
| 159 | ++++ | +++ |
| 160 | +++ | ++ |
| 161 | +++ | +++ |
| 162 | ++++ | ++++ |
| 163 | ++++ | +++ |
| 164 | ++++ | +++ |
| 165 | +++ | +++ |
| 166 | +++ | ++ |
| 167 | ++++ | ++++ |
| 168 | +++ | +++ |
| 169 | ++ | ++ |
| 170 | +++ | +++ |
| 171 | ++ | ++ |
| 172 | +++ | ++ |
| 173 | ++ | ++ |
| 174 | +++ | +++ |
| 175 | +++ | +++ |
| 176 | ++ | ++ |
| 177 | +++ | +++ |
| 178 | ++++ | ++++ |
| 179 | +++ | +++ |
| 180 | +++ | +++ |
| 181 | +++ | +++ |
| 182 | ++++ | ++++ |
| 183 | ++++ | ++++ |
| 184 | +++ | +++ |
| 185 | +++ | +++ |
| 186 | +++ | +++ |
| 187 | +++ | +++ |
| 188 | ++++ | +++ |
| 189 | ++++ | ++++ |
| 190 | ++++ | ++++ |
| 191 | ++++ | +++ |
| 192 | +++ | ++ |
| 193 | +++ | +++ |
| 194 | ++++ | +++ |
| 195 | ++++ | ++++ |
| 196 | ++++ | ++++ |

TABLE 46-continued

BRM and BRG1 Inhibition Data for Compounds of the Invention

| Compound No. | BRM $IP_{50}$ (μM)* | BRG1 $IP_{50}$ (μM)* |
|---|---|---|
| 197 | ++++ | +++ |
| 198 | +++ | +++ |
| 199 | +++ | +++ |
| 200 | +++ | +++ |
| 201 | ++++ | +++ |
| 202 | +++ | +++ |
| 203 | +++ | +++ |
| 204 | +++ | +++ |
| 205 | +++ | +++ |
| 206 | ++++ | +++ |
| 207 | +++ | +++ |
| 208 | +++ | +++ |
| 209 | +++ | +++ |
| 210 | +++ | +++ |
| 211 | +++ | +++ |
| 212 | ++++ | ++++ |
| 213 | +++ | +++ |
| 214 | ++ | ++ |
| 215 | +++ | +++ |
| 216 | +++ | +++ |
| 217 | +++ | +++ |
| 218 | +++ | +++ |
| 219 | +++ | +++ |
| 220 | +++ | +++ |
| 221 | +++ | +++ |
| 222 | +++ | ++ |
| 223 | +++ | +++ |
| 224 | +++ | +++ |
| 225 | +++ | +++ |
| 226 | ++++ | +++ |
| 227 | +++ | +++ |
| 228 | ++++ | +++ |
| 229 | ++ | ++ |
| 230 | +++ | ++ |
| 231 | +++ | +++ |
| 232 | +++ | +++ |
| 233 | ++++ | +++ |
| 234 | +++ | +++ |
| 235 | +++ | +++ |
| 236 | +++ | +++ |
| 237 | +++ | +++ |
| 238 | +++ | +++ |
| 239 | +++ | +++ |
| 240 | ++++ | +++ |
| 241 | +++ | ++ |
| 242 | +++ | +++ |
| 243 | +++ | ++ |
| 244 | +++ | +++ |
| 245 | +++ | +++ |
| 246 | ++++ | +++ |
| 247 | +++ | +++ |
| 248 | +++ | +++ |
| 249 | +++ | +++ |
| 250 | +++ | +++ |
| 252 | +++ | +++ |
| 253 | +++ | +++ |
| 254 | +++ | +++ |
| 255 | ++++ | ++++ |
| 256 | +++ | +++ |
| 257 | +++ | +++ |
| 258 | +++ | +++ |
| 259 | +++ | +++ |
| 260 | +++ | +++ |
| 261 | ++++ | ++++ |
| 262 | +++ | +++ |
| 263 | +++ | +++ |
| 264 | +++ | +++ |
| 265 | +++ | +++ |
| 266 | +++ | +++ |
| 267 | ++ | ++ |
| 268 | +++ | ++ |
| 269 | +++ | +++ |
| 270 | +++ | +++ |
| 271 | +++ | ++ |
| 272 | +++ | ++ |
| 273 | +++ | ++ |

TABLE 46-continued

BRM and BRG1 Inhibition Data for Compounds of the Invention

| Compound No. | BRM $IP_{50}$ (μM)* | BRG1 $IP_{50}$ (μM)* |
|---|---|---|
| 274 | +++ | +++ |
| 275 | +++ | +++ |
| 276 | +++ | +++ |
| 277 | ++++ | +++ |
| 278 | +++ | +++ |
| 279 | +++ | +++ |
| 280 | +++ | +++ |
| 281 | +++ | +++ |
| 282 | ++++ | ++++ |
| 283 | +++ | +++ |
| 284 | +++ | +++ |
| 285 | +++ | +++ |
| 286 | +++ | +++ |
| 287 | ++++ | +++ |
| 288 | +++ | +++ |
| 289 | +++ | +++ |
| 290 | ++++ | +++ |
| 291 | +++ | +++ |
| 292 | ++ | ++ |
| 293 | ++++ | ++++ |
| 294 | +++ | +++ |
| 295 | ++++ | ++++ |
| 296 | +++ | +++ |
| 297 | +++ | ++ |
| 298 | +++ | +++ |
| 299 | ++++ | +++ |
| 300 | +++ | +++ |
| 301 | +++ | +++ |
| 302 | +++ | +++ |
| 303 | ++++ | +++ |
| 304 | +++ | +++ |
| 305 | +++ | +++ |
| 306 | +++ | +++ |
| 307 | +++ | +++ |
| 308 | +++ | +++ |
| 309 | +++ | +++ |
| 310 | +++ | ++ |
| 311 | +++ | +++ |
| 312 | +++ | +++ |
| 313 | ++ | ++ |
| 314 | +++ | +++ |
| 315 | +++ | +++ |
| 316 | ++++ | +++ |
| 317 | ++ | ++ |
| 318 | +++ | +++ |
| 319 | +++ | +++ |
| 320 | ++++ | +++ |
| 321 | +++ | ++ |
| 322 | +++ | +++ |
| 323 | +++ | +++ |
| 324 | +++ | +++ |
| 325 | ++++ | ++++ |
| 326 | ++++ | +++ |
| 327 | +++ | +++ |
| 328 | +++ | ++ |
| 329 | ++++ | +++ |
| 330 | ++ | ++ |
| 331 | ++++ | ++++ |
| 332 | +++ | ++ |
| 333 | ++++ | ++++ |
| 334 | ++++ | ++++ |
| 335 | +++ | +++ |
| 336 | +++ | +++ |
| 337 | +++ | +++ |
| 338 | +++ | +++ |
| 339 | +++ | +++ |
| 340 | +++ | +++ |
| 341 | +++ | ++ |
| 342 | ++++ | ++++ |
| 343 | +++ | ++ |
| 344 | +++ | +++ |
| 345 | ++ | ++ |
| 346 | ++ | ++ |
| 347 | +++ | +++ |
| 348 | +++ | +++ |
| 349 | +++ | +++ |

TABLE 46-continued

BRM and BRG1 Inhibition Data for Compounds of the Invention

| Compound No. | BRM $IP_{50}$ (μM)* | BRG1 $IP_{50}$ (μM)* |
|---|---|---|
| 350 | ++++ | ++++ |
| 351 | +++ | +++ |
| 352 | ++++ | ++++ |
| 353 | +++ | ++ |
| 354 | +++ | +++ |
| 355 | +++ | +++ |
| 356 | +++ | +++ |
| 357 | ++++ | ++++ |
| 358 | ++++ | ++++ |
| 359 | ++++ | ++++ |
| 360 | +++ | +++ |
| 361 | +++ | +++ |
| 362 | ++ | ++ |
| 363 | +++ | +++ |
| 364 | +++ | +++ |
| 365 | +++ | +++ |
| 366 | ++++ | +++ |
| 367 | +++ | +++ |
| 368 | +++ | +++ |
| 369 | ++++ | +++ |
| 370 | +++ | +++ |
| 371 | ++++ | ++++ |
| 372 | ++++ | +++ |
| 373 | ++++ | +++ |
| 374 | +++ | +++ |
| 375 | +++ | +++ |
| 376 | +++ | +++ |
| 377 | ++++ | +++ |
| 378 | ++++ | +++ |
| 379 | ++++ | ++++ |
| 380 | ++++ | ++++ |
| 381 | ++++ | +++ |
| 382 | +++ | +++ |
| 383 | +++ | ++ |
| 384 | ++++ | ++++ |
| 385 | +++ | +++ |
| 386 | ++++ | ++++ |
| 387 | +++ | +++ |
| 388 | +++ | ++ |
| 389 | +++ | +++ |
| 390 | +++ | +++ |
| 391 | ++++ | ++++ |
| 392 | +++ | +++ |
| 393 | +++ | +++ |
| 394 | +++ | +++ |
| 395 | ++ | ++ |
| 396 | ++++ | +++ |
| 397 | ++ | ++ |
| 398 | ++ | ++ |
| 399 | +++ | +++ |
| 400 | ++++ | ++++ |
| 401 | ++ | ++ |
| 402 | ++++ | +++ |
| 403 | +++ | +++ |
| 404 | ++++ | +++ |
| 405 | ++++ | ++++ |
| 406 | ++++ | ++++ |
| 407 | ++++ | ++++ |
| 408 | ++++ | ++++ |
| 409 | ++++ | ++++ |
| 410 | ++++ | ++++ |
| 411 | +++ | +++ |
| 412 | ++++ | ++++ |
| 413 | ++++ | ++++ |
| 414 | ++++ | ++++ |
| 415 | +++ | +++ |
| 416 | ++++ | ++++ |
| 417 | ++++ | +++ |
| 418 | +++ | +++ |
| 419 | +++ | ++ |
| 420 | +++ | +++ |
| 421 | +++ | +++ |
| 422 | +++ | +++ |
| 423 | ++++ | ++++ |
| 424 | +++ | +++ |
| 425 | +++ | +++ |

TABLE 46-continued

BRM and BRG1 Inhibition Data for Compounds of the Invention

| Compound No. | BRM $IP_{50}$ (μM)* | BRG1 $IP_{50}$ (μM)* |
|---|---|---|
| 426 | +++ | +++ |
| 427 | +++ | +++ |
| 428 | +++ | +++ |
| 429 | ++++ | +++ |
| 430 | ++++ | ++++ |
| 431 | +++ | +++ |
| 432 | +++ | +++ |
| 433 | +++ | +++ |
| 434 | +++ | +++ |
| 435 | ++++ | ++++ |
| 436 | +++ | +++ |
| 437 | ++ | ++ |
| 438 | ++++ | ++++ |
| 439 | ++++ | ++++ |
| 440 | +++ | +++ |
| 441 | ++++ | ++++ |
| 442 | ++++ | ++++ |
| 443 | ++++ | +++ |
| 444 | ++ | ++ |
| 445 | +++ | ++ |
| 446 | +++ | +++ |
| 447 | +++ | +++ |
| 448 | +++ | +++ |
| 449 | +++ | +++ |
| 450 | +++ | +++ |
| 451 | ++ | ++ |
| 452 | +++ | +++ |
| 453 | +++ | +++ |
| 454 | ++++ | +++ |
| 455 | +++ | +++ |
| 456 | +++ | +++ |
| 457 | +++ | +++ |
| 458 | ++++ | +++ |
| 459 | +++ | +++ |
| 460 | +++ | +++ |
| 461 | ++ | ++ |
| 462 | +++ | +++ |
| 463 | +++ | +++ |
| 464 | +++ | ++ |
| 465 | +++ | +++ |
| 466 | +++ | +++ |
| 467 | +++ | +++ |
| 468 | ++ | ++ |
| 469 | ++ | ++ |
| 470 | +++ | ++ |
| 471 | ++ | ++ |
| 472 | +++ | +++ |
| 473 | +++ | ++ |
| 474 | +++ | +++ |
| 475 | ++++ | ++++ |
| 476 | +++ | +++ |
| 477 | ++ | ++ |
| 478 | +++ | +++ |
| 479 | +++ | +++ |
| 480 | +++ | ++ |
| 481 | ++ | ++ |
| 482 | +++ | +++ |
| 483 | +++ | +++ |
| 484 | ++ | ++ |
| 485 | ++++ | ++++ |
| 486 | +++ | +++ |
| 487 | +++ | +++ |
| 488 | ++ | ++ |
| 489 | +++ | +++ |
| 490 | +++ | ++ |
| 491 | +++ | +++ |
| 492 | +++ | +++ |
| 493 | ++ | ++ |
| 494 | +++ | +++ |
| 495 | +++ | ++ |
| 496 | ++ | ++ |
| 497 | +++ | ++ |
| 498 | ++ | ++ |
| 499 | ++++ | ++++ |
| 500 | +++ | ++ |
| 501 | +++ | ++ |

TABLE 46-continued

BRM and BRG1 Inhibition Data for Compounds of the Invention

| Compound No. | BRM $IP_{50}$ (μM)* | BRG1 $IP_{50}$ (μM)* |
|---|---|---|
| 502 | +++ | +++ |
| 503 | ++ | ++ |
| 504 | +++ | +++ |
| 505 | ++ | ++ |
| 506 | +++ | ++ |
| 507 | +++ | +++ |
| 508 | +++ | +++ |
| 509 | ++ | ++ |
| 510 | +++ | +++ |
| 511 | ++++ | ++++ |
| 512 | ++ | ++ |
| 513 | +++ | ++ |
| 514 | ++ | ++ |
| 515 | +++ | ++ |
| 516 | +++ | +++ |
| 517 | +++ | +++ |
| 518 | ++++ | ++++ |
| 519 | +++ | +++ |
| 520 | +++ | ++ |
| 521 | ++++ | +++ |
| 522 | ++ | ++ |
| 523 | +++ | +++ |
| 524 | ++++ | +++ |
| 525 | +++ | +++ |
| 526 | +++ | +++ |
| 527 | +++ | +++ |
| 528 | ++ | ++ |
| 529 | ++++ | +++ |
| 530 | +++ | +++ |
| 531 | +++ | +++ |
| 532 | +++ | +++ |
| 533 | +++ | +++ |
| 534 | +++ | +++ |
| 535 | +++ | ++ |
| 536 | +++ | +++ |
| 537 | +++ | +++ |
| 538 | ++++ | ++++ |
| 539 | +++ | +++ |
| 540 | ++++ | ++++ |
| 541 | ++++ | ++++ |
| 542 | +++ | +++ |
| 543 | +++ | +++ |
| 544 | ++++ | ++++ |
| 545 | +++ | ++ |
| 546 | ++++ | ++++ |
| 547 | +++ | ++ |
| 548 | ++ | ++ |
| 549 | ++++ | +++ |
| 550 | ++ | ++ |
| 551 | +++ | +++ |
| 552 | +++ | +++ |
| 553 | +++ | +++ |
| 554 | +++ | ++ |
| 555 | +++ | +++ |
| 556 | +++ | ++ |
| 557 | +++ | +++ |
| 558 | ++++ | ++++ |
| 559 | ++ | ++ |
| 560 | +++ | +++ |
| 561 | ++++ | ++++ |
| 562 | ++++ | +++ |
| 563 | ++++ | ++++ |
| 564 | ++++ | ++++ |
| 565 | +++ | +++ |
| 566 | +++ | +++ |
| 567 | +++ | +++ |
| 568 | +++ | +++ |
| 569 | ++++ | ++++ |
| 570 | +++ | +++ |
| 571 | ++++ | +++ |
| 572 | +++ | +++ |
| 573 | +++ | +++ |
| 574 | +++ | +++ |
| 575 | +++ | +++ |
| 576 | ++++ | +++ |
| 577 | ++++ | +++ |

TABLE 46-continued

BRM and BRG1 Inhibition Data for Compounds of the Invention

| Compound No. | BRM $IP_{50}$ (μM)* | BRG1 $IP_{50}$ (μM)* |
|---|---|---|
| 578 | +++ | ++ |
| 579 | ++ | ++ |
| 580 | ++ | ++ |
| 581 | ++ | ++ |
| 582 | ++++ | ++++ |
| 583 | +++ | +++ |
| 584 | ++++ | ++++ |
| 585 | ++++ | +++ |
| 586 | +++ | +++ |
| 587 | ++++ | ++++ |
| 588 | +++ | ++ |
| 589 | +++ | ++ |
| 590 | +++ | +++ |
| 591 | +++ | +++ |
| 592 | +++ | +++ |
| 593 | +++ | +++ |
| 594 | +++ | ++ |
| 595 | +++ | +++ |
| 596 | ++++ | +++ |
| 597 | +++ | ++ |
| 598 | +++ | +++ |
| 599 | +++ | +++ |
| 600 | ++++ | ++++ |
| 601 | ++++ | +++ |
| 602 | ++++ | ++++ |
| 603 | ++++ | ++++ |
| 604 | ++ | ++ |
| 605 | ++ | ++ |
| 606 | +++ | ++ |
| 607 | +++ | +++ |
| 608 | +++ | ++ |
| 609 | +++ | +++ |
| 610 | +++ | +++ |
| 611 | +++ | +++ |
| 612 | +++ | +++ |
| 613 | +++ | ++ |
| 614 | +++ | +++ |
| 615 | ++++ | ++++ |
| 616 | ++++ | ++++ |
| 617 | +++ | ++ |
| 618 | +++ | +++ |
| 619 | ++++ | +++ |
| 620 | +++ | +++ |
| 621 | ++ | ++ |
| 622 | ++++ | +++ |
| 623 | ++ | ++ |
| 624 | ++ | ++ |
| 625 | ++ | ++ |
| 626 | ++ | ++ |
| 627 | +++ | ++ |
| 628 | ++ | ++ |
| 629 | ++ | ++ |
| 630 | +++ | +++ |
| 631 | +++ | +++ |
| 632 | +++ | +++ |
| 633 | +++ | +++ |
| 634 | +++ | +++ |
| 635 | ++ | ++ |
| 636 | +++ | +++ |
| 637 | +++ | +++ |
| 638 | ++ | ++ |
| 639 | +++ | +++ |
| 640 | +++ | ++ |
| 641 | ++ | ++ |
| 642 | ++ | ++ |
| 643 | +++ | +++ |
| 644 | ++ | ++ |
| 645 | +++ | +++ |
| 646 | ++ | ++ |
| 647 | +++ | +++ |
| 648 | ++ | ++ |
| 649 | +++ | +++ |
| 650 | +++ | ++ |
| 651 | ++ | + |
| 652 | +++ | +++ |
| 653 | +++ | +++ |

TABLE 46-continued

BRM and BRG1 Inhibition Data for Compounds of the Invention

| Compound No. | BRM $IP_{50}$ (μM)* | BRG1 $IP_{50}$ (μM)* |
|---|---|---|
| 654 | +++ | +++ |
| 655 | ++ | ++ |
| 656 | ++ | ++ |
| 657 | +++ | ++ |
| 658 | +++ | +++ |
| 659 | +++ | ++ |
| 660 | ++ | ++ |
| 661 | ++ | ++ |
| 662 | ++++ | ++++ |
| 663 | ++ | ++ |
| 664 | +++ | ++ |
| 665 | ++ | ++ |
| 666 | +++ | +++ |
| 667 | +++ | ++ |
| 668 | +++ | +++ |
| 669 | ++ | ++ |
| 670 | +++ | ++ |
| 671 | +++ | ++ |
| 672 | +++ | +++ |
| 673 | +++ | +++ |
| 674 | +++ | +++ |
| 675 | +++ | +++ |
| 676 | +++ | +++ |
| 677 | ++ | ++ |
| 678 | ++ | ++ |
| 679 | +++ | +++ |
| 680 | +++ | ++ |
| 681 | ++++ | +++ |
| 682 | ++ | ++ |
| 683 | +++ | +++ |
| 684 | +++ | +++ |
| 685 | +++ | ++ |
| 686 | +++ | +++ |
| 687 | +++ | ++ |
| 688 | +++ | +++ |
| 689 | ++ | ++ |
| 690 | +++ | ++ |
| 691 | +++ | ++ |
| 692 | +++ | +++ |
| 693 | ++++ | +++ |
| 694 | +++ | +++ |
| 695 | ++++ | ++++ |
| 696 | ++ | ++ |
| 697 | +++ | +++ |
| 698 | +++ | +++ |
| 699 | +++ | +++ |
| 700 | +++ | +++ |
| 701 | ++++ | +++ |
| 702 | +++ | ++ |
| 703 | ++ | ++ |
| 704 | +++ | +++ |
| 705 | +++ | +++ |
| 706 | ++ | ++ |
| 707 | +++ | +++ |
| 708 | ++++ | ++++ |
| 709 | +++ | +++ |
| 710 | +++ | +++ |
| 711 | +++ | +++ |
| 712 | +++ | +++ |
| 713 | ++++ | ++++ |
| 714 | +++ | +++ |
| 715 | +++ | +++ |
| 716 | +++ | +++ |
| 717 | +++ | +++ |
| 718 | +++ | +++ |
| 719 | ++++ | ++++ |
| 720 | +++ | +++ |
| 721 | +++ | +++ |
| 722 | +++ | +++ |
| 723 | ++++ | ++++ |
| 724 | +++ | +++ |
| 725 | +++ | +++ |
| 726 | ++++ | ++++ |
| 727 | ++++ | +++ |
| 728 | +++ | +++ |
| 729 | +++ | +++ |

TABLE 46-continued

BRM and BRG1 Inhibition Data for Compounds of the Invention

| Compound No. | BRM $IP_{50}$ (μM)* | BRG1 $IP_{50}$ (μM)* |
|---|---|---|
| 730 | ++++ | ++++ |
| 731 | ++++ | ++++ |
| 732 | +++ | +++ |
| 733 | ++++ | ++++ |
| 734 | ++++ | ++++ |
| 735 | +++ | +++ |
| 736 | ++++ | ++++ |
| 737 | ++++ | ++++ |
| 738 | ++++ | ++++ |
| 739 | ++++ | ++++ |
| 740 | ++++ | ++++ |
| 741 | +++ | +++ |
| 742 | +++ | +++ |
| 743 | +++ | +++ |
| 744 | +++ | +++ |
| 745 | ++++ | ++++ |
| 746 | ++++ | ++++ |
| 747 | ++ | ++ |
| 748 | ++++ | ++++ |
| 749 | ++ | ++ |
| 750 | +++ | +++ |
| 751 | +++ | +++ |
| 752 | +++ | +++ |
| 753 | ++++ | +++ |
| 754 | ++++ | +++ |
| 755 | +++ | +++ |
| 756 | +++ | ++ |
| 757 | ++ | ++ |
| 758 | ++++ | ++++ |
| 759 | +++ | +++ |
| 760 | ++ | ++ |
| 761 | +++ | +++ |
| 762 | +++ | +++ |
| 763 | ++++ | ++++ |
| 764 | ++++ | ++++ |
| 765 | +++ | ++ |
| 766 | ++++ | ++++ |
| 767 | ++++ | +++ |
| 768 | ++ | ++ |
| 769 | +++ | +++ |
| 770 | ++++ | +++ |
| 771 | +++ | +++ |
| 772 | ++++ | ++++ |
| 773 | ++++ | ++++ |
| 774 | ++++ | ++++ |
| 775 | ++++ | +++ |
| 776 | +++ | +++ |
| 777 | +++ | +++ |
| 778 | +++ | ++ |
| 779 | ++ | ++ |
| 780 | ++ | ++ |
| 781 | +++ | ++ |
| 782 | ++ | ++ |
| 783 | +++ | ++ |
| 784 | +++ | +++ |
| 785 | +++ | +++ |
| 786 | ++++ | +++ |
| 787 | +++ | +++ |
| 788 | ++ | ++ |
| 789 | ++ | ++ |
| 790 | +++ | +++ |
| 791 | +++ | +++ |
| 792 | ++ | ++ |
| 793 | +++ | +++ |
| 794 | ++ | ++ |
| 795 | +++ | ++ |
| 796 | ++ | ++ |
| 797 | ++ | ++ |
| 798 | ++ | ++ |
| 799 | +++ | ++ |
| 800 | +++ | ++ |
| 801 | ++ | ++ |
| 802 | +++ | +++ |
| 803 | +++ | ++ |
| 804 | ++ | ++ |
| 805 | ++ | ++ |

TABLE 46-continued

BRM and BRG1 Inhibition Data for Compounds of the Invention

| Compound No. | BRM IP$_{50}$ (μM)* | BRG1 IP$_{50}$ (μM)* |
|---|---|---|
| 806 | +++ | +++ |
| 807 | +++ | ++ |
| 808 | +++ | +++ |
| 809 | ++ | ++ |
| 810 | +++ | +++ |
| 811 | +++ | ++ |
| 812 | ++ | ++ |
| 813 | +++ | ++ |
| 814 | +++ | ++ |
| 815 | ++ | ++ |
| 816 | +++ | +++ |
| 817 | +++ | +++ |
| 818 | +++ | +++ |
| 819 | +++ | +++ |
| 820 | ++ | ++ |
| 821 | +++ | +++ |
| 822 | +++ | ++ |
| 823 | ++++ | +++ |
| 824 | ++ | ++ |
| 825 | ++++ | +++ |
| 826 | +++ | +++ |
| 827 | ++++ | +++ |

"+" indicates inhibitory effect of ≥1 μM;
"++" indicates inhibitory effect of ≥0.1 μM;
"+++" indicates inhibitory effect of ≥0.01 μM,
"++++" indicates inhibitory effect of <0.01 μM Example 242. Synthesis of Compound A BRG1/BRM Inhibitor compound A has the structure:

Compound A

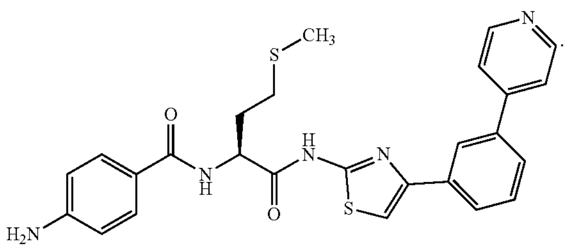

Compound A was synthesized as shown in Scheme 13 below.

Scheme 13. Synthesis of Compound A

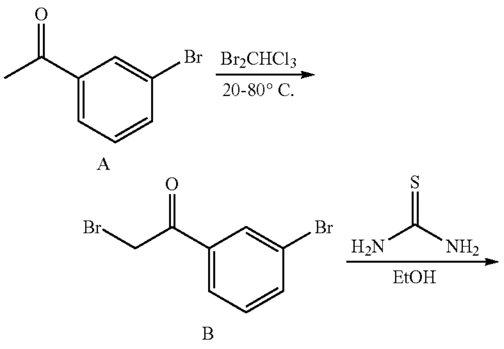

-continued

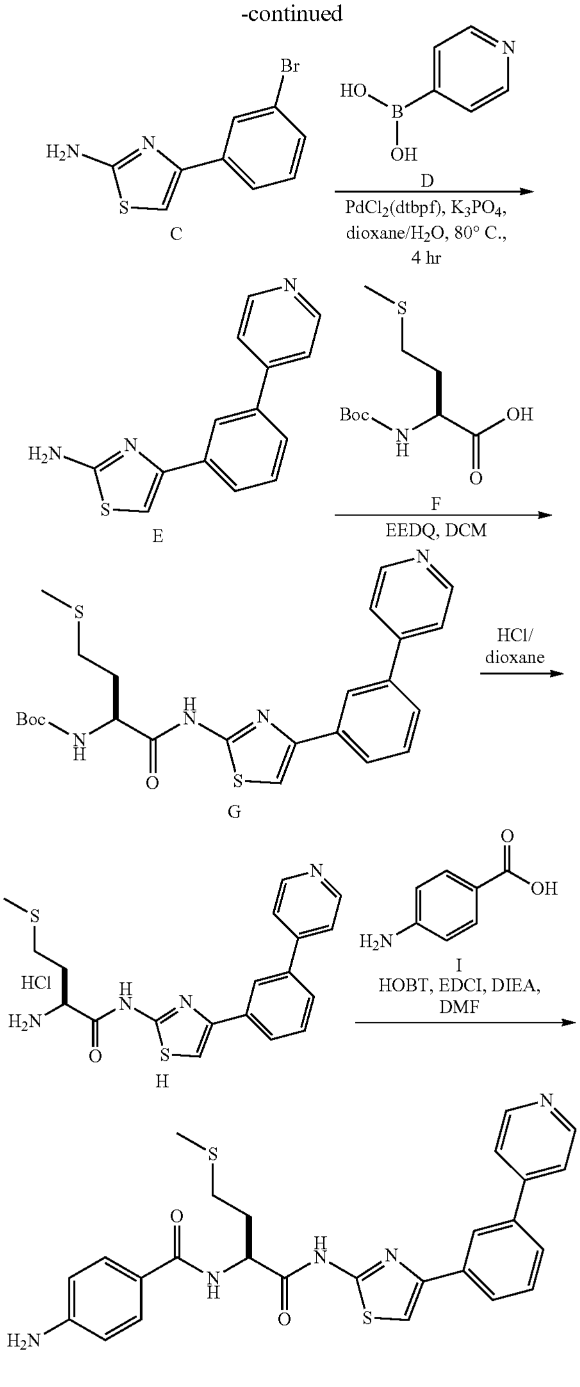

The ATPase catalytic activity of BRM or BRG-1 in the presence of compound A was measured by the in vitro biochemical assay using ADP-Glo™ (Promega, V9102). The ADP-Glo™ kinase assay is performed in two steps once the reaction is complete. The first step is to deplete any unconsumed ATP in the reaction. The second step is to convert the reaction product ADP to ATP, which will be utilized by the luciferase to generate luminesce and be detected by a luminescence reader, such as Envision.

The assay reaction mixture (10 μL) contains 30 nM of BRM or BRG1, 20 nM salmon sperm DNA (from Invitrogen, UltraPure™ Salmon Sperm DNA Solution, cat #15632011), and 400 μM of ATP in the ATPase assay buffer, which comprises of 20 mM Tris, pH 8, 20 mM $MgCl_2$, 50 mM NaCl, 0.1% Tween-20, and 1 mM fresh DTT (Pierce™ DTT (Dithiothreitol), cat #20290). The reaction is initiated by the addition of the 2.5 μL ATPase solution to 2.5 μL ATP/DNA solution on low volume white Proxiplate-384 plus plate (PerkinElmer, cat #6008280) and incubates at room temperature for 1 hour. Then following addition of 5 μL of ADP-Glo™ Reagent provided in the kit, the reaction incubates at room temperature for 40 minutes. Then 10 μL of Kinase Detection Reagent provided in the kit is added to convert ADP to ATP, and the reaction incubates at room temperature for 60 minutes. Finally, luminescence measurement is collected with a plate-reading luminometer, such as Envision.

BRM and BRG1 were synthesized from high five insect cell lines with a purity of greater than 90%. Compound A was found to have an $IP_{50}$ of 10.4 nM against BRM and 19.3 nM against BRG1 in the assay.

Example 243. Effects of BRG1/BRM ATPase Inhibition on the Growth of Uveal Melanoma and Hematological Cancer Cell Lines Procedure: Uveal melanoma cell lines (92-1, MP41, MP38, MP46), prostate cancer cell lines (LNCAP), lung cancer cell lines (NCI-H1299), and immortalized embryonic kidney lines (HEK293T) were plated into 96 well plates with growth media (see Table 47). BRG1/BRM ATPase inhibitor, Compound A, was dissolved in DMSO and added to the cells in a concentration gradient from 0 to 10 micromolar at the time of plating. Cells were incubated at 37 degrees Celsius for 3 days. After three days of treatment, the media was removed from the cells, and 30 microliters of TrypLE (Gibco) was added to cells for 10 minutes. Cells were detached from the plates, and resuspended with the addition of 170 microliters of growth media. Cells from two DMSO-treated control wells were counted, and the initial number of cells plated at the start of the experiment, were re-plated into fresh-compound containing plates for an additional four days at 37 degrees Celsius. At day 7, cells were harvested as described above. On day 3 and day 7, relative cell growth was measured by the addition of Cell-titer glo (Promega), and luminescence was measured on an Envision plate reader (Perkin Elmer). The concentration of compound at which each cell line's growth was inhibited by 50% ($GI_{50}$), was calculated using Graphpad Prism, and is plotted below. For multiple myeloma cell lines (OPM2, MM1S, LP1), ALL cell lines (TALL1, JURKAT, RS411), DLBCL cell lines (SUDHL6, SUDHL4, DB, WSUDLCL2, PFEIFFER), AML cell lines (OCIAML5), MDS cell lines (SKM1), ovarian cancer cell lines (OV7, TYKNU), esophageal cancer cell lines (KYSE150), rhabdoid tumor lines (RD, G402, G401, HS729, A204), liver cancer cell lines (HLF, HLE, PLCRPF5), and lung cancer cell lines (SW1573, NCIH2444), the above methods were performed with the following modifications: Cells were plated in 96 well plates, and the next day, BRG1/BRM ATPase inhibitor, Compound A, was dissolved in DMSO and added to the cells in a concentration gradient from 0 to 10 micromolar. At the time of cell splitting on days 3 and 7, cells were split into new 96 well plates, and fresh compound was added four hours after re-plating.

Table 47 lists the tested cell lines and growth media used.

TABLE 47

Cell Lines and Growth Media

| Cell Line | Source | Growth Media |
|---|---|---|
| 92-1 | SIGMA | RPMI1640 + 20% FBS |
| A204 | ATCC | McCoy's 5A + 10% FBS |
| DB | ATCC | RPMI1640 + 10% FBS |
| G401 | ATCC | McCoy's 5A + 10% FBS |
| G402 | ATCC | McCoy's 5A + 10% FBS |
| HEK293T | ATCC | DMEM + 10% FBS |
| HLE | JCRB | DMEM + 10% FBS |
| HLF | JCRB | DMEM + 10% FBS |
| HS729 | ATCC | DMEM + 10% FBS |
| JURKAT | ATCC | RPMI1640 + 10% FBS |
| KYSE150 | DSMZ | RPMI1640/Ham's F12 + 10% FBS |
| LNCAP | ATCC | RPMI1640 + 10% FBS |
| LP1 | DSMZ | IMDM + 20% FBS |
| MM1S | ATCC | RPMI1640 + 10% FBS |
| MP38 | ATCC | RPMI1640 + 20% FBS |
| MP41 | ATCC | RPMI1640 + 20% FBS |
| MP46 | ATCC | RPMI1640 + 20% FBS |
| NCIH1299 | ATCC | RPMI1640 + 10% FBS |
| NCIH2444 | ATCC | RPMI1640 + 20% FBS |
| OCIAML5 | DSMZ | alpha-MEM + 20% FBS + 10 ng/ml GM-CSF |
| OPM2 | DSMZ | RPMI1640 + 10% FBS |
| OV7 | ECACC | DMEM/Ham's F12 (1:1) + 2 mM Glutamine + 10% FBS + 0.5 ug/ml hydrocortisone + 10 ug/ml insulin |
| PFEIFFER | ATCC | RPMI1640 + 10% FBS |
| PLCPRF5 | ATCC | EMEM + 10% FBS |
| RD | ATCC | DMEM + 10% FBS |
| RS411 | ATCC | RPMI1640 + 10% FBS |
| SKM1 | JCRB | RPMI1640 + 10% FBS |
| SUDHL4 | DSMZ | RPMI1640 + 10% FBS |
| SUDHL6 | ATCC | RPMI1640 + 20% FBS |
| SW1573 | ATCC | DMEM + 10% FBS |
| TALL1 | JCRB | RPMI1640 + 10% FBS |
| TYKNU | JCRB | EMEM + 20% FBS |
| WSUDLCL2 | DSMZ | RPMI1640 + 10% FBS |

Results: As shown in FIG. 1, the uveal melanoma and hematologic cancer cell lines were more sensitive to BRG1/BRM inhibition than the other tested cell lines. Inhibition of the uveal melanoma and hematologic cancer cell lines was maintained through day 7.

Example 244. Comparison of BRG1/BRM Inhibitors to Clinical PKC and MEK Inhibitors in Uveal Melanoma Cell Lines Procedure: Uveal melanoma cell lines, 92-1 or MP41, were plated in 96 well plates in the presence of growth media (see Table 47). BAF ATPase inhibitors (Compound A), PKC inhibitor (LXS196; MedChemExpress), or MEK inhibitor (Selumetinib; Selleck Chemicals) were dissolved in DMSO and added to the cells in a concentration gradient from 0 to 10 micromolar at the time of plating. Cells were incubated at 37 degrees Celsius for 3 days. After three days of treatment, cell growth was measured with Cell-titer glow (Promega), and luminescence was read on an Envision plate reader (Perkin Elmer).

Figure 2A:
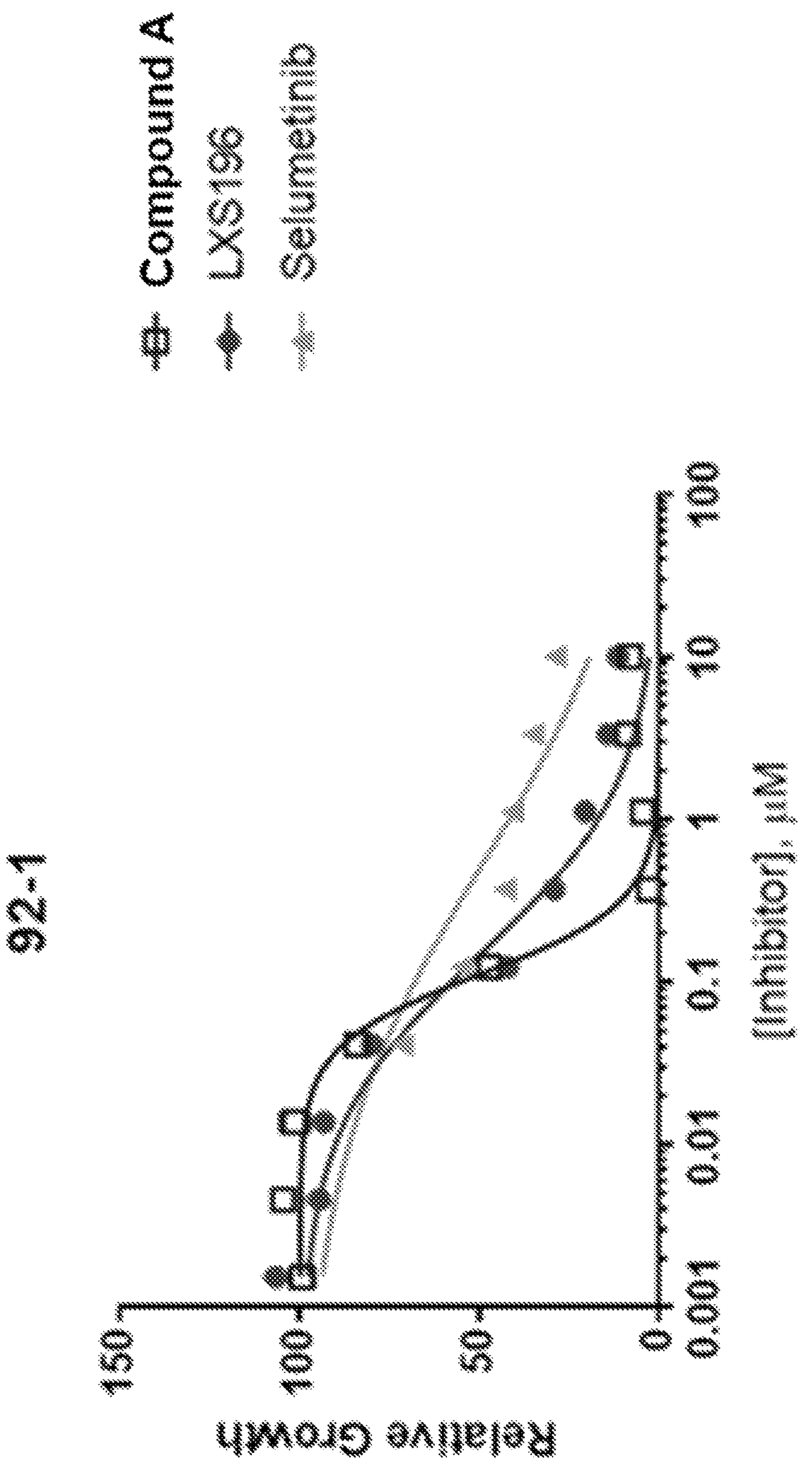
FIG. 2A is a graph illustrating inhibition of cell proliferation of uveal melanoma cell line 92-1 by a BRG1/BRM inhibitor (Compound A), a MEK inhibitor (Selumetinib), and a PKC inhibitor (LXS196).
Figure 2B:
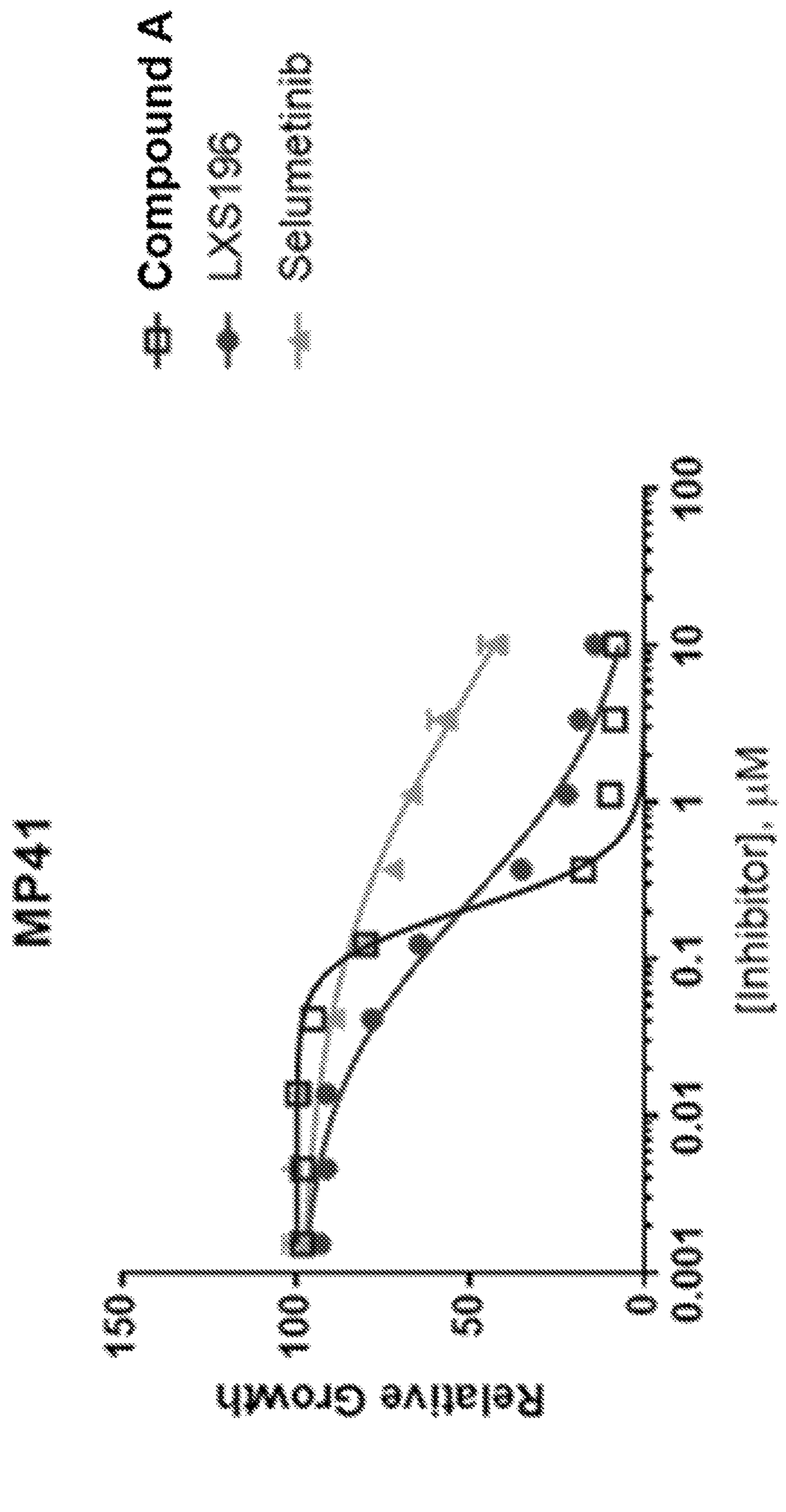
FIG. 2B is a graph illustrating inhibition of cell proliferation of uveal melanoma cell line MP41 by a BRG1/BRM inhibitor (Compound A), a MEK inhibitor (Selumetinib), and a PKC inhibitor (LXS196).

Results: As shown in FIG. 2A and FIG. 2B, Compound A showed comparable growth inhibition of uveal melanoma cells as the clinical PKC and MEK inhibitors. Further, compound A was found to result in a faster onset of inhibition than the clinical PKC and MEK inhibitors.

Example 245. Effects of BRG1/BRM ATPase Inhibition on the Growth of Uveal Melanoma, Hematological Cancer, Prostate Cancer, Breast Cancer, and Ewing's Sarcoma Cell Lines Procedure: All cell lines described above in Example 243 were also tested as described above with Compound 67. In addition, the following cell lines were also tested as follows. Briefly, for Ewing's sarcoma cell lines (CADOES1, RDES, SKES1), retinoblastoma cell lines (WERIRB1), ALL cell lines (REH), AML cell lines (KASUMI1), prostate cancer cell lines (PC3, DU145, 22RV1), melanoma cell lines (SH4, SKMEL28, WM115, COLO829, SKMEL3, A375), breast cancer cell lines (MDAMB415, CAMA1, MCF7, BT474, HCC1419, DU4475, BT549), B-ALL cell lines (SUPB15), CML cell lines (K562, MEG01), Burkitt's lymphoma cell lines (RAMOS2G64C10, DAUDI), mantle cell lymphoma cell lines (JEKO1, REC1), bladder cancer cell lines (HT1197), and lung cancer cell lines (SBC5), the above methods were performed with the following modifications: Cells were plated in 96 well plates, and the next day, BRG1/BRM ATPase inhibitor, Compound 67, was dissolved in DMSO and added to the cells in a concentration gradient from 0 to 10 micromolar. At the time of cell splitting on days 3 and 7, cells were split into new 96 well plates, and fresh compound was added four hours after re-plating.

Table 48 lists the tested cell lines and growth media used.

TABLE 48

Cell Lines And Growth Media

| Cell Line | Source | Growth Media |
|---|---|---|
| 22RV1 | ATCC | RPMI1640 + 10% FBS |
| A375 | ATCC | DMEM + 10% FBS |
| BT474 | ATCC | Hybricare medium + 1.5 g/L sodium bicarbonate + 10% FBS |
| BT549 | ATCC | RPMI1640 + 0.023 IU/ml insulin + 10% FBS |
| CADOES1 | DSMZ | RPMI1640 + 10% FBS |
| CAMA1 | ATCC | EMEM + 10% FBS |
| COLO829 | ATCC | RPMI1640 + 10% FBS |
| DAUDI | ATCC | RPMI1640 + 10% FBS |
| DU145 | ATCC | EMEM + 10% FBS |
| DU4475 | ATCC | RPMI1640 + 10% FBS |
| HCC1419 | ATCC | RPMI1640 + 10% FBS |
| HT1197 | ATCC | EMEM + 10% FBS |
| JEKO1 | ATCC | RPMI1640 + 20% FBS |
| K562 | ATCC | IMDM + 10% FBS |
| KASUMI1 | ATCC | RPMI1640 + 10% FBS |
| MCF7 | ATCC | EMEM + 0.01 mg/ml bovine insulin + 10% FBS |
| MDAMB415 | ATCC | Leibovitz's L-15 + 2 mM L-glutamine + 10 mcg/ml insulin + 10 mcg/ml glutathione + 15% FBS |
| MEG01 | ATCC | RPMI1640 + 10% FBS |
| PC3 | ATCC | F-12K + 10% FBS |
| RAMOS2G64C10 | ATCC | RPMI1640 + 10% FBS |
| RDES | ATCC | RPMI1640 + 15% FBS |
| REC1 | ATCC | RPMI1640 + 10% FBS |
| REH | ATCC | RPMI1640 + 10% FBS |
| SBC5 | JCRB | EMEM + 10% FBS |
| SH4 | ATCC | DMEM + 10% FBS |
| SKES1 | ATCC | McCoy's 5A + 15% FBS |
| SKMEL28 | ATCC | EMEM + 10% FBS |
| SKMEL3 | ATCC | McCoy's 5A + 15% FBS |
| SUPB15 | ATCC | IMDM + 4 mM L-glutamine + 1.5 g/L sodium bicarbonate + 0.05 mM 2-mercaptoethanol + 20% FBS |
| WERIRB1 | ATCC | RPMI1640 + 10% FBS |
| WM115 | ATCC | EMEM + 10% FBS |

Figure 3:
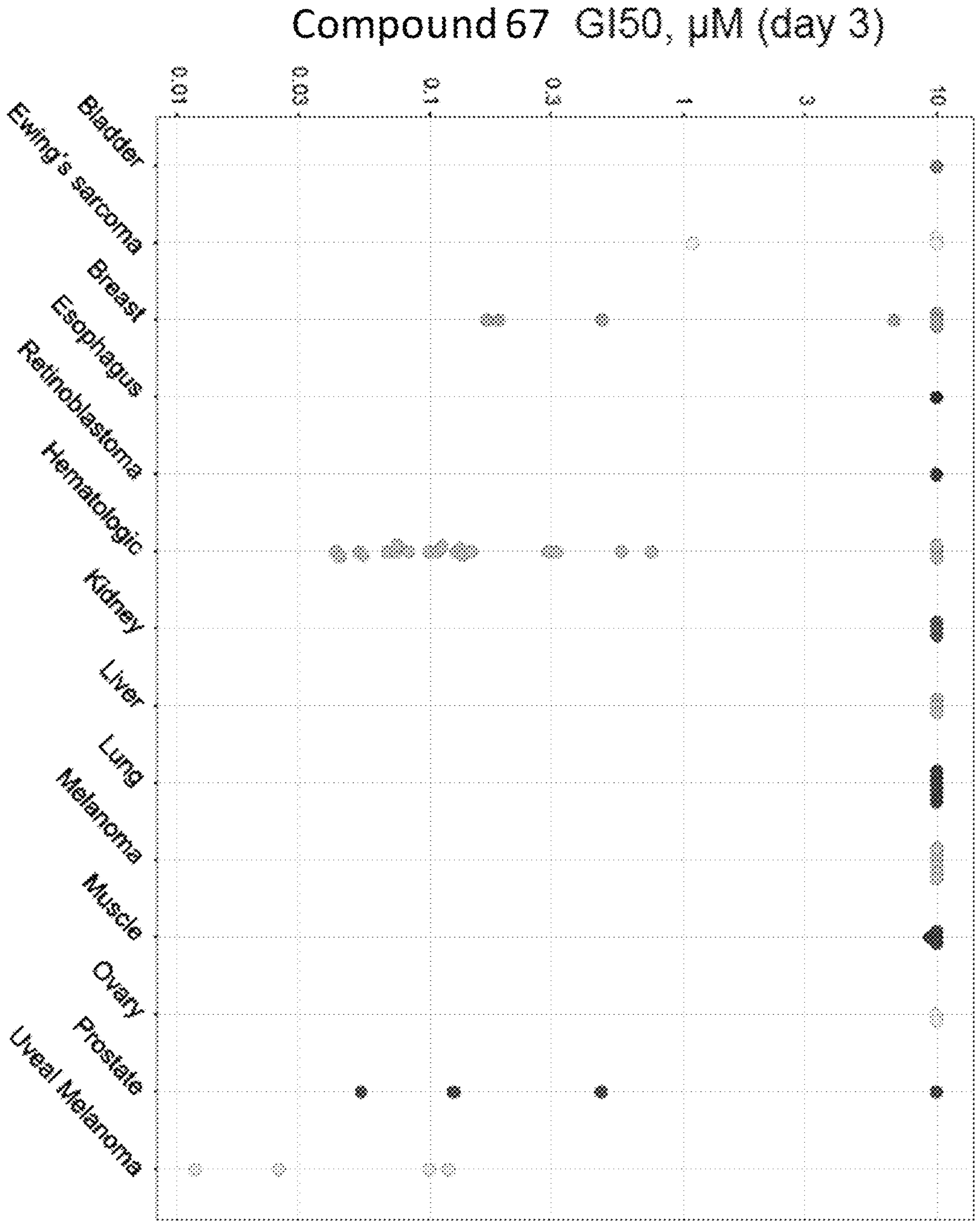
FIG. 3 is a graph illustrating inhibition of cell proliferation of several cancer cell lines by a BRG1/BRM inhibitor (Compound 67).

Results: As shown in FIG. 3, the uveal melanoma, hematologic cancer, prostate cancer, breast cancer, and Ewing's sarcoma cell lines were more sensitive to BRG1/BRM inhibition than the other tested cell lines. Inhibition of the uveal melanoma, hematologic cancer, prostate cancer, breast cancer, and Ewing's sarcoma cell lines was maintained through day 7.

Example 246. Effects of BRG1/BRM ATPase Inhibition on the Growth of Cancer Cell Lines Procedure: A pooled cell viability assay was performed using PRISM (Profiling Relative Inhibition Simultaneously in Mixtures) as previously described ("High-throughput identification of genotype-specific cancer vulnerabilities in mixtures of barcoded tumor cell lines", Yu et al, Nature Biotechnology 34, 419-423, 2016), with the following modifications. Cell lines were obtained from the Cancer Cell Line Encyclopedia (CCLE) collection and adapted to RPMI-1640 medium without phenol red, supplemented with 10% heat-inactivated fetal bovine serum (FBS), in order to apply a unique infection and pooling protocol to such a big compendium of cell lines. A lentiviral spin-infection protocol was executed to introduce a 24 nucleotide-barcode in each cell line, with an estimated multiplicity of infection (MOI) of 1 for all cell lines, using blasticidin as selection marker. Over 750 PRISM cancer cell lines stably barcoded were then pooled together according to doubling time in pools of 25. For the screen execution, instead of plating a pool of 25 cell lines in each well as previously described (Yu et al.), all the adherent or all the suspension cell line pools were plated together using T25 flasks (100,000 cells/flask) or 6-well plates (50,000 cells/well), respectively. Cells were treated with either DMSO or compound in a 8-point 3-fold dose response in triplicate, starting from a top concentration of 10 μM. As control for assay robustness, cells were treated in parallel with two previously validated compounds, the pan-Raf inhibitor AZ-628, and the proteasome inhibitor bortezomib, using a top concentration of 2.5 μM and 0.039 μM, respectively.

Figure 4:
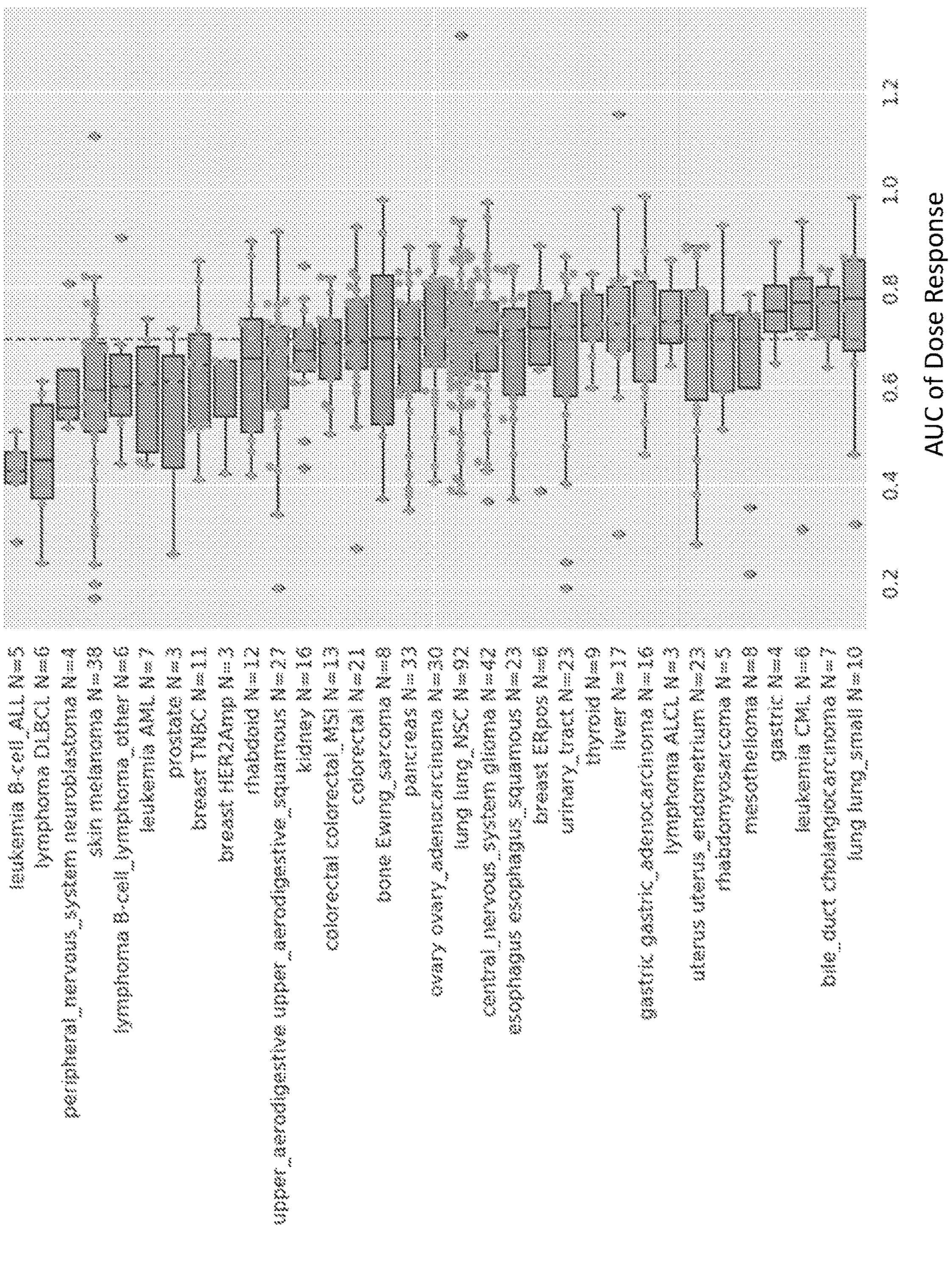
FIG. 4 is a graph illustrating the area under the curves (AUCs) calculated from dose-response curves for cancer cell lines treated with a BRG1/BRM inhibitor (Compound 67).

Following 3 days of treatment with compounds, cells were lysed, genomic DNA was extracted, barcodes were amplified by PCR and detected with Next-Generation Sequencing. Cell viability was determined by comparing the counts of cell-line specific barcodes in treated samples to those in the DMSO-control and Day 0 control. Dose-response curves were fit for each cell line and corresponding area under the curves (AUCs) were calculated and compared to the median AUC of all cell lines (FIG. 4). Cell lines with AUCs less than the median were considered most sensitive.

Example 247. Effects of BRG1/BRM ATPase Inhibitors on the Growth of Uveal Melanoma Cell Lines Procedure: Uveal melanoma cell lines (92-1, MP41, MP38, MP46) and Non-small cell lung cancer cells (NCIH1299) were plated into 96 well plates with growth media (see Table 47). BRG1/BRM ATPase inhibitor, compound 67, was dissolved in DMSO and added to the cells in a concentration gradient from 0 to 10 micromolar at the time of plating. Cells were incubated at 37° C. for 3 days. After three days of treatment, cell growth was measured with Cell-titer glow (Promega), and luminescence was read on an Envision plate reader (Perkin Elmer).

Figure 5:
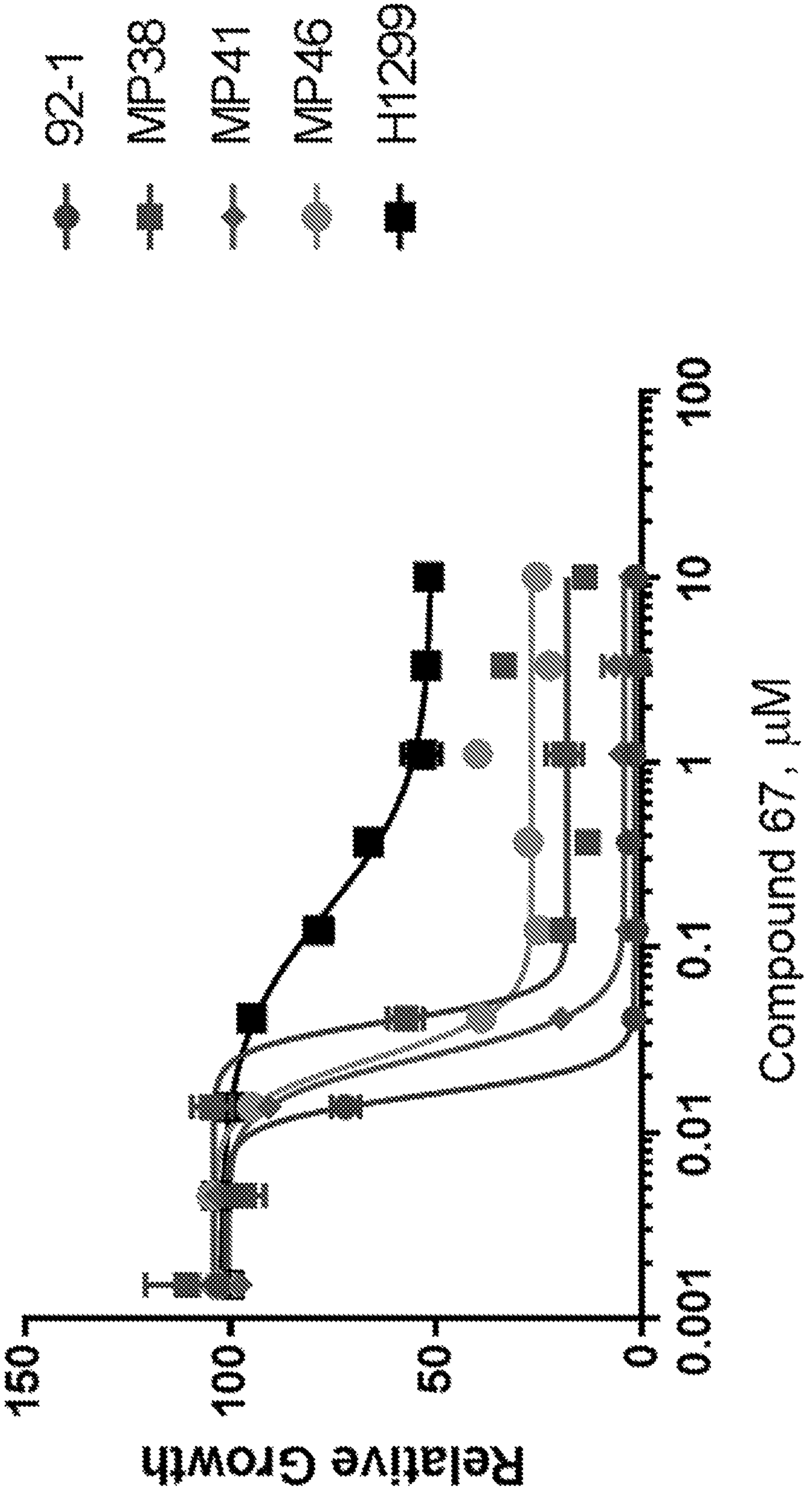
FIG. 5 is a graph illustrating inhibition of cell proliferation of uveal melanoma and non-small cell lung cancer cell lines by a BRG1/BRM inhibitor (compound 67).

Results: As shown in FIG. 5, compound 67 resulted in potent growth inhibition in the uveal melanoma cell lines.

Example 248. Comparison of BRG1/BRM Inhibitors to Clinical PKC and MEK Inhibitors in Uveal Melanoma Cell Lines Procedure: Uveal melanoma cell lines, 92-1 or MP41, were plated in 96 well plates in the presence of growth media (see Table 47). BAF ATPase inhibitor (compound 67), PKC inhibitor (LXS196; MedChemExpress), and MEK inhibitor (Selumetinib; Selleck Chemicals) were dissolved in DMSO and added to the cells in a concentration gradient from 0 to 10 micromolar at the time of plating. Cells were incubated at 37° C. for 3 days. After three days of treatment, cell growth was measured with Cell-titer glow (Promega), and luminescence was read on an Envision plate reader (Perkin Elmer).

Figure 6A:
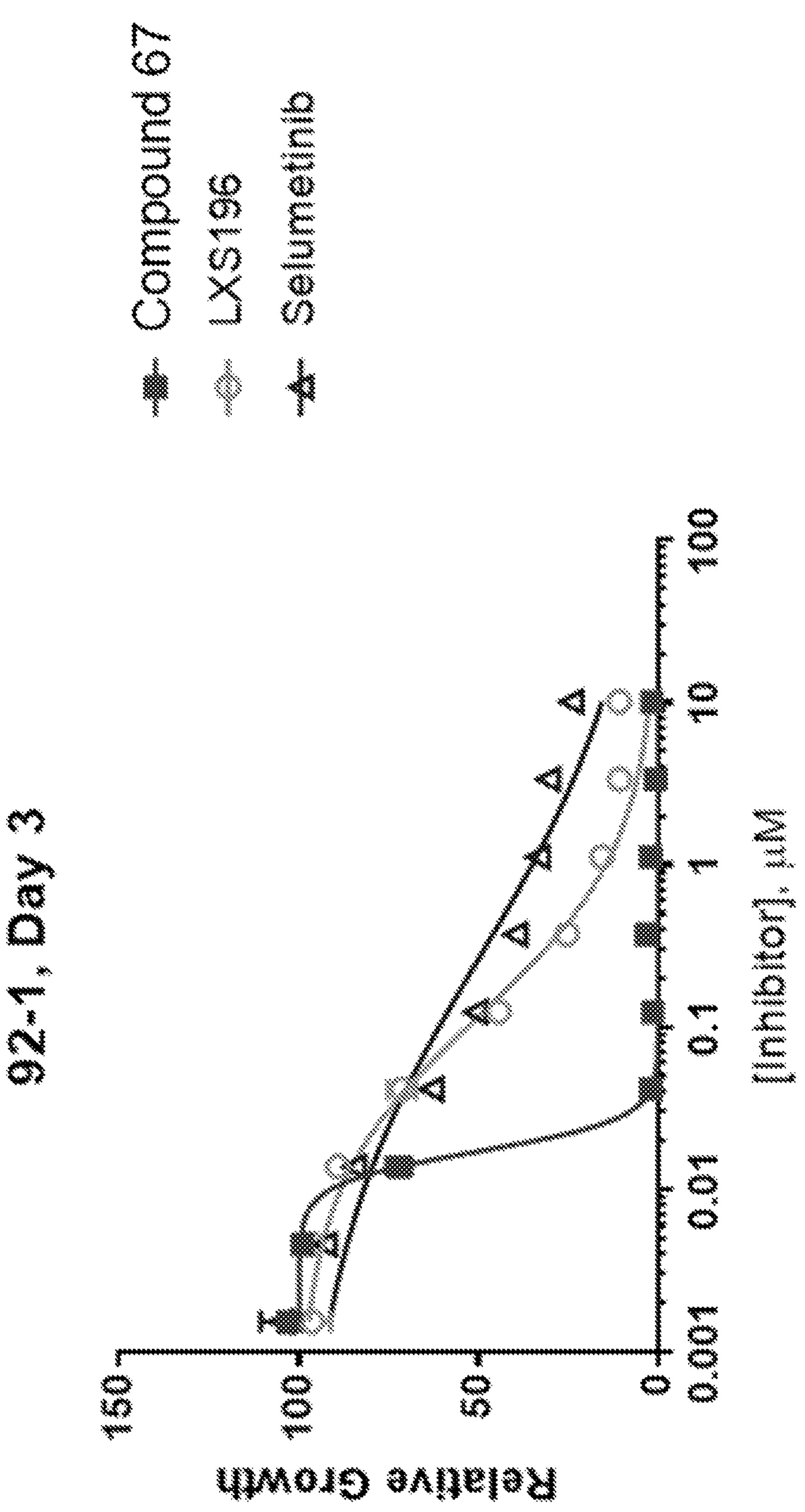
FIG. 6A is a graph illustrating inhibition of cell proliferation of uveal melanoma cell line 92-1 by a BRG1/BRM inhibitor (compound 67), a MEK inhibitor (Selumetinib), and a PKC inhibitor (LXS196).
Figure 6B:
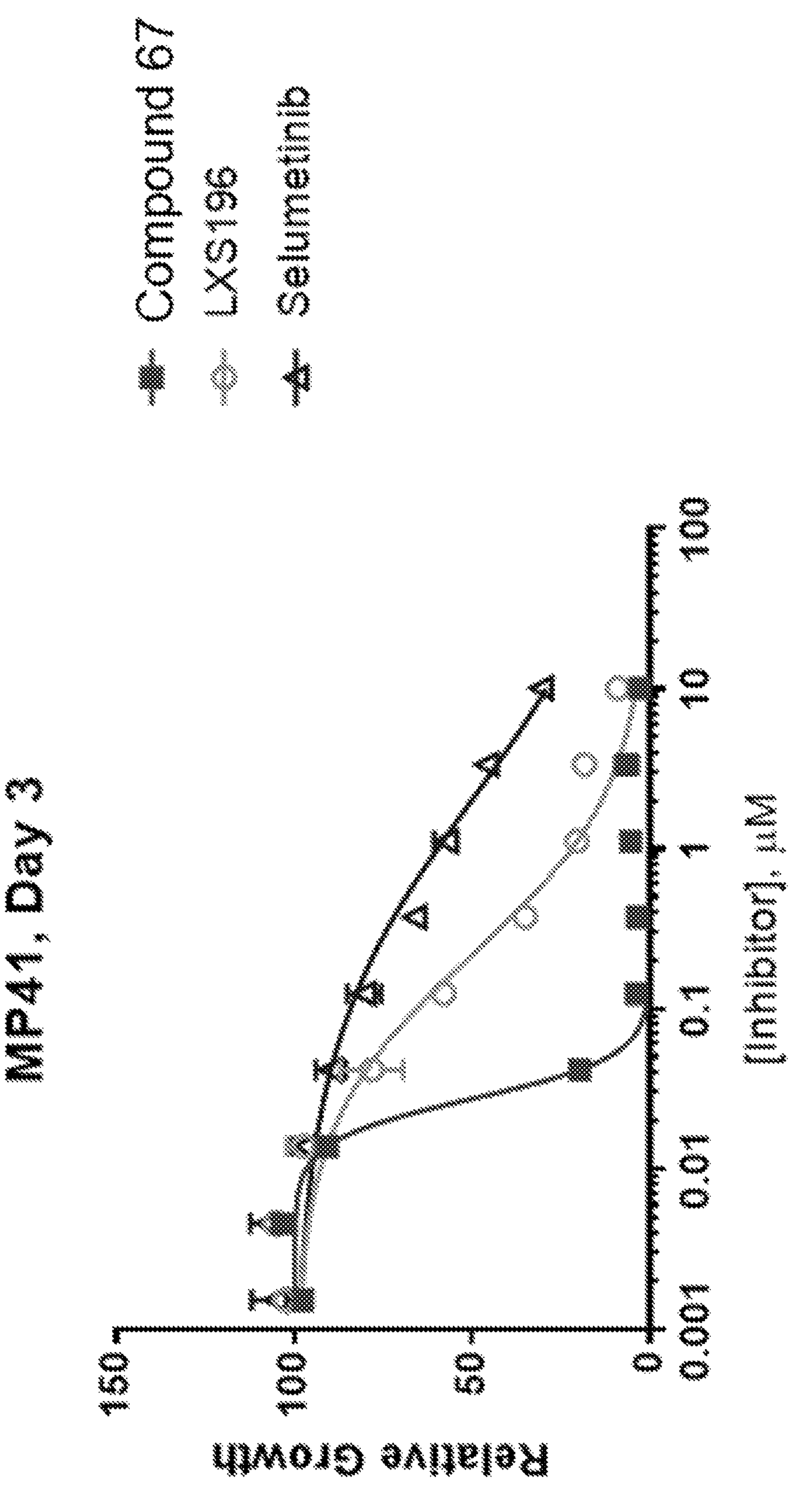
FIG. 6B is a graph illustrating inhibition of cell proliferation of uveal melanoma cell line MP41 by a BRG1/BRM inhibitor (compound 67), a MEK inhibitor (Selumetinib), and a PKC inhibitor (LXS196).

Results: As shown in FIG. 6A and FIG. 6B, compound 67 showed more potent effects on growth inhibition of uveal melanoma cells as compared to the clinical PKC and MEK inhibitors. Further, compound 67 was found to result in a faster onset of growth inhibition than the clinical PKC and MEK inhibitors.

Example 249. BRG1/BRM ATPase Inhibitors are Effective at Inhibiting the Growth of PKC Inhibitor-Resistant Cells Procedure: MP41 uveal melanoma cells were made resistant to the PKC inhibitor (LXS196; MedChemExpress), by long-term culture in growth media (see Table 47) containing increasing concentrations of the compound, up to 1 micromolar. After 3 months, sensitivity of the parental MP41 cells and the PKC inhibitor (PKCi)-resistant cells to the PKC inhibitor (LXS196) or the BRG1/BRM ATPase inhibitor (compound 67) was tested in a 7-day growth inhibition assay as described above in Example 2.

Figure 7A:
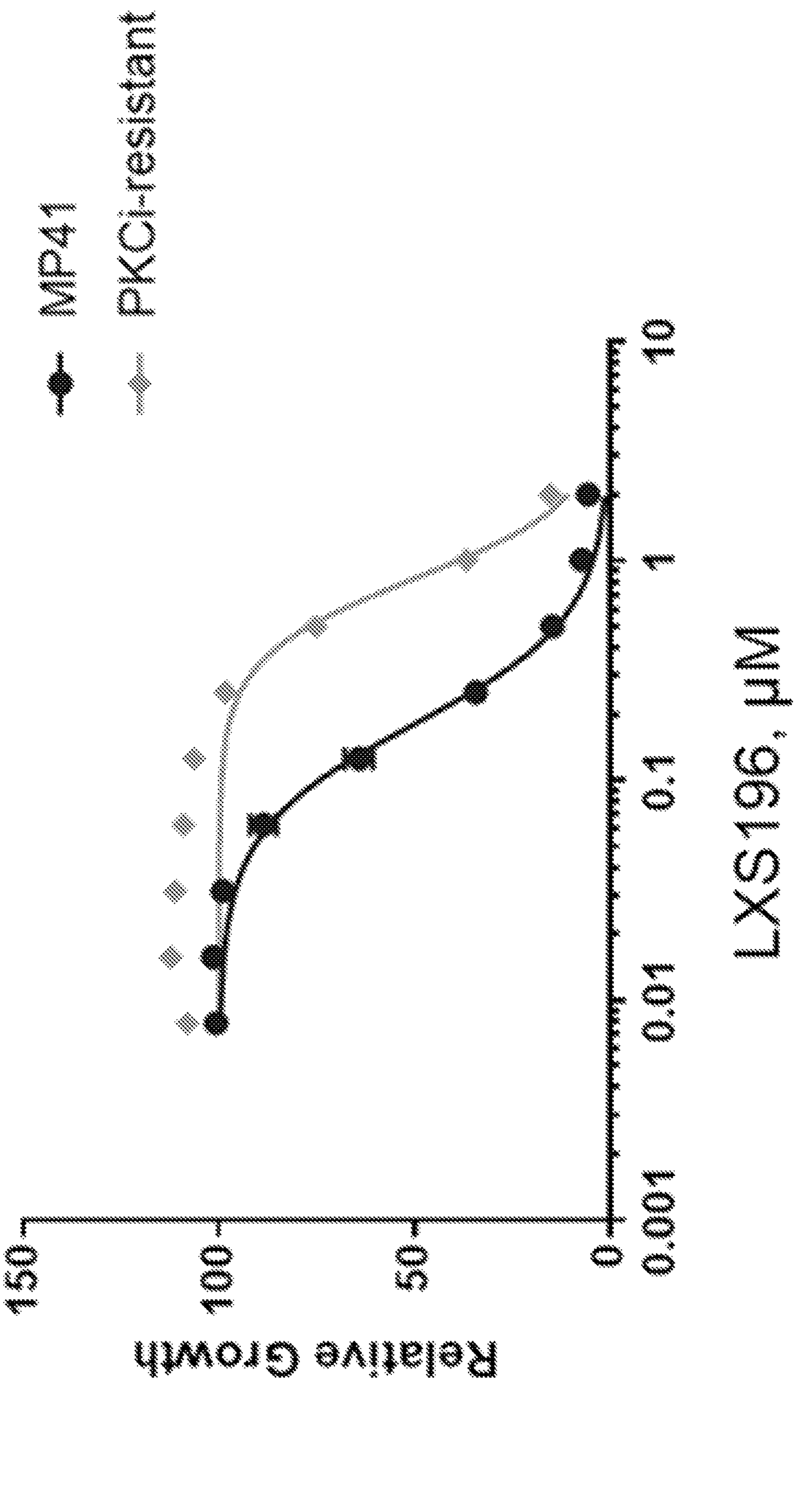
FIG. 7A is a graph illustrating inhibition of cell proliferation of parental and PKC-inhibitor refractory uveal melanoma cell lines by a PKC inhibitor (LXS196).
Figure 7B:
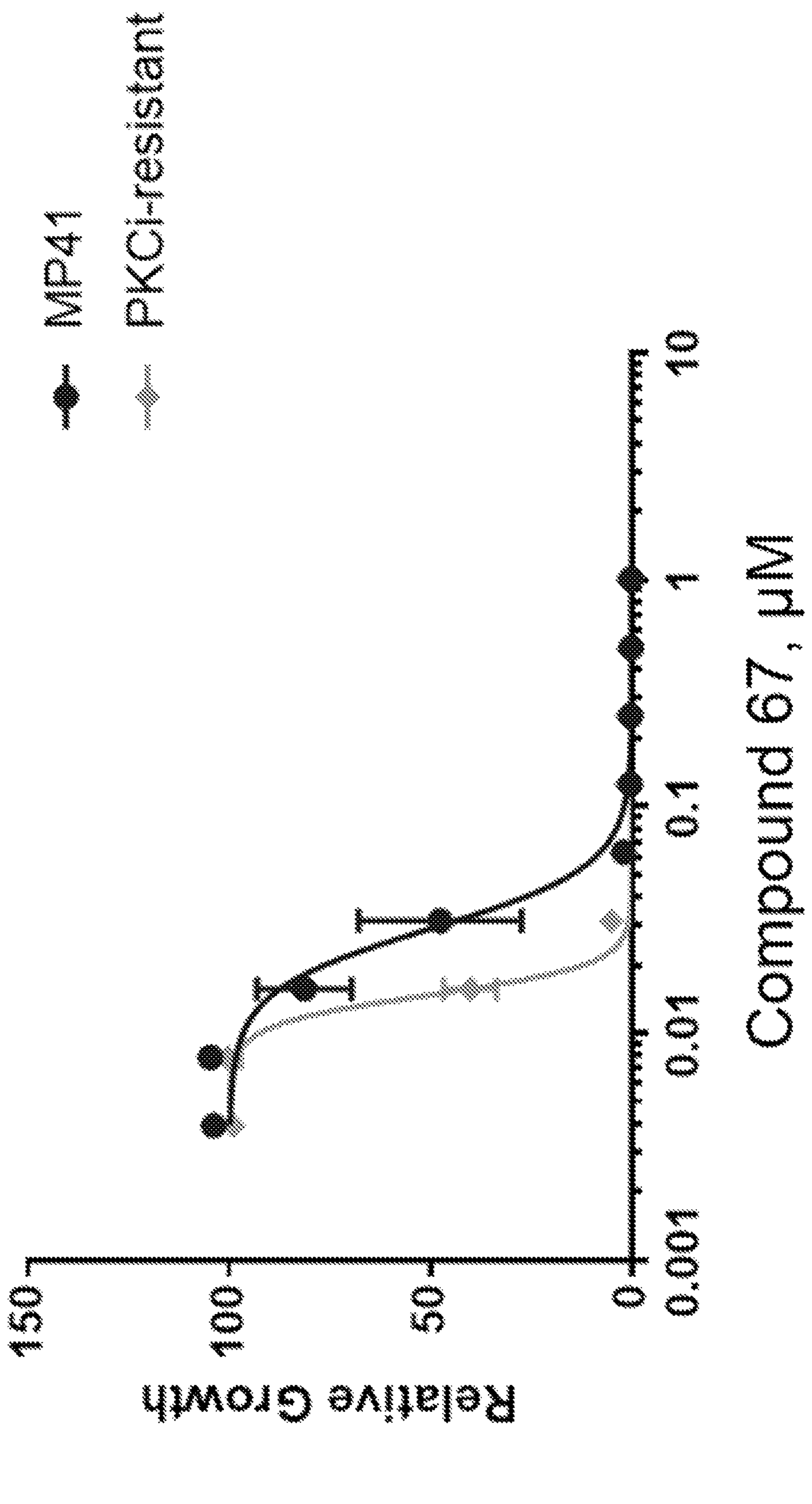
FIG. 7B is a graph illustrating inhibition of cell proliferation of parental and PKC-inhibitor refractory uveal melanoma cell lines by a BRG1/BRM inhibitor (compound 67).

Results: While the PKCi-resistant cells could tolerate growth at higher concentrations of LXS196 than could the parental MP41 cell line (FIG. 7A), the BRG1/BRM ATPase inhibitor (compound 67) still resulted in strong growth inhibition of both the PKCi-resistant and parental cell lines (FIG. 7B). The PKCi-resistant cells were more sensitive to compound 67 than were the parental MP41 cells (FIG. 7B).

Example 250. BRG1/BRM ATPase Inhibitors Cause Uveal Melanoma Tumor Growth Inhibition In Vivo Procedure: Nude mice (Envigo) were engrafted subcutaneously in the axillary region with $5\times10^6$ 92-1 uveal melanoma cells in 50% Matrigel. Tumors were grown to a mean of ~200 $mm^3$, at which point mice were grouped and dosing was initiated. Mice were dosed once daily by oral gavage with vehicle (20% 2-Hydroxypropyl-β-Cyclodextrin) or increasing doses of compound 320. Tumor volumes and body weights were measured over the course of 3 weeks, and doses were adjusted by body weight to achieve the proper dose in terms of mg/kg. At this time, animals were sacrificed, and tumors were dissected and imaged.

Figure 8A:
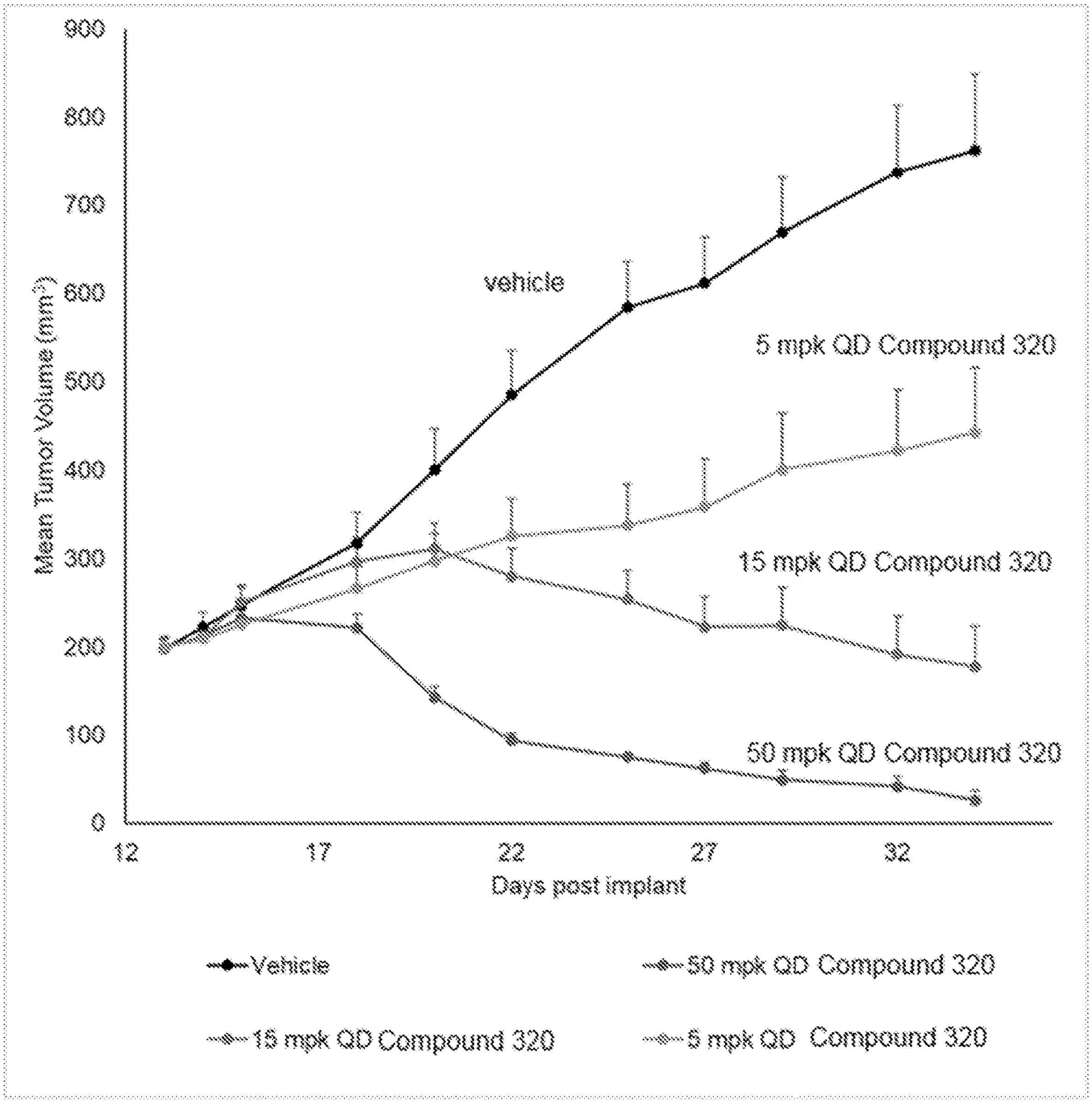
FIG. 8A is a graph illustrating inhibition of tumor growth in mice engrafted with uveal melanoma cell lines by a BRG1/BRM inhibitor (compound 320).
Figure 8B:
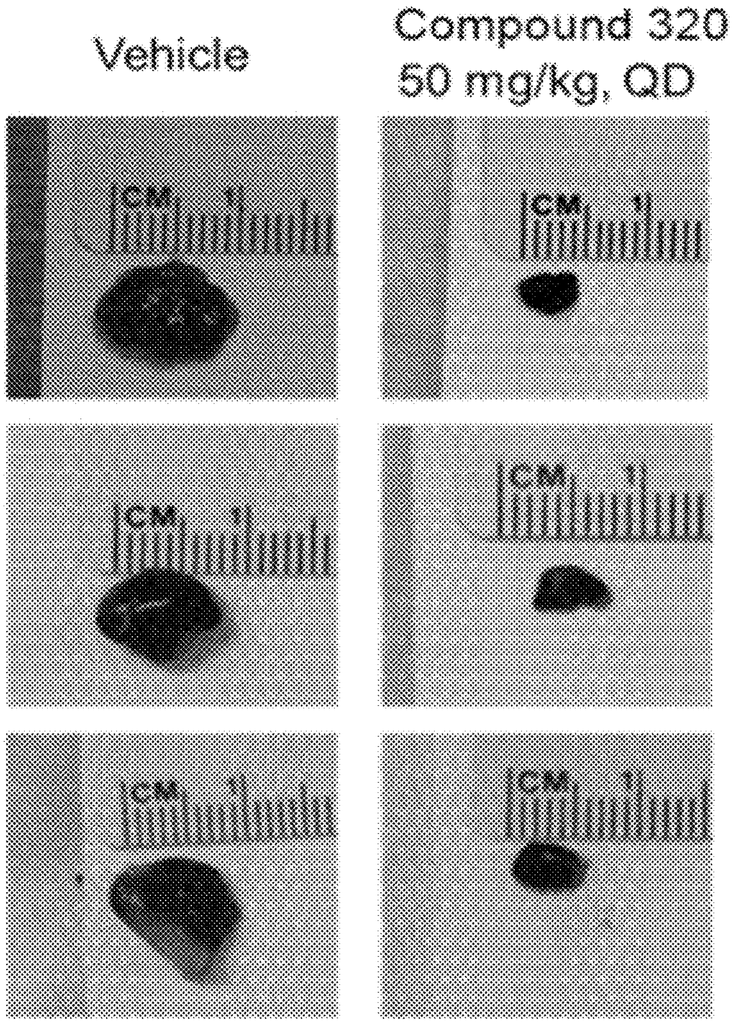
FIG. 8B is an illustration of the size of tumors from mice engrafted with uveal melanoma cell lines and dosed with a BRG1/BRM inhibitor (compound 320).
Figure 8C:
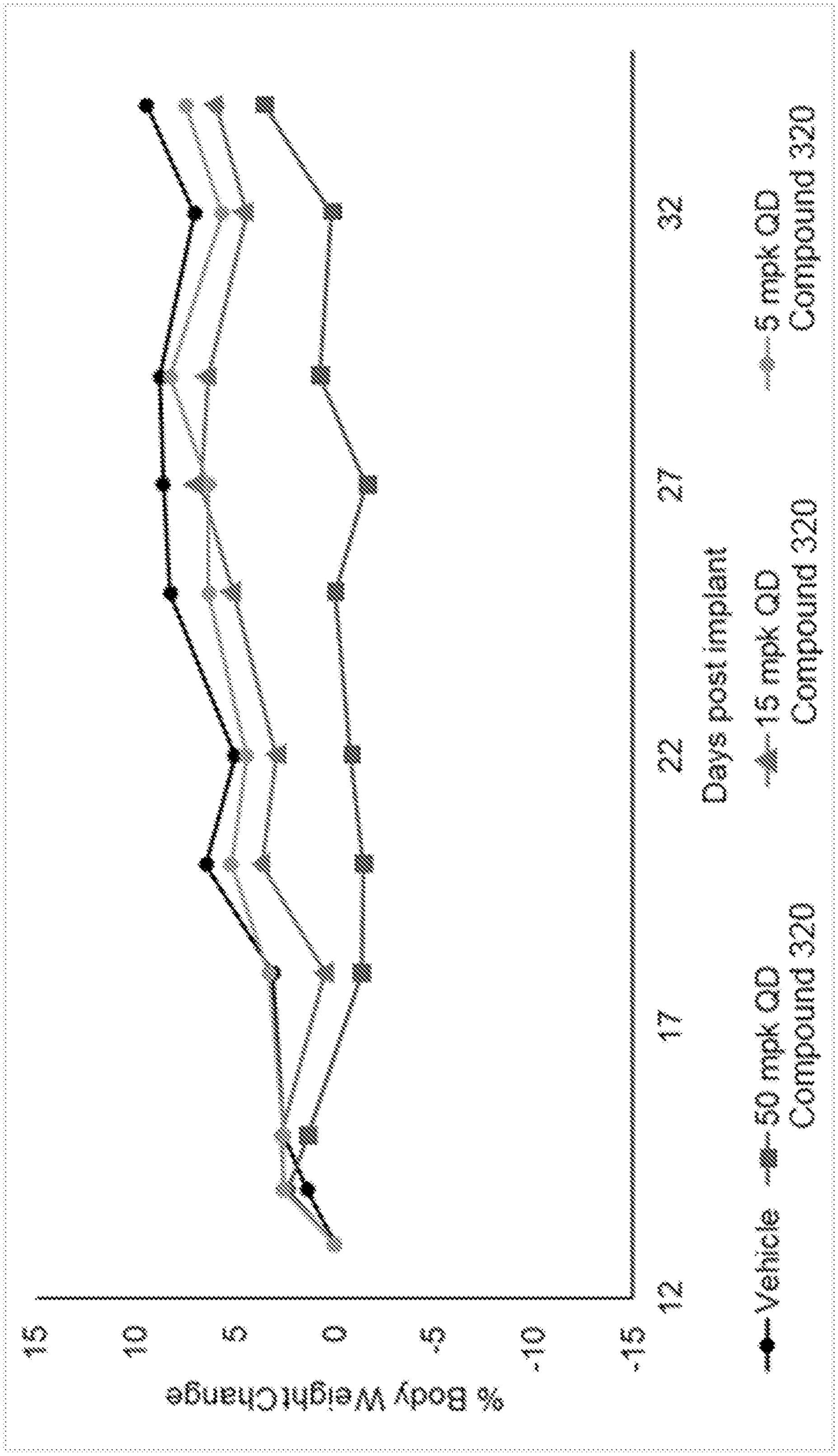
FIG. 8C is a graph illustrating body weight change of mice engrafted with uveal melanoma cell lines and dosed with a BRG1/BRM inhibitor (compound 320).

Results: Treatment with compound 320 led to tumor growth inhibition in a dose-dependent manner with tumor regression observed at the highest (50 mg/kg) dose. (FIG. 8A and FIG. 8B). All treatments were well tolerated with no body weight loss observed (FIG. 8C).

OTHER EMBODIMENTS

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

The invention claimed is:

1. A compound having the structure:

Formula Ia

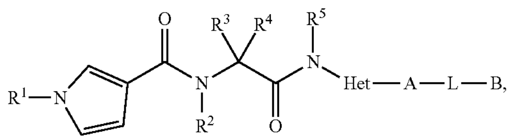

wherein $R^1$ is H, optionally substituted $C_1$-$C_6$ acyl, optionally substituted $C_1$-$C_6$ alkyl, optionally substituted $C_3$-$C_8$ cycloalkyl, optionally substituted $C_1$-$C_6$ heteroalkyl, optionally substituted $C_2$-$C_9$ heterocyclyl, or —$SO_2R^6$;

each of $R^2$ and $R^5$ is, independently, H or optionally substituted $C_1$-$C_6$ alkyl;

$R^3$ is H and $R^4$ is H $R^6$ is optionally substituted $C_1$-$C_6$ alkyl or —$NR^7R^8$;

$R^7$ and $R^8$ are, independently, optionally substituted $C_1$-$C_6$ alkyl;

Het is optionally substituted 5-membered heteroarylene, optionally substituted 6-membered heteroarylene, or

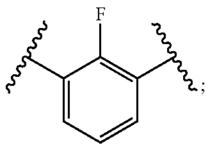 [SMILES: *c1cccc(*)c1F]

A is optionally substituted $C_6$-$C_{10}$ arylene, optionally substituted $C_2$-$C_9$ heterocyclylene, or optionally substituted $C_2$-$C_9$ heteroarylene;

L is absent, —O—, optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted $C_2$-$C_9$ heterocyclylene, optionally substituted $C_2$-$C_9$ heteroarylene, or optionally substituted $C_2$-$C_9$ heteroaryl $C_1$-$C_6$ alkylene; and B is H, halogen, cyano, optionally substituted $C_6$-$C_{10}$ aryl, optionally substituted $C_3$-$C_{10}$ cycloalkyl, optionally substituted $C_2$-$C_9$ heterocyclyl, or optionally substituted $C_2$-$C_9$ heteroaryl;

or a pharmaceutically acceptable salt thereof.

2. The compound of claim 1, wherein $R^2$ is H.

3. The compound of claim 1, wherein $R^5$ is H.

4. The compound of claim 1, wherein Het is

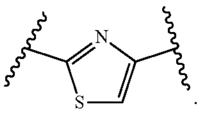 [SMILES: *c1csc(*)n1]

5. The compound of claim 1, wherein L is absent.

6. The compound of claim 1, wherein A is optionally substituted $C_2$-$C_9$ heteroarylene.

7. The compound of claim 6, wherein A is

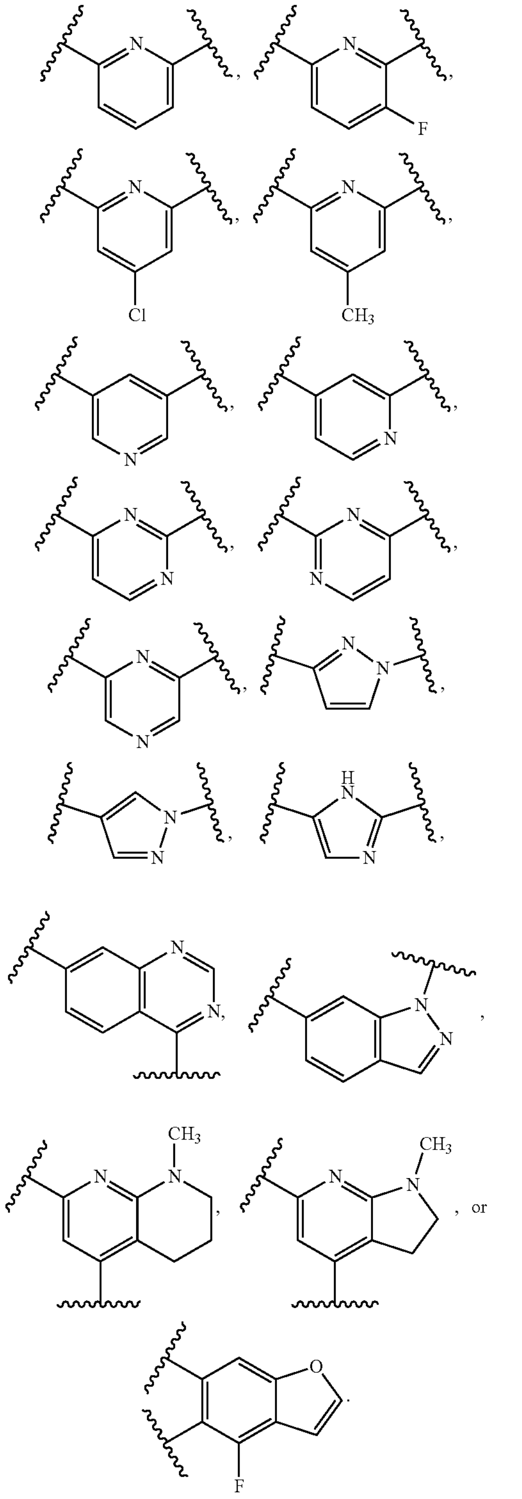

8. The compound of claim 1, wherein B is optionally substituted $C_2$-$C_9$ heterocyclyl.

9. The compound of claim 8, wherein B is

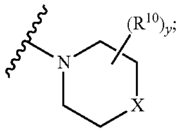

X' is O or $C(R^{10})_2$; y is 0, 1, 2, 3, 4, 5, 6, 7, or 8; and each $R^{10}$ is, independently, H, halogen, cyano, amino, hydroxyl, allyl, heteroallyl, optionally substituted $C_{1-6}$ alkyl, or optionally substituted $C_{1-6}$ heteroalkyl.

10. The compound of claim 9, wherein B is

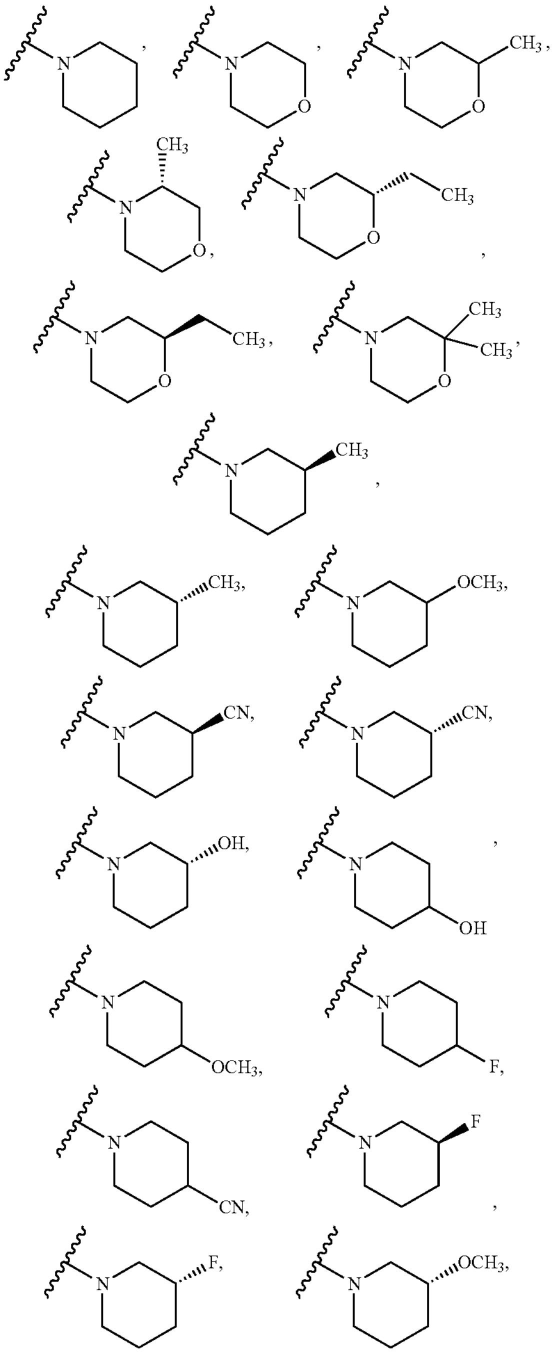

-continued
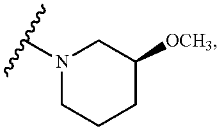 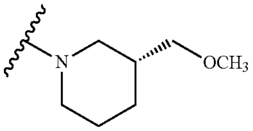,
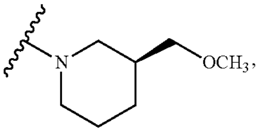 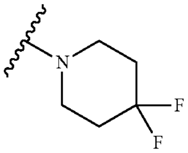,
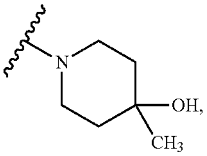 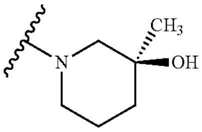,
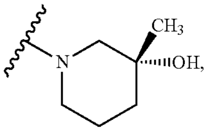 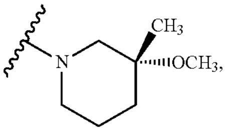
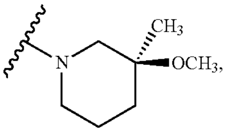 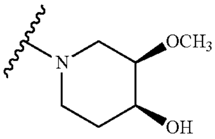,
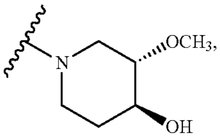 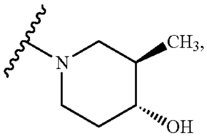
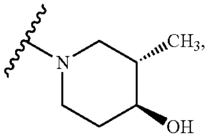 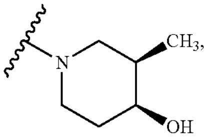
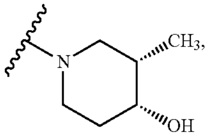 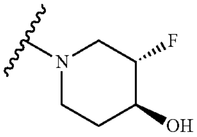,
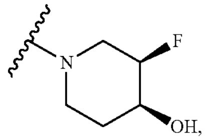 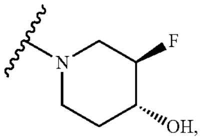
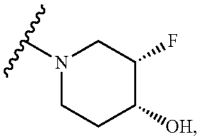 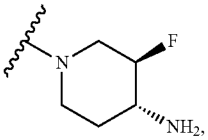
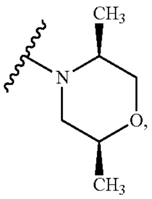 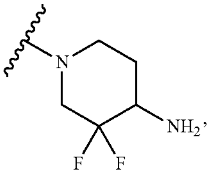
-continued
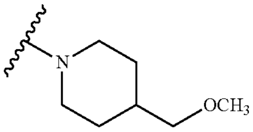,
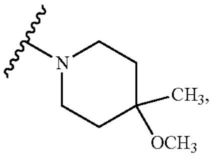 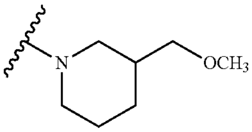,
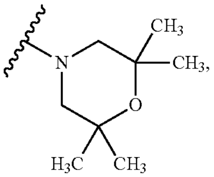 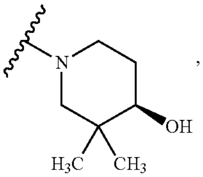,
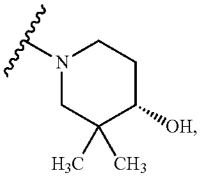 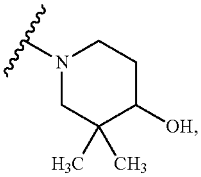
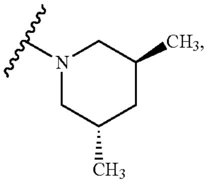 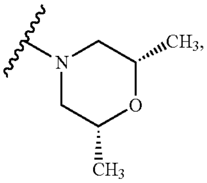 or
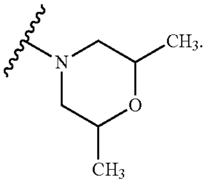
11. The compound of claim 1, wherein $R^1$ is —$SO_2R^6$.
12. The compound of claim 11, wherein $R^6$ is optionally substituted $C_1$-$C_6$ alkyl.
13. The compound of claim 12, wherein $R^6$ is methyl, iso-propyl, or
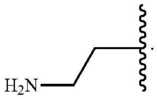

14. The compound of claim 1, wherein the compound has the structure of any one of compounds:
| # | Compound |
|---|---|
| 1 | 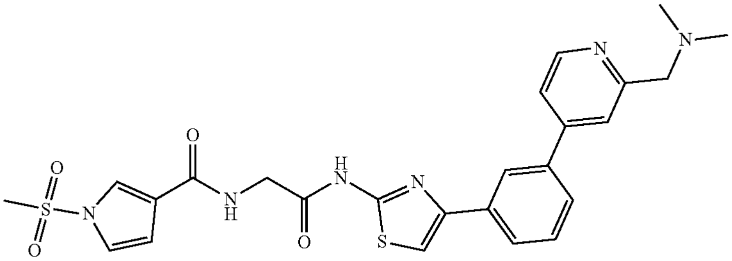 |
| 2 | 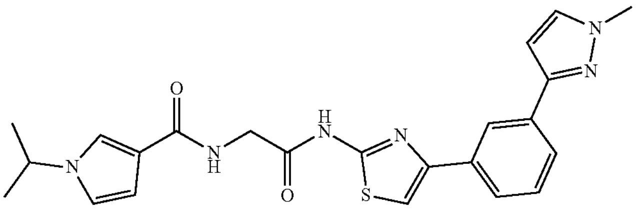 [SMILES: CC(C)n1ccc(C(=O)NCC(=O)Nc2nc(-c3cccc(-c4ccn(C)n4)c3)cs2)c1] |
| 4 | 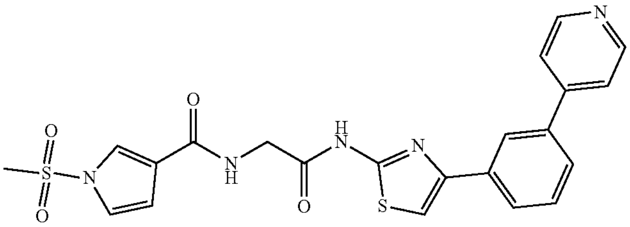 [SMILES: CS(=O)(=O)n1ccc(C(=O)NCC(=O)Nc2nc(-c3cccc(-c4ccncc4)c3)cs2)c1] |
| 6 | 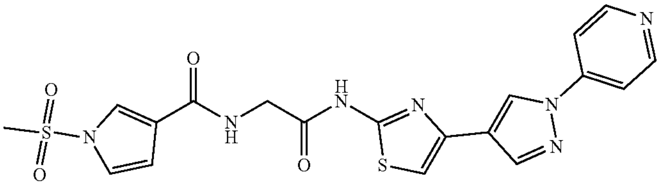 [SMILES: CS(=O)(=O)n1ccc(C(=O)NCC(=O)Nc2nc(-c3cnn(-c4ccncc4)c3)cs2)c1] |
| 7 | 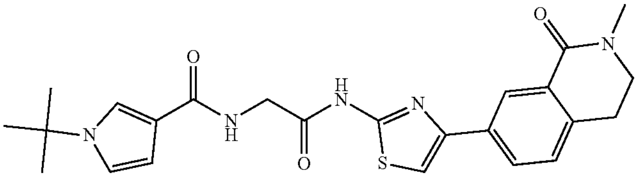 [SMILES: CN1CCc2ccc(-c3csc(NC(=O)CNC(=O)c4ccn(C(C)(C)C)c4)n3)cc2C1=O] |
| 8 | 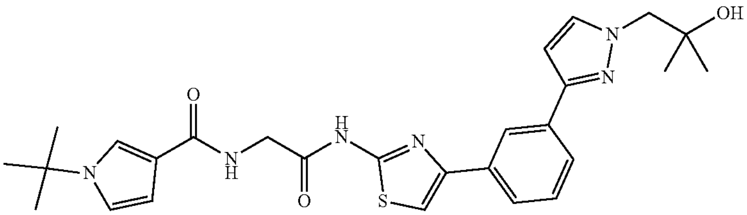 [SMILES: CC(C)(O)Cn1ccc(-c2cccc(-c3csc(NC(=O)CNC(=O)c4ccn(C(C)(C)C)c4)n3)c2)n1] |
| 9 | 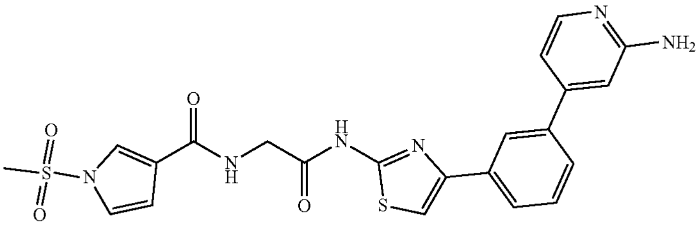 [SMILES: CS(=O)(=O)n1ccc(C(=O)NCC(=O)Nc2nc(-c3cccc(-c4ccnc(N)c4)c3)cs2)c1] |

-continued
| # | Compound |
|---|---|
| 10 | 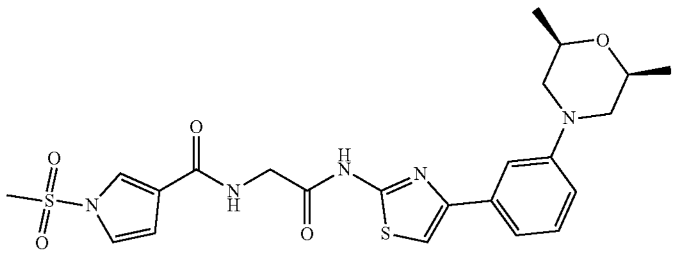 |
| 11 | 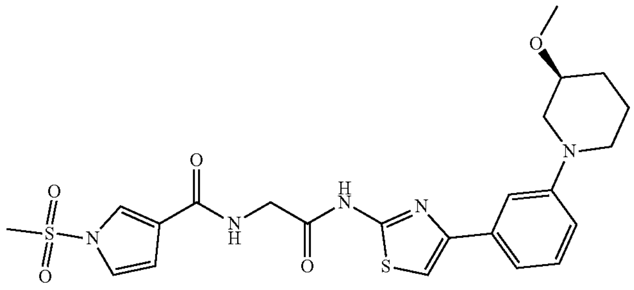 [SMILES: CO[C@H]1CCCN(c2cccc(-c3csc(NC(=O)CNC(=O)c4ccn(S(C)(=O)=O)c4)n3)c2)C1] |
| 12 | 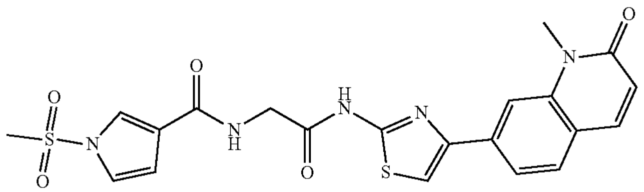 [SMILES: Cn1c(=O)ccc2ccc(-c3csc(NC(=O)CNC(=O)c4ccn(S(C)(=O)=O)c4)n3)cc21] |
| 13 | 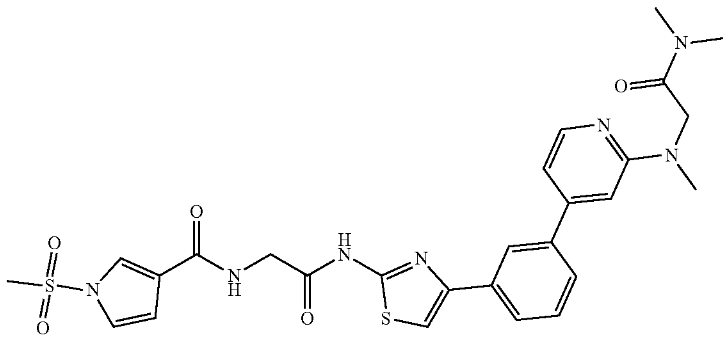 |
| 14 | 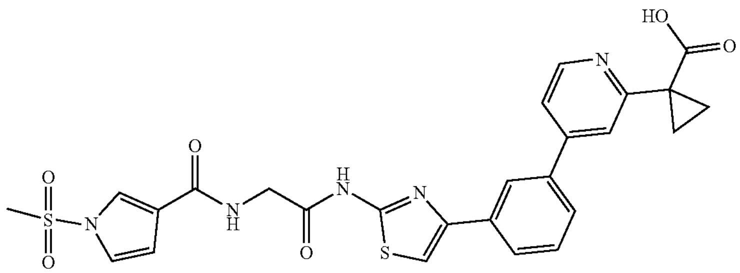 [SMILES: CS(=O)(=O)n1ccc(C(=O)NCC(=O)Nc2nc(-c3cccc(-c4ccnc(C5(C(=O)O)CC5)c4)c3)cs2)c1] |

-continued
| # | Compound |
|---|---|
| 15 | 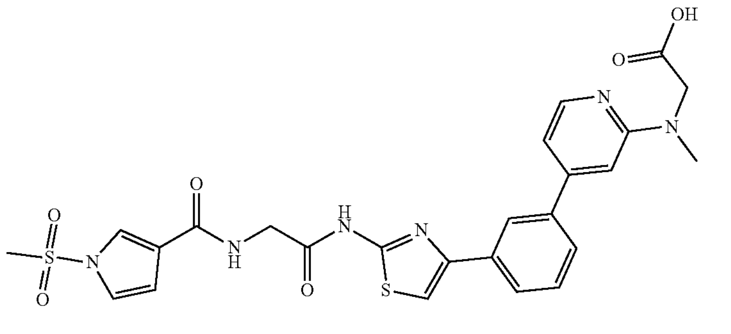 |
| 16 | 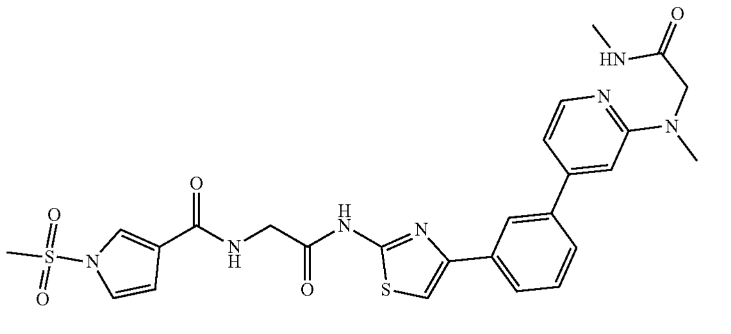 |
| 17 | 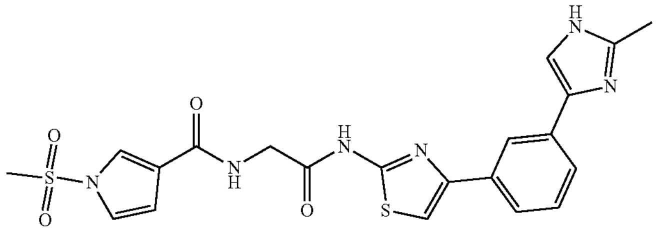 |
| 18 | 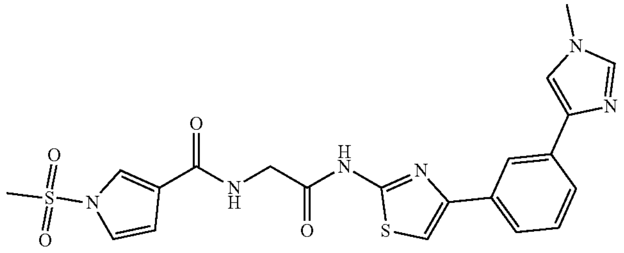 [SMILES: Cn1cnc(-c2cccc(-c3csc(NC(=O)CNC(=O)c4ccn(S(C)(=O)=O)c4)n3)c2)c1] |
| 19 | 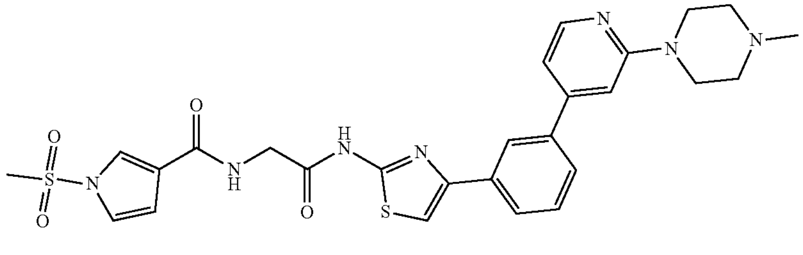 |

-continued
| # | Compound |
|---|---|
| 20 | 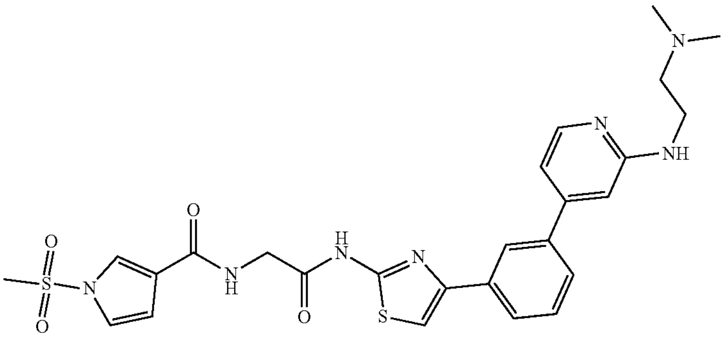 |
| 21 | 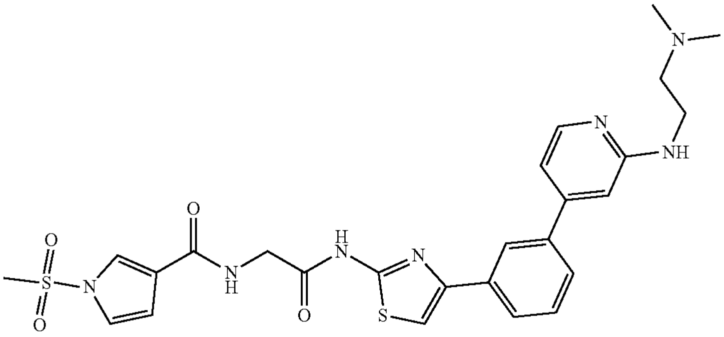 |
| 22 | 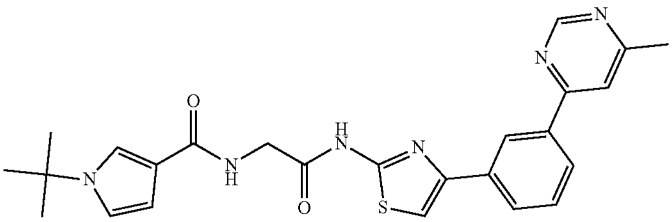 [SMILES: Cc1cc(-c2cccc(-c3csc(NC(=O)CNC(=O)c4ccn(C(C)(C)C)c4)n3)c2)ncn1] |
| 23 | 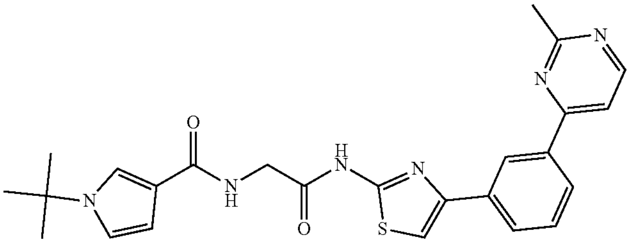 [SMILES: Cc1nccc(-c2cccc(-c3csc(NC(=O)CNC(=O)c4ccn(C(C)(C)C)c4)n3)c2)n1] |
| 24 | 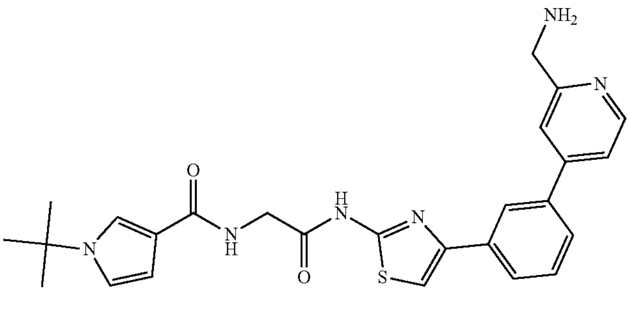 [SMILES: CC(C)(C)n1ccc(C(=O)NCC(=O)Nc2nc(-c3cccc(-c4ccnc(CN)c4)c3)cs2)c1] |

-continued
| # | Compound |
|---|---|
| 25 | 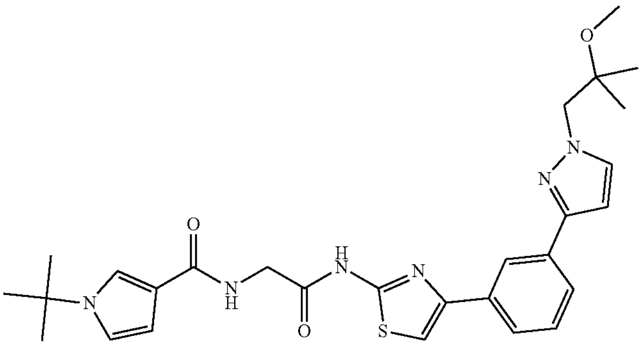 [SMILES: COC(C)(C)Cn1ccc(-c2cccc(-c3csc(NC(=O)CNC(=O)c4ccn(C(C)(C)C)c4)n3)c2)n1] |
| 26 | 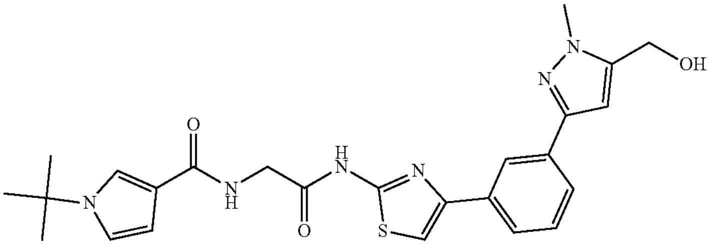 [SMILES: Cn1nc(-c2cccc(-c3csc(NC(=O)CNC(=O)c4ccn(C(C)(C)C)c4)n3)c2)cc1CO] |
| 27 | 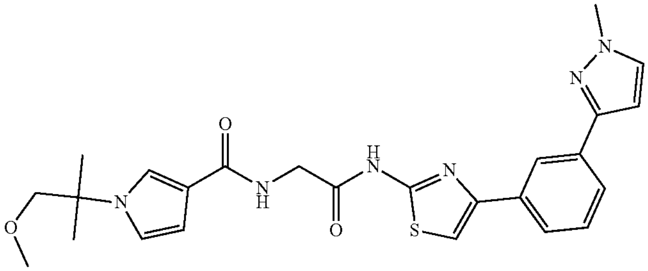 [SMILES: COCC(C)(C)n1ccc(C(=O)NCC(=O)Nc2nc(-c3cccc(-c4ccn(C)n4)c3)cs2)c1] |
| 28 | 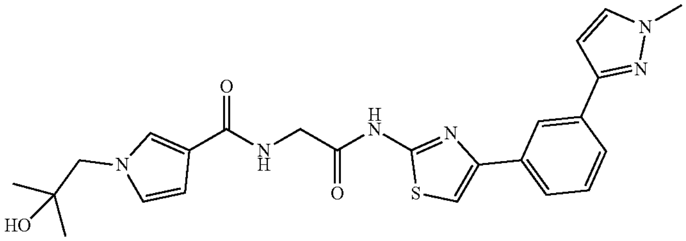 [SMILES: Cn1ccc(-c2cccc(-c3csc(NC(=O)CNC(=O)c4ccn(CC(C)(C)O)c4)n3)c2)n1] |
| 29 | 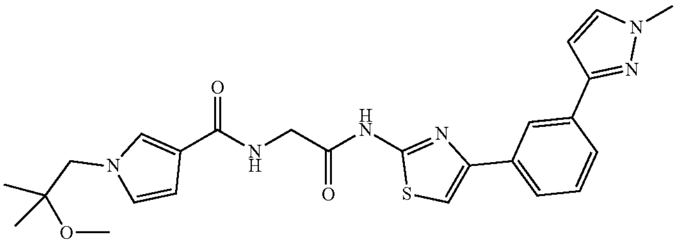 [SMILES: COC(C)(C)Cn1ccc(C(=O)NCC(=O)Nc2nc(-c3cccc(-c4ccn(C)n4)c3)cs2)c1] |

-continued
| # | Compound |
|---|---|
| 30 | 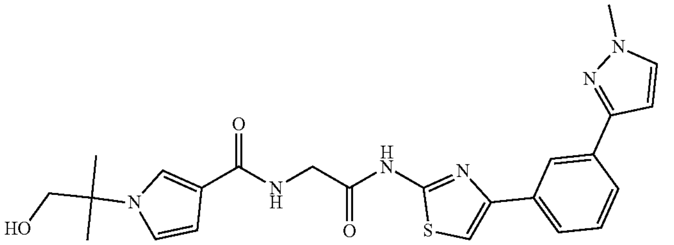 [SMILES: Cn1ccc(-c2cccc(-c3csc(NC(=O)CNC(=O)c4ccn(C(C)(C)CO)c4)n3)c2)n1] |
| 33 | 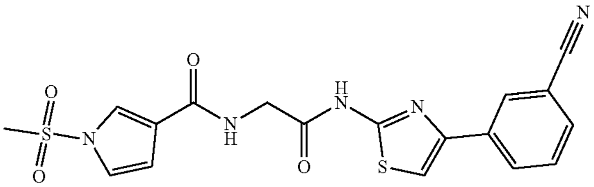 [SMILES: CS(=O)(=O)n1ccc(C(=O)NCC(=O)Nc2nc(-c3cccc(C#N)c3)cs2)c1] |
| 34 | 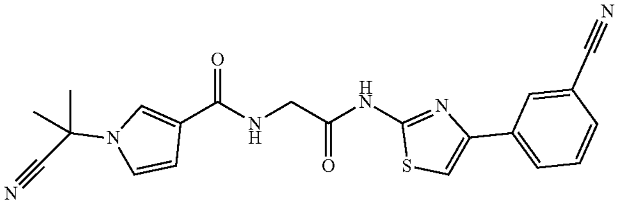 [SMILES: CC(C)(C#N)n1ccc(C(=O)NCC(=O)Nc2nc(-c3cccc(C#N)c3)cs2)c1] |
| 35 | 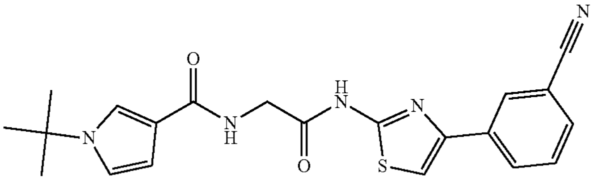 |
| 38 | 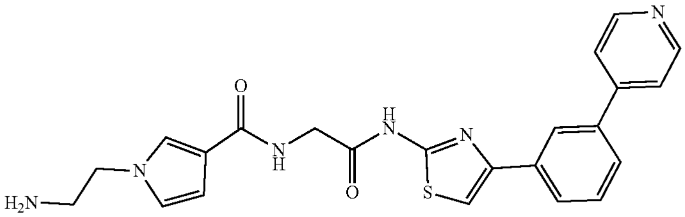 [SMILES: NCCn1ccc(C(=O)NCC(=O)Nc2nc(-c3cccc(-c4ccncc4)c3)cs2)c1] |
| 39 | 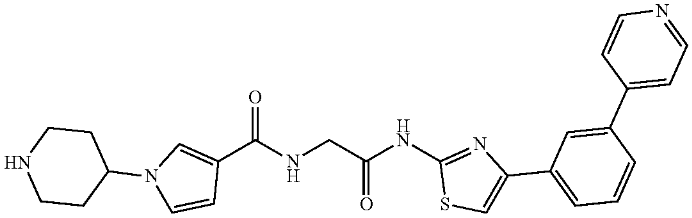 [SMILES: O=C(CNC(=O)c1ccn(C2CCNCC2)c1)Nc1nc(-c2cccc(-c3ccncc3)c2)cs1] |
| 40 | 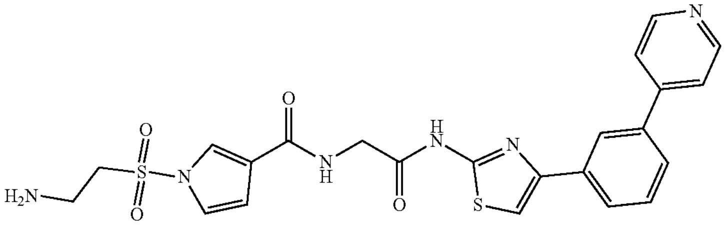 [SMILES: NCCS(=O)(=O)n1ccc(C(=O)NCC(=O)Nc2nc(-c3cccc(-c4ccncc4)c3)cs2)c1] |

-continued
| # | Compound |
|---|---|
| 41 | 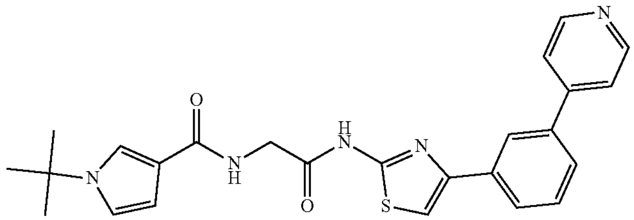 [SMILES: CC(C)(C)n1ccc(C(=O)NCC(=O)Nc2nc(-c3cccc(-c4ccncc4)c3)cs2)c1] |
| 42 | 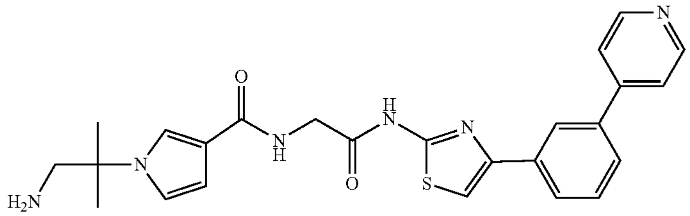 [SMILES: CC(C)(CN)n1ccc(C(=O)NCC(=O)Nc2nc(-c3cccc(-c4ccncc4)c3)cs2)c1] |
| 43 | 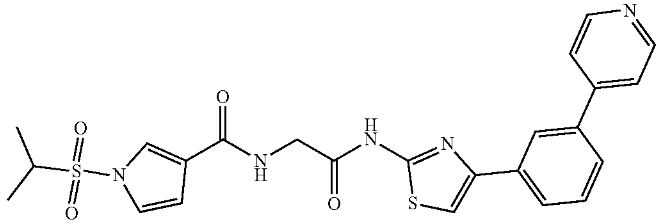 |
| 47 | 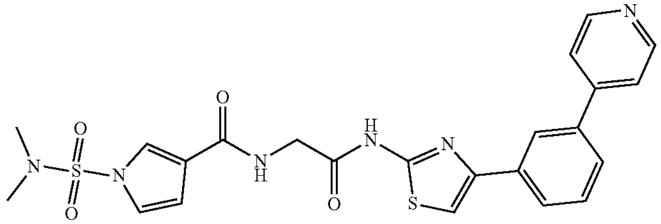 [SMILES: CN(C)S(=O)(=O)n1ccc(C(=O)NCC(=O)Nc2nc(-c3cccc(-c4ccncc4)c3)cs2)c1] |
| 48 | 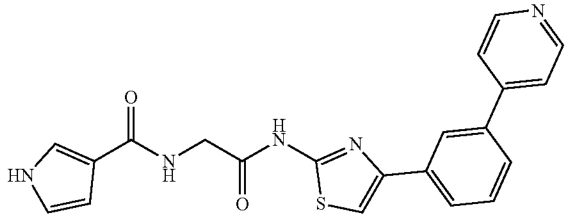 [SMILES: O=C(CNC(=O)c1cc[nH]c1)Nc1nc(-c2cccc(-c3ccncc3)c2)cs1] |
| 49 | 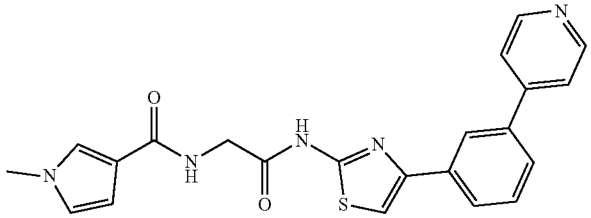 [SMILES: Cn1ccc(C(=O)NCC(=O)Nc2nc(-c3cccc(-c4ccncc4)c3)cs2)c1] |
| 50 | 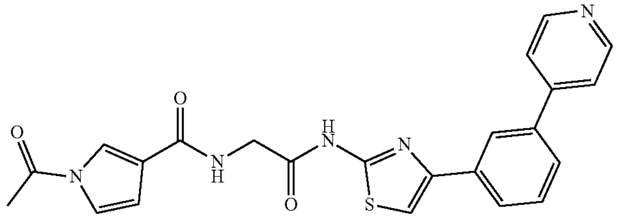 [SMILES: CC(=O)n1ccc(C(=O)NCC(=O)Nc2nc(-c3cccc(-c4ccncc4)c3)cs2)c1] |

-continued
| # | Compound |
|---|---|
| 53 | 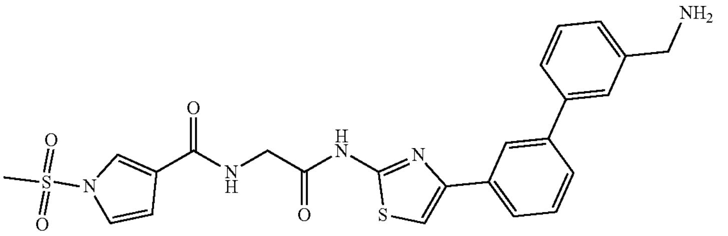 [SMILES: CS(=O)(=O)n1ccc(C(=O)NCC(=O)Nc2nc(-c3cccc(-c4cccc(CN)c4)c3)cs2)c1] |
| 54 | 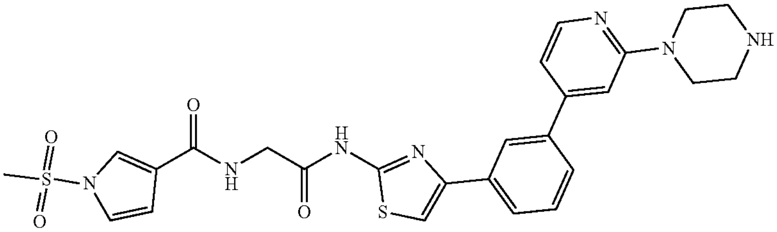 [SMILES: CS(=O)(=O)n1ccc(C(=O)NCC(=O)Nc2nc(-c3cccc(-c4ccnc(N5CCNCC5)c4)c3)cs2)c1] |
| 55 | 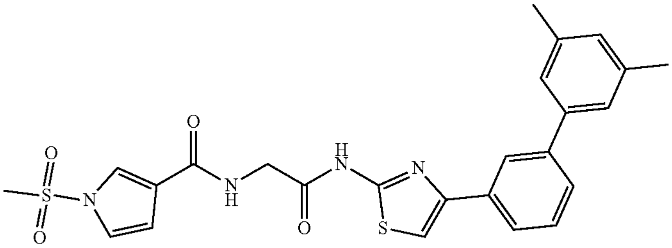 |
| 56 | 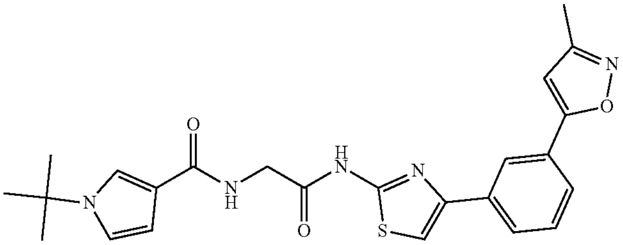 [SMILES: Cc1cc(-c2cccc(-c3csc(NC(=O)CNC(=O)c4ccn(C(C)(C)C)c4)n3)c2)on1] |
| 57 | 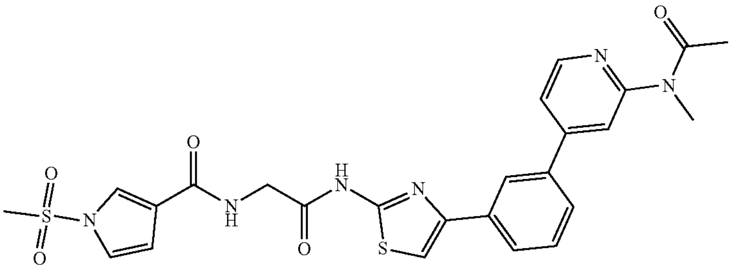 [SMILES: CC(=O)N(C)c1cc(-c2cccc(-c3csc(NC(=O)CNC(=O)c4ccn(S(C)(=O)=O)c4)n3)c2)ccn1] |
| 58 | 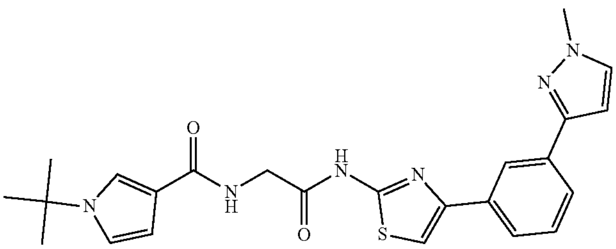 [SMILES: Cn1ccc(-c2cccc(-c3csc(NC(=O)CNC(=O)c4ccn(C(C)(C)C)c4)n3)c2)n1] |

-continued
| # | Compound |
|---|---|
| 81 | 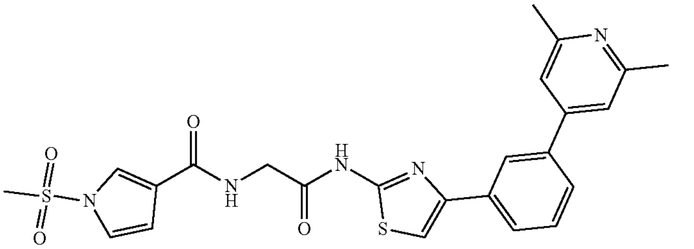 |
| 82 | 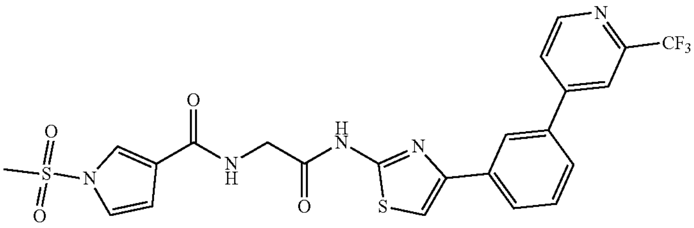 [SMILES: CS(=O)(=O)n1ccc(C(=O)NCC(=O)Nc2nc(-c3cccc(-c4ccnc(C(F)(F)F)c4)c3)cs2)c1] |
| 83 | 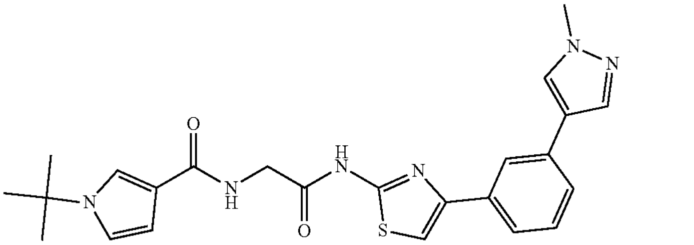 [SMILES: Cn1cc(-c2cccc(-c3csc(NC(=O)CNC(=O)c4ccn(C(C)(C)C)c4)n3)c2)cn1] |
| 84 | 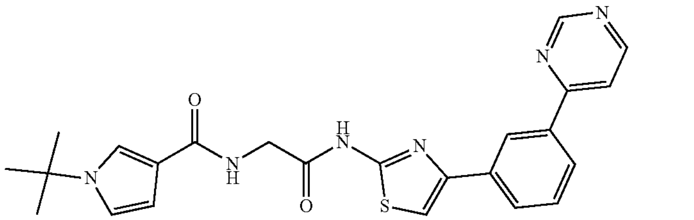 |
| 85 | 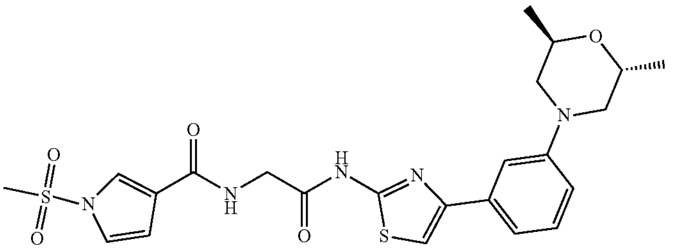 |
| 86 | 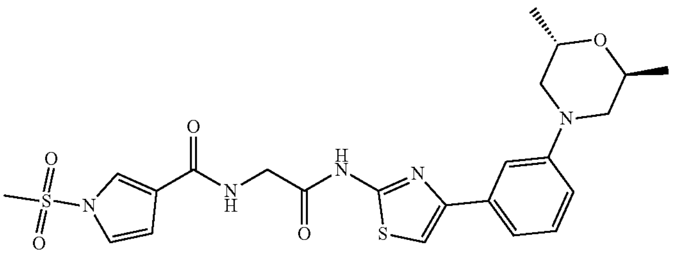 |

-continued
| # | Compound |
|---|---|
| 87 | 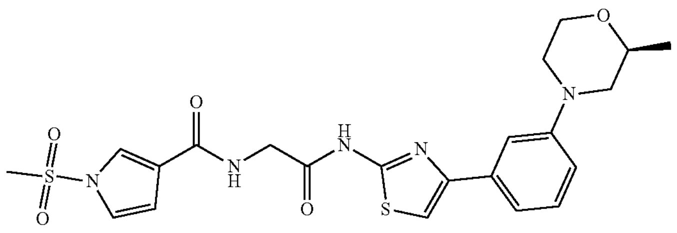 |
| 88 | 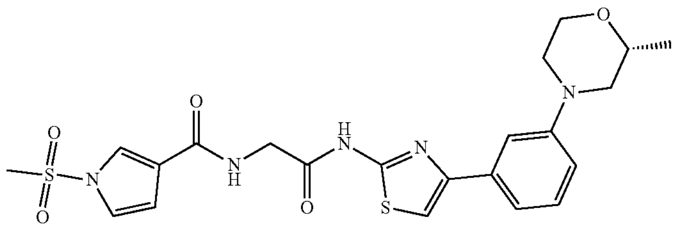 |
| 89 | 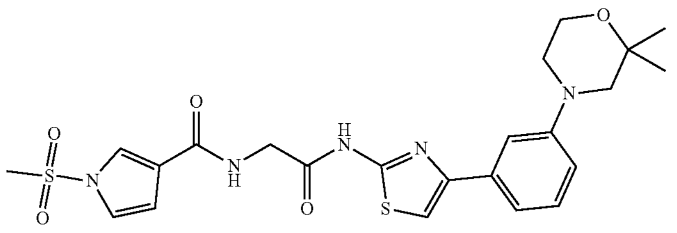 |
| 90 | 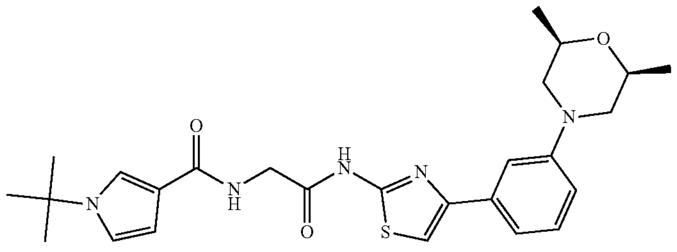 [SMILES: C[C@@H]1CN(c2cccc(-c3csc(NC(=O)CNC(=O)c4ccn(C(C)(C)C)c4)n3)c2)C[C@H](C)O1] |
| 91 | 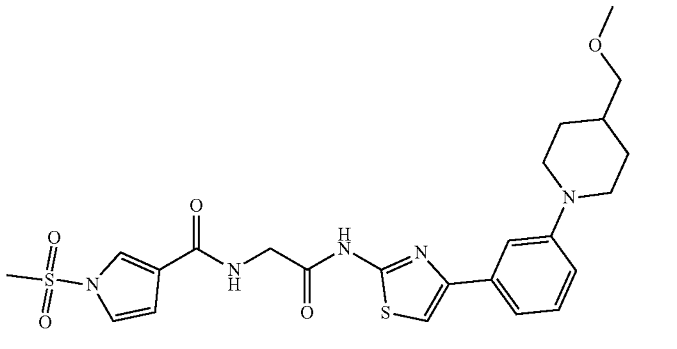 [SMILES: COCC1CCN(c2cccc(-c3csc(NC(=O)CNC(=O)c4ccn(S(C)(=O)=O)c4)n3)c2)CC1] |

-continued
| # | Compound |
|---|---|
| 92 | 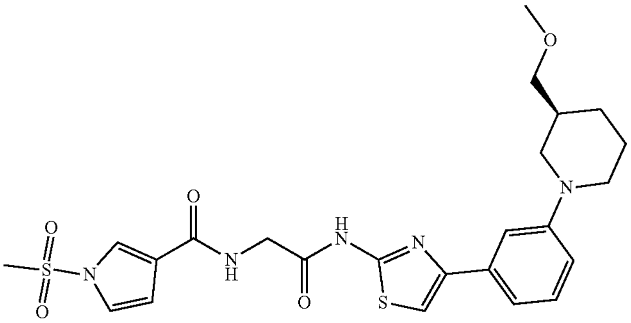 [SMILES: COC[C@H]1CCCN(c2cccc(-c3csc(NC(=O)CNC(=O)c4ccn(S(C)(=O)=O)c4)n3)c2)C1] |
| 93 | 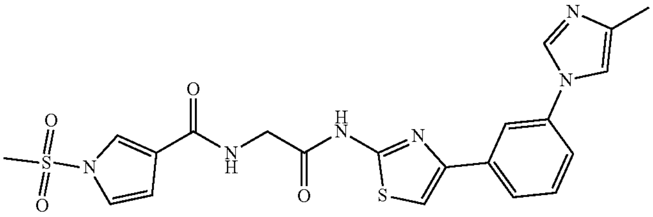 |
| 94 | 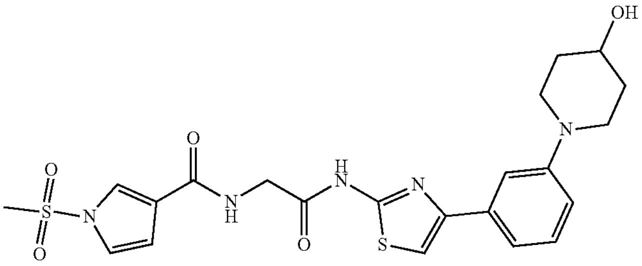 |
| 95 | 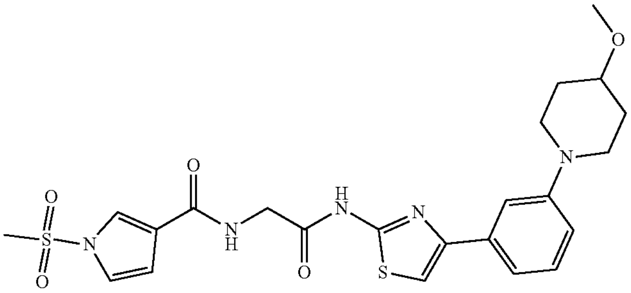 [SMILES: COC1CCN(c2cccc(-c3csc(NC(=O)CNC(=O)c4ccn(S(C)(=O)=O)c4)n3)c2)CC1] |
| 96 | 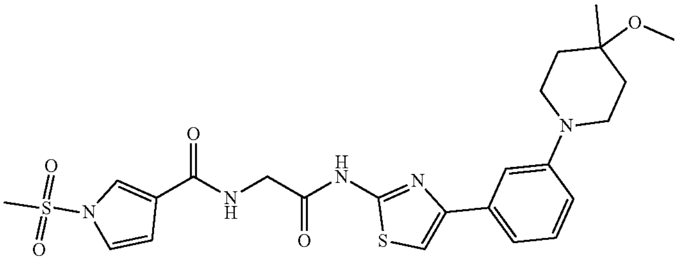 |

-continued
| # | Compound |
|---|---|
| 97 | 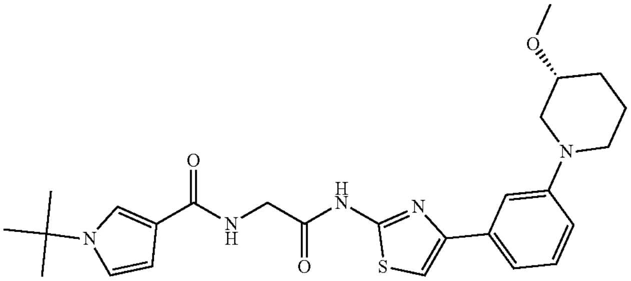 [SMILES: CO[C@@H]1CCCN(c2cccc(-c3csc(NC(=O)CNC(=O)c4ccn(C(C)(C)C)c4)n3)c2)C1] |
| 98 | 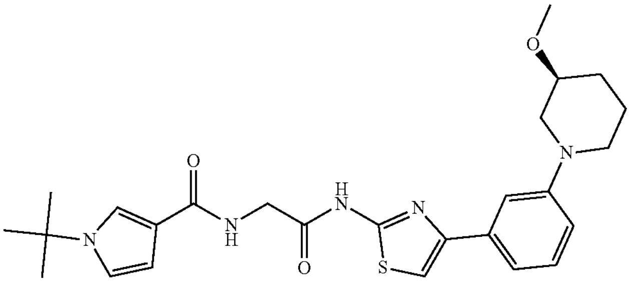 [SMILES: CO[C@H]1CCCN(c2cccc(-c3csc(NC(=O)CNC(=O)c4ccn(C(C)(C)C)c4)n3)c2)C1] |
| 99 | 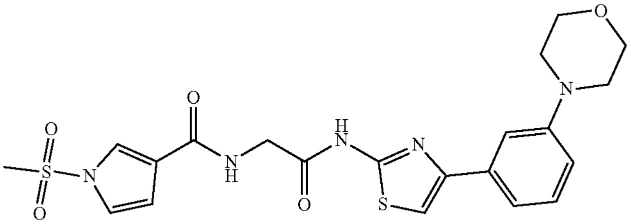 [SMILES: CS(=O)(=O)n1ccc(C(=O)NCC(=O)Nc2nc(-c3cccc(N4CCOCC4)c3)cs2)c1] |
| 100 | 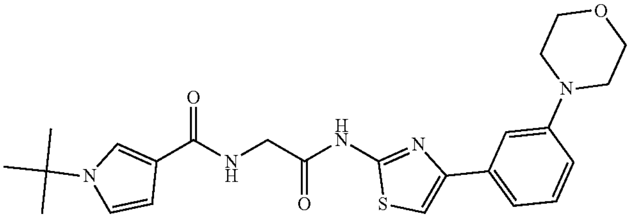 [SMILES: CC(C)(C)n1ccc(C(=O)NCC(=O)Nc2nc(-c3cccc(N4CCOCC4)c3)cs2)c1] |
| 101 | 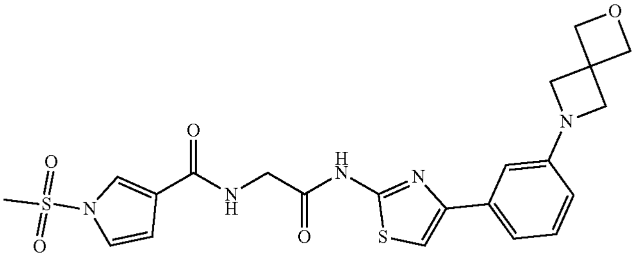 [SMILES: CS(=O)(=O)n1ccc(C(=O)NCC(=O)Nc2nc(-c3cccc(N4CC5(COC5)C4)c3)cs2)c1] |
| 102 | 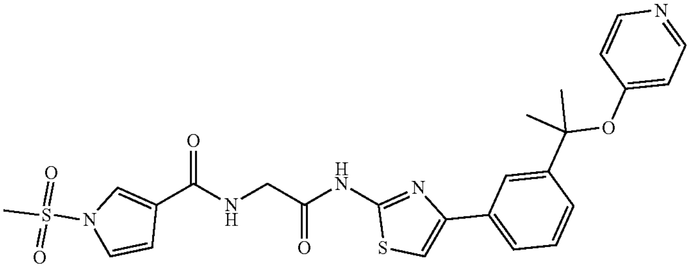 [SMILES: CC(C)(Oc1ccncc1)c1cccc(-c2csc(NC(=O)CNC(=O)c3ccn(S(C)(=O)=O)c3)n2)c1] |

-continued
| # | Compound |
|---|---|
| 103 | 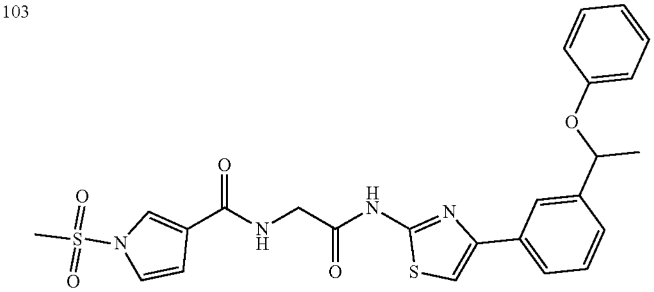 |
| 104 | 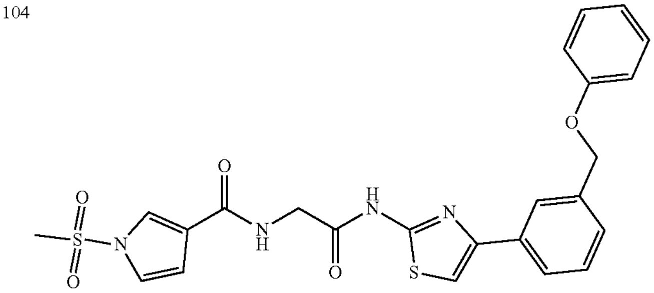 |
| 105 | 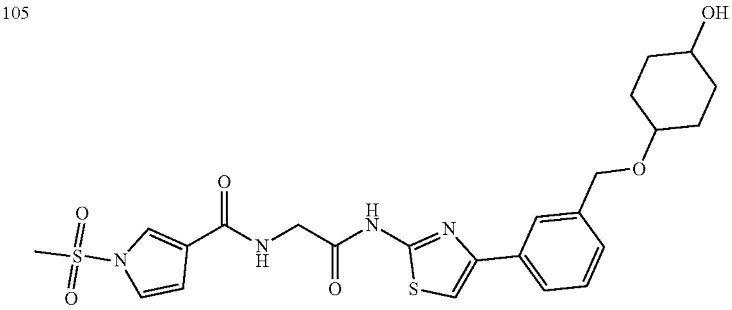 |
| 106 | 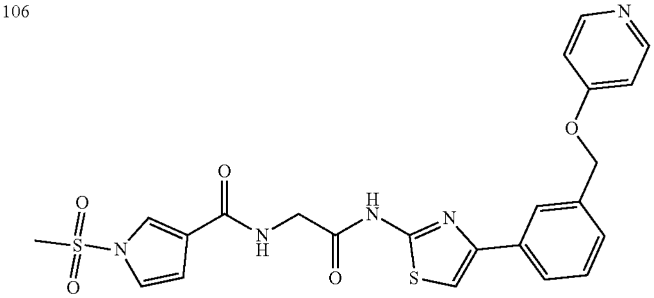 |
| 107 | 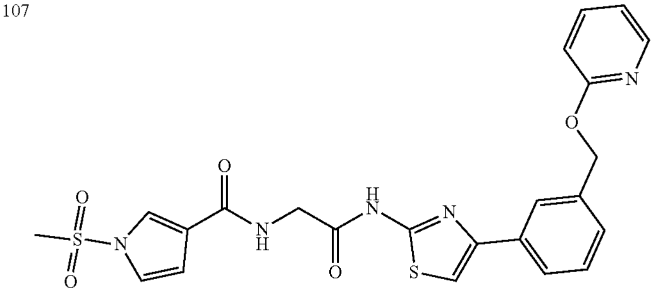 |

-continued
| # | Compound |
|---|---|
| 108 | 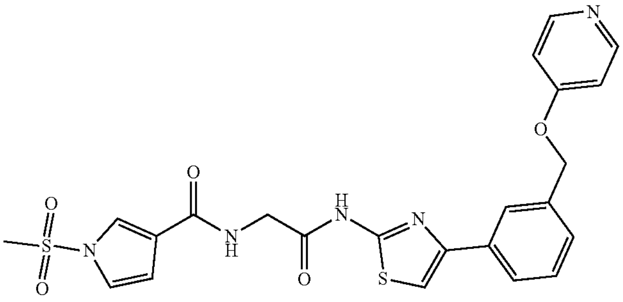 |
| 109 | 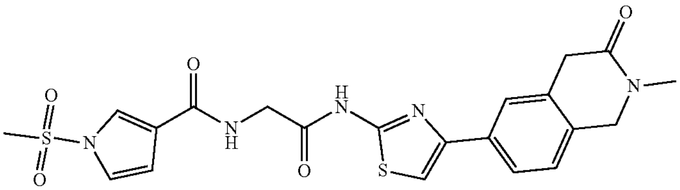 |
| 110 | 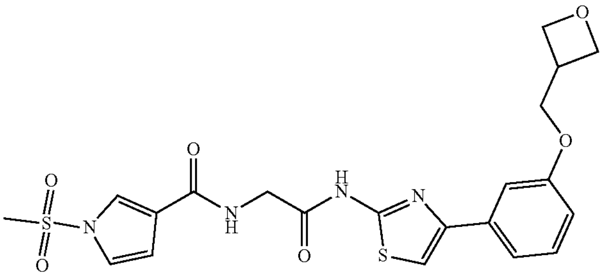 [SMILES: CS(=O)(=O)n1ccc(C(=O)NCC(=O)Nc2nc(-c3cccc(OCC4COC4)c3)cs2)c1] |
| 111 | 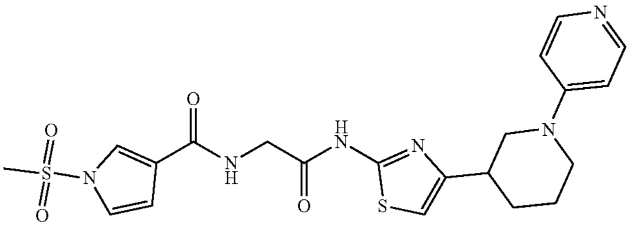 [SMILES: CS(=O)(=O)n1ccc(C(=O)NCC(=O)Nc2nc(C3CCCN(c4ccncc4)C3)cs2)c1] |
| 112 | 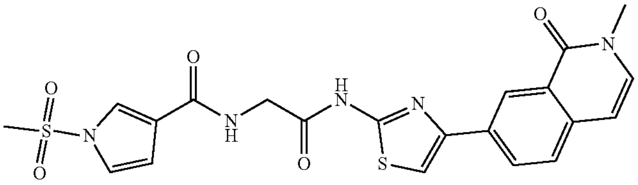 [SMILES: Cn1ccc2ccc(-c3csc(NC(=O)CNC(=O)c4ccn(S(C)(=O)=O)c4)n3)cc2c1=O] |
| 113 | 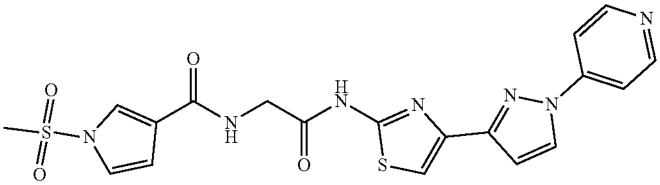 [SMILES: CS(=O)(=O)n1ccc(C(=O)NCC(=O)Nc2nc(-c3ccn(-c4ccncc4)n3)cs2)c1] |

-continued
| # | Compound |
|---|---|
| 114 | 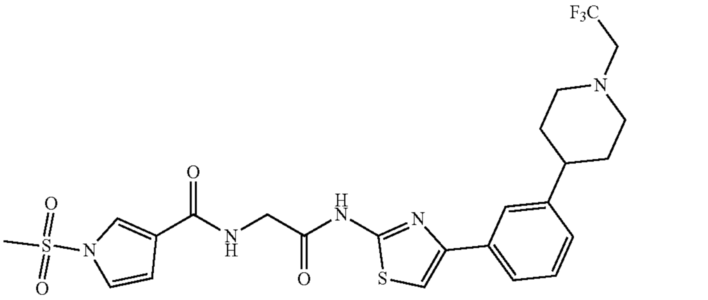 [SMILES: CS(=O)(=O)n1ccc(C(=O)NCC(=O)Nc2nc(-c3cccc(C4CCN(CC(F)(F)F)CC4)c3)cs2)c1] |
| 115 | 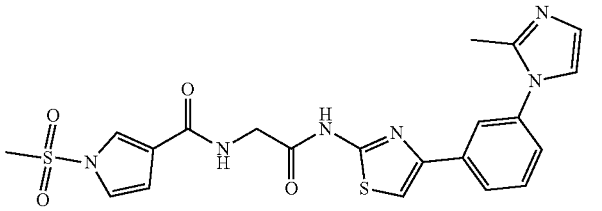 [SMILES: Cc1nccn1-c1cccc(-c2csc(NC(=O)CNC(=O)c3ccn(S(C)(=O)=O)c3)n2)c1] |
| 116 | 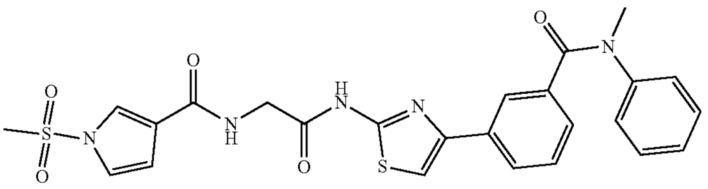 [SMILES: CN(C(=O)c1cccc(-c2csc(NC(=O)CNC(=O)c3ccn(S(C)(=O)=O)c3)n2)c1)c1ccccc1] |
| 117 | 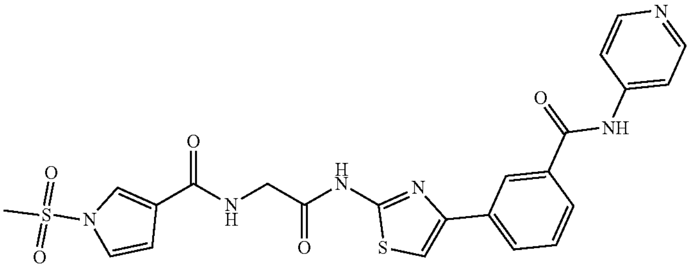 [SMILES: CS(=O)(=O)n1ccc(C(=O)NCC(=O)Nc2nc(-c3cccc(C(=O)Nc4ccncc4)c3)cs2)c1] |
| 118 | 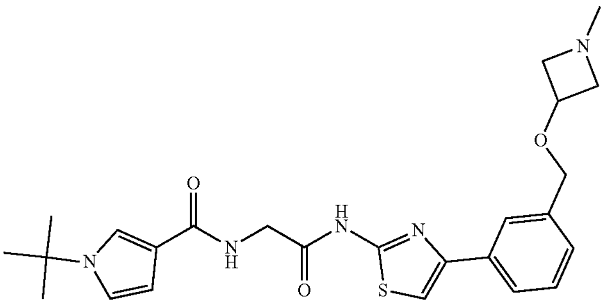 [SMILES: CN1CC(OCc2cccc(-c3csc(NC(=O)CNC(=O)c4ccn(C(C)(C)C)c4)n3)c2)C1] |
| 119 | 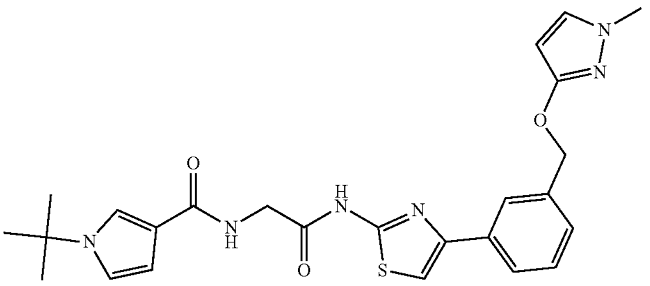 [SMILES: Cn1ccc(OCc2cccc(-c3csc(NC(=O)CNC(=O)c4ccn(C(C)(C)C)c4)n3)c2)n1] |

-continued
| # | Compound |
|---|---|
| 120 | 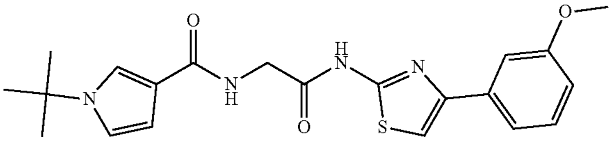 [SMILES: COc1cccc(-c2csc(NC(=O)CNC(=O)c3ccn(C(C)(C)C)c3)n2)c1] |
| 121 | 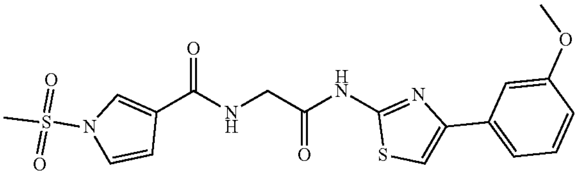 [SMILES: COc1cccc(-c2csc(NC(=O)CNC(=O)c3ccn(S(C)(=O)=O)c3)n2)c1] |
| 122 | 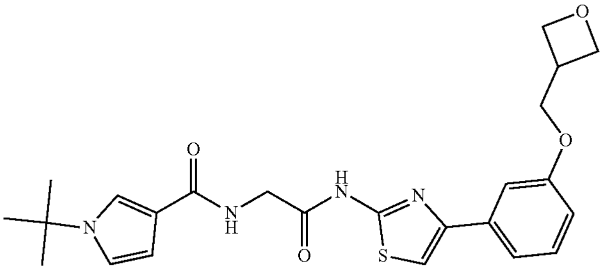 [SMILES: CC(C)(C)n1ccc(C(=O)NCC(=O)Nc2nc(-c3cccc(OCC4COC4)c3)cs2)c1] |
| 123 | 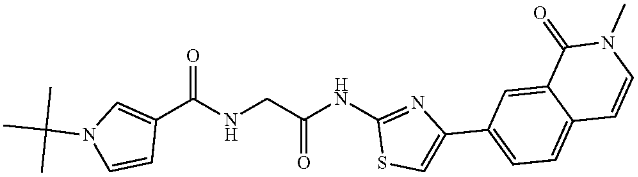 [SMILES: Cn1ccc2ccc(-c3csc(NC(=O)CNC(=O)c4ccn(C(C)(C)C)c4)n3)cc2c1=O] |
| 124 | 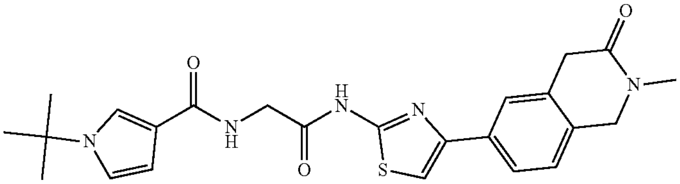 [SMILES: CN1Cc2ccc(-c3csc(NC(=O)CNC(=O)c4ccn(C(C)(C)C)c4)n3)cc2CC1=O] |
| 125 | 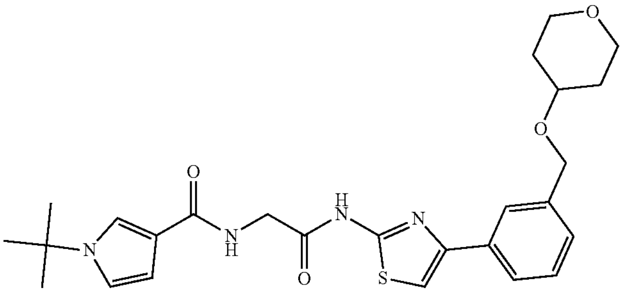 [SMILES: CC(C)(C)n1ccc(C(=O)NCC(=O)Nc2nc(-c3cccc(COC4CCOCC4)c3)cs2)c1] |
| 126 | 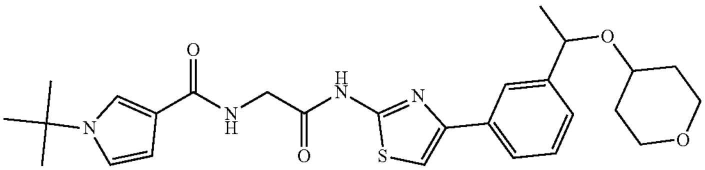 [SMILES: CC(OC1CCOCC1)c1cccc(-c2csc(NC(=O)CNC(=O)c3ccn(C(C)(C)C)c3)n2)c1] |

-continued
| # | Compound |
|---|---|
| 127 | 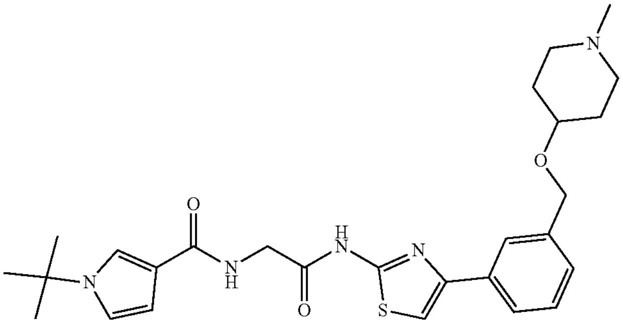 [SMILES: CN1CCC(OCc2cccc(-c3csc(NC(=O)CNC(=O)c4ccn(C(C)(C)C)c4)n3)c2)CC1] |
| 128 | 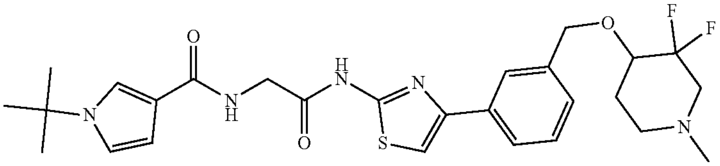 [SMILES: CN1CCC(OCc2cccc(-c3csc(NC(=O)CNC(=O)c4ccn(C(C)(C)C)c4)n3)c2)C(F)(F)C1] |
| 129 | 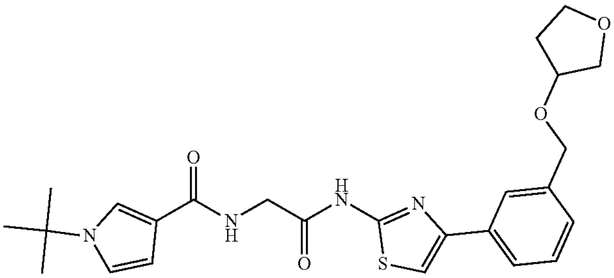 [SMILES: CC(C)(C)n1ccc(C(=O)NCC(=O)Nc2nc(-c3cccc(COC4CCOC4)c3)cs2)c1] |
| 130 | 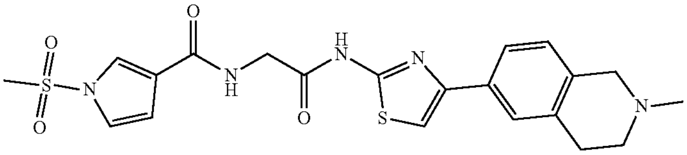 |
| 131 | 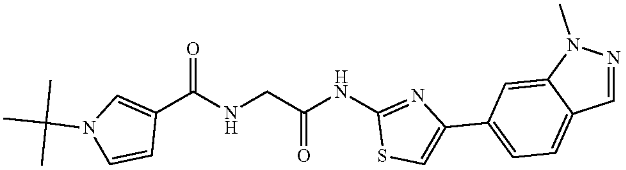 [SMILES: Cn1ncc2ccc(-c3csc(NC(=O)CNC(=O)c4ccn(C(C)(C)C)c4)n3)cc21] |
| 132 | 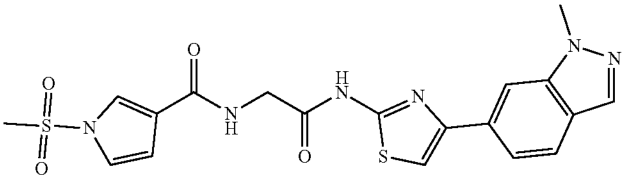 [SMILES: Cn1ncc2ccc(-c3csc(NC(=O)CNC(=O)c4ccn(S(C)(=O)=O)c4)n3)cc21] |
| 133 | 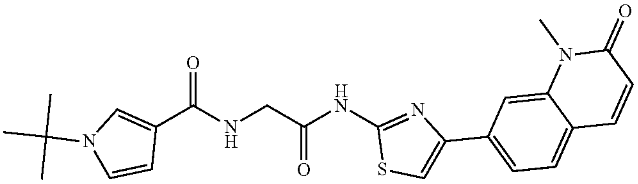 [SMILES: Cn1c(=O)ccc2ccc(-c3csc(NC(=O)CNC(=O)c4ccn(C(C)(C)C)c4)n3)cc21] |

-continued
| # | Compound |
|---|---|
| 134 | 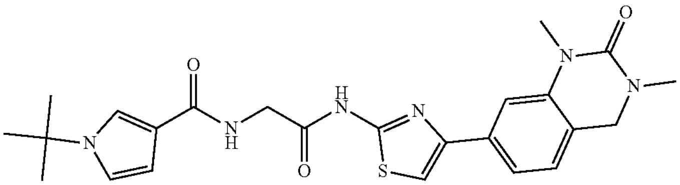 [SMILES: CN1Cc2ccc(-c3csc(NC(=O)CNC(=O)c4ccn(C(C)(C)C)c4)n3)cc2N(C)C1=O] |
| 135 | 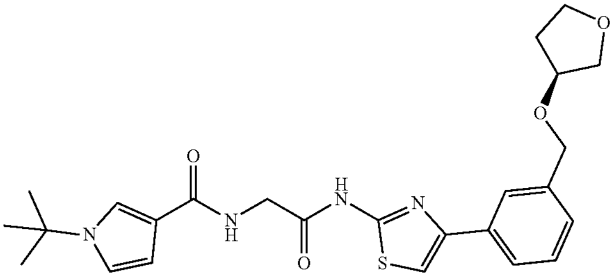 [SMILES: CC(C)(C)n1ccc(C(=O)NCC(=O)Nc2nc(-c3cccc(CO[C@H]4CCOC4)c3)cs2)c1] |
| 136 | 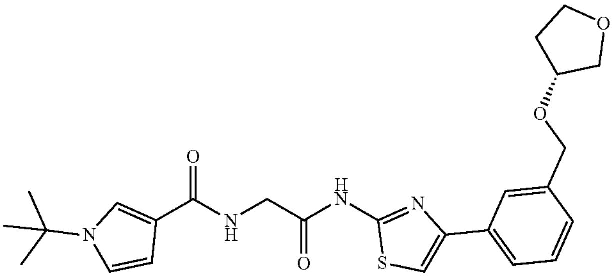 [SMILES: CC(C)(C)n1ccc(C(=O)NCC(=O)Nc2nc(-c3cccc(CO[C@@H]4CCOC4)c3)cs2)c1] |
| 137 | 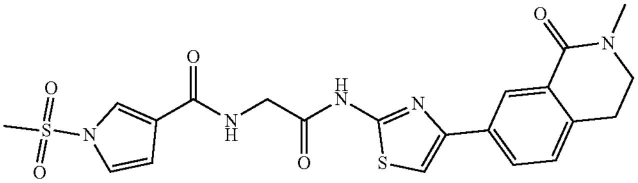 [SMILES: CN1CCc2ccc(-c3csc(NC(=O)CNC(=O)c4ccn(S(C)(=O)=O)c4)n3)cc2C1=O] |
| 138 | 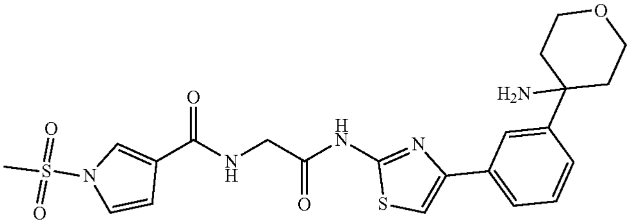 [SMILES: CS(=O)(=O)n1ccc(C(=O)NCC(=O)Nc2nc(-c3cccc(C4(N)CCOCC4)c3)cs2)c1] |
| 139 | 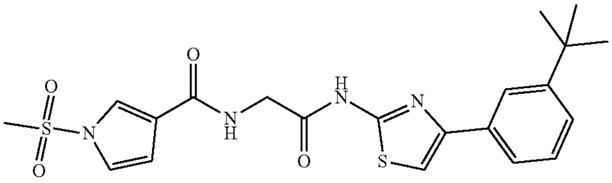 [SMILES: CC(C)(C)c1cccc(-c2csc(NC(=O)CNC(=O)c3ccn(S(C)(=O)=O)c3)n2)c1] |
| 140 | 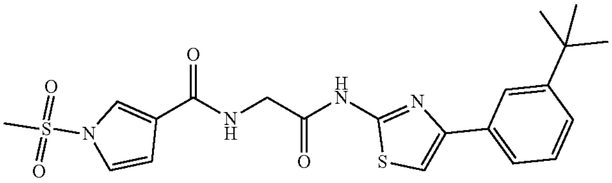 [SMILES: CC(C)(C)c1cccc(-c2csc(NC(=O)CNC(=O)c3ccn(S(C)(=O)=O)c3)n2)c1] |

-continued
| # | Compound |
|---|---|
| 141 | 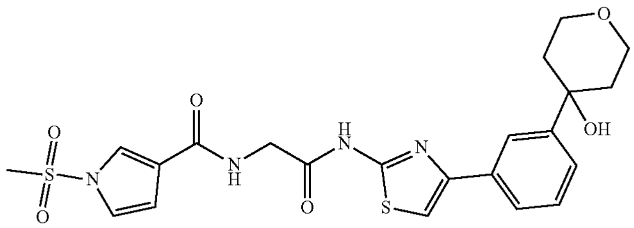 [SMILES: CS(=O)(=O)n1ccc(C(=O)NCC(=O)Nc2nc(-c3cccc(C4(O)CCOCC4)c3)cs2)c1] |
| 142 | 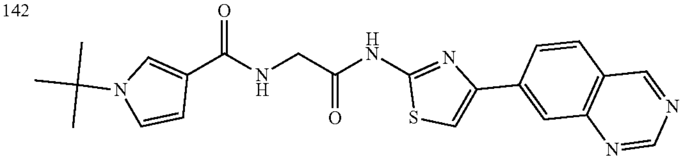 |
| 143 | 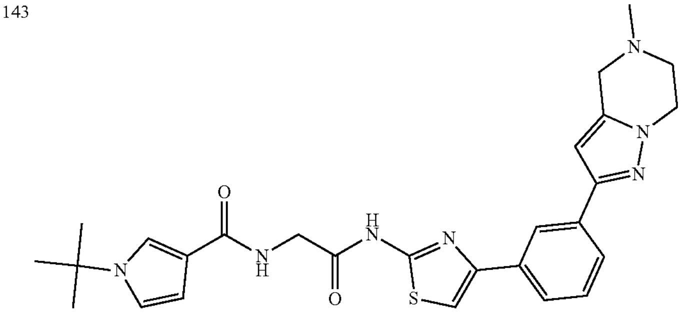 |
| 144 | 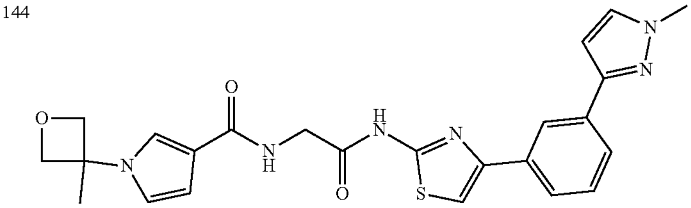 |
| 145 | 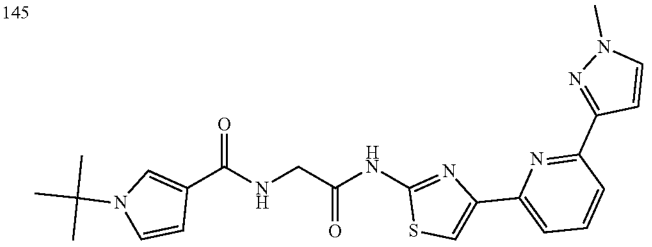 |
| 146 | 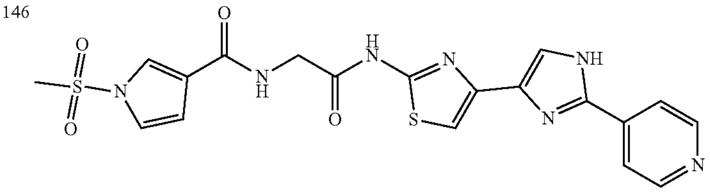 |

-continued
| # | Compound |
|---|---|
| 147 | 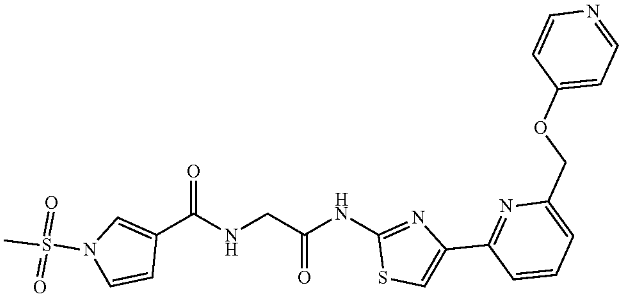 [SMILES: CS(=O)(=O)n1ccc(C(=O)NCC(=O)Nc2nc(-c3cccc(COc4ccncc4)n3)cs2)c1] |
| 148 | 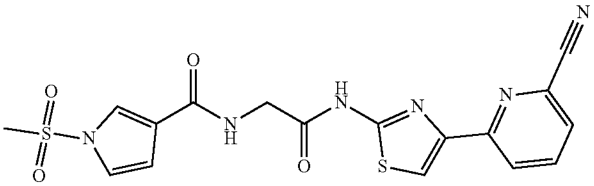 [SMILES: CS(=O)(=O)n1ccc(C(=O)NCC(=O)Nc2nc(-c3cccc(C#N)n3)cs2)c1] |
| 149 | 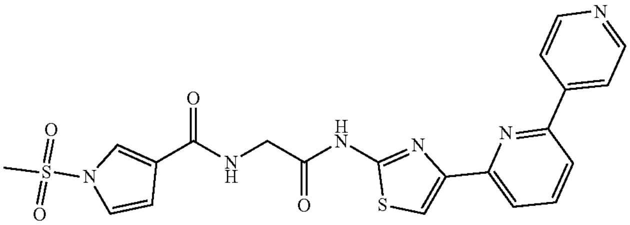 [SMILES: CS(=O)(=O)n1ccc(C(=O)NCC(=O)Nc2nc(-c3cccc(-c4ccncc4)n3)cs2)c1] |
| 150 | 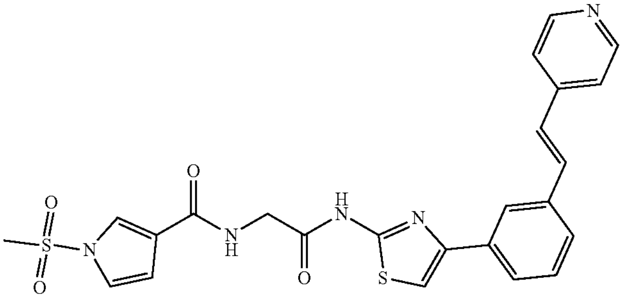 [SMILES: CS(=O)(=O)n1ccc(C(=O)NCC(=O)Nc2nc(-c3cccc(/C=C/c4ccncc4)c3)cs2)c1] |
| 151 | 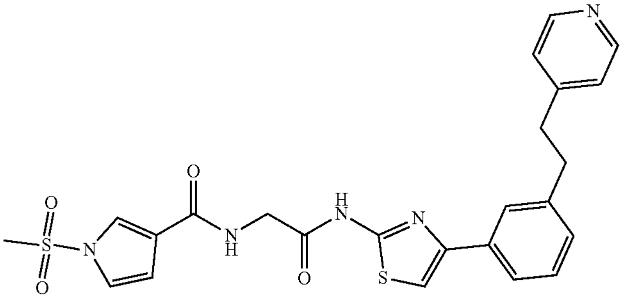 [SMILES: CS(=O)(=O)n1ccc(C(=O)NCC(=O)Nc2nc(-c3cccc(CCc4ccncc4)c3)cs2)c1] |
| 152 | 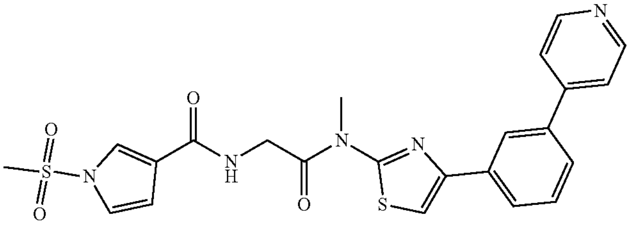 [SMILES: CN(C(=O)CNC(=O)c1ccn(S(C)(=O)=O)c1)c1nc(-c2cccc(-c3ccncc3)c2)cs1] |

-continued
| # | Compound |
|---|---|
| 154 | 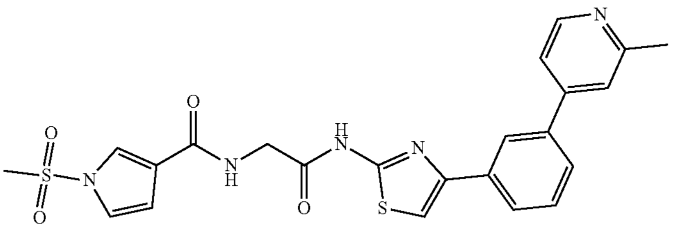 |
| 155 | 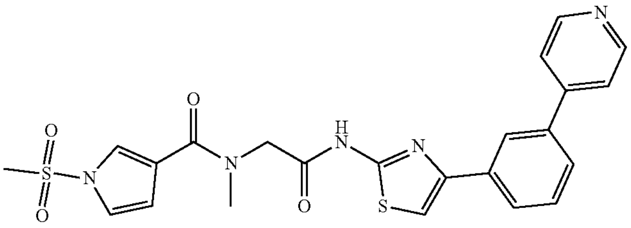 [SMILES: CN(CC(=O)Nc1nc(-c2cccc(-c3ccncc3)c2)cs1)C(=O)c1ccn(S(C)(=O)=O)c1] |
| 156 | 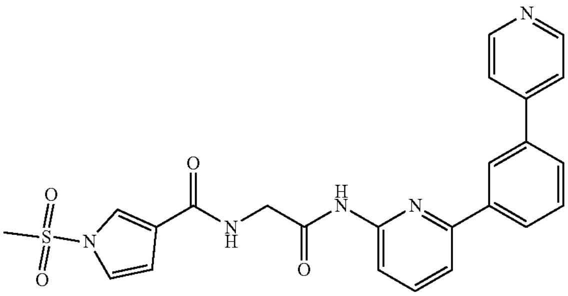 [SMILES: CS(=O)(=O)n1ccc(C(=O)NCC(=O)Nc2cccc(-c3cccc(-c4ccncc4)c3)n2)c1] |
| 157 | 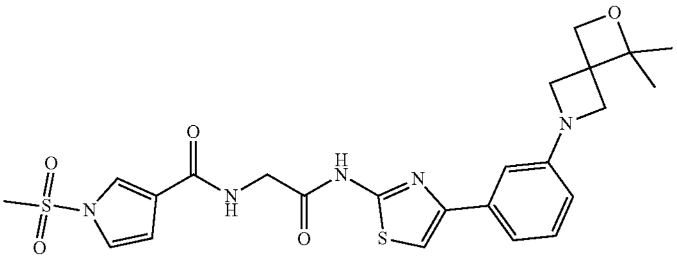 |
| 158 | 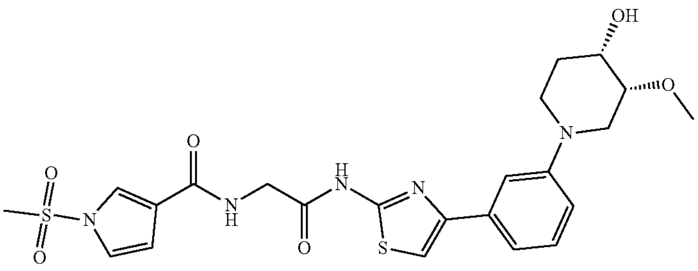<br>(±) |

-continued
| # | Compound |
|---|---|
| 159 | 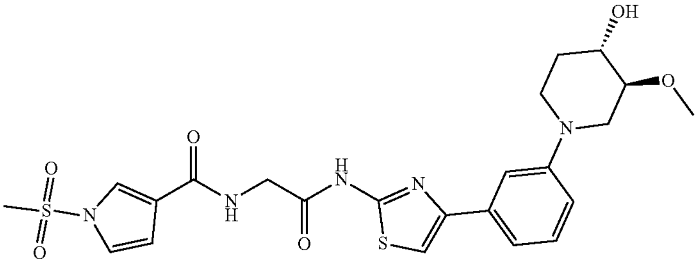 (±) |
| 160 | 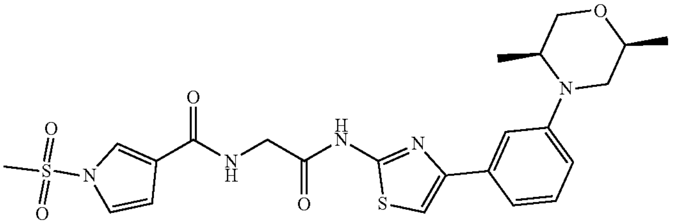 |
| 161 | 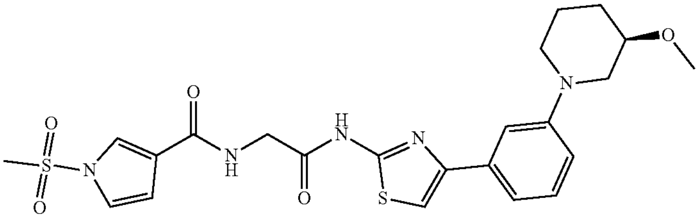 |
| 162 | 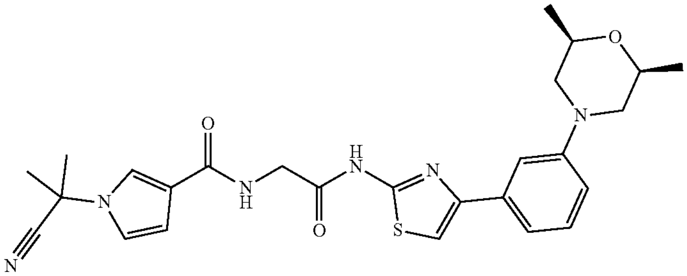 [SMILES: C[C@@H]1CN(c2cccc(-c3csc(NC(=O)CNC(=O)c4ccn(C(C)(C)C#N)c4)n3)c2)C[C@H](C)O1] |
| 163 | 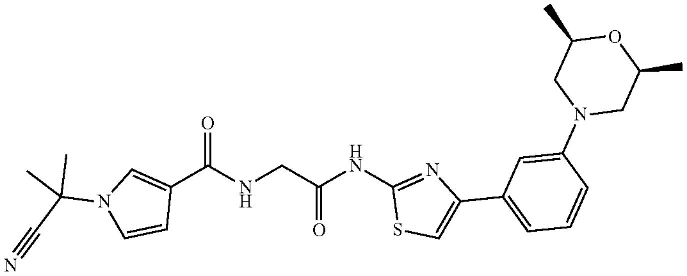 [SMILES: C[C@@H]1CN(c2cccc(-c3csc(NC(=O)CNC(=O)c4ccn(C(C)(C)C#N)c4)n3)c2)C[C@H](C)O1] |
| 164 | 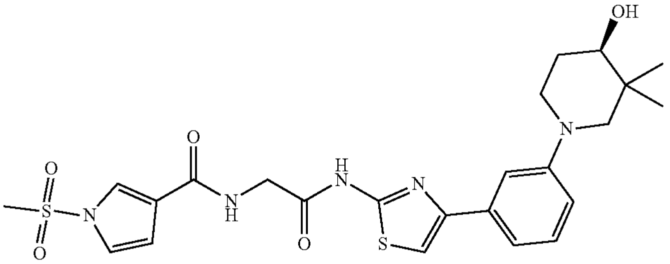 |

-continued
| # | Compound |
|---|---|
| 165 | 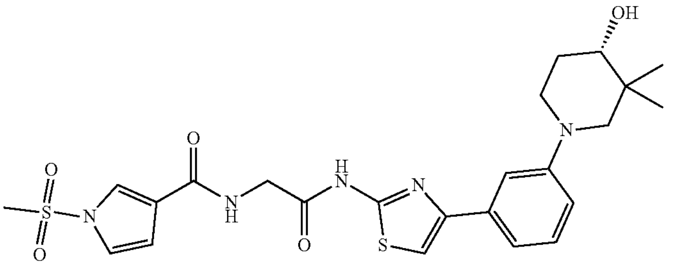 |
| 166 | 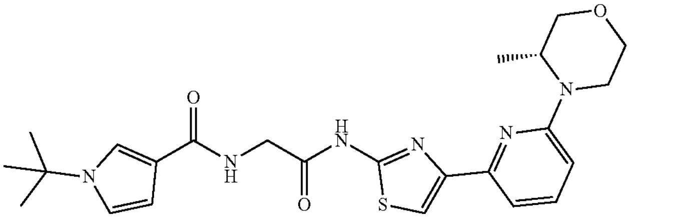 [SMILES: C[C@@H]1COCCN1c1cccc(-c2csc(NC(=O)CNC(=O)c3ccn(C(C)(C)C)c3)n2)n1] |
| 168 | 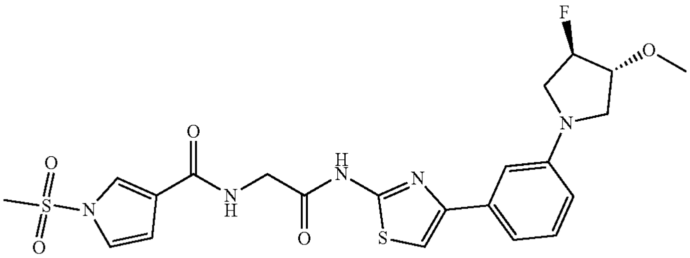 |
| 169 | 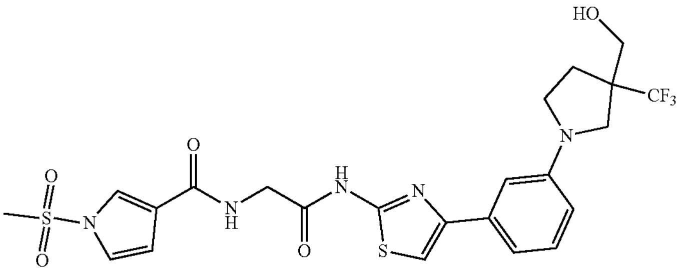 [SMILES: CS(=O)(=O)n1ccc(C(=O)NCC(=O)Nc2nc(-c3cccc(N4CCC(CO)(C(F)(F)F)C4)c3)cs2)c1] |
| 170 | 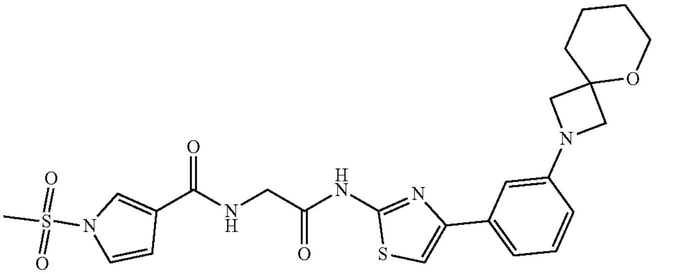 [SMILES: CS(=O)(=O)n1ccc(C(=O)NCC(=O)Nc2nc(-c3cccc(N4CC5(CCCCO5)C4)c3)cs2)c1] |

-continued
| # | Compound |
|---|---|
| 171 | 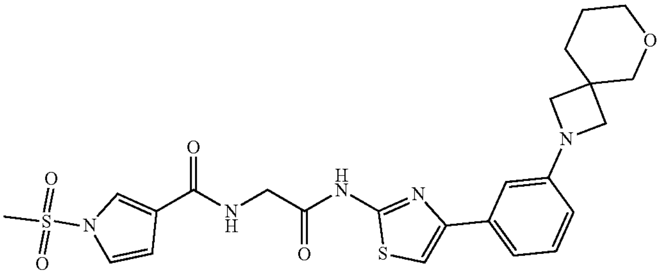 [SMILES: CS(=O)(=O)n1ccc(C(=O)NCC(=O)Nc2nc(-c3cccc(N4CC5(CCCOC5)C4)c3)cs2)c1] |
| 172 | 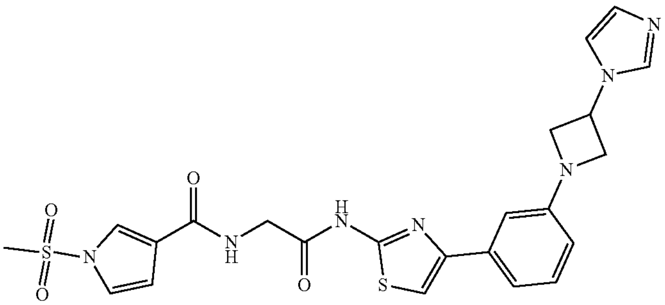 [SMILES: CS(=O)(=O)n1ccc(C(=O)NCC(=O)Nc2nc(-c3cccc(N4CC(n5ccnc5)C4)c3)cs2)c1] |
| 173 | 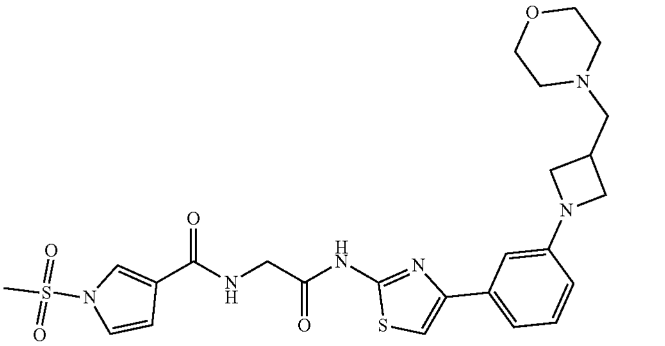 [SMILES: CS(=O)(=O)n1ccc(C(=O)NCC(=O)Nc2nc(-c3cccc(N4CC(CN5CCOCC5)C4)c3)cs2)c1] |
| 174 | 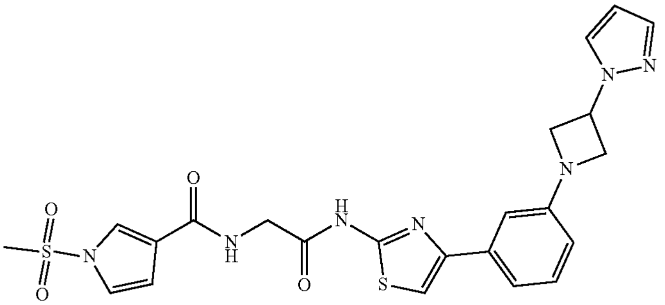 [SMILES: CS(=O)(=O)n1ccc(C(=O)NCC(=O)Nc2nc(-c3cccc(N4CC(n5cccn5)C4)c3)cs2)c1] |
| 175 | 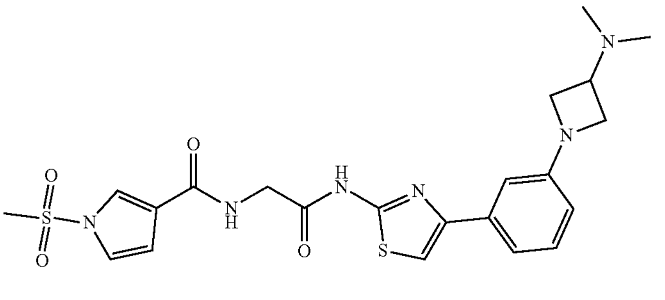 |

-continued
| # | Compound |
|---|---|
| 176 | 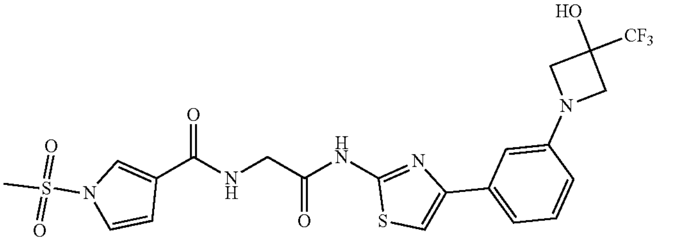 [SMILES: CS(=O)(=O)n1ccc(C(=O)NCC(=O)Nc2nc(-c3cccc(N4CC(O)(C(F)(F)F)C4)c3)cs2)c1] |
| 177 | 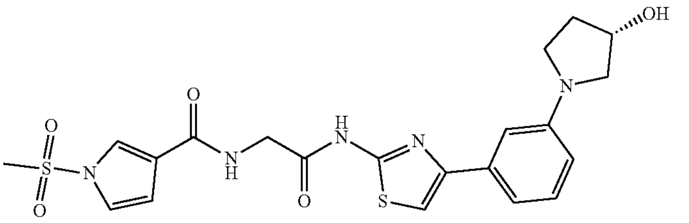 [SMILES: CS(=O)(=O)n1ccc(C(=O)NCC(=O)Nc2nc(-c3cccc(N4CC[C@H](O)C4)c3)cs2)c1] |
| 178 | 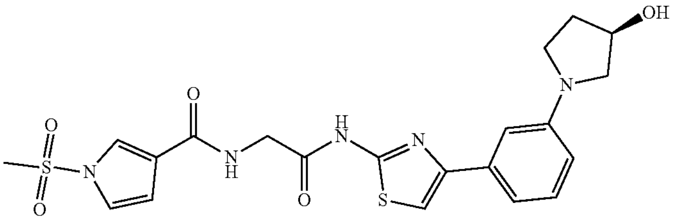 [SMILES: CS(=O)(=O)n1ccc(C(=O)NCC(=O)Nc2nc(-c3cccc(N4CC[C@@H](O)C4)c3)cs2)c1] |
| 179 | 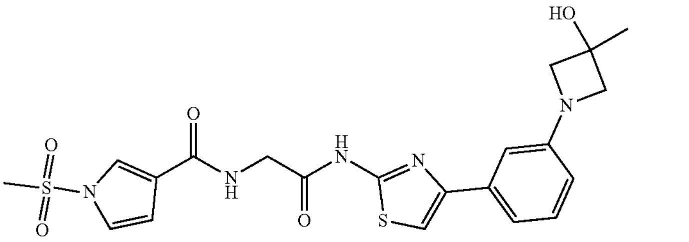 |
| 180 | 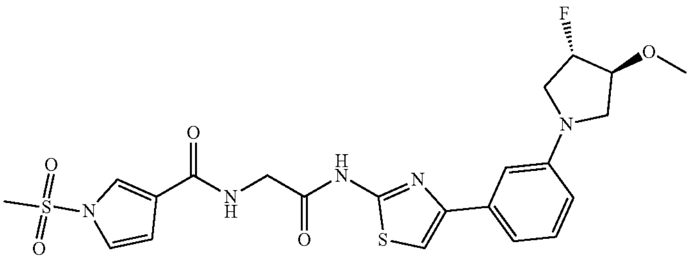 |
| 181 | 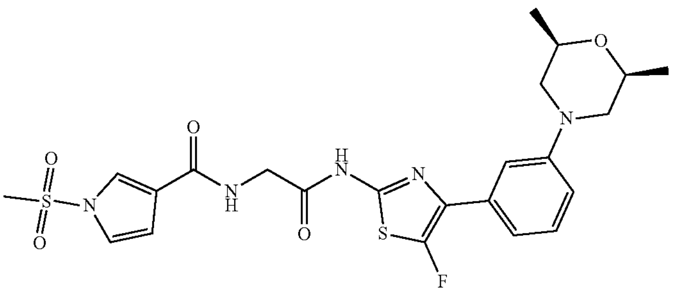 |

-continued
| # | Compound |
|---|---|
| 182 | 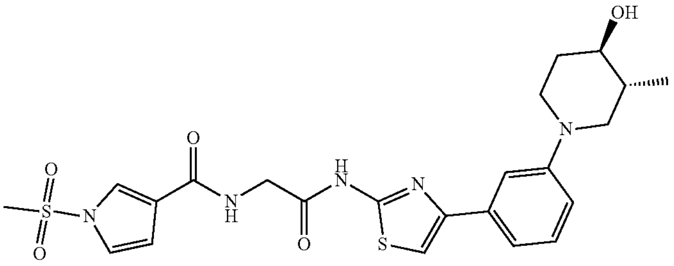 |
| 183 | 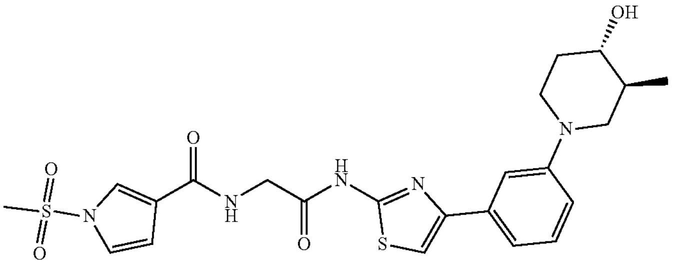 |
| 184 | 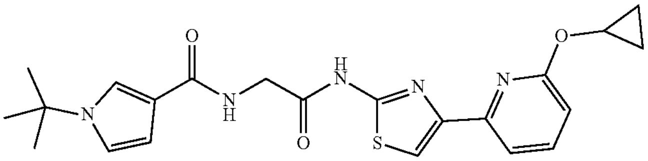 [SMILES: CC(C)(C)n1ccc(C(=O)NCC(=O)Nc2nc(-c3cccc(OC4CC4)n3)cs2)c1] |
| 185 | 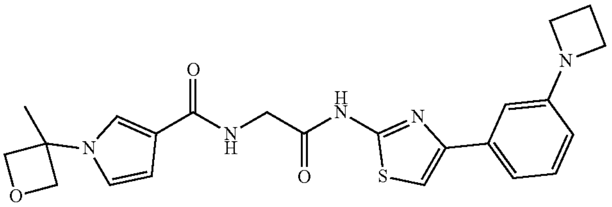 [SMILES: CC1(n2ccc(C(=O)NCC(=O)Nc3nc(-c4cccc(N5CCC5)c4)cs3)c2)COC1] |
| 186 | 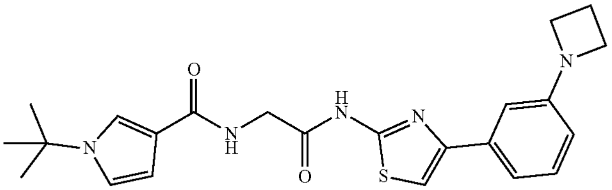 [SMILES: CC(C)(C)n1ccc(C(=O)NCC(=O)Nc2nc(-c3cccc(N4CCC4)c3)cs2)c1] |
| 187 | 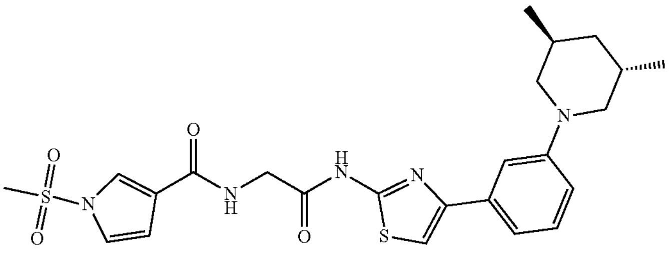 (±) |

-continued
| # | Compound |
|---|---|
| 188 | 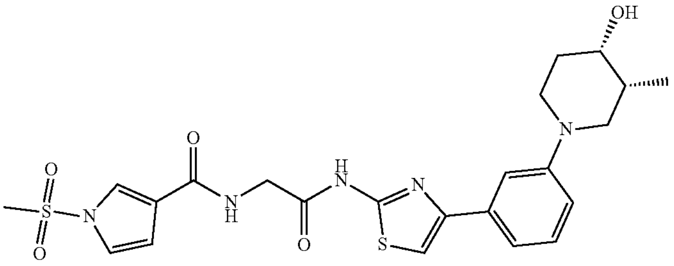 |
| 189 | 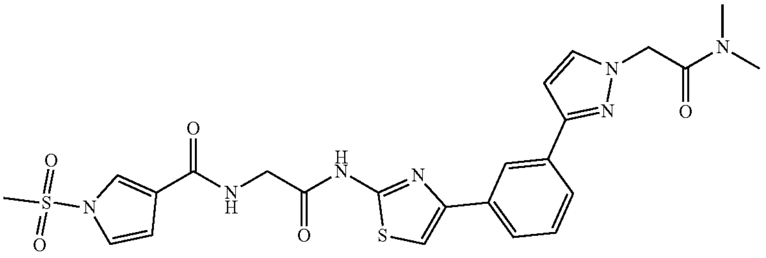 |
| 190 | 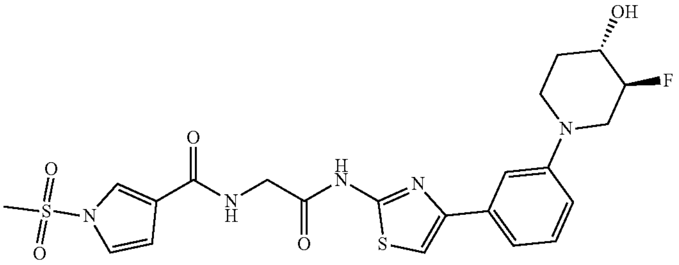 [SMILES: CS(=O)(=O)n1ccc(C(=O)NCC(=O)Nc2nc(-c3cccc(N4CC[C@H](O)[C@@H](F)C4)c3)cs2)c1] |
| 191 | 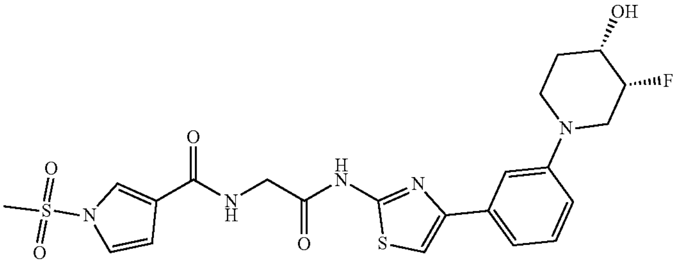 [SMILES: CS(=O)(=O)n1ccc(C(=O)NCC(=O)Nc2nc(-c3cccc(N4CC[C@H](O)[C@H](F)C4)c3)cs2)c1] |
| 193 | 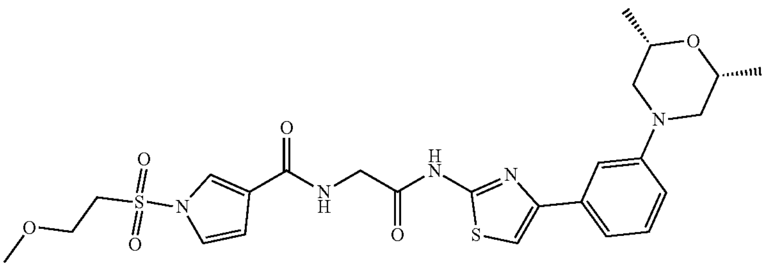 |

-continued
| # | Compound |
|---|---|
| 194 | 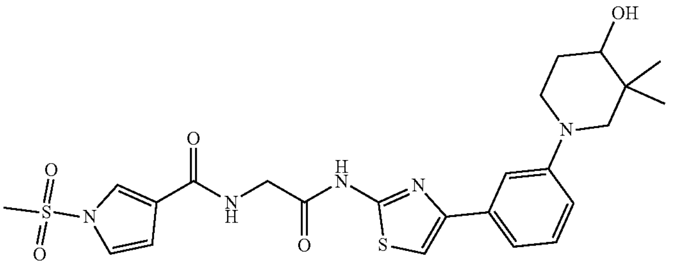 (±) |
| 195 | 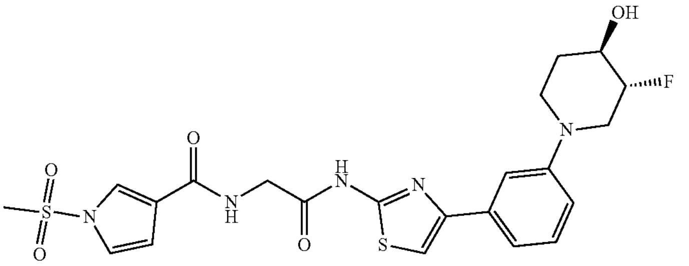 [SMILES: CS(=O)(=O)n1ccc(C(=O)NCC(=O)Nc2nc(-c3cccc(N4CC[C@@H](O)[C@H](F)C4)c3)cs2)c1] |
| 196 | 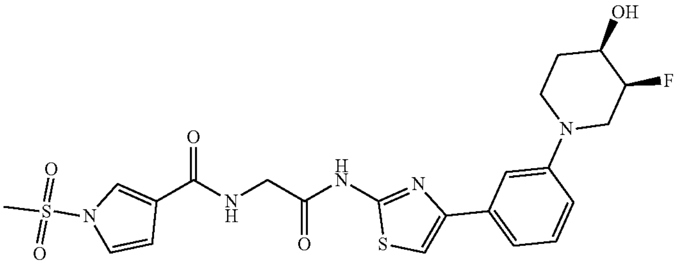 [SMILES: CS(=O)(=O)n1ccc(C(=O)NCC(=O)Nc2nc(-c3cccc(N4CC[C@@H](O)[C@@H](F)C4)c3)cs2)c1] |
| 167 | 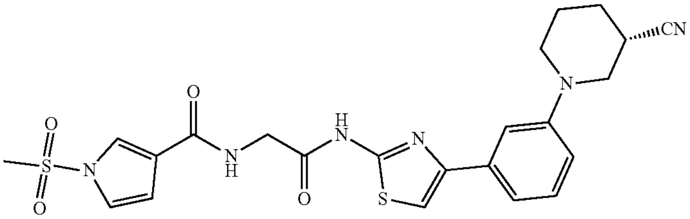 [SMILES: CS(=O)(=O)n1ccc(C(=O)NCC(=O)Nc2nc(-c3cccc(N4CCC[C@H](C#N)C4)c3)cs2)c1] |
| 168 | 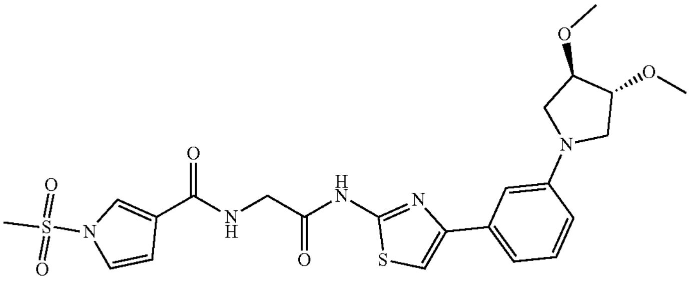 (±) |

-continued
| # | Compound |
|---|---|
| 199 | 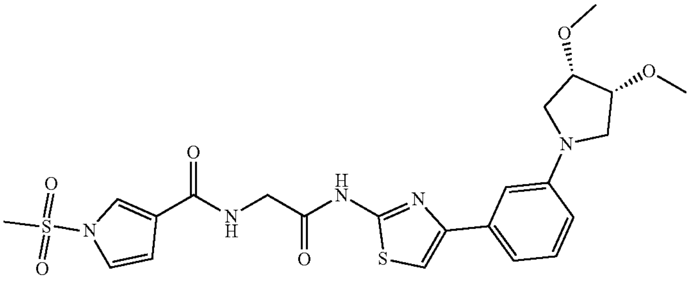 |
| 200 | 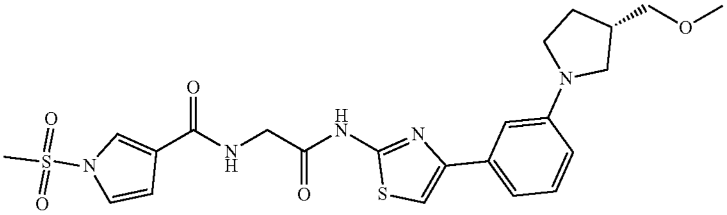 |
| 201 | 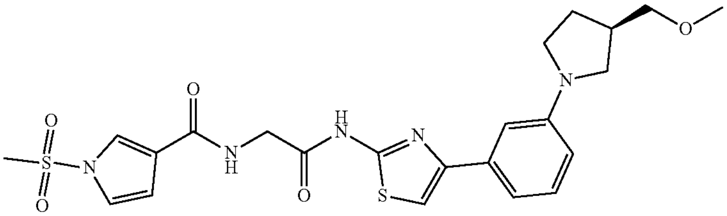 |
| 202 | 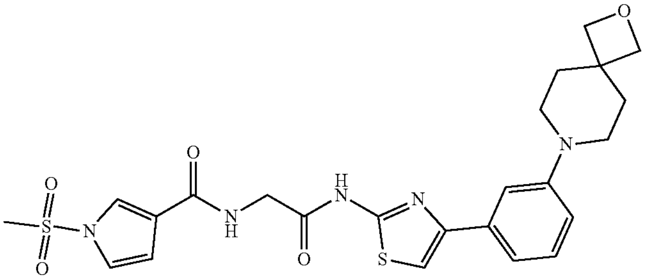 [SMILES: CS(=O)(=O)n1ccc(C(=O)NCC(=O)Nc2nc(-c3cccc(N4CCC5(CC4)COC5)c3)cs2)c1] |
| 203 | 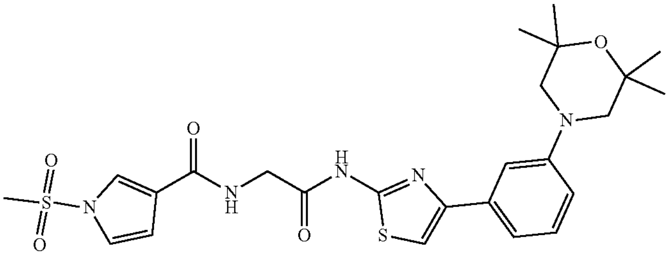 |
| 204 | 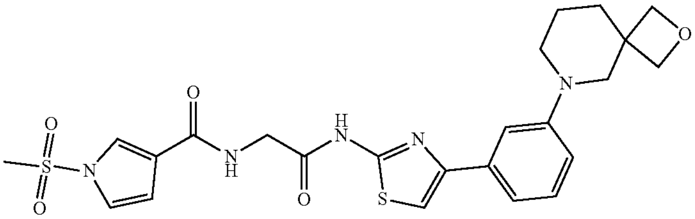 [SMILES: CS(=O)(=O)n1ccc(C(=O)NCC(=O)Nc2nc(-c3cccc(N4CCCC5(COC5)C4)c3)cs2)c1] |

-continued
| # | Compound |
|---|---|
| 205 | 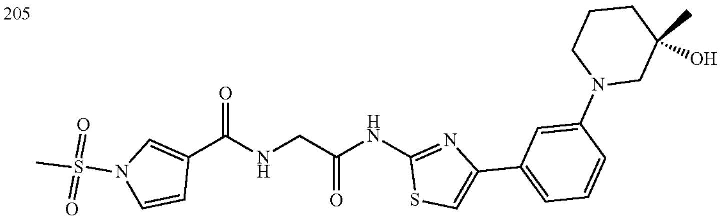 |
| 206 | 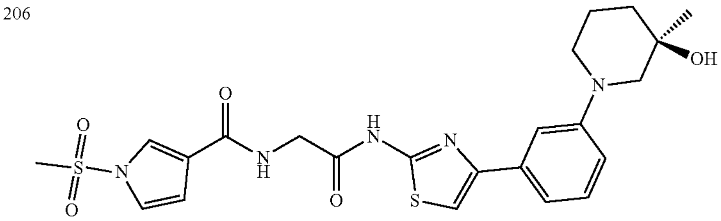 |
| 207 | 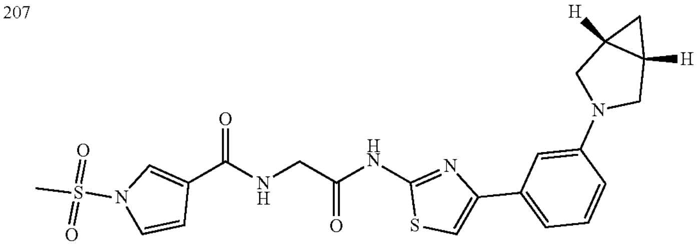 |
| 208 | 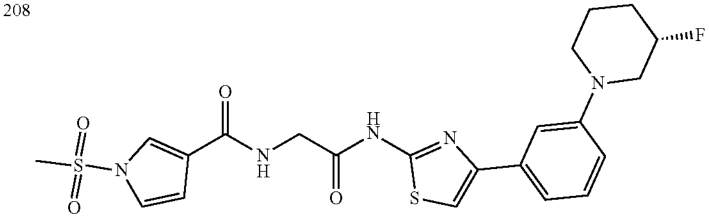 |
| 209 | 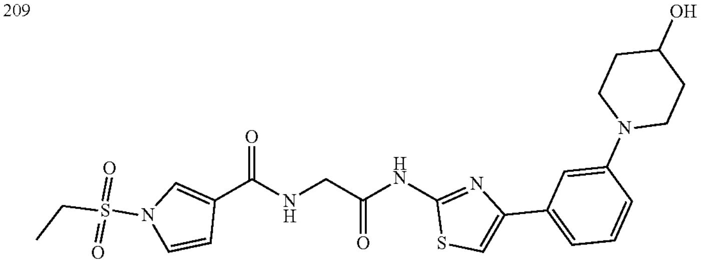 |
| 210 | 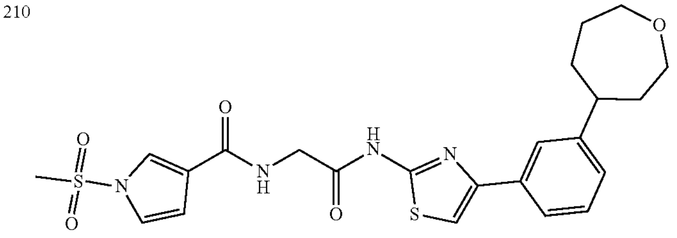 |

-continued
| # | Compound |
|---|---|
| 211 | 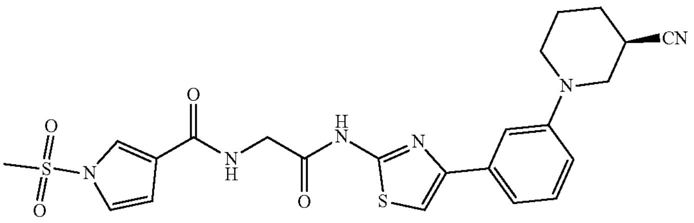 |
| 212 | 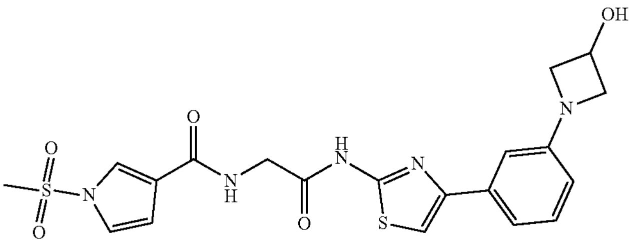 [SMILES: CS(=O)(=O)n1ccc(C(=O)NCC(=O)Nc2nc(-c3cccc(N4CC(O)C4)c3)cs2)c1] |
| 213 | 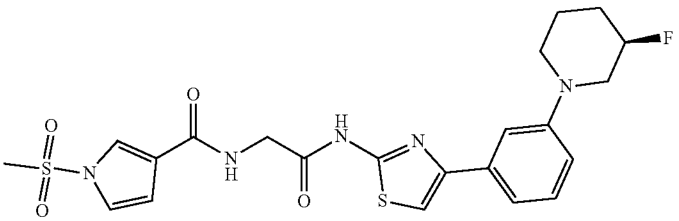 [SMILES: CS(=O)(=O)n1ccc(C(=O)NCC(=O)Nc2nc(-c3cccc(N4CCC[C@@H](F)C4)c3)cs2)c1] |
| 214 | 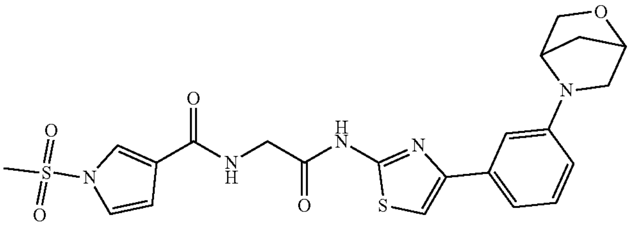 [SMILES: CS(=O)(=O)n1ccc(C(=O)NCC(=O)Nc2nc(-c3cccc(N4CC5CC4CO5)c3)cs2)c1] |
| 215 | 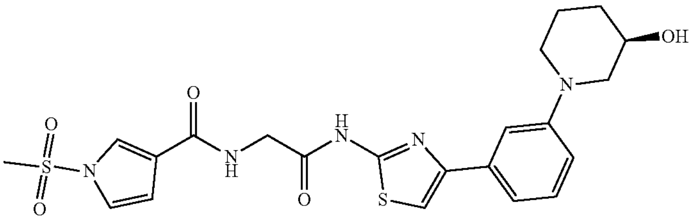 |
| 216 | 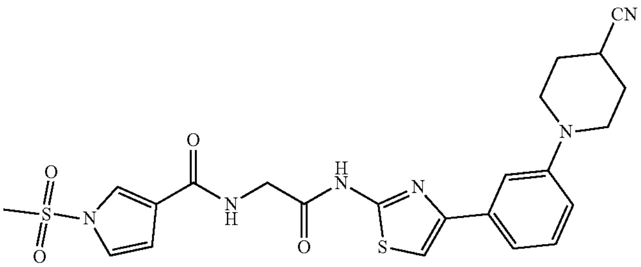 [SMILES: CS(=O)(=O)n1ccc(C(=O)NCC(=O)Nc2nc(-c3cccc(N4CCC(C#N)CC4)c3)cs2)c1] |

-continued
| # | Compound |
|---|---|
| 217 | 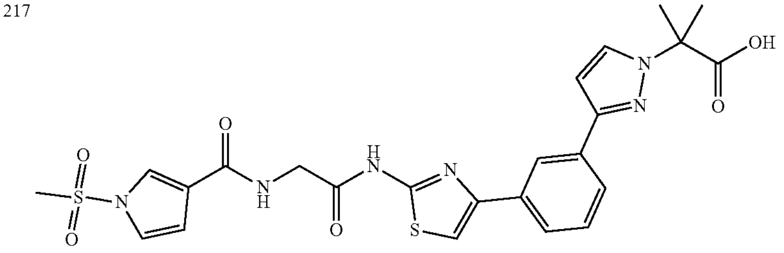 |
| 218 | 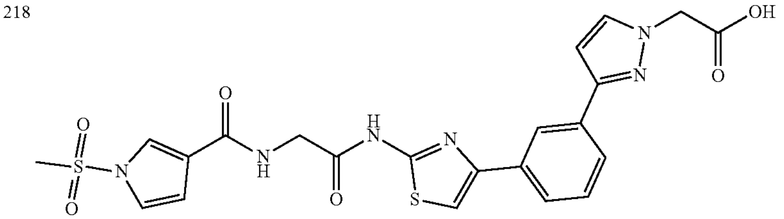 |
| 219 | 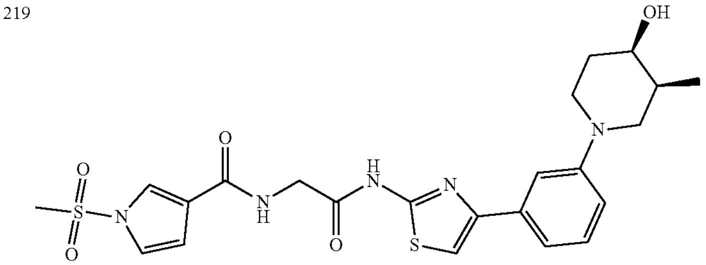 |
| 220 | 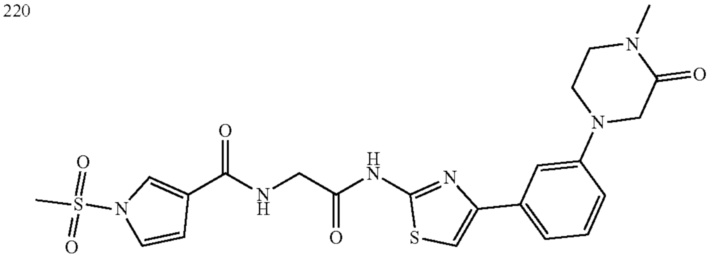 |
| 221 | 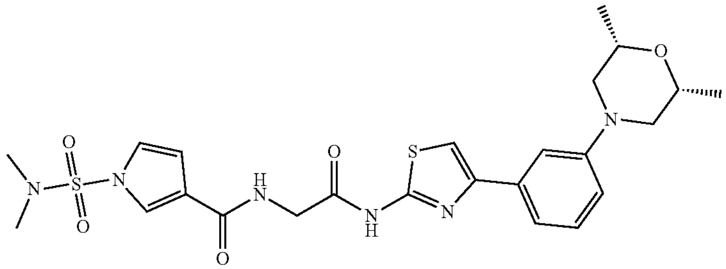 |
| 222 | 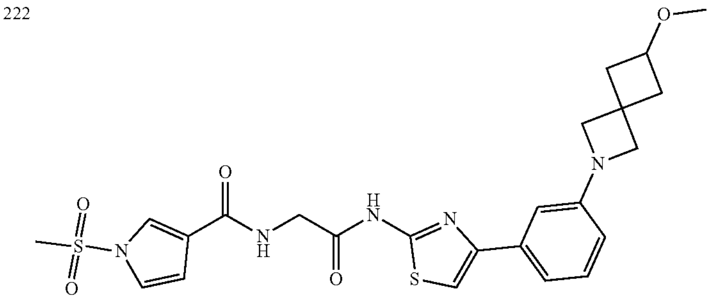 |

-continued
| # | Compound |
|---|---|
| 223 | 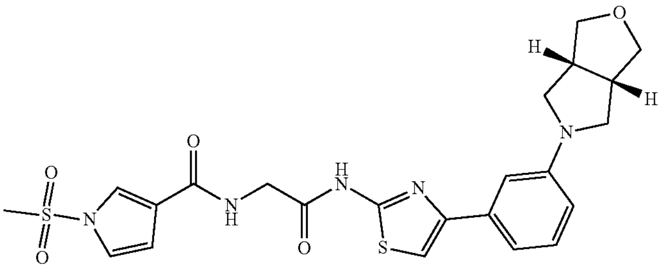 [SMILES: CS(=O)(=O)n1ccc(C(=O)NCC(=O)Nc2nc(-c3cccc(N4C[C@H]5COC[C@H]5C4)c3)cs2)c1] |
| 224 | 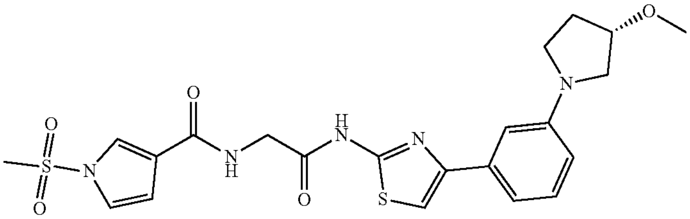 |
| 225 | 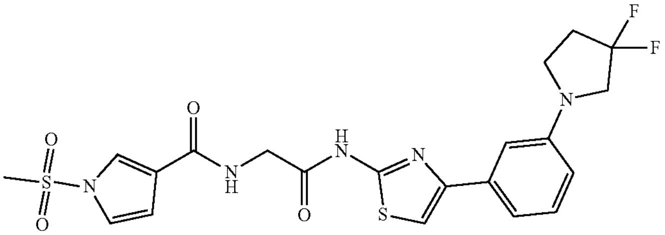 [SMILES: CS(=O)(=O)n1ccc(C(=O)NCC(=O)Nc2nc(-c3cccc(N4CCC(F)(F)C4)c3)cs2)c1] |
| 226 | 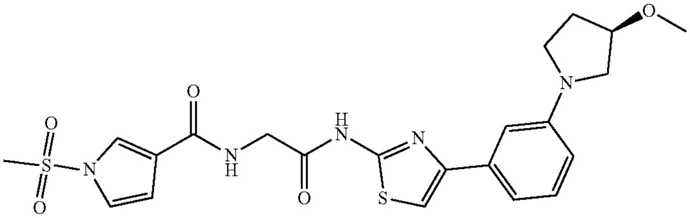 |
| 227 | 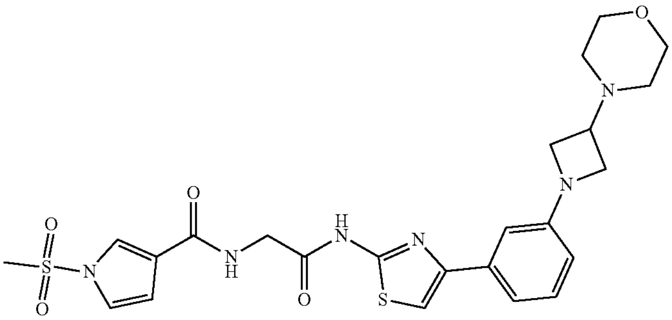 [SMILES: CS(=O)(=O)n1ccc(C(=O)NCC(=O)Nc2nc(-c3cccc(N4CC(N5CCOCC5)C4)c3)cs2)c1] |
| 228 | 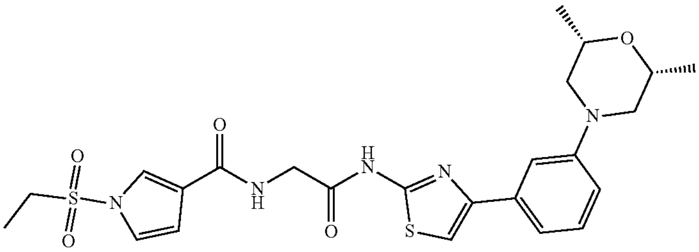 [SMILES: CCS(=O)(=O)n1ccc(C(=O)NCC(=O)Nc2nc(-c3cccc(N4C[C@@H](C)O[C@@H](C)C4)c3)cs2)c1] |

-continued
| # | Compound |
|---|---|
| 229 | 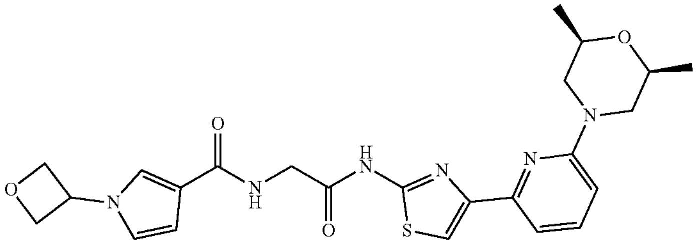 [SMILES: C[C@@H]1CN(c2cccc(-c3csc(NC(=O)CNC(=O)c4ccn(C5COC5)c4)n3)n2)C[C@H](C)O1] |
| 230 | 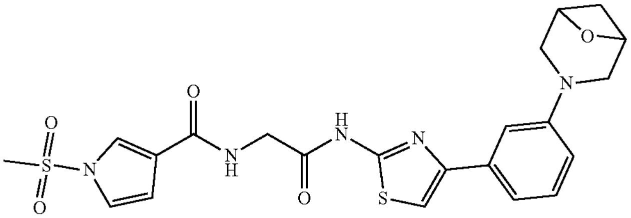 [SMILES: CS(=O)(=O)n1ccc(C(=O)NCC(=O)Nc2nc(-c3cccc(N4CC5CC(C4)O5)c3)cs2)c1] |
| 231 | 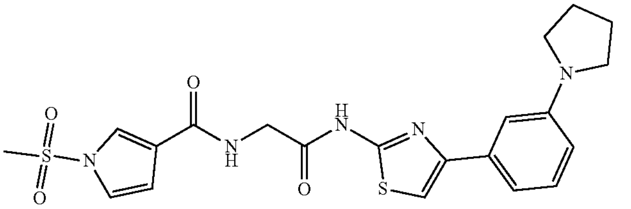 [SMILES: CS(=O)(=O)n1ccc(C(=O)NCC(=O)Nc2nc(-c3cccc(N4CCCC4)c3)cs2)c1] |
| 232 | 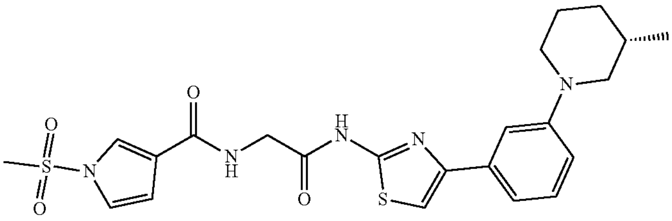 |
| 233 | 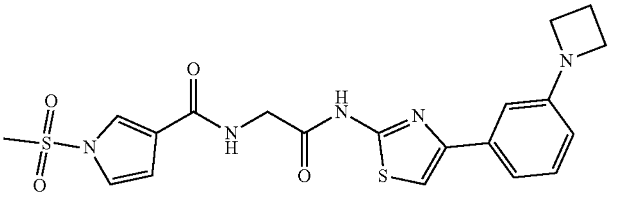 [SMILES: CS(=O)(=O)n1ccc(C(=O)NCC(=O)Nc2nc(-c3cccc(N4CCC4)c3)cs2)c1] |
| 234 | 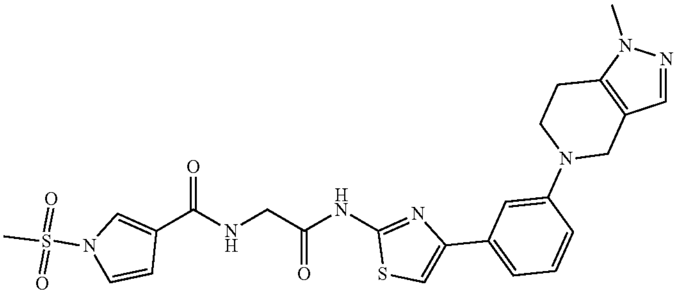 [SMILES: Cn1ncc2c1CCN(c1cccc(-c3csc(NC(=O)CNC(=O)c4ccn(S(C)(=O)=O)c4)n3)c1)C2] |

-continued
| # | Compound |
|---|---|
| 235 | 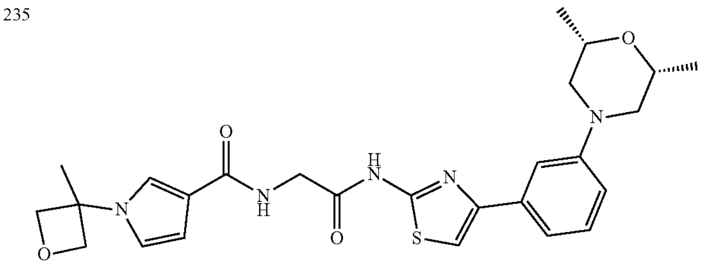 |
| 236 | 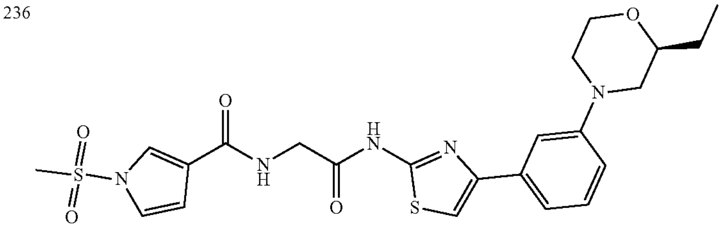 |
| 237 | 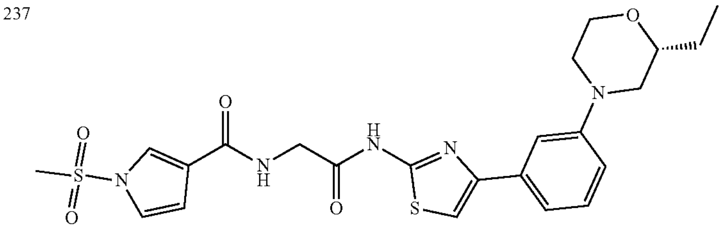 |
| 238 | 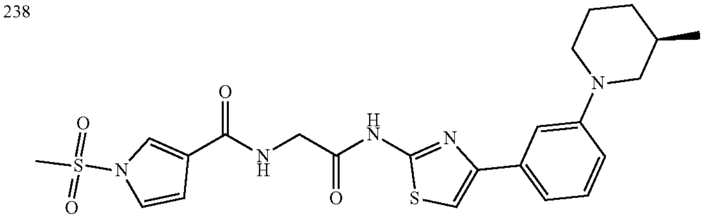 |
| 239 | 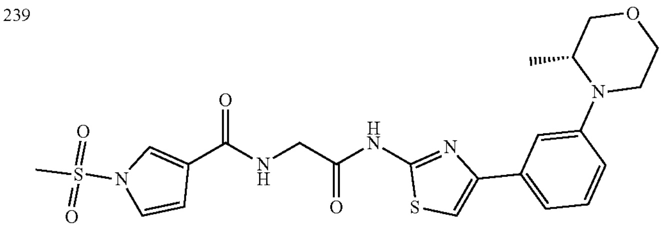 |
| 241 | 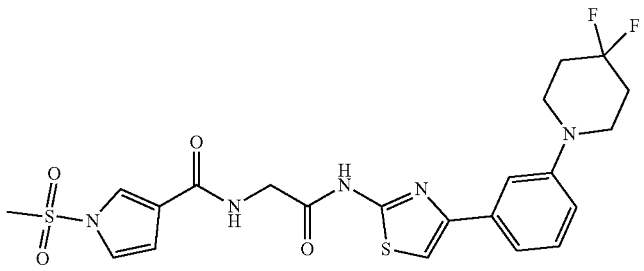 [SMILES: CS(=O)(=O)n1ccc(C(=O)NCC(=O)Nc2nc(-c3cccc(N4CCC(F)(F)CC4)c3)cs2)c1] |

-continued
| # | Compound |
|---|---|
| 242 | 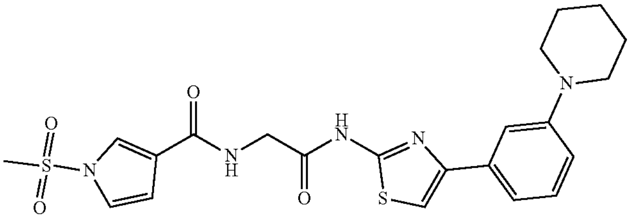 [SMILES: CS(=O)(=O)n1ccc(C(=O)NCC(=O)Nc2nc(-c3cccc(N4CCCCC4)c3)cs2)c1] |
| 243 | 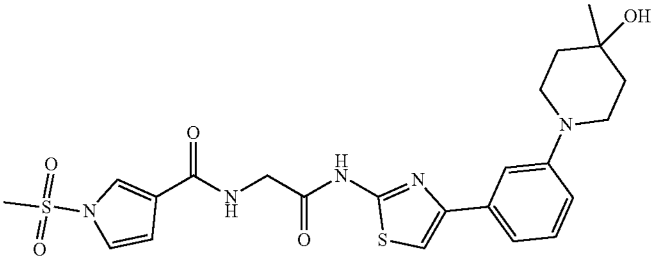 [SMILES: CC1(O)CCN(c2cccc(-c3csc(NC(=O)CNC(=O)c4ccn(S(C)(=O)=O)c4)n3)c2)CC1] |
| 244 | 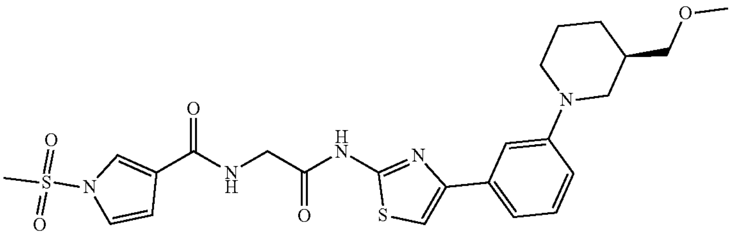 |
| 245 | 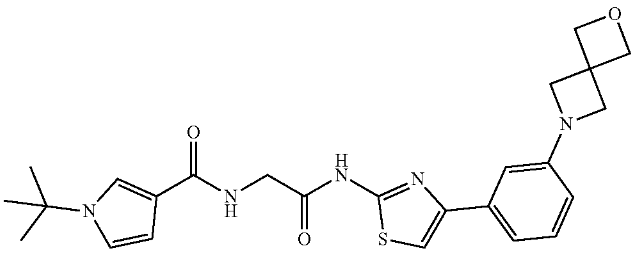 [SMILES: CC(C)(C)n1ccc(C(=O)NCC(=O)Nc2nc(-c3cccc(N4CC5(COC5)C4)c3)cs2)c1] |
| 246 | 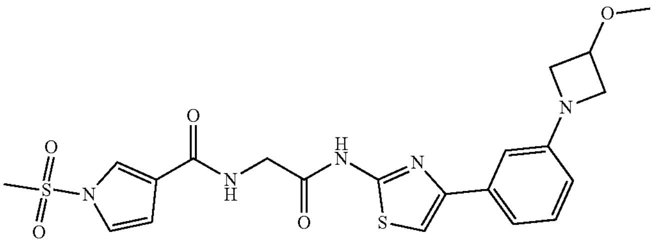 |
| 247 | 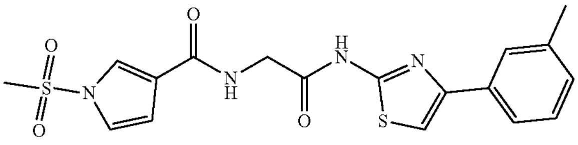 [SMILES: Cc1cccc(-c2csc(NC(=O)CNC(=O)c3ccn(S(C)(=O)=O)c3)n2)c1] |
| 248 | 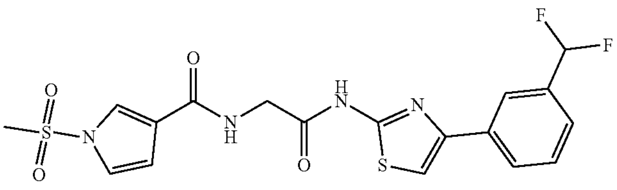 [SMILES: CS(=O)(=O)n1ccc(C(=O)NCC(=O)Nc2nc(-c3cccc(C(F)F)c3)cs2)c1] |

-continued
| # | Compound |
|---|---|
| 249 | 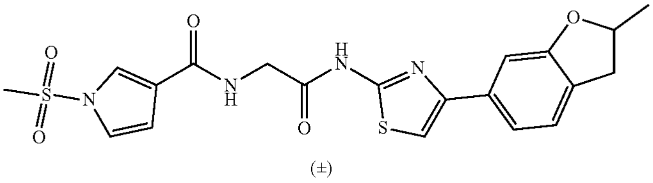 |
| 250 | 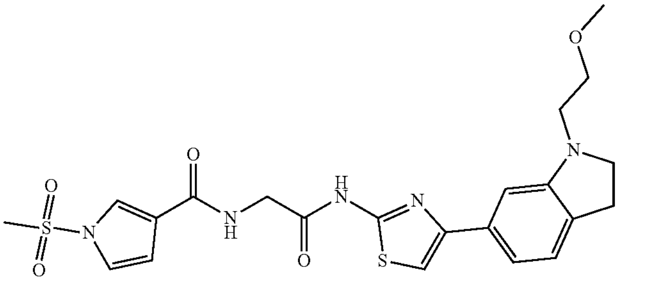 [SMILES: COCCN1CCc2ccc(-c3csc(NC(=O)CNC(=O)c4ccn(S(C)(=O)=O)c4)n3)cc21] |
| 251 | 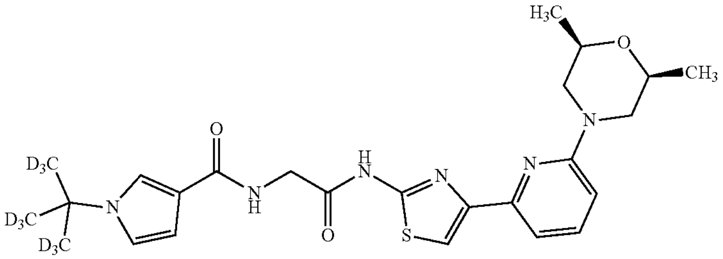 [SMILES: [2H]C([2H])([2H])C(n1ccc(C(=O)NCC(=O)Nc2nc(-c3cccc(N4C[C@@H](C)O[C@@H](C)C4)n3)cs2)c1)(C([2H])([2H])[2H])C([2H])([2H])[2H]] |
| 252 | 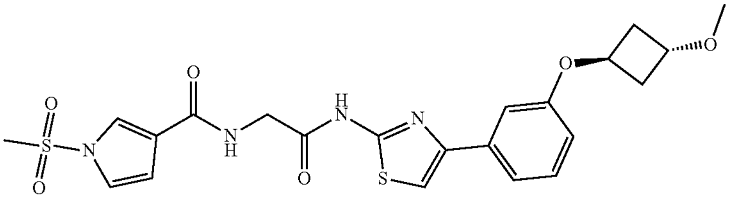 |
| 253 | 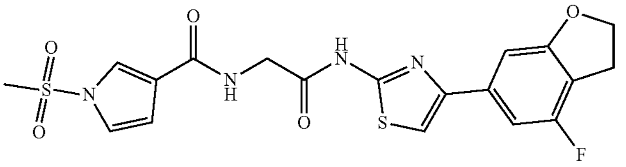 [SMILES: CS(=O)(=O)n1ccc(C(=O)NCC(=O)Nc2nc(-c3cc(F)c4c(c3)OCC4)cs2)c1] |
| 254 | 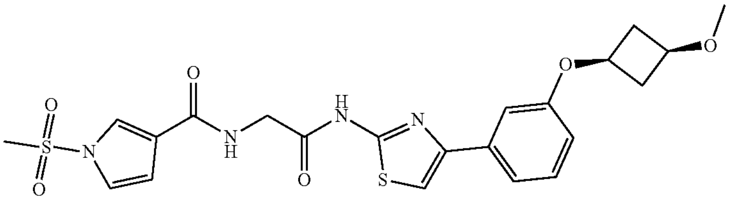 |
| 255 | 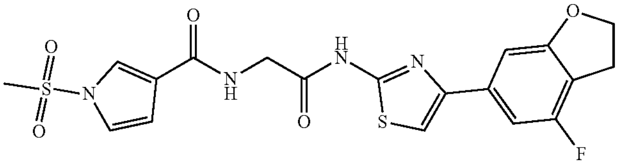 [SMILES: CS(=O)(=O)n1ccc(C(=O)NCC(=O)Nc2nc(-c3cc(F)c4c(c3)OCC4)cs2)c1] |

-continued
| # | Compound |
|---|---|
| 256 | 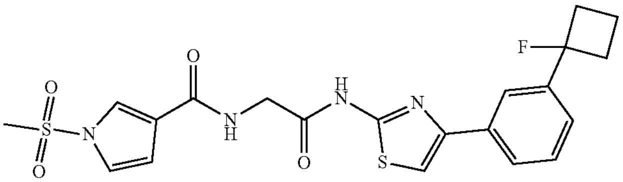 [SMILES: CS(=O)(=O)n1ccc(C(=O)NCC(=O)Nc2nc(-c3cccc(C4(F)CCC4)c3)cs2)c1] |
| 257 | 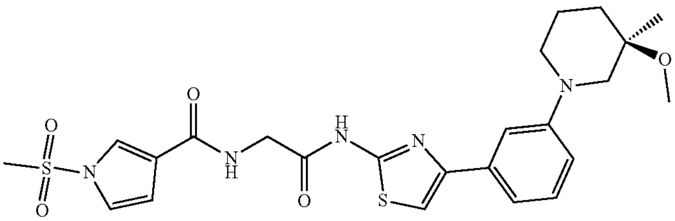 |
| 258 | 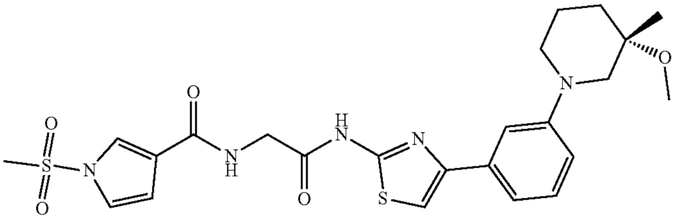 |
| 259 | 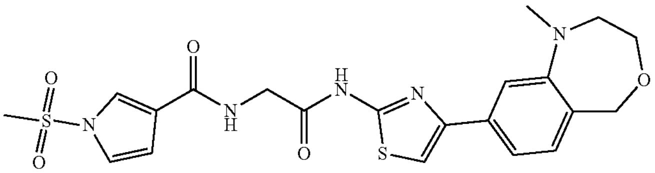 [SMILES: CN1CCOCc2ccc(-c3csc(NC(=O)CNC(=O)c4ccn(S(C)(=O)=O)c4)n3)cc21] |
| 260 | 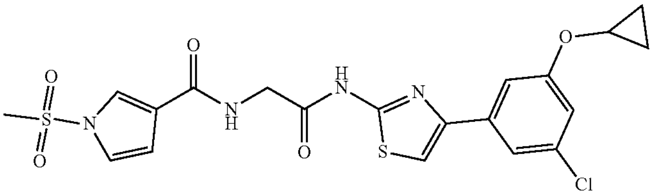 [SMILES: CS(=O)(=O)n1ccc(C(=O)NCC(=O)Nc2nc(-c3cc(Cl)cc(OC4CC4)c3)cs2)c1] |
| 261 | 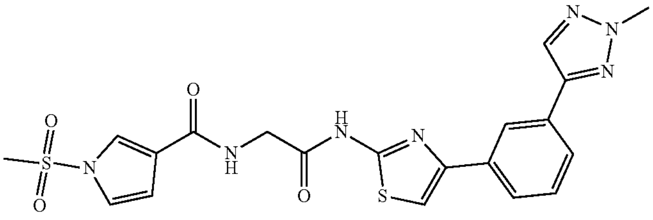 |
| 262 | 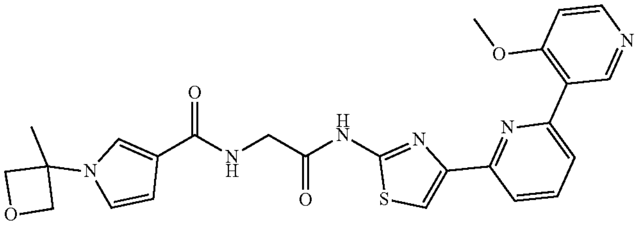 [SMILES: COc1ccncc1-c1cccc(-c2csc(NC(=O)CNC(=O)c3ccn(C4(C)COC4)c3)n2)n1] |

-continued
| # | Compound |
|---|---|
| 263 | 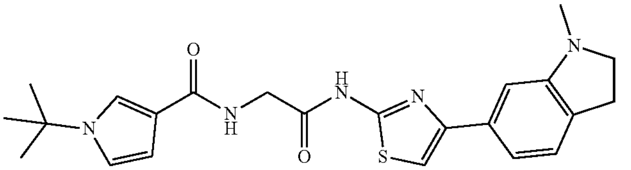 [SMILES: CN1CCc2ccc(-c3csc(NC(=O)CNC(=O)c4ccn(C(C)(C)C)c4)n3)cc21] |
| 264 | 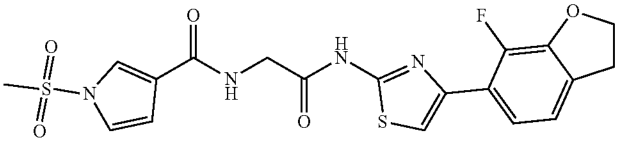 [SMILES: CS(=O)(=O)n1ccc(C(=O)NCC(=O)Nc2nc(-c3ccc4c(c3F)OCC4)cs2)c1] |
| 265 | 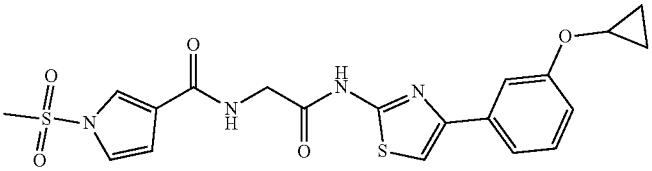 [SMILES: CS(=O)(=O)n1ccc(C(=O)NCC(=O)Nc2nc(-c3cccc(OC4CC4)c3)cs2)c1] |
| 266 | 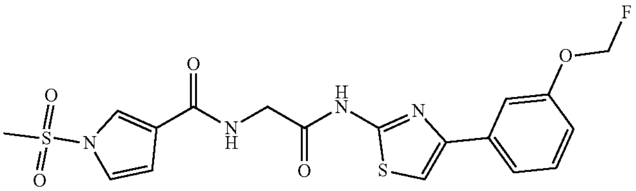 [SMILES: CS(=O)(=O)n1ccc(C(=O)NCC(=O)Nc2nc(-c3cccc(OCF)c3)cs2)c1] |
| 267 | 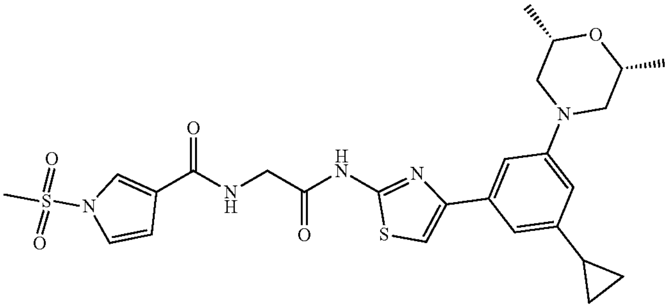 |
| 268 | 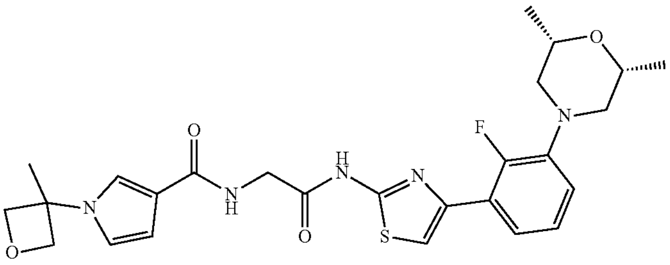 [SMILES: C[C@@H]1CN(c2cccc(-c3csc(NC(=O)CNC(=O)c4ccn(C5(C)COC5)c4)n3)c2F)C[C@H](C)O1] |
| 269 | 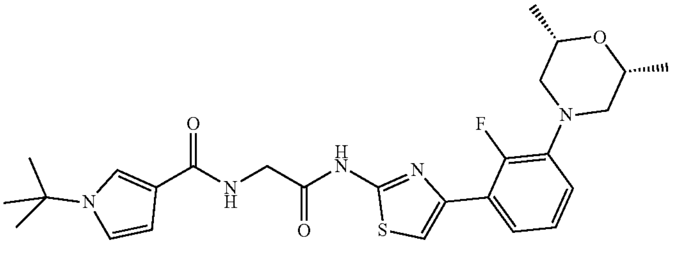 [SMILES: C[C@@H]1CN(c2cccc(-c3csc(NC(=O)CNC(=O)c4ccn(C(C)(C)C)c4)n3)c2F)C[C@H](C)O1] |

-continued
| # | Compound |
|---|---|
| 270 | 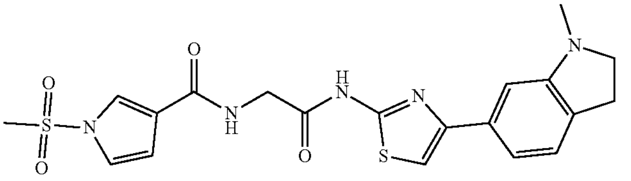 [SMILES: CN1CCc2ccc(-c3csc(NC(=O)CNC(=O)c4ccn(S(C)(=O)=O)c4)n3)cc21] |
| 271 | 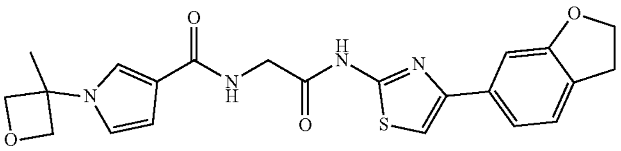 [SMILES: CC1(n2ccc(C(=O)NCC(=O)Nc3nc(-c4ccc5c(c4)OCC5)cs3)c2)COC1] |
| 272 | 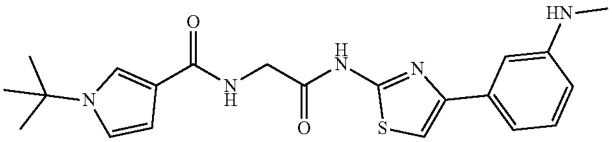 [SMILES: CNc1cccc(-c2csc(NC(=O)CNC(=O)c3ccn(C(C)(C)C)c3)n2)c1] |
| 273 | 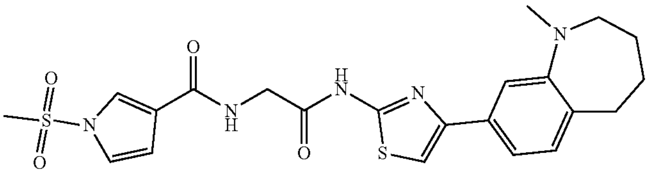 [SMILES: CN1CCCCc2ccc(-c3csc(NC(=O)CNC(=O)c4ccn(S(C)(=O)=O)c4)n3)cc21] |
| 274 | 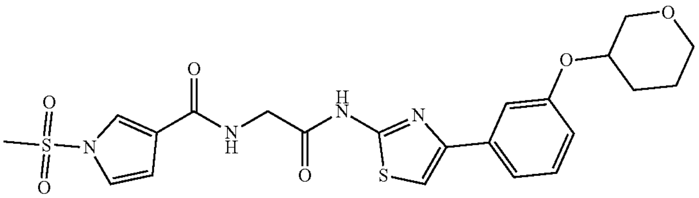 (±) |
| 275 | 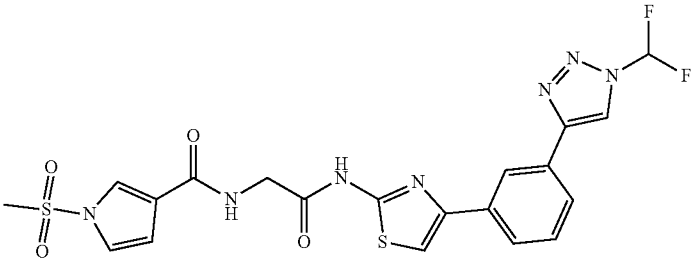 [SMILES: CS(=O)(=O)n1ccc(C(=O)NCC(=O)Nc2nc(-c3cccc(-c4cn(C(F)F)nn4)c3)cs2)c1] |
| 276 | 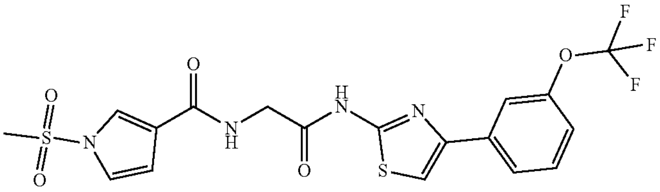 [SMILES: CS(=O)(=O)n1ccc(C(=O)NCC(=O)Nc2nc(-c3cccc(OC(F)(F)F)c3)cs2)c1] |

-continued
| # | Compound |
|---|---|
| 277 | 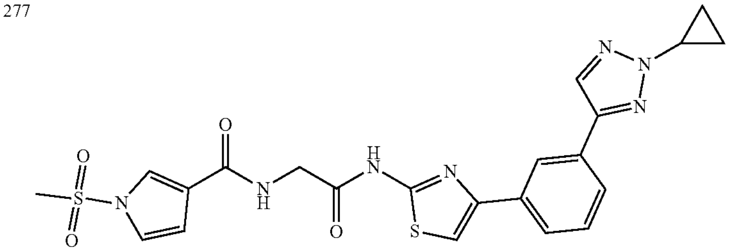 |
| 278 | 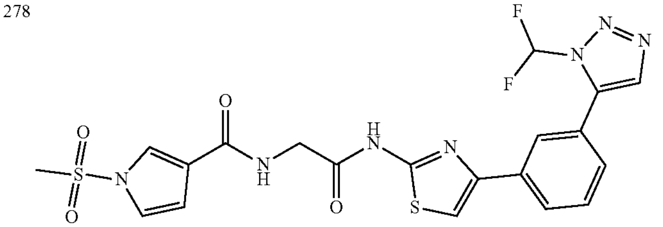 |
| 279 | 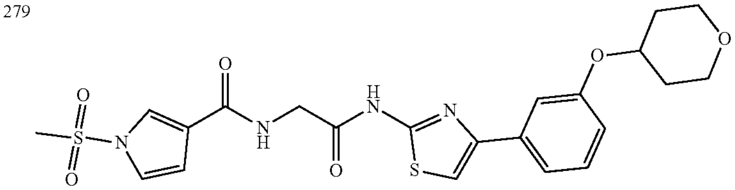 |
| 280 | 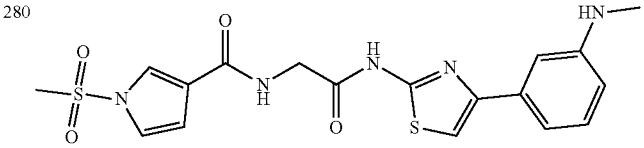 |
| 281 | 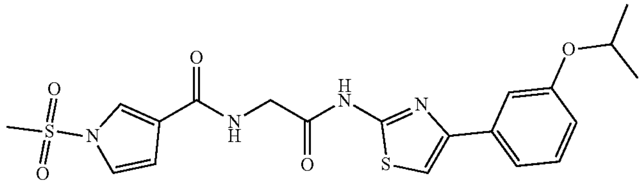 [SMILES: CC(C)Oc1cccc(-c2csc(NC(=O)CNC(=O)c3ccn(S(C)(=O)=O)c3)n2)c1] |
| 282 | 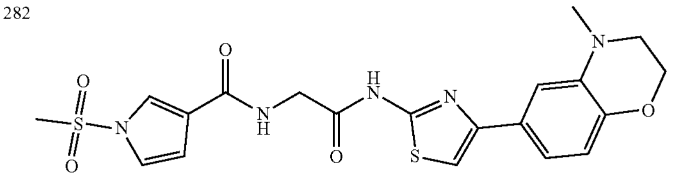 |
| 283 | 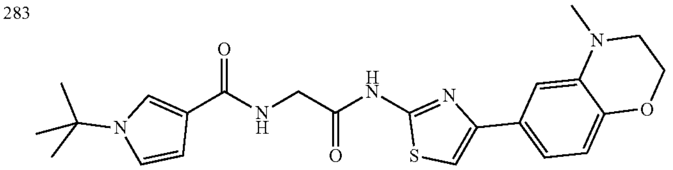 |

-continued
| # | Compound |
|---|---|
| 284 | 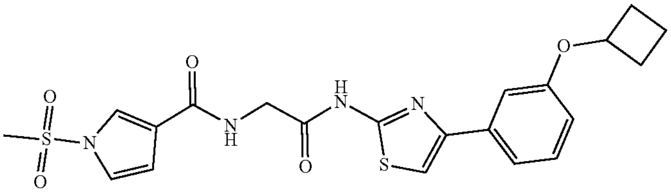 [SMILES: CS(=O)(=O)n1ccc(C(=O)NCC(=O)Nc2nc(-c3cccc(OC4CCC4)c3)cs2)c1] |
| 285 | 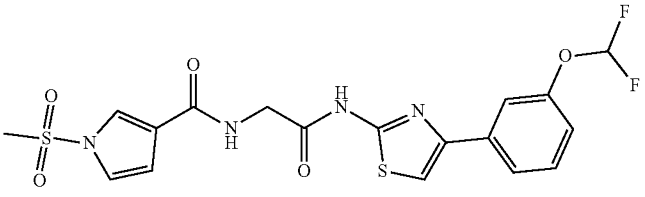 [SMILES: CS(=O)(=O)n1ccc(C(=O)NCC(=O)Nc2nc(-c3cccc(OC(F)F)c3)cs2)c1] |
| 286 | 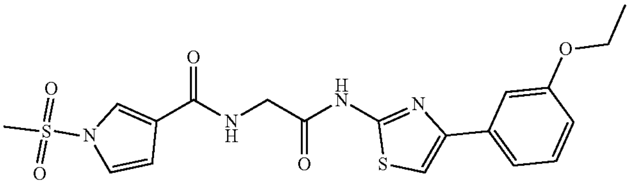 [SMILES: CCOc1cccc(-c2csc(NC(=O)CNC(=O)c3ccn(S(C)(=O)=O)c3)n2)c1] |
| 287 | 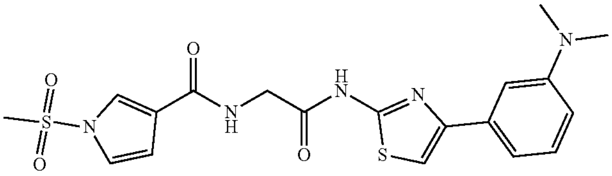 |
| 288 | 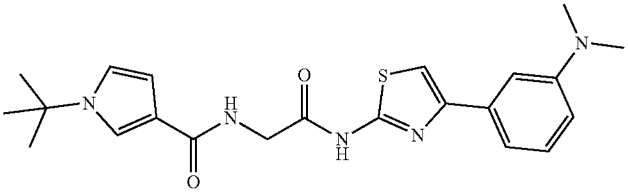 [SMILES: CN(C)c1cccc(-c2csc(NC(=O)CNC(=O)c3ccn(C(C)(C)C)c3)n2)c1] |
| 289 | 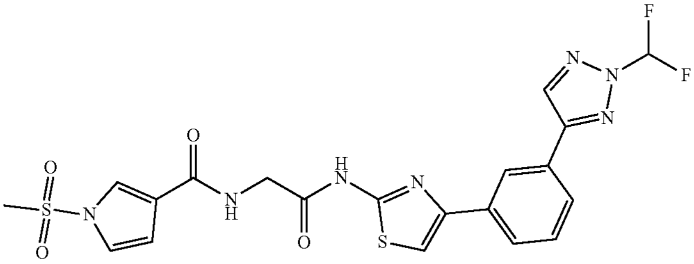 [SMILES: CS(=O)(=O)n1ccc(C(=O)NCC(=O)Nc2nc(-c3cccc(-c4cnn(C(F)F)n4)c3)cs2)c1] |
| 290 | 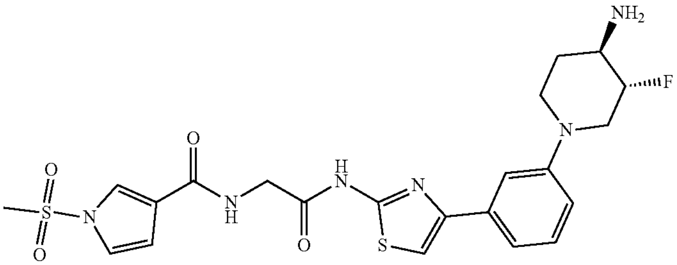 [SMILES: CS(=O)(=O)n1ccc(C(=O)NCC(=O)Nc2nc(-c3cccc(N4CC[C@@H](N)[C@H](F)C4)c3)cs2)c1] |

-continued
| # | Compound |
|---|---|
| 291 | 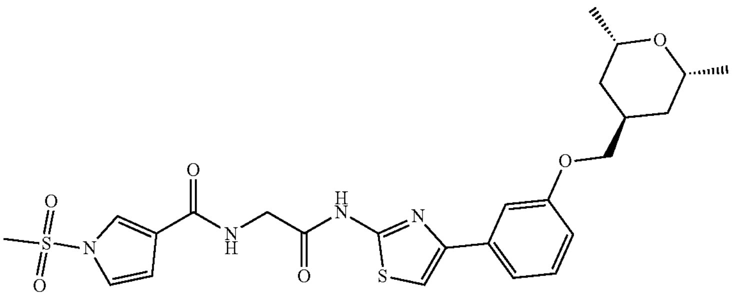 |
| 292 | 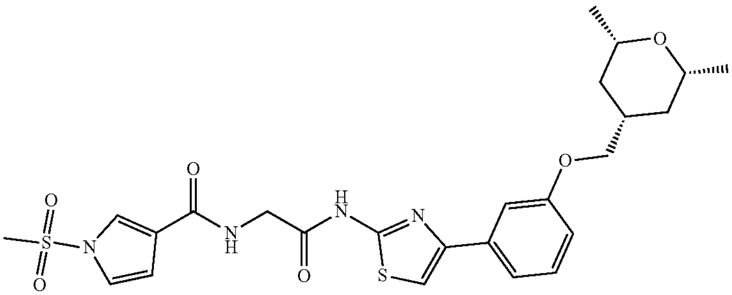 |
| 293 | 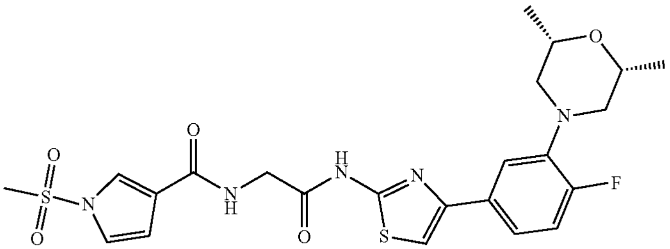 |
| 294 | 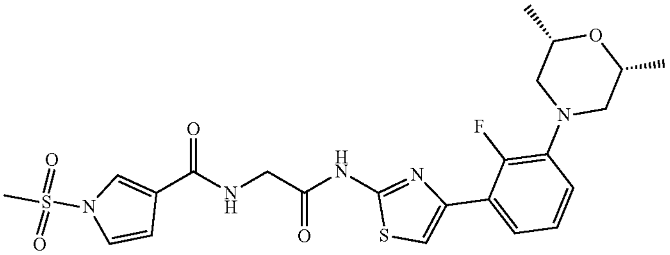 |
| 295 | 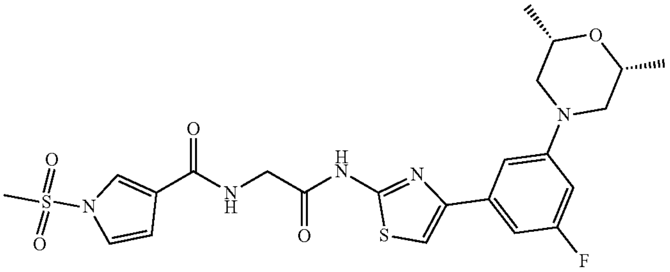 |

-continued
| # | Compound |
|---|---|
| 296 | 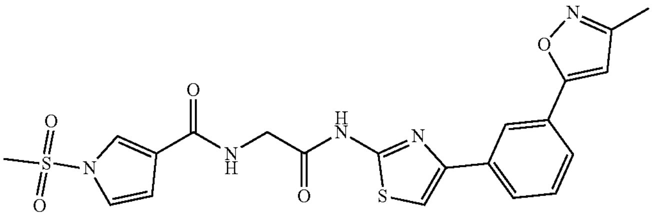 |
| 297 | 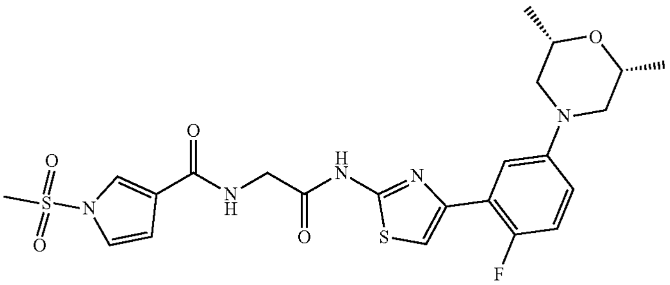 |
| 298 | 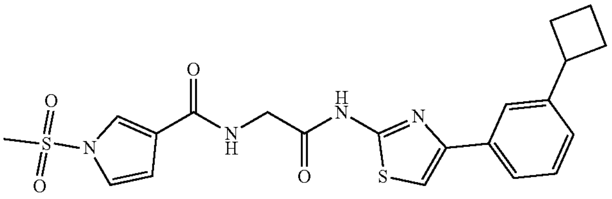 [SMILES: CS(=O)(=O)n1ccc(C(=O)NCC(=O)Nc2nc(-c3cccc(C4CCC4)c3)cs2)c1] |
| 299 | 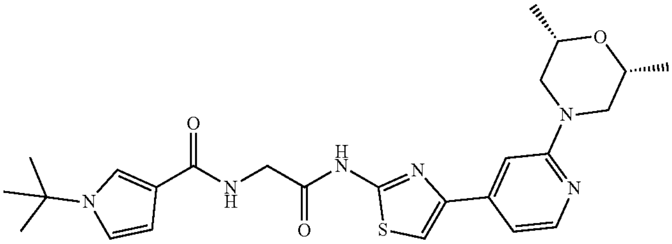 [SMILES: C[C@@H]1CN(c2cc(-c3csc(NC(=O)CNC(=O)c4ccn(C(C)(C)C)c4)n3)ccn2)C[C@H](C)O1] |
| 300 | 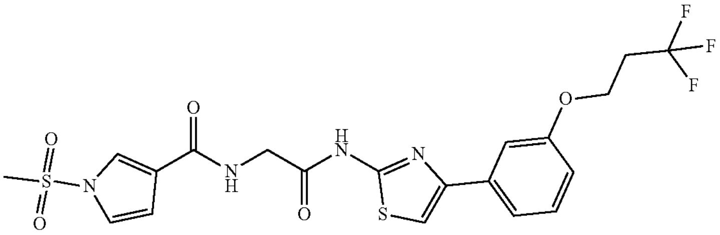 [SMILES: CS(=O)(=O)n1ccc(C(=O)NCC(=O)Nc2nc(-c3cccc(OCCC(F)(F)F)c3)cs2)c1] |
| 301 | 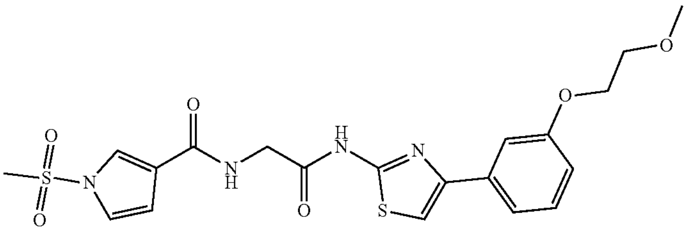 |

-continued
| # | Compound |
|---|---|
| 302 | 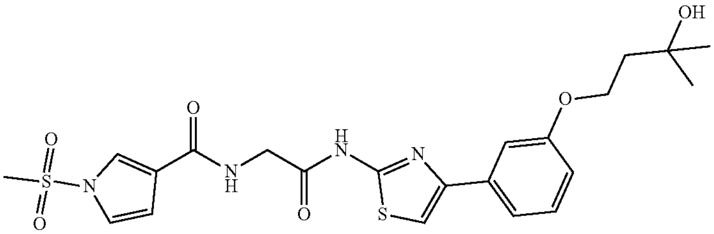 [SMILES: CC(C)(O)CCOc1cccc(-c2csc(NC(=O)CNC(=O)c3ccn(S(C)(=O)=O)c3)n2)c1] |
| 303 | 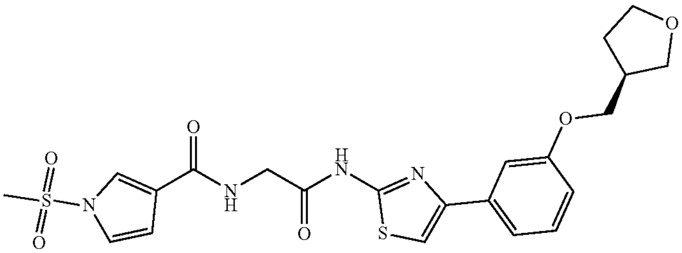 [SMILES: CS(=O)(=O)n1ccc(C(=O)NCC(=O)Nc2nc(-c3cccc(OC[C@H]4CCOC4)c3)cs2)c1] |
| 304 | 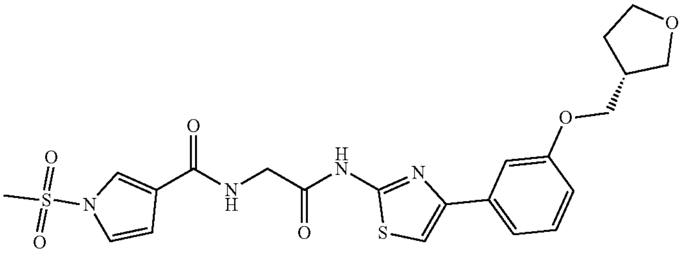 [SMILES: CS(=O)(=O)n1ccc(C(=O)NCC(=O)Nc2nc(-c3cccc(OC[C@@H]4CCOC4)c3)cs2)c1] |
| 305 | 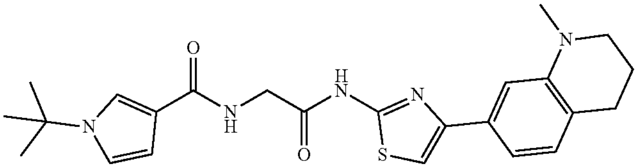 [SMILES: CN1CCCc2ccc(-c3csc(NC(=O)CNC(=O)c4ccn(C(C)(C)C)c4)n3)cc21] |
| 306 | 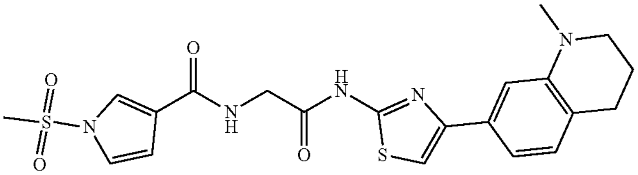 [SMILES: CN1CCCc2ccc(-c3csc(NC(=O)CNC(=O)c4ccn(S(C)(=O)=O)c4)n3)cc21] |
| 307 | 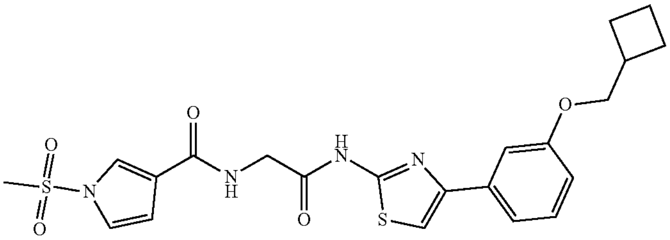 [SMILES: CS(=O)(=O)n1ccc(C(=O)NCC(=O)Nc2nc(-c3cccc(OCC4CCC4)c3)cs2)c1] |
| 308 | 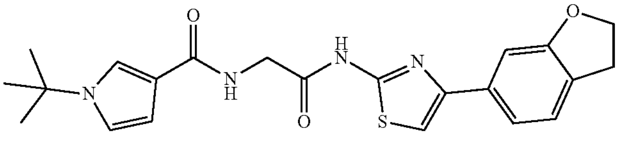 [SMILES: CC(C)(C)n1ccc(C(=O)NCC(=O)Nc2nc(-c3ccc4c(c3)OCC4)cs2)c1] |

-continued
| # | Compound |
|---|---|
| 309 | 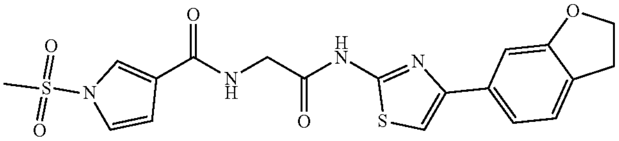 [SMILES: CS(=O)(=O)n1ccc(C(=O)NCC(=O)Nc2nc(-c3ccc4c(c3)OCC4)cs2)c1] |
| 310 | 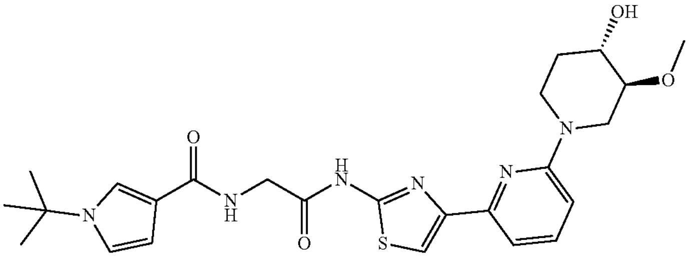 (±) |
| 311 | 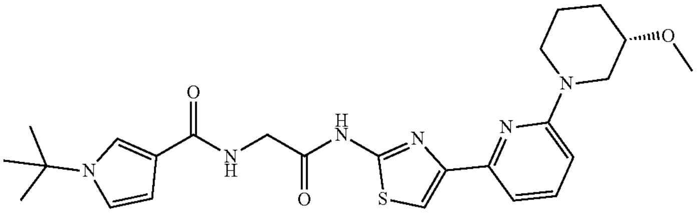 [SMILES: CO[C@H]1CCCN(c2cccc(-c3csc(NC(=O)CNC(=O)c4ccn(C(C)(C)C)c4)n3)n2)C1] |
| 312 | 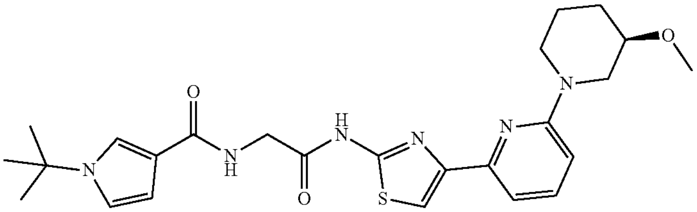 [SMILES: CO[C@@H]1CCCN(c2cccc(-c3csc(NC(=O)CNC(=O)c4ccn(C(C)(C)C)c4)n3)n2)C1] |
| 313 | 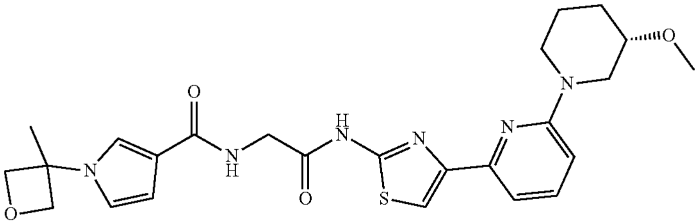 [SMILES: CO[C@H]1CCCN(c2cccc(-c3csc(NC(=O)CNC(=O)c4ccn(C5(C)COC5)c4)n3)n2)C1] |
| 314 | 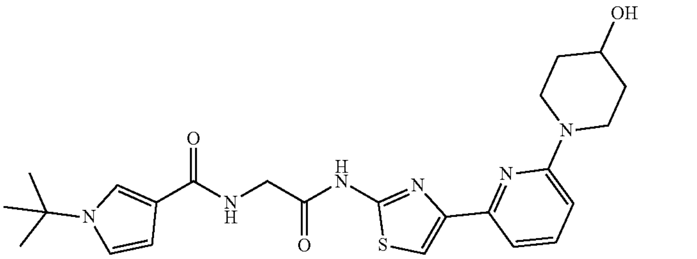 |
| 315 | 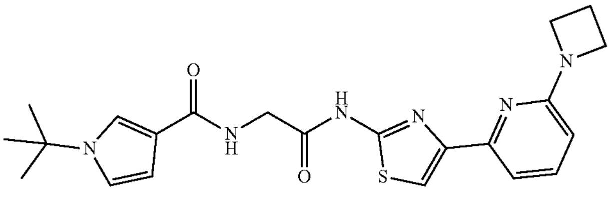 [SMILES: CC(C)(C)n1ccc(C(=O)NCC(=O)Nc2nc(-c3cccc(N4CCC4)n3)cs2)c1] |

-continued
| # | Compound |
|---|---|
| 316 | 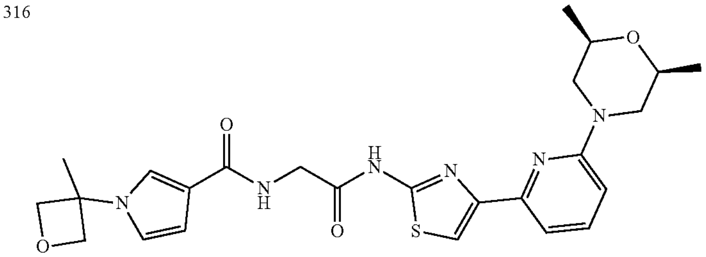 |
| 317 | 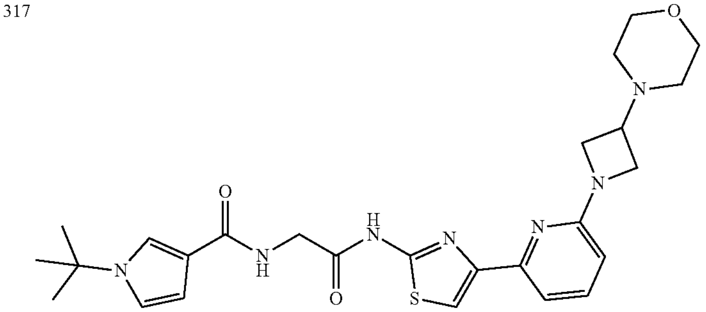 |
| 318 | 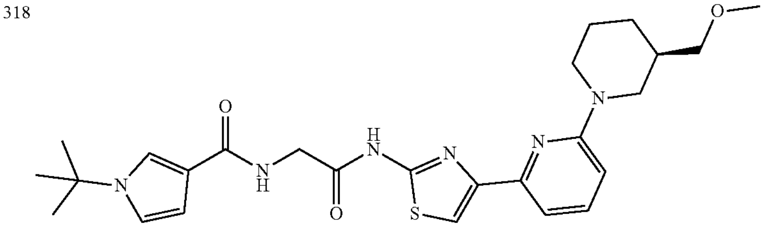 |
| 319 | 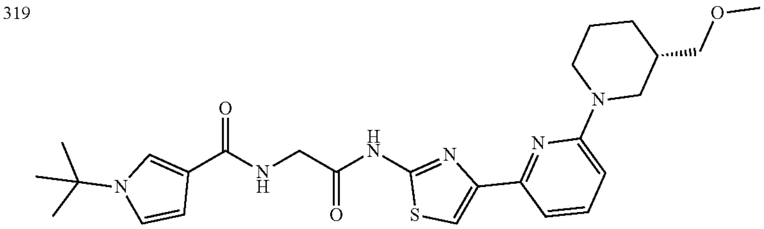 |
| 320 | 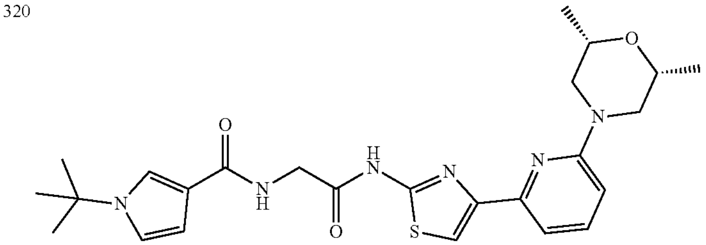 |
| 321 | 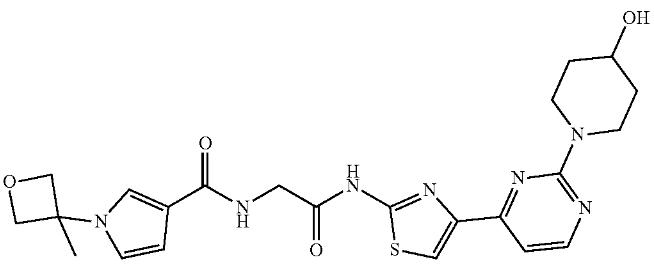 [SMILES: CC1(n2ccc(C(=O)NCC(=O)Nc3nc(-c4ccnc(N5CCC(O)CC5)n4)cs3)c2)COC1] |

-continued
| # | Compound |
|---|---|
| 322 | 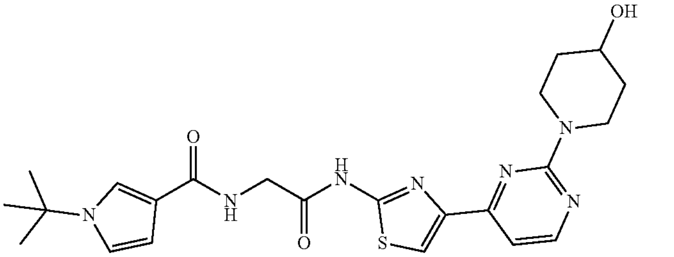 [SMILES: CC(C)(C)n1ccc(C(=O)NCC(=O)Nc2nc(-c3ccnc(N4CCC(O)CC4)n3)cs2)c1] |
| 324 | 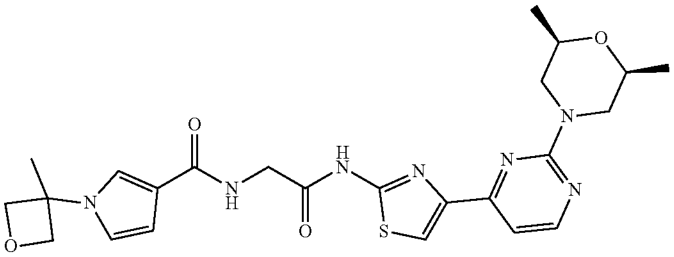 |
| 325 | 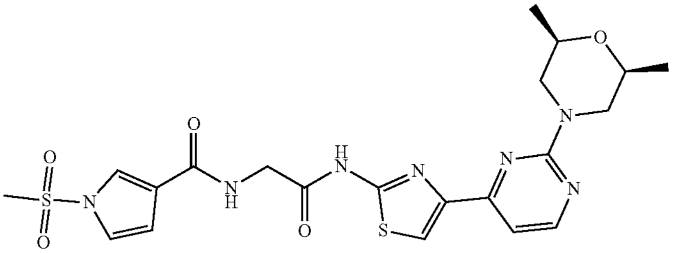 |
| 326 | 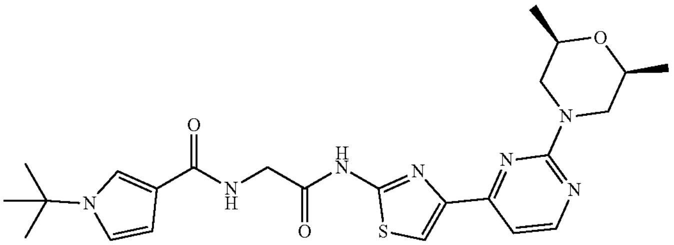 [SMILES: C[C@@H]1CN(c2nccc(-c3csc(NC(=O)CNC(=O)c4ccn(C(C)(C)C)c4)n3)n2)C[C@H](C)O1] |
| 327 | 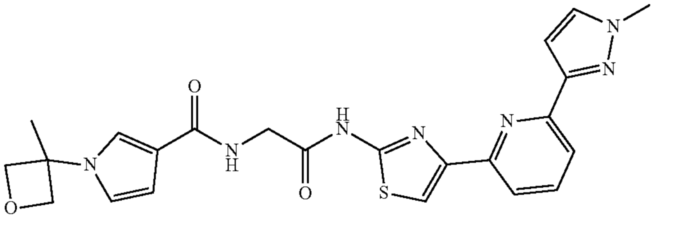 [SMILES: Cn1ccc(-c2cccc(-c3csc(NC(=O)CNC(=O)c4ccn(C5(C)COC5)c4)n3)n2)n1] |
| 328 | 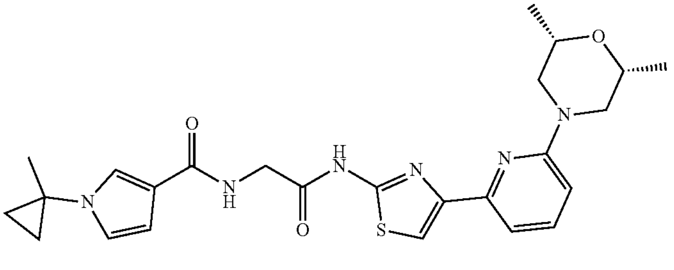 |

-continued
| # | Compound |
|---|---|
| 329 | 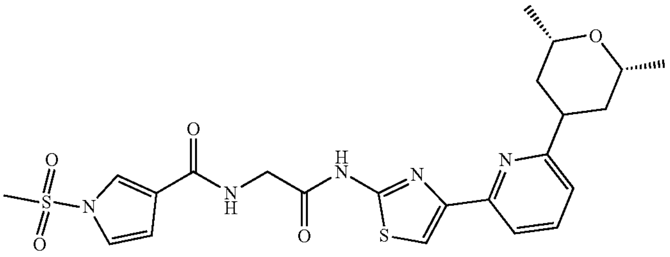 |
| 330 | 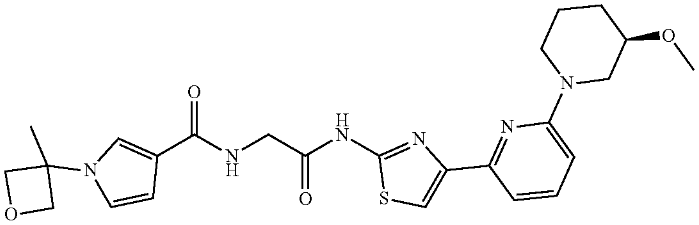 [SMILES: CO[C@@H]1CCCN(c2cccc(-c3csc(NC(=O)CNC(=O)c4ccn(C5(C)COC5)c4)n3)n2)C1] |
| 331 | 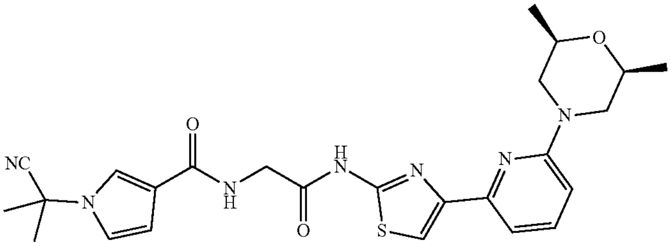 [SMILES: C[C@@H]1CN(c2cccc(-c3csc(NC(=O)CNC(=O)c4ccn(C(C)(C)C#N)c4)n3)n2)C[C@H](C)O1] |
| 332 | 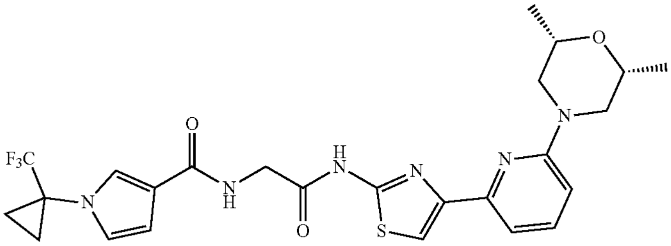 [SMILES: C[C@@H]1CN(c2cccc(-c3csc(NC(=O)CNC(=O)c4ccn(C5(C(F)(F)F)CC5)c4)n3)n2)C[C@H](C)O1] |
| 333 | 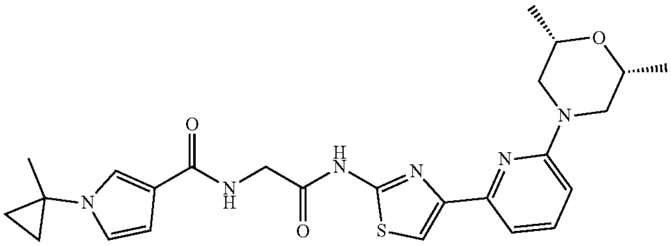 [SMILES: C[C@@H]1CN(c2cccc(-c3csc(NC(=O)CNC(=O)c4ccn(C5(C)CC5)c4)n3)n2)C[C@H](C)O1] |
| 334 | 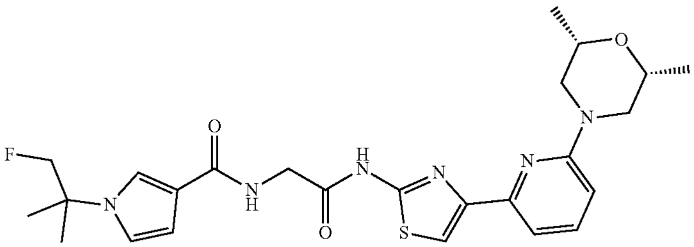 [SMILES: C[C@@H]1CN(c2cccc(-c3csc(NC(=O)CNC(=O)c4ccn(C(C)(C)CF)c4)n3)n2)C[C@H](C)O1] |

-continued
| # | Compound |
|---|---|
| 336 | 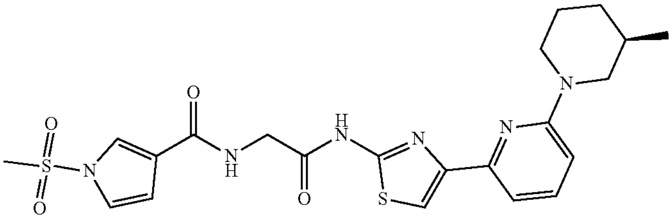 |
| 337 | 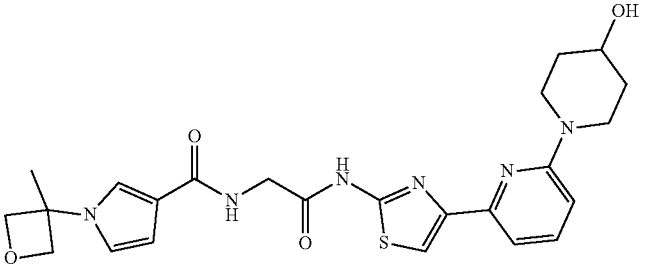 [SMILES: CC1(n2ccc(C(=O)NCC(=O)Nc3nc(-c4cccc(N5CCC(O)CC5)n4)cs3)c2)COC1] |
| 339 | 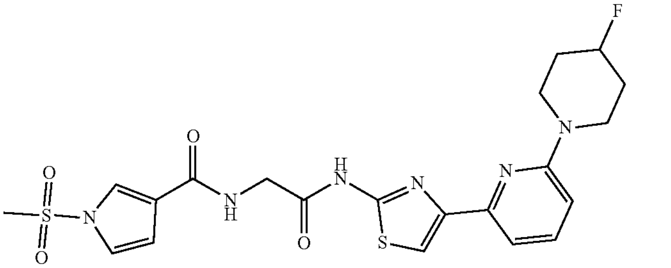 [SMILES: CS(=O)(=O)n1ccc(C(=O)NCC(=O)Nc2nc(-c3cccc(N4CCC(F)CC4)n3)cs2)c1] |
| 340 | 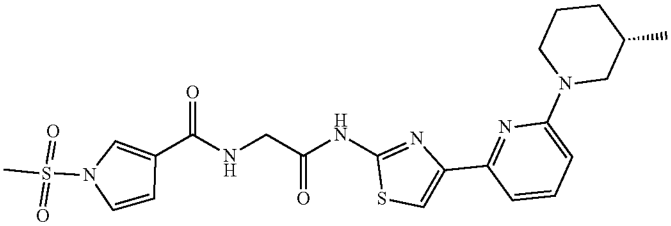 |
| 341 | 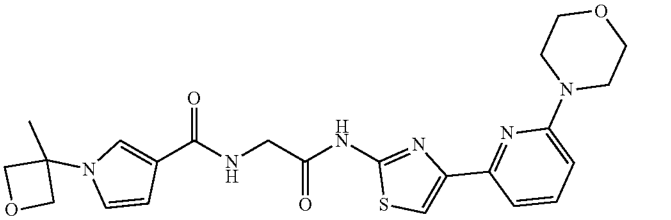 [SMILES: CC1(n2ccc(C(=O)NCC(=O)Nc3nc(-c4cccc(N5CCOCC5)n4)cs3)c2)COC1] |
| 342 | 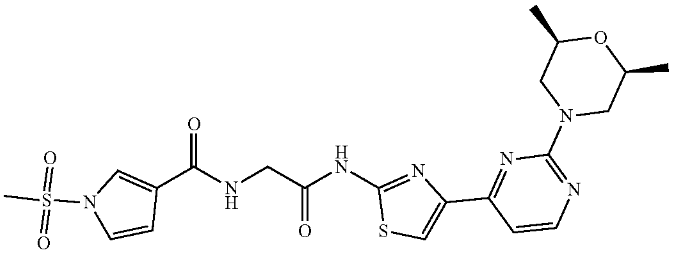 |

-continued
| # | Compound |
|---|---|
| 343 | 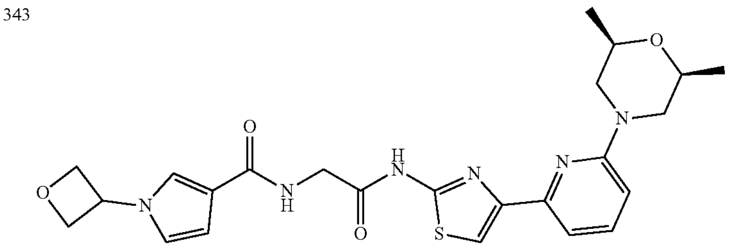 |
| 349 | 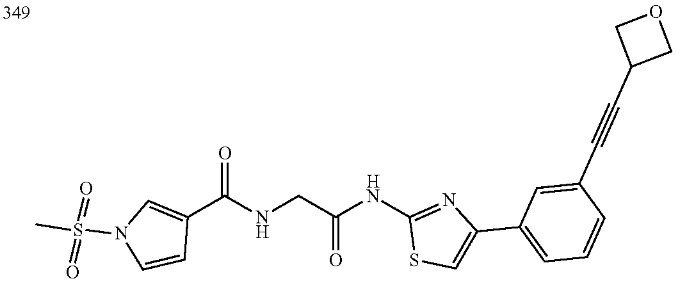 |
| 350 | 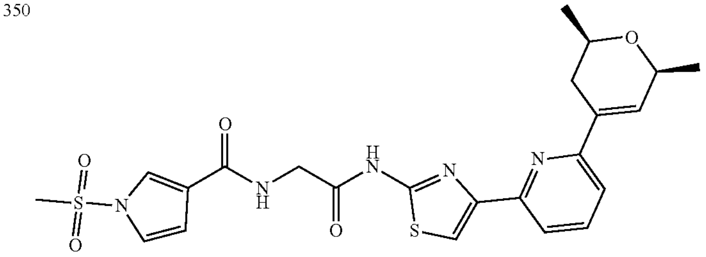 (±) |
| 361 | 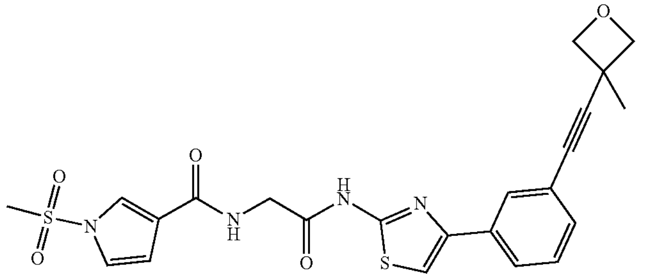 [SMILES: CC1(C#Cc2cccc(-c3csc(NC(=O)CNC(=O)c4ccn(S(C)(=O)=O)c4)n3)c2)COC1] |
| 362 | 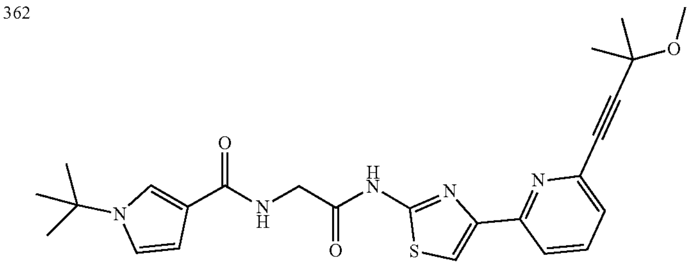 |

-continued
| # | Compound |
|---|---|
| 363 | 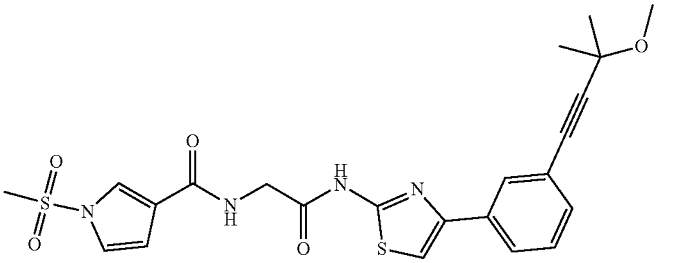 |
| 374 | 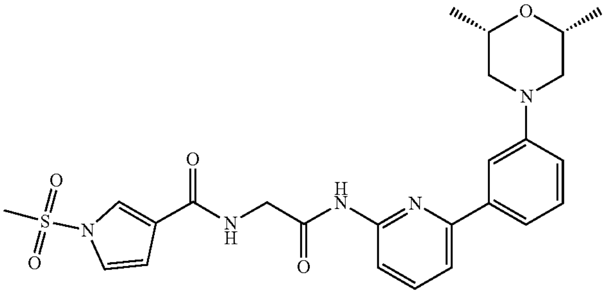 |
| 378 | 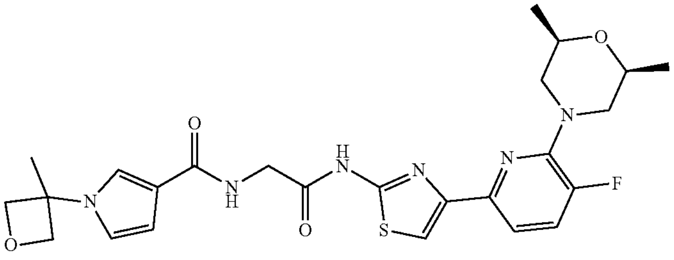 [SMILES: C[C@@H]1CN(c2nc(-c3csc(NC(=O)CNC(=O)c4ccn(C5(C)COC5)c4)n3)ccc2F)C[C@H](C)O1] |
| 379 | 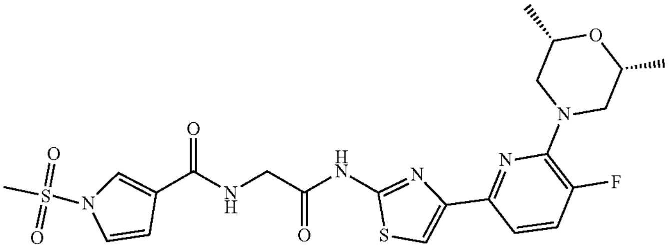 |
| 382 | 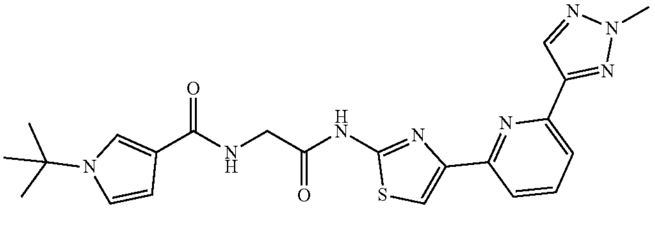 [SMILES: Cn1ncc(-c2cccc(-c3csc(NC(=O)CNC(=O)c4ccn(C(C)(C)C)c4)n3)n2)n1] |
| 383 | 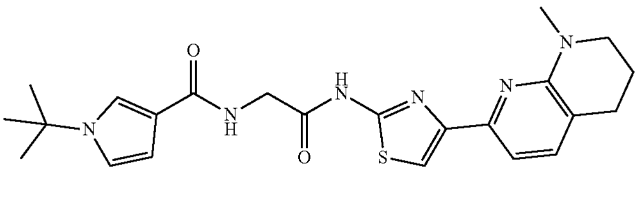 [SMILES: CN1CCCc2ccc(-c3csc(NC(=O)CNC(=O)c4ccn(C(C)(C)C)c4)n3)nc21] |

-continued
| # | Compound |
|---|---|
| 384 | 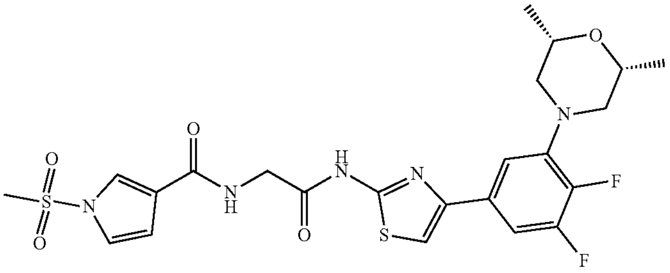 |
| 385 | 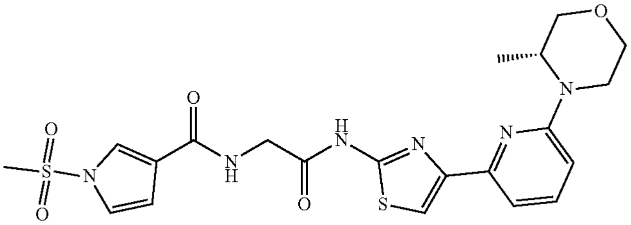 [SMILES: C[C@@H]1COCCN1c1cccc(-c2csc(NC(=O)CNC(=O)c3ccn(S(C)(=O)=O)c3)n2)n1] |
| 386 | 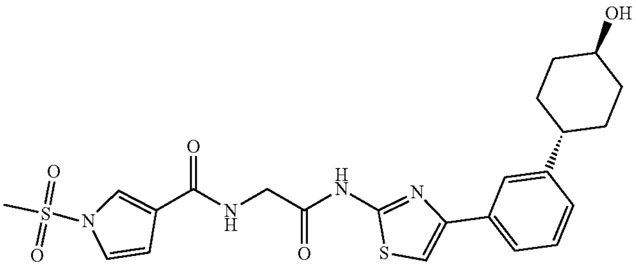 [SMILES: CS(=O)(=O)n1ccc(C(=O)NCC(=O)Nc2nc(-c3cccc([C@H]4CC[C@H](O)CC4)c3)cs2)c1] |
| 387 | 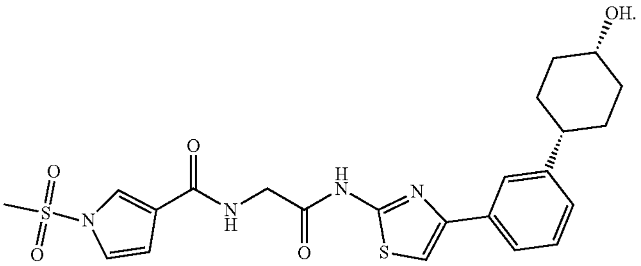 [SMILES: CS(=O)(=O)n1ccc(C(=O)NCC(=O)Nc2nc(-c3cccc([C@H]4CC[C@@H](O)CC4)c3)cs2)c1] |
| 388 | 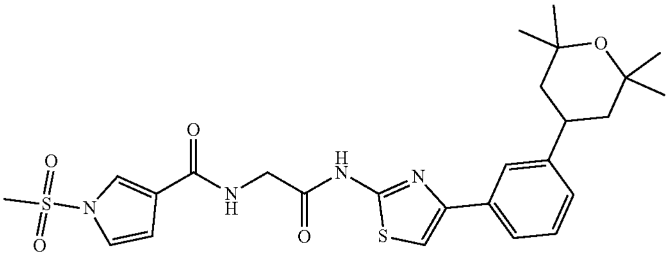 |

-continued
| # | Compound |
|---|---|
| 389 | 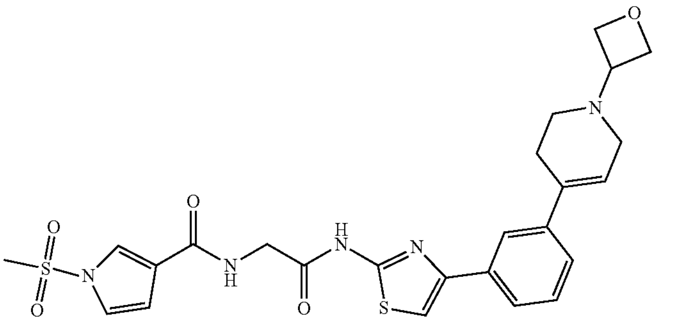 [SMILES: CS(=O)(=O)n1ccc(C(=O)NCC(=O)Nc2nc(-c3cccc(C4=CCN(C5COC5)CC4)c3)cs2)c1] |
| 390 | 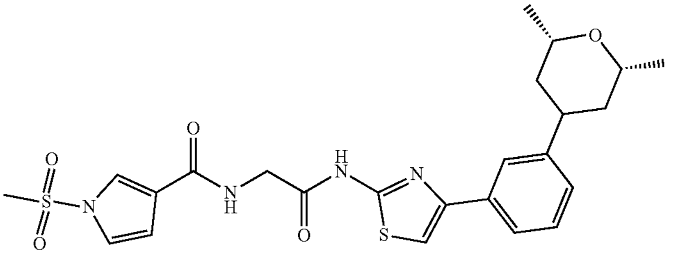 |
| 391 | 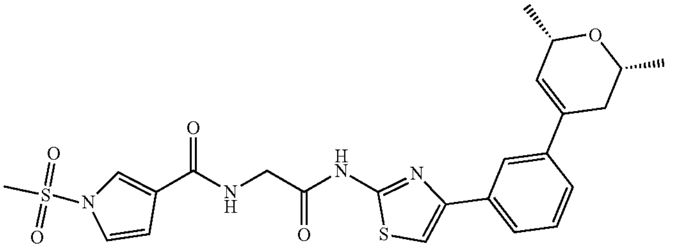 ± |
| 392 | 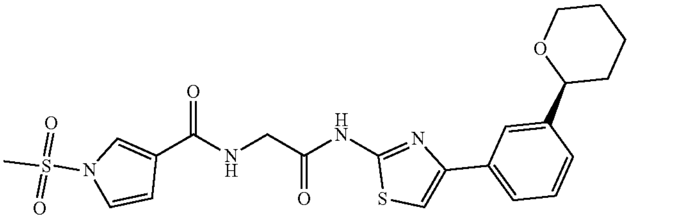 [SMILES: CS(=O)(=O)n1ccc(C(=O)NCC(=O)Nc2nc(-c3cccc([C@@H]4CCCCO4)c3)cs2)c1] |
| 393 | 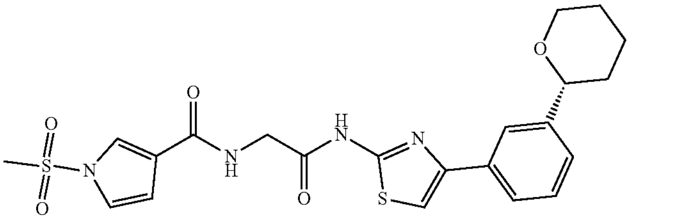 [SMILES: CS(=O)(=O)n1ccc(C(=O)NCC(=O)Nc2nc(-c3cccc([C@H]4CCCCO4)c3)cs2)c1] |
| 394 | 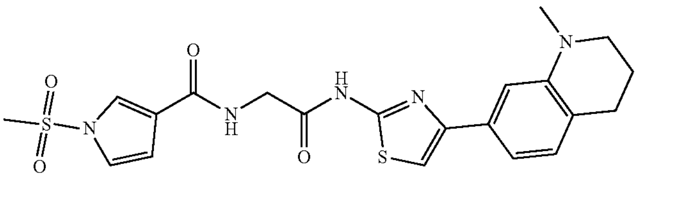 [SMILES: CN1CCCc2ccc(-c3csc(NC(=O)CNC(=O)c4ccn(S(C)(=O)=O)c4)n3)cc21] |

-continued
| # | Compound |
|---|---|
| 395 | 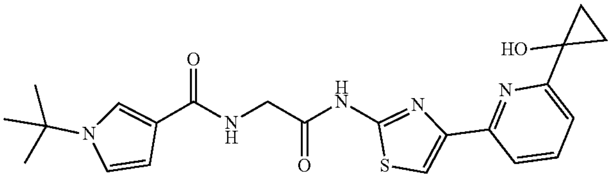 [SMILES: CC(C)(C)n1ccc(C(=O)NCC(=O)Nc2nc(-c3cccc(C4(O)CC4)n3)cs2)c1] |
| 396 | 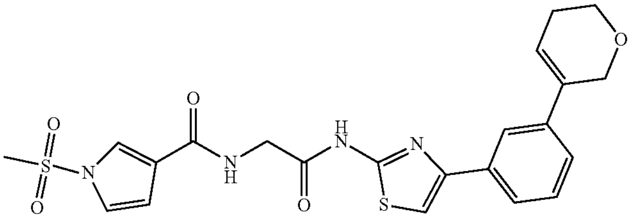 [SMILES: CS(=O)(=O)n1ccc(C(=O)NCC(=O)Nc2nc(-c3cccc(C4=CCCOC4)c3)cs2)c1] |
| 398 | 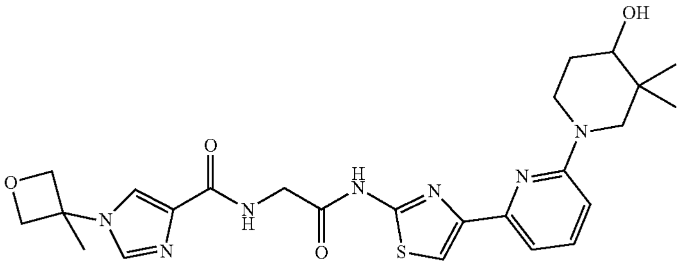 [SMILES: CC1(C)CN(c2cccc(-c3csc(NC(=O)CNC(=O)c4cn(C5(C)COC5)cn4)n3)n2)CCC1O] |
| 399 | 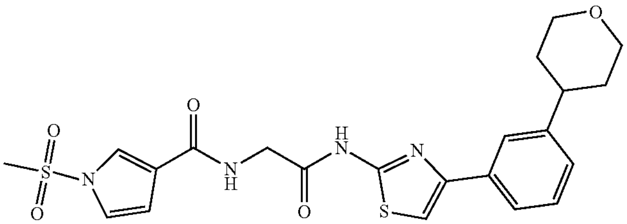 [SMILES: CS(=O)(=O)n1ccc(C(=O)NCC(=O)Nc2nc(-c3cccc(C4CCOCC4)c3)cs2)c1] |
| 400 | 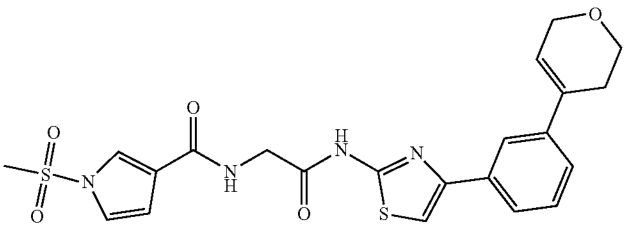 [SMILES: CS(=O)(=O)n1ccc(C(=O)NCC(=O)Nc2nc(-c3cccc(C4=CCOCC4)c3)cs2)c1] |
| 401 | 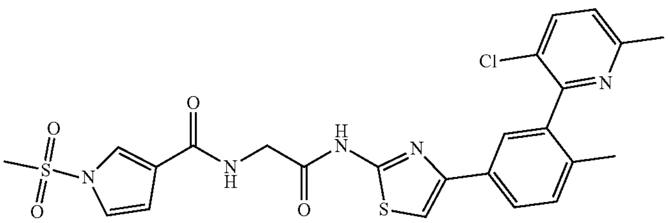 |

-continued
| # | Compound |
|---|---|
| 402 | 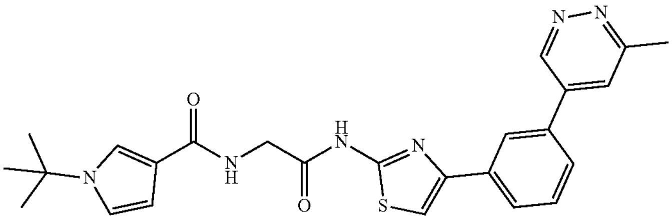 [SMILES: Cc1cc(-c2cccc(-c3csc(NC(=O)CNC(=O)c4ccn(C(C)(C)C)c4)n3)c2)cnn1] |
| 403 | 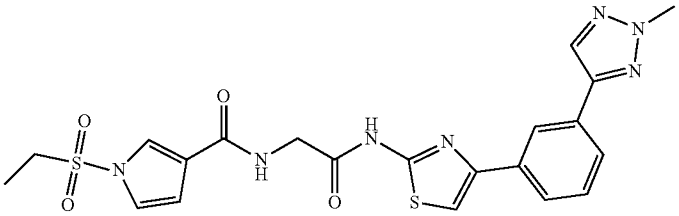 [SMILES: CCS(=O)(=O)n1ccc(C(=O)NCC(=O)Nc2nc(-c3cccc(-c4cnn(C)n4)c3)cs2)c1] |
| 404 | 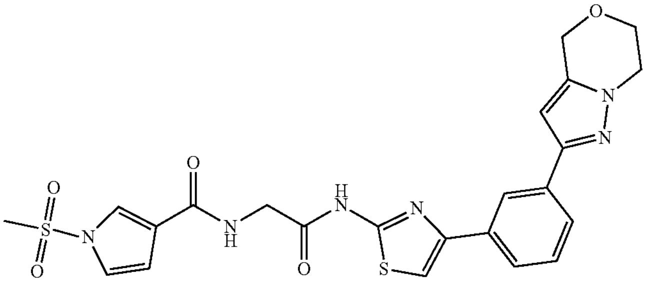 [SMILES: CS(=O)(=O)n1ccc(C(=O)NCC(=O)Nc2nc(-c3cccc(-c4cc5n(n4)CCOC5)c3)cs2)c1] |
| 405 | 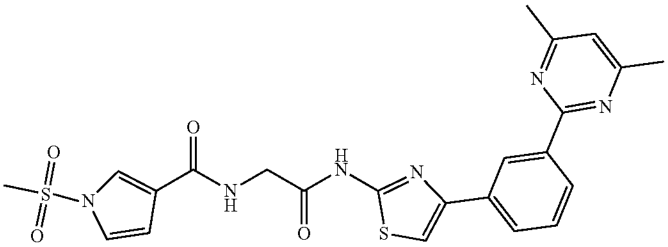 |
| 406 | 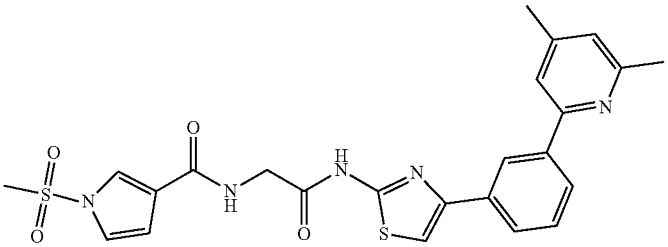 |
| 407 | 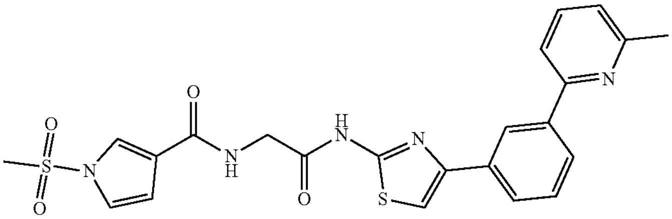 |

-continued
| # | Compound |
|---|---|
| 408 | 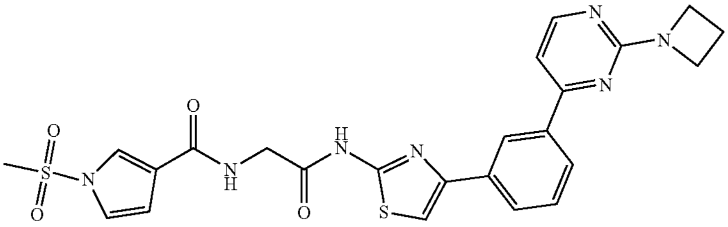 [SMILES: CS(=O)(=O)n1ccc(C(=O)NCC(=O)Nc2nc(-c3cccc(-c4ccnc(N5CCC5)n4)c3)cs2)c1] |
| 409 | 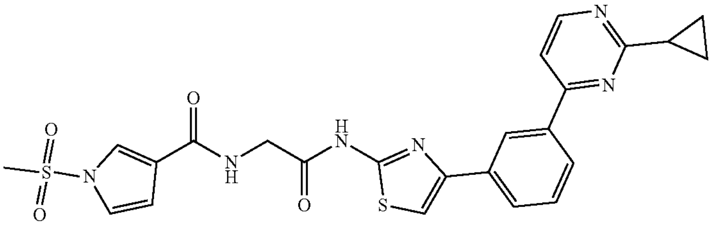 [SMILES: CS(=O)(=O)n1ccc(C(=O)NCC(=O)Nc2nc(-c3cccc(-c4ccnc(C5CC5)n4)c3)cs2)c1] |
| 410 | 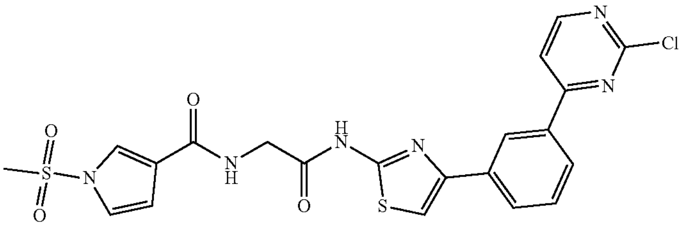 [SMILES: CS(=O)(=O)n1ccc(C(=O)NCC(=O)Nc2nc(-c3cccc(-c4ccnc(Cl)n4)c3)cs2)c1] |
| 411 | 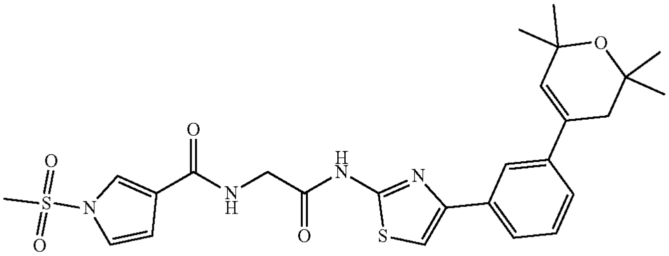 |
| 412 | 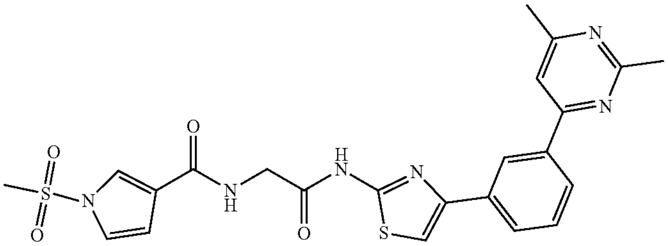 |
| 413 | 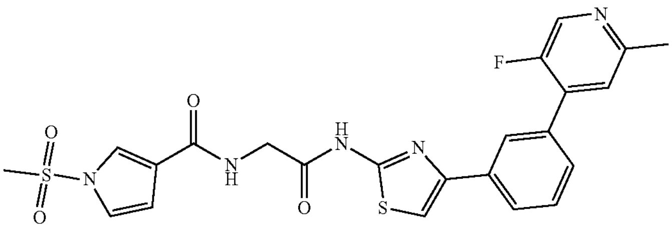 |

-continued
| # | Compound |
|---|---|
| 414 | 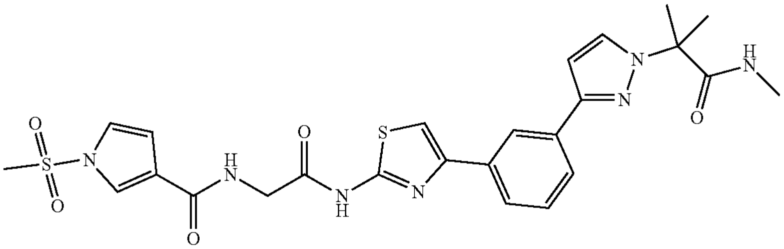 |
| 415 | 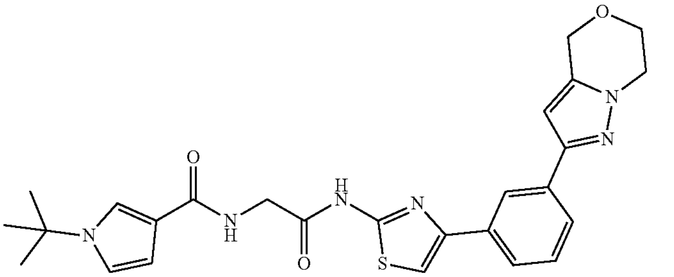 [SMILES: CC(C)(C)n1ccc(C(=O)NCC(=O)Nc2nc(-c3cccc(-c4cc5n(n4)CCOC5)c3)cs2)c1] |
| 416 | 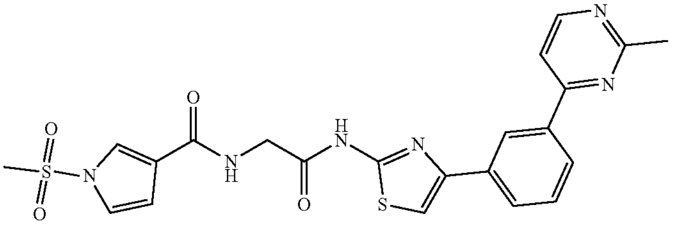 |
| 417 | 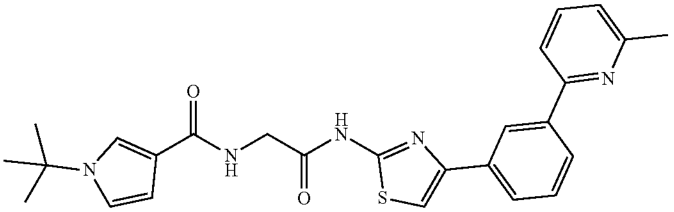 [SMILES: Cc1cccc(-c2cccc(-c3csc(NC(=O)CNC(=O)c4ccn(C(C)(C)C)c4)n3)c2)n1] |
| 418 | 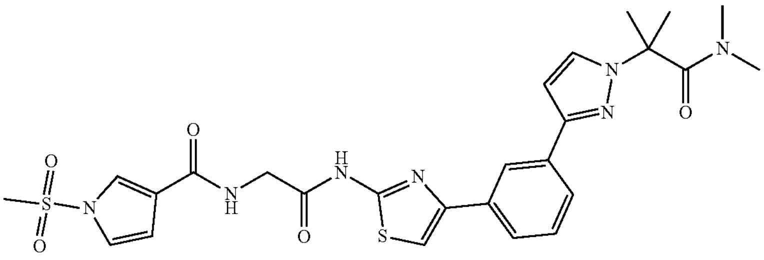 |
| 419 | 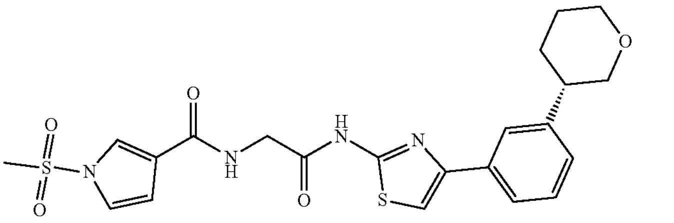 [SMILES: CS(=O)(=O)n1ccc(C(=O)NCC(=O)Nc2nc(-c3cccc([C@@H]4CCCOC4)c3)cs2)c1] |

-continued
| # | Compound |
|---|---|
| 420 | 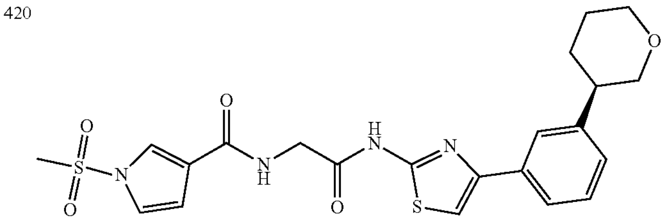 |
| 421 | 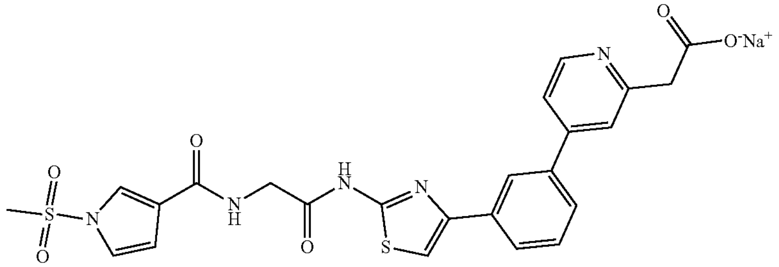 |
| 422 | 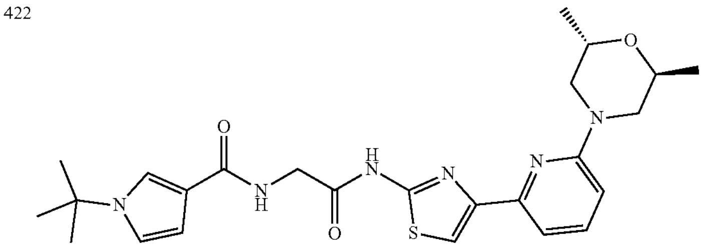 |
| 423 | 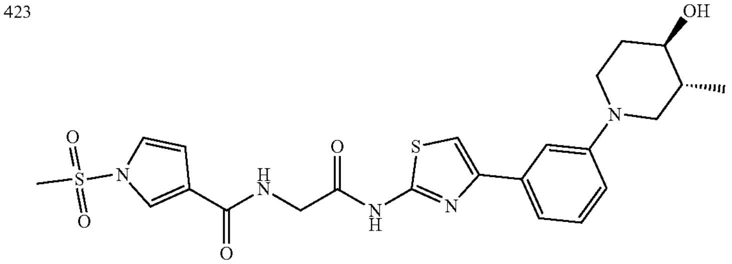 |
| 424 | 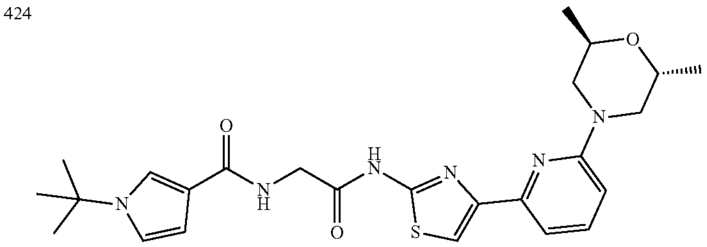 |
| 425 | 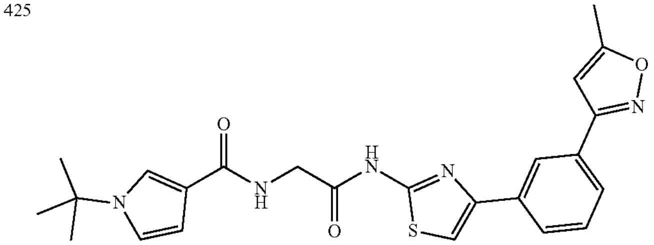 |

-continued
| # | Compound |
|---|---|
| 426 | 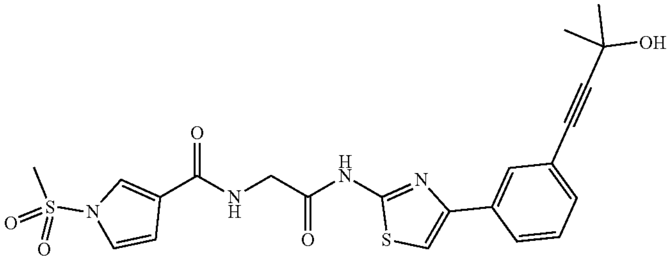 [SMILES: CC(C)(O)C#Cc1cccc(-c2csc(NC(=O)CNC(=O)c3ccn(S(C)(=O)=O)c3)n2)c1] |
| 427 | 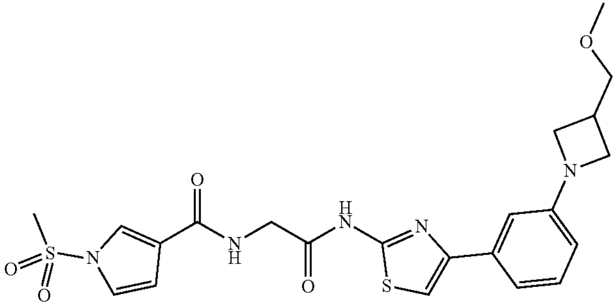 [SMILES: COCC1CN(c2cccc(-c3csc(NC(=O)CNC(=O)c4ccn(S(C)(=O)=O)c4)n3)c2)C1] |
| 428 | 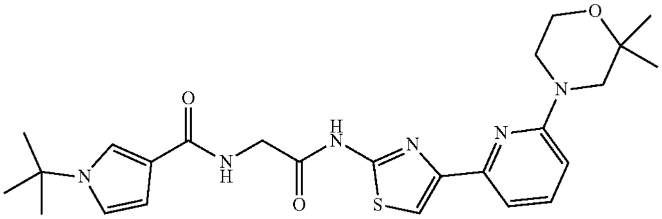 [SMILES: CC1(C)CN(c2cccc(-c3csc(NC(=O)CNC(=O)c4ccn(C(C)(C)C)c4)n3)n2)CCO1] |
| 429 | 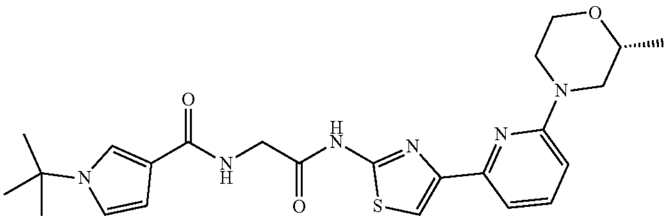 [SMILES: C[C@@H]1CN(c2cccc(-c3csc(NC(=O)CNC(=O)c4ccn(C(C)(C)C)c4)n3)n2)CCO1] |
| 431 | 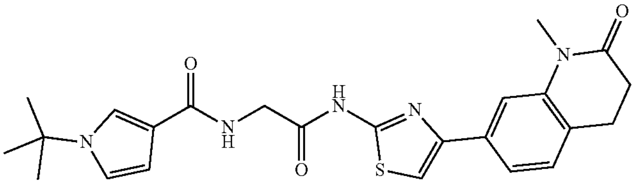 [SMILES: CN1C(=O)CCc2ccc(-c3csc(NC(=O)CNC(=O)c4ccn(C(C)(C)C)c4)n3)cc21] |
| 432 | 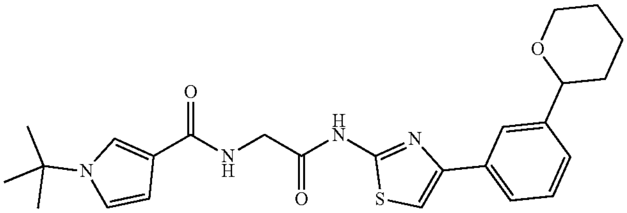 [SMILES: CC(C)(C)n1ccc(C(=O)NCC(=O)Nc2nc(-c3cccc(C4CCCCO4)c3)cs2)c1] |

-continued
| # | Compound |
|---|---|
| 433 | 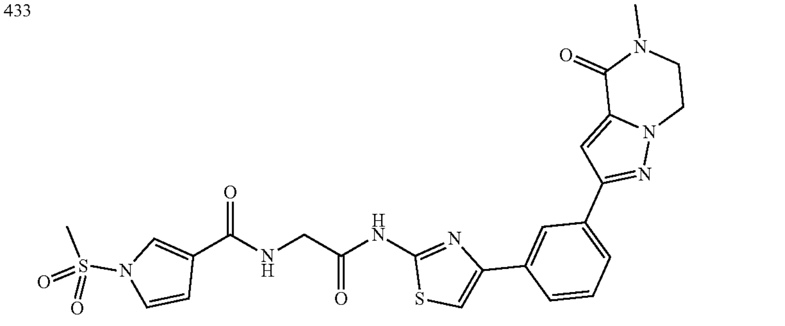 |
| 434 | 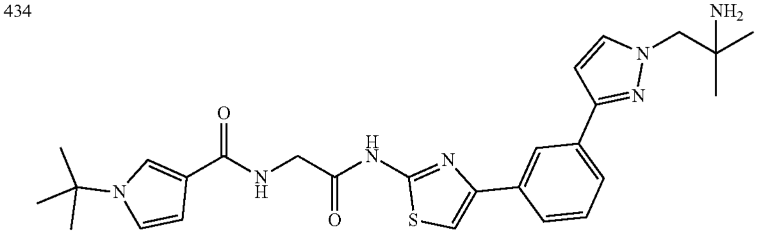 |
| 435 | 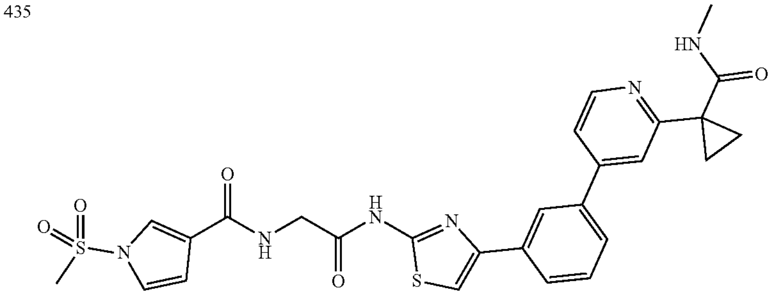 |
| 437 | 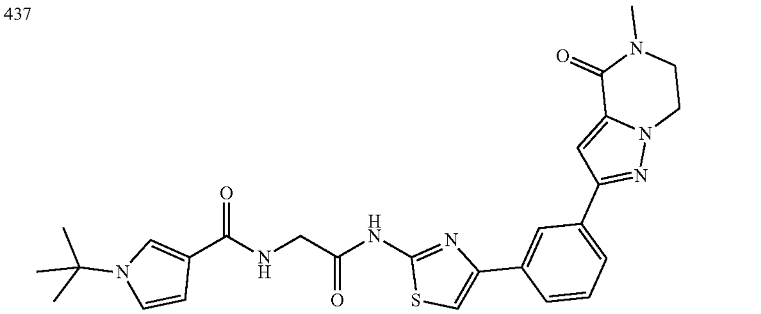 |
| 439 | 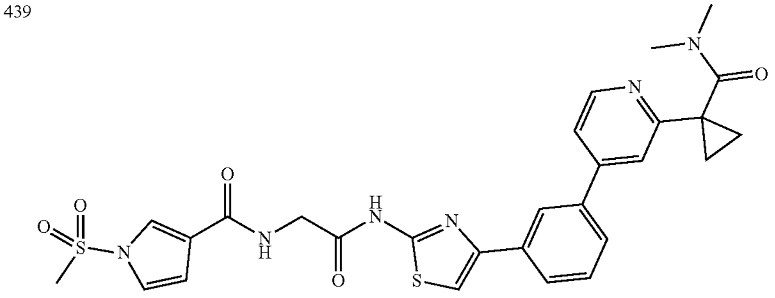 |

-continued
| # | Compound |
|---|---|
| 440 | 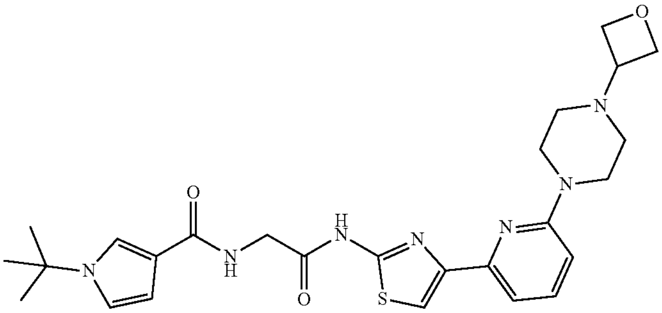 [SMILES: CC(C)(C)n1ccc(C(=O)NCC(=O)Nc2nc(-c3cccc(N4CCN(C5COC5)CC4)n3)cs2)c1] |
| 441 | 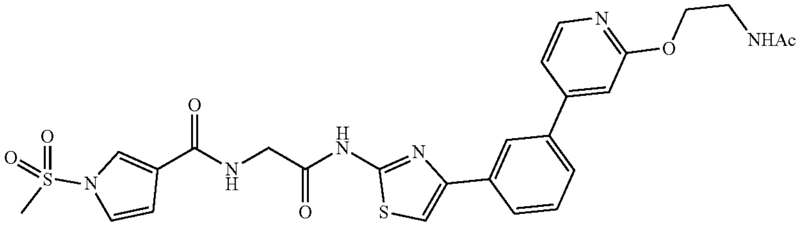 [SMILES: CC(=O)NCCOc1cc(-c2cccc(-c3csc(NC(=O)CNC(=O)c4ccn(S(C)(=O)=O)c4)n3)c2)ccn1] |
| 442 | 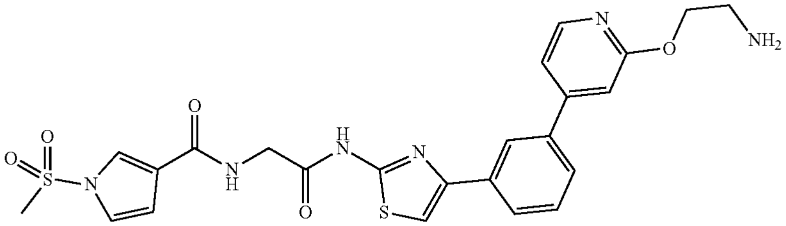 [SMILES: CS(=O)(=O)n1ccc(C(=O)NCC(=O)Nc2nc(-c3cccc(-c4ccnc(OCCN)c4)c3)cs2)c1] |
| 445 | 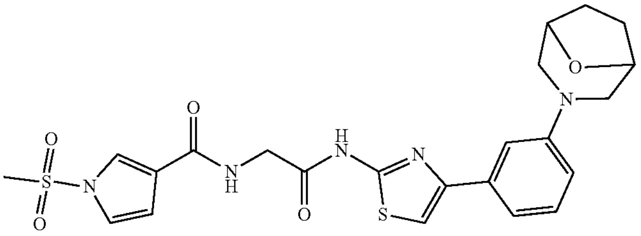 [SMILES: CS(=O)(=O)n1ccc(C(=O)NCC(=O)Nc2nc(-c3cccc(N4CC5CCC(C4)O5)c3)cs2)c1] |
| 446 | 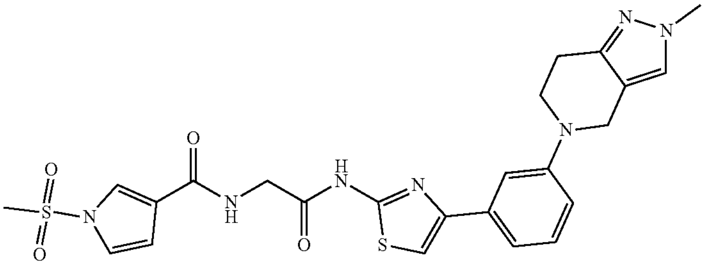 |
| 447 | 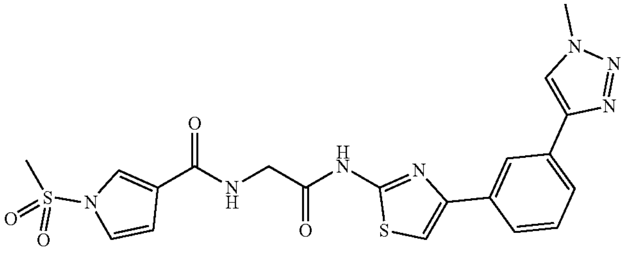 [SMILES: Cn1cc(-c2cccc(-c3csc(NC(=O)CNC(=O)c4ccn(S(C)(=O)=O)c4)n3)c2)nn1] |

-continued
| # | Compound |
|---|---|
| 448 | 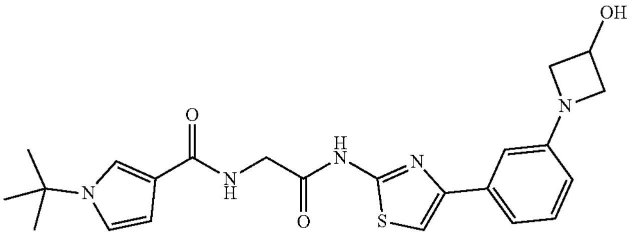 [SMILES: CC(C)(C)n1ccc(C(=O)NCC(=O)Nc2nc(-c3cccc(N4CC(O)C4)c3)cs2)c1] |
| 449 | 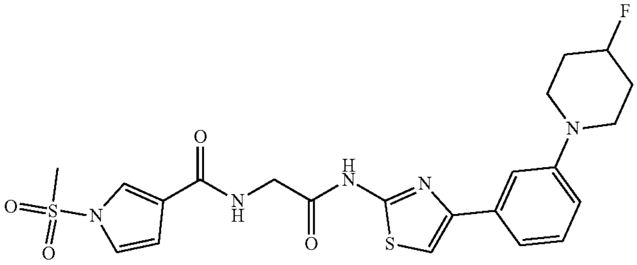 [SMILES: CS(=O)(=O)n1ccc(C(=O)NCC(=O)Nc2nc(-c3cccc(N4CCC(F)CC4)c3)cs2)c1] |
| 450 | 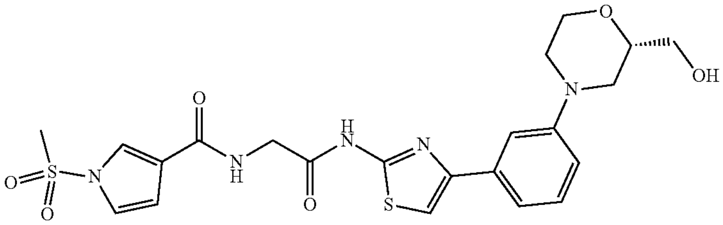 [SMILES: CS(=O)(=O)n1ccc(C(=O)NCC(=O)Nc2nc(-c3cccc(N4CCO[C@H](CO)C4)c3)cs2)c1] |
| 451 | 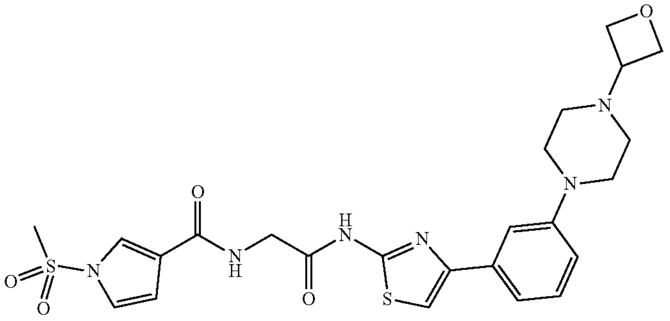 [SMILES: CS(=O)(=O)n1ccc(C(=O)NCC(=O)Nc2nc(-c3cccc(N4CCN(C5COC5)CC4)c3)cs2)c1] |
| 452 | 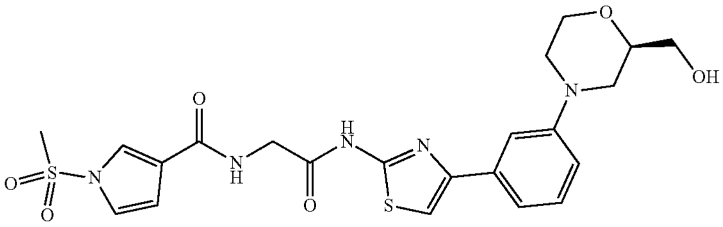 [SMILES: CS(=O)(=O)n1ccc(C(=O)NCC(=O)Nc2nc(-c3cccc(N4CCO[C@@H](CO)C4)c3)cs2)c1] |
| 455 | 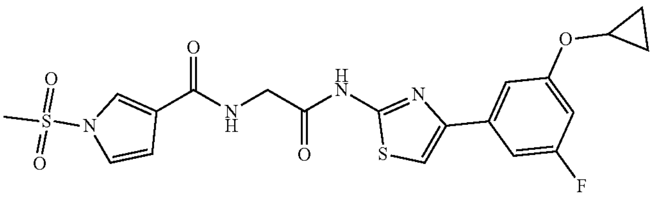 [SMILES: CS(=O)(=O)n1ccc(C(=O)NCC(=O)Nc2nc(-c3cc(F)cc(OC4CC4)c3)cs2)c1] |

-continued
| # | Compound |
|---|---|
| 457 | 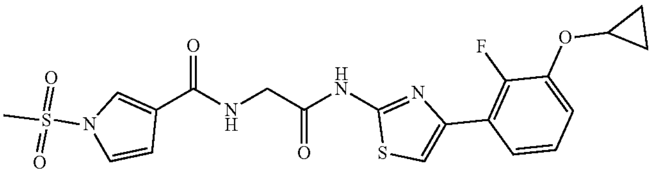 [SMILES: CS(=O)(=O)n1ccc(C(=O)NCC(=O)Nc2nc(-c3cccc(OC4CC4)c3F)cs2)c1] |
| 458 | 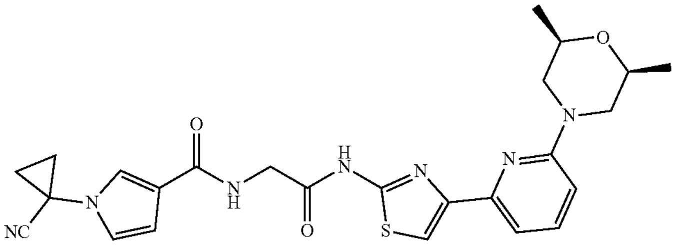 [SMILES: C[C@@H]1CN(c2cccc(-c3csc(NC(=O)CNC(=O)c4ccn(C5(C#N)CC5)c4)n3)n2)C[C@H](C)O1] |
| 460 | 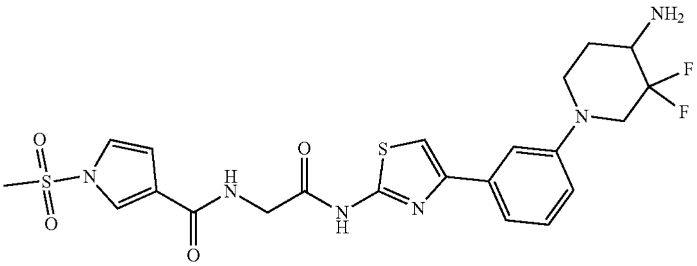 [SMILES: CS(=O)(=O)n1ccc(C(=O)NCC(=O)Nc2nc(-c3cccc(N4CCC(N)C(F)(F)C4)c3)cs2)c1] |
| 463 | 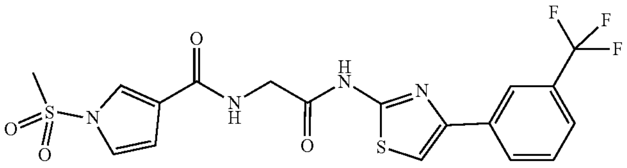 [SMILES: CS(=O)(=O)n1ccc(C(=O)NCC(=O)Nc2nc(-c3cccc(C(F)(F)F)c3)cs2)c1] |
| 464 | 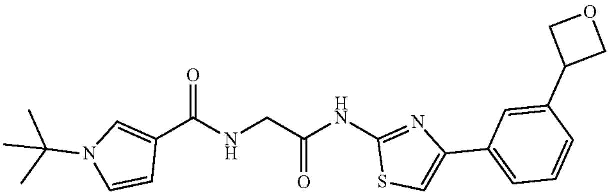 [SMILES: CC(C)(C)n1ccc(C(=O)NCC(=O)Nc2nc(-c3cccc(C4COC4)c3)cs2)c1] |
| 465 | 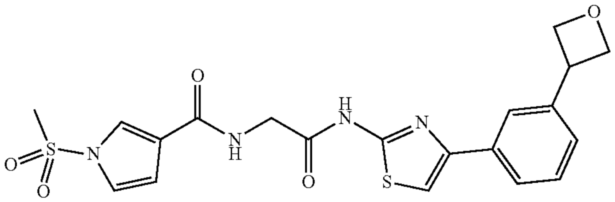 [SMILES: CS(=O)(=O)n1ccc(C(=O)NCC(=O)Nc2nc(-c3cccc(C4COC4)c3)cs2)c1] |

-continued
| # | Compound |
|---|---|
| 467 | 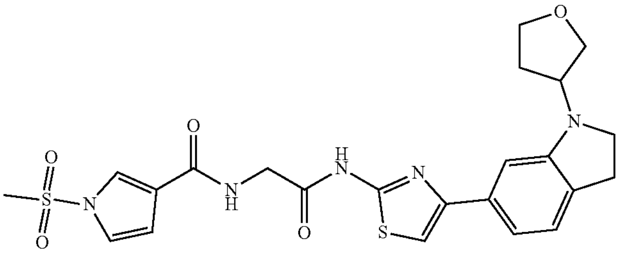<br>(±) |
| 468 | 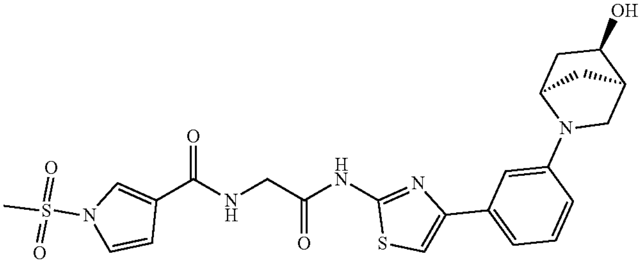<br>(±) |
| 469 | 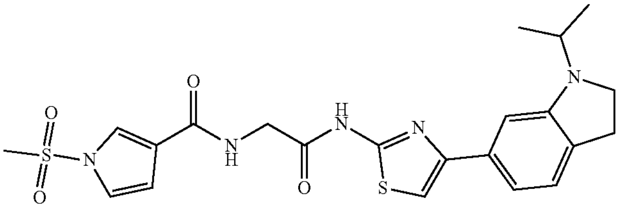 [SMILES: CC(C)N1CCc2ccc(-c3csc(NC(=O)CNC(=O)c4ccn(S(C)(=O)=O)c4)n3)cc21] |
| 470 | 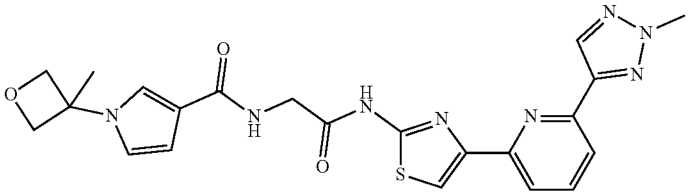 [SMILES: Cn1ncc(-c2cccc(-c3csc(NC(=O)CNC(=O)c4ccn(C5(C)COC5)c4)n3)n2)n1] |
| 471 | 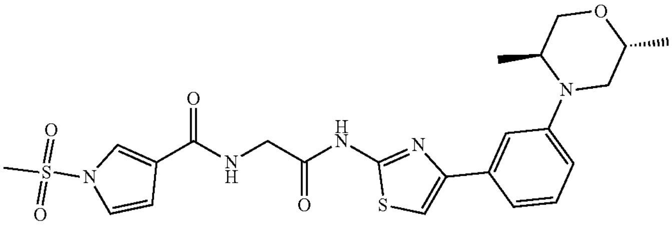 |
| 472 | 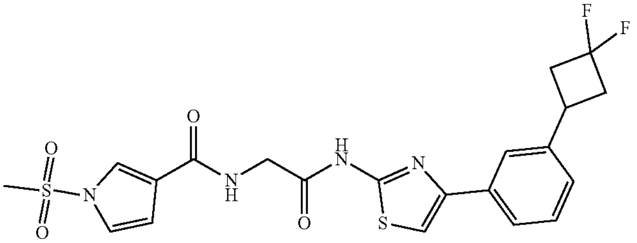 [SMILES: CS(=O)(=O)n1ccc(C(=O)NCC(=O)Nc2nc(-c3cccc(C4CC(F)(F)C4)c3)cs2)c1] |

-continued
| # | Compound |
|---|---|
| 473 | 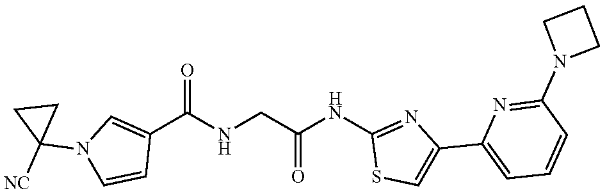 [SMILES: N#CC1(n2ccc(C(=O)NCC(=O)Nc3nc(-c4cccc(N5CCC5)n4)cs3)c2)CC1] |
| 474 | 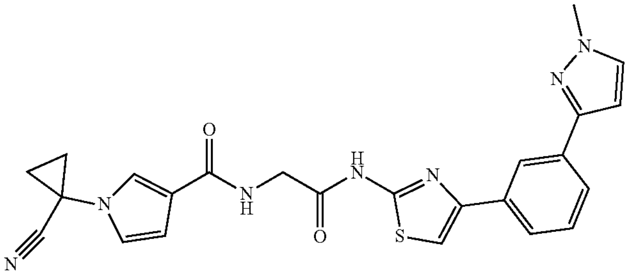 [SMILES: Cn1ccc(-c2cccc(-c3csc(NC(=O)CNC(=O)c4ccn(C5(C#N)CC5)c4)n3)c2)n1] |
| 475 | 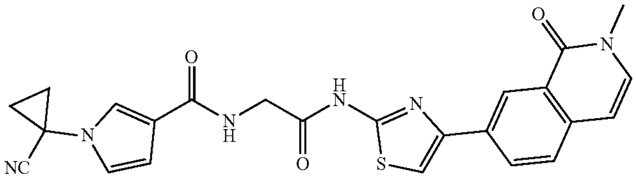 [SMILES: Cn1ccc2ccc(-c3csc(NC(=O)CNC(=O)c4ccn(C5(C#N)CC5)c4)n3)cc2c1=O] |
| 476 | 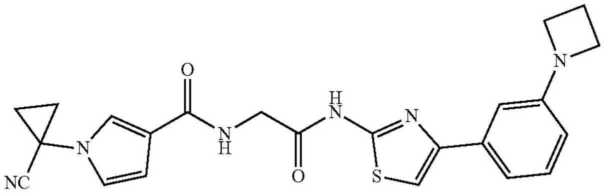 [SMILES: N#CC1(n2ccc(C(=O)NCC(=O)Nc3nc(-c4cccc(N5CCC5)c4)cs3)c2)CC1] |
| 477 | 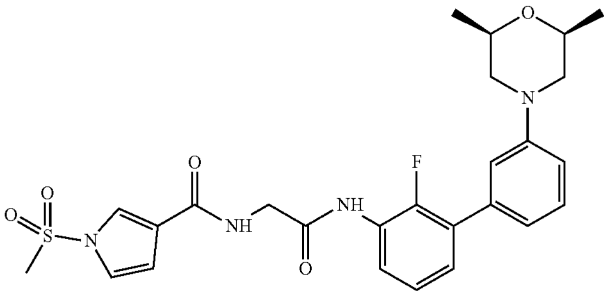 [SMILES: C[C@@H]1CN(c2cccc(-c3cccc(NC(=O)CNC(=O)c4ccn(S(C)(=O)=O)c4)c3F)c2)C[C@H](C)O1] |
| 478 | 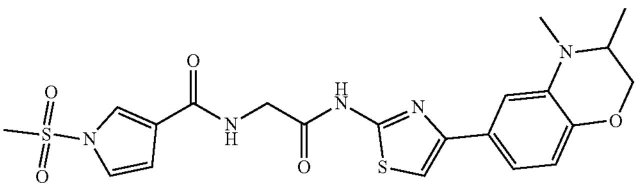 (±) |

-continued
| # | Compound |
|---|---|
| 479 | 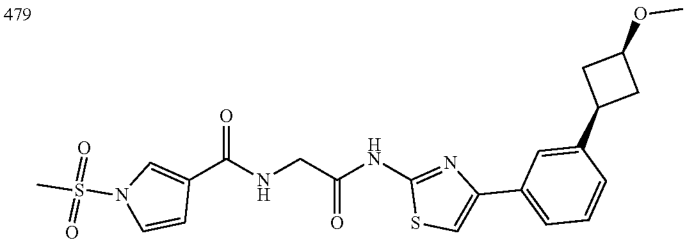 |
| 480 | 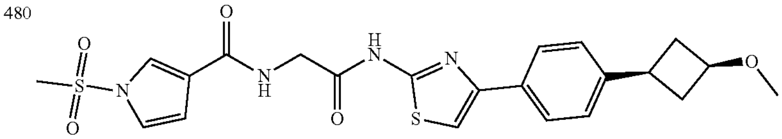 |
| 481 | 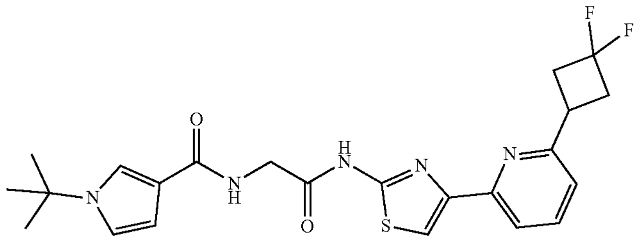 [SMILES: CC(C)(C)n1ccc(C(=O)NCC(=O)Nc2nc(-c3cccc(C4CC(F)(F)C4)n3)cs2)c1] |
| 482 | 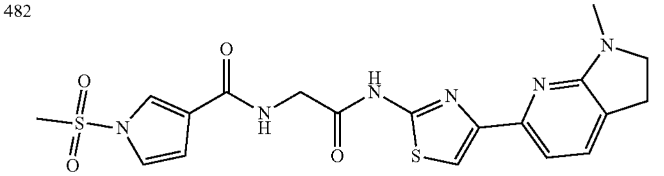 |
| 483 | 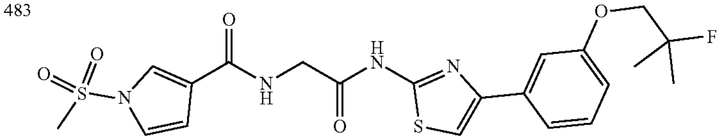 |
| 484 | 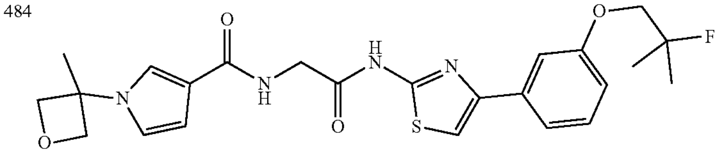 |
| 486 | 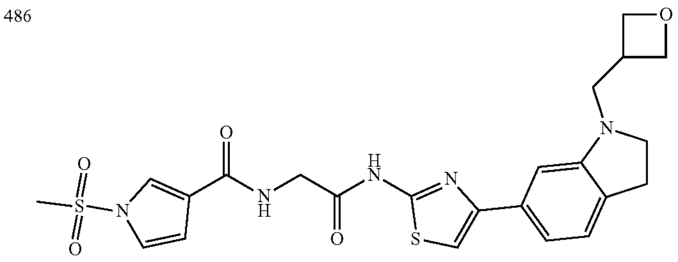 |

-continued
| # | Compound |
|---|---|
| 487 | 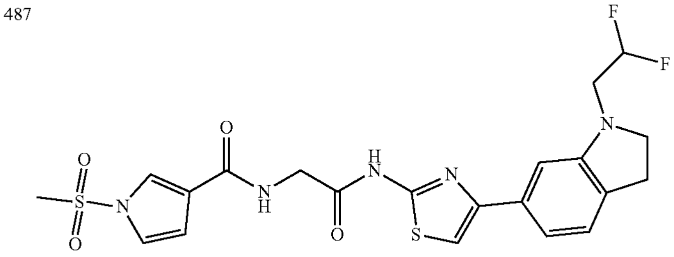 |
| 489 | 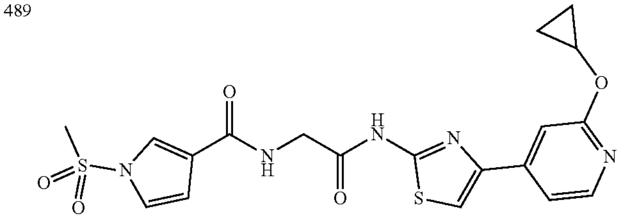 |
| 490 | 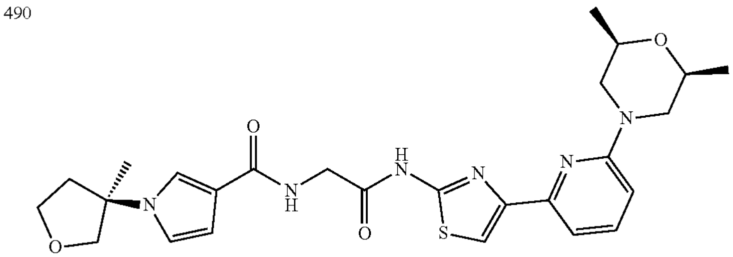 |
| 491 | 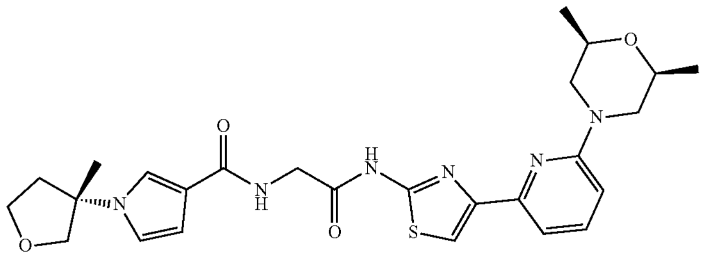 [SMILES: C[C@@H]1CN(c2cccc(-c3csc(NC(=O)CNC(=O)c4ccn([C@@]5(C)CCOC5)c4)n3)n2)C[C@H](C)O1] |
| 492 | 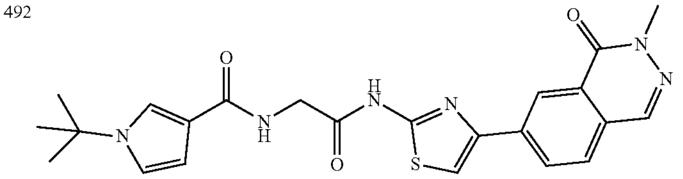 |
| 493 | 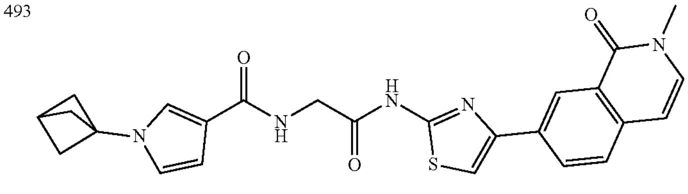 |
| 494 | 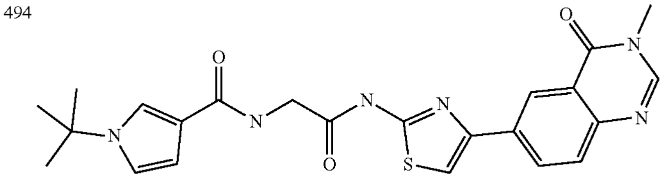 |

-continued
| # | Compound |
|---|---|
| 495 | 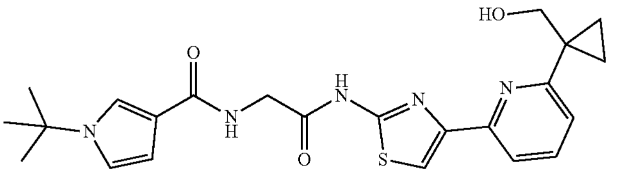 [SMILES: CC(C)(C)n1ccc(C(=O)NCC(=O)Nc2nc(-c3cccc(C4(CO)CC4)n3)cs2)c1] |
| 496 | 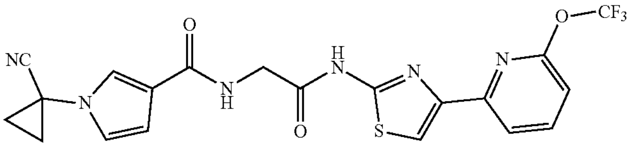 [SMILES: N#CC1(n2ccc(C(=O)NCC(=O)Nc3nc(-c4cccc(OC(F)(F)F)n4)cs3)c2)CC1] |
| 497 | 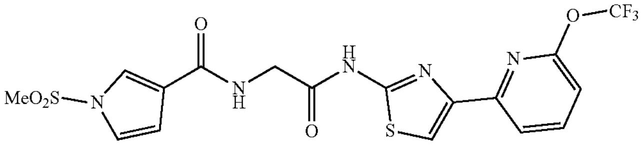 [SMILES: CS(=O)(=O)n1ccc(C(=O)NCC(=O)Nc2nc(-c3cccc(OC(F)(F)F)n3)cs2)c1] |
| 498 | 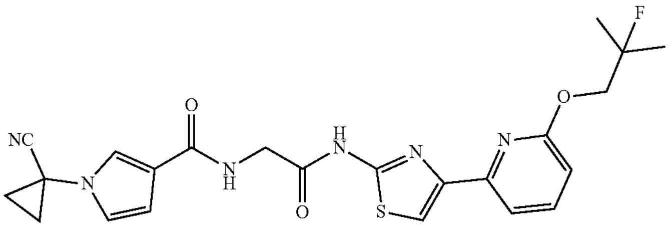 [SMILES: CC(C)(F)COc1cccc(-c2csc(NC(=O)CNC(=O)c3ccn(C4(C#N)CC4)c3)n2)n1] |
| 499 | 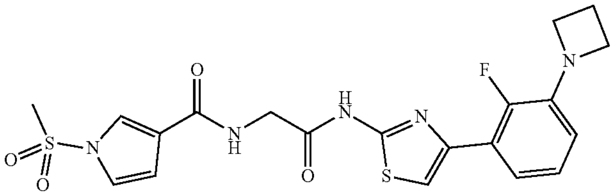 [SMILES: CS(=O)(=O)n1ccc(C(=O)NCC(=O)Nc2nc(-c3cccc(N4CCC4)c3F)cs2)c1] |
| 500 | 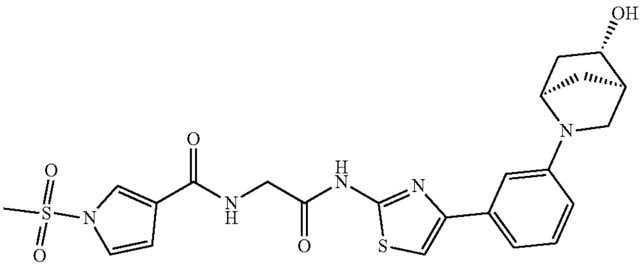 (±) |
| 501 | 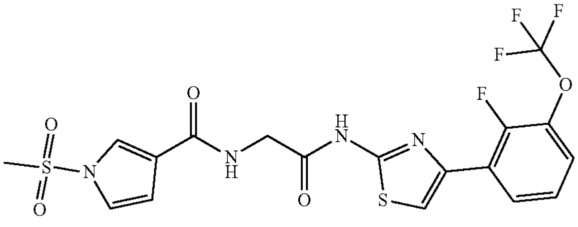 [SMILES: CS(=O)(=O)n1ccc(C(=O)NCC(=O)Nc2nc(-c3cccc(OC(F)(F)F)c3F)cs2)c1] |

-continued
| # | Compound |
|---|---|
| 502 | 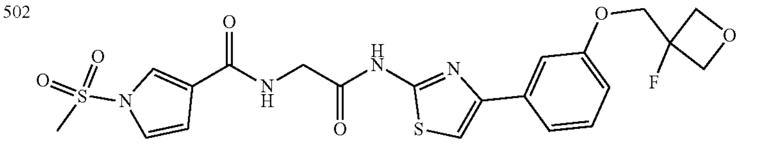 |
| 503 | 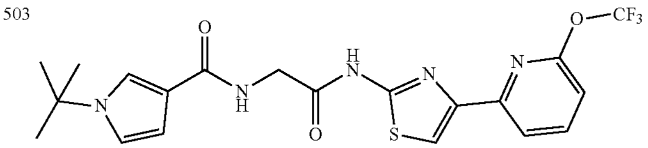 |
| 504 | 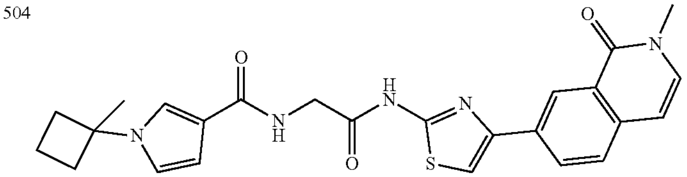 |
| 505 | 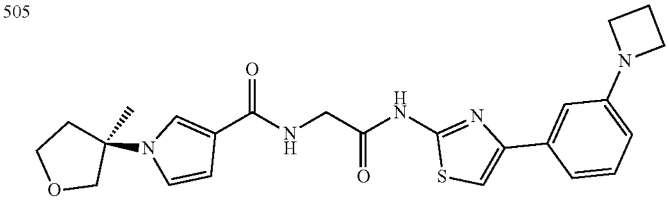 |
| 506 | 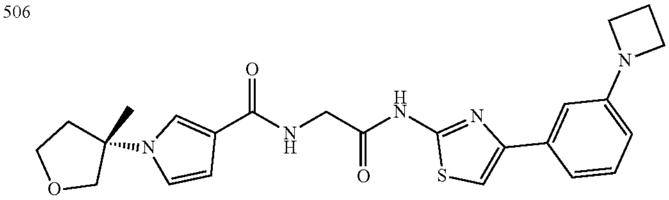 |
| 507 | 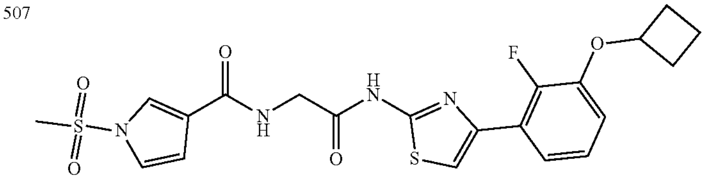 |
| 508 | 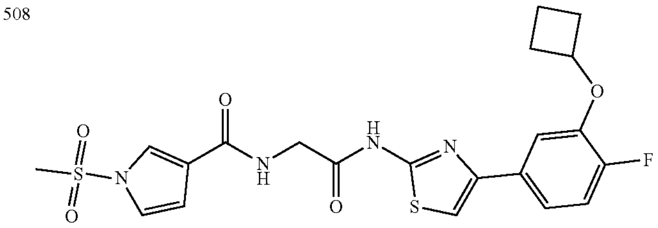 |
| 509 | 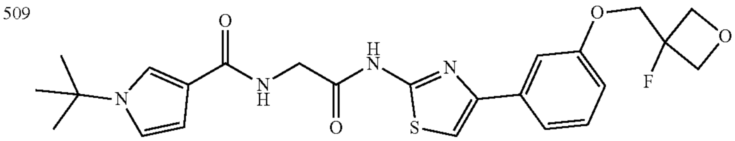 |

-continued
| # | Compound |
|---|---|
| 510 | 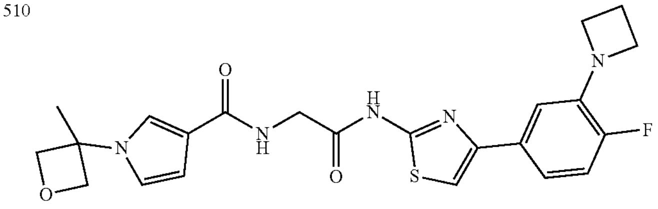 |
| 511 | 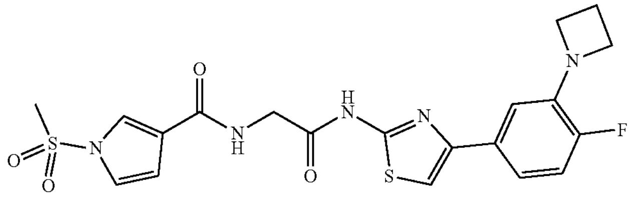 [SMILES: CS(=O)(=O)n1ccc(C(=O)NCC(=O)Nc2nc(-c3ccc(F)c(N4CCC4)c3)cs2)c1] |
| 512 | 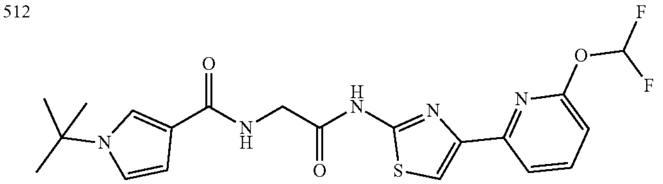 |
| 514 | 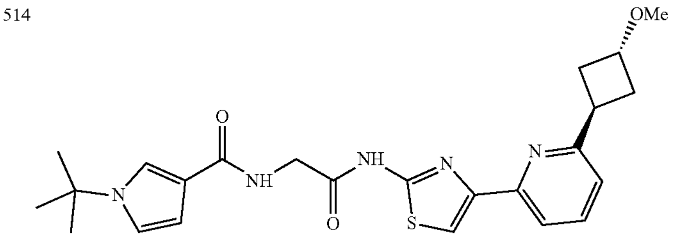 |
| 515 | 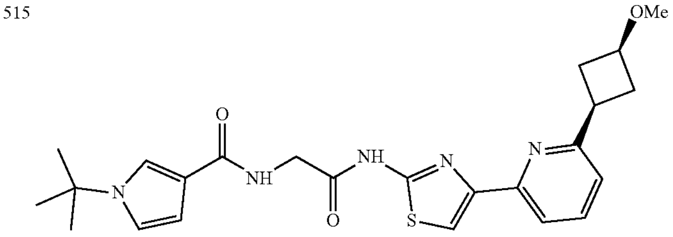 |
| 516 | 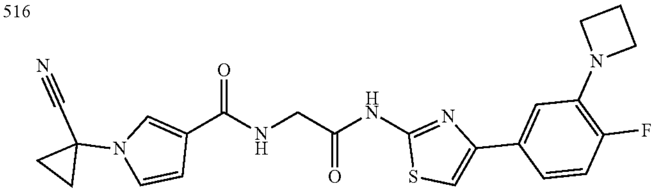 |
| 517 | 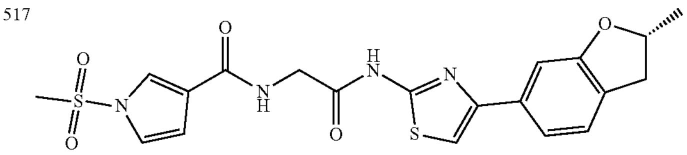 |

-continued
| # | Compound |
|---|---|
| 518 | 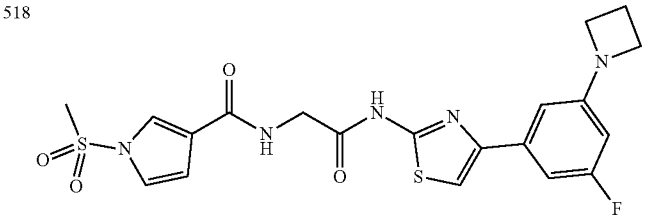 |
| 519 | 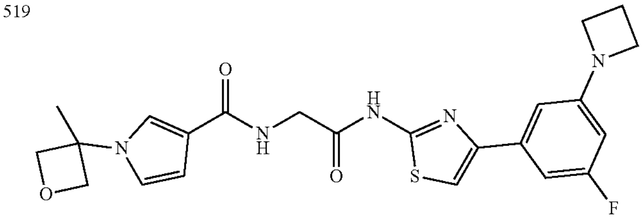 |
| 520 | 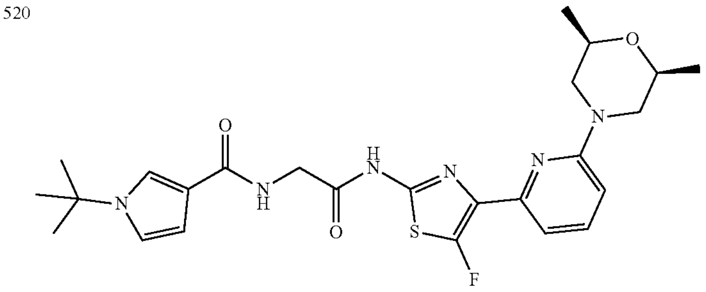 |
| 521 | 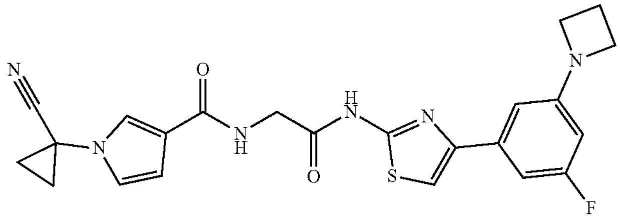 [SMILES: N#CC1(n2ccc(C(=O)NCC(=O)Nc3nc(-c4cc(F)cc(N5CCC5)c4)cs3)c2)CC1] |
| 522 | 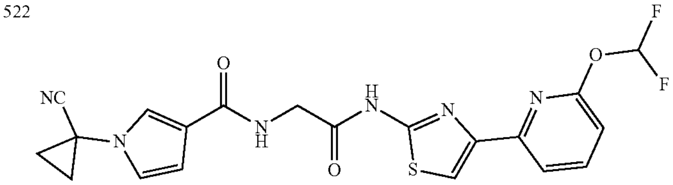 |
| 523 | 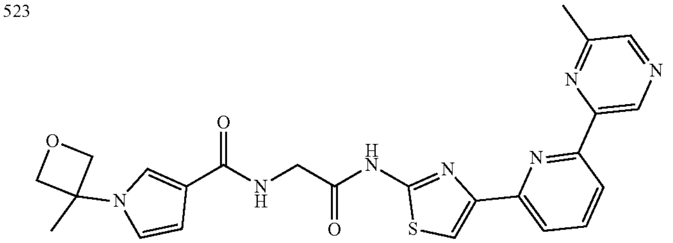 |

-continued
| # | Compound |
|---|---|
| 524 | 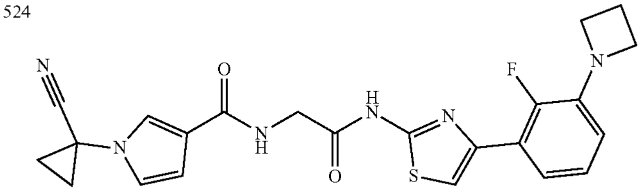 |
| 525 | 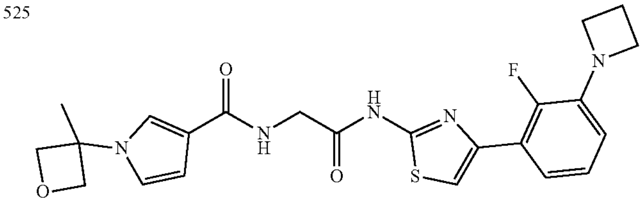 |
| 526 | |
| 527 | 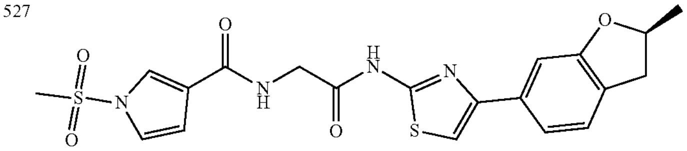 |
| 528 | 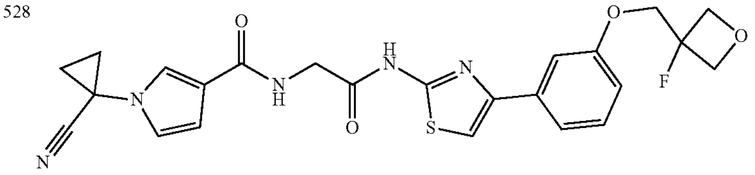 |
| 529 | 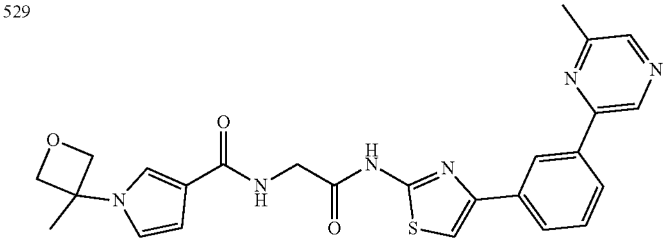 |
| 530 | 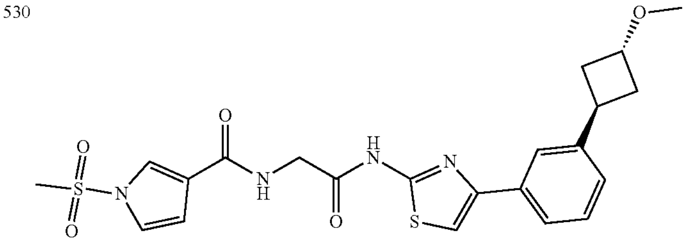 |
| 531 | 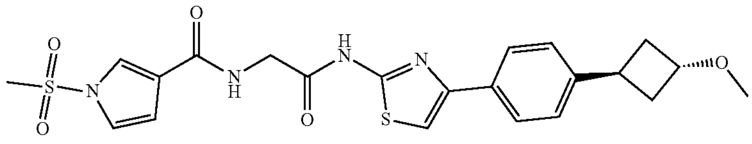 |

-continued
| # | Compound |
|---|---|
| 533 | 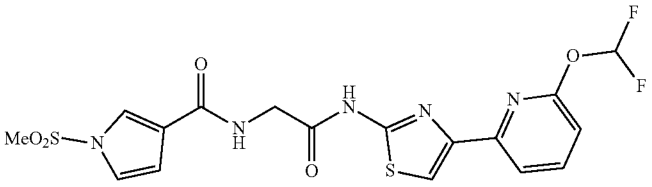 [SMILES: CS(=O)(=O)n1ccc(C(=O)NCC(=O)Nc2nc(-c3cccc(OC(F)F)n3)cs2)c1] |
| 535 | 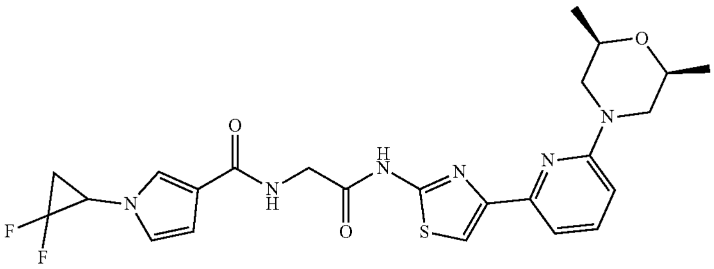 (±) |
| 538 | 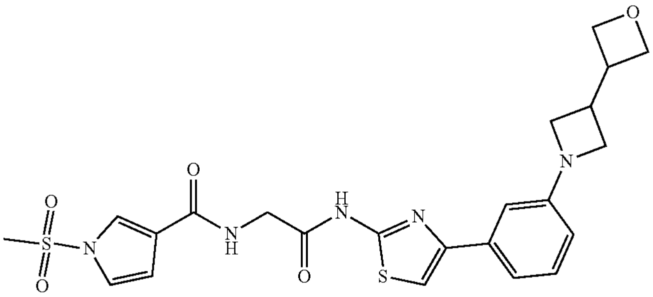 [SMILES: CS(=O)(=O)n1ccc(C(=O)NCC(=O)Nc2nc(-c3cccc(N4CC(C5COC5)C4)c3)cs2)c1] |
| 541 | 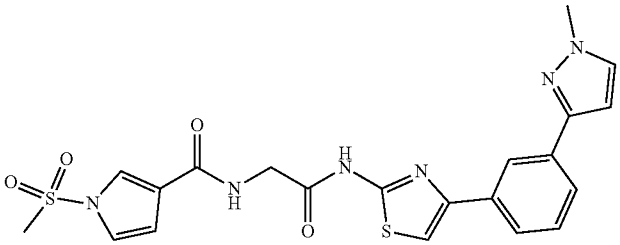 [SMILES: Cn1ccc(-c2cccc(-c3csc(NC(=O)CNC(=O)c4ccn(S(C)(=O)=O)c4)n3)c2)n1] |
| 542 | 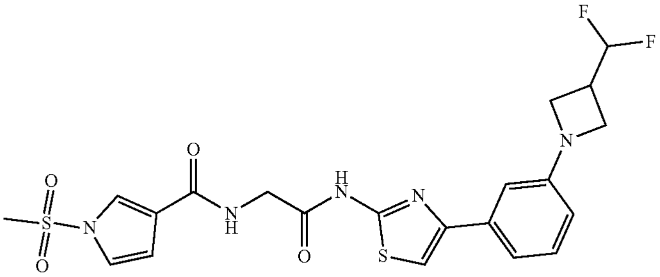 [SMILES: CS(=O)(=O)n1ccc(C(=O)NCC(=O)Nc2nc(-c3cccc(N4CC(C(F)F)C4)c3)cs2)c1] |

-continued
| # | Compound |
|---|---|
| 543 | 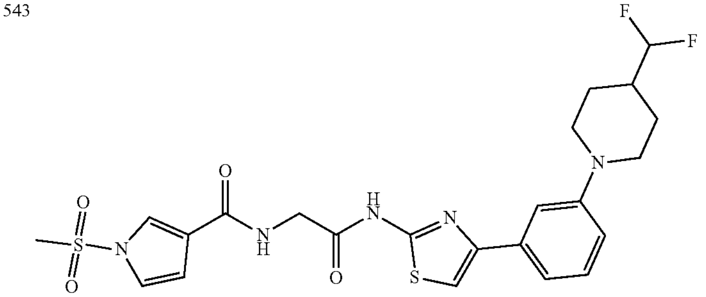 |
| 544 | 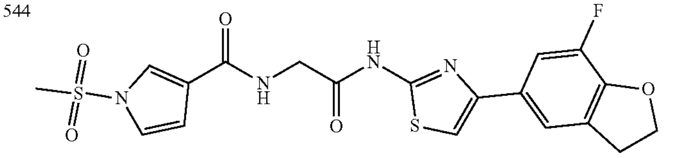 |
| 546 | 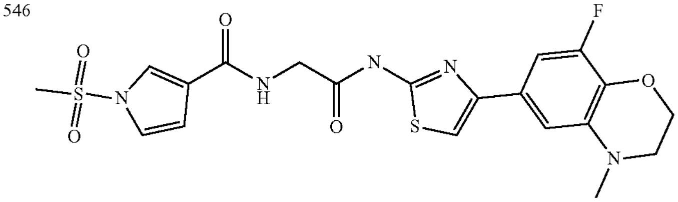 |
| 547 | 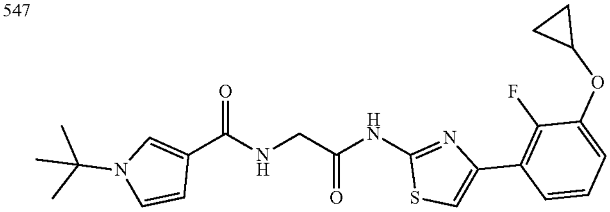 |
| 548 | 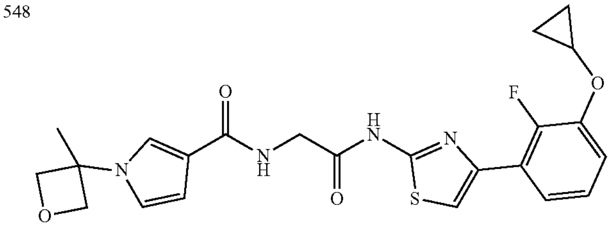 |
| 550 | 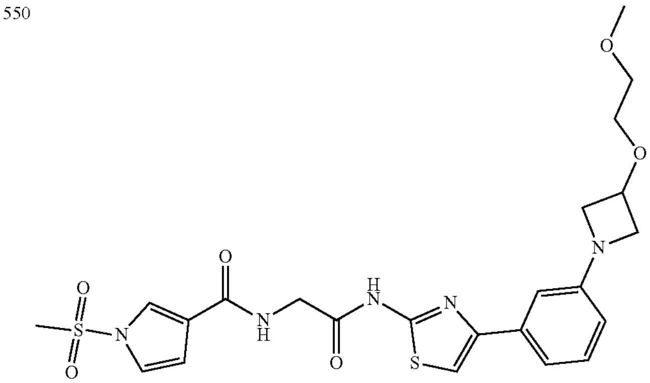 |

-continued
| # | Compound |
|---|---|
| 552 | 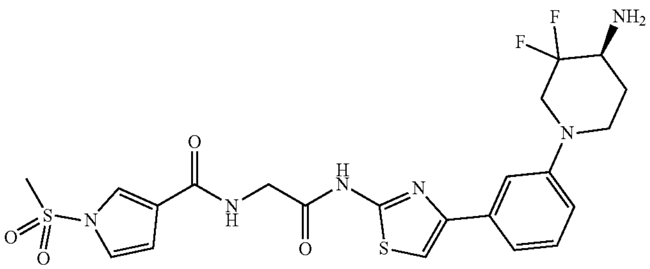 |
| 553 | 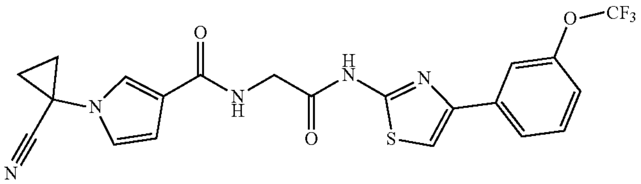 [SMILES: N#CC1(n2ccc(C(=O)NCC(=O)Nc3nc(-c4cccc(OC(F)(F)F)c4)cs3)c2)CC1] |
| 554 | 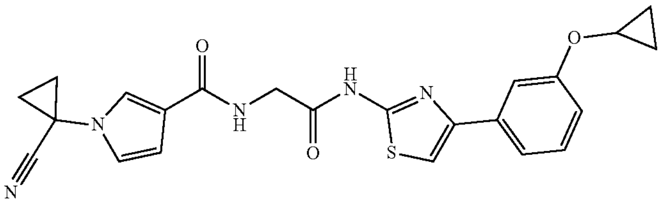 [SMILES: N#CC1(n2ccc(C(=O)NCC(=O)Nc3nc(-c4cccc(OC5CC5)c4)cs3)c2)CC1] |
| 555 | 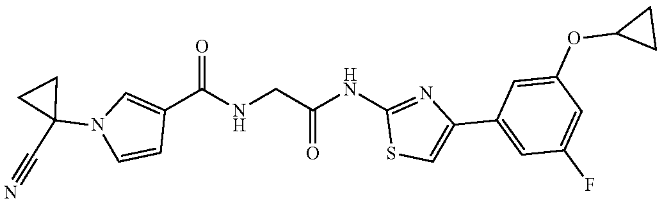 [SMILES: N#CC1(n2ccc(C(=O)NCC(=O)Nc3nc(-c4cc(F)cc(OC5CC5)c4)cs3)c2)CC1] |
| 556 | 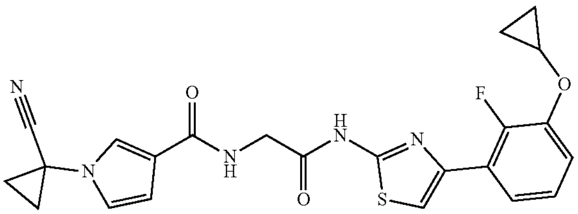 [SMILES: N#CC1(n2ccc(C(=O)NCC(=O)Nc3nc(-c4cccc(OC5CC5)c4F)cs3)c2)CC1] |
| 558 | 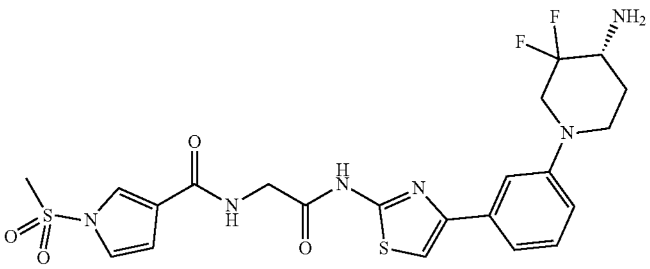 [SMILES: CS(=O)(=O)n1ccc(C(=O)NCC(=O)Nc2nc(-c3cccc(N4CC[C@@H](N)C(F)(F)C4)c3)cs2)c1] |
| 559 | 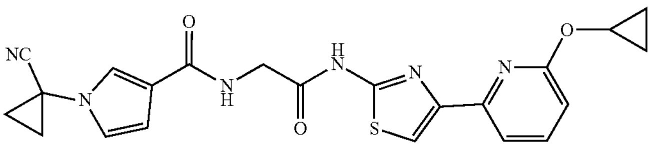 [SMILES: N#CC1(n2ccc(C(=O)NCC(=O)Nc3nc(-c4cccc(OC5CC5)n4)cs3)c2)CC1] |

-continued
| # | Compound |
|---|---|
| 562 | 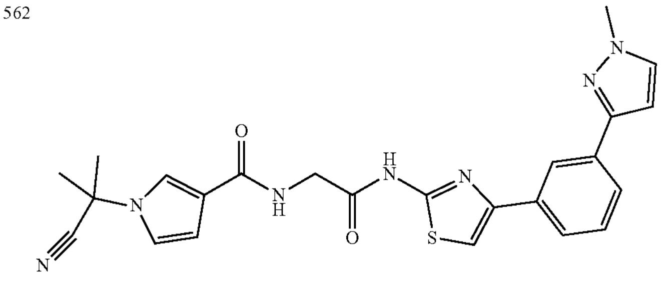 |
| 565 | 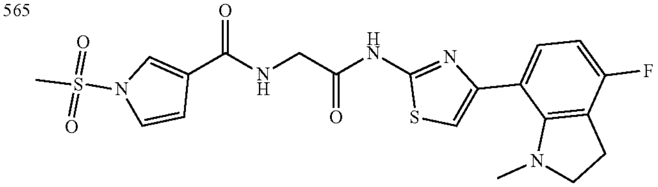 |
| 566 | 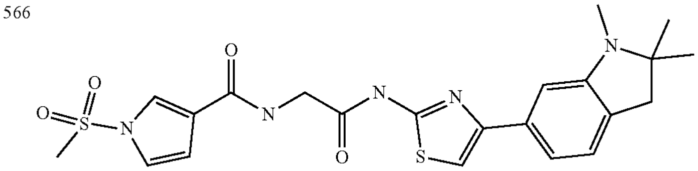 |
| 569 | 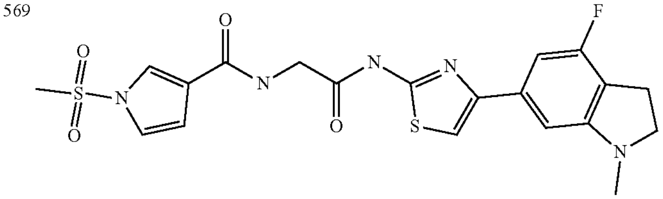 |
| 571 | 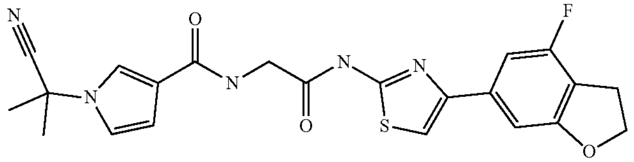 |
| 574 | 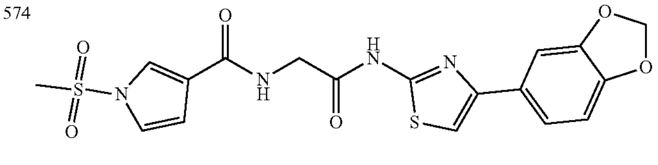 |
| 575 | 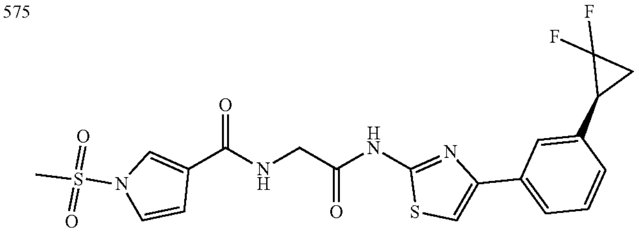 |

-continued
| # | Compound |
|---|---|
| 576 | 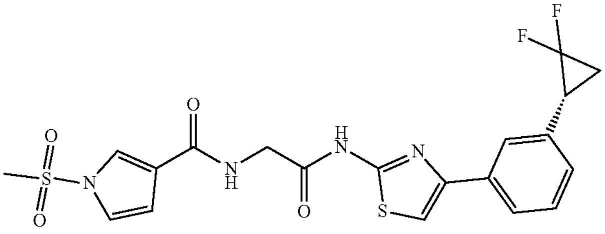 [SMILES: CS(=O)(=O)n1ccc(C(=O)NCC(=O)Nc2nc(-c3cccc([C@H]4CC4(F)F)c3)cs2)c1] |
| 578 | 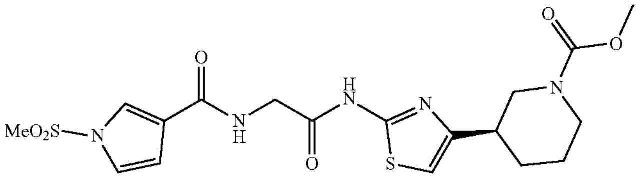 [SMILES: COC(=O)N1CCC[C@@H](c2csc(NC(=O)CNC(=O)c3ccn(S(C)(=O)=O)c3)n2)C1] |
| 579 | 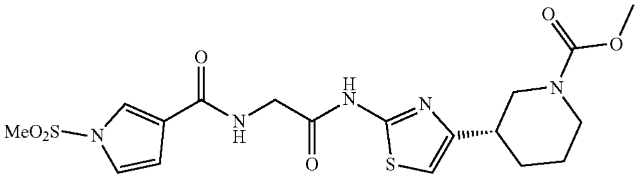 [SMILES: COC(=O)N1CCC[C@H](c2csc(NC(=O)CNC(=O)c3ccn(S(C)(=O)=O)c3)n2)C1] |
| 580 | 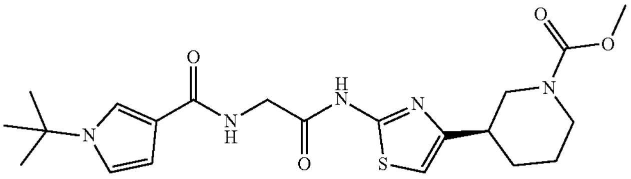 [SMILES: COC(=O)N1CCC[C@@H](c2csc(NC(=O)CNC(=O)c3ccn(C(C)(C)C)c3)n2)C1] |
| 581 | 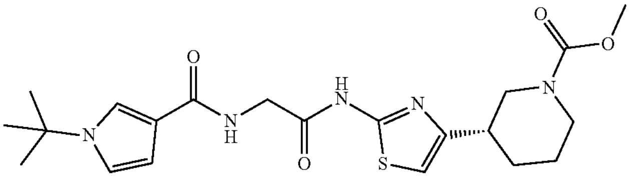 [SMILES: COC(=O)N1CCC[C@H](c2csc(NC(=O)CNC(=O)c3ccn(C(C)(C)C)c3)n2)C1] |
| 582 | 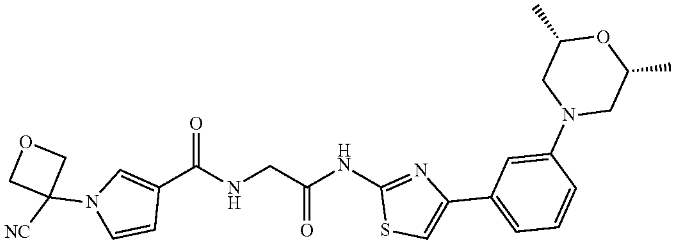 [SMILES: C[C@@H]1CN(c2cccc(-c3csc(NC(=O)CNC(=O)c4ccn(C5(C#N)COC5)c4)n3)c2)C[C@H](C)O1] |
| 585 | 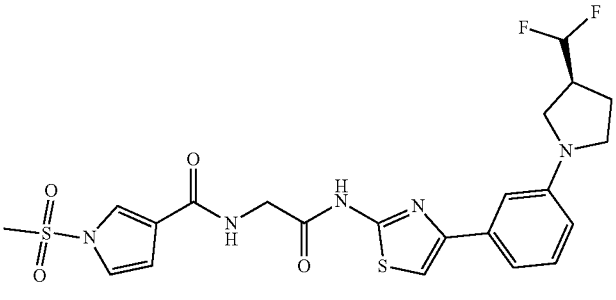 [SMILES: CS(=O)(=O)n1ccc(C(=O)NCC(=O)Nc2nc(-c3cccc(N4CC[C@H](C(F)F)C4)c3)cs2)c1] |

-continued
| # | Compound |
|---|---|
| 586 | 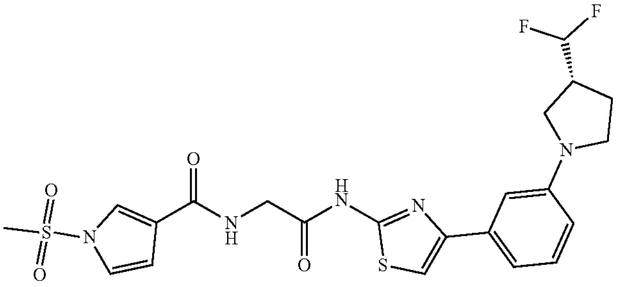 [SMILES: CS(=O)(=O)n1ccc(C(=O)NCC(=O)Nc2nc(-c3cccc(N4CC[C@@H](C(F)F)C4)c3)cs2)c1] |
| 590 | 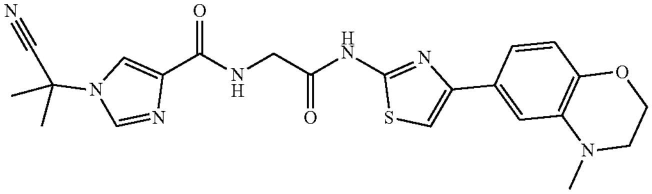 [SMILES: CN1CCOc2ccc(-c3csc(NC(=O)CNC(=O)c4cn(C(C)(C)C#N)cn4)n3)cc21] |
| 595 | 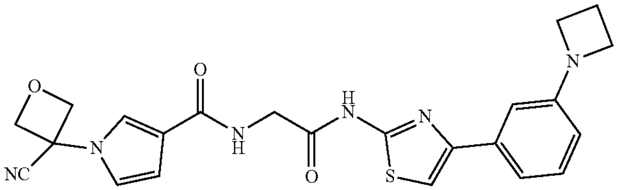 [SMILES: N#CC1(n2ccc(C(=O)NCC(=O)Nc3nc(-c4cccc(N5CCC5)c4)cs3)c2)COC1] |
| 597 | 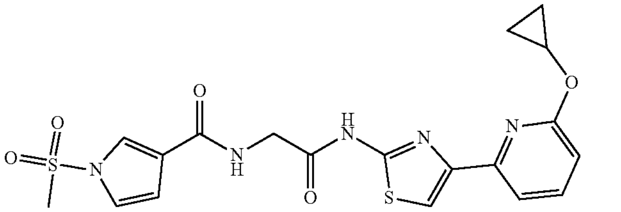 [SMILES: CS(=O)(=O)n1ccc(C(=O)NCC(=O)Nc2nc(-c3cccc(OC4CC4)n3)cs2)c1] |
| 601 | 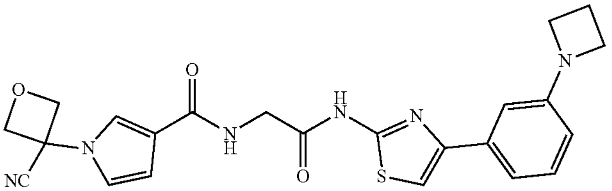 [SMILES: N#CC1(n2ccc(C(=O)NCC(=O)Nc3nc(-c4cccc(N5CCC5)c4)cs3)c2)COC1] |
| 602 | 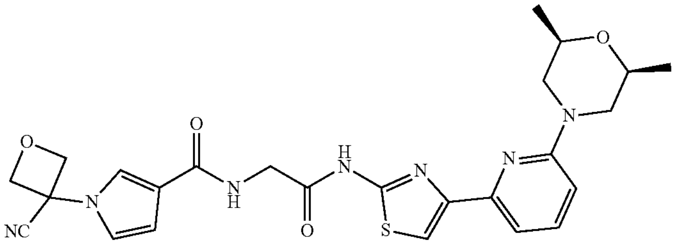 [SMILES: C[C@@H]1CN(c2cccc(-c3csc(NC(=O)CNC(=O)c4ccn(C5(C#N)COC5)c4)n3)n2)C[C@H](C)O1] |
| 607 | 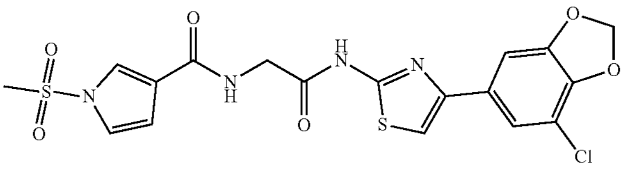 [SMILES: CS(=O)(=O)n1ccc(C(=O)NCC(=O)Nc2nc(-c3cc(Cl)c4c(c3)OCO4)cs2)c1] |

-continued
| # | Compound |
|---|---|
| 608 | 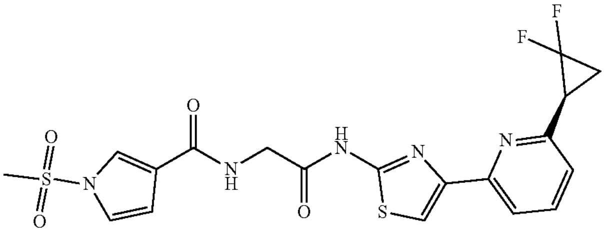 [SMILES: CS(=O)(=O)n1ccc(C(=O)NCC(=O)Nc2nc(-c3cccc([C@@H]4CC4(F)F)n3)cs2)c1] |
| 609 | 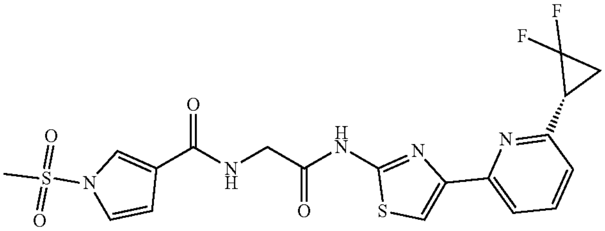 [SMILES: CS(=O)(=O)n1ccc(C(=O)NCC(=O)Nc2nc(-c3cccc([C@H]4CC4(F)F)n3)cs2)c1] |
| 612 | 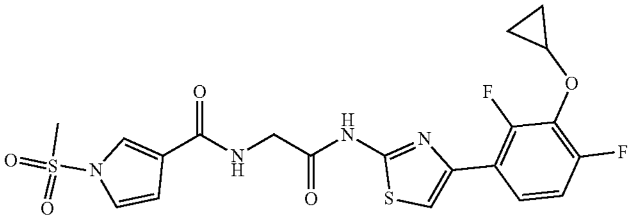 [SMILES: CS(=O)(=O)n1ccc(C(=O)NCC(=O)Nc2nc(-c3ccc(F)c(OC4CC4)c3F)cs2)c1] |
| 614 | 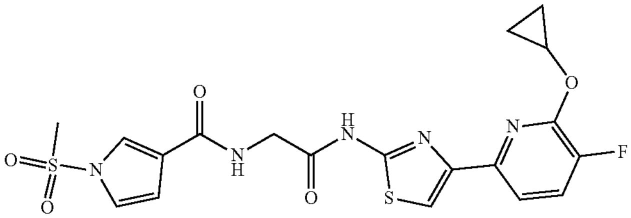 [SMILES: CS(=O)(=O)n1ccc(C(=O)NCC(=O)Nc2nc(-c3ccc(F)c(OC4CC4)n3)cs2)c1] |
| 616 | 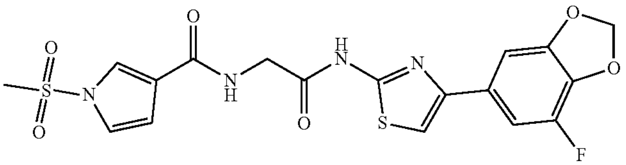 |
| 618 | 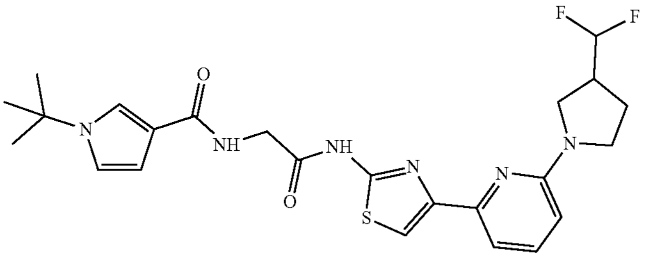 [SMILES: CC(C)(C)n1ccc(C(=O)NCC(=O)Nc2nc(-c3cccc(N4CCC(C(F)F)C4)n3)cs2)c1] |
| 619 | 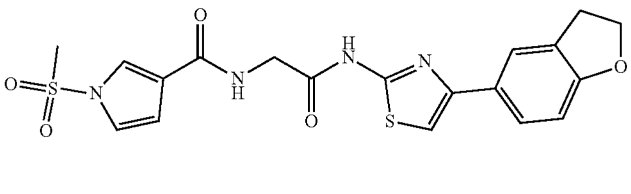 [SMILES: CS(=O)(=O)n1ccc(C(=O)NCC(=O)Nc2nc(-c3ccc4c(c3)CCO4)cs2)c1] |

-continued
| # | Compound |
|---|---|
| 620 | 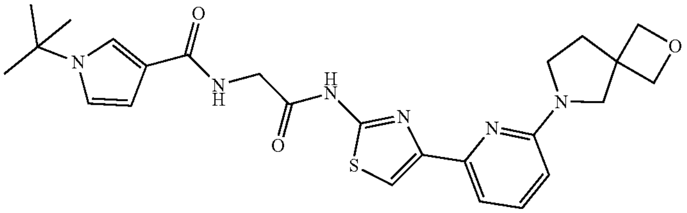 [SMILES: CC(C)(C)n1ccc(C(=O)NCC(=O)Nc2nc(-c3cccc(N4CCC5(COC5)C4)n3)cs2)c1] |
| 621 | 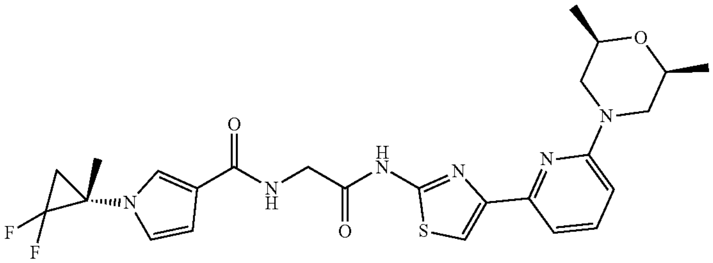 [SMILES: C[C@@H]1CN(c2cccc(-c3csc(NC(=O)CNC(=O)c4ccn([C@@]5(C)CC5(F)F)c4)n3)n2)C[C@H](C)O1] |
| 622 | 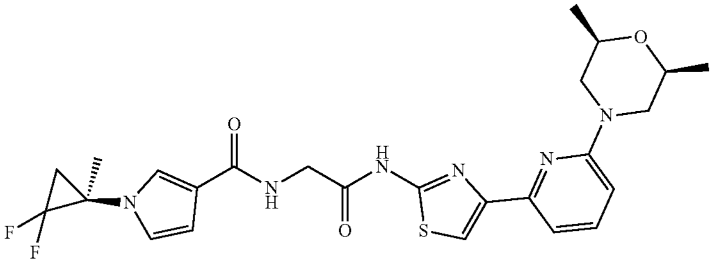 [SMILES: C[C@@H]1CN(c2cccc(-c3csc(NC(=O)CNC(=O)c4ccn([C@]5(C)CC5(F)F)c4)n3)n2)C[C@H](C)O1] |
| 623 | 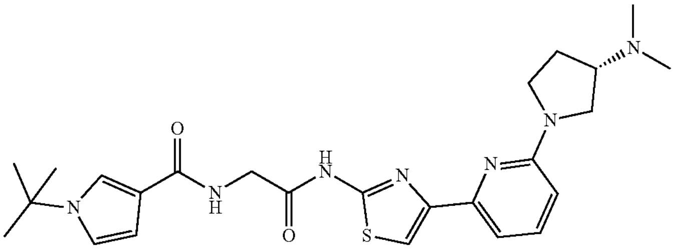 [SMILES: CN(C)[C@H]1CCN(c2cccc(-c3csc(NC(=O)CNC(=O)c4ccn(C(C)(C)C)c4)n3)n2)C1] |
| 624 | 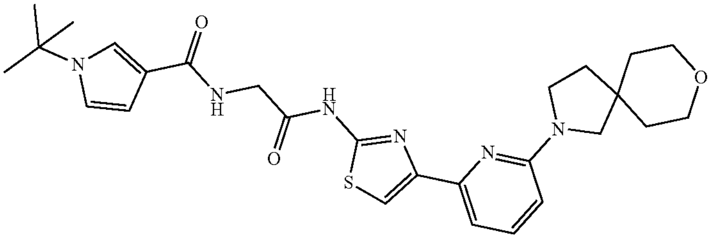 [SMILES: CC(C)(C)n1ccc(C(=O)NCC(=O)Nc2nc(-c3cccc(N4CCC5(CCOCC5)C4)n3)cs2)c1] |
| 625 | 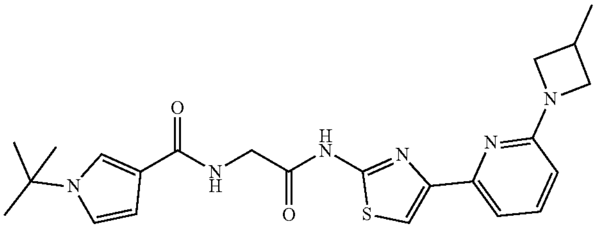 [SMILES: CC1CN(c2cccc(-c3csc(NC(=O)CNC(=O)c4ccn(C(C)(C)C)c4)n3)n2)C1] |

-continued
| # | Compound |
|---|---|
| 626 | 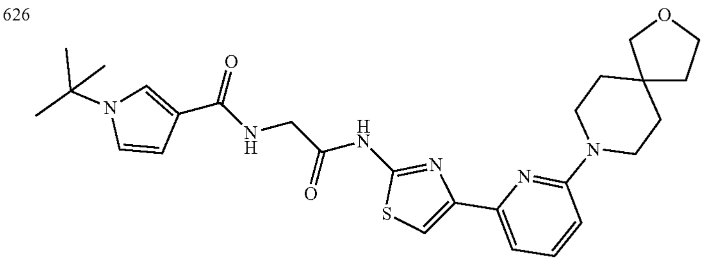 |
| 627 | 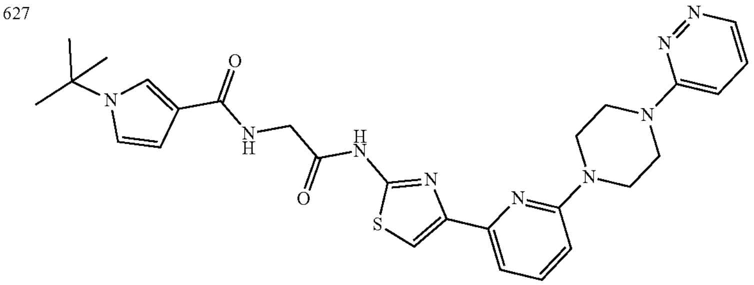 |
| 628 | 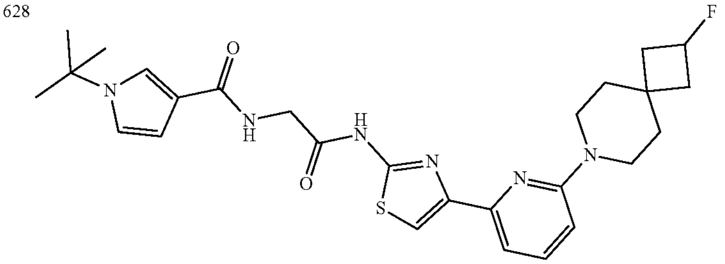 |
| 629 | 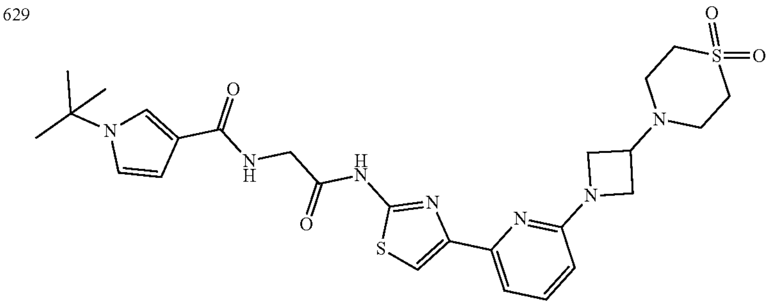 |
| 630 | 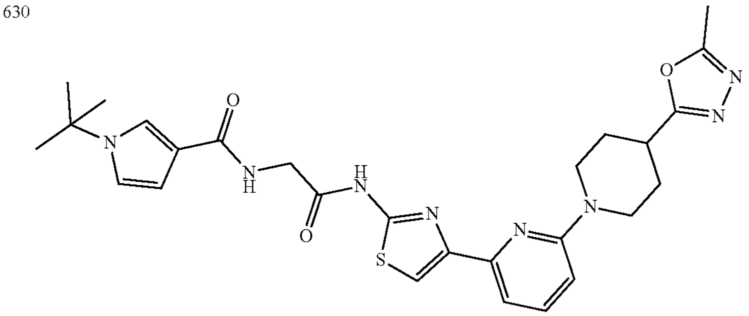 |

-continued
| # | Compound |
|---|---|
| 631 | 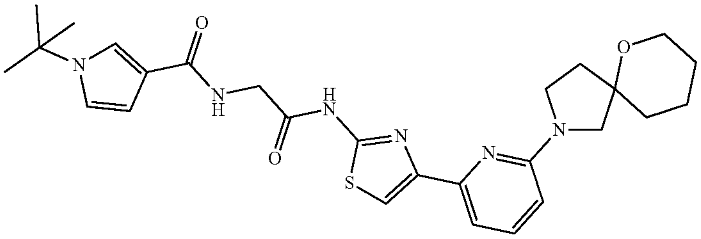 [SMILES: CC(C)(C)n1ccc(C(=O)NCC(=O)Nc2nc(-c3cccc(N4CCC5(CCCCO5)C4)n3)cs2)c1] |
| 632 | 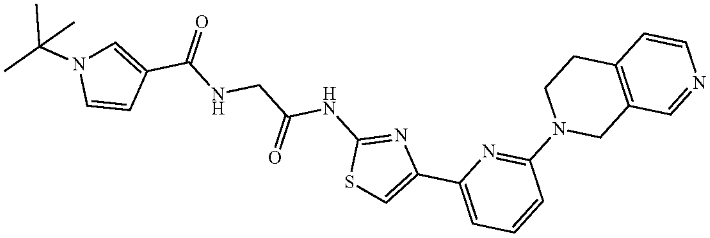 [SMILES: CC(C)(C)n1ccc(C(=O)NCC(=O)Nc2nc(-c3cccc(N4CCc5ccncc5C4)n3)cs2)c1] |
| 633 | 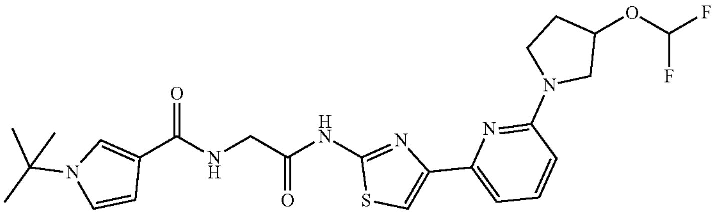 [SMILES: CC(C)(C)n1ccc(C(=O)NCC(=O)Nc2nc(-c3cccc(N4CCC(OC(F)F)C4)n3)cs2)c1] |
| 634 | 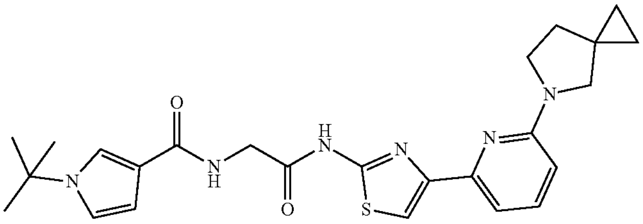 [SMILES: CC(C)(C)n1ccc(C(=O)NCC(=O)Nc2nc(-c3cccc(N4CCC5(CC5)C4)n3)cs2)c1] |
| 635 | 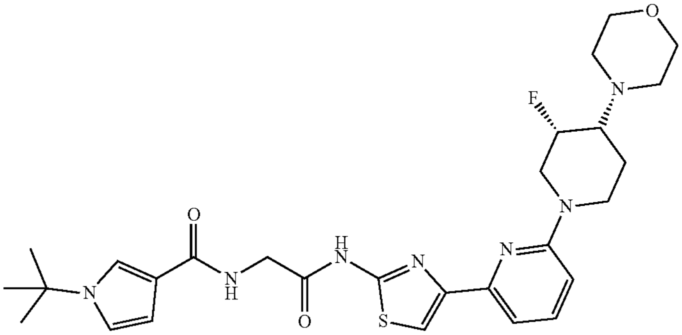 |
| 636 | 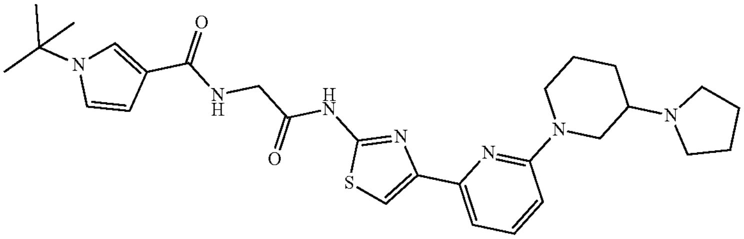 [SMILES: CC(C)(C)n1ccc(C(=O)NCC(=O)Nc2nc(-c3cccc(N4CCCC(N5CCCC5)C4)n3)cs2)c1] |

-continued
| # | Compound |
|---|---|
| 637 | 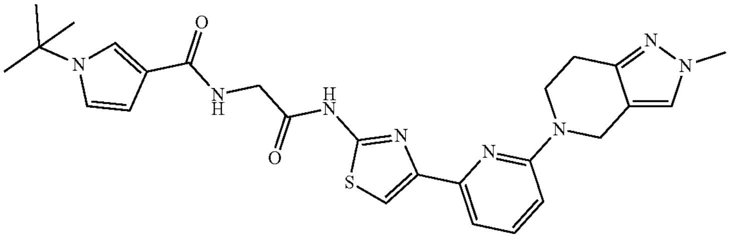 [SMILES: Cn1cc2c(n1)CCN(c1cccc(-c3csc(NC(=O)CNC(=O)c4ccn(C(C)(C)C)c4)n3)n1)C2] |
| 638 | 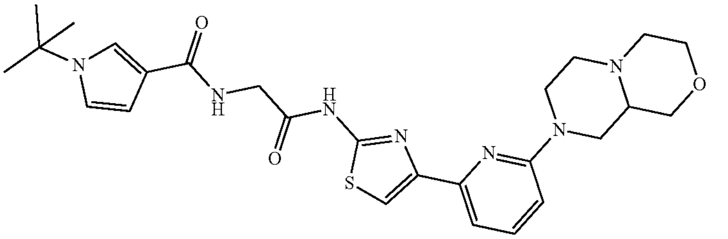 [SMILES: CC(C)(C)n1ccc(C(=O)NCC(=O)Nc2nc(-c3cccc(N4CCN5CCOCC5C4)n3)cs2)c1] |
| 639 | 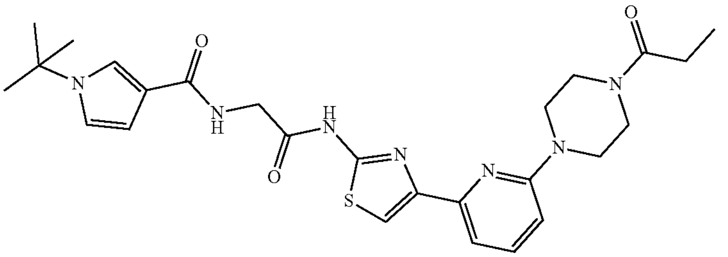 [SMILES: CCC(=O)N1CCN(c2cccc(-c3csc(NC(=O)CNC(=O)c4ccn(C(C)(C)C)c4)n3)n2)CC1] |
| 640 | 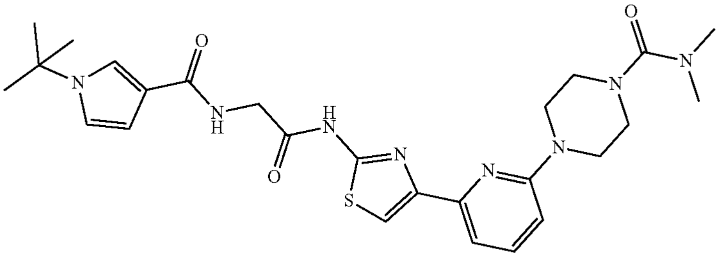 [SMILES: CN(C)C(=O)N1CCN(c2cccc(-c3csc(NC(=O)CNC(=O)c4ccn(C(C)(C)C)c4)n3)n2)CC1] |
| 641 | 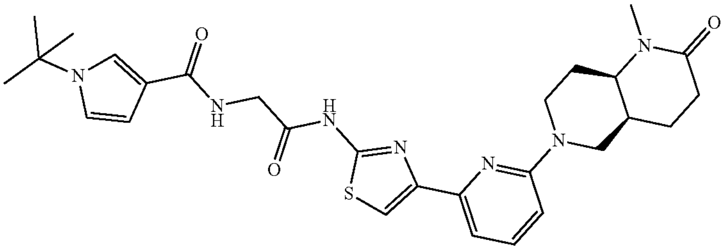 [SMILES: CN1C(=O)CC[C@H]2CN(c3cccc(-c4csc(NC(=O)CNC(=O)c5ccn(C(C)(C)C)c5)n4)n3)CC[C@H]21] |
| 642 | 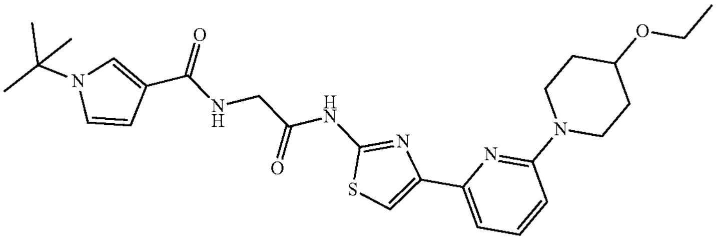 [SMILES: CCOC1CCN(c2cccc(-c3csc(NC(=O)CNC(=O)c4ccn(C(C)(C)C)c4)n3)n2)CC1] |

-continued
| # | Compound |
| --- | --- |
| 643 | 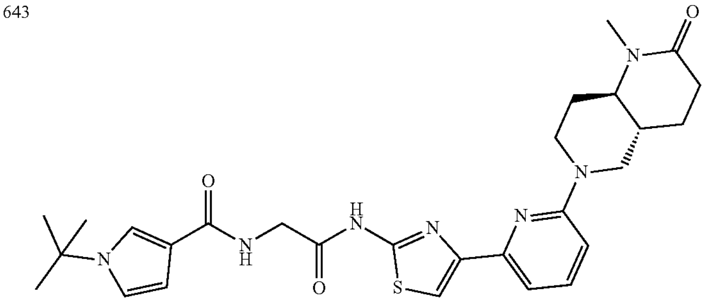 |
| 644 | 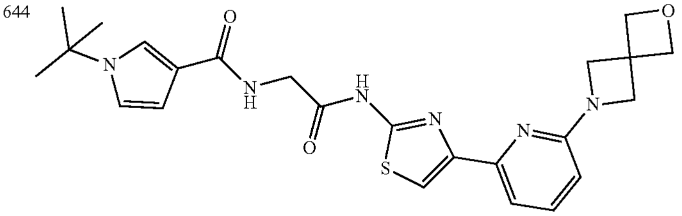 |
| 645 | 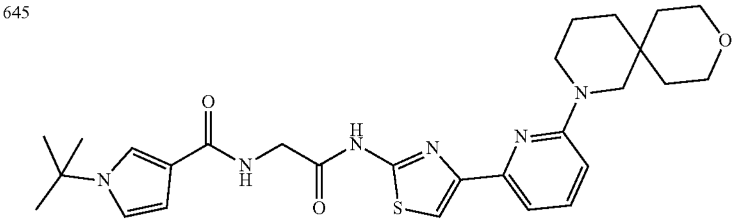 |
| 646 | 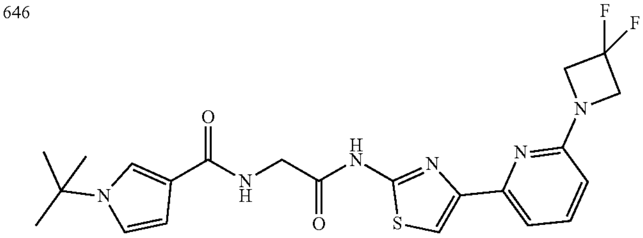 |
| 647 | 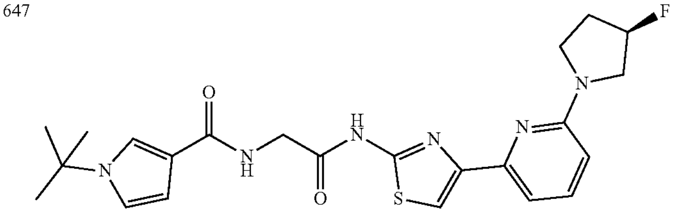 |
| 648 | 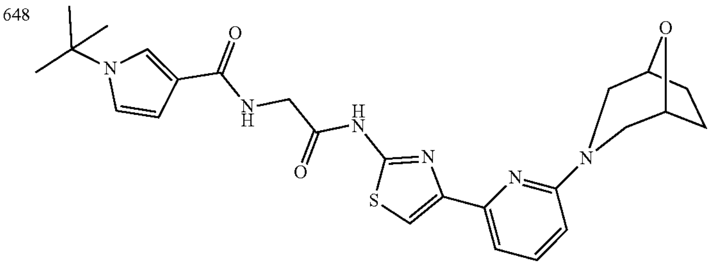 |

-continued
| # | Compound |
|---|---|
| 649 | 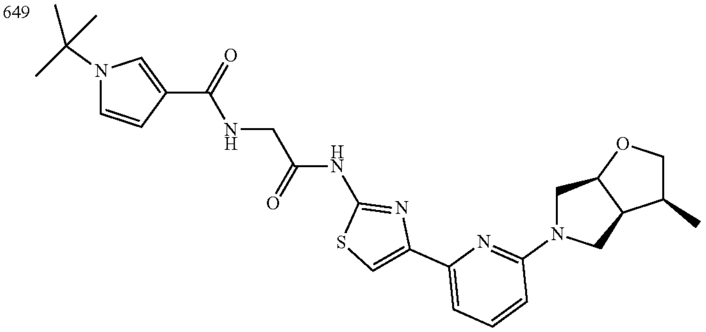 (±) |
| 650 | 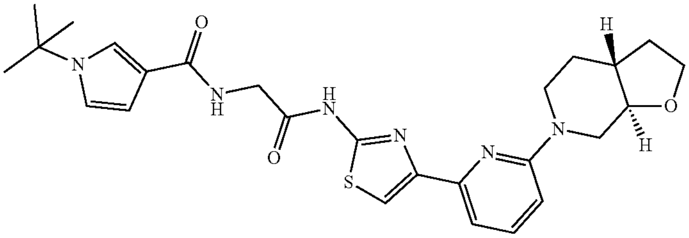 (±) |
| 651 | 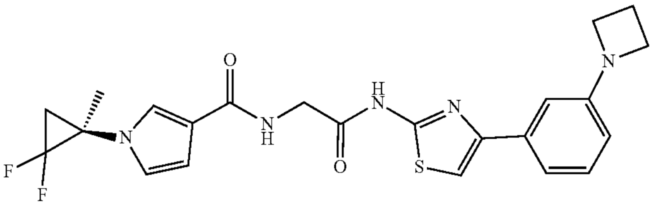 [SMILES: C[C@@]1(n2ccc(C(=O)NCC(=O)Nc3nc(-c4cccc(N5CCC5)c4)cs3)c2)CC1(F)F] |
| 652 | 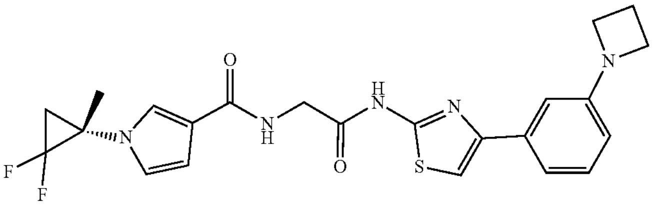 [SMILES: C[C@]1(n2ccc(C(=O)NCC(=O)Nc3nc(-c4cccc(N5CCC5)c4)cs3)c2)CC1(F)F] |
| 653 | 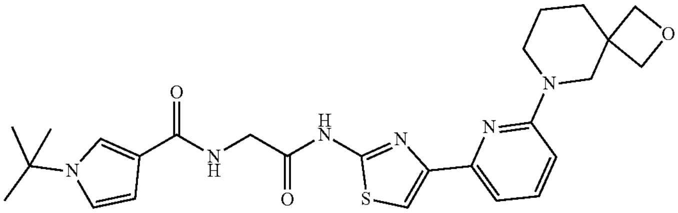 [SMILES: CC(C)(C)n1ccc(C(=O)NCC(=O)Nc2nc(-c3cccc(N4CCCC5(COC5)C4)n3)cs2)c1] |
| 654 | 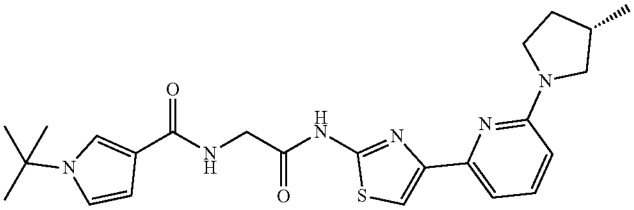 [SMILES: C[C@H]1CCN(c2cccc(-c3csc(NC(=O)CNC(=O)c4ccn(C(C)(C)C)c4)n3)n2)C1] |

-continued
| # | Compound |
| --- | --- |
| 655 | 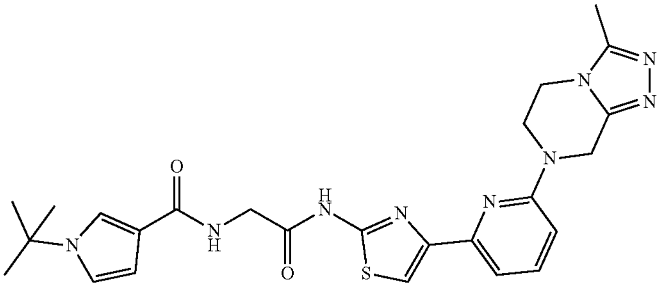 [SMILES: Cc1nnc2n1CCN(c1cccc(-c3csc(NC(=O)CNC(=O)c4ccn(C(C)(C)C)c4)n3)n1)C2] |
| 656 | 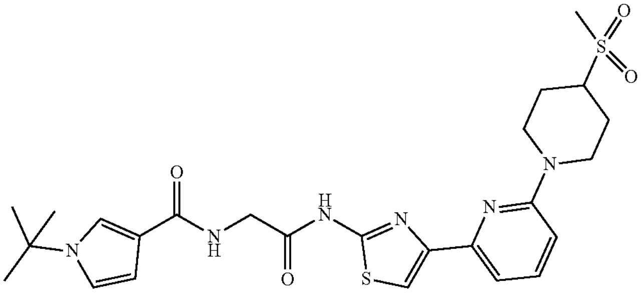 [SMILES: CC(C)(C)n1ccc(C(=O)NCC(=O)Nc2nc(-c3cccc(N4CCC(S(C)(=O)=O)CC4)n3)cs2)c1] |
| 657 | 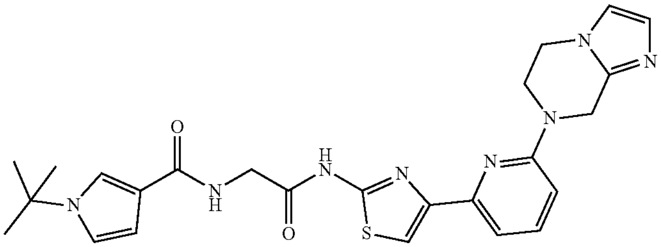 [SMILES: CC(C)(C)n1ccc(C(=O)NCC(=O)Nc2nc(-c3cccc(N4CCn5ccnc5C4)n3)cs2)c1] |
| 658 | 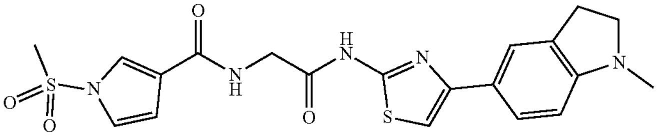 [SMILES: CN1CCc2cc(-c3csc(NC(=O)CNC(=O)c4ccn(S(C)(=O)=O)c4)n3)ccc21] |
| 659 | 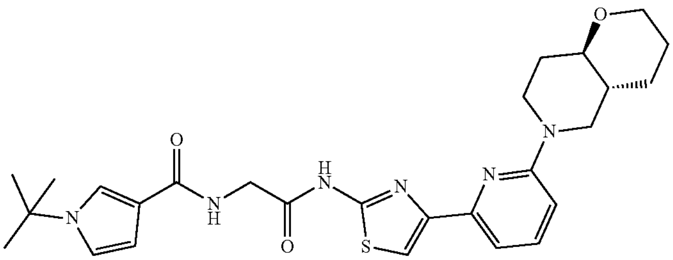 [SMILES: CC(C)(C)n1ccc(C(=O)NCC(=O)Nc2nc(-c3cccc(N4CC[C@H]5OCCC[C@@H]5C4)n3)cs2)c1] |
| 660 | 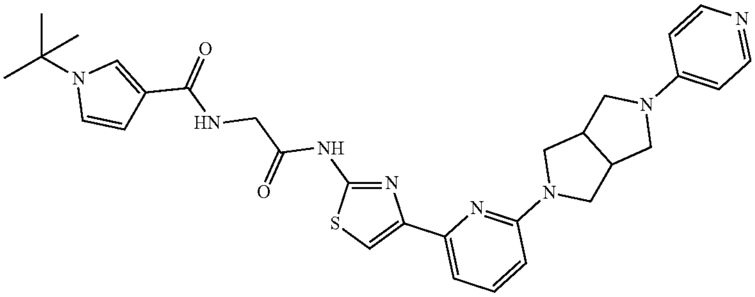 [SMILES: CC(C)(C)n1ccc(C(=O)NCC(=O)Nc2nc(-c3cccc(N4CC5CN(c6ccncc6)CC5C4)n3)cs2)c1] |

-continued
| # | Compound |
|---|---|
| 661 | 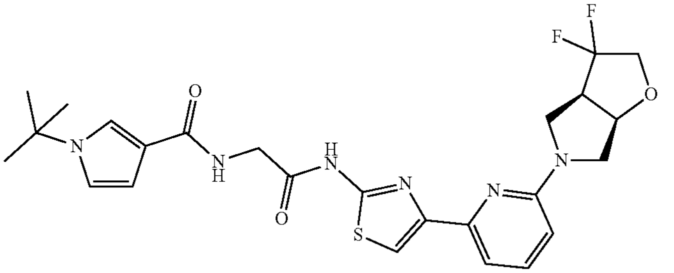 [SMILES: CC(C)(C)n1ccc(C(=O)NCC(=O)Nc2nc(-c3cccc(N4C[C@@H]5OCC(F)(F)[C@@H]5C4)n3)cs2)c1] |
| 662 | 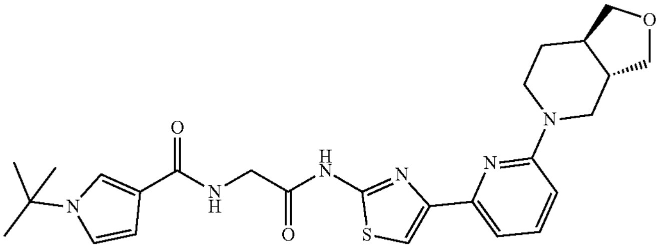 [SMILES: CC(C)(C)n1ccc(C(=O)NCC(=O)Nc2nc(-c3cccc(N4CC[C@H]5COC[C@@H]5C4)n3)cs2)c1] |
| 663 | 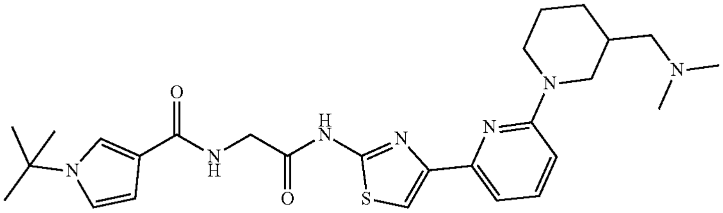 [SMILES: CN(C)CC1CCCN(c2cccc(-c3csc(NC(=O)CNC(=O)c4ccn(C(C)(C)C)c4)n3)n2)C1] |
| 664 | 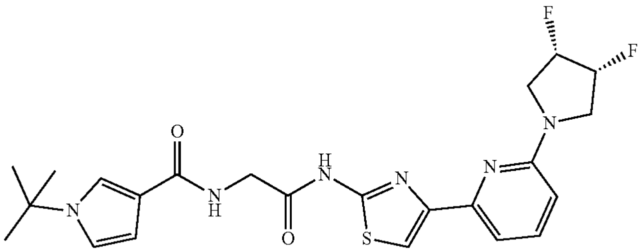 [SMILES: CC(C)(C)n1ccc(C(=O)NCC(=O)Nc2nc(-c3cccc(N4C[C@@H](F)[C@@H](F)C4)n3)cs2)c1] |
| 665 | 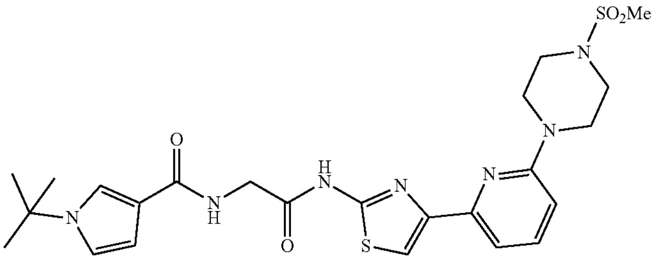 [SMILES: CC(C)(C)n1ccc(C(=O)NCC(=O)Nc2nc(-c3cccc(N4CCN(S(C)(=O)=O)CC4)n3)cs2)c1] |
| 667 | 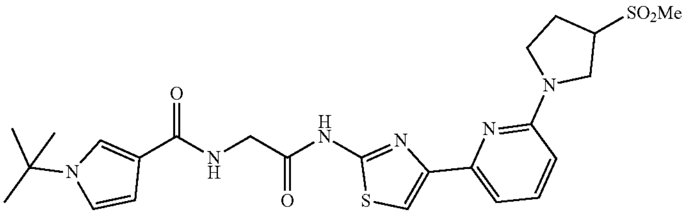 [SMILES: CC(C)(C)n1ccc(C(=O)NCC(=O)Nc2nc(-c3cccc(N4CCC(S(C)(=O)=O)C4)n3)cs2)c1] |

-continued
| # | Compound |
|---|---|
| 668 | 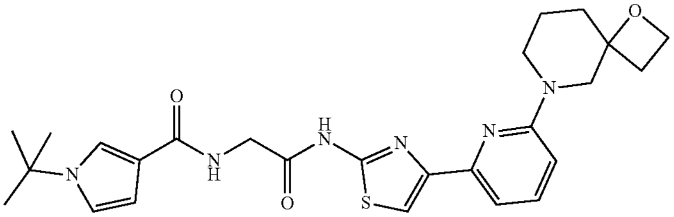 [SMILES: CC(C)(C)n1ccc(C(=O)NCC(=O)Nc2nc(-c3cccc(N4CCCC5(CCO5)C4)n3)cs2)c1] |
| 669 | 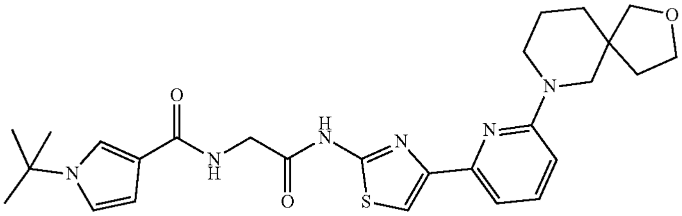 [SMILES: CC(C)(C)n1ccc(C(=O)NCC(=O)Nc2nc(-c3cccc(N4CCCC5(CCOC5)C4)n3)cs2)c1] |
| 670 | 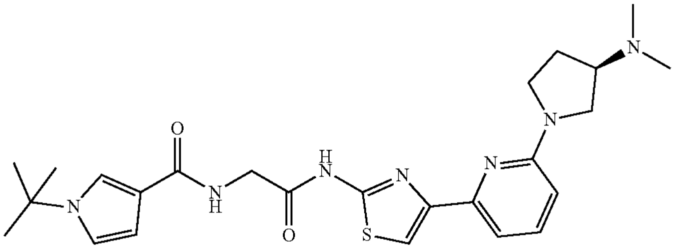 [SMILES: CN(C)[C@@H]1CCN(c2cccc(-c3csc(NC(=O)CNC(=O)c4ccn(C(C)(C)C)c4)n3)n2)C1] |
| 671 | 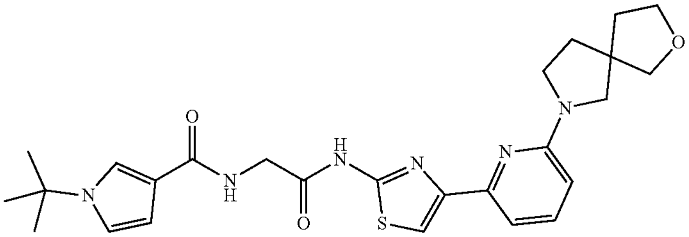 [SMILES: CC(C)(C)n1ccc(C(=O)NCC(=O)Nc2nc(-c3cccc(N4CCC5(CCOC5)C4)n3)cs2)c1] |
| 672 | 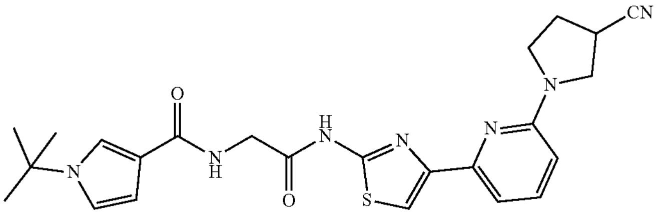 [SMILES: CC(C)(C)n1ccc(C(=O)NCC(=O)Nc2nc(-c3cccc(N4CCC(C#N)C4)n3)cs2)c1] |
| 673 | 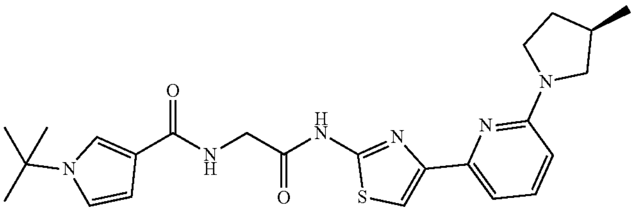 [SMILES: C[C@@H]1CCN(c2cccc(-c3csc(NC(=O)CNC(=O)c4ccn(C(C)(C)C)c4)n3)n2)C1] |

-continued
| # | Compound |
|---|---|
| 674 | 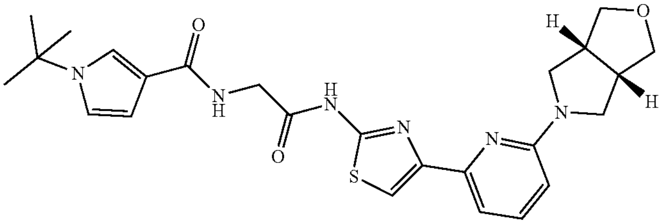 [SMILES: CC(C)(C)n1ccc(C(=O)NCC(=O)Nc2nc(-c3cccc(N4C[C@H]5COC[C@H]5C4)n3)cs2)c1] |
| 675 | 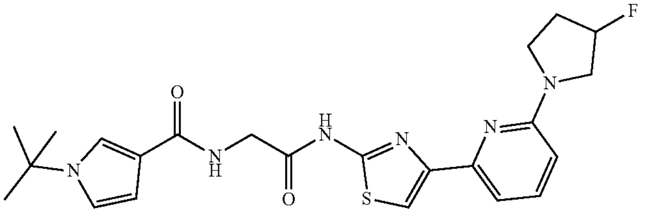 [SMILES: CC(C)(C)n1ccc(C(=O)NCC(=O)Nc2nc(-c3cccc(N4CCC(F)C4)n3)cs2)c1] |
| 676 | 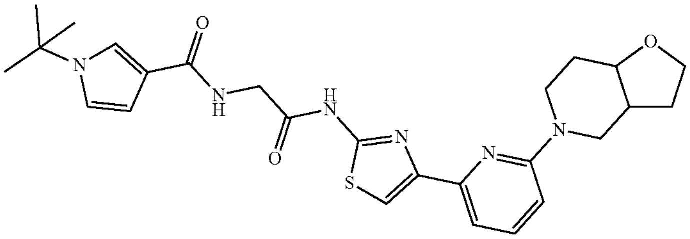 [SMILES: CC(C)(C)n1ccc(C(=O)NCC(=O)Nc2nc(-c3cccc(N4CCC5OCCC5C4)n3)cs2)c1] |
| 677 | 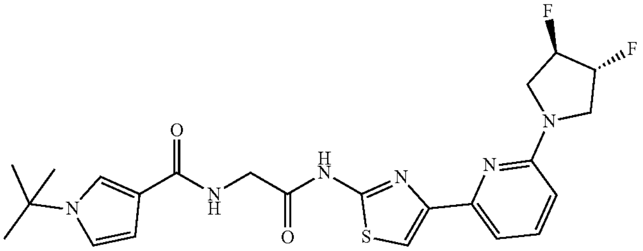 [SMILES: CC(C)(C)n1ccc(C(=O)NCC(=O)Nc2nc(-c3cccc(N4C[C@@H](F)[C@H](F)C4)n3)cs2)c1] |
| 678 | 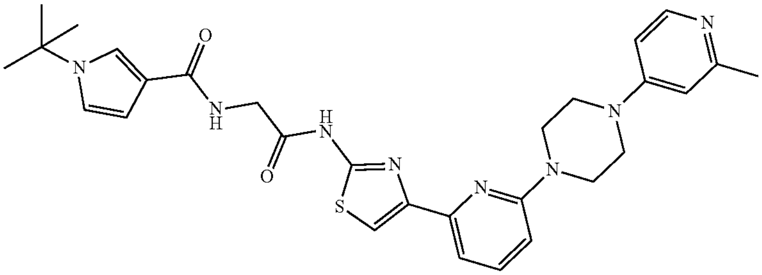 [SMILES: Cc1cc(N2CCN(c3cccc(-c4csc(NC(=O)CNC(=O)c5ccn(C(C)(C)C)c5)n4)n3)CC2)ccn1] |
| 679 | 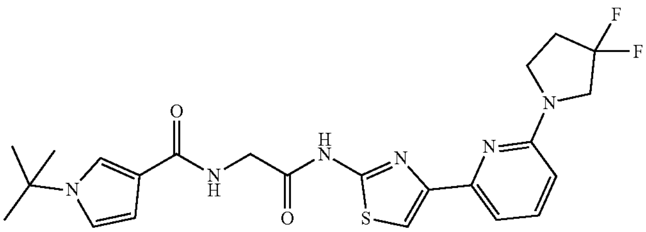 [SMILES: CC(C)(C)n1ccc(C(=O)NCC(=O)Nc2nc(-c3cccc(N4CCC(F)(F)C4)n3)cs2)c1] |

-continued
| # | Compound |
|---|---|
| 680 | 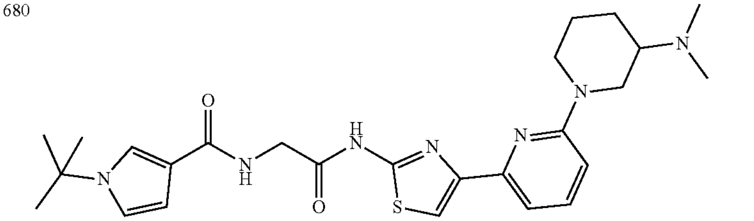 |
| 681 | 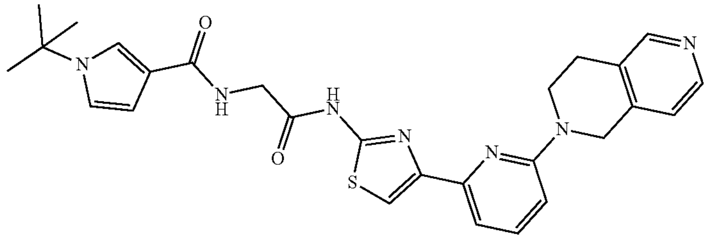 [SMILES: CC(C)(C)n1ccc(C(=O)NCC(=O)Nc2nc(-c3cccc(N4CCc5cnccc5C4)n3)cs2)c1] |
| 682 | 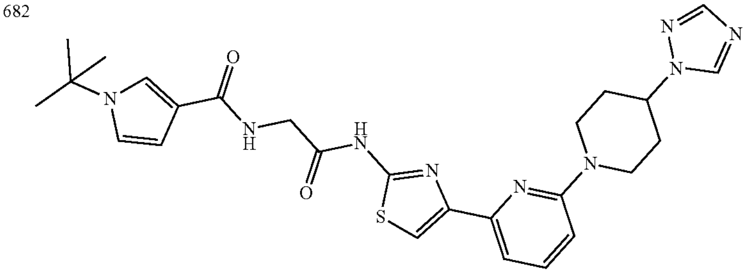 |
| 683 | 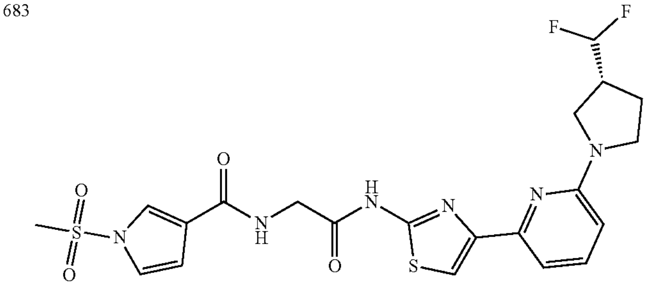 |
| 684 | 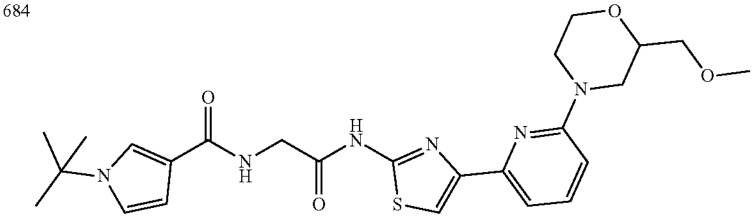 |
| 685 | 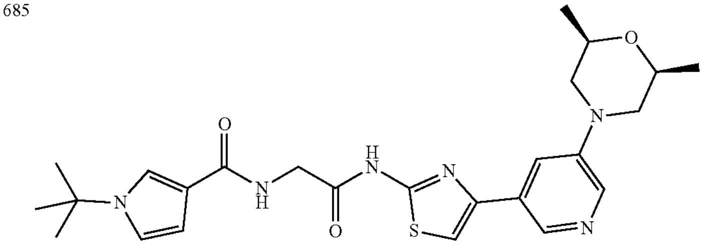 |

-continued
| # | Compound |
|---|---|
| 686 | 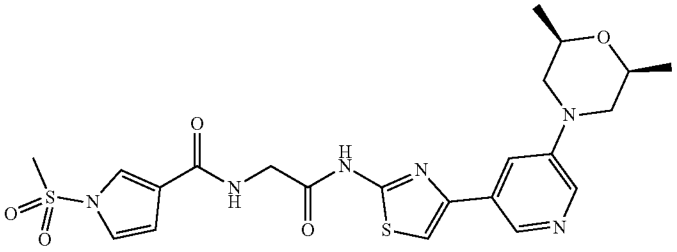 [SMILES: C[C@@H]1CN(c2cncc(-c3csc(NC(=O)CNC(=O)c4ccn(S(C)(=O)=O)c4)n3)c2)C[C@H](C)O1] |
| 687 | 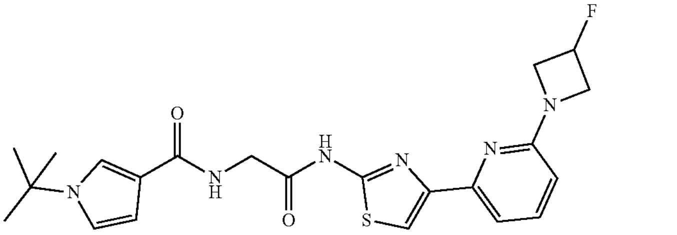 [SMILES: CC(C)(C)n1ccc(C(=O)NCC(=O)Nc2nc(-c3cccc(N4CC(F)C4)n3)cs2)c1] |
| 689 | 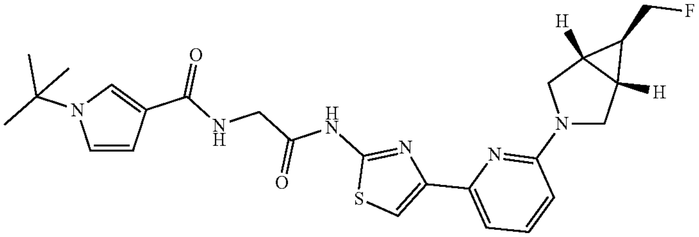 [SMILES: CC(C)(C)n1ccc(C(=O)NCC(=O)Nc2nc(-c3cccc(N4C[C@@H]5[C@@H](CF)[C@@H]5C4)n3)cs2)c1] |
| 690 | 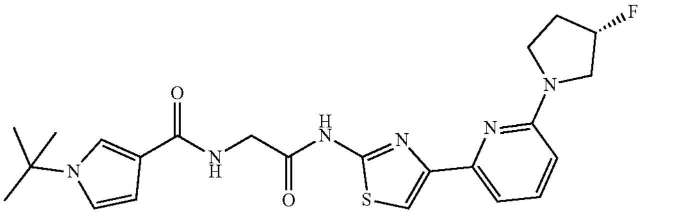 [SMILES: CC(C)(C)n1ccc(C(=O)NCC(=O)Nc2nc(-c3cccc(N4CC[C@H](F)C4)n3)cs2)c1] |
| 692 | 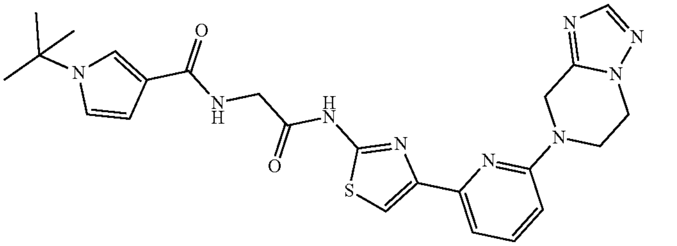 [SMILES: CC(C)(C)n1ccc(C(=O)NCC(=O)Nc2nc(-c3cccc(N4CCn5ncnc5C4)n3)cs2)c1] |
| 693 | 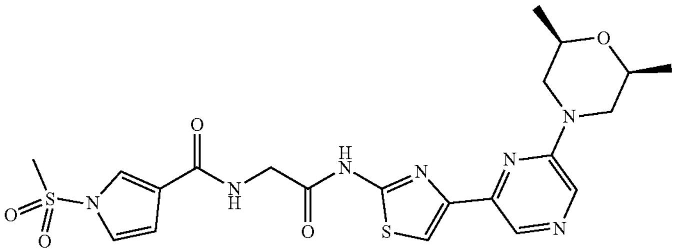 [SMILES: C[C@@H]1CN(c2cncc(-c3csc(NC(=O)CNC(=O)c4ccn(S(C)(=O)=O)c4)n3)n2)C[C@H](C)O1] |

-continued
| # | Compound |
|---|---|
| 694 | 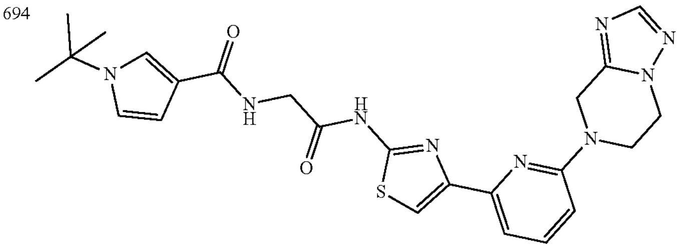 |
| 696 | 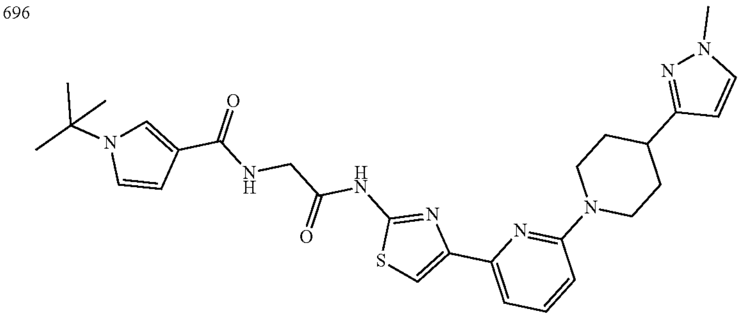 |
| 697 | 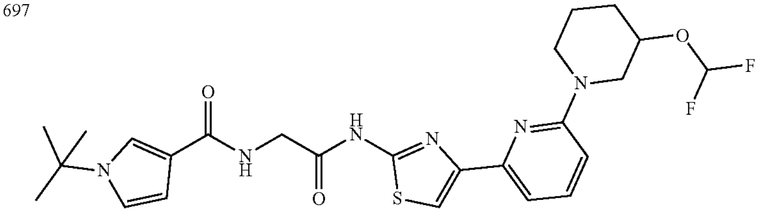 |
| 698 | 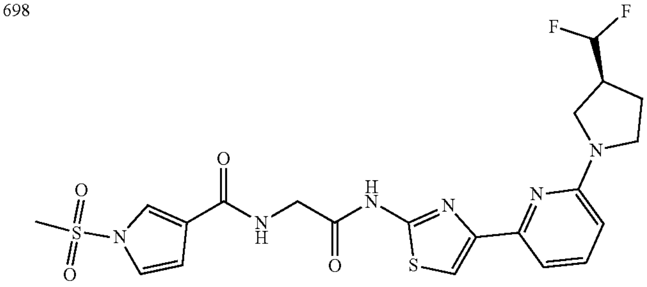 |
| 700 | 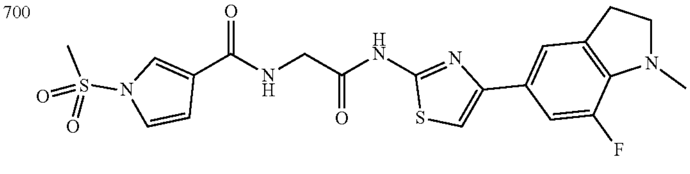 |
| 701 | 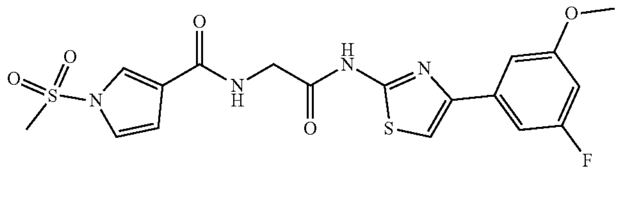 [SMILES: COc1cc(F)cc(-c2csc(NC(=O)CNC(=O)c3ccn(S(C)(=O)=O)c3)n2)c1] |

-continued
| # | Compound |
|---|---|
| 702 | 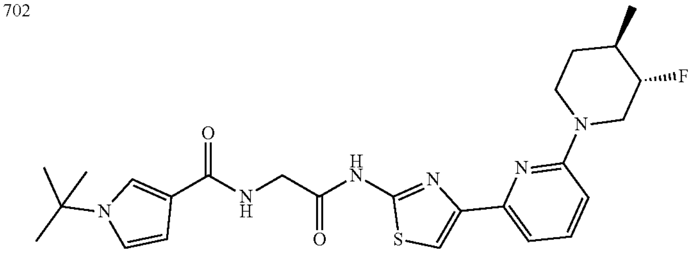 (±) |
| 703 | 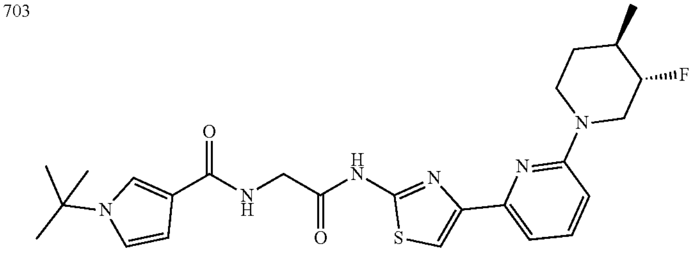 (±) |
| 704 | 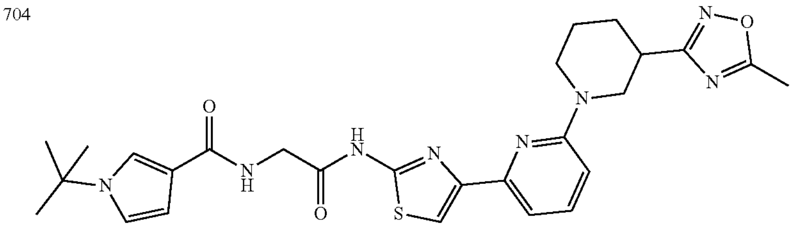 |
| 705 | 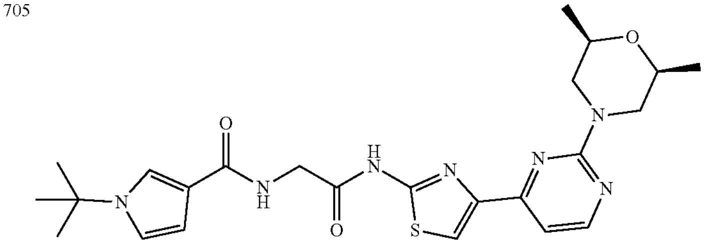 |
| 706 | 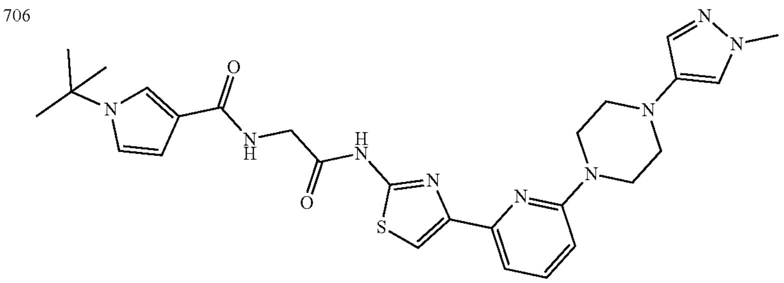 |

-continued
| # | Compound |
|---|---|
| 709 | 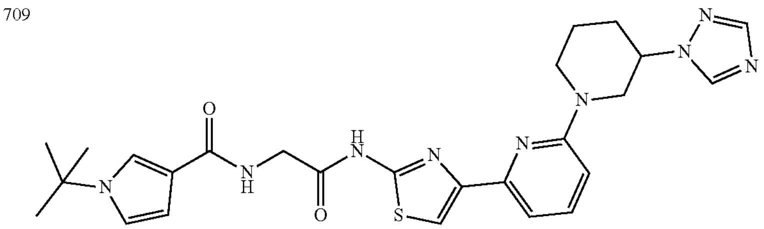 |
| 711 | 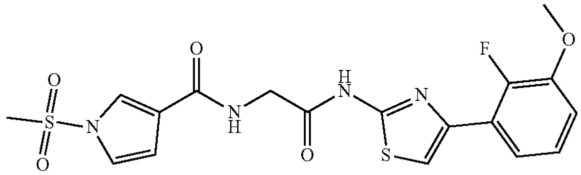 [SMILES: COc1cccc(-c2csc(NC(=O)CNC(=O)c3ccn(S(C)(=O)=O)c3)n2)c1F] |
| 715 | 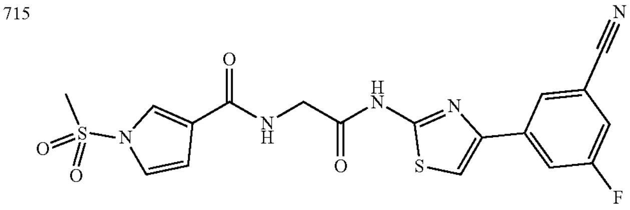 |
| 717 | 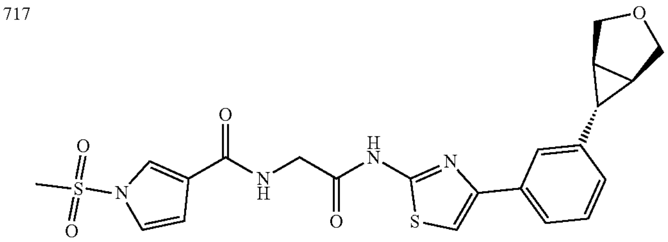 |
| 718 | 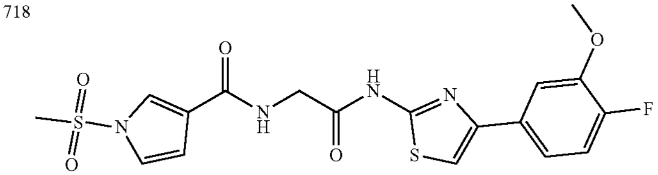 |
| 719 | 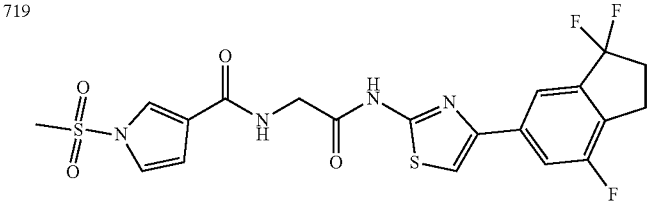 |
| 720 | 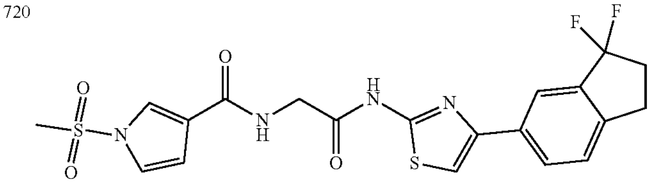 |

-continued
| # | Compound |
|---|---|
| 722 | 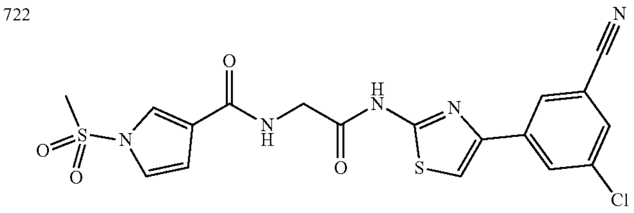 |
| 724 | 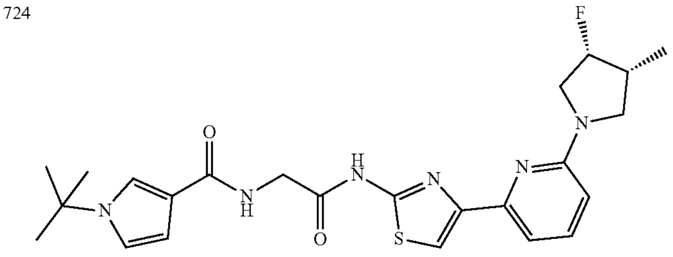 (±) |
| 727 | 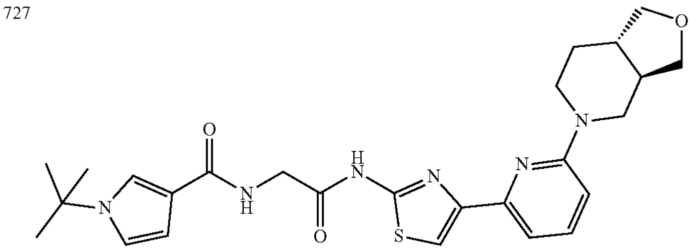 |
| 729 | 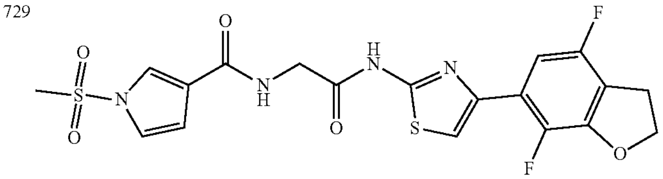 |
| 731 | 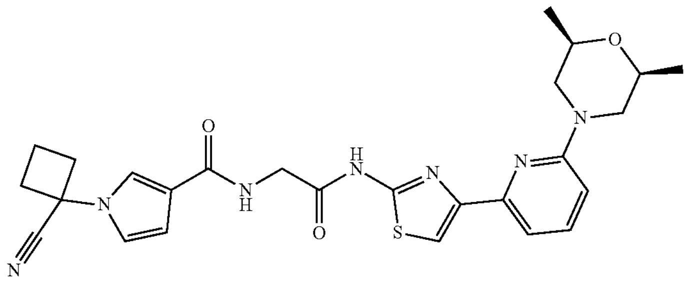 [SMILES: C[C@@H]1CN(c2cccc(-c3csc(NC(=O)CNC(=O)c4ccn(C5(C#N)CCC5)c4)n3)n2)C[C@H](C)O1] |
| 736 | 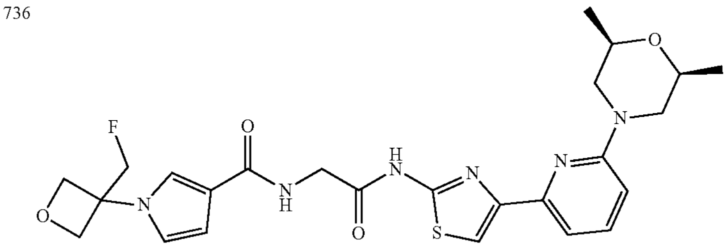 |

-continued
| # | Compound |
|---|---|
| 737 | 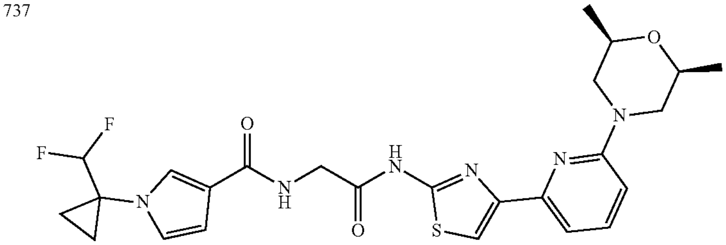 |
| 743 | 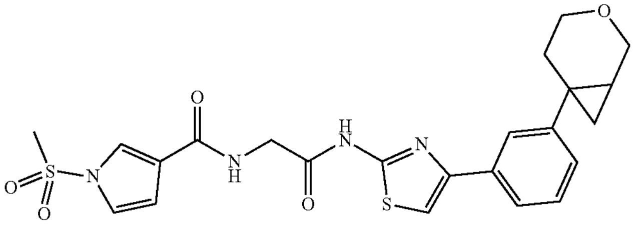 (±) |
| 744 | 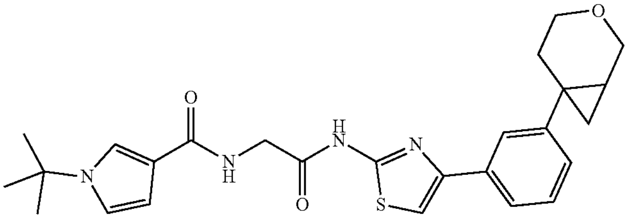 (±) |
| 745 | 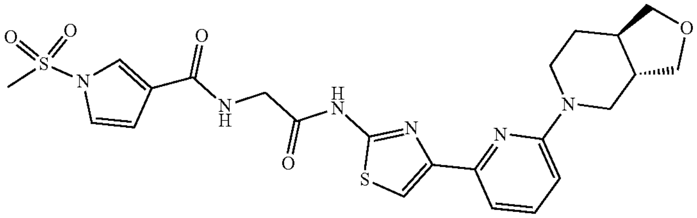 [SMILES: CS(=O)(=O)n1ccc(C(=O)NCC(=O)Nc2nc(-c3cccc(N4CC[C@H]5COC[C@@H]5C4)n3)cs2)c1] |
| 746 | 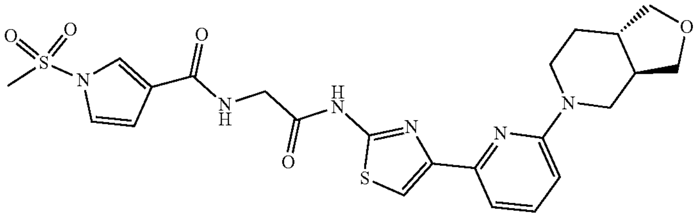 [SMILES: CS(=O)(=O)n1ccc(C(=O)NCC(=O)Nc2nc(-c3cccc(N4CC[C@@H]5COC[C@H]5C4)n3)cs2)c1] |
| 747 | 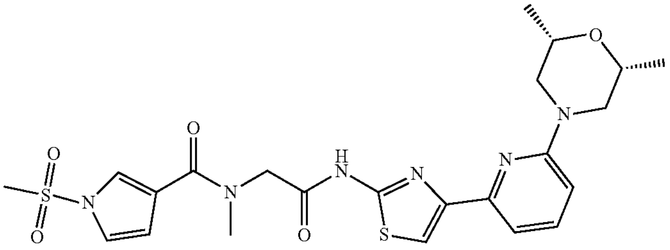 |

-continued
| # | Compound |
|---|---|
| 748 | 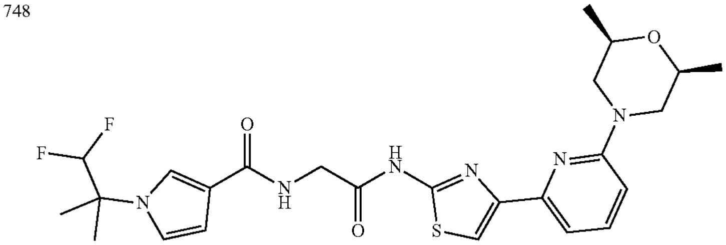 |
| 749 | 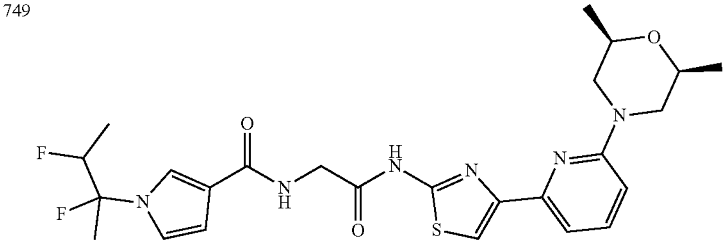 |
| 750 | 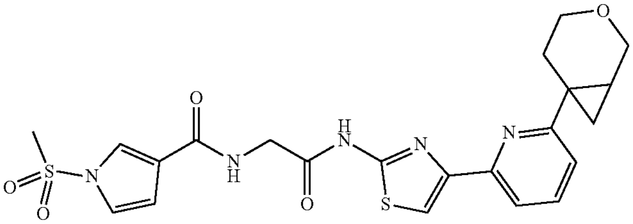 [SMILES: CS(=O)(=O)n1ccc(C(=O)NCC(=O)Nc2nc(-c3cccc(C45CCOCC4C5)n3)cs2)c1] |
| 751 | 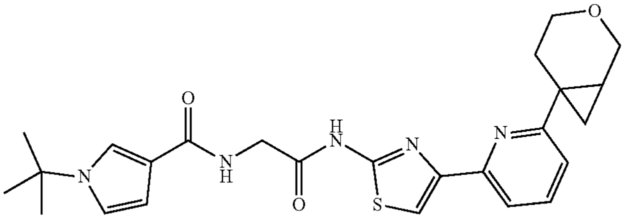 [SMILES: CC(C)(C)n1ccc(C(=O)NCC(=O)Nc2nc(-c3cccc(C45CCOCC4C5)n3)cs2)c1] |
| 752 | 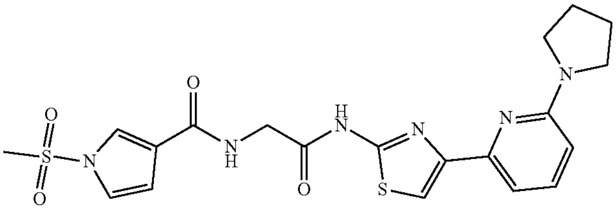 [SMILES: CS(=O)(=O)n1ccc(C(=O)NCC(=O)Nc2nc(-c3cccc(N4CCCC4)n3)cs2)c1] |
| 753 | 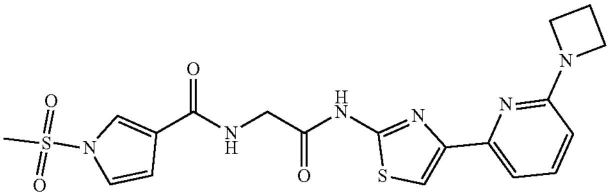 [SMILES: CS(=O)(=O)n1ccc(C(=O)NCC(=O)Nc2nc(-c3cccc(N4CCC4)n3)cs2)c1] |

-continued
| # | Compound |
|---|---|
| 754 | 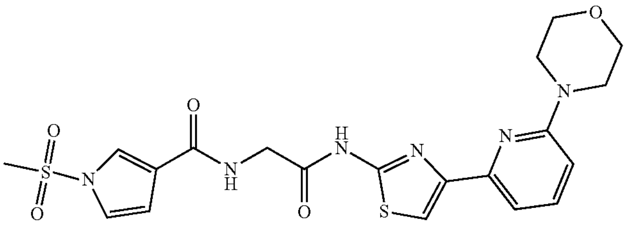 [SMILES: CS(=O)(=O)n1ccc(C(=O)NCC(=O)Nc2nc(-c3cccc(N4CCOCC4)n3)cs2)c1] |
| 757 | 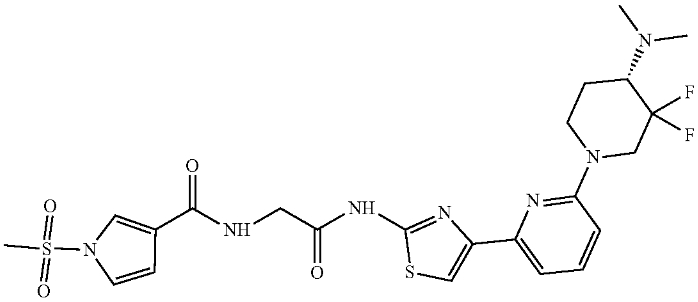 [SMILES: CN(C)[C@H]1CCN(c2cccc(-c3csc(NC(=O)CNC(=O)c4ccn(S(C)(=O)=O)c4)n3)n2)CC1(F)F] |
| 760 | 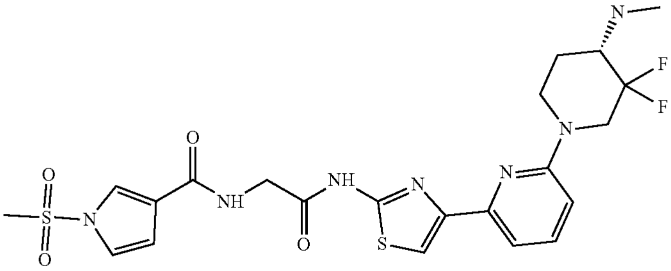 [SMILES: CN[C@H]1CCN(c2cccc(-c3csc(NC(=O)CNC(=O)c4ccn(S(C)(=O)=O)c4)n3)n2)CC1(F)F] |
| 761 | 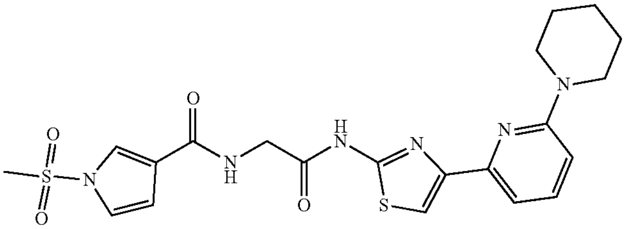 [SMILES: CS(=O)(=O)n1ccc(C(=O)NCC(=O)Nc2nc(-c3cccc(N4CCCCC4)n3)cs2)c1] |
| 762 | 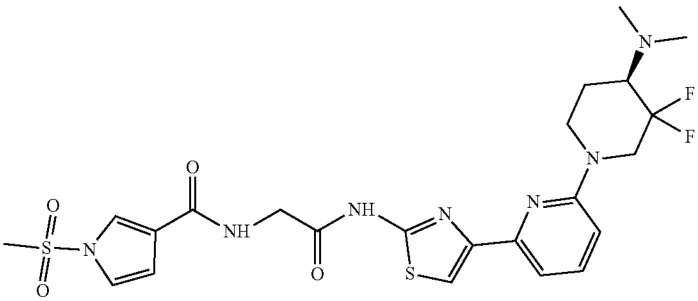 [SMILES: CN(C)[C@@H]1CCN(c2cccc(-c3csc(NC(=O)CNC(=O)c4ccn(S(C)(=O)=O)c4)n3)n2)CC1(F)F] |

-continued

| # | Compound |
|---|---|
| 763 | 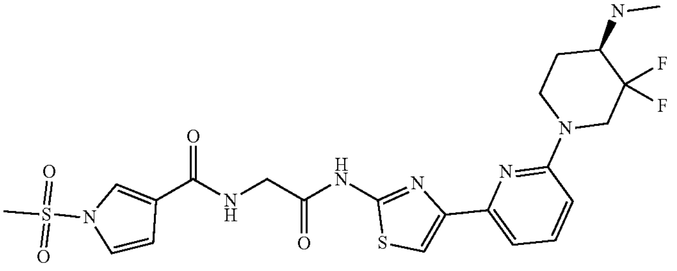 [SMILES: CN[C@@H]1CCN(c2cccc(-c3csc(NC(=O)CNC(=O)c4ccn(S(C)(=O)=O)c4)n3)n2)CC1(F)F] |
| 764 | 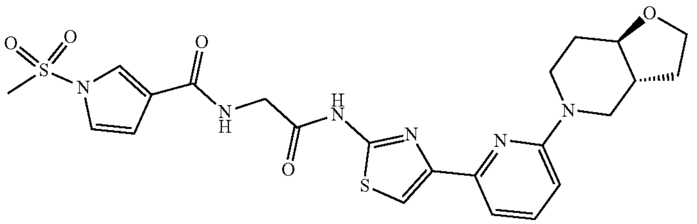 [SMILES: CS(=O)(=O)n1ccc(C(=O)NCC(=O)Nc2nc(-c3cccc(N4CC[C@H]5OCC[C@@H]5C4)n3)cs2)c1] |
| 765 | 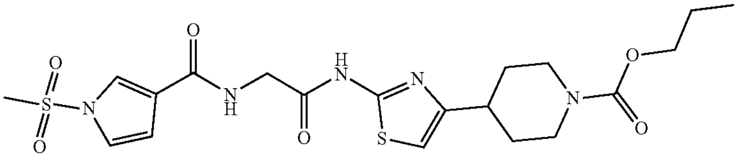 [SMILES: CCCOC(=O)N1CCC(c2csc(NC(=O)CNC(=O)c3ccn(S(C)(=O)=O)c3)n2)CC1] |
| 766 | 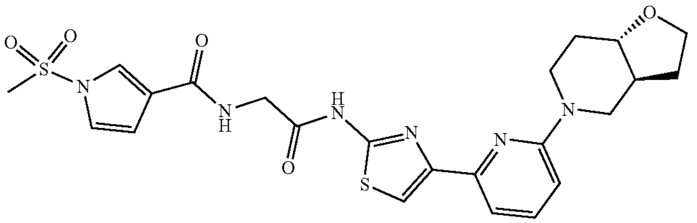 [SMILES: CS(=O)(=O)n1ccc(C(=O)NCC(=O)Nc2nc(-c3cccc(N4CC[C@@H]5OCC[C@H]5C4)n3)cs2)c1] |
| 771 | 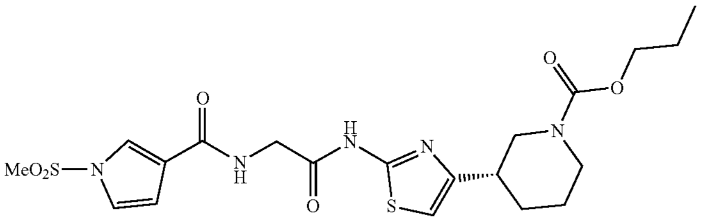 [SMILES: CCCOC(=O)N1CCC[C@H](c2csc(NC(=O)CNC(=O)c3ccn(S(C)(=O)=O)c3)n2)C1] |
| 776 | 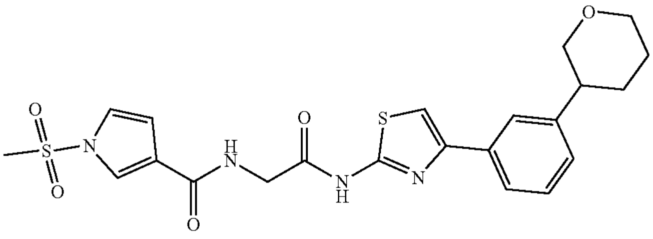 [SMILES: CS(=O)(=O)n1ccc(C(=O)NCC(=O)Nc2nc(-c3cccc(C4CCCOC4)c3)cs2)c1] |

15. A pharmaceutical composition comprising a compound of claim 1 and a pharmaceutically acceptable excipient.

16. A method of treating melanoma, prostate cancer, breast cancer, bone cancer, renal cell carcinoma, or a hematologic cancer in a subject in need thereof, the method comprising administering to the subject an effective amount of a compound of claim 1.

* * * * *